United States Patent
Patturajan

(10) Patent No.: US 7,033,790 B2
(45) Date of Patent: Apr. 25, 2006

(54) PROTEINS AND NUCLEIC ACIDS ENCODING SAME

(75) Inventor: Meera Patturajan, Branford, CT (US)

(73) Assignee: CuraGen Corporation, New Haven, CT (US)

( * ) Notice: Subject to any disclaimer, the term of this patent is extended or adjusted under 35 U.S.C. 154(b) by 403 days.

(21) Appl. No.: 10/114,270

(22) Filed: Apr. 2, 2002

(65) Prior Publication Data

US 2004/0030110 A1 Feb. 12, 2004

Related U.S. Application Data

(60) Provisional application No. 60/281,086, filed on Apr. 3, 2001, provisional application No. 60/281,136, filed on Apr. 3, 2001, provisional application No. 60/281,863, filed on Apr. 5, 2001, provisional application No. 60/281,906, filed on Apr. 5, 2001, provisional application No. 60/282,020, filed on Apr. 6, 2001, provisional application No. 60/282,930, filed on Apr. 10, 2001, provisional application No. 60/282,934, filed on Apr. 10, 2001, provisional application No. 60/283,512, filed on Apr. 12, 2001, provisional application No. 60/283,710, filed on Apr. 13, 2001, provisional application No. 60/284,234, filed on Apr. 17, 2001, provisional application No. 60/285,325, filed on Apr. 19, 2001, provisional application No. 60/285,381, filed on Apr. 20, 2001, provisional application No. 60/285,609, filed on Apr. 20, 2001, provisional application No. 60/285,748, filed on Apr. 23, 2001, provisional application No. 60/285,890, filed on Apr. 23, 2001, provisional application No. 60/286,068, filed on Apr. 24, 2001, provisional application No. 60/286,292, filed on Apr. 25, 2001, provisional application No. 60/287,213, filed on Apr. 27, 2001, provisional application No. 60/288,257, filed on May 2, 2001, provisional application No. 60/294,164, filed on May 29, 2001, provisional application No. 60/294,484, filed on May 30, 2001, provisional application No. 60/298,952, filed on Jun. 18, 2001, provisional application No. 60/299,237, filed on Jun. 19, 2001, provisional application No. 60/299,276, filed on Jun. 19, 2001, provisional application No. 60/318,750, filed on Sep. 12, 2001, provisional application No. 60/324,800, filed on Sep. 25, 2001, provisional application No. 60/324,802, filed on Sep. 25, 2001, provisional application No. 60/325,684, filed on Sep. 27, 2001, provisional application No. 60/330,143, filed on Oct. 17, 2001, provisional application No. 60/332,115, filed on Nov. 21, 2001, provisional application No. 60/332,131, filed on Nov. 14, 2001, provisional application No. 60/332,240, filed on Nov. 14, 2001, provisional application No. 60/332,779, filed on Nov. 14, 2001, provisional application No. 60/337,621, filed on Dec. 4, 2001, provisional application No. 60/345,783, filed on Jan. 3, 2002, and provisional application No. 60/350,251, filed on Jan. 16, 2002.

(51) Int. Cl.
   *C07H 21/04* (2006.01)
   *C12P 21/06* (2006.01)
   *C07K 1/00* (2006.01)
   *C12N 15/00* (2006.01)

(52) U.S. Cl. .................. 435/69.1; 435/320.1; 536/23.1; 530/350

(58) Field of Classification Search .............. 435/320.1, 435/69.1; 536/23.1; 530/350
   See application file for complete search history.

(56) References Cited

U.S. PATENT DOCUMENTS

| 5,858,707 | A  | 1/1999  | Guimarães et al. | ........ 435/69.1 |
| 5,871,697 | A  | 2/1999  | Rothberg et al.  | .......... 422/68.1 |
| 6,025,196 | A  | 2/2000  | Sladek et al.    | ............ 435/320.1 |
| 6,057,101 | A  | 5/2000  | Nandabalan et al.| ........... 435/6 |
| 6,083,693 | A  | 7/2000  | Nandabalan et al.| ........... 435/6 |
| 6,153,188 | A  | 11/2000 | Wilson et al.    | ............. 424/94.6 |
| 6,265,216 | B1 | 7/2001  | Bennett et al.   | ............. 435/375 |

FOREIGN PATENT DOCUMENTS

| CN | 1287170   | 3/2001 |
| CN | 1296952   | 5/2001 |
| CN | 1315336   | 10/2001 |
| DE | 198 41 413| 9/1999 |
| EP | 0 351 826 | 9/1994 |
| EP | 0 856 583 | 8/1998 |
| EP | 1 033 405 | 9/2000 |
| EP | 1 067 182 | 1/2001 |
| EP | 1 074 617 | 2/2001 |
| EP | 1 130 094 | 9/2001 |

(Continued)

OTHER PUBLICATIONS

Alderborn, et al. (2000). "Determination of single–nucleotide polymorphisms by real–time pyrophosphate DNA sequencing." *Genome Res* 10(8): 1249–58.

Bindoff, et al. (1989). "Familial intermittent ataxia due to a defect of the E1 component of pyruvate dehydrogenase complex," *J Neurol Sci* 93(2–3): 311–8.

Biswas and Russell (1997). "Expression clonging and characterization of oxidative 17beta– and 3alpha– hydroxysteroid dehydrogenases from rat and human prostate," *J Biol Chem* 272(25): 15959–66.

Bonaglia, et al. (2001), "Disruption of the ProSAP2 gene in a t(12;22)(q24.1;q13.3) is associated with the 22q13.3 deletion syndrome." *Am J Hum Genet* 69(2): 261–8.

(Continued)

*Primary Examiner*—Jon Weber
*Assistant Examiner*—Sheridan K. Snedden
(74) *Attorney, Agent, or Firm*—Daniel K. Rieger; George M. Yahwak

(57) ABSTRACT

The present invention provides novel isolated polynucleotides and small molecule target polypeptides encoded by the polynucleotides. Antibodies that immunospecifically bind to a novel small molecule target polypeptide or any derivative, variant, mutant or fragment of that polypeptide, polynucleotide or antibody are disclosed, as are methods in which the small molecule target polypeptide, polynucleotide and antibody are utilized in the detection and treatment of a broad range of pathological states. More specifically, the present invention discloses methods of using recombinantly expressed and/or endogenously expressed proteins in various screening procedures for the purpose of identifying therapeutic antibodies and therapeutic small molecules associated with diseases.

7 Claims, No Drawings

FOREIGN PATENT DOCUMENTS

| | | |
|---|---|---|
| JP | 8-283295 | 10/1996 |
| JP | 10-313866 | 12/1998 |
| JP | 2000-184884 | 7/2000 |
| WO | WO 91/17171 | 11/1991 |
| WO | WO 93/21328 | 10/1993 |
| WO | WO 94/02616 | 2/1994 |
| WO | WO 95/02054 | 1/1995 |
| WO | WO 95/21252 | 8/1995 |
| WO | WO 95/24924 | 9/1995 |
| WO | WO 95/31539 | 11/1995 |
| WO | WO 95/34202 | 12/1995 |
| WO | WO 96/05302 | 2/1996 |
| WO | WO 96/12735 | 5/1996 |
| WO | WO 96/27015 | 9/1996 |
| WO | WO 97/09421 | 3/1997 |
| WO | WO 97/11162 | 3/1997 |
| WO | WO 97/19167 | 5/1997 |
| WO | WO 97/30084 | 8/1997 |
| WO | WO 97/37044 | 10/1997 |
| WO | WO 97/37676 | 10/1997 |
| WO | WO 97/44466 | 11/1997 |
| WO | WO 98/07859 | 2/1998 |
| WO | WO 98/11254 | 3/1998 |
| WO | WO 98/14466 | 4/1998 |
| WO | WO 98/32878 | 7/1998 |
| WO | WO 98/35040 | 8/1998 |
| WO | WO 98/36054 | 8/1998 |
| WO | WO 98/45408 | 10/1998 |
| WO | WO 98/45704 | 10/1998 |
| WO | WO 98/53064 | 11/1998 |
| WO | WO 98/53071 | 11/1998 |
| WO | WO 99/00507 | 1/1999 |
| WO | WO 99/04265 | 1/1999 |
| WO | WO 99/05298 | 2/1999 |
| WO | WO 99/16788 | 4/1999 |
| WO | WO 99/26973 | 6/1999 |
| WO | WO 99/31134 | 6/1999 |
| WO | WO 91/12340 | 8/1999 |
| WO | WO 99/42592 | 8/1999 |
| WO | WO 99/57132 | 11/1999 |
| WO | WO 99/60986 | 12/1999 |
| WO | WO 99/61469 | 12/1999 |
| WO | WO 99/64459 | 12/1999 |
| WO | WO 99/66051 | 12/1999 |
| WO | WO 00/01811 | 1/2000 |
| WO | WO 00/06698 | 2/2000 |
| WO | WO 00/06728 | 2/2000 |
| WO | WO 00/06776 | 2/2000 |
| WO | WO 00/08137 | 2/2000 |
| WO | WO 00/08143 | 2/2000 |
| WO | WO 00/09689 | 2/2000 |
| WO | WO 00/11191 | 3/2000 |
| WO | WO 00/11204 | 3/2000 |
| WO | WO 00/12679 | 3/2000 |
| WO | WO 00/12711 | 3/2000 |
| WO | WO 00/14223 | 3/2000 |
| WO | WO 00/14225 | 3/2000 |
| WO | WO 00/15793 | 3/2000 |
| WO | WO 00/16805 | 3/2000 |
| WO | WO 00/20448 | 4/2000 |
| WO | WO 00/21999 | 4/2000 |
| WO | WO 00/23615 | 4/2000 |
| WO | WO 00/28054 | 5/2000 |
| WO | WO 00/53756 | 9/2000 |
| WO | WO 00/55173 | 9/2000 |
| WO | WO 00/55180 | 9/2000 |
| WO | WO 00/55199 | 9/2000 |
| WO | WO 00/55318 | 9/2000 |
| WO | WO 00/55350 | 9/2000 |
| WO | WO 00/58473 | 10/2000 |
| WO | WO 00/63351 | 10/2000 |
| WO | WO 00/64479 | 11/2000 |
| WO | WO 00/73323 | 12/2000 |
| WO | WO 00/73454 | 12/2000 |
| WO | WO 00/73469 | 12/2000 |
| WO | WO 00/73801 | 12/2000 |
| WO | WO 00/76530 | 12/2000 |
| WO | WO 00/78921 | 12/2000 |
| WO | WO 00/78953 | 12/2000 |
| WO | WO 00/78959 | 12/2000 |
| WO | WO 00/78971 | 12/2000 |
| WO | WO 00/78974 | 12/2000 |
| WO | WO 01/00784 | 1/2001 |
| WO | WO 01/00828 | 1/2001 |
| WO | WO 01/02563 | 1/2001 |
| WO | WO 01/02600 | 1/2001 |
| WO | WO 01/04283 | 1/2001 |
| WO | WO 01/04311 | 1/2001 |
| WO | WO 01/07628 | 2/2001 |
| WO | WO 01/09316 | 2/2001 |
| WO | WO 01/09345 | 2/2001 |
| WO | WO 01/12662 | 2/2001 |
| WO | WO 01/16318 | 3/2001 |
| WO | WO 01/18176 | 3/2001 |
| WO | WO 01/18207 | 3/2001 |
| WO | WO 01/19854 | 3/2001 |
| WO | WO 01/22920 | 4/2001 |
| WO | WO 01/23547 | 4/2001 |
| WO | WO 01/27158 | 4/2001 |
| WO | WO 01/27257 | 4/2001 |
| WO | WO 01/32876 | 5/2001 |
| WO | WO 01/34643 | 5/2001 |
| WO | WO 01/34809 | 5/2001 |
| WO | WO 01/38484 | 5/2001 |
| WO | WO 01/38503 | 5/2001 |
| WO | WO 01/38541 | 5/2001 |
| WO | WO 01/40794 | 6/2001 |
| WO | WO 01/44281 | 6/2001 |
| WO | WO 01/49728 | 7/2001 |
| WO | WO 01/49848 | 7/2001 |
| WO | WO 01/53312 | 7/2001 |
| WO | WO 01/53454 | 7/2001 |
| WO | WO 01/53455 | 7/2001 |
| WO | WO 01/53468 | 7/2001 |
| WO | WO 01/53490 | 7/2001 |
| WO | WO 01/54477 | 8/2001 |
| WO | WO 01/54733 | 8/2001 |
| WO | WO 01/55202 | 8/2001 |
| WO | WO 01/55301 | 8/2001 |
| WO | WO 01/55304 | 8/2001 |
| WO | WO 01/55308 | 8/2001 |
| WO | WO 01/55312 | 8/2001 |
| WO | WO 01/55320 | 8/2001 |
| WO | WO 01/55368 | 8/2001 |
| WO | WO 01/55402 | 8/2001 |
| WO | WO 01/55411 | 8/2001 |
| WO | WO 01/55441 | 8/2001 |
| WO | WO 01/57182 | 8/2001 |
| WO | WO 01/57188 | 8/2001 |
| WO | WO 01/57190 | 8/2001 |
| WO | WO 01/57220 | 8/2001 |
| WO | WO 01/57270 | 8/2001 |
| WO | WO 01/57272 | 8/2001 |
| WO | WO 01/57275 | 8/2001 |
| WO | WO 01/57276 | 8/2001 |
| WO | WO 01/57278 | 8/2001 |
| WO | WO 01/59063 | 8/2001 |
| WO | WO 01/59080 | 8/2001 |
| WO | WO 01/59127 | 8/2001 |
| WO | WO 01/61016 | 8/2001 |
| WO | WO 01/64875 | 9/2001 |

| | | |
|---|---|---|
| WO | WO 01/64895 | 9/2001 |
| WO | WO 01/66559 | 9/2001 |
| WO | WO 01/66689 | 9/2001 |
| WO | WO 01/68701 | 9/2001 |
| WO | WO 01/68848 | 9/2001 |
| WO | WO 01/72295 | 10/2001 |
| WO | WO 01/72836 | 10/2001 |
| WO | WO 01/74901 | 10/2001 |
| WO | WO 01/75067 | 10/2001 |
| WO | WO 01/77126 | 10/2001 |
| WO | WO 01/77155 | 10/2001 |
| WO | WO 01/77172 | 10/2001 |
| WO | WO 01/77174 | 10/2001 |
| WO | WO 01/79294 | 10/2001 |
| WO | WO 01/79449 | 10/2001 |
| WO | WO 01/79455 | 10/2001 |
| WO | WO 01/79468 | 10/2001 |
| WO | WO 01/79552 | 10/2001 |
| WO | WO 01/81363 | 11/2001 |
| WO | WO 01/81555 | 11/2001 |
| WO | WO 01/81559 | 11/2001 |
| WO | WO 01/83771 | 11/2001 |
| WO | WO 01/88188 | 11/2001 |

OTHER PUBLICATIONS

Brodie, et al. (2001), "Aromatase and COX–2 expression in human breast cancers," *J Steroid Biochem Mol Biol* 79(1–5): 41–7.

Brueggemeier, et al. (2001), "Molecular pharmacology of aromatase and its regulation by endogenous and exogenous agents," *J Steroid Biochem Mol Biol* 79(1–5): 75–84.

Burkman, et al. (2001), "Current perspectives on benefits and risks of hormone replacement therapy," *Am J Obstet Gynecol* 185(2 Suppl): S13–23.

Casley, et al. (2002), "Beta–amyloid inhibits integrated mitochondrial respiration and key enzyme activites." *J Neurochem* 80(1): 91–100.

Chi, et al. (2000), "Potassium channel openers prevent beta–amyloid toxicity in bovine vascular endothelial cells." *Neurosci Lett* 290(1): 9–12.

Colom, et al. (1998), "Role of potassium channels in amyloid–induced cell death," *J Neurochem* 70(5): 1925–34.

De Lorenzo, et al. (1999), "What is Drosophila telling us about cancer?" *Cancer Metastasis Rev* 18(2): 295–311.

Dircks and Sul (1997), "Mammalian mitochondrial glycerol–3–phosphate acyltransferase," *Biochim Biophys Acta* 1348(1–2): 17–26.

Dukes and Philipson (1996), "K+ channels; generating excitement in pancreatic beta–cells," *Diabetes* 45(7): 845–53.

Ericsson, et al. (1997), "Identification of glycerol–3–phosphate acyltransferase as an adipocyte determination and differentiation factor 1– and sterol regulatory element–binding protein–responsive gene," *J Biol Chem* 272(11): 7298–305.

Gaillard, et al. (2001), "Glucocorticoid and type 1 interferon interactions at the blood–brain barrier: relevance for drug therapies for multiple sclerosis," *Neuroreport* 12(10): 2189–93.

Greenberg (1997), "Calcium channels in neurological disease." *Ann Neurol* 42(3): 275–82.

Gupta, et al. (2000), "Cerebral antioxidant status and free radical generation following glutathione depletion and subsequent recovery." *Mol Cell Biochem* 209(1–2): 55–61.

Holinka (2001). "Design and conduct of clinical trials in hormone replacement therapy." *Ann N Y Acad Sci* 943: 89–108.

Iwasaki, et al. (1997), "aex–3 encodes a novel regulator of presynaptic activity in C. elegans." *Neuron* 18(4): 613–22.

Jhamandas, et al, (2001). "Cellular mechanisms for amyloid beta–protein activation of rat cholinergic basal forebrain neurons." *J Neurophysiol* 86(3): 1312–20.

Krugel, et al, (2001). "Deafferentation of the septo–hippocampal pathway in rats as a model of the metabolic events in Alzheimer's disease," *Int J Dev Neurosci* 19(3): 263–77.

Li and Dryhurst (2001). "Oxidative metabolites of 5–S–cysteinyldopamine inhibit the pyruvate dehydrogenase complex." *J Neural Transm* 108(12): 1363–74.

Lusini, et al, (2001). "Altered glutathione anti–oxidant metabolism during tumor progression in human renal–cell carcinoma." *Int J Cancer* 91(1): 55–9.

Matsumoto, et al. (2001). "Early complications of high–dose methylprednisolone sodium succinate treatment in the follow–up of acute cervical spinal cord injury," *Spine* 26(4): 426–30.

Moulard, et al. (2001), "Ion channel variation causes epilepsies," *Brain Res Brain Res Rev* 36(2–3): 275–84.

Ohtsuka, et al, (1993). "A somatic cell mutant defective in phosphatidylglycerophosphate synthase, with impaired phosphatidylglycerol and cardiolipin biosynthesis," *J Biol Chem* 268(30): 22908–13.

Penning, et al. (2000), "Human 3alpha–hydroxysteroid dehydrogenase isoforms (AKR1C1–AKR1C4) of the aldo–keto reductase superfamily: functional plasticity and tissue distribution reveals roles in the inactivation and formation of male and female sex hormones." *Biochem J* 351(Pt 1): 67–77.

Perry, et al. (1998), "Prospective study of serum gamma-–glutamyltransferase and risk of NIDDM." *Diabetes Care* 21(5): 732–7.

Piccini, et al. (2000), "Endogenous APP derivatives oppositely modulate apoptosis through an autocrine loop." *Neuroreport* 11(7): 1375–9.

Pittenger, et al. (1999), "Multilineage potential of adult human mesenchymal stem cells." *Science* 284(5411): 143–7.

Rekha, et al., (1998), "Inhibition of human class 3 aldehyde dehydrogenase, and sensitization of tumor cells that express significant amounts of this enzyme to oxazaphosphorines, by chlorpropamide analogues," *Biochem Pharmacol* 55(4): 465–74.

Richmond, et al. (2001), "An open form of syntaxin bypasses the requirement for UNC–13 in vesicle priming." *Nature* 412(6844): 338–41.

Shimabukuro, et al. (1998), "Troglitazone lowers islet fat and restores beta cell function of Zucker diabetic fatty rats," *J Biol Chem* 273(6): 3547–50.

Shimizu–Nishikawa, et al. (1995), "Cloning and expression of SEZ–6, a brain–specific and seizure–related cDNA." *Brain Res Mol Brain Res* 28(2): 201–10.

Shimkets, et al. (1999). "Gene expression analysis by transcript profiling coupled to a gene database query." *Nat Biotechnol* 17(8): 798/–803.

Song, et al. (1999), "Human munc13 is a diaclglycerol receptor that induces apoptosis and may contribute to renal cell injury in hyperglycemia." *Mol Biol Cell* 10(5): 1609–19.

Sugiyama, et al. (2001), "Characterization of the efflux transport of 17beta–estradiol–D–17beta– glucuronide from the brain across the blood–brain barrier." *J Pharmacol Exp Ther* 298(1): 316–22.

Sun, et al. (2001). "Transcript map of the 8p23 putative tumor suppressor region." *Genomics* 75(1–3): 17–25.

Tam, et al. (2000). "Voltage–gated calcium channels direct neuronal migration in Caenorhabditis elegans." *Dev Biol* 226(1): 104–17.

Upadhya, et al. (2000). "Mutations in a NiMA–related kinase gene, Nek1, cause pleiotropic effects including a progressive polycystic kidney disease in mice," *Proc Natl Acad Sci U S A* 97(1): 217–21.

Velarde, et al. (2001). "Activation of MAPK by modified low–density lipoproteins in vascular smooth muscle cells." *J Appl Physiol* 91(3): 1412–20.

Yu, S. P., Z. S. Farhangrazi, et al. (1998), "Enhancement of outward potassium current may participate in beta–amyloid peptide–induced cortical neuronal death." *Neurobiol Dis* 5(2): 81–8.

Zhang, et al. (1998), "A splicing variant of a death domain protein that is regulated by a mitogen–activated kinase is a substrate for c–Jun N–terminal kinase in the human central nervous system." *Proc Natl Acad Sci U S A* 95(5): 2586–91.

Zhu, et al. (2001). "Activation of MKK6, an upstream activator of p38, in Alzheimer's disease," *J Neurochem* 79(2): 311–8.

GenBank Accession No.: A05225 (Jun. 16, 2000).
GenBank Accession No.: A41253 (Jul. 10, 1998).
GenBank Accession No.: A41675 (Sep. 24, 1999).
GenBank Accession No.: A48082 (Jun. 16, 2000).
GenBank Accession No.: A48713 (Nov. 5, 1999).
GenBank Accession No.: A54325 (Jul. 16, 1999).
GenBank Accession No.: AAB12000 (Oct. 7, 1996).
GenBank Accession No.: AAB27797 (Sep. 30, 1993).
GenBank Accession No.: AAB27845 (Oct. 13, 1993).
GenBank Accession No.: AAB27846 (Oct. 13, 1993).
GenBank Accession No.: AAB28677 (Dec. 18, 1993).
GenBank Accession No.: AAB31365 (Sep. 23, 1994).
GenBank Accession No.: AAB31516 (Oct. 24, 1994).
GenBank Accession No.: AAB31517 (Oct. 24, 1994).
GenBank Accession No.: AAB31518 (Oct. 24, 1994).
GenBank Accession No.: AAB31563 (Feb. 28, 1995).
GenBank Accession No.: AAB31564 (May 16, 1995).
GenBank Accession No.: AAB31700 (Apr. 4, 2001).
GenBank Accession No.: AAB37805 (May 22, 2002).
GenBank Accession No.: AAB38111 (Dec. 6, 1996).
GenBank Accession No.: AAB38114 (Dec. 6, 1996).
GenBank Accession No.: AAB40646 (Jan. 14, 1997).
GenBank Accession No.: AAB40996 (Jan. 17, 1997).
GenBank Accession No.: AAB41695 (Feb. 1, 1997).
GenBank Accession No.: AAB42919 (Feb. 7, 1997).
GenBank Accession No.: AAB43007 (Feb. 7, 1997).
GenBank Accession No.: AAB43129 (Feb. 7, 1997).
GenBank Accession No.: AAB43444 (Feb. 7, 1997).
GenBank Accession No.: AAB43498 (Feb. 7, 1997).
GenBank Accession No.: AAB43663 (Feb. 7, 1997).
GenBank Accession No.: AAB44257 (Feb. 7, 1997).
GenBank Accession No.: AAB47271 (Feb. 13, 1997).
GenBank Accession No.: AAB47279 (Aug. 31, 1999).
GenBank Accession No.: AAB50936 (Mar. 28, 1997).
GenBank Accession No.: AAB51184 (May 10, 2000).
GenBank Accession No.: AAB58156 (Feb. 1, 2000).
GenBank Accession No.: AAB58981 (Jan. 9, 2002).
GenBank Accession No.: AAB59006 (Jun. 6, 1997).
GenBank Accession No.: AAB60094 (Jul. 20, 1995).
GenBank Accession No.: AAB61616 (Jun. 25, 1997).
GenBank Accession No.: AAB63803 (Jul. 22, 1997).
GenBank Accession No.: AAB64943 (Aug. 1, 1997).
GenBank Accession No.: AAB65229 (May 3, 2002).
GenBank Accession No.: AAB65602 (Aug. 4, 1997).
GenBank Accession No.: AAB65656 (May 1, 2002).
GenBank Accession No.: AAB65661 (Aug. 5, 1997).
GenBank Accession No.: AAB70163 (Sep. 16, 1997).
GenBank Accession No.: AAB74727 (Oct. 8, 1997).
GenBank Accession No.: AAB76865 (Oct. 8, 1997).
GenBank Accession No.: AAB80256 (Oct. 8, 1997).
GenBank Accession No.: AAB85482 (Jun. 19, 2002).
GenBank Accession No.: AAB85483 (Jun. 19, 2002).
GenBank Accession No.: AAB85779 (Jun. 19, 2002).
GenBank Accession No.: AAB87552 (Nov. 27, 1997).
GenBank Accession No.: AAB88341 (May 22, 2202).
GenBank Accession No.: AAB88462 (Dec. 9, 1997).
GenBank Accession No.: AAB92909 (Dec. 29, 1997).
GenBank Accession No.: AAB92953 (Dec. 29, 1997).
GenBank Accession No.: AAB93303 (Aug. 14, 2001).
GenBank Accession No.: AAB93332 (Oct. 8, 1999).
GenBank Accession No.: AAB93393 (Dec. 30, 1997).
GenBank Accession No.: AAB93480 (Dec. 29, 1997).
GenBank Accession No.: AAB94391 (Jan. 24, 2001).
GenBank Accession No.: AAB94727 (Jan. 2, 1998).
GenBank Accession No.: AAB95123 (Aug. 8, 2001).
GenBank Accession No.: AAB95504 (Jan. 12, 1998).
GenBank Accession No.: AAE03702 (Sep. 29, 1999).
GenBank Accession No.: AAE03711 (Sep. 29, 1999).
GenBank Accession No.: AAE03717 (Sep. 29, 1999).
GenBank Accession No.: AAE03718 (Sep. 29, 1999).
GenBank Accession No.: AAE03719 (Sep. 29, 1999).
GenBank Accession No.: AAE04101 (Sep. 29, 1999).
GenBank Accession No.: AAE05100 (Sep. 29, 1999).
GenBank Accession No.: AAE05951 (Sep. 29, 1999).
GenBank Accession No.: AAE06572 (Sep. 29, 1999).
GenBank Accession No.: AAE07183 (Sep. 29, 1999).
GenBank Accession No.: AAE07184 (Sep. 29, 1999).
GenBank Accession No.: AAE09698 (Sep. 29, 1999).
GenBank Accession No.: AAE09713 (Sep. 29, 1999).
GenBank Accession No.: AAE10313 (Sep. 29, 1999).
GenBank Accession No.: AAE10314 (Sep. 29, 1999).
GenBank Accession No.: AAE10440 (Sep. 29, 1999).
GenBank Accession No.: AAE11767 (Sep. 29, 1999).
GenBank Accession No.: AAE11774 (Sep. 29, 1999).
GenBank Accession No.: AAE12023 (Sep. 29, 1999).
GenBank Accession No.: AAE13280 (Sep. 29, 1999).
GenBank Accession No.: AAE13610 (Sep. 29, 1999).
GenBank Accession No.: AAE13611 (Sep. 29, 1999).
GenBank Accession No.: AAE13612 (Sep. 29, 1999).
GenBank Accession No.: AAE13613 (Sep. 29, 1999).
GenBank Accession No.: AAE13614 (Sep. 29, 1999).
GenBank Accession No.: AAE13839 (Sep. 29, 1999).
GenBank Accession No.: AAE14268 (Sep. 29, 1999).
GenBank Accession No.: AAE14270 (Sep. 29, 1999).
GenBank Accession No.: AAE15156 (Sep. 29, 1999).
GenBank Accession No.: AAE15434 (Sep. 29, 1999).
GenBank Accession No.: AAF82757 (Aug. 14, 2000).
GenBank Accession No.: AAG00176 (Aug. 16, 2000).
GenBank Accession No.: AAG14814 (Sep. 19, 2000).
GenBank Accession No.: AAG21988 (Mar. 20, 2002).
GenBank Accession No.: AAG31821 (Dec. 4, 2000).

GenBank Accession No.: AAG31822 (Mar. 15, 2001).
GenBank Accession No.: AAG31823 (Nov. 19, 2000).
GenBank Accession No.: AAG32461 (Oct. 31, 2001).
GenBank Accession No.: AAG32463 (Oct. 31, 2001).
GenBank Accession No.: AAG38279 (Feb. 7, 2001).
GenBank Accession No.: AAG38280 (Feb. 7, 2001).
GenBank Accession No.: AAG38281 (Feb. 7, 2001).
GenBank Accession No.: AAG39994 (Dec. 13, 2000).
GenBank Accession No.: AAG54391 (Mar. 21, 2001).
GenBank Accession No.: AAG54392 (Mar. 21, 2001).
GenBank Accession No.: AAH17046 (Nov. 9, 2001).
GenBank Accession No.: AAH18060 (Dec. 6, 2001).
GenBank Accession No.: AAH119201 (Dec. 11, 2001).
GenBank Accession No.: AAH19217 (Dec. 11, 2001).
GenBank Accession No.: AAH19916 (Jan. 22, 2002).
GenBank Accession No.: AAH20744 (Jan. 22, 2002).
GenBank Accession No.: AAH21577 (Jan. 22, 2002).
GenBank Accession No.: AAH21605 (Jan. 22, 2002).
GenBank Accession No.: AAH21843 (Jan. 22, 2002).
GenBank Accession No.: AAH22601 (Feb. 4, 2002).
GenBank Accession No.: AAH24675 (Mar. 12, 2002).
GenBank Accession No.: AAH25795 (Mar. 13, 2002).
GenBank Accession No.: AAH25836 (Mar. 13, 2002).
GenBank Accession No.: AAL18245 (Dec. 1, 2001).
GenBank Accession No.: AAL35261 (Nov. 25, 2001).
GenBank Accession No.: AAL37173 (Dec. 2, 2001).
GenBank Accession No.: AAL40267 (Dec. 11, 2001).
GenBank Accession No.: AAL40268 (Dec. 11, 2001).
GenBank Accession No.: AAL50041 (Dec. 21, 2001).
GenBank Accession No.: AAL50045 (Dec. 21, 2001).
GenBank Accession No.: AAL50049 (Dec. 21, 2001).
GenBank Accession No.: AAL50637 (Dec. 27, 2001).
GenBank Accession No.: AAL56246 (Jan. 1, 2002).
GenBank Accession No.: AAL56247 (Jan. 1, 2002).
GenBank Accession No.: AAL56988 (Jun. 25, 2002).
GenBank Accession No.: AAL60921 (Apr. 3, 2002).
GenBank Accession No.: AAL61267 (Apr. 3, 2002).
GenBank Accession No.: AAL61329 (Apr. 3, 2002).
GenBank Accession No.: AAL61330 (Apr. 3, 2002).
GenBank Accession No.: AAL61393 (Apr. 3, 2002).
GenBank Accession No.: AAL61437 (Apr. 3, 2002).
GenBank Accession No.: AAL61440 (Apr. 3, 2002).
GenBank Accession No.: AAL61470 (Apr. 3, 2002).
GenBank Accession No.: AAL61478 (Apr. 3, 2002).
GenBank Accession No.: AAL61485 (Apr. 3, 2002).
GenBank Accession No.: AAL68829 (Jan. 29, 2002).
GenBank Accession No.: AAL83910 (Jun. 12, 2002).
GenBank Accession No.: AAL83911 (Jun. 12, 2002).
GenBank Accession No.: AAL87040 (Mar. 13, 2002).
GenBank Accession No.: AAM01599 (Mar. 20, 2002).
GenBank Accession No.: AAM13856 (Apr. 21, 2002).
GenBank Accession No.: AAM23509 (May 9, 2002).
GenBank Accession No.: AAM25845 (May 9, 2002).
GenBank Accession No.: AAM25563 (May 9, 2002).
GenBank Accession No.: AAM25720 (May 9, 2002).
GenBank Accession No.: AAM26263 (Jun. 14, 2002).
GenBank Accession No.: AAM38736 (May 29, 2002).
GenBank Accession No.: AAM38737 (May 29, 2002).
GenBank Accession No.: AAM38836 (May 29, 2002).
GenBank Accession No.: AAM38956 (May 29, 2002).
GenBank Accession No.: AAM39210 (May 23, 2002).
GenBank Accession No.: AAM39211 (May 23, 2002).
GenBank Accession No.: AAM39365 (May 23, 2002).
GenBank Accession No.: AAM39431 (May 23, 2002).
GenBank Accession No.: AAM39688 (May 23, 2002).
GenBank Accession No.: AAM39844 (May 23, 2002).
GenBank Accession No.: AAM40140 (May 23, 2002).
GenBank Accession No.: AAM40523 (May 23, 2002).
GenBank Accession No.: AAM40622 (May 23, 2002).
GenBank Accession No.: AAM40661 (May 23, 2002).
GenBank Accession No.: AAM41217 (May 23, 2002).
GenBank Accession No.: AAM41474 (May 23, 2002).
GenBank Accession No.: AAM41630 (May 23, 2002).
GenBank Accession No.: AAM43573 (May 24, 2002).
GenBank Accession No.: AAM43645 (May 24, 2002).
GenBank Accession No.: AAM48169 (Jun. 6, 2002).
GenBank Accession No.: AAM52238 (Jun. 18, 2002).
GenBank Accession No.: AAM53608 (Jun. 17, 2002).
GenBank Accession No.: AAM65987 (Jun. 26, 2002).
GenBank Accession No.: BAB84586 (Feb. 7, 2002).
GenBank Accession No.: BAB84587 (Feb. 7, 2002).
GenBank Accession No.: BAB84864 (Feb. 15, 2002).
GenBank Accession No.: BAB85520 (Mar. 23, 2002).
GenBank Accession No.: BAB85521 (Mar. 23, 2002).
GenBank Accession No.: BC022180 (Jan. 28, 2002).
GenBank Accession No.: CAB69291 (Jan. 21, 2000).
GenBank Accession No.: CAB69300 (Jan. 21, 2000).
GenBank Accession No.: CAB69577 (Jan. 22, 2000).
GenBank Accession No.: CAC17064 (Nov. 23, 2000).
GenBank Accession No.: CAC27252 (Jan. 25, 2001).
GenBank Accession No.: CAC27312 (Jan. 25, 2001).
GenBank Accession No.: CAC39529 (May 29, 2001).
GenBank Accession No.: CAC43514 (Jul. 3, 2001).
GenBank Accession No.: CAC51146 (Aug. 15, 2001).
GenBank Accession No.: CAC60190 (Aug. 30, 2001).
GenBank Accession No.: CAC60191 (Aug. 30, 2001).
GenBank Accession No.: CAD10244 (Oct. 26, 2001).
GenBank Accession No.: CAD20990 (Jan. 16, 2002).
GenBank Accession No.: CAD28475 (Mar. 20, 2002).
GenBank Accession No.: CAD28545 (Mar. 20, 2002).
GenBank Accession No.: I56506 (Aug. 20, 1999).
GenBank Accession No.: JC4937 (Sep. 8, 2000).
GenBank Accession No.: JC6095 (Sep. 20, 1999).
GenBank Accession No.: JE0343 (Jun. 9, 2000).
GenBank Accession No.: O14581 (Oct. 16, 2001).
GenBank Accession No.: O35786 (May 30, 2000).
GenBank Accession No.: O35942 (Jun. 15, 2002).
GenBank Accession No.: O46629 (Jun. 15, 2002).
GenBank Accession No.: O67632 (Oct. 16, 2001).
GenBank Accession No.: O74431 (Jun. 15, 2002).
GenBank Accession No.: O75748 (Aug. 20, 2001).
GenBank Accession No.: O75795 (Oct. 16, 2001).
GenBank Accession No.: O76100 (Oct. 16, 2001).
GenBank Accession No.: O88416 (Jun. 15, 2002).
GenBank Accession No.: O88587 (Oct. 16, 2001).
GenBank Accession No.: O97580 (Jun. 15, 2002).
GenBank Accession No.: P04374 (Jun. 15, 2002).
GenBank Accession No.: P05092 (Jun. 15, 2002).
GenBank Accession No.: P07314 (Jun. 15, 2002).
GenBank Accession No.: P08133 (Jun. 15, 2002).
GenBank Accession No.: P08559 (Jun. 15, 2002).
GenBank Accession No.: P14060 (Oct. 16, 2001).
GenBank Accession No.: P14769 (Jun. 15, 2002).
GenBank Accession No.: P15848 (May 30, 2000).
GenBank Accession No.: P17516 (Jun. 15, 2002).
GenBank Accession No.: P19440 (Jun. 15, 2002).
GenBank Accession No.: P20735 (Jun. 15, 2002).
GenBank Accession No.: P21708 (Oct. 16, 2001).

GenBank Accession No.: P21964 (Oct. 16, 2001).
GenBank Accession No.: P22734 (Jun. 15, 2002).
GenBank Accession No.: P22792 (Oct. 16, 2001).
GenBank Accession No.: P26284 (Jun. 15, 2002).
GenBank Accession No.: P27361 (Oct. 16, 2001).
GenBank Accession No.: P27365 (Jul. 15, 1999).
GenBank Accession No.: P29294 (Oct. 16, 2001).
GenBank Accession No.: P29804 (Jun. 15, 2002).
GenBank Accession No.: P30839 (Oct. 16, 2001).
GenBank Accession No.: P31662 (Oct. 16, 2001).
GenBank Accession No.: P31948 (Oct. 16, 2001).
GenBank Accession No.: P33727 (Jul. 15, 1998).
GenBank Accession No.: P35486 (Jun. 15, 2002).
GenBank Accession No.: P41279 (Jun. 15, 2002).
GenBank Accession No.: P43353 (Jun. 15, 2002).
GenBank Accession No.: P47740 (Jul. 15, 1999).
GenBank Accession No.: P48448 (Jul. 15, 2002).
GenBank Accession No.: P51954 (Oct. 16, 2001).
GenBank Accession No.: P51955 (Jun. 15, 2002).
GenBank Accession No.: P51956 (Jun. 15, 2002).
GenBank Accession No.: P55084 (Jun. 15, 2002).
GenBank Accession No.: P58182 (Oct. 16, 2001).
GenBank Accession No.: P78329 (Jun. 15, 2002).
GenBank Accession No.: P80508 (Jun. 15, 2002).
GenBank Accession No.: P97441 (Jun. 15, 2002).
GenBank Accession No.: P97468 (Oct. 16, 2001).
GenBank Accession No.: P97564 (Jul 15, 1999).
GenBank Accession No.: Q00973 (Jun. 15, 2002).
GenBank Accession No.: Q07174 (Jun. 15, 2002).
GenBank Accession No.: Q08469 (Oct. 16, 2001).
GenBank Accession No.: Q09199 (Jun. 15, 2002).
GenBank Accession No.: Q09200 (Jun. 15, 2002).
GenBank Accession No.: Q10468 (Jun. 15, 2002).
GenBank Accession No.: Q14541 (Jun. 15, 2002).
GenBank Accession No.: Q15622 (Oct. 16, 2001).
GenBank Accession No.: Q15746 (Jun. 15, 2002).
GenBank Accession No.: Q21286 (Oct. 16, 2001).
GenBank Accession No.: Q60928 (Jun. 15, 2002).
GenBank Accession No.: Q61586 (Oct. 16, 2001).
GenBank Accession No.: Q62941 (Jun. 15, 2002).
GenBank Accession No.: Q63099 (Dec. 15, 1998).
GenBank Accession No.: Q63562 (Jun. 15, 2002).
GenBank Accession No.: S01786 (Jun. 22, 1999).
GenBank Accession No.: S52844 (Sep. 10, 1999).
GenBank Accession No.: S57219 (Sep. 20, 1999).
GenBank Accession No.: T42759 (Sep. 2, 2000).
SWALL (SPTR) Accession No.: O00360 (Jul. 1, 1997).
SWALL (SPTR) Accession No.: O00406 (Jul. 1, 1997).
SWALL (SPTR) Accession No.: O08873 (Jul. 1, 1997).
SWALL (SPTR) Accession No.: O09040 (Jul. 1, 1997).
SWALL (SPTR) Accession No.: O14528 (Jan. 1, 1998).
SWALL (SPTR) Accession No.: O14795 (Jan. 1, 1998).
SWALL (SPTR) Accession No.: O15013 (Jan. 1, 1998).
SWALL (SPTR) Accession No.: O15293 (Jan. 1, 1998).
SWALL (SPTR) Accession No.: O35533 (Jan. 1, 1998).
SWALL (SPTR) Accession No.: O35814 (Jan. 1, 1998).
SWALL (SPTR) Accession No.: O35956 (Jan. 1, 1998).
SWALL (SPTR) Accession No.: O54981 (Jun. 1, 1998).
SWALL (SPTR) Accession No.: O57379 (Jun. 1, 1998).
SWALL (SPTR) Accession No.: O60447 (Aug. 1, 1998).
SWALL (SPTR) Accession No.: O60634 (Aug. 1, 1998).
SWALL (SPTR) Accession No.: O70177 (Aug. 1, 1998).
SWALL (SPTR) Accession No.: O75539 (Nov. 1, 1998).
SWALL (SPTR) Accession No.: O88370 (Nov. 1, 1998).
SWALL (SPTR) Accession No.: O88377 (Nov. 1, 1998).
SWALL (SPTR) Accession No.: O88763 (Nov. 1, 1998).
SWALL (SPTR) Accession No.: O88904 (Nov. 1, 1998).
SWALL (SPTR) Accession No.: O94839 (May 1, 1999).
SWALL (SPTR) Accession No.: O95194 (Jun. 15, 2002).
SWALL (SPTR) Accession No.: O95742 (May 1, 1999).
SWALL (SPTR) Accession No.: O96899 (May 1, 1999).
SWALL (SPTR) Accession No.: P78356 (May 1, 1997).
SWALL (SPTR) Accession No.: P97366 (May 1, 1997).
SWALL (SPTR) Accession No.: Q13078 (Nov 1, 1996).
SWALL (SPTR) Accession No.: Q15134 (Nov. 1, 1996).
SWALL (SPTR) Accession No.: Q15604 (Nov. 1, 1996).
SWALL (SPTR) Accession No.: Q15735 (Nov. 1, 1996).
SWALL (SPTR) Accession No.: Q19101 (Nov. 1, 1996).
SWALL (SPTR) Accession No.: Q60792 (Nov. 1, 1996).
SWALL (SPTR) Accession No.: Q60850 (Nov. 1, 1996).
SWALL (SPTR) Accession No.: Q60864 (Nov. 1, 1996).
SWALL (SPTR) Accession No.: Q62768 (Nov. 1, 1996).
SWALL (SPTR) Accession No.: Q62769 (Nov. 1, 1996).
SWALL (SPTR) Accession No.: Q62770 (Nov. 1, 1996).
SWALL (SPTR) Accession No.: Q62944 (Nov. 1, 1996).
SWALL (SPTR) Accession No.: Q90WD8 (Dec. 1, 2001).
SWALL (SPTR) Accession No.: Q90ZZ7 (Dec. 1, 2001).
SWALL (SPTR) Accession No.: Q91674 (Nov. 1, 1996).
SWALL (SPTR) Accession No.: Q91766 (Jul. 15, 1999).
SWALL (SPTR) Accession No.: Q91V22 (Dec. 1, 2001).
SWALL (SPTR) Accession No.: Q91V24 (Dec. 1, 2001).
SWALL (SPTR) Accession No.: Q91W00 (Dec. 1, 2001).
SWALL (SPTR) Accession No.: Q91WG0 (Dec. 1, 2001).
SWALL (SPTR) Accession No.: Q91XH4 (Dec. 1, 2001).
SWALL (SPTR) Accession No.: Q91XU3 (Dec. 1, 2001).
SWALL (SPTR) Accession No.: Q91YP4 (Dec. 1, 2001).
SWALL (SPTR) Accession No.: Q91Z03 (Dec. 1, 2001).
SWALL (SPTR) Accession No.: Q91Z18 (Dec. 1, 2001).
SWALL (SPTR) Accession No.: Q920P7 (Dec. 1, 2001).
SWALL (SPTR) Accession No.: Q920Q9 (Dec. 1, 2001).
SWALL (SPTR) Accession No.: Q920S2 (Dec. 1, 2001).
SWALL (SPTR) Accession No.: Q920Y8 (Dec. 1, 2001).
SWALL (SPTR) Accession No.: Q920Y9 (Dec. 1, 2001).
SWALL (SPTR) Accession No.: Q920Z0 (Dec. 1, 2001).
SWALL (SPTR) Accession No.: Q921N9 (Dec. 1, 2001).
SWALL (SPTR) Accession No.: Q923L3 (Dec. 1, 2001).
SWALL (SPTR) Accession No.: Q924C5 (Dec. 1, 2001).
SWALL (SPTR) Accession No.: Q925G9 (Dec. 1, 2001).
SWALL (SPTR) Accession No.: Q92953 (Dec. 15, 1998).
SWALL (SPTR) Accession No.: Q92964 (Feb. 1, 1997).
SWALL (SPTR) Accession No.: Q95157 (Nov. 1, 1997).
SWALL (SPTR) Accession No.: Q95JS0 (Dec. 1, 2001).
SWALL (SPTR) Accession No.: Q95JS1 (Dec. 1, 2001).
SWALL (SPTR) Accession No.: Q95K03 (Dec. 1, 2001).
SWALL (SPTR) Accession No.: Q95KB4 (Dec. 1, 2001).
SWALL (SPTR) Accession No.: Q95KH3 (Dec. 1, 2001).
SWALL (SPTR) Accession No.: Q95L11 (Dec. 1, 2001).
SWALL (SPTR) Accession No.: Q969E9 (Dec. 1, 2001).
SWALL (SPTR) Accession No.: Q969S0 (Dec. 1, 2001).
SWALL (SPTR) Accession No.: Q96A71 (Oct. 1, 1996).
SWALL (SPTR) Accession No.: Q96A75 (Dec. 1, 2001).
SWALL (SPTR) Accession No.: Q96AQ5 (Jun. 15, 2002).
SWALL (SPTR) Accession No.: Q96C77 (Dec. 1, 2001).
SWALL (SPTR) Accession No.: Q96C87 (Dec. 1, 2001).
SWALL (SPTR) Accession No.: Q96CN4 (Dec. 1, 2001).
SWALL (SPTR) Accession No.: Q96DD0 (Dec. 1, 2001).
SWALL (SPTR) Accession No.: Q96DN9 (Dec. 1, 2001).
SWALL (SPTR) Accession No.: Q96DQ1 (Dec. 1, 2001).

SWALL (SPTR) Accession No.: Q96DT8 (Dec. 1, 2001).
SWALL (SPTR) Accession No.: Q96EF6 (Jun. 15, 2002).
SWALL (SPTR) Accession No.: Q96F06 (Dec. 1, 2001).
SWALL (SPTR) Accession No.: Q96GA7 (Dec. 1, 2001).
SWALL (SPTR) Accession No.: Q96GX5 (Dec. 1, 2001).
SWALL (SPTR) Accession No.: Q96H81 (Dec. 1, 2001).
SWALL (SPTR) Accession No.: Q96IB2 (Feb. 1, 1996).
SWALL (SPTR) Accession No.: Q96J70 (Dec. 1, 2001).
SWALL (SPTR) Accession No.: Q96J92 (Dec. 1, 2001).
SWALL (SPTR) Accession No.: Q96J99 (Dec. 1, 2001).
SWALL (SPTR) Accession No.: Q96JB8 (Dec. 1, 2001).
SWALL (SPTR) Accession No.: Q96JW0 (Dec. 1, 2001).
SWALL (SPTR) Accession No.: Q96K33 (Dec. 1, 2001).
SWALL (SPTR) Accession No.: Q96KS1 (Dec. 1, 2001).
SWALL (SPTR) Accession No.: Q96KV8 (Dec. 1, 2001).
SWALL (SPTR) Accession No.: Q96L96 (Dec. 1, 2001).
SWALL (SPTR) Accession No.: Q96LQ4 (Dec. 1, 2001).
SWALL (SPTR) Accession No.: Q96MC0 (Dec. 1, 2001).
SWALL (SPTR) Accession No.: Q96NA6 (Dec. 1, 2001).
SWALL (SPTR) Accession No.: Q96P71 (Dec. 1, 2001).
SWALL (SPTR) Accession No.: Q96PY6 (Dec. 1, 2001).
SWALL (SPTR) Accession No.: Q96PZ3 (Dec. 1, 2001).
SWALL (SPTR) Accession No.: Q96Q03 (Dec. 1, 2001).
SWALL (SPTR) Accession No.: Q96Q44 (Dec. 1, 2001).
SWALL (SPTR) Accession No.: Q96QN9 (Dec. 1, 2001).
SWALL (SPTR) Accession No.: Q96QU9 (Dec. 1, 2001).
SWALL (SPTR) Accession No.: Q96RM4 (Dec. 1, 2001).
SWALL (SPTR) Accession No.: Q96RZ3 (Dec. 1, 2001).
SWALL (SPTR) Accession No.: Q96S25 (Dec. 1, 2001).
SWALL (SPTR) Accession No.: Q96S58 (Dec. 1, 2001).
SWALL (SPTR) Accession No.: Q96SJ5 (Dec. 1, 2001).
SWALL (SPTR) Accession No.: Q99028 (Jun. 1, 1994).
SWALL (SPTR) Accession No.: Q99578 (May 1, 1997).
SWALL (SPTR) Accession No.: Q99726 (May 30, 2000).
SWALL (SPTR) Accession No.: Q99788 (Jul. 15, 1998).
SWALL (SPTR) Accession No.: Q99JX6 (Jun. 1, 2001).
SWALL (SPTR) Accession No.: Q99JY0 (Jun. 1, 2001).
SWALL (SPTR) Accession No.: Q99K72 (Jun. 1, 2001).
SWALL (SPTR) Accession No.: Q99L64 (Jun. 1, 2001).
SWALL (SPTR) Accession No.: Q99L66 (Jun. 1, 2001).
SWALL (SPTR) Accession No.: Q99P45 (Jun. 1, 2001).
SWALL (SPTR) Accession No.: Q99PH3 (Jun. 1, 2001).
SWALL (SPTR) Accession No.: Q99PH4 (Jun. 1, 2001).
SWALL (SPTR) Accession No.: Q99BK47 (Jun. 1, 2001).
SWALL (SPTR) Accession No.: Q99BRC7 (Jun. 1, 2001).
SWALL (SPTR) Accession No.: Q99BR13 (Jun. 1, 2001).
SWALL (SPTR) Accession No.: Q99BRU4 (Jun. 1, 2001).
SWALL (SPTR) Accession No.: Q9BT40 (Jun. 1, 2001).
SWALL (SPTR) Accession No.: Q9BUT9 (Jun. 1, 2001).
SWALL (SPTR) Accession No.: Q9BXD3 (Jun. 1, 2001).
SWALL (SPTR) Accession No.: Q9BXT0 (Jun. 15, 2002).
SWALL (SPTR) Accession No.: Q9BYB0 (Jun. 1, 2001).
SWALL (SPTR) Accession No.: Q9BYS8 (Jun. 1, 2001).
SWALL (SPTR) Accession No.: Q9BZC4 (Jun. 1, 2001).
SWALL (SPTR) Accession No.: Q9C036 (Jun. 1, 2001).
SWALL (SPTR) Accession No.: Q9C037 (Jun. 1, 2001).
SWALL (SPTR) Accession No.: Q9CQB2 (Jun. 1, 2001).
SWALL (SPTR) Accession No.: Q9CQF4 (Jun. 1, 2001).
SWALL (SPTR) Accession No.: Q9CWJ5 (Jun. 1, 2001).
SWALL (SPTR) Accession No.: Q9CX04 (Jun. 1, 2001).
SWALL (SPTR) Accession No.: Q9CZH9 (Jun. 1, 2001).
SWALL (SPTR) Accession No.: Q9D413 (Jun. 1, 2001).
SWALL (SPTR) Accession No.: Q9D5V2 (Jun. 1, 2001).
SWALL (SPTR) Accession No.: Q9D6J4 (Jun. 1, 2001).
SWALL (SPTR) Accession No.: Q9D811 (Jun. 1, 2001).
SWALL (SPTR) Accession No.: Q9D8D7 (Jun. 1, 2001).
SWALL (SPTR) Accession No.: Q9D995 (Jun. 1, 2001).
SWALL (SPTR) Accession No.: Q9D9F2 (Jun. 1, 2001).
SWALL (SPTR) Accession No.: Q9D9N4 (Jun. 1, 2001).
SWALL (SPTR) Accession No.: Q9D9V0 (Jun. 1, 2001).
SWALL (SPTR) Accession No.: Q9DA07 (Jun. 1, 2001).
SWALL (SPTR) Accession No.: Q9DBB9 (Jun. 1, 2001).
SWALL (SPTR) Accession No.: Q9DBU1 (Jun. 1, 2001).
SWALL (SPTR) Accession No.: Q9DBY7 (Jun. 1, 2001).
SWALL (SPTR) Accession No.: Q9EPQ8 (Mar. 1, 2001).
SWALL (SPTR) Accession No.: Q9EPR4 (Mar. 1, 2001).
SWALL (SPTR) Accession No.: Q9ESB5 (Mar. 1, 2001).
SWALL (SPTR) Accession No.: Q9GMY0 (Mar. 1, 2001).
SWALL (SPTR) Accession No.: Q9H2J7 (Oct. 16, 2001).
SWALL (SPTR) Accession No.: Q9H3F5 (Mar. 1, 2001).
SWALL (SPTR) Accession No.: Q9H4A3 (Mar. 1, 2001).
SWALL (SPTR) Accession No.: Q9H511 (Mar. 1, 2001).
SWALL (SPTR) Accession No.: Q9H6S4 (Mar. 1, 2001).
SWALL (SPTR) Accession No.: Q9H7F0 (Oct. 16, 2001).
SWALL (SPTR) Accession No.: Q9H7K5 (Mar. 1, 2001).
SWALL (SPTR) Accession No.: Q9H8E4 (Mar. 1, 2001).
SWALL (SPTR) Accession No.: Q9HB16 (Jun. 15, 2002).
SWALL (SPTR) Accession No.: Q9HBS6 (Mar. 1, 2001).
SWALL (SPTR) Accession No.: Q9HBW7 (Mar. 1, 2001).
SWALL (SPTR) Accession No.: Q9HBW8 (Mar. 1, 2001).
SWALL (SPTR) Accession No.: Q9HBY2 (Mar. 1, 2001).
SWALL (SPTR) Accession No.: Q9HCE6 (Mar. 1, 2001).
SWALL (SPTR) Accession No.: Q9HCL2 (Oct. 16, 2001).
SWALL (SPTR) Accession No.: Q9HCS2 (Jun. 15, 2002).
SWALL (SPTR) Accession No.: Q9JHB2 (Oct. 1, 2000).
SWALL (SPTR) Accession No.: Q9JHJ7 (Oct. 16, 2001).
SWALL (SPTR) Accession No.: Q9JIH7 (Oct. 1, 2000).
SWALL (SPTR) Accession No.: Q9JJF7 (Oct. 1, 2000).
SWALL (SPTR) Accession No.: Q9JLU4 (Oct. 1, 2000).
SWALL (SPTR) Accession No.: Q9JMC1 (Oct. 1, 2000).
SWALL (SPTR) Accession No.: Q9N0C8 (Oct. 1, 2000).
SWALL (SPTR) Accession No.: Q9NPW7 (Oct. 1, 2000).
SWALL (SPTR) Accession No.: Q9NQ11 (Oct. 16, 2001).
SWALL (SPTR) Accession No.: Q9NR73 (Oct. 1, 2000).
SWALL (SPTR) Accession No.: Q9NS54 (Aug. 1, 1990).
SWALL (SPTR) Accession No.: Q9NV21 (Jun. 15, 2002).
SWALL (SPTR) Accession No.: Q9NVP7 (Jun. 15, 2002).
SWALL (SPTR) Accession No.: Q9NVT3 (Oct. 1, 2000).
SWALL (SPTR) Accession No.: Q9NYN1 (Oct. 1, 2000).
SWALL (SPTR) Accession No.: Q9P0P8 (Oct. 1, 2000).
SWALL (SPTR) Accession No.: Q9P0U7 (Oct. 1, 2000).
SWALL (SPTR) Accession No.: Q9P2J3 (Oct. 16, 2001).
SWALL (SPTR) Accession No.: Q9P2N7 (Oct. 16, 2001).
SWALL (SPTR) Accession No.: Q9QUL7 (Oct. 16, 2001).
SWALL (SPTR) Accession No.: Q9QUQ8 (May 1, 2000).
SWALL (SPTR) Accession No.: Q9QWX5 (May 1, 2000).
SWALL (SPTR) Accession No.: Q9QXA2 (May 1, 2000).
SWALL (SPTR) Accession No.: Q9QY39 (May 1, 2000).
SWALL (SPTR) Accession No.: Q9QY54 (May 1, 2000).
SWALL (SPTR) Accession No.: Q9QY55 (May 1, 2000).
SWALL (SPTR) Accession No.: Q9QYG9 (May 1, 2000).
SWALL (SPTR) Accession No.: Q9QYH1 (May 1, 2000).
SWALL (SPTR) Accession No.: Q9QYU3 (May 1, 2000).
SWALL (SPTR) Accession No.: Q9QZM8 (Jun. 15, 2002).
SWALL (SPTR) Accession No.: Q9QZR3 (May 1, 2000).
SWALL (SPTR) Accession No.: Q9QZR5 (Oct. 16, 2001).
SWALL (SPTR) Accession No.: Q9R0A5 (Oct. 16, 2001).
SWALL (SPTR) Accession No.: Q9R110 (May 1, 2000).

SWALL (SPTR) Accession No.: Q9R189 (May 1, 2000).
SWALL (SPTR) Accession No.: Q9R1U7 (May 1, 2000).
SWALL (SPTR) Accession No.: Q9TSY7 (May 1, 2000).
SWALL (SPTR) Accession No.: Q9TXI7 (May 1, 2000).
SWALL (SPTR) Accession No.: Q9U7C9 (May 1, 2000).
SWALL (SPTR) Accession No.: Q9UDT9 (May 1, 2000).
SWALL (SPTR) Accession No.: Q9UFG7 (May 1, 2000).
SWALL (SPTR) Accession No.: Q9UGU0 (Jan. 1, 1998).
SWALL (SPTR) Accession No.: Q9UIZ3 (May 1, 2000).
SWALL (SPTR) Accession No.: Q9UJ96 (May 1, 2000).
SWALL (SPTR) Accession No.: Q9UJK1 (May 1, 1999).
SWALL (SPTR) Accession No.: Q9UN80 (May 1, 2000).
SWALL (SPTR) Accession No.: Q9UPQ7 (May 1, 2000).
SWALL (SPTR) Accession No.: Q9VAX9 (May 1, 2000).
SWALL (SPTR) Accession No.: Q9W429 (May 1, 2000).
SWALL (SPTR) Accession No.: Q9W6R2 (Nov. 1, 1999).
SWALL (SPTR) Accession No.: Q9W6R3 (Nov. 1, 1999).
SWALL (SPTR) Accession No.: Q9WTW8 (Nov. 1, 1999).
SWALL (SPTR) Accession No.: Q9WUU6 (Oct. 16, 2001).
SWALL (SPTR) Accession No.: Q9WUY7 (Nov. 1, 1999).
SWALL (SPTR) Accession No.: Q9WV40 (Nov. 1, 1999).
SWALL (SPTR) Accession No.: Q9WV47 (Nov. 1, 1999).
SWALL (SPTR) Accession No.: Q9WV59 (Nov. 1, 1999).
SWALL (SPTR) Accession No.: Q9WVT0 (Nov. 1, 1999).
SWALL (SPTR) Accession No.: Q9XS59 (Oct. 16, 2001).
SWALL (SPTR) Accession No.: Q9Y137 (Nov. 1, 1999).
SWALL (SPTR) Accession No.: Q9Y3K0 (Nov. 1, 1999).
SWALL (SPTR) Accession No.: Q9Y5K0 (Nov. 1, 1999).
SWALL (SPTR) Accession No.: Q9Y698 (May 30, 2000).
SWALL (SPTR) Accession No.: Q9Y6M0 (Oct.16, 2001).
SWALL (SPTR) Accession No.: Q9Z1N9 (May 1, 1999).
SWALL (SPTR) Accession No.: Q9Z2Z7 (May 1, 1999).

PROTEINS AND NUCLEIC ACIDS ENCODING SAME

RELATED APPLICATIONS

This application claims priority to U.S. Ser. No. 60/281,086, filed on Apr. 3, 2001; U.S. Ser. No. 60/281,136, filed on Apr. 3, 2001; U.S. Ser. No. 60/281,863, filed on Apr. 5, 2001; U.S. Ser. No. 60/281,906, filed on Apr. 5, 2001; U.S. Ser. No. 60/282,020, filed on Apr. 6, 2001; U.S. Ser. No. 60/282,930, filed on Apr. 10, 2001; U.S. Ser. No. 60/282,934, filed on Apr. 10, 2001; U.S. Ser. No. 60/283,512, filed on Apr. 12, 2001; U.S. Ser. No. 60/283,710, filed on Apr. 13, 2001; U.S. Ser. No. 60/284,234, filed on Apr. 17, 2001; U.S. Ser. No. 60/285,325, filed on Apr. 19, 2001; U.S. Ser. No. 60/285,381, filed on Apr. 20, 2001; U.S. Ser. No. 60/285,609, filed on Apr. 20, 2001; U.S. Ser. No. 60/285,748, filed on Apr. 23, 2001; U.S. Ser. No. 60/285,890, filed on Apr. 23, 2001; U.S. Ser. No. 60/286,068, filed on Apr. 24, 2001; U.S. Ser. No. 60/286,292, filed on Apr. 25, 2001; U.S. Ser. No. 60/287,213, filed on Apr. 27, 2001; U.S. Ser. No. 60/288,257, filed on May 2, 2001; U.S. Ser. No. 60/294,164, filed on May 29, 2001; U.S. Ser. No. 60/294,484, filed on May 30, 2001; U.S. Ser. No. 60/298,952, filed on Jun. 18, 2001; U.S. Ser. No. 60/299,237, filed on Jun. 19, 2001; U.S. Ser. No. 60/299,276, filed on Jun. 19, 2001; U.S. Ser. No. 60/318,750, filed on Sep. 12, 2001; U.S. Ser. No. 60/324,800, filed on Sep. 25, 2001; U.S. Ser. No. 60/324,802, filed on Sep. 25, 2001; U.S. Ser. No. 60/325,684, filed on Sep. 27, 2001; U.S. Ser. No. 60/330,143, filed on Oct. 17, 2001; U.S. Ser. No. 60/332,115, filed on Nov. 21, 2001; U.S. Ser. No. 60/332,131, filed on Nov. 14, 2001; U.S. Ser. No. 60/332,240, filed on Nov. 14, 2001; U.S. Ser. No. 60/332,779, filed on Nov. 14, 2001; U.S. Ser. No. 60/337,621, filed on Dec. 4, 2001; U.S. Ser. No. 60/345,783, Jan. 3, 2002; U.S. Ser. No. 60/350,251, filed on Jan. 16, 2002; each of which is incorporated by reference in its entirety.

FIELD OF THE INVENTION

The present invention relates to novel polypeptides that are targets of small molecule drugs and that have properties related to stimulation of biochemical or physiological responses in a cell, a tissue, an organ or an organism. More particularly, the novel polypeptides are gene products of novel genes, or are specified biologically active fragments or derivatives thereof. Methods of use encompass diagnostic and prognostic assay procedures as well as methods of treating diverse pathological conditions.

BACKGROUND

Eukaryotic cells are characterized by biochemical and physiological processes which under normal conditions are exquisitely balanced to achieve the preservation and propagation of the cells. When such cells are components of multicellular organisms such as vertebrates, or more particularly organisms such as mammals, the regulation of the biochemical and physiological processes involves intricate signaling pathways. Frequently, such signaling pathways are constituted of extracellular signaling proteins, cellular receptors that bind the signaling proteins and signal transducing components located within the cells.

Signaling proteins may be classified as endocrine effectors, paracrine effectors or autocrine effectors. Endocrine effectors are signaling molecules secreted by a given organ into the circulatory system, which are then transported to a distant target organ or tissue. The target cells include the receptors for the endocrine effector, and when the endocrine effector binds, a signaling cascade is induced. Paracrine effectors involve secreting cells and receptor cells in close proximity to each other, for example two different classes of cells in the same tissue or organ. One class of cells secretes the paracrine effector, which then reaches the second class of cells, for example by diffusion through the extracellular fluid. The second class of cells contains the receptors for the paracrine effector; binding of the effector results in induction of the signaling cascade that elicits the corresponding biochemical or physiological effect. Autocrine effectors are highly analogous to paracrine effectors, except that the same cell type that secretes the autocrine effector also contains the receptor. Thus the autocrine effector binds to receptors on the same cell, or on identical neighboring cells. The binding process then elicits the characteristic biochemical or physiological effect.

Signaling processes may elicit a variety of effects on cells and tissues including by way of nonlimiting example induction of cell or tissue proliferation, suppression of growth or proliferation, induction of differentiation or maturation of a cell or tissue, and suppression of differentiation or maturation of a cell or tissue.

Many pathological conditions involve dysregulation of expression of important effector proteins. In certain classes of pathologies the dysregulation is manifested as diminished or suppressed level of synthesis and secretion protein effectors. In a clinical setting a subject may be suspected of suffering from a condition brought on by diminished or suppressed levels of a protein effector of interest. Therefore there is a need to be able to assay for the level of the protein effector of interest in a biological sample from such a subject, and to compare the level with that characteristic of a nonpathological condition. There further is a need to provide the protein effector as a product of manufacture. Administration of the effector to a subject in need thereof is useful in treatment of the pathological condition, or the protein effector deficiency or suppression may be favorably acted upon by the administration of another small molecule drug product. Accordingly, there is a need for a method of treatment of a pathological condition brought on by a diminished or suppressed levels of the protein effector of interest.

Small molecule targets have been implicated in various disease states or pathologies. These targets may be proteins, and particularly enzymatic proteins, which are acted upon by small molecule drugs for the purpose of altering target function and achieving a desired result. Cellular, animal and clinical studies can be performed to elucidate the genetic contribution to the etiology and pathogenesis of conditions in which small molecule targets are implicated in a variety of physiologic, pharmacologic or native states. These studies utilize the core technologies at CuraGen Corporation to look at differential gene expression, protein-protein interactions, large-scale sequencing of expressed genes and the association of genetic variations such as, but not limited to, single nucleotide polymorphisms (SNPs) or splice variants in and between biological samples from experimental and control groups. The goal of such studies is to identify potential avenues for therapeutic intervention in order to prevent, treat the consequences or cure the conditions.

In order to treat diseases, pathologies and other abnormal states or conditions in which a mammalian organism has been diagnosed as being, or as being at risk for becoming, other than in a normal state or condition, it is important to identify new therapeutic agents. Such a procedure includes at least the steps of identifying a target component within an affected tissue or organ, and identifying a candidate therapeutic agent that modulates the functional attributes of the target. The target component may be any biological macromolecule implicated in the disease or pathology. Commonly the target is a polypeptide or protein with specific functional attributes. Other classes of macromolecule may be a nucleic acid, a polysaccharide, a lipid such as a complex lipid or a glycolipid; in addition a target may be a sub-cellular structure or extra-cellular structure that is comprised of more than one of these classes of macromolecule. Once such a target has been identified, it may be employed in a screening assay in order to identify favorable candidate therapeutic agents from among a large population of substances or compounds.

In many cases the objective of such screening assays is to identify small molecule candidates; this is commonly approached by the use of combinatorial methodologies to develop the population of substances to be tested. The implementation of high throughput screening methodologies is advantageous when working with large, combinatorial libraries of compounds.

SUMMARY OF THE INVENTION

The invention is based in part upon the discovery of nucleic acid sequences encoding novel polypeptides. These nucleic acids and polypeptides, as well as derivatives, homologs, analogs and fragments thereof, will hereinafter be collectively designated as "NOVX" nucleic acid, which represents the nucleotide sequence selected from the group consisting of SEQ ID NO: 2n−1, wherein n is an integer between 1 and 106, or polypeptide sequences, which represents the group consisting of SEQ ID NO: 2n, wherein n is an integer between 1 and 106.

In one aspect, the invention provides an isolated polypeptide comprising a mature form of a NOVX amino acid. One example is a variant of a mature form of a NOVX amino acid sequence, wherein any amino acid in the mature form is changed to a different amino acid, provided that no more than 15% of the amino acid residues in the sequence of the mature form are so changed. The amino acid can be, for example, a NOVX amino acid sequence or a variant of a NOVX amino acid sequence, wherein any amino acid specified in the chosen sequence is changed to a different amino acid, provided that no more than 15% of the amino acid residues in the sequence are so changed. The invention also includes fragments of any of these. In another aspect, the invention also includes an isolated nucleic acid that encodes a NOVX polypeptide, or a fragment, homolog, analog or derivative thereof.

Also included in the invention is a NOVX polypeptide that is a naturally occurring allelic variant of a NOVX sequence. In one embodiment, the allelic variant includes an amino acid sequence that is the translation of a nucleic acid sequence differing by a single nucleotide from a NOVX nucleic acid sequence. In another embodiment, the NOVX polypeptide is a variant polypeptide described therein, wherein any amino acid specified in the chosen sequence is changed to provide a conservative substitution. In one embodiment, the invention discloses a method for determining the presence or amount of the NOVX polypeptide in a sample. The method involves the steps of: providing a sample; introducing the sample to an antibody that binds immunospecifically to the polypeptide; and determining the presence or amount of antibody bound to the NOVX polypeptide, thereby determining the presence or amount of the NOVX polypeptide in the sample. In another embodiment, the invention provides a method for determining the presence of or predisposition to a disease associated with altered levels of a NOVX polypeptide in a mammalian subject. This method involves the steps of: measuring the level of expression of the polypeptide in a sample from the first mammalian subject; and comparing the amount of the polypeptide in the sample of the first step to the amount of the polypeptide present in a control sample from a second mammalian subject known not to have, or not to be predisposed to, the disease, wherein an alteration in the expression level of the polypeptide in the first subject as compared to the control sample indicates the presence of or predisposition to the disease.

In a further embodiment, the invention includes a method of identifying an agent that binds to a NOVX polypeptide. This method involves the steps of: introducing the polypeptide to the agent; and determining whether the agent binds to the polypeptide. In various embodiments, the agent is a cellular receptor or a downstream effector.

In another aspect, the invention provides a method for identifying a potential therapeutic agent for use in treatment of a pathology, wherein the pathology is related to aberrant expression or aberrant physiological interactions of a NOVX polypeptide. The method involves the steps of: providing a cell expressing the NOVX polypeptide and having a property or function ascribable to the polypeptide; contacting the cell with a composition comprising a candidate substance; and determining whether the substance alters the property or function ascribable to the polypeptide; whereby, if an alteration observed in the presence of the substance is not observed when the cell is contacted with a composition devoid of the substance, the substance is identified as a potential therapeutic agent. In another aspect, the invention describes a method for screening for a modulator of activity or of latency or predisposition to a pathology associated with the NOVX polypeptide. This method involves the following steps: administering a test compound to a test animal at increased risk for a pathology associated with the NOVX polypeptide, wherein the test animal recombinantly expresses the NOVX polypeptide. This method involves the steps of measuring the activity of the NOVX polypeptide in the test animal after administering the compound of step; and comparing the activity of the protein in the test animal with the activity of the NOVX polypeptide in a control animal not administered the polypeptide, wherein a change in the activity of the NOVX polypeptide in the test animal relative to the control animal indicates the test compound is a modulator of latency of, or predisposition to, a pathology associated with the NOVX polypeptide. In one embodiment, the test animal is a recombinant test animal that expresses a test protein transgene or expresses the transgene under the control of a promoter at an increased level relative to a wild-type test animal, and wherein the promoter is not the native gene promoter of the transgene. In another aspect, the invention includes a method for modulating the activity of the NOVX polypeptide, the method comprising introducing a cell sample expressing the NOVX polypeptide with a compound that binds to the polypeptide in an amount sufficient to modulate the activity of the polypeptide.

The invention also includes an isolated nucleic acid that encodes a NOVX polypeptide, or a fragment, homolog, analog or derivative thereof. In a preferred embodiment, the nucleic acid molecule comprises the nucleotide sequence of a naturally occurring allelic nucleic acid variant. In another embodiment, the nucleic acid encodes a variant polypeptide, wherein the variant polypeptide has the polypeptide sequence of a naturally occurring polypeptide variant. In another embodiment, the nucleic acid molecule differs by a single nucleotide from a NOVX nucleic acid sequence. In one embodiment, the NOVX nucleic acid molecule hybridizes under stringent conditions to the nucleotide sequence selected from the group consisting of SEQ ID NO: 2n−1, wherein n is an integer between 1 and 106, or a complement of the nucleotide sequence. In another aspect, the invention provides a vector or a cell expressing a NOVX nucleotide sequence.

In one embodiment, the invention discloses a method for modulating the activity of a NOVX polypeptide. The method includes the steps of: introducing a cell sample expressing the NOVX polypeptide with a compound that binds to the polypeptide in an amount sufficient to modulate the activity of the polypeptide. In another embodiment, the invention includes an isolated NOVX nucleic acid molecule comprising a nucleic acid sequence encoding a polypeptide comprising a NOVX amino acid sequence or a variant of a mature form of the NOVX amino acid sequence, wherein any amino acid in the mature form of the chosen sequence is changed to a different amino acid, provided that no more than 15% of the amino acid residues in the sequence of the mature form are so changed. In another embodiment, the invention includes an amino acid sequence that is a variant of the NOVX amino acid sequence, in which any amino acid specified in the chosen sequence is changed to a different amino acid, provided that no more than 15% of the amino acid residues in the sequence are so changed.

In one embodiment, the invention discloses a NOVX nucleic acid fragment encoding at least a portion of a NOVX polypeptide or any variant of the polypeptide, wherein any amino acid of the chosen sequence is changed to a different amino acid, provided that no more than 10% of the amino acid residues in the sequence are so changed. In another embodiment, the invention includes the complement of any of the NOVX nucleic acid molecules or a naturally occurring allelic nucleic acid variant. In another embodiment, the invention discloses a NOVX nucleic acid molecule that encodes a variant polypeptide, wherein the variant polypeptide has the polypeptide sequence of a naturally occurring polypeptide variant. In another embodiment, the invention discloses a NOVX nucleic acid, wherein the nucleic acid molecule differs by a single nucleotide from a NOVX nucleic acid sequence.

In another aspect, the invention includes a NOVX nucleic acid, wherein one or more nucleotides in the NOVX nucleotide sequence is changed to a different nucleotide provided that no more than 15% of the nucleotides are so changed. In one embodiment, the invention discloses a nucleic acid fragment of the NOVX nucleotide sequence and a nucleic acid fragment wherein one or more nucleotides in the NOVX nucleotide sequence is changed from that selected from the group consisting of the chosen sequence to a different nucleotide provided that no more than 15% of the nucleotides are so changed. In another embodiment, the invention includes a nucleic acid molecule wherein the nucleic acid molecule hybridizes under stringent conditions to a NOVX nucleotide sequence or a complement of the NOVX nucleotide sequence. In one embodiment, the invention includes a nucleic acid molecule, wherein the sequence is changed such that no more than 15% of the nucleotides in the coding sequence differ from the NOVX nucleotide sequence or a fragment thereof.

In a further aspect, the invention includes a method for determining the presence or amount of the NOVX nucleic acid in a sample. The method involves the steps of: providing the sample; introducing the sample to a probe that binds to the nucleic acid molecule; and determining the presence or amount of the probe bound to the NOVX nucleic acid molecule, thereby determining the presence or amount of the NOVX nucleic acid molecule in the sample. In one embodiment, the presence or amount of the nucleic acid molecule is used as a marker for cell or tissue type.

In another aspect, the invention discloses a method for determining the presence of or predisposition to a disease associated with altered levels of the NOVX nucleic acid molecule of in a first mammalian subject. The method involves the steps of: measuring the amount of NOVX nucleic acid in a sample from the first mammalian subject; and comparing the amount of the nucleic acid in the sample of step (a) to the amount of NOVX nucleic acid present in a control sample from a second mammalian subject known not to have or not be predisposed to, the disease; wherein an alteration in the level of the nucleic acid in the first subject as compared to the control sample indicates the presence of or predisposition to the disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

The present invention provides novel nucleotides and polypeptides encoded thereby. Included in the invention are the novel nucleic acid sequences, their encoded polypeptides, antibodies, and other related compounds. The sequences are collectively referred to herein as "NOVX nucleic acids" or "NOVX polynucleotides" and the corresponding encoded polypeptides are referred to as "NOVX polypeptides" or "NOVX proteins." Unless indicated otherwise, "NOVX" is meant to refer to any of the novel sequences disclosed herein. Table 1 provides a summary of the NOVX nucleic acids and their encoded polypeptides.

TABLE 1

Sequences and Corresponding SEQ ID Numbers

| NOVX Assignment | Internal Identification | SEQ ID NO (nucleic acid) | SEQ ID NO (polypeptide) | Homology |
| --- | --- | --- | --- | --- |
| 1a | CG55912-01 | 1 | 2 | CACNG4 |
| 2a | CG55918-01 | 3 | 4 | Zinc Transporter |
| 2b | CG55918_02 | 5 | 6 | Zinc Transporter |
| 3a | CG56641-02 | 7 | 8 | Thrombospondin |
| 4a | CG56832-01 | 9 | 10 | Guanylate Kinase |
| 4b | CG56832-02 | 11 | 12 | Guanylate Kinase |

TABLE 1-continued

Sequences and Corresponding SEQ ID Numbers

| NOVX Assignment | Internal Identification | SEQ ID NO (nucleic) acid) | SEQ ID NO (polypeptide) | Homology |
|---|---|---|---|---|
| 4c | CG56832-03 | 13 | 14 | Guanylate Kinase |
| 5a | CG58618-01 | 15 | 16 | Catechol O-Methyltransferase |
| 5b | CG58618-02 | 17 | 18 | Catechol O-Methyltransferase |
| 6a | CG59580-01 | 19 | 20 | GPCR |
| 7a | CG59611-01 | 21 | 22 | GPCR |
| 8a | CG59617-01 | 23 | 24 | GPCR |
| 9a | CG59826-01 | 25 | 26 | Transformation Sensitive Protein IEF SSP 3521 |
| 10a | CG59839-01 | 27 | 28 | Cation Transporting ATPase |
| 11a | CG59847-01 | 29 | 30 | Intracellular Protein |
| 12a | CG59905-01 | 31 | 32 | Sushi Containing Membrane Protein |
| 13a | CG59930-01 | 33 | 34 | Leucine Rich Repeat |
| 13b | CG59930-02 | 35 | 36 | Leucine Rich Repeat |
| 14a | CG59934-01 | 37 | 38 | Leucine Rich Repeat |
| 14b | CG59934-02 | 39 | 40 | Leucine Rich Repeat |
| 15a | CG88565-01 | 41 | 42 | UDP N-Acetylglucosamine Transporter |
| 16a | CG88623-01 | 43 | 44 | Potassium Channel Alpha Subunit |
| 17a | CG88645-01 | 45 | 46 | Cardiac Potassium Channel Subunit(KV6.2) |
| 18a | CG88738-01 | 47 | 48 | Synaptotagmin Interacting Protein STIP1 |
| 19a | CG88902-01 | 49 | 50 | UDP Glucuronosyltransferase |
| 19b | CG88902-02 | 51 | 52 | UDP Glucuronosyltransferase |
| 20a | CG89048_01 | 53 | 54 | Kelch |
| 20b | CG89048_02 | 55 | 56 | Kelch |
| 21a | CG89098-01 | 57 | 58 | Cytoplasmic G-box Protein |
| 22a | CG89126-01 | 59 | 60 | Cytochrome P-450 |
| 23a | CG89367_01 | 61 | 62 | db1/cdc24rhoGEF |
| 24a | CG89645-01 | 63 | 64 | Mitochondrial Protein |
| 25a | CG89677-01 | 65 | 66 | Arylsulfatase B |
| 26a | CG89697_01 | 67 | 68 | RIS |
| 26b | CG89697_01 | 69 | 70 | RIS |
| 27a | CG90001-01 | 71 | 72 | Peptidylprolyl Isomerase A |
| 28a | CG90011-01 | 73 | 74 | ATP Specific Succinyl Coa Synthetase Beta Subunit Precursor |
| 29a | CG90204-01 | 75 | 76 | Semaphorin Cytoplasmic Domain |
| 30a | CG90385-01 | 77 | 78 | Mitogen Activated Kinase |
| 30b | CG90385-02 | 79 | 80 | Mitogen Activated Kinase |
| 31a | CG90635-01 | 81 | 82 | Nuclear Body-Associated Kinase 2B |
| 32a | CG90729-01 | 83 | 84 | Proline Rich Inositol Polyphosphate 5 Phophotase |
| 33a | CG90760-01 | 85 | 86 | Transcription Factor 20 |
| 34a | CG90770-01 | 87 | 88 | 9530058B02R1K Lysosomal |
| 35a | CG91002-01 | 89 | 90 | Steroid Dehydrogenase |
| 35b | CG91002_02 | 91 | 92 | Steroid Dehydrogenase |
| 36a | CG91298-01 | 93 | 94 | Phosphatidylglycerophosphate Synthase |
| 37a | CG91383-01 | 95 | 96 | Aldehyde Dehydrogenase |
| 38a | CG91403-01 | 97 | 98 | Proline Rich Synapse Associated Protein 2 |
| 39a | CG91434-01 | 99 | 100 | Aldehyde Dehydrogenase |
| 40a | CG91484-01 | 101 | 102 | GPCR |
| 41a | CG91514-01 | 103 | 104 | Telokin |
| 42a | CG91587-01 | 105 | 106 | Tripartite Motif Protein TRIM4 Isoform Alpha |
| 43a | CG91631_01 | 107 | 108 | NAG5 |
| 44a | CG91643_01 | 109 | 110 | Protein Kinase-ERK1 |
| 45a | CG91911-01 | 111 | 112 | Mitogen-Activated Protein Kinase Kinase Kinase 8 |
| 46a | CG91931-01 | 113 | 114 | Rab-like Small GTPases |
| 47a | CG91941-01 | 115 | 116 | Serine/Threonine-Protein Kinase |
| 48a | CG91951-01 | 117 | 118 | Serine/Threonine-Protein Kinase |
| 49a | CG92025-01 | 119 | 120 | Gamma-Glutamyltransferase |
| 49b | CG92025-02 | 121 | 122 | Gamma-Glutamyltransferase |
| 50a | CG92078-01 | 123 | 124 | Yolk Sac Permease-Like YSPL-1 Form |

TABLE 1-continued

Sequences and Corresponding SEQ ID Numbers

| NOVX Assignment | Internal Identification | SEQ ID NO (nucleic) acid) | SEQ ID NO (polypeptide) | Homology |
|---|---|---|---|---|
| 51a | CG92088-01 | 125 | 126 | UDP-galactose: beta-d-galactosyl-1,4-glucosylceramide alpha-1,3-galactosyltransferase (iGb(3) synthase) |
| 52a | CG92142-01 | 127 | 128 | Glycerol-3-Phosphate Acyltransferase |
| 53a | CG92152_01 | 129 | 130 | Plasminogen Activator SPA |
| 54a | CG92228-01 | 131 | 132 | Transmembrane Tryptase |
| 54b | CG92228-02 | 133 | 134 | Transmembrane Tryptase |
| 55a | CG92425-01 | 135 | 136 | Retinol Dehydrogenase |
| 55b | CG92425-02 | 137 | 138 | Retinol Dehydrogenase |
| 56a | CG92477_01 | 139 | 140 | Secretin |
| 57a | CG92499-01 | 141 | 142 | Seven Transmembrane Domain Protein |
| 57b | CG92499-02 | 143 | 144 | Seven Transmembrane Domain Protein |
| 58a | CG92541-01 | 145 | 146 | Munc13-4 |
| 59a | CG92662-01 | 147 | 148 | Prostaglandin-E2 9-Reductase |
| 60a | CG92683-01 | 149 | 150 | C2PA |
| 60b | CG92683-02 | 151 | 152 | C2PA |
| 61a | CG92694-01 | 153 | 154 | Long Chain 2-Ketoacyl-CoA Thiolase |
| 62a | CG92896-01 | 155 | 156 | Phosphatidylinositol 5-Phosphate 4-Kinase |
| 62b | CG92896-02 | 157 | 158 | Phosphatidylinositol 5-Phosphate 4-Kinase |
| 63a | CG92987_01 | 159 | 160 | Annexin VI |
| 64a | CG93042_01 | 161 | 162 | GPCR |
| 65a | CG93265-01 | 163 | 164 | L-Serine Dehydratase |
| 65b | CG93265-02 | 165 | 166 | L-Serine Dehydratase |
| 66a | CG93464_01 | 167 | 168 | Phosphatidylinositol 3-Kinase |
| 66b | CG93464_02 | 169 | 170 | Phosphatidylinositol 3-Kinase |
| 66c | CG93464_03 | 171 | 172 | Phosphatidylinositol 3-Kinase |
| 67a | CG93495-01 | 173 | 174 | MAP Kinase-Activating Death Domain Protein |
| 68a | CG93529-01 | 175 | 176 | Macrophage ABC Transporter |
| 69a | CG93594-01 | 177 | 178 | Phosphatidylinositol-Specific Phospholipase C |
| 70a | CG93669-01 | 179 | 180 | Serine/Threonine Kinase NEK3 |
| 70b | CG93669-02 | 181 | 182 | Serine/Threonine Kinase NEK3 |
| 70c | CG93669-03 | 183 | 184 | Serine/Threonine Kinase NEK3 |
| 71a | CG93896-01 | 185 | 186 | NEK |
| 71b | CG93896-02 | 187 | 188 | NEK |
| 72a | CG93939-01 | 189 | 190 | Sodium-And Chloride-Dependent Transporter NTT4 |
| 73a | CG94245-01 | 191 | 192 | Hepatocyte Nuclear Factor 4 |
| 74a | CG94302-01 | 193 | 194 | MUNC13-1 (KIAA1032) |
| 75a | CG94356-01 | 195 | 196 | Carboxylesterase |
| 76a | CG94421_01 | 197 | 198 | Kelch-BTB |
| 77a | CG94465-01 | 199 | 200 | Protein Kinase |
| 77b | CG94465-02 | 201 | 202 | Protein Kinase |
| 77c | CG94465-03 | 203 | 204 | Protein Kinase |
| 78a | CG94511-01 | 205 | 206 | Pyruvate Dehydrogenase |
| 79a | CG94551-01 | 207 | 208 | MUNC13-3 |
| 80a | CG94682_02 | 209 | 210 | Renal Organic Anion Transporter 1 |
| 81a | CG90214_01 | 211 | 212 | Beta 1,4N-Acetylgalactosaminyltransferase |

Table 1 indicates homology of NOVX nucleic acids to known protein families. Thus, the nucleic acids and polypeptides, antibodies and related compounds according to the invention corresponding to a NOVX as identified in column 1 of Table 1 will be useful in therapeutic and diagnostic applications implicated in, for example, pathologies and disorders associated with the known protein families identified in column 5 of Table 1.

NOVX nucleic acids and their encoded polypeptides are useful in a variety of applications and contexts. The various NOVX nucleic acids and polypeptides according to the invention are useful as novel members of the protein families according to the presence of domains and sequence relatedness to previously described proteins. Additionally, NOVX nucleic acids and polypeptides can also be used to identify proteins that are members of the family to which the NOVX polypeptides belong.

Consistent with other known members of the family of proteins, identified in column 5 of Table 1, the NOVX polypeptides of the present invention show homology to, and contain domains that are characteristic of, other members of such protein families. Details of the sequence relatedness and domain analysis for each NOVX are presented in Example A.

The NOVX nucleic acids and polypeptides can also be used to screen for molecules, which inhibit or enhance NOVX activity or function. Specifically, the nucleic acids and polypeptides according to the invention may be used as targets for the identification of small molecules that modulate or inhibit diseases associated with the protein families listed in Table 1.

The NOVX nucleic acids and polypeptides are also useful for detecting specific cell types. Details of the expression analysis for each NOVX are presented in Example 83. Accordingly, the NOVX nucleic acids, polypeptides, antibodies and related compounds according to the invention will have diagnostic and therapeutic applications in the detection of a variety of diseases with differential expression in normal vs. diseased tissues, e.g. a variety of cancers.

Additional utilities for NOVX nucleic acids and polypeptides according to the invention are disclosed herein.

The present invention is based on the identification of biological macromolecules differentially modulated in a pathologic state, disease, or an abnormal condition or state. Among the pathologies or diseases of present interest include metabolic diseases including those related to endocrinologic disorders, cancers, various tumors and neoplasias, inflammatory disorders, central nervous system disorders, and similar abnormal conditions or states. In very significant embodiments of the present invention, the biological macromolecules implicated in the pathologies and conditions are proteins and polypeptides, and in such cases the present invention is related as well to the nucleic acids that encode them. Methods that may be employed to identify relevant biological macromolecules include any procedures that detect differential expression of nucleic acids encoding proteins and polypeptides associated with the disorder, as well as procedures that detect the respective proteins and polypeptides themselves. Significant methods that have been employed by the present inventors, include GeneCalling® technology and SeqCalling™ technology, disclosed respectively, in U.S. Pat. No. 5,871,697, and in U.S. Ser. No. 09/417,386, filed Oct. 13, 1999, each of which is incorporated herein by reference in its entirety. GeneCalling® is also described in Shimkets, et al., "Gene expression analysis by transcript profiling coupled to a gene database query" Nature Biotechnology 17:198–803 (1999).

The invention provides polypeptides and nucleotides encoded thereby that have been identified as having novel associations with a disease or pathology, or an abnormal state or condition, in a mammal. The present invention further identifies a set of proteins and polypeptides, including naturally occurring polypeptides, precursor forms or proproteins, or mature forms of the polypeptides or proteins, which are implicated as targets for therapeutic agents in the treatment of various diseases, pathologies, abnormal states and conditions. A target may be employed in any of a variety of screening methodologies in order to identify candidate therapeutic agents which interact with the target and in so doing exert a desired or favorable effect. The candidate therapeutic agent is identified by screening a large collection of substances or compounds in an important embodiment of the invention. Such a collection may comprise a combinatorial library of substances or compounds in which, in at least one subset of substances or compounds, the individual members are related to each other by simple structural variations based on a particular canonical or basic chemical structure. The variations may include, by way of nonlimiting example, changes in length or identity of a basic framework of bonded atoms; changes in number, composition and disposition of ringed structures, bridge structures, alicyclic rings, and aromatic rings; and changes in pendent or substituents atoms or groups that are bonded at particular positions to the basic framework of bonded atoms or to the ringed structures, the bridge structures, the alicyclic structures, or the aromatic structures.

A polypeptide or protein described herein, and that serves as a target in the screening procedure, includes the product of a naturally occurring polypeptide or precursor form or proprotein. The naturally occurring polypeptide, precursor or proprotein includes, e.g., the full-length gene product, encoded by the corresponding gene. The naturally occurring polypeptide also includes the polypeptide, precursor or proprotein encoded by an open reading frame described herein. A "mature" form of a polypeptide or protein arises as a result of one or more naturally occurring processing steps as they may occur within the cell, including a host cell. The processing steps occur as the gene product arises, e.g., via cleavage of the amino-terminal methionine residue encoded by the initiation codon of an open reading frame, or the proteolytic cleavage of a signal peptide or leader sequence. Thus, a mature form arising from a precursor polypeptide or protein that has residues 1 to N, where residue 1 is the N-terminal methionine, would have residues 2 through N remaining. Alternatively, a mature form arising from a precursor polypeptide or protein having residues 1 to N, in which an amino-terminal signal sequence from residue 1 to residue M is cleaved, includes the residues from residue M+1 to residue N remaining. A "mature" form of a polypeptide or protein may also arise from non-proteolytic post-translational modification. Such non-proteolytic processes include, e.g., glycosylation, myristylation or phosphorylation. In general, a mature polypeptide or protein may result from the operation of only one of these processes, or the combination of any of them.

As used herein, "identical" residues correspond to those residues in a comparison between two sequences where the equivalent nucleotide base or amino acid residue in an alignment of two sequences is the same residue. Residues are alternatively described as "similar" or "positive" when the comparisons between two sequences in an alignment show that residues in an equivalent position in a comparison are either the same amino acid or a conserved amino acid as defined below.

As used herein, a "chemical composition" relates to a composition including at least one compound that is either synthesized or extracted from a natural source. A chemical compound may be the product of a defined synthetic procedure. Such a synthesized compound is understood herein to have defined properties in terms of molecular formula, molecular structure relating the association of bonded atoms to each other, physical properties such as chromatographic or spectroscopic characterizations, and the like. A compound extracted from a natural source is advantageously analyzed by chemical and physical methods in order to provide a representation of its defined properties, including its molecular formula, molecular structure relating the association of bonded atoms to each other, physical properties such as chromatographic or spectroscopic characterizations, and the like.

As used herein, a "candidate therapeutic agent" is a chemical compound that includes at least one substance shown to bind to a target biopolymer. In important embodiments of the invention, the target biopolymer is a protein or polypeptide, a nucleic acid, a polysaccharide or proteoglycan, or a lipid such as a complex lipid. The method of identifying compounds that bind to the target effectively eliminates compounds with little or no binding affinity, thereby increasing the potential that the identified chemical compound may have beneficial therapeutic applications. In cases where the "candidate therapeutic agent" is a mixture of more than one chemical compound, subsequent screening procedures may be carried out to identify the particular substance in the mixture that is the binding compound, and that is to be identified as a candidate therapeutic agent.

As used herein, a "pharmaceutical agent" is provided by screening a candidate therapeutic agent using models for a disease state or pathology in order to identify a candidate exerting a desired or beneficial therapeutic effect with relation to the disease or pathology. Such a candidate that successfully provides such an effect is termed a pharmaceutical agent herein. Nonlimiting examples of model systems that may be used in such screens include particular cell lines, cultured cells, tissue preparations, whole tissues, organ preparations, intact organs, and nonhuman mammals. Screens employing at least one system, and preferably more than one system, may be employed in order to identify a pharmaceutical agent. Any pharmaceutical agent so identified may be pursued in further investigation using human subjects.

NOVX Nucleic Acids and Polypeptides
NOVX Clones

NOVX nucleic acids and their encoded polypeptides are useful in a variety of applications and contexts. The various NOVX nucleic acids and polypeptides according to the invention are useful as novel members of the protein families according to the presence of domains and sequence relatedness to previously described proteins. Additionally, NOVX nucleic acids and polypeptides can also be used to identify proteins that are members of the family to which the NOVX polypeptides belong.

The NOVX genes and their corresponding encoded proteins are useful for preventing, treating or ameliorating medical conditions, e.g., by protein or gene therapy. Pathological conditions can be diagnosed by determining the amount of the new protein in a sample or by determining the presence of mutations in the new genes. Specific uses are described for each of the NOVX genes, based on the tissues in which they are most highly expressed. Uses include developing products for the diagnosis or treatment of a variety of diseases and disorders.

The NOVX nucleic acids and proteins of the invention are useful in potential diagnostic and therapeutic applications and as a research tool. These include serving as a specific or selective nucleic acid or protein diagnostic and/or prognostic marker, wherein the presence or amount of the nucleic acid or the protein are to be assessed, as well as potential therapeutic applications such as the following: (i) a protein therapeutic, (ii) a small molecule drug target, (iii) an antibody target (therapeutic, diagnostic, drug targeting/cytotoxic antibody), (iv) a nucleic acid useful in gene therapy (gene delivery/gene ablation), and (v) a composition promoting tissue regeneration in vitro and in vivo (vi) biological defense weapon.

In one specific embodiment, the invention includes an isolated polypeptide comprising an amino acid sequence selected from the group consisting of: (a) a mature form of the amino acid sequence selected from the group consisting of SEQ ID NO: 2n, wherein n is an integer between 1 and 106; (b) a variant of a mature form of the amino acid sequence selected from the group consisting of SEQ ID NO: 2n, wherein n is an integer between 1 and 106, wherein any amino acid in the mature form is changed to a different amino acid, provided that no more than 15% of the amino acid residues in the sequence of the mature form are so changed; (c) an amino acid sequence selected from the group consisting of SEQ ID NO: 2n, wherein n is an integer between 1 and 106; (d) a variant of the amino acid sequence selected from the group consisting of SEQ ID NO:2n, wherein n is an integer between 1 and 106 wherein any amino acid specified in the chosen sequence is changed to a different amino acid, provided that no more than 15% of the amino acid residues in the sequence are so changed; and (e) a fragment of any of (a) through (d).

In another specific embodiment, the invention includes an isolated nucleic acid molecule comprising a nucleic acid sequence encoding a polypeptide comprising an amino acid sequence selected from the group consisting of: (a) a mature form of the amino acid sequence given SEQ ID NO: 2n, wherein n is an integer between 1 and 106; (b) a variant of a mature form of the amino acid sequence selected from the group consisting of SEQ ID NO: 2n, wherein n is an integer between 1 and 106 wherein any amino acid in the mature form of the chosen sequence is changed to a different amino acid, provided that no more than 15% of the amino acid residues in the sequence of the mature form are so changed; (c) the amino acid sequence selected from the group consisting of SEQ ID NO: 2n, wherein n is an integer between 1 and 106; (d) a variant of the amino acid sequence selected from the group consisting of SEQ ID NO: 2n, wherein n is an integer between 1 and 106, in which any amino acid specified in the chosen sequence is changed to a different amino acid, provided that no more than 15% of the amino acid residues in the sequence are so changed; (e) a nucleic acid fragment encoding at least a portion of a polypeptide comprising the amino acid sequence selected from the group consisting of SEQ ID NO: 2n, wherein n is an integer between 1 and 106 or any variant of said polypeptide wherein any amino acid of the chosen sequence is changed to a different amino acid, provided that no more than 10% of the amino acid residues in the sequence are so changed; and (f) the complement of any of said nucleic acid molecules.

In yet another specific embodiment, the invention includes an isolated nucleic acid molecule, wherein said nucleic acid molecule comprises a nucleotide sequence selected from the group consisting of: (a) the nucleotide sequence selected from the group consisting of SEQ ID NO: 2n−1, wherein n is an integer between 1 and 106; (b) a nucleotide sequence wherein one or more nucleotides in the nucleotide sequence selected from the group consisting of SEQ ID NO: 2n−1, wherein n is an integer between 1 and 106 is changed from that selected from the group consisting of the chosen sequence to a different nucleotide provided that no more than 15% of the nucleotides are so changed; (c) a nucleic acid fragment of the sequence selected from the group consisting of SEQ ID NO: 2n−1, wherein n is an integer between 1 and 106; and (d) a nucleic acid fragment wherein one or more nucleotides in the nucleotide sequence selected from the group consisting of SEQ ID NO: 2n−1, wherein n is an integer between 1 and 106 is changed from that selected from the group consisting of the chosen sequence to a different nucleotide provided that no more than 15% of the nucleotides are so changed.

One aspect of the invention pertains to isolated nucleic acid molecules that encode NOVX polypeptides or biologically active portions thereof. Also included in the invention are nucleic acid fragments sufficient for use as hybridization probes to identify NOVX-encoding nucleic acids (e.g., NOVX mRNAs) and fragments for use as PCR primers for the amplification and/or mutation of NOVX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded, but preferably is comprised double-stranded DNA.

An NOVX nucleic acid can encode a mature NOVX polypeptide. As used herein, a "mature" form of a polypeptide or protein disclosed in the present invention is the product of a naturally occurring polypeptide or precursor form or proprotein. The naturally occurring polypeptide, precursor or proprotein includes, by way of nonlimiting example, the full-length gene product, encoded by the corresponding gene. Alternatively, it may be defined as the polypeptide, precursor or proprotein encoded by an ORF described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide or protein include the cleavage of the N-terminal methionine residue encoded by the initiation codon of an ORF, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

The term "probes", as utilized herein, refers to nucleic acid sequences of variable length, preferably between at least about 10 nucleotides (nt), 100 nt, or as many as approximately, e.g., 6,000 nt, depending upon the specific use. Probes are used in the detection of identical, similar, or complementary nucleic acid sequences. Longer length probes are generally obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies.

The term "isolated" nucleic acid molecule, as utilized herein, is one, which is separated from other nucleic acid molecules which are present in the natural source of the nucleic acid. Preferably, an "isolated" nucleic acid is free of sequences which naturally flank the nucleic acid (i.e., sequences located at the 5'- and 3'-termini of the nucleic acid) in the genomic DNA of the organism from which the nucleic acid is derived. For example, in various embodiments, the isolated NOVX nucleic acid molecules can contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue from which the nucleic acid is derived (e.g., brain, heart, liver, spleen, etc.). Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the invention, e.g., a nucleic acid molecule having the nucleotide sequence SEQ ID NO: 2n−1, wherein n is an integer between 1 and 106, or a complement of this aforementioned nucleotide sequence, can be isolated using standard molecular biology techniques and the sequence information provided herein. Using all or a portion of the nucleic acid sequence of SEQ ID NO: 2n−1, wherein n is an integer between 1 and 106 as a hybridization probe, NOVX molecules can be isolated using standard hybridization and cloning techniques (e.g., as described in Sambrook, et al., (eds.), MOLECULAR CLONING: A LABORATORY MANUAL $2^{nd}$ Ed., Cold Spring Harbor Laboratory Press, Cold Spring Harbor, N.Y., 1989; and Ausubel, et al., (eds.), CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to NOVX nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment of the invention, an oligonucleotide comprising a nucleic acid molecule less than 100 nt in length would further comprise at least 6 contiguous nucleotides SEQ ID NO: 2n−1, wherein n is an integer between 1 and 106, or a complement thereof. Oligonucleotides may be chemically synthesized and may also be used as probes.

In another embodiment, an isolated nucleic acid molecule of the invention comprises a nucleic acid molecule that is a complement of the nucleotide from the group consisting of SEQ ID NO: 2n−1, wherein n is an integer between 1 and 106, or a portion of this nucleotide sequence (e.g., a fragment that can be used as a probe or primer or a fragment encoding a biologically-active portion of an NOVX polypeptide). A nucleic acid molecule that is complementary to the nucleotide sequence from the group consisting of SEQ ID NO: 2n−1, wherein n is an integer between 1 and 106 is one that is sufficiently complementary to the nucleotide sequence from the group consisting of SEQ ID NO: 2n−1, wherein n is an integer between 1 and 106 that it can hydrogen bond with little or no mismatches to the nucleotide sequence from the group consisting of SEQ ID NO: 2n−1, wherein n is an integer between 1 and 106, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

A full-length NOVX clone is identified as containing an ATG translation start codon and an in-frame stop codon. Any disclosed NOVX nucleotide sequence lacking an ATG start codon therefore encodes a truncated C-terminal fragment of the respective NOVX polypeptide, and requires that the corresponding full-length cDNA extend in the 5' direction of the disclosed sequence. Any disclosed NOVX nucleotide sequence lacking an in-frame stop codon similarly encodes a truncated N-terminal fragment of the respective NOVX polypeptide, and requires that the corresponding full-length cDNA extend in the 3' direction of the disclosed sequence.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of NOVX polypeptides. Isoforms can be expressed in different tissues of the same organism as a result of, for example, alternative splicing of RNA. Alternatively, isoforms can be encoded by different genes. In the invention, homologous nucleotide sequences include nucleotide sequences encoding for an NOVX polypeptide of species other than humans, including, but not limited to: vertebrates, and thus can include, e.g., frog, mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding human NOVX protein. Homologous nucleic acid sequences include those nucleic acid sequences that encode conservative amino acid substitutions (see below) in SEQ ID NO: 2n–1, wherein n is an integer between 1 and 106, as well as a polypeptide possessing NOVX biological activity. Various biological activities of the NOVX proteins are described below.

An NOVX polypeptide is encoded by the open reading frame ("ORF") of an NOVX nucleic acid. An ORF corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bona fide cellular protein, a minimum size requirement is often set, e.g., a stretch of DNA that would encode a protein of 50 amino acids or more.

The nucleotide sequences determined from the cloning of the human NOVX genes allows for the generation of probes and primers designed for use in identifying and/or cloning NOVX homologues in other cell types, e.g. from other tissues, as well as NOVX homologues from other vertebrates. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence SEQ ID NO: 2n–1, wherein n is an integer between 1 and 106; or an anti-sense strand nucleotide sequence of SEQ ID NO: 2n–1, wherein n is an integer between 1 and 106.

Probes based on the human NOVX nucleotide sequences can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissues which mis-express an NOVX protein, such as by measuring a level of an NOVX-encoding nucleic acid in a sample of cells from a subject e.g., detecting NOVX mRNA levels or determining whether a genomic NOVX gene has been mutated or deleted.

"A polypeptide having a biologically-active portion of an NOVX polypeptide" refers to polypeptides exhibiting activity similar, but not necessarily identical to, an activity of a polypeptide of the invention, including mature forms, as measured in a particular biological assay, with or without dose dependency. A nucleic acid fragment encoding a "biologically-active portion of NOVX" can be prepared by isolating a portion SEQ ID NO: 2n–1, wherein n is an integer between 1 and 106, that encodes a polypeptide having an NOVX biological activity (the biological activities of the NOVX proteins are described below), expressing the encoded portion of NOVX protein (e.g., by recombinant expression in vitro) and assessing the activity of the encoded portion of NOVX.

NOVX Nucleic Acid and Polypeptide Variants

The invention further encompasses nucleic acid molecules that differ from the nucleotide sequences shown in SEQ ID NO: 2n−1, wherein n is an integer between 1 and 106 due to degeneracy of the genetic code and thus encode the same NOVX proteins as that encoded by the nucleotide sequences shown in SEQ ID NO: 2n−1, wherein n is an integer between 1 and 106. In another embodiment, an isolated nucleic acid molecule of the invention has a nucleotide sequence encoding a protein having an amino acid sequence shown in SEQ ID NO: 2n, wherein n is an integer between 1 and 106.

In addition to the human NOVX nucleotide sequences shown in SEQ ID NO: 2n−1, wherein n is an integer between 1 and 106, it will be appreciated by those skilled in the art that DNA sequence polymorphisms that lead to changes in the amino acid sequences of the NOVX polypeptides may exist within a population (e.g., the human population). Such genetic polymorphism in the NOVX genes may exist among individuals within a population due to natural allelic variation. As used herein, the terms "gene" and "recombinant gene" refer to nucleic acid molecules comprising an open reading frame (ORF) encoding an NOVX protein, preferably a vertebrate NOVX protein. Such natural allelic variations can typically result in 1–5% variance in the nucleotide sequence of the NOVX genes. Any and all such nucleotide variations and resulting amino acid polymorphisms in the NOVX polypeptides, which are the result of natural allelic variation and that do not alter the functional activity of the NOVX polypeptides, are intended to be within the scope of the invention.

Moreover, nucleic acid molecules encoding NOVX proteins from other species, and thus that have a nucleotide sequence that differs from the human SEQ ID NO: 2n−1, wherein n is an integer between 1 and 106 are intended to be within the scope of the invention. Nucleic acid molecules corresponding to natural allelic variants and homologues of the NOVX cDNAs of the invention can be isolated based on their homology to the human NOVX nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO: 2n−1, wherein n is an integer between 1 and 106. In another embodiment, the nucleic acid is at least 10, 25, 50, 100, 250, 500, 750, 1000, 1500, or 2000 or more nucleotides in length. In yet another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding NOVX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel, et al., (eds.), CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequences SEQ ID NO: 2n−1, wherein n is an integer between 1 and 106, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO: 2n−1, wherein n is an integer between 1 and 106, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art. See, e.g., Ausubel, et al. (eds.), 1993, CURRENT PROTOCOLS IN MOLECULAR BIOLOGY, John Wiley & Sons, NY, and Kriegler, 1990; GENE TRANSFER AND EXPRESSION, A LABORATORY MANUAL, Stockton Press, NY.

In a third embodiment, a nucleic acid that is hybridizable to the nucleic acid molecule comprising the nucleotide sequences SEQ ID NO: 2n−1, wherein n is an integer between 1 and 106, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50C. Other conditions of low stringency that may be used are well known in the art (e.g., as employed for cross-species hybridizations). See, e.g., Ausubel, et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981. Proc Natl Acad Sci USA 78: 6789–6792.

Conservative Mutations

In addition to naturally-occurring allelic variants of NOVX sequences that may exist in the population, the skilled artisan will further appreciate that changes can be introduced by mutation into the nucleotide sequences SEQ ID NO: 2n–1, wherein n is an integer between 1 and 106, thereby leading to changes in the amino acid sequences of the encoded NOVX proteins, without altering the functional ability of said NOVX proteins. For example, nucleotide substitutions leading to amino acid substitutions at "nonessential" amino acid residues can be made in the sequence SEQ ID NO: 2n, wherein n is an integer between 1 and 106. A "non-essential" amino acid residue is a residue that can be altered from the wild-type sequences of the NOVX proteins without altering their biological activity, whereas an "essential" amino acid residue is required for such biological activity. For example, amino acid residues that are conserved among the NOVX proteins of the invention are predicted to be particularly non-amenable to alteration. Amino acids for which conservative substitutions can be made are well-known within the art.

Another aspect of the invention pertains to nucleic acid molecules encoding NOVX proteins that contain changes in amino acid residues that are not essential for activity. Such NOVX proteins differ in amino acid sequence from SEQ ID NO: 2n–1, wherein n is an integer between 1 and 106 yet retain biological activity. In one embodiment, the isolated nucleic acid molecule comprises a nucleotide sequence encoding a protein, wherein the protein comprises an amino acid sequence at least about 45% homologous to the amino acid sequences SEQ ID NO: 2n, wherein n is an integer between 1 and 106. Preferably, the protein encoded by the nucleic acid molecule is at least about 60% homologous to SEQ ID NO: 2n, wherein n is an integer between 1 and 106; more preferably at least about 70% homologous SEQ ID NO: 2n, wherein n is an integer between 1 and 106; still more preferably at least about 80% homologous to SEQ ID NO: 2n, wherein n is an integer between 1 and 106; even more preferably at least about 90% homologous to SEQ ID NO: 2n, wherein n is an integer between 1 and 106; and most preferably at least about 95% homologous to SEQ ID NO: 2n, wherein n is an integer between 1 and 106.

An isolated nucleic acid molecule encoding an NOVX protein homologous to the protein of SEQ ID NO: 2n, wherein n is an integer between 1 and 106 can be created by introducing one or more nucleotide substitutions, additions or deletions into the nucleotide sequence of SEQ ID NO: 2n–1, wherein n is an integer between 1 and 106, such that one or more amino acid substitutions, additions or deletions are introduced into the encoded protein.

Mutations can be introduced into SEQ ID NO: 2n–1, wherein n is an integer between 1 and 106 standard techniques, such as site-directed mutagenesis and PCR-mediated mutagenesis. Preferably, conservative amino acid substitutions are made at one or more predicted, nonessential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in the NOVX protein is replaced with another amino acid residue from the same side chain family. Alternatively, in another embodiment, mutations can be introduced randomly along all or part of an NOVX coding sequence, such as by saturation mutagenesis, and the resultant mutants can be screened for NOVX biological activity to identify mutants that retain activity. Following mutagenesis SEQ ID NO: 2n–1, wherein n is an integer between 1 and 106, the encoded protein can be expressed by any recombinant technology known in the art and the activity of the protein can be determined.

The relatedness of amino acid families may also be determined based on side chain interactions. Substituted amino acids may be fully conserved "strong" residues or fully conserved "weak" residues. The "strong" group of conserved amino acid residues may be any one of the following groups: STA, NEQK, NHQK, NDEQ, QHRK, MILV, MILF, HY, FYW, wherein the single letter amino acid codes are grouped by those amino acids that may be substituted for each other. Likewise, the "weak" group of conserved residues may be any one of the following: CSA, ATV, SAG, STNK, STPA, SGND, SNDEQK, NDEQHK, NEQHRK, HFY, wherein the letters within each group represent the single letter amino acid code.

In one embodiment, a mutant NOVX protein can be assayed for (i) the ability to form protein:protein interactions with other NOVX proteins, other cell-surface proteins, or biologically-active portions thereof, (ii) complex formation between a mutant NOVX protein and an NOVX ligand; or (iii) the ability of a mutant NOVX protein to bind to an intracellular target protein or biologically-active portion thereof; (e.g. avidin proteins).

In yet another embodiment, a mutant NOVX protein can be assayed for the ability to regulate a specific biological function (e.g., regulation of insulin release).

Antisense Nucleic Acids

Another aspect of the invention pertains to isolated antisense nucleic acid molecules that are hybridizable to or complementary to the nucleic acid molecule comprising the nucleotide sequence of SEQ ID NO: 2n–1, wherein n is an integer between 1 and 106, or fragments, analogs or derivatives thereof. An "antisense" nucleic acid comprises a nucleotide sequence that is complementary to a "sense" nucleic acid encoding a protein (e.g., complementary to the coding strand of a double-stranded cDNA molecule or complementary to an mRNA sequence). In specific aspects, antisense nucleic acid molecules are provided that comprise a sequence complementary to at least about 10, 25, 50, 100, 250 or 500 nucleotides or an entire NOVX coding strand, or to only a portion thereof. Nucleic acid molecules encoding fragments, homologs, derivatives and analogs of an NOVX protein of SEQ ID NO: 2n, wherein n is an integer between 1 and 106, or antisense nucleic acids complementary to an NOVX nucleic acid sequence of SEQ ID NO: 2n–1, wherein n is an integer between 1 and 106, are additionally provided.

In one embodiment, an antisense nucleic acid molecule is antisense to a "coding region" of the coding strand of a nucleotide sequence encoding an NOVX protein. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding the NOVX protein. The term "noncoding region" refers to 5' and 3' sequences which flank the coding region that are not translated into amino acids (i.e., also referred to as 5' and 3' untranslated regions).

Given the coding strand sequences encoding the NOVX protein disclosed herein, antisense nucleic acids of the invention can be designed according to the rules of Watson and Crick or Hoogsteen base pairing. The antisense nucleic acid molecule can be complementary to the entire coding region of NOVX mRNA, but more preferably is an oligonucleotide that is antisense to only a portion of the coding or noncoding region of NOVX mRNA. For example, the antisense oligonucleotide can be complementary to the region surrounding the translation start site of NOVX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described farther in the following subsection).

The antisense nucleic acid molecules of the invention are typically administered to a subject or generated in situ such that they hybridize with or bind to cellular mRNA and/or genomic DNA encoding an NOVX protein to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other. See, e.g., Gaultier, et al., 1987. *Nucl. Acids Res.* 15: 6625–6641. The antisense nucleic acid molecule can also comprise a 2'-o-methylribonucleotide (See, e.g., Inoue, et al. 1987. *Nucl. Acids Res.* 15: 6131–6148) or a chimeric RNA-DNA analogue (See, e.g., Inoue, et al., 1987. *FEBS Lett.* 215: 327–330.

Ribozymes and PNA Moieties

Nucleic acid modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haselhoff and Gerlach 1988. *Nature* 334: 585–591) can be used to catalytically cleave NOVX mRNA transcripts to thereby inhibit translation of NOVX mRNA. A ribozyme having specificity for an NOVX-encoding nucleic acid can be designed based upon the nucleotide sequence of an NOVX cDNA disclosed herein (i.e., SEQ ID NO: 2n–1, wherein n is an integer between 1 and 106). For example, a derivative of a Tetrahymena L-19 IVS RNA can be constructed in which the nucleotide sequence of the active site is complementary to the nucleotide sequence to be cleaved in an NOVX-encoding mRNA. See, e.g., U.S. Pat. No. 4,987,071 to Cech, et al. and U.S. Pat. No. 5,116,742 to Cech, et al. NOVX mRNA can also be used to select a catalytic RNA having a specific ribonuclease activity from a pool of RNA molecules. See, e.g., Bartel et al., (1993) *Science* 261:1411–1418.

Alternatively, NOVX gene expression can be inhibited by targeting nucleotide sequences complementary to the regulatory region of the NOVX nucleic acid (e.g., the NOVX promoter and/or enhancers) to form triple helical structures that prevent transcription of the NOVX gene in target cells. See, e.g., Helene, 1991. *Anticancer Drug Des.* 6: 569–84; Helene, et al. 1992. *Ann. N.Y. Acad. Sci.* 660:27–36; Maher, 1992. *Bioassays* 14: 807–15.

In various embodiments, the NOVX nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. See, e.g., Hyrup, et al., 1996. *Bioorg Med Chem* 4: 5–23. As used herein, the terms "peptide nucleic acids" or "PNAs" refer to nucleic acid mimics (e.g., DNA mimics) in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, et al., 1996. supra; Perry-O'Keefe, et al., 1996. *Proc. Natl. Acad. Sci. USA* 93: 14670–14675.

PNAs of NOVX can be used in therapeutic and diagnostic applications. For example, PNAs can be used as antisense or antigene agents for sequence-specific modulation of gene expression by, e.g., inducing transcription or translation arrest or inhibiting replication. PNAs of NOVX can also be used, for example, in the analysis of single base pair mutations in a gene (e.g., PNA directed PCR clamping; as artificial restriction enzymes when used in combination with other enzymes, e.g., $S_1$ nucleases (See, Hyrup, et al., 1996.supra); or as probes or primers for DNA sequence and hybridization (See, Hyrup, et al., 1996, supra; Perry-O'Keefe, et al., 1996. supra).

In another embodiment, PNAs of NOVX can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NOVX can be generated that may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (see, Hyrup, et al., 1996. supra). The synthesis of PNA-DNA chimeras can be performed as described in Hyrup, et al., 1996. supra and Finn, et al., 1996. *Nucl Acids Res* 24: 3357–3363. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA. See, e.g., Mag, et al., 1989. *Nucl Acid Res* 17: 5973–5988. PNA monomers are then coupled in a stepwise manner to produce a chimeric molecule with a 5' PNA segment and a 3' DNA segment. See, e.g., Finn, et al., 1996. supra. Alternatively, chimeric molecules can be synthesized with a 5' DNA segment and a 3' PNA segment. See, e.g., Petersen, et al., 1975. *Bioorg. Med. Chem. Lett.* 5: 1119–11124.

In other embodiments, the oligonucleotide may include other appended groups such as peptides (e.g., for targeting host cell receptors in vivo), or agents facilitating transport across the cell membrane (see, e.g., Letsinger, et al., 1989. *Proc. Natl. Acad. Sci. U.S.A.* 86: 6553–6556; Lemaitre, et al., 1987. *Proc. Natl. Acad. Sci.* 84: 648–652; PCT Publication No. WO88/09810) or the blood-brain barrier (see, e.g., PCT Publication No. WO 89/10134). In addition, oligonucleotides can be modified with hybridization triggered cleavage agents (see, e.g., Krol, et al., 1988. *BioTechniques* 6:958–976) or intercalating agents (see, e.g., Zon, 1988. *Pharm. Res.* 5: 539–549). To this end, the oligonucleotide may be conjugated to another molecule, e.g., a peptide, a hybridization triggered cross-linking agent, a transport agent, a hybridization-triggered cleavage agent, and the like.

NOVX Polypeptides

A polypeptide according to the invention includes a polypeptide including the amino acid sequence of NOVX polypeptides whose sequences are provided in SEQ ID NO: 2n, wherein n is an integer between 1 and 106. The invention also includes a mutant or variant protein any of whose residues may be changed from the corresponding residues shown in SEQ ID NO: 2n, wherein n is an integer between 1 and 106 while still encoding a protein that maintains its NOVX activities and physiological functions, or a functional fragment thereof.

In general, an NOVX variant that preserves NOVX-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated NOVX proteins, and biologically-active portions thereof, or derivatives, fragments, analogs or homologs thereof. Also provided are polypeptide fragments suitable for use as immunogens to raise anti-NOVX antibodies. In one embodiment, native NOVX proteins can be isolated from cells or tissue sources by an appropriate purification scheme using standard protein purification techniques. In another embodiment, NOVX proteins are produced by recombinant DNA techniques. Alternative to recombinant expression, an NOVX protein or polypeptide can be synthesized chemically using standard peptide synthesis techniques.

An "isolated" or "purified" polypeptide or protein or biologically-active portion thereof is substantially free of cellular material or other contaminating proteins from the cell or tissue source from which the NOVX protein is derived, or substantially free from chemical precursors or other chemicals when chemically synthesized. The language "substantially free of cellular material" includes preparations of NOVX proteins in which the protein is separated from cellular components of the cells from which it is isolated or recombinantly-produced. In one embodiment, the language "substantially free of cellular material" includes preparations of NOVX proteins having less than about 30% (by dry weight) of non-NOVX proteins (also referred to herein as a "contaminating protein"), more preferably less than about 20% of non-NOVX proteins, still more preferably less than about 10% of non-NOVX proteins, and most preferably less than about 5% of non-NOVX proteins. When the NOVX protein or biologically-active portion thereof is recombinantly-produced, it is also preferably substantially free of culture medium, i.e., culture medium represents less than about 20%, more preferably less than about 10%, and most preferably less than about 5% of the volume of the NOVX protein preparation.

The language "substantially free of chemical precursors or other chemicals" includes preparations of NOVX proteins in which the protein is separated from chemical precursors or other chemicals that are involved in the synthesis of the protein. In one embodiment, the language "substantially free of chemical precursors or other chemicals" includes preparations of NOVX proteins having less than about 30% (by dry weight) of chemical precursors or non-NOVX chemicals, more preferably less than about 20% chemical precursors or non-NOVX chemicals, still more preferably less than about 10% chemical precursors or non-NOVX chemicals, and most preferably less than about 5% chemical precursors or non-NOVX chemicals.

Biologically-active portions of NOVX proteins include peptides comprising amino acid sequences sufficiently homologous to or derived from the amino acid sequences of the NOVX proteins (e.g., the amino acid sequence shown in SEQ ID NO: 2n, wherein n is an integer between 1 and 106) that include fewer amino acids than the full-length NOVX proteins, and exhibit at least one activity of an NOVX protein. Typically, biologically-active portions comprise a domain or motif with at least one activity of the NOVX protein. A biologically-active portion of an NOVX protein can be a polypeptide which is, for example, 10, 25, 50, 100 or more amino acid residues in length. Moreover, other biologically-active portions, in which other regions of the protein are deleted, can be prepared by recombinant techniques and evaluated for one or more of the functional activities of a native NOVX protein.

In an embodiment, the NOVX protein has an amino acid sequence shown SEQ ID NO: 2n, wherein n is an integer between 1 and 106. In other embodiments, the NOVX protein is substantially homologous to SEQ ID NO: 2n, wherein n is an integer between 1 and 106, and retains the functional activity of the protein of SEQ ID NO: 2n, wherein n is an integer between 1 and 106, yet differs in amino acid sequence due to natural allelic variation or mutagenesis, as described in detail, below. Accordingly, in another embodiment, the NOVX protein is a protein that comprises an amino acid sequence at least about 45% homologous to the amino acid sequence SEQ ID NO: 2n, wherein n is an integer between 1 and 106, and retains the functional activity of the NOVX proteins of SEQ ID NO: 2n, wherein n is an integer between 1 and 106.

Determining Homology Between Two or More Sequences

To determine the percent homology of two amino acid sequences or of two nucleic acids, the sequences are aligned for optimal comparison purposes (e.g. gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch, 1970. *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA from the group consisting of SEQ ID NO: 2n–1, wherein n is an integer between 1 and 106.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides NOVX chimeric or fusion proteins. As used herein, an NOVX "chimeric protein" or "fusion protein" comprises an NOVX polypeptide operatively-linked to a non-NOVX polypeptide. An "NOVX polypeptide" refers to a polypeptide having an amino acid sequence corresponding to an NOVX protein SEQ ID NO: 2n, wherein n is an integer between 1 and 106, whereas a "non-NOVX polypeptide" refers to a polypeptide having an amino acid sequence corresponding to a protein that is not substantially homologous to the NOVX protein, e.g., a protein that is different from the NOVX protein and that is derived from the same or a different organism. Within an NOVX fusion protein the NOVX polypeptide can correspond to all or a portion of an NOVX protein. In one embodiment, an NOVX fusion protein comprises at least one biologically-active portion of an NOVX protein. In another embodiment, an NOVX fusion protein comprises at least two biologically-active portions of an NOVX protein. In yet another embodiment, an NOVX fusion protein comprises at least three biologically-active portions of an NOVX protein. Within the fusion protein, the term "operatively-linked" is intended to indicate that the NOVX polypeptide and the non-NOVX polypeptide are fused in-frame with one another. The non-NOVX polypeptide can be fused to the N-terminus or C-terminus of the NOVX polypeptide.

In one embodiment, the fusion protein is a GST-NOVX fusion protein in which the NOVX sequences are fused to the C-terminus of the GST (glutathione S-transferase) sequences. Such fusion proteins can facilitate the purification of recombinant NOVX polypeptides.

In another embodiment, the fusion protein is an NOVX protein containing a heterologous signal sequence at its N-terminus. In certain host cells (e.g. mammalian host cells), expression and/or secretion of NOVX can be increased through use of a heterologous signal sequence.

In yet another embodiment, the fusion protein is an NOVX-immunoglobulin fusion protein in which the NOVX sequences are fused to sequences derived from a member of the immunoglobulin protein family. The NOVX-immunoglobulin fusion proteins of the invention can be incorporated into pharmaceutical compositions and administered to a subject to inhibit an interaction between an NOVX ligand and an NOVX protein on the surface of a cell, to thereby suppress NOVX-mediated signal transduction in vivo. The NOVX-immunoglobulin fusion proteins can be used to affect the bioavailability of an NOVX cognate ligand. Inhibition of the NOVX ligand/NOVX interaction may be useful therapeutically for both the treatment of proliferative and differentiative disorders, as well as modulating (e.g. promoting or inhibiting) cell survival. Moreover, the NOVX-immunoglobulin fusion proteins of the invention can be used as immunogens to produce anti-NOVX antibodies in a subject, to purify NOVX ligands, and in screening assays to identify molecules that inhibit the interaction of NOVX with an NOVX ligand.

An NOVX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). An NOVX-encoding nucleic acid can be cloned into such an expression vector such that the fusion moiety is linked in-frame to the NOVX protein.

NOVX Agonists and Antagonists

The invention also pertains to variants of the NOVX proteins that function as either NOVX agonists (i.e., mimetics) or as NOVX antagonists. Variants of the NOVX protein can be generated by mutagenesis (e.g., discrete point mutation or truncation of the NOVX protein). An agonist of the NOVX protein can retain substantially the same, or a subset of, the biological activities of the naturally occurring form of the NOVX protein. An antagonist of the NOVX protein can inhibit one or more of the activities of the naturally occurring form of the NOVX protein by, for example, competitively binding to a downstream or upstream member of a cellular signaling cascade which includes the NOVX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the NOVX proteins.

Variants of the NOVX proteins that function as either NOVX agonists (i.e., mimetics) or as NOVX antagonists can be identified by screening combinatorial libraries of mutants (e.g., truncation mutants) of the NOVX proteins for NOVX protein agonist or antagonist activity. In one embodiment, a variegated library of NOVX variants is generated by combinatorial mutagenesis at the nucleic acid level and is encoded by a variegated gene library. A variegated library of NOVX variants can be produced by, for example, enzymatically ligating a mixture of synthetic oligonucleotides into gene sequences such that a degenerate set of potential NOVX sequences is expressible as individual polypeptides, or alternatively, as a set of larger fusion proteins (e.g., for phage display) containing the set of NOVX sequences therein. There are a variety of methods which can be used to produce libraries of potential NOVX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NOVX sequences. Methods for synthesizing degenerate oligonucleotides are well-known within the art. See, e.g., Narang, 1983. *Tetrahedron* 39: 3; Itakura, et al., 1984. *Annu. Rev. Biochem.* 53: 323; Itakura, et al., 1984. *Science* 198: 1056; Ike, et al., 1983. *Nucl. Acids Res.* 11: 477.

Polypeptide Libraries

In addition, libraries of fragments of the NOVX protein coding sequences can be used to generate a variegated population of NOVX fragments for screening and subsequent selection of variants of an NOVX protein. In one embodiment, a library of coding sequence fragments can be generated by treating a double stranded PCR fragment of an NOVX coding sequence with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with $S_1$ nuclease, and ligating the resulting fragment library into an expression vector. By this method, expression libraries can be derived which encodes N-terminal and internal fragments of various sizes of the NOVX proteins.

Various techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NOVX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify NOVX variants. See, e.g., Arkin and Yourvan, 1992. *Proc. Natl. Acad. Sci. USA* 89: 7811–7815; Delgrave, et al., 1993. *Protein Engineering* 6:327–331.

NOVX Antibodies

The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated protein of the invention intended to serve as an antigen, or a portion or fragment thereof, can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO: 2n, wherein n is an integer between 1 and 106, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of NOVX that is located on the surface of the protein, e.g., a hydrophilic region. A hydrophobicity analysis of the human NOVX protein sequence will indicate which regions of a NOVX polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each incorporated herein by reference in their entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). It is an objective, especially important in therapeutic applications of monoclonal antibodies, to identify antibodies having a high degree of specificity and a high binding affinity for the target antigen.

After the desired hybridoma cells are identified, the clones can be subcloned by limiting dilution procedures and grown by standard methods (Goding,1986). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann et al., *Nature*, 332:323–327 (1988); Verhoeyen et al., *Science*. 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.* 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368 812–13 (1994)); Fishwild et al,(*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit. Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature*, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5): 1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994). Antibodies with more than two valencies are contemplated. For example, trispecific antibodies can be prepared. Tutt et al., *J. Immunol.* 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., *J. Exp Med.*, 176: 1191–1195 (1992) and Shopes, *J. Immunol.*, 148: 2918–2922 (1992). Homodimeric antibodies with enhanced anti-tumor activity can also be prepared using heterobifunctional cross-linkers as described in Wolff et al. *Cancer Research*, 53: 2560–2565 (1993). Alternatively, an antibody can be engineered that has dual Fc regions and can thereby have enhanced complement lysis and ADCC capabilities. See Stevenson et al., *Anti-Cancer Drug Design*, 3: 219–230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon–14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

Immunoliposomes

The antibodies disclosed herein can also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286–288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

Diagnostic Applications of Antibodies Directed Against the Proteins of the Invention Antibodies directed against a protein of the invention may be used in methods known within the art relating to the localization and/or quantitation of the protein (e.g., for use in measuring levels of the protein within appropriate physiological samples, for use in diagnostic methods, for use in imaging the protein, and the like). In a given embodiment, antibodies against the proteins, or derivatives, fragments, analogs or homologs thereof, that contain the antigen binding domain, are utilized as pharmacologically-active compounds (see below).

An antibody specific for a protein of the invention can be used to isolate the protein by standard techniques, such as immunoaffinity chromatography or immunoprecipitation. Such an antibody can facilitate the purification of the natural protein antigen from cells and of recombinantly produced antigen expressed in host cells. Moreover, such an antibody can be used to detect the antigenic protein (e.g., in a cellular lysate or cell supernatant) in order to evaluate the abundance and pattern of expression of the antigenic protein. Antibodies directed against the protein can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Therapeutics

Antibodies of the invention, including polyclonal, monoclonal, humanized and fully human antibodies, may used as therapeutic agents. Such agents will generally be employed to treat or prevent a disease or pathology in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous ligand to which it naturally binds. In this case, the antibody binds to the target and masks a binding site of the naturally occurring ligand, wherein the ligand serves as an effector molecule. Thus the receptor mediates a signal transduction pathway for which ligand is responsible.

Alternatively, the effect may be one in which the antibody elicits a physiological result by virtue of binding to an effector binding site on the target molecule. In this case the target, a receptor having an endogenous ligand which may be absent or defective in the disease or pathology, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Pharmaceutical Compositions of Antibodies

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

If the anti genic protein is intracellular and whole antibodies are used as inhibitors, internalizing antibodies are preferred. However, liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889–7893 (1993). The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

ELISA Assay

An agent for detecting an analyte protein is an antibody capable of binding to an analyte protein, preferably an antibody with a detectable label. Antibodies can be polyclonal, or more preferably, monoclonal. An intact antibody, or a fragment thereof (e.g., $F_{ab}$ or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Thory of Enzyme Immunoassays", P. Tijssen, Elsevier Science Publishers, Amsterdam, 1985. Furthermore, in vivo techniques for detection of an analyte protein include introducing into a subject a labeled anti-an analyte protein antibody. For example, the antibody can be labeled with a radioactive marker whose presence and location in a subject can be detected by standard imaging techniques.

NOVX Recombinant Expression Vectors and Host Cells

Another aspect of the invention pertains to vectors, preferably expression vectors, containing a nucleic acid encoding an NOVX protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NOVX proteins, mutant forms of NOVX proteins, fusion proteins, etc.).

The recombinant expression vectors of the invention can be designed for expression of NOVX proteins in prokaryotic or eukaryotic cells. For example, NOVX proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the NOVX expression vector is a yeast expression vector. Examples of vectors for expression in yeast *Saccharomyces cerivisae* include pYepSec1 (Baldari, et al., 1987. *EMBO J.* 6: 229–234), pMFa (Kuijan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, NOVX can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Baneri, et al., 1983. *Cell* 33: 729–740; Queen and Baltimore, 1983. *Cell* 33: 741–748), neuron-specific promoters (e.g., the neurofilament promoter; Byrne and Ruddle, 1989. *Proc. Nat. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873, 316 and European Application Publication No. 264,166). Developmentally-regulated promoters are also encompassed, e.g., the murine hox promoters (Kessel and Gruss, 1990. *Science* 249: 374–379) and the c-fetoprotein promoter (Campes and Tilghman, 1989. *Genes Dev.* 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to NOVX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews-Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, NOVX protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding NOVX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) NOVX protein. Accordingly, the invention further provides methods for producing NOVX protein using the host cells of the invention. In one embodiment, the method comprises culturing the host cell of invention (into which a recombinant expression vector encoding NOVX protein has been introduced) in a suitable medium such that NOVX protein is produced. In another embodiment, the method further comprises isolating NOVX protein from the medium or the host cell.

Transgenic NOVX Animals

The host cells of the invention can also be used to produce non-human transgenic animals. For example, in one embodiment, a host cell of the invention is a fertilized oocyte or an embryonic stem cell into which NOVX protein-coding sequences have been introduced. Such host cells can then be used to create non-human transgenic animals in which exogenous NOVX sequences have been introduced into their genome or homologous recombinant animals in which endogenous NOVX sequences have been altered. Such animals are useful for studying the function and/or activity of NOVX protein and for identifying and/or evaluating modulators of NOVX protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous NOVX gene has been altered by homologous recombination between the endogenous gene and an exogenous DNA molecule introduced into a cell of the animal, e.g., an embryonic cell of the animal, prior to development of the animal.

A transgenic animal of the invention can be created by introducing NOVX-encoding nucleic acid into the male pronuclei of a fertilized oocyte (e.g., by microinjection, retroviral infection) and allowing the oocyte to develop in a pseudopregnant female foster animal. The human NOVX cDNA sequences SEQ ID NO: 2n–1, wherein n is an integer between 1 and 106 can be introduced as a transgene into the genome of a non-human animal. Alternatively, a non-human homologue of the human NOVX gene, such as a mouse NOVX gene, can be isolated based on hybridization to the human NOVX cDNA (described further supra) and used as a transgene. Intronic sequences and polyadenylation signals can also be included in the transgene to increase the efficiency of expression of the transgene. A tissue-specific regulatory sequence(s) can be operably-linked to the NOVX transgene to direct expression of NOVX protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the NOVX transgene in its genome and/or expression of NOVX mRNA in tissues or cells of the animals. A transgenic founder animal can then be used to breed additional animals carrying the transgene. Moreover, transgenic animals carrying a transgene-encoding NOVX protein can further be bred to other transgenic animals carrying other transgenes.

To create a homologous recombinant animal, a vector is prepared which contains at least a portion of an NOVX gene into which a deletion, addition or substitution has been introduced to thereby alter, e.g., functionally disrupt, the NOVX gene. The NOVX gene can be a human gene (e.g., the cDNA of SEQ ID NO: 2n–1, wherein n is an integer between 1 and 106), but more preferably, is a non-human homologue of a human NOVX gene. For example, a mouse homologue of human NOVX gene of SEQ ID NO: 2n–1, wherein n is an integer between 1 and 106 can be used to construct a homologous recombination vector suitable for altering an endogenous NOVX gene in the mouse genome. In one embodiment, the vector is designed such that, upon homologous recombination, the endogenous NOVX gene is functionally disrupted (i.e., no longer encodes a functional protein; also referred to as a "knock out" vector).

Alternatively, the vector can be designed such that, upon homologous recombination, the endogenous NOVX gene is mutated or otherwise altered but still encodes functional protein (e.g., the upstream regulatory region can be altered to thereby alter the expression of the endogenous NOVX protein). In the homologous recombination vector, the altered portion of the NOVX gene is flanked at its 5'- and 3'-termini by additional nucleic acid of the NOVX gene to allow for homologous recombination to occur between the exogenous NOVX gene carried by the vector and an endogenous NOVX gene in an embryonic stem cell. The additional flanking NOVX nucleic acid is of sufficient length for successful homologous recombination with the endogenous gene. Typically, several kilobases of flanking DNA (both at the 5'- and 3'-termini) are included in the vector. See, e.g., Thomas, et al., 1987. *Cell* 51: 503 for a description of homologous recombination vectors. The vector is ten introduced into an embryonic stem cell line (e.g., by electroporation) and cells in which the introduced NOVX gene has homologously-recombined with the endogenous NOVX gene are selected. See, e.g., Li, et al., 1992. *Cell* 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. *Curr. Opin. Biotechnol.* 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. *Proc. Natl. Acad. Sci. USA* 89: 6232–6236. Another example of a recombinase system is the FLP recombinase system of *Saccharomyces cerevisiae*. See, O'Gorman, et al., 1991. *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The NOVX nucleic acid molecules, NOVX proteins, and anti-NOVX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EC™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an NOVX protein or anti-NOVX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Screening and Detection Methods

The isolated nucleic acid molecules of the invention can be used to express NOVX protein (e.g., via a recombinant expression vector in a host cell in gene therapy applications), to detect NOVX mRNA (e.g., in a biological sample) or a genetic lesion in an NOVX gene, and to modulate NOVX activity, as described further, below. In addition, the NOVX proteins can be used to screen drugs or compounds that modulate the NOVX protein activity or expression as well as to treat disorders characterized by insufficient or excessive production of NOVX protein or production of NOVX protein forms that have decreased or aberrant activity compared to NOVX wild-type protein (e.g.; diabetes (regulates insulin release); obesity (binds and transport lipids); metabolic disturbances associated with obesity, the metabolic syndrome X as well as anorexia and wasting disorders associated with chronic diseases and various cancers, and infectious disease (possesses anti-microbial activity) and the various dyslipidemias. In addition, the anti-NOVX antibodies of the invention can be used to detect and isolate NOVX proteins and modulate NOVX activity. In yet a further aspect, the invention can be used in methods to influence appetite, absorption of nutrients and the disposition of metabolic substrates in both a positive and negative fashion.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to NOVX proteins or have a stimulatory or inhibitory effect on, e.g., NOVX protein expression or NOVX protein activity. The invention also includes compounds identified in the screening assays described herein. In one embodiment, the invention provides assays for screening candidate or test compounds which bind to or modulate the activity of the membrane-bound form of an NOVX protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37:1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865–1869) or on phage (Scott and Smith, 1990. *Science* 249: 386–390; Devlin, 1990. *Science* 249: 404–406; Cwirla, et al., 1990. *Proc. Natl. Acad. Sci. U.S.A.* 87: 6378–6382; Felici, 1991. *J. Mol. Biol.* 222: 301–310; Ladner, U.S. Pat. No. 5,233,409.).

In one embodiment, an assay is a cell-based assay in which a cell which expresses a membrane-bound form of NOVX protein, or a biologically-active portion thereof, on the cell surface is contacted with a test compound and the ability of the test compound to bind to an NOVX protein determined. The cell, for example, can of mammalian origin or a yeast cell. Determining the ability of the test compound to bind to the NOVX protein can be accomplished, for example, by coupling the test compound with a radioisotope or enzymatic label such that binding of the test compound to the NOVX protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of NOVX protein, or a biologically-active portion thereof, on the cell surface with a known compound which binds NOVX to form an assay mixture, contacting the assay mixture with a test compound, and determining the ability of the test compound to interact with an NOVX protein, wherein determining the ability of the test compound to interact with an NOVX protein comprises determining the ability of the test compound to preferentially bind to NOVX protein or a biologically-active portion thereof as compared to the known compound.

In another embodiment, an assay is a cell-based assay comprising contacting a cell expressing a membrane-bound form of NOVX protein, or a biologically-active portion thereof, on the cell surface with a test compound and determining the ability of the test compound to modulate (e.g., stimulate or inhibit) the activity of the NOVX protein or biologically-active portion thereof. Determining the ability of the test compound to modulate the activity of NOVX or a biologically-active portion thereof can be accomplished, for example, by determining the ability of the NOVX protein to bind to or interact with an NOVX target molecule. As used herein, a "target molecule" is a molecule with which an NOVX protein binds or interacts in nature, for example, a molecule on the surface of a cell which expresses an NOVX interacting protein, a molecule on the surface of a second cell, a molecule in the extracellular milieu, a molecule associated with the internal surface of a cell membrane or a cytoplasmic molecule. An NOVX target molecule can be a non-NOVX molecule or an NOVX protein or polypeptide of the invention. In one embodiment, an NOVX target molecule is a component of a signal transduction pathway that facilitates transduction of an extracellular signal (e.g. a signal generated by binding of a compound to a membrane-bound NOVX molecule) through the cell membrane and into the cell. The target, for example, can be a second intercellular protein that has catalytic activity or a protein that facilitates the association of downstream signaling molecules with NOVX.

Determining the ability of the NOVX protein to bind to or interact with an NOVX target molecule can be accomplished by one of the methods described above for determining direct binding. In one embodiment, determining the ability of the NOVX protein to bind to or interact with an NOVX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising an NOVX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting an NOVX protein or biologically-active portion thereof with a test compound and determining the ability of the test compound to bind to the NOVX protein or biologically-active portion thereof. Binding of the test compound to the NOVX protein can be determined either directly or indirectly as described above. In one such embodiment, the assay comprises contacting the NOVX protein or biologically-active portion thereof with a known compound which binds NOVX to form an assay mixture, contacting the assay mixture with a test compound, and determining the ability of the test compound to interact with an NOVX protein, wherein determining the ability of the test compound to interact with an NOVX protein comprises determining the ability of the test compound to preferentially bind to NOVX or biologically-active portion thereof as compared to the known compound.

In still another embodiment, an assay is a cell-free assay comprising contacting NOVX protein or biologically-active portion thereof with a test compound and determining the ability of the test compound to modulate (e.g. stimulate or inhibit) the activity of the NOVX protein or biologically-active portion thereof. Determining the ability of the test compound to modulate the activity of NOVX can be accomplished, for example, by determining the ability of the NOVX protein to bind to an NOVX target molecule by one of the methods described above for determining direct binding. In an alternative embodiment, determining the ability of the test compound to modulate the activity of NOVX protein can be accomplished by determining the ability of the NOVX protein further modulate an NOVX target molecule. For Example, the catalytic/enzymatic activity of the target molecule on an appropriate substrate can be determined as described, supra.

In yet another embodiment, the cell-free assay comprises contacting the NOVX protein or biologically-active portion thereof with a known compound which binds NOVX protein to form an assay mixture, contacting the assay mixture with a test compound, and determining the ability of the test compound to interact with an NOVX protein, wherein determining the ability of the test compound to interact with an NOVX protein comprises determining the ability of the NOVX protein to preferentially bind to or modulate the activity of an NOVX target molecule.

The cell-free assays of the invention are amenable to use of both the soluble form or the membrane-bound form of NOVX protein. In the case of cell-free assays comprising the membrane-bound form of NOVX protein, it may be desirable to utilize a solubilizing agent such that the membrane-bound form of NOVX protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl)dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the invention, it may be desirable to immobilize either NOVX protein or its target molecule to facilitate separation of complexed from uncomplexed forms of one or both of the proteins, as well as to accommodate automation of the assay. Binding of a test compound to NOVX protein, or interaction of NOVX protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-NOVX fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or NOVX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of NOVX protein binding or activity determined using standard techniques.

Other techniques for immobilizing proteins on matrices can also be used in the screening assays of the invention. For example, either the NOVX protein or its target molecule can be immobilized utilizing conjugation of biotin and streptavidin. Biotinylated NOVX protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with NOVX protein or target molecules, but which do not interfere with binding of the NOVX protein to its target molecule, can be derivatized to the wells of the plate, and unbound target or NOVX protein trapped in the wells by antibody conjugation. Methods for detecting such complexes, in addition to those described above for the GST-immobilized complexes, include immunodetection of complexes using antibodies reactive with the NOVX protein or target molecule, as well as enzyme-linked assays that rely on detecting an enzymatic activity associated with the NOVX protein or target molecule.

In another embodiment, modulators of NOVX protein expression are identified in a method wherein a cell is contacted with a candidate compound and the expression of NOVX mRNA or protein in the cell is determined. The level of expression of NOVX mRNA or protein in the presence of the candidate compound is compared to the level of expression of NOVX mRNA or protein in the absence of the candidate compound. The candidate compound can then be identified as a modulator of NOVX mRNA or protein expression based upon this comparison. For example, when expression of NOVX mRNA or protein is greater (i.e., statistically significantly greater) in the presence of the candidate compound than in its absence, the candidate compound is identified as a stimulator of NOVX mRNA or protein expression. Alternatively, when expression of NOVX mRNA or protein is less (statistically significantly less) in the presence of the candidate compound than in its absence, the candidate compound is identified as an inhibitor of NOVX mRNA or protein expression. The level of NOVX mRNA or protein expression in the cells can be determined by methods described herein for detecting NOVX mRNA or protein.

In yet another aspect of the invention, the NOVX proteins can be used as "bait proteins" in a two-hybrid assay or three hybrid assay (see, e.g., U.S. Pat. No. 5,283,317; Zervos, et al., 1993. *Cell* 72: 223–232; Madura, et al., 1993. *J. Biol. Chem.* 268: 12046–12054; Bartel, et al., 1993. *Biotech-* niques 14: 920–924; Iwabuchi, et al., 1993. *Oncogene* 8: 1693–1696; and Brent WO 94/10300), to identify other proteins that bind to or interact with NOVX ("NOVX-binding proteins" or "NOVX-bp") and modulate NOVX activity. Such NOVX-binding proteins are also likely to be involved in the propagation of signals by the NOVX proteins as, for example, upstream or downstream elements of the NOVX pathway.

The two-hybrid system is based on the modular nature of most transcription factors, which consist of separable DNA-binding and activation domains. Briefly, the assay utilizes two different DNA constructs. In one construct, the gene that codes for NOVX is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an NOVX-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with NOVX.

The invention further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Some of these applications are described in the subsections, below.

Chromosome Mapping

Once the sequence (or a portion of the sequence) of a gene has been isolated, this sequence can be used to map the location of the gene on a chromosome. This process is called chromosome mapping. Accordingly, portions or fragments of the NOVX sequences, SEQ ID NO: 2n–1, wherein n is an integer between 1 and 106, or fragments or derivatives thereof, can be used to map the location of the NOVX genes, respectively, on a chromosome. The mapping of the NOVX sequences to chromosomes is an important first step in correlating these sequences with genes associated with disease.

Briefly, NOVX genes can be mapped to chromosomes by preparing PCR primers (preferably 15–25 bp in length) from the NOVX sequences. Computer analysis of the NOVX, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the NOVX sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. See, e.g., D'Eustachio, et al., 1983. *Science* 220: 919–924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the NOVX sequences to design oligonucleotide primers, sub-localization can be achieved with panels of fragments from specific chromosomes. Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see, Verma, et al., HUMAN CHROMOSOMES: A MANUAL OF BASIC TECHNIQUES (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, e.g., in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, e.g., Egeland, et al., 1987. *Nature,* 325: 783–787.

Moreover, differences in the DNA sequences between individuals affected and unaffected with a disease associated with the NOVX gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The NOVX sequences of the invention can also be used to identify individuals from minute biological samples. In this technique, an individual's genomic DNA is digested with one or more restriction enzymes, and probed on a Southern blot to yield unique bands for identification. The sequences of the invention are useful as additional DNA markers for RFLP ("restriction fragment length polymorphisms," described in U.S. Pat. No. 5,272,057).

Furthermore, the sequences of the invention can be used to provide an alternative technique that determines the actual base-by-base DNA sequence of selected portions of an individual's genome. Thus, the NOVX sequences described herein can be used to prepare two PCR primers from the 5'- and 3'-termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the invention can be used to obtain such identification sequences from individuals and from tissue. The NOVX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences can comfortably provide positive individual identification with a panel of perhaps 10 to 1,000 primers that each yield a noncoding amplified sequence of 100 bases. If predicted coding sequences, such as those in SEQ ID NO: 2n−1, wherein n is an integer between 1 and 106 are used, a more appropriate number of primers for positive individual identification would be 500–2,000.

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining NOVX protein and/or nucleic acid expression as well as NOVX activity, in the context of a biological sample (e.g., blood, serum, cells, tissue) to thereby determine whether an individual is afflicted with a disease or disorder, or is at risk of developing a disorder, associated with aberrant NOVX expression or activity. The disorders include metabolic disorders, diabetes, obesity, infectious disease, anorexia, cancer-associated cachexia, cancer, neurodegenerative disorders, Alzheimer's Disease, Parkinson's Disorder, immune disorders, and hematopoietic disorders, and the various dyslipidemias, metabolic disturbances associated with obesity, the metabolic syndrome X and wasting disorders associated with chronic diseases and various cancers. The invention also provides for prognostic (or predictive) assays for determining whether an individual is at risk of developing a disorder associated with NOVX protein, nucleic acid expression or activity. For example, mutations in an NOVX gene can be assayed in a biological sample. Such assays can be used for prognostic or predictive purpose to thereby prophylactically treat an individual prior to the onset of a disorder characterized by or associated with NOVX protein, nucleic acid expression, or biological activity.

Another aspect of the invention provides methods for determining NOVX protein, nucleic acid expression or activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of NOVX in clinical trials.

These and other agents are described in further detail in the following sections.

Diagnostic Assays

An exemplary method for detecting the presence or absence of NOVX in a biological sample involves obtaining a biological sample from a test subject and contacting the biological sample with a compound or an agent capable of detecting NOVX protein or nucleic acid (e.g., mRNA, genomic DNA) that encodes NOVX protein such that the presence of NOVX is detected in the biological sample. An agent for detecting NOVX mRNA or genomic DNA is a labeled nucleic acid probe capable of hybridizing to NOVX mRNA or genomic DNA. The nucleic acid probe can be, for example, a full-length NOVX nucleic acid, such as the nucleic acid of SEQ ID NO: 2n−1, wherein n is an integer between 1 and 106, or a portion thereof, such as an oligonucleotide of at least 15, 30, 50, 100, 250 or 500 nucleotides in length and sufficient to specifically hybridize under stringent conditions to NOVX mRNA or genomic DNA. Other suitable probes for use in the diagnostic assays of the invention are described herein.

An agent for detecting NOVX protein is an antibody capable of binding to NOVX protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect NOVX mRNA, protein, or genomic DNA in a biological sample in vitro as well as in vivo. For example, in vitro techniques for detection of NOVX mRNA include Northern hybridizations and in situ hybridizations. In vitro techniques for detection of NOVX protein include enzyme linked immunosorbent assays (ELISAs), Western blots, immunoprecipitations, and immunofluorescence. In vitro techniques for detection of NOVX genomic DNA include Southern hybridizations. Furthermore, in vivo techniques for detection of NOVX protein include introducing into a subject a labeled anti-NOVX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting NOVX protein, mRNA, or genomic DNA, such that the presence of NOVX protein, mRNA or genomic DNA is detected in the biological sample, and comparing the presence of NOVX protein, mRNA or genomic DNA in the control sample with the presence of NOVX protein, mRNA or genomic DNA in the test sample. The invention also encompasses kits for detecting the presence of NOVX in a biological sample. For example, the kit can comprise: a labeled compound or agent capable of detecting NOVX protein or mRNA in a biological sample; means for determining the amount of NOVX in the sample; and means for comparing the amount of NOVX in the sample with a standard. The compound or agent can be packaged in a suitable container. The kit can further comprise instructions for using the kit to detect NOVX protein or nucleic acid.

Prognostic Assays

The diagnostic methods described herein can furthermore be utilized to identify subjects having or at risk of developing a disease or disorder associated with aberrant NOVX expression or activity. For example, the assays described herein, such as the preceding diagnostic assays or the following assays, can be utilized to identify a subject having or at risk of developing a disorder associated with NOVX protein, nucleic acid expression or activity. Alternatively, the prognostic assays can be utilized to identify a subject having or at risk for developing a disease or disorder. Thus, the invention provides a method for identifying a disease or disorder associated with aberrant NOVX expression or activity in which a test sample is obtained from a subject and NOVX protein or nucleic acid (e.g., mRNA, genomic DNA) is detected, wherein the presence of NOVX protein or nucleic acid is diagnostic for a subject having or at risk of developing a disease or disorder associated with aberrant NOVX expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NOVX expression or activity. For example, such methods can be used to determine whether a subject can be effectively treated with an agent for a disorder. Thus, the invention provides methods for determining whether a subject can be effectively treated with an agent for a disorder associated with aberrant NOVX expression or activity in which a test sample is obtained and NOVX protein or nucleic acid is detected (e.g., wherein the presence of NOVX protein or nucleic acid is diagnostic for a subject that can be administered the agent to treat a disorder associated with aberrant NOVX expression or activity).

The methods of the invention can also be used to detect genetic lesions in an NOVX gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding an NOVX-protein, or the misexpression of the NOVX gene. For example, such genetic lesions can be detected by ascertaining the existence of at least one of: (i) a deletion of one or more nucleotides from an NOVX gene; (ii) an addition of one or more nucleotides to an NOVX gene; (iii) a substitution of one or more nucleotides of an NOVX gene, (iv) a chromosomal rearrangement of an NOVX gene; (v) an alteration in the level of a messenger RNA transcript of an NOVX gene, (vi) aberrant modification of an NOVX gene, such as of the methylation pattern of the genomic DNA, (vii) the presence of a non-wild-type splicing pattern of a messenger RNA transcript of an NOVX gene, (viii) a non-wild-type level of an NOVX protein, (ix) allelic loss of an NOVX gene, and (x) inappropriate post-translational modification of an NOVX protein. As described herein, there are a large number of assay techniques known in the art which can be used for detecting lesions in an NOVX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran, et al., 1988. *Science* 241: 1077–1080; and Nakazawa, et al., 1994. *Proc. Natl. Acad. Sci. USA* 91: 360–364), the latter of which can be particularly useful for detecting point mutations in the NOVX-gene (see, Abravaya, et al., 1995. *Nucl. Acids Res.* 23: 675–682). This method can include the steps of collecting a sample of cells from a patient, isolating nucleic acid (e.g., genomic, mRNA or both) from the cells of the sample, contacting the nucleic acid sample with one or more primers that specifically hybridize to an NOVX gene under conditions such that hybridization and amplification of the NOVX gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (see, Guatelli, et al., 1990. *Proc. Natl. Acad. Sci. USA* 87: 1874–1878), transcriptional amplification system (see, Kwoh, et al., 1989. *Proc. Natl. Acad. Sci. USA* 86: 1173–1177); QP Replicase (see, Lizardi, et al, 1988. *BioTechnology* 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an NOVX gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in NOVX can be identified by hybridizing a sample and control nucleic acids, e.g., DNA or RNA, to high-density arrays containing hundreds or thousands of oligonucleotides probes. See, e.g., Cronin, et al., 1996. *Human Mutation* 7: 244–255; Kozal, et al., 1996. *Nat. Med.* 2: 753–759. For example, genetic mutations in NOVX can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NOVX gene and detect mutations by comparing the sequence of the sample NOVX with the corresponding wild-type (control) sequence. Examples of sequencing reactions include those based on techniques developed by Maxim and Gilbert, 1977. *Proc. Natl. Acad. Sci. USA* 74: 560 or Sanger, 1977. *Proc. Natl. Acad. Sci. USA* 74: 5463. It is also contemplated that any of a variety of automated sequencing procedures can be utilized when performing the diagnostic assays (see, e.g., Naeve, et al., 1995. *Biotechniques* 19: 448), including sequencing by mass spectrometry (see, e.g., PCT International Publication No. WO 94/16101; Cohen, et al., 1996. *Adv. Chromatography* 36: 127–162; and Griffin, et al., 1993. *Appl. Biochem. Biotechnol.* 38: 147–159).

Other methods for detecting mutations in the NOVX gene include methods in which protection from cleavage agents is used to detect mismatched bases in RNA/RNA or RNA/DNA heteroduplexes. See, e.g., Myers, et al., 1985. *Science* 230: 1242. In general, the art technique of "mismatch cleavage" starts by providing heteroduplexes of formed by hybridizing (labeled) RNA or DNA containing the wild-type NOVX sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with $S_1$ nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. *Proc. Natl. Acad. Sci. USA* 85: 4397; Saleeba, et al., 1992. *Methods Enzymol.* 217: 286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NOVX cDNAs obtained from samples of cells. For example, the mutY enzyme of *E. coli* cleaves A at G/A mismatches and the thymidine DNA glycosylase from HeLa cells cleaves T at G/T mismatches. See, e.g., Hsu, et al., 1994. *Carcinogenesis* 15: 1657–1662. According to an exemplary embodiment, a probe based on an NOVX sequence, e.g. a wild-type NOVX sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in NOVX genes. For example, single strand conformation polymorphism (SSCP) may be used to detect differences in electrophoretic mobility between mutant and wild type nucleic acids. See, e.g., Orita, et al., 1989. *Proc. Natl. Acad. Sci. USA:* 86: 2766; Cotton, 1993. *Mutat. Res.* 285: 125–144; Hayashi, 1992. *Genet. Anal. Tech. Appl.* 9: 73–79. Single-stranded DNA fragments of sample and control NOVX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. *Trends Genet.* 7: 5.

In yet another embodiment, the movement of mutant or wild-type fragments in polyacrylamide gels containing a gradient of denaturant is assayed using denaturing gradient gel electrophoresis (DGGE). See, e.g., Myers, et al., 1985. *Nature* 313: 495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. *Biophys. Chem.* 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. *Nature* 324: 163; Saiki, et al., 1989. *Proc. Natl. Acad. Sci. USA* 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization; see, e.g., Gibbs, et al., 1989. *Nucl. Acids Res.* 17: 2437–2448) or at the extreme 3'-terminus of one primer where, under appropriate conditions, mismatch can prevent, or reduce polymerase extension (see, e.g., Prossner, 1993. *Tibtech.* 11: 238). In addition it may be desirable to introduce a novel restriction site in the region of the mutation to create cleavage-based detection. See, e.g., Gasparini, et al., 1992. *Mol. Cell Probes* 6: 1. It is anticipated that in certain embodiments amplification may also be performed using Taq ligase for amplification. See, e.g. Barany, 1991. *Proc. Natl. Acad. Sci. USA* 88: 189. In such cases, ligation will occur only if there is a perfect match at the 3'-terminus of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an NOVX gene.

Furthermore, any cell type or tissue, preferably peripheral blood leukocytes, in which NOVX is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on NOVX activity (e.g., NOVX gene expression), as identified by a screening assay described herein can be administered to individuals to treat (prophylactically or therapeutically) disorders (The disorders include metabolic disorders, diabetes, obesity, infectious disease, anorexia, cancer-associated cachexia, cancer, neurodegenerative disorders, Alzheimer's Disease, Parkinson's Disorder, immune disorders, and hematopoietic disorders, and the various dyslipidemias, metabolic disturbances associated with obesity, the metabolic syndrome X and wasting disorders associated with chronic diseases and various cancers.) In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NOVX protein, expression of NOVX nucleic acid, or mutation content of NOVX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. *Clin. Exp. Pharmacol. Physiol.,* 23: 983–985; Linder, 1997. *Clin. Chem.,* 43: 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome PREGNANCY ZONE PROTEIN PRECURSOR enzymes CYP2D6 and CYP2C 19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of NOVX protein, expression of NOVX nucleic acid, or mutation content of NOVX genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an NOVX modulator, such as a modulator identified by one of the exemplary screening assays described herein.

Monitoring of Effects During Clinical Trials

Monitoring the influence of agents (e.g., drugs, compounds) on the expression or activity of NOVX (e.g., the ability to modulate aberrant cell proliferation and/or differentiation) can be applied not only in basic drug screening, but also in clinical trials. For example, the effectiveness of an agent determined by a screening assay as described herein to increase NOVX gene expression, protein levels, or upregulate NOVX activity, can be monitored in clinical trails of subjects exhibiting decreased NOVX gene expression, protein levels, or downregulated NOVX activity.

Alternatively, the effectiveness of an agent determined by a screening assay to decrease NOVX gene expression, protein levels, or downregulate NOVX activity, can be monitored in clinical trails of subjects exhibiting increased NOVX gene expression, protein levels, or upregulated NOVX activity. In such clinical trials, the expression or activity of NOVX and, preferably, other genes that have been implicated in, for example, a cellular proliferation or immune disorder can be used as a "read out" or markers of the immune responsiveness of a particular cell.

By way of example, and not of limitation, genes, including NOVX, that are modulated in cells by treatment with an agent (e.g., compound, drug or small molecule) that modulates NOVX activity (e.g., identified in a screening assay as described herein) can be identified. Thus, to study the effect of agents on cellular proliferation disorders, for example, in a clinical trial, cells can be isolated and RNA prepared and analyzed for the levels of expression of NOVX and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of NOVX or other genes. In this manner, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of an NOVX protein, mRNA, or genomic DNA in the preadministration sample; (iii) obtaining one or more post-administration samples from the subject; (iv) detecting the level of expression or activity of the NOVX protein, mRNA, or genomic DNA in the post-administration samples; (v) comparing the level of expression or activity of the NOVX protein, mRNA, or genomic DNA in the pre-administration sample with the NOVX protein, mRNA, or genomic DNA in the post administration sample or samples; and (vi) altering the administration of the agent to the subject accordingly. For example, increased administration of the agent may be desirable to increase the expression or activity of NOVX to higher levels than detected, ie., to increase the effectiveness of the agent. Alternatively, decreased administration of the agent may be desirable to decrease expression or activity of NOVX to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant NOVX expression or activity. The disorders include cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, obesity, transplantation, adrenoleukodystrophy, congenital adrenal hyperplasia, prostate cancer, neoplasm; adenocarcinoma, lymphoma, uterus cancer, fertility, hemophilia, hypercoagulation, idiopathic thrombocytopenic purpura, immunodeficiencies, graft versus host disease, AIDS, bronchial asthma, Crohn's disease; multiple sclerosis, treatment of Albright Hereditary Ostoeodystrophy, and other diseases, disorders and conditions of the like.

These methods of treatment will be discussed more fully, below.

Disease and Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to: (i) an aforementioned peptide, or analogs, derivatives, fragments or homologs thereof, (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989. *Science* 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g. from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the invention provides a method for preventing, in a subject, a disease or condition associated with an aberrant NOVX expression or activity, by administering to the subject an agent that modulates NOVX expression or at least one NOVX activity. Subjects at risk for a disease that is caused or contributed to by aberrant NOVX expression or activity can be identified by, for example, any or a combination of diagnostic or prognostic assays as described herein. Administration of a prophylactic agent can occur prior to the manifestation of symptoms characteristic of the NOVX aberrancy, such that a disease or disorder is prevented or, alternatively, delayed in its progression. Depending upon the type of NOVX aberrancy, for example, an NOVX agonist or NOVX antagonist agent can be used for treating the subject. The appropriate agent can be determined based on screening assays described herein. The prophylactic methods of the invention are further discussed in the following subsections.

Therapeutic Methods

Another aspect of the invention pertains to methods of modulating NOVX expression or activity for therapeutic purposes. The modulatory method of the invention involves contacting a cell with an agent that modulates one or more of the activities of NOVX protein activity associated with the cell. An agent that modulates NOVX protein activity can be an agent as described herein, such as a nucleic acid or a protein, a naturally-occurring cognate ligand of an NOVX protein, a peptide, an NOVX peptidomimetic, or other small molecule. In one embodiment, the agent stimulates one or more NOVX protein activity. Examples of such stimulatory agents include active NOVX protein and a nucleic acid molecule encoding NOVX that has been introduced into the cell. In another embodiment, the agent inhibits one or more NOVX protein activity. Examples of such inhibitory agents include antisense NOVX nucleic acid molecules and anti-NOVX antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of an NOVX protein or nucleic acid molecule. In one embodiment, the method involves administering an agent (e.g., an agent identified by a screening assay described herein), or combination of agents that modulates (e.g., up-regulates or down-regulates) NOVX expression or activity. In another embodiment, the method involves administering an NOVX protein or nucleic acid molecule as therapy to compensate for reduced or aberrant NOVX expression or activity.

Stimulation of NOVX activity is desirable in situations in which NOVX is abnormally downregulated and/or in which increased NOVX activity is likely to have a beneficial effect. One example of such a situation is where a subject has a disorder characterized by aberrant cell proliferation and/or differentiation (e.g., cancer or immune associated disorders). Another Example of such a situation is where the subject has a gestational disease (e.g., preclampsia).

Determination of the Biological Effect of the Therapeutic

In various embodiments of the invention, suitable in vitro or in vivo assays are performed to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Prophylactic and Therapeutic Uses of the Compositions of the Invention

The NOVX nucleic acids and proteins of the invention are useful in potential prophylactic and therapeutic applications implicated in a variety of disorders including, but not limited to: metabolic disorders, diabetes, obesity, infectious disease, anorexia, cancer-associated cancer, neurodegenerative disorders, Alzheimer's Disease, Parkinson's Disorder, immune disorders, hematopoietic disorders, and the various dyslipidemias, metabolic disturbances associated with obesity, the metabolic syndrome X and wasting disorders associated with chronic diseases and various cancers.

As an example, a cDNA encoding the NOVX protein of the invention may be useful in gene therapy, and the protein may be useful when administered to a subject in need thereof. By way of non-limiting example, the compositions of the invention will have efficacy for treatment of patients suffering from: metabolic disorders, diabetes, obesity, infectious disease, anorexia, cancer-associated cachexia, cancer, neurodegenerative disorders, Alzheimer's Disease, Parkinson's Disorder, immune disorders, hematopoietic disorders, and the various dyslipidemias.

Both the novel nucleic acid encoding the NOVX protein, and the NOVX protein of the invention, or fragments thereof, may also be useful in diagnostic applications, wherein the presence or amount of the nucleic acid or the protein are to be assessed. A further use could be as an anti-bacterial molecule (i.e., some peptides have been found to possess anti-bacterial properties). These materials are further useful in the generation of antibodies, which immunospecifically-bind to the novel substances of the invention for use in therapeutic or diagnostic methods.

Sequence Analyses

The sequence of NOVX was derived by laboratory cloning of cDNA fragments, by in silico prediction of the sequence. cDNA fragments covering either the full length of the DNA sequence, or part of the sequence, or both, were cloned. In silico prediction was based on sequences available in CuraGen's proprietary sequence databases or in the public human sequence databases, and provided either the full length DNA sequence, or some portion thereof.

The laboratory cloning was performed using one or more of the methods summarized below:

SeqCalling™ Technology: cDNA was derived from various human samples representing multiple tissue types, normal and diseased states, physiological states, and developmental states from different donors. Samples were obtained as whole tissue, primary cells or tissue cultured primary cells or cell lines. Cells and cell lines may have been treated with biological or chemical agents that regulate gene expression, for example, growth factors, chemokines or steroids. The cDNA thus derived was then sequenced using CuraGen Corporation's SeqCalling technology which is disclosed in full in U.S. Ser. No. 09/417,386 filed Oct. 13, 1999, and Ser. No. 09/614,505 filed Jul. 11, 2000. Sequence traces were evaluated manually and edited for corrections if appropriate. cDNA sequences from all samples were assembled together, sometimes including public human sequences, using bioinformatics programs to produce a consensus sequence for each assembly. Each assembly is included in CuraGen Corporation's database. Sequences were included as components for assembly when the extent of identity with another component was at least 95% over 50 bp. Each assembly represents a gene or portion thereof and includes information on variants, such as splice forms single nucleotide polymorphisms (SNPs), insertions, deletions and other sequence variations.

Variant sequences are also included in this application. A variant sequence can include a single nucleotide polymorphism (SNP). A SNP can, in some instances, be referred to as a "cSNP" to denote that the nucleotide sequence containing the SNP originates as a cDNA. A SNP can arise in several ways. For example, a SNP may be due to a substitution of one nucleotide for another at the polymorphic site. Such a substitution can be either a transition or a transversion. A SNP can also arise from a deletion of a nucleotide or an insertion of a nucleotide, relative to a reference allele. In this case, the polymorphic site is a site at which one allele bears a gap with respect to a particular nucleotide in another allele. SNPs occurring within genes may result in an alteration of the amino acid encoded by the gene at the position of the SNP. Intragenic SNPs may also be silent, when a codon including a SNP encodes the same amino acid as a result of the redundancy of the genetic code. SNPs occurring outside the region of a gene, or in an intron within a gene, do not result in changes in any amino acid sequence of a protein but may result in altered regulation of the expression pattern. Examples include alteration in temporal expression, physiological response regulation, cell type expression regulation, intensity of expression, and stability of transcribed message.

Presented information includes that associated with genomic clones, public genes and ESTs sharing sequence identity with the disclosed sequence and CuraGen Corporation's Electronic Northern bioinformatic tool.

EXAMPLES

Example 1

The NOV1 clone was analyzed, and the nucleotide and encoded polypeptide sequences are shown in Table 1A.

TABLE 1A

NOV1 Sequence Analysis

| | | |
|---|---|---|
| NOV1a, | SEQ ID NO:1 | 1173 bp |
| CG55912-01 DNA Sequence | AATATAGCCGGTCCTGTCCCCGTGTTAACTGGAGTGCTGAAGCGCTGGAACGAAATGC | |
| | GGGGCCTCTGGTGCGAGAAGGGGGTGCAGGTGCTGCTGACGACGGTGGGCGCCTTCGC | |
| | CGCCTTCGGCCTCATGACCATCGCCATCAGCACTGACTACTGGCTCTACACGGGGCAA | |
| | CAAGAGCGAAAATCTGTCTCAAAAAATAAAAGAAGTAAGAAGGACCCCGGCGGCCTCA | |
| | CGCACTCGGCCCTCTGGAGGATCTGCTGCCTGGAAGGGTTGAAAAGAGGCGTCTGCGT | |
| | GAAGATCAATCATTTCCCGGAGGACACGGACTACGACCACGACAGCGCGGAGTATCTA | |
| | CTCCGTACGGTCCGGGCCTCCAGCATCTTCCCCATCCTTAGCGCCATCCTGCTGCTGC | |
| | TCGGGGGTGTGTGCGTGGCGGCCTCCCGCGTCTACAAGTCCAAGAGGAACATCATTCT | |
| | GGGCGCAGGGATCCTGTTCGTGGCAGCAGGTCTGAGCAACATCATCGGCGTGATCGTG | |
| | TACATCTCCGCCAACGCGGGCGAGCCGGGCCGAAGCAGAGCCAAGAAAAACCACTACT | |
| | CGTACGGCTGGTCCTTCTACTTCGGCGGGCTGTCGTTCATCCTGGCCGAGGTGATAGG | |
| | CGTGCTGGCCGTCAACATCTACATCGAGCCAGCCGAGGCGCACTGCCAGTCTCGGAGC | |
| | GGGACCGCGGGGGGTCGTCCGGCTTCCTCACGCTGCACAACGCCTTCCCCAAGGAGGC | |
| | GGGCGGCGGCGTCACGGTCACGTTCACCCGGCCGCCCGCCCCGCCCGCCCCACGCCAC | |
| | CCCGGCCAACACCAACTCCACGGACATCTCCATGTACACGCTCAGCCGCGACCCCTCC | |
| | AAGGGCAGCCCCCATTCCAATGCCACCACCCCCACCCCCACTAGCCTCAAGGATAGGA | |
| | AAAACTCATTTGTGTCCATAAAAATAAAGGTAAAAAAGAAAAAAAGAAATATATATAT | |
| | ATATATATATACGCTCAACAGGAAAACCACGCCTGTGTAGGGGCGCGGCGGGGGAGCC | |
| | GAGGGGCGTGTCCGCGGCGCGTGCGGGCGCGCGTGCATCGAGGCTGCCGGGGTCGGGG | |
| | GCGCCCCGCTTTCCCCCGTGAGCGCGCTGGAGACTGCTGGGCCCGCCCCACGCCCAC | |
| | CCTCCCCGCCCCC | |
| NOV1a, | ORF Start: ATG at 55 | ORF Stop: TAG at 1024 |
| | SEQ ID NO:2 | 323 aa MW at 35342.3 kD |
| CG55912-01 Protein Sequence | MRGLWCEKGVQVLLTTVGAFAAFGLMTIAISTDYWLYTCQQERKSVSKNKRSKKDPGG | |
| | LTHSGLWRICCLEGLKRGVCVKINHFPEDTDYDHDSAEYLLRTVRASSIFPILSAILL | |
| | LLGGVCVAASRVYKSKRNIILGAGILPVAAGLSNIIGVIVYTSANAGEPGRSRAKKNH | |
| | YSYGWSFYFGGLSFILAEVIGVLAVNIYIEPAEAHCQSRSGTAGGRPASSRCTTPSPR | |
| | RRAAASRSRSPGRPPRPREATPANTNSTDISMYTLSRDPSKCSPHSNATTPTPTSLKD | |
| | RKNSFVSIKIKVKKKRNIYIYIYTLNRKTTPV | |

Further analysis of the NOV1a protein yielded the following properties shown in Table 1B.

TABLE 1B

Protein Sequence Properties NOV1a

| | |
|---|---|
| PSort analysis: | 0.6400 probability located in plasma membrane; 0.4600 probability located in Golgi body; 0.3700 probability located in endoplasmic reticulum (membrane); |

TABLE 1B-continued

Protein Sequence Properties NOV1a

| | |
|---|---|
| SignalP analysis: | 0.1000 probability located in endoplasmic reticulum (lumen) Cleavage site between residues 22 and 23 |

A search of the NOV1a protein against the Geneseq database, a proprietary database that contains sequences published in patents and patent publication, yielded several homologous proteins shown in Table 1C.

TABLE 1C

Geneseq Results for NOV1a

| Geneseq Identifier | Protein/Organism/Length [Patent #, Date] | NOV1a Residues/ Match Residues | Identities/ Similarities for the Matched Region | Expect Value |
|---|---|---|---|---|
| AAY70462 | Human membrane channel protein-12 (MECHP-12)-*Homo sapiens*, 323 aa. [WO200012711-A2, 09-MAR-2000] | 7 . . . 323<br>5 . . . 323 | 183/327 (55%)<br>233/327 (70%) | 5e−93 |
| ABB11805 | Human voltage gated Ca channel subunit homologue, SEQ ID NO: 2175-*Homo sapiens*, 325 aa. [WO200157188-A2, 09-AUG-2001] | 7 . . . 323<br>7 . . . 325 | 183/327 (55%)<br>233/327 (70%) | 1e−92 |
| AAY84376 | A human voltage-gated calcium channel designated CACNGLIKE1-*Homo sapiens*, 323 aa. [WO200014223-A1, 16-MAR-2000] | 7 . . . 323<br>5 . . . 323 | 183/327 (55%)<br>233/327 (70%) | 1e−92 |
| AAY84374 | A human a neuronal voltage-gated calcium chanel polypeptide-*Homo sapiens*, 315 aa. [WO200014225-A1, 16-MAR-2000] | 6 . . . 323<br>4 . . . 315 | 173/324 (53%)<br>217/324 (66%) | 9e−86 |
| AAB43007 | Human ORFX ORF2771 polypeptide sequence SEQ ID NO: 5542-*Homo sapiens*, 315 aa. [WO200058473-A2, 05-OCT-2000] | 6 . . . 323<br>4 . . . 315 | 173/324 (53%)<br>217/324 (66%) | 9e−86 |

In a BLAST search of public sequence datbases, the NOV1a protein was found to have homology to the proteins shown in the BLASTP data in Table 1D.

TABLE 1D

Public BLASTP Results for NOV1a

| Protein Accession Number | Protein/Organism/Length | NOV1a Residues/ Match Residues | Identities/ Similarities for the Matched Portion | Expect Value |
|---|---|---|---|---|
| AAL50041 | VOLTAGE-DEPENDENT CALCIUM CHANNEL GAMMA-8 SUBUNIT-*Rattus norvegicus* (Rat), 421 aa. | 2 . . . 275<br>11 . . . 317 | 226/309 (73%)<br>234/309 (75%) | e−113 |
| AAL50045 | VOLTAGE-DEPENDENT CALCIUM CHANNEL GAMMA-8 SUBUNIT-*Mus musculus* (Mouse). 423 aa. | 2 . . . 275<br>11 . . . 317 | 225/309 (72%)<br>234/309 (74%) | e−113 |
| AAL50049 | VOLTAGE-DEPENDENT CALCIUM CHANNEL GAMMA-8 SUBUNIT-*Homo sapiens* (Human), 426 aa. | 2 . . . 275<br>11 . . . 318 | 227/309 (73%)<br>234/309 (75%) | e−112 |
| Q9BXT0 | CALCIUM CHANNEL GAMMA SUBUNIT 8-*Homo sapiens* (Human), 414 aa (fragment). | 3 . . . 275<br>1 . . . 306 | 228/309 (73%)<br>235/309 (75%) | e−112 |
| Q9Y698 | Voltage-dependent calcium channel gamma-2 subunit (Neuronal voltage-gated calcium channel gamma-2 subunit)-*Homo sapiens* (Human), 323 aa. | 7 . . . 323<br>5 . . . 323 | 183/327 (55%)<br>233/327 (70%) | 3e−92 |

PFam analysis predicts that the NOV1a protein contains the domains shown in the Table 1e.

TABLE 1E

Domain Analysis of NOV1a

| Pfam Domain | NOV1a Match Region | Identities/ Similarities for the Matched Region | Expect Value |
|---|---|---|---|
| PMP22_Claudin: domain 1 of 1 | 8 . . . 198 | 51/198 (26%) 161/198 (81%) | 7.6e−53 |

Example 2

The NOV2 clone was analyzed, and the nucleotide and encoded polypeptide sequences are shown in Table 2A.

TABLE 2A

NOV2 Sequence Analysis

NOV2a, CG55918-01 DNA Sequence

SEQ ID NO:3   116 bp

AAATGGGAGCCAGGTCATACACGGGATCTCTGTGGCAGGAACGGGCTGGCTGGATTCC
TCTGCCCCTGGACTTGCAGGCCATTGAGCTGGCTGCCCAGAGCAACCATCACTGCCAT
GCTCAGAAGGGTCCTGACAGTCACTGTGACCCCAAGAAGGGGAAGGCCCAGCGCCAGC
TGTATGTAGCCTCTGCCATCTGCCTGTTGTTCATGATCGGAGAAGTCGTTGGTGGGTA
CCTGGCACACAGCTTGGCTGTCATGACTGACGCAGCACACCTGCTCACTGACTTTGCC
AGCATGCTCATCAGCCTCTTCTCCCTCTGGATGTCCTCCCGGCCAGCCACCAAGACCA
TGAACTTTGGCTGGCAGAGAGCTGAGATCTTGGGAGCCCTGGTCTCTGTACTGTCCAT
CTGGGTCGTGACGGGGGTACTGGTGTACCTGGCTGTGGAGCGGCTGATCTCTGGGGAC
TATGAAATTGACGGGGGGACCATGCTGATCACGTCGGGCTGCGCTGTGGCTGTGAACA
TCATGATGGGGTTGACCCTTCACCAGTCTGGCCATGGGCACAGCCACCGCACCACCAA
CCAGCAGGAGGAGAACCCCAGCGTCCGAGCTGCCTTCATCCATGTGATCGGCGACTTT
ATGCAGAGCATGGGTGTCCTAGTGGCAGCCTATATTTTATACTTCAAGCCAGAATACA
AGTATGTAGACCCCATCTGCACCTTCGTCTTCTCCATCCTGGTCCTGGGGACAACCTT
GACCATCCTGAGAGATGTGATCCTGGTGTTGATGGAAGGTACCCCCAAGGGCGTTGAC
TTCACAGCTGTTCGTCATCTGCTGCTGTCGGTGGAGGGGGTAGAAGCCCTGCACAGCC
TGCATATCTGGGCACTGACGGTGGCCCAGCCTGTTCTGTCTGTCCACATCGCCATTGC
TCAGAATACAGACGCCCAGGCTGTGCTGAAGACAGCCAGCAGCCGCCTCCAAGGGAAG
TTCCACTTCCACACCGTGACCATCCAGATCGAGGACTACTCGGAGGACATGAAGGACT
GTCAGGCATGCCAGGGCCCCTCAGACTGACTGCTCAGCCAGCCACCAACTGGGGCATG
AACAGGACCTGCAG

ORF Start: ATG at 3   ORF Stop: TGA at 1071
SEQ ID NO:4   356 aa  MW at 38698.4 kD NOV2a, CG55918-01 Protein Sequence MGARSYTGSLWQEGAGWIPLPLDLQAIELAAQSNHHCHAQKGPDSHCDPKKGKAQRQL
YVASAICLLFMIGEVVGGYLAHSLAVMTDAAHLLTDFASMLISLFSLWMSSRPATKTM
NFGWQRAEILGALVSVLSIWVVTGVLVYLAVERLISGDYEIDGGTMLITSGCAVAVNI
MMGLTLHQSGHGHSHGTTNQQEENPSVRAAFIHVIGDFMQSMGVLVAAYILYFKPEYK
YVDPICTFVFSILVLGTTLTILRDVILVLMEGTPKGVDFTAVRDLLLSVEGVEALHSL
HIWALTVAQPVLSVHIAIAQNTDAQAVLKTASSRLQGKFHFHTVTIQIEDYSEDMKDC

TABLE 2A-continued

NOV2 Sequence Analysis

QACQGPSD

NOV2b,
CG55918-02 DNA Sequence

SEQ ID NO:5       11154 bp

<u>AA</u>ATGGGAGCCAGGTCATACACGGGATCTCTGTGGCAGGAAGGGGCTGGCTGGATTCC
TCTGCCCCGACCTGGCCTGGACTTGCAGGCCATTGAGCTGGCTGCCCAGAGCAACCAT
CACTGCCATGCTCAGAAGGGTCCTGACAGTCACTGTGACCCCAAGAAGGGGAAGGCCC
AGCGCCAGCTGTATGTAGCCTCTGCCATCTGCCTGTTGTTCATGATCGGAGAAGTCGT
TGATGATGAAACTGAGGCACGTTCAGGTGGGTACCTGGCACACAGCTTGGCTGTCATG
ACTGACGCAGCACACCTGCTCACTGACTTTGCCAGCATGCTCATCAGCCTCTTCTCCC
TCTGGATGTCCTCCCGGCCAGCCACCAAGACCATGAACTTTGGCTGGCAGAGAGCTGA
GATCTTGGGAGCCCTGGTCTCTGTACTGTCCATCTGGGTCGTGACGGGGGTACTGGTG
TACCTGGCTGTGGAGCGGCTGATCTCTGGGGACTATGAAATTGACGGGGGGACCATGC
TGATCACGTCGGGCTGCGCTGTGGCTGTGAACATCATAATGCGGTTGACCCTTCACCA
GTCTGGCCATGGGCACAGCCACGGCACCACCAACCAGCAGGAGGAGAACCCCAGCGTC
CGAGCTGCCTTCATCCATGTGATCGGCGACTTTATGCAGAGCATGGGTGTCCTAGTGG
CAGCCTATATTTTATACTTCAAGCCAGAATACAAGTATGTAGACCCCATCTGCACCTT
CGTCTTCTCCATCCTGGTCCTGGGGACAACCTTGACCATCCTGAGAGATGTGATCCTG
GTGTTGATGGAAGGGACCCCCAAGGGCGTTGACTTCACAGCTGTTCGTGATCTGCTGC
TGTCGGTGGAGGGGTAGAAGCCCTGCACAGCCTGCATATCTGGGCACTGACGGTGGC
CCAGCCTGTTCTGTCTGTCCACATCGCCATTGGCCCCCAGCTCAGA<u>ATACAGACGCCC</u>
<u>AGGCTGTGCTGAAGACAGCCAGCAGCCGCCTCCAAGGGAAGTTCCACTTCCACACCGT</u>
<u>GACCATCCAGATCGAGGACTACTCGGAGGACATGAAGGACTGTCAGGCATGCCAGGGC</u>
<u>CCCTCAGACTGACTGCTCAGCCAGGCACCAACTGGGGCATGAACAGGACCTG</u>

NOV2b,
CG55918-02 Protien Sequence

ORF Start: ATG at 3       ORF Stop: at 9721
SEQ ID NO:6       323 aa MW at 35057.5 kD MGARSYTGSLWQEGAGWIPLPRPGLDLQAIELAAQSNHHCHAQKGPDSHCDPKKGKAQ
RQLYVASAICLLFMIGEVVGGYLAHSLAVMTDAAHLLTDFASMLISLFSLWMSSRPAT
KTMNFGWQRAEILGALVSVLSIWVVTGVLVYLAVERLISGDYEIDGGTMLITSGCAVA
VNIIMGLTLHQSCHGHSHGTTNQQEENPSVRAAFIHVIGDFMQSMGVLVAAYILYFKP
EYKYVDPICTFVFSILVLGTTLTILRDVILVLMEGTPKGVDFTAVRDLLLSVECVEAL
HSLHIWALTVAQPVLSVHIAIGPQLRIQTPRLC Sequence comparison of the above protein sequences yields the following sequence relationships shown in Table 2B.

TABLE 2B

Comparison of NOV2a against NOV2b.

| Protein Sequence | NOV2a Residues/ Match Residues | Identities/ Similarities for the Matched Region |
|---|---|---|
| NOV2b | 1 ... 308 | 288/311 (92%) |
|  | 1 ... 311 | 289/311 (92%) |

Further analysis of the NOV2a protein yielded the following properties shown in Table 2C.

TABLE 2C

Protein Sequence Properties NOV2a

| | |
|---|---|
| PSort analysis: | 0.6000 probability located in plasma membrane; 0.4000 probability located in Golgi body; 0.3000 probability located in endoplasmic reticulum (membrane); 0.3000 probability located in microbody (peroxisome) |
| SignalP analysis: | Cleavage site between residues 40 and 41 |

A search of the NOV2a protein against the Geneseq database, a proprietary database that contains sequences published in patents and patent publication, yielded several homologous proteins shown in Table 2D.

TABLE 2D

Geneseq Results for NOV2a

| Geneseq Identifier | Protein/Organism/Length [Patent #, Date] | NOV2a Residues/ Match Residues | Identities/ Similarities for the Matched Region | Expect Value |
|---|---|---|---|---|
| AAB60094 | Human transport protein TPPT-14-*Homo sapiens*, 320 aa. [WO200078953-A2, 28-DEC-2000] | 35 . . . 356 <br> 2 . . . 320 | 171/322 (53%) <br> 232/322 (71%) | 6e–97 |
| AAG31823 | *Arabidopsis thaliana* protein fragment SEQ ID NO: 38281-*Arabidopsis thaliana*, 359 aa. [EP1033405-A2, 06-SEP-2000] | 46 . . . 339 <br> 27 . . . 357 | 105/331 (31%) <br> 180/331 (53%) | 1e–46 |
| AAG31822 | *Arabidopsis thaliana* protein fragment SEQ ID NO: 38280-*Arabidopsis thaliana*, 375 aa. [EP1033405-A2, 06-SEP-2000] | 46 . . . 339 <br> 43 . . . 373 | 105/331 (31%) <br> 180/331 (53%) | 1e–46 |
| AAG31821 | *Arabidopsis thaliana* protein fragment SEQ ID NO: 38279-*Arabidopsis thaliana*, 385 aa. [EP1033405-A2, 06-SEP-2000] | 46 . . . 339 <br> 53 . . . 383 | 105/331 (31%) <br> 180/331 (53%) | 1e–46 |
| ABB53142 | Human 0RF48 protein-*Homo sapiens*, 144 aa. [WO200177155-A2, 18-OCT-2001] | 35 . . . 176 <br> 1 . . . 142 | 84/142 (59%) <br> 105/142 (73%) | 7e–42 |

In a BLAST search of public sequence datbases, the NOV2a protein was found to have homology to the proteins shown in the BLASTP data in Table 2E.

TABLE 2E

Public BLASTP Results for NOV2a

| Protein Accession Number | Protein/Organism/Length | NOV2a Residues/ Match Residues | Identities/ Similarities for the Matched Portion | Expect Value |
|---|---|---|---|---|
| Q62941 | Zinc transporter 2 (ZnT-2)-*Rattus norvegicus* (Rat), 359 aa. | 1 . . . 356 <br> 1 . . . 359 | 290/360 (80%) <br> 327/360 (90%) | e–167 |
| Q9BRI3 | SIMILAR TO ZINK TRANSPORTER 2-*Homo sapiens* (Human), 323 aa. | 4 . . . 356 <br> 17 . . . 323 | 303/356 (85%) <br> 304/356 (85%) | e–166 |
| P97441 | Zinc transporter 3 (ZnT-3)-*Mus musculus* (Mouse), 388 aa. | 19 . . . 355 <br> 40 . . . 386 | 193/350 (55%) <br> 242/350 (69%) | e–107 |
| Q99726 | Zinc transporter 3 (ZnT-3)-*Homo sapiens* (Human), 388 aa. | 19 . . . 354 <br> 40 . . . 385 | 189/349 (54%) <br> 239/349 (68%) | e–105 |
| CAD28545 | HYPOTHETICAL 35.1 KDA PROTEIN-*Homo sapiens* (Human), 320 aa. | 35 . . . 356 <br> 2 . . . 320 | 170/322 (52%) <br> 230/322 (70%) | 2e–95 |

PFam analysis predicts that the NOV2a protein contains the domains shown in the Table 2F.

TABLE 2F

Domain Analysis of NOV2a

| Pfam Domain | NOV2a Match Region | Identities/ Similarities for the Matched Region | Expect Value |
|---|---|---|---|
| Cation_efflux: domain 1 of 1 | 58 . . . 345 | 105/322 (33%) <br> 257/322 (80%) | 4.1e–109 |

Example 3

The NOV3 clone was analyzed, and the nucleotide and encoded polypeptide sequences are shown in Table 3A.

TABLE 3A

NOV3 Sequence Analysis

| | |
|---|---|
| NOV3a, <br><br> CG56641-01 DNA Sequence | SEQ ID NO:7                 1814 bp <br> <u>TCACCTCTGACCCGCAGCACTTCGTGGCCCTGGGGGCCGGTCCATCATCAATGGGAAC</u> <br> <u>TGGGCTGTGGATCCCCTGGGTCCTACAGGGCCGGCGGGACCGTCTTTCGATATAACC</u> <br> <u>GTCCTCCCAGGCAGGAGGGCAAAGGGGAGAGTCTGTCGGCTGAAGGCCCCACCACCCA</u> <br> <u>GCCTGTGGATGTCTATGTGATGACTTTCAGGAGCAAAACCCAGGCGTTTTTTATCAG</u> <br> TATGTCATCTCTTCACCTCCTCCAATCCTTGAGAACCCCACCCCAGAGCCCCCTGTCC <br> CCCAGCTTCACCCGGGTAACACTCTGACCCCTGCACTTGGAAGGAGGAGGGAGAGGCT <br> GCAGGGCTGGCTCGGGGCAGTGGGGTGGCATCTGATTCGCCTGCTCCCCTGCACAGAG <br> ATTCTGACGGTGGAGCCCCCACTTGCTCCGGCACCCCGCCCAGCCCGGACCCCAGGCA <br> CCCTCCAGCGTCAGGTGCGGATCCCCCAGATGCCCGCCCCGCCCCATCCCAGGACACC <br> CCTGGGGTCTCCAGCTGCGTACTGGAAACGAGTGCGACACTCTGCATGCTCAGCGTCC <br> TGCGCGAAAGGTTCCTCTGAGGCCCCCACGTCCAGTGTCTCTTCCATCTCTCCTGCCA <br> CGGCAGCCCCACACATCTCATCTATGTCTCCGCCTCTTCCCTGCCCTGCTGGTGCCTG <br> CAGCTGGGAGGCTGGCGAGTGGACATCCTCCAGCCGCTCCTGTGGCCCCGGCACCCAG <br> CACCGCCAGCTGCAGTCCCGGCAGGAATTTGGGGCGGGTGGCTCCTCGGTGCCCCCGG <br> AGCGCTGTGGACATCTCCCCCCGCCCAACATCACCCAGTCTTGCCAGCTGCGCCTCTG <br> TGGCCATTGGGAAGTTGGCTCTCCTTGGAGCCAGTGCTCCGTGCGGTGCGCCCGGGGC <br> CAGAGAAGCCGGCAGGTTCGCTGTGTTGGGAACAATGGTGATGAAGTGAGCGAGCAGG <br> AGTGTGCGTCAGGCCCCCCGCAGCCCCCCAGCAGAGAGGCCTGTCACATGGGGCCCTG <br> TACTACTGCCTGGTTCCACAGCGACTCGAGCTCCAAGGTGTCAGCCGAGTGTGGGACG <br> GGAATCCAGCGGCGCTCTGTGGTCTGCCTTGGGAGTGGGGCAGCCCTCGGGCCAGGCC <br> AGGGGGAAGCAGGAGCAGGAACTGGGCAGAGCTGTCCAACAGGAAGCCGGCCCCCTGA <br> CATGCGCGCCTGCAGCCTGGGGCCCTGTGAGAGAACTTGGCGCTGGTACACAGGGCCC <br> TGGGGTGAGTCCTCCTCCCAATGTGCCTCTGGCACACACCGTAGAGACATCATCTGTG <br> TATCCAAACTGGGGACGGAGTTCAACGTGACTTCTCCGAGCAACTGTTCTCACCTCCC <br> CAGGCCCCCTGCCCTGCAGCCCTGTCAAGGGCAGGCCTGCCAGGACCGATGGTTTTCC <br> ACGCCCTGGAGCCCATGTTCTCGCTCCTGCCAAGGGGAACGCAGACACGGGAGGTCC <br> AGTGCCTGAGCACCAACCAGACCCTCACCACCCGATGCCCTCCTCAACTGCGGCCCTC <br> CAGGAAGCGCCCCTGTAACAGCCAACCCTGCGATGATCAATGCAAGGACAGCTCTCCA <br> CATTGCCCCCTGGTGGTACAGGCCCGGCTCTGCGTCTACCCCTACTACACAGCCACCT <br> GTTGCCGCTCTTGCGCACATGTCCTGGAGCGGTCTCCCCAGGATCCCTCCTGA<u>AAGGG</u> <br> <u>GTCCGGGGCACCTTCACGGTTTTCTGTGCCACCATCGGTCACCCATTGATCGGCCCAC</u> <br> <u>TCTGAACCCCCTGCCT</u> |
| | ORF Start: ATG at 194      ORF Stop: TGA at 1733 <br> SEQ ID NO:8                  513 aa MW at 55199.7 kD |
| NOV3a, <br><br> CG56641-01 Protein Sequence | MIFQEEWPGVFYQYVISSPPPILENPTPEPPVPQLQPCKTLTPALGRRRSRLQCWLGA <br><br> VCWHLIRLLPCTEILRVEPPLAPAPRPARTPGTLQRQVRIPQMPAPPHPRTPLGSPAA |

TABLE 3A-continued

NOV3 Sequence Analysis

YWKRVCHSACSASCGKGSSEAPTSSVSSISAATAAPHISSMSPPLPCPAGACSWEAGE

WTSCSRSCGPGTQHRQLQCRQEFCGGGSSVPPERCGHLPRPNITQSCQLRLCGHWEVG

SPWSQCSVRCGRGQRSRQVRCVGNNGDEVSEQECASGPPQPPSREACDMGPCTTAWFH

SDWSSKVSAECGTGIQRRSVVCLGSGAALGPGQGEACAGTGQSCPTGSRPPDMPACSL

GPCERTWRWYTGPWGECSSECGSGTQRRDIICVSRLGTEFNVTSPSNCSHLPRPPALQ

PCQGQACQDRWFSTPWSPCSRSCQGCTQTREVQCLSTNQTLSTRCPPQLRPSRKRPCN

SQPCDDQCKDSSPHCPLVVQARLCVYPYYTATCCRSCAHVLERSPQDPS

Further analysis of the NOV3a protein yielded the following properties shown in Table 3B.

TABLE 3B

Protein Sequence Properties NOV3a

| | |
|---|---|
| PSort analysis: | 0.3000 probability located in microbody (peroxisome); 0.3000 probability located in nucleus; 0.1000 probability located in mitochondrial matrix space; 0.1000 probability located in lysosome (lumen) |
| SignalP analysis: | Cleavage site between residues 26 and 27 |

A search of the NOV3a protein against the Geneseq database, a proprietary database that contains sequences published in patents and patent publication, yielded several homologous proteins shown in Table 3C.

TABLE 3C

Geneseq Results for NOV3a

| Geneseq Identifier | Protein/Organism/Length [Patent #, Date] | NOV3a Residues/ Match Residues | Identities/ Similarities for the Matched Region | Expect Value |
|---|---|---|---|---|
| AAB50936 | ADAM protein #2-*Homo sapiens*, 491 aa. [WO200073323-A2, 07-DEC-2000] | 1 . . . 513<br>1 . . . 491 | 454/528 (85%)<br>455/528 (85%) | 0.0 |
| AAE09698 | Human gene 9 encoding novel protein HUCMO06, SEQ ID NO: 45-*Homo sapiens*, 372 aa. [WO200155202-A1, 02-AUG-2001] | 160 . . . 513<br>13 . . . 372 | 347/360 (96%)<br>347/360 (96%) | 0.0 |
| AAE09713 | Human gene 9 encoding novel protein HUCMO06, SEQ ID NO: 60-*Homo sapiens*, 260 aa. [WO200155202-A1, 02-AUG-2001] | 160 . . . 403<br>13 . . . 258 | 234/246 (95%)<br>235/246 (95%) | e–147 |
| AAU32725 | Novel human secreted protein #3216-*Homo sapiens*, 416 aa. [WO200179449-A2, 25-OCT-2001] | 229 . . . 500<br>9 . . . 293 | 224/285 (78%)<br>226/285 (78%) | e–130 |
| AAB94727 | Human protein sequence SEQ ID NO: 15753-*Homo sapiens*, 538 aa. [EP1074617-A2, 07-FEB-2001] | 1 . . . 507<br>32 . . . 530 | 218/528 (41%)<br>287/528 (54%) | e–112 |

In a BLAST search of public sequence datbases, the NOV3a protein was found to have homology to the proteins shown in the BLASTP data in Table 3D.

TABLE 3D

Public BLASTP Results for NOV3a

| Protein Accession Number | Protein/Organism/Length | NOV3a Residues/ Match Residues | Identities/ Similarities for the Matched Portion | Expect Value |
|---|---|---|---|---|
| Q9HBS6 | HYPOTHETICAL 25.7 KDA PROTEIN-*Homo sapiens* (Human), 237 aa. | 281 . . . 513<br>1 . . . 237 | 232/237 (97%)<br>232/237 (97%) | e−146 |
| Q91YP4 | SIMILAR TO HYPOTHETICAL PROTEIN FLJ13710-*Mus musculus* (Mouse), 235 aa. | 281 . . . 513<br>1 . . . 235 | 200/237 (84%)<br>210/237 (88%) | e−122 |
| Q9H8E4 | PLACE2000373 PROTEIN-*Homo sapiens* (Human), 538 aa. | 1 . . . 507<br>32 . . . 530 | 218/528 (41%)<br>287/528 (54%) | e−111 |
| Q96H81 | HYPOTHETICAL 51.1 KDA PROTEIN-*Homo sapiens* (Human), 454 aa. | 1 . . . 423<br>32 . . . 442 | 172/440 (39%)<br>232/440 (52%) | 2e−81 |
| Q9UFG7 | HYPOTHETICAL 12.5 KDA PROTEIN-*Homo sapiens* (Human), 111 aa (fragment). | 407 . . . 513<br>1 . . . 111 | 107/111 (96%)<br>107/111 (96%) | 2e−62 |

PFam analysis predicts that the NOV3a protein contains the domains shown in the Table 3E.

TABLE 3E

Domain Analysis of NOV3a

| Pfam Domain | NOV3a Match Region | Identities/ Similarities for the Matched Region | Expect Value |
|---|---|---|---|
| tsp_1: domain 1 of 4 | 170 . . . 226 | 15/62 (24%)<br>39/62 (63%) | 0.18 |
| tsp_1: domain 2 of 4 | 230 . . . 284 | 18/62 (29%)<br>41/62 (66%) | 0.00028 |
| tsp_1: domain 3 of 4 | 357 . . . 413 | 10/62 (16%)<br>35/62 (56%) | 1.4 |
| tsp_1: domain 4 of 4 | 419 . . . 468 | 14/55 (25%)<br>34/55 (62%) | 0.0035 |

Example 4

The NOV4 clone was analyzed, and the nucleotide and encoded polypeptide sequences are shown in Table 4A.

TABLE 4A

NOV4 Sequence Analysis

NOV4a,
CG56832-01 DNA Sequence

SEQ ID NO:9      1396 bp

```
TTCTCCCTCCACTGCCAGACAATATCCCTGAGAGTGAGGAAGCAATGAGGATTGTTTG
TTTAGTGAAAAACCAACAGCCCCTGGGAGCCACCATCAAGCGCCACGAGATGACAGGG
GACATCTTGGTGGCCAGGATCATCCACGGTGGGCTGGCGGAGAGAAGTGGGTTGCTAT
ATGCTGGAGACAAACTGGTAGAAGTGAATGGAGTTTCAGTTGAGGGACTGGACCCTGA
ACAAGTGATCCATATTCTGGCCATGTCTCGAGGCACAATCATGTTCAAGGTGGTTCCA
GTCTCTGACCCTCCTGTGAATAGCCAGCAGATGGTGTACGTCCGTGCCATGACTGAGT
ACTGGCCCCAGGAGGATCCCGACATCCCCTGCATGGACGCTGGATTGCCTTTCCAGAA
GGGGCACATCCTCCAGATTGTGGACCAGAATGATGCCCTCTGGTGGCAGGCCCGAAAA
ATCTCAGACCCTGCTACCTGCGCTGGGCTTGTCCCTTCTAACCACCTTCTGAAGAGGA
AGCAACGGGAATTCTGGTGGTCTCAGCCGTACCAGCCTCACACCTGCCTCAAGTCAAC
CCTATACAAGGAGGAGTTTGTTGGCTACGGTCAGAAGTTCTTTATAGGTAGCCCGCTG
CATGCCAGTGTGTGCTGCACCGGCAGCTGCTACAGTGCAGTGGGTGCCCCTTACGAGG
```

TABLE 4A-continued

NOV4 Sequence Analysis

AGGTGGTGAGGTACCAGCGACGCCCTTCAGACAAGTACCGCCTCATAGTGCTCATGGG
ACCCTCTGGTGTTGGAGTAAATGACCTCAGAAGACAACTTATTGAATTTAATCCCAGC
CATTTTCAAAGTGCTGTGCCACACACTACTCGTACTAAAAAGAGTTACGAAATGAATG
GGCGTGAGTATCACTATGTGTCCAAGGAAACATTTGAAAACCTCATATATAGTCACAG
GATGCTGGAGTATGGTGAGTACAAAGGCCACCTGTATGGCACTAGTGTGGATGCTGTT
CAAACAGTCCTTGTCGAAGGAAAGATCTGTGTCATGGACCTAGAGCCTCAGGATATTC
AAGGGGTTCGAACCCATGAACTGAAGCCCTATGTCATATTTATAAAGCCATCGAATAT
GAGGTGTATGAAACAATCTCGGAAAAATGCCAAGGTTATTACTGACTACTATGTGGAC
ATGAAGTTCAAGGATGAAGACCTACAAGAGATGGAAAATTTAGCCCAAAGAATGGAAA
CTCAGTTTGGCCAATTTTTTGATCATGTGATTGTGAATGACAGCTTGCACGATGCATG
TGCCCAGTTGTTGTCTGCCATACAGAAGGCTCAGGAGGAGCCTCAGTGGGTACCAGCA
ACATGGATTTCCTCAGATACTGAGTCTCAATGAGACTTCTTGTTTAATGCTGGAGTTT
TAAC

| | |
|---|---|
| | ORF Start: ATG at 45     ORF Stop: TGA at 1365 |
| | SEQ ID NO:10     440 aa MW at 50266.1 kD |

NOV4a,

CG56832-01 Protein Sequence

MRIVCLVKNQQPLGATIKRHEMTGDILVARIIHGGLAERSGLLYAGDKLVEVNGVSVE
GLDPEQVIHILAMSRGTIMFKVVPVSDPPVNSQQMVYVRAMTEYWPQEDPDIPCMDAG
LPFQKGDILQIVDQNDALWWQARKISDPATCAGLVPSNHLLRKQREFWWSQPYQPHT
CLKSTLYKEEFVGYGQKFFIGSPLHASVCCTGSCYSAVGAPYEEVVRYQRRPSDKYRL
IVLMGPSGVGVNELRRQLIEFNPSHFQSAVPHTTRTKKSYEMNGREYHYVSKETFENL
IYSHRMLEYGEYKGHLYGTSVDAVQTVLVEGKICVMDLEPQDIQGVRTHELKPYVIFI
KPSNMRCMKQSRKNAKVITDYYVDMKFKDEDLQEMENLAQRMETQFGQFFDHVIVNDS
LHDACAQLLSAIQKAQEEPQWVPATWISSDTESQ

NOV4b,

CG56832-02 DNA Sequence

SEQ ID NO:11     1371 bp
<u>CA</u>ATGAGGATTGTTTGTTTAGTGAAAAACCAACAGCCCCTGGGAGCCACCATCAAGCG
CCACGAGATGACAGGGGACATCTTGGTGGCCAGGATCATCCACGGTGGGCTGGCGGAG
AGAAGTGGGTTGCTATATGCTGGAGACAAGCTGGTAGAAGTGAATGGAGTTTCAGTTG
AGGGACTGGACCCTGAACAAGTGATCCATATTCTCGCCATGTCTCGAGGCACAATCAT
GTTCAAGGTGGTTCCAGTCTCTGACCCTCCTGTGAATAGCCAGCAGATGGTGTACGTC
CGTGCCATGACTGAGTACTGGCCCCAGGAGGATCCCGACATCCCCTGCATGGACGCTG
GATTGCCTTTCCAGAAGGGGACATCCTCCAGATTGTGGACCAGAATGATGCCCTCTG
GTGGCAGGCCCGAAAAATCTCAGACCCTGCTACCTGCGCTGGGCTTGTCCCTTCTAAC
CACCTTCTGAAGAGGAAGCAACGGGAATTCTGGTGGTCTCAGCCGTACCAGCCTCACA
CCTGCCTCAAGTCAACCCTATACAAGGAGGAGTTTGTTGGCTACGGTCAGAAGTTCTT
TATAGCTGGCTTCCGCCGCAGCATGCGCCTTTGTCGCAGGAAGTCTCACCTCAGCgCG
CTGCATGCCAGTGTGTGCTGCACCGGCAGCTGCTACAGTGCAGTGGGTGCCCCTTACG
AGGAGGTGGTGAGGTACCAGCGACGCCCTTCAGACAAGTACCGCCTCATAGTGCTCAT
GGGACCCTCTGGTGTTGGAGTAAATGAGCTCAGAAGACAACTTATTGAATTTAATCCC
AGCCATTTTCAAAGTGCTGTGCCACACACTACTCGTACTAAAAAGAGTTACGAAATGA
ATGGGCGTGAGTATCACTATGTGTCCAAGGAAACATTTGAAAACCTCATATATAGTCA

TABLE 4A-continued

NOV4 Sequence Analysis

|  | |
|---|---|
|  | CAGGATGCTGGAGTATGGTGAGTACAAAGGCCACCTGTATGGCACTAGTGTGGATGCT |
|  | GTTCAAACAGTCCTTGTCGAAGGAAAGATCTGTGTCATGGACCTAGAGCCTCAGGATA |
|  | TTCAAGGGGTTCGAACCCATGAACTGAAGCCCTATGTCATATTTATAAAGCCATCGAA |
|  | TATGAGGTGTATGAAACAATCTCGGAAAAATGCCAAGGTTATTACTGACTACTATGTG |
|  | GACATGAAGTTCAAGGATGAAGACCTACAAGAGATGGAAAATTTAGCCCAAAGAATGG |
|  | AAACTCAGTTTGGCCAATTTTTTGATCATGTGATTGTGAATGACAGCTTGCACGATGC |
|  | ATGTGCCCAGTTGTTGTCTGCCATACAGAAGGCTCAGCAGGAGCCTCAGTGGGTACCA |
|  | GCAACATGGATTTCCTCAGATACTGAGTCTCAATGAG |
| NOV4b, | ORF Start: ATG at 3         ORF Stop: TGA at 1368 |
|  | SEQ ID NO:12            455 aa MW at 52165.4 kD |
| CG56832-02 Protien Sequence | MRIVCLVKNQQPLGATIKRHEMTGDILVARIIHGGLAERSGLLYAGDKLVEVNGVSVE |
|  | GLDPEQVIHILAMSRGTIMFKVVPVSDPPVNSQQMVYVRAMTEYWPQEDPDIPCMDAG |
|  | LPFQKGDILQIVDQNDALWWQARKISDPATCAGLVPSNHLLRKQREFWWSQPYQPHT |
|  | CLKSTLYKEEFVGYGQKFFIAGFRRSMRLCRRKSHLSPLHASVCCTGSCYSAVGAPYE |
|  | EVVRYQRRPSDKYRLIVLMGPSGVGVNELRRQLIEFNPSHFQSAVPHTTRTKKSYEMN |
|  | GREYHYVSKETFENLIYSHRMLEYGEYKGHLYGTSVDAVQTVLVEGKICVMDLEPQDI |
|  | QGVRTHELKPYVIFIKPSNMRCMKQSRKNAKVITDYYVDMKFKDEDLQEMENLAQRME |
|  | TQFGQFFDHVIVNDSLHDACAQLLSAIQKAQEEPQWVPATWISSDTESQ |
| NOV4c, | SEQ ID NO:13            1935 bp |
|  | <u>TCAGAAGCTCCGGCAGGGAGG</u>ATGATACAGTCAGACAAAGGAGCAGATCCACCAGACA |
| CG56832-03 DNA Sequence | AGAAGGACATGAAGCTTTCTACAGCCACCAATCCACAGAATGGTCTCTCCCAGATCCT |
|  | GAGGCTTGTGCTGCAAGAGCTGAGTCTGTTCTACGGCACAGATGTGAATGGAGTGTGT |
|  | CTCTTGTACGATCTCCTCCACTCGCCGTGGCTTCAGGCTCTGCTAAAGATTTATGACT |
|  | GCCTCCAGGAATTTAAAGAAAAGAAACTAGTTCCTGCCACACCACATGCACAGGTGTT |
|  | ATCCTATGAGGTAGTGGAGTTATTACGTGAAACCCCTACTTCCCCTGAGATCCAAGAG |
|  | CTGAGACAAATGCTCCAGGCTCCACACTTCAAGGCATTGCTCAGTGCCCATGACACGA |
|  | TAGCTCAGAAAGATTTTGAACCCCTTCTCCCTCCACTGCCAGACAATATCCCTGACAG |
|  | TGAGGAAGCAATGAGGATTGTTTGTTTAGTGAAAAACCAACAGCCCCTGGGAGCCACC |
|  | ATCAAGCCCCACGAGATGACAGGGGACATCTTGGTGGCCAGGATCATCCACGGTGGGC |
|  | TGGCGGAGAGAAGTGGGTTGCTATATGCTGGAGACAAACTGGTAGAAGTGAATGGAGT |
|  | TTCAGTTGAGGGACTGGACCCTGAACAAGTGATCCATATTCTGGCCATGTCTCGAGGC |
|  | ACAATCATGTTCAAGGTGGTTCCAGTCTCTGACCCTCCTGTGAATAGCCAGCAGATGG |
|  | TGTACGTCCGTGCCATGACTGAGTACTGGCCCCAGGAGGATCCCGACATCCCCTGCAT |
|  | GGACGCTGGATTGCCTTTCCAGAAGGGGGACATCCTCCAGATTGTGGACCAGAATGAT |
|  | GCCCTCTGGTGGCAGGCCCGAAAAATCTCAGACCCTGCTACCTGCGCTGGGCTTGTCC |
|  | CTTCTAACCACCTTCTGAAGAGGAAGCAACGGGAATTCTGGTGGTCTCAGCCCTACCA |
|  | GCCTCACACCTGCCTCAAGTCAACCCTAGAAGATGACATGAAGATTGATGAGAAATGT |
|  | GTGGAAGCAGACAAGGAGGAGTTTGTTGGCTACGGTCAGAAGTTCTTTATAGCTGGCT |
|  | TCCGCCGCAGCATGCGCCTTTGTCGCAGGAAGTCTCACCTCAGCCCGCTGCATGCCAG |
|  | AGGTACCAGCGACGCCCTTCAGACAAGTACCGCCTCATAGTGCTCATGGGTCCCTCTG |

TABLE 4A-continued

NOV4 Sequence Analysis

```
GTGTTGGAGTAAATGAGCTCAGAAGACAACTTATTGAATTTAATCCCAGCCATTTTCA

AAGTGCTGTGCCAACTACTCGTACTAAAAAGAGTTACGAAATGAATGGGCGTGAGTAT

CACTATGTGTCCAAGGAAACATTTGAAAACCTCATATATAGTCACAGGATGCTGGAGT

ATGGTGAGTACAAAGGCCACCTGTATGGCACTAGTGTGGATGCTGTTCAAACAGTCCT

TGTCGAAGGAAAGATCTGTGTCATGGACCTAGAGCCTCAGGATATTCAAGGGGTTCGA

ACCCATGAACTGAAGCCCTATGTCATATTTATAAAGCCATCGAATATGAGCTGTATGA

AACAATCTCGGAAAAATGCCAAGGTTATTACTGACTACTATGTGGACATGAAGTTCAA

GGATGAAGACCTACAAGAGATGGAAAATTTAGCCCAAAGAATGGAAACTCAGTTTGGC

CAATTTTTTGATCATGTGATTGTGAATGACAGCTTGCACGATGCATGTGCCCAGTTGT

TGTCTGCCATACAGAAGGCTCAGGAGGAGCCTCAGTCGGTACCAGCAACATGGATTTC

CTCAGATACTGAGTCTCAATGAGACTTCTTGTTTAATGCTGGAGTTTTAACACTGIAC

CCTTGATACAGCGATCCATAG
```

ORF Start: ATG at 22          ORF Stop: TGA at 1876
SEQ ID NO:14                  618 aa MW at 70539.2 kD NOV4c, CG56832-03 Protein Sequence

MIQSDKGADPPDKKDMKLSTATNPQNGLSQILRLVLQELSLFYGRDVNGVCLLYDLLH

SPWLQALLKIYDCLQEFKEKKLVPATPHAQVLSYEVVELLRETPTSPEIQELRQMLQA

PHFKALLSAHDTIAQKDFEPLLPPLPDNIPESEEAMRIVCLVKMQQPLGATIKRHEMT

GDILVARIIHGGLAERSGLLYAGDKLVEVNGVSVEGLDPEQVIHILAMSRGTIMFKVV

PVSDPPVNSQQMVYVRAMTEYWPQEDPDIPCMDAGLPFQKGDILQIVDQNDALWWQAR

KISDPATCAGLVPSNHLLKRKQREFWWSQPYQPHTCLKSTLEDDMKIDEKCVFADKEE

FVGYGQKFFIAGFRRSMRLCRRKSHLSPLHASVCCTGSCYSAVGAPYEEVVRYQRRPS

DKYRLIVLMGPSGVGVNELRRQLIEFNPSHFQSAVPTTRTKKSYEMNGREYHYVSKET

FENLIYSHRMLEYGEYKGHLYGTSVDAVQTVLVEGKICVMDLEPQDIQGVRTHELKPY

VIFIKPSNMRCMKQSRKNAKVITDYYVDMKFKDEDLQEMENLAQRMETQFGQFFDHVI

VNDSLHDACAQLLSAIQKAQEEPQWVPATWISSDTESQ

Sequence comparison of the above protein sequences yields the following sequence relationships shown in Table 4B.

TABLE 4B

Comparison of NOV4a against NOV4b and NOV4c.

| Protein Sequence | NOV4a Residues/ Match Residues | Identities/ Similarities for the Matched Region |
|---|---|---|
| NOV4b | 1 ... 440 | 439/455 (96%) |
|  | 1 ... 455 | 439/455 (96%) |
| NOV4c | 1 ... 440 | 437/468 (93%) |
|  | 152 ... 618 | 437/468 (93%) |

Further analysis of the NOV4a protein yielded the following properties shown in Table 4C.

TABLE 4C

Protein Sequence Properties NOV4a

| PSort analysis: | 0.6500 probability located in cytoplasm; 0.1000 probability located in mitochondrial matrix space; 0.1000 probability located in lysosome (lumen); 0.0587 probability located in microbody (peroxisome) |
| SignalP analysis: | No Known Signal Sequence Predicted |

A search of the NOV4a protein against the Geneseq database, a proprietary database that contains sequences published in patents and patent publication, yielded several homologous proteins shown in Table 4D.

TABLE 4D

Geneseq Results for NOV4a

| Geneseq Identifier | Protein/Organism/Length [Patent #, Date] | NOV4a Residues/ Match Residues | Identities/ Similarities for the Matched Region | Expect Value |
|---|---|---|---|---|
| AAE11774 | Human kinase (PKIN)-8 protein-*Homo sapiens*, 442 aa. [WO200181555-A2, 01-Nov-2001] | 1 . . . 440<br>1 . . . 442 | 437/442 (98%)<br>438/442 (98%) | 0.0 |
| AAU07123 | Human novel human protein, NHP #23-*Homo sapiens*, 576 aa. [WO200161016-A2, 23-AUG-2001] | 1 . . . 435<br>137 . . . 576 | 195/443 (44%)<br>292/443 (65%) | e−105 |
| AAU07119 | Human novel human protein, NHP #19-*Homo sapiens*, 560 aa. [WO200161016-A2, 23-AUG-2001] | 1 . . . 407<br>137 . . . 548 | 186/415 (44%)<br>278/415 (66%) | 2e−99 |
| AAU07115 | Human novel human protein, NHP #15-*Homo sapiens*, 520 aa. [WO200161016-A2, 23-AUG-2001] | 1 . . . 367<br>137 . . . 505 | 167/372 (44%)<br>254/372 (67%) | 5e−90 |
| AAU07111 | Human novel human protein, NHP #11-*Homo sapiens*, 473 aa. [WO200161016-A2, 23-AUG-2001] | 1 . . . 330<br>137 . . . 468 | 149/335 (44%)<br>225/335 (66%) | 3e−78 |

In a BLAST search of public sequence datbases, the NOV4a protein was found to have homology to the proteins shown in the BLASTP data in Table 4E.

TABLE 4E

Public BLASTP Results for NOV4a

| Protein Accession Number | Protein/Organism/Length | NOV4a Residues/ Match Residues | Identities/ Similarities for the Matched Portion | Expect Value |
|---|---|---|---|---|
| Q96JB8 | MEMBRANE PROTEIN PALMITOYLATED 4-*Homo sapiens* (Human), 637 aa. | 1 . . . 440<br>152 . . . 637 | 438/486 (90%)<br>438/486 (90%) | 0.0 |
| Q96Q44 | ALS2CR5 PROTEIN-*Homo sapiens* (Human), 593 aa. | 1 . . . 440<br>152 . . . 593 | 426/455 (93%)<br>426/455 (93%) | 0.0 |
| Q9QYH1 | DLG6 ALPHA-*Rattus norvegicus* (Rat), 441 aa. | 1 . . . 439<br>1 . . . 441 | 363/441 (82%)<br>395/441 (89%) | 0.0 |
| Q920P7 | MDLG6B-*Mus musculus* (Mouse), 479 aa. | 1 . . . 439<br>1 . . . 479 | 369/479 (77%)<br>399/479 (83%) | 0.0 |
| Q9QYG9 | DLG6 GAMMA-*Rattus norvegicus* (Rat), 423 aa. | 1 . . . 439<br>1 . . . 423 | 348/441 (78%)<br>380/441 (85%) | 0.0 |

PFam analysis predicts that the NOV4a protein contains the domains shown in the Table 4F.

TABLE 4F

Domain Analysis of NOV4a

| Pfam Domain | NOV4a Match Region | Identities/ Similarities for the Matched Region | Expect Value |
|---|---|---|---|
| PDZ: domain 1 of 1 | 3 . . . 83 | 25/84 (30%)<br>59/84 (70%) | 4.3e−09 |
| SH3: domain 1 of 1 | 94 . . . 159 | 19/68 (28%)<br>47/68 (69%) | 0.002 |
| Guanylate_kin: domain 1 of 1 | 266 . . . 370 | 40/108 (37%)<br>79/108 (73%) | 1e−32 |
| I_LWEQ: domain 1 of 1 | 403 . . . 420 | 6/18 (33%)<br>15/18 (83%) | 6.3 |

Example 5

The NOV5 clone was analyzed, and the nucleotide and encoded polypeptide sequences are shown in Table 5A.

TABLE 5A

NOV5 Sequence Analysis

| | |
|---|---|
| NOV5a,<br><br>CG58618-01 DNA Sequence | SEQ ID NO:15        894 bp<br>ACACAAATAGGCAAATTGTGGGTATGGGATTCCCTCCCTACCTCCCTCCACCCCAGGG<br>CCCAGGTAGCGACCATGTCCCTGCCATTGCATTGGCCTTCCTGCCACTGGTGGTAAC<br>ATTGCTGGTCCGGTACCCGCACTACTTCCCATTCCTGGTGCGCACGGTCTTGCTGCGA<br>AGCCTCCGAGACTGCCTGTCAGGGCTGCGGATCGAGGACCCGGCCTTCAGCPACGTGC<br>TCACCCATGCCCTGCCCGGTGACCCTGGTCACATCCTCACCACCCTGGACCACTGGAG<br>CAGCCGCTGCCAGTACTTGAGCCACATCGGGCCTGTCAAAGGTCAGATCCTGATGCGG<br>CTGGTGGAGGAGAAGGCCCCTGCTTGTGTGCTGGAATTGGGAACCTACTCTGCATACT<br>CTACCCTGCTTATTGCCCGAGCCCTGCCCCCTGCGCGTCGCCTTCTTACTGTGGAGCG<br>GGACCCACGCACGGCAGCAGTGGCTGAAAAACTCATCCGCCTGGCCGGCTTTGATGAG<br>CACCACGTGGAGCTCATCCTGGGCAGCTCACAGGACGTCATCCCGTGCCTACGCACCC<br>AGTATCAGCTCAGTCCCCAGACCTCCTCCTCCTGGCACACCGGCCACGATGTTACCT<br>GAGGGACCTGCAGCTGCTGGAGGCCCATGCCCTACTGCCAGCACGTGCCACCGTGCTG<br>GCTGACCATGTGCTCTTCCCTGGTGCACCCCGCTTCTTGCAGTATGCTAAGAGCTGTG<br>GCCGCTACCGCTGCCGCCTCCACCACACTGCCTTCCAGACTTCCCTGCCATCAAGGA<br>TGGAATAGCTCAGCTCACCTATCCTGGACCAGGCTGAGGTCCACGCCCAGCGGTACTT<br>ACTGATGCCCACCCCCACCCCCAC |
| | ORF Staff: ATG at 73     ORF Stop: TGA at 847<br>SEQ ID NO:16        258 aa MW at 28694.2 kD |
| NOVA5a,<br><br>CG58618-01 Protein Sequence | MSPAIALAFLPLVVTLLVRYRHYFRLLVRTVLLRSLRDCLSGLRIEERAFSYVLTHAL<br>PGDPGHILTTLDHWSSRCEYLSHMGPVKGQILMRLVEEKAPACVLELGTYCGYSTLLI<br>ARALPPGGRLLTVERDPRTAAVAEKLIRLAGFDEHQVELIVGSSEDVIPCLRTQYQLS<br>RADLVLLAHRPRCYLRDLQLLEAHALLPAGATVLADHVLFPGAPRFLQYAKSCGRYRC<br>RLHHTGLPDFPAIKDGIAQLTYAGPG |
| NOV5b,<br><br>CG5818-02 DNA Sequence | SEQ ID NO:17 897 bp<br>AAATAGGCAAATTGTGGGTATGGGATTCCCTCCCTACCTCCCTCCACCCCAGGGCCCA<br>GGTAGGGACCATGTCCCTGCCATTGCATTGGCCTTCCTGCCACTGGTGGTAACATTG<br>CTGGTGCGGTACCGGCACTACTTCCGATTGCTGGTGCGCACGGTCTTGCTGCGAAGCC<br>TCCGAGACTGCCTGTCAGGGCTGCGGATCGAGGACCGGGCCTTCAGCTACGTGCTCAC<br>CCATGCCCTGCCCGGTGACCCTGGTCACATCCTCACCACCCTGGACCACTGGAGCAGC<br>CGCTGCGAGTACTTGAGCCACATGGGGCCTGTCAAAGGTCAGATCCTGATGCGGCTGG<br>TGGAGGAGAAGGCCCCTCCTTGTGTGCTGGAATTGGGAACCTACTCTCGATACTCTAC<br>CCTGCTTATTGCCCGAGCCCTGCCCCCTGGGGTCGCCTTCTTACTGTGGAGCGGGAC<br>CCACGCACGCCAGCAGTCCCTGAAAAACTCATCCGCCTCCCCGGCTTTGATGACCACA<br>TGGTGGAGCTCATCGTGGGCAGCTCAGAGGACGTGATCCCGTGCCTACGCACCCAGTA<br>TCAGCTGAGTCGGGCAGACCTGGTGCTCCTGGCACACCGGCCACGATGTTACCTGAGG<br>GACCTGCAGCTGCTGGAGGCCCATGCCCTACTGCCAGCACGTGCCACCGTGCTGGCTG<br>ACCATGTGCTCTTCCCTGGTGCACCCCGCTTCTTGCAGTATGCTAAGAGCTGTGGCCG<br>CTACCGCTGCCGCCTCCACCACACTGGCCTTCCAGACTTCCCCGCCATCAAGGATGGA<br>ATAGCTCAGCTCACCTATGCTGGACCAGGCTGAGGTCCAGGCCCAGGGGTACTTACTG<br>ATGCCCACCCCCACAATTTGCCTATTT |

TABLE 5A-continued

NOV5 Sequence Analysis

| | |
|---|---|
| NOV5b, | ORF Staff: ATG at 69     ORF Stop: TGA at 843 |
| | SEQ ID NO:18     258 aa MW at 28697.3 kD |
| | MSPAIALAFLPLVVTLLVRYRHYFRLLVRTVLLRSLEDCLSGLRIEERAFSYVLTHAL |
| CG58618-02 Protein Sequence | PGDPGHILTTLDHWSSRCEYLSHMGPVKGQILMRLVEEKAPACVLELGTYCGYSTLLI |
| | ARALPPGGRLLTVERDPRTAAVAEKLIRLAGFDEHMVELIVGSSEDVIPCLRTQYQLS |
| | RADLVLLAHRPRCYLRDLQLLEAHALLPAGATVLADHVLFPGAPRFLQYAKSCGRYRC |
| | RLHHTGLPDFPAIKDGIAQLTYAGPG |

Sequence comparison of the above protein sequences yields the following sequence relationships shown in Table 5B.

TABLE 5B

Comparison of NOV5a against NOV5b.

| Protein Sequence | NOV5a Residues/ Match Residues | Identities/ Similarities for the Matched Region |
|---|---|---|
| NOV5b | 1 . . . 258 | 244/258 (94%) |
| | 1 . . . 258 | 244/258 (94%) |

Further analysis of the NOV5a protein yielded the following properties shown in Table 5C.

TABLE 5C

Protein Sequence Properties NOV5a

| | |
|---|---|
| PSort analysis: | 0.8200 probability located in endoplasmic reticulum (membrane); 0.1900 probability located in plasma membrane; 0.1000 probability located in endoplasmic reticulum (lumen); 0.1000 probability located in outside |
| SignalP analysis: | Cleavage site between residues 42 and 43 |

A search of the NOV5a protein against the Geneseq database, a proprietary database that contains sequences published in patents and patent publication, yielded several homologous proteins shown in Table 5D.

TABLE 5D

Geneseq Results for NOV5a

| Geneseq Identifier | Protein/Organism/Length [Patent #, Date] | NOV5a Residues/ Match Residues | Identities/ Similarities for the Matched Region | Expect Value |
|---|---|---|---|---|
| AAE07183 | Catechol-O-methyltransferase-like human enzyme #1-*Homo sapiens*, 258 aa. [WO200157220-A2, 09-AUG-2001] | 1 . . . 258<br>1 . . . 258 | 257/258 (99%)<br>257/258 (99%) | e-148 |
| AAE07184 | Catechol-O-methyltransferase-like human enzyme #2-*Homo sapiens*, 168 aa. [WO200157220-A2, 09-AUG-2001] | 91 . . . 258<br>1 . . . 168 | 167/168 (99%)<br>167/168 (99%) | 6e-94 |
| AAW70989 | Murine catechol-O-methyltransferase (COMT)-Mus sp, 265 aa. [WO9832878-A1, 30-JUL-1998] | 4 . . . 258<br>5 . . . 259 | 93/257 (36%)<br>149/257 (57%) | 5e-43 |
| AAB43663 | Human cancer associated protein sequence SEQ ID NO: 1108-*Homo sapiens*, 299 aa. [WO200055350-A1, 21-SEP-2000] | 4 . . . 258<br>38 . . . 294 | 94/259 (36%)<br>151/259 (58%) | 7e-42 |
| AAW70988 | Human catechol-O-methyltransferase (COMT)-*Homo sapiens*, 271 aa. [WO9832878-A1, 30-JUL-1998] | 4 . . . 258<br>10 . . . 266 | 94/259 (36%)<br>151/259 (58%) | 7e-42 |

In a BLAST search of public sequence datbases, the NOV5a protein was found to have homology to the proteins shown in the BLASTP data in Table 5E.

TABLE 5E

Public BLASTP Results for NOV5a

| Protein Accession Number | Protein/Organism/Length | NOV5a Residues/ Match Residues | Identities/ Similarities for the Matched Portion | Expect Value |
|---|---|---|---|---|
| Q91XH4 | CATECHOL-O-METHYLTRANSFERASE-*Mus musculus*(Mouse), 265 aa. | 4 ... 258 5 ... 259 | 94/257 (36%) 150/257 (57%) | 3e−43 |
| O88587 | Catechol O-methyltransferase, membrane-bound form (EC 2.1.1.6) (MB-COMT) [Contains: Catechol O-methyltransferase, soluble form (S-COMT)]-*Mus musculus*(Mouse), 265 aa. | 4 ... 258 5 ... 259 | 93/257 (36%) 149/257 (57%) | 1e−42 |
| P21964 | Catechol O-methyltransferase, membrane-bound form (EC 2.1.1.6) (MB-COMT) [Contains: Catechol O-methyltransferase, soluble form (S-COMT)]-*Homo sapiens*(Human), 271 aa. | 4 ... 258 10 ... 266 | 94/259 (36%) 151/259 (58%) | 2e−41 |
| P22734 | Catechol O-methyltransferase, membrane-bound form (EC 2.1.1.6) (MB-COMT) [Contains: Catechol O-methyltransferase, soluble form (S-COMT)]-*Rattus norvegicus*(Rat), 264 aa. | 4 ... 257 5 ... 258 | 91/256 (35%) 151/256 (58%) | 2e−41 |
| Q99028 | Catechol-O-methyltransferase, soluble form (EC 2.1.1.6) (S-COMT)-*Sus scrofa*(Pig), 186 aa (fragment). | 77 ... 258 2 ... 181 | 77/182 (42%) 116/182 (63%) | 2e−36 |

PFam analysis predicts that the NOV5a protein contains the domains shown in the Table 5F.

TABLE 5F

Domain Analysis of NOV5a

| Pfam Domain | NOV5a Match Region | Identities/ Similarities for the Matched Region | Expect Value |
|---|---|---|---|
| Methyltransf_3: domain 1 of 1 | 55 ... 252 | 49/218 (22%) 109/218 (50%) | 8.9e−05 |

Example 6

The NOV6 clone was analyzed, and the nucleotide and encoded polypeptide sequences are shown in Table 6A.

TABLE 6A

NOV6 Sequence Analysis

| NOV6a, CG59580-01 DNA Sequence | SEQ ID NO:19 1115 bp<br>TCTTGACTGTAGAATATAAGTGAGAATATTTCTGATATGTTTGTAATGCATGCTTGTG<br>TCATGTTCTCTTTCTCTCTCTTTTGGAAGTCACATCAACAAGATGAAACCAGGGAATG<br>AGACACAAATTTCACAATTCCTTCTCCTGGGACTTTCAGAGGAACCAGAATTGCAGCC<br>CTTCCTCTTTGGGCTATTTCTGTCCATGTACCTGGTCACCGTGCTCGGGAACCTGCTC<br>ATCATCCTGGCCACAATCTCAGACTCCCACCTCCACACCCCCATGTACTTCTTCCTCT<br>CCAACCTGTCCTTTGCAGACATCTGTTTTGTGTCTACCACTGTCCCAAAGATGCTGGT<br>GAACATCCAGACAGAGAGCAGAGTCATCACCTATGCAGACTGCATCACCCAGATGTGC<br>TTTTTTATACTCTTTGTAGTGTTGGACAGCTTACTCCTGACTGTGATGGCCTATGACC |
|---|---|

TABLE 6A-continued

NOV6 Sequence Analysis

|  |  |
|---|---|
|  | GGTTTGTGGCCATCTGTCACCCCCTGCACTACACAGTCATTATGAACTCCTGGCTCTG |
|  | TGGACTGCTGGTTCTGGTGTCCTGGATCGTGAGCATCCTATATTCTCTGTTACAAAGC |
|  | ATAATGGCATTGCAGCTGTCCTTCTGTACAGAATTGAAAATCCCTCATTTTTTCTGTG |
|  | AACTTAATCAGGTCATCCACCTTGCCTGTTCCGACACTTTTATTAATGACATGATCAT |
|  | GAATTTTACAAGTGTGCTGCTGGGTGGGGGATGCCTCGCTGGAATATTTACTTACTTT |
|  | AAGATACTTTGTTGCATATGTTCGATCTCATCAGCTCAGGGGATGAATAAAGCACTTT |
|  | CCACCTGTGCATCTCACCTCTCAGTTGTCTCCTTATTTTATTGTACAGGCGTAGGTGT |
|  | GTACCTTAGTTCTGCTGCAACCCATAACTCACTCTCAAATGCTGCAGCCTCGGTGATG |
|  | TACACTGTGGTCACCTCCATGCTCAACCCCTTCATCTACAGCCTGAGGAATAAAGACA |
|  | TAAACAGAGCTCTGAATCGATTCTTCAGAGAGCAGAAACAGGAGGGCCATTTTCCAGA |
|  | AGTTCTTGAGATTTCAGAGCTCTAAATCCCCTAGCCAGAAATTATGATTCATGGATCA |
|  | GATTGTGAAAGTA |
| NOV6a, | ORF Start: ATG at 50        ORF Stop: TAA at 1067 |
|  | SEQ ID NO:20               339 aa MW at 37821.1 kD |
| CG59580-01 Protein Sequence | MLVSCSLSLSFGSHINKMKPGNETQISQFLLLGLSEEPELQPFLFGLFLSMYLVTVLG |
|  | NLLIILATISDSHLHTPMYFFLSNLSFADICFVSTTVPKMLVNIQTQSRVITYADCIT |
|  | QMCFFILFVVLDSLLLTVMAYDRFVAICHPLHYTVIMNSWLCCLLVLVSWIVSILYSL |
|  | LQSIMALQLSFCTELKIPHFFCELNQVIHLACSDTFINDMMMNFTSVLLGGGCLAGIF |
|  | TYFKILCCICSISSAQCMNKALSTCASELSVVSLFYCTGVCVYLSSAATHNSLSNAAA |
|  | SVMYTVVTSMLNPFIYSLRNKDINRALNRFFREOKQEGHFPEVLEISEL |

Further analysis of the NOV6a protein yielded the following properties shown in Table 6B.

TABLE 6B

Protein Sequence Properties NOV6a

| | |
|---|---|
| PSort analysis: | 0.6000 probability located in plasma membrane; 0.4000 probability located in Golgi body; 0.3000 probability located in endoplasmic reticulum (membrane); 0.3000 probability located in microbody (peroxisome) |
| SignalP analysis: | Cleavage site between residues 69 and 70 |

A search of the NOV6a protein against the Geneseq database, a proprietary database that contains sequences published in patents and patent publication, yielded several homologous proteins shown in Table 6C.

TABLE 6C

Geneseq Results for NOV6a

| Geneseq Identifier | Protein/Organism/Length [Patent #, Date] | NOV6a Residues/ Match Residues | Identities/ Similarities for the Matched Region | Expect Value |
|---|---|---|---|---|
| AAG72100 | Human olfactory receptor polypeptide, SEQ ID NO: 1781-*Homo sapiens*, 314 aa. [WO200127158-A2, 19-APR-2001] | 18 ... 330<br>1 ... 314 | 312/314 (99%)<br>313/314 (99%) | e-179 |
| AAG72195 | Human olfactory receptor polypeptide, SEQ ID NO: 1876-*Homo sapiens*, 309 aa. [WO200127158-A2, 19-APR-2001] | 18 ... 322<br>1 ... 306 | 244/306 (79%)<br>267/306 (86%) | e-136 |

TABLE 6C-continued

Geneseq Results for NOV6a

| Geneseq Identifier | Protein/Organism/Length [Patent #, Date] | NOV6a Residues/ Match Residues | Identities/ Similarities for the Matched Region | Expect Value |
|---|---|---|---|---|
| ABG29229 | Novel human diagnostic protein #29220-*Homo sapiens*, 788 aa. [WO200175067-A2, 11-OCT-2001] | 16 . . . 322 478 . . . 785 | 239/308 (77%) 264/308 (85%) | e−133 |
| ABG26552 | Novel human diagnostic protein #26543-*Homo sapiens*, 379 aa. [WO200175067-A2, 11-OCT-2001] | 16 . . . 322 69 . . . 376 | 239/308 (77%) 264/308 (85%) | e−133 |
| ABG29229 | Novel human diagnostic protein #29220-*Homo sapiens*. 788 aa. [WO200175067-A2, 11-OCT-2001] | 16 . . . 322 478 . . . 785 | 239/308 (77%) 264/308 (85%) | e−133 |

In a BLAST search of public sequence datbases, the NOV6a protein was found to have homology to the proteins shown in the BLASTP data in Table 6D.

TABLE 6D

Public BLASTP Results for NOV6a

| Protein Accession Number | Protein/Organism/ Length | NOV6a Residues/ Match Residues | Identities/ Similarities for the Matched Portion | Expect Value |
|---|---|---|---|---|
| O14581 | Olfactory receptor 7A17-*Homo sapiens* (Human), 309 aa. | 18 . . . 322 1 . . . 306 | 244/306 (79%) 267/306 (86%) | e−136 |
| O76100 | Olfactory receptor 7A10 (OST027)-*Homo sapiens*(Human), 309 aa. | 18 . . . 322 1 . . . 306 | 238/306 (77%) 262/306 (84%) | e−132 |
| Q15622 | Olfactory receptor 7A5 (Olfactory receptor TPCR92)-*Homo sapiens* (Human), 319 aa. | 18 . . . 330 1 . . . 314 | 232/314 (73%) 260/314 (81%) | e−127 |
| Q95157 | Olfactory receptor-like protein OLF4-*Canis familiaris* (Dog), 309 aa. | 18 . . . 322 1 . . . 306 | 216/306 (70%) 254/306 (82%) | e−121 |
| Q9JHB2 | M12 ODORANT RECEPTOR-*Mus musculus*(Mouse), 309 aa. | 18 . . . 324 1 . . . 308 | 220/308 (71%) 258/308 (83%) | e−121 |

PFam analysis predicts that the NOV6a protein contains the domains shown in the Table 6E.

TABLE 6E

Domain Analysis of NOV6a

| Pfam Domain | NOV6a Match Region | Identities/ Similarities for the Matched Region | Expect Value |
|---|---|---|---|
| Bac_export_3: domain 1 of 1 | 138 . . . 221 | 18/87 (21%) 52/87 (60%) | 8.4 |
| 7tm_1:domain 1 of 1 | 58 . . . 306 | 55/269 (20%) 182/269 (68%) | 5.9e−38 |

Example 7

The NOV7 clone was analyzed, and the nucleotide and encoded polypeptide sequences are shown in Table 7A.

TABLE 7A

NOV7 Sequence Analysis

NOV7a,
CG59611-01 DNA
Sequence

SEQ ID NO:21   982 bp

```
ATGAATGGAGGGGTTTAACTATTCCAGAGTATCTGAATTCATGTTACTTGGACTTACT
GATTCTCCTGAACTCCAGATATTCTTTTTTGTGGTGTTTTCTGTCTTCTATTTAATGA
CCATGTTGGGCAACTGCCTGATTTTACTCACTGTCCTATCCACCTCACACCTTCACTC
TCGCACGTACTTCCTGCTCAGCAACCTGTCTCATATTGACATGTGCCTGTCCTCCTTT
GCCACACCAAAGATGATTATGGACTTTTTGCTCTGCGTAAGACCATCTCTTTTGAAG
GCTGCATTTCTCAGATCTTTTTTTTACACCTCTTCAATGGGACTGAGATTGTGCTGCT
GATCTCCATGTCTTTTGACAGGTATATTGCCATATGTAAACCTCTCCGCTATTCAACA
ATTATGAGCCAAAGAGTGTGTGTTGAGCTTGTGGCAGTTTCTTGTTGGACAGTGGGCT
```

TABLE 7A-continued

NOV7 Sequence Analysis

```
TTCTACATACAATGAGCCAATTAAGTTTTTCCCTCTATTTGCCCTTCTGTGTTCCCAA
TGTTGTAGACAGTTTTTTCTGTGATCTTCCTTTGGTCATCCAGTTAGCTTGTATAGAT
ATTTATGTTCTTGGGACCTCCATGATTTCAACCAGTGGTGTGACTGCTCTTACAAGTT
TTCTGCTTTTGCTCACCTCCTACATCATTGTTCTTAATACTATCAGGGACTACTCCTC
CACAGGATCCTCCAAGGCTCTTTCTACCTGTACAGCACATTTTATTGTTCTGTTAATG
TTCTTTGGGCCCTGTATTTTCATTTATGTGTGGCCTTCCACAAACTTCCTGGTAGACA
AAATTCTCTCTGTTTTCTATACCATCTTCACTCCCTTTCTGAATCCACTTATCTATAC
TTTGAGAAACCAGGAAGTGAAGACAGCAATGAAGAAGAAACTGAATATTCAGTATTTC
AGTCTTGGGAAAACTGCTCCGTGATACTTCATGCAATGAATAGCGATCTCCTTT
```

| | | |
|---|---|---|
| | ORF Start: ATG at 5 | ORF Stop: TGA at 950 |
| | SEQ ID NO:22 | 315 aa MW at 35742.0 kD |
| NOV7a, | MEGFNYSRVDEFMLLGLTDSPELQIFFFVVFSVFYLMTMLGNCLILLTVLSTSHLHSR | |
| CG59611-01 Protein Sequence | TYFLLSNLSHIDMCLSSFATPKMIMDFFALRKTISFEGCISQIFFLHLFNGTEIVLLI | |
| | SMSFDRYIAICKPLRYSTIMSQRVCVELVAVSCWTVQFLHTMSQLSFSLYLPFCVPNV | |
| | VDSFFCDLPLVIQLACIDIYVLGTSMISTSGVTALTSFLLLLTSYIIVLNTIRDYSST | |
| | GSSKALSTCTAHFIVVLMFFGPCIFIYVWPSTNFLVDKILSVFYTIFTPFLNPLIYTL | |
| | RNQEVKTAMKKKLNIQYFSLGKTAP | |

Further analysis of the NOV7a protein yielded the following properties shown in Table 7B.

TABLE 7B

Protein Sequence Properties NOV7a

| | |
|---|---|
| PSort analysis: | 0.6000 probability located in plasma membrane; 0.4000 probability located in Golgi body; 0.3000 probability located in endoplasmic reticulum (membrane); 0.3000 probability located in microbody (peroxisome) |

TABLE 7B-continued

Protein Sequence Properties NOV7a

| | |
|---|---|
| SignalP analysis: | Cleavage site between residues 52 and 53 |

A search of the NOV7a protein against the Geneseq database, a proprietary database that contains sequences published in patents and patent publication, yielded several homologous proteins shown in Table 7C.

TABLE 7C

Geneseq Results for NOV7a

| Geneseq Identifier | Protein/Organism/Length [Patent #, Date] | NOV7a Residues/ Match Residues | Identities/ Similarities for the Matched Region | Expect Value |
|---|---|---|---|---|
| AAG71880 | Human olfactory receptor polypeptide, SEQ ID NO: 1561-*Homo sapiens*, 314 aa. [WO200127158-A2, 19-APR-2001] | 1 . . . 315<br>1 . . . 314 | 312/315 (99%)<br>313/315 (99%) | e−178 |
| AAG72471 | Human OR-like polypeptide query sequence, SEQ ID NO: 2152-*Homo sapiens*, 314 aa. [WO200127158-A2, 19-APR-2001] | 1 . . . 315<br>1 . . . 314 | 304/315 (96%)<br>307/315 (96%) | e−173 |
| AAG71767 | Human olfactory receptor polypeptide, SEQ ID NO: 1448-*Homo sapiens*. 314 aa. [WO200127158-A2, 19-APR-2001] | 1 . . . 315<br>1 . . . 314 | 304/315 (96%)<br>307/315 (96%) | e−173 |
| AAG71495 | Human olfactory receptor polypeptide, SEQ ID NO: 1176-*Homo sapiens*, 313 aa. [WO200127158-A2, 19-APR-2001] | 1 . . . 315<br>1 . . . 313 | 294/315 (93%)<br>299/315 (94%) | e−164 |

TABLE 7C-continued

Geneseq Results for NOV7a

| Geneseq Identifier | Protein/Organism/Length [Patent #, Date] | NOV7a Residues/ Match Residues | Identities/ Similarities for the Matched Region | Expect Value |
|---|---|---|---|---|
| AAG71508 | Human olfactory receptor polypeptide, SEQ ID NO: 1189-*Homo sapiens*, 291 aa. [WO200127158-A2, 19-APR-2001] | 1 . . . 292<br>1 . . . 291 | 280/292 (95%)<br>283/292 (96%) | e-159 |

In a BLAST search of public sequence datbases, the NOV7a protein was found to have homology to the proteins shown in the BLASTP data in Table 7D.

TABLE 7D

Public BLASTP Results for NOV7a

| Protein Accession Number | Protein/Organism/ Length | NOV7a Residues/ Match Residues | Identities/ Similarities for the Matched Portion | Expect Value |
|---|---|---|---|---|
| AAL61393 | OLFACTORY RECEPTOR MOR246-5-*Mus musculus* (Mouse), 326 aa. | 1 . . . 315<br>1 . . . 314 | 262/315 (83%)<br>278/315 (88%) | e-147 |
| AAL61267 | OLFACTORY RECEPTOR MOR247-1-*Mus musculus* (Mouse), 318 aa. | 5 . . . 301<br>6 . . . 301 | 205/297 (69%)<br>252/297 (84%) | e-118 |
| AAL61437 | OLFACTORY RECEPTOR MOR246-2-*Mus musculus* (Mouse), 324 aa. | 1 . . . 314<br>1 . . . 312 | 193/314 (61%)<br>247/314 (78%) | e-109 |
| AAL61440 | OLFACTORY RECEPTOR MOR246-4-*Mus musculus* (Mouse), 321 aa. | 5 . . . 314<br>5 . . . 312 | 188/310 (60%)<br>239/310 (76%) | e-107 |
| AAL61478 | OLFACTORY RECEPTOR MOR246-6-*Mus musculus* (Mouse), 323 aa. | 1 . . . 301<br>1 . . . 300 | 180/301 (59%)<br>234/301 (76%) | e-105 |

PFam analysis predicts that the NOV7a protein contains the domains shown in the Table 7E.

TABLE 7E

Domain Analysis of NOV7a

| Pfam Domain | NOV7a Match Region | Identities/ Similarities for the Matched Region | Expect Value |
|---|---|---|---|
| 7tm_1: domain 1 of 1 | 41 . . . 288 | 51/276 (18%)<br>174/276 (63%) | 3.3e-19 |

Example 8

The NOV8 clone was analyzed, and the nucleotide and encoded polypeptide sequences are shown in Table 8A.

TABLE 8A

NOV8 Sequence Analysis

| NOV8a, CG59617-01 DNA Sequence | SEQ ID NO:23    963 bp<br>CTGCAAAAAGACATGGGAAAGACCAAAAACACATCGCTGGACACTGTGGTGAGAGATT<br>TCATTCTTCTGGGTTTGTCTCACCCCCCGAATATAAGAAGCCTCCTCTTCCTGGTCTT<br>CTTCGTCATTTACATCCTCACTCAGCTGGGGAACCTGCTCATTCTGCTCACCGTGTGG<br>GCTGACCCGAAGCTCCGTGCTCGCCCCATGTACATTCTTCTGGGAGTGCTCTCATTCC<br>TGGACATGTGGCTCTCCTCAGTCATCGTTCCTGGAATTATTTTAAACTTCACTCCTGC<br>CAACAAGGCTATCCCGTTTGGTGGCTGTGTGGCTCAACTGTATTTCTTTCACTTCCTG<br>GGCAGCACCCAGTGCTTCCTCTACACCTTGATGGCCTATGACAGGTACCTGGCAATAT<br>GTCAGCCCCTGCGCTACCCAGTGCTCATGAATGGGAGGTTATGCACAGTCCTTGTGGC<br>TGGAGCTTGGGTCGCCGGCTCCATGCATGGGTCTATCCAGGCCACCCTGACCTTCCGC<br>CTGCCCTACTGTGGGCCCAATCAGGTAGATTACTTTATCTGTGACATCCCCGCAGTAT |
|---|---|

TABLE 8A-continued

NOV8 Sequence Analysis

|  |  |
|---|---|
|  | TGAGACTGGCCTGTGCTGACACAACTGTCAATGAGCTTGTGACCTTTGTGGACATCGG |
|  | GGTAGTGGCCGCCAGTTGCTTCATGTTAATTCTGCTCTCGTATGCCAACATAGTAAAT |
|  | GCCATCCTGAAGATACGCACCACTGATGGGAGGCGCCGGGCCTTCTCCACCTGTGGCT |
|  | CCCACCTAATCGTGGTCACAGTCTACTATGTCCCCTGTATTTTCATCTACCTTAGGGC |
|  | TGGCTCCAAAGGCCCCCTGGATGGGGCAGCGGCTGTGTTTTACACTGTTGTCACTCCA |
|  | TTACTGAACCCCCTCATCTATACACTGAGGAACCAGGAAGTGAAGTCTGCCCTGAAGA |
|  | GGATAACAGCAGGTCAAGGGACTGAATGAAAATAA |
| NOV8a, | ORF Start: ATG at 13  ORF Stop: at 853 |
|  | SEQ ID NO:24  280 aa MW at 30929.4 kD |
|  | MGKTKNTSLDTVVRDFILLGLSHPPNIRSLLFLVFFVIYILTQLGNLLILLTVWADPK |
| CG59617-01 Protein Sequence | LRARPMYILLGVLSFLDMWLSSVIVPGIILNFTPANKAIPFGGCVAQLYFFHFLGSTQ |
|  | CFLYTLMAYDRYLAICQPLRYPVLMNGRLCTVLVAGAWVAGSMHGSIQATLTFRLPYC |
|  | GPNQVDYFICDIPAVLRLACADTTVNELVTFVDIGVVAASCFMLILLSYANIVNAILK |
|  | IRTTDGRRRAFSTCGSHLIVVTVYYVPCIF1YLRAGSKGPLDGAAAVF |

Further analysis of the NOV8a protein yielded the following properties shown in Table 8B.

TABLE 8B

Protein Sequence Properties NOV8a

| PSort analysis: | 0.6000 probability located in plasma membrane; 0.4000 probability located in Golgi body; 0.3000 probability located in endoplasmic reticulum (membrane); 0.3000 probability located in microbody (peroxisome) |
|---|---|

TABLE 8B-continued

Protein Sequence Properties NOV8a

| SignalP analysis: | Cleavage site between residues 56 and 57 |
|---|---|

A search of the NOV8a protein against the Geneseq database, a proprietary database that contains sequences published in patents and patent publication, yielded several homologous proteins shown in Table 8C.

TABLE 8C

Geneseq Results for NOV8a

| Geneseq Identifier | Protein/Organism/Length [Patent #, Date] | NOV8a Residues/ Match Residues | Identities/ Similarities for the Matched Region | Expect Value |
|---|---|---|---|---|
| AAG72301 | Human olfactory receptor polypeptide. SEQ ID NO: 1982-*Homo sapiens*, 318 aa. [WO200127158-A2, 19-APR-2001] | 1 . . . 280 | 279/280 (99%) | e−161 |
| AAG72302 | Human olfactory receptor polypeptide, SEQ ID NO: 1983-*Homo sapiens*, 310 aa. [WO200127158-A2, 19-APR-2001] | 1 . . . 280 1 . . . 280 | 261/280 (93%) 269/280 (95%) | e−151 |
| AAY90874 | Human G protein-coupled receptor GTAR14-5 SEQ ID NO: 6-*Homo sapiens*, 310 aa. [WO200021999-A1, 20-APR-2000] | 1 . . . 280 1 . . . 280 | 261/280 (93%) 269/280 (95%) | e−151 |
| AAG72708 | Murine OR-like polypeptide query sequence, SEQ ID NO: 2390-*Mus musculus*, 324 aa. [WO200127158-A2, 19-APR-2001] | 1 . . . 280 7 . . . 286 | 252/280 (90%) 268/280 (95%) | e−149 |
| AAG73014 | Olfactory receptor-like polypeptide, SEQ ID NO: 2696-Unidentified, 318 aa. [WO200127158-A2, 19-APR-2001] | 1 . . . 280 1 . . . 280 | 249/280 (88%) 263/280 (93%) | e−146 |

In a BLAST search of public sequence datbases, the NOV8a protein was found to have homology to the proteins shown in the BLASTP data in Table 8D.

TABLE 8D

Public BLASTP Results for NOV8a

| Protein Accession Number | Protein/ Organism/ Length | NOV8a Residues/ Match Residues | Identities/ Similarities for the Matched Portion | Expect Value |
|---|---|---|---|---|
| AAL61330 | OLFACTORY RECEPTOR MOR223-6- Mus musculus (Mouse), 318 aa. | 1 . . . 280<br>1 . . . 280 | 252/280 (90%)<br>268/280 (95%) | e−149 |
| Q62944 | TASTE BUD RECEPTOR PROTEIN TB 641- Rattus norvegicus (Rat), 318 aa. | 1 . . . 280<br>1 . . . 280 | 249/280 (88%)<br>263/280 (93%) | e−146 |
| AAL61485 | OLFACTORY RECEPTOR MOR223-9- Mus musculus (Mouse), 318 aa. | 1 . . . 280<br>1 . . . 280 | 248/280 (88%)<br>263/280 (93%) | e−146 |
| AAL61329 | OLFACTORY RECEPTOR MOR223-5- Mus musculus (Mouse), 313 aa. | 11 . . . 280<br>7 . . . 276 | 202/270 (74%)<br>232/270 (85%) | e−118 |
| AAL61470 | OLFACTORY RECEPTOR MOR223-8- Mus musculus (Mouse), 310 aa. | 11 . . . 280<br>7 . . . 275 | 169/270 (62%)<br>199/270 (73%) | 3e−94 |

PFam analysis predicts that the NOV8a protein contains the domains shown in the Table 8E.

TABLE 8E

Domain Analysis of NOV8a

| Pfam Domain | NOV8a Match Region | Identities/ Similarities for the Matched Region | Expect Value |
|---|---|---|---|
| 7tm_1: domain 1 of 1 | 45 . . . 253 | 42/215 (20%)<br>149/215 (69%) | 1.5e−23 |

Example 9

The NOV9 clone was analyzed, and the nucleotide and encoded polypeptide sequences are shown in Table 9A.

TABLE 9A

NOV9 Sequence Analysis

NOV9a,  SEQ ID NO:25    1704 bp

CG59826-01 DNA Sequence

GCCGCGCTGTGCTATGAAGCAGGTCAATGAGCTGAAAGAGAACGCCAACAAGGCCCTG

GGCGTGGAAAACATCGACAATGCCTTACAGTGCTACTCTGAAGCCATTAAGCTGGATC

CCCACAACCACGTGCTCTACACCAACTGTTCTGCCACCTATGCCAAGAAAGGAGACTA

CCAGAAGGCTTACAAGGACCGCTGCAAGACCGTCGACCTAAAATTTGACTGGGCCAAG

GGATATTCACGAAAAGCAGCAGCTCTAGAGTTCTTAAACCGATTTGAAGAAGCCAAGG

GAACCTACGAGGAGAGCTTAAAACACGAGGCAGATAACCCTCAACTGAAAGAGGGTTT

ACAGAATATGGAGGCCAGGTTGGCAGAGAGAAAATGTATGAATGCTTTCAACATGCCC

AATCTGAAACAGAAGTTGGAGAGTGATCCCAGGACAAGGACACTGCTCAGTGATCCTA

CCTACCGGGAGCTGATAGAGCAACTAAAAAACAAGCCTTCTGATCTGGGCACAAAACT

ACGAGATCCCCGGATCCTGACCACTCTCAGTGTCCTCCTTGAGGTCGATCGGGGCAGT

ATGGATGAGGAGGAACAGGTTGCAACACCTTCACCACCACCCCTTCCCAAAAAGGAGA

CCAAGCCAGAGCCAGTGGAAGAAGATCTTCCAGAGAATAAGAAGCAGGCACTGAAAGA

AAAAGAGCTGAGGAACGATGCCTACAAGAAGAAAGACAGACTGACAGCCTTGAAGCAT

TACGACAAAGCCAAGGAGCTGGACCCCAGCAACATGACTTACATTACCAATCAAGCAG

CGGTATACTTTGAAAAGGGCGACTACAATAAGTGTTGGGAGCTTTGTGAGAAGTCCAT

TGAAGTGGGGAGAGAAAACAGAGAAGACTATCTACAGATTGCCAAAGTGTGTGCTCGA

ATTGGCAACTCCTACTTCAAAGAAGAAAAGTACAAGGATGCCATCCATTTCTATAACA

TABLE 9A-continued

NOV9 Sequence Analysis

|  |  |
|---|---|
|  | AGTCTCTGGCAGAGCACCGAACTCCAGATGTGCTCAAGAAATGCCAGCAGGCAGAGAA |
|  | AATCCTGAAGGAGCAAGAACGGCTGGCCTACATAAACCCCGACCTGGCTTTAGAAGAG |
|  | AAGAACAAAGGCAACGAGTGTTTTCAGAAAGGGGACTATCCCCACGCCATGAAGCATT |
|  | ATACGGAAGCCATCAAAAGGAACCCGAAAGATGCCAAATTATACAGCAATCGAGCTGC |
|  | CTGTTACACCAAACTCCTGGATTTCCAGCTGGCACTCAAGGACTGTGAAGAATGTATC |
|  | CAGCTAGAACCGACCTTCATCAAGGGTTATACACGGAAAGCCGTTGCCCTGGAAGCGA |
|  | TGAAGGACTACACCAAAGTCATGGATGTGTACCGGAAGGCGCTAGACCCGGACTCCAG |
|  | CTGTAAGGAGGCGGCAGACGGCTACCAGCGCTGTATGATGGCGCAGTACAACCGGCAC |
|  | CACAGCCCCGAAGATGTGAAGCGACGAGCCATGGCCGACCCCGAGGTGCAGCAGATCA |
|  | TGAGTGACATAGCCATGCACCTTATCCTGGAGCAGATGCAGAAGGACCCCCAGGCACT |
|  | CAGCGAACACTTAAAGAATCCTGTAATCGCAAAGAAGATCCAGAAGCTGATGGATGTG |
|  | GGTCTGATTGCAATTCGACAATGACTTGTCCATCCCCGCTTCCCTTCGCCCTCATGCG |
|  | GAAAGAGGAGCGGGGACCGCGG |
|  | ORF Start: ATG at 14      ORF Stop:TGA at 1646 |
|  | SEQ ID NO:26      544 aa MW at 62861.1 kD |
| NOV9a, | MKQVNELKEKGNKALGVENIDNALQCYSEAIKLDPHNHVLYSNCSATYAKKGDYQKAY |
| CG59826-01 Protein Sequence | KDGCKTVDLKFDWCKGYSRKAAALEFLNRFEEAKGTYEESLKHEADNPQLKEGLQNME |
|  | ARLAERKCMNAFNMPNLKQKLESDPRTRTLLSDPTYRELIEQLKNKPSDLGTKLRDPR |
|  | ILTTLSVLLEVDRGSMDEEEQVATPSPPPLPKKETKPEPVEEDLPENKKQALKEKBLR |
|  | NDAYKKKDRLTALKHYDKAKELDPSNMTYITNQAAVYFEKGDYNKCWELCEKSIEVGR |
|  | ENREDYLQIAKVCARIGNSYFKEEKYKDAIHFYNKSLAEHRTPDVLKKCQQAEKILKE |
|  | QERLAYINPDLALEEKNKGNECFQKGDYPHAMKHYTEAIKRNPKDAKLYSNRAACYTK |
|  | LLDFQLALKDCEECIQLEPTFIKGYTRKAVALEAMKDYTKVMDVYRKALDPDSSCKEA |
|  | ADGYQRCMMAQYNRHHSPEDVKRRAMADPEVQQIMSDIAMHLILEQMQKDPQALSEHL |
|  | KNPVIAKKIQKLMDVGLIAIRQ |

Further analysis of the NOV9a protein yielded the following properties shown in Table 9B.

TABLE 9B

Protein Sequence Properties NOV9a

| PSort analysis: | 0.4500 probability located in cytoplasm; 0.3000 probability located in microbody (peroxisome); 0.1000 probability located in mitochondrial matrix space; 0.1000 probability located in lysosome (lumen) |
|---|---|

TABLE 9B-continued

Protein Sequence Properties NOV9a

| SignalP analysis: | No Known Signal Sequence Predicted |
|---|---|

A search of the NOV9a protein against the Geneseq database, a proprietary database that contains sequences published in patents and patent publication, yielded several homologous proteins shown in Table 9C.

TABLE 9C

Geneseq Results for NOV9a

| Geneseq Identifier | Protein/Organism/Length [Patent #, Date] | NOV9a Residues/ Match Residues | Identities/ Similarities for the Matched Region | Expect Value |
|---|---|---|---|---|
| AAY07058 | Renal cancer associated antigen precursor sequence-*Homo sapiens*, 543 aa. [WO9904265-A2, 28-JAN-1999] | 1 ... 543<br>1 ... 543 | 500/543 (92%)<br>515/543 (94%) | 0.0 |
| ABB57064 | Mouse ischaemic condition related protein sequence SEQ ID NO: 127-*Mus musculus*, 543 aa. [WO200188188-A2, 22-NOV-2001] | 1 ... 543<br>1 ... 543 | 488/543 (89%)<br>509/543 (92%) | 0.0 |
| ABG18854 | Novel human diagnostic protein #18845-*Homo sapiens*, 629 aa. [WO200175067-A2, 11-OCT-2001] | 1 ... 538<br>33 ... 572 | 472/540 (87%)<br>499/540 (92%) | 0.0 |
| ABG18854 | Novel human diagnostic protein #18845-*Homo sapiens*, 629 aa. [WO200175067-A2, 11-OCT-2001] | 1 ... 538<br>33 ... 572 | 472/540 (87%)<br>499/540 (92%) | 0.0 |
| ABG18853 | Novel human diagnostic protein #18844-*Homo sapiens*, 319 aa. [WO200175067-A2, 11-OCT-2001] | 26 ... 348<br>1 ... 313 | 279/323 (86%)<br>290/323 (89%) | e−160 |

In a BLAST search of public sequence datbases, the NOV9a protein was found to have homology to the proteins shown in the BLASTP data in Table 9D.

TABLE 9D

Public BLASTP Results for NOV9a

| Protein Accession Number | Protein/Organism/Length | NOV9a Residues/ Match Residues | Identities/ Similarities for the Matched Portion | Expect Value |
|---|---|---|---|---|
| P31948 | Stress-induced-phosphoprotein 1 (STI1) (Hsp70/Hsp90-organizing protein) (Transformation-sensitive protein IEF SSP 3521)-*Homo sapiens* (Human), 543 aa. | 1 ... 543<br>1 ... 543 | 500/543 (92%)<br>515/543 (94%) | 0.0 |
| O35814 | P60 PROTEIN-*Rattus norvegicus* (Rat), 543 aa. | 1 ... 543<br>1 ... 543 | 489/543 (90%)<br>509/543 (93%) | 0.0 |
| Q99L66 | STRESS-INDUCED PHOSPHOPROTEIN 1-*Mus musculus* (Mouse), 543 aa. | 1 ... 543<br>1 ... 543 | 488/543 (89%)<br>509/543 (92%) | 0.0 |
| Q60864 | MSTI1-*Mus musculus* (Mouse), 543 aa. | 1 ... 543<br>1 ... 543 | 488/543 (89%)<br>509/543 (92%) | 0.0 |
| O54981 | HSP70/HSP90 ORGANIZING PROTEIN-*Cricetulus griseus* (Chinese hamster), 543 aa. | 1 ... 543<br>1 ... 543 | 485/543 (89%)<br>508/543 (93%) | 0.0 |

PFam analysis predicts that the NOV9a protein contains the domains shown in the Table 9E.

TABLE 9E

Domain Analysis of NOV9a

| Pfam Domain | NOV9a Match Region | Identities/ Similarities for the Matched Region | Expect Value |
|---|---|---|---|
| TPR: domain 1 of 8 | 4 ... 37 | 11/34 (32%)<br>25/34 (74%) | 0.0001 |
| TPR: domain 2 of 8 | 72 ... 105 | 9/34 (26%)<br>25/34 (74%) | 0.07 |
| TPR: domain 3 of 8 | 225 ... 258 | 13/34 (38%)<br>23/34 (68%) | 18 |
| TPR: domain 4 of 8 | 259 ... 292 | 9/34 (26%)<br>24/34 (71%) | 4.5 |
| TPR: domain 5 of 8 | 300 ... 333 | 12/34 (35%)<br>26/34 (76%) | 7e−05 |
| TPR: domain 6 of 8 | 360 ... 393 | 10/34 (29%)<br>26/34 (76%) | 7.4e−06 |
| TPR: domain 7 of 8 | 394 ... 427 | 11/34 (32%)<br>29/34 (85%) | 7.5e−08 |
| TPR: domain 8 of 8 | 428 ... 461 | 8/34 (24%)<br>26/34 (76%) | 0.89 |

Example 10

The NOV10 clone was analyzed, and the nucleotide and encoded polypeptide sequences are shown in Table 10A.

TABLE 10A

NOV10 Sequence Analysis

| | |
|---|---|
| NOV10a, CG59839-01 DNA Sequence | SEQ ID NO: 27      2649 bp<br>CAACTGATTTTAAACTCTACAGAGATGCCTACTTGTTTCTACTATGTCTTGTGGCAGT<br><br>TGCTGGCATTGGGTTTATCTACACTATTATTAATAGCATTTTAAATGAGGTACAAGTT<br><br>GGGGTCATAATTATCGAGTCTCTTGATATTATCACAATTACTGTGCCCCCTGCACTTC<br><br>CTGCTGCAATGACTGCTGGTATTGTGTATGCTCAGAGAAGACTGAAAAAAATCGGTAT<br><br>TTTCTGTATCAGTCCTCAAAGAATAAATATTTGTGGACAGCTCAATCTTGTTTGCTTT<br><br>GACAAGACTGGAACTCTAACTGAAGATGGTTTAGATCTTTGGGGGATTCAACGAGTGG<br><br>AAAATGCACGATTTCTTTCACCAGAAGAAAATGTGTGCAATGAGATGTTGGTAAAATC<br><br>CCAGTTTGTTGCTTGTATGGCTACTTGTCATTCACTTACAAAAATTGAAGGAGTGCTC<br><br>TCTGGTGATCCACTTGATCTGAAAATGTTTGAGGCTATTGGATGGATTCTGGAAGAAG<br><br>CAACTGAAGAAGAAACAGCACTTCATAATCGAATTATGCCCACAGTGGTTCGTCCTCC<br><br>CAAACAACTGCTTCCTGAATCTACCCCTGCAGGAAACCAAGAAATGGAGCTGTTTGAA<br><br>CTTCCAGCTACTTATGAGATAGGAATTGTTCGCCAGTTCCCATTTTCTTCTGCTTTGC<br><br>AACGTATGAGTGTGGTTGCCAGGGTGCTGGGGGATAGGAAAATGGACGCCTACATGAA<br><br>AGGAGCGCCCGAGGCCATTGCCGGTCTCTGTAAACCTGAAACAGTTCCTGTCGATTTT<br><br>CAAAACGTTTTGGAAGACTTCACTAAACAGGGCTTCCGTGTGATTGCTCTTGCACACA<br><br>GAAAATTGGAGTCAAAACTGACATGGCATAAAGTACAGAATATTAGCAGAGATGCAAT<br><br>TGAGAACAACATGGATTTTATGGGATTAATTATAATGCAGAACAAATTAAAGCAAGAA<br><br>ACCCCTGCAGTACTTGAAGATTTGCATAAAGCCAACATTCGCACCGTCATGGTCACAG<br><br>GTGACAGTATGTTGACTGCTGTCTCTGTGGCCAGAGATTGTGGAATGATTCTACCTCA<br><br>GGATAAAGTGATTATTGCTGAAGCATTACCTCCAAAGGATGGGAAAGTTGCCAAAATA<br><br>AATTGGCATTATGCAGACTCCCTCACGCAGTGCAGTCATCCATCAGCAATTGACCCAG<br><br>AGGCTATTCCGGTTAAATTGGTCCATGATAGCTTAGAGGATCTTCAAATGACTCGTTA<br><br>TCATTTTGCAATGAATGGAAAATCATTCTCAGTGATACTGGAGCATTTTCAAGACCTT<br><br>GTTCCTAAGTTGATGTTGCATGGCACCGTGTTTGCCCGTATGGCACCTGATCAGAAGA<br><br>CACAGTTGATAGAAGCATTGCAAAATGTTGATTATTTTGTTGGGATGTGTGGTGATGG<br><br>CGCAAATGATTGTGGTGCTTTGAAGAGGGCACACGGAGGCATTTCCTTATCGGAGCTC<br><br>GAAGCTTCAGTGGCATCTCCCTTTACCTCTAAGACTCCTAGTATTTCCTGTGTGCCAA<br><br>ACCTTATCAGGGAAGGCCGTGCTGCTTTAATAACTTCCTTCTGTGTGTTTAAATTCAT<br><br>GGCATTGTACAGCATTATCCAGTACTTCAGTGTTACTCTGCTGTATTCTATCTTAAGT<br><br>AACCTAGGAGACTTCCAGTTTCTCTTCATTGATCTGGCAATCATTTTGGTAGTGGTAT<br><br>TTACAATGAGTTTAAATCCTGCCTGGAAAGAACTTGTGGCACAAAGACCACCTTCGGG<br><br>TCTTATATCTGGGCCCTTCTCTTCTCCGTTTTGTCTCAGATTATCATCTGCATTGGA<br><br>TTTCAATCTTTGGGTTTTTTTGGGTCAAACAGCAACCTTGGTATGAAGTGTGGCATC<br><br>CAAAATCAGATGCTTGTAATACAACAGGAAGCGGGTTTTGGAATTCTTCACACGTAGA<br><br>CAATGAAACCGAACTTGATGAACTAATATACAAAATTATGAAAATACCACAGTGTTTT |

TABLE 10A-continued

NOV10 Sequence Analysis

| | |
|---|---|
| | TTATTTCCAGTTTTCAGTACCTCATAGTGGCAATTGCCTTTTCAAAAGGAAAACCCTT |
| | CAGGCAACCTTGCTACAAAAATTATTTTTTTGTTTTTTCTGTGATTTTTTTATATATT |
| | TTTATATTATTCATCATGTTGTATCCAGTTGCCTCTGTTGACCAGGTTCTTCAGATAG |
| | TGTGTGTACCATATCAGTGGCGTGTAACTATGCTCATCATTGTTCTTGTCAATGCCTT |
| | TGTGTCTATCACAGTGGAGGAGTCAGTGGATCGGTGGGGAAAATGCTGCTTACCCTGG |
| | GCCCTGGGCTGTAGAAAGAAGACACCAAAGGCAAAGTACATGTATCTGGCGCAGGAGC |
| | TCTTGGTTGATCCAGAATGGCCACCAAAACCTCAGACAACCACAGAAGCTAAAGCTTT |
| | AGTTAAGGAGAATGGATCATGTCAAATCATCACCATAACATAGCAGTGAATCAGTCTC |
| | AGTGGTATTGCTGATAGCAGTATTCAGGAATATGTGATTTTAGGAGTTTCTGATCCTG |
| | TGTGTCAGAATGGCACTAGTTCAGTTTATGTCCCTTCTGATATGTAGCTTATTTGAC |
| | AGCTTTGCTCTTCCTTAAAATAAAAAAAAAAAAAAAAAAA |
| NOV10a, CG59839-01 Protein Sequence | ORF Start: ATG at 183     ORF Stop: TAG at 2055<br>SEQ ID NO: 28           624 aa   MW at 69590.1 kD<br>MTAGIVYAQRRLKKIGIFCISPQRINICGQLNLVCFDKTGTLTEDGLDLWGIQRVENA<br>RFLSPEENVCNEMLVKSQFVACMATCHSLTKIEGVLSGDPLDLKMFEAIGWILEEATE<br>EETALHNRIMPTVVRPPKQLLPESTPAGNQEMELFELPATYEIGIVRQFPFSSALQRM<br>SVVARVLGDRKMDAYMKGAPEAIAGLCKPETVPVDFQNVLEDFTKQGFRVIALAHRKL<br>ESKLTWHKVQNISRDAIENNMDFMGLIIMQNKLKQETPAVLEDLHKANIRTVMVTGDS<br>MLTAVSVARDCGMILPQDKVIIAEALPPKDGKVAKINWHYADSLTQCSHPSAIDPEAI<br>PVKLVHDSLEDLQMTRYHFAMNGKSFSVILEHFQDLVPKLMLHGTVFARMAPDQKTQL<br>IEALQNVDYFVGMCGDGANDCGALKRAHGGISLSELEASVASPFTSKTPSISCVPNLI<br>REGRAALITSFCVFKFMALYSIIQYFSVTLLYSILSNLGDFQFLFIDLAIILVVVFTM<br>SLNPAWKELVAQRPPSGLISGALLFSVLSQIIICIGFQSLGFFWVKQQPWYEVWHPKS<br>DACNTTGSGFWNSSHVDNETELDELIYKIMKIPQCFLFPVFSTS |

Further analysis of the NOV10a protein yielded the following properties shown in Table 10B.

TABLE 10B

Protein Sequence Properties NOV10a

| | |
|---|---|
| PSort analysis: | 0.6000 probability located in plasma membrane; 0.4617 probability located in mitochondrial inner membrane; 0.4000 probability located in Golgi body; 0.3000 probability located in endoplasmic reticulum (membrane) |
| SignalP analysis: | No Known Signal Sequence Predicted |

A search of the NOV10a protein against the Geneseq database, a proprietary database that contains sequences published in patents and patent publication, yielded several homologous proteins shown in Table 10C.

TABLE 10C

Geneseq Results for NOV10a

| Geneseq Identifier | Protein/Organism/Length [Patent #, Date] | NOV10a Residues/ Match Residues | Identities/ Similarities for the Matched Region | Expect Value |
|---|---|---|---|---|
| AAB40996 | Human ORFX ORF760 polypeptide sequence SEQ ID NO:1520-*Homo sapiens*, 692 aa. [WO200058473-A2, 05-OCT-2000] | 48 . . . 604<br>2 . . . 558 | 557/557 (100%)<br>557/557 (100%) | 0.0 |

TABLE 10C-continued

Geneseq Results for NOV10a

| Geneseq Identifier | Protein/Organism/Length [Patent #, Date] | NOV10a Residues/ Match Residues | Identities/ Similarities for the Matched Region | Expect Value |
|---|---|---|---|---|
| AAM93525 | Human polypeptide, SEQ ID NO: 3259-*Homo sapiens*, 505 aa. [EP1130094-A2, 05-SEP-2001] | 261 . . . 604 1 . . . 344 | 341/344 (99%) 341/344 (99%) | 0.0 |
| AAU23078 | Novel human enzyme polypeptide #164-*Homo sapiens*, 476 aa. [WO200155301-A2, 02-AUG-2001] | 297 . . . 604 8 . . . 315 | 308/308 (100%) 308/308 (100%) | 0.0 |
| AAM93906 | Human polypeptide, SEQ ID NO: 4053-*Homo sapiens*, 842 aa. [EP1130094-A2, 05-SEP-2001] | 1 . . . 573 139 . . . 691 | 263/575 (45%) 370/575 (63%) | e−138 |
| AAM79751 | Human protein SEQ ID NO 3397-*Homo sapiens*, 666 aa. [WO200157190-A2, 09-AUG-2001] | 39 . . . 573 1 . . . 515 | 241/537 (44%) 342/537 (62%) | e−124 |

In a BLAST search of public sequence datbases, the NOV10a protein was found to have homology to the proteins shown in the BLASTP data in Table 10D.

TABLE 10D

Public BLASTP Results for NOV10a

| Protein Accession Number | Protein/ Organism/ Length | NOV10a Residues/ Match Residue | Identities/ Similarities for the Matched Portion | Expect Value |
|---|---|---|---|---|
| Q9H7F0 | Probable cation-transporting ATPase 3 (EC 3.6.3.-)-*Homo sapiens* (Human), 684 aa (fragment). | 1 . . . 624 61 . . . 684 | 624/624 (100%) 624/624 (100%) | 0.0 |
| Q96KS1 | HYPOTHETICAL 77.3 KDA PROTEIN-*Homo sapiens* (Human), 701 aa. | 1 . . . 499 185 . . . 680 | 482/499 (96%) 486/499 (96%) | 0.0 |
| Q9NQ11 | Probable cation-transporting ATPase 1 (EC 3.6.1.-)-*Homo sapiens* (Human), 1180 aa. | 1 . . . 573 477 . . . 1029 | 264/575 (45%) 371/575 (63%) | e−138 |
| O74431 | Probable cation-transporting ATPase C1672.11C (EC 3.6.3.-)-*Schizosaccharomyces pombe* (Fission yeast), 1315 aa. | 1 . . . 588 583 . . . 1181 | 250/609 (41%) 367/609 (60%) | e−124 |
| Q21286 | Probable cation-transporting ATPase K07E3.7 in chromosome X (EC 3.6.3.-)-*Caenorhabditis elegans*, 1152 aa. | 1 . . . 573 467 . . . 1034 | 248/587 (42%) 351/587 (59%) | e−122 |

PFam analysis predicts that the NOV10a protein contains the domains shown in the Table 10E.

TABLE 10E

Domain Analysis of NOV10a

| Pfam Domain | NOV10a Match Region | Identities/ Similarities for the Matched Region | Expect Value |
|---|---|---|---|
| Hydrolase: domain 1 of 1 | 31 . . . 443 | 40/423 (9%) 247/423 (58%) | 0.009 |
| Hemagglutinin: domain 1 of 1 | 555 . . . 561 | 4/7 (57%) 7/7 (100%) | 8.9 |

Example 11

The NOV11 clone was analyzed, and the nucleotide and encoded polypeptide sequences are shown in Table 11A.

TABLE 11A

| NOV11 Sequence Analysis | |
|---|---|
| NOV11a, CG59847-01 DNA Sequence | SEQ ID NO: 29  3880 bp<br>CTAACATCATCATGACAGGATCAAATTCACACATAACAATATTAACTTTAAATGTAAA<br>TGGACTAAATGCTCCAATTAAAAGACACAGACTGGCAAATTGGATAAAGAGTCAAGAC<br>CCATCAGTGTGCTGTATTCAGGAAACCCATCTCATGTGCAGAGACACACATAGGCTCA<br>AAATAAAAGGATGGAGGAAGATCTATCAAAAACAAAAAAAGGCAGGGGTTGCAACCCT<br>AGTCTCTGATAAAACAGACAAACCAATAAAGATCAAAAGAGACAAAGAAGGCCATTAC<br>ATAATGGTAAAGGGATCAATTCAACAAGAAGAGCTAACTATCCTAAATATATATGCAC<br>CCAATACAGCAGCACCCACATTCATAAAGCAAGTCCTGAGTGACCTACAAAGAGACTT<br>AGACTCCCACACATTAATAATGGGAGACTTTAACACCCCACTGTCAACATTAGACAGA<br>TCAACGAGACAGAAAGTCAACAAGGATACCCAGGAATTGAACTCAGCTCTGCACCAAG<br>TGGACCTAATAGACATCTATACAACTCTCCACCCCAAATCAACAGAATATACATTTTT<br>TTCAGCACCACACCCCACCTATTCCAAAATTGACCACATACTGGGAAGTAAAGCTCTC<br>CTCAGCAAATGTAAAAGAACAGAAATTATAACAAACTATCTCTCAGACCACAGTGCAA<br>TCAAACTAGAACTCAGGATTCAGAATCTCACTCAAAACTGCTCAACTACATGGAAACT<br>GAACAACCTGCTCCTGAATGACTACTGGGTACATAACGAAATGAAGGCAGAAATAAAG<br>ATGTTCTTTGAAACCAACAAGAACAAAGACACAACATACCAGAATCTCTGGGACGCAT<br>TCAAAGGAGTGTGTAGAGGGAAATTTATAGCACTAAATGCCCACAAGAGAAAGCAGGA<br>AAGATCCAAAATTGACATCCTAACATCACAATTAAAAGAACTAGAAAAGCAAGAGCAA<br>ACACACTCAAAAGGTAGCAGAAGGCAAGAAATAACTAAAATCAGAGCAGAACTGAAGG<br>AAATAGAGACACGAAAAACCCTTCAAAAAATTAATGAATCCAGGAGCATCAACAAAAC<br>AGATAGACCACTAGCAAGACTAATAAAGAAAAAAGAGAGAAGAATCAAATAGACGCA<br>ATAAAAAATGATAAAGGGGATATCACCACCGATCCCACAGAAATACAAACTACCATCA<br>GAGAATACTACAAACACCTCTACGCAAATAAACTAGAAAATCTAGAAGAAATGGATAA<br>ATTCCTCGACACATACACTCTCCCAAGACTAAACCAGGAAGAAGTTGAATCTCTGAAT<br>AGACCAATAACAGGATCTGAAACTGTGGCAATAATCAATAGCTTACCAACCAAAAGA<br>GTCCAGGACCAGATGGATTCACAGCTGAATTCTACCAGAGGTACAAGGAGGAACTGGT<br>ACCATTCCCTCTGAAACTATTCCAATCAATAGAAAAAGAGGGAATCCTCCCTAACTCA<br>TTTTATGAGGCCAGCATCATTCTGATACCAAAGCCTGGCAGAGACACAACCAAAAAAG<br>AGAATTTTAGACCAATATCCTTGATGAACATTGATGCAAAAATCCTCAATAAAATACT<br>GGCAAAACGAATCCAGCAGCACAGCAAAAAGCTTATCCACCATGATCAAGTGGGCTTC<br>ATCCCTGGGATGCAAGGCTGGTTCAATATATGCAAATCAATAAATGTAATCCAGCATA<br>TAAACAGAGCCAAAGACAAAAACCACATGATTATCTCAATAGATGCAGAAAAGGCCTT<br>TGACAAAATTCAACAACGCTTCATGCTAAAAACTCTCAATAAATCAGGTATTGATGGG<br>ACGTATTTCAAAATAATAAGAGCTATCTATGACAAACCCACAGCCAATATCATACTGA<br>ATGGACAAAAACTGGAAGCATTCCCTTTGAAAACCGGCACAAGACAGGGATACCCTCT<br>CTCACCACTCCTATTCAACATAGTGTTGGAAGTTCTGGCCAGGGCAATTAGGCAGGAG<br>AAGGAAATAAAGTGTATTCAATTAGGAAAAGAGGAAGTCAAATTGTCCCTGTTTGCAG<br>ACGACATGATTGTATATCTAGAAAACCCCATTGTCTCAGCCCAAAATCTCCTTAAGCT<br>GATAAGCAACTTCAGCAAAGTCTCAGGATACAAAATCAATGTACAAAAATCACAAGCA |

TABLE 11A-continued

NOV11 Sequence Analysis

TTCTTCTACACCAACTACAGACAAACAGAGAGCCAAATCATGAGTGAACTCCCATTCA

CAATTGCTTCAAAGAGAATAAAATACCTAGGAATCCAACTTACAAGGGATGTGAAGGA

CCTCTTCAAGGAGAACTACAAACCACTGCTCAAGGAAATAAAAGAGGATACAAACAAA

TGGAAGAACATTCCATGCTCATGGGTAGGAAGAATCAATATCGTGAAAATGGCCATAC

TGCCCAAGGTAATTTACAGATTCAATGCCATCCCCATCAAGCTACCAATGCCTTTCTT

CACAGAATTGGAAAAAACTACTTTAAAGTTCATATGGAACCAAAAAAGAGCCTGCATC

GCCAAGTCAATCCTAAGCCAAAAGGACAAAGCTGGAGGCATCACATTACCTGACTTCA

CACTACACTACAAGGCTACAGTAACCAAAACAGCATGGTACTGGTACCAAAACAGAGA

TATAGATCAATGGAACAGAACAGAGCCCTCAGAAATAATGCCGCATATCTACAACTAT

CGGATCTTTGACAAACCTGAGAAAAACAAGCAATGGGAAAGGATTCCCTATTTAATA

AATGGTGCTGGGAAACCTGCCTAGCCATATGTAGAAAGCTGAAACTGGATCCCTTCCT

TACACCTTATACAAAAATCAATTCAAGATGGATTAAAGACTTAAACGTTAGACCTAAA

ACCATAAAAACTCTAGAAGAAAACCTAGGCATTACCATTCAGGACGTAGCTATGGGCA

AGGACTTCATGTCTAAAACACCAAAAGCAATGGCAACAAAAGCCAAAATTGACAAATG

GGATCTAATTAAACTAAAGAGCTTCTGCACAGCAAAAGAAACTACCATCAGAGTGAAC

AGGCAACCTACAAAATGGGAGAAAATTTTTGCAGCCTACTCATCTGACAAAGGGCTAA

TATCCAGAATCTACAATGAACTCAAACAAATTTACAAGAAAAAAACAAACAACCCCAT

CAAAAAGTGGGCAAAGGACATGAACAGACACTTCTCAAAAGAAGACATTTATGCAGCC

AAAAAACACATGAAAAAATGCTCATCATCACTGGCCATCAGAGAAATGCAAATCAAAA

CCACAATGAGATACCATCTCACACCAGTTAGAATGGCAATCATTAAAAAGTCAGGAAA

CAACAGGTGCTGGAGAGGATGTGGAGAAATAGGAACACTTTTACACTGTTGGTGGGAC

TGTAAACTAGTTCAACCCTTGTGGAAGTCAGTGTGGCGATTCCTCAGGGATCTAGACC

TAGAAATACCATTTGACCCAGCCATCCCATTACTGGGTATATACCCAAAGGACTATAA

ATCATGCTGCTATAAAGATACATGCACACATATGTTTATTGCAGCACTATTCACAATA

GAAAGACTTGGAACCAACCCAAAGACTTGGAACCAACCCAAATGTCCAACAATGATAG

ACTGGATTAAGAAAATGTGGCACATATACACCATGGAATACTATGCAGCCATAAAAAA

TGAAGAGTTCATGTCCTTTGTAGGGACATGGATGAAATTGGAAATCATCATTCTCAGT

AAACTATCGCAAGAACAAAAAACCAAACACCGCATATTCTCACTCATAGGTGGGAATT

GAACAATGAGATCACATGGACACAGGAAGGGGAACATCACACTCTGGGGACT

NOV11a,
CG59847-01 Protein Sequence

ORF Start: ATG at 12        ORF Stop: TGA at 3828
SEQ ID NO: 30               1272 aa  MW at 148630.6 kD
MTGSNSHITILTLNVNGLNAPIKRHRLANWIKSQDPSVCCIQETHLMCRDTHRLKIKG

WRKIYQKQKKAGVATLVSDKTDKPIKIKRDKEGHYIMVKGSIQQEELTILNIYAPNTG

APTFIKQVLSDLQRDLDSHTLIMGDFNTPLSTLDRSTRQKVNKDTQELNSALHQVDLI

DIYRTLHPKSTEYTFFSAPHPTYSKIDHILGSKALLSKCKRTEIITNYLSDHSAIKLE

LRIQNLTQNCSTTWKLNNLLLNDYWVHNEMKAEIKMFFETNKNKDTTYQNLWDAFKGV

CRGKFIALNAHKRKQERSKIDILTSQLKELEKQEQTHSKGSRRQEITKIRAELKEIET

RKTLQKINESRSINKTDRPLARLIKKKREKNQIDAIKNDKGDITTDPTEIQTTIREYY

KHLYANKLENLEEMDKFLDTYTLPRLNQEEVESLNRPITGSETVAIINSLPTKKSPGP

DGFTAEFYQRYKEELVPFPLKLFQSIEKEGILPNSFYEASIILIPKPGRDTTKKENFR

TABLE 11A-continued

NOV11 Sequence Analysis

```
PISLMNIDAKILNKILAKRIQQHSKKLIHHDQVGFIPGMQGWFNICKSINVIQHINRA
KDKNHMIISIDAEKAFDKIQQRFMLKTLNKSGIDGTYFKIIRAIYDKPTANIILNGQK
LEAFPLKTGTRQGYPLSPLLFNIVLEVLARAIRQEKEIKCIQLGKEEVKLSLFADDMI
VYLENPIVSAQNLLKLISNFSKVSGYKINVQKSQAFFYTNYRQTESQIMSELPFTIAS
KRIKYLGIQLTRDVKDLFKENYKPLLKEIKEDTNKWKNIPCSWVGRINIVKMAILPKV
IYRFNAIPIKLPMPFFTELEKTTLKFIWNQKRACIAKSILSQKDKAGGITLPDFTLHY
KATVTKTAWYWYQNRDIDQWNRTEPSEIMPHIYNYRIFDKPEKNKQWGKDSLFNKWCW
ETWLAICRKLKLDPFLTPYTKINSRWIKDLNVRPKTIKTLEENLGITIQDVAMGKDFM
SKTPKAMATKAKIDKWDLIKLKSFCTAKETTIRVNRQPTKWEKIFAAYSSDKGLISRI
YNELKQIYKKKTNNPIKKWAKDMNRHFSKEDIYAAKKHMKKCSSSLAIREMQIKTTMR
YHLTPVRMAIIKKSGNNRCWRGCGEIGTLLHCWWDCKLVQPLWKSVWRFLRDLDLEIP
FDPAIPLLGIYPKDYKSCCYKDTCTHMFIAALFTIERLGTNPKTWNQPKCPTMIDWIK
KMWHIYTMEYYAAIKNEEFMSFVGTWMKLEIIILSKLSQEQKTKHRIFSLIGGN
```

Further analysis of the NOV11a protein yielded the following properties shown in Table 11B.

TABLE 11B

| | Protein Sequence Properties NOV11a |
|---|---|
| PSort analysis: | 0.5500 probability located in endoplasmic reticulum (membrane); 0.1900 probability located in lysosome (lumen); 0.1363 probability located in microbody (peroxisome); 0.1000 probability located in endoplasmic reticulum (lumen) |
| SignalP analysis: | No Known Signal Sequence Predicted |

A search of the NOV11a protein against the Geneseq database, a proprietary database that contains sequences published in patents and patent publication, yielded several homologous proteins shown in Table 11C.

TABLE 11C

Geneseq Results for NOV11a

| Geneseq Identifier | Protein/Organism/Length [Patent #, Date] | NOV11a Residues/ Match Residues | Identities/ Similarities for the Matched Region | Expect Value |
|---|---|---|---|---|
| AAB64943 | Human secreted protein sequence encoded by gene 7 SEQ ID NO:121 - Homo sapiens, 1280 aa. [WO200076530-A1, 21 Dec. 2000] | 1..1272 6..1280 | 1205/1281 (94%) 1213/1281 (94%) | 0.0 |
| ABG14889 | Novel human diagnostic protein #14880 - Homo sapiens, 1284 aa. [WO200175067-A2, 11 Oct. 2001] | 1..1272 10..1284 | 1196/1281 (93%) 1218/1281 (94%) | 0.0 |
| ABG10795 | Novel human diagnostic protein #10786 - Homo sapiens, 1284 aa. [WO200175067-A2, 11 Oct. 2001] | 1..1272 10..1284 | 1196/1281 (93%) 1218/1281 (94%) | 0.0 |
| ABG09636 | Novel human diagnostic protein #9627 - Homo sapiens, 1284 aa. [WO200175067-A2, 11 Oct. 2001] | 1..1272 10..1284 | 1196/1281 (93%) 1218/1281 (94%) | 0.0 |
| ABG06053 | Novel human diagnostic protein #6044 - Homo sapiens, 1284 aa. [WO200175067-A2, 11-OCT-2001] | 1..1272 10..1284 | 1196/1281 (93%) 1218/1281 (94%) | 0.0 |

In a BLAST search of public sequence datbases, the NOV11a protein was found to have homology to the proteins shown in the BLASTP data in Table 11D.

TABLE 11D

Public BLASTP Results for NOV11a

| Protein Accession Number | Protein/Organism/Length | NOV11a Residues/ Match Residues | Identities/ Similarities for the Matched Portion | Expect Value |
|---|---|---|---|---|
| O00360 | PUTATIVE P150 - *Homo sapiens* (Human), 1275 aa. | 1..1272 1..1275 | 1209/1281 (94%) 1224/1281 (95%) | 0.0 |
| Q9YSK0 | HYPOTHETICAL 149.0 KDA PROTEIN - *Homo sapiens* (Human), 1275 aa. | 1..1272 1..1275 | 1208/1281 (94%) 1226/1281 (95%) | 0.0 |
| Q9UN80 | HYPOTHETICAL 149.0 KDA PROTEIN - *Homo sapiens* (Human), 1275 aa. | 1..1272 1..1275 | 1207/1281 (94%) 1226/1281 (95%) | 0.0 |
| Q15604 | ORF2 CONTAINS A REVERSE TRANSCRIPTASE DOMAIN - *Homo sapiens (Human)*, 1275 aa. | 1..1272 1..1275 | 1205/1281 (94%) 1224/1281 (95%) | 0.0 |
| AAL50637 | HYPOTHETICAL 149.0 KDA PROTEIN - *Homo sapiens* (Human), 1275 aa. | 1..1272 1..1275 | 1206/1281 (94%) 1223/1281 (95%) | 0.0 |

PFam analysis predicts that the NOV1a protein contains the domains shown in the Table 11E.

TABLE 11E

Domain Analysis of NOV11a

| Pfam Domain | NOV11a Match Region | Identities/ Similarities for the Matched Region | Expect Value |
|---|---|---|---|
| AP_endonucleas1: domain 1 of 1 | 8..234 | 79/297 (27%) 202/297 (68%) | 1e-83 |
| rvt: domain 1 of 1 | 494..764 | 84/278 (30%) 218/278 (78%) | 1.1e-71 |

Example 12

The NOV12 clone was analyzed, and the nucleotide and encoded polypeptide sequences are shown in Table 12A.

TABLE 12A

NOV12 Sequence Analysis

| NOV12a, CG59905-01 DNA Sequence | SEQ ID NO: 31  3145 bp<br>ATTTTACTTGCTGGATCTTCAGCCTTGACCTGTATGGCAAATGGCTTATGGGACCGAT<br>CCCTGCCCAAGTGTTTGGCTATATCCTGTGGACACCCAGGGGTCCCTGCCAACGCCGT<br>CCTCACTGGAGAGCTGTTTACCTATGGCGCCGTCGTGCACTACTCCTGCAGAGGGAGC<br>GAGAGCCTCATAGGCAACGACACGAGAGTGTGCCAGGAAGACAGTCACTCGAGCGGGG<br>CACTGCCCCACTGCACAGGAAATAATCCTGGATTCTGTGGTGATCCGGGGACCCCAGC<br>ACATGGGTCTCGGCTTGGTGATGACTTTAAGACAAAGAGTCTTCTCCGCTTCTCCTGT<br>GAAATGGGGCACCAGCTGAGGGGCTCCCCTGAACGCACGTGTTTGCTCAATGGGTCAT<br>GGTCAGGACTGCAGCCGGTGTGTGAGGCCGTGTCCTGTGGCAACCCTGGCACACCCAC<br>CAACGGAATGATTGTCAGTAGTGATGGCATTCTGTTCTCCAGCTCGGTCATCTATGCC<br>TGCTGGGAAGGCTACAAGACCTCAGGGCTCATGACACGGCATTGCACAGCCAATGGGA<br>CCTGGACAGGCACTGCTCCCGACTGCACAATTATAAGTTGTGGGGATCCAGGCACACT<br>AGCAAATGGCATCCAGTTTGGGACCGACTTCACCTTCAACAAGACTGTGAGCTATCAG<br>TGTAACCCAGGCTATGTCATGGAAGCAGTCACATCCGCCACTATTCGCTGTACCAAAG |

TABLE 12A-continued

NOV12 Sequence Analysis

ACGGCAGGTGGAATCCGAGCAAACCTGTCTGCAAAGCCGTGCTGTGTCCTCAGCCGCC
GCCGGTGCAGAATGGAACAGTGGAGGGAAGTGATTTCCGCTGGGGCTCCAGCATAAGT
TACAGCTGCATGGACGGTTACCAGCTCTCTCACTCCGCCATCCTCTCCTGTGAAGGTC
GCGGGGTGTGGAAAGGAGAGATCCCCAGTGTCTGCCTGTGTTCTGCGGAGACCCTGGC
ATCCCCGCAGAAGGGCGACTTAGTGGGAAAAGTTTCACCTATAAGTCCGAAGTCTTCT
TCCAGTGCAAATCTCCATTTATACTCGTGGGATCCTCCAGAAGAGTCTGCCAAGCTGA
CGGCACGTGGAGCGGCATACAACCCACCTGCATTGGTAATAATTATCATACAGCTCTG
GGGATACCTGGGAGTATTTGGAGATGAGGACGCTTCATTCCGAAATTGGGTCATTTGT
GATTACATAGAAAGTGTTTCCATAGACAGTTTTCTGTACAAGGTTGGAAGCACGGTTT
TTTTCAGGTGCAGAAAAGGCTACCATATTCAAGGTTCCACGACTCGCACCTGCCTTGC
CAATTTAACATGGAGTGGGATACAGACCGAATGTATACCTCATGCCTGCAGACAGCCA
GAAACCCCGGCACACGCGGATGTGAGAGCCATCGATCTTCCTACTTTCGGCTACACCT
TAGTGTACACCTGCCATCCAGGCTTTTTCCTCGCAGGGGATCTCAGCACAGAACATG
TAAAGCAGACATGAAATGGACAGGAAAGTCGCCTGTGTGTAAAATTCCTTCAGATGTC
TTTTTCGTCAATTCACTGTGGAAGGGGTATTATGAATATTTAGGGAAAAGACAACCCG
CCACTCTAACTGTTGACTGGTTCAATGCAACAAGCAGTAAGGTGAATGCCACCTTCAG
CGAAGCCTCGCCAGTGGAGCTGAAGTTGACAGGCATTTACAAGAAGGAGGAGGCCCAC
TTACTCCTGAAAGCTTTTCAAATTAAAGGCCAGGCAGATATTTTTGTAAGCAAGTTCG
AAAATGACAACTGGGGACTAGATGGTTATGTGTCATCTGGACTTGAAAGAGGAGGATT
TACTTTTCAAGGTGACATTCATGGAAAAGACTTTGGAAAATTTAAGCTAGAAAGGCAA
GGATGGGTCACAATATTCTTGAGCCTATTTCTTCATCTTAAATCTCAGTATAGAAGTT
CCCAAGGTTGTTACGAGATTGAGAGGCCACATCCTTTAAACCCAGATCAAGACTCTTC
CAGTCATTACCACGGCACCAGCAGTGGCTCTGTGGCGGCTGCCATTCTGGTTCCTTTC
TTTGCTCTAATTTTATCAGGGTTTGCATTTTACCTCTACAAACACAGAACGAGACCAA
AAGTTCAATACAATGGCTATGCTGGGCATGAAAACAGCAATGGACAAGCATCGTTTGA
AAACCCCATGTATGATACAAACTTAAAACCCACAGAAGCCAAGGCTAAAACCACACAC
GGGCTGCTCACGTCTCTGGACTCCAAGAGAAAGATGGTTATAACCCTGGCAGAGTCTT
TACCCGCCCTGCGAACCTGCCTGTTGATCTGCTTCCCACTCCTCTTTAGACTTGCTCG
TGAATCTTCAGCACAGCCATTTGTTTTGAGTATTCAAACACATAAAAAGATATCTGGC
AACTTCCCACTTCTTATGACTTCTCAGACACCTTGTAACGGAGCTTCCCTTGGAGGTG
GACAAACTTCTCACTCACAAGAGAGACGGAGAGCAACAGAGAGAGATGGGCAGGGATT
GATTCGAGGATTGGCTGACTCGATTATGGAGGGTGAGAAGTCCCAGGACAGGCCGTCT
GCAAGGCGTAAACCCAGGGAAGCTGCTGGTATGGCTCGGTTCAAGTCCAAAGGCCTCA
GCACCAAGGAAACCAAGGTGATAACTCTCAGTTCGGGTCAAAGTCCTGGGAGTCTGCA
AGGCCTCTCATTGAGTAAGTCTCACAAGATCCGATGGTTTTATAAAGGGCAGTTCCCC
TGCACAAGCTCTCTTCTCTGCCACCACGCGTTTGCTGTTCATTCACCTTTCACCATGA
TTGTGAGGCCTCCCAGCCATGTGGAACTGTGCAAAGAGGATGTTCAAAGGGCATCTTG
GACCAGGAGGAGGAAGCCCATTGTGAGGATGGCAAAGAACAATAAATGGAAGGCCCGT
GGAACCCTGAGCGGCTGCCCCATCACTGTCCTCTCCATCCTTTCCATGCTTCCCATGG

TABLE 12A-continued

NOV12 Sequence Analysis

| | |
|---|---|
| | TGCATGGCTCTCAGGCTCTCCAAGCACCATGAGCTCCTGGCGCGTATGGCCTGGCCCC<br><br>TGAGTGTGGAGTCTGTGGACTTTAAATGTGCCTTTACTCAGCCAGCATCTCCCTGGCT<br><br>GGGTGCGATGTTG |
| NOV12a,<br>CG59905-01 Protein Sequence | ORF Start: ATG at 34     ORF Stop: TGA at 3046<br>SEQ ID NO: 32          1004 aa MW at 109752.7 kD<br>MANGLWIDRSLPKCLAISCGHPGVPANAVLTGELFTYGAVVHYSCRGSESLIGNDTRVC<br><br>QEDSHWSGALPHCTGNNPGFCGDPGTPAHGSRLGDDFKTKSLLRFSCEMGHQLRGSPE<br><br>RTCLLNGSWSGLQPVCEAVSCGNPGTPTNGMIVSSDGILFSSSVIYACWEGYKTSGLM<br><br>TRHCTANGTWTGTAPDCTIISCGDPGTLANGIQFGTDFTFNKTVSYQCNPGYVMEAVT<br><br>SATIRCTKDGRWNPSKPVCKAVLCPQPPPVQNGTVEGSDFRWGSSISYSCMDGYQLSH<br><br>SAILSCEGRGVWKCEIPSVCLCSAETLASPQKGDLVGKVSPISPKSSSSANLHLYSWD<br><br>PPEESAKLTARGAAYNPPALVIIIQLWGYLGVFGDEDASFRNWVICDYIESVSTDSF<br><br>LYKVGSTVFFRCRKGYHIQGSTTRTCLANLTWSGIQTECIPHACRQPETPAHADVRAI<br><br>DLPTFGYTLVYTCHPGFFLAGGSEHRTCKADMKWTGKSPVCKIPSDVFFVNSLWKGYY<br><br>EYLGKRQPATLTVDWFNATSSKVNATFSEASPVELKLTGIYKKEEAHLLLKAFQIKGQ<br><br>ADIFVSKFENDNWGLDGYVSSGLERGGFTFQGDIHGKDFGKFKLERQGWVTIFLSLFL<br><br>HLKSQYRSSQGCYEIERPHPLNPDQDSSSNYNGTSSGSVAAAILVPFFALILSGFAFY<br><br>LYKHRTRPKVQYNGYAGHENSNGQASFENPMYDTNLKPTEAKAKTTHGLLTSLDSKRK<br><br>MVITLAESLPALRTCLLICFPLLFRLARESSAQPFVLSIQTHKKISGNFPLIMTSQTP<br><br>CNGASLGGGQTSHSQERRRATERDGQGLIRGLADSIMEGEKSQDRPSARRKPREAAGM<br><br>ARFKSKGLSTKETKVITLSSGQSPGSLQGLSLSKSHKIRWFYKGQFPCTSSLLCHHAF<br><br>AVHSPFTMIVRPPSHVELCKEDVQRASWTRRRKPIVRMAKNNKWKARGTLSGCPITVL<br><br>SILSMLPMVHGSQALQAP |

Further analysis of the NOV12a protein yielded the following properties shown in Table 12B.

TABLE 12B

Protein Sequence Properties NOV12a

| | |
|---|---|
| PSort analysis: | 0.6000 probability located in nucleus; 0.6000 probability located in plasma membrane; 0.4000 probability located in Golgi body; 0.3000 probability located in in endoplasmic reticulum (membrane) |
| SignalP analysis: | No Known Signal Sequence Predicted |

A search of the NOV12a protein against the Geneseq database, a proprietary database that contains sequences published in patents and patent publication, yielded several homologous proteins shown in Table 12C.

TABLE 12C

Geneseq Results for NOV12a

| Geneseq Indentifier | Protein/Organism/Length [Patent #, Date] | NOV12a Residues/ Match Residues | Identities/ Similarities for the Matched Region | Expect Value |
|---|---|---|---|---|
| AAU00816 | Human Immunoglobulin superfamily, IgSF, protein #2 - *Homo sapiens*, 613 aa. [WO200118176-A1, 15 Mar. 2001] | 3..204<br>375..576 | 118/202 (58%)<br>152/202 (74%) | 4e-75 |
| AAG68264 | Human POLY11 protein sequence SEQ ID NO:22 - *Homo sapiens*, 2050 | 3..498<br>775..1242 | 147/507 (28%)<br>223/507 (42%) | 2e-64 |

TABLE 12C-continued

Geneseq Results for NOV12a

| Geneseq Indentifier | Protein/Organism/Length [Patent #, Date] | NOV12a Residues/ Match Residues | Identities/ Similarities for the Matched Region | Expect Value |
|---|---|---|---|---|
| | aa. [WO200179294-A2, 25 Oct. 2001] | | | |
| AAU19902 | Novel human calcium-binding protein #11 - *Homo sapiens*, 1139 aa. [WO200155304-A2, 02 Aug. 2001] | 3..498 270..737 | 147/507 (28%) 223/507 (42%) | 2e-64 |
| AAG66398 | Receptor 222 - Unidentified, 979 aa. [CN1296952-A, 30 May 2001] | 3..498 110..577 | 147/507 (28%) 223/507 (42%) | 2e-64 |
| AAU16963 | Human novel secreted protein, SEQ ID 204 - *Homo sapiens*, 1139 aa. [WO200155441-A2, 02 Aug. 2001] | 3..498 270..737 | 147/507 (28%) 223/507 (42%) | 2e-64 |

In a BLAST search of public sequence datbases, the NOV12a protein was found to have homology to the proteins shown in the BLASTP data in Table 12D.

TABLE 12D

Public BLASTP Results for NOV12a

| Protein Accession Number | Protein/Organism/Length | NOV12a Residues/ Match Residues | Identities/ Similarities for the Matched Portion | Expect Value |
|---|---|---|---|---|
| Q96Q03 | KIAA1884 PROTEIN - *Homo sapiens* (Human), 946 aa (fragment). | 6..739 221..932 | 375/757 (49%) 480/757 (62%) | 0.0 |
| Q96RM4 | CUB AND SUSHI MULTIPLE DOMAINS 1 PROTEIN - *Homo sapiens* (Human), 3508 aa. | 1..328 2786..3113 | 312/328 (95%) 313/328 (95%) | 0.0 |
| Q923L3 | CSMD1 - *Mus musculus* (Mouse), 3564 aa. | 1..328 2842..3169 | 279/328 (85%) 297/328 (90%) | e-176 |
| Q96QU9 | CUB AND SUSHI MULTIPLE DOMAINS PROTEIN 1 SHORT FORM - *Homo sapiens* (Human), 3389 aa. | 408..739 3058..3375 | 300/347 (86%) 302/347 (86%) | e-174 |
| Q96PZ3 | KIAA1894 PROTEIN - *Homo sapiens* (Human), 514 aa (fragment). | 218..739 2..500 | 239/544 (43%) 310/544 (56%) | e-125 |

PFam analysis predicts that the NOV12a protein contains the domains shown in the Table 12E.

TABLE 12E

Domain Analysis of NOV12a

| Pfam Domain | NOV12a Match Region | Identities/ Similarities for the Matched Region | Expect Value |
|---|---|---|---|
| sushi: domain 1 of 7 | 18..71 | 18/63 (29%) 43/63 (68%) | 2.9e-11 |
| sushi: domain 2 of 7 | 79..132 | 15/63 (24%) 41/63 (65%) | 4e-11 |
| sushi: domain 3 of 7 | 137..191 | 20/64 (31%) 41/64 (64%) | 1.4e-08 |
| sushi: domain 4 of 7 | 196..251 | 21/65 (32%) 46/65 (71%) | 5.2e-14 |
| sushi: domain 5 of 7 | 256..310 | 20/64 (31%) 45/64 (70%) | 4e-09 |
| myosin_head: domain 1 of 1 | 398..417 | 8/22 (36%) 16/22 (73%) | 8.1 |
| sushi: domain 6 of 7 | 395..445 | 18/62 (29%) 39/62 (63%) | 3.2e-07 |
| sushi: domain 7 of 7 | 450..505 | 18/64 (28%) 41/64 (64%) | 1.4e-09 |

Example 13

The NOV13 clone was analyzed, and the nucleotide and encoded polypeptide sequences are shown in Table 13A.

TABLE 13A

NOV13 Sequence Analysis

| | |
|---|---|
| NOV13a, CG59930-01 DNA Sequence | SEQ ID NO: 33    1463 bp<br>TGGCACGAGGATTACATTTCACTTGGTTACAGCTGACTGGGGATTTTAATCATTTGGA<br>GCCACACTGAAAAAAAAATTTCCCCCTGCAATCTACTCTTAACTGATAGTCGCTAACT<br>TTGGTTATGTGTGTCTATTCAGAATATTACATTAATTGATTTCTCAAACAAAGGTCCT<br>TTCTGAAATGGTATCTATGATTCAGCTATTCAAAACCTAATGAAGTTGGTGACTATGA<br>CAATGTGGAGAAATCATGACAGAAAATGTGGTTTGTACTGGGGCTGTCAATGCTGTAA<br>AGGAAGTTTGGGAAAAAAGAATAAAGAAACTCAATGAAGACCTGAAGCGAGAGAAGGA<br>ATTTCAACACAAGCTAGTGCGGATCTGGGAAGAACGAGTAAGCTTAACCAAGCTAAGA<br>GAAAAGGTCACCAGGGAAGATGGAAGAGTCATTTTGAAGATAGAAAAGAGGAATGGA<br>AGACCCTCCTTCTTCTCTGCTGAAACTGAATCAACTACAGGAATGGCAACTTCATAG<br>AACTGGTTTGCTGAAAATTCCTGAATTCATTGGAAGATTCCAGAACCTCATTGTGTTA<br>GATTTATCTCGAAACACAATTTCAGAGATACCACCAGGGATTGGACTGCTTACTAGAC<br>TTCAGGAACTGATTCTCAGCTACAACAAAATCAAGACTGTCCCCAAGGAACTAAGTAA<br>TTGTGCCAGCTTGGAGAAACTAGAACTGGCTGTTAACAGAGATATATGTGATCTTCCA<br>CAAGAGCTCAGCAATCTGCTAAAACTTACTCACCTTGATCTGAGTATGAACGATTTTA<br>CTACAATCCCTCTTGCTGTGTTGAACATGCCTGCCCTTGAGTGGCTGGACATGGGAAG<br>CAACAAACTTGAACAACTTCCTGATACTATAGAAAGAATGCAAAATCTACATACGTTA<br>TGGCTGCAACGAAATGAAATAACATGCTTGCCTCAAACAATCAGCAATATGAAAAATC<br>TGGGTACTCTTGTTCTCAGCAACAATAAACTGCAAGATATTCCAGTATGCATGGAAGA<br>AATGGCAAATCTGAGGTTTGTCAACTTCAGAGACAACCCACTGAAATTGAAAGTATCA<br>CTTCCTCCCAGTGAAGGCACAGATGAAGAAGAGGAACGGGAATTATTTGGCCTTCAGT<br>TTATGCACACATACATACAAGAGTCACGGAGAAGAGCAGATCACCAAGTCAACGGTTC<br>AACTACTTTACCAATCTCCATAAATACGGATGGATAATATAATTCAAGATGCCCTTCT<br>AAAGAGGATTACTTTGGTGAATTCTCTAATGTTTGGATTTCTGAAGTAAAAAGAAAAG<br>CTATTACCAAAGTTTAATGAGGCCACAGCATTTTTTAAAGTTCATATTATTTGCTATT<br>TAAAGTATATATTTTTTTGATATAAAAATATAATTAAAAATTTTTTGGTGCAAAAAAA<br>AAAAAAAAAAAAA |
| NOV13a, CG59930-01 Protein Sequence | ORF Start: ATG at 248  ORF Stop: TAA at 1253<br>SEQ ID NO: 34    335 aa  MW at 38792.5kD<br>MTENVVCTGAVNAVKEVWEKRIKKLNEDLKREKEFQHKLVRIWEERVSLTKLREKVTR<br>EDGRVILKIEKEEWKTLPSSLLKLNQLQEWQLHRTGLLKIPEFIGRFQNLIVLDLSRN<br>TISEIPPGIGLLTRLQELILSYNKIKTVPKELSNCASLEKLELAVNRDICDLPQELSN<br>LLKLTHLDLSMNDFTTIPLAVLNMPALEWLDMGSNKLEQLPDTIERMQNLHTLWLQRN<br>EITCLPQTISNMKNLGTLVLSNNKLQDIPVCMEEMANLRFVNFRDNPLKLKVSLPPSE<br>GTDEEEERELFGLQFMHTYIQESRRRADHQVNGSTTLPISINTDG |
| NOV13b, CG59930-02 DNA Sequence | SEQ ID NO: 35    1276 bp<br>CTAGAATTCAGCGGCCGCTGAATTCTAGCTGAAAAAAAAATTTCCCCCTGCAATCTAC<br>TCTTAACTGATAGTCGCTAACTTTGGTTATGTGTGGTAAGTATTTGACAATGTCTATT<br>CAGAATATTACATTAATTGATTTCTCAAACAAAGGTCCTTTCTGAAATGGTATCTATG<br>ATTCAGCTATTCAAAACCTAATGAAGTTGGTGACTATGACAATGTGGAGAAATCATGA<br>CAGAAAATGTGGTTTGTACTGGGGCTGTCAATGCTGTAAAGGAAGTTTGGGAAAAAAG |

TABLE 13A-continued

NOV13 Sequence Analysis

AATAAAGAAACTCAATGAAGACCTGAAGCGAGAGAAGGAATTTCAACACAAGCTAGTG

CGGATCTGGGAAGAACGAGTAAGCTTAACCAAGCTAAGAGAAAAGGTCACCAGGGAAG

ATGGAAGAGTCATTTTGAAGATAGAAAAAGAGGAATGGAAGACCCTCCCTTCTTCTCT

GCTGAAACTGAATCAACTACAGGAATGGCAACTTCATAGAACTGGTTTGCTGAAAATT

CCTGAATTCATTGGAAGATTCCAGAACCTCATTGTGTTAGATTTATCTCGAAACACAA

TTTCAGAGATACCACCAGGGATTGGACTGCTTACTAGACTTCAGGAACTGATTCTCAG

CTACAACAAAATCAAGACTGTCCCCAAGGAACTAAGTAATTGTGCCAGCTTGGAGAAA

CTAGAACTGGCTGTTAACAGAGATATATGTGATCTTCCACAAGAGCTCAGCAATCTGC

TAAAACTTACTCACCTTGATCTGAGTATGAACGATTTTACTACAATCCCTCTTGCTGT

GTTGAACATGCCTGCCCTTGAGTGGCTGGACATGGGAAGCAACAAACTTGAACAACTT

CCTGATACTATAGAAAGAATGCAAAATCTACATACGTTATGGCTGCAACGAAATGAAA

TAACATGCTTGCCTCAAACAATCAGCAATATGAAAAATCTGGGTACTCTTGTTCTCAG

CAACAATAAACTGCAAGATATTCCAGTATGCATGGAAGAAATGGCAAATCTGAGGTTT

GTCAACTTCAGAGACAACCCACTGAAATTGAAAGTATCACTTCCTCCCAGTGAAGGCA

CAGATGAAGAAGAGGAACGGGAATTATTTGGCCTTCAGTTTATGCACACATACATACA

AGAGTCACGGAGAAGAGCAGATCACCAAGTCAACGGTTCAACTACTTTACCAATCTCC

ATAAATACGGATGGATAATATAATTCAAGATGCCCTTTTAAAGAGGATTACTTTGGTG

| | |
|---|---|
| | ORF Start: ATG at 229  ORF Stop: TAA at 1234<br>SEQ ID NO: 36         335 aa  MW at 38792.5kD |
| NOV13b<br>CG59930-02 Protein Sequence | MTENVVCTGAVNAVKEVWEKRIKKLNEDLKREKEFQHKLVRIWEERVSLTKLREKVTR |
| | EDGRVILKIEKEEWKTLPSSLLKLNQLQEWQLHRTGLLKIPEFIGRFQNLIVLDLSRN |
| | TISEIPPGIGLLTRLQELILSYNKIKTVPKELSNCASLEKLELAVNRDICDLPQELSN |
| | LLKLTHLDLSMNDFTTIPLAVLNMPALEWLDMGSNKLEQLPDTIERMQNLHTLWLQRN |
| | EITCLPQTISNMKNLGTLVLSNNKLQDIPVCMEEMANLRFVNFRDNPLKLKVSLPPSE |
| | GTDEEEERELFGLQFMHTYIQESRRRADHQVNGSTTLPISINTDG |

Sequence comparison of the above protein sequences yields the following sequence relationships shown in Table 13B.

TABLE 13B

Comparison of NOV13a against NOV13b.

| Protein Sequence | NOV13a Residues/<br>Match Residues | Identities/Similarities<br>for the Matched Region |
|---|---|---|
| NOV13b | 1..335<br>1..335 | 335/335 (100%)<br>335/335 (100%) |

Further analysis of the NOV13a protein yielded the following properties shown in Table 13C.

TABLE 13C

Protein Sequence Properties NOV13a

| | |
|---|---|
| PSort analysis: | 0.6500 probability located in cytoplasm; 0.1000 probability located in mitochondrial matrix space; 0.1000 probability located in lysosome (lumen); 0.0000 probability located in endoplasmic reticulum (membrane) |
| SignalP analysis: | No Known Signal Sequence Predicted |

A search of the NOV13a protein against the Geneseq database, a proprietary database that contains sequences published in patents and patent publication, yielded several homologous proteins shown in Table 13D.

TABLE 13D

Geneseq Results for NOV13a

| Geneseq Identifier | Protein/Organism/Length [Patent #, Date] | NOV13a Residues/ Match Residues | Identities/ Similarities for the Matched Region | Expect Value |
|---|---|---|---|---|
| AAU70173 | Rat secreted factor protein encoded by DNA clone P0269__H08 - *Rattus norvegicus*, 142 aa. [WO200174901-A2, 11 Oct. 2001] | 1..140<br>1..141 | 116/141 (82%)<br>127/141 (89%) | 2e−59 |
| AAU21299 | Human novel foetal antigen, SEQ ID NO 1543 - *Homo sapiens*, 133 aa. [WO200155312-A2, 02 Aug. 2001] | 1..120<br>6..125 | 110/120 (91%)<br>114/120 (94%) | 7e−58 |
| AAB31563 | Amino acid sequence of a human SGT4-1 polypeptide - *Homo sapiens*, 371 aa. [WO200078959-A1, 28 Dec. 2000] | 10..316<br>39..355 | 108/318 (33%)<br>186/318 (57%) | 1e−48 |
| AAB31564 | Amino acid sequence of a human SGT4-2 polypeptide - *Homo sapiens*, 226 aa. [WO200078959-A1, 28 Dec. 2000] | 110..316<br>3..210 | 78/208 (37%)<br>132/208 (62%) | 2e−38 |
| ABG04747 | Novel human diagnostic protein #4738 - *Homo sapiens*, 1271 aa. [WO200175067-A2, 11 Oct. 2001] | 64..281<br>65..281 | 68/218 (31%)<br>117/218 (53%) | 5e−25 |

In a BLAST search of public sequence datbases, the NOV13a protein was found to have homology to the proteins shown in the BLASTP data in Table 13E.

TABLE 13E

Public BLASTP Results for NOV13a

| Protein Accession Number | Protein/Organim/Length | NOV13a Residues/ Match Residues | Identities/ Similarities for the Matched Portion | Expect Value |
|---|---|---|---|---|
| Q96DD0 | SIMILAR TO RIKEN CDNA 2010005E21 GENE - *Homo sapiens* (Human), 335 aa. | 1..335<br>1..335 | 335/335 (100%)<br>335/335 (100%) | 0.0 |
| Q9D8D7 | 2010005E21RIK PROTEIN - *Mus musculus* (Mouse), 175 aa. | 1..175<br>1..175 | 156/175 (89%)<br>167/175 (95%) | 1e−84 |
| CAD20990 | LEUCINE-RICH REPEAT-CONTAINING 2 PROTEIN - *Mus musculus* (Mouse), 371 aa. | 11..316<br>10..355 | 117/346 (33%)<br>188/346 (53%) | 4e−51 |
| Q9CX04 | 2400002D05RIK PROTEIN - *Mus musculus* (Mouse), 371 aa. | 11..316<br>10..355 | 117/346 (33%)<br>188/346 (53%) | 4e−51 |
| Q9BYS8 | LEUCINE-RICH REPEAT-CONTAINING 2 PROTEIN - *Homo sapiens* (Human), 371 aa. | 10..316<br>39..355 | 108/318 (33%)<br>186/318 (57%) | 2e−48 |

PFam analysis predicts that the NOV13a protein contains the domains shown in the Table 13F.

TABLE 13F

Domain Analysis of NOV13a

| Pfam Domain | NOV13a Match Region | Identities/ Similarities for the Matched Region | Expect Value |
|---|---|---|---|
| LRR: domain 1 of 7 | 107..129 | 12/25 (48%)<br>20/25 (80%) | 0.00049 |
| LRR: domain 2 of 7 | 130..152 | 9/25 (36%)<br>20/25 (80%) | 0.0094 |
| LRR: domain 3 of 7 | 153..176 | 10/26 (38%)<br>17/26 (65%) | 75 |
| LRR: domain 4 of 7 | 177..199 | 9/25 (36%)<br>18/25 (72%) | 0.12 |
| LRR: domain 5 of 7 | 200..222 | 8/25 (32%)<br>20/25 (80%) | 0.54 |
| LRR: domain 6 of 7 | 223..245 | 8/25 (32%)<br>19/25 (76%) | 0.021 |
| LRR: domain 7 of 7 | 246..268 | 9/25 (36%)<br>16/25 (64%) | 10 |

Example 14

The NOV14 clone was analyzed, and the nucleotide and encoded polypeptide sequences are shown in Table 14A.

TABLE 14A

NOV14 Sequence Analysis

| | |
|---|---|
| NOV14a,<br>CG59934-01 DNA Sequence | SEQ ID NO: 37    1933 bp<br>CTCCTTTCCACTTCTTTCCCCAGTCTGAGAAGAATACAGAAAGCCCCAAAGCCCTGGG<br>TCTTGGTCCTGCCGCATGTTGGAGCTCGCTGTCCAGTGCTGGGGTCACTATGCCCTGG<br>TCACTGTGCCCTGGTCACTGTGCCATGCTGTGTGATGATCAAGTTTCTCTTCCTGTTC<br>TCTCTCCCTCCTCGAATCTAGAAGATGCTCCCTGGAGCCTGGCTGCTCTGGACCTCCC<br>TCCTGCTCCTGGCCAGGCCTGCCCAGCCCTGTCCCATGGGTTGTGACTGCTTCGTCCA<br>GGAGGTGTTCTGCTCAGATGAGGAGCTTGCCACCGTCCCGCTGGACATCCCGCCATAT<br>ACGAAAAACATCATCTTTGTGGAGACCTCGTTCACCACATTGGAAACCAGAGCTTTTG<br>GCAGTAACCCCAACTTGACCAAGGTGGTCTTCCTCAACACTCAGCTCTGCCAGTTTAG<br>GCCGGATGCCTTTGGGGGCTGCCCAGGCTGGAGGACCTGGAGGTCACAGGCAGTAGC<br>TTCTTGAACCTCAGCACCAACATCTTCTCCAACCTGACCTCGCTGGGCAAGCTCACCC<br>TCAACTTCAACATGCTGGAGGCTCTGCCCGAGGGTCTTTTCCAGCACCTGGCTGCCCT<br>GGAGTCCCTCCACCTGCAGGGGAACCAGCTCCAGGCCCTGCCCAGGAGGCTCTTCCAG<br>CCTCTGACCCATCTGAAGACACTCAACCTGGCCCAGAACCTCCTGGCCCAGCTCCCGG<br>AGGAGCTGTTCCACCCACTCACCAGCCTGCAGACCCTGAAGCTGAGCAACAACGCGCT<br>CTCTGGTCTCCCCCAGGGTGTGTTTGGCAAACTGGGCAGCCTGCAGGAGCTCTTCCTG<br>GACAGCAACAACATCTCGGAGCTGCCCCCTCAGGTGTTCTCCCAGCTCTTCTGCCTAG<br>AGAGGCTGTGGCTGCAACGCAACGCCATCACGCACCTGCCGCTCTCCATCTTTGCCTC<br>CCTGGGTAATCTGACCTTTCTGAGCTTGCAGTGGAACATGCTTCGGGTCCTGCCTGCC<br>GGCCTCTTTGCCCACACCCCATGCCTGGTTGGCCTGTCTCTGACCCATAACCAGCTGG<br>AGACTGTCGCTGAGGGCACCTTTGCCCACCTGTCCAACCTGCGTTCCCTCATGCTCTC<br>ATACAATGCCATTACCCACCTCCCAGCTGGCATCTTCAGAGACCTGGAGGAGTTGGTC<br>AAACTCTACCTGGGCAGCAACAACCTTACGGCGCTGCACCCAGCCCTCTTCCAGAACC<br>TGTCCAAGCTGGAGCTGCTCAGCCTCTCCAAGAACCAGCTGACCACACTTCCGGAGGG<br>CATCTTCGACACCAACTACAACCTGTTCAACCTGGCCCTGCACGGTAACCCCTGGCAG<br>TGCGACTGCCACCTGGCCTACCTCTTCAACTGGCTGCAGCAGTACACCGATCGGCTCC<br>TGAACATCCAGACCTACTGCGCTGGCCCTGCCTACCTCAAAGGCCAGGTGGTGCCCGC<br>CTTGAATGAGAAGCAGCTGGTGTGTCCCGTCACCCGGGACCACTTGGGCTTCCAGGTC<br>ACGTGGCCGGACGAAAGCAAGGCAGGGGGCAGCTGGGATCTGGCTGTGCAGGAAAGGG<br>CAGCCCGGAGCCAGTGCACCTACAGCAACCCCGAGGGCACCGTGGTGCTCGCCTGTGA<br>CCAGGCCCAGTGTCGCTGGCTGAACGTCCAGCTCTCTCCTTGGCAGGGCTCCCTGGGA<br>CTGCAGTACAATGCTAGTCAGGAGTGGGACCTGAGGTCGAGCTGCGGTTCTCTGCGGC<br>TCACCGTGTCTATCGAGGCTCGGGCAGCAGGGCCCTAGTAGCAGCGCATACAGGAGCT<br>GGGGAAGGGGCTTTGGGGCCTGCCCACGCGACAGGTAGGGCGGAGGGGAGCTGAGT<br>CTCCGAAGCTTGGCTTTAC<br><br>ORF Start: ATG at 199    ORF Stop: TAG at 1834<br>SEQ ID NO: 38    545 aa    MW at 60613.9 kD |
| NOV14a,<br>CG59934-01 Protein Sequence | MLPGAWLLWTSLLLLARPAQPCPMGCDCFVQEVFCSDEELATVPLDIPPYTKNIIFVE<br>TSFTTLETRAFGSNPNLTKVVFLNTQLCQFRPDAFGGLPRLEDLEVTGSSFLNLSTNI<br>FSNLTSLGKLTLNFNMLEALPEGLFQHLAALESLHLQGNQLQALPRRLFQPLTHLKTL |

TABLE 14A-continued

NOV14 Sequence Analysis

|  |  |
| --- | --- |
|  | NLAQNLLAQLPEELFHPLTSLQTLKLSNNALSGLPQGVFGKLGSLQELFLDSNNISEL |
|  | PPQVFSQLFCLERLWLQRNAITHLPLSIFASLGNLTFLSLQWNMLRVLPAGLFAHTPC |
|  | LVGLSLTHNQLETVAEGTFAHLSNLRSLMLSYNAITHLPAGIFRDLEELVKLYLGSNN |
|  | LTALHPALFQNLSKLELLSLSKNQLTTLPEGIFDTNYNLFNLALHGNPWQCDCHLAYL |
|  | FNWLQQYTDRLLNIQTYCAGPAYLKGQVVPALNEKQLVCPVTRDHLGFQVTWPDESKA |
|  | GGSWDLAVQERAARSQCTYSNPEGTVVLACDQAQCRWLNVQLSPWQGSLGLQYNASQE |
|  | WDLRSSCGSLRLTVSIEARAAGP |
| NOV14b, CG59934-02 DNA Sequence | SEQ ID NO: 39             11719 bp <br> <u>CCATGCTGTGTGATGATCAAGTTTCTCTTCCTGTTCTCTCTCCCTCCTCGAATCTAGA</u> <br> <u>AG</u>ATGCTCCCTGGAGCCTGGCTGCTCTGGACCTCCCTCCTGCTCCTGGCCAGGCCTGC <br> CCAGCCCTGTCCCATGGGTTGTGACTGCTTCGTCCAGGAGGTGTTCTGCTCAGATGAG <br> GAGCTTGCCACCGTCCCACTGGACATCCCGCCATATACGAAAAACATCATCTTTGTGG <br> AGACCTCGTTCACCACATTGGAAACCAGAGCTTTTGGCAGTAACCCCAACTTGACCAA <br> GGTGGTCTTCCTCAACACTCAGCTCTGCCAGTTTAGGCCGGATGCCTTCAGGGGCTG <br> CCCAGGCTGGAGGACCTGGAGGTCACAGGCAGTAGCTTCTTGAACCTCAGCACCAACA <br> TCTTCTCCAACCTGACCTCGCTGGGCAAGCTCACCCTCAACTTCAACATGCTGGAGGC <br> TCTGCCCGAGGGTCTTTTCCAGCACCTGGCTGCCCTGGAGTCCCTCCACCTGCAGGGG <br> AACCAGCTCCAGGCCCTGCCCAGGAGGCTCTTCCAGCCTCTGACCCATCTGAAGACAC <br> TCAACCTGGCCCAGAACCTCCTGGCCCAGCTCCCGGAGGAGCTGTTCCACCCACTCAC <br> CAGCCTGCAGACCCTGAAGCTGAGCAACAACGCGCTCTCTGGTCTCCCCCAGGGTGTG <br> TTTGGCAAACTGGGCAGCCTGCAGGAGCTCTTCCTGGACAGCAACAACATCTCGGAGC <br> TGCCCCCTCAGGTGTTCTCCCAGCTCTTCTGCCTAGAGAGGCTGTGGCTGCAACGCAA <br> CGCCATCACGCACCTGCCGCTCTCCATCTTTGCCTTCCTGGGTAATCTGACCTTTCTG <br> AGCTTGCAGTGGAACATGCTTCGGGTCCTGCCTGCCGGCCTCTTTGCCCACACCCCGT <br> GCCTGGTTGGCCTGTCTCTGACCCATAACCAGCTGGAGACTGTCGCTGAGGGCACCTT <br> TGCCCACCTGTCCAACCTGCGTTCCCTCATGCTCTCATACAATGCCATTACCCACCTC <br> CCAGCTGGCATCTTCAGAGACCTGGAGGAGTTGGTCAAACTCTACCTGGGCAGCAACA <br> ACCTTACGGCGCTGCACCCAGCCCTCTTCCAGAACCTGTCCAAGCTGGAGCTGCTCAG <br> CCTCTCCAAGAACCAGCTGACCACACTTCCGGAGGGCATCTTCGACACCAACTACAAC <br> CTGTTCAACCTGGCCCTGCACGGTAACCCCTGGCAGTGCGACTGCCACCTGGCCTACC <br> TCTTCAACTGGCTGCAGCAGTACACCGATCGGCTCCTGAACATCCAGACCTACTGCGC <br> TGGCCCTGCCTACCTCAAAGGCCAGGTGGTGCCCGCCTTGAATGAGAAGCAGCTGGTG <br> TGTCCCGTCACCCGGGACCACTTGGGCTTCCAGGTCACGTGGCCGGACGAAAGCAAGG <br> CAGGGGGCAGCTGGGATCTGGCTGTGCAGGAAAGGGCAGCCCGGAGCCAGTGCACCTA <br> CAGCAACCCCGAGGGCACCGTGGTGCTCGCCTGTGACCAGGCCCAGTGTCGCTGGCTG <br> AACGTCCAGCTCTCTCCTCAGCAGGGCTCCCTGGGACTGCAGTACAATGCTAGTCAGG <br> AGTGGGACCTGAGGTCGAGCTGCGGTTCTCTGCGGCTCACCGTGTCTATCGAGGCTCG <br> GGCAGCAGGGCCCTAG<u>TAGCAGCGCATACAGGAGCTG</u> |
|  | ORF Start: ATG at 61        ORF Stop: TAG at 1696 <br> SEQ ID NO: 40               545 aa  MW at 60715.1 kD |

TABLE 14A-continued

NOV14 Sequence Analysis

| | |
|---|---|
| NOV14b, CG59934-02 Protein Sequence | MLPGAWLLWTSLLLLARPAQPCPMGCDCFVQEVFCSDEELATVPLDIPPYTKNIIFVE<br>TSFTTLETRAFGSNPNLTKVVFLNTQLCQFRPDAFRGLPRLEDLEVTGSSFLNLSTNI<br>FSNLTSLGKLTLNFNMLEALPEGLFQHLAALESLHLQGNQLQALPRRLFQPLTHLKTL<br>NLAQNLLAQLPEELFHPLTSLQTLKLSNNALSGLPQGVFGKLGSLQELFLDSNNISEL<br>PPQVFSQLFCLERLWLQRNAITHLPLSIFAFLGNLTFLSLQWNMLRVLPAGLFAHTPC<br>LVGLSLTHNQLETVAEGTFAHLSNLRSLMLSYNAITHLPAGIFRDLEELVKLYLGSNN<br>LTALHPALFQNLSKLELLSLSKNQLTTLPEGIFDTNYNLFNLALHGNPWQCDCHLAYL<br>FNWLQQYTDRLLNIQTYCAGPAYLKGQVVPALNEKQLVCPVTRDHLGFQVTWPDESKA<br>GGSWDLAVQERAARSQCTYSNPEGTVVLACDQAQCRWLNVQLSPQQGSLGLQYNASQE<br>WDLRSSCGSLRLTVSIEARAAGP |

Sequence comparison of the above protein sequences yields the following sequence relationships shown in Table 14B.

TABLE 14B

Comparison of NOV14a against NOV14b.

| Protein Sequence | NOV14a Residues/ Match Residues | Identities/Similarities for the Matched Region |
|---|---|---|
| NOV14b | 1..545<br>1..545 | 492/545 (90%)<br>492/545 (90%) |

Further analysis of the NOV14a protein yielded the following properties shown in Table 14C.

TABLE 14C

Protein Sequence Properties NOV14a

| | |
|---|---|
| PSort analysis: | 0.8493 probability located in lysosome (lumen); 0.3700 probability located in outside; 0.1325 probability located in microbody (peroxisome); 0.1000 probability located in endoplasmic reticulum (membrane) |
| SignalP analysis: | Cleavage site between residues 22 and 23 |

A search of the NOV14a protein against the Geneseq database, a proprietary database that contains sequences published in patents and patent publication, yielded several homologous proteins shown in Table 14D.

TABLE 14D

Geneseq Results for NOV14a

| Geneseq Identifier | Protein/Organism/Length [Patent #, Date] | NOV14a Residues/ Match Residues | Identities/ Similarities for the Matched Region | Expect Value |
|---|---|---|---|---|
| ABB53264 | Human polypeptide #4 - *Homo sapiens*, 581 aa. [WO200181363-A1, 01 Nov. 2001] | 22..439<br>25..468 | 148/444 (33%)<br>213/444 (47%) | 4e−56 |
| AAY69183 | Amino acid sequence of murine glycoprotein V (GP V) - Mus sp, 566 aa. [WO200008137-A2, 17 Feb. 2000] | 1..427<br>1..454 | 150/455 (32%)<br>205/455 (44%) | 2e−50 |
| AAY69184 | Amino acid sequence of a human glycoprotein V (GP V) - *Homo sapiens*, 560 aa. [WO200008137-A2, 17 Feb. 2000] | 1..449<br>1..476 | 152/500 (30%)<br>212/500 (42%) | 3e−47 |
| AAR71294 | Human glycoprotein V - *Homo sapiens*, 560 aa. [WO9502054-A, 19 Jan. 1995] | 1..449<br>1..476 | 152/500 (30%)<br>212/500 (42%) | 3e−47 |
| AAR85889 | WD-40 domain-contg. rat insulin-like growth factor binding protein - *Rattus rattus*, 603 aa. [WO9521252-A2, 10 Aug. 1995] | 22..444<br>41..601 | 171/564 (30%)<br>221/564 (38%) | 3e−41 |

In a BLAST search of public sequence datbases, the NOV14a protein was found to have homology to the proteins shown in the BLASTP data in Table 14E.

TABLE 14E

Public BLASTP Results for NOV14a

| Protein Accession Number | Protein/Organism/Length | NOV14a Residues/ Match Residues | Identities/ Similarities for the Matched Portion | Expect Value |
| --- | --- | --- | --- | --- |
| P22792 | Carboxypeptidase N 83 kDa chain (Carboxypeptidase N regulatory subunit) - *Homo sapiens* (Human), 536 aa (fragment). | 23..531 2..511 | 459/521 (88%) 466/521 (89%) | 0.0 |
| AAH25836 | SIMILAR TO CARBOXYPEPTIDASE N, POLYPEPTIDE 2, 83KD - *Mus musculus* (Mouse), 562 aa. (fragment). | 1..545 16..562 | 368/547 (67%) 434/547 (79%) | 0.0 |
| Q9DBB9 | 1300018K11RIK PROTEIN - *Mus musculus* (Mouse), 570 aa. | 1..545 24..570 | 368/547 (67%) 434/547 (79%) | 0.0 |
| BAB84586 | LIB - *Rattus norvegicus* (Rat), 578 aa. | 22..439 25..468 | 148/444 (33%) 210/444 (46%) | 4e−59 |
| BAB84587 | LIB - *Homo sapiens* (Human), 581 aa. | 22..439 25..468 | 148/444 (33%) 213/444 (47%) | 1e−55 |

PFam analysis predicts that the NOV14a protein contains the domains shown in the Table 14F.

TABLE 14F

Domain Analysis of NOV14a

| Pfam Domain | NOV14a Match Region | Identities/ Similarities for the Matched Region | Expect Value |
| --- | --- | --- | --- |
| LRRNT: domain 1 of 1 | 21..48 | 12/31 (39%) 19/31 (61%) | 0.00049 |
| LRR: domain 1 of 13 | 74..97 | 9/25 (36%) 16/25 (64%) | 1.9e+02 |
| LRR: domain 2 of 13 | 98..121 | 7/25 (28%) 16/25 (64%) | 1.5e+02 |
| LRR: domain 3 of 13 | 122..145 | 9/25 (36%) 18/25 (72%) | 1 |
| LRR: domain 4 of 13 | 146..169 | 10/25 (40%) 19/25 (76%) | 0.0093 |
| LRR: domain 5 of 13 | 170..193 | 10/25 (40%) 18/25 (72%) | 0.022 |
| LRR: domain 6 of 13 | 194..217 | 13/25 (52%) 21/25 (84%) | 0.00021 |
| LRR: domain 7 of 13 | 218..241 | 12/25 (48%) 22/25 (88%) | 0.0004 |
| LRR: | 242..265 | 9/25 (36%) | 0.29 |

TABLE 14F-continued

Domain Analysis of NOV14a

| Pfam Domain | NOV14a Match Region | Identities/ Similarities for the Matched Region | Expect Value |
| --- | --- | --- | --- |
| domain 8 of 13 | | 18/25 (72%) | |
| LRR: domain 9 of 13 | 266..289 | 10/25 (40%) 20/25 (80%) | 0.067 |
| LRR: domain 10 of 13 | 290..313 | 7/25 (28%) 19/25 (76%) | 0.79 |
| LRR: domain 11 of 13 | 314..337 | 10/25 (40%) 20/25 (80%) | 0.00072 |
| LRR: domain 12 of 13 | 338..361 | 11/25 (44%) 18/25 (72%) | 0.015 |
| LRR: domain 13 of 13 | 362..385 | 10/25 (40%) 17/25 (68%) | 0.15 |
| LRRCT: domain 1 of 1 | 395..446 | 20/55 (36%) 41/55 (75%) | 2e−12 |

Example 15

The NOV15 clone was analyzed, and the nucleotide and encoded polypeptide sequences are shown in Table 15A.

TABLE 15A

NOV15 Sequence Analysis

NOV15a, CG88565-01 DNA Sequence

SEQ ID NO: 41    1068 bp

GCTTGCTTCCCCAACCCTGCACCGGCCATGCGCCCGGCCTTGGCGGTGGGCCTGGTGT

TCGCAGGCTGCTGCAGTAACGTGATCTTCCTAGAGCTCCTGGCCCGGAAGCATCCAGG

ATGTGGGAACATTGTGACATTTGCACAATTTTTATTTATTGCTGTGGAAGGCTTCCTC

TTTGAAGCTGATTTGGGAAGGAAGCCACCAGCTATCCCAATAAGGTATTATGCCATAA

TGGTGACCATGTTCTTCACCGTGAGCGTGGTGAACAACTATGCCCTGAATCTCAACAT

TGCCATGCCCCTGCATATGATATTTAGATCCGGTTCTCTAATTGCCAACATGATTCTA

TABLE 15A-continued

NOV15 Sequence Analysis

```
GGAATTATCATTTTGAAGAAAAGGTACAGTATATTCAAATATACCTCCATTGCCCTGG
TGTCTGTGGGGATATTTATTTGCACTTTTATGTCAGCAAAGCACGTGACTTCCCAGTC
CAGCTTGAGTGAGAATGATGGATTCCAGGCATTTGTGTGGTGGTTACTAGGCATTGGG
GCATTGACTTTTGCTCTTCTGATGTCAGCAAGGATGGGCGTATTCCAAGAGACTCTCT
ACAAACGATTTGGGAAACACTCCAAGGAGGCTTTGTTTTATAATCACGCCCTTCCACT
TCCGGGTTTCGTCTTCTTGGCTTCTGATATTTATGACCATGCAGTTCTATTCAATAAG
TCTGAGTTATATGAAATTCCCGTCATCGGAGTGACCCTGCCCATCATGTGGTTCTACC
TCCTCATGAACATCATCACTCAGTATGTGTGCATCCGGGGTGTGTTTATCCTCACCAC
AGAATGCGCCTCCCTCACCGTCACGCTCGTCGTGACCCTACGCAAATTTGTGAGCCTC
ATCTTTTGCATCTTGTACTTCCAGAACCCCTTCACCCTGTGGCACTGGCTGGGCACCT
TGTTTGTCTTCATTGGGACCTTAATGTACACAGAGGTGTGGAACAACCTAGGGACCAC
AAAAAGTGAGCCTCAGAAGGACAGCAAGAAGAACTGAGGCCTGTCTGGAGTACGTAGA
CCAGTGTCGTCGTGAGGGTGGGAC
```

NOV15a, CG88565-01 Protein Sequence

ORF Start: ATG at 28  ORF Stop: TGA at 1021
SEQ ID NO: 42          331 aa   MW at 37423.1 kD

```
MRPALAVGLVFAGCCSNVIFLELLARKHPGCGNIVTFAQPLFIAVEGFLFEADLGRKP
PAIPIRYYAIMVTMFFTVSVVNNYALNLNIAMPLHMIFRSGSLIANMILGIIILKKRY
SIFKYTSIALVSVGIFICTFMSAKQVTSQSSLSENDGFQAPVWWLLGIGALTFALLMS
ARMGIFQETLYKRFGKHSKEALFYNHALPLPGFVFLASDIYDHAVLFNKSELYEIPVI
GVTLPIMWFYLLMNIITQYVCIRGVFILTTECASLTVTLVVTLRKFVSLIFSILYFQN
PFTLWHWLGTLFVFIGTLMYTEVWNNLGTTKSEPQKDSKKN
```

Further analysis of the NOV15a protein yielded the following properties shown in Table 15B.

TABLE 15B

Protein Sequence Properties NOV15a

| | |
|---|---|
| PSort analysis: | 0.6400 probability located in plasma membrane; 0.4600 probability located in Golgi body; 0.3700 probability located in endoplasmic reticulum (membrane); 0.1000 probability located in endoplasmic reticulum (lumen) |
| SignalP analysis: | Cleavage site between residues 22 and 23 |

A search of the NOV15a protein against the Geneseq database, a proprietary database that contains sequences published in patents and patent publication, yielded several homologous proteins shown in Table 15C.

TABLE 15C

Geneseq Results for NOV15a

| Geneseq Identifier | Protein/Organism/Length [Patent #, Date] | NOV15a Residues/ Match Residues | Identities/ Similarities for the Matched Region | Expect Value |
|---|---|---|---|---|
| AAB88341 | Human membrane or secretory protein clone PSEC0055 - *Homo sapiens*, 331 aa. [EP1067182-A2, 10 Jan. 2001] | 1..331<br>1..331 | 331/331 (100%)<br>331/331 (100%) | 0.0 |
| AAB74727 | Human membrane associated protein MEMAP-33 - *Homo sapiens*, 331 aa. [WO200112662-A2, 22 Feb. 2001] | 1..331<br>1..331 | 331/331 (100%)<br>331/331 (100%) | 0.0 |

TABLE 15C-continued

Geneseq Results for NOV15a

| Geneseq Identifier | Protein/Organism/Length [Patent #, Date] | NOV15a Residues/ Match Residues | Identities/ Similarities for the Matched Region | Expect Value |
|---|---|---|---|---|
| AAB94391 | Human protein sequence SEQ ID NO:14953 - *Homo sapiens*, 331 aa. [EP1074617-A2, 07 Feb. 2001] | 1..331 1..331 | 331/331 (100%) 331/331 (100%) | 0.0 |
| AAM96349 | Human reproductive system related antigen SEQ ID NO: 5007 - *Homo sapiens*, 241 aa. [WO200155320-A2, 02 Aug. 2001] | 29..255 7..233 | 212/227 (93%) 220/227 (96%) | e-120 |
| AAB93332 | Human protein sequence SEQ ID NO:12434 - *Homo sapiens*, 185 aa. [EP1074617-A2, 07 Feb. 2001] | 69..250 1..182 | 182/182 (100%) 182/182 (100%) | e-100 |

In a BLAST search of public sequence datbases, the NOV15a protein was found to have homology to the proteins shown in the BLASTP data in Table 15D.

TABLE 15D

Public BLASTP Results for NOV15a

| Protein Accession Number | Protein/Organism/Length | NOV15a Residues/ Match Residues | Identities/ Similarities for the Matched Portion | Expect Value |
|---|---|---|---|---|
| Q969S0 | MRNA, SIMILAR TO YEAST YEA4P COMPLETE CDS (UNKNOWN) (PROTEIN FOR MGC:14552) (CDNA FLJ14697 FIS, CLONE NT2RP2005812) - *Homo sapiens* (Human), 331 aa. | 1..331 1..331 | 331/331 (100%) 331/331 (100%) | 0.0 |
| Q95KB4 | HYPOTHETICAL 37.4 KDA PROTEIN - *Macaca fascicularis* (Crab eating macaque) (Cynomolgus monkey), 331 aa. | 1..331 1..331 | 327/331 (98%) 330/331 (98%) | 0.0 |
| Q9JJF7 | BRAIN CDNA, CLONE MNCB-4414, SIMILAR TO NM_005827 UDP-GALACTOSE TRANSPORTER RELATED (*HOMO SAPIENS*) - *Mus musculus* (Mouse), 331 aa. | 1..331 1..331 | 301/331 (90%) 316/331 (94%) | e-178 |
| Q9W429 | CG3774 PROTEIN - *Drosophila melanogaster* (Fruit fly), 352 aa. | 1..317 5..328 | 174/324 (53%) 237/324 (72%) | e-101 |
| Q96K33 | CDNA FLJ14820 FIS, CLONE OVARC1000335 - *Homo sapiens* (Human), 185 aa. | 69..250 1..182 | 182/182 (100%) 182/182 (100%) | e-100 |

PFam analysis predicts that the NOV15a protein contains the domains shown in the Table 15E.

TABLE 15E

Domain Analysis of NOV15a

| Pfam Domain | NOV15a Match Region | Identities/ Similarities for the Matched Region | Expect Value |
|---|---|---|---|
| cytochrome_b_C: domain 1 of 1 | 257..288 | 9/38 (24%) 24/38 (63%) | 7.2 |
| DUF6: domain 1 of 1 | 136..312 | 23/177 (13%) 110/177 (62%) | 3.1 |
| CbiM: domain 1 of 1 | 183..323 | 28/199 (14%) 93/199 (47%) | 9.1 |

Example 16

The NOV16 clone was analyzed, and the nucleotide and encoded polypeptide sequences are shown in Table 16A.

TABLE 16A

NOV16 Sequence Analysis

| | |
|---|---|
| NOV16a, CG88623-01 DNA Sequence | SEQ ID NO: 43  1455 bp<br>CAGCCAGGAGGAAAAAGCTAGGCGTCCACTTTCCGCAGCCATGCTCAAACAGAGTGAG AGGAGACGGTCCTGGAGCTACAGGCCCTGGAACACGACGGAGCTGAATGTGAACGTGG GTGGCCACAGCTACCAGCTGGACTACTGCGAGCTGGCCGGCTTCCCCAAGACGCGCCT AGGTCGCCTGGCCACCTCCACCAGCCGCAGCCGCCAGCTAAGCCTGTGCGACGACTAC GAGGAGCAGACAGACGAATACTTCTTCGACCGCGACCCGGCCGTCTTCCAGCTGGTCT ACAATTTCTACCTGTCCGGGGTGCTGCTGGTGCTCGACGGGCTGTGTCCGCGCCGCTT CCTGGAGGAGCTGGGCTACTGGGGCGTGCGGCTCAAGTACACGCCCACGCTGCTGCCGC ATCTGCTTCGAGGAGCGGCGCGACGAGCTGAGCGAACGGCTCAAGATCCAGCACGAGC TGCGCGCGCAGGCGCAGGTCGAGGAGGCGGAGGAACTCTTCCGCGACATGCGCTTCTA CGGCCCGCAGCGGCGCCGCCTCTGGAACCTCATGGAGAAGCCATTCTCCTCGGTGGCC GCCAAGGCCATCGGGGTGGCCTCCAGCACCTTCGTGCTCGTCTCCGTGGTGGCGCTGG CGCTCAACACCGTGGAGGAGATGCAGCAGCACTCGGGGCAGGGCGAGGGCGGCCCAGA CCTGCGGCCCATCCTGGAGCACGTGGACATGCTGTGCATGGGCTTCTTCACGCTCGAG TACCTGCTGCGCCTAGCCTCCACGCCCGACCTGAGGCGCTTCGCGCGCAGCGCCCTCA ACCTGGTGGACCTGGTGGCCATCCTGCCGCTCTACCTTCAGCTGCTGCTCGAGTGCTT CACGGGCGAGGGCCACCAACGCGGCCAGACGGTGGGCAGCGTGGGTAAGGTGGGTCAG GTGTTGCGCGTCATGCGCCTCATGCGCATCTTCCGCATCCTCAAGCTGGCGCGCCACT CCACCGGACTGCGTGCCTTCGGCTTCACGCTGCGCCAGTGCTACCAGCAGGTGGGCTG CCTGCTGCTCTTCATCGCCATGGGCATCTTCACTTTCTCTGCGGCTGTCTACTCTGTG GAGCACGATGTGCCCAGCACCAACTTCACTACCATCCCCCACTCCTGGTGGTGGGCCG CGGTGAGCATCTCCACCGTGGGCTACGGAGACATGTACCCAGAGACCCACCTGGGCAG GTTTTTTGCCTTCCTCTGCATTGCTTTTGGGATCATTCTCAACGGGATGCCCATTTCC ATCCTCTACAACAAGTTTTCTGATTACTACAGCAAGCTGAAGGCTTATGAGTATACCA CCATACGCAGGGAGAGGGGAGAGGTGAACTTCATGCAGAGAGCCAGAAAGAAGATAGC TGAGTGTTTGCTTGGAAGCAACCCACAGCTCACCCCAAGACAAGAGAATTAGTATTTT ATAGG |
| NOV16a, CG88623-01 Protein Sequence | ORF Start: ATG at 41  ORF Stop: TAG at 1442<br>SEQ ID NO: 44  467 aa  MW at 53892.6 kD<br>MLKQSERRRSWSYRPWNTTELNVNVGGHSYQLDYCELAGFPKTRLGRLATSTSRSRQL SLCDDYEEQTDEYFFDRDPAVFQLVYNFYLSGVLLVLDGLCPRRFLEELGYWGVRLKY TPRCCRICFEERRDELSERLKIQHELRAQAQVEEAEELFRDMRFYGPQRRRLWNLMEK PFSSVAAKAIGVASSTFVLVSVVALALNTVEEMQQHSGQGEGGPDLRPILEHVEMLCM GFFTLEYLLRLASTPDLRRFARSALNLVDLVAILPLYLQLLLECFTGEGHQRGQTVGS VGKVGQVLRVMRLMRIFRILKLARHSTGLRAFGFTLRQCYQQVGCLLLFIAMGIFTFS AAVYSVEHDVPSTNFTTIPHSWWWAAVSISTVGYGDMYPETHLGRFFAFLCIAFGIIL NGMPISILYNKFSDYYSKLKAYEYTTIRRERGEVNFMQRARKKIAECLLGSNPQLTPR QEN |

Further analysis of the NOV16a protein yielded the following properties shown in Table 16B.

TABLE 16B

| Protein Sequence Properties NOV16a | |
|---|---|
| PSort analysis: | 0.6000 probability located in plasma membrane; 0.4120 probability located in mitochondrial inner membrane; 0.4000 probability located in Golgi body; 0.3000 probability located in endoplasmic reticulum (membrane) |

TABLE 16B-continued

| Protein Sequence Properties NOV16a | |
|---|---|
| SignalP analysis: | No Known Signal Sequence Predicted |

A search of the NOV16a protein against the Geneseq database, a proprietary database that contains sequences published in patents and patent publication, yielded several homologous proteins shown in Table 16C.

TABLE 16C

Geneseq Results for NOV16a

| Geneseq Identifier | Protein/Organism/Length [Patent #, Date] | NOV16a Residues/ Match Residues | Identities/ Similarities for the Matched Region | Expect Value |
|---|---|---|---|---|
| AAE13614 | Human Kv10.1 protein variant #4 (Q77E) - *Homo sapiens*, 545 aa. [WO200179455-A1, 25 Oct. 2001] | 21..467 99..545 | 447/447 (100%) 447/447 (100%) | 0.0 |
| AAE13610 | Human KvlO.1 protein - *Homo sapiens*, 545 aa. [WO200179455-A1, 25 Oct. 2001] | 21..467 99..545 | 447/447 (100%) 447/447 (100%) | 0.0 |
| AAE13613 | Human Kv10.1 protein variant #3 (V518M) - *Homo sapiens*, 545 aa. [WO200179455-A1, 25 Oct. 2001] | 21..467 99..545 | 446/447 (99%) 447/447 (99%) | 0.0 |
| AAE13612 | Human Kv10.1 protein variant #2 (M285L) - *Homo sapiens*, 545 aa. [WO200179455-A1, 25 Oct. 2001] | 21..467 99..545 | 446/447 (99%) 447/447 (99%) | 0.0 |
| AAE13611 | Human Kv10.1 protein variant #1 (L99V) - *Homo sapiens*, 545 aa. [WO200179455-A1, 25 Oct. 2001] | 21..467 99..545 | 446/447 (99%) 447/447 (99%) | 0.0 |

In a BLAST search of public sequence datbases, the NOV16a protein was found to have homology to the proteins shown in the BLASTP data in Table 16D.

TABLE 16D

Public BLASTP Results for NOV16a

| Protein Accession Number | Protein/Organism/Length | NOV16a Residues/ Match Residues | Identities/ Similarities for the Matched Portion | Expect Value |
|---|---|---|---|---|
| AAL83910 | VOLTAGE-GATED POTASSIUM CHANNEL KV11.1 - *Homo sapiens* (Human), 545 aa. | 21..467 99..545 | 447/447 (100%) 447/447 (100%) | 0.0 |
| Q95L11 | VOLTAGE-GATED POTASSIUM CHANNEL ALPHA SUBUNIT KV2.2 - *Oryctolagus cuniculus* (Rabbit), 911 aa. | 21..436 37..438 | 169/416 (40%) 266/416 (63%) | 1e-92 |
| Q63099 | Voltage-gated potassium channel protein Kv2.2 (CDRK) - *Rattus norvegicus* (Rat), 802 aa. | 21..436 37..438 | 167/416 (40%) 266/416 (63%) | 5e-92 |
| Q9BXD3 | POTASSIUM VOLTAGE-GATED CHANNEL, SHAB-RELATED SUBFAMILY, MEMBER 2 - *Homo sapiens* (Human), 911 aa. | 21..436 37..438 | 167/416 (40%) 266/416 (63%) | 2e-91 |
| Q92953 | Voltage-gated potassium channel protein Kv2.2 - *Homo sapiens* (Human), 806 aa. | 21..436 37..438 | 167/416 (40%) 265/416 (63%) | 2e-91 |

PFam analysis predicts that the NOV16a protein contains the domains shown in the Table 16E.

TABLE 16E

Domain Analysis of NOV16a

| Pfam Domain | NOV16a Match Region | Identities/ Similarities for the Matched Region | Expect Value |
|---|---|---|---|
| K_tetra: domain 1 of 1 | 19..125 | 41/112 (37%) 72/112 (64%) | 4.8e-18 |

TABLE 16E-continued

Domain Analysis of NOV16a

| Pfam Domain | NOV16a Match Region | Identities/ Similarities for the Matched Region | Expect Value |
|---|---|---|---|
| ion_trans: domain 1 of 1 | 223..414 | 49/226 (22%) 156/226 (69%) | 1.8e-26 |

Example 17

The NOV17 clone was analyzed, and the nucleotide and encoded polypeptide sequences are shown in Table 17A.

TABLE 17A

NOV17 Sequence Analysis

| | |
|---|---|
| NOV17a, CG88645-01 DNA Sequence | SEQ ID NO: 45    1651 bp<br>ATGGCGGCCAACATGTACCGGGTCGGATCGGGCCGAAAGTCCCCCGGGCGGCCAGCCA<br>TGACCTTCGGGCGCAGCGGGGCGGCCTCGGTGGTGCTGAACGTGGGCGGCGCCCGGTA<br>TTCGCTGTCCCGGGAGCTGCTGAAGGACTTCCCGCTGCGCCGCGTGAGCCGGCTGCAC<br>GGCTGCCGCTCCGAGCGCGACGTGCTCGAGGTGTGCGACGACTACGACCGCGAGCGCA<br>ACGAGTACTTCTTCGACCGGCACTCGGAGGCCTTCGGCTTCATCCTGCTCTACGTGCG<br>CGGCCACGGCAAGCTGCGCTTCGCGCCGCGGATGTGCGAGCTCTCCTTCTACAACGAG<br>ATGATCTACTGGGGCCTGGAGGGCGCGCACCTCGAGTACTGCTGCCAGCGCCGCCTCG<br>ACGACCGCATGTCCGACACCTACACCTTCTACTCGGCCGACGAGCCGGGCGTGCTGGG<br>CCGCGACGAGGCGCGCCCCGGCGCGCGAGGCGGCTCCCTCCAGGCGCTGGCTGGAGCG<br>CATGCGGCGGACCTTCGAGGAGCCCACGTCGTCGCTGGCCGCAGGCGCTGGCTGGAGC<br>GCATGCGGCGGACCTTCGAGGAGCCCACGTCGTCGCTGGCCGCGCAGATCCTGGCTAG<br>CGTGTCGGTGGTGTTCGTGATCGTGTCCATGGTGGTGCTGTGCGCCAGCACGTTGCCC<br>GACTGGCGCAACGCAGCCGCCGACAACCGCAGCCTGGATGACCGGAGCAGGTACTCCG<br>CCGGCCCTGGGAGGGAGCCCTCCGGGTGTTCTCTTGACAGGATAATTGAAGCTATCTG<br>CATAGGTTGGTTCACTGCCGAGTGCATCGTGAGGTTCATTGTCTCCAAAAACAAGTGT<br>GAGTTTGTCAAGAGACCCCTGAACATCATTGATTTACTGGCAATCACGCCGTATTACA<br>TCTCTGTGTTGATGACAGTGTTTACAGGCGAGAACTCTCAACTCCAGAGGGCTGGAGT<br>CACCTTGAGGGTACTTAGAATGATGAGGATTTTTTGGGTGATTAAGCTTGCCCGTCAC<br>TTCATTGGTCTTCAGACACTCGGTTTGACTCTCAAACGTTGCTACCGAGAGATGGTTA<br>TGTTACTTGTCTTCATTTGTGTTGCCATGGCAATCTTTAGTGCACTTTCTCAGCTTCT<br>TGAACATGGGCTGGACCTGGAAACATCCAACAAGGACTTTACCAGCATTCCTGCTGCC<br>TGCTGGTGGGTGATTATCTCTATGACTACAGTTGGCTATGGAGATATGTATCCTATCA<br>CAGTGCCTGGAAGAATTCTTGGAGGAGTTTGTGTTGTCAGTGGAATTGTTCTATTGGC<br>ATTACCTATCACTTTTATCTACCATAGCTTTGTGCAGTGTTATCATGAGCTCAAGTTT<br>AGATCTGCTAGGGGCCCACCGGTGGAGCAGCTGCCCCCAGACCCCTTGACCCGGTGGT<br>GCTTCCACCCTGCCGGAAGCACCTTGTGTGGCCCCGCCAACAGCATGGCGGTTGCATC<br>CCCAGGAAGCAGGCCCGCAGCGCCCGGAGGGGTTTCCTGAGGACAGAGGCCCTTGTC<br>CTGATTGTCGCAGCAGGCCCTGTCGATGGACTTAACTGTGAAAATCACCCTTTCAGGG<br>GTGGATGCAAGGACTTCTGAGGGCGGA |

TABLE 17A-continued

NOV17 Sequence Analysis

| | |
|---|---|
| NOV 17a,<br>CG88645-01 Protein Sequence | ORF Start: ATG at 1     ORF Stop: TGA at 1642<br>SEQ ID NO: 46     547 aa    MW at 60771.7 kD<br>MAANMYRVGSGRKSPGRPAMTFGRSGAASVVLNVGGARYSLSRELLKDFPLRRVSRLH<br>GCRSERDVLEVCDDYDRERNEYFFDRHSEAFGFILLYVRGHGKLRFAPRMCELSFYNE<br>MIYWGLEGAHLEYCCQRRLDDRMSDTYTFYSADEPGVLGRDEARPGARGGSLQALAGA<br>HAADLRGAHVVAGRRRWLERMRRTFEEPTSSLAAQILASVSVVFVIVSMVVLCASTLP<br>DWRNAAADNRSLDDRSRYSAGPGREPSGCSLDRIIEAICIGWFTAECIVRFIVSKNKC<br>EFVKRPLNIIDLLAITPYYISVLMTVFTGENSQLQRAGVTLRVLRMMRIFWVIKLARH<br>FIGLQTLGLTLKRCYREMVMLLVFICVAMAIFSALSQLLEHGLDLETSNKDFTSIPAA<br>CWWVIISMTTVGYGDMYPITVPGRILGGVCVVSGIVLLALPITFIYHSFVQCYHELKF<br>RSARGPPVEQLPPDPLTRWCFHPAGSTLCGPANSMAVASPGSRPAAPGGGFLRTEALV<br>LIVAAGPVDGLNCENHPFRGGCKDF |

Further analysis of the NOV 17a protein yielded the following properties shown in Table 17B.

TABLE 17B

| Protein Sequence Properties NOV17a | |
|---|---|
| PSort analysis: | 0.6000 probability located in plasma membrane; 0.4000 probability located in Golgi body; 0.3000 probability located in endoplasmic reticulum (membrane); 0.3000 probability located in microbody (peroxisome) |
| SignalP analysis: | No Known Signal Sequence Predicted |

A search of the NOV17a protein against the Geneseq database, a proprietary database that contains sequences published in patents and patent publication, yielded several homologous proteins shown in Table 17C.

TABLE 17C

Geneseq Results for NOV17a

| Geneseq Indentifier | Protein/Organism/Length [Patent #, Date] | NOV17a Residues/ Match Residues | Identities/ Similarities for the Matched Region | Expect Value |
|---|---|---|---|---|
| ABG11444 | Novel human diagnostic protein #11435 - *Homo sapiens*, 466 aa. [WO200175067-A2, 11 Oct. 2001] | 23..473<br>12..426 | 188/453 (41%)<br>271/453 (59%) | 6e-90 |
| ABG11444 | Novel human diagnostic protein #11435 - *Homo sapiens*, 466 aa. [WO200175067-A2, 11 Oct. 2001] | 23..473<br>12..426 | 188/453 (41%)<br>271/453 (59%) | 6e-90 |
| AAY50341 | Human Kv6.2 protein - *Homo sapiens*, 466 aa. [DE19841413-C1, 23 Sep. 1999] | 23..473<br>12..426 | 188/453 (41%)<br>271/453 (59%) | 6e-90 |
| AAY44568 | Mouse Voltage-gated Potassium channel monomer, Kv6.2 variant #3 - Mus sp, 506 aa. [WO200001811-A1, 13 Jan. 2000] | 30..463<br>60..463 | 180/446 (40%)<br>263/446 (58%) | 9e-89 |
| AAY44566 | Mouse Voltage-gated Potassium channel monomer, Kv6.2 variant #1 - Mus sp, 506 aa. [WO200001811-A1, 13 Jan. 2000] | 30..463<br>60..463 | 180/446 (40%)<br>263/446 (58%) | 9e-89 |

In a BLAST search of public sequence datbases, the NOV17a protein was found to have homology to the proteins shown in the BLASTP data in Table 17D.

TABLE 17D

Public BLASTP Results for NOV17a

| Protein Accession Number | Protein/Organism/Length | NOV17a Residues/ Match Residues | Identities/ Similarities for the Matched Portion | Expect Value |
|---|---|---|---|---|
| BAB85520 | VOLTAGE-GATED K+ CHANNEL 6.3 - *Homo sapiens* (Human), 436 aa. | 20..468 1..425 | 422/449 (93%) 422/449 (93%) | 0.0 |
| BAB85521 | VOLTAGE-GATED K+ CHANNEL 6.3 - *Rattus norvegicus* (Rat), 345 aa. | 108..468 1..334 | 319/361 (88%) 325/361 (89%) | e-178 |
| Q9UJ96 | CARDIAC POTASSIUM CHANNEL SUBUNIT (KV6.2) - *Homo sapiens* (Human), 466 aa. | 23..473 12..426 | 188/453 (41%) 271/453 (59%) | 2e-89 |
| Q9QYU3 | CARDIAC POTASSIUM CHANNEL SUBUNIT (KV6.2) - *Rattus rattus* (Black rat), 480 aa. | 19..482 18..448 | 190/470 (40%) 275/470 (58%) | 5e-89 |
| AAL83911 | VOLTAGE-GATED POTASSIUM CHANNEL KV6.3 - *Homo sapiens* (Human), 519 aa. | 30..463 61..465 | 182/448 (40%) 262/448 (57%) | 2e-87 |

PFam analysis predicts that the NOV 17a protein contains the domains shown in the Table 17E.

TABLE 17E

Domain Analysis of NOV17a

| Pfam Domain | NOV17a Match Region | Identities/ Similarities for the Matched Region | Expect Value |
|---|---|---|---|
| K_tetra: domain 1 of 1 | 28..135 | 42/112 (38%) 78/112 (70%) | 4.6e-24 |
| ion_trans: domain 1 of 1 | 264..451 | 49/226 (22%) 141/226 (62%) | 2.3e-24 |

Example 18

The NOV18 clone was analyzed, and the nucleotide and encoded polypeptide sequences are shown in Table 18A.

TABLE 18A

NOV18 Sequence Analysis

| | |
|---|---|
| NOV18a, CG88738-01 DNA Sequence | SEQ ID NO: 47  1178 bp<br>CCGGTGCGTCCGCCTAGCCCCGCTCCGCCTGAGGCCGTCAGGGCTCCCGAGGATGGAA<br>GATTCCCAGGAGACATCGCCGTCCTCCAACAACTCCTCGGAGGAGCTCAGCTCTGCTC<br>TGCACCTGTCCAAGGGCATGTCGATCTTCCTCGACGTAAGTACAGATGATGATGGAAA<br>ATTATCCTTTGAAGAATTCAAAGCATATTTTGCAGATGGTGTTCTCAGTGGAGAAGAA<br>TTACACGAGCTTTTCCATACCATTGATACACATAATACTAATAATCTTGACACAGAAG<br>AGCTATGTGAATATTTTTCTCAGCACTTGGGCGAGTATGAGAATGTACTAGCAGCACT<br>TGAAGACCTGAATCTTTCCATCCTGAAGGCAATGGGCAAAACAAAGAAAGACTACCAA<br>GAAGCCTCCAATTTGGAACAATTCGTAACTAGATTTTTATTGAAGGAAACCCTGAATC<br>AGCTGCAGTCTCTCCAGAATTCCCTGGAATGTGCCATGGAAACTACTGAGGAGCAAAC<br>CCGTCAAGAAAGGCAAGGGCCAGCCAAGCCAGAAGTCCTGTCGATTCAATGGCCTCGA<br>AAACGATCAAGCCGCCGAGTCCAGAGACACAACAGCTTCTCCCCAAACAGCCCTCAGT<br>TTAATGTCAGCGGTCCAGGCTTATTAGAAGAAGACAACCAGTGGATGACCCAGATAAA |

TABLE 18A-continued

NOV18 Sequence Analysis

|  |  |
|---|---|
|  | TAGACTCCAGAAATTAATTGATAGACTGGAAAAGAAGGATCTCAAACTCGAACCACCA |
|  | GAAGAAGAAATTATTGAAGGGAATACTAAATCTCACATCATGCTTGTGCAGCGGCAGA |
|  | TGTCTGTGATAGAAGAGGACCTGGAAGAATTCCAGCTCGCTCTGAAACACTACGTGGA |
|  | GAGTGCTTCCTCCCAAAGTGGATGCTTGCGTATTTCTATACAGAAGCTTTCAAATGAA |
|  | TCTCGCTACATGATCTATGAGTTCTGGGAGAATAGTAGTGTATGGAATAGCCACCTTC |
|  | AGACAAATTATAGCAAGACATTCCAAAGAAGTAATGTGGATTTCTTGGAAACTCCAGA |
|  | ACTCACATCTACAATGCTAGTTCCTGCTTCGTGGTGGATCCTGAACAACTAGATGTTC |
|  | CTAGACATTTTCTTTATGGTTCCAAGTGCAAAACAGGTGTTCTTATCTAAAACGTCAA |
|  | TTAGAAAATTATCTGCGG |
|  | ORF Start: ATG at 53    ORF Stop: TAG at 1094 |
|  | SEQ ID NO: 48    347 aa  MW at 40006.0 kD |
| NOV18a, CG88738-01 Protein Sequence | MEDSQETSPSSNNSSEELSSALHLSKGMSIFLDVSTDDDGKLSFEEFKAYFADGVLSG |
|  | EELHELFHTIDTHNTNNLDTEELCEYFSQHLGEYENVLAALEDLNLSILKAMGKTKKD |
|  | YQEASNLEQFVTRFLLKETLNQLQSLQNSLECAMETTEEQTRQERQGPAKPEVLSIQW |
|  | PGKRSSRRVQRHNSFSPNSPQFNVSGPGLLEEDNQWMTQINRLQKLIDRLEKKDLKLE |
|  | PPEEEIIEGNTKSHIMLVQRQMSVIEEDLEEFQLALKHYVESASSQSGCLRISIQKLS |
|  | NESRYMIYEFWENSSVWNSHLQTNYSKTFQRSNVDFLETPELTSTMLVPASWWILNN |

Further analysis of the NOV18a protein yielded the following properties shown in Table 18B.

TABLE 18B

Protein Sequence Properties NOV18a

| | |
|---|---|
| PSort analysis: | 0.4500 probability located in cytoplasm; 0.3000 probability located in microbody (peroxisome): 0.1000 probability located in mitochondrial matrix space: 0.1000 probability located in lysosome (lumen) |
| SignalP analysis: | No Known Signal Sequence Predicted |

A search of the NOV18a protein against the Geneseq database, a proprietary database that contains sequences published in patents and patent publication, yielded several homologous proteins shown in Table 18C.

TABLE 18C

Geneseq Results for NOV18a

| Geneseq Identifier | Protein/Organism/Length [Patent #, Date] | NOV18a Residues/ Match Residues | Identities/ Similarities for the Matched Region | Expect Value |
|---|---|---|---|---|
| AAM43573 | Human polypeptide SEQ ID NO 251 - Homo sapiens, 385 aa. [WO200155308-A2, 02 Aug. 2001] | 27..347 60..384 | 157/329 (47%) 215/329 (64%) | 2e-79 |
| AAM40140 | Human polypeptide SEQ ID NO 3285 - Homo sapiens, 260 aa. [WO200153312-A1, 26 Jul. 2001] | 89..342 1..254 | 108/255 (42%) 148/255 (57%) | 5e-48 |
| AAU19958 | Novel human calcium-binding protein #67 - Homo sapiens, 250 aa. [WO200155304-A2, 02 Aug. 2001] | 27..193 60..234 | 92/175 (52%) 121/175 (68%) | 9e-41 |
| AAM43645 | Human polypeptide SEQ ID NO 323 - Homo sapiens, 250 aa. [WO200155308-A2, 02 Aug. 2001] | 27..193 60..234 | 92/175 (52%) 121/175 (68%) | 9e-41 |
| AAB95504 | Human protein sequence SEQ ID NO:18060 - Homo sapiens, 149 aa. [EP1074617-A2, 07 Feb. 2001] | 42..156 2..116 | 74/115 (64%) 92/115 (79%) | 2e-34 |

In a BLAST search of public sequence datbases, the NOV18a protein was found to have homology to the proteins shown in the BLASTP data in Table 18D.

TABLE 18D

Public BLASTP Results for NOV18a

| Protein Accession Number | Protein/Organism/Length | NOV18a Residues/ Match Residues | Identities/ Similarities for the Matched Portion | Expect Value |
|---|---|---|---|---|
| Q9ESB5 | NEURONAL CALCIUM BINDING PROTEIN NECAB1 - *Rattus norvegicus* (Rat), 352 aa. | 1..347 1..351 | 330/351 (94%) 336/351 (95%) | 0.0 |
| Q9HBW8 | NEURONAL CALCIUM BINDING PROTEIN NECAB1 - *Homo sapiens* (Human), 255 aa (fragment). | 93..347 1..255 | 255/255 (100%) 255/255 (100%) | e-145 |
| Q96P71 | NIP1 - *Homo sapiens* (Human), 362 aa. | 27..347 37..361 | 157/329 (47%) 215/329 (64%) | 5e-79 |
| Q9HBW7 | NEURONAL CALCIUM BINDING PROTEIN NECAB3 - *Homo sapiens* (Human), 362 aa. | 27..347 37..361 | 156/329 (47%) 214/329 (64%) | 3e-78 |
| Q9D6J4 | 2900010M17RIK PROTEIN - *Mus musculus* (Mouse), 329 aa. | 27..347 28..328 | 148/326 (45%) 202/326 (61%) | 7e-71 |

PFam analysis predicts that the NOV18a protein contains the domains shown in the Table 18E.

TABLE 18E

Domain Analysis of NOV18a

| Pfam Domain | NOV18a Match Region | Identities/ Similarities for the Matched Region | Expect Value |
|---|---|---|---|
| efhand: domain 1 of 2 | 26..54 | 12/29 (41%) 22/29 (76%) | 1.2 |
| efhand: domain 2 of 2 | 60..88 | 7/29 (24%) 20/29 (69%) | 0.99 |
| DUF176: domain 1 of 1 | 248..339 | 23/105 (22%) 53/105 (50%) | 0.25 |

Example 19

The NOV19 clone was analyzed, and the nucleotide and encoded polypeptide sequences are shown in Table 19A.

TABLE 19A

NOV19 Sequence Analysis

| NOV19a, CG88902-01 DNA Sequence | SEQ ID NO: 49  3050 bp<br>AAAATATTAATTTTTAACTTCTGTGCTTATATTGTCATTTCAACTCCTTGCTTAGTAA<br>CTACAAAACCATTGCAGATCAGTGTGTGAGGGAACTGCCATCATGAGGTCTGACAAGT<br>CAGCTTTGGTATTTCTGCTCCTGCAGCTCTTCTGTGTTGGCTGTGGATTCTGTGGGAA<br>AGTCCTGGTGTGGCCCTGTGACATGAGCCATTGGCTTAATGTCAAGGTCATTCTAGAA<br>GAGCTCATAGTGAGAGGCCATGAGGTAACAGTATTGACTCACTCAAAGCCTTCGTTAA<br>TTGACTACAGGAAGCCTTCTGCATTGAAATTTGAGGTGGTCCATATGCCACAGGACAG<br>AACAGAAGAAATGAAATATTTGTTGACCTAGCTCTGAATGTCTTGCCAGGCTTATCA<br>ACCTGGCAATCAGTTATAAAATTAAATGATTTTTTTGTTGAAATAAGAGGAACTTTAA<br>AAATGATGTGTGAGAGCTTTATCTACAATCAGACGCTTATGAAGAAGCTACAGGAAAC<br>CAACTACGATGTAATGCTTATAGACCCTGTGATTCCCTGTGGAGACCTGATGGCTGAG<br>TTGCTTGCAGTCCCTTTTGTGCTCACACTTAGAATTTCTGTAGGAGGCAATATGGAGC<br>GAAGCTGTGGGAAACTTCCAGCTCCACTTTCCTATGTACCTGTGCCTATGACAGGACT<br>AACAGACAGAATGACCTTTCTGGAAAGAGTAAAAAATTCAATGCTTTCAGTTTTGTTC |

TABLE 19A-continued

NOV19 Sequence Analysis

CACTTCTGGATTCAGGATTACGACTATCATTTTTGGGAAGAGTTTTATAGTAAGGCAT

TAGGTAGACCCACTACATTATGTGAGACTGTGGGAAAAGCTGAGATATGGCAAATACG

AACATATTGGGATTTTGAATTTCCTCAACCATACCAACCTAACTTTGAGTTTGTTGGA

GGATTGCACTGTAAACCTGCCAAAGCTTTGCCTAAGGAAATGGAAAATTTTGTCCAGA

GTTCAGGGGAAGATGGTATTGTGGTGTTTTCTCTGGGGTCACTGTTTCAAAATGTTAC

AGAAGAAAAGGCTAATATCATTGCTTCAGCCCTTGCCCAGATCCCACAGAAGGTGTTA

TGGAGGTACAAAGGAAAAAAACCATCCACATTAGGAGCCAATACTCGGCTGTATGATT

GGATACCCCAGAATGATCTTCTTGGTCATCCCAAAACCAAAGCTTTTATCACTCATGG

TGGAATGAATGGGATCTATGAAGCTATTTACCATGGGTCCCTATGGTGGGAGTTCCC

ATATTTGGTGATCAGCTTGATAACATAGCTCACATGAAGGCCAAAGGAGCAGCTGTAG

AAATAAACTTCAAAACTATGACAAGCGAAGATTTACTGAGGGCTTTGAGAACAGTCAT

TACCGATTCCTCTTATAAAGAGAATGCTATGAGATTATCAAGAATTCACCATGATCAA

CCTGTAAAGCCCCTAGATCGAGCAGTCTTCTGGATCGAGTTTGTCATGCGCCACAAAG

GAGCCAAGCACCTGCGATCAGCTGCCCATGACCTCACCTGGTTCCAGCACTACTCTAT

AGATGTGATTGGGTTCCTGCTGGCCTGTGTGGCAACTGCTATATTCTTGTTCACAAAA

TGTTTTTTATTTTCCTGTCAAAAATTTAATAAAACTAGAAAGATAGAAAAGAGGGAAT

AGATCTTTCCAAATTCAAGAAAGACCTGATGGGGTAATCCTGTTAATTCCAGCCACAT

AGAATTTGGTGAAAACCTTGCTATTTTCATATTATCTATTCTGTTATTTTATCTTAGC

TATATAGCCTAGAATTCCACGATCATGAGGTTGTGAGTATATCTCATTCTTTCGTTGT

ATTTTCCTAGGTGTCTTTACTCTCTTCTCTCACTTTGTGACACAAGGACATGAATACA

TCTAAATTTTCCTATTTCTGATATGACTGTTTTGATGATGTCATTACTTCTATAACCT

TAAGTGATAGGGTGACATGCAATATGATTATTCCTGGTGTGCGCCCAAACACATGGAT

ATAAAGAGGTAAAAAACTTAAAATTCACAAAATTCAGTAAACCACACAAATCAGGTAA

GTGTTCTATGAGATTAGCTGGCTATGAGAAACATAATGATGTTTCTTTTTCAATTTAA

ATAAGCCCTTCTACATAGCCAGCATCAGTGATCTCAGAAAATAAATTGCTAATAATGA

TGACATGGCATTATGCTTAGAAAAGTTTGCTGTATTTCCATAGACCTCATCTAGATGT

CATGGCCTACATTTCTGCCATCACTCAACCAATACTTTTTCTGTTTTCTTGATGATA

AAAAGACCTTTCTCATGATTGCCATCAAATAACAAAAGAAACTATTTTTTTTCTCACA

TAGAGAACATGTCAGTAAGATATTCAAGGTGAACAGATTATTTTTGGGATTAGTAACT

ATTTGAAATATGTGGTGATAATTACTGAGTTTATAAAATTTATTTGATAGTACACTTA

AAGAAGATTTATATGTTTATTCTTTAAAAATGATGAATACTCATAATTCTTATCTCTA

TAATCAAAAGTATAATTTACTGTAGAAAAATAAAGAGATGCTTGTTCTGAAAGTAAGA

TCAGTGAACTGCTTTTCAGTCTCAATCTTTGAGAATTGTAAATTCATCAAATAATTGC

TTACATAGTAAAAATTTAAGGTATTAGAAAACCTGCATAACAAATAGTATTATATATT

AAATATTTTGATATGTAAAGCTCTACACAAAGCTAAATATAGTGTAATAATGTTTACA

CTAATAAGCAAATATGTTAATCTTCTCATTTTTTTACTGTCATATAATCTTAGTGATA

TGCCTATTAATAGTTTTAAATAAATAAATTGGCTCATCTGGCTTTTTGAAAATTTTGA

TABLE 19A-continued

NOV19 Sequence Analysis

AATTCTTACAGATGTTGATTAGGTATATCTACAAATTAATTTCAATTTTAAAATGATG
ATATAAAAATAAATATAAGTATTTTTCTTGTGTATGTATACAATAAATATAAATAAAA
TTGTTTACTGTTTTGAAAAAAAAAAAAAAAAAA

NOV19a,
CG88902-01 Protein Sequence

ORF Start: ATG at 101          ORF Stop: TAG at 1682
SEQ ID NO: 50                  527 aa   MW at 60268.8 kD
MRSDKSALVFLLLQLFCVGCGFCGKVLVWPCDMSHWLNVKVILEELIVRGHEVTVLTH
SKPSLIDYRKPSALKFEVVHNPQDRTEENEIFVDLALNVLPGLSTWQSVIKLNDFFVE
IRGTLKMMCESFIYNQTLMKKLQETNYDVMLIDPVIPCGDLMAELLAVPFVLTLRISV
GGNMERSCGKLPAPLSYVPVPMTGLTDRMTFLERVKNSMLSVLFHFWIQDYDYHFWEE
FYSKALGRPTTLCETVGKAEIWQIRTYWDFEFPQPYQPNFEFVGGLHCKPAKALPKEM
ENFVQSSGEDGIVVFSLGSLFQNVTEEKANIIASALAQIPQKVLWRYKGKKPSTLGAN
TRLYDWIPQNDLLGHPKTKAFITHGGMNGIYEAIYHGVPMVGVPIFGDQLDNIAHMKA
KGAAVEINFKTMTSEDLLRALRTVITDSSYKENAMRLSRIHHDQPVKPLDRAVFWIEF
VMRHKGAKHLRSAAHDLTWFQHYSIDVIGFLLACVATAIFLFTKCFLFSCQKFNKTRK
IEKRE NOV19b,
CG88902-02 DNA Sequence SEQ ID NO: 51                  1705 bp
ACTACAAAACCATTGCAGATCAGTGTGTGAGGGAACTGCCATCATGAGGTCTGACAAG
TCAGCTTTGGTATTTCTGCTCCTGCAGCTCTTCGTGTTGGCTGTGGATTCTGTGGGA
AAGTCCTGGTGTGGCCCTGTGACATGAGCCATTGGCTTAATGTCAAGGTCATTCTAGA
AGAGCTCATAGTGAGAGGCCATGAGGTAACAGTATTGACTCACTCAAAGCCTTCGTTA
ATTGACTACAGGAAGCCTTCTGCATTGAAATTTGAGGTGGTCCATATGCCACAGGACA
GAACAGAAGAAAATGAAATATTTGTTGACCTAGCTCTGAATGTCTTGCCAGGCTTATC
AACCTGGCAATCAGTTATAAAATTAAATGATTTTTTTGTTGAAATAAGAGGAACTTTA
AAAATGATGTGTGAGAGCTTTATCTACAATCAGACGCTTATGAAGAAGCTACAGGAAA
CCAACTACGATGTAATGCTTATAGACCCTGTGATTCCCTGTGGAGACCTGATGGCTGA
GTTGCTTGCAGTCCCTTTTGTGCTCACACTTAGAATTTCTGTAGGAGGCAATATGGAG
CGAAGCTGTGGGAAACTTCCAGCTCCACTTTCCTATGTACCTGTGCCTATGACAGGAC
TAACAGACAGAATGACCTTTCTGGAAAGAGTAAAAAATTCAATGCTTTCAGTTTTGTT
CCACTTCTGGATTCAGGATTACGACTACCATTTTTGGGAAGAGTTTTATAGTAAGGCA
TTAGGAAGGCCCACTACATTATGTGAGACTGTGGGAAAAGCTGAGATATGGCTAATAC
GAACATATTGGGATTTTGAATTTCCTCAACCATACCAACCTAACTTTGAGTTTGTTGG
AGGATTGCACTGTAAACCTGCCAAAGCTTTGCCTAAGGAAATGGAAAATTTTGTCCAG
AGTTCAGGGGAAGATGGTATTGTGGTGTTTTCTCTGGGGTCACTGTTTCAAAATGTTA
CAGAAGAAAAGGCTAATATCATTGCTTCAGCCCTTGCCCAGATCCCACAGAAGGTGTT
ATGGAGGTACAAAGGAAAAAAACCATCCACATTAGGAGCCAATACTCGGCTGTATGAT
TGGATACCCCAGAATGATCTTCTTGGTCATCCCAAAACCAAAGCTTTTATCACTCATG
GTGGAATGAATGGGATCTATGAAGCTATTTACCATGGGTCCCTATGGTGGGAGTTCC
CATATTTGGTGATCAGCTTGATAACATAGCTCACATGAAGGCCAAAGGAGCAGCTGTA
GAAATAAACTTCAAAACTATGACAAGCGAAGATTTACTGAGGGCTTTGAGAACAGTCA
TTACCGATTCCTCTTATAAAGAGAATGCTATGAGATTATCAAGAATTCACCATGATCA

TABLE 19A-continued

NOV19 Sequence Analysis

```
ACCTGTAAAGCCCCTAGATCGAGCAGTCTTCTGGATCGAGTTTGTCATGCGCCACAAA
GGAGCCAAGCACCTGCGATCAGCTGCCCATGACCTCACCTGGTTCCAGCACTACTCTA
TAGATGTGATTGGGTTCCTGCTGACCTGTGTGGCAACTGCTATATTCTTGTTCACAAA
ATGTTTTTTATTTTCCTGTCAAAAATTTAATAAAACTAGAAAGATAGAAAAGAGGGAA
TAGATCTTTCCAAATTCAAGAAAGACCTGATGGGGTAATCCTGTTAATTCCAGCCACA
TAGAATTTGGTGAAAACCTTGCT
```

NOV19b,
CG88902-02 Protein Sequence

ORF Start: ATG at 44    ORF Stop: TAG at 1625
SEQ ID NO: 52           527 aa   MW at 60283.8 kD

```
MRSDKSALVFLLLQLFCVGCGFCGKVLVWPCDMSHWLNVKVILEELIVRGHEVTVLTH
SKPSLIDYRKPSALKFEVVHMPQDRTEENEIFVDLALNVLPGLSTWQSVIKLNDFFVE
IRGTLKMMCESFIYNQTLMKKLQETNYDVMLIDPVIPCGDLMAELLAVPFVLTLRISV
GGNMERSCGKLPAPLSYVPVPMTGLTDRMTFLERVKNSMLSVLFHFWIQDYDYHFWEE
FYSKALGRPTTLCETVGKAEIWLIRTYWDFEFPQPYQPNFEFVGGLHCKPAKALPKEM
ENFVQSSGEDGIVVFSLGSLFQNVTEEKANIIASALAQIPQKVLWRYKGKKPSTLGAN
TRLYDWIPQNDLLGHPKTKAFITHGGMNGIYEAIYHGVPMVGVPIFGDQLDNIAHMKA
KGAAVEINFKTMTSEDLLRALRTVITDSSYKENAMRLSRIHHDQPVKPLDRAVFWIEF
VMRHKGAKHLRSAAHDLTWFQHYSIDVIGFLLTCVATAIFLFTKCFLFSCQKFNKTRK
IEKRE
```

Sequence comparison of the above protein sequences yields the following sequence relationships shown in Table 19B.

TABLE 19B

Comparison of NOV19a against NOV19b.

| Protein Sequence | NOV19a Residues/ Match Residues | Identities/Similarities for the Matched Region |
|---|---|---|
| NOV19b | 1..527 | 525/527 (99%) |
|  | 1..527 | 525/527 (99%) |

Further analysis of the NOV 19a protein yielded the following properties shown in Table 19C.

TABLE 19C

Protein Sequence Properties NOV19a

| PSort analysis: | 0.4600 probability located in plasma membrane; 0.3700 probability located in endoplasmic reticulum (membrane); 0.3000 probability located in lysosome (membrane); 0.1840 probability located in microbody (peroxisome) |
|---|---|
| SignalP analysis: | Cleavage site between residues 24 and 25 |

A search of the NOV 19a protein against the Geneseq database, a proprietary database that contains sequences published in patents and patent publication, yielded several homologous proteins shown in Table 19D.

TABLE 19D

Geneseq Results for NOV19a

| Geneseq Identifier | Protein/Organism/Length [Patent #, Date] | NOV19a Residues/ Match Residues | Identities/ Similarities for the Matched Region | Expect Value |
|---|---|---|---|---|
| AAE15434 | Human drug metabolising enzyme (DME)-1 - *Homo sapiens*, 527 aa. [WO200179468-A2, 25 Oct. 2001] | 1..527<br>1..527 | 525/527 (99%)<br>525/527 (99%) | 0.0 |
| AAU29284 | Human PRO polypeptide sequence #261 - *Homo sapiens*, 527 aa. [WO200168848-A2, 20 Sep. 2001] | 1..527<br>1..527 | 525/527 (99%)<br>525/527 (99%) | 0.0 |
| AAB28677 | Human carbohydrate-modifying enzyme Incyte ID No:2912330CD1 - *Homo sapiens*, 529 aa. [WO200063351-A2, 26 Oct. 2000] | 3..527<br>2..529 | 367/528 (69%)<br>414/528 (77%) | 0.0 |

TABLE 19D-continued

Geneseq Results for NOV19a

| Geneseq Identifier | Protein/Organism/Length [Patent #, Date] | NOV19a Residues/ Match Residues | Identities/ Similarities for the Matched Region | Expect Value |
|---|---|---|---|---|
| AAW47126 | Uridine diphospho-glucuronosyltransferase 2B17 (UGT2B17) enzyme - *Homo sapiens*, 530 aa. [WO9744466-A1, 27 Nov. 1997] | 9..527 8..530 | 326/523 (62%) 400/523 (76%) | 0.0 |
| AAY78933 | Human UDP-glucuronosyltransferase 2B4 amino acid sequence - *Homo sapiens*, 528 aa. [WO200006776-A1, 10 Feb. 2000] | 3..527 2..528 | 332/528 (62%) 393/528 (73%) | 0.0 |

In a BLAST search of public sequence datbases, the NOV19a protein was found to have homology to the proteins shown in the BLASTP data in Table 19E.

TABLE 19E

Public BLASTP Results for NOV19a

| Protein Accession Number | Protein/Organism/Length | NOV19a Residues/ Match Residues | Identities/ Similarities for the Matched Portion | Expect Value |
|---|---|---|---|---|
| Q9H6S4 | CDNA: FLJ21934 FIS, CLONE HEP04364 - *Homo sapiens* (Human), 449 aa. | 79..527 1..449 | 448/449 (99%) 448/449 (99%) | 0.0 |
| Q9R110 | UDP GLUCURONOSYLTRANSFERASE UGT2A3 - *Cavia porcellus* (Guinea pig), 530 aa. | 1..527 1..530 | 377/530 (71%) 435/530 (81%) | 0.0 |
| AAH25795 | RIKEN CDNA 2010321J07 GENE - *Mus musculus* (Mouse), 534 aa. | 1..527 1..531 | 358/533 (67%) 427/533 (79%) | 0.0 |
| Q9D811 | 2010321J07RIK PROTEIN - *Mus musculus* (Mouse), 534 aa. | 1..527 1..531 | 357/533 (66%) 427/533 (79%) | 0.0 |
| O75795 | UDP-glucuronosyltransferase 2B17 precursor, microsomal (EC 2.4.1.17) (UDPGT) (C19-steroid specific UDP-glucuronosyltransferase) - *Homo sapiens* (Human), 530 aa. | 9..527 8..530 | 326/523 (62%) 400/523 (76%) | 0.0 |

PFam analysis predicts that the NOV19a protein contains the domains shown in the Table 19F.

TABLE 19F

Domain Analysis of NOV19a

| Pfam Domain | NOV19a Match Region | Identities/ Similarities for the Matched Region | Expect Value |
|---|---|---|---|
| UDPGT: | 24..525 | 305/507 (60%) | 1.1e-284 |
| domain 1 of 1 | | 426/507 (84%) | |

Example 20

The NOV20 clone was analyzed, and the nucleotide and encoded polypeptide sequences are shown in Table 20A.

TABLE 20A

NOV20 Sequence Analysis

NOV20a, CG89048-01 DNA Sequence

SEQ ID NO: 53      1855 bp

GGTGCCATGGAGATGGAGAGCGCGGCGGCCTCCACACGTTTCCACCAGCCTCACATGG
AGAGGAAGATGAGTGCGATGGCCTGTGAGATCTTCAACGAGCTTAGGCTAGAGGGCAA

GCTCTGCGACGTGGTCATCAAGGTCAATGGCTTTGAGTTCAGTGCCCATAAGAGCGTC

CTCTGTAGCTGCAGTTCCTACTGTAGGGCTTTGTTTACAAGTGGCTGGAACAACACTG

AAAAGAAGGTATACAACATCCCTGGCATTTCTCCCGACATGATGAAGCTAATCATTGA

GTATGCATACACCCGGACCGTGCCTATCACACCGGACAATGTGGAGAAACTGCTTGCT

GCTGCAGACCAGTTTAACATCATGGGTATCGTCAGGGGTTGCTGCGAGTTCCTCAAGT

CAGAGCTGTGCTTGGATAATTGTATCGGCATCTGTAAGTTCACGGACTACTACTACTG

TCCTGAGCTGAGGCAGAAGGCCTACATGTTCATACTGCACAACTTTGAGGAGATGGTG

AAAGTCTCGGCAGAATTTTTAGAGCTCTCGGTCACTGAACTTAAGGATATCATTGAGA

AAGATGAGCTCAATGTCAAACAGGAAGATGCTGTATTTGAGGCCATTTTAAAGTGGAT

TTCTCATGACCCCCAAAATAGAAAGCAGCACATTTCAATTTTGCTTCCTAAGGTCCGC

CTGGCCCTAATGCATGCTGAGTACTTCATGAACAATGTTAAGATGAATGACTATGTCA

AAGACAGTGAGGAATGCAAACCAGTCATCATTAATGCCCTAAAGGCCATGTATGACCT

CAACATGAATGGACCCTCTAATTCTGATTTCACCAACCCACTCACCAGACCACGCTTG

CCCTATGCCATCCTCTTTGCAATTGGTGGCTGGAGTGGTGGGAGCCCCACCAATGCCA

TTGAGGCATATGACGCTCGGGCAGACAGATGGGTGAATGTTACTTGTGAGGAAGAGAG

TCCCCGTGCCTACCATGGGGCAGCCTATTTGAAAGGCTATGTGTATATCATTGGGGGG

TTTGATAGTGTAGACTATTTCAATAGTGTTAAGCGTTTTGACCCAGTCAAGAAAACTT

GGCATCAGGTGGCCCCGATGCACTCCAGACGTTGCTATGTCAGTGTGACAGTCCTCGG

CAATTTTATTTATGCCATGGAGGATTTGATGGCTACGTGCGTCTAAACACTGCTGAA

CGTTATGAGCCAGAGACCAATCAATGGACACTCATCGCCCCCATGCACGAACAGAGGA

GTGATGCAAGCGCCACAACACTTTATGGGAAGGTATACATATGTGGTGGGTTTAATGG

AAACGAGTGCCTGTTCACAGCAGAAGTGTATAACACTGAAAGTAATCAGTGGACAGTC

ATAGCACCCATGAGAAGCAGGAGGAGTGGAATAGGCGTGATTGCTTATGGAGAACATG

TATATGCGGTAGGTGGCTTTGATGGAGCTAATCGACTTAGGAGTGCCGAAGCCTACAG

CCCTGTGGCTAACACTTGGCGCACAATCCCCACTATGTTTAATCCTCGTAGCAATTTT

GGCATCGAGGTGGTGGATGACCTCTTGTTTGTGGTGGGTGGCTTTAATGGTTTTACCA

CCACCTTTAATGTTGAGTGCTATGATGAAAAGACCGATGAGTGGTATGATGCTCATGA

CATGAGTATATACCGCAGTGCTCTGAGCTGCTGTGTAGTACCAGGGCTGGCCAATGTT

GAGGAATATGCAGCTAGACGGGACAACTTCCCAGGATTAGCACTGCGAGATGAAGTAA

AATATTCTGCTTCGACAAGTACCCTACCTGTATGAGCCTCTTCATTTAGCTAATAAA

ORF Start: ATG at 7    ORF Stop: TGA at 1831
SEQ ID NO: 54      608 aa    MW at 68855.6 kD

NOV20a, CG89048-01 Protein Sequence

MEMESAAASTRFHQPHMERKMSAMACEIFNELRLEGKLCDVVIKVNGFEFSAHKSVLC
SCSSYCRALFTSGWNNTEKKVYNIPGISPDMMKLIIEYAYTRTVPITPDNVEKLLAAA

DQFNIMGIVRGCCIFLKSELCLDNCIGICKFTDYYYCPELRQKAYMFILHNFEEMVKV

SAEFLELSVTELKDIIEKDELNVKQEDAVFEAILKWISHDPQNRKQHISILLPKVRLA

LMHAEYFMNNVKMNDYVKDSEECKPVIINALKAMYDLNMNGPSNSDFTNPLTRPRLPY

AILFAIGGWSGGSPTNAIEAYDARADRWVNVTCEEESPRAYHGAAYLKGYVYIIGGFD

TABLE 20A-continued

NOV20 Sequence Analysis

| | |
|---|---|
| | SVDYFNSVKRFDPVKKTWHQVAPMHSRRCYVSVTVLGNFIYAMGGFDGYVRLNTAERY |
| | EPETNQWTLIAPMHEQRSDASATTLYGKVYICGGFNGNECLFTAEVYNTESNQWTVIA |
| | PMRSRRSGIGVIAYGEHVYAVGGFDGANRLRSAEAYSPVANTWRTIPTMFNPRSNFGI |
| | EVVDDLLFVVGGFNGFTTTFNVECYDEKTDEWYDAHDMSIYRSALSCCVVPGLANVEE |
| | YAARRDNFPGLALRDEVKYSASTSTLPV |
| NOV20b, CG89048-02 DNA Sequence | SEQ ID NO: 55    1875 bp<br>GGTGCCATGGAGATGGAGAGCGCGGCGGCCTCCACACGTTTCCACCAGCCTCACATGG |
| | AGAGGAAGATGAGTGCGATGGCCTGTGAGATCTTCAACGAGCTTAGACTAGAGGGCAA |
| | GCTCTGCGACGTGGTCATCAAGGTCAATGGCTTTGAGTTCAGTGCCCATAAGAACATC |
| | CTCTGTAGCTGCAGTTCCTACTTTAGAGCTTTGTTTACAAGTGGCTGGAACAACACTG |
| | AAAAGAAGGTATACAACATCCCTGGCATTTCTCCTGACATGATGAAGCTAATCATTGA |
| | GTATGCATACACCCGGACCGTGCCTATCACACCGGACAATGTGGAGAAACTGCTTGCT |
| | GCTGCAGACCAGTTTAACATCATGGGTATCGTCAGGGGTTGCTGCGAGTTCCTCAAGT |
| | CAGAGCTGTGCTTGGATAATTGTATCGGCATCTGTAAGTTCACGGACTACTACTACTG |
| | TCCTGAGCTGAGGCAGAAGGCCTACATGTTCATACTGCACAACTTTGAGGAGATGGTG |
| | AAAGTCTCGGCAGAATTTTTAGAGCTCTCGGTCACTGAACTTAAGGATATCATTGAGA |
| | AAGATGAGCTCAATGTCAAACAGGAAGATGCTGTATTTGAGGCCATTTTAAAGTGGAT |
| | TTCTCATGACCCCCAAAATAGAAAGCAGCACATTTCAATTTTGCTTCCTAAGGTTCGC |
| | CTGGCCCTAATGCATGCTGAGTACTTCATGAACAATGTTAAGATGAATGACTATGTCA |
| | AAGACAGTGAGGAATGCAAACCAGTCATCATTAATGCCCTAAAGGCCATGTATGACCT |
| | CAACATGAATGGACCCTCTAATTCTGATTTCACCAACCCACTCACCAGACCACGCTTG |
| | CCCTATGCCATCCTCTTTGCAATTGGTGGCTGGAGTGGTGGGAGCCCCACCAATGCCA |
| | TTGAGGCATATGACGCTCGGGCAGACAGATGGGTGAATGTTACTTGTGAGGAAGAGAG |
| | TCCCCGTGCCTACCATGGGGCAGCCTATTTGAAAGGCTATGTGTATATCATTGGGGGG |
| | TTTGATAGTGTAGACTATTTCAATAGTGTTAAGCGTTTTGACCCAGTCAAGAAAACTT |
| | GGCATCAGGTGGCCCCGATGCACTCCAGACGTTGCTATGTCAGTGTGACAGTCCTCGG |
| | CAATTTTATTTATGCCATGGGAGGATTTGATGGCTACGTGCGTCTAAACACTGCTGAA |
| | CGTTATGAGCCAGAGACCAATCAATGGACACTCATCGCCCCCATGCACGAACAGAGGA |
| | GTGATGCAAGCGCCACAACACTTTATGGGAAGGTCTACATATGTGGTGGGTTTAATGG |
| | AAACGAGTGCCTGTTCACAGCAGAAGTGTATAAAACTGAAAGTAATCAGTGGACAGTC |
| | ATAGCACCCATGAGAAGCAGGAGGAGTGGAATAGGCGTGATTGCTTATGGAGAACATG |
| | TATATGCGGTAGGTGGCTTTGATGGAGCTAATCGACTTAGGAGTGCCGAAGCCTACAG |
| | CCCTGTGGCTAACACTTGGCGCACAATCCCCACTATGTTTAATCCTCGTAGCAATTTT |
| | GGCATCGAGGTGGTGGATGACCTCTTGTTTGTGGTGGGTGGCTTTAATGGTTTTACCA |
| | CCACCTTTAATGTTGAGTGCTATGATGAAAAGACCGATGAGTGGTATGATGCTCATGA |
| | CATGAGTATATACCGCAGTGCTCTGAGCTGCTGTGTAGTACCAGGGCTGGCCAATGTT |
| | GAGGAATATGCAGCTAGACGGGACAACTTCCCAGGATTAGCACTGCGAGATGAAGTAA |
| | AATATTCTGCTTCGACAAGTACCCTACCTGTATGAGCCTCTTCATTTAGCTAAGGGCG |
| | AATTCCAGCACATGTGGGC |
| | ORF Start: ATG at 7 ORF Stop: TGA at 1831 |

TABLE 20A-continued

NOV20 Sequence Analysis

NOV20b,
CG89048-02
Protein Sequence

SEQ ID NO: 56    608 aa MW at 68954.8 kD

MEMESAAASTRFHQPHMERKMSAMACEIFNELRLEGKLCDVVIKVNGFEFSAHKNILC

SCSSYFRALFTSGWNNTEKKVYNIPGISPDMMKLIIEYAYTRTVPITPDNVEKLLAAA

DQFNIMGIVRGCCEFLKSELCLDNCIGICKFTDYYYCPELRQKAYMFILHNFEEMVKV

SAEFLELSVTELKDIIEKDELNVKQEDAVFEAILKWISHDPQNRKQHISILLPKVRLA

LMHAEYFMNNVKMNDYVKDSEECKPVIINALKAMYDLNMNGPSNSDFTNPLTRPRLPY

AILFAIGGWSGGSPTNAIEAYDARADRWVNVTCEEESPRAYHGAAYLKGYVYIIGGFD

SVDYFNSVKRFDPVKKTWHQVAPMHSRRCYVSVTVLGNFIYAMGGFDGYVRLNTAERY

EPETNQWTLIAPMHEQRSDASATTLYGKVYICGGFNGNECLFTAEVYKTESNQWTVIA

PMRSRRSGIGVIAYGEHVYAVGGFDGANRLRSAEAYSPVANTWRTIPTMFNPRSNFGI

EVVDDLLFVVGGFNGFTTTFNVECTDEKTDEWYDAHDMSIYRSALSCCVVPGLANVEE

YAARRDNFPGLALRDEVKYSASTSTLPV

Sequence comparison of the above protein sequences yields the following sequence relationships shown in Table 20B.

TABLE 20B

Comparison of NOV20a against NOV20b.

| Protein Sequence | NOV20a Residues/ Match Residues | Identities/Similarities for the Matched Region |
|---|---|---|
| NOV20b | 1..608 1..608 | 604/608 (99%) 606/608 (99%) |

Further analysis of the NOV20a protein yielded the following properties shown in Table 20C.

TABLE 20C

Protein Sequence Properties NOV20a

| PSort analysis: | 0.4500 probability located in cytoplasm; 0.1000 probability located in mitochondrial matrix space; 0.1000 probability located in lysosome (lumen); 0.0923 probability located in microbody (peroxisome) |
| SignalP analysis: | No Known Signal Sequence Predicted |

A search of the NOV20a protein against the Geneseq database, a proprietary database that contains sequences published in patents and patent publication, yielded several homologous proteins shown in Table 20D.

TABLE 20D

Geneseq Results for NOV20a

| Geneseq Identifier | Protein/Organism/Length [Patent #, Date] | NOV20a Residues/ Match Residues | Identities/ Similarities for the Matched Region | Expect Value |
|---|---|---|---|---|
| ABG03507 | Novel human diagnostic protein #3498 - Homo sapiens, 816 aa. [WO200175067-A2, 11 Oct. 2001] | 15..554 221..758 | 203/544 (37%) 291/544 (53%) | e-101 |
| ABG03507 | Novel human diagnostic protein #3498 - Homo sapiens, 816 aa. [WO200175067-A2, 11 Oct. 2001] | 15..554 221..758 | 203/544 (37%) 291/544 (53%) | e-101 |
| AAB92953 | Human protein sequence SEQ ID NO:11635 - Homo sapiens, 609 aa. [EP1074617-A2, 07 Feb. 2001] | 15..554 44..581 | 201/544 (36%) 288/544 (51%) | 2e-99 |
| AAM38956 | Human polypeptide SEQ ID NO 2101 - Homo sapiens, 587 aa. [WO200153312-A1, 26 Jul. 2001] | 25..554 36..564 | 193/535 (36%) 297/535 (55%) | 3e-99 |
| AAM78511 | Human protein SEQ ID NO 1173 - Homo sapiens, 593 aa. [WO200157190-A2, 09 Aug. 2001] | 3..554 19..570 | 201/562 (35%) 301/562 (52%) | 6e-97 |

In a BLAST search of public sequence datbases, the NOV20a protein was found to have homology to the proteins shown in the BLASTP data in Table 20E.

TABLE 20E

Public BLASTP Results for NOV20a

| Protein Accession Number | Protein/Organism/Length | NOV20a Residues/ Match Residues | Identities/ Similarities for the Matched Portion | Expect Value |
|---|---|---|---|---|
| Q96MC0 | CDNA FLJ32662 FIS, CLONE TESTI1000064, WEAKLY SIMILAR TO FUGU RUBRIPES SEX COMB ON MIDLEG-LIKE 2 PROTEIN (SCML2) GENE - Homo sapiens (Human), 614 aa. | 1..608 1..608 | 604/608 (99%) 606/608 (99%) | 0.0 |
| Q9D5V2 | 4921517C11RIK PROTEIN - Mus musculus (Mouse), 608 aa. | 1..608 1..608 | 598/608 (98%) 602/608 (98%) | 0.0 |
| Q9DA07 | 4921517C11RIK PROTEIN - Mus musculus (Mouse), 608 aa. | 1..608 1..608 | 597/608 (98%) 602/608 (98%) | 0.0 |
| Q9W6R2 | KETCH PROTEIN - Fugu rubripes (Japanese pufferfish) (Takifugu rubripes), 518 aa (fragment). | 66..578 1..511 | 255/513 (49%) 353/513 (68%) | e-152 |
| Q9W6R3 | KELCH PROTEIN - Fugu rubripes (Japanese pufferfish) (Takifugu rubripes), 531 aa (fragment). | 65..589 1..523 | 251/525 (47%) 333/525 (62%) | e-141 |

PFam analysis predicts that the NOV20a protein contains the domains shown in the Table 20F.

TABLE 20F

Domain Analysis of NOV20a

| Pfam Domain | NOV20a Match Region | Identities/ Similarities for the Matched Region | Expect Value |
|---|---|---|---|
| K_tetra: domain 1 of 1 | 41..134 | 16/112 (14%) 49/112 (44%) | 7.6 |
| BTB: domain 1 of 1 | 23..136 | 35/143 (24%) 91/143 (64%) | 1.2e-25 |
| Kelch: domain 1 of 5 | 328..373 | 14/47 (30%) 40/47 (85%) | 68e-10 |
| Kelch: domain 2 of 5 | 375..420 | 15/47 (32%) 38/47 (81%) | 4e-10 |
| Colipase_C: domain 1 of 1 | 422..438 | 9/17 (53%) 10/17 (59%) | 5.5 |
| Kelch: domain 3 of 5 | 422..467 | 15/47 (32%) 37/47 (79%) | 1.2e-09 |
| Kelch: domain 4 of 5 | 469..514 | 16/47 (34%) 36/47 (77%) | 5.5e-08 |
| Kelch: domain 5 of 5 | 516..561 | 13/47 (28%) 37/47 (79%) | 8.5e-09 |

Example 21

The NOV21 clone was analyzed, and the nucleotide and encoded polypeptide sequences are shown in Table 21A.

TABLE 21A

NOV21 Sequence Analysis

| | |
|---|---|
| NOV21a, CG89098-01 DNA Sequence | SEQ ID NO:57        903 bp<br>CCGGGCCTGGCGGGGGGACCATGGGCGCCTCGGTCTCCAGGGGCCGGGCCGCCCGGGT<br><br>CCCCGCGCCGGAGCCGGAACCCGAAGAGGCGCTGGACCTGAGCCAACTACCCCCAGAG<br><br>CTGCTTCTGGTGGTGCTGAGCCACGTCCCCCCGCGCACGCTGCTCGGGCGCTGCCGCC<br><br>AAGTGTGCCGGGGCTGGCGAGCCCTGGTGGACGGCCAGGCCCTGTGGCTGCTGATCCT<br><br>GGCCCGCGACCACGGCGCCACCGGCCGCGCGCTGCTGCACCTCGCCCGCAGCTGCCAG<br><br>TCTCCCGCCCGTAACGCCAGGCCTTGCCCCCTGGGCCGCTTCTGCGCGCGCAGACCCA<br><br>TCGGACGCAACCTTATTCGCAACCCCTGCGGCGAAGGCCTCCGAAAGTGGATGGTGCA |

TABLE 21A-continued

NOV21 Sequence Analysis

|  |  |
|---|---|
|  | ACACGGTGGGGACGGCTGGGTGGTGGAGGAAAACAGGACAACCGTGCCTGGGGCCCCT<br><br>TCTCAGACGTGCTTCGTGACTTCATTCAGCTGGTGTTGCAAGAAGCAGGTCTTGGACC<br><br>TAGAGGAGGAGGGTCTGTGGCCAGAACTGCTGGATAGTGGCAGGATTGAGATTTGTGT<br><br>CTCTGACTGGTGGGGAGCCCGACACGACAGCGGCTGTATGTACAGACTCCTCGTCCAA<br><br>CTTCTAGACGCCAACCAGACTGTTCTAGATAAATTCTCTGCTGTGCCTGATCCCATCC<br><br>CGCAGTGGAACAACAATGCCTGCCTTCACGTGACCCACGTGTTCTCCAACATCAAGAT<br><br>GGGCGTCCGCTTTGTGTCTTTCGAACACCGGGGCCAGGACACACAGTTCTGGGCTGGC<br><br>CACTATGGAGCCCGTGTGACCAACTCCAGTGTGATCGTGCGAGTCCGTCTGTCCTAGT<br><br>CCAGCACTACCCTTCTTGCAAGACAGCCTGACT |
| NOV21a,<br>CG89098-01 Protein Sequence | ORF Start: ATG at 21  ORF Stop: TAG at 867<br>SEQ ID NO:58        282 aa MW at 31494.9 kD<br>MGASVSRGRAARVPAPEPEPEEALDLSQLPPELLLVVLSHVPPRTLLGRCRQVCRGWR<br><br>ALVDGQALWLLILARDHGATGRALLHLARSCQSPARNARPCPLGRFCARRPIGRNLIR<br><br>NPCGEGLRKWMVQHGGDGWVVEENRTTVPGAPSQTCFVTSFSWCCKKQVLDLEEEGLW<br><br>PELLDSGRIEICVSDWWGARHDSGCMYRLLVQLLDANQTVLDKFSAVPDPIPQWNNNA<br><br>CLHVTHVFSNIKMGVRFVSFEHRGQDTQFWAGHYGARVTNSSVIVRVRLS |

Further analysis of the NOV21a protein yielded the following properties shown in Table 21B.

TABLE 21B

| Protein Sequence Properties NOV21a | |
|---|---|
| PSort analysis: | 0.4500 probability located in cytoplasm; 0.2436 probability located in lysosome (lumen); 0.1644 probability located in microbody (peroxisome); 0.1000 probability located in mitochondrial matrix space |
| SignalP analysis: | Cleavage site between residues 13 and 14 |

A search of the NOV21a protein against the Geneseq database, a proprietary database that contains sequences published in patents and patent publication, yielded several homologous proteins shown in Table 21C.

TABLE 21C

| Geneseq Results for NOV21a | | | | |
|---|---|---|---|---|
| Geneseq Identifier | Protein/Organism/Length [Patent #, Date] | NOV21a Residues/ Match Residues | Identities/ Similarities for the Matched Region | Expect Value |
| ABG23890 | Novel human diagnostic protein #23881 - *Homo sapiens*, 194 aa. [WO200175067-A2, 11 Oct. 2001] | 121..259<br>27..176 | 123/151 (81%)<br>126/151 (82%) | 1e-64 |
| ABG23890 | Novel human diagnostic protein #23881 - *Homo sapiens*, 194 aa. [WO200175067-A2, 11 Oct. 2001] | 121..259<br>27..176 | 123/151 (81%)<br>126/151 (82%) | 1e-64 |
| AAY91629 | Human secreted protein sequence encoded by gene 23 SEQ ID NO:302 - *Homo sapiens*, 331 aa. [WO200006698-A1, 10 Feb. 2000] | 18..282<br>42..300 | 111/272 (40%)<br>151/272 (54%) | 2e-49 |
| AAM39365 | Human polypeptide SEQ ID NO 2510 - *Homo sapiens*, 295 aa. [WO200153312-A1, 26 Jul. 2001] | 10..277<br>26..293 | 117/284 (41%)<br>155/284 (54%) | 4e-47 |
| AAY83046 | F-box protein FBP-6 - *Homo sapiens* 338 aa [WO200012679-A1, 09 Mar. 2000] | 2..282<br>26..307 | 113/295 (38%)<br>155/295 (52%) | 9e-47 |

In a BLAST search of public sequence datbases, the NOV2a protein was found to have homology to the proteins shown in the BLASTP data in Table 21D.

TABLE 21D

Public BLASTP Results for NOV21a

| Protein Accession Number | Protein/Organism/Length | NOV21a Residues/ Match Residues | Identities/ Similarities for the Matched Portion | Expect Value |
|---|---|---|---|---|
| Q96C87 | SIMILAR TO F-BOX ONLY PROTEIN 17 - *Homo sapiens* (Human), 283 aa. | 1..282 1..283 | 282/283 (99%) 282/283 (99%) | e-170 |
| Q9N0C8 | UNNAMED PROTEIN PRODUCT - *Macaca fascicularis* (Crab eating macaque) (Cynomolgus monkey), 280 aa. | 1..282 1..280 | 271/284 (95%) 272/284 (95%) | e-160 |
| Q96EF6 | SIMILAR TO F-BOX ONLY PROTEIN 17 - *Homo sapiens* (Human), 278 aa. | 1..282 1..278 | 165/286 (57%) 201/286 (69%) | 5e-91 |
| Q96LQ4 | CDNA FLJ25205 FIS, CLONE REC05844, HIGHLY SIMILAR TO *MUS MUSCULUS* F-BOX PROTEIN FBX17 MRNA - *Homo sapiens* (Human), 287 aa. | 1..282 10..287 | 165/286 (57%) 201/286 (69%) | 5e-91 |
| Q9QZM8 | F-BOX PROTEIN FBX17 - *Mus musculus* (Mouse), 242 aa. | 24..233 16..237 | 132/222 (59%) 160/222 (71%) | 1e-73 |

PFam analysis predicts that the NOV21a protein contains the domains shown in the Table 21E.

TABLE 21E

Domain Analysis of NOV21a

| Pfam Domain | NOV21a Match Region | Identities/ Similarities for the Matched Region | Expect Value |
|---|---|---|---|
| F-box: domain 1 of 1 | 24..72 | 16/49 (33%) 37/49 (76%) | 1.5e-07 |

Example 22

The NOV22 clone was analyzed, and the nucleotide and encoded polypeptide sequences are shown in Table 22A.

TABLE 22A

NOV22 Sequence Analysis

NOV22a, CG89126-01 DNA Sequence

SEQ ID NO: 59    1634 bp
ACTGCTCCTGACAGAAGGATGCCACAGCTGAGCCTGTCCTCGCTGGGCCTTTGGCCAA

TGGCAGCATCCCCGTGGCTGCTCCTGCTGCTGGTTGGGGCCTCCTGGCTCCTGGCCCG

CATCCTGGCCTGGACCTACACCTTCTATGACAACTGCTGCCGCCTCCAGTGTTTCCCA

CAGCCCCCAAAACAGAACTGGTTTTGGGGTCACCTGGGCCTGGTCACCCCCACGGAAG

AGGGCATGAAGACATTGACCCAGCTGGTGGCCACATATCCCCAGGGCTTTAAGGTCTG

GCTGGGTCCCATCATCCCCTTCATCGTTTTATGCCACCCTGACACCATCCGGTCTATC

ACCAATGCCTCAGCTGCCATTGTACCCAAGGATAATCTCTTCTACAGCTTCCTGAAGC

CCTGGCTGGGGATGGGCTCCTGCTGAGTGGCGGTGACAAGTGGAGCCGCCACCGTCG

GATGCTGACGCCCGCCTTCCATTTCAACATCCTGAAGTCCTATATAACGATCTTCAAC

AAGAGTGCAAACATCATGCTTGACAAGTGGCAGCACCTGGCCTCAGAGGGCAGCAGTC

GTCTGGACATGTTTGAGCACATCAGCCTCATGACCTTGGACAGTCTGCAGAAATGTGT

TABLE 22A-continued

NOV22 Sequence Analysis

```
CTTCAGCTTTGAAAGCAATTGTCAGGAGAAACCCAGTGAATATATTGCCGCCATCTTG

GAGCTCAGTGCCTTTGTAGAAAAGAGAAACCAGCAGATTCTCTTGCATATTGACTTCC

TGTATTATCTCACCCCTGATGGGCAGCGCTTCCACAGGGCCTGCAGACTGGTGCACGA

CTTCACAGATGCCGTCATCCAGGAGCGGCGCCGCACCCTCCCTAGCCAGGGTGTTGAT

GATTTCCTCCAAGCCAAGGCCAAGTCCAAGACTTTAGACTTCATTGATGTGCTTCTGC

TGAGCAAGGATGAAGACGGGAAGAAGTTATCTGATGAGGACATAAGAGCAGAAGCTGA

CACCTTTATGTTTGAGGGCCATGACACCACAGCCAGTGGTCTCTCCTGGGTCCTGTAC

CACCTTGCAAAGCACCCAGAATACCAGGAGCGCTGCCGGCAAGAAGTGCAAGAGCTTC

TGAAGGACCGTGAACCTATAGAGATTGAATGGGACGACCTGGCCCAGCTGCCCTTCCT

GACCATGTGCATTAAGGAGAGCCTGCGGTTGCATCCCCCAGTCCCGGTCATCTCCCGC

GGCTGCACCCAGGACTTTGTGCTCCCAGACGGCCGCGTCATCCCCAAAGGCATTATCT

GCCTCATCAGTGTTTTTGGAACCCATCACAACCCAGCTGTGTGGCCGGACCCTGAGGT

CTACGACCCCTTCCGCTTTGACCCAGAGAACATCAAGGAGAGGTCACCTCTGGCTTTT

ATTCCCTTCTCGGCAGGGCCCAGGAACTGCATCGGGCAGACGTTCGCGATGGCGGAGA

TGAAGGTGGTCCTGGCGCTCACGCTGCTGCGCTTCCGCGTCCTGCCTGACCACACCGA

GCCCCGCAGGAAGCCGGAGCTGGTCCTGCGCGCAGAGGGCGGACTTTGGCTGCGGGTG

GAGCCCCTGAGCTGAGTTCTGCAGAGACCCACTCTGACCCCACTAAAATGACCCCTGA

TTCATCAAAA
```

ORF Start: ATG at 19   ORF Stop: TGA at 1579
SEQ ID NO: 60          520 aa MW at 59618.3 kD NOV22a,
CG89126-01
Protein Sequence

```
MPQLSLSSLGLWPMAASPWLLLLLVGASWLLARILAWTYTFYDNCCRLQCFPQPPKQN

WFWGHLGLVTPTEEGMKTLTQLVATYPQGFKVWLGPIIPFIVLCHPDTIRSITNASAA

IVPKDNLFYSFLKPWLGDGLLLSGGDKWSRHRRMLTPAFHFNILKSYITIFNKSANIM

LDKWQHLASEGSSRLDMFEHISLMTLDSLQKCVFSFESNCQEKPSEYIAAILELSAFV

EKRNQQILLHIDFLYYLTPDGQRFHRACRLVHDFTDAVIQERRRTLPSQGVDDFLQAK

AKSKTLDFIDVLLLSKDEDGKKLSDEDIRAEADTPMFEGHDTTASGLSWVLYHLAKHP

EYQERCRQEVQELLKDREPIEIEWDDLAQLPFLTMCIKESLRLHPPVPVISRGCTQDF

VLPDGRVIPKGIICLISVFGTHHNPAVWPDPEVYDPFRFDPENIKERSPLAFIPFSAG

PRNCIGQTFAMAEMKVVLALTLLRFRVLPDHTEPRRKPELVLRAEGGLWLRVEPLS
```

Further analysis of the NOV22a protein yielded the following properties shown in Table 22B.

TABLE 22B

| Protein Sequence Properties NOV22a | |
|---|---|
| PSort analysis: | 0.8200 probability located in outside; 0.4362 probability located in lysosome (lumen); 0.2522 probability located in microbody (peroxisome); 0.1000 probability located in endoplasmic reticulum (membrane) |
| SignalP analysis: | Cleavage site between residues 37 and 38 |

A search of the NOV22a protein against the Geneseq database, a proprietary database that contains sequences published in patents and patent publication, yielded several homologous proteins shown in Table 22C.

TABLE 22C

Geneseq Results for NOV22a

| Geneseq Identifier | Protein/Organism/Length [Patent #, Date] | NOV22a Residues/ Match Residues | Identities/ Similarities for the Matched Region | Expect Value |
|---|---|---|---|---|
| AAB85779 | Human drug metabolizing enzyme (ID No. 6825202CD1) - *Homo sapiens*, 524 aa. [WO200159127-A2, 16 Aug. 2001] | 1..519<br>1..519 | 467/519 (89%)<br>488/519 (93%) | 0.0 |
| ABG28261 | Novel human diagnostic protein #28252 - *Homo sapiens*, 728 aa. [WO200175067-A2, 11 Oct. 2001] | 1..520<br>209..728 | 468/520 (90%)<br>487/520 (93%) | 0.0 |
| ABG28261 | Novel human diagnostic protein #28252 - *Homo sapiens*, 728 aa. [WO200175067-A2, 11 Oct. 2001] | 1..520<br>209..728 | 468/520 (90%)<br>487/520 (93%) | 0.0 |
| AAB65229 | Human PRO1129 (UNQ568) protein sequence SEQ ID NO:264 - *Homo sapiens*, 524 aa. [WO200073454-A1, 07 Dec. 2000] | 1..520<br>1..520 | 448/520 (86%)<br>476/520 (91%) | 0.0 |
| AAB87552 | Human PRO1129 - *Homo sapiens*, 524 aa. [WO200116318-A2, 08 Mar. 2001] | 1..520<br>1..520 | 448/520 (86%)<br>476/520 (91%) | 0.0<br>0.0 |

In a BLAST search of public sequence datbases, the NOV22a protein was found to have homology to the proteins shown in the BLASTP data in Table 22D.

TABLE 22D

Public BLASTP Results for NOV22a

| Protein Accession Number | Protein/Organism/Length | NOV22a Residues/ Match Residues | Identities/ Similarities for the Matched Portion | Expect Value |
|---|---|---|---|---|
| O60634 | CYTOCHROME P-450 - *Homo sapiens* (Human), 520 aa. | 1..520<br>1..520 | 474/520 (91%)<br>494/520 (94%) | 0.0 |
| Q96AQ5 | CYTOCHROMEP 450, SUBFAMILY IVF, POLYPEPTIDE 11 - *Homo sapiens* (Human), 524 aa. | 1..519<br>1..519 | 466/519 (89%)<br>488/519 (93%) | 0.0 |
| Q9HBI6 | CYP4F11 - *Homo sapiens* (Human), 524 aa. | 1..519<br>1..519 | 465/519 (89%)<br>488/519 (93%) | 0.0 |
| P78329 | Cytochrome P450 4F2 (EC 1.14.13.30) (CYPIVF2) (Leukotriene-B4 omega-hydroxylase) (Leukotriene B4 20-monooxygenase) (Cytochrome P450-LTB-omega) - *Homo sapiens* (Human), 520 aa. | 1..520<br>1..520 | 468/520 (90%)<br>487/520 (93%) | 0.0 |
| Q9HCS2 | CYTOCHROME P450 (CYTOCHROME P450 ISOFORM 4F12) - *Homo sapiens* (Human), 524 aa. | 1..520<br>1..520 | 448/520 (86%)<br>476/520 (91%) | 0.0 |

PFam analysis predicts that the NOV22a protein contains the domains shown in the Table 22E.

TABLE 22E

Domain Analysis of NOV22a

| Pfam Domain | NOV22a Match Region | Identities/ Similarities for the Matched Region | Expect Value |
|---|---|---|---|
| ATP-synt_8: domain 1 of 1 | 1..62 | 17/66 (26%)<br>33/66 (50%) | 5.6 |
| p450: domain 1 of 1 | 52..519 | 162/515 (31%)<br>381/515 (74%) | 3.2e-145 |

Example 23

The NOV23 clone was analyzed, and the nucleotide and encoded polypeptide sequences are shown in Table 23A.

TABLE 23A

NOV23 Sequence Analysis

SEQ ID NO:61 3764 bp

| NOV23a, CG89367-01 DNA Sequence | <u>ACGGTGCTGGTCTGAGCTGGACCTTGTCTG</u>ATGGCTTCCTCCAACCCTCCTCCACAGC<br>CTGCCATAGGAGATCAGCTGGTTCCAGGAGTCCCAGGCCCCTCCTCTGAGGCAGAGGA<br>CGACCCAGGAGAGGCGTTTGAGTTTGATGACAGTGATGATGAAGAGGACACCAGCGCA<br>GCCCTGGGCGTCCCCAGCCTTGCTCCTGAGAGGGACACAGACCCCCCACTGATCCACT<br>TGGACTCCATCCCTGTCACTGACCCAGACCCAGCAGCTGCTCCACCCGGCACAGGGGT<br>GCCAGCCTGGGTGAGCAATGGGGATGCTGCGGATTCAGCCTTCTCCGGGGCCCGGCAC<br>TCCAGCTGGAAGCGGAAGAGTTCCCGTCGCATTGACCGGTTCACTTTCCCCGCCCTGG<br>AAGAGGATGTGATTTATGACGATGTCCCCTGCGAGAGCCCAGATGCGCATCAGCCCGG<br>GGCAGAGAGGAACCTGCTCTACGAGGATGCGCACCGGGCTGGGGCCCCTCGGCAGGCG<br>GAGGACCTAGGCTGGAGCTCCAGTGAGTTCGAGAGCTACAGCGAGGACTCGGGGGAGG<br>AGGCCAAGCCGGAGGTCGAGGTCGAGCCCGCCAAGCACCGAGTGTCCTTCCAGCCCAA<br>GATGACCCAGCTCATGAAGGCCGCCAAGAGCGGGACCAAGGATGGGCTGGAGAAGACA<br>CGGATGGCCGTGATGCGCAAAGTCTCCTTCCTGCACAGGAAGGACGTCCTCGGTGACT<br>CGGAGGAGGAGGACATGGGGCTCCTGGAGGTCAGCGTTTCGGACATCAAGCCCCCAGC<br>CCCAGAGCTGGGCCCCATGCCAGAGGGCCTGAGCCCTCAGCAGGTGGTCCGGAGGCAT<br>ATCCTGGGCTCCATCGTGCAGAGCGAAGGCAGCTACGTGGAGTCTCTGAAGCGGATAC<br>TCCAGGACTACCGCAACCCCCTGATGGAGATGGAGCCCAAGGCGCTGAGCGCCCGCAA<br>GTGCCAGGTGGTGTTCTTCCGCGTGAAGGAGATCCTGCACTGCCACTCCATGTTCCAG<br>ATCGCCCTGTCCTCCCGCGTGGCTGAGTGGGATTCCACCGAGAAGATCGGGGACCTCT<br>TCGTGGCCTCGTTTTCCAAGTCCATGGTGCTAGATGTGTACAGTGACTACGTGAACAA<br>CTTCACCAGTGCCATGTCCATCATCAAGAAGGCCTGCCTCACCAAGCCTGCCTTCCTC<br>GAGTTCCTCAAGCGACGGCAGGTGTGCAGCCCAGACCGTGTCACCCTCTACGGGCTGA<br>TGGTCAAGCCCATCCAGAGGTTCCCACAGTTCATACTCCTGCTTCAGGACATGCTGAA<br>GAACACCCCCAGGGGCCATCCGGACAGGCTGTCGCTGCAGCTGGCCCTCACAGAGCTG<br>GAGACGCTGGCTGAGAAGCTGAACGAGCAGAAGCGGCTGGCTGACCAGGTGGCTGAGA<br>TCCAGCAGCTGACCAAGAGCGTCAGTGACCGCAGCAGCCTCAACAAGCTGTTGACCTC<br>AGGCCAGCGGCAGCTGCTCCTGTGTGAGACGTTGACGGAGACCGTGTACGGTGACCGA<br>GGGCAGCTAATTAAGTCCAAGGAGCGTCGGGTCTTCCTGCTCAACGACATGCTTGTCT<br>GTGCCAACATCAACTTCAAGCCTGCCAACCACAGGGGCCAGCTGGAGATTAGCAGCCT<br>GGTGCCCCTGGGGGCCAAGTATGTGGTGAAGTGGAACACGGCGCTGCCCCAGGTGCAG<br>GTGGTGGAGGTGGGCCAGGACGGTGGCACCTATGACAAGGACAATGTGCTCATCCAGC<br>ACTCAGGCGCCAAGAAGGCCTCTGCCTCAGGGCAGGCTCAGAATAAGGTGTACCTCGG<br>CCCCCCACGCCTCTTCCAGGAGCTGCAGGACCTGCAGAAGGACCTGGCCGTGGTGGAG<br>CAGATCACGCTTCTCATCAGCACGCTGCACGGCACCTACCAGAACCTGAACATGACTG<br>TGGCTCAAGACTGGTGCCTGGCCCTGCAGAGGCTGATGCGGGTGAAGGAGGAAGAGAT<br>CCACTCGGCCAACAAGTGCCGTCTCAGGCTCCTGCTTCCTGGGAAACCCGACAAGTCC<br>GGCCGCCCCATTAGCTTCATGGTGGTTTTCATCACCCCCAACCCCCTGAGCAAGATTT<br>CCTGGGTCAACAGGTTACATTTGGCCAAAATCGGACTCCGGGAGGAGAACCAGCCAGG<br>CTGGCTATGCCCGGATGAGGACAAGAAGAGCAAAGCCCCATTCTGGTGCCCGATCCTG<br>GCCTGCTGCATCCCTGCCTTCTCCTCCCGGGCACTCAGCCTGCAGCTTGGGGCCCTGG<br>TCCACAGTCCTGTCAACTGTCCCCTGCTGGGTTTCTCAGCAGTCAGCACCTCCCTTCC<br>ACAGGGCTACCTCTGGGTCGGGGCGGACAGGAAGGCGCAGGGGGCCAGGTGGAAATC<br>TTTTCCTTGAACCGGCCCTCGCCCCGCACCGTCAAGTCCTTCCCACTGGCAGCCCCTG<br>TGCTCTGCATGGAGTATATCCCGGAGCTGGAGGAGGAGGCGGAGAGCAGAGACGAGAG<br>CCCGACAGTTGCTGACCCCTCGGCCACGGTGCATCCAACCATCTGCCTCGGGCTCCAG<br>GATGGCAGCATCCTCCTCTACAGCAGTGTGGACACTGGCACCCAGTGCCTGGTGAGCT<br>GCAGGAGCCCAGGTCTGCAGCCTGTGCTCTGCCTGCGACACAGCCCCTTCCACCTGCT<br>CGCTGGCCTGCAGGATGGGACCCTTGCTGCTTACCCTCGGACCAGCGGAGGTGTCCTG<br>TGGGACCTGGAGAGCCCTCCCGTGTGCCTGACTGTGGGGCCCGGGCCTGTCCGCACCC<br>TGTTGAGCCTGGAGGATGCCGTGTGGGCCAGCTGTGGGCCCCGGGTCACTGTCCTGGA<br>AGCCACCACCCTGCAGCCTCAGCAAAGCTTCGAGGCGCACCAGGACGAGGCAGTGAGC<br>GTGACACACATGGTGAAGGCGGGCAGCGGCGTCTGGATGGCCTTCTCCTCCGGCACCT<br>CCATCCGCCTCTTCCACACTGAGACCCTGGAGCATCTGCAAGAGATCAACATCGCCAC<br>CAGGACCACCTTCCTCCTGCCAGGCCAGAAGCACTTGTGTGTCACCAGCCTCCTGATC<br>TGCCAGGGTCTGCTCTGGGTGGGCACTGACCAGGGTGTCATCGTCCTGCTGCCCGTGC<br>CTCGGCTGGAAGGCATCCCCAAGATCACAGGGAAAGGCATGGTCTCACTCAATGGGCA<br>CTGTGGGCCTGTGGCCTTCCTGGCTGTGGCTACCAGCATCCTGGCCCCTGACATCCTG<br>CGGAGTGACCAGGAGGAGGCTGAGGGGCCCCGGGCTGAGGAGGACAAGCCAGACGGGC<br>AGGCACACGAGCCCATGCCCGACAGCCACGTGGGCCGAGAGCTGACCCGCAAGAAGGG<br>CATCCTCTTGCAGTACCGCCTGCGCTCCACCGCACACCTCCCGGGCCCGCTGCTCTCC<br>ATGCGGGAGCCGGCGCCTGCTGATGGCGCAGCTTTGGAGCACAGCGAGGAGGACGGCT<br>CCATTTACGAGATGGCCGACCCCCGACGTCTGGGTGCGCAGCCGCCCTGCGCCCG<br>CGACGCCCACCGCAAGGAGATTTGCTCTGTGGCCATCATCTGGGGCGGGCAGGGCTAC<br>CGCAACTTTGGCAGCGCTCTGGGCAGCAGTGGGAGGCAGGCCCCGTGTGGGGAGACGG<br>ACAGCACCCTCCTCATCTGGCAGGTGCCCTTGATGCTATAG<u>CGCCTCCCCTC</u> |

ORF Start: ATG at 31 ORF Stop: TAG at 3751
SEQ ID NO: 62 1240 aa MW at 135723.2 kD

| NOV23a, G89367-01 Protein Sequence | MASSNPPPQPAIGDQLVPGVPGPSSEAEDDPGEAFEFDDSDDEEDTSAALGVPSLAPE<br>RDTDPPLIHLDSIPVTDPDPAAAPPGTGVPAWVSNGDAADSAFSGARHSSWKRKSSRR<br>IDRFTFPALEEDVIYDDVPCESPDAHQPGAERNLLYEDAHRAGAPRQAEDLGWSSSEF<br>ESYSEDSGEEAKPEVEVEPAKHRVSFQPKMTQLMKAAKSGTKDGLEKTRMAVMRKVSF<br>LHRKDVLGDSEEEDMGLLEVSVSDIKPPAPSLGPMPEGLSPQQVVRRHILGSIVQSEG |

TABLE 23A-continued

NOV23 Sequence Analysis

```
SYVESLKRILQDYRNPLMEMEPKALSARKCQVVFFRVKEILHCHSMFQIALSSRVAEW
DSTEKIGDLFVASFSKSMVLDVYSDYVNNFTSAMSIIKKACLTKPAFLEFLKRRQVCS
PDRVTLYGLMVKPIQRFPQFILLLQDMLKNTPRGHPDRLSLQLALTELETLAEKLNEQ
KRLADQVAEIQQLTKSVSDRSSLNKLLTSGQRQLLLCETLTETVYGDRGQLIKSKERR
VFLLNDMLVCANINFKPANHRGQLEISSLVPLGPKYVVKWNTALPQVQVVEVGQDGGT
YDKDNVLIQHSGAKKASASGQAQNKVYLGPPRLFQELQDLQKDLAVVEQITLLISTLH
GTYQNLNMTVAQDWCLALQRLMRVKEEEIHSANKCRLRLLLPGKPDKSGRPISFMVVF
ITPNPLSKISWVNRLHLAKIGLREENQPGWLCPDEDKKSKAPFWCPILACCIPAFSSR
ALSLQLGALVHSPVNCPLLGFSAVSTSLPQGYLWVGGGQEGAGGQVEIFSLNRPSPRT
VKSFPLAAPVLCMEYIPELEEEAESRDESPTVADPSATVHPTICLGLQDGSILLYSSV
DTGTQCLVSCRSPGLQPVLCLRHSPFHLLAGLQDGTLAAYPRTSGGVLWDLESPPVCL
TVGPGPVRTLLSLEDAVWASCGPRVTVLEATTLQPQQSFEAHQDEAVSVTHMVKAGSG
VWMAFSSGTSIRLFHTETLEHLQEINIATRTTFLLPGQKHLCVTSLLICQGLLWVGTD
QGVIVLLPVPRLEGIPKITGKGMVSLNGHCGPVAFLAVATSILAPDILRSDQEEAEGP
RAEEDKPDGQAHEPMPDSHVGRELTRKKGILLQYRLRSTAHLPGPLLSMREPAPADGA
ALEHSEEDGSIYEMADDPDVWVRSRPCARDAHRKEICSVAIISGGQGYRNFGSALGSS
GRQAPCGETDSTLLIWQVPLML
```

Further analysis of the NOV23a protein yielded the following properties shown in Table 23B.

TABLE 23B

Protein Sequence Properties NOV23a

| | |
|---|---|
| PSort analysis: | 0.7600 probability located in nucleus; 0.3000 probability located in microbody (peroxisome); 0.1000 probability located in mitochondrial matrix space; 0.1000 probabilty located in lysosome (lumen) |
| SignalP analysis: | No Known Signal Sequence Predicted |

A search of the NOV23a protein against the Geneseq database, a proprietary database that contains sequences published in patents and patent publication, yielded several homologous proteins shown in Table 23C.

TABLE 23C

Geneseq Results for NOV23a

| Geneseq Identifier | Protein/Organism/Length [Patent #, Date] | NOV23a Residues/ Match Residues | Identities/ Similarities for the Matched Region | Expect Value |
|---|---|---|---|---|
| AAB92909 | Human protein sequence SEQ ID NO:11539 - *Homo sapiens*, 596 aa. [EP1074617-A2, 07 Feb. 2001] | 433..1022 1..585 | 583/590 (98%) 583/590 (98%) | 0.0 |
| ABG08838 | Novel human diagnostic protein #8829 - *Homo sapiens*, 1129 aa. [WO200175067-A2, 11 Oct. 2001] | 150..1239 14..1127 | 510/1143 (44%) 691/1143 (59%) | 0.0 |
| ABG08838 | Novel human diagnostic protein #8829 - *Homo sapiens*, 1129 aa. [WO200175067-A2, 11 Oct. 2001] | 150..1239 14..1127 | 510/1143 (44%) 691/1143 (59%) | 0.0 |
| ABG08836 | Novel human diagnostic protein #8827 - *Homo sapiens*, 988 aa. [WO200175067-A2, 11 Oct. 2001] | 211..1239 1..986 | 479/1042 (45%) 645/1042 (60%) | 0.0 |
| ABG08836 | Novel human diagnostic protein #8827 - *Homo sapiens*, 988 aa. [WO200175067-A2, 11 Oct. 2001] | 211..1239 1..986 | 479/1042 (45%) 645/1042 (60%) | 0.0 |

In a BLAST search of public sequence datbases, the NOV23a protein was found to have homology to the proteins shown in the BLASTP data in Table 23D.

TABLE 23D

Public BLASTP Results for NOV23a

| Protein Accession Number | Protein/Organism/Length | NOV23a Residues/ Match Residues | Identities/ Similarities for the Matched Portion | Expect Value |
|---|---|---|---|---|
| Q9HCE6 | KIAA1626 PROTEIN - Homo sapiens (Human), 1284 aa (fragment). | 1..1240 6..1284 | 1239/1279 (96%) 1240/1279 (96%) | 0.0 |
| AAH21843 | HYPOTHETICAL 77.6 KDA PROTEIN - Mus musculus (Mouse), 720 aa (fragment). | 524..1240 1..720 | 664/720 (92%) 688/720 (95%) | 0.0 |
| Q9NVT3 | CDNA FLJ10521 FIS, CLONE NT2RP2000841 - Homo sapiens (Human), 596 aa. | 433..1022 1..585 | 583/590 (98%) 583/590 (98%) | 0.0 |
| Q9GMY0 | HYPOTHETICAL 63.8 KDA PROTEIN - Macaca fascicularis (Crab eating macaque) (Cynomolgus monkey), 567 aa. | 208..773 1..566 | 563/566 (99%) 564/566 (99%) | 0.0 |
| O15013 | KIAA0294 PROTEIN - Homo sapiens (Human), 1121 aa. | 150..1239 6..1119 | 510/1143 (44%) 691/1143 (59%) | 0.0 |

PFam analysis predicts that the NOV23a protein contains the domains shown in the Table 23E.

TABLE 23E

Domain Analysis of NOV23a

| Pfam Domain | NOV23a Match Region | Identities/ Similarities for the Matched Region | Expect Value |
|---|---|---|---|
| RhoGEF: domain 1 of 1 | 281..463 | 60/209 (29%) 135/209 (65%) | 2.8e-33 |

Example 24

The NOV24 clone was analyzed, and the nucleotide and encoded polypeptide sequences are shown in Table 24A.

TABLE 24A

NOV24 Sequence Analysis

NOV24a CG89645-01 DNA Sequence

SEQ ID NO: 63    750 bp

GTTATAAGCGCCATGGCTATGACTAGTGTCAAATTGCTTGCCATTGTTTTAAGAAAGC

CAGATACCTGGATTGGACTCTGGGGTGTTCTCCGAGGGACACCTTCGTCACACAAACT

CTGTACTTCCTGGAATCGATATAGCACTAAGTTATGTGCACCAAATTATAAAAGACTT

ATCCATAATATTTTCTCACTGAAATTCTCAGGGCTTTTAATATCTCCAGAATATATTT

TTCCATTTTCCATAAGACTCAAAAGTAATAAAAGCTCTAATAAATCTACTACAAAGTC

ACTGCAAAAAGTAGAAGATGAAGAGGACTCTGAGGAAGACAGCAATCATGATGAGATG

AGTGAGCAGGAAGAGGAGCTTGAGGATGACCCTACGATAGTCAAAGACTATCAAGACC

TGGAAAAAGCAGTGCAGTCTTTTTGGTATGACGATGTCCTGAAGACAGGCCTAGATAT

TGGGAGAAACAAAGTGGAAGATGCGTTCTACAAAGGTGAACTCAGGCTGAATGGGGAA

AAGTTATGGAAGAAAAACAGAACGGTCAAAGTGGGAGATACACTGGATCTTCTCATTG

GAGAGGATAAAGAAGGAGGAACCGAGACAGTGATGAGGATTCTCCTGAAAAAAGTGTT

TABLE 24A-continued

NOV24 Sequence Analysis

|  |  |
|---|---|
|  | TGAAGACAAAGTGAAAAACACAGTGGTGTTACGGCGGTGGAAAAACTTAAAGTTGCCT |
|  | AGGAAGAGAATGTCTAAATAAACGGATTGCTTTTTGCAATACAGCTGCTTTCTA |
| NOV24a,<br>CG89645-01<br>Protein Sequence | ORF Start: ATG at 13    ORF Stop: TAA at 715<br>SEQ ID NO: 64           234 aa MW at 27161.9 kD<br>MAMTSVKLLAIVLRKPDTWIGLWGVLRGTPSSHKLCTSWNRYSTKLCAPNYKRLIHNI<br>FSLKFSGLLISPEYIFPFSIRLKSNKSSNKSTTKSLQKVEDEEDSEEDSNHDEMSEQE<br>EELEDDPTIVKDYQDLEKAVQSFWYDDVLKTGLDIGRNKVEDAFYKGELRLNGEKLWK<br>KNRTVKVGDTLDLLIGEDKEGGTETVMRILLKKVFEDKVKNTVVLRRWKNLKLPRKRM<br>SK |

Further analysis of the NOV24a protein yielded the following properties shown in Table 24B.

TABLE 24B

Protein Sequence Properties NOV24a

| PSort analysis: | 0.6213 probability located in mitochondrial matrix space; 0.3222 probability located in mitochondrial inner membrane; 0.3222 probability located in mitochondrial intermembrane space; 0.3222 probability located in mitochondrial outer membrane |
|---|---|
| SignalP analysis: | Cleavage site between residues 15 and 16 |

A search of the NOV24a protein against the Geneseq database, a proprietary database that contains sequences published in patents and patent publication, yielded several homologous proteins shown in Table 24C.

TABLE 24C

Geneseq Results for NOV24a

| Geneseq Identifier | Protein/Organism/Length [Patent #, Date] | NOV24a Residues/ Match Residues | Identities Similarities for the Matched Region | Expect Value |
|---|---|---|---|---|
| AAM01599 | Peptide #281 encoded by probe for measuring human breast gene expression - *Homo sapiens*, 245 aa. [WO200157270-A2, 09 Aug. 2001] | 1..211<br>18..245 | 211/228 (92%)<br>211/228 (92%) | e-117 |
| AAM26263 | Peptide #300 encoded by probe for measuring placental gene expression - *Homo sapiens*, 245 aa. [WO200157272-A2, 09 Aug. 2001] | 1..211<br>18..245 | 211/228 (92%)<br>211/228 (92%) | e-117 |
| AAM13856 | Peptide #290 encoded by probe for measuring cervical gene expression - *Homo sapiens*, 245 aa. [WO200157278-A2, 09 Aug. 2001] | 1..211<br>18..245 | 211/228 (92%)<br>211/228 (92%) | e-117 |
| AAM65987 | Human bone marrow expressed probe encoded protein SEQ ID NO: 26293 - *Homo sapiens*, 245 aa. [WO200157276-A2, 09 Aug. 2001] | 1..211<br>18..245 | 211/228 (92%)<br>211/228 (92%) | e-117 |
| AAM53608 | Human brain expressed single exon probe encoded protein SEQ ID NO: 25713 - *Homo sapiens*, 245 aa. [WO200157275-A2, 09 Aug. 2001] | 1..211<br>18..245 | 211/228 (92%)<br>211/228 (92%) | e-117 |

In a BLAST search of public sequence datbases, the NOV24a protein was found to have homology to the proteins shown in the BLASTP data in Table 24D.

TABLE 24D

Public BLASTP Results for NOV24a

| Protein Accession Number | Protein/Organism/Length | NOV24a Residues/ Match Residues | Identities/ Similarities for the Matched Portion | Expect Value |
|---|---|---|---|---|
| Q9P0P8 | HSPC230 (SIMILAR TO HYPOTHETICAL PROTEIN) - *Homo sapiens* (Human), 240 aa. | 1..234 1..240 | 198/241 (82%) 213/241 (88%) | e-106 |
| Q9CQF4 | 1700021F05RIK PROTEIN (RIKEN CDNA 1700021F05 GENE) - *Mus musculus* (Mouse), 240 aa. | 1..234 1..240 | 167/241 (69%) 194/241 (80%) | 3e-89 |
| Q9VAX9 | CG4884 PROTEIN - *Drosophila melanogaster* (Fruit fly), 189 aa. | 99..231 47..176 | 44/134 (32%) 78/134 (57%) | 1e-11 |
| Q9U7C9 | PUTATIVE CALMODULIN- BINDING PROTEIN CAM-BP-38 - *Dictyostelium discoideum* (Slime mold), 340 aa. | 80..174 99..190 | 29/99 (29%) 51/99 (51%) | 0.003 |
| O67632 | Tyrosyl-tRNA synthetase (EC 6.1.1.1) (Tyrosine--tRNA ligase) (TYRRS) - *Aquifex aeolicus*, 392 aa. | 94..193 291..385 | 23/100 (23%) 48/100 (48%) | 0.14 |

PFam analysis predicts that the NOV24a protein contains the domains shown in the Table 24E.

TABLE 24E

Domain Analysis of NOV24a

| Pfam Domain | NOV24a Match Region | Identities/ Similarities for the Matched Region | Expect Value |
|---|---|---|---|
| No Significant Matches Found | | | |

Example 25

The NOV25 clone was analyzed, and the nucleotide and encoded polypeptide sequences are shown in Table 25A.

TABLE 25A

NOV25 Sequence Analysis

NOV25a, CG89677-01 DNA Sequence

SEQ ID NO: 65   1835 bp
TCATCTCCCCGATTCCCTTCCCCTCTCCTCCCTCCTCTCCTTCCTCTCCTCCTTCCTC

TTCTCCTTTCCCCATCCCGGTCAGGGGCGGGCGCTGGAGCCAGCAGGCCTCCCCACAT

CATCTTCATCCTCACGGACGACCAAGGCTACCACGACGTGGGCTACCATGGTTCAGAT

ATCGAGACCCCTACGCTGGACAGGCTGGCGGCCAAGGGGGTCAAGTTGGAGAATTATT

ACATCCAGCCCATCTGCACGCCTTCGCGGAGCCAGCTCCTCACTGGCAGGTACCAGAT

CCACACAGGACTCCAGCATTCCATCATCCGCCCACAGCAGCCCAACTGCCTGCCCCTG

GACCAGGTGACACTGCCACAGAAGCTGCAGGAGGCAGGTTATTCCACCCATATGGTGG

GCAAGTGGCACCTGGGCTTCTACCGGAAGGAGTGTCTGCCCACCCGTCGGGGCTTCGA

CACCTTCCTGGGCTCGCTCACGGGCAATGTGGACTATTACACCTATGACAACTGTGAT

GGCCCAGGCGTGTGCGGCTTCGACCTGCACGAGGGTGAGAATGTGGCCTGGGGGCTCA

GCGGCCAGTACTCCACTATGCTTTATGCCCAGCGCGCCAGCCATATCCTGGCCAGCCA

CAGCCCTCAGCGTCCCCTCTTCCTCTATGTGGCCTTCCAGGCAGTACACACACCCCTG

TABLE 25A-continued

NOV25 Sequence Analysis

CAGTCCCCTCGTGAGTACCTGTACCGCTACCGCACCATGGGCAATGTGGCCCGGCGGA

AGTACGCGGCCATGGTGACCTGCATGGATGAGGCTGTGCGCAACATCACCTGGGCCCT

CAAGCGCTACGGTTTCTACAACAACAGTGTCATCATCTTCTCCAGTGACAATGGTGGC

CAGACTTTCTCGGGGGGCAGCAACTGGCCGCTCCGAGGACGCAAGGGCACTTATTGGG

AAGGTGGCGTGCGGGGCCTAGGCTTTGTCCACAGTCCCCTGCTCAAGCGAAAGCAACG

GACAAGCCGGGCACTGATGCACATCACTGACTGGTACCCGACCCTGGTGGGTCTGGCA

GGTGGTACCACCTCAGCAGCCGATGGGCTAGATGGCTACGACGTGTGGCCGGCCATCA

GCGAGGGCCGGGCCTCACCACGCACGGAGATCCTGCACAACATTGACCCACTCTACAA

CCATGCCCAGCATGGCTCCCTGGAGGGCGGCTTTGGCATCTGGAACACCGCCGTGCAG

GCTGCCATCCGCGTGGGTGAGTGGAAGCTGCTGACAGGAGACCCCGGCTATGGCGATT

GGATCCCACCGCAGACACTGGCCACCTTCCCGGGTAGCTGGTGGAACCTGGAACGAAT

GGCCAGTGTCCGCCAGGCCGTGTGGCTCTTCAACATCAGTGCTGACCCTTATGAACGG

GAGGACCTGGCTGGCCAGCGGCCTGATGTGGTCCGCACCCTGCTGGCTCGCCTGGCCG

AATATAACCGCACAGCCATCCCGGTACGCTACCCAGCTGAGAACCCCCGGGCTCATCC

TGACTTTAATGGGGGTGCTTGGGGGCCCTGGGCCAGTGATGAGGAAGAGGAGGAAGAG

GAAGGGAGGGCTCGAAGCTTCTCCCGGGGTCGTCGCAAGAAAAAATGCAAGATTTGCA

AGCTTCGATCCTTTTTCCGTAAACTCAACACCAGGCTAATGTCCCAACGGATCTGATG

GTGGGGAGGGAGAAAACTGTCCTTTAGAGGATCTTCCCCACTCCGGCTTGGCCCTGCT

GTTTCTCAGGGAGAAGCCTGTCACATCTCCATCTACAGGGAGTTGGAGGGTGTAGAGT

CCCTTGGTTGAACAGGGTAGGGAGCCTGGATAGGAGT

NOV25a,
CG89677-01
Protein Sequence

ORF Start: at 1    ORF Stop: TGA at 1678
SEQ ID NO: 66      559 aa MW at 62814.5 kD
SSPRFPSPLLPPLLPLLLPLLLSPSRSGAGAGASRPPHIIFILTDDQGYHDVGYHGSD

IETPTLDRLAAKGVKLENYYIQPICTPSRSQLLTGRYQIHTGLQHSIIRPQQPNCLPL

DQVTLPQKLQEAGYSTHMVGKWHLGFYRKECLPTRRGFDTFLGSLTGNVDYYTYDNCD

GPGVCGFDLHEGENVAWGLSGQYSTMLYAQRASHILASHSPQRPLFLYVAFQAVHTPL

QSPREYLYRYRTMGNVARRKYAAMVTCMDEAVRNITWALKRYGFYNNSVIIFSSDNGG

QTFSGGSNWPLRGRKGTYWEGGVRGLGFVHSPLLKRKQRTSRALMHITDWYPTLVGLA

GGTTSAADGLDGYDVWPAISEGRASPRTEILHNIDPLYNHAQHGSLEGGFGIWNTAVQ

AAIRVGEWKLLTGDPGYGDWIPPQTLATFPGSWWNLERMASVRQAVWLFNISADPYER

EDLAGQRPDVVRTLLARLAEYNRTAIPVRYPAENPRAHPDFNGGAWGPWASDEEEEEE

EGRARSFSRGRRKKKCKICKLRSFFRKLNTRLMSQRI

Further analysis of the NOV25a protein yielded the following properties shown in Table 25B.

TABLE 25B

Protein Sequence Properties NOV25a

| | |
|---|---|
| PSort analysis: | 0.8650 probability located in lysosome (lumen); 0.4419 probability located in outside; 0.2799 probability located in microbody (peroxisome); 0.1000 probability located in endoplasmic reticulum (membrane) |
| SignalP analysis: | Cleavage site between residues 30 and 31 |

A search of the NOV25a protein against the Geneseq database, a proprietary database that contains sequences published in patents and patent publication, yielded several homologous proteins shown in Table 25C.

TABLE 25C

Geneseq Results for NOV25a

| Geneseq Identifier | Protein/Organism/Length [Patent #, Date] | NOV25a Residues/ Match Residues | Identities/ Similarities for the Matched Region | Expect Value |
|---|---|---|---|---|
| AAB85482 | Human 25278 sulfatase polypeptide - Homo sapiens, 569 aa. [WO200155411-A2, 02 Aug. 2001] | 31..559 41..569 | 525/529 (99%) 526/529 (99%) | 0.0 |
| AAB85483 | Human 23553 sulfatase polypeptide - Homo sapiens, 599 aa. [WO200155411-A2, 02 Aug. 2001] | 37..539 76..580 | 321/505 (63%) 406/505 (79%) | 0.0 |
| AAB51184 | Human sulfatase protein B SEQ ID NO:13 - Homo sapiens, 533 aa. [US6153188-A, 28 Nov. 2000] | 1..513 8..532 | 296/535 (55%) 367/535 (68%) | e-164 |
| AAU29061 | Human PRO polypeptide sequence #38 - Homo sapiens, 515 aa. [WO200168848-A2, 20 Sep. 2001] | 37..384 76..424 | 244/349 (69%) 288/349 (81%) | e-155 |
| AAB44257 | Human PRO708 (UNQ372) protein sequence SEQ ID NO:114 - Homo sapiens, 515 aa. [WO200053756-A2, 14 Sep. 2000] | 37..384 76..424 | 244/349 (69%) 288/349 (81%) | e-155 |

In a BLAST search of public sequence datbases, the NOV25a protein was found to have homology to the proteins shown in the BLASTP data in Table 25D.

TABLE 25D

Public BLASTP Results for NOV25a

| Protein Accession Number | Protein/Organism/Length | NOV25a Residues/ Match Residues | Identities/ Similarities for the Matched Portion | Expect Value |
|---|---|---|---|---|
| CAC60190 | SEQUENCE 6 FROM PATENT WO0155411 - Homo sapiens (Human), 569 aa. | 31..559 41..569 | 525/529 (99%) 526/529 (99%) | 0.0 |
| CAC60191 | SEQUENCE 8 FROM PATENT WO0155411 - Homo sapiens (Human), 599 aa. | 37..539 76..580 | 321/505 (63%) 406/505 (79%) | 0.0 |
| P33727 | Arylsulfatase B precursor (EC 3.1.6.12) (ASB) (N-acetylgalactosamine-4-sulfatase) (G4S) - Felis silvestris catus (Cat), 535 aa. | 1..513 8..534 | 297/532 (55%) 370/532 (68%) | e-169 |
| P15848 | Arylsulfatase B precursor (EC 3.1.6.12) (ASB) (N-acetylgalactosamine-4-sulfatase) (G4S) - Homo sapiens (Human), 533 aa. | 1..513 8..532 | 297/535 (55%) 369/535 (68%) | e-165 |
| KJHUAB | N-acetylgalactosamine-4-sulfatase (EC 3.1.6.12) precursor [validated] - human, 533 aa. | 1..513 8..532 | 296/535 (55%) 369/535 (68%) | e-165 |

PFam analysis predicts that the NOV25a protein contains the domains shown in the Table 25E.

TABLE 25E

Domain Analysis of NOV25a

| Pfam Domain | NOV25a Match Region | Identities/ Similarities for the Matched Region | Expect Value |
|---|---|---|---|
| Sulfatase: domain 1 of 1 | 37..461 | 147/543 (27%) 322/543 (59%) | 1.4e-96 |

Example 26

The NOV26 clone was analyzed, and the nucleotide and encoded polypeptide sequences are shown in Table 26A.

TABLE 26A

NOV26 Sequence Analysis

| | |
|---|---|
| NOV26a, CG89697-01 DNA Sequence | SEQ ID NO: 67      862 bp<br>GCTGGGTCAGGAAAGCCTGCATCCCGCTCCCCTGGGCCCCGACGGGCGGGCGCACTGC<br><br>GCGGGGCCCACCGGCCGCAGACCTGCGTGGCCGTCCAGGGCGTCGCCATGTCCTCGGT<br><br>GTTTGGAAAACCCCGCGCGGGCAGCGGGCCTCAGAGCGCGCCCCTCGAGGTCAACCTG<br><br>GCCATCCTGGGGCGCCGCGGGGCTGGCAAGTCTGAGGACACCTACAGCTCCGAGGAGA<br><br>CTGTGGACCACCAGCCTGTCCACCTGAGGGTCATGGACACTGCAGACCTGGACACCCC<br><br>CAGGAACTGCGAGCGCTACCTGAACTGGGCCCATGCCTTCCTGGTGGTGTACAGCGTC<br><br>GACAGCCGCCAGAGCTTTGATAGCAGCAGCAGCTACCTGGAGCTGCTTGCCTTGCACG<br><br>CGAAGGAGACACAGCGCAGCATCCCTGCCCTGCTGCTGGGCAACAAGCTGGACATGGC<br><br>TCAGTACAGGCAAGTCACCAAGGCAGAGGGTGTGGCTTTGGCAGGCAGGTTTGGGTGC<br><br>CTGTTTTTCGAGGTCTCTGCCTGTCTGGACTTTGAGCACGTGCAGCATGTCTTCCACG<br><br>AGGCAGTGCGAGAGGCACGGCGGGAGCTGGAGAAGAGCCCCCTGACCCGGCCCCTCTT<br><br>CATCTCCGAGGAGAGGGCCCTGCCCCACCAGGCCCCGCTCACCGCGCGGCATGGGCTG<br><br>GCCAGCTGCACCTTCAACACGCTCTCCACCATCAACCTGAAGGAGATGCCCACTGTGG<br><br>CCCAGGCCAAGCTGGTCACCGTGAAGTCATCCCGGGCCCAGAGCAAGCGCAAGGCGCC<br><br>TACCCTGACTCTCCTGAAGGGCTTCAAGATCTTCTGAGGCCCCCTCCCCA |
| NOV26a, CG89697-01 Protein Sequence | ORF Start: ATG at 106      ORF Stop: TGA at 847<br>SEQ ID NO: 68      247 aa      MW at 27424.0kD<br>MSSVFGKPRAGSGPQSAPLEVNLAILGRRGAGKSEDTYSSEETVDHQPVHLRVMDTAD<br><br>LDTPRNCERYLNWAHAFLVVYSVDSRQSFDSSSSYLELLALHAKETQRSIPALLLGNK<br><br>LDMAQYRQVTKAEGVALAGRFGCLFFEVSACLDFEHVQHVFHEAVREARRELEKSPLT<br><br>RPLFISEERALPHQAPLTARHGLASCTFNTLSTINLKEMPTVAQAKLVTVKSSRAQSK<br><br>RKAPTLTLLKGFKIF |
| NOV26b, CG89697-02 DNA Sequence | SEQ ID NO: 69      1101 bp<br>GCTGGGTCAGGAAAGCCTGCATCCCGCTCCCCTGGGCCCCGACGGGCGGGCGCACTGC<br><br>GCGGGGCCCACCGGCCGCAGACCTGCGTGGCCGTCCAGGGCGTCGCCATGTCCTCGGT<br><br>GTTTGGAAAACCCCGCGCGGGCAGCGGGCCTCAGAGCGCGCCCCTCGAGGTCAACCTG<br><br>GCCATCCTGGGGCGCCGCGGGGCTGGCAAGTCTGAGGACACCTACAGCTCCGAGGAGA<br><br>CTGTGGACCACCAGCCTGTCCACCTGAGGGTCATGGACACTGCAGACCTGGACACCCC<br><br>CAGGAACTGCGAGCGCTACCTGAACTGGGCCCATGCCTTCCTGGTGGTGTACAGCGTC<br><br>GACAGCCGCCAGAGCTTTGATAGCAGCAGCAGCTACCTGGAGCTGCTTGCCTTGCACG<br><br>CGAAGGAGACACAGCGCAGCATCCCTGCCCTGCTGCTGGGCAACAAGCTGGACATGGC<br><br>TCAGTACAGGCAAGTCACCAAGGCAGAGGGTGTGGCTTTGGCAGGCAGGTTTGGGTGC<br><br>CTGTTTTTCGAGGTCTCTGCCTGTCTGGACTTTGAGCACGTGCAGCATGTCTTCCACG<br><br>AGGCAGTGCGAGAGGCACGGCGGGAGCTGGAGAAGAGCCCCCTGACCCGGCCCCTCTT<br><br>CATCTCCGAGGAGAGGGCCCTGCCCCACCAGGCCCCGCTCACCGCGCGGCATGGGCTG<br><br>GCCAGCTGCACCTTCAACACGCTCTCCACCATCAACCTGAAGGAGATGCCCACTGTGG<br><br>CCCAGGCCAAGCTGGTCACCGTGAAGTCATCCCGGGCCCAGAGCAAGCGCAAGGCGCC |

TABLE 26A-continued

NOV26 Sequence Analysis

```
              TACCCTGACTCTCCTGAAGGGCTTCAAGATCTTCTGAGGCCCCCTCCCCAGGAAGCCT

AGGCTCGGTGGCTGGACAGGACTGCAGCAGGACAGGGACTGGCTTCTCACCACCAGCC

TTTCCGTCTGATGGACAGCAGACCCCGCCTCCAGCACCAAGCAGTGTCCCTACACTCA

ATTCACTGTGTGAGCTGGAGTGGCAGGCAGGGATGCTGCTTCTGTTCCCTCCAGGCCT

TGGTCTTCATGGTAACCACCGCGTCTGTGGCCGTAGAGGGAAACAGCCACTGTGAAC

ORF Start: ATG at 106          ORF Stop: TGA at 847
              SEQ ID NO: 70         247 aa  MW at 27424.0kD
NOV26b,       MSSVFGKPRAGSGPQSAPLEVNLAILGRRGAGKSEDTYSSEETVDHQPVHLRVMDTAD
CG89697-02
Protein Sequence LDTPRNCERYLNWAHAFLVVYSVDSRQSFDSSSSYLELLALHAKETQRSIPALLLGNK

LDMAQYRQVTKAEGVALAGRFGCLFFEVSACLDFEHVQHVFHEAVREARRELEKSPLT

RPLFISEERALPHQAPLTARHGLASCTFNTLSTINLKEMPTVAQAKLVTVKSSRAQSK

RKAPTLTLLKGFKIF
```

Sequence comparison of the above protein sequences yields the following sequence relationships shown in Table 26B.

TABLE 26B

Comparison of NOV26a against NOV26b.

| Protein Sequence | NOV26a Residues/ Match Residues | Identities/Similarities for the Matched Region |
|---|---|---|
| NOV26b | 1..247<br>1..247 | 234/247 (94%)<br>234/247 (94%) |

Further analysis of the NOV26a protein yielded the following properties shown in Table 26C.

TABLE 26C

Protein Sequence Properties NOV26a

| PSort analysis: | 0.4500 probability located in cytoplasm; 0.3200 probability located in microbody (peroxisome); 0.1000 probability located in mitochondrial matrix space; 0.1000 probability located in lysosome (lumen) |
|---|---|
| SignalP analysis: | No Known Signal Sequence Predicted |

A search of the NOV26a protein against the Geneseq database, a proprietary database that contains sequences published in patents and patent publication, yielded several homologous proteins shown in Table 26D.

TABLE 26D

Geneseq Results for NOV26a

| Geneseq Identifier | Protein/Organism/Length [Patent #, Date] | NOV26a Residues/ Match Residues | Identities/ Similarities for the Matched Region | Expect Value |
|---|---|---|---|---|
| ABB17201 | Human nervous system related polypeptide SEQ ID NO 5858 - *Homo sapiens*, 142 aa. [WO200159063-A2, 16 Aug. 2001] | 35..172<br>5..142 | 125/138 (90%)<br>127/138 (91%) | 4e-67 |
| ABG20939 | Novel human diagnostic protein #20930 - *Homo sapiens*, 1048 aa. [WO200175067-A2, 11 Oct. 2001] | 123..247<br>924..1048 | 124/125 (99%)<br>124/125 (99%) | 4e-65 |
| ABG20939 | Novel human diagnostic protein #20930 - *Homo sapiens*, 1048 aa. [WO200175067-A2, 11 Oct. 2001] | 123..247<br>924..1048 | 124/125 (99%)<br>124/125 (99%) | 4e-65 |
| ABB57198 | Mouse ischaemic condition related protein sequence SEQ ID NO:484 - *Mus musculus*, 217 aa. [WO200188188-A2, 22 Nov. 2001] | 20..167<br>20..184 | 58/168 (34%)<br>88/168 (51%) | 2e-19 |
| AAM40661 | Human polypeptide SEQ ID NO 5592 - *Homo sapiens*, 227 aa. [WO200153312-A1, 26 Jul. 2001] | 20..166<br>34..197 | 54/166 (32%)<br>80/166 (47%) | 2e-18 |

In a BLAST search of public sequence datbases, the NOV26a protein was found to have homology to the proteins shown in the BLASTP data in Table 26E.

TABLE 26E

Public BLASTP Results for NOV26a

| Protein Accession Number | Protein/Organism/Length | NOV26a Residues/ Match Residues | Identities/ Similarities for the Matched Portion | Expect Value |
|---|---|---|---|---|
| Q9NYN1 | RIS - Homo sapiens (Human), 266 aa. | 1..247 1..266 | 247/266 (92%) 247/266 (92%) | e-135 |
| AAH18060 | RIC (DROSOPHILA)-LIKE, EXPRESSED IN NEURONS - Homo sapiens (Human), 217 aa. | 20..167 20..184 | 58/168 (34%) 90/168 (53%) | 1e-19 |
| Q99578 | RIN PROTEiN (RIBA) - Homo sapiens (Human), 217 aa. | 20..167 20..184 | 58/168 (34%) 90/168 (53%) | 1e-19 |
| Q92964 | RIN - Homo sapiens (Human), 217 aa. | 20..167 20..184 | 59/170 (34%) 91/170 (52%) | 3e-19 |
| Q9QWX5 | GTP-BINDING PROTEIN ROC2 - Mus musculus (Mouse), 217 aa. | 20..167 20..184 | 58/168 (34%) 88/168 (51%) | 4e-19 |

PFam analysis predicts that the NOV26a protein contains the domains shown in the Table26F.

TABLE 26F

Domain Analysis of NOV26a

| Pfam Domain | NOV26a Match Region | Identities/ Similarities for the Matched Region | Expect Value |
|---|---|---|---|
| ras: domain 1 of 1 | 22 ... 203 | 56/216 (26%) 126/216 (58%) | 1.5e-14 |

Example 27

The NOV27 clone was analyzed, and the nucleotide and encoded polypeptide sequences are shown in Table 27A.

TABLE 27A

NOV27 Sequence Analysis

NOV27a, CG90001-01 DNA Sequence

SEQ ID NO: 71    500 bp

CCATGGTCAACCCCACCGTGTCCTTCAACATCACTGTCAATGGTGAGCCCTTGGGCTG

TGTCTCCTTCAAGCTGTTTGCAGACAAGTTTCCAAAGACAGCAGAAAACTTTCGTGCT

CTGAGCACTGGAGAGAAAGGATTTGATTATAAATGTTCCTCCTTTCACAGAATTATTC

CAGGGTTTATGTGTCAGGGTGGTGACTTCACACGCCATAATGGCACTGGTGGCAAGTC

CATCTACGGGGAGAAATTTGATGATGAGAACTTCATCCTAAAGCATACAGGTCCTGGC

ATCTTGTCCATGGCAAATGCTGGACCCAACACAAATGATTCCCAGTTTTTCATCTGCA

CTGCCAAGACTGAGTGGTTGGATGGCAAGCCCATGGTCTTTGGCAAGGTGAAAGATGG

CATGAATATTGTGGAGGCCATGGAGCACTTCGGGTCTGGGAATGGCAAGACCATCAAG

AAGATCACCATCGCTGACTGTACACAACTTGACTAA

ORF Staff: ATG at 3    ORF Stop: TAA at 498
SEQ ID NO: 72    165 aa    MW at 18022.4 kD NOV27a, CG90001-01 Protein Sequence MVNPTVSFNITVNGEPLGCVSFKLFADKFPKTAENFRALSTGEKGFDYKCSSFHRIIP
GFMCQGGDFTRHNGTGGKSIYGEKFDDENFILKHTGPGILSMANAGPNTNDSQFFICT
AKTEWLDGKPMVFGKVKDGMNIVEAMEHFGSGNGKTIKKITIADCTQLD Further analysis of the NOV27a protein yielded the following properties shown in Table 27B.

TABLE 27B

Protein Sequence Properties NOV27a

| | |
|---|---|
| PSort analysis: | 0.6400 probability located in microbody (peroxisome); 0.4500 probability located in cytoplasm; 0.1000 probability located in mitochondrial matrix space; 0.1000 probability located in lysosome (lumen) |
| SignalP analysis: | No Known Signal Sequence Predicted |

A search of the NOV27a protein against the Geneseq database, a proprietary database that contains sequences published in patents and patent publication, yielded several homologous proteins shown in Table 27C.

TABLE 27C

Geneseq Results for NOV27a

| Geneseq Identifier | Protein/ Organism/ Length [Patent #, Date] | NOV27a Residues/ Match Residues | Identities/ Similarities for the Matched Region | Expect Value |
|---|---|---|---|---|
| ABG29337 | Novel human diagnostic protein #29328 - Homo sapiens, 162 aa. [WO200175067-A2, 11 OCT. 2001] | 1 . . . 165 1 . . . 162 | 151/165 (91%) 156/165 (94%) | 6e−87 |
| ABG12722 | Novel human diagnostic protein #12713 - Homo sapiens, 162 aa. [WO200175067-A2, 11 OCT. 2001] | 1 . . . 165 1 . . . 162 | 151/165 (91%) 156/165 (94%) | 6e−87 |
| ABG29337 | Novel human diagnostic protein #29328 - Homo sapiens, 162 aa. [WO200175067-A2, 11 OCT. 2001] | 1 . . . 165 1 . . . 162 | 151/165 (91%) 156/165 (94%) | 6e−87 |
| ABG12722 | Novel human diagnostic protein #12713 - Homo sapiens, 162 aa. [WO200175067-A2, 11 OCT. 2001] | 1 . . . 165 1 . . . 162 | 151/165 (91%) 156/165 (94%) | 6e−87 |
| AAU01195 | Human cyclophilin A protein - Homo sapiens, 165 aa. [WO200132876-A2, 10 MAY 2001] | 1 . . . 165 1 . . . 165 | 145/165 (87%) 152/165 (91%) | 7e−82 |

In a BLAST search of public sequence datbases, the NOV27a protein was found to have homology to the proteins shown in the BLASTP data in Table 27D.

TABLE 27D

Public BLASTP Results for NOV27a

| Protein Accession Number | Protein/ Organism/ Length | NOV27a Residues/ Match Residues | Identities/ Similarities for the Matched Portion | Expect Value |
|---|---|---|---|---|
| CAC39529 | SEQUENCE 26 FROM PATENT WO0132876 - Homo sapiens (Human), 165 aa. | 1 . . . 165 1 . . . 165 | 145/165 (87%) 152/165 (91%) | 2e−81 |
| Q9CWJ5 | PEPTIDYLPROLYL ISOMERASE A - Mus musculus (Mouse), 164 aa. | 1 . . . 164 1 . . . 164 | 144/164 (87%) 151/164 (91%) | 7e−81 |
| Q9BRU4 | PEPTIDYLPROLYL ISOMERASE A (CYCLOPHILIN A) - Homo sapiens (Human), 165 aa. | 1 . . . 165 1 . . . 165 | 144/165 (87%) 151/165 (91%) | 7e−81 |
| P05092 | Peptidyl-prolyl cis-trans isomerase A (EC 5.2.1.8) (PPIase) (Rotamase) (Cyclophilin A) (Cyclosporin A-binding protein) - Homo sapiens (Human),, 164 aa. | 2 . . . 165 1 . . . 164 | 144/164 (87%) 151/164 (91%) | 7e−81 |
| P04374 | Peptidyl-prolyl cis-trans isomerase A (EC 5.2.1.8) (PPIase) (Rotamase) (Cyclophilin A) (Cyclosporin A-binding protein) - Bos taurus (Bovine), and, 163 aa. | 2 . . . 164 1 . . . 163 | 144/163 (88%) 150/163 (91%) | 7e−81 |

PFam analysis predicts that the NOV27a protein contains the domains shown in the Table 27E.

TABLE 27E

Domain Analysis of NOV27a

| Pfam Domain | NOV27a Match Region | Identities/ Similarities for the Matched Region | Expect Value |
|---|---|---|---|
| pro_isomerase: domain 1 of 1 | 5 . . . 165 | 109/180 (61%) 147/180 (82%) | 3.8e−97 |

Example 28

The NOV28 clone was analyzed, and the nucleotide and encoded polypeptide sequences are shown in Table 28A.

TABLE 28A

NOV28 Sequence Analysis

| NOV28a, CG90011-01 DNA Sequence | SEQ ID NO: 73   1388 bp |
|---|---|

AAATGGTGGCCTCCATGTTCTTCCGCCCGCTGTTGGTGGCCGCCACCCTTCGGACCAC

ACTGCGGGCTGCTGCTCAGGTTCTGGGAAGTTCTGGATTGTTTAATAACCATGGACTC

CAAGTACAGCAGCAACAGCAAAGGAATCTCTCACTACATGAATACATGAGTATGGAAT

TATTGCAAGAAACTGGTGTCTCTGTTCCCAAAGGATATGTGGCAAAGAGACCAGATGA

AGCTTATGCAATTGCCAAAAAATTAGGTTCAAAAGATGTTGTGATGAAGGCACAGGTT

TTAGCTGGTGGTAGAGGAAAAGGAACATTTGAAAGTGGCCTCAAAGGAGGAGTGAAGA

TGGTTTTCTCTCCAGAAGAAGCAAAAGCTGTTCCTTCACAAATGATTAGGAAACAGTT

GTTTACCAAGCAAATGGGAGAAAAGGGCAGAATATGCAATCAGGTATTGGTCTGTGAG

AGAAAATATCCCAAGAGAGTGCTACTTTGCAATAACAATGGAAAGGTCATTTCAAG

GTCTTGTATTAATAGGAAGTTTACATAGTGGGGCCAACATTGAAGATGTTGCTGCTGA

GACTCCTGAAGCAATAATTAAAGTACCTATTGATATTGTAGAAGGTATCAAAGAGGAA

CAAGCTCTCCAGCTTGCACAGAAGATGGGATTTCCATCTAATATTGTGGCTTCAGCAG

CAGAAAACATGATCAAGCTTTACAGCCTTTTTCTGAAATACGATGCAACCATGATAGA

AATAAATTCAATGGTGGAAGATTCAGATGGAGCTGCATTGTGTAAGGATGCAAAGATC

AATTTTGACTCTAATTCAGCCTATCGCCAAAAGAAAATGTTTGATCTACAGGACTGGA

CCCAGGAAGATGAAAGGAACAAAGATGCTGCTAAGGCAGATCTCAACTACACTGGCCT

CGATGGAAGTATAGGCTGCCTAGTAAATGGTGCTGGTTTGGCTATGGCCACAATGGAT

ATAATAAAACTTCATGGAGAGACTCCAGCTAATTTCCTTGTTGGTGGTGGTGCTACAG

TCCATCAAGTAACAGAAGCATTTAAGCCTATCACTTCAGATAAAAAGGTACTGGCTAT

TCTGGTCAACATTTGTGGAGGAATCATGCACTGTGATATTACAGCAAAGGGTATAGTC

ATGGCAGTAAAAAGTTTGGAAATTAAAATACCTGTTGTGGTACAGTTACAAGGTACAC

AAGTTGATGATGTTAAGGCACTAAAAGCAGACAGTGGACTTAAAATACTTGCTTGTGA

TGATTTGGTGGAAGCTGCTAGAGTGCTTGTAAAGCTCTCTGAAATAGTGAAGCAAGCA

AAGCAAGCGCATGTGGATGTGAAATTTCAATTGCCAATATGATCTGAAAACCCA

| | ORF Start: ATG at 3 | ORF Stop: TGA at 1374 |
|---|---|---|
| | SEQ ID NO: 74   457 aa | MW at 49653.4 kD |
| NOV28a, CG90011-01 Protein Sequence | MVASMFFRPLLVAATLRTTLRAAAQVLGSSGLFNNHGLQVQQQQQRNLSLHEYMSMEL LQETGVSVPKGYVAKRPDEAYAIAKKLGSKDVVMKAQVLAGGRGKGTFESGLKGGVKM | |

TABLE 28A-continued

NOV28 Sequence Analysis

VFSPEEAKAVPSQMIRKQLFTKQMGEKGRICNQVLVCERKYPKRECYFAITMERSFQG

LVLIGSLHSGANIEDVAAETPEAIIKVPIDIVEGIKEEQALQLAQKMGFPSNIVASAA

ENMIKLYSLFLKYDATMIEINSMVEDSDGAALCKDAKINFDSNSAYRQKKMFDLQDWT

QEDERNKDAAKADLNYTGLDGSIGCLVNGAGLAMATMDIIKLHGETPAMFLVGGGATV

HQVTEAFKPITSDKKVLAILVNICGGIMHCDITAKGIVMAVKSLEIKIPVVVQLQGTQ

VDDVKALDADSGLKILACDDLVEAARVLVKLSEIVKQAKQAHVDVKFQLPI

Further analysis of the NOV28a protein yielded the following properties shown in Table 28B.

TABLE 28B

Protein Sequence Properties NOV28a

| | |
|---|---|
| PSort analysis: | 0.7464 probability located in mitochondrial inner membrane; 0.6000 probability located in mitochondrial matrix space; 0.6000 probability located in mitochondrial intermembrane space; 0.6000 probability located in mitochondrial outer membrane |
| SignalP analysis: | Cleavage site between residues 25 and 26 |

A search of the NOV28a protein against the Geneseq database, a proprietary database that contains sequences published in patents and patent publication, yielded several homologous proteins shown in Table 28C.

TABLE 28C

Geneseq Results for NOV28a

| Geneseq Identifier | Protein/ Organism/ Length [Patent #, Date] | NOV28a Residues/ Match Residues | Identities/ Similarities for the Matched Region | Expect Value |
|---|---|---|---|---|
| AAB70163 | DNA encoding human synthetase #13 - *Homo sapiens*, 463 aa. [WO200107628-A2, 01 FEB. 2001] | 1 . . . 457<br>1 . . . 463 | 403/463 (87%)<br>421/463 (90%) | 0.0 |
| AAG66501 | ATP-specific succinyl-CoA synthetase 51 - Unidentified, 463 aa. [WO200155402-Al, 02 AUG. 2001] | 1 . . . 457<br>1 . . . 463 | 403/463 (87%)<br>421/463 (90%) | 0.0 |
| AAM41474 | Human polypeptide SEQ ID NO 6405 - *Homo sapiens*, 485 aa. WO200153312-Al, 26 JUL. 2001] | 1 . . . 457<br>23 . . . 485 | 403/463 (87%)<br>421/463 (90%) | 0.0 |
| AAM39688 | Human polypeptide SEQ ID NO 2833 - *Homo sapiens*, 463 aa. [WO200153312-Al, 26 JUL. 2001] | 1 . . . 457<br>1 . . . 463 | 403/463 (87%)<br>421/463 (90%) | 0.0 |
| AAB93393 | Human protein sequence SEQ ID NO: 12573 - *Homo sapiens*, 463 aa. [EP1074617-A2, 07 FEB. 2001] | 1 . . . 457<br>1 . . . 463 | 401/463 (86%)<br>421/463 (90%) | 0.0 |

In a BLAST search of public sequence datbases, the NOV28a protein was found to have homology to the proteins shown in the BLASTP data in Table 28D.

TABLE 28D

Public BLASTP Results for NOV28a

| Protein Accession Number | Protein/ Organism/ Length | NOV28a Residues/ Match Residues | Identities/ Similarities for the Matched Portion | Expect Value |
|---|---|---|---|---|
| Q9P2R7 | ATP SPECIFIC SUCCINYL COA SYNTHETASE BETA SUBUNIT - *Homo sapiens* (Human), 463 aa. | 1 . . . 457<br>1 . . . 463 | 402/463 (86%)<br>421/463 (90%) | 0.0 |
| Q9NV21 | CDNA FLJ10985 FIS, CLONE PLACE1001817, HIGHLY SIMILAR | 1 . . . 457<br>1 . . . 463 | 401/463 (86%)<br>421/463 (90%) | 0.0 |

TABLE 28D-continued

Public BLASTP Results for NOV28a

| Protein Accession Number | Protein/ Organism/ Length | NOV28a Residues/ Match Residues | Identities/ Similarities for the Matched Portion | Expect Value |
|---|---|---|---|---|
| | TO *HOMO SAPIENS* ATP-SPECIFIC SUCCINYL-COA SYNTHETASE BETA SUBUNIT MRNA - *Homo sapiens* (Human), 463 aa. | | | |
| O95194 | ATP-SPECIFIC SUCCINYL-COA SYNTHETASE BETA SUBUNIT - *Homo sapiens* (Human), 426 aa (fragment). | 33 ... 457 1 ... 426 | 380/426 (89%) 396/426 (92%) | 0.0 |
| Q9NVP7 | CDNA FLJ10596 FIS, CLONE NT2RP2004799, MODERATELY SIMILAR TO PROBABLE SUCCINYL-COA LIGASE - *Homo sapiens* (Human), 441 aa. | 1 ... 457 1 ... 441 | 382/458 (83%) 402/458 (87%) | 0.0 |
| O97580 | ATP-SPECIFIC SUCCINYL-COA SYNTHETASE BETA SUBUNIT - *Sus scrofa* (Pig), 425 aa (fragment). | 34 ... 457 1 ... 425 | 366/425 (86%) 393/425 (92%) | 0.0 |

PFam analysis predicts that the NOV28a protein contains the domains shown in the Table 28E.

TABLE 28E

Domain Analysis of NOV28a

| Pfam Domain | NOV28a Match Region | Identities/ Similarities for the Matched Region | Expect Value |
|---|---|---|---|
| ATP-grasp: domain 1 of 1 | 76 ... 252 | 70/191 (37%) 144/191 (75%) | 7.9e-44 |
| ligase-CoA: domain 1 of 1 | 300 ... 436 | 84/150 (56%) 120/150 (80%) | 8e-57 |

Example 29

The NOV29 clone was analyzed, and the nucleotide and encoded polypeptide sequences are shown in Table 29A.

TABLE 29A

NOV29 Sequence Analysis

NOV29a, CG90204-01 DNA Sequence

SEQ ID NO: 75    3170 bp

```
GAAGGCAGGGGGGCTCGGAGAAGACGGACTCTGCTTTCGCTCCCCCTTTCTTCCCCAT
CCCTAACATGGGCTTTGCCCTGGAGCGCTTCGCAGAAGCCGTGGACCCGGCTCTGGAG
TGCAAACTGTGCGGCCAGGTGCTTGAAGAGCCCCTGTGCACGCCGTGCGGGCACGTCT
TCTGCGCCAGCTGCCTGTTGCCCTGGGCGGTGCGGAGGCGCCGGTGCCCGCTGCAGTG
CCAGCCCTTGGCGCCCGGCGAGCTGTACCGGGTGCTGCCGCTGCGCAGCCTCATCCAG
AAGCTGCGAGTCCAGTGCGACTACCGCGCCCGCGGCTGCGGCCACTCGGTCAGGCTGC
ACGAGCTGGAGGCGCACGTCGAGCACTGCGACTTCGGCCCTGCCCGCCGGCTCCGCAG
CCGCGGGGCTGCGCTTCGGGGCTGGGCGGTGGTGAGGTGCCCGCGCGGGGGGCTGC
GGTCCGACACCCAGGGCTGGCCGGGGCGGGGCGCGCGCGGGGGCCGCCGGGCGGCC
GCTGGGGCCGCGGGCGGGGACCCGGGCCTCGGGTCCTCGCCTGGAGGCGGCGCGAGAA
GGCGCTGCTGGCGCAGCTCTGGGCGCTGCAGGGCGAGGTGCAGCTCACGGCGCGCAGG
TACCAGGAGAAGTTCACCCAATACATGGCTCACGTCCGCAACTTCGTCGGCGACCTCG
```

TABLE 29A-continued

NOV29 Sequence Analysis

GTGGCGGCCACCGCAGGGATGGAGAGCATAAGCCATTCACTATTGTGTTAGAAAGAGA

AAATGACACTTTGGGATTCAATATTATAGGAGGTCGACCAAATCAGAATAATCAGGAA

GGAACATCGACTGAAGGAATTTACGTTTCAAAAATTTTAGAAAATGGACCTGCTGACA

GAGCAGATGGCCTGGAGATTCATGACAAAATCATGGAGGTCAATGGGAAGGATCTTTC

AAAGGCCACTCATGAAGAGGCAGTGGAAGCTTTTCGCAATGCCAAGGAGCCCATTGTG

GTGCAGGTGTTAAGGCGAACACCTCTTAGTAGACCAGCCTATGGGATGGCTTCAGAAG

TGCAGCTTATGAATGCCAGCACTCAGACGGACATCACCTTCGAACACATCATGGCTCT

GGCCAAGCTTCGTCCACCTACCCCTCCACATGAATTTTATGAGGACAATGAGTATATT

TCCAGCTTGCCTGCTGATGCAGACAGAACAGAAGACTTTGAATATGAGGAGGTCGAGT

TGTGTCGTGTTAGCAGTCAAGAGAAGCTGGGCCTGACAGTCTGTTACCGAACAGATGA

TGAAGAAGACACCAGCATTTATGTCAGCGAGGTTGACCCAAATAGCATTGCTGCCAAA

GACGGCCGGATTCGAGAAGGGGATCGGATTTTGCAAATAAATGGGGAAGATGTCCAGA

ATCGAGAAGAAGCAGTGGCCTTGCTGTCTAACGATGAGTGTAAGAGAATCGTGCTGCT

TGTTGCAAGGCCAGAGATTCAGCTGGATGAAGGCTGGCTGGAAGATGAAAGGAATGAA

TTCTTAGAGGAGTTAAACTTGGAGATGTTGGAAGAAGAGCATAATGAAGCAATGCAGC

CCACTGCCAATGAGGTGGAGCAGCCAAAAAAGCAAGAAGAAGAAGAAGGCACAACAGA

CACTGCAACATCCTCATCCAACAACCATGAGAAGGACAGTGGAGTAGGACGTACAGAT

GAAAGCTTGCGAAATGATGAGAGCTCAGAGCAGGAGAATGCAGCCGAGGACCCCAATA

GCACATCTTTGAAGAGCAAGAGAGACCTGGGGCAGAGCCAAGACACTCTGGGAAGTGT

TGAACTTCAGTACAATGAGAGCCTCGTATCTGGTGAATACATTGACTCAGACTGCATT

GGCAACCCAGATGAGGACTGTGAAAGATTCAGGCAGCTCTTGGAGCTCAAATGCAAGA

TTCGAAATCATGGAGAGTATGACCTGTATTACTCAAGCAGCACAATTGAATGCAATCA

AGGGGAGCAAGAGGGAGTGGAGCATGAGCTACAGTTGCTTAATGAAGAACTGAGAAAC

ATTGAGCTTGAGTGTCAGAATATCATGCAGGCTCACAGGCTCCAGAAAGTGACAGACC

AGTATGGAGACATCTGGACATTGCATGATGGAGGATTCCGGAATTATAACACCAGCAT

AGATATGCAAAGGGGAAAGCTAGATGACATCATGGAGCATCCAGAAAAGTCTGACAAG

GACAGTTCTAGTGCTTACAACACAGCTGAGAGCTGCAGAAGTACTCCGCTCACTGTAG

ACCGTTCCCCTGACAGTTCCCTTCCAAGGGTGATCAACCTCACCAATAAGAAAAACCT

GAGAAGCACAATGGCAGCCACCCAGTCCTCTTCCGGACAGAGCAGTAAAGAGTCGACC

TCCACCAAAGCCAAAACCACTGAGCAAGGTTGTAGCGCTGAAAGCAAGGAGAAGGTTT

TAGAAGGCAGCAAGCTTCCTGATCAAGAGAAGGCAGTCAGCGAACACATCCCTTACCT

CTCTCCTTACCACAGCTCCTCATATAGATATGCAAACATCCCAGCACACGCCCGGCAT

TATCAAAGCTACATGCAGTTAATTCAACAGAAATCTGCAGTCGAGTATGCTCAGAGTC

AGCTCAGCTTGGTGAGCATGTGCAAGGAGTCTCAGAAGTGTTCAGAGCCCAAGATGGA

ATGGAAGGTGAAAATTAGGAGCGACGGGACACGGTACATCACAAAGAGACCCGTGCGA

GACCGAATCCTGAAGGAACGTGCCTTAAAGATCAAGGAAGAGCGGAGTGGCATGACCA

CAGACGATGACACCATGAGCGAGATGAAAATGGGGCGCTACTGGAGCAAAGAGGAGAG

AAAGCAGCACCTGGTTAGGGCCAAAGAGCAGCGCCGTCGCCGTGAGTTCATGATGCGA

AGCAGGTTAGAGTGTCTCAAGGAGAGCCCTCAGAGCGGCAGTGAGGGCAAGAAGGAGA

TABLE 29A-continued

NOV29 Sequence Analysis

|  |  |
|---|---|
|  | TCAATATCATTGAACTGAGTCACAAAAAGATGATGAAAAAGAGAAACAAGAAAATTTT |
|  | GGACAACTGGATGACAATCCAAGAACTGATGACCCATGGGGCCAAGTCTCCAGATGGC |
|  | ACGAGAGTCCATAATGCCTTCTTGTCGGTGACCACTGTATGACCGAATGAATGGAATG |
|  | CATGCGACTGATTTTAGGAGGATGCTACCAGTTTCGGT |
|  | ORF Start: ATG at 66      ORF Stop: TGA at 3114 |
|  | SEQ ID NO: 76    1016 aa     MW at 114909.3 kD |
| NOV29a, CG90204-01 Protein Sequence | MGFALERFAEAVDPALECKLCGQVLEEPLCTPCGHVFCASCLLPWAVRRRRCPLQCQP LAPGELYRVLPLRSLIQKLRVQCDYRARGCGHSVRLHELEAHVEHCDFGPARRLRSRG GCASGLGGGEVPARGGCGPTPRAGRGGGARGGPPGGRWGRGRGPGPRVLAWRRREKAL LAQLWALQGEVQLTARRYQEKFTQYMAHVRNFVGDLGGGHRRDGEHKPFTIVLEREND TLGFNIIGGRPNQNNQEGTSTEGIYVSKILENGPADRADGLEIHDKIMEVNGKDLSKA THEEAVEAFRNAKEPIVVQVLRRTPLSRPAYGMASEVQLMNASTQTDITFEHIMALAK LRPPTPPHEFYEDNEYISSLPADADRTEDFEYEEVELCRVSSQEKLGLTVCYRTDDEE DTSIYVSEVDPNSIAAKDGRIREGDRILQINGEDVQNREEAVALLSNDECKRIVLLVA RPEIQLDEGWLEDERNEFLEELNLEMLEEEHNEAMQPTANEVEQPKKQEEEEGTTDTA TSSSNNHEKDSGVGRTDESLRNDESSEQENAAEDPNSTSLKSKRDLGQSQDTLGSVEL QYNESLVSGEYIDSDCEGNPDEDCERFRQLLELKCKIRNHGEYDLYYSSSTIECNQGE QEGVEHELQLLNEELRNIELECQNIMQAHRLQKVTDQYGDIWTLHDGGFRNYNTSIDM QRGKLDDIMEHPEKSDKDSSSAYNTAESCRSTPLTVDRSPDSSLPRVINLTNKKNLRS TMAATQSSSGQSSKESTSTKAKTTEQGCSAESKEKVLEGSKLPDQEKAVSEHIPYLSP YHSSSYRYANIPAHARHYQSYMQLIQQKSAVEYAQSQLSLVSMCKESQKCSEPKMEWK VKIRSDGTRYITKRPVRDRILKERALKIKEERSGMTTDDDTMSEMKMGRYWSKEERKQ HLVRAKEQRRRREFMMRSRLECLKESPQSGSEGKKEINIIELSHKKMMKKRNKKILDN WMTIQELMTHGAKSPDGTRVHNAFLSVTTV |

Further analysis of the NOV29a protein yielded the following properties shown in Table 29B.

TABLE 29B

Protein Sequence Properties NOV29a

| | |
|---|---|
| PSort analysis: | 0.9800 probability located in nucleus; 0.3000 probability located in microbody (peroxisome); 0.1000 probability located in mitochondrial matrix space; 0.1000 probability located in lysosome (lumen) |
| SignalP analysis: | No Known Signal Sequence Predicted |

A search of the NOV29a protein against the Geneseq database, a proprietary database that contains sequences published in patents and patent publication, yielded several homologous proteins shown in Table 29C.

TABLE 29C

Geneseq Results for NOV29a

| Geneseq Identifier | Protein/Organism/Length [Patent #, Date] | NOV29a Residues/ Match Residues | Identities/ Similarities for the Matched Region | Expect Value |
|---|---|---|---|---|
| ABB11704 | Human semaphorin domain-associated protein homologue, SEQ ID NO:2074 - *Homo sapiens*, 1098 aa. [WO200157188-A2, 09-AUG-2001] | 1..1016 33..1098 | 610/1076 (56%) 780/1076 (71%) | 0.0 |

TABLE 29C-continued

Geneseq Results for NOV29a

| Geneseq Identifier | Protein/Organism/Length [Patent #, Date] | NOV29a Residues/ Match Residues | Identities/ Similarities for the Matched Region | Expect Value |
|---|---|---|---|---|
| AAM25720 | Human protein sequence SEQ ID NO:1235 - *Homo sapiens,* 1098 aa. [WO200153455-A2, 26-JUL-2001] | 1..1016 33..1098 | 608/1076 (56%) 778/1076 (71%) | 0.0 |
| AAU17405 | Novel signal transduction pathway protein, Seq ID 970—*Homo sapiens,* 439 aa. [WO200154733-A1, 02-AUG-2001] | 376..742 27..395 | 231/370 (62%) 303/370 (81%) | e-132 |
| AAM25485 | Human protein sequence SEQ ID NO:1000 - *Homo sapiens.* 206 aa [WO200153455-A2, 26-JUL-2001] | 641..838 9..206 | 196/198 (98%) 196/198 (98%) | e-110 |
| AAM93242 | Human polypeptide, SEQ ID NO: 2673 - *Homo sapiens,* 320 aa. [EP1130094-A2, 05-SEP-2001] | 376..602 4..232 | 148/230 (64%) 190/230 (82%) | 1e-78 |

In a BLAST search of public sequence datbases, the NOV29a protein was found to have homology to the proteins shown in the BLASTP data in Table 29D.

TABLE 29D

Public BLASTP Results for NOV29a

| Protein Accession Number | Protein/Organism/Length | NOV29a Residues/ Match Residues | Identities/ Similarites for the Matched Portion | Expect Value |
|---|---|---|---|---|
| Q9UPQ7 | KIAA1095 PROTEIN - *Homo sapiens* (Human), 1098 aa (fragment). | 1..1016 33..1098 | 611/1076 (56%) 781/1076 (71%) | 0.0 |
| Q9QY55 | SEMAPHORIN CYTOPLASMIC DOMAIN-ASSOCIATED PROTEIN 3A - *Mus musculus* (Mouse), 1063 aa. | 1..1016 1..1063 | 610/1077 (56%) 776/1077 (71%) | 0.0 |
| Q9QY54 | SEMAPHORIN CYTOPLASMIC DOMAIN-ASSOCIATED PROTEIN 3B - *Mus musculus* (Mouse), 1011 aa. | 1..1016 1..1011 | 597/1050 (56%) 759/1050 (71%) | 0.0 |
| Q91Z03 | SIMILAR TO SEMAF CYTOPLASMIC DOMAIN ASSOCIATED PROTEIN 3 - *Mus musculus* (Mouse), 654 aa. | 376..1016 4..654 | 412/657 (62%) 521/657 (78%) | 0.0 |
| Q9QY39 | HYPOTHETICAL 77.1 KDA PROTEIN - *Mus musculus* (Mouse), 686 aa. | 344..1016 1..686 | 334/710 (47%) 446/710 (62%) | e-166 |

PFam analysis predicts that the NOV29a protein contains the domains shown in the Table 29E.

TABLE 29E

Domain Analysis of NOV29a

| Pfam Domain | NOV29a Match Region | Identities/ Similarities for the Matched Region | Expect Value |
|---|---|---|---|
| FYVE: domain 1 of 1 | 33 ... 46 | 6/14 (43%) 11/14 (79%) | 3.5 |
| zf-C3HC4: domain 1 of 1 | 18 ... 56 | 15/55 (27%) 32/55 (58%) | 2.7e-06 |
| PDZ: domain 1 of 2 | 224 ... 313 | 31/93 (33%) 80/93 (86%) | 2.8e-20 |
| prion: domain 1 of 1 | 111 ... 333 | 57/249 (23%) 79/249 (32%) | 4 |
| PDZ: domain 2 of 2 | 382 ... 466 | 29/87 (33%) 66/87 (76) | 3.9e-15 |

Example 30

The NOV30 clone was analyzed, and the nucleotide and encoded polypeptide sequences are shown in Table 30A.

TABLE 30A

NOV30 Sequence Analysis

| | |
|---|---|
| NOV30a,<br>CG90385-01 DNA Sequence | SEQ ID NO: 77    4071 bp<br>ATGTCCCACACTCAGGCCGACCTGGCCCTGCGGCCCCCGCCTCCTCTTGCCACCGCGG<br>GGCAGCCCCGCCTCCGGCCCCCTCCTCGCCGAGCGCGCCGCTTCTCCGGGAAGGCTGA<br>GCCCCGGCCGCGCTCTTCTCGTCTCAGCCGCCGTAGCTCAGTCGACTTGGGGCTGCTG<br>AGCTCTTGGTCCCTGCCAGCCTCACCCGCTCCGGACCCCCCCGATCCTCCGGACTCCG<br>CTGGACCCAGCGAGCCCCTCTGAAGGCTGCGGAAGACTCCGCGCGTCCCGAGCTCCCG<br>GTGGACCGAGGGAGCCCCTGTGAAGGCTGCGGAAGACTCCGCGCGTCCCGAGCTCCCG<br>GACTCTGCAGTGGCCCCCGGGTCCAGGGAGCCGCTAAGCGTCCCTGAACCTGTGGCCC<br>TAGAGCGGCGCCGGGAGCAGGAAGAAAAGCAGGACATGGAGACCCAGGCTGTGGCAAC<br>GTCCCCCGATGGCCGATACCTCAAGTTTGACATCGAGATTCGACGTGCCTCCTTCAAG<br>ACGGTGTATCCAGGGCTAGACACCGACACCACAGTGGAGGTAGCCTGGTGTGACCTCG<br>AGACTCGGAAACTGTCTAGAGCTGAGCGGCAGCGCTTCTCAGACGACGTGCAGATGCT<br>CAAGGGGCTGCAGCACCCCAACATCGTCCGCTTCTATGATTCGTGGAAGTCGGTGCTG<br>AGGGGCCAGGTTTGCATCGTGCTGGTCACCGAACTCATGACCTCCGGCACGCTCAAGA<br>CACATAGGCTAGGAGAATGCTGGCAGAAGATGCGCAGGCGGCAGCAGGGTGCGGCAGG<br>GGGGAACTTCCCAGTGGGGGGCTCCTTCCCGGAGGACGTGTCCCCCCACCAGGACTCT<br>GGCTATGCGCCCTCCCCCAGGTACCTGAGGCGGTTCCCGGAGATGAAGCCGCGGGTCC<br>TTCAGCGCTGGAGCCGCCAAATCCTGCGGGGACTTCATTTCCTACACTCCCGGGTTCC<br>TCCCATCCTCCTCCGGGATCTCAAGTGCGACAATGTCTTTATCACGGGACCTACTGCC<br>TCTGTCAAAATCGGGGACCTGGACCTGGCCACGCTCAAGCGCGCCTCCTTTGCCAAGA<br>GTGTCATCGGCACCCCGGAATTCATGGCCCCCGAGATGTACGACGAAAAGTACGATGA<br>GGCCGTGCACGTCTACGCGTTCGGCATGTGCATGCTGGAGATGGCCACCTCTGAGTAC<br>CCGTACTCCGAGTGCCAGAATGCCGCGCAAATCTACCGCAAGGTCACTTCGGGCAGAA<br>AGCCGAACAGCTTCCACAAGGTGAAGATACCCGAGGTCAAGGAGATCATTGAAGGCTG<br>CATCCGCACCGATAAGAACGAGACCTTCACCATCCAGCACCTCCTGGCCCACGCCTTC<br>TTCCGCGAGGAGCGCGGTGTGCACCTGCAACTAGCCGACGACGACGACGGCGACAAGC<br>CGGGCCTCAAGCTCTGCCTGCGCATGGACGACGCCCGGCGCGCGGGGCGCCCACGGGA<br>CAACCAGGCCATCGAGTTCCTGTTCCAGCTGGGCCGGGACGCGGCCGAGGAGGTGGCA<br>CAGGAGATGGTGGCTCTCGGCTTGGTCTCTGAAGCCGATTACCAGCCACTGGCCCGTG<br>CAGTACGTGAACGCGTTGCTGCCATCCAGCGAAAGCGTGAGAAGCTGCGTAAAGCAAG<br>GGAATTGGAGGCACTCCCACCAGAGCCAGGACCTCCACCAGCAACTGTGCCCATGGCC<br>CCCGGTCCCCCAGTCTCTTCCCCCCTCAGCCTGAGGAOCCAGAGGCAGACCAGCACC<br>AGCCCTTCCTTTTCCGCCACCCCACCTACTCATCTACCACTTCGCATTCCGAGACTGA<br>TGGCTACCTCAGCTCCTCCGCCTTCCTGGATCCCTCAGACCCTGCCCTTCAGCCCCCT<br>GGGGGGGTGCCATCCACCCTGGCTGAGTCCCATCTCTGCCTCCCCTCGGCTTTTGCCC<br>TATCCATTCCACGTTCTGGCCCTGGAAGTGACTTTTCCCCCGGGGACAGCTATGCCTC<br>AGATGCAGCTTCAGGCCTTAGCGATGTGGGAGAAGGGATGGGACAAATGAGGAGACCC<br>CCACCGAGGAATCTCCGGCGCAGACCCCGATCCCGGCTGCGGGTCACTAGTGTCTCAG<br>ACCAGAATGACAGAGTGGTTGAGTGCGAGCTACAGACCCATAACAGCAAGATCGTGAC |

TABLE 30A-continued

NOV30 Sequence Analysis

CTTCCGATTTCATCTGGATGGGGACAGCCCGCAAGACATTGCAGCTGCCATGGTATAT
AACGAGTTCATTCTGCCTTCGCAGCGAGATGGATTTCTCAGACCGATTCGGGAGATTA
TCCAGCGACTGGAGACCCTCTTGAACAGAGACACTCGCCCCATGGAGCCTCCTGAAGA
CACCCTAAGCCCCAGCACACCCGAGTTTCCCGTCCCACTCTCTCAGTGTCCCTGGAG
TTCTCTCCCCACGACTTCTCCACCTACGTTCTCTCCCACTTGTTCTCAGGGGAAGCCA
GGCTGGCGCCCATCTCTGAAGAGGGAAAGCCGCAGCTTCTTCGGCGTTTCCAAGTGAC
TTCATCCAAGCAACCCGCTGAGCCTCTTCCCTTGCAGCCAACATCCCCCACTCTCTCT
GGTTCTCCAAAACCTTCAACCCCTCAGCTCACTTCAGAGAGCTCAGATACACAGGACA
GTGCTGCAGCCGCCCCAGAGACCAGGGAAGCTCTGGCTGAGAGCCACCGTGCAGCTGA
GGGTCTGGGGCTGGAGTTGAGGAGGAAGGAGATGATGGGAAGGAACCCCAAGTTGGG
GGCAGCCCCCAACCCCTGAGCCATCCCAGCCCAGTGTGGATGAACTACTCCTACAGCA
GCCTGTGTTTGAGCAGCGAGGAGTCAGAAAGCAGTGGGGAAGATGAGGAGTTCTGGGC
TGAGCTGCAGAGTCTTCGGCAGAAGCACTTGTCAGAGGTCGAAACACTACAGACACTA
CAGAAAAAAGAAATTGAAGATTTGTACAGCCCGCTGGGGAAGCAGCCCCCACCGGGTA
TTGTCCCCCCAGCTGCTATGCTGTCCAGCCGCCAGCGCCGCCTCTCCAACGCCAGCTT
CCCCACCTCCCGCCGCAACAGCCTACAGCGCTCTGAGCCCCCAGGCCCTGGCATCATG
CGAAGGAACTCTCTGAGTGGCAGCAGCACCGGCTCCCAGGAGCAGCGCGCAAGCAAGG
GGGTGACATTCGCCGGGGATGTTGGCAGGATGTTTGGAGTTGTCGCCACAGAGACGAT
TGAAGACGCCCTGCTTCACTTGGCCCAGCAGAATGACCAAGCACTCAGGGAGGCTTCG
GGGCGGCTGGCCCCCTTCAGCGAGCCCCAGATCGTGGAATTTGTTTTTCTCCTGTCTG
AACAATGGTGTCTGGAGAAATCTGTGAGCTACCAGGCTGTAGAAATCCTAGAAAGGTT
TATGGTAAAACACGCAGAGAAGATCTGCAGGCAAGCCACAATCAGGATAACCCCTAAT
AAGAGAGAGTCTCAGAATTGGAGGGCTCTGAAACAGCAGCTTCTCAACAAGTTTACTC
TCCGTCTTGTGTCAGGTCTTCAGCTGGCCAGCAAACTTTCCTTCCGAAACAAAATAAT
CAGCAACATTACAGTCTTGAATTTCCTCCAGGCTCTAGGCTATCTACACACTAAAGAA
GAACTGCTGGAATCAGAGCTTGATGTTTTGAAGTCCTTGAACTTCCGAATTAATCTGC
CCACTCCCCTGGCATATGTGGAGACGCTCCTAGAGGTTTTAGGATACAATGGCTCTTT
GGTTCCAGCCATGAGGCTGCATGCAACCTGCCTGACACTGCTCGACCTGGTCTATCTT
CTGCATGAACCCATATATCAGAGCCTGTTGACGGCTTCAATTGAGAACTCCACTCCCA
GTCAGCTGCAAGGGGAAAAGTTTACTTCAGTGAAGGAAGACTTCATGCTGTTGCCAGT
AGGAATCATTGCAGCAAGTGCTTTCATCCAAAACCATGAGTGTTGGAGCCAGGTATGC
ACCACTGAGCAGGACCAGCATGAGAGAGTTAAGGTGCACCAGCATGCCCTTTTTGTCA
TATCAGCCTGA

ORF Start: ATG at 1    ORF Stop: TGA at 4069
SEQ ID NO: 78          1356 aa    MW at 150401.9kD NOV30a,
CG90385-01 Protein Sequence MSQTEADLALRPPPPLGTAGQPRLGPPPRRARRFSGKAEPRPRSSRLSRRSSVDLGLL
SSWSLPASPAPDPPDPPDSAGPGPARSPPPSSKEPPEGTWTEGAPVKAAEDSARPELP
DSAVGTGSRETLRVTEAVALERRREGEEKEDMETQAVATSPDGRYLKFDIEIGRGSFK
TVYRGLDTDTTVEVAWCELQTRKLSRAERQRFSEEVEMLKGLQHPNIVRFYDSWKSVL
RGQVCIVLVTELMTSGTLKTHRLGECWQKMRRRQQGAAGGNFPVGGSFPEDVSPHQDS TABLE 30A-continued NOV30 Sequence Analysis

|  |  |
| --- | --- |
|  | GYAPSPRYLRRFREMKPRVLQRWSRQILRGLHFLHSRVPPILHRDLKCDNVFITGPTG |
|  | SVKIGDLGLATLKRASFAKSVIGTTEFMATEMYEEKYDEAVDVYAFGMCMLEMATSEY |
|  | PYSECQNAAQIYRKVTSGRKPNSFHKVKIPEVKEIIEGCIRTDKNERFTIQDLLAHAF |
|  | FREERGVHVELAEEDDGEKPGLKLWLRMEDARRGGRPRDNQAIEFLFQLGRDAAEEVA |
|  | QEMVALGLVCEADYQPVARAVRERVAAIQRKREKLRKARELEALPPEPGPPPATVPMA |
|  | PGPPSVFPPEPEEPEADQHQPFLFRHASYSSTTSDCETDGYLSSSGFLDASDPALQPP |
|  | GGVPSSLAESHLCLPSAFALSIPRSGPGSDFSPGDSYASDAASGLSDVGEGMGQMRRP |
|  | PGRNLRRRPRSRLRVTSVSDQNDRVVECQLQTHNSKMVTFRFDLDGDSPEEIAAAMVY |
|  | NEFILPSERDGFLRRIREIIQRVETLLKRDTGPMEAAEDTLSPQHTRVSGPTLSVSLE |
|  | FSPHDFSTYVLSHLFSGEARLAPISEEGKPQLVGRFQVTSSKEPAEPLPLQPTSPTLS |
|  | GSPKPSTPQLTSESSDTEDSAGGGPETREALAESDRAAEGLGAGVEEEGDDGKEPQVG |
|  | GSPQPLSHPSPVWMNYSYSSLCLSSEESESSGEDEEFWAELQSLRQKHLSEVETLQTL |
|  | QKKEIEDLYSRLGKQPPPGIVAPAAMLSSRQRRLSKGSFPTSRRNSLQRSEPPGPGIM |
|  | RRNSLSGSSTGSQEQRASKGVTFAGDVGRMFGVVATETIEDALLHLAQQNEQAVREAS |
|  | GRLGRFREPQIVEFVFLLSEQWCLEKSVSYQAVEILERFMVKQAENICRQATIRITPN |
|  | KRESQNWRALKQQLVNKFTLRLVSCVQLASKLSFRNKIISNITVLNFLQALGYLHTKE |
|  | ELLESELDVLKSLNFRINLPTPLAYVETLLEVLGYNGCLVPAMRLHATCLTLLDLVYL |
|  | LHEPIYESLLRASIENSTPSQLQGEKFTSVKEDFMLLAVGIIAASAFIQNHECWSQVC |
|  | TTEQDQHERVKDEHALFVISA |
| NOV30b,<br>CG90385-02 DNA Sequence | SEQ ID NO: 79     4019 bp<br>AATTTTCTACCCTTCGGCGCCCTGCTCTTTCCTCATGTTGGCAATCCCCGGCCACGGA |
|  | GACCACCGTCCTCATGTCCCAGACTGAGGCCGACCTGGCCCTGCGGCCCCCGCCTCCT |
|  | CTTGGCACCCCGGGGCAGCCCCGCCTCGCGCCCCCTCCTCGCCGAGCGCGCCGCTTCT |
|  | CCGGGAAGGCTGAGCCCCGCCGCGCTCTTCTCCTCTCAGCCGCCGTAGCTCACTCGA |
|  | CTTGGGGCTGCTGAGCTCTTGGTCCCTCCCACCCTCACCCGCTCCGGACCCCCCCGAT |
|  | CCTCCGGACTCCGCTGCTCCTGGCCCCCCGAGGACCCCACCGCCTAGCTCCAAAGAAC |
|  | CCCCCGAGGGCACGTGGACCGAGGGAGCCCCTGTGAAGGCTGCGGAAGACTCCGCGCG |
|  | TCCCGACCTCCCGCACTCTGCACTCCGCCCGGCGTCCAGGGACCCGCTAAGGGTCCCT |
|  | GAAGCTCTGGCCCTAGAGCGGCGGCGCGAGCAGGAAGAAAAGSAGGACATGGAGACCC |
|  | AGGCTGTGGCAACGTCCCCCGATGGCCGATACCTCAAGTTTGACATCGAGATTGGACG |
|  | TGGCTCCTTCAAGACGGTGTATCGAGGGCTAGACACCGACACCACAGTGGAGGTGGCC |
|  | TGGTGTGAGCTGCACGTGCGGACTCGGAAACTCTCTAGACCTGAGCCGCAGCGCTTCT |
|  | CAGAGGAGGTGGAGATGCTCAAGGGGCTGCAGCACCCCAACATCGTCCGCTTCTATGA |
|  | TTCGTGGAAGTCGGTGCTGAGGGCCCAGGTTTGCATCCTGCTGGTCACCGAACTCATG |
|  | ACCTCGGGCACGCTCAAGACGTACCTGAGGCGGTTCCGGGAGATGAAGCCGCGGGTCC |
|  | TTCAGCGCTCGACCCGCCAAATCCTGCGGGACTTCATTTCCTACACTCCCCGGTTCC |
|  | TCCCATCCTGCACCGGGATCTCAAGTGCGACAATGTCTTTATCACGGGACCTACTGGC |
|  | TCTGTCAAAATCCGCGACCTGGCCCTGGCCACGCTCAAGCGCGCCTCCTTTGCCAAGA |
|  | GTGTCATCGGTACCCCGGAATTCATGGCCCCCGACATGTACCAGGAAAAGTACGATGA |

TABLE 30A-continued

| NOV30 Sequence Analysis |
|---|
| GGCCGTCGACGTGTACGCGTTCGGCATGTGCATGCTGGAGATGGCCACCTCTGAGTAC |
| CCGTACTCCCAGTGCCAGAATGCCGCGCAAATCTACCGCAAGGTCACTTCGGTGAGAG |
| GGATGGGGCTCGCCGGAAAGGCAATTCCAGACGTGAAGGACATCATTGAACCCTGCAT |
| CCGCACGGATAAGAACGAGAGGTTCACCATCCAGGACCTCCTGGCCCACGCCTTCTTC |
| CGCGAGGAGCCCGGTGTGCACGTCGAACTAGCGGAGGACGACGACGGCGAGAAGCCGG |
| GCCTCAAGCTCTGGCTGCGCATGGAGGACGCGCGGCGCGGGGGCGCCCACGGGACAA |
| CCAGGCCATCGAGTTCCTGTTCCAGCTGGGCCGGGACGCCGCCGAGGAGCTGGCACAG |
| GAGATGGTGAGCCGAGGATTGGTCTGTGAAGCCGATTACCAGCCAGTGGCCCGTGCAG |
| TACGTGAACGGGTTGCTGCCATCCAGCGAAAGCGTCAGAAGCTGCGTAAACCAAGGGA |
| ACGGGTTGCTGCCATCCAGCGAAAGCGTGAGAAGCTGCGTAAAGCAAGGGAATTGGAG |
| GCACTCCCACCAGAGCCAGGACCTCCACCAGCAACTGTGCCCATGGCCCCGGTCCCC |
| CCAGTCTCTTCCCCCCTGAGCCTGAGGAGCCAGAGGCAGACCAGCACCAGCCCTTCCT |
| TTTCCGCCACGCCAGCTACTCATCCTCTCCCTCCAACAGCTATGCCTCAGATGCAGCT |
| TCAGGCCTTAGCGATGTGGCAGAAGGGATGGGACAAATGAGGAGACCCCCTGGGAGGA |
| ATCTCCGGCGCAGACCCCGATCCCGGCTGCGGGTCACTAGTCAGCATGATGAAGAGGG |
| CTTGACCTTCTCCCCTCTGCTGACTTTGAATCTCAAGGTCTCAGACCAGAATGACAGA |
| GTGGTTGAGTGCCAGCTACAGACCCATAACAGCAAGATGCTGACCTTCCGATTTGATC |
| TGGATCGGGACAGCCCGGAAGAGATTGCAGCTGCCATGGTGTATAACCAGTTCATTCT |
| GCCTTCGGAGCGAGATGGATTTCTCACACGGATTCGGGAGATTATCCAGCGAGTGGAG |
| ACCCTGTTGAAGAGAGACCCCATCACTTCTCCCCCATGTCATCCCAGCCCCTCCCCAT |
| TCTCCCCCATTTCTTCCCAGGTCTCCTCAAATCCCTCTCCACACCCCACCAGCTCTCC |
| ACTTCCATTCTCCTCCAGCACACCCGAGTTTCCCGTCCCACTCTCTCAGTGTCCCTGG |
| AGTTCTCTCCCCACGACTTCTCCACCTACGTTCTCTCCCACTTGTTCTCAGCTCACTC |
| TTAGTTCCCCTTTCTTTCCTCCGTGCCCCTCCACTTCTTCCTTCCCCTCCACCACAGC |
| AGCCCCTCTCCTTTCTCTCGCTAGTGCCTTCTCACTGCCTGTGATCACTGTGGCCCAG |
| TCCCTGCTGGCCTTCTCCACCTCCTCATCTTCTCCTGGAACTCCTTTGTCTCGTGGAA |
| ACCCATTTTCCCCTGGAACCCCCATTTCCCCAGGTCCCATCTTCCCCATCACTTCTCC |
| CCCATGTCATCCCAGCCCCTCCCCATTCTCCCCCATTTCTTCCCAGGTCTCCTCAAAT |
| CCCTCTCCACACCCCACCAGCTCTCCACTTCCATTCTCCTCCAGCACACCCGAGTTTC |
| CGGTCCCACTCTCTCAGTGTCCCTGGAGTTCTCTCCCCACGACTTCTCCACCTACGTT |
| CTCTCCCACTTGTTCTCAGGTCGGGACTGTCGTCTCAACATACCCTCCTTCCCAGAAG |
| AGCTCCAGAGCAGCACCTCCCTGGAGCACACGAGCTGGACAGCCTTCTCCACCTCCTC |
| ATCTTCTCCTGGAACTCCTTTGTCTCCTGGAAACCCATTTTCCCCTGGAACCCCCATT |
| TCCCCACGTCCCATCTTCCCCATCACTTCTCCCCCATGTCATCCCAGCCCCTCCCCAT |
| TCTCCCCCATTTCTTCCCAGGTCTCCTCAAATCCCTCTCCACACCCCACCAGCTCTCC |
| ACTTCCATTCTCCTCCAGCACACCCGAGTTTCCGGTCCCACTCTCTCAGTGTCCCTGG |
| AGTTCTCTCCCCACGACTTCTCCACCTACGTTCTCTCGTTGGGCCTTTCCAAGTGACT |
| TCATCCAAGGAACCGCCTGAGCCTCTTCCCTTGCAGCCAACATCCCCCACTCTCTCTG |

TABLE 30A-continued

NOV30 Sequence Analysis

GTTCTCCAAAACCTTCAACCCCTCAGCTCACTTCAGAGAGCTCAGATACAGAGGACAG

TGCTGGAGGCGGGCCAGAGAGGCACTTGTCAGAGGTGGAAACACTACAGACACTACAG

AAAAAAGAAATTGAAGATTTGTACAGCCGGCTGGCGAAGCAGCCCCCACCGGGTATTG

TGGCCCCACCTGCTATGCTGTCCAGCCGCCAGCCCCGCCTCTCCAAGGCCAGCTTCCC

CACCTCCCGCCGCAACAGCCTACAGCGCTCTGAGCCCTGCTGCGTGCCTGCAATCCCA

GCTACTCAGCAGGCTGAGGCAGGAGAATTTCTTGAGCCTGGGAGGCCCACGTTGCAGA

ATCATTCTCCCTCTGCCCTTCGACAGAATTCCTCTTCTCCTCCTTCCCATAACCTGTT

TTTAACAGCATCCAACCCACCCATTCTTTCTGCAACCTCAAGATGCTGCATGAGCTTC

CATACCTCACTGGGAAGTTGGATCTTCATTCTTAAGCCTCCCATGTATACATGTTAAA

TACATTTGTAATCTTTTTCTCATATTAATTAATCTGCCTTATCTCAGTCACTTTTCAG

CGAACTTGTAGGTAGTCACTCACATAAGGATCCTCCAGTTTACATAGTTTTGTAAATG

TCAGGTCACCCTGTCCCACTAGACCACCAAGCTCCTGCAGGACACCTGGGATTTAACT

TTTTTTTTTTTTTTTTT

ORF Start: ATG at 72    ORF Stop: TAA At 3825
SEQ ID NO: 80           1251 aa    MW at 137141.7kD NOV30b,
CG90385-02 Protein Sequence

MSQTEADLALRPPPPLGTAGQPRLGPPPRRARRFSGKAEPRPRSSRLSRRSSVDLGLL

SSWSLPASPAPDPPDPPDSAGPGPARSPPPSSKEPPEGTWTEGAPVKAAEDSARPELP

DSAVGTGSRETLRVTEAVALERRREGEEKEDMETGAVATSTDGRYLKFDIEIGRGSFK

TVYRGLDTDTTVEVAWCELGVRTRKLSRAERGRFSEEVSMLKGLGHTNIVRFYDSWKS

VLRGQVCIVLVTELMTSGTLKTYLRRFREMKPRVLQRWSRQILRGLHFLHSRVPPILH

RDLKCDNVFITGPTGSVKIGDLGLATLKRASFAKSVIGTPEFMAPEMYEEKYDEAVDV

YAFGMCMLEMATSEYPYSECQNAAQIYRKVTSVRGMGLAGKAIPEVKEIIEGCIRTDK

NERFTIQDLLAHAFFREERGVHVELAEEDDGEKPGLKLWLRMEDARRGGRPRDNQAIE

FLFQLGRDAAEEVAQEMVSGGLVCEADYQPVARAVRERVAAIQRKREKLRKARERVAA

IQRKREKLRKARELEALTTETGTTTATVTMATCTTSVFTTETEETEADGHGTFLFRHA

SYSSSTSNSYASDAASGLSDVGEGMGGMRRTTGRNLRRRTRSRLRVTSGHDESGLTFS

PLLTLNLKVSDQNDRVVECQLQTHNSKMVTFRFDLDGDSPEEIAAAMVYNEFILPSER

DGFLRRIREIIQRVETLLKRDPITSPPCHPSPSPFSPISSQVSSNPSPHPTSSPLPFS

SSTPEFPVPLSQCPWSSLPTTSPPTFSPTCSQVTLSSPFFPPCPSTSSFPSTTAAPLL

SLASAFSLAVMTVAGQSLLAFSTSSSSPGTPLSPGNPFSPGTPISPGIFPITSPPCHP

SPSPFSPISSQVSSNPSPHPTSSPLPFSSSTPEFPVPLSQCPWSSLPTTSPPTFSPTC

SQVGTVVSTYPPSQKSSRAAPPWSTGAGQPSPPPHLLLELLCLLETHFPLEPPFPQVP

SSPSLLPHVIPAPPHSPPFLPRSPQIPLHTPPALHFHSPPAHPSFRSHSLSVPGVLSP

RLLHLRSLVGRFQVTSSKEPAEPLPLQPTSPTLSGSPKPSTPQLTSESSDTEDSAGGG

PERHLSEVETLQTLQKKEIEDLYSRLGKQPPPGIVAPAAMLSSRQRRLSKGSFPTSRR

NSLQRSEPWCVPAIPATQEAEAGEFLEPGRRRLQNHSPSALRQNSSSPPSHNLFLTGS

KPPILSATSRWWMSFHTSLGSWIFILKPPMYTC

Sequence comparison of the above protein sequences yields the following sequence relationships shown in Table 30B.

TABLE 30B

Comparison of NOV30a against NOV30b.

| Protein Sequence | NOV30a Residues/ Match Residues | Identities/Similarities for the Matched Region |
| --- | --- | --- |
| NOV30b | 1 . . . 551 | 419/553 (75%) |
| | 1 . . . 507 | 420/553 (75%) |

Further analysis of the NOV30a protein yielded the following properties shown in Table 30C.

TABLE 30C

Protein Sequence Properties NOV30a

| | |
| --- | --- |
| PSort analysis: | 0.8500 probability located in endoplasmic reticulum (membrane); 0.8200 probability located in nucleus; 0.4400 probability located in plasma membrane; 0.3000 probability located in microbody (peroxisome) |
| SignalP analysis: | No Known Signal Sequence Predicted |

A search of the NOV30a protein against the Geneseq database, a proprietary database that contains sequences published in patents and patent publication, yielded several homologous proteins shown in Table 30D.

TABLE 30D

Geneseq Results for NOV30a

| Geneseq Identifier | Protein/Organism/Length [Patent #, Date] | NOV30a Residues/ Match Residues | Identities/ Similarities for the Matched Region | Expect Value |
| --- | --- | --- | --- | --- |
| AAU03531 | Human protein kinase #31 - *Homo sapiens*, 1513 aa. [WO200138503-A2, 31 MAY 2001] | 1 . . . 895<br>1 . . . 850 | 781/898 (86%)<br>788/898 (86%) | 0.0 |
| AAB65656 | Novel protein kinase, SEQ ID NO: 183 - *Homo sapiens*, 1920 aa. [WO200073469-A2, 07 DEC. 2000] | 20 . . . 630<br>97 . . . 667 | 336/638 (52%)<br>402/638 (62%) | e-169 |
| AAM40523 | Human polypeptide SEQ ID NO 5454 - *Homo sapiens*, 470 aa. [WO200153312-A1, 26 JUL. 2001] | 67 . . . 556<br>34 . . . 467 | 299/491 (60%)<br>357/491 (71%) | e-164 |
| AAM38736 | Human polypeptide SEQ ID NO 1881 - *Homo sapiens*, 502 aa. [WO200153312-A1, 26 JUL. 2001] | 161 . . . 630<br>4 . . . 451 | 298/497 (59%)<br>350/497 (69%) | e-158 |
| AAM38737 | Human polypeptide SEQ ID NO 1882 - *Homo sapiens*, 591 aa. [WO200153312-A1, 26 JUL. 2001] | 298 . . . 630<br>185 . . . 540 | 223/360 (61%)<br>265/360 (72%) | e-117 |

In a BLAST search of public sequence datbases, the NOV30a protein was found to have homology to the proteins shown in the BLASTP data in Table 30E.

TABLE 30E

Public BLASTP Results for NOV30a

| Protein Accession Number | Protein/Organism/Length | NOV30a Residues/ Match Residues | Identities/ Similarities for the Matched Portion | Expect Value |
| --- | --- | --- | --- | --- |
| Q96DT8 | SERINE/THREONINE PROTEIN KINASE (EC 2.7.1.37) - *Homo sapiens* (Human), 1231 aa. | 1 . . . 895<br>1 . . . 850 | 781/898 (86%)<br>788/898 (86%) | 0.0 |
| Q96J92 | HYPOTHETICAL 134.7 KDA PROTEIN - *Homo sapiens* (Human), 1243 aa. | 1 . . . 895<br>13 . . . 862 | 781/898 (86%)<br>788/898 (86%) | 0.0 |
| Q9H4A3 | HYPOTHETICAL 250.8 KDA PROTEIN - *Homo sapiens* (Human), 2382 aa. | 20 . . . 686<br>97 . . . 730 | 349/701 (49%)<br>423/701 (59%) | e-170 |
| Q9JIH7 | PROTEIN KINASE WNK1 - *Rattus norvegicus* (Rat), 2126 aa. | 38 . . . 630<br>68 . . . 668 | 344/654 (52%)<br>416/654 (63%) | e-170 |
| Q9D995 | 5430417M23RIK PROTEIN (RIKEN CDNA 5430417M23 GENE) - *Mus musculus* (Mouse), 334 aa. | 1075 . . . 1333<br>19 . . . 277 | 226/259 (87%)<br>243/259 (93%) | e-125 |

PFam analysis predicts that the NOV30a protein contains the domains shown in the Table 30F.

TABLE 30F

Domain Analysis of NOV30a

| Pfam Domain | NOV30a Match Region | Identities/ Similarities for the Matched Region | Expect Value |
| --- | --- | --- | --- |
| pkinase: domain 1 of 2 | 162 . . . 253 | 28/92 (30%) 64/92 (70%) | 8.7e-09 |
| pkinase: domain 2 of 2 | 297 . . . 465 | 56/208 (27%) 136/208 (65%) | 1.5e-40 |

TABLE 30F-continued

Domain Analysis of NOV30a

| Pfam Domain | NOV30a Match Region | Identities/ Similarities for the Matched Region | Expect Value |
| --- | --- | --- | --- |
| Ca_channel_B: domain 1 of 1 | 678 . . . 732 | 10/55 (18%) 33/55 (60%) | 4 |
| cyclin: domain 1 of 1 | 1112 . . . 1236 | 31/152 (20%) 76/152 (50%) | 0.4 |

Example 31

The NOV31 clone was analyzed, and the nucleotide and encoded polypeptide sequences are shown in Table 31A.

TABLE 31A

NOV31 Sequence Analysis

| | |
| --- | --- |
| NOV31a, CG90635-01 DNA SEQUENCE | SEQ ID NO:81    7961 bp<br>CTGTCTAATTCTTCCTTTCTCTCAATATAGGTATGGCATCACAGCTGCAAGTGTTTTC<br><br>GCCCCCATCAGTGTCGTCGAGTGCCTTCTGCAGTGCGAACAAACTGAAAATACAGCCC<br><br>TCTGGCTQGGATGTTTCAGQACAGAGTAGCAACGACAAATATTATACCCACAGCAAAA<br><br>CCCTCCCAGCCACACAAGGGCAAGCCAACTCCTCTCACCAGGTACCAAATTTCAACAT<br><br>CCCTGCTTACGACCAGGGCCTCCTCCTCCCAGCTCCTGCAGTGGAGCATATTGTTGTA<br><br>ACAGCCGCTGATAGCTCGGGCAGTGCTGCTACATCAACCTTCCAAAGCAGCCAGACCC<br><br>TGACTCACAGAAGCAACGTTTCTTTGCTTGAGCCATATCAAAAATGTGGATTGAAACG<br><br>AAAAACTGAGGAAGTTGACAGCAACGGTAGTGTGCAGATCATAGAAQAACATCCCCCT<br><br>CTCATGCTGCAAAACAGGACTGTCGTGGGTGCTGCTGCCACAACCACCACTGTGACCA<br><br>CAAAGAGTAGCAGTTCCAGCGGAGAAGGCGATTACCAGCTGGTCCAGCATGAGATCCT<br><br>TTGCTCTATGACCAATAGCTATGAAGTCTTGGAGTTCCTAGGCCGGGGGACATTTGGA<br><br>CAGGTCGCTAAGTGCTGGAAGAGGAQCACCAACGAAATTGTGGCTATTAAAATCTTGA<br><br>AGAACCACCCCTCCTATGCCAGACAAGGACAGATTGAAGTGACCATCCTTTCCCGCCT<br><br>AAGCAGTGAAAATGCTGATGAGTATAATTTTGTCCGTTCATACGAGTGCTTTCAGCAT<br><br>AAGCAGTGAAAATGCTGATGAGTATAATTTTGTCCGTTCATACGAGTGCTTTCAGCAT<br><br>AAGAATCACACCTGCCTTGTTTTTGAAATGTTGGAGCAGAACTTATATGATTTTCTAA<br><br>AGCAAAACAAATTTAGCCCACTGCCACTCAAGTACATCAGACCAATCTTGCAGCAGGT<br><br>GGCCACAGCCTTGATGAAGCTCAAGAGTCTTGGTCTGATCCACGCTGACCTTAAGCCT<br><br>GAAAACATCATGCTGGTTGATCCAGTTCGCCAGCCCTACCGAGTGAAGGTCATTGACT<br><br>TTGGTTCTGTCAGTCACGTTTCCAAAGCTGTGTGCTCAACCTACTTACAGTCACGTTA<br><br>CTACAGAGCTCCTGAAATTATCCTTCGATTACCATTCTGTGAAGCTATTGACATGTGG<br><br>TCACTGGCCTQTGTAATAGCTGAGCTGTTCCTGCGATGGCCTCTTTATCCTGGTGCTT<br><br>CAGAATACGAGCACATTCGTTATATTTCACAAACACAAGGCTTGCCAGCTCAATATCT<br><br>TCTCAGTGCCGGAACAAAAACAACCAGCTTTTTCAACAGAGATCCTAATTTGGGGTAC<br><br>CCACTGTGGAGGCTTAACACACCTCAAGAACATGAACTGCAGACTGGAATAAAATCAA<br><br>AAGAAGCTCGGAAGTACATTTTTAATTGCTTAGATGACATGGCTCAGGTGAATATGTC |

TABLE 31A-continued

NOV31 Sequence Analysis

TACAGACCTGGAGGGAACAGACATGTTGGCAGACAAGGCACACCCAAGAGAATACATT
GATCTGTTAAAGAAAATGCTCACAATTGATGCAGATAACAGAATTACCCCTCTAAAAA
CTCTTAACCATCAGTTTGTGACAATGACTCACCTTTTGGATTTTCCACATAGCAATCA
GAGTGTTAAGTCTTGTTTTCACAACATQGAGATCTGCAAGCGGAGGCTTCACATGTAT
GATACAGTGAGTCACATCAAGAGTCCCTTCAGTACACATGTTGCCCCAAATACAAGCA
CAAATCTAACCATGAGCTTCAGCAATCAGCTCAATACAGTGCACAATCAGGCCAGTGT
TCTAGCTTCCAGTTCTACTGCAGCAGCTGCTACTCTTTCTCTGGCTAATTCAGATGTC
TCACTACTAAACTACCAGTCAGCTTTGTACCCATCATCTGCTGCACCAGTTCCTGGAG
TTCCCCAGCAGCGTGTTTCCTTGCACCCTGGAACCACCCAGATTTGCACTCACACAGA
TCCATTCCAACAGACATTTATAGTATGTCCACOTGCCTTTCAAAGTGGACTACAAGCA
ACAACAAAGCATTCTGGATTCCCTGTGACOATGGATAATGCTGTACCGATTGTACCCC
AGGCACCAGCTCCTCAGCCACTACAGATTCAGTCAGGAGTTCTCACGCAGGGAAGCTG
TACACCACTAATGGTACCAACTCTCCACCCTCAAGTAGCCACCATCACACCGCAGTAT
GCGGTGCCCTTTACTCTGAGCTGCGCAGCCGGCCGGCCGGCGCTGGTTGAACAGACTG
CCGCTGTACTGCAGGCCTGGCCTGGAGGGACTCAGCAAATTCTCCTGCCTTCAACTTG
GCAACAGTTGCCTGGGGTACCTCTACACAACTCTGTCCAGCCCACAGCAATGATTCCA
GAGGCCATGGCGAGTGGACAGCAGCTACCTGACTCGAGGAGGAATGCCCACTCTCATG
GCAACCAGTACAGCACTATCATGCAGCAGCCATCCTTGCTGACTAACCATGTQACATT
GGCCACTGCTCAGCCTCTGAATGTTGGTGTTGCCCATGTTGTCAGACAACAACAATCC
AGTTCCCTCCCTTCGAAGAAGAATAAGCAGTCAGCTCCAGTCTCTTCCAAGTCCTCTC
TAGATGTTCTGCCTTCCCAAGTCTATTCTCTGGTTGGGAGCAGTCCCCTCCGCACCAC
ATCTTCTTATAATTCCTTCGTCCCTGTCCAAGATCAGCATCAGCCCATCATCATTCCA
GATACTCCCAGCCCTCCTGTGAGTGTCATCACTATCCGAAGTGACACTGATGAGGAAG
AGGACAACAAATACAAGCCCAGTAGCTCTGGACTGAAGCCAAGGTCTAATGTCATCAG
TTATGTCACTGTCAATGATTCTCCACACTCTGACTCTTCTTTGAGCAGCCCTTATTCC
ACTGATACCCTGAGTGCTCTCCCAGGCAATAGTGGATCCGTTTTGGAGGGGCCTGGCA
GAGTTGTGGCAGATGGCACTGGCACCCCCACTATCATTCTGCCTCCACTGAAAACTCA
GCTTGGTGACTGCACTGTAGCAACCCAGCCCTCAGGTGGTCTCCTGAGCAATAAGACT
AAGCCACTCGCTTCAGTCAGTGCGCAGTCATCTCGATOCTGTATCACCCCCACAGGGT
ATCGAGCTCAACGCGGGGGCACCAGTGCAGCACAACCACTCAATCTTAGCCAGAACCA
GCAGTCATCGCCGGCTCCAACCTCACAGGAGAGAAGCAGCAACCCACCCCCCCGCAGG
CAGCAGGCGTTTGTGGCCCCTCTCTCCCAAGCCCCCTACACCTTCCAGCATGGCAGCC
CGCTACACTCGACAGGGCACCCACACCTTGCCCCGGCCCCTGCTCACCTGCCAAGCCA
GGCTCATCTGTATACGTATGCTGCCCCGACTTCTCCTGCTGCACTGGGCTCAACCAGC
TCCATTGCTCATCTTTTCTCCCCACACGGTTCCTCAAGOCATGCTGCAGCCTATACCA
CTCACCCTAGCACTTTGGTGCACCAGGTCCCTGTCAGTGTTGGGCCCAGCCTCCTCAC
TTCTGCCAGCGTGGCCCCTGCTCAGTACCAACACCAGTTTGCCACCCAATCCTACATT
GGGTCTTCCCGAGGCTCAACAATTTACACTGGATACCCGCTGAGTCCTACCAAGATCA
GCCAGTATTCCTACTTATAGTTGGTGAGCATGAGGGAGGAGGAATCATGGCTACCTTC

TABLE 31A-continued

NOV31 Sequence Analysis

TCCTGGCCCTGCGTTCTTAATATTGGGCTATGGAGAGATCCTCCTTTACCCTCTTGAA

ATTTCTTAGCCAGCAACTTGTTCTGCAGGGGCCCACTGAAGCAGAAGGTTTTTCTCTG

GGGGAACCTGTCTCAGTGTTGACTGCATTGTTGTAGTCTTCCCAAAGTTTGCCCTATT

TTTAAATTCATTATTTTTGTCACAGTAATTTTGGTACTTGGAAGAGTTCAGATGCCCA

TCTTCTGCAGTTACCAAGGAAGAGAGATTGTTCTGAAGTTACCCTCTGAAAAATATTT

TGTCTCTCTGACTTGATTTCTATAAATGCTTTTAAAAACAAGTGAAGCCCCTCTTTAT

TTCATTTTGTGTTATTGTGATTGCTGGTCAGGAAAAATGCTGATAGAAGGAGTTGAAA

TCTGATGACAAAAAAAGAAAAATTACTTTTTGTTTGTTTATAAACTCAGACTTGCCTA

TTTTATTTTAAAAGCGGCTTACACAATCTCCCTTTTGTTTATTGGACATTTAAACTTA

CAGAGTTTCAGTTTTGTTTTAATGTCATATTATACTTAATGGGCAATTGTTATTTTTG

CAAAACTCGTTACGTATTACTCTGTCTTACTATTGAGATTCTCTCAATTCCTCCTGTG

TTTGTTATAAAGTAGTGTTTAAAAGGCAGCTCACCATTTGCTCGTAACTTAATGTGAG

AGAATCCATATCTGCGTGAAAACACCAAGTATTCTTTTTAAATGAAOCACCATGAATT

CTTTTTTAAATTATTTTTTAAAAGTCTTTCTCTCTCTGATTCACCTTAAATTTTTTA

TCGAAAAAGCCATTAAGGTGGTTATTATTACATGGTGGTGGTCGTTTTATTATATGCA

AAATCTCTGTCTATTATCAGATACTGGCATTGATGAGCTTTGCCPAAAGATTAGTATG

AATTTTCACTAATACACCTCTGTTTTGCTCATCTCTCCCTTCTGTTTTATGTGATTTG

TTTGGGGAOAAAGCTAAAAAAACCTCAAACCAGATAAGAACATTTCTTGTGTATAGCT

TTTATACTTCAAAGTAGCTTCCTTTGTATGCCAGCAGCAAATTGAATGCTCTCTTATT

AAGACTTATATAATAAGTGCATGTAGGAATTCCAAAAAATATTTTAAAAATTTATTAC

TGAATTTAAAAATATTTPAGAAGTTTTGTAATGGTCGTCTTTTAATATTTTACATAAT

TAAATATGTACATATTGATTAGAAAAATATAACAAGCAATTTTTCCTGCTAACCCAAA

ATGTTATTTGTAATCAAATGTGTAGTGATTACACTTGAATTGTCTACTTAGTCTGTAT

GTGATCCTCCAGTGTTATCCCGGACATGGATTGATGTCTCCATTGTATTTAAACCAAA

ATGAACTGATACTTGTTGGAATGTATGTGAACTAATTGCAATTATATTAGAGCATATT

ACTGTAGTGCTGAATGAGCAGGGGCATTGCCTGCAAGGAGAGGAGACCCTTGGAATTG

TTTTGCACAGGTGTGTCTGGTGAGGAGTTTTTCAGTCTGTGTCTCTTCCTTCCCTTTC

TTCCTCCTTCCCTTATTGTAGTGCCTTATATGATAATGTAGTGGTTAATAGACTTTAC

AGTGAGCTTGCCTTAGGATGGACCAGCAAGCCCCGTGGACCCTAAGTTGTTCACCGG

GATTTATCACAACAGCATTAGTAGCTGTATTGTGTAATGCATTGTTCTCAGTTTCCCT

GCCAACATTGAAAAATAAAAACAGCAGCTTTTCTCCTTTACCACCACCTCTACCCCTT

TCCATTTTGGATTCTCGGCTGAGTTCTCACAGAAGCATTTTCCCCATGTGGCTCTCTC

ACTGTGCGTTGCTACCTTGCTTCTCTGAGAATTCAGGAAGCAGGTGAGAGGAGTCAAG

CCAATATTAAATATGCATTCTTTTAAAGTATGTGCAATCACTTTTAGAATGAATTTTT

TTTTCCTTTTCCCATOTGGCACTCCTTCCTGCACATAGTTGACATTCCTAGTAAAATA

TTTGCTTGTTGAAAAAAACATGTTAACAGATGTGTTTATACCAAAGAGCCTCTTGTAT

TGCTTACCATGTCCCCATACTATGACGAGAAGTTTTCTGGTGCCGCTGGTGACAAGGA

ACTCACAGAAAOGTTTCTTAGCTGCTGAAGAATATAGACAAGOAACCAAAGCCTGTTC

AGTCATTGAGGCTTTTGAGGTTTCTTTTTTAACAGCTTGTATAGTCTTGGGGCCCTTC

TABLE 31A-continued

NOV31 Sequence Analysis

AAGCTGTGAAATTGTCCTTGTACTCTCAGCTCCTGCATGATCTGGGTCAACTAGAAG

GTACTGGGGATGGGGACATTCCTGCCCATAAAGGATTTGGGGAAAGAAGATTAATCCT

AAAATACAGGTGTGTTCCATCCGAATTGAAAATGATATATTTGACATATAATTTTAGG

ACTGGTTCTGTGTAGATAGACATGGTGTCAAGGAGGTCCACCATGGAGATCGGAGATT

TCATGGAGCCTGGTCAGCCAGCTCTGTACCAGGTTGAACACCGAGGAGCTGTCAAAGT

ATTTGGAGTTTCTTCATTGTAAGCAGTAAGGGCTTCCAAGATGGGGCAGGTAGTCCGT

ACAGCCTACCAGGAACATGTTGTGTTTTCTTTATTTTTTAAAATCATTATATTGAGTT

GTGTTTTCAGCACTATATTGGTCAACATACCCAAGCAGTTTGTATAATTTCTCTCACT

AGTGTCATACAGTTTTCTGCTCAACATGTGTGATCTTTGTGTCTCCTTTTTGCCAAGC

ACATTCTGATTTTCTTGTTGGAACACAGCTCTAGTTTCTAAAGGACAAATTTTFTGTT

CCTTGTCTTTTTTCTGTAAGCGACAAGATTTGTTGTTTTTGTAAGAAATGAGATGCAG

GAAAGAAACCAAATCCCATTCCTGCACCCCAGTCCAATAAGCAGATACCACTTAAGA

TAGGAGTCTAAACTCCACAGAAAAGGATAATACCAAGAGCTTGTATTGTTACCTTAGT

CACTTCCCTAGCAGTGTGTCCCTTTAAAAACTAGAGATTTTTCAGTCTTAGTCTGCAA

ACTGGCATTTCCGATTTTCCAGCATAAAAATCCACCTGTGTCTGCTGAATCTGTATGT

ATGTGCTCACTGTGGCTTTAGATTCTGTCCCTGGGGTTACCCCTGTTCGCCCTGACAG

GAAGGGAGGAAGCCTGGTGAATTTAGTGAGCAGCTGGCCTGGGTCACAGTGACCTGAC

CTCAAACCAGCTTAAGGCTTTAAGTCCTCTCTCAGAACTTGGCATTTCCAACTTCTTC

CTTTCCGGGTGAGAGAAGAAGCGGAGAAGGGTTCAGTGTAGCCACTCTGGGCTCATAG

GGACACTTGTCACTCCACAGTTTTTAATAGCTCCCAGGAGGTGATATTATTTTCAGT

GCTCAGCTGAAATACCAACCCCAGGAATAAGAACTCCATTTCAAACAGTTCTGGCCAT

TCTGAGCCTGCTTTTGTCATTGCTCATCCATTGTCCTCCACTAGAGGGGCTAAGCTTG

ACTGCCCTTAGCCAGGCAACCACAGTAATGTGTGTTTCTTCAGCATTATTATGCAAA

AATTCACTAGTTGAGATGGTTTGTTTTAGGATAGGAAATGAAATTGCCTCTCAGTGAC

AGGAGTGGCCCGAGCCTGCTTCCTATTTTGATTTTTTTTTTTTTAACTGATAGATGG

TGCAGCATGTCTACATGGTTGTTGTTGCTAAACTTTATATAATGTGTGGTTTCAATT

CAGCTTGAAAAATAATCTCACTACATGTAGCAGTACATTATATGTACATTATATGTAA

TGTTAGTATTTCTGCTTTGAATCCTTGATATTGCAATGGAATTCCTACTTTATTAAAT

GTATTTCATATGCTAGTTATTCTGTCCGATTTAAACTTTTTTTGCTTTCTCCCTTTTT

TTGGTTGTGCGCTTTCTTTTACAACAAGCCTCTAGAAACAGATAGTTTCTGAGAATTA

CTCAGCTATGTTTGTAATGCAGATGTACTTAGGGAGTATGTAAAATAATCATTTTAAC

AAAAGAAATAGATATTTAAAATTTAATACTAACTATGGCAAAAGGGTCCATTGTGTAA

AACATAGTTTATCTTTGGATTCAATGTTTGTCTTTCGTTTTACAAAGTAGCTTGTATT

TTCAGTATTTTCTACATAATATGGTAAAATGTAGAGCAATTGCAATGCATCAATAAAA

TGGGTAAATTTTCTG

ORF Start: ATG at 33  ORF Stop: TAG at 3672
SEQ ID NO: 82  1213 aa  MW at 131132.5kD NOV31a,
CG90635-01 Protein Sequence

MASQLQVFSPPSVSSSAFCSAKKLKIEPSGWDVSGQSSNDKYYTHSKTLPATQGQANS

SHQVANFNIPAYDQGLLLPAPAVEHIVVTAADSSGSAATSTFQSSQTLTHRSNVSLLE

PYQKCGLKRKSEEVDSNGSVQIIEEHPPLMLQNRTVVGAAATTTTVTTKSSSSSGEGD

TABLE 31A-continued

NOV31 Sequence Analysis

YQLVQHEILCSMTNSYEVLEFLGRGTFGQVAKCWKRSTKEIVAIKILKNHPSYARQGQ

IEVSILSRLSSENADEYNFVRSYECFQHKNHTCLVFEMLEQNLYDFLKQNKFSPLPLK

YIRPILQQVATALMKLKSLGLIHADLKPENIMLVDPVRQPYRVKVIDFGSASHVSKAV

CSTYLQSRYYRAPEIILGLPFCEAIDMWSLGCVIAELFLGWPLYPGASEYEQIRYISQ

TQGLPAEYLLSAGTKTTRFFNRDPNLGYPLWRLKTPEEHELETGIKSKEARKYIFNCL

DDMAQVNMSTDLEGTDMLAEKADRREYIDLLKKMLTIDADKRITPLKTLNHQFVTMTH

LLDFPHSNQSVKSCFQNMEICKRRVHMYDTVSQIKSPFTTHVAPNTSTNLTMSFSNQL

NTVHNQASVLASSSTAAAATLSLANSDVSLLNYQSALYPSSAAPVPGVAQQGVSLQPG

TTQICTQTDPFQQTFIVCPPAFQSGLQATTKHSGFPVRMDNAVPIVPQAPAAQPLQIQ

SGVLTQGSCTPLMVATLHPQVATITPQYAVPFTLSCAAGRPALVEQTAAVLQAWPGGT

QQILLPSTWQQLPGVALHNSVQPTAMIPEAMGSGQQLADWRRNAHSHGNQYSTIMQQP

SLLTNHVTLATAQPLNVGVAHVVRQQQSSSLPSKKNKQSAPVSSKSSLDVLPSQVYSL

VGSSPLRTTSSYNSLVPVQDQHQPIIIPDTPSPPVSVITIRSDTDEEEDNKYKPSSSG

LKPRSNVISYVTVNDSPDSDSSLSSPYSTDTLSALRGNSGSVLEGPGRVVADGTGTRT

IIVPPLKTQLGDCTVATQASGGLLSNKTKPVASVSGQSSGCCITPTGYRAQRGGTSAA

QPLNLSQNQQSSAAPTSQERSSNPAPRRQQAFVAPLSQAPYTFQHGSPLHSTGHPHLA

PAPAHLPSQAHLYTYAAPTSAAALGSTSSIAHLFSPQGSSRHAAAYTTHPSTLVHQVP

VSVGPSLLTSASVAPAQYQHQFATQSYIGSSRGSTIYTGYPLSPTKISQYSYL

Further analysis of the NOV31a protein yielded the following properties shown in Table 31B.

TABLE 31B

Protein Sequence Properties NOV31a

| | |
|---|---|
| PSort analysis: | 0.4974 probability located in mitochondrial matrix space; 0.3000 probability located in microbody (peroxisome); 0.2147 probability located in mitochondrial inner membrane; 0.2147 probability located in mitochondrial intermembrane space |

TABLE 31B-continued

Protein Sequence Properties NOV31a

| | |
|---|---|
| SignalP analysis: | No Known Signal Sequence Predicted |

A search of the NOV31a protein against the Geneseq database, a proprietary database that contains sequences published in patents and patent publication, yielded several homologous proteins shown in Table 31C.

TABLE 31C

Geneseq Results for NOV31a

| Geneseq Identifier | Protein/Organism/Length [Patent #, Date] | NOV31a Residues/ Match Residues | Identities/ Similarities for the Matched Region | Expect Value |
|---|---|---|---|---|
| AAE11767 | Human kinase (PKIN)-1 protein- Homo sapiens, 1210 aa. [WO200181555-A2, 01 NOV. 2001] | 1 ... 1213 1 ... 1210 | 1206/1213 (99%) 1208/1213 (99%) | 0.0 |
| AAB65661 | Novel protein kinase, SEQ ID NO: 188 - Homo sapiens, 1171 aa. [WO200073469-A2, 07 DEC. 2000] | 1 ... 1213 8 ... 1171 | 771/1259 (61%) 893/1259 (70%) | 0.0 |
| AAY53013 | Human secreted protein clone co155_12 protein sequence SEQ ID NO:32 - Homo sapiens, 654 aa. [WO9957132-A1, 11 NOV. 1999] | 574 ... 1213 1 ... 654 | 617/663 (93%) 624/663 (94%) | 0.0 |
| AAM25563 | Human protein sequence SEQ ID NO:1078 - Homo sapiens, 590 aa. [WO200153455-A2, 26 JUL. 2001] | 196 ... 850 1 ... 575 | 468/656 (71%) 513/656 (77%) | 0.0 |

TABLE 31C-continued

Geneseq Results for NOV31a

| Geneseq Identifier | Protein/Organism/Length [Patent #, Date] | NOV31a Residues/ Match Residues | Identities/ Similarities for the Matched Region | Expect Value |
|---|---|---|---|---|
| AAW00215 | Drug resistance-associated protein kinase - *Homo sapiens*, 1160 aa. [WO9627015-A2, 06 SEP. 1996] | 10 . . . 1186<br>6 . . . 1160 | 563/1268 (44%)<br>718/1268 (56%) | 0.0 |

In a BLAST search of public sequence datbases, the NOV31a protein was found to have homology to the proteins shown in the BLASTP data in Table 31 D.

TABLE 31D

Public BLASTP Results for NOV31a

| Protein Accession Number | Protein/Organism/Length | NOV31a Residues/ Match Residues | Identities/ Similarities for the Matched Portion | Expect Value |
|---|---|---|---|---|
| Q9QUQ8 | NUCLEAR BODY ASSOCIATED KINASE 2B - *Mus musculus* (Mouse), 1210 aa. | 1 . . . 1213<br>1 . . . 1210 | 1179/1213 (97%)<br>1195/1213 (98%) | 0.0 |
| O88904 | HOMEODOMAIN-INTERACTING PROTEIN KINASE 1 - *Mus musculus* (Mouse), 1209 aa. | 1 . . . 1213<br>1 . . . 1209 | 1177/1213 (97%)<br>1194/1213 (98%) | 0.0 |
| Q9QZR3 | NUCLEAR BODY ASSOCIATED KINASE 2A - *Mus musculus* (Mouse), 1165 aa. | 1 . . . 1213<br>1 . . . 1165 | 1134/1213 (93%)<br>1150/1213 (94%) | 0.0 |
| Q9QZR5 | Homeodomain-interacting protein kinase 2 (EC 2.7.1.-) (Nuclear body associated kinase 1) (Sialophorin tail associated nuclear serine/threonine kinase) - *Mus musculus* (Mouse), 1196 aa. | 1 . . . 1213<br>8 . . . 1196 | 792/1258 (62%)<br>918/1258 (72%) | 0.0 |
| Q99P45 | HOMEODOMAIN-INTERACTING PROTEIN KINASE 2B - *Mus musculus* (Mouse), 1196 aa. | 1 . . . 1213<br>8 . . . 1196 | 791/1258 (62%)<br>917/1258 (72%) | 0.0 |

PFam analysis predicts that the NOV31a protein contains the domains shown in the Table 31E.

TABLE 31E

Domain Analysis of NOV31a

| Pfam Domain | NOV31a Match Region | Identities/ Similarities for the Matched Region | Expect Value |
|---|---|---|---|
| pkinase: domain 1 of 2 | 190 . . . 411 | 85/235 (36%)<br>170/235 (72%) | 1.9e-48 |
| pkinase: domain 2 of 2 | 492 . . . 518 | 13/30 (43%)<br>20/30 (67%) | 0.013 |

Example 32

The NOV32 clone was analyzed, and the nucleotide and encoded polypeptide sequences are shown in Table 32A.

TABLE 32A

NOV32 Sequence Analysis

| NOV32a, CG90729-01 DNA Sequence | SEQ ID NO: 83　　　　3157 BP<br>TGGTTCCCGGGAGCGGTAGAGCTGGACCCGGACCCAAGGCAGTCCAGGCTCCCCGGGG<br><br>CTGCACACATGGAGGGCCAGAGCAGCAGGCGCAGCAGGAGGCCACGGACCCGCGCTGG<br><br>CCTGGGTTCCCTGCCCATGCCCCACGGTGTTGCCCAAACTGCGGCACCCTCCAAGGTG |
|---|---|

TABLE 32A-continued

NOV32 Sequence Analysis

GACTCAAGTTTTCAGCTCCCAGCAAAGAAGAACGCAGCCCTAGGACCCTCGGAACCAA
GGTTGCCTCTGGCACCTGTAGGGCCACGGGCAGCTATGTCAGCTTCCTCGGAAGGACC
GAGGCTGCCTCTGGCATCTCCCCGACCAATCCTGGCTCCACTGTGTACCCCTGAAGGG
CAGAAAACAGCTACTGCCCACCGCAGCTCCAGCCTGGCCCCAACATCTGTGGGCCAGC
TGGTGATGTCTGCCTCACCTGGACCAAAGCCTCCCCCAGCGACCACAQGCTCAGTTCT
GGCTCCGACGTCCCTGGCGCTGGTGATGCCTGCCTCAGCAGGGCCAACATCTCCCCCA
GTCACCCTGGGGCCCAATCTGGCCCCAACCTCCAGAGACCAGAAGCAGGAGCCACCTG
CCTCCGTGGGACCCAAGCCAACACTGGCAGCCTCTGGCCTGAGCCTCGCCCTGGCTTC
TGAGGAGCAGCCCCCAGAACTCCCCTCCACCCCTTCCCCGGTGCCCAGTCCAGTTCTG
TCTCCAACTCAGGAACAGGCCCTGGCTCCAGCATCCACCGCATCAGGCGCAGCCTCTG
TGGGACAGACATCAGCTAGAAAGAGCGATGCCCCAGCCCCTAGACCTCTCCCTGCTTC
TGAGGGGCATCTCCAGCCTCCAGCTCAGACATCTGCTCCTACAGGCTCCCCACCCTGC
ATCCAAACCTCCCCAGACCCTCGGCTCTCCCCCTCCTTCCGAGCCCGGCCTGAGGCCC
TCCACAGCAGCCCTCAGGATCCTCTTTTGCCACGGCCACCCCAGACCTTGCCCTTGGA
TGTGGGCCACGGTCCTTCAGACCCTCGCACTCACTCCCCTQGACTTCTGTCCCCCACC
TTCCGGCCTCGGGCCCCCTCAGGCCAGACTCTGCCCCCACCTCTGCCCAAGCCACCCC
GATCACCCAGCCGTTCCCCAAGCCACTCCCCGAATCGCTCTCCCTGTGTTCCCCCAGC
CCCTCACATGGCCCTCCCAACGCTTGGCACACAGAGTACAGGGCCTGGCAGGTGCCTG
AGCCCCAACCTTCAGGCCCAAGAAGCCCCAGCCCCAGTCACCACCTCCTCTTCTACAT
CCACCCTGTCATCCTCCCCTTGGTCAGCTCAGCCTACCTGGAACAGCGACCCCGGCTT
CCGGATCACTGTGGTCACATGGAACGTGGGCACTGCCATGCCCCCAGACGATGTCACA
TCCCTCCTCCACCTGCGCCCTGCTGACGACACCGACGCCGCAGACATGATCGCCATAG
GGTTGCACGAAGTGAACTCCATGCTCAACAAGCGACTCAAGGACGCCCTCTTCACGGA
CCAGTGGAGTGAGCTGTTCATGGATGCGCTAGGGCCCTTCAACTTCCTGCTGGTGAGT
TCGGTGAGGATGCAGGGTCTCATCCTGCTGCTGTTCCCCAAGTACTACCACCTGCCCT
TCCTGCGAGACGTGCAGACCGACTGCACGCGCACTGGCCTGGGCGGCTACTGGGGTAA
CAAGGGTGGCGTGAGCGTGCGCCTGGCGGCCTTCGGGCACATGCTCTGCTTCCTGAAC
TGCCACTTCCCTGCGCATATGGACAAGGCGGAGCAGCGCAAAGACAACTTCCAGACCA
TCCTCAGCCTCCAGCAGTTCCAAGGGCCGGGCGCACAGGGCATCCTGGATCATGACCT
CGTGTTCTGGTTCGGGGACCTGAACTTCCGCATTGACAGCTATCACCTGGACTTTGTC
AAGTTTGCCATCGACAGTGACCAGCTCCAPCAGCTCTGGGAGAAGGACCAGCTCAACA
TGGCCAAGAACACCTGGCCCATTCTGAAGGGCTTTCACGACGGGCCCCTCAACTTCGC
TCCCACCTTCAAGTTTGATGTGGGTACCAACAAATACGATACCAGTGCCAAGAAACGG
AAGCCACCTTCGACAGACCGTATCCTATCCAACGTCAACCCTCCAGGTCGGGGTCCCA
GCCCCTCAGGACGGAAGAGCCACCGACTCCAGGTGACGCACCACAGCTACCGCAGCCA
CATGGAATACACAGTCAGCCACCACAAGCCTGTGGCTGCCCAGTTCCTCCTGCACTTT
GCCTTCAGGGACGACATGCCACTGGTGCGGCTCGACQTCGCAGATGAGTGGGTGCGGC
CCGAGCAGGCGGTGCTGAGGTACCCCATGGAAACAGTGTTCGCCCGCAGCTCCTGGGA
CTGGATCGGCTTATACCGGGTGGGTTTCCCCCATTCCAAGGACTATGTGCCTTATGTC

TABLE 32A-continued

NOV32 Sequence Analysis

```
TGGGCCAAACATGAAGATCTGGATGGGAATACCTACCAGGTAACATTCAGTGAGGAAT

CACTCCCCAAGGGCCATGGAGACTTCATCCTGGGCTACTATAGTCACAACCACAGCAT

CCTGATCGGCATCACTGAACCCTTCCAGATCTCQCTGCCTTCCTCGGAGTTGGCCAGC

AGCAGCACAGACAGCTCAGGCACCAGCTCAGAGGGAGAGGATGACAGCACACTGGAGC

TCCTTGCACCCAAGTCCCGCAGCCCCAGTCCTGGCAAGTCCAAGCGACACCGCAGCCG

CAGCCCGGGACTGGCCAGGTTCCCTGGGCTTGCCCTACCGCCCTCATCCCGTGAACGC

CGTGGTGCCAGCCGTACCCCCTCACCCCAGAGCCGCCGCCTGTCCCGAGTGGCTCCTG

ACAGGAGCAGTAATGGCAGCAGCCGGGGCAGTAGTGAAGAGGQGCCCTCTGGGTTGCC

TGGCCCCTGGGCCTTCCCACCAGCTGTGCCTCGAAGCCTGCGCCTGTTGCCCCCCTTG

CGCCTACAGACTGTAGACCCTGCTGGTGGTGGCTCCTGGGGACCTGATCGGGAGGCCC

TGGCGCCCAACAGCCTGTCTCCTAGTCCCCAGGGCCATCGGGGCTGGAGCAAGGGGG

CCTGGGGCCCTGAGGGTGGGGTAGCCAGATGGGCCAAGGTCACCACCATTCTGCCTCA

ATCTTTTGCAAGCCCACCTCCCTCT

ORF Start: ATG at 67       ORF Stop: TGA at 3085
SEQ ID NO: 84              1006 aa    MW at 107195.5kD
```

NOV32a,
CG90729-01 Protein Sequence

```
MEGQSSRGSRRPGTRAGLGSLPMPQGVAQTGAPSKVDSSFQLPAKKNAALGPSEPRLA

LAPVGPRAAMSASSEGPRLALASPRPILAPLCTPEGQKTATAHRSSSLAPTSVGQLVM

SASAGPKPPPATTGSVLAPTSLGLVMPASAGPRSPPVTLGPNLAPTSRDQKQEPPASV

GPKPTLAASGLSLALASEEQPPELPSTPSPVPSFVLSPTQEQALAPASTASGAASVGQ

TSARKRDAPAPRPLPASEGHLQPPAQTSGPTGSPPCIQTSPDPRLSPSFRARPEALHS

SPEDPVLPRPPQTLFLDVCQGPSEPGTHSPCLLSFTFRPGAPSGQTVPPPLPKPPRSP

SRSPSHSPNRSPCVPPAPDMALPRLGTQSTGPGRCLSPNLQAQEAPAPVTTSSSTSTL

SSSPWSAQPTWKSDPGFRITVVTWNVGTAMPPDDVTSLLHLGGGDDSDGADMIAIGLQ

EVNSMLNKRLKDALFTDQWSELFMDALGPFNFVLVSSVRMQGVILLLFAKYYHLPFLR

DVQTDCTRTGLGGYWGNKGGVSVRLAAFGHMLCFLNCHLPAHMDKAEQRKDNFQTILS

LQQFQGPGAQGILDHDLVFWFGDLNFRIESYDLHFVKFAIDSDQLHQLWEKDQLNMAK

NTWPILKGFQEGPLNFAPTFKFDVGTNKYDTSAKKRKPAWTDRILWKVKAPGGGPSPS

GRKSHRLQVTQHSYRSHMEYTVSDHKPVAAQFLLQFAFRDDMPLVRLEVADEWVRPEQ

AVVRYRMETVFARSSWDWIGLYRVGFRHCKDYVAYVWAKHEDVDGNTYQVTFSEESLP

KGHGDFILGYYSHNHSILIGITEPFQISLPSSELASSSTDSSGTSSEGEDDSTLELLA

PKSRSPSPGKSKRHRSRSPGLARFPGLALRPSSRERRGASRSPSPQSRRLSRVAPDRS

SNGSSRGSSEEGPSGLPGPWAFPPAVPRSLGLLPALRLETVDPGGGGSWGPDREALAP

NSLSPSPQGHRGLEEGGLGP
```

Further analysis of the NOV32a protein yielded the following properties shown in Table 32B.

TABLE 32B

Protein Sequence Properties NOV32a

| | |
|---|---|
| PSort analysis: | 0.8500 probability located in endoplasmic reticulum (membrane); 0.8200 probability located in nucleus; 0.4400 probability located in plasma membrane; 0.1297 probability located in microbody (peroxisome) |

TABLE 32B-continued

Protein Sequence Properties NOV32a

| | |
|---|---|
| SignalP analysis: | No Known Signal Sequence Predicted |

A search of the NOV32a protein against the Geneseq database, a proprietary database that contains sequences published in patents and patent publication, yielded several homologous proteins shown in Table 32C.

TABLE 32C

Geneseq Results for NOV32a

| Geneseq Identifier | Protein/Organism/Length [Patent #, Date] | NOV32a Residues/ Match Resideus | Identities/ Similarities for the Matched Region | Expect Value |
|---|---|---|---|---|
| AAB27845 | Sequence homologous to protein fragment encoded by gene 4 - Homo sapiens, 381 aa. [WO200055199-A1, 21 Sep. 2000] | 613 . . . 993<br>1 . . . 381 | 381/381 (100%)<br>381/381 (100%) | 0.0 |
| AAG73981 | Human colon cancer antigen protein SEQ ID NO:4745 - Homo sapiens, 279 aa. [WO200122920-A2, 05 Apr. 2001] | 481 . . . 735<br>3 . . . 257 | 253/255 (99%)<br>254/255 (99%) | e-153 |
| AAB27846 | Protein fragment encoded by gene 4 - Homo sapiens, 382 aa. [WO200055199-A1, 21 Sep. 2000] | 613 . . . 993<br>1 . . . 382 | 260/382 (68%)<br>262/382 (68%) | e-145 |
| AAB27797 | Human secreted protein #4 - Homo sapiens, 255 aa. [WO200055199-A1, 21 Sep. 2000] | 504 . . . 735<br>1 . . . 232 | 230/232 (99%)<br>231/232 (99%) | e-139 |
| AAW97094 | Phosphatidylinositol 4,5-bisphosphate 5-phosphatase - Homo sapiens, 372 aa. [WO9900507-A1, 07 Jan. 1999] | 488 . . . 839<br>1 . . . 355 | 167/355 (47%)<br>221/355 (62%) | 2e-92 |

In a BLAST search of public sequence datbases, the NOV32a protein was found to have homology to the proteins shown in the BLASTP data in Table 32D.

TABLE 32D

Public BLASTP Results for NOV32a

| Protein Accession Number | Protein/Organism/Length | NOV32a Residues/ Match Residues | Identities/ Similarities for the Matched Portion | Expect Value |
|---|---|---|---|---|
| Q9UDT9 | WUGSC:H_DJ412A9.2 PROTETN - Homo sapiens (Human), 1056 aa (fragment). | 1 . . . 1006<br>13 . . . 1056 | 1005/1044 (96%)<br>1006/1044 (96%) | 0.0 |
| Q9JMC1 | PROLINE-RICH INOSITOL POLYPHOSPHATE 5-PHOSPHATASE - Rattus norvegicus (Rat), 1001 aa. | 1 . . . 1006<br>1 . . . 1001 | 842/1008 (83%)<br>884/1008 (87%) | 0.0 |
| Q15735 | PHOSPHATIDYLINOSITOL (4,5)BISPHOSPHATE 5-PHOSPHATASE HOMOLOG - Homo sapiens (Human), 397 aa (fragment). | 613 . . . 1006<br>4 . . . 397 | 394/394 (100%)<br>394/394 (100%) | 0.0 |
| O09040 | PUTATIVE PHOSPHATASE (PUTATIVE PHOSPHOINOSITIDE 5-PHOSPHATASE TYPE II) - Mus musculus (Mouse), 468 aa. | 425 . . . 843<br>34 . . . 454 | 201/423 (47%)<br>262/423 (61%) | e-108 |
| Q9BT40 | SKIP FOR SKELETAL MUSCLE AND KIDNEY ENRICHED INOSITOL PHOSPHATASE - Homo sapiens (Human), 448 aa. | 425 . . . 839<br>16 . . . 431 | 196/418 (46%)<br>258/418 (60%) | e-107 |

PFam analysis predicts that the NOV32a protein contains the domains shown in the Table 32E.

TABLE 32E

Domain Analysis of NOV32a

| Pfam Domain | NOV32a Match Region | Identities/ Similarities for the Matched Region | Expect Value |
|---|---|---|---|
| IPPc: domain 1 of 2 | 56...412 | 6/357 (2%) 249/357 (70%) | 5.9e+04 |

TABLE 32E-continued

Domain Analysis of NOV32a

| Pfam Domain | NOV32a Match Region | Identities/ Similarities for the Matched Region | Expect Value |
|---|---|---|---|
| IPPc: domain 2 of 2 | 421...736 | 128/424 (30%) 249/424 (59%) | 8.9e−108 |

Example 33

The NOV33 clone was analyzed, and the nucleotide and encoded polypeptide sequences are shown in Table 33A.

TABLE 33A

NOV33 Sequence Analysis

| | |
|---|---|
| NOV33a, CG90760-01 DNA Sequence | SEQ ID NO: 85    6261 bp<br>AAATTCAAACCAGTCAGCTTCATCTGGGCTCTGATTCATCTTTATTCCCTCCATCAT<br>CTAGACTTGATTTTATTTGTACCAAGGAGATGCGTGTCTAATGTTTTTCTTTCTTCTA<br>TTTCTAGGAGGGCTGTTGGCCTGCTGCTGTGCTGCTGAACAGTATGCAGTCCTTTCGG<br>GAGCAAAGCAGTTACCACGGAAACCAGCAAAGCTACCCACAGGAGGTACACGGCTCAT<br>CCCGGCTAGAAGAGTTCAGCCCTCGTCAGGCCCAGATGTTCCAGAATTTTGGAGGTAC<br>AGGTGGCAGTAGTGCCAGCAGTCGCAGTGGCAGTCGTCGTGOACGACGAGGAGCAGCA<br>GCTGCTGCGGCAGCGATGGCTAGCGACACCTCTGGCCATCAAGGTTACCAGGGTTTCA<br>GGAAAGAGGCTGGAGATTTTTACTACATGGCAGGCAACAAAGACCCCGTGACTACAGG<br>AACCCCACAGCCTCCTCAGCGAAGGCCTTCTGGGCCTCTCCACAGCTATGGACCCCCC<br>CAGGGGAGCAGCTTTGGCAATCAGTATGGGAGTGAGGGTCATGTGGGCCAGTTTCAAG<br>CACAGCACTCTGGCCTTGGCGGTGTGTCACATTATCAGCAGGATTACACTGGGCCTTT<br>CTCTCCAGGGAGTCCTCAGTACCAACACCACGCTTCCAGCCACCAGCACCACCAGCAA<br>GTCCAGCAGTTGAGACAACAGCTTTACCAGTCCCATCAGCCCCTQCCACAGGCCACTG<br>GCCAACCAGCATCCAGCTCATCCCATCTACAGCCAATCCAGCGGCCCTCAACTCTGCC<br>ATCCTCTGCTCCTGGTTACCAGTTAAGAGTCGGTCAGTTTGGCCAACACTATCAGTCT<br>TCTGCTTCCTCCTCCTCCTCCTCCTTCCCTTCACCACAGCGTTTTAGCCAGTCTG<br>GACAGAGCTATGATGGCAGTTACAATGTGAATGCTGGATCTCAGTATGAAGGACACAA<br>TGTGGGTTCTAATGCACAGGCTTATGGAACACAATCCAATTACAOCTATCAGCCTCAA<br>TCTATGAAGAATTTTGAACAGGCAAAGATTCCACAAGGGACCCAACAGGGGCAGCAGC<br>AGCAGCAACCGCAGCAACAACAACACCCTTCTCAGCATGTGATGCAGTATACTAACGC<br>TGCCACCAAGCTGCCCCTGCAAAGCCAACTGGOGCAGTACAACCAGCCTGAGGTTCCT<br>GTGAGGTCCCCCATGCAGTTTCACCAGAACTTCAGCCCCATTTCTAACCCTTCTCCAG<br>CTGCCTCTGTCGTTCAGTCTCCAAGCTGTAGTTCTACCCCATCTCCTCTCATGCAGAC<br>TGGGGAGAATCTCCAGTGTGCGCAAGGCAGTGTGCCTATCCGTTCCAGAAACAGAATT<br>TTACAGTTAATGCCTCAACTCAGTCCAACCCCATCAATGATGCCCAGTCCTAATTCTC<br>ATGCTGCAGGCTTCAAAGGGTTTGGACTAGAACGCGTACCAGAAAAGCCACTGACAGA<br>TCCTGGGTTCAGTACTTTGAGTGCTCTCAGTACTCAAGTGGCCAATCTTCCTAACACT<br>GTCCAGCACATGTTACTTTCTGATGCCCTGACTCCTCAGAAGAAGACCTCCAAGAGGC<br>CCTCATCTTCCAAGAAACCAGAPAGCTGCACAAATTCTGAACGCTCCTCACAACCTGA |

TABLE 33A-continued

NOV33 Sequence Analysis

AGAACAGCTGAACTCCCCTATGGCAGAGTCATTAGATGGAGGCTGCTCCAGCAGTTCA

GAGGATCAAGGCCAGAGAGTGCGGCAACTAAGTGGCCAGACCACCAGCTCTCACACCA

CCTACAAGGGTGGAGCCTCTGAGAAAGCTGGCTCCTCACCGGCACAAGGTGCTCAGAA

TGAACCCCCCAGACTCAATGCTAGTCCTGCCGCAAGAGAAGAGGCCACCTCACCAGGC

GCTAAGCACATGCCATTGTCATCCGACGCGAACCCAAAGCTTAATGACAACACTGTTG

GGGTGATTGTCTCCCGGGAAGCCATGACAGGTCGGGTAGAAAAGCCTGGTGGACAAGA

TAAAGGCTCCCAAGAGGAPGATCCTGCAGCCACTCAAAGGCCACCTAGCAATGGTGGG

GCAAAGGAAACCAGTCATGCATCACTTCCCCAGCCAGAGCCTCCAGGAGGAGGAGGGA

GCAAAGCAAACAAOAATGGCGATAACAACTCCAACCATAATGGACAAGGAAATGGCCA

GAGTGGCCACTCTGCAGCGGGCCCTGGTTTTACGAGCAGAACTGAGCCTAGCAAATCT

CCTGGAAGTCTGCGCTATAGTTACAAAGATAGTTTCCGGTCAGCCGTGCCACGAAATG

TCAGTGGCTTTCCTCAGTATCCTACAGGGCAAGAAAAGGGAGATTTCACTGGCCATGG

GGAACGAAAGGGTAGAAATGAAAAATTCCCAAGCCTCCTGCAGCAAGTGCTTCAGGGT

TACCACCACCACCCTGACAGQAGATATTCTAGGAGTACTCAAGAGCATCAGGGGATGG

CTGGTAGCCTAQAACGAACCACAAGGCCCAATGTCTTGGTTAGTCAAACCAATGAATT

AGCTAGCAGGGCCTTCTGAACAAAAGCATTGCGTCTCTATTAGAAAATCCCCACTGG

GGCCCCTGGGAAAGGAAATCAAGCAGCACAGCTCCTGAAATCAAACAGATCAATTTGA

CTGACTATCCAATTCCCAGAAAGTTTGAAATAGAGCCTCAGTCATCAGCACATOAGCC

TGGGGGTTCCCTCTCTGAAACAAGATCAGTGATCTCTGATATTTCTCCACTAAGACAG

ATTGTCAGGGACCCAGGGGCTCACTCACTGGGACACATGAGTGCCGACACCAGAATTG

GGAGGAATGACCGTCTCAATCCAACTTTAAGTCAGTCGGTCATTCTTCCTGGTGGTTT

GGTGTCCATGGAAACCAAGCTGAAATCCCAGAGCGCGCAGATAAAAGAGGAAGACTTT

GAACAGTCTAAATCTCAAQCTAGTTTCAACAACAAGAAATCPGCAGACCACTGCCATC

CTCCTAGCATCAACCATGAGTCTTACCGCGGCAATGCCAGCCCTGGAGCACCAACCCA

TGATTCCCTTTCAGACTATGGCCCGCAAGACAGCAGACCCACGCCAATGCGGCGCGTC

CCTGGCAGAGTrGGTGCTCCGGAGGGCATGAGGGGTCGGTCCCCTTCTCAATATCATC

ACTTTGCAGAAAAATTGAAAATGTCTCCTCGGCGGAGCAGAGGCCCAGGGGAGACCC

TCATCACATGAATCCACACATGACCTTTTCAGAGAGGGCTAACCGGAGTTCTTTACAC

ACTCCCTTTTCTCCCAACTCAGAAACCCTCGCCTCTGCTTATCATGCAAATACTCGGG

CTCATGCTTATCGGGACCCTAACGCACCTTTQAATTCTCAGCTGCATTATAAGAGACA

GATGTACCAACAGCAACCAGAGGAGTATAAAGACTCQAGCAGCCOTTCTGCTCAGGGA

GTAATTGCTGCAGCACAGCACACGCAGGAGGGGCCACCGAAGAGTCCAAGGCAGCAGC

AGTTTCTTGACAGAGTACGGAGCCCTCTGAAAAATQACAAAGATGGTATGATGTATGG

CCCACCAGTGGGGACTTACCATGACCCCAGTGCCCAGGAGGCTGGGCGCTGCCTAATG

TCTACTGATGGTCTCCCTAACAAGGCCATGGAATTAAAGCATGGCPCCCAGAAGTTAC

AAGAATCCTCTTGGCATCTTTCTCGGCAAACTTCTCCAGCCAAAAGCAGCGGTCCTCC

AGGAATGTCCAGTCAAAAAAGCTATGGGCCGCCCCATGAGACTGATGGACATGGACTA

GCTGAGGCTACACAGTCATCCAAACCTCGTAGTGTTATCCTGACACTTCCAGGCCAGG

AGGATCATTCTTCTCAAAACCCCTTAATCATGAGGAGGCGTGTTCQTTCTTTTATCTC

TABLE 33A-continued

NOV33 Sequence Analysis

TCCCATTCCCAGTAACAGACAGTCACAAGATGTAAAGAACAGTAGCACTGAAGATAAA

GGTCGCCTCCTTCACTCATCAAAAGAAGCCGCTGATAAAGCATTCAATTCCTATCCCC

ATCTTTCTCACAGTCAGGATATCAAGTCTATCCCTAAGAGAGATTCCTCCAAGGACCT

TCCAAGTCCAGATAGTAGAAACTGCCCTCCTCTTACCCTCACAAGCCCTGCTAAGACC

AAAATACTGCCCCCACGGAAAGGACGGGGATTGAAATTGGAAGCTATACTTCACAAGA

TTACATCCCCAAATATTAGGAGGAGCGCATCTTCGAACAGTGCCGAGGCTGCGGCAGA

CACGGTTACGCTTGATGATATACTGTCTTTGAAGAGTGGTCCTCCTGAAGGTGGGAGT

GTTGCTGTTCAGGATGCTGACATAGAGAAGAGAAAAGGTGAOGTCGCTTCGCACCTAG

TCAGTCCAGCAAACCAGGAGTTGCACGTAGAGAAACCTCTTCCAAGGTCTTCAGAAGA

GTGGCGTGGCACCGTGGATGACAAAGTGAAGACAGAGACACATGCAGAAACAGTTACT

GCCGGAAAGGAACCCCTGGTGCCATGACATCCACAACCTCACAGAAGCCTGGTAGTA

ACCAAGGGAGACCAGATGGTTCCCTGGGTGGAACAGCACCTTTAATCTTTCCAGACTC

AAAGAATGTACCTCCAGTGGGCATATTGGCCCCTGAGGCAAACCCCAAGGCTGAAGAG

AAGGAGAACGATACAGTGACGATTTCACCGAAGCAAGAGGGTTTCCCTCCAAAGGGAT

ATTTCCCATCAGGAAAGAACAAGGGGAGACCCATTGGTAGTGTGAATAAGCAAAAGAA

ACAGCAGCACCCACCGCCTCCACCCCCTCAGCCCCCACAGATACCAGAAGGTTCTGCA

GATGGAGAGCCAAAGCCAAAAAAACAGAGGCAAAGGAGGGACAGAACGAAGCCTGGGG

CCCAGCCGAGGAAGCGAAAAACCAAACAAGCAGTTCCCATTGTGGAACCCCAAGAACC

TGAGATCAAACTAAAATATGCCACCCAGCCACTGGATAAAACTGATGCCAAGAACAAG

TCTTTTTACCCTTACATCCATGTAGTAAATAAGTGTGAACTTGGAGCCGTTTGTACAA

TCATCAATGCTGAGGAAGAAGAACAGACCAAATTAGTGAGGGGCAGGAAGGGTCAGAG

GTCACTGACCCCTCCACCTAGCAGCACTGAAAGCAAGGCGCTCCCGGCCTCGTCCTTT

ATGCTGCAGGGACCTCTTGTGACAGAGTCTTCGCTTATGCGGCACCTGCTTTGCTGTC

TGTGTGGCAAGTGGGCCAGTTACCGGAACATCGGTGACCTCTTTGGACCTTTPTATCC

CCAAGATPATGCAGCCACTCTCCCGAAGAATCCACCTCCTAAGAGGGCCACAGAAATG

CAGAGCAAACTTAACGTACGGCACAAAAGTGCTTCTAATCGCTCCAAGACCGACACTG

AGGAGGAGGAAGAGCAGCACCACCAGCAGAAQGAGCAGAGAAGCCTCCCCCCACACCC

CAGGTTTAAGCGGCGCCACCGCTCGGAAGACTGTGGTGGAGGCCCTCGGTCCCTGTCC

AGGGGCCTCCCTTCTAAAAAAGCAGCCACTGAGGGCAGCAGTGAAAACACTGTTTTGG

ACTCGAAGCCCTCCGTGCCCACCACTTCAGAAGGTGGCCCTGACCTGGAGTTACAAAT

CCCTGAACTACCTCTTGACAGCAATGAATTTTGGGTCCATGAGGGTTGTATTCTCTGG

GCCAATGGAATCTACCTGGTTTGTGGCAGGCTCTATGGCCTGCAGGAAGCGCTGGAAA

TGAGAAGGTGGTGGACACTCGTGATGGAATGGAAATCGTCCTACCGTGCAGCCACACC

CAACAAAGGCTGCTCCTTCCGATACCATTACCCGTGTGCCATTGATGCAGATTGTTTG

CTACATGAGGAGAACTTCTCGGTGAGGTGCCCTAAGCAACAAGGTGAGACTGTGGAGA

TGAGAAGGTGGTGGACACTCGTGATGGAATGGAAATCGTCCTACCGTGCAGCCACACC

CTGCCCTGCCCCGCCCCGCCCCGCCCGCGTGCCTGCCCATGCCAGCACTTCCTTAAGT

TCTCACATCACACTCAAACCAGTGACACCACAGGAAAGAAAGACCCAAGACGTTGCAA

TGGCTGTTTGGATCCACACAATCTCCATAGTGACAATGTGGGGGGAGGGGCCACGCCT

TABLE 33A-continued

NOV33 Sequence Analysis

GGGATGATGGGGAAAGGGTGGGGGGATTAAAAGGGAGGGATAAATATATATATAT

| | |
|---|---|
| NOV33a, CG90760-01 Protein Sequence | ORF Start: ATG at 160   ORF Stop: TGA at 6211<br>SEQ ID NO: 86        2017 aa   MW at 218079.6kD<br>MQSFREQSSYHGNQQSYPQEVHGSSRLEEFSPRQAQMFQNFCGTCGSSCSSCSCSCGG |

RRGAAAAAAAMASETSGHQGYQGFRKEAGDFYYMAGNKDPVTTGTPQPPQRRPSGPVQ

SYGPPQGSSPCNQYGSEGEVCQFQAQHSGLCGVSHYQQDYTGPESPCSAQYQQQASSQ

QQQQQVQQLRQQLYQSHQPLPQATGQPASSSSHLQPMQRPSTLPSSAAGYQLRVCQFC

QHYQSSASSSSSSFPSPQRFSQSGQSYDGSYNVNAGSQYEGHNVGSNAQAYGTQSNY

SYQPQSMKNFEQAKIPQGTQQGQQQQQPQQQQHPSQHVMQYTNAATKLPLQSQVGQYN

QPEVFVRSPMQFHQNFSPISNPSPAASVVQSPSCSSTPSPLMQTGENLQCCQGSVPMG

SRNRILQLMPQLSPTPSMMPSPNSEAACFKGFCLEGVPEKRLTDPCLSSLSALSTQVA

NLPNTVQHMLLSDALTPQKKTSKRPSSSKKADSCTNSEGSSQPEEQLKSPMAESLDGG

CSSSSEDQGERVRQLSGQSTSSDTTYKGGASEKAGSSPAQCAQNEPPRLNASPAAREE

ATSPGAKDMPLSSDCNPKVNEKTVGVIVSREAMTGRVEKFCCQDKCSQEDDPAATQRP

PSNGGAKETSHASLPQPEPPGGGGSKGNKNGDNNSNHNGEGNGQSGHSAAGPGFTSRT

EPSKSPGSLRYSYKDSFGSAVPRNVSGFPQYPTGQEKGDFTGHGERKGRNEKFPSLLQ

EVLQGYHHHPDRRYSRSTQEHQGMAGSLEGTTRPNVLVSQTNELASRGLLNKSIGSLL

ENPHWGPWERKSSSTAPEMKQINLTDYPIPRKFEIEPQSSAHEPGGSLSERRSVICDI

SPLRQIVRDPGAHSLGHMSADTRIGRNDRLNPTLSQSVILPGGLVSMETKLKSQSGQI

KEEDFEQSKSQASFNNKKSGDHCHPPSIKHESYRGNASPGAATHDSLSDYGPQDSRPT

PMRRVPGRVGGREGMRGRSPSQYHDFAEKLKMSPGRSRGPGGDPHHMNPHMTFSERAN

RSSLHTPFSPNSETLASAYHANTRAHAYGDPNAGLNSQLHYKRQMYQQQPEEYKDWSS

GSAGGVIAAAQHRQEGPRKSPRQQQFLDRVRSPLKNDKDGMMYGPPVGTYHDPSAQEA

GRCLMSSDGLPNKGMELKHGSQKLQESCWDLSRQTSPAKSSGPPGMSSQKRYGPPHET

DGHGLAEATQSSKPGSVMLRLPGQEDHSSQNPLIMRRRVRSFISPIPSKRQSQDVKNS

STEDKCRLLESSKEGADKAFNSYAHLSHSQDIKSIPKRDSSKDLPSPDSRNCPAVTLT

SPAKTKILPPRKGRGLKLEAIVQKITSPNIRRSASSNSAEAGGDTVTLDDILSLKSGP

PEGGSVAVQDADIEKRKGEVASDLVSPANQELHVEKPLPRSSEEWRGSVDDKVKTETH

AETVTAGKEPPGAMTSTTSQKPGSNQGRPDGSLGGTAPLIFPDSKNVPPVGILAPEAN

PKAEEKENDTVTISPKQEGPPPKGYFPSGKKKCRPIGSVNKQKKQQQPPPPPQPPQI

PEGSADGEPKPKKQRQRRERRKPGAQPRKRKTKQAVPIVEPQEPEIKLKYATQPLDKT

DAKNKSFYPYIHVVNKCELGAVCTIINAEEEEQTKLVRGRKGQRSLTPPPSSTESKAL

PASSFMLQGPVVTESSVMGHLVCCLCGKWASYRNMGDLFGPFYPQDYAATLPKNPPPK

RATEMQSKVKVRHKSASNGSKTDTEEEEEQQQQQKEQRSLAAHPRFKRRHRSEDCGGG

PRSLSRGLPCKKAATEGSSEKTVLDSKPSVPTTSEGGPELELQIPELPLDSNEFWVHE

GCILWANGIYLVCGRLYGLQEALEIAREMKCSHCQEAGATLGCYNKGCSFRYHYPCAI

DADCLLHEENFSVRCPKQQGETVEMRRWWTLVMEWKSSYRAATPCPAPPRPARVPAHA

STSLSSHITLKPVTPQERKTQDVGMAVSMDTISIVTMWGEGGGVG

Further analysis of the NOV33a protein yielded the following properties shown in Table 33B.

TABLE 33B

Protein Sequence Properties NOV33a

| | |
|---|---|
| PSort analysis: | 0.9700 probability located in nucleus; 0.3000 probability located in microbody (peroxisome); 0.1000 probability located in mitochondrial matrix space; 0.1000 probability located in lysosome (lumen) |

TABLE 33B-continued

Protein Sequence Properties NOV33a

| | |
|---|---|
| SignalP analysis: | No Known Signal Sequence Predicted |

A search of the NOV33a protein against the Geneseq database, a proprietary database that contains sequences published in patents and patent publication, yielded several homologous proteins shown in Table 33C.

TABLE 33C

Geneseq Results for NOV33a

| Geneseq Identifier | Protein/Organism/Length [Patent #, Date] | NOV33a Residues/ Match Residues | Identities/ Similarities for the Matched Region | Expect Value |
|---|---|---|---|---|
| AAB40646 | Human ORFX ORF410 polypeptide sequence SEQ ID NO:820 - *Homo sapiens*, 494 aa. [WO200058473-A2, 05 Oct. 2000] | 1559 . . . 1933 98 . . . 491 | 133/416 (31%) 196/416 (46%) | 2e-48 |
| AAY51611 | Human HSGT1 protein - *Homo sapiens*, 1798 aa. [WO200008143-A2, 17 Feb. 2000] | 1 . . . 594 1 . . . 522 | 179/625 (28%) 248/625 (39%) | 8e-36 |
| ABG19553 | Novel human diagnostic protein #19544 - *Homo sapiens*, 901 aa. [WO200175067-A2, 11 Oct. 2001] | 161 . . . 592 407 . . . 801 | 106/451 (23%) 158/451 (34%) | 4e-11 |
| ABG19553 | Novel human diagnostic protein #19544 - *Homo sapiens*, 901 aa. [WO200175067-A2, 11 Oct. 2001] | 161 . . . 592 407 . . . 801 | 106/451 (23%) 158/451 (34%) | 4e-11 |
| AAE13839 | Human lung tumour-specific protein SCC2-29 - *Homo sapiens*, 4019 aa. [WO200172295-A2, 04 Oct. 2001] | 1851 . . . 1930 3537 . . . 3616 | 30/81 (37%) 45/81 (55%) | 9e-10 |

In a BLAST search of public sequence datbases, the NOV33a protein was found to have homology to the proteins shown in the BLASTP data in Table 33D.

TABLE 33D

Public BLASTP Results for NOV33a

| Protein Accession Number | Protein/Organism/Length | Nov33a Residues/ Match Residues | Identities/ Similarities for the Matched Portion | Expect Value |
|---|---|---|---|---|
| Q9EPQ8 | STROMELYSIN-1 PDGF-RESPONSIVE ELEMENT BINDING PROTEIN - *Mus musculus* (Mouse), 1965 aa. | 1 . . . 1933 1 . . . 1960 | 1781/1965 (90%) 1828/1965 (92%) | 0.0 |
| O14528 | KIAA0292 (DJ257I20.4) - *Homo sapiens* (Human), 1716 aa (fragment). | 245. . .1963 1. . .1698 | 1692/1719 (98%) 1694/1719 (98%) | 0.0 |
| Q9UGU0 | DJ597B2.1 (TRANSCRIPTION FACTOR 20 (AR1, KIAA0292)) - *Homo sapiens* (Human), 1641 aa (fragment). | 245. . .1885 1. . .1641 | 1641/1641 (100%) 1641/1641 (100%) | 0.0 |
| Q13078 | AR1 - *Homo sapiens* (Human), 935 aa (fragment). | 1083. . .2017 1. . .935 | 935/935 (100%) 935/935 (100%) | 0.0 |
| Q60792 | STROMELYSIN PDGF RESPONSIVE ELEMENT BINDING PROTEIN TRANSCRIPTION FACTOR - *Mus musculus* (Mouse),937 aa. | 988 . . . 1902 1 . . . 913 | 839/915 (91%) 863/915 (93%) | 0.0 |

PFam analysis predicts that the NOV33a protein contains the domains shown in the Table 33E.

TABLE 33E

Domain Analysis of NOV33a

| Pfam Domain | NOV33a Match Region | Identities/ Similarities for the Matched Region | Expect Value |
|---|---|---|---|
| Flu_PB1: domain 1 of 1 | 920...935 | 7/16 (44%) 13/16 (81%) | 3.4 |
| Integrase_Zn: domain 1 of 1 | 1886...1894 | 4/9 (44%) 9/9 (100%) | 6.9 |
| PHD: domain 1 of 1 | 1886...1932 | 12/53 (23%) 24/53 (45%) | 0.81 |

Example 34

The NOV34 clone was analyzed, and the nucleotide and encoded polypeptide sequences are shown in Table 34A.

TABLE 34A

NOV34 Sequence Analysis

| | |
|---|---|
| NOV34a, CG90770-01 DNA SEQUENCE | SEQ ID NO: 87    549 bp<br>GGGCCGGCGGCAGTCTGGGAGCGGCGCGCCATGTACACCATCATCAACCGGCCCAGCA<br><br>AGTTGGTCGCGCAGCGCCGCACAGGTCTCACGCAGCAGCAGGTGAAGGGCCAGCTCCA<br><br>GGAGCTCCTGAAAAGCCGGCAGCCCGCCCCGCCGACCTTCCAGCCCCAGCGGGCGCAG<br><br>CCCTTCGCGCAGCCGCTCGGACCCTGGCCCCTGTCGAGTGCAGGGCCAAGGCTTGTGT<br><br>TCAATCGTGTGAATCGCCCGCGGGACCCCTCCAAGTCCCCATCCCTCCAGGGGACCCA<br><br>GGAGACCTACACACTGCCCCACAAGGAGAATGTCCCCTTTGTGTCCGAAGCCTGGCAC<br><br>CAGGTGCCGCAGCAGCTGGATGGTGGCCCAGCCCGTGAGGGCGGGACAAGGCCTCTGC<br><br>AGTGGGTGGAGAGGATCCCCAATCCCCGGCTGCAGAACTTCGTGCCCATTGACTTGGA<br><br>CGAGTCGTGGGCGCACCACTTCCTGGCTAGAATCACCAGCTGTTCCTAGCGGCTGCTG<br><br>GGAGGGAGCGCTGCTATGGTCTACCTA |
| NOV34a, CG90770-01 Protein Sequence | ORF Start: ATG at 31    ORF Stop: TAG at 511<br>SEQ ID NO: 88    160 aa    MW at 18139.5kD<br>MYTIINGPSKLVAQRRTGLTQQQVKGQLQELLKSRQPAPPTLQPQRAQPFAQPLGWP<br><br>LSSAGPRLVFNRVNRRDPSKSPSLQGTQETYTLAHKENVRFVSEAWQQVRQQLDGGP<br><br>AGEGGTRPVQWVERIPNPRLQNFVPIDLDEWWAQHFLARITSCS |

Further analysis of the NOV34a protein yielded the following properties shown in Table 34B.

TABLE 34B

Protein Sequence Properties NOV34a

| | |
|---|---|
| PSort analysis: | 0.8127 probability located in lysosome (lumen); 0.4687 probability located in microbody (peroxisome); 0.3600 probability located in mitochondrial matrix space; 0.0000 probability located in endoplasmic reticulum (membrane) |

TABLE 34B-continued

Protein Sequence Properties NOV34a

| | |
|---|---|
| SignalP analysis: | No Known Signal Sequence Predicted |

A search of the NOV34a protein against the Geneseq database, a proprietary database that contains sequences published in patents and patent publication, yielded several homologous proteins shown in Table 34C.

TABLE 34C

Geneseq Results for NOV34a

| Geneseq Identifier | Protein/Organism/Length [Patent #, Date] | NOV34a Residues/ Match Residues | Identities/ Similarities for the Matched Region | Expect Value |
|---|---|---|---|---|
| AAB43129 | Human ORFX ORF2893 polypeptide sequence SEQ ID NO: 5786-*Homo sapiens*, 159 aa. [WO200058473-A2, 05-OCT-2000] | 1 . . . 160<br>1 . . . 159 | 123/162 (75%)<br>127/162 (77%) | 4e−63 |
| AAB59006 | Breast and ovarian cancer associated antigen protein sequence SEQ ID 714-*Homo sapiens*, 200 aa. [WO200055173-A1, 21-SEP-2000] | 40 . . . 160<br>72 . . . 200 | 97/129 (75%)<br>103/129 (79%) | 3e−51 |
| ABG06662 | Novel human diagnostic protein #6653-*Homo sapiens*, 63 aa. [WO200175067-A2, 11-OCT-2001] | 85 . . . 146<br>1 . . . 62 | 56/62 (90%)<br>60/62 (96%) | 9e−28 |
| ABG06662 | Novel human diagnostic protein #6653- -*Homo sapiens*, 63 aa. [WO200175067-A2, 11-OCT-2001] | 85 . . . 146<br>1 . . . 62 | 56/62 (90%)<br>60/62 (96%) | 9e−28 |
| AAM82721 | Human immune/haematopoietic antigen SEQ ID NO: 10314-*Homo sapiens*, 101 aa. [WO200157182-A2, 09-AUG-2001] | 22 . . . 99<br>13 . . . 87 | 53/80 (66%)<br>59/80 (73%) | 3e−21 |

In a BLAST search of public sequence datbases, the NOV34a protein was found to have homology to the proteins shown in the BLASTP data in Table 34D.

TABLE 34D

Public BLASTP Results for NOV34a

| Protein Accession Number | Protein/Organism/Length | NOV34a Residues/ Match Residues | Identities/ Similarities for the Matched Portion | Expect Value |
|---|---|---|---|---|
| Q96KV8 | C349E10.1.1 (NOVEL PROTEIN, ISOFORM 1)-*Homo sapiens* (Human), 160 aa. | 1 . . . 160<br>1 . . . 160 | 137/160 (85%)<br>144/160 (89%) | 1e−76 |
| Q9BUT9 | HYPOTHETICAL 22.4 KDA PROTEIN-*Homo sapiens* (Human), 207 aa (fragment). | 1 . . . 160<br>48 . . . 207 | 137/160 (85%)<br>144/160 (89%) | 1e−76 |
| Q9CQB2 | 9530058B02RIK PROTEIN-*Mus musculus* (Mouse), 160 aa. | 1 . . . 160<br>1 . . . 160 | 121/160 (75%)<br>134/160 (83%) | 1e−66 |
| Q96J99 | HTB-*Homo sapiens* (Human), 113 aa. | 83 . . . 148<br>1 . . . 66 | 58/66 (87%)<br>64/66 (96%) | 2e−30 |
| Q969E9 | C349E10.1.2 (NOVEL PROTEIN, ISOFORM 2) (SIMILAR TO RIKEN CDNA 9530058B02 GENE)-*Homo sapiens* (Human), 75 aa. | 1 . . . 61<br>1 . . . 61 | 51/61 (83%)<br>53/61 (86%) | 4e−22 |

PFam analysis predicts that the NOV34a protein contains the domains shown in the Table 34E.

TABLE 34E

Domain Analysis of NOV34a

| Pfam Domain | NOV34a Match Region | Identities/ Similarities for the Matched Region | Expect Value |
|---|---|---|---|
| No Significant Matches Found | | | |

Example 35

The NOV35 clone was analyzed, and the nucleotide and encoded polypeptide sequences are shown in Table 35A.

TABLE 35A

| NOV35 Sequence Analysis | |
|---|---|
| NOV35a, CG91002-01 DNA Sequence | SEQ ID NO: 89    1255 bp<br>GCGAGTGTTTCCTGCAATATTGGATTGGCATGACAGGCTGGAGCTGCCTTGTGACAG<br>GAGCAGGAGGGTTTCTGGGTCAGAGGATCATCCGCCTCTTGGTGGAGGAGAAGGAGCT<br>GAAGGAGATCAGGGCCTTGGACAAGGCCTTCAGACCAAAGCTGAGCGAGGAATTTTCT<br>GAGCTCCAGAACAAGACCAAGCTGACAGTGCTGGAAGGAGACATTCTGGATGAGCCAT<br>TCCTCAAGAGAGCCTGCCACGACATGTCGGTCATCATCCACACTGCCTCTATCATATA<br>TGTCATCGGTGTCACTCACAGAGACTCCATCATGAATGTCAATGTGAAAGGTACACAG<br>CTTCTGTTGGACCCCTGTGTCCAAGCTACAGTGCCAGTCTTCATCTACACCAGTACCC<br>CAGAGGTACCCGGQCCCAATTCCTACAAGGAAATCATCCAGAACAGTCACGAAGAACA<br>GCCTCTGCAAAACACATGGTACCCTCCATACCCACACAGCAAAAAGCTTGCTGAGAAG<br>GCTGTGCTCGCGGCTAATGGGTGGACTCTGAAAAACGGTGGCACCTTGTACACTTGTG<br>CCTTAAGACCAATGTTTATCTATGGGAAGGAACCCCAATCCTTTCTGCCGGTATAAA<br>TGAGGCCCTAAACAACCATCGGATCCTGTCAAGTTTCAGCAAGTTCTCCAGAGTCAAC<br>CCACTCTATATTGGAAACATGGCCTCGGCCCACATTCTGGCCTTGAGGCCCTGCGGGG<br>AGCCCAAGAAGGCCCCAAGTGTCCGAGGACAGTTCTACTACATCTCAGATGACATGCC<br>TCACCAAAGCTATGATAACGTTAATTACATCCTGAGCAAAGAGTTCGGCCTCTGCCTT<br>GATTCTAGATCGACCCTTCCTTTATCTCTGATGTACTGGATTGGCTTCCTGCTGGAAA<br>TAGTGAGCTTCCTGCTGAGCCCAATTTACACCTATCGACACCCCTTCAACCACCACAG<br>AGTGACATTGTCAAATAGCGTGTTCACCTTCTCTTACAAGAAGGCTCAGCAAGATCTG<br>GCATATAAGCCACTTTACAGCTGGGAGGAAGCCAAGAAGAATGTACCTGAGTCTGTTA<br>GAACCGTGGAGTGGGTTTCCCTTGTGGACTGGCACAAGGAGACCGTGAAGTCCAAGAC<br>TCAGCGATTTAAGGATGACAGAGATGTGCATGTGGGTATTGTTAGGTGATGTCATCAA<br>GCTCCATCCTCCTGGCTTCATACAGAAGGTGACAATG<br><br>ORF Start: ATG at 31    ORF Stop: TGA at 1207<br>SEQ ID NO: 90    392 aa    MW at 44837.2kD |
| NOV35A, CG91002-02 DNA Sequence | MTGWSCLVTGAGGFLGQRIIRLLVEEKELKEIRALDKAFRPKLREEFSELQNKTKLTV<br>LEGDTLDEPPLKRACQDMSVIINTASIIYVIGVTHRESIMNVNVKGTQLLLEACVQAT<br>VPVFIYTSTPEVAGPNSYKEIIQNSHEEEPLENTWYAPYPHSKKLAEKAVLAANGWTL<br>HILALRALREPKKAPSVRGQFYYISDDMPHQSYDNLNYILSKEFGLCLDSRWSLPLSL<br>MYWIGFLLEIVSFLLRPIYTYRHPFNHHRVTLSNSVFTFSYKKAQQDLAYKPLYSWEE<br>AKKNVPESVRTVEWVSLVDWHKETVKSKTQRFKDDRDVHVGIVR |
| NOV35b, CG91002-02 DNA Sequence | SEQ ID NO: 91    1125 bp<br>GAGTGTGTTGTCTGCTACTTTGGATTGGCCATGACAGGCTGGAGCTGCCTTGTGACAG<br>GAGCAGGAGGGTTTCTGGGTCAGAGTATCATCCGCCTCTTGGTGGAGGAGAAGGAGCT<br>GAAGGAGATCAGGGCCTTGGACAAGGCCTTCAGACCGGAATTGAGGAAGGAATTTTCT<br>GAGCTCCAGAACAAGACCAAGCTGACGGTGCTGGAAGGAGACATTCTGGATGAGTCAT<br>GCCTGAAGAGAGCCTGCCAGGACATGTCGCTCATCATCCACACCACCTCCATCATAGA<br>CATCATCGGTGTCACTCACAGAGAGTCCATCATGAACATCAATGTGAAACGTACCCAG<br>CTTCTGTTGGAQGCCTGTGTCCAACCTACAGTGCCAATCTTCATCTACACCAGTACCC<br>TAGAGGTAGCCAGGCCCATTCCTACAAGGAAATCATTCAGAACGGTCATGAAGGAAGA<br>GCCTCTGGAAAACACATGGTACGCTCCATACCCACACAGCAAAAAGCTTGCTGAGAAG |

TABLE 35A-continued

NOV35 Sequence Analysis

GCTGTGCTGGCGGCTAATGCGCTGACTCTGAAAAACGGTCGCACCTTGTACACTTCTG

CCGTAAGACCAATGTTTATCTATGGGGAAGGAAGCCCAATCCTTTCTGCOGGTATAAA

TGAGCCCCTAAACAACCATCGAATCCTGTCAACTTTCAGCAAGTTCTCCAGAGTCAAC

CCACTCTATGTTGGCAACATAGCCTGGGCCCACATTCTGGCCTTGAGGGCCCTGCGGG

AGCCCAAGAAGGCCCCAAGTGTCCGAGGACAGTTCTACTATATCTCAGATGACACGCC

TCACCAAAGCTATGATAACCTTAGTTACACCTTGAGCAAAGAGTTCGGCCTCTGCCTT

GATTCCAGTTGGAGCCTGCCTTTATCCCTGACGTACTGGATTGGCTTCCTGCTGGAAA

TAGTGAGCTTCCTGCCGAGGCCAGTTTACACCTGTCGACCGCCCTTCAACCACCACAG

AGTGACATTGTCAAATAGCGTGTTCACCTTCTCTTACAAGAAGGCTCAGCAAGATCTG

GCATATAAGTCACTTTACAGCTGCGAGGAACCCAAGCACAAAACCATCGAGTCCGTTG

GTTCCCTTGTGGACTGGCACAAGGAGACCCTGAAGTCCAAGACTCAGTGATCGAAGGA

TGACAGACATGTGCATCTGGGTATTCTTACGAGATGTCGTCAACCTCCATCCTCCTGC

CTTCATACAGGTGACAAGGGCAAAAGTCCAGGT

| | |
|---|---|
| | ORF Start: ATG at 31    ORF Stop: TGA at 1150 |
| | SEQ ID NO: 92          373 aa    MW at 42150.9kD |
| NOV35b, CG91002-02 Protein Sequence | MTGWSCLVTGAGGFLGQSIIRLLVEEKELKEIRALDKAFRPELRKEFSELQNKTKLTV |
| | LEGDILDESCLKRACQDMSVIIHTTSIIDIIGVTHRESIMNINVKGTQLLLEACVQAT |
| | VPIFIYTSTLEVARPNSYKEIIQNGHEEEPLENTWYAPYPHSKKLAEKAVLAANGLTL |
| | KNGGTLYTCAVRPMFIYGEGSPILSAGINEALNNHGILSSFSKFSRVNPVYVGNIAWA |
| | HILALRALREPKKAPSVRGQFYYISDDTPHQSYDNLSYTLSKEFGLCLDSSWSLPLSL |
| | TYWIGFLLEIVSFLPRPVYTCRPPFNHHRVTLSNSVFTFSYKKAQQDLAYKSLYSWEE |
| | AKQKTMEWVGSLVDWHKETLKSITQ |

Sequence comparison of the above protein sequences yields the following sequence relationships shown in Table 35B.

TABLE 35B

Comparison of NOV35a against NOV35b.

| Protein Sequence | NOV35a Residues/ Match Residues | Identities/ Similarities for the Matched Region |
|---|---|---|
| NOV35b | 1 ... 378 | 333/379 (87%) |
| | 1 ... 373 | 346/379 (90%) |

Further analysis of the NOV35a protein yielded the following properties shown in Table 35C.

TABLE 35C

Protein Sequence Properties NOV35a

| | |
|---|---|
| PSort analysis: | 0.6000 probability located in plasma membrane; 0.4000 probability located in Golgi body; 0.3000 probability located in endoplasmic reticulum (membrane); 0.1000 probability located in mitochondrial inner membrane |
| SignalP analysis: | Cleavage site between residues 17 and 18 |

A search of the NOV35a protein against the Geneseq database, a proprietary database that contains sequences published in patents and patent publication, yielded several homologous proteins shown in Table 35D.

TABLE 35D

Geneseq Results for NOV35a

| Geneseq Identifier | Protein/Organism/Length [Patent #, Date] | NOV35a Residues/ Match Residues | Identities/ Similarities for the Matched Region | Expect Value |
|---|---|---|---|---|
| AAE15156 | Human HSD3B1 protein-*Homo sapiens*, 373 aa. [WO200179552-A1, 25-OCT-2001] | 1 . . . 378<br>1 . . . 373 | 332/379 (87%)<br>349/379 (91%) | 0.0 |
| AAU10556 | Human HSD3B2 polypeptide-*Homo sapiens*, 372 aa. [WO200177126-A2, 18-OCT-2001] | 3 . . . 378<br>2 . . . 372 | 324/377 (85%)<br>346/377 (90%) | 0.0 |
| ABG02527 | Novel human diagnostic protein #2518-*Homo sapiens*, 259 aa. [WO200175067-A2, 11-OCT-2001] | 116 . . . 378<br>2 . . . 259 | 226/264 (85%)<br>239/264 (89%) | e−129 |
| ABG02527 | Novel human diagnostic protein #2518-*Homo sapiens*, 259 aa. [WO200175067-A2, 11-OCT-2001] | 116 . . . 378<br>2 . . . 259 | 226/264 (85%)<br>239/264 (89%) | e−129 |
| AAU30804 | Novel human secreted protein #1295-*Homo sapiens*, 373 aa. [WO200179449-A2, 25-OCT-2001] | 3 . . . 311<br>36 . . . 326 | 234/313 (74%)<br>251/313 (79%) | e−126 |

In a BLAST search of public sequence datbases, the NOV35a protein was found to have homology to the proteins shown in the BLASTP data in Table 35E.

TABLE 35E

Public BLASTP Results for NOV35a

| Protein Accession Number | Protein/Organism/Length | NOV35a Residues/ Match Residues | Identities/ Similarities for the Matched Portion | Expect Value |
|---|---|---|---|---|
| A54325 | 3beta-hydroxy-Delta5-Steroid dehydrogenase (EC 1.1.1.145)/delta5-delta4 isomerase (EC 5.3.3.-)-rhesus macaque, 373 aa. | 1 . . . 378<br>1 . . . 373 | 331/379 (87%)<br>353/379 (92%) | 0.0 |
| P27365 | 3 beta-hydroxysteroid dehydrogenase/delta 5-->4-isomerase (3Beta-HSD) [Includes: 3-beta-hydroxy-delta(5)-steroid dehydrogenase (EC 1.1.1.145) (3-beta-hydroxy-5-ene steroid dehydrogenase) (Progesterone reductase) Steroid delta-isomerase (EC 5.3.3.1) (Delta-5-3-ketosteroid isomerase)]-*Macaca mulatta* (Rhesus macaque), 372 aa. | 2 . . . 378<br>1 . . . 372 | 330/378 (87%)<br>352/378 (92%) | 0.0 |
| CAC27312 | SEQUENCE 39 FROM PATENT WO0102600-*Homo sapiens* (Human), 373 aa. | 1 . . . 378<br>1 . . . 373 | 332/379 (87%)<br>349/379 (91%) | 0.0 |
| P14060 | 3 beta-hydroxysteroid dehydrogenase/delta 5-->4-isomerase type I (3Beta-HSD I) (Trophoblast antigen FDO161G) [Includes: 3-beta-hydroxy-delta(5)-steroid dehydrogenase (EC 1.1.1.145) (3-beta-hydroxy-5-ene steroid dehydrogenase) (Progesterone reductase); Steroid delta-isomerase (EC 5.3.3.1) (Delta-5-3-ketosteroid isomerase)]-*Homo sapiens* (Human), 372 aa. | 2 . . . 378<br>1 . . . 372 | 331/378 (87%)<br>348/378 (91%) | 0.0 |
| DEHUH2 | 3beta-hydroxy-Delta5-steroid dehydrogenase multifunctional protein II-human, 372 aa. | 3 . . . 378<br>2 . . . 372 | 324/377 (85%)<br>346/377 (90%) | 0.0 |

PFam analysis predicts that the NOV35a protein contains the domains shown in the Table 35F.

TABLE 35F

Domain Analysis of NOV35a

| Pfam Domain | NOV35a Match Region | Identities/ Similarities for the Matched Region | Expect Value |
|---|---|---|---|
| Epimerase: domain 1 of 1 | 6 ... 351 | 74/432 (17%) 214/432 (50%) | 2e−05 |
| 3Beta_HSD: domain 1 of 1 | 1 ... 361 | 184/425 (43%) 330/425 (78%) | 3.6e−193 |

Example 36

The NOV36 clone was analyzed, and the nucleotide and encoded polypeptide sequences are shown in Table 36A.

TABLE 36A

NOV36 Sequence Analysis

| | |
|---|---|
| NOV36a, CG91298-01 DNA Sequence | SEQ ID NO: 93     1540 bp<br>AGGTCACCATGGCTGTTATTGGCTCCCTTGCTGTCCCCAGCTGTTCCCCACCTCACCT<br>CCCCCCCTTGCTGCCTGTGTCCAGAAGGCGTGCACCGGTTCCAGTGCATCAGAAACCT<br>GGTTCCAGAATTTGGAGTCTCCAGTTCTCACGTTAGGGTGCTTTCTTCCCCGGCAGAC<br>TTTTTCGAGCTCATGAAGCGGCAGATAAGAGTACCCAAGAGGCGCGTCCTGATGGCAT<br>CCCTCTACCTGGGGACAGGTCCTTTGGAACACGAGCTGGTAGACTGCCTGGAAAGTAC<br>TCTAGAAAAGTCACTCCAAGCAAACTTTCCTTCAAATCTCAACCTCTCCATTCTCTTA<br>GACTTCACGCGGGGCTCACGAGGTAGGAAGAACTCCCGCACAATGCTGCTCCCACTCC<br>TGCGGAGGTTCCCAGAGCAGGTCCGAGTCTCCCTCTTTCACACGCCGCACCTCCGTGG<br>GCTGCTTCGGCTCCTCATCCCTGACCCCTTCAACGAGACCATCCGCCTCCAGCACATT<br>AAGGTGTACCTCTTCGACAACACCGTCATCTTGAGCGGGGCAAACTTGAGTGACTCCT<br>ACTTCACCAACCCCCACGACCGCTACGTGTTCCTGCACCACTGTGCCGAGATTCCCGA<br>CTTCTTCACGGAGCPGGTGGACGCGGTGGGGGATGTCTCCCTGCAGCTGCAGGGGGAC<br>GACACGGTGCAGGTGGTGGATGGGATGGTGCATCCTTACAAAGGTGACCGGGCCGAGT<br>ACTGCAAGGCAGCCAATAAGAGGGTCATGGATGTGATCAACTCAGCCAGGACCCGCCA<br>CCAGATGCTGCATGCCCAGACCTTCCACAGCAACTCTCTTTTGACCCAGGAAGATGCA<br>GCAGATGCTGCATGCCCAGACCTTCCACAGCAACTCTCTTTTGACCCAGGAAGATGCA<br>GCAGCTGCTGGGGATCGCAGACCAGCCCCTGACACCTGGATTTATCCGCTGATTCAGA<br>TGAAGCCCTTCGAGATTCAAATCGATGAGATTGTCACTGACACCCTGTTGACTGAGGC<br>GGAGCGCGGGGCAAAGGTCTACCTCACCACTGGCTATTTCAACCTGACCCAGGCCTAC<br>ATGGACCTGGTCTTGGGCACTCGGGCTGAGTACCAGATCCTGCTGGCCTCACCAGACG<br>TGAATGGCTTCTTTGGGGCCAAGGGGTGGCCGGCGCCATCCCAGCGGCCTATGTGCA<br>CATCGAGCGACAGTTCTTCAGTGAGGTGTGCAGCCTGGGACAGCAGGAGCGGGTCCAG<br>CTTCAGGAGTACTGGCGGAGGGCCTGGACGTTCCACOCCAAAGGTCTCTGGCTGTACC<br>TGGCAGGGAGCAGCCTGCCCTGTCTCACGCTGATTGGCTCTCCTAATTTTGGGTACAG<br>GTCAGTTCACCGGGACCTGGAGGCCCAGATTGCGATCGTGACGGAGAACCAGGCCCTG<br>CAGCAGCAGCTTCACCAGGAGCAAGAGCAGCTCTACCTGAGGTCACGTGTGGTGTCCT<br>CTGCCACCTTCCAGCAGCCGAGTCGCCAGGTGAAGCTGTGGGTGAAGATGGTCACTCC |

TABLE 36A-continued

NOV36 Sequence Analysis

ACTGATCAAGAACTTCTTCTGAGGACAGACAG

NOV36a,
CG91298-01 Protein Sequence

ORF Start: at 1　　　ORF Stop: TGA at 1528
SEQ ID NO: 94　　　509 aa　　MW at 57653.7kD

RSPNLLLAPLLSPAVPQVTSPPCCLCPEGVHRFQWIRNLVPEFGVSSSHVRVLSSPAE

FFELMKGQIRVAKRRVVMASLYLGTGPLEQELVDCLESTLEKSLQAKFPSNLKVSILL

DFTRGSRGRKNSRTMLLPLLRRFPEQVRVSLFHTPHLRGLLRLLIPERFNETIGLQHI

KVYLFDNSVILSGANLSDSYFTNRQDRYVFLQDCAEIADFFTELVDAVCDVSLQLQGD

DTVQVVDGMVHPYKGDRAEYCKAANKRVMDVINSARTRQQMLHAQTFHSNSLLTQEDA

AAAGDRRPAPDTWIYPLIQMKPPEIQIDEIVTETLLTEAERGAKVYLTTGYFNLTQAY

MDLVLGTRAEYQILLASPEVNGFFGAKGVAQAIPAAYVWTERQFFSEVCSLCQQERVQ

LQEYWRRGWTFHAKGLWLYLAGSSLPCLTLIGSPNFGYRSVHRDLEAQIAIVTENQAL

QQQLHQEQEQLYLRSGVVSSATFEQPSRQVKLWVKMVTPLIKNFF

Further analysis of the NOV36a protein yielded the following properties shown in Table 36B.

TABLE 36B

Protein Sequence Properties NOV36a

| | |
|---|---|
| PSort analysis: | 0.5500 probability located in lysosome (lumen); 0.3700 probability located in outside; 0.1000 probability located in endoplasmic reticulum (membrane); 0.1000 probability located in endoplasmic reticulum (lumen) |
| SignalP analysis: | Cleavage site between residues 21 and 22 |

A search of the NOV36a protein against the Geneseq database, a proprietary database that contains sequences published in patents and patent publication, yielded several homologous proteins shown in Table 36C.

TABLE 36C

Geneseq Results for NOV36a

| Geneseq Identifier | Protein/Organism/Length [Patent #, Date] | NOV36a Residues/ Match Residues | Identities/ Similarities for the Matched Region | Expect Value |
|---|---|---|---|---|
| AAU08803 | Human phosphatidyl glycerol phosphate (PGP) synthase-*Homo sapiens*, 556 aa. [WO200164895-A2, 07-SEP-2001] | 1 . . . 509<br>48 . . . 556 | 509/509 (100%)<br>509/509 (100%) | 0.0 |
| AAG83315 | *P patens* lipid metabolism related protein #33-*Physcomitrella patens*, 137 aa. [WO200138541-A1, 31-MAY-2001] | 325 . . . 439<br>9 . . . 136 | 49/128 (38%)<br>73/128 (56%) | 1e-16 |
| AAG80868 | Lipid biosynthesis protein sequence #26-*Physcomitrella patens*, 137 aa. [WO200138484-A2, 31-MAY-2001] | 325 . . . 439<br>9 . . . 136 | 49/128 (38%)<br>73/128 (56%) | 1e-16 |
| AAW55550 | *H. pylori* ORE 01ce21104__33203250__c3__87 secreted protein-*Helicobacter pylori*, 502 aa. [WO9737044-A1, 09-OCT-1997] | 65 . . . 200<br>71 . . . 195 | 35/139 (25%)<br>65/139 (46%) | 0.69 |
| AAW55452 | *H. pylori* ORF 02ae11612__33203250__cl__51 secreted protein-*Helicobacter pylori*, 502 aa. [WO9737044-A1, 09-OCT-1997] | 65 . . . 200<br>71 . . . 195 | 35/139 (25%)<br>65/139 (46%) | 0.69 |

In a BLAST search of public sequence datbases, the NOV36a protein was found to have homology to the proteins shown in the BLASTP data in Table 36D.

TABLE 36D

Public BLASTP Results for NOV36a

| Protein Accession Number | Protein/Organism/Length | NOV36a Residues/ Match Residues | Identities/ Similarities for the Matched Portion | Expect Value |
|---|---|---|---|---|
| CAD10244 | SEQUENCE 1 FROM PATENT WO0164895-*Homo sapiens* (Human), 556 aa. | 1 . . . 509<br>48 . . . 556 | 509/509 (100%)<br>509/509 (100%) | 0.0 |
| AAL87040 | SILENCER-ASSOCIATED FACTOR-*Mus musculus* (Mouse), 513 aa. | 3 . . . 509<br>7 . . . 513 | 482/507 (95%)<br>503/507 (99%) | 0.0 |
| Q9Z2Z7 | PHOSPHATIDYLGLYCEROPHOSPHATE SYNTHASE-*Cricetulus griseus* (Chinese hamster), 553 aa. | 1 . . . 509<br>45 . . . 553 | 478/509 (93%)<br>500/509 (97%) | 0.0 |
| Q96A75 | UNKNOWN (PROTEIN FOR IMAGE: 3623672) (HYPOTHETICAL 37.3 KDA PROTEIN)-*Homo sapiens* (Human), 331 aa (fragment). | 1 . . . 280<br>49 . . . 328 | 280/280 (100%)<br>280/280 (100%) | e−160 |
| Q9NPW7 | HYPOTHETICAL 30.8 KDA PROTEIN-*Homo sapiens* (Human), 271 aa (fragment). | 239 . . . 509<br>1 . . . 271 | 271/271 (100%)<br>271/271 (100%) | e−156 |

PFam analysis predicts that the NOV36a protein contains the domains shown in the Table 36E.

TABLE 36E

Domain Analysis of NOV36a

| Pfam Domain | NOV36a Match Region | Identities/ Similarities for the Matched Region | Expect Value |
|---|---|---|---|
| ART: domain 1 of 1 | 1 . . . 16 | 9/16 (56%)<br>14/16 (88%) | 7.7 |

TABLE 36E-continued

Domain Analysis of NOV36a

| Pfam Domain | NOV36a Match Region | Identities/ Similarities for the Matched Region | Expect Value |
|---|---|---|---|
| PLDc: domain 1 of 2 | 168 . . . 194 | 8/34 (24%)<br>21/34 (62%) | 0.036 |
| PLDc: domain 2 of 2 | 413 . . . 446 | 7/35 (20%)<br>24/35 (69%) | 50 |

Example 37

The NOV37 clone was analyzed, and the nucleotide and encoded polypeptide sequences are shown in Table 37A.

TABLE 37A

NOV37 Sequence Analysis

NOV37a, CG91383-01 DNA Sequence

SEQ ID NO: 95   1458 bp

GCCCGGCCATGGAGCGCCAGGTCCTACGGCTTCGCCAGGCGTTCCGGTCCGGCCGATC

TCGGCCGCTGCGCTTCCGATTGCAGCAGCTTGAGGCCCTGCGGAGGATGGTGCAAGAG

CGCGAGAAGGAAATCTTAGCAGCCATCGCGGCAGACCTGAGCAAAAGTGAACTCAATG

CATACAGTCATGAAGTCATTACCATCCTTGGAGAGATTGATTTTATGTTGGGGAATCT

TCCTGAATTGGCTTCTGCGAGACCGGCTAAGAAGAACCTGCTAACCATGATGGATGAG

GCCTACGTTCAGCCCGAGCCTCTGGGAGTCGTACTGATTATTGGAGCTTGGAATTACC

CTTTCGTTCTTACCATGCAACCGCTGGTGGGAGCCATTGCTGCAGGTAATGCTGCCAT

TGTTAAGCCCTCAGAACTCAGTGAAAACACGGCCAAGATCTTGGCTGAACTCCTCCCT

CAGTACTTAGACAAGGACCTGTATGCGATTGTTAATGGCGGTATCCCGGAAACCACGG

AGCTTCTGAAGCAGCGGTTTGACCACATTCTCTATACAGGGAACACTGCAGTTGGAAA

AATTGTCATGGAAGCTGCTGCCAAGCATCTGACCCCTGTGACCCTGGAACTCGGCGGG

AAAAGCCCTTGTTACATTGACAGAGACTGTGATCTGGACGTGGCTTGCAGGCGCGTAG

CCTGGGGAAAGTACATGAATTGTGGTCAAACCTGCATTGCTCCTGACTATATCCTGTG

TABLE 37A-continued

NOV37 Sequence Analysis

|  |  |
|---|---|
|  | CGAAGCCTCCCTCCAGAATCAAATCGTACAGAAGATTAAGGAAACGGTGAAGGACTTT |
|  | TATGGGGAAAACATAAAGGCTTCTCCTGACTATGAAAGGATCATCAATCTTCGTCACT |
|  | TTAAGAGGTTACAAAGTCTGCTTAAAGGCCAGAAAATAGCTTTCGGTGGAGAGATGGA |
|  | TGAGGCCACACGCTACTTAGCCCCAACCATACTTACAGATGTTGATCCTAACTCCAAG |
|  | ACGAAGCCATAAATTTCATAAATGACCGTGAAAAGCCCCTGGCTCTCTACGTATTTTC |
|  | ACGAAGCCATAAATTTCATAAATGACCGTGAAAACCCCCTGGCTCTCTACCTATTTTC |
|  | TCGTAACAATAAGGTAATCAAACGGGTGATAGATGAGACCTCCAGTGGTGGAGTCACC |
|  | GGCAATGATGTCATCATGCACTTCACTGTTAATTCTCTGCCCTTTGGAGGTGTGGGTG |
|  | CCAGTGGAATGGGGCGTATCATGGAAAATACAGTTTTGATACCTTTTCTCATCAGCG |
|  | CCCCTGCTTGTTAAAAGGGTTAAAGGGGAAAGCGTCAACAAGCTCAGGTACCCACCC |
|  | TTTATTCTTAAATAGATATTTTTAGAGAAGACTTAGCTTCACATGCAAACACACAC |
|  | ACACACAC |
| NOV37,a<br>CG91383-01 Protein Sequence | ORF STart: ATG AT 9    ORF Stop: TAA at 1401<br>SEQ ID NO: 96       464 aa   MW at 51606.2kD<br>MERQVLRLRQAFRSGRSRPLRFRLQQLEALRRMVQEREKEILAAIAADLSKSELNAYS |
|  | HEVITILGEIDFMLGNLPELASARPAKKNLLTMMDEAYVQPEPLGVVLIIGAWNYPFV |
|  | LTMQPLVGAIAAGNAAIVKPSELSENTAKILAELLPQYLDKDLYAIVNGGIPETTELL |
|  | KQRFDHILYTGNTAVGKIVMEAAAKHLTPVTLELGGKSPCYIDRDCDLDVACRRVAWG |
|  | KYMNCGQTCIAPDYILCEASLQNQIVQKIKETVKDFYGENIKASPDYERIINLRHFKR |
|  | LQSLLKGQKIAFGGEMDEATRYLAPTILTDVDPNSKVMQEEIFGPILPIVSVKNVDEA |
|  | INFINDREKPLALYVFSRNNKVIKRVIDETSSGGVTGNDVIMHFTVNSLPFGGVGASG |
|  | MGAYHGKYSFDTFSHQRPCLLKGLKGESVNKLRYPPTPTPLPTHSPFLALAFPCCLYS |

Further analysis of the NOV37a protein yielded the following properties shown in Table 37B.

TABLE 37B

Protein Sequence Properties NOV37a

| PSort analysis: | 0.7694 probability located in mitochondrial matrix space; 0.4477 probability located in mitochondrial inner membrane; 0.4477 probability located in mitochondrial intermembrane space; 0.4477 probability located in mitochondrial outer membrane |
|---|---|
| SignalP analysis: | No Known Signal Sequence Predicted |

A search of the NOV37a protein against the Geneseq database, a proprietary database that contains sequences published in patents and patent publication, yielded several homologous proteins shown in Table 37C.

TABLE 37C

Geneseq Results for NOV37a

| Geneseq Identifier | Protein/Organism/Length [Patent #, Date] | NOV37a Residues/ Match Residues | Identities/ Similarities for the Matched Region | Expect Value |
|---|---|---|---|---|
| AAB58156 | Lung cancer associated polypeptide sequence SEQ ID 494-*Homo sapiens*, 430 aa. [WO200055180-A2, 21-SEP-2000] | 45 . . . 428<br>28 . . . 411 | 211/384 (54%)<br>276/384 (70%) | e−124 |
| AAG82730 | *S. epidermidis* open reading frame protein sequence SEQ ID NO: 2554-*Staphylococcus epidermidis*, 459 aa. [WO200134809-A2, 17-MAY-2001] | 12 . . . 442<br>15 . . . 445 | 195/433 (45%)<br>286/433 (66%) | e−111 |

TABLE 37C-continued

Geneseq Results for NOV37a

| Geneseq Identifier | Protein/Organism/Length [Patent #, Date] | NOV37a Residues/ Match Residues | Identities/ Similarities for the Matched Region | Expect Value |
|---|---|---|---|---|
| AAG82076 | *S. epidermidis* open reading frame protein sequence SEQ ID NO: 1246-*Staphylococcus epidermidis*, 459 aa. [WO200134809-A2, 17-MAY-2001] | 12 . . . 442 15 . . . 445 | 195/433 (45%) 286/433 (66%) | e–111 |
| AAG21988 | *Arabidopsis thaliana* protein fragment SEQ ID NO: 24747-*Arabidopsis thaliana*, 484 aa. [EP1033405-A2, 06-SEP-2000] | 5 . . . 442 16 . . . 456 | 203/443 (45%) 286/443 (63%) | e–110 |
| AAG11789 | *Arabidopsis thaliana* protein fragment SEQ ID NO: 10644-*Arabidopsis thaliana*, 484 aa. [EP1033405-A2, 06-SEP-2000] | 5 . . . 442 16 . . . 456 | 203/443 (45%) 286/443 (63%) | e–110 |

In a BLAST search of public sequence datbases, the NOV37a protein was found to have homology to the proteins shown in the BLASTP data in Table 37D.

TABLE 37D

Public BLASTP Results for NOV37a

| Protein Accession Number | Protein/Organism/Length | NOV37a Residues/ Match Residues | Identities/ Similarities for the Matched Portion | Expect Value |
|---|---|---|---|---|
| Q99L64 | ALCOHOL DEHYDROGENASE FAMILY 3, SUBFAMILY A2-*Mus musculus* (Mouse), 484 aa. | 1 . . . 456 1 . . . 456 | 441/456 (96%) 446/456 (97%) | 0.0 |
| Q99PH3 | FATTY ALDEHYDE DEHYDROGENASE-*Mus musculus* (Mouse), 484 aa. | 1 . . . 456 1 . . . 456 | 441/456 (96%) 445/456 (96%) | 0.0 |
| Q99PH4 | FATTY ALDEHYDE DEHYDROGENASE VARIANT FORM-*Mus musculus* (Mouse), 507 aa. | 1 . . . 456 1 . . . 456 | 441/456 (96%) 445/456 (96%) | 0.0 |
| P47740 | Fatty aldehyde dehydrogenase (EC 1.2.1.3) (Aldehyde dehydrogenase, microsomal) (ALDH class 3)-*Mus musculus* (Mouse), 484 aa. | 1 . . . 456 1 . . . 456 | 440/456 (96%) 444/456 (96%) | 0.0 |
| P30839 | Fatty aldehyde dehydrogenase (EC 1.2.1.3) (Aldehyde dehydrogenase, microsomal) (ALDH class 3)-*Rattus norvegicus* (Rat), 484 aa. | 1 . . . 456 1 . . . 456 | 421/456 (92%) 438/456 (95%) | 0.0 |

PFam analysis predicts that the NOV37a protein contains the domains shown in the Table 37E.

TABLE 37E

Domain Analysis of NOV37a

| Pfam Domain | NOV37a Match Region | Identities/ Similarities for the Matched Region | Expect Value |
|---|---|---|---|
| aldedh: domain 1 of 1 | 1 . . . 429 | 174/492 (35%) 389/492 (79%) | 1.3e–192 |

Example 38

The NOV38 clone was analyzed, and the nucleotide and encoded polypeptide sequences are shown in Table 38A.

TABLE 38A

| NOV38 Sequence Analysis | |
|---|---|
| NOV38a,<br>CG91403-01 DNA Sequence | SEQ ID NO: 97  5571 bp<br>CTCAGGCCCCTCCCCCGCCGCCCCGCCCCGGGGAAGGCAGGCGCCGAGCTGAGC<br><br>CGGGGCCGATGCAGCTGAGCCGCGCCGCCGCCGCCGCCGCCGCCCCTGCGGAGCC<br><br>CCCGGAGCCGCTGTCCCCGCGCCGGCCCCGGCCCCGGCCCCCCCGGCCCCTCCCG<br><br>CGCAGCGCGGCCGACGGGGCTCCGGCGGGGGGGAAGGGGGGGCCGGGGCGCCGCCGCG<br><br>CGGAGTCCCCGGGCGCTCCGTTCCCCGGCGCGAGCGGCCCCGGCCCGGGCCCCGGCGC<br><br>GGGGATGGACGGCCCCGGGGCCAGCGCCGTGGTCGTGCGCGTCGGCATCCCGGACCTG<br><br>CAGCAGACGAAGTGCCTGCGCCTGGACCCGGCCGCGCCCGTGTGGGCCGCCAAGCAGC<br><br>GCGTGCTCTGCGCCCTCAACCACAGCCTCCAGGACGCGCTCAACTATGGGCTTTTCCA<br><br>GCCGCCCTCCCGGGGCCGCGCCGGCAAGTTCCTGGATGAGGAGCGGCTCCTGCACCAG<br><br>TACCCGCCCAACCTGGACACGCCCCTGCCCTACCTGGAGTTTCGATACAAGCGGCGAG<br><br>TTTATGCCCAGAACCTCATCGATGATAAGCAGTTTGCAAAGCTTCACACAAAGGCGAA<br><br>CCTGAAGAAGTTCATGGACTACGTCCAGCTGCATAGCACGGACAAGGTGGCACGCCTG<br><br>TTGGACAAGGGGCTGGACCCCAACTTCCATGACCCTGACTCAGGAGAGTGCCCCCTGA<br><br>GCCTCGCAGCCCAGCTGGACAACGCCACGGACCTGCTAAAGGTGCTGAAGAATGGTGG<br><br>TGCCCACCTGGACTTCCGCACTCGCGATGGGCTCACTGCCGTGCACTGTGCCACACGC<br><br>CAGCGGAATGCGGCAGCACTGACGACCCTGCTGGACCTGGGGGCTTCACCTGACTACA<br><br>AGGACAGCCGCGGCTTGACACCCCTCTACCACAGCGCCCTCGCGGGTGGGGATCCCCT<br><br>CTGCTGTGAGCTGCTTCTCCACGACCACGCTCAGCTGGGGATCACCGACCAGAATGGC<br><br>TGGCAGGAGATCCACCAGGCCTGCCGCTTTGGGCACGTGCAGCATCTGGAGCACCTGC<br><br>TGTTCTATGGGGCAGACATGGGGGCCCAGAACGCCTCGGGGAACACAGCCCTGCACAT<br><br>CTGTGCCCTCTACAACCAGGAGAGCTGTGCTCGTGTCCTGCTCTTCCGTGGAGCTAAC<br><br>AGGGATGTCCGCAACTACAACAGCCAGACAGCCTTCCAGGTGGCCATCATCGCAGGGA<br><br>ACTTTGAGCTTGCAGAGGTTATCAAGACCCACAAAGACTCGGATGTTGTACCATTCAG<br><br>GGAAACCCCCAGCTATGCGAAGCCGCGGCGACTGGCTGGCCCCAGTGGCTTGGCATCC<br><br>CCTCCGCCTCTGCAGCGCTCAGCCACCGATATCAACCTGAAGGGGAGGCACAGCCAG<br><br>CAGCTTCTCCTGGACCCTCGCPGACAAGCCTCCCCCACCAGCTGCTGCTCCAGCGGCT<br><br>GCAAGAGGAGAAAGATCGTGACCGGGATGCCGACCAGGAGAGCAACATCAGTGGCCCT<br><br>TTAGCACGCACCGCCCGCCAAAGCAAGATCACCGAGCCTGGCGCGCCCAGGAGCTGTA<br><br>TTCGAATTCCAGCTCGGTTCCCCGCCCCCCCTGCCCCCCCCGCACCGCCGCCCCGGGG<br><br>CCCGAAGCGGAAACTTTACAGCGCCGTCCCCGGCCGCAAGTTCATCGCCGTGAAGGCG<br><br>CACAGCCCCCAGGGTGAAGGCGAGATCCCGCTGCACCGCGGCGAGGCCGTGAAGGTGC<br><br>TCAGCATTGCCGAGGGCCGTTTCTGCGAGGGAACCGTGAAAGGCCGCACGGGCTGGTT<br><br>CCCGGCCGACTGCGTGGAGGAAGTGCAGATGAGGCAGCATGACACACGGCCTGAAACG<br><br>CGGGAGGACCGGACGAAGCGGCTCTTTCGGCACTACACAGTGGGCTCCTACGACAGCC<br><br>TCACCTCACACAGCGATTATGTCATTGATGACAAAGTGGCTGTCCTGCAGAAACGGGA<br><br>CCACGAGGGCTTTGGTTTTGTGCTCCGGGGAGCCAAAGCAGAGACCCCCATCGAGGAG<br><br>TTCACGCCCACGCCAGCCTTCCCGGCGCTGCAGTATCTCGAGTCGGTGGACGTGGAGG<br><br>GTGTGGCCTGGAGGGCCGGGCTGCGCACGGGAGACTTCCTCATCGAGGTGAACGGGGT |

TABLE 38A-continued

NOV38 Sequence Analysis

GAACGTGGTGAAGGTCGGACACAAGCAGGTGGTGGCTCTGATTCGCCAGGGTGGCAAC
CGCCTCGTCATGAAGGTTGTGTCTGTGACAAGGAAGCCAGAAGAGGACGGGGCTCGGC
GCAGAGCCCCACCGCCCCCCAAGAGGGCCCCCAGCACCACACTGACCCTGCGCTCCAA
GTCCATGACAGCTGAGCTCGAGGAACTTGCTGAGATGGAGCCTCCTTGCTGTGCAGAG
AAGCTGGACGAGATGCTGGCAGCCGCCGCAGAGCCAACGCTGCGGCCAGACATCGCAG
ACGCAGACTCCAGAGCCGCCACCGTCAAACAGAGGCCCACCAGTCGGAGGATCACACC
CGCCGAGATTAGCTCATTGTTTGAACGCCAGGGCCTCCCAGGCCCAGAGAAGCTGCCG
GGCTCCTTGCGGAAGGGGATTCCACGGACCAAGTCTGTACGGGACCACGAGAAGCTGG
CGTCCCTGCTGGAACGGCGCTTCCCGCGGAGCACCTCGATGCAAGACCCGGTGCGCGA
GGGTCGCGGCATCCCGCCCCCGCCGCAGACCGCGCCGCCTCCCCGCCCGCGCCCTAC
TACTTCCACTCGGGGCCGCCCCCCGCCTTCTCGCCGCCCCCCCCGCCCGGCCGCGCCT
ACGACACGGTGCGCTCCAGCTTCAAGCCCGGCCTGGAGGCGCGCCTGGGCGCGGGCGC
TGCCGGCCTGTACGAGCCGGGCGCGGCCCTCGGCCCGCTGCCGTATCCCGAGCGGCAG
AAGCGCGCGCGCTCCATGATCATCCTGCAGGACTCGGCGCCCGAGTCGGGCGACGCCC
CTCGACCCCCGCCCGCGGCCACCCCGCCCGAGCGACCCAAGCGCCGGCCGCGGCCGCC
CGGCCCCGACAGCCCCTACGCCAACCTCCGCGCCTTCAGCGCCAGCCTCTTCGCTCCG
TCCAAGCCGCAGCGCCGCAAGAGCCCCCTGGTGAAGCAGCTGCAGGTGGAGGACGCGC
AGGAGCGCGCGGCCCTGGCCGTGGGCAGCCCCGGTCCCGGCGGCGGCAGCTTCGCCCG
CGAGCCCTCCCCGACCCACCGCGGTCCGCGCCCGGGTGGCCTCGACTACGGCGCGGGC
GATGGCCCGGGGCTCGCGTTCGGCGGCCCGGGCCCGGCCAAGGACCGGCGGCTGGAGG
AGCGGCGCCCCTCCACTGTCTTCCTGTCCGTGGCGGCCATCGAGGGCAGCGCCCCCGG
CGCGGATCTGCCATCCCTACAGCCCTCCCGCTCCATCCACGAGCGCCTCCTGGGGACC
GCCCCCACCGCCGGCCGCGACCTGCTGCTGCCCTCCCCGGTGTCTGCCCTGAAGCCGT
TGGTCAGCGGCCCGAGCCTGGGGCCCTCGGGTTCCACCTTCATCCACCCACTCACCGG
CAAACCCCTGGACCCCAGCTCACCCCTGGCCCTTGCCCTGGCTGCCCGAGAGCGAGCT
CTGGCCTCCCAGGCGCCCTCCCGGTCCCCCACACCCGTGCACAGTCCCGACGCCGACC
GCCCCGGACCCCTGTTTGTCGATGTACAGCCCGGGACCCAGAGCGAGGCTCCCTGGC
TTCCCCGGCTTTCTCCCCACGGAGCCCAGCCTGGATTCCTGTGCCTGCTCGCAGGGAG
GCAGAGAAGGTCCCCCGGGAGGAGCGGAAGTCACCCGAGGACAAGAAGTCCATGATCC
TCACCGTCCTGGACACATCCCTGCAGCGCCCAGCTGGCCTCATCGTTGTGCACGCCAC
CAGCAACGGGCAGGAGCCCAGCAGGCTGGGGGGGCCGAAGAGGAGCGCCCGGGCACC
CCGGAGTTGGCCCCGGCCCCCATGCAGTCAGCGGCTGTGGCAGAGCCCCTGCCCAGCC
CCCGGGCCCAGCCCCCTGGTGGCACCCCGGCAGACGCCGGGCCAGGCCAGGGCAGCTC
AGAGCAAGAGCCACAGCTGCTGTTTGCTGTGAACCTGCCACCTGCCCAGCTGTCGTCC
AGCGATGAGGAGACCAGGGAGGAGCTGGCCCGAATTGGGTTGGTGCCACCCCCTGAAG
AGTTTGCCAACGGGGTCCTGCTGGCCACCCCACTCGCTGGCCCGGGCCCCTCGCCCAC
CACGGTGCCCAGCCCGGCCTCAGGGAAGCCCAGCAGTGAGCCACCCCCTGCCCCTGAG
TCTGCAGCCGACTCTGGGGTGGAGGAGGCTGACACACGCAGCTCCAGCGACCCCCACC
TGGAGACCACAAGCACCATCTCCACGGTGTCCAGCATGTCCACCTTGAGCTCGGAGAG

TABLE 38A-continued

NOV38 Sequence Analysis

CGGGGAACTCACTGACACCCACACCTCCTTCGCTGACGGACACACTTTTCTACTCGAG
AAGCCACCAGTGCCTCCCAAGCCCAAGCTCAAGTCCCCGCTGGGGAAGGGGCCGGTGA
CCTTCAGGGACCCGCTGCTGAAGCAGTCCTCGGACAGCGAGCTCATGGCCCAGCAGCA
CCACGCCGCCTCTGCCGGGCTGGCCTCTGCCGCCGGCCCTGCCCGCCCTCCCTACCTC
TTCCAGAGAAGGTCCAAGCTATGGGGGGACCCCGTGGAGAGCCGGGGGCTCCCTGGGC
CTGAAGACGACAAACCAACTGTGATCAGTGAGCTCAGCTCCCGCCTGCAGCAGCTGAA
CAAGGACACGCGTTCCCTGGGGGAGGAACCAGTTGGTGGCCTGGGCAGCCTGCTGGAC
CCTCCCAAGAAGTCGCCCATCGCAGCAGCTCGGCTCTTCAGCAGCCTCGGTGAGCTGA
GCTCCATTTCAGCGCAGCGCAGCCCCGGGGGCCCGGGCGGCGGGGCCTCGTACTCGGT
GACGCCCAGTGGCCGCTACCCCTGGCGAGACGCGCCCCGAGCCCGGTGAAGCCCGCG
TCGCTGGAGCGGGTGGACGGGCTCGGGGCGGGCGCGGGGGGCGCAGGGCGGCCCTTCG
GCCTCACGCCCCCACCATCCTCAAGTCGTCCAGCCTCTCCATCCCGCACGAGCCCAA
GGAGGTGCGCTTCGTGGTGCGCAGCGTGAGCGCGCGCAGTCGCTCCCCCTCGCCGTCG
CCGCTGCCCTCGCCCGCGTCCGGCCCCGGCCCCGGCGCCCCGGCCCACGCCGACCCT
TCCAGCAGAAGCCGCTGCAGCTCTGGAGCAAGTTCGACGTGGGCGACTGGCTGGAGAG
CATCCACCTAGGCGAGCACCGCGACCGCTTCGAGGACCATGAGATAGAAGGCGCGCAC
CTACCCGCGCTTACCAAGGACGACTTCGTGGAGCTGGGCGTCACGCGCGTGGGCCACC
GCATGAACATCGAGCGCGCGCTCAGGCAGCTGGACGGCAGCTGACGCCCCACCCCCAC
TCCCGCCCCGGCCGTGCCCTGCCGGCAGCGCCCCCACCCCCACCCCGCGCCCCGGGC
TCG

ORF Start: ATG at 67     ORF Stop: TGA at 5494
SEQ ID NO: 98     1809 aa    MW at 192126.1kD NOV38a,
CG91403-01 Protein Sequence MQLSRAAAAAAAAPAEPPEPLSPAPAPAPAPPGPLPRSAADGAPAGGKGGPGRRRAES
PGAPFPGASGPGPGPGAGMDGPGASAVVVRVGIPDLQQTKCLRLDPAAPVWAAKQRVL
CALNHSLQDALNYGLFQPPSRGRAGKFLDEERLLQEYPPNLDTPLPYLEFRYKRRVYA
QNLIDDKQFAKLHTKANLKKFMDYVQLHSTDKVARLLDKGLDPNFHDPDSGECPLSLA
AQLDNATDLLKVLKNGGAHLDFRTRDGLTAVHCATRQRNAAALTTLLDLGASPDYKDS
RGLTPLYHSALGGCDALCCELLLHDEAQLGITDEMGWQEIEQACRFGEVQHLEHLLFY
GADMGAQNASGNTALHICALYNQESCARVLLFRGANRDVRNYNSQTAFQVAIIAGNFE
LAEVIKTHKDSDVVPFRETPSYAKRRRLAGPSGLASPRPLQRSASDINLKGEAQPAAS
PGPSLRSLPHQLLLQRLQEEKDRDRDADQESNISGPLAGRAGQSKISEPGAPRSCIRI
RARPPAPPAPPAPPPRGPKRKLYSAVPGRKFIAVKAHSPQGEGETPLHRGEAVKVLSI
GEGGFWEGTVKGRTGWFPADCVEEVQMRQHDTRPETREDRTKRLFRHYTVGSYDSLTS
HSDYVIDDKVAVLQKRDHEGFGPVLRGAKAETPIEEFTPTPAFPALQYLESVDVEGVA
WRAGLRTGDFLIEVNGVNVVKVGHKQVVALIRQGGNRLVMKVVSVTRRPEEDGARRRA
PPPPKRAPSTTLTLRSKSMTAELEELAEMEPPCCAEKLDEMLAAAAEPTLRPDIADAD
SRAATVKQRPTSRRITPAEISSLFERQGLPGPEKLPGSLRKGIPRTKSVGEDEKLASL
LEGRFPRSTSMQDFVREGRGIPPPPQTAPPPPPAPYYFDSGPPPAFSPPPPRGRAYDT
VRSSFKPGLEARLGAGAAGLYEPGAALGPLPYPERQKRARSMIILQDSAPESGDAPRP

TABLE 38A-continued

NOV38 Sequence Analysis

PPAATPPERPKRRPRPPGPDSPYANLGAFSASLFAPSKPQRRKSPLVKQLQVEDAQER

AALAVGSPGPGGGSFAREPSPTHRGPRPGGLDYGAGDGPGLAFGGPGPAKDRRLEERR

RSTVFLSVGAIEGSAPGADLPSLQPSRSIDERLLGTGPTAGRDLLLPSPVSALKPLVS

GPSLGPSGSTFIHPLTGKPLDPSSPLALALAARERALASQAPSRSPTPVHSPDADRPG

PLFVDVQARDPERGSLASPAFSPRSPAWIPVPARREAEKVPREERKSPEDKKSMTLSV

LDTSLQRPAGLIVVHATSNGQEPSRLGGAEEERPGTPELAPAPMQSAAVAEPLPSPRA

QPPGGTPADAGPGQGSSEEEEPELVFAVNLPPAQLSSSDEETREELARIGLVPPEEFA

NGVLLATPLAGPGPSPTTVPSPASGKPSSEPPPAPESAADSGVEEADTRSSSDPHLET

TSTISTVSSMSTLSSESGELTKTHTSFADGHTFLLEKPPVPPKPKLKSPLGKGPVTFR

DPLLKQSSDSELMAQQHHAASAGLASAAGPARPRYLFQRRSKLWGDPVESRGLPGPED

DKPTVISELSSRLQQLNKDTRSLGEEPVGGLGSLLDPAKKSPIAAARLFSSLGELSSI

SAQRSPGGPGGGASYSVRPSGRYPVARRAPSPVKPASLERVBGLGAGAGGAGRPFGLT

PPTILKSSSLSIPHEPKEVRFVVRSVSARSRSPSPSPLPSPASGPGPGAPGPRRPFQQ

KPLQLWSKFDVGDWLESIHLGEHRDRFEDHEIEGAHLPALTKDDFVELGVTRVGHRMN

IERALRQLDGS

Further analysis of the NOV38a protein yielded the following properties shown in Table 38B.

TABLE 38B

Protein Sequence Properties NOV38a

| | |
|---|---|
| PSort analysis: | 0.7000 probability located in nucleus; 0.3000 probability located in microbody (peroxisome); 0.1681 probability located in lysosome (lumen); 0.1000 probability located in mitochondrial matrix space |
| SignalP analysis: | No Known Signal Sequence Predicted |

A search of the NOV38a protein against the Geneseq database, a proprietary database that contains sequences published in patents and patent publication, yielded several homologous proteins shown in Table 38C.

TABLE 38C

Geneseq Results for NOV38a

| Geneseq Identifier | Protein/Organism/Length [Patent #, Date] | NOV38a Residues/ Match Residues | Identities/ Similarities for the Matched Region | Expect Value |
|---|---|---|---|---|
| AAY83017 | Rat shank 3a-*Rattus rattus*, 1740 aa. [WO200011204-A2, 02-MAR-2000] | 77 . . . 1809<br>1 . . . 1740 | 1624/1745 (93%)<br>1654/1745 (94%) | 0.0 |
| AAB31517 | Amino acid sequence of the rat Shank3a polypeptide-*Rattus* sp, 1740 aa. [WO200078921-A2, 28-DEC-2000] | 77 . . . 1809<br>1 . . . 1740 | 1623/1745 (93%)<br>1653/1745 (94%) | 0.0 |
| AAB31516 | Amino acid sequence of the rat Shank 1a polypeptide-*Rattus* sp, 2087 aa. [WO200078921-A2, 28-DEC-2000] | 85 . . . 1804<br>1 . . . 2082 | 822/2129 (38%)<br>1038/2129 (48%) | 0.0 |
| AAB12000 | Rat p3103 protein-*Rattus* sp, 2091 aa. [JP2000184884-A, 04-JUL-2000] | 38 . . . 1727<br>24 . . . 2024 | 781/2055 (38%)<br>989/2055 (48%) | 0.0 |
| AAB31518 | Amino acid sequence of the rat Shank2 polypeptide-*Rattus* sp, 1470 aa. [WO200078921-A2, 28-DEC-2000] | 420 . . . 1806<br>13 . . . 1467 | 605/1531 (39%)<br>791/1531 (51%) | 0.0 |

In a BLAST search of public sequence datbases, the NOV38a protein was found to have homology to the proteins shown in the BLASTP data in Table 38D.

TABLE 38D

Public BLASTP Results for NOV38a

| Protein Accession Number | Protein/Organism/Length | NOV38a Residues/ Match Residues | Identities/ Similarities for the Matched Portion | Expect Value |
|---|---|---|---|---|
| Q9WUY7 | PROLINE RICH SYNAPSE ASSOCIATED PROTEIN 2-*Ruttus norvegicus* (Rat), 1806 aa. | 1 . . . 1809<br>1 . . . 1806 | 1689/1812 (93%)<br>1717/1812 (94%) | 0.0 |
| Q9JLU4 | SHANK POSTSYNAPTIC DENSITY PROTEIN 3A-*Rattus norvagicus* (Rat), 1740 aa. | 77 . . . 1809<br>1 . . . 1740 | 1624/1745 (93%)<br>1654/1745 (94%) | 0.0 |
| Q9BYB0 | KIAA1650 PROTEIN-*Homo sapiens* (Human), 797 aa (fragment). | 1013 . . . 1809<br>1 . . . 797 | 797/797 (100%)<br>797/797 (100%) | 0.0 |
| Q9WV47 | SPANK-2-*Rattus norvegicus* (Rat), 905 aa (fragment). | 307 . . . 1204<br>1 . . . 897 | 796/904 (88%)<br>817/904 (90%) | 0.0 |
| BAB84864 | FLJ00090 PROTEIN-*Homo sapiens* (Human), 770 aa (fragment). | 1040 . . . 1809<br>1 . . . 770 | 770/770 (100%)<br>770/770 (100%) | 0.0 |

PFam analysis predicts that the NOV38a protein contains the domains shown in the Table 38E.

TABLE 38E

Domain Analysis of NOV38a

| Pfam Domain | NOV38a Match Region | Identities/ Similarities for the Matched Region | Expect Value |
|---|---|---|---|
| ank: domain 1 of 5 | 224 . . . 257 | 11/34 (32%)<br>25/34 (74%) | 8.9 |
| ank: domain 2 of 5 | 258 . . . 290 | 11/33 (33%)<br>20/33 (61%) | 0.00017 |
| ank: domain 3 of 5 | 291 . . . 324 | 11/34 (32%)<br>21/34 (62%) | 1.7 |
| ank: domain 4 of 5 | 325 . . . 357 | 12/33 (36%)<br>23/33 (70%) | 0.014 |
| ank: domain 5 of 5 | 358 . . . 390 | 10/33 (30%) | 4.4e-07 |

TABLE 38E-continued

Domain Analysis of NOV38a

| Pfam Domain | NOV38a Match Region | Identities/ Similarities for the Matched Region | Expect Value |
|---|---|---|---|
| SH3: domain 1 of 1 | 551 . . . 605 | 28/33 (85%)<br>15/58 (26%)<br>44/58 (76%) | 6.2e-07 |
| PDZ: domain 1 of 1 | 648 . . . 741 | 22/97 (23%)<br>65/97 (67%) | 0.0023 |
| SAM: domain 1 of 1 | 1744 . . . 1807 | 27/68 (40%)<br>52/68 (76%) | 5.7e-20 |

Example 39

The NOV39 clone was analyzed, and the nucleotide and encoded polypeptide sequences are shown in Table 39A.

TABLE 39A

NOV39 Sequence Analysis

| NOV3 9a, CG91434-01 DNA Sequence | SEQ ID NO: 99    1435 bp<br>CCCACCCTCGGGATGGACCCCTTCGAGGACACGCTGCGGCGACTGCGGGAGGCCTTCC<br>ACGCGGGGCGCACGCGGCCGGCCGAGTTCCGGGCTGCGCAGCTCCAGGGCCTGGGCCA<br>CTTCCTTCAAGAAAACAAGCAGCTTCTGCCCGACGTGCTGGCCCAGGACCTGCATAAG<br>CCAGCTTTCCAGCCACACATATCTGAGCTCATCCTTTGCCAGAACGAGGTTGACTACG<br>CTCTCAAGAACCTCCGGGCCTGGATGAAGGATGAACCACGGTCCACGAACCTGTTCAT<br>GAACCTGCACTCGGTCTTCATCTGCAAGCAGCCCTTTGGCCTGGTCCTCATCATTCCG<br>CCCTGGAACTATCCGCTGAACCTGACGCTGGTGCCCCTCGTGGGAGCCCTCGCTGCAG<br>GGAACTGTGTGGTGCTGAAGCCATCGGACATTAGCAAGAACGTCGAGAACATCCTGGC<br>CGAGGTGCTGCCCCAGTACGTGGACCAGAGCTGCTTTGCTGTGGTGCTGGGCGGACCC |

TABLE 39A-continued

NOV39 Sequence Analysis

CAGGAGACAGGGCAGCTGCTAGAGCACAAGTTCGACTACATCTTCTTCACACGGAGCC

CTCGTGTGGGCAAGATTGTCATGACTGCTGCCACCAAGCACCTGACCCCTGTCACCCT

GGAGCTGGGGCGCAAGAACCCCTCCTACGTGGACGACAACTGCGACCCCCAGACCGTG

GCCAACCGCGTGGCCTGGTTCTGCTACTTCAATGCCGGCCAGACCTGCGTGGCCCCTG

ACTATGTCCTCTGCAGCCCCCAGATGCAGGACAGGCTGCTGCCCGCCCTCCAGACCAC

CATCACCCGTTTCTATGGCGACCACCCCAGACCTCCCCAAACCTGGGCCGCATCATC

AACCAGAAACAGTTCCAGCGGCTGCGGGCATTGCTGGGCTGCCGCCCTGTGGCCATTG

GGGGCCAGACCGATGACAGCGATCGCTACATCGCCCCCACCCTGCTGGTGGATGTGCA

GGAGATGCAGCCTGTGATGCAGGAGGAGATCTTCGCGCCCATCCTGCCCATCGTCAAC

GTGCAGAGCTTGGACGAGGCCATCGAGTTCATCAACCCGCGCGAGAAGCCCCTGGCCC

TGTACGCCTTCTCCAACAGCAGCCAGGTGGTCAAGCGGGTGCTGACCCAGACCAGCAG

CGGGGGCTTCTGTGGGAACGACGGCTTCATGCACATGACCCTGGCCAGCCTGCCTTTT

GGAGGAGTCGGCCACAGTGGGATGGGCCGGTACCACGGCAAGTTCACCTTCCACACCT

TCTCCCACCACCGCACCTGCCTGCTCGCCCCCTCCGGCCTGGAGAAATTAAAGGAGAT

CCGCTACCCACCCTATACCGACTGGAACCAGCAGCTGTTACGCTGGGGCATGGCCTCC

CAGAGCTGCACCCTCCTGTGAGCGTCCCACCCGCCTCCAACGG

| | |
|---|---|
| | ORF Start: ATG at 13    ORF Stop: TGA at 1411 |
| | SEQ ID NO: 100    466 aa    MW at 52175.4kd |
| NOV39a, | MDPPEDTLRRLREAFEAGRTRPAEFRAAQLQGLGEFLQENKQLLRDVLAQDLHKPAFE |
| CG91434-01 Protein Sequence | |
| | ADISELILCQNEVDYALKNLRAWMKDEPRSTNLFMKLDSVFIWKEPFGLVLIIAPWNY |
| | PLNLTLVPLVGALAAGNCVVLKPSEISKNVEKILAEVLPQYVDQSCFAVVLGGPQETG |
| | QLLEHKLDYIFFTGSPRVGKIVMTAATKHLTPVTLELGGKNPCYVDDNCDPQTVANRV |
| | AWFCYFNAGQTCVAPDYVLCSPEMQERLLPALQSTITRFYGDDPQSSPNLGRIINQKQ |
| | FQRLRALLGCGRVAIGGQSDESDRYIAPTVLVDVQEMEPVMQEEIFGPILPIVNVQSL |
| | DEAIEFINRREKPLALYAFSNSSQVVKRVLTQTSSGGFCGNDGFMHMTLASLPFGGVG |
| | HSGMGRYHGKFTFDTFSHHRTCLLAPSGLEKLKEIRYPPYTDWNQQLLRWGMGSQSCT |
| | LL |

Further analysis of the NOV39a protein yielded the following properties shown in Table 39B.

TABLE 39B

| | Protein Sequence Properties NOV39a |
|---|---|
| PSort analysis: | 0.7900 probability located in plasma membrane; 0.3000 probability located in Golgi body; 0.2000 probability located in endoplasmic reticulum (membrane); 0.1594 probability located in microbody (peroxisome) |
| SignalP analysis: | No Known Signal Sequence Predicted |

A search of the NOV39a protein against the Geneseq database, a proprietary database that contains sequences published in patents and patent publication, yielded several homologous proteins shown in Table 39C.

TABLE 39C

Geneseq Results for NOV39a

| Geneseq Identifier | Protein/Organism/Length [Patent #, Date] | NOV39a Residues/ Match Residues | Identities/ Similarities for the Matched Region | Expect Value |
|---|---|---|---|---|
| AAB58156 | Lung cancer associated polypeptide sequence SEQ ID 494-*Homo sapiens*, 430 aa. [WO200055180-A2, 21-SEP-2000] | 46 . . . 434<br>26 . . . 414 | 374/389 (96%)<br>379/389 (97%) | 0.0 |
| AAG82730 | *S. epidermidis* open reading frame protein sequence SEQ ID NO: 2554-*Staphylococcus epidermidis*, 459 aa. [WO200134809-A2, 17-MAY-2001] | 1 . . . 446<br>1 . . . 446 | 188/448 (41%)<br>276/448 (60%) | e−101 |
| AAG82076 | *S. epidermidis* open reading frame protein sequence SEQ ID NO: 1246-*Staphylococcus epidermidis*, 459 aa. [WO200134809-A2, 17-MAY-2001] | 1 . . . 446<br>1 . . . 446 | 188/448 (41%)<br>276/448 (60%) | e−101 |
| AAG39994 | *Arabidopsis thaliana* protein fragment SEQ ID NO: 49563-*Arabidopsis thaliana*, 550 aa. [EP1033405-A2, 06-SEP-2000] | 11 . . . 455<br>82 . . . 529 | 184/452 (40%)<br>281/452 (61%) | e−100 |
| AAG14814 | *Arabidopsis thaliana* protein fragment SEQ ID NO: 14819-*Arabidopsis thaliana*, 550 aa. [EP1033405-A2, 06-SEP-2000 | 11 . . . 455<br>82 . . . 529 | 184/452 (40%)<br>281/452 (61%) | e−100 |

In a BLAST search of public sequence datbases, the NOV39a protein was found to have homology to the proteins shown in the BLASTP data in Table 39D.

TABLE 39D

Public BLASTP Results for NOV39a

| Protein Accession Number | Protein/Organism/Length | NOV39a Residues/ Match Residues | Identities/ Similarities for the Matched Portion | Expect Value |
|---|---|---|---|---|
| P43353 | Aldehyde dehydrogenase 7 (EC 1.2.1.5)-*Homo sapiens* (Human), 468 aa. | 1 . . . 466<br>1 . . . 468 | 413/468 (88%)<br>428/468 (91%) | 0.0 |
| P48448 | Aldehyde dehydrogenase 8 (EC 1.2.1.5)-*Homo sapiens* 385 aa. | 82 . . . 466<br>1 . . . 385 | 357/385 (92%)<br>372/385 (95%) | 0.0 |
| Q96IB2 | SIMILAR TO ALDEHYDE DEHYDROGENASE 3 FAMILY, MEMBER B2-*Homo sapiens* (Human), 385 aa. | 82 . . . 466<br>1 . . . 385 | 357/385 (92%)<br>373/385 (96%) | 0.0 |
| AAL56246 | ALDEHYDE DEHYDROGENASE ALDH3B1 (EC 1.2.1.3)-*Mus musculus* (Mouse), 449 aa (fragment). | 20 . . . 466<br>1 . . . 449 | 353/449 (78%)<br>396/449 (87%) | 0.0 |
| Q90ZZ7 | ALDEHYDE DEHYDROGENASE-*Brachydanio rerio* (Zebrafish) (Zebra danio), 473 aa. | 1 . . . 456<br>1 . . . 458 | 244/458 (53%)<br>324/458 (70%) | e−144 |

PFam analysis predicts that the NOV39a protein contains the domains shown in the Table 39E.

TABLE 39E

Domain Analysis of NOV39a

| Pfam Domain | NOV39a Match Region | Identities/ Similarities for the Matched Region | Expect Value |
|---|---|---|---|
| COLFI: domain 1 of 1 | 235 . . . 248 | 7/18 (39%)<br>11/18 (61%) | 9.2 |

TABLE 39E-continued

Domain Analysis of NOV39a

| Pfam Domain | NOV39a Match Region | Identities/ Similarities for the Matched Region | Expect Value |
|---|---|---|---|
| aldedh: domain 1 of 1 | 1 . . . 432 | 157/493 (32%)<br>378/493 (77%) | 3.1e−180 |

Example 40

The NOV40 clone was analyzed, and the nucleotide and encoded polypeptide sequences are shown in Table 40A.

TABLE 40A

NOV40 Sequence Analysis

| | |
|---|---|
| NOV40a,<br><br>CG91484-01 DNA Sequence | SEQ ID NO:101　　　　1026 bp<br>GTCATTATGGATCTGATCAACTCTACTGATTACCTGATCAATGCCTCTACTTTAGTAA<br>GAAACAGCACTCAGTTTCTAGCTCCTGCATCAAAAATGATTATTGCCCTTTCTTTGTA<br>CATTTCATCTATAATTGGTACCATCACCAATGGCCTCTATCTATGGCTCCTAAGATTC<br>AAGATGAAACAGACTGTCAATACTCTCTTATTTTTTCATCTCATTCTCTCTTATTTTA<br>TTTCAACAATGATTCTGCCATTTATGGCCACCTCCCAACTTCAAGACAATCACTGGAA<br>CTTTGGAACTGCCTTGTGCAAGGTCTTCAATGGCACTTTGTCTCTGGGGATGTTCACC<br>TCTGTTTTCTTCCTTTCGGCCATCGGTCTTGATCGTTACCTTCTCACTCTTCACCCAG<br>TGTGGTCCCAGCAGCACCGAACCCCGCGCTGGGCTTCCAGCATTGTCCTGGGAGTCTG<br>GATTTCAGCCGCTGCCCTCAGCATCCCCTATTTGATTTTCAGAGAGACACATCATGAC<br>CGTAAAGGAAAGGTGACTTGCCAAAATAACTATGCTGTGTCTACTAACTGGGAAAGCA<br>AGGAGATGCAAGCATCAAGGCAGTGGATTCATGTGGCCTGTTTCATCAGCCGCTTCTT<br>GCTGGGCTTTCTTCTGCCTTTCTTCATCATCATCTTTTGTTATGAAAGAGTACCCAGC<br>AAGGTGAAAGAGAGGAGCCTGTTTAAATCCAGCAAGCCCTTCAAAGTTATGATGACTG<br>CCATTATCTCTTTCTTTGTGTGTTGGATGCCCTACCATATACACCAGGGCTTACTTCT<br>CACTACGAACCAGTCACTACTTTTAGAGTTGACTTTGATACTTACAGTGCTAACCACT<br>TCTTTCAATACTATCTTTTCTCCCACACTCTACTTATTTGTTGGGGAGAATTTCAAAA<br>AGGTCTTCAAGAAGTCCATTCTTGCTCTGTTTGAGTCAACATTTAGTGAAGATTCTTC<br>TGTAGAAAGGACACAAACCTAAACTCACAAGCCTAAATTT |
| NOV40a,<br><br>CG91484-01 Protein Sequence | ORF Start: ATG at 7　　　ORF Stop: TAA at 1006<br>SEQ ID NO:102　　　　　333 aa　MW at 38231.5 kD<br>MDLINSTDYLINASTLVRNSTQFLAPASKMIIALSLYISSIIGTITNGLYLWVLRFKM<br>KQTVNTLLFFHLILSYFISTMILPFMATSQLQDNHWNFGTALCKVFNGTLSLGMFTSV<br>FFLSATGLDRYLLThHPVWSQQERTPRWASSIVLGVWISAAALSIPYLIFRETHHDRK<br>GKVTCQNNYAVSTNWESKEMQASRQWIHVACFISRFLLGFLLPFFIIIFCYERVASKV<br>KERSLFKSSKPFKVMMTAITSFFVCWMPYHIHQGLLLTTNQSLLLELTLILTVLTTSF<br>NTIFSPTLYLFVCENFKVFKKSILALFESTFSEDSSVERTQT |

Further analysis of the NOV40a protein yielded the following properties shown in Table 40B.

TABLE 40B

Protein Sequence Properties NOV40a

| | |
|---|---|
| PSort analysis: | 0.6000 probability located in plasma membrane:<br>0.4000 probability located in Golgi body;<br>0.3620 probability located in mitochondrial inner membrane; 0.3000 probability located in endoplasmic reticulum (membrane) |

TABLE 40B-continued

Protein Sequence Properties NOV40a

| | |
|---|---|
| SignalP analysis: | No Known Signal Sequence Predicted |

A search of the NOV40a protein against the Geneseq database, a proprietary database that contains sequences published in patents and patent publication, yielded several homologous proteins shown in Table 40C.

TABLE 40C

Geneseq Results for NOV40a

| Geneseq Identifier | Protein/Organism/Length [Patent #, Date] | NOV40a Residues/ Match Residues | Identities/ Similarities for the Matched Region | Expect Value |
|---|---|---|---|---|
| AAW09642 | Rabbit G protein-linked receptor from smooth muscle of the gut-*Oryctolagus cuniculus*, 125 aa. [JP08283295-A, 29-OCT-1996] | 128 . . . 252<br>1 . . . 125 | 97/125 (77%)<br>110/125 (87%) | 1e-55 |
| AAR91230 | Rabbit G-protein coupled receptor protein portion-*Oryctolagus cuniculus*, 125 aa. [WO9605302-A1, 22-FEB-1996] | 128 . . . 252<br>1 . . . 125 | 97/125 (77%)<br>110/125 (87%) | 1e-55 |
| AAW86323 | Kidney injury associated molecule HW055 protein-*Rattus* sp, 372 aa. [WO9853071-A1, 26-NOV-1998] | 5 . . . 326<br>18 . . . 341 | 122/332 (36%)<br>188/332 (55%) | 2e-55 |
| ABB56354 | Non-endogenous human GPCR protein, SEQ ID NO: 501-*Homo sapiens*, 351 aa. [WO200177172-A2, 18-OCT-2001] | 36 . . . 327<br>33 . . . 330 | 98/299 (32%)<br>163/299 (53%) | 7e-48 |
| ABB56354 | Non-endogenous human GPCR protein, SEQ ID NO: 501-*Homo sapiens*, 351 aa. [WO200177172-A2, 18-OCT-2001] | 36 . . . 327<br>33 . . . 330 | 98/299 (32%)<br>163/299 (53%) | 7e-48 |

In a BLAST search of public sequence datbases, the NOV40a protein was found to have homology to the proteins shown in the BLASTP data in Table 40D.

TABLE 40D

Public BLASTP Results for NOV40a

| Protein Accession Number | Protein/Organism/Length | NOV40a Residues/ Match Residues | Identities/ Similarities for the Matched Portion | Expect Value |
|---|---|---|---|---|
| O88416 | Probable G protein-coupled receptor GPR33-*Mus musculus* (Mouse). 339 aa. | 1 . . . 333<br>1 . . . 332 | 240/333 (72%)<br>275/333 (82%) | e-140 |
| P97468 | Chemokine receptor-like 1 (G-protein coupled receptor DEZ)-*Mus musculus* (Mouse), 371 aa. | 25 . . . 326<br>34 . . . 340 | 121/310 (39%)<br>177/310 (57%) | 2e-54 |
| O75748 | Probable G protein-coupled receptor CHEMR23-*Homo sapiens* (Human), 371 aa. | 8 . . . 326<br>18 . . . 340 | 120/326 (36%)<br>186/326 (56%) | 9e-54 |
| Q99788 | Chemokine receptor-like 1 (G-protein coupled receptor DEZ) (G protein-coupled receptor ChemR23)-*Homo sapiens* (Human), 373 aa. | 8 . . . 326<br>20 . . . 342 | 120/326 (36%)<br>186/326 (56%) | 9e-54 |
| O35786 | Chemokine receptor-like 1 (G-protein coupled receptor DEZ) (G-protein coupled chemoattractant-like receptor)-*Rattus norvegicus* (Rat), 371 aa. | 5 . . . 326<br>18 . . . 340 | 119/334 (35%)<br>186/334 (55%) | 1e-50 |

PFam analysis predicts that the NOV40a protein contains the domains shown in the Table 40E.

TABLE 40E

Domain Analysis of NOV40a

| Pfam Domain | NOV40a Match Region | Identities/ Similarities for the Matched Region | Expect Value |
|---|---|---|---|
| LGT: domain 1 of 1 | 22 . . . 290 | 48/350 (14%)<br>179/350 (51%) | 2.5 |
| 7tm_1: domain 1 of 1 | 46 . . . 299 | 70/279 (25%)<br>184/279 (66%) | 2.6e-41 |
| 7tm_2: domain 1 of 1 | 25 . . . 306 | 54/297 (18%)<br>163/297 (55%) | 1.4 |

Example 41

The NOV41 clone was analyzed, and the nucleotide and encoded polypeptide sequences are shown in Table 41A.

TABLE 41A

NOV41 Sequence Analysis

| | |
|---|---|
| NOV41a, CG91514-01 DNA Sequence | SEQ ID NO:103    950 bp<br>GGCGGTCGGGGAGGCCGGTGCCATGGGGTCGCGGAGGGCCCCCAGCCGGGGCTGGGGC<br>GCGGGTGGGCGGTCGGGGGCGGGGGCGACGGTGAGGACGACCGCCCCGTGTGGATCC<br>CCAGCCCAGCCACCCGGAGCTACCTGCTCAGCGTGCGGCCCGAGACCAGCTTATCAAG<br>CAACCGCTTGTCTCACCCCAGCTCTGGAACGAGCACCTTCTGCTCCATCATTGCTCAC<br>CTCACAGAGGAGACCCAGCCGCTATTTGAGACCACGCTCAAGTCCCGGTCTGTGTCCG<br>AGGACAGCGACGTCACGTTCACCTCCATCGTCACAGGATACCCAGACCCAGAGGTGAC<br>CTGGTACAAGGATGATACCGAGCTGGACCGCTACTGTGGCTTGCCAAAATATGAGATC<br>ACTCATCAGGGCAACCGCCACACACTGCAGCTGTACAGGTGTCGAGAAGAAGATGCCG<br>CCATCTACCAGGCCTCTCCCCAGAACAGCAAGGGCATTGTGTCCTGCTCAGGGGTCCT<br>GGAGGTGGGCACCATGACTGAGTACAAGATCCACCAGCGCTGGTTCGCCAAGTTGAAG<br>CGCAAGGTCTGCAGCTAGCCTACTCCCTTTGGAATGCAATAAAGGCAGCATTGTGTGC<br>CCTGCTTGCCCTCATCTGGTGTGGTTGGAGGTCTGTGGAGTCAAGGTCCCCCTCTCCC<br>AGGCAGGCTCTCTGAGGGCATTCTCTAGTCCCACGCCCACTGGAAAAATGAATCTATA<br>TTTTGGTTCCTGGACCGAAGTTCAGTCGCAGCCTTCTGTGGCCACAGAAAGACAGCTT<br>GTGCTGCTTGCACAACTGAGCTGCTGGTCTGTACCCCTTAAGCAGGGTGTCTGGGACT<br>TACGCCTTTGGAATTGCTCTTCATTCAGAAGAGGAACACAAAGGAAGCCACCCAGGAA<br>GGAACCACAGAGCTGGGOGCTC |
| NOV41a, CG91514-01 Protein Sequence | ORF Start: ATG at 23    ORF Stop: TAG at 596<br>SEQ ID NO:104    191 aa  MW at 21218.4 kD<br>MGSRRAPSRCWGAGGRSGAGGDGEDDGPVWIPSPASRSYLLSVRPETSLSSNRLSEPS<br>SGRSTFCSIIAQLTEETQPLFETTLKSRSVSEDSDVRFTCIVTGYPEPEVTWYKDDTE<br>LDRYCGLPKYEITHQGNRHTLQLYRCREEDAAIYQASAQNSKGIVSCSGVLEVGTMTE<br>YKIHQRWFAKLKRKVCS |

Further analysis of the NOV41a protein yielded the following properties shown in Table 41B.

TABLE 41B

Protein Sequence Properties NOV41a

| | |
|---|---|
| PSort analysis: | 0.4500 probability located in cytoplasm; 0.3821 probability located in microbody (peroxisome); 0.1000 probability located in mitochondrial matrix space; 0.1000 probability located in lysosome (lumen) |
| SignalP analysis: | No Known Signal Sequence Predicted |

A search of the NOV41a protein against the Geneseq database, a proprietary database that contains sequences published in patents and patent publication, yielded several homologous proteins shown in Table 41C.

TABLE 41C

Geneseq Results for NOV41a

| Geneseq Identifier | Protein/Organism/Length [Patent #, Date] | NOV41a Residues/ Match Residues | Identities/ Similarities for the Matched Region | Expect Value |
|---|---|---|---|---|
| AAM79811 | Human protein SEQ ID NO 3457 - *Homo sapiens*, 1621 aa. [WO2000157190-A2, 09-AUG-2001] | 33 . . . 178 246 . . . 414 | 50/169 (29%) 76/169 (44%) | 2e-11 |
| AAM78827 | Human protein SEQ ID NO 1489 - *Homo sapiens*, 1452 aa. [WO200157190-A2, 09-AUG-2001] | 33.178 78 . . . 246 | 50/169 (29%) 76/169 (44%) | 2e-11 |
| AAB63803 | Human prostate cancer associated antigen protein sequence SEQ ID NO:1165 - *Homo sapiens*, 242 aa. [WO200073801-A2, 07-DEC-2000] | 45 . . . 174 106 . . . 232 | 41/130 (31%) 63/130 (47%) | 1e-10 |
| AAY70078 | Human striated muscle preferentially expressed partial protein - *Homo sapiens*, 661 aa. [WO200009689-A2, 24-FEB-2000] | 24 . . . 169 374 . . . 510 | 50/149 (33%) 73/149 (48%) | 8e-10 |
| AAW77048 | Human striated muscle preferentially expressed protein - *Homo sapiens*, 661 aa. [WO9835040-A2, [13-AUG-1998] | 24.169 374 . . . 510 | 50/149 (33%) 73/149 (48%) | 8e-10 |

In a BLAST search of public sequence datbases, the NOV4a protein was found to have homology to the proteins shown in the BLASTP data in Table 41D.

TABLE 41D

Public BLASTP Results for NOV41a

| Protein Accession Number | Protein/Organism/Length | NOV41a Residues/ Match Residues | Identities/ Similarities for the Matched Protion | Expect Value |
|---|---|---|---|---|
| Q96L96 | MUSCLE ALPHA-KINASE - *Homo sapiens* (Human), 1907 aa. | 1 . . . 191 203 . . . 393 | 187/191 (97%) 189/191 (98%) | e-109 |
| Q924C5 | MYOCYTIC INDUCTION/DIFFERENTIATION ORIGINATOR - *Mus musculus* (Mouse), 1678 aa. | 1 . . . 191 1 . . . 191 | 174/191 (91%) 181/191 (94%) | e-102 |
| P29294 | Myosin light chain kinase, smooth muscle (EC 2.7.1.117) (MLCK) [Contains: Telokin] - *Oryctolagus cuniculus* (Rabbit), 1147 aa. | 45 . . . 1174 1009 . . . 1136 | 42/130 (32%) 61/130 (46%) | 2e-11 |
| Q15746 | Myosin light chain kinase, smooth muscle and non-muscle isozymes (EC 2.7.1.117) (MLCK) [Contains: Telokin (Kinase related protein) (KRP)] - *Homo sapiens* (Human), 1914 aa. | 77 . . . 186 414 . . . 521 | 37/110 (33%) 59/110 (53%) | 2e-11 |
| A41675 | telokin - rabbit, 155 aa. | 45 . . . 174 17 . . . 144 | 42/130 (32%) 61/130 (46%) | 3e-11 |

PFam analysis predicts that the NOV41a protein contains the domains shown in the Table 41E.

TABLE 41E

Domain Analysis of NOV41a

| Pfam Domain | NOV41a Match Region | Identities/ Similarities for the Matched Region | Expect Value |
|---|---|---|---|
| ig: domain 1 of 1 | 91 . . . 154 | 14/67 (21%) 49/67 (73%) | 7.8e-07 |

Example 42

The NOV42 clone was analyzed, and the nucleotide and encoded polypeptide sequences are shown in Table 42A.

TABLE 42A

NOV42 Sequence Analysis

| | |
|---|---|
| NOV42a | SEQ ID NO:105    1680 bp |
| CG91587-01 DNA Sequence | <u>TGCAGGTGCGTTGTACCCTTTTACGTGAGGCGGTGACGGCGGTTCGGAAGTCCTCTGG</u> |
| | CCTCCCCGCGGCCGCTCGCAGCTTGCTGGCCTCTCCCGCGCCTCACGTCGGACTCCGT |
| | CTCCGCGGCACGGAAGCAGCATCCAAGCTGAGGACATCCACCAGGAGTTGACCTGCCC |
| | CATCTGCCTCGACTATTTCCACCACCCGGTGTCCATCGACTCCGGCCACAACTTCTGC |
| | CGCGGCTGCCTGCACCGCAACTGCGCGCCGGGCGGCGGCCCGTTCCCCTGCCCCGAAT |
| | GTCGGCACCCATCGGCGCCCGCCGCCCTGCGACCCAACTGCGCCCTCGCCAGGCTGAC |
| | TGACAAGACGCAGCGCCGGCGCCTGGGCCCCGTCCCCCGGGCCTGTGCGGCCGCCAC |
| | TCGCAGCCGCTGCGGCTCTTCTGCCAGGACGACCAGCGaCCAGTGTGCCTGGTGTGCA |
| | GGGAGTCCCAGGAGCACCAGACTCACGCCATGGCACCCATCCACGAGGCCTTCGAGAG |
| | CTACCGGACAGGTAACTTTGACATCCACGTGGATGAATCCAAGAGAAGACTAATTACC |
| | CTGCTCTTGTACCATTCTAAGCAGGACGAGAAACTTCTTAAGTCTCAGCGTAATCTCG |
| | TGGCCAAGATGAAGAAAGTCATGCATTTACAGGATGTAGAAGTGAAGAACGCCACACA |
| | GTGCAAGGATAAGATAAAGAGTCAGCGAATGAGAATCAGCACGCAGTTTTCAAAGCTG |
| | CACAACTTCCTGGTTGAAGAAGAGGACCTCTTTCTTCAGAGATTCAACAAAGAAGAAG |
| | AAGAGACGAAGAAGAAGCTGAATGAGAACACGTTAAAACTCAATCAAACTATCGCTTC |
| | ATTGAAGAAGCTCATCTTAGAGGTGGGGCAGAAGAGCCAGGCTCCCACCCTGGAGCTG |
| | CTTCAGAATCCAAAAGAAGTGTTGACCAGGAGTGAGATCCAGGATGTGAACTATTCCC |
| | TTGAACCTGTGAAGGTGAAGACAGTGTGCCAGATACCATTGATGAAGGAAATGCTAAA |
| | CCGATTCCAAGTGGCTGTAAACCTAGCTGAAGACACAGCTCATCCCAAACTCGTCTTC |
| | TCCCAGGAAGGCAGATACGTGAAAAATACAGCATCAGCCAGTTCTTGGCCAACTGCTT |
| | TTGTAGAGAGATTTCAGCACTTACCCTGTGTTCTGGGAAAAAACGTTTTCACCTCAGG |
| | GAAACATTACTGGGAAGTTGAGAGTAGACATAGTCTGGACCTTGCTGTTGGGGTGTGT |
| | CGGGAGGACGTCATGGGAATTACTGATCGTTCAAAAATGTCCCCAGATGTGGGCATCT |
| | GGGCGATTTATTGCAGTGCTQCTCCCTATTGCCCCTTGATAGGCTTCCCTCCAACTCC |
| | CACCCAGCAAGAGCCAGCTCTCCACCGAGTGGGGGTTNACCTGGATCGTGGGACTGGG |
| | AATGTCTCCTTCTACAGCGCTGTGGACGGAGTGCACCTGCACACCTTTTCTTGTTCTT |
| | <u>CTGTCTCACGCCTCCGGCCATTTTTTTGGTTGAGTCCATTAGCATCTTTACTCATTCC</u> |
| | <u>ACCACTGACTGATACGAAATGAGGCTTTTCTTCCCCTGACCAAAACTCCTTCCCTGTA</u> |
| | <u>GTCCAGCTGAGGGACACACATCCCTGGGCCCTCTTCTGCCCTTCATGTCTCTATCC</u> |
| | ORF Staff: at 29    ORF Stop: at 1478 |
| | SEQ ID NO:106    483 aa  MW at 55196.9 kD |
| NOV42a | MEAEDIQEELTCPICLDYFQDPVSIECGHNFCRCCLHRNWAPGGGPFPCPECRHPSAP |
| CG91587-01 Protein Sequence | AALRPNWALARLTEKTQRRRLGPVPPGLCGRHWEPLRLFCEDDQRPVCLVCRESQEHQ |
| | THANAPIDEAFESYRTGHFDIHVDHWKRRLIRLLLYHSKQEEKLLKSQRNLVAKNKKV |
| | MHLQDVEVKNATQWKDKIKSQRMRISTEFSKLENFLVEEEDLFLQRLNKEEEETKKKL |
| | HEHTLKLNQTIASLKKLILEVGEKSQAPTLELLQNPKEVLTRSEIQDVNYSLEAVKVK |

TABLE 42A-continued

NOV42 Sequence Analysis

TVCQIPLMKEMLKRFQVAVNLAEDTAHPKLVFSQEGRYVKNTASASSWPTAFVERFQH

LPCVLGKNVFTSGKHYWEVESRDSLEVAVGVCREDVMGITDRSKMSPDVGIWAIYWSA

AGYWPLIGFPGTPTQQEPALHRVGVXLDRGTGNVSFYSAVDGVHLHTFSCSSVSRLRP

FFWLSPLASLVIPPVTDRK

Further analysis of the NOV42a protein yielded the following properties shown in Table 42B.

TABLE 42B

Protein Sequence Properties NOV42a

| | |
|---|---|
| PSort analysis: | 0.5050 probability located in cytoplasm; 0.3117 probability located in microbody (peroxisome); 0.1000 probability located in mitochondrial matrix space; 0.1000 probability located in lysosome (lumen) |
| SignalP analysis: | No Known Signal Sequence Predicted |

A search of the NOV42a protein against the Geneseq database, a proprietary database that contains sequences published in patents and patent publication, yielded several homologous proteins shown in Table 42C.

TABLE 42C

Geneseq Results for NOV42a

| Geneseq Identifier | Protein/Organism/Length [Patent #, Date] | NOV42a Residues/ Match Residues | Identities/ Similarities for the Matched Region | Expect Value |
|---|---|---|---|---|
| ABB11609 | Human secreted protein homologue, SEQ ID NO:1979 - *Homo sapiens*, 326 aa. [WO200157188-A2, 09 Aug. 2001] | 261 . . . 483<br>6 . . . 245 | 221/240 (92%)<br>221/240 (92%) | e−124 |
| AAB42919 | Human ORFX ORF2683 polypeptide sequence SEQ ID NO:5366 - *Homo sapiens*, 477 aa. [WO200058473-A2, 05 Oct. 2000] | 3 . . . 480<br>7 . . . 472 | 183/501 (36%)<br>264/501 (52%) | 2e−76 |
| AAR15148 | Ro/SSA autoantigen - *Homo sapiens*, 475 aa. [WO9117171-A, 14 Nov. 1991] | 8 . . . 466<br>12 . . . 446 | 173/468 (36%)<br>244/468 (51%) | 4e−67 |
| AAB43498 | Human cancer associated protein sequence SEQ ID NO:943 - *Homo sapiens*, 580 aa. [WO200055350-A1, 21 Sep. 2000] | 3 . . . 480<br>74 . . . 560 | 169/519 (32%)<br>248/519 (47%) | 1e−64 |
| AAW78921 | Human haemochromatosis protein RoRet - *Homo sapiens*, 465 aa. [WO9814466-A1, 09 Apr. 1998] | 6 . . . 481<br>10 . . . 465 | 160/490 (32%)<br>233/490 (46%) | 5e−58 |

In a BLAST search of public sequence datbases, the NOV42a protein was found to have homology to the proteins shown in the BLASTP data in Table 42D.

TABLE 42D

Public BLASTP Results for NOV42a

| Protein Accession Number | Protein/Organism/Length | NOV42a Residues/ Match Residues | Identities/ Similarities for the Matched Portion | Expect Value |
|---|---|---|---|---|
| Q9C037 | TRIPARTITE MOTIF PROTEIN TRIM4 ISOFORM ALPHA - *Homo sapiens* (Human), 500 aa. | 1 . . . 483<br>1 . . . 500 | 482/500 (96%)<br>482/500 (96%) | 0.0 |
| Q9C036 | TRIPARTITE MOTIF PROTEIN TRIM4 ISOFORM BETA - *Homo sapiens* (Human), 474 aa. | 1 . . . 483<br>1 . . . 474 | 456/500 (91%)<br>456/500 (91%) | 0.0 |

TABLE 42D-continued

Public BLASTP Results for NOV42a

| Protein Accession Number | Protein/Organism/Length | NOV42a Residues/ Match Residues | Identities/ Similarities for the Matched Portion | Expect Value |
|---|---|---|---|---|
| Q96F06 | SIMILAR TO TRIPARTITE MOTIF PROTEIN 4 - *Homo sapiens* (Human), 294 aa. | 1 ... 306<br>1 ... 280 | 280/306 (91%)<br>280/306 (91%) | e−162 |
| JE0343 | terf protein - rat, 477 aa. | 3 ... 480<br>7 ... 472 | 198/498 (39%)<br>274/498 (54%) | 6e−82 |
| Q9WV59 | RING FINGER PROTEIN TERF - *Rattus norvegicus* (Rat), 477 aa | 3 ... 480<br>7 ... 472 | 198/498 (39%)<br>274/498 (54%) | 7e−82 |

PFam analysis predicts that the NOV42a protein contains the domains shown in the Table 42E.

TABLE 42E

Domain Analysis of NOV42a

| Pfam Domain | NOV42a Match Region | Identities/ Similarities for the Matched Region | Expect Value |
|---|---|---|---|
| zf-C3HC4: domain 1 of 1 | 12 ... 52 | 18/54 (33%)<br>37/54 (69%) | 2.1e−15 |
| zf-B_box: domain 1 of 1 | 82 ... 123 | 19/48 (40%)<br>33/48 (69%) | 5.5e−12 |
| SNAP 25: domain 1 of 1 | 111 ... 275 | 36/217 (17%)<br>85/217 (39%) | 2.3 |
| SPRY: domain 1 of 1 | 360 ... 480 | 33/157 (21%)<br>82/157 (52%) | 3.5e−12 |

Example 43

The NOV43 clone was analyzed, and the nucleotide and encoded polypeptide sequences are shown in Table 43A.

TABLE 43A

NOV43 Sequence Analysis

| NOV43a, | SEQ ID NO:107  2295 bp |
|---|---|
| | CACCAGAAATGGATCCTTTCCCAANGCTGCTCCCCATCACAAGCCCTTCCTTTCATCC |
| CG91631-01 DNA Sequence | CATTCCTGCCGGTTCAGCGANCCGGAGTCGCCCAGGCCTGAACTCCTACCCAGGTCCC |
| | CGGCCCCCGCCCCGGCCCGCGAGACACCGGAGCCACCCCCCGGGGTGGNGNAGCGGAG |
| | CGCGGCCTAGACTCAAGTCTGGGTTTCAGCTGCCGCCAGCCCTATTGCTGCTGTTGCT |
| | GTTCTCTGTCCTTGGCCCAGGGNATGGAGGCCTTTTCCTGACTGATTACTCCACCTGC |
| | TCACCCCGCAAGCTGAGTCCTTTCCGCTCCTTTGCCAGCACCGAGCTCTTCCACTTCC |
| | ATGTTCCTGAGGACACATTCCTGGCTGTTTGGAACCTCATCATCTTCAAGGAGCAAGG |
| | GGGAACTTTTGGGGACCACTGCCCAGACCAAAGTGTGACTGTGTATTTCCGGTCCGGG |
| | GCACCCCCTGTCATCAATCCCCTGCATACACACTTCCCAGGGGACACAGCTGTGCCTG |
| | GGGTTTTCTCACTGACCCTCAGCTGGACACTGCCCAACCGCACCTCAGGCATCTTTAA |
| | CGTCAGCAGCCCCTTACCTGGGGACTGGTTCTTGGCTGCCCACCTTCCCAGGCCCAC |
| | GGCCACATCTCTGTCAAGGGTCTCCAGGATGAGTGTCAGTACCTCCTTCAGCCGCAGC |
| | TGATTGTCCGGCGTTTGCTGGACGTCGCTGTGCTGGTTCCTGGCCGGCCCTCAGAGCA |
| | AACCCTCTCCCCACACAATCGCTCAGCCCTGTACAAGGTCTTTGTGCCCAGCTTCACT |
| | TACAGGGTTTCAGCACAGCTGGTGTGTGTGGGGGGCCGTGGGGTATCTGCCTGCCCCC |
| | TGTCACTGCGTCTGCGTCCCAAAGCCCCACCCCTGCACAACTCAAGCTCTGTGGCCTG |
| | TGGAGGTGCCTCAGGATGCCAGCTGGAGCTGGCACTGCCCCCCTGGGGGCACTGGGTC |
| | TACGTGCGTGTGGAAACATCATCCCGGGGCCCTGGTAGGACCATCCGCTTCCAGCTGT |

TABLE 43A-continued

NOV43 Sequence Analysis

```
GTGTGCAGTTGCAAGAGTGCCCACAGCCCGGCCTGCTCCGAGCCCTGGTCCCTGGAGC
TGCCATGAACATGCCCCAGTCCCTGGGCAACCAGCCACTGCCCCCAGAACCGCCATCC
CTTGGAACCCCTGCGGAGGGGCCTGGGACCACGTCCCCACCCGAGCACTGCTGGCCAG
TGCGCCCGACTCTGCGCAACGAGCTGGACACCTTCTCTGTCCACTTCTACATCTTCTT
TGGCCCAAGTGTGGCCCTTCCCCCTGAGCGCCCAGCCGTGTTCGCCATGAGGCTGTTG
CCAGTGCTGGACAGTGGAGGCGTCCTCAGCCTGGAGCTCCAGCTCAATGCGAGCTCCG
TGCGCCAGGAAAACGTGACGGTGTTTGGATGCTTGACTCACGAGGTGCCCTTGAGCCT
GGGGGATGCAGCAGTGACCTGTTCCAAAGAGTCCCTGGCCGGCTTCCTCCTCTCTGTC
AGTGCCACCACCAGGGTTGCCAGGCTGCGAATCCCATTCCCGCAGACGGGGACCTGGT
TCCTGGCCCTCCGCTCCCTGTGCGGGGTGGGGCCTCGGTTCGTGCGGTGCCGCAACGC
GACGGCCGAGGTGCGGATGCGCACCTTCCTGTCCCCATGCGTGGACGACTGCGGGCCC
TACGGCCAGTGCAAGCTGCTGCGCACACACAATTATCTGTACGCAGCCTGCGAGTGCA
AGGCCGGGTGGAGAGGCTGGGGCTGCACCGACAGTGCAGATGCGCTCACCTATGGATT
CCAGCTGCTGTCCACACTCCTGCTCTGCCTGAGCAACCTCATGTTTCTGCCACCTGTG
GTCCTGGCCATTCGGAGTCGATATGTGCTGGAAGCTGCAGTCTACACCTTCACCATGT
TCTTCTCCACGTTCTATCATGCCTGTGACCAGCCAGGCATCGTGGTTTTCTGCATCAT
GGACTACGATGTGCTGCAGTTCTGTGATTTCCTGGGCTCCTTAATGTCCGTGTGGGTC
ACTGTCATTGCCATGGCTCGTTTACAGCCCGTGGTCAAGCAGGTGCTGTATTTGCTGG
GAGCTATGCTGCTGTCCATGGCTCTGCAGCTTGACCGACATGGACTCTGGAACCTGCT
TGGACCCAGTCTCTTCGCCCTGGGGATCTTGGCCACAGCCTGGAACCCCATAGAGATG
AACAAATCATCAGCGCTATTCTCCAGTTGCTCAGCAGGGCAAGGATTTGTGCCTGGCC
TTCCAGGTACTTTTGGAGTAAGAGGATGCTGAG
```

|  |  |
|---|---|
| | ORF Start: at 258    ORF Stop: end of sequence |
| | SEQ ID NO:108    761 aa  MW at 82335.7 kD |
| NOV43a, | MDPFPXLLPITSPSFHPIPAGSAXRSRPGLNSYPGPRPPPRPARHRSHPPGWXSGARP |
| CG91631-01 Protein Sequence | RLKSGFQLPPALLLLLLFSVLGPXGGLFLTDYSTCSPRKLSPFRSFASTELFHFHVP |
| | EDTFLAVWNLIIFKEQGGTFGDHCPDQSVTVYFRSGAPPVINPLHTHFPGDTAVPGVF |
| | SLTLSWTLPNRTSGIFNVSSPLPGDWFLAAHLPQAHGHISVKGLQDECQYLLQPQLIV |
| | RRLLDVAVLVPGRPSEQTLSPHNRSALYKVFVPSFTYRVSAQLVCVGCRGVSACPLSL |
| | RLRPKAPPLHNSSSVACGGASGCQLELALPPWGHWVYVRVETSSRGPGRTIRFQLCVQ |
| | LQECPQPGLLRALVPGAAMNMPQSLGNQPLPPEPPSLGTPAEGPGTTSPPEHCWPVRP |
| | TLRNELDTFSVHFYIFFGPSVALPPERPAVFAMRLLPVLDSGGVLSLELQLNASSVRQ |
| | ENVTVFGCLTHEVPLSLGDAAVTCSKESLAGFLLSVSATTRVARLRIPFPQTGTWFLA |
| | LRSLCGVGPRFVRCRNATAEVRMRTFLSPCVDDCGPYGQCKLLRTHNYLYAACECKAG |
| | WRGWGCTDSADALTYGFQLLSTLLLCLSNLMFLPPVVLAIRSRYVLEAAVYTFTMFFS |
| | TFYHACDQPGIVVFCIMDYDVLQFCDFLGSLMSVWVTVIAMARLQPVVKQVLYLLGAM |
| | LLSMALQLDRHGLWNLLGPSLFALGILATAWNPIEMNKSSALFSSCSAGQGFVPGLPG |
| | TFGVRGC |

Further analysis of the NOV43a protein yielded the following properties shown in Table 43B.

TABLE 43B

| Protein Sequence Properties NOV43a | |
|---|---|
| PSort analysis: | 0.6000 probability located in plasma membrane; 0.4000 probability located in Golgi body; 0.3000 probability located in endoplasmic reticulum (membrane); 0.3000 probability located in microbody (peroxisome) |
| SignalP analysis: | No Known Signal Sequence Predicted |

A search of the NOV43a protein against the Geneseq database, a proprietary database that contains sequences published in patents and patent publication, yielded several homologous proteins shown in Table 43C.

TABLE 43C

Geneseq Results for NOV43a

| Geneseq Identifier | Protein/Organism/Length [Patent #, Date] | NOV43a Residues/ Match Residues | Identities/ Similarities for the Matched Region | Expect Value |
|---|---|---|---|---|
| AAM93940 | Human polypeptide, SEQ ID NO: 4122 - *Homo sapiens*, 338 aa. [EP1130094-A2, 05 Sep. 2001] | 367 . . . 639 1 . . . 273 | 273/273 (100%) 273/273 (100%) | e−162 |
| ABB11995 | Human M83 protein homologue, SEQ ID NO:2365 - *Homo sapiens*, 728 aa. [WO200157188-A2, 09 Aug. 2001] | 89 . . . 727 3 . . . 630 | 270/641 (42%) 381/641 (59%) | e−144 |
| AAY21590 | Human secreted protein (clone C544-1) - *Homo sapiens*, 310 aa. [WO9926973-A1, 03 Jun. 1999] | 536 . . . 727 9 . . . 200 | 114/192 (59%) 149/192 (77%) | 4e−70 |
| AAW52985 | *Homo sapiens* clone C544_1 protein - *Homo sapiens*, 229 aa. [WO9807859-A2, 26 Feb. 1998] | 536 . . . 727 9 . . . 200 | 113/192 (58%) 148/192 (76%) | 1e−69 |
| AAY52590 | Human prostate growth-associated membrane protein PGAMP-2 - *Homo sapiens*, 410 aa. [WO9961469-A2, 02 Dec. 1999] | 611 . . . 727 1 . . . 117 | 117/117 (100%) 117/117 (100%) | 2e−62 |

In a BLAST search of public sequence datbases, the NOV43a protein was found to have homology to the proteins shown in the BLASTP data in Table 43D.

TABLE 43D

Public BLASTP Results for NOV43a

| Protein Accession Number | Protein/Organism/Length | NOV43a Residues/ Match Residues | Identities/ Similarities for the Matched Portion | Expect Value |
|---|---|---|---|---|
| Q9P0U7 | NAG-5 PROTEIN - *Homo sapiens* (Human), 704 aa. | 1 . . . 639 1 . . . 639 | 639/639 (100%) 639/639 (100%) | 0.0 |
| O75539 | HYPOTHETICAL 63.6 KDA PROTEIN - *Homo sapiens* (Human), 585 aa (fragment). | 120 . . . 639 1 . . . 520 | 520/520 (100%) 520/520 (100%) | 0.0 |
| Q9HBY2 | NASOPHARYNGEAL CARCINOMA RELATED PROTEIN - *Homo sapiens* (Human), 338 aa. | 367 . . . 639 1 . . . 273 | 273/273 (100%) 273/273 (100%) | e−162 |
| Q96S25 | M83 - *Homo sapiens* (Human), 771 aa. | 71 . . . 727 21 . . . 673 | 277/666 (41%) 390/666 (57%) | e−145 |
| AAH21557 | TRANSMEMBRANE PROTEIN 8 (FIVE MEMBRANE-SPANNING DOMAINS) - *Homo sapiens* (Human), 771 aa. | 71 . . . 727 21 . . . 673 | 275/665 (41%) 386/665 (57%) | e−145 |

PFam analysis predicts that the NOV43a protein contains the domains shown in the Table 43E.

TABLE 43E

Domain Analysis of NOV43a

| Pfam Domain | NOV43a Match Region | Identities/ Similarities for the Matched Region | Expect Value |
|---|---|---|---|
| No Significant Matches Found | | | |

Example 44

The NOV44 clone was analyzed, and the nucleotide and encoded polypeptide sequences are shown in Table 44A.

TABLE 44A

NOV44 Sequence Analysis

SEQ ID NO: 109   1147 bp

NOV44a,
CG91643-01 DNA Sequence

ATGGCGGCGGCGGCGGCTCAGGGGGCGGGGCGGGGAGCCCCGTAGAACCGAGGGGG
TCGGCCCGGGGGTCCCGGGGGAGGTGGAGATGGTGAAGGGGCAGCCGTTCGACGTGGG
CCCGCGCTACACGCAGTTGCAGTACATCGGCGAGGGCGCGTACGGCATGGTCAGCTCG
GCCTATGACCACGTGCGCAAGACTCGCGTGGCCATCAAGAAGATCAGCCCCTTCGAAC
ATCAGACCTACTGCCAGCGCACGCTCCGGGAGATCCAGATCCTGCTGCGCTTCCGCCA
TGAGAATGTCATCGGCATCCGAGACATTCTGCGGGCGTCCACCCTGGAAGCCATGAGA
GATGTCTACATTGTGCAGGACCTGATGGAGACTGACCTGTACAAGTTGCTGAAAAGCC
AGCAGCTGAGCAATGACCATATCTGCTACTTCCTCTACCAGATCCTGCGGGGCCTCAA
GTACATCCACTCCGCCAACGTGCTCCACCGAGATCTAAAGCCCTCCAACCTGCTCAGC
AACACCACCTGCGACCTTAAGATTTGTGATTTCGGCCTGGCCCGGATTGCCGATCCTG
AGCATGACCACACCGGCTTCCTGACGGAGTATGTGGCTACGCGCTGGTACCGGGCCCC
AGAGATCATGCTGAACTCCAAGGGCTATACCAAGTCCATCGACATCTGGTCTGTGGGC
TGCATTCTGGCTGAGATGCTCTCTAACCGGCCCATCTTCCCTGGCAAGCACTACCTGG
ATCAGCTCAACCACATTCTGGGCATCCTGGGCTCCCCATCCCAGGAGGACCTGAATTG
TATCATCAACATGAAGGCCCGAAACTACCTACAGTCTCTGCCCTCCAAGACCAAGGTG
GCTTGGGCCAAGCTTTTCCCCAAGTCAGACTCCAAAGCCCTTGACCTGCTGGACCGGA
TGTTAACCTTTAACCCCAATAAACGGATCACAGTGGCCGAGGAGCCCTTCACCTTCGC
CATGGAGCTGGATGACCTACCTAAGGAGCGGCTGAAGGAGCTCATCTTCCAGGAGACA
GCACGCTTCCAGCCCGGAGTGCTGGAGGCCCCCTAGCCCAGACAGACATCTCTGCACC
CTGGGGCCTGGACCTGCCTCCTGCCTGCCCCTCTCCCGCCAGACT

ORF Start: ATG at 1   ORF Stop: TAG at 1078
SEQ ID NO: 110   359 aa   MW at 40747.5kD NOV44a,
CG91643-01 Protein Sequence MAAAAAQGGGGEPRRTEGVGPGVPGEVEMVKGQPFDVGPRYTQLQYIGEGAYGMVSS
AYDHVRKTRVAIKKISPFEHQTYCQRTLREIQILLRFRHENVIGIRDILRASTLEAMR
DVYIVQDLMETDLYKLLKSQQLSNDHICYFLYQILRGLKYIHSANVLHRDLKPSNLLS
NTTCDLKICDFGLARIADPEHDHTGFLTEYVATRWYRAPEIMLNSKGYTKSIDIWSVG
CILAEMLSNRPIFPGKHYLDQLNHILGILGSPSQEDLNCIINMKARNYLQSLPSKTKV
AWAKLFPKSDSKALDLLDRMLTFNPNKRITVAEEPFTFAMELDDLPKERLKELIFQET
ARFQPGVLEAP Further analysis of the NOV44a protein yielded the following properties shown in Table 44B.

TABLE 44B

Protein Sequence Properties NOV44a

| PSort analysis: | 0.4500 probability located in cytoplasm; 0.3000 probability located in microbody (peroxisome); 0.1924 probability located in lysosome (lumen); 0.1000 probability located in mitochondrial matrix space |
|---|---|

TABLE 44B-continued

Protein Sequence Properties NOV44a

| SignalP analysis: | No Known Signal Sequence Predicted |
|---|---|

A search of the NOV44a protein against the Geneseq database, a proprietary database that contains sequences published in patents and patent publication, yielded several homologous proteins shown in Table 44C.

TABLE 44C

Geneseq Results for NOV44a

| Geneseq Identifier | Protein/Organism/Length [Patent #, Date] | NOV44a Residues/ Match Residues | Identities/ Similarities for the Matched Region | Expect Value |
|---|---|---|---|---|
| AAG67618 | Amino acid sequence of a human protein - *Homo sapiens*, 379 aa. [WO200109316-A1, 08 Feb. 2001] | 1 ... 359<br>1 ... 379 | 359/379 (94%)<br>359/379 (94%) | 0.0 |
| AAG67439 | Amino acid sequence of a human polypeptide - *Homo sapiens*, 379 aa. [WO200109345-A1, 08 Feb. 2001] | 1 ... 359<br>1 ... 379 | 359/379 (94%)<br>359/379 (94%) | 0.0 |
| AAY70778 | EGFP-Erk1 fusion protein construct - Chimeric - *Homo sapiens*, 631 aa. [WO200023615-A2, 27 Apr. 2000] | 1 ... 359<br>253 ... 631 | 359/379 (94%)<br>359/379 (94%) | 0.0 |
| AAY42413 | Extracellular signal Regulated Kinase (ERK)1 mutant - *Homo sapiens*, 379 aa. [WO9942592-A1, 26 Aug. 1999] | 1 ... 359<br>1 ... 379 | 359/379 (94%)<br>359/379 (94%) | 0.0 |
| AAW85006 | Erk1-green flourescent protein fusion product - Chimeric - *Aequorea victoria*, 631 aa. [WO9845704-A2, 15 Oct. 1998] | 1 ... 359<br>253 ... 631 | 359/379 (94%)<br>359/379 (94%) | 0.0 |

In a BLAST search of public sequence datbases, the NOV44a protein was found to have homology to the proteins shown in the BLASTP data in Table 44D.

TABLE 44D

Public BLASTP Results for NOV44a

| Protein Accession Number | Protein/Organism/Length | NOV44a Residues/ Match Residues | Identities/ Similarities for the Matched Portion | Expect Value |
|---|---|---|---|---|
| A48082 | MAP kinase 3 (EC 2.7.1.-) - human, 379 aa. | 1 ... 359<br>1 ... 379 | 359/379 (94%)<br>359/379 (94%) | 0.0 |
| P27361 | Mitogen-activated protein kinase 3 (EC 2.7.1.-) (Extracellular signal- regulated kinase 1) (ERK- 1) (Insulin-stimulated MAP2 kinase) (MAP kinase 1) (MAPK 1) (p44-ERK1) (ERT2) (p44-MAPK) (Microtubule- associated protein-2 kinase) - *Homo sapiens* (Human), 379 aa. | 1 ... 359<br>1 ... 379 | 358/379 (94%)<br>358/379 (94%) | 0.0 |
| CAB69291 | SEQUENCE 38 FROM PATENT WO9845704 - unidentified, 630 aa (fragment). | 1 ... 358<br>253 ... 630 | 358/378 (94%)<br>358/378 (94%) | 0.0 |
| CAB69300 | SEQUENCE 56 FROM PATENT WO9845704 - unidentified, 624 aa. | 2 ... 359<br>3 ... 380 | 346/378 (91%)<br>347/378 (91%) | 0.0 |
| P21708 | Mitogen-activated protein kinase 3 (EC 2.7.1.-) (Extracellular signal- regulated kinase 1) (ERK-1) (Insulin-stimulated MAP2 kinase) (MAP kinase 1) (MAPK 1) (P44-ERK1) (ERT2) (P44-MAPK) (Microtubule- associated protein-2 kinase) (MNK1) - *Rattus norvegicus* (Rat), 380 aa. | 2 ... 359<br>3 ... 380 | 346/378 (91%)<br>347/378 (91%) | 0.0 |

PFam analysis predicts that the NOV44a protein contains the domains shown in the Table 44E.

TABLE 44E

Domain Analysis of NOV44a

| Pfam Domain | NOV44a Match Region | Identities/ Similarities for the Matched Region | Expect Value |
|---|---|---|---|
| pkinase: domain 1 of 1 | 42 ... 323 | 94/302 (31%) 234/302 (77%) | 2e-78 |

Example 45

The NOV45 clone was analyzed, and the nucleotide and encoded polypeptide sequences are shown in Table 45A.

TABLE 45A

NOV45 Sequence Analysis

NOV45a,
CG91911-01 DNA Sequence

SEQ ID NO:111   2496 bp

TATGTCAGTTTCCCATGGGTCTTGAATGCAAATACAAATATCGTAAACTAAATATTTG
TGTTTTCTTTCCTAGACTCTCCAGAAAGAGCAACAGTAATGGAGTACATGAGCACTGG
AAGTGACAATAAAGAAGAGATTGATTTATTAATTAAACATTTAAATGTGTCTGATGTA
ATAGACATTATGGAAAATCTTTATGCAAGTGAAGAGCCAGCAGTTTATGAACCCAGTC
TAATGACCATGTGTCAAGACAGTAATCAAAACGATGAGCGTTCTAAGTCTCTGCTGCT
TAGTGGCCAAAAGGTACCATGGTTGTCATCAGTCAAATACGGAACTGTGGAGGATTTG
CTTGCTTTTGAAAACCATATATCCAACACTGCAAAGCATTTTTATGTTCAACGACCAC
AGGAATATGGTATTTTATTAAACATGGTAATCACTCCCCAAAATGGACGTTACCAAAT
AGATTCCGATGTTCTCCTGATCCCCTGGAAGCTGACTTACAGGAATATTGGTTCTGAT
TTTATTCCTCGGGGCGCCTTTGGAAAGGTATACTTGGCACAAGATATAAAGACGAAGA
AAAGAATGGCGTGTAAACTGATCCCAGTAGATCAATTTAAGCCATCTGATGTGGAAAT
CCAGGCTTCCTTCCGGCACGAGAACATCGCAGAGCTGTATGGCGCAGTCCTGTGGGGT
GAAACTGTCCATCTCTTTATGGAAGCAGGCGAGGGTCTGTTCTGGAGAAACTGG
AGAGCTGTGGACCAATGAGAGAATTTGAAATTATTTGGGTGACAAAGCATGTTCTCAA
GGGACTTGATTTTCTACACTCAAAGAAAGTGATCCATCATGATATTAAACCTAGCAAC
ATTCTTTTCATGTCCACAAAAGCTGTTTTGGTGGATTTTGGCCTAAGTGTTCAAATCA
CCGAAGATGTCTATTTTCCTAAGGACCTCCGAGGAACAGAGATTTACATGAGCCCAGA
GGTCATCCTGTGCAGGGGCCATTCAACCAAAGCAGACATCTACAGCCTGGGGGCCACG
CTCATCCACATGCAGACGGGCACCCCACCCTGGGTGAAGCGCTACCCTCGCTCAGCCT
ATCCCTCCTACCTGTACATAATCCACAAGCAAGCACCTCCACTGGAAGACATTGCAGA
TGACTGCAGTCCAGGGATGAGAGAGCTGATAGAAGCTTCCCTGGAGAGAAACCCCAAT
CACCGCCCAAGAGCCGCAGACCTACTAAAACATGAGGCCCTGAACCCGCCCAGAGAGG
ATCAGCCACGCTGTCAGAGTCTGGACTCTGCCCTCTTGGAGCGCAAGAGGCTGCTGAG
TAGGAAGGAGCTGGAACTTCCTGAGAACATTGCTGATTCTTCGTGCACAGGAAGCACC
GAGGAATCTGAGATGCTCAAGAGGCAACGCTCTCTCTACATCGACCTCGGCGCTCTGG
CTGGCTACTTCAATCTTGTTCGGGGACCACCAACGCTTGAATATGGCTGAAGGATGCC
ATGTTTGCTCTAAATTAAGACAGCATTGATCTCCTGGAGGCTGGTTCTGCTGCCTCTA
CACAGGGGCCCTGTACAGTGAATGGTGCCATTTTCGAAGGAGCAGTGTGACCTCCTGT

TABLE 45A-continued

NOV45 Sequence Analysis

GACCCGTGAATGTGCCTCCAAGCGGCCCTGTGTGTTTGACATGTGAAGCTATTTGATA
TGCACCAGGTCTCAAGGTTCTCATTTCTCAGGTGACGTGATTCTAAGGCAGGAATTTG
AGAGTTCACAGAAGGATCGTGTCTGCTGACTGTTTCATTCACTGTGCACTTTGCTCAA
AATTTTAAAAATACCAATCACAAGGATAATAGAGTAGCCTAAAATTACTATTCTTGGT
TCTTATTTAAGTATGGAATATTCATTTTACTCAGAATAGCTGTTTTGTGTATATTGGT
GTATATTATATAACTCTTTGAGCCTTTATTGGTAAATTCTGGTATACATTGAATTCAT
TATAATTTGGGTGACTAGAACAACTTGAAGATTGTAGCAATAAGCTGGACTAGTGTCC
TAAAAATGGCTAACTGATGAATTAGAAGCCATCTGACAGCAGGCCACTAGTGACAGTT
TCTTTTGTGTTCCTATGGAAACATTTTATACTGTACATGCTATGCTGAAGACATTCAA
AACGTGATGTTTTGAATGTGGATAAAACTGTGTAAACCACATAATTTTTGTACATCCC
AAAGGATGAGAATGTGACCTTTAAGAAAAATGAAAACTTTTGTAAATTATTGATGATT
TTGTAATTCTTATGACTAAATTTTCTTTTAAGCATTTGTATATTAAAATAGCATACTG
TGTATGTTTTATATCAAATGCCTTCATGAATCTTTCATACATATATATATTTGTAACA
TTGTAAAGTATGTGAGTAGTCTTATGTAAAGTATGTTTTTACATTATGCAAATAAAAC
CCAATACTTTTGTCCAATGTGGTTGGTCAAATCAACTGAATAAATTCAGTATTTTGCC
TT

ORF Start: ATG at 97     ORF Stop: TGA at 1498
SEQ ID NO:112     467 aa   MW at 53071.2 kD NOV45a, CG91911-01 Protein Sequence MEYMSTGSDNKEEIDLLIKHLNVSDVIDIMENLYASEEPAVYEPSLMTMCQDSNQNDE
RSKSLLLSGQKVPWLSSVKYGTVEDLLAFENHISNTAKHFYVQRPQEYGILLNMVITP
QNGRYQIDSDVLLIPWKLTYRNIGSDFIPRGAFGKVYLAQDIKTKKRMACKLIPVDQF
KPSDVEIQACFRHENIAELYGAVLWGETVHLFMEAGEGGSVLEKLESCGPMREFEIIW
VTKHVLKGLDFLHSKKVIHHDIKPSNIVFMSTKAVLVDFGLSVQMTEDVYFPKDLRGT
EIYMSPEVILCRGHSTKADIYSLGATLIHMQTGTPPWVKRYPRSAYPSYLYIIHKQAP
PLEDIADDCSPGMRELIEASLERNPNHRPRAADLLKHEALNPPREDQPRCQSLDSALL
ERKRLLSRKELELPENIADSSCTGSTEESEMLKRQRSLYIDLGALAGYFNLVRGPPTL
EYG Further analysis of the NOV45a protein yielded the following properties shown in Table 45B.

TABLE 45B

Protein Sequence Properties NOV45a

| | |
|---|---|
| PSort analysis: | 0.6500 probability located in cytoplasm; 0.1000 probability located in mitochondrial matrix space; 0.1000 probability located in lysosome (lumen); 0.0000 probability located in endoplasmic reticulum (membrane) |
| SignalP analysis: | No Known Signal Sequence Predicted |

A search of the NOV45a protein against the Geneseq database, a proprietary database that contains sequences published in patents and patent publication, yielded several homologous proteins shown in Table 45C.

TABLE 45C

Geneseq Results for NOV45a

| Geneseq Identifier | Protein/Organism/Length [Patent #, Date] | NOV45a Residues/ Match Residues | Identities/ Similarities for the Matched Region | Expect Value |
|---|---|---|---|---|
| AAE10313 | Human Tp12 protein - *Homo sapiens*, 467 aa. [WO200166559-A1, 13 Sep. 2001] | 1 . . . 467<br>1 . . . 467 | 462/467 (98%)<br>464/467 (98%) | 0.0 |
| AAE05951 | Human cot oncoprotein encoded by D14497 oncogene - *Homo sapiens*, 467 aa. [U.S. 6265216-B1, 24 Jul. 2001] | 1 . . . 467<br>1 . . . 467 | 461/467 (98%)<br>463/467 (98%) | 0.0 |
| AAY79244 | Human COT - *Homo sapiens*, 467 aa. [WO200011191-A2, 02 Mar. 2000] | 1 . . . 467<br>1 . . . 467 | 461/467 (98%)<br>463/467 (98%) | 0.0 |
| AAE10314 | Rat Tp12 protein - *Rattus* sp, 467 aa. [WO200166559-A1, 13 Sep. 2001] | 1 . . . 467<br>1 . . . 467 | 435/467 (93%)<br>452/467 (96%) | 0.0 |
| AAY79243 | Rat TPL-2 - *Rattus norvegicus*, 467 aa. [WO200011191-A2, 02 Mar. 2000] | 1 . . . 467<br>1 . . . 467 | 435/467 (93%)<br>452/467 (96%) | 0.0 |

In a BLAST search of public sequence datbases, the NOV45a protein was found to have homology to the proteins shown in the BLASTP data in Table 45D.

TABLE 45D

Public BLASTP Results for NOV45a

| Protein Accession Number | Protein/Organism/Length | NOV45a Residues/ Match Residues | Identities/ Similarities for the Matched Portion | Expect Value |
|---|---|---|---|---|
| A48713 | serine/threonine-specific protein kinase cot, 58K form - human, 467 aa. | 1 . . . 467<br>1 . . . 467 | 462/467 (98%)<br>464/467 (98%) | 0.0 |
| P41279 | Mitogen-activated protein kinase kinase kinase 8 (EC 2.7.1.-) (COT proto-oncogene serine/threonine-protein kinase) (C-COT) (Cancer osaka thyroid oncogene) - *Homo sapiens* (Human), 467 aa. | 1 . . . 467<br>1 . . . 467 | 461/467 (98%)<br>463/467 (98%) | 0.0 |
| Q63562 | Mitogen-activated protein kinase kinase kinase 8 (EC 2.7.1.-) (Tumor progression locus 2) (TPL-2) - *Rattus norvegicus* (Rat), 467 aa. | 1 . . . 467<br>1 . . . 467 | 435/467 (93%)<br>452/467 (96%) | 0.0 |
| Q07174 | Mitogen-activated protein kinase kinase kinase 8 (EC 2.7.1.-) (COT proto-oncogene serine/threonine-protein kinase) (C-COT) (Cancer osaka thyroid oncogene) - *Mus musculus* (Mouse), 467 aa. | 1 . . . 467<br>1 . . . 467 | 432/467 (92%)<br>453/467 (96%) | 0.0 |
| A41253 | kinase-related transforming protein (EC 2.7.1.-) - human, 415 aa. | 1 . . . 397<br>1 . . . 397 | 374/397 (94%)<br>376/397 (94%) | 0.0 |

PFam analysis predicts that the NOV45a protein contains the domains shown in the Table 45E.

TABLE 45E

Domain Analysis of NOV45a

| Pfam Domain | NOV45a Match Region | Identities/ Similarities for the Matched Region | Expect Value |
|---|---|---|---|
| pkinase: domain 1 of 1 | 146 . . . 388 | 74/279 (27%)<br>187/279 (67%) | 4.7e−54 |

Example 46

The NOV46 clone was analyzed, and the nucleotide and encoded polypeptide sequences are shown in Table 46A.

TABLE 46A

NOV46 Sequence Analysis

| | |
|---|---|
| NOV46a, CG91931-01 DNA Sequence | SEQ ID NO:113    568 bp<br>GACGAGCTGATGAGCGTGCGTCTGCGCGAGGCCCAGGCCCTGGCCGAGGGCCGCGAGC<br>TGCGGCAGCGCGTGGTGGAACTTGAGACGCAGGTGGACTCGGGGCAGAGGGAGGAAGG<br>CCGCATCCAGGGCCAGCTGAACCACTCGGACTCATCGCAGTACATCCGCGAGCTCAAG<br>GACCAGATCGAGGAGCTGAAGGCCGAGGTGCAGGTGCGGCTGCTGAAGGGCCCGCCGC<br>CCTTCGAGGACCCGCTGGCTTTCGATGGGCTGAGCCTGGCGCGGCACTTGGACGAGGA<br>CTCGCTGCCGTCGTCGGACGAGGAGCTACTTGGCGTAGGCGTGGGCGCTGCCCTGCAG<br>GACGCATTGTATCCTCTGTCCCCGCGCGATGCGCGCTTCTTCCGCCGTCTGGAGCGGC<br>CGGCCAAGGACAGCGAGGGCGCAGGACGCATTGTATCCTCTGTCCCCGCGCGATGCGC<br>GCTTCTTCCGCCGTCTGGAGCGGCCGGCCAAGGACAGCGAGGGCAGCTCAGACAGCGA<br>CGCCGATGAGCTGGCCGCGCCCTACAGCCAGGGTCTGGACAACTGA |
| NOV46a, CG91931-01 Protein Sequence | ORF Start: ATG at 10    ORF Stop: TGA at 529<br>SEQ ID NO:114    173 aa   MW at 19187.3 kD<br>MSVRLREAQALAEGRELRQRVVELETQVDSGQREEGRIQGQLNHSDSSQYIRELKDQI<br>EELKAEVQVRLLKGPPPFEDPLAFDGLSLARHLDEDSLPSSDEELLGVGVGAALQDAL<br>YPLSPRDARFFRRLERPAKDSEGAGRIVSSVPARCALLPPSGAAGQGQRGQLRQRRR |

Further analysis of the NOV46a protein yielded the following properties shown in Table 46B.

TABLE 46B

Protein Sequence Properties NOV46a

| | |
|---|---|
| PSort analysis: | 0.5680 probability located in mitochondrial matrix space; 0.2832 probability located in mitochondrial inner membrane; 0.2832 probability located in mitochondrial intermembrane space; 0.2832 probability located in mitochondrial outer membrane |
| SignalP analysis: | No Known Signal Sequence Predicted |

A search of the NOV46a protein against the Geneseq database, a proprietary database that contains sequences published in patents and patent publication, yielded several homologous proteins shown in Table 46C.

TABLE 46C

Geneseq Results for NOV46a

| Geneseq Identifier | Protein/Organism/Length [Patent #, Date] | NOV46a Residues/ Match Residues | Identities/ Similarities for the Matched Region | Expect Value |
|---|---|---|---|---|
| AAM84422 | Human immune/haematopoietic antigen SEQ ID NO:12015 - *Homo sapiens*, 110 aa. [WO200157182-A2, 09 Aug. 2001] | 66 ... 102<br>74 ... 110 | 24/37 (64%)<br>24/37 (64%) | 4e–05 |
| AAW33887 | Flea saliva protein PfspM(B)900 - *Ctenocephalides felis*, 900 aa. [WO9737676-A1, 16 Oct. 1997] | 2 ... 66<br>517 ... 581 | 24/67 (35%)<br>40/67 (58%) | 0.13 |
| AAW82361 | Flea saliva protein PfspM(B)-900 - *Ctenocephalides* sp, 900 aa. [WO9845408-A2, 15 Oct. 1998] | 2 ... 66<br>517 ... 581 | 24/67 (35%)<br>40/67 (58%) | 0.23 |
| AAY59273 | Mouse huntingtin-interacting protein (mHIP1a) - *Mus* sp, 1068 aa. [WO9960986-A2, 02 Dec. 1999] | 3 ... 80<br>563 ... 646 | 26/84 (30%)<br>43/84 (50%) | 0.51 |
| AAY93405 | Amino acid sequence of a filament-like protein 3 - *Lycopersicon esculentum*, 582 aa. [WO200028054-A2, 18 May 2000] | 12 ... 67<br>312 ... 372 | 19/61 (31%)<br>34/61 (55%) | 0.67 |

In a BLAST search of public sequence datbases, the NOV46a protein was found to have homology to the proteins shown in the BLASTP data in Table 46D.

TABLE 46D

Public BLASTP Results for NOV46a

| Protein Accession Number | Protein/Organism/Length | NOV46a Residues/ Match Residues | Identities/ Similarities for the Matched Portion | Expect Value |
| --- | --- | --- | --- | --- |
| Q96CN4 | SIMILAR TO ECOTROPIC VIRAL INTEGRATION SITE 5 - Homo sapiens (Human), 794 aa. | 1 . . . 140 644 . . . 776 | 121/140 (86%) 127/140 (90%) | 3e−60 |
| Q9D9F2 | 1700084G18RIK PROTEIN - Mus musculus (Mouse), 133 aa. | 1 . . . 142 1 . . . 133 | 99/144 (68%) 107/144 (73%) | 1e−41 |
| O60447 | EVI-5 HOMOLOG - Homo sapiens (Human), 810 aa. | 1 . . . 104 648 . . . 746 | 55/106 (51%) 70/106 (65%) | 5e−19 |
| P97366 | EVI-5 - Mus musculus (Mouse), 809 aa. | 1 . . . 104 648 . . . 746 | 53/106 (50%) 70/106 (66%) | 5e−18 |
| Q19101 | HYPOTHETICAL 53.2 KDA PROTEIN - Caenorhabditis elegans, 466 aa. | 1 . . . 64 266 . . . 331 | 25/66 (37%) 41/66 (61%) | 0.006 |

PFam analysis predicts that the NOV46a protein contains the domains shown in the Table 46E.

TABLE 46E

Domain Analysis of NOV46a

| Pfam Domain | NOV46a Match Region | Identities/ Similarities for the Matched Region | Expect Value |
| --- | --- | --- | --- |
| No Significant Matches Found | | | |

Example 47

The NOV47 clone was analyzed, and the nucleotide and encoded polypeptide sequences are shown in Table 47A.

TABLE 47A

NOV47 Sequence Analysis

NOV47a

CG91941-01 DNA Sequence

SEQ ID NO:115          1387 bp
CGCGACTCTGGCGACTGGCCGGCCATGCCGTCCCGGGCTGAGAACTATGAAGTGTTGT

ACACCATTGGCACAGGCTCCTATGGCCGCTGCCAGAAGATCCAGCGGAAGAGTGACGG

CAAGATATTAGTTTGGAAAGAACTTGATTATGGCTTCATGACAGAAGCTGAGAAACAG

ATGCTTATTTCTGAAGTGAATTTGCTTCGTGAACTGAAACATCCAAACATCGTTCATT

ACTATGATCGTATTATTGACCGGACCAACACAACACTGTACGTTGTAATGGAATATTG

TGAAGGAGGGGATCTGGCTAGTGTAATTACAAAGGGAACCATGGAAAGGCAATACTTA

GATGAAGAGTTTGTTCTTCGAGTGATGACTCAGTTGACTCTGGCCCTGAAGGAATGCC

ACAGACGAAGTGGTGGTGATCATACTGTATTGCGTGGGGATCTGAAACCAGCCAATGT

TTTCCTGGATGGCAAGCAAAACGTCAAGCTTGGAGATTTGGGGCTAGCCAGAATATTA

AACCACGACACGAGTTTTGCAAAAACATTTGTTGGCATACCTTATTACATGTCTCCTG

AACAAATGAATCGCATGTCCTACAATGAGAAACCAGATATCTGGTCATTGGGCTGCTT

GCTGTATGAGTTATGTGCATTAATGCCTCCATTTACAGCTTTTAGCCAGAAAGAACTC

GCTGGGAAAATCAGAGAAGGCAAATTCAGGCGAATTCTATACCGTTACTCTGATGAAT

TABLE 47A-continued

NOV47 Sequence Analysis

|  |  |
|---|---|
|  | TGAATGAAATTATTATGAGGATGTTAAACTTAAAGGATTACCATCAACCTTCTGTTGA |
|  | AGAAATTCTTGAGAACCCTTTAATAGCAGATTTGGTTGCACAAGAGCAAAGAAGAAAT |
|  | CTTGAGAGAAGAGGGCGACAATTAGGAGAGCCAGAAAAATTGCTGGATTCCAGCCCTG |
|  | TATTGAGTGAGCTGAAACTAAAGGAAATTCAGTTAGAGGAGCAAGAGCGAGCTCTCAA |
|  | AGCAGGAGAAGAAAGATTGGAGCAGAAAGAACAGGAGCTTTGTGTTTGTGAGAGACTA |
|  | GCAGAGGACAGACTGGCTATACCAGAAAATCTGTTGAAGAATTACAGCTTGCTAAAGG |
|  | AACAGAAGTTCCTGTCTCTGGCAAGTAGTCCAGAACTTCTTAATCTTCCATCCTCAGT |
|  | AATTAAGAAGAAAGTTCATTTCAGTGGGGAAAGTAAAGAGAATGTCATGAGGAGTGAG |
|  | AATCCTGAGAGTCAGCTCACATCTAAGTCCAAGTGCAAGGACCTGAAGTGCTTCATGC |
|  | TTCATGCTGCCCAGCTGCGGGCTCAAGCCCTGTCAGATATTGAGAAAAATTACCAACT |
|  | GAAAAGCAGACAGATCCTGGGCATGCGCTAGCCAGGTAGAGAGACACAGAGCT |
|  | ORF Start: ATG at 25      ORF Stop: TAG at 1363 |
|  | SEQ ID NO:116      446 aa   MW at 51598.9 kD |
| NOV47a, | MPSRAENYEVLYTIGTGSYGRCQKIQRKSDGKILVWKELDYGFMTEAEKQMLISEVNL |
| CG91941-01 Protein Sequence | LRELKHPNIVHYYDRIIDRTNTTLYVVMEYCEGGDLASVITKGTMERQYLDEEFVLRV |
|  | MTQLTLALKECHRRSGGDHTVLRGDLKPANVFLDGKQNVKLGDLGLARILNHDTSFAK |
|  | TFVGIPYYMSPEQMNRMSYNEKPDIWSLGCLLYELCALMPPFTAFSQKELAGKIREGK |
|  | FRRILYRYSDELNEIIMRMLNLKDYHQPSVEEILENPLIADLVAEEQRRNLERRGRQL |
|  | GEPEKLLDSSPVLSELKLKEIQLEEQERALKAGEERLEQKEQELCVCERLAEDRLAIP |
|  | ENLLKNYSLLKEQKFLSLASSPELLNLPSSVIKKKVHFSGESKENVMRSENPESQLTS |
|  | KSKCKDLKCFMLHAAQLRAQALSDIEKNYQLKSRQILGMR |

Further analysis of the NOV47a protein yielded the following properties shown in Table 47B.

TABLE 47B

Protein Sequence Properties NOV47a

| | |
|---|---|
| PSort analysis: | 0.6500 probability located in cytoplasm; 0.1000 probability located in mitochondrial matrix space; 0.1000 probability located in lysosome (lumen); 0.0000 probability located in endoplasmic reticulum (membrane) |
| SignalP analysis: | No Known Signal Sequence Predicted |

A search of the NOV47a protein against the Geneseq database, a proprietary database that contains sequences published in patents and patent publication, yielded several homologous proteins shown in Table 47C.

TABLE 47C

Geneseq Results for NOV47a

| Geneseq Identifier | Protein/Organism/Length [Patent #, Date] | NOV47a Residues/ Match Residues | Identities/ Similarities for the Matched Region | Expect Value |
|---|---|---|---|---|
| AAU03547 | Human protein kinase #47 - *Homo sapiens*, 446 aa. [WO200138503-A2, 31 May 2001] | 1 . . . 446<br>1 . . . 446 | 421/448 (93%)<br>427/448 (94%) | 0.0 |
| AAY92330 | Human N1K1 protein - *Homo sapiens*, 445 aa. [WO200020448-A2, 13 Apr. 2000] | 1 . . . 446<br>1 . . . 445 | 412/446 (92%)<br>424/446 (94%) | 0.0 |
| AAY59148 | Human NEK2 protein fragment - *Homo sapiens*, 336 aa. [WO9966051-A2, 23 Dec. 1999] | 1 . . . 336<br>1 . . . 336 | 313/336 (93%)<br>321/336 (95%) | 0.0 |

TABLE 47C-continued

Geneseq Results for NOV47a

| Geneseq Identifier | Protein/Organism/Length [Patent #, Date] | NOV47a Residues/ Match Residues | Identities/ Similarities for the Matched Region | Expect Value |
|---|---|---|---|---|
| AAY59147 | E. nidulans NIMA protein fragment - Emericella nidulans, 360 aa. [WO9966051-A2, 23 Dec. 1999] | 3 . . . 316<br>6 . . . 342 | 131/338 (38%)<br>189/338 (55%) | 4e-61 |
| AAU03545 | Human protein kinase #45 - Homo sapiens, 649 aa. [WO200138503-A2, 31 May 2001] | 6 . . . 275<br>2 . . . 263 | 106/272 (38%)<br>158/272 (57%) | 9e-48 |

In a BLAST search of public sequence datbases, the NOV47a protein was found to have homology to the proteins shown in the BLASTP data in Table 47D.

TABLE 47D

Public BLASTP Results for NOV47a

| Protein Accession Number | Protein/Organism/Length | NOV47a Residues/ Match Residues | Identities/ Similarities for the Matched Portion | Expect Value |
|---|---|---|---|---|
| P51955 | Serine/threonine-protein kinase NEK2 (EC 2.7.1.-) (NimA-related protein kinase 2) (NimA-like protein kinase 1) (HSPK 21) - Homo sapiens (Human), 445 aa. | 1 . . . 446<br>1 . . . 445 | 412/446(92%)<br>424/446(94%) | 0.0 |
| Q91Z18 | NIMA (NEVER IN MITOSIS GENE A)-RELATED EXPRESSED KINASE 2 - Mus musculus (Mouse), 443 aa. | 1 . . . 446<br>1 . . . 443 | 367/446(82%)<br>403/446(90%) | 0.0 |
| Q921N9 | SIMILAR TO NIMA (NEVER IN MITOSIS GENE A)-RELATED EXPRESSED KINASE 2 - Mus musculus (Mouse), 443 aa. | 1 . . . 446<br>1 . . . 443 | 366/446(82%)<br>402/446(90%) | 0.0 |
| O35942 | Serine/threonine-protein kinase NEK2 (EC 2.7.1.-) (NimA-related protein kinase 2) - Mus musculus (Mouse), 443 aa. | 1 . . . 446<br>1 . . . 443 | 365/446(81%)<br>401/446(89%) | 0.0 |
| Q96QN9 | NEK2B PROTEIN KINASE - Homo sapiens (Human), 384 aa. | 1 . . . 370<br>1 . . . 370 | 341/370(92%)<br>352/370(94%) | 0.0 |

PFam analysis predicts that the NOV47a protein contains the domains shown in the Table 47E.

TABLE 47E

Domain Analysis of NOV47a

| Pfam Domain | NOV47a Match Region | Identities/ Similarities for the Matched Region | Expect Value |
|---|---|---|---|
| pkinase: domain 1 of 1 | 8 . . . 271 | 90/302 (30%)<br>204/302 (68%) | 2.5e-57 |

Example 48

The NOV48 clone was analyzed, and the nucleotide and encoded polypeptide sequences are shown in Table 48A.

TABLE 48A

| NOV48 Sequence Analysis | |
|---|---|
| NOV48a,<br>CG91951-01 DNA Sequence | SEQ ID NO:117    1432 bp<br><u>CGTGACTCTGGCGACTGGCTGGCC</u>ATGCCGTCCCGGGCTGAGAACTATGAAGTGTTGG<br>ACACCATTGGCACAGGCTCCTCTGGCCGCTGCCAGAAGATCCAGAGGAAGAGTGACGG<br>CAAGATACTAGCTTGGAAAGAACTTGATTATGGCTTCATGACAGAAGCTGACAAACAG<br>ATGCTTATTTCTGAAGTGAATTTGCTTTGTAAACTGAAAAATCCAAACATCGTTCATT<br>ACTATGATCGTATTATTGACCGGACCAACACAACACTGTACATTGTAATGGAATATTG<br>TGAAGAAGGAGACCTGGCTAGTGTAATTACAAAGGGAACCAAGGAAAGGCAATACTTA<br>GATGAAGAGTTTGTTCTTCGAGTGACGACTCAGTTGACTCTGGCCCTGAAGGAATGCC<br>ACAGACGAAGTGGTGGTGATCATACTGTAGTGCGTCGGGGTCTGAAACCAGCCAGTGT<br>TTTCCTGGATGGCAAGCAAAACGTCAAGCTTGGAGATTTGGGGCTAGCCAGAATATTA<br>AACCACGACACGAGTTTTGCAAAAACATTTGTTGGCATACCTTATTACATGTCTCCTG<br>AACAAACGAATCACATGTCCTACAATGAGAAACCAGATATCTGGTCATTGGGCTGCTT<br>GCCGTATGAGTCGCGTGCATTAATGCCTCCATTTACAGCTTTTAGCCAGAAAGAACTC<br>GCTGGGAAAATCAGAGAAGGCAAATTCAGGCGAATTCTATACCATTACTCTGATGAAT<br>TGAATGAAATTATTATGAGGATGTTAAAGGATTACCATCGACCTTCTGTTGAAGAAAT<br>TCTCGAGAACCCTTTAATAGCAGATTTGGTTGCAGAAGAGCAAAGAAGAAATCTTGAG<br>AGAAGAGGGCGACAATTAGGAGAGCCAGAAAAATTGCCGGATTCCAGCCTTGTATTGA<br>GTGAGCTGAAACTAAAGGAAATTCAGTTAGAGGAGCAAGAGCGAGCTCTCAAAGCAGG<br>AGAAGAAAGGTTGGAGCAGAAAGAACAGGAGCTTTGTGTTTGTGAGAGACTAGCAGAG<br>GACAGACTGGCTATACCAGAAAATCTGTTGAAGAATTACAGCTTGCTAAAGGAACAGA<br>AGTTCCTGTCTCTGGCAAGTAGTCCAGAACTTCTTAATCTTCCATCCTCAGTAATTAA<br>GAAGAAAGTTCATTTCAGTGGGGAAAGTAAAGAGAATGTCATGAGGAGTGAGAATTCT<br>GAGAGTCAGCTCACATCTAAGTCCAAGTGCAAGGACCTGAAGGTCCTTGCTTCATGCT<br>TCATGCTGCCCAGCGTGCAAGGACCTGAAGGTCCTTGCTTCATGCTTCATGCTGCCCA<br>GCTGCGGGCTCAAGCCCTGTCAGATTTTGAGAAAAATTATCAACTAAAAAGCAGACAG<br>ATCCTGGGCATGCGCTAG<u>CCGGGTAGAGAGACACAGAGCT</u> |
| NOV48a<br>CG91951-01 Protein Sequence | ORF Start: ATG at 25    ORF Stop: TAG at 1408<br>SEQ ID NO:118    461 aa  MW at 52904.2 kD<br>MPSRAENYEVLDTIGTGSSGRCQKIQRKSDGKILAWKELDYGFMTEAEKQMLISEVNL<br>LCKLKNPNIVHYYDRIIDRTNTTLYIVMEYCEEGDLASVITKGTKERQYLDEEFVLRV<br>TTQLTLALKECHRRSGGDHTVVRRGLKPASVFLDGKQNVKLGDLGLARILNHDTSFAK<br>TFVGIPYYMSPEQTNHMSYNEKPDIWSLGCLPYESRALMPPFTAFSQKELAGKIREGK<br>FRRILYHYSDELNEIIMRMLKDYHRPSVEEILENPLIADLVAEEQRRNLERRGRQLGE<br>PEKLPDSSLVLSELKLKEIQLEEQERALKAGEERLEQKEQELCVCERLAEDRLAIPEN<br>LLKNYSLLKEQKFLSLASSPELLNLPSSVIKKKVHFSGESKENVMRSENSESQLTSKS<br>KCKDLKVLASCFMLPSVQGPEGPCFMLHAAQLRAQALSDFEKNYQLKSRQILGMR |

Further analysis of the NOV48a protein yielded the following properties shown in Table 48B.

TABLE 48B

| Protein Sequence Properties NOV48a | |
|---|---|
| PSort analysis: | 0.6500 probability located in cytoplasm; 0.1000 probability located in mitochondrial matrix space; 0.1000 probability located in lysosome (lumen); 0.0000 probability located in endoplasmic reticulum (membrane) |

TABLE 48B-continued

| Protein Sequence Properties NOV48a | |
|---|---|
| SignalP analysis: | No Known Signal Sequence Predicted |

A search of the NOV48a protein against the Geneseq database, a proprietary database that contains sequences published in patents and patent publication, yielded several homologous proteins shown in Table 48C.

TABLE 48C

Geneseq Results for NOV48a

| Geneseq Identifier | Protein/Organism/Length [Patent #, Date] | NOV48a Residues/ Match Residues | Identities/ Similarities for the Matched Region | Expect Value |
|---|---|---|---|---|
| AAU03547 | Human protein kinase #47 - *Homo sapiens*, 446 aa. [WO200138503-A2, 31 May 2001] | 1 . . . 461<br>1 . . . 446 | 429/461 (93%)<br>431/461 (93%) | 0.0 |
| AAY92330 | Human N1K1 protein - *Homo sapiens*, 445 aa. [WO200020448-A2, 13 Apr. 2000] | 1 . . . 461<br>1 . . . 445 | 396/463 (85%)<br>410/463 (88%) | 0.0 |
| AAY59148 | Human NEK2 protein fragment - *Homo sapiens*, 336 aa. [WO9966051-A2, 23 Dec. 1999] | 1 . . . 334<br>1 . . . 336 | 297/336 (88%)<br>307/336 (90%) | e−166 |
| AAY59147 | *E. nidulans* NIMA protein fragment - *Emericella nidulans*, 360 aa. [WO9966051-A2, 23 Dec. 1999] | 3 . . . 314<br>6 . . . 342 | 126/338 (37%)<br>185/338 (54%) | 4e−55 |
| AAU07102 | Human novel human protein, NHP #2 - *Homo sapiens*, 1214 aa. [WO200161016-A2, 23 Aug. 2001] | 6 . . . 276<br>2 . . . 274 | 106/282 (37%)<br>148/282 (51%) | 7e−42 |

In a BLAST search of public sequence datbases, the NOV48a protein was found to have homology to the proteins shown in the BLASTP data in Table 48D.

TABLE 48D

Public BLASTP Results for NOV48a

| Protein Accession Number | Protein/Organism/Length | NOV48a Residues/ Match Residues | Identities/ Similarities for the Matched Portion | Expect Value |
|---|---|---|---|---|
| P51955 | Serine/threonine-protein kinase NEK2 (EC 2.7.1.-) (NimA-related protein kinase 2) (NimA-like protein kinase 1) (HSPK 21) - *Homo sapiens* (Human), 1445aa. | 1 . . . 461<br>1 . . . 445 | 396/463 (85%)<br>410/463 (88%) | 0.0 |
| Q91Z18 | NIMA (NEVER IN MITOSIS GENE A)-RELATED EXPRESSED KINASE 2 - *Mus musculus* (Mouse), 443 aa. | 1 . . . 461<br>1 . . . 443 | 354/463 (76%)<br>391/463 (83%) | 0.0 |
| O35942 | Serine/threonine-protein kinase NEK2 (EC 2.7.1-) (NimA-related protein kinase 2) - *Mus musculus* (Mouse), 443 aa. | 1 . . . 461<br>1 . . . 443 | 353/463 (76%)<br>390/463 (83%) | 0.0 |
| Q921N9 | SIMILAR TO NIMA (NEVER IN MITOSIS GENE A)-RELATED EXPRESSED KINASE 2 - *Mus musculus* (Mouse), 443 aa. | 1 . . . 461<br>1 . . . 443 | 353/463 (76%)<br>390/463 (83%) | 0.0 |
| Q96QN9 | NEK2B PROTEIN KINASE - *Homo sapiens* (Human), 384 aa. | 1 . . . 368<br>1 . . . 370 | 325/370 (87%)<br>338/370 (90%) | 0.0 |

PFam analysis predicts that the NOV48a protein contains the domains shown in the Table 48E.

TABLE 48E

Domain Analysis of NOV48a

| Pfam Domain | NOV48a Match Region | Identities/ Similarities for the Matched Region | Expect Value |
|---|---|---|---|
| pkinase: domain 1 of 1 | 8 ... 269 | 87/302 (29%) 196/302(65%) | 1.5e-42 |

Example 49

The NOV49 clone was analyzed, and the nucleotide and encoded polypeptide sequences are shown in Table 49A.

TABLE 49A

NOV49 Sequence Analysis

NOV49a,

CG92025-01 DNA Sequence

SEQ ID NO:119    1861 bp

AGCCATGAACAAGAAGTTAGTGGTGCTCCCCCTGCTCGCCGTGGTCCTGGTGCTCGTC

ATTCTCGCCCTCTCTCTCTGGCTGCCCTCGGCCTCCAAGGAACCTGACAACCATOTGT

ACACCAGGGCTGCCATGGCCGCGGATCCCAAGCAGTGCTTCGAGATTCGGAGGGGCAG

GGACACACTGCCGCACGGTGGCTCTGCAGTGGATGGAGCCATTGCAGCCCTGTTGTGT

GTGGGGCTCATGAATGCCCACAGCATGGGCATCGGGGTTGGCCTCTTCCTCACCATCT

ACAACACCACCACTCATGAGGTCGGTGGGCCTGCCTACCTGCTTCTTCTAGGAAAAGC

TGAGCTCATCAATCCCCGCGAGGTGGCCCCCAGGCTGGCCTTTGCCAGCATGTTCAAC

AGCTCGCAGCAGTCCCAGAAGGGAGGCCTGTCGGTGGCGGTGCCTGGGGAGATCCGAG

GCTATGAGCTCGCACACCACCGGCATCGCCGGCTGCCCTGGGCTCGCCTCTTCCAGCC

CAGCATCCAGCTCGCCCGCCAGGGCTTCCCTGTGGGCAAGGGCTTGGCGGCAGTCCTG

GAAAACAACCGGACTGTCATCCAQCAGCAGCCTGTCTTGCTCTGCCCCGGTGAGATGT

TCTGCCGGGATAGAAAGGTGCTTCGGGAGGGGAGAGACTGACCCTGCCGCGGCTGGC

TGACACCTATGAGATGCTCGCCATCGAGGGTGCCCAGGCCTTCTACAACGGCAGCCTC

ATGCCCCACATTCTGAAGCACATCCAGGCCGCTGGTGACTCGGTAACCTCAGCAGGGG

GCATTGTGACAGCTGAGCACCTGAACAAGTACCGTGCTGAGCTGATCGAGCACCCGCT

GAACATCACCCTGGGAGACGCGGTGCTGTACATGCCCAGTGCGCGCCTCAGCCGGCCC

GTGCTGCCCCTCATCCTCAACATCCTCAAAGGTCGGTACAACTTCTCCCGGGAGAGCC

TGGAGACCCCCGAGCAGAAGGGCCTCACGTACCACCGCATCGTAGAQGCTTTCCGGTT

TGCCTACGCCAAGAGGACCCTGCTTCGGGACCCCAAGTTTGTGGATGTGACTGAGGTA

CAGGTGGTCCGCAACATGACCTCTCAGTTCTTCGCTGCCCAGCTCCGGTCCCAGATCT

CTGACCACACCACTCACCCGATCTCCTACTACAAGCCCGAGTTCTACACGCCGGATGA

CGGGGGCACTGCTCACCTGTCTGTCGTCGCAGAGGACGGCAGTGCTGTGTCCGCCACC

AGCACCATCAACCTCAGCTTTGGCTCCAACGTCTGCTCCCCCGTCAGTGGGATCCTGT

TCAATAATGAATGGACGACTTCAGCTCTCCCAGCATTCACCAATGAGTTTGGGCACC

CCCCTCACCTGCCAATTTCATCCAGCCAGGTGGCAAGCAGCCGCTCTTGTCCATGTGC

CTGACGATCATGGTGGGCCAGGACGGCCAGGTCCGGATGGTGGTGGGAGCTGCTGGGG

GCACGCAGATCACCACAGACACTGCACTGGTATGTGTCGCCATCATCTACAACCTCTG

TABLE 49A-continued

NOV49 Sequence Analysis

```
GTTCGGCTATGACGTGAAGAGGGCCGTGGAGGAGCCCCGGCTGCACAACAAGCTTCTG

CCCAACGTCACGACAGTGGAGAGAAACATTGACCAGGTGGGCCAGGGGTTCGAGAAAC

TGAGTCACCAGGCAGTGACTGCACCCCTGGAGACCCGGCACCATCACACCCAGATCCC

GTCCACCTTCATCGCTGTGGTGCAAGCCATCGTCCGCACGGCTGGTGGCTGGGCAGCT

GCCTCGGACTCCAGGAAAGGCGGGGAACCTGCTGGCTACTGATTGCTCCAGGCAGACA

AGGCT
```

| | |
|---|---|
| NOV49a, <br> CG92025-01 Protein Sequence | ORF Start: ATG at 5     ORF Stop: TGA at 1838 <br> SEQ ID NO:120     611 aa   MW at 65845.9 kD <br> MKKKLVVLCLLAVVLVLVIVGLCLWLPSASKEPDNHVYTRAAMAADAKQCLETCRGRD <br><br> TLRDGGSAVDAAIAALLCVGLMNAESMGTGVGLFLTIYNSTTHEVGGPAYLLLLGKAE <br><br> VINAREVAPRLAFASMFNSSEQSQKGGLSVAVPGEIRGYELAHQRHGRLPWARLFQPS <br><br> IQLARQGFPVGKGLAAVLENKRTVIEQQPVLLCPGEVFCRDRKVLREGERLTLPRLAD <br><br> TYEMIAIEGAQAFYNGSLMAQIVKDTQAAGEWVTSAGCIVTAEDLNNYRAELIEHPLN <br><br> ISLGDAVLYMPSARLSGPVLALILNILKGGYMFSRESVETPEQKGLTYHRIVEAFRFA <br><br> YAKPTLLGDPKFVDVTEVQVVRNNTSEFFAAQLRSQISDHTTHPISYYKPEFYTPDDG <br><br> GTAHLSVVAEDCSAVSATSTINLSFGSKVCSPVSGILFNNEWTTSALPAFTNEFGAPP <br><br> SPANFIQPCCKQPLLSMCLTIMVGQDGQVRMVVGAAGGTQITTDTALVCVAIIYNLWF <br><br> GYDVKRAVEEPRTNKLLPNVTTVERNIDQVGQGLEKLSITQAVTAALETRHEETQIAS <br><br> TFIAVVQAIVRTAGGWAAASDSRKGCEPAGY |
| NOV49b <br> CG92025-02 DNA Sequence | SEQ ID NO:121     2089 bp <br> <u>CGGGGCAAGTGAGGTGCTGCCGTCATCCACGCTGGACAGTTCAGTGATTTGCCTGAGG</u> <br><br> <u>CCCACAGCAGAGTTCAACTGGAGACAGAGAAACCAGCTAGACGCAGAGGGACGTAAC</u> <br><br> <u>ACGGAGTCCCCCACAAAGGTCTGGGCTCCGCGTGCTTCAGGTAACCTCCCTTGACCTT</u> <br><br> <u>CAGGAGAACGAGAAGGCTGCCTGATCAGAGAGTCCCTGAAGAAGATTCTGTGGCTACA</u> <br><br> <u>GGCTTCAGCAGAGTGTGAGCGAGACCCCGGTTATTTCCTCAGCTATTTCCACCAAATC</u> <br><br> <u>CTCCTGTCTTTCGTGGCCAACACCCCAGGCAACCCTTGGCGCCCCCGTCTGCTCCTGG</u> <br><br> <u>ACGCAGAGCC</u>ATGAAGAAGAACTTAGTGGTCCTGGGCCTGCTGGCCGTCGTCCTGGTG <br><br> CTGGTCATTCTCGGCCTCTGTCTCTGGCTGCCCTCAGCCTCCAAGGAACCTGACAACC <br><br> ATGTGTACACCACGGCTGCCGTCGCCGCGGATGCCAAGCAGTGCTCGAAGATTGGGAG <br><br> GGATGCACTGCGGGACCGTGGCTCTGCGGTGGATGCAGCCATTGCAGCCCTGTTGTGT <br><br> GTGGGGCGCATGAATGCCCACAGCATGGGCATCGGGGTGGCCTCTTCCTCAGCATCT <br><br> ACAACAGCACCACACGAAAAGCTGAGGTCATCAACGCCCGCGAGGTGGCCCCCACGCT <br><br> GGCCTTTGCCACCATGTTCAACAGCTCCGAGCAGTCCCAGAAGCGGGGCTGTCGGTG <br><br> GCGGTGCCTGCGCAGATCCGAGGCTATCAGCTCGCACACCAGCCGCATGCGCCGCTCC <br><br> CCTGGGCTCGCCTCTTCCAGCCCAGCATCCAGCTGGCCCGCCAGGGCTTCCCCGTGGG <br><br> CAAGGGCTTGGCCGCAGCCCTGGAAAACAAGCGGACCGTCATCCAGCAGCAGCCTGTC <br><br> TTGTGTGAGGTGTTCTGCCGGGATAGAAACGTGCAAGCGGAGGGGAGAGACTGACCC <br><br> TGCCCCAGCTGGCTGACACCTACGACACGCTGGCCATCGAGGGTGCCCAGGCCTTCTA <br><br> CAACGGCAGCCTCACGGCCCAGATTGTGAAGGACATCCAGGCGGCCGGGGGCATTGTG <br><br> ACAGCTGAGGACCTGAACAACTACCGTGCTGACCTGATCGAGCACCCGCTGAACATCA |

TABLE 49A-continued

NOV49 Sequence Analysis

```
GCCTGGGAGACGCGGTGCTGTACATGCCCAGTGCGCCGCTCAGCGGGCCCGTGCTGGC

CCTCATCCTCAACATCCTCAAAGGGTACAACTTCTCCCGGGAGAGCGTGGAGAGCCCC

GAGCAGAAGCGCCTGACGTACCACCGCATCGTAGAGGCTTTCCGGTTTGCCTACGCCA

AGAGGACCCTGCTTCGGGACCCCAACTTTGTGGATCTCACTCAGGTCGTCCGCAACAT

GACCTCCGACTTCTTCGCTGCCCAGCTCCGGGCCCAGATCTCTGACGACACCACTCAC

CCGATCTCCTACTACAAGCCCGAGTTCTACACGCCGGATGACGGGGGCACTGCTCACC

TGTCTGTCCTCGCAGACGACGGCAGTGCTGTGTCCGCCACCAGCACCATCAACCTCTA

CTTTGGCTCCAAGGTCTGCTCCCCGGTCAGTGGGATCCTGTTCAATAATGAATGGACG

ACTTCAGCTCTCCCAGCATTCACCAATGAGTTTGGGCCACCCCCCTCACCTGCCAATT

TCATCCAGCCAGGGAAGCAGCCGCTCTTGTCCATGTGCCTCACGATCATGGTGGGCCA

GGACGGCCAGGTCCGGATGGTGGTGCGAGCTGCTGGGGGCACGCAGATCACCACAGAC

ACTGCACTGGCCATCATCTACAACCTCTCGTTCGGCTATGACGTCAAGAGGGCCGTGC

AGGAGCCCCGGCTGCACAACAAGCTTCTGCCCAACGTCACGACAGTGGAGAGAAACAT

TGACCAGGCAGTGACTGCAGCCCTGGACACCCGGCACCATCACACCCAGATCCCGTCC

ACCTTCATCGCTGTGGTGCAAGCCATCGTCCGCATGGCTGGTGGCTGGGCAGCTGCCT

CGGACTCCAGGAAAGGCGGCGAACCTCCTGGCTACTGATTGCTCCAGGCAGACAAGGC

T
```

SEQ ID NO:122
NOV49b,
CG92025-01 Protein Sequence

ORF Start: ATG at 359  ORF Stop: TGA at 2066
569 aa  MW at 61411.7 kD

```
MKKKLVVLGLLAVVLVLVIVGLCLWLPSASKEPDNHVYTRAAVAADAKQCSKIGRDAL

RDGGSAVDAAIAALLCVCLMNAIISMCIGGGLFLTIYNSTTRKAEVINAREVAPRLAFA

TMFNSSEQSQKGGLSVAVPGEIRGYELAHQRHGRLPWARLFQPSIQLARQGFFPVGKGL

AAALENKRTVIEQQPVLCEVFCRDRKVLREGERLTLPQLAETYETLAIEEGAQAFYNGS

LTAQIVKDIQAAGGIVTAEDLNNYRAELIEHPLNISLGDAVLYMPSAPLSGPVLALIL

NTLKGYNFSRESVESPEQKGLTYHRIVEAFREAYAKRTLLGDPKFVDVTEVVRNMTSE

FFAAQLRAQISDDTTHPISYYKPEFYTPDDGGTAHLSVVAEDGSAVSATSTINLYFGS

KVCSPVSGILPNNEWTTSALPAFTNEFGAPPSPANFIQPGKQPLLSMCLTIMVGQDGQ

VRNVVGAAGGTQITTDTALAIIYNLWFGYDVEAVEEPRLHNKLLPNVTTVERNIQDQA

VTAALETRHHHTQIASTFTAVVQAIVRMAGGWAAASDSRKGGEPAGY
```

Sequence comparison of the above protein sequences yields the following sequence relationships shown in Table 49B.

TABLE 49B

Comparison of NOV49a against NOV49b.

| Protein Sequence | NOV49a Residues/ Match Residues | Identities/Similarites for the Matched Region |
|---|---|---|
| NOV49b | 27 ... 611 | 525/585 (89%) |
|  | 27 ... 569 | 531/585 (90%) |

Further analysis of the NOV49a protein yielded the following properties shown in Table 49C.

TABLE 49C

Protein Sequence Properties NOV49a

| PSort analysis: | 0.4600 probability located in plasma membrane; 0.1305 probability located in microbody (peroxisome); 0.1000 probability located in endoplasmic reticulum (membrane); 0.1000 probability located in endoplasmic reticulum (lumen) |
|---|---|
| SignalP analysis: | Cleavage site between residues 32 and 33 |

A search of the NOV49a protein against the Geneseq database, a proprietary database that contains sequences published in patents and patent publication, yielded several homologous proteins shown in Table 49D.

TABLE 49D

Geneseq Results for NOV49a

| Geneseq Identifier | Protein/Organism/Length [Patent #, Date] | NOV49a Residues/ Match Residues | Identities/ Similarities for the Matched Region | Expect Value |
|---|---|---|---|---|
| ABG30234 | Novel human diagnostic protein #30225 - *Homo sapiens*, 605 aa. [WO200175067-A2, 11 Oct. 2001] | 1 . . . 611<br>37 . . . 605 | 538/611 (88%)<br>547/611 (89%) | 0.0 |
| ABG30234 | Novel human diagnostic protein #30225 - *Homo sapiens*, 605 aa. [WO200175067-A2, 11 Oct. 2001] | 1 . . . 611<br>37 . . . 605 | 538/611 (88%)<br>547/611 (89%) | 0.0 |
| ABG30235 | Novel human diagnostic protein #30226 - *Homo sapiens*, 623 aa. [WO200175067-A2, 11 Oct. 2001] | 1 . . . 611<br>48 . . . 623 | 537/616 (87%)<br>546/616 (88%) | 0.0 |
| ABG30235 | Novel human diagnostic protein #30226 - *Homo sapiens*, 623 aa. [WO200175067-A2, 11 Oct. 2001] | 1 . . . 611<br>48 . . . 623 | 537/616 (87%)<br>546/616 (88%) | 0.0 |
| ABG30240 | Novel human diagnostic protein #30231 - *Homo sapiens*, 639 aa. [WO200175067-A2, 11 Oct. 2001] | 1 . . . 611<br>64 . . . 639 | 538/616 (87%)<br>546/616 (88%) | 0.0 |

In a BLAST search of public sequence datbases, the NOV49a protein was found to have homology to the proteins shown in the BLASTP data in Table 49E.

TABLE 49E

Public BLASTP Results for NOV49a

| Protein Accession Number | Protein/Organism/Length | NOV49a Residues/ Match Residues | Identities/ Similarities for the Matched Portion | Expect Value |
|---|---|---|---|---|
| P19440 | Gamma-glutamyltranspeptidase 1 precursor (EC 2.3.2.2) (Gamma-glutamyltransferase 1) - *Homo sapiens* (Human), 569 aa. | 1 . . . 611<br>1 . . . 569 | 538/611 (88%)<br>547/611 (89%) | 0.0 |
| P20735 | Gamma-glutamyltranspeptidase precursor (EC 2.3.2.2) (Gamma-glutamyltransferase) (GGT) - *Sus scrofa* (Pig), 568 aa. | 1 . . . 611<br>1 . . . 568 | 464/611 (75%)<br>505/611 (81%) | 0.0 |
| P07314 | Gamma-glutamyltranspeptidase precursor (EC 2.3.2.2) (Gamma-glutamyltransferase) (GGT) - *Rattus norvegicus* (Rat), 568 aa. | 1 . . . 611<br>1 . . . 568 | 436/611 (71%)<br>503/611 (81%) | 0.0 |
| A05225 | gamma-glutamyltransferase (EC 2.3.2.2) precursor - rat, 568 aa. | 1 . . . 611<br>1 . . . 568 | 435/611 (71%)<br>501/611 (81%) | 0.0 |
| Q60928 | Gamma-glutamyltranspeptidase precursor (EC 2.3.2.2) (Gamma-glutamyltransferase) (GGT) - *Mus musculus* (Mouse), 568 aa. | 1 . . . 611<br>1 . . . 568 | 436/611 (71%)<br>498/611 (81%) | 0.0 |

PFam analysis predicts that the NOV49a protein contains the domains shown in the Table 49F.

TABLE 49F

Domain Analysis of NOV49a

| Pfam Domain | NOV49a Match Region | Identities/ Similarities for the Matched Region | Expect Value |
|---|---|---|---|
| G_glu_transpept: domain 1 of 1 | 57 . . . 607 | 253/618 (41%)<br>486/618 (79%) | 6.2e-227 |

Example 50

The NOV50 clone was analyzed, and the nucleotide and encoded polypeptide sequences are shown in Table 50A.

TABLE 50A

| NOV50 Sequence Analysis | |
|---|---|
| NOV50a, CG92078-01 DNA Sequence | SEQ ID NO:123    2014 bp<br>GCAGCATGAGCCGATCACCCCTCAATCCCAGCCAACTCCGATCAGTGCGCTCCCAGGA<br>TGCCCTGGCCCCCTTGCCTCCACCTCCTCCCCAGAATCCCTCCACCCACTCTTCGGAC<br>CCTTTGTGTGGATCTCTGCCTTGGGGCCTCAGCTGTCTTCTGGCTCTGCAGCATGTCT<br>TGGTCATGGCTTCTCTGCTCTGTGTCTCCCACCTCCTCCTGCTTTGCAGTCTCTCCCC<br>AGGAGGACTCTCTTACTCCCCTTCTCAGCTCCTGGCCTCCAGCTTCTTTTCATGTGGT<br>ATGTCTACCATCCTGCAAACTTGGATCCGCAGCAGGAGCCTGCCTCTTCTCCAGGCTC<br>CATCCTTAGACTTCCTTATCCCTGCTCTGGTGCTGACCAGCCAGAAGCTACCCCGGGC<br>CATCCAGACACCTGGAAACGCCTCCCTCATGCTGCACCTTTGTAGGCGACCTAGCTGC<br>CATGGCCTGGGGCACTGGAACACTTCTCTCCAGGAGCTGCTGGTAGTATCTGCGCTGC<br>TGCAGGCCATGATGGGGCTGCTGGGGAGTCCCGGCCACCTGTTCCCCCACTGTGGGCC<br>CCTGGTGCTGGCTCCCAGCCTGGTTGTGGCACGGCTCTCTGCCTTTCCCCAACAGGGA<br>GTTTCCTCCTCTCACCCAGCCTGGACTGCAATGCCGATCTCGGCTCACCACTGGCTTT<br>TGGCTTCTGTCTACCCCTGCAAGGCTGGCTCAGAAGGTTCTGGGGGAGGAGTTCTTTT<br>CTCACTCTCGCCCCTCAGGTGCTGATCCCAGTGGCCTGTGTCTCGATTGTTTCTGCCT<br>TTGTGGGATTCACTGTTATCCCCCAGGAACTGTCTGCCCCCACCAAGGCACCATGGAT<br>TTGGCTGCCTCACCCAGGTGTCTGGAATTGGCCTTTGCTGACGCCCAGAGCTCTGGCT<br>GCAGGCATCTCCATGGCCTTGGCAGCCTCCACCAGTTCCCTGGGCTGCTATGCCCTGT<br>GTGGCCGGCTGCTGCATTTGCCTCCCCCACCTCCACATGCCTGCAGTCCAGGGCTGAG<br>CCTGGAGGGGCTGGGCACTGTGCTGGCCGCGCTCCTGGGAAGCCCCATGGGCACTGCA<br>TCCAGCTTCCCCAACGTGGGCAAAGTGGGTCTTATCCAGCAGGCTGGATCTCAGCAAG<br>TGGCTCACTTAGTGGGGCTACTCTGCGTGCCGCTTGGACTCTCCCCCAGGTTGGCTCA<br>GCTCCTCACCACCATCCCACTGCCTGTTGTTGGTGGTGGGCTGCTGGGGGTGACCCAG<br>GCTGTGGTTTTGTCTGCTGGATTCTCCAGCTTCTACCTGGCTGACATAGACTCTGGGC<br>GAAATATCTTCATTGTGGGCTTCTCCATCTTCATGGCCTTGCTGCTGCCAAGATGGTT<br>TCGGGAAGCCCAGTCCTGTTCACCACAGGTCACTCACTGCTGATCGAGCCCCTTGGA<br>TGTATTACTGCACAGCCCATCTTCCTGGCTGGACTCTCAGGCTTCCTACTAGACAACA<br>CGATTCCGGGCACACAGCTTGAGCGAGGCCTAGGTCAAGGGCTACCATCTCCTTTCAC<br>TGCCCAAGAGGCTCGAATGCCTCACAACCCCACCGACAAGGCTGCTCAAGTGTACAGA<br>CTTCCTTTCCCCATCCAAAACCTCTGTCCCTGCATCCCCCAGCCTCTCCACTGCCTCT<br>GCCCACTGCCTGAAGACCCTGGGGATGAGGAAGGAGGCTCCTCTGAGCAGCAAGAGAT<br>GGCAGACTTCCTGCGTGGCTCAGGGGAGCATGCCCTGAATCTAGCAGAGAAGGGTTTA<br>GGTCCAGAAATGACCAGAACGCGTACTTCTGCCCTGGTTAATTTAGCCCTAACTCTCA<br>TCTGCTGGAGAGTCAGCTCCCAAACTGTTCTTTCGTGTAGGCAGAGGATATCTCTGTG<br>TGTATTACATCGGACTGTCTAGAGGTTCCATTTCCCAATAGG |
| NOV50a, CG92078-01 Protein Sequence | ORF Start: ATG at 6    ORF Stop: TGA at 1992<br>SEQ ID NO:124    662 aa  MW at 70138.5 kD<br>MSRSPLNPSQLRSVQSQDALAPLPPPAPQNPSTHSWDPLCGSLPWGLSCLLALQHVLV<br>MASLLCVSHLLLLCSLSPGGLSYSPSQLLASSFPSCGMSPILQTWMCSRRLPLVQAPS<br>LEFLIPALVLTSQKLPRAIQTPGNASLMHLCRGPSCECLGHWNTSLQEVVVVSGLLQ |

TABLE 50A-continued

NOV50 Sequence Analysis

CMMGLLGSPGHVFPHCGPLVLAPSLVVACLSAFPQEGVLLLSPSLECNGMTSAHHWGE

ASQLCLLALECSLHPLPFGFCLPLGCWLRRFWGRSSFLSLAPQVLIPVACVWTVSAFV

GFSVIPQELSAPTKAPWIWLPHPGVVNWPLLTPRALAAGISMALAASTSSLGCYALCG

RLLHLRPPFPHACSRGLSLEGLGSVLAGLLGSPMGTASSFFNVGKVGLIQQAGSQQVA

HLVCIZCVGLGLSPRLAQLLTTTPLPVVGGGVLCVTQAVVLSACFSSFYLADIDSCRN

IFIVGFSIPMALLLPRWFREAPVLFSTGHSLLMEPLGCITAQPIFLACLSGFLLENTI

RGTQLERGLGQGLPSPFTAQEANPQKPREKAAQVYRLPFPIQNLCPCIPQPLHCLCP

LPEDPGDEEGGSSEQQEMADLLRGSGEHALNIAEKGLGPEMTRTRTSALVNLALTLIC

Further analysis of the NOV50a protein yielded the following properties shown in Table 50B.

TABLE 50B

Protein Sequence Properties NOV50a

| | |
|---|---|
| PSort analysis: | 0.6000 probability located in plasma membrane; 0.4000 probability located in Golgi body; 0.3000 probability located in endoplasmic reticulum (membrane); 0.3000 probability located in microbody (peroxisome) |
| SignalP analysis: | Cleavage site between residues 17 and 18 |

A search of the NOV50a protein against the Geneseq database, a proprietary database that contains sequences published in patents and patent publication, yielded several homologous proteins shown in Table 50C.

TABLE 50C

Geneseq Results for NOV50a

| Geneseq Identifier | Protein/Organism/Length [Patent #, Date] | NOV50a Residues/ Match Residues | Identities/ Similarities for the Matched Region | Expect Value |
|---|---|---|---|---|
| AAW73924 | Nucleobase permease Yspl1 - Mus sp, 611 aa. [US5858707-A, 12 Jan. 1999] | 1 ... 617<br>1 ... 608 | 435/629 (69%)<br>480/629 (76%) | 0.0 |
| AAE06572 | Human protein having hydrophobic domain, HP03700 - *Homo sapiens*, 243 aa. [WO200149728-A2, 12 Jul. 2001] | 1 ... 232<br>1 ... 243 | 215/244 (88%)<br>219/244 (89%) | e-116 |
| AAM23509 | Murine EST encoded protein SEQ ID NO: 1034 - *Mus musculus*, 148 aa. [WO200154477-A2, 02 Aug. 2001] | 474 ... 617<br>1 ... 144 | 121/144 (84%)<br>125/144 (86%) | 3e-64 |
| AAG54392 | *Arabidopsis thaliana* protein fragment SEQ ID NO: 69348 - *Arabidopsis thaliana*, 525 aa. [EP1033405-A2, 06 Sep. 2000] | 25 ... 569<br>10 ... 521 | 139/567 (24%)<br>239/567 (41%) | 3e-32 |
| AAG54391 | *Arabidopsis thaliana* protein fragment SEQ ID NO: 69347 - *Arabidopsis thaliana*, 527 aa. [EP1033405-A2, 06 Sep. 2000] | 25 ... 569<br>12 ... 523 | 139/567 (24%)<br>239/567 (41%) | 3e-32 |

In a BLAST search of public sequence datbases, the NOV50a protein was found to have homology to the proteins shown in the BLASTP data in Table 50D.

TABLE 50D

Public BLASTP Results for NOV50a

| Protein Accession Number | Protein/Organism/Length | NOV50a Residues/ Match Residues | Identities/ Similarities for the Matched Portion | Expect Value |
|---|---|---|---|---|
| Q60850 | YOLK SAC PERMEASE-LIKE YSPL-1 FORM 1 (YOLK SAC PERMEASE-LIKE YSPL-1 FORM 4) (YOLK SAC PERMEASE-LIKE YSPL-1 FORM 3) (YOLK SAC PERMEASE-LIKE YSPL- 1 FORM 2) - Mus musculus (Mouse), 611 aa. | 1 . . . 617<br>1 . . . 608 | 435/629 (69%)<br>480/629 (76%) | 0.0 |
| CAC51146 | SEQUENCE 22 FROM PATENT WO0149728 - Homo sapiens (Human), 243 aa. | 1 . . . 232<br>1 . . . 243 | 215/244 (88%)<br>219/244 (89%) | e-115 |
| Q96NA6 | CDNA FLJ31168 FIS, CLONE KIDNE1000152, MODERATELY SIMILAR TO MUS MUSCULUS YOLK SAC PERMEASE-LIKE MOLECULE 1 (YSPL-1) MRNA - Homo sapiens (Human), 212 aa. | 1 . . . 232<br>1 . . . 212 | 184/244 (75%)<br>188/244 (76%) | 2e-92 |
| Q9EPR4 | SODIUM-DEPENDENT VITAMIN C TRANSPORTER TYPE 2 - Mus musculus (Mouse), 647 aa. | 44 . . . 531<br>97 . . . 578 | 160/513 (31%)<br>252/513 (48%) | 7e-60 |
| Q9WTW8 | SODIUM-COUPLED ASCORBIC ACID TRANSPORTER SVCT2 - Rattus norvegicus (Rat), 592 aa. | 44 . . . 531<br>42 . . . 523 | 160/513 (31%)<br>252/513 (48%) | 7e-60 |

PFam analysis predicts that the NOV50a protein contains the domains shown in the Table 50E.

TABLE 50E

Domain Analysis of NOV50a

| Pfam Domain | NOV50a Match Region | Identities/ Similarities for the Matched Region | Expect Value |
|---|---|---|---|
| Sulfate_transp: domain 1 of 1 | 202 . . . 483 | 53/352 (15%)<br>176/352 (50%) | 8.8 |
| xan_ur_permease: domain 1 of 1 | 46 . . . 484 | 117/477 (25%)<br>341/477 (71%) | 5.8e−59 |

Example 51

The NOV51 clone was analyzed, and the nucleotide and encoded polypeptide sequences are shown in Table 51A.

TABLE 51A

NOV51 Sequence Analysis

| NOV51a, | SEQ ID NO:125　　　　　1037 bp |
|---|---|
| | TTACTGATGCCCCCTCCCGCCCCCAQCGCCTGGAACAGAATCTTCTGGCGGCAGATCC |
| CG92088-01 DNA Sequence | TACTTACACTTGGCCTCTTAGGCCTGTTTCTGTATGGCCTCCCTAAATTCAGGCATCT |
| | CGAAGCCCTCATCCCCATGGCCGTCTGCCCTTCGGCCACAATGTCCCAGCTCAGACAC |
| | AACTTCACAGGTGCCCTGCGTCCCTCGGCCCGGCCTGAAGTTCTGACCTGTACCCCCT |
| | GGGGGGCTCCCATTATTTGGGATGGCTCTTTCGACCCACATGTGGCCAAGCAAGAGGC |

TABLE 51A-continued

NOV51 Sequence Analysis

```
TAGACAGCAGAACCTCACCATTCGGCTGACTATCTTTGCTGTAGGCAGCTACCTGGAG
AAGTACCTGGACCGCTTCCTGCAGACGCCGCAGCAGCACTTCATGGCGGCCCAGAGCG
TGATCTACTACGTGTTCACCGAGCTTCCGGCAGCGGTGCCCCGCGTGGCGCTGCCCCC
GCGACGCCGGCTGCCCGTGGAGCGCGTGGCGCGCGAGCGGCGCTGGCAAGACGTGTCG
ATGGCGCGCATGCGCACGTTGCACGCGGCGCTGGGCCGGCTGCCGGGCCGCGAGGCGC
ACTTCATGTTCTGCATCGACGTGGACCAGCACTTCAGCGGCACTTTTGGGCCCGACGC
GCTGGCCGAGTCGGTCGCGCAGCTCCACTCCTCCCACTACCACTCGCCGTCGTGGCTC
CTCCCCTTCGAACGCGACGCGCATTCGCCCGCCGCGATGCCGTGGGGCCAGGGCGACT
TCTATAACCACCCGGCGGTGTTCGGGGGCAGCGTGGCGGCGCTGCGCGGGCTGACGGC
GCACTGTGCGGGGGGCCTGGACTGGCACCGCGCGCGGCCTGGAGGCGCGCTGGCAC
GACGAGAGCCACCTCAACAACTTCTTCTCCCTGCACAACCCCGCCAAGGTGCTGTCGC
CCGAGTTCTCCTCGAGCCCGGACATCCGCCCGCGGCCCGAGATCCGCCCCCCGCGACT
GCTGTGGGCGCCCAAGGGGTACCGGCTGCTGCGGAACTAGCGCCGCCGCCG
```

| | |
|---|---|
| | ORF Start: ATG at 7     ORF Stop: TAG at 1024 |
| | SEQ ID NO:126     339 aa MW at 38627.2 kD |
| NOV51a, | MPPPAPRAWKRIFWRQILLTLGLLGLFLYGLPKFRULEALIPMGVCPSATMSQLRDNF |
| CG92088-01 Protein Sequence | TGALRPWARPEVLTCTPWGAPIIWDGSPDPDVAKQEARQQNLTIGLTIFAVCRYLEKY |
| | LERFLETPEQEFMAGQSVMYYVPTELPGAVPRVALGPGRRLPVERVARERRWQDVSMA |
| | RRTLHAALGGLPGREATIFNFCMDVDQHFSCTFGPEALAESVAQLHSWHYHWPSWLLP |
| | FERDAHSAAAMAWGQGDFYNHAAVFGGSVAALRGLTAHCAGGLDWDRARGLEARWHDE |
| | SHLNKFFWLHRPAKVLSPEFCWSPDIGPRAEIRRPRLLWAPKGYRLLRN |

Further analysis of the NOV51a protein yielded the following properties shown in Table 51B.

TABLE 51B

Protein Sequence Properties NOV51a

| | |
|---|---|
| PSort analysis: | 0.8650 probability located in lysosome (lumen); 0.5565 probability located in outside; 0.3880 probability located in microbody (peroxisome); 0.1000 probability located in endoplasmic reticulum (membrane) |
| SignalP analysis: | Cleavage site between residues 33 and 34 |

A search of the NOV51a protein against the Geneseq database, a proprietary database that contains sequences published in patents and patent publication, yielded several homologous proteins shown in Table 51C.

TABLE 51C

Geneseq Results for NOV51a

| Geneseq Identifier | Protein/ Organism/ Length [Patent #, Date] | NOV51a Residues/ Match Residues | Identities/ Similarities for the Matched Region | Expect Value |
|---|---|---|---|---|
| AAW13639 | Murine alpha(1,3)-galactosyltransferase - Mus sp, 394 aa. [WO9709421-A1, 13 Mar. 1997] | 64 . . . 339<br>117 . . . 392 | 126/276 (45%)<br>175/276 (62%) | 1e-70 |
| AAR45935 | A glycosyltransferase - Homo sapiens, 394 aa. [WO9402616-A, 03 Feb. 1994] | 64 . . . 339<br>117 . . . 392 | 126/276 (45%)<br>175/276 (62%) | 1e-70 |
| AAR13750 | GDP-Fuc:[beta-D-Gal(1,4/1,3)]-D-GlcNAc(/Glc)alpha(1,3/1,4) - fucosyltransferase - Mus musculus, 394 aa. [WO9112340-A, 22 Aug. 1991] | 64 . . . 339<br>117 . . . 392 | 126/276 (45%)<br>175/276 (62%) | 1e-70 |

TABLE 51C-continued

Geneseq Results for NOV51a

| Geneseq Identifier | Protein/ Organism/ Length [Patent #, Date] | NOV51a Residues/ Match Residues | Identities/ Similarities for the Matched Region | Expect Value |
|---|---|---|---|---|
| AAR80016 | Marmoset alpha-1,3-galactosyltransferase - *Callithrix jacchus*, 376 aa. [WO9524924-A1, 21 Sep. 1995] | 53 . . . 338<br>82 . . . 373 | 127/292 (43%)<br>181/292 (61%) | 3e−70 |
| AAR90573 | Pig alpha(1,3)-galactosyltransferase - *Sus scrofa*, 359 aa. [WO9534202-A1, 21 Dec. 1995] | 64 . . . 339<br>82 . . . 357 | 124/276 (44%)<br>172/276 (61%) | 4e−70 |

In a BLAST search of public sequence datbases, the NOV51a protein was found to have homology to the proteins shown in the BLASTP data in Table 51D.

TABLE 51D

Public BLASTP Results for NOV51a

| Protein Accession Number | Protein/Organism/Length | NOV51a Residues/ Match Residues | Identities/ Similarities for the Matched Portion | Expect Value |
|---|---|---|---|---|
| AAF82757 | IGB3 SYNTHASE - *Rattus norvegicus* (Rat), 339 aa. | 7 . . . 338<br>7 . . . 338 | 229/332 (68%)<br>263/332 (78%) | e−137 |
| P14769 | N-acetyllactosaminide alpha-1,3-galactosyltransferase (EC 2.4.1.151) (Galactosyltransferase) (UDP-galactose:beta-D-galactosyl-1,4-N-acetyl-D-glucosaminide alpha-1,3-galactosyltransferase) - *Bos taurus* (Bovine), 368 aa. | 64 . . . 339<br>91 . . . 366 | 125/276 (45%)<br>177/276 (63%) | 2e−71 |
| Q91V22 | ALPHA-1,3-GALACTOSYLTRANSFERASE - *Mus musculus* (Mouse), 371 aa. | 64 . . . 339<br>94 . . . 369 | 126/276 (45%)<br>175/276 (62%) | 3e−70 |
| Q91W00 | UNKNOWN (PROTEIN FOR MGC:11545) - *Mus musculus* (Mouse), 372 aa. | 64 . . . 339<br>95 . . . 370 | 126/276 (45%)<br>175/276 (62%) | 3e−70 |
| Q9DBU1 | GLYCOPROTEIN GALACTOSYLTRANSFERASE ALPHA 1,3 - *Mus musculus* (Mouse), 406 aa. | 64 . . . 339<br>129 . . . 404 | 126/276 (45%)<br>175/276 (62%) | 3e−70 |

PFam analysis predicts that the NOV51a protein contains the domains shown in the Table 51E.

TABLE 51E

Domain Analysis of NOV51a

| Pfam Domain | NOV51a Match Region | Identities/ Similarities for the Matched Region | Expect Value |
|---|---|---|---|
| No Significant Matches Found | | | |

Example 52

The NOV52 clone was analyzed, and the nucleotide and encoded polypeptide sequences are shown in Table 52A.

TABLE 52A

| NOV52 Sequence Analysis | |
|---|---|
| NOV52a, CG92142-01 DNA Sequence | SEQ ID NO:127　　2684 bp<br>ATCAGAATTTTGAGTTCTAGTATTTACTCTCTCGATTCCTTGTTAATTTAAATGGTAC<br>CTATTTTTTATAGCACATGATTTGGGAATTACACTTTGTGACATGGATGAATCTGCAC<br>TGACCCTTGGTACAATAGATGTTTCTTATCTGCCACATTCATCAGAATACAGTGTTGC<br>TCGATGTAAGCACACAAGTGAGGAATGGGTAGAGTGTGGCTTTAGACCCACCATCTTC<br>ACATCTGCAACTTTAAAATGGAAAGAAACCCTAATGAGTCGGAAAAGGCCATTTGTTG<br>GAAGATGTTGTTACTCCTGCACTCCCCAGAGCTCCGACAAATTTTTCAACCCCAGTAT<br>CCCGTCTTTGGGTTTGCGGAATGTTATTTATATCAATCAAACTCACACAAGACACCCC<br>GGATGGCTTGCAAGACGCCTTTCTTACGTTCTTTTTATTCAAGAGCGAGATGTGCATA<br>AGGGCATGTTTGCCACCAATGTCACTGAAAATCTGCTGAACAGCACTACAGTACAAGA<br>CGCAATTGCAGAAGTGGCTGCTGAATTAAACCCTGATGGTTCTCCCCAGCAGCAATCA<br>AAACCCGTTAACAAAGTCAAAAGAAAGCTAAAACGATTCTTCAACAAATCGTTGCCA<br>CTCTCTCACCGGCAATGATCAGACTGACTGGGTGGGTGCTGCTAAAACTCTTCAACAG<br>CTTCTTTTCCAACATTCAAATTCACAAACGTCAACTTGACATGCTTAAAGCTGCAACT<br>GAGACGAATTTGCCGCTTCTGTTTCTACCAGTTCATAGATCCCATATTGACTATCTGC<br>TGCTCACTTTCATTCTCTTCTOCCATAACATCAAACCACCATACATTGCTTCAGGCAA<br>TAATCTCAACATCCCAATCTTCAGTACCTTGATCCATAACCTTGGGCGCTTCTTCATA<br>CGACGAACGCTCGATGAAACACCAGATGGACGGAAAGATGTTCTCTATACAGCTTTGC<br>TCCATGGGCATATAGTTGAATTACTTCGACAGCAGCAATTCTTCGAGATCTTCCTGGA<br>AGGCACACGTTCTAGGAGTGGAAAAACCTCTTGTGCTCGGGCACCACTTTTGTCAGTT<br>GTGGTAGATACTCTGTCTACCAATGTCATCCCAGACATCTTGATAATACCTGTTGGAA<br>TCTCCTATGATCGCATTATCGAAGGTCACTACAATGGTCAACAACTGGGCAAACCTAA<br>GAAGAATCACAGCCTGTGGAGTGTAGCAAGACGTGTTATTAGAATGTTACGAAAAAAC<br>TATGGTTGTGTCCGAGTGGATTTTCCACAGCCATTTTCCTTAAAGGAATATTTAGAAA<br>GCCAAAGTCAGAAACCGGTGTCTGCTCTACTTTCCCTGCACCAACCGTTGTTACCAGC<br>TATACTTCCTTCAAGACCCACTGATGCTGCTGATCAAGGTAGAGACACCTCCATTAAT<br>CAGTCCAGAAATGCAACACATGAATCCCTACCAAGGAGGTTGATTGCAAATCTGGCTG<br>AGCATATTCTATTCACTGCTAGCAAGTCCTGTGCCATTATGTCCACACACATTGTCGC<br>TTGCCTCCTCCTCTACAGACACACCCACGGAATTGATCTCTCCACATTGGTCGAACAC<br>TTCTTTGTGATGAAAGAGGAAGTCCTGGCTCGTGATTTTGACCTCOGCTTCTCAGGAA<br>ATTCAGAAGATGTAGTAATGCATGCCATACAGCTGCTCGCAAATTCTCTCACAATCAC<br>CCACACTAGCAGGAACGATGAGTTTTTTATCACCCCCAGCACAACTGTCCCATCACTC<br>TTCGAACTCAACTTCTACAGCAATGCGGTACTTCATGTCTTTATCATCGAGGCCATCA<br>TAGCTTGCAGCCTTTATGCAGTTCTGAACAAGAGGGGACTGGGGGGTCCCACTACCAC<br>CCCACCTAACCTGATCAGCCAGGAGCAGCTGGTGCGGAAGGCGGCCAGCCTCTGCTAC<br>CTTCTCTCCAATGAAGGCACCATCTCACTGCCTTGCCAGACATTTTACCAAGTCTGCC<br>ATGAAACAGTAGGAAAGTTTATCCAGTATGGCATTCTTACAGTGGCAGAGCACGATGA<br>CCAGGAAGATATCAGTCCTAGTCTTGCTGAGCAGCAGTGGGACAAGAAGCTTCCTGAA<br>CCTTTGTCTTGGAUAAGTGATGAACAAGATCAAGACAGTGACTTTGGGCAGGAACAGC |

TABLE 52A-continued

NOV52 Sequence Analysis

GAGATTCCTACCTGAAGGTGAGCCAATCCAAGGAGCACCAGCAGTTTATCACCTTCTT

ACAGACACTCCTTGGGCCTTTGCTGGAGGCCTACAGCTCTGCTGCCATCTTTGTTCAC

AACTTCAGTGGTCCTGTTCCAGAACCTGAGTATCTGCAAAAGTTGCACAAATACCTAA

TAACCAGAACAGAAAGAAATGTTGCAGTATATGCTGAGAGTGCCACATATTGTCTTGT

GAAGAATGCTGTGAAAATGTTTAAGCATATTGGGGTTTTCAAGGAGACCAAACAAAAG

AGAGTGTCTGTTTTAGAACTGAGCAGCACTTTTCTACCTCAATGCAACCGACAAAAAC

TTCTAGAATATATTCTGAGTrTTGTGGTGCTGTAGGTAACGTGTGGCACTGCTGGCAA

ATGAAGGTCATGAGATGAGTTCCTTGTAGGTACCAGCTTCTGGCTCAAGAGTTGAAGG

TGCCGTCGCAGGGTCA

| | |
|---|---|
| | ORF Start: ATG at 101  ORF Stop: TAG at 2585 |
| | SEQ ID NO:128  828 aa MW at 93835.7 kD |
| NOV52a, | MDESALTLGTIDVSYLPHSSEYSVGRCKHTSEEWVECGFRPTIFRSATLKWKESLMSR |
| CG92142-01 Protein Sequence | KRPFVGRCCYSCTPQSWDKFFNPSIPSLGLRNVIYINETHTRERGWLARRLSYVLFIQ |
| | ERDVHKGMFATNVTENVLNSSRVQEAIAEVAAELNPDGSAQQQSKAVNKVKKKAKRIL |
| | QEMVATVSPAMIRLTCNVLLKLPNSFFWNIQIEKGQLEMVKAATETNLPLLFLPVHRS |
| | HIDYLLLTFILFCHNIKAPYIASGNNLNIPIFSTLIHKLGGFFIRRRLDETPDGRKDV |
| | LYRALLHGHIVELLRQQQFLEIFLEGTRSRSGKTSCARAGLLSVVVDTLSTNVIPDIL |
| | IIPVGISYDRIIEGHYNGEQLGKPKKNESLWSVARGVIRMLRKNYGCVRVDFAQPFSL |
| | KEYLESQSQKPVSALLSLEQALLPAILPSRRSDAADEGRDTSINESRNATDESLRRRL |
| | IANLAEEILFTASKSCAIMSTHIVACLLLYRHRQGIDLSTLVEDFFVMKEEVLARDFD |
| | LGFSGNSEDVVMHAIQLLGNCVTITHTSRNDEFFITPSTTVPSVFELNFYSNGVLHVF |
| | IMEAIIACSLYAVLHKRGLGGPTSTPPNLISQEQLVRKAASLCYLLSNEGTTSLPCQT |
| | FYQVCHETVGKFIQYGILTVAEHDDQEDISPSLAEQQWDKKLPEPLSWRSDEEDEDSD |
| | FGEEQRDCYLKVSQSKEHQQFITFLQRLLGPLLEAYSSAAIFVHNFSCPVPEPEYLQK |
| | LHKYLTTRTERNVAVYAESATYCLVKNAVKMFKDIGVFKETKQKRVSVLELSSTFLPQ |
| | CNRQKLLEYILSFVVL |

Further analysis of the NOV52a protein yielded the following properties shown in Table 52B.

TABLE 52B

Protein Sequence Properties NOV52a

| | |
|---|---|
| PSort analysis: | 0.8500 probability located in endoplasmic reticulum (membrane); 0.4400 probability located in plasma membrane; 0.3000 probability located in nucleus; 0.1000 probability located in mitochondrial inner membrane |

TABLE 52B-continued

Protein Sequence Properties NOV52a

| | |
|---|---|
| SignalP analysis: | No Known Signal Sequence Predicted |

A search of the NOV52a protein against the Geneseq database, a proprietary database that contains sequences published in patents and patent publication, yielded several homologous proteins shown in Table 52C.

TABLE 52C

Geneseq Results for NOV52a

| Geneseq Identifier | Protein/ Organism/ Length [Patent #, Date] | NOV52a Residues/ Match Residues | Identities/ Similarities for the Matched Region | Expect Value |
|---|---|---|---|---|
| ABB11171 | Human sn-glycerol-3-P acyltransferase homologue, SEQ ID NO:1541 - *Homo sapiens*, 156 aa. [WO200157188-A2, 09 AUG. 2001] | 89 ... 233<br>12 ... 156 | 145/145 (100%)<br>145/145 (100%) | 8e−78 |
| ABG23092 | Novel human diagnostic protein #23083 - *Homo sapiens*, 807 aa. [WO200175067-A2, 11 OCT. 2001] | 178 ... 822<br>142 ... 799 | 209/678 (30%)<br>324/678 (46%) | 8e−72 |
| ABG23092 | Novel human diagnostic protein #23083 - *Homo sapiens*, 807 aa. [WO200175067-A2, 11 OCT. 2001] | 178 ... 822<br>142 ... 799 | 209/678 (30%)<br>324/678 (46%) | 8e−72 |
| AAY72134 | *E. coli* glycerol-3-phosphate acyltransferase with ER retention sequence - *Escherichia coli*, 827 aa. [WO200078974-A2, 28 DEC. 2000] | 131 ... 410<br>234 ... 499 | 89/281 (31%)<br>146/281 (51%) | 1e−30 |
| AAY72133 | *Escherichia coli* glycerol-3-phosphate acyltransferase (GPAT) - *Escherichia coli*, 827 aa. [WO200078974-A2, 28 DEC. 2000] | 131 ... 410<br>234 ... 499 | 89/281 (31%)<br>146/281 (51%) | 1e−30 |

In a BLAST search of public sequence datbases, the NOV52a protein was found to have homology to the proteins shown in the BLASTP data in Table 52D.

TABLE 52D

Public BLASTP Results for NOV52a

| Protein Accession Number | Protein/Organism/Length | NOV52a Residues/ Match Residues | Identities/ Similarities for the Matched Portion | Expect Value |
|---|---|---|---|---|
| Q9HCL2 | Glycerol-3-phosphate acyltransferase, mitochondrial precursor (EC 2.3.1.15) (GPAT) - *Homo sapiens* (Human), 828 aa. | 1 ... 828<br>1 ... 828 | 828/828 (100%)<br>828/828 (100%) | 0.0 |
| AAH19201 | GLYCEROL-3-PHOSPHATE ACYLTRANSFERASE, MITOCHONDRIAL - *Mus musculus* (Mouse), 827 aa. | 1 ... 828<br>1 ... 827 | 769/828 (92%)<br>799/828 (95%) | 0.0 |
| Q61586 | Glycerol-3-phosphate acyltransferase, mitochondrial precursor (EC 2.3.1.15) (GPAT) (P90) - *Mus musculus* (Mouse), 827 aa. | 1 ... 828<br>1 ... 827 | 767/828 (92%)<br>799/828 (95%) | 0.0 |
| P97564 | Glycerol-3-phosphate acyltransferase, mitochondrial precursor (EC 2.3.1.15) (GPAT) - *Rattus norvegicus* (Rat), 828 aa. | 1 ... 828<br>1 ... 828 | 760/828 (91%)<br>794/828 (95%) | 0.0 |
| Q9Y137 | BCDNA:GH07066 PROTEIN - *Drosophila melanogaster* (Fruit fly), 850 aa. | 163 ... 809<br>194 ... 820 | 196/654 (29%)<br>353/654 (53%) | 1e−81 |

PFam analysis predicts that the NOV52a protein contains the domains shown in the Table 52E.

TABLE 52E

Domain Analysis of NOV52a

| Pfam Domain | NOVA52a Match Region | Identities/Similarities for the Matched Region | Expect Value |
|---|---|---|---|
| Acyltransferase: domain 1 of 1 | 215 ... 412 | 47/207 (23%) 151/207 (73%) | 6.4e−34 |

Example 53

The NOV53 clone was analyzed, and the nucleotide and encoded polypeptide sequences are shown in Table 53A.

TABLE 53A

NOV53 Sequence Analysis

| | |
|---|---|
| NOV53a, CG92152-01 DNA Sequence | SEQ ID NO:129  906 bp<br>AGTAACCTGGAAGATTATGAATGAACTTACATGCAAGAAAAGTACTGAGAAATGTGGC<br>ATCCCTCCATTTAGTCCCCAGTGGCTTTCCAGAAGAATCGCAGGAGGGGAAGAAGCCT<br>GCCCCCACTGTTGGCCATGGCAGGTGGGTCTGAGGTTTCTAGGCGATTACCAATGTGG<br>AGGTGCCATCATCAACCCAGTGTGGATTCTGACCGCAGCCCACTGTGTGCAAAAGAAT<br>AATCCACTCTCCTGGACTATTATTGCTGGGGACCATGACAGAAACCTGAAGGAATCAA<br>CAGAGCAGGTGAAAAAATGTTTTTACATAATAGTGCATGAAGACTTTAACACACTAAG<br>TTATGACTCTGACATTGCCCTAATACAACTAAGCTCTCCTCTGGAGTACAACTCGGTG<br>GTGAGGCCAGTATGTCTCCCACACAGCGCAGAGCCTCTATTTTCCTCGGAGATCTGTG<br>CTGTGACCGGATGGGGAAGCATCAGTGATGGTGGCCTAGCAAGTCGCCTACAGCAGAT<br>TCAAGTGCATGTGTTAGAAAGAGAGGTCTGTGAACACACTTACTATTCTGCCCATCCA<br>GGAGGGATCACAGAGAAGATGATCTGTGCTGGCTTTGCAGCATCTGGAGAGAAAGATT<br>TCTGCCAGGGAGACTCTGGTGGGCCACTAGTATGTAGACATGAAAATGGTCCCTTTGT<br>CCTCTATGGCATTGTCAGCTGGGGAGCTGGCTGTGTCCAGCCATGGAAGCCGGGTGTA<br>TTTGCCAGAGTGATGATCTTCTTGGACTGGATCCAATCAAAAATCAATGGTAAATTGT<br>TTTCAAATGTTATTAAAACAATAACCTCTTTCTTTAGAGTGGGTTTGGGAACAGTGAG<br>TGTGGTATAAATTAGCATGAAAGAGAAAACCATAGA |
| NOV53a, CG92152-01 Protein Sequence | ORF Start: ATG at 17  ORF Stop: TAA at 878<br>SEQ ID NO:130  287 aa MW at 31625.0 kD<br>MNELTCKKSTEKCGIPPFSPQWLSRRIAGGEEACPHCWPWQVGLRFLGDYQCGGAIIN<br>PVWILTAAHCVQKNNPLSWTIIAGDHDRNLKESTEQVKKCFYIIVHEDFNTLSYDSDI<br>ALIQLSSPLEYNSVVRPVCLPHSAEPLFSSEICAVTGWGSISDGGLASRLQQIQVHVL<br>EREVCEHTYYSAHPGGITEKMICAGFAASGEKDFCQGDSGGPLVCRHENGPFVLYGIV<br>SWGAGCVQPWKPGVFARVMIFLDWIQSKINGKLFSNVIKTITSFFRVGLGTVSVV |

Further analysis of the NOV53a protein yielded the following properties shown in Table 53B.

TABLE 53B

Protein Sequence Properties NOV53a

| | |
|---|---|
| PSort analysis: | 0.6564 probability located in microbody (peroxisome); 0.1000 probability located in mitochondrial matrix space; 0.1000 probability located in lysosome (lumen); 0.0000 probability located in endoplasmic reticulum (membrane) |

TABLE 53B-continued

Protein Sequence Properties NOV53a

| | |
|---|---|
| SignalP analysis: | No Known Signal Sequence Predicted |

A search of the NOV53a protein against the Geneseq database, a proprietary database that contains sequences published in patents and patent publication, yielded several homologous proteins shown in Table 53C.

TABLE 53C

Geneseq Results for NOV53a

| Geneseq Identifier | Protein/ Organism/ Length [Patent #, Date] | NOV53a Residues/ Match Residues | Identities/ Similarities for the Matched Region | Expect Value |
|---|---|---|---|---|
| ABG24246 | Novel human diagnostic protein #24237 - *Homo sapiens*, 913 aa. [WO200175067-A2, 11 OCT. 2001] | 13 ... 268<br>506 ... 743 | 196/257 (76%)<br>201/257 (77%) | e–110 |
| ABG24246 | Novel human diagnostic protein #24237 - *Homo sapiens*, 913 aa. [WO200175067-A2, 11 OCT. 2001] | 13 ... 268<br>506 ... 743 | 196/257 (76%)<br>201/257 (77%) | e–110 |
| ABG19887 | Novel human diagnostic protein #19878 - *Homo sapiens*, 1576 aa. [WO200175067-A2, 11 OCT. 2001] | 13 ... 262<br>1345 ... 1576 | 194/251 (77%)<br>199/251 (78%) | e–109 |
| ABG14588 | Novel human diagnostic protein #14579 - *Homo sapiens*, 1576 aa. [WO200175067-A2, 11 OCT. 2001] | 13 ... 262<br>1345 ... 1576 | 194/251 (77%)<br>199/251 (78%) | e–109 |
| ABG10218 | Novel human diagnostic protein #10209 - *Homo sapiens*, 1576 aa. [WO200175067-A2, 11 OCT. 2001] | 13 ... 262<br>1345 ... 1576 | 194/251 (77%)<br>199/251 (78%) | e–109 |

In a BLAST search of public sequence datbases, the NOV53a protein was found to have homology to the proteins shown in the BLASTP data in Table 53D.

TABLE 53D

Public BLASTP Results for NOV53a

| Protein Accession Number | Protein/Organism/Length | NOV53a Residues/ Match Residues | Identities/ Similarities for the Matched Portion | Expect Value |
|---|---|---|---|---|
| Q91674 | POLYPROTEIN - *Xenopus laevis* (African clawed frog), 1524 aa. | 13 ... 259<br>570 ... 814 | 130/248 (52%)<br>175/248 (70%) | 2e–76 |
| Q9BK47 | SEA STAR REGENERATION-ASSOCIATED PROTEASE SRAP - *Luidia foliolata*, 267 aa. | 13 ... 261<br>18 ... 264 | 108/255 (42%)<br>152/255 (59%) | 8e–52 |
| O96899 | PLASMINOGEN ACTIVATOR SPA - *Scolopendra subspinipes*, 277 aa. | 12 ... 273<br>19 ... 276 | 115/269 (42%)<br>163/269 (59%) | 1e–51 |
| Q90WD8 | OVIDUCTIN - *Bufo japonicus* (Japanese toad), 974 aa. | 11 ... 261<br>574 ... 818 | 99/253 (39%)<br>150/253 (59%) | 2e–49 |
| CAC17064 | SEQUENCE 3 FROM PATENT WO0065067 - *Homo sapiens* (Human), 492 aa. | 26 ... 263<br>255 ... 492 | 107/245 (43%)<br>148/245 (59%) | 3e–49 |

PFam analysis predicts that the NOV53a protein contains the domains shown in the Table 53E.

TABLE 53E

Domain Analysis of NOV53a

| Pfam Domain | NOV53a Match Region | Identities/ Similarities for the Matched Region | Expect Value |
|---|---|---|---|
| trypsin: domain 1 of 1 | 27 . . . 257 | 108/263 (41%) 180/263 (68%) | 2.8e−79 |

Example 54

The NOV54 clone was analyzed, and the nucleotide and encoded polypeptide sequences are shown in Table 54A.

TABLE 54A

NOV54 Sequence Analysis

NOV54a,
CG92228-01 DNA Sequence

SEQ ID NO:131    1155 bp
TTATTCTCCTGCCTCAGCCTCCTGAGTAGCTGAGATTATAGGCATGTGCCACCACGCC
TGGCTAATTTTTGTATTTTTAGTAGAGACTGGGTTTCACCATGTTGGTCACGCTGGTC
TCAAACTTGTGACCTTGCCAGAAGCCCAGCTGGCTTCACCTCTCAATGGCCCTTGTGG
GCGGCCCACAGTCTCATCTGGTATTGCCTCAGGCTGGGGGGCTAGTGTGGGGCAGTGG
CCCTGGCAGGTCAGCATCCGCCAGGGCTTGATTCACGTCTGCTCAGATACCCTCATCT
CAGAGGAGTGGGTGCTGACAGTGGCGATCTGCTTCCCGTCCTCCTGCCTCAGCCTCCC
GAGTAGCTGGGACTTCAGGTGCACATCACTACACCAGGCGCAGGCCTCCTTTCTTTT
CCCCATAGGACCTGGACTACTTTTTCATATACTCTGTGGCTAGGATCGATTACAGTAG
GTGACTCAACGAAACGTGTGAAGTACTACGTGTCCAAAATCGTCATCCATCCCAAGTA
CCAAGATACAACGGCAGACGTCGCCTTGTTGAAACTGTCCTCTCAAGTCACCTTCACT
TCTGCCATCCTGCCTATTTGCTTGCCCAGTGTCACAAACCAGTTGGCAATTCCACCCT
TTTGTTGGGTGACCGGATGGGAAAAGTTAAGGAAAGTTCACTTCAGGAAGCAGAAGT
ACCCATTATTGACCGCCAGGCTTGTGAACAGCTCTACGGTGATTCTGGAGGGCCTCTG
TCGTGTCACATTGATGGTGTATGGATCCAGACACGACTAGTAAGCTGGGGATTAGAAT
GTGGTAAATCTCTTCCTGGAGTCTACACCAATGTAATCTACTACCAAAAATGGATTAA
TGCCACTATTTCAAGAGCCAACAATCTAGACTTCTCTGACTTCTTGTTCCCTATTGTC
CTACTCTCTCTGGCTCTCCTGCGTCCCTCCTGTGCCTTTGGACCTAACACTATACACA
GAGTAGGCACTGTAGCTGAAGCTGTTGCTTGCATACAGGGCTGGGAAGAGAATGCATG
GAGATTTAGTCCCAGGGGCAGATAACTCACAGGAGAGCCACTGCTAACCCTGGGTGAC
TTTATTTACAATTTGAAATGATTTTGTTTTTAAGGTTTTTGATTTTGGAAGTT

ORF Start: ATG at 44    ORF Stop: TAA at 1067
SEQ ID NO:132    341 aa  MW at 37339.7 kD NOV54a,
CG92228-01 Protein Sequence MCHHAWLIFVFLVETGFHHVGQAGLKLVTLPEAQLASPLNGPCGRPTVSSGIASGWGA
SVGQWPWQVSIRQGLIHVCSDTLISEEWVLTVAICFPSSCLSLPSSWGLQVHITTPGA
GLLSFPHRTWTTFSYTVWLGSITVGDSRKRVKYYVSKIVIHPKYQDTTADVALLKLSS
QVTPTSAILPICLPSVTKQLAIPPFCWVTGWGKVKESSLQEAEVPIIDRQACEQLYGD
SGGPLSCHIDGVWIQTGVVSWGLECGKSLPGVYTNVIYYQKWINATISRANNLDFSDF
LFPIVLLSLALLRPSCAFGPNTIHRVGTVAEAVACIQGWEENAWRFSPRGR NOV54b, SEQ ID NO:133    1022 bp
TCTGAGGACAGAGACATGGGCCCTGCTGGCTGTGCCTTCACGCTGCTCCTTCTGCTGG

TABLE 54A-continued

NOV54 Sequence Analysis

| | |
|---|---|
| CG92228-02 DNA Sequence | GGATCTCAGTGTGTGGGCAACCTGTATACTCCAGCCGCGTTGTAGGTGGCCAGGATGC |
| | TGCTGCAGGGCGCTCGCCTTGGCAGGTCAGCCTACACTTTGACCACAACTTTATCTGT |
| | GGAGGTTCCCTCGTCAGTGAGAGGTTGATACTGACAGCAGCTCACTGCATAGCAACCT |
| | ATACTGTGTGGCTAGGATCGATTACAGTAGCTGACTCAACGAAACGTGTGAAGTACTA |
| | CGTGTCCAAAATCGTCATCCATCCCAAGTACCAAGATACAACCGCACACGTCGCCTTG |
| | TTGAAACTGTCCTCTCAAGTCACCTTCACTTCTGCCATCCTGCCTATTTGCTTGCCCA |
| | GTGTCACAAAGCAGTTCGCAATTCCACCCTTTTGTTGGGTGACCGGATCGCGAAAAGT |
| | TAAGGAAAGTTCAGATAGAGATTACCATTCTGCCCTTCAGGAAGCAGAAGTACCCATT |
| | ATTGACCGCCAGGCTTGTGAACAGCTCTACAATCCCATCGGTATCTTCTTGCCAGCAC |
| | TGGAGCCAGTCATCAAGGAACACAAGATTTGTGCTCCTGATACTCAAAACATGAACGA |
| | TAGTTGCAAGGGTGATTCTGGAGGGCCTCTGTCGTGTCACATTGATGGTGTATGGATC |
| | CAGACAGGAGTAGTAAGCTGGGGATTAGAATGTGGTAAATCTCTTCCTGGAGTCTACA |
| | CCAATGTAATCTACTACCAAAAATGGATTAATGCCACTATTTCAAGAGCCAACAATCT |
| | AGACTTCTCTGACTTGTTCTTCCCTATTGTCCTACTCTCTCTGGCTCTCCTCCGTCCC |
| | TCCTGTGCCTTTGGACCTAACACTATACACAGAGTAGGCACTGTAGCTGAAGCTGTTG |
| | CTTGCATACAGGGCTGGGAAGAGAATGCATGGAGATTTAGTCCCAGGGGCAGATAACT |
| | CACAGGAGAGCCACTGCTAACCCTGGGTGACTTTAT |
| | ORF Start: ATG at 16      ORF Stop: TAA at 982 |
| | SEQ ID NO:134      322 aa MW at 35193.2 kD |
| NOV54b, | MGPAGCAFTLLLLLGISVCGQPVYSSRVVGGQDAAAGRWPWQVSLHFDHNFICGGSLV |
| CG92228-02 Protein Sequence | SERLILTAAHCIATYTVWLGSITVGDSRKRVKYYVSKIVIHPKYQDTTADVALLKLSS |
| | QVTFTSAILPICLPSVTKQLAIPPFCWVTGWGKVKESSDRDYHSALQEAEVPIIDRQA |
| | CEQLYNPIGIFLPALEPVIKEDKICAGDTQNMKDSCKGDSGGPLSCHIDGVWIQTGVV<br>C[ ]QLYNPIGI FLPALEPVI KEDKICAGDTQNMKDSCKGDSGG-<br>PLSCHIDCVNIQTCVV |
| | SWGLECGKSLPGVYTNVIYYQKWINATISRANNLDFSDFLFPIVLLSLALLRPSCAFG |
| | PNTIHRVGTVAEAVACIQGWEENAWRFSPRGR |

Sequence comparison of the above protein sequences yields the following sequence relationships shown in Table 54B.

TABLE 54B

Comparison of against NOV54b.

| Protein Sequence | NOV54a Residues/<br>Match Residues | Identities/<br>Similarities for<br>the Matched Region |
|---|---|---|
| NOV54b | 43 . . . 341 | 233/338 (68%) |
| | 19 . . . 322 | 243/338 (70%) |

Further analysis of the NOV54a protein yielded the following properties shown in Table 54C.

TABLE 54C

Protein Sequence Properties NOV54a

| | |
|---|---|
| PSort analysis: | 0.7300 probability located in plasma membrane; 0.6400 probability located in endoplasmic reticulum (membrane); 0.3200 probability located in microbody (peroxisome); 0.1000 probability located in endoplasmic reticulum (lumen) |
| SignalP analysis: | Cleavage site between residues 24 and 25 |

A search of the NOV54a protein against the Geneseq database, a proprietary database that contains sequences published in patents and patent publication, yielded several homologous proteins shown in Table 54D.

TABLE 54D

Geneseq Results for NOV54a

| Geneseq Identifier | Protein/ Organism/ Length [Patent #, Date] | NOV54a Residues/ Match Residues | Identities/ Similarities for the Matched Region | Expect Value |
|---|---|---|---|---|
| AAW77297 | Amino acid sequence of long isoform of HELA2 - *Homo sapiens*, 314 aa. [WO9836054-A1, 20 AUG. 1998] | 20 . . . 304 13 . . . 309 | 117/322 (36%) 170/322 (52%) | 3e-48 |
| AAB80256 | Human PR0303 protein - *Homo sapiens*, 314 aa. [WO200104311-A1, 18 JAN. 2001] | 20 . . . 304 13 . . . 309 | 116/322 (36%) 170/322 (52%) | 1e-47 |
| AAU01569 | Human secreted protein immunogenic epitope encoded by gene #9 - *Homo sapiens*, 315 aa. [WO200123547-A1, 05 APR. 2001] | 20 . . . 304 13 . . . 309 | 116/322 (36%) 170/322 (52%) | 1e-47 |
| AAU02223 | Human extracellular serine protease TADG-16 - *Homo sapiens*, 314 aa. [WO200127257-A1, 19 APR. 2001] | 20 . . . 304 13 . . . 309 | 116/322 (36%) 170/322 (52%) | 1e-47 |
| AAY91871 | Human cancer-specific gene protein, Pro104 - *Homo sapiens*, 327 aa. [WO200016805-A1, 30 MAR. 2000] | 20 . . . 304 26 . . . 322 | 116/322 (36%) 170/322 (52%) | 1e-47 |

In a BLAST search of public sequence datbases, the NOV54a protein was found to have homology to the proteins shown in the BLASTP data in Table 54E.

TABLE 54E

Public BLASTP Results for NOV54a

| Protein Accession Number | Protein/Organism/Length | NOV54a Residues/ Match Residues | Identities/ Similarities for the Matched Portion | Expect Value |
|---|---|---|---|---|
| Q9Y6M0 | Testisin precursor (EC 3.4.21.-) (Eosinophil serine protease 1) (ESP-1) - *Homo sapiens* (Human), 314 aa. | 20 . . . 304 13 . . . 309 | 116/322 (36%) 170/322 (52%) | 3e-47 |
| Q9JHJ7 | Testisin precursor (EC 3.4.21.-) (Tryptase 4) - *Mus musculus* (Mouse), 324 aa. | 31 . . . 305 34 . . . 324 | 115/315 (36%) 157/315 (49%) | 1e-43 |
| Q920S2 | TESTIS SERINE PROTEASE-1 - *Mus musculus* (Mouse), 322 aa. | 39 . . . 305 39 . . . 322 | 101/308 (32%) 149/308 (47%) | 6e-38 |
| Q9D4I3 | 4931440B09RIK PROTEIN - *Mus musculus* (Mouse), 282 aa. | 42 . . . 305 2 . . . 282 | 100/305 (32%) 147/305 (47%) | 1e-37 |
| Q9QUL7 | Tryptase gamma precursor (EC 3.4.21.-) (Transmembrane tryptase) - *Mus musculus* (Mouse), 311 aa. | 43 . . . 305 18 . . . 285 | 103/302 (34%) 128/302 (42%) | 1e-35 |

PFam analysis predicts that the NOV54a protein contains the domains shown in the Table 54F.

TABLE 54F

Domain Analysis of NOV54a

| Pfam Domain | NOV54a Match Region | Identities/ Similarities for the Matched Region | Expect Value |
|---|---|---|---|
| trypsin: domain 1 of 1 | 52 . . . 275 | 89/284 (31%) 163/284 (57%) | 1.2e-48 |

Example 55

The NOV55 clone was analyzed, and the nucleotide and encoded polypeptide sequences are shown in Table 55A.

TABLE 55A

NOV55 Sequence Analysis

| | |
|---|---|
| NOV55a,<br>CG92425-01 DNA Sequence | SEQ ID NO:135          991 bp<br><u>TCCCTCTTGGCCATCACATTCCCCTTGCCCT</u>ATGGCGGCCCTCACAGACCTCTCATTT<br>ATGTATCGCTGGTTCAAGAACTGCAATCTGGTTGCCAACCTCTCAGAGAAGTACGTCT<br>TCATCACAGGCTGTGACTCTGCCTTCGCGAACCTCCTGGCCAAACAGCTGGTTGATCG<br>GGGCATGCAGGTGCTGGCTGCTTGCTTCACTGAGGAGGGATCCCAGAAACTTCAGCGG<br>GATACCTCCTATCGGCTGCAGACCACCCTACTGGATGTCACCAAGAGCGAAAGCATCA<br>AGGCGGCGCCCAGTGGGTCAGCGACAAAGTGGGCGAACAAGGTCTCTCGGCCCTGGT<br>GAACAATGCTGGTGTGGGCCTGCCCAGTCGTCCCAACGAATGGCTGACCAACGATGAC<br>TTTGTGAAGGTGATTAATGTGAACCTGGTGCCACPGATCGAAGTGACCCTTCACATGC<br>TGCCCATGGTCAAGAGAGCCCGGGGCAGGGTTGTCAACATGTCCAGCTCTGGTGGTCG<br>TGTCGCTCTCATTGGTCGTCGCTACTGCGTCTCCAACTTTGGCCTTGACGCCTTCTCT<br>GACAGCATAAGGCGTGAGCTCTACTACTTTGGGGTGAAAGTCTGCATCATTGAGCCAG<br>GGAACTATCGGACAGCCATTCTCGGCAAGGAGAACCTGGAGTCACGCATGCGAAAGCT<br>TTGGGAGAGGCTGCCTCAGGACACCCGGGACACCTACGGAGAGCATTATATGCCTCTT<br>ATCCTAAAGGCATTAGAGAGCCTTCTAAATGGCTCTGAPATGAAGGATCAGATTGTCA<br>TCAACAGCATCGAGCATGCTATTGTTTCCCGGAGCCCTCCCATCCGCTACAACCCTGG<br>CCTGGATGCCAAACTCCTCTACATCCCTCTGGCTAAGTTGCCCACCCCTGTGACAGAT<br>TTCATCCTAAGCCGCTACCTTCCAAGGCCAGCCGACAGTGTCTAA<u>ACTCGGGAGGATC</u><br><u>AATGG</u> |
| NOV55a,<br>CG92425-01 Protein Sequence | ORF Start: ATG at 32          ORF Stop: TAA at 971<br>SEQ ID NO:136          313 aa MW AT 34973.1 kD<br>MAALTDLSFMYRWFKNCNLVGNLSEKYVFITGCDSGFGNLLAKQLVDRGMQVLAACFT<br>EEGSQKLQRDTSYRLQTTLLDVTKSESIKAAAQWVRDKVGEQGLWALVNNAGVGLPSG<br>PNEWLTKDDFVKVINVNLVGLIEVTLHMLPMVKRARGRVVNMSSSGGRVAVICGGYCV<br>SKFGVEAFSDSIRRELYYFGVKVCIIEPGNYRTAILGKENLESRMRKLWERLPQETRD<br>SYGEDYMALILKALESLVMGSEMKDQIVINSMEHAIVSRSPRIRYNPGLDAKLLYIPL<br>AKLPTPVTDFILSRYLPRPADSV |
| NOV55b,<br>CG92425-02 DNA Sequence | SEQ ID NO:137          991 bp<br><u>TCCCTCTTGGCCATCACATTCCCCTTGCCCT</u>ATGGCGGCCCTCACAGACCTCTCATTT<br>ATGTATCGCTGGTTCAAGAACTGCAATCTGGTTGGCAACCTCTCAGAGAAGTACGTCT<br>TCATCACAGGCTGTGACTCTGGCTTCGGGAACCTGCTGGCCAAACAGCTGGTTGATCG<br>GGGCATGCAGGTGCTGGCTGCTTGCTTCACTGAGGAGGGATCCCAGAAACTTCAGCGG<br>GATACCTCCTATCGGCTGCAGACCACCCTACTGGATGTCACCAAGAGCGAAAGCATCA<br>AGGCGGCGCCCAGTGGGTGAGGGACAAAGTGGGCGAACAAGGCCTCTGGGCCCTGGT<br>GAACAATGCTGGTGTGGGCCTGCCCAGTGGTCCCAACGAATCGCTGACCAAGGATGAC<br>TTTGTGAAGGTGATTAATGTGAACCTGGTGGGACTGATCGAAGTGACCCTTCACATGC<br>TGCCCATGGTCAAGAGAGCCCGGGGCAGGGTTGTCAACATGTCCAGCTCTGGTGGTCG<br>TGTGGCTGTCATTGGTGGTGGCTACTGCGTCTCCAAGTTTGGCGTTGAGGCCTTCTCT |

TABLE 55A-continued

NOV55 Sequence Analysis

```
GACAGCATAAGGCGTGAGCTCTACTACTTTGGGGTGAAAGTCTGCATCATTGAGCCAG

GGAACTATCGGACAGCCATTCTCGGCAAGGAGAACCTGGAGTCACGCATGCGAAAGCT

TTGGGAGAGGCTGCCTCAGGAGACCCGGGACAGCTACGGAGAGGATTATTTCCGCATC

TATACTGACAAGTTAAAAAACATAATGCAGGTGGCAGAGCCCAGAGTCAGAGATGTCA

TCAACAGCATGGAGCATGCTATTGTTTCCCGGAGCCCTCGCATCCGCTACAACCCTGG

CCTGGATGCCAAACTCCTCTACATCCCTCTGGCTAAGTTCCCCACCCCTGTCACAGAT

TTCATCCTAAGCCGGTACCTTCCAAGGCCAGCGGACAGTGTCTAAACTGGGGAGGATC

AATGG
```

| | | |
|---|---|---|
| | ORF Start: ATG at 32 | ORF Stop: TAA at 971 |
| | SEQ ID NO:138 | 313 aa MW AT 25262.4 kD |
| NOV55b, | MAALTDLSFMYRWFKNCNLVGNLSEKYVFITGCDSGFGNLLAKQLVDRGMQVLAACFT | |
| CG9425-02 Protein Sequence | EEGSQKLQRDTSYRLQTTLLDVTKSESIKAAAQWVRDKVGEQGLWALVNNAGVGPLSG | |
| | PNEWLTKDDFVKVINVNLVGLIEVTLHMLPMVKRARGRVVNMSSSGGRVAVIGGGYCV | |
| | SKFGVEAFSDSIRRELYYFGVKVCIIEPGNYRTAILGKENLESRMRKLWERLPQETRD | |
| | SYGEDYFRIYTDKLKNIMQVAEPRVRDVINSMEHAIVSRSPRIRYNPGLDAKLLYIPL | |
| | AKLPTPVTDFILSRYLPRPADSV | |

Sequence comparison of the above protein sequences yields the following sequence relationships shown in Table 55B.

TABLE 55B

Comparison of NOV55a against NOV55b.

| Protein Sequence | NOV55a Residues/ Match Residues | Identities/ Similarities for the Matched Region |
|---|---|---|
| NOV55b | 1...313 | 294/313 (93%) |
| | 1...313 | 302/313 (95%) |

Further analysis of the NOV55a protein yielded the following properties shown in Table 55C.

TABLE 55C

Protein Sequence Properties NOV55a

| PSort analysis: | 0.5813 probability located in mitochondrial matrix space; 0.3000 probability located in microbody (peroxisome); 0.2927 probability located in mitochondrial inner membrane; 0.2927 probability located in mitochondrial intermembrane space |
|---|---|
| SignalP analysis: | No Known Signal Sequence Predicted |

A search of the NOV55a protein against the Geneseq database, a proprietary database that contains sequences published in patents and patent publication, yielded several homologous proteins shown in Table 55D.

TABLE 55D

Geneseq Results for NOV55a

| Geneseq Identifier | Protein/Organism/Length [Patent #, Date] | NOV55a Residues Match Residues | Identities/ Similarities for the Matched Region | Expect Value |
|---|---|---|---|---|
| AAM41630 | Human polypeptide SEQ ID NO 6561 - Homo sapiens, 360 aa. [WO200153312-A1, 26 Jul. 2001] | 1..313 48..360 | 294/313 (93%) 302/313 (95%) | e−169 |
| AAM39844 | Human polypeptide SEQ ID NO 2989 - Homo sapiens, 313 aa. [WO200153312-A1, 26 Jul. 2001] | 1..313 1..313 | 294/313 (93%) 302/313 (95%) | e−169 |
| AAY02003 | A retinol dehydrogenase nrotein of the invention - Mus sp, 318 aa. [WO9916788-A1, 08 Apr. 1999] | 1..309 5..314 | 170/310 (54%) 227/310 (72%) | 9e−94 |
| AAW18335 | Murine liver p32 11-cis-retinol dehydrogenase - Mus musculus, 317 aa. [WO9719167-A1, 29 May 1997] | 1..302 5..306 | 169/302 (55%) 219/302 (71%) | 9e−94 |
| AAY02002 | A retinol dehydrogenase protein of the invention - Mus sp, 317 aa. [WO9916788-A1, 08 Apr. 1999] | 1..302 5..306 | 168/302 (55%) 219/302 (71%) | 2e−93 |

In a BLAST search of public sequence datbases, the NOV55a protein was found to have homology to the proteins shown in the BLASTP data in Table 55E.

TABLE 55E

Public BLASTP Results for NOV55a

| Protein Accession Number | Protein/Organism/Length | NOV55a Residues/ Match Residues | Identities/ Similarities for the Matched Portion | Expect Value |
|---|---|---|---|---|
| P50169 | Retinol dehydrogenase type I (EC 1.1.1.105) (RODH I) - *Rattus norvegicus* (Rat), 317 aa. | 1..310 5..314 | 170/310 (54%) 236/310 (75%) | 4e-99 |
| P55006 | Retinol dehydrogenase type III (EC 1.1.1.105) (RODHIII) - *Rattus norvegicus* (Rat), 317 aa. | 1..310 5..314 | 169/310 (54%) 235/310 (75%) | 9e-98 |
| AAK30001 | RETINOL DEHYDROGENASE TYPE 1 - *Mus musculus* (Mouse), 317 aa. | 1..302 5..306 | 166/302 (54%) 224/302 (73%) | 3e-96 |
| AAH18263 | SIMILAR TO RETINOL DEHYDROGENASE TYPE 6 - *Mus musculus* (Mouse), 318 aa. | 1..309 5..314 | 173/309 (55%) 226/310 (72%) | 5e-94 |
| O75452 | STEROL/RETINOL DEHYDROGENASE - *Homo sapiens* (Human), 317 aa. | 1..313 5..317 | 162/313 (51%) 231/313 (73%) | 6e-94 |

PFam analysis predicts that the NOV55a protein contains the domains shown in the Table 55F.

TABLE 55F

Domain Analysis of NOV55a

| Pfam Domain | NOV55a Match Region | Identities/ Similarities for the Matched Region | Expect Value |
|---|---|---|---|
| adh_short: domain 1 of 1 | 24..265 | 78/275 (28%) 178/275 (65%) | 5.4e-42 |

Example 56

The NOV56 clone was analyzed, and the nucleotide and encoded polypeptide sequences are shown in Table 56A.

TABLE 56A

NOV56 Sequence Analysis

NOV56A,
CG92477-01 DNA Sequence

SEQ ID NO:139  1553 bp
<u>TTTTAATG</u>TGGTTCGTGACTGAGCCAATTCTCTGGGCATTTTTCCTATTCTTAATGCT

AATGACTATCCACTGCTGGTCCTCTTATCTGTTTACTCAAAAACACAAACTGACTCTC

ATCCTTGTGTTTCAGGATGTCATCAGTATAGCTGACAATATCCTTAATTCAGCCTCAG

TAACCAACTGGACAGTCTTACTGCGGGAAGAAAAGTATGCCAGCTCACCGTTACTAGA

GACATTAGAAAACATCAGCACTCTCGTGCCTCCGACAGCTCTTCCTCTGAATTTTTCT

CGGAAATTCATTGACTGGAAAGGGATTCCAGTGAACAAAAGCCAACTCAAAAGGGGTT

ACAGCTATCAGATTAAAATGTGTCCCCAAAATACATCTATTCCCATCAGACGCCGTGT

GTTAATTGGGTCAGACCAATTCCAGAGATCCCTTCCAGAAACTATTATCAGCATGGCC

TCGTTGACTCTGGCGAACATTCTACCCCTTTCCAAAAATGCAAATGCTCAGGTCAATG

GACCTGTGATATCCACGGTTATTCAAAACTATTCCATAAATGAAGTTTTCCTATTTTT

TTCCAAGATAGAGTCAAACCTGAGCCAGCCTCATTGTGTGTTTGGGATTTCAGTCAT

TTGCAGPCCAACGATGCAGGCTCCCACCTAGTGAATGAAACTCAAGACATCGTGACGT

TABLE 56A-continued

NOV56 Sequence Analysis

```
                        GCCAATGTACTCACTTCACCTCCTTCTCCATGTTGATGTCACCTTTTGTCCCCTCTAC

AATCTTCCCCGTTGTAAAATGGATCACCTATGTGGGACTGGGTATCTCCATTGGAAGT

CTCATTTTATGCCTGATCATCGAGGCTTTGTTTTGGAAGCAGATTAAAAAAACCCAAA

CCTCTCACACACGTCGTATTTGCATGGTGAACATAGCCCTGTCCCTCTTGATTGCTGA

TGTCTGGTTTATTGTTGGTGCCACAGTGGACACCACGGTGAACCCTTCTGGAGTCTGC

ACAGCTGCTGTGTTCTTTACACACTTCTTCTACCTCTCTTTGTTCTTCTGGATGCTCA

TGCTTGCCATCCTGCTCCCTTACCGGATCATCCTCGTGTTCCATCACATGGCCCAGCA

TTTGATGATGGCTGTTGCATTTTGCCTCCGTTATGGGTGCCCTCTCATTATATCTGTC

ATTACCATTGCTGTCACGCAACCTAGCAATACCTACAAAAGGAAAGATGTGTGTTGGC

TTAACTGGTCCAATCGAAGCAAACCACTCCTGGCTTTTGTTGTCCCTGCACTGCCTAT

TGTGGCTGTGAACTTCGTTGTCGTGCTGCTAGTTCTCACAAAGCTCTGGAGGCCGACT

GTTGGGAAAGACTGAGTCGGGATGACAAGGCCACCATCGTCCCCGTGCGGAAGAGCC

TCCTCATTCTGACCCCTCTGCTACGGCTCACCTGGGCCTTTGGAATAGGAACAATAGT

GGACAGCCAGAATCTGGCTTGGCATGTTATTTTTGCTTTACTCAATCCATTCCAGCTG

AGAACAGTAACAATAACCTATTGTATTGTCAAGTGATTGGAATAA

ORF Start: ATG at 6      ORF Stop: TGA at 1542
                        SEQ ID NO:140             512 aa MW at 57687.7 kD
NOV56a,                 MWFVTEPILWAFFLFLMLMTIHCWSSYLFTQKHKTLTLVFQDVISIADNILNTSASVT CG92477-01 Protein Sequence  NWTVLLREEKYASSRLLETLENISTLVPPTALPLNFSRKFIDWKGIPVNKSQLKRGYS

YQIKMCPQNTSIPIRGRVLIGSDQBQRSLPETIISMASLTLGNILPVSKNGNAQVNGP

VISTVIQNYSINEVFLFFSKIESNLSQPHCVFWDFSHLQWNDAGCELVNETQDIVTCQ

CTHLTSFSMLMSPFVPSTIPPVVKWITYVGLGTSIGSLILCLIIEALFWKQIKKSQTS

HTRRICMVNIALSLLIADVWFIVGATVDTTVNPSGVCTAAVFFTHFFYLSLFFWMLML

GILLAYRIILVFHHMAQHLMMAVGFCLCYCCPLIISVITIAVTQPSNTYKRKDVCWLN

WSNGSKPLLAFVVPALAIVAVNIVVVLLVLTKLWRPTVGERLSRDDKATIVRVGKSLL

ILTPLLGLTWGFGIGTIVDSQNLAWHVIFALLNAFQVRTVTITYCIVK
```

Further analysis of the NOV56a protein yielded the following properties shown in Table 56B.

TABLE 56B

Protein Sequence Properties NOV56a

| | |
|---|---|
| PSort analysis: | 0.6850 probability located in endoplasmic reticulum (membrane); 0.6400 probability located in plasma membrane; 0.4600 probability located in Golgi body; 0.1000 probability located in endoplasmic reticulum (lumen) |
| SignalP analysis: | Cleavage site between residues 24 and 25 |

A search of the NOV56a protein against the Geneseq database, a proprietary database that contains sequences published in patents and patent publication, yielded several homologous proteins shown in Table 56C.

TABLE 56C

Geneseq Results for NOV56a

| Geneseq Identifier | Protein/Organism/Length [Patent #, Date] | NOV56a Residues/ Match Residues | Identities/ Similarities for the Matched Region | Expect Value |
|---|---|---|---|---|
| AAG68126 | Human 7TM-GPCR protein sequence SEQ ID NO:6 - Homo sapiens, 928 aa. [WO200168701-A2, 20 Sep. 2001] | 42..502 195..655 | 459/461 (99%) 461/461 (99%) | 0.0 |
| AAE12023 | Human G-protein coupled receptor, GCREC-2 - Homo sapiens, 910 aa. [WO200172836-A2, 04 Oct. 2001] | 42..500 372..830 | 456/459 (99%) 459/459 (99%) | 0.0 |
| AAB61616 | Human protein HP10678 - Homo sapiens, 542 aa. [WO200102563-A2, 11 Jan. 2001] | 21..500 10..491 | 196/491 (39%) 297/491 (59%) | 3e-95 |
| AAY57288 | Human GPCR protein (HGPRP) sequence (clone ID 3036563) - Homo sapiens, 807 aa. [WO200015793-A2, 23 Mar. 2000] | 44..510 256..729 | 187/480 (38%) 283/480 (58%) | 8e-94 |
| AAU04581 | Human G-protein coupled receptor like protein, GPCR #12 - Homo sapiens, 1346 aa. [WO200153454-A2, 26 Jul/ 2001] | 44..510 795..1268 | 187/480 (38%) 282/480 (57%) | 1e-93 |

In a BLAST search of public sequence datbases, the NOV56a protein was found to have homology to the proteins shown in the BLASTP data in Table 56D.

TABLE 56D

Public BLASTP Results for NOV56a

| Protein Accession Number | Protein/Organism/Length | NOV56a Residues/ Match Residues | Identities/ Similarities for the Matched Portion | Expect Value |
|---|---|---|---|---|
| AAH19217 | HYPOTHIETICAL 101.5 KDA PROTEIN - Mus musculus (Mouse), 908 aa. | 39..500 368..828 | 349/462 (75%) 410/462 (88%) | 0.0 |
| Q96DQ1 | CDNA FLJ30646 FIS, CLONE CTONG2004716, WEAKLY SIMILAR TO RATTUS NORVEGICUS SEVEN TRANSMEMBRANE RECEPTOR - Homo sapiens (Human), 302 aa. | 42..283 60..301 | 240/242 (99%) 242/242 (99%) | e-138 |
| Q9WVT0 | SEVEN TRANSMEMBRANE RECEPTOR - Rattus norvegicus (Rat), 1349 aa. | 40..510 791..1271 | 191/487 (39%) 294/487 (60%) | 9e-98 |
| CAC27252 | SEQUENCE 29 FROM PATENT WO0102563 - Homo sapiens (Human), 542 aa. | 21..500 10..491 | 196/491 (39%) 297/491 (59%) | 8e-95 |
| Q9UIZ3 | DJ365O12.1 (KIAA0758 PROTEIN) - Homo sapiens (Human), 1346 aa. | 44..510 795..1268 | 187/480 (38%) 283/480 (58%) | 2e-93 |

PFam analysis predicts that the NOV56a protein contains the domains shown in the Table 56E.

TABLE 56E

Domain Analysis of NOV56a

| Pfam Domain | NOV56a Match Region | Identities/ Similarities for the Matched Region | Expect Value |
|---|---|---|---|
| GPS: domain 1 of 1 | 200..250 | 24/56 (43%) 40/56 (71%) | 3e-12 |
| 7tm_2: domain 1 of 1 | 252..511 | 75/290 (26%) 193/290 (67%) | 9.4e-20 |

Example 57

The NOV57 clone was analyzed, and the nucleotide and encoded polypeptide sequences are shown in Table 57A.

TABLE 57A

NOV57 Sequence Analysis

| NOV57a, CG92499-01 DNA Sequence | SEQ ID NO:141    2320 bp<br>TTCAGAAGGAAATATCATCAGCAGAAGCTCCTAAAAAATAATGAGTCCTTGGATGAAG<br>GCTTGAGGCTACACACAGTGAATCTGAGACAACTGGGTCATTGTCTTGCCATGGAGGA<br>ACCCAAAGGCTACTACTGGCCATCTATCCAACCTTCTGAATACGTTCTTCCTTGTCCA<br>GACAAGCCTGGGTTTTCTGCTTCTCGGATATGTTTTTACAATGCTACCAACCCATTGG<br>TAACCTACTGGGGACCTGTTGATATCTCCAACTGTTTAAAAGAAGCAAATGAACTTGC<br>TAACCAGATTTTAAATTTAACTGCTGATGGCCAGAACTTAACCTCAGCCAATATTACC<br>AACATTGTGGAACAGGTCAAAACAATTGTGAATAAAGAAGAAAACATTGATATAACAC<br>TTGGCTCAACTCTAATGAATATATTTTCTAATATCTTAAGCAGTTCAGACAGTGACTT<br>GCTTGAGTCATCTTCTGAAGCTTTAAAAACAATTGATGAATTGGCCTTCAACATAGAC<br>CTAAATAGCACATCACATGTGAATATTACAACTCGGAACTTGGCTCTCAGCGTATCAT<br>CCCTGTTACCAGGGACAAATGCAATTTCAAATTTTAGCATTGGTCTTCCAAGCAATAA<br>TGAATCGTATTTCCACATGGATTTTGAGAGTCGACAAGTGGATCCACTGGCATCTGTA<br>ATTTTGCCTCCAAACTTACTTGAGAATTTAAGTCCAGAAGATTCTGTATTAGTTAGAA<br>GAGCACAGTTTACTTTCTTCAACAAAACTGGACTTTTCCAGGATGTAGGACCCCAAAG<br>AAAAACTTTAGTGAGTTATGTGATGGCGTGCAGTATTGCAAACATTACTATCCAGAAT<br>CTGAAGGATCCTGTTCAAATAAAAATCAAACATACAAGAACTCAGGAAGTGCATCATC<br>CCATCTGTGCCTTCTGCGATCTGAACAAAAACAAAAGTTTTCCAGGATGCAACACGTC<br>AGGATGTGTTGCACACAGAGATTCAGATGCAAGTGACACAGTCTGCCTGTGTAACCAC<br>TTCACACACTTTCGAGTTCTGATGGACCTTCCAAGAAGTCCCTCACAGTTACATGCAA<br>GAAACACTAAAGTCCTCACTTTCATCAGCTATATTGGGTGTCGAATATCTGCTATTTT<br>TTCAGCAGCAACTCTCCTGACATATGTTGCTTTTGAGAAATTGCGAAGGGATTATCCC<br>TCCAAAATCTTGATCAACCTGAGCACAGCCCTGCTGTTCCTGAATCTCCTCTTCCTCC<br>TAGATGGCTGGATCACCTCCTTCAATQTCCATGGACTTTGCATTGCTGTTGCAGTCCT<br>GTTGCATTTCTTCCTTCTGGCAACCTTTACCTGGATGCGGCTAGAAGCAATTCACATG<br>TACATTGCTCTAGTTAAAGTATTTAACACTTACATTCGCCGATACATTCTAAAATTCT<br>GCATCATTGGCTGCGGTTTGCCTGCCTTAGTGGTGTCAGTTGTTCTAGCGAGCAGAAA<br>CAACAATCAAGTCTATGGAAAAGAAAGTTATCGCAAAGAAAAAGGTGATGAATTCTGT<br>TGGATTCAAGATCCAGTCATATTTTATGTGACCTGTGCTGGGTATTTTGGAGTCATGT<br>TTTTTCTGAACATTGCCATGTTCATTGTGGTAATGGTGCAGATCTGTGGCAGCAATGG<br>CAAGAGAAGCAACCGGACCCTGAGAGAAGAAGTGTTAAGGAACCTGCGCAGTGTGGTT<br>AGCTTGACCTTTCTGTTGCGCATGACATGGGGTTTTGCATTCTTTGCCTGGGGACCCT<br>TAAATATCCCCTTCATGTACCTCTTCTCCATCTTCAATTCATTACAAGGCTTATTTAT<br>ATTCATCTTCCACTGTCCTATGAACGAGAATGTTCAGAAACAGTGGCGGCGGCATCTC<br>TGCTGTGGTAGATTTCGGTTAGCACATAACTCAGATTCGAGTAAGACAGCTACCAATA<br>TCATCAAGAAAGTTCTCATAATCTAGGAAAATCTTTGTCTTCAAGCTCCATTGGTTC<br>CAACTCAACCTATCTTACATCCAAATCTAAATCCAGCTCTAACCACCTATTTCAAAAG<br>GAATAGCCACACAGATTATGTCTCCTATAACTTTCCTCCCCAAAGTGGTTCTCCGACG<br>GGTTCCTTGAAAGTCTTTTAAAATGCCCTTTATGGAAAAAATCAAACCCCTCCCCGGT |
|---|---|

TABLE 57A-continued

NOV57 Sequence Analysis

TTTTTGGGGGGTTTGGGGTCTCCCCTTTTTATTTTTTAAATTGGGGGGGTTTTTTAA

AAAAAATTTATTTTTGGGGGGTTTTTTTTTATTAAAAAAAAAAAAAAAACAATTTTTTA

NOV57a,

ORF Start: ATG at 109     ORF Stop: TAG at 2092
SEQ ID NO:142     661 aa MW at 74148.5 kD
MEEPKGYYWPSIQPSEYVLPCPDKPGFSASRICFYNATNPLVTYWGPVDISNCLKEAN
MEEPKGYYWPS I QPSEYVLPCPDKPGFSASRI CPYNATNPLVrYWGPVD ISN-
CLKEAN CG92499-01 Protein Sequence     EVANQILNLTADGQNLTSANITNTVEQVKRIVNKBENIDITLGSTLMNIFSNILSSSD

SDLLESSSEALKTIDELAFKIDLNSTSHVNITTRNLALSVSSLLPGTNAISNFSIGLP

SNNESYFQMDFESGQVDPLASVILPPNLLENLSPEDSVLVRRAQFTFFNKTGLFQDVG

PQRKTLVSYVMACSIGNITTQNLKDPVQIKIKHTRTQEVHHPICAFWDLNKNKSFGGW

NTSGCVAHRDSDASETVCLCNHFTHFGVLMDLPRSASQLDARNTKVLTFISYIGCGIS

AIFSAATLLTYVAFSKLRRDYPSKILMNLSTALLFLNLLFLLDGWITSFNVDGLCIAV

AVLLHFFLLATFTWMGLEAIHMYIALVKVFNTYIRRYILKFCIIGWGLPALVVSVVLA

SRNNNEVYGKESYGKEKGDEFCWIQDPVXFYVTCAGYFGVMFFLNIAMFIVVMVQICG

RNGKRSNRTLRBEVLRNLRSVVSLTFLLGMTWGFAFFAWGPLNIPFMYLFSIFNSLQG

LFIFIFHCAMKENVQKQWRRHLCCGRFRLADNSDWSKTATNITKKSSDNLGKSLSSSS

IGSNSTYLTSKSKSSSNHLFQKE

NOV57b,

SEQ ID NO:143     2428 bp
GGATGAGCCAAGCTTGGTGCTTTCGCCCCTTCTAGTTTACAATGCTACCAACAATACT

CG92499-02 DNA Sequence     AATTTAGAAGGAAAAATCATTCAGCAGAACCTCCTAAAAAATAATGAGTCCTTGGATG

AAGGCTTGAGGCTACATACAGTGAATGTCACACAACTGGGTCATTGTCTTGCCATGCA

GGAACCCAAAGGCTACTACTGGCCATCTATCCAACCTTCTGAATACGTTCTTCCTTGT

CCAGACAAGCCTGGCTTTTCTGCTTCTCGGATATGTTTTTACAATGCTACCAACCCAT

TGGTAACCTACTGGCGACCTGTTGATATCTCCAACTGTTTAAAACAAGCAAATGAAGT

TGCTAACCAGATTPTAAATTTAACTGCPGATGGGCAGAACTTAACCTCAGCCAATATT

ACCAACATTGTGGAACAGGTCAAAAGAATTGTGAATAAAGAAGAAAACATTGATATAA

CACTTGGCTCAACTCTAATGAATATATTTTCTAATATCTTAAGCAGTTCAGACAGTCA

CTTGCTTGAGTCATCTTCTGAAGCTTTAAAAACAATTQATGAATTGGCCTTCAAGATA

GACCTAAATACCACATCACATGTGAATATTACAACTCCGAACTTGGCTCTCAGCGTAT

CATCCCTCTTACCAGGGACAAATGCAATTTCAAATTTTAGCATTGGTCTTCCAAGCAA

TAATGAATCGTATTTCCAGGTACACATGCATTTTGAGAGTGGACAACTCGATCCACTG

GCATCTGTAATTTTCCCTCCAAACTTACTTGACAATTTAAGTCCAGAACATTCTGTAT

TAGTTAGAAGAGCACAGTTTACTTTCTTCAACAAAACTGGACTTTTCCAGGATGTAGG

ACCCCAAAGAAAAACTTTAGTGAGTTATGTGATGGCGTGCAGTATTGGAAACATTACT

ATCCAGAATCTGAAGGATCCTGTTCAAATAAAAATCAAACATTATAGAGAAGAAACTG

ACCTGCTGTTTTCACACTGTTTGTTGATTCCTTCAACAGAAAGTTTTCGAGGATGGAA

CACGTCAGGATGTGTTGCACACAGAGATTCAGATGCAACTGAGACAGTCTGCCTGTGT

AACCACTTCACACACTTTGGAGTTCTGATGGACCTTCCAAGAAGTGCCTCACAGTTAG

ATGCAAGAAACACTAAAGTCCTCACTTTCATCAGCTATATTGGGTGTGGAATATCTGC

TATTTTTTCAGCAGCAACTCTCCTGACATATGTTGCTTTTGAGAAATTGCGAAGGGAT

TABLE 57A-continued

NOV57 Sequence Analysis

TATCCCTCCAAAATCTTGATGAACCTGAGCACAGCCCTGCTGTTCCTCAATCTCCTCT

TCCTCCTAGATGGCTGGATCACCTCCTTCAATGTGGATGGACTTTGCATTGCTGTTGC

AGTCCTGTTCCATTTCTTCCTTCTCGCAACCTTTACCTGGATGCGGCTAGAAGCAATT

CACATCTACATTGCTCTAGTTAAAGTATTTAACACTTACATTCCCCGATACATTCTAA

AATTCTGCATCATTGGCTGGGGTTTGCCTGCCTTAGTGGTGTCAGTTGTTCTAGCGAG

CAGAAACAACAATCAAGTCTATGGAAAAGAAAGTTATGGGAAAGAAAAAGGTGATGAA

TGTTGGATTCAAGATCCAGTCATATTTTATGTGACCTGTGCTGGGTATTTTGGAGTCA

TGTTTTTTCTGAACATTGCCATGTTCATTGTGGTAATGGTGCAGATCTCTGGGAGGAA

TGGCAAGAGAAGCAACCGGACCCTGAGAGAACAAGTCTTAAGGAACCTGCGCACTGTG

GTTAGCTTGACCTTTCTGTTGGGCATGACATGGGGTTTTGCATTCTTTCCCTGGGGAC

CCTTAAATATCCCCTTCATCTACCTCTTCTCCATCTTCAATTCATTACAAGGTTTATT

TATATTCATCTTCCACTCTGCTATCAAGGAGAATGTTCACAAACAGTCGCGGCAGCAT

CTCTGCTGTGGTAGATTTCGGTTAGCACATAACTCAGATTGGAGTAAGACAGCTACCA

ATATCATCAAGAAAAGTTCTGATAATCTAGGAAAATCTTTGTCTTCAAGCTCCATTGG

TTCCAACTCAACCTATCTTACATCCAAATCTAAATCCACCTCTACCACCTATTTCAAA

AGGAATAGCCACACAGACAGTGCTTCCATGGACAAGTCCTTGTCAAAACTGGCCCATG

CTGATGGAGATCAAACATCAATCATCCCTGTCCATCAGGTCATTGATAAGGTCAAGGG

TTATTCCAATGCTCATTCACACAACTTCTATAAAAATATTATCATGTCAGACACCTTC

AGCCACAGCACAAAGTTTTAATGTCTTTAAGAAAAAGAAATCAATCTGCAGAAATGTG

AAGATTTGCAAGCAGTGTAAACTGCAACTAGTGATGTAAATGTGCTATTA

ORF Start: ATG at 170     ORF Stop: TAA at 2339
SEQ ID NO:144     723 aa MW at 80895.8 kD NOV57b,
CG92499-02 Protein Sequence

MEEPKGYYWPSIQPSEYVLPCPDKPGFSASRICFYNATNPLVTYWCPVDISNCLKEAN

EVANQILNLTANCQNLTSANTTNIVEQVKRIVNKEENIDITLCSTLMNIFSNILSSSD

SDLLESSSEALKTIDELAFKIDLNSTSHVNITTRNLALSVSSLLPGTNAISNFSIGLP

SNNESYFQVQMDFESGQVDPLASVILPPNLLENLSPEDSVLRRAQPTFFNKTGLFQD

VGPQRKTLVSYVMACSIGNITIQNLKDPVQIKIKHYREETDLLFSHCLLIPSTESFGG

WNTSGCVAHRDSDASETVCLCNHFTHFGVLNDLPRSASQLDARNTKVLTPISYIGCGI

SAIFSAATLLTYVAFEKLRRDYPSKILMNLSTALLFLNLLFLLDGWITSFNVDGLCIA

VAVLLHFFLLATFTWNCLEAIHMYIALVKVFNTYIRRYILKFCIICWGLPALVVSVVL

ASRNNNEVYGKESYGKEKGDECWIQDPVIFYVTCAGYFGVMFFLNIAMFIVVMVQICG

RNGKRSNRTLREEVLRNLRSVVSLTFLLGMTWCFAFFAWGPLNIPFMYLFSTFNSLQG

LFIFIFHCAKKENVQKQWRQHLCCGRFRLADNSDWSKTATNIIKKSSDNLCKSLSSSS

IGSNSTYLTSKSKSSSTTYFKRNSHTDSASMDKSLSKLAHADGDQTSIIPVHQVIDKV

KGYCNAHSDNFYKNIIMSDTFSESTKF

Sequence comparison of the above protein sequences yields the following sequence relationships shown in Table 57B.

TABLE 57B

Comparison of NOV57a against NOV57b.

| Protein Sequence | NOV57a Residues/ Match Residues | Identitites/Similarities for the Matched Region |
|---|---|---|
| NOV57b | 1..624<br>1..624 | 536/627 (85%)<br>542/627 (85%) |

Further analysis of the NOV57a protein yielded the following properties shown in Table 57C.

TABLE 57C

Protein Sequence Properties NOV57a

| PSort analysis: | 0.6000 probability located in plasma membrane; 0.4000 probability located in Golgi body; 0.3000 probability located in endoplasmic reticulum (membrane); 0.0300 probability located in mitochondrial inner membrane |
|---|---|
| SignalP analysis: | No Known Signal Sequence Predicted |

A search of the NOV57a protein against the Geneseq database, a proprietary database that contains sequences published in patents and patent publication, yielded several homologous proteins shown in Table 57D.

TABLE 57D

Geneseq Results for NOV57a

| Geneseq Identifier | Protein/Organism/Length [Patent #, Date] | NOV57a Residues/ Match Residues | Identities Similarities for the Matched Region | Expect Value |
|---|---|---|---|---|
| AAU00719 | Human novel G-protein coupled receptor, NGPCR#29 - *Homo sapiens*, 1192 aa. [WO200118207-A1, 15 Mar. 2001] | 1..660<br>499..1158 | 655/660 (99%)<br>657/660 (99%) | 0.0 |
| AAU00210 | Human novel G-protein coupled recentor NGPCR#21 - *Homo sapiens*, 1221 aa. [WO200118207-A1, 15 Mar. 2001] | 1..660<br>499..1158 | 655/660 (99%)<br>657/660 (99%) | 0.0 |
| AAU00207 | Human novel G-protein coupled receptor, NGPCR#18 - *Homo sapiens*, 1193 aa. [WO200118207-A1, 15 Mar. 2001] | 1..660<br>500..1159 | 655/660 (99%)<br>657/660 (99%) | 0.0 |
| AAU00206 | Human novel G-protein coupled receptor, NGPCR#17 - *Homo sapiens*, 1222 aa. [WO200118207-A1, 15 Mar. 2001] | 1..660<br>500..1159 | 655/660 (99%)<br>657/660 (99%) | 0.0 |
| AAU00199 | Human novel G-protein coupled receptor, NGPCR#10 - *Homo sapiens*, 1221 aa. [WO200118207-A1, 15 Mar. 2001] | 1..660<br>528..1187 | 655/660 (99%)<br>657/660 (99%) | 0.0 |

In a BLAST search of public sequence datbases, the NOV57a protein was found to have homology to the proteins shown in the BLASTP data in Table 57E.

TABLE 57E

Public BLASTP Results for NOV57a

| Protein Accession Number | Protein/Organism/Length | NOV57a Residues/ Match Residues | Identities/ Similarities for the Matched Value Portion | Expect Value |
|---|---|---|---|---|
| Q96JW0 | CDNA FLJ14937 FIS, CLONE PLACE1010231, WEAKLY SIMILAR TO CELL SURFACE GLYCOPROTEIN EMR1 PRECURSOR - *Homo sapiens* (Human), 512 aa. | 183..660<br>1..478 | 473/478 (98%)<br>475/478 (98%) | 0.0 |
| Q9Y3K0 | DJ287G14.2 (PUTATTVE NOVEL SEVEN TRANSMEMBRANE DOMAIN PROTEIN) - *Homo sapiens* (Human), 541 aa (fragment). | 183..660<br>1..478 | 472/478 (98%)<br>475/478 (98%) | 0.0 |
| CAB69577 | SEQUENCE 1 FROM PATENT EP0805204 - unidentified, 1038 aa (fragment). | 78..655<br>391..968 | 278/588 (47%)<br>396/588 (67%) | e-155 |

TABLE 57E-continued

Public BLASTP Results for NOV57a

| Protein Accession Number | Protein/Organism/Length | NOV57a Residues/ Match Residues | Identities/ Similarities for the Matched Value Portion | Expect Value |
| --- | --- | --- | --- | --- |
| O00406 | G-PROTEIN-COUPLED RECEPTOR HE6 PRECURSOR - *Homo sapiens* (Human), 1014 aa. | 78..655 367..944 | 278/588 (47%) 396/588 (67%) | e-155 |
| CAC43514 | SEQUENCE 1 FROM PATENT WO0144281 - *Homo sapiens* (Human), 528 aa. | 221..591 135..507 | 135/385 (35%) 210/385 (54%) | 1e-57 |

PFam analysis predicts that the NOV57a protein contains the domains shown in the Table 57F.

TABLE 57F

Domain Analysis of NOV57a

| Pfam Domain | NOV57a Match Region | Identities/ Similarities for the Matched | Expect Value |
| --- | --- | --- | --- |
| HRM: domain 1 of 1 | 3 ... 58 | 18/79 (23%) 38/79 (48%) | 9.6 |
| GPS: domain 1 of 1 | 272 ... 325 | 25/55 (45%) 44/55 (80%) | 2.1e-16 |
| LHC: domain 1 of 1 | 404 ... 422 | 6/21 (29%) 15/21 (71%) | 5.7 |
| DUF32: domain 1 of 1 | 486 ... 542 | 14/163 (9%) 42/163 (26%) | 1.1 |
| 7tm_2: domain 1 of 1 | 334 ... 594 | 74/281 (26%) 200/281 (71%) | 1.3e-59 |

Example 58

The NOV58 clone was analyzed, and the nucleotide and encoded polypeptide sequences are shown in Table 58A.

TABLE 58A

NOV58 Sequence Analysis

| | |
| --- | --- |
| NOV58a, CG92541-01 DNA Sequence | SEQ ID NO:145      4483 bp<br>CCCCTGACAGAGCGTGGCAGCCCCAGGCTCTTTGCATAATCCTGTGGCTTCGCTGTCT<br>TCACCCAGCACCACCGGACAGGGAAGGGCAGAGAAGGCCACCATGGCGACACTCCTCT<br>CCCATCCGCAGCAGCGCCCTCCCTTCTTGCGCCAOCCCATCAACATAAGGCGCCGCAG<br>AGTCAGAGATCTACAGGATCCCCGCCCCAAATGGCCCCGAAGGATCCAGCCTCCATCC<br>CACCACTTCTCCCCCGAGCAGCCGGCCCTGCTCTACGAGGACGCACTCTACACTGTCT<br>TGCACCCCCTGGGTCATCCTGAGCCCAACCATGTGACGGACGCCTCTGACCTGCTGCG<br>ATACCTGCAGGAGGCCTTCCACGTGGACCCCGAGGAGCACCAGCAGACACTGCAGCGG<br>GTCAGGGAGCTTGAGAAGCCAATATTTTGTCTGAAGGCAACAGTGAAACAGGCCAAGG<br>GCATTCTGGGCAAAGATGTCAGTGGGTTCAGCGACCCCTACTGCCTGCTGGGCATTGA<br>GCAGGGGTAGGTGTGCCAGGCCCCAGCCCCGGTCCCGQCATCGGCAGAAGGCTGTG<br>GTGAGGCACACCATCCCCGACGAGGAGACCCACCGCACGCAGGTCATCACCCAGACAC<br>TCAACCCCGTCTGCGACGAGACCTTCATCCTGGAGTTTCAGGACATCACCAATGCGAG<br>CTTTCATCTGCACATGTCGGACCTGGACACTGTGGAGTCTGTCCQACAGAAGCTTGGG<br>GAGCTCACGGATCTGCATGGGCTTCGCACGATCTTTAAAGAGGCCCGGAACGACAAAG<br>GCCAGGACGACTTTCTGCGGAACGTGGTTCTGAGGCTGCAGGACCTGCCCTGCCGAGA<br>CGACCAGTGGTACCCCCTGCAACCCCGCACTGAGACCTACCCAGACCGAGGCCAGTGC<br>CACCTCCAGTTCCAACTCATCCATAAGCGGCAGAGAGCCACTTCGGCCAGCCGCTCGC<br>AGCCGAGCTACACCGTGCACCTCCACCTCCTGCAGCAGCTTGTGTCCCACGAGGTCAC |

TABLE 58A-continued

NOV58 Sequence Analysis

CCAGCACCAGGCGGGAAGCACCTCCTGGGACGGGTCGCTGAGTCCCCAGGCTGCCACC

GTCCTCTTTCTGCACGCCACACAGAACGACCTATCCGACTTCCACCAGTCCATCGCGC

AGTGGCTGGCCTACAGCCGCCTCTACCACAGCCTGGAGTTCCCCAGCACCTGCCTCCT

GCACCCCATCACCAGCATCGACTACCAQTGGATCCAGGGTCGGCTCAACGCAGAACAG

CAGGAGGAGCTGGCCGCCTCATTCAACTCCCTGATGACCTACGGCCTCTCCCTCATCC

GGACGTTCCGCTCTCTCATCCACCTCTCTGTCTCGGACTCCCCAGCCAGACTCCAGTC

TCTTCTAAGGGTCCTGCTACAGATGTGCAAGATGAAGGCCTTTCCAGAACTGTGCCCC

AACACCGCCCCATTGCCCCACCTGGTGACTGAGGCCCTGCAGACTGGCACCACTGAAT

GGTTCCACCTGAAGCACCAGCACCATCAACCCATGGTGCAGGGCATCCCCGACGCAGG

CAAGGCCTTCCTGCGCCTCGTACAGGATGTCATTGGCGACCTGCACCAGTGCCAGCGC

ACATGGACAAGATCTTCCACAGTACCCTCAAGATCCACCTCTTCTCCATGGCTTTCC

GGGAGCTGCAGTGCCTGGTGCCCAAGCGGGTCCAGGACCACACCACGGTTGTGGCTGA

TGTAGTGTCCCCAGACATGGGCGAGAGTCTGTTCCAGCTCTACATCAGCCTCAAGGAG

CTCTGCCAGCTGCCCATCAGCTCCTCAGAGAGGGATGGAGTCCTCGCCCTGGATAATT

TCCACCGCTGCTTCCAGCCCGCCATCCCCTCCTGGCTGCAGAAGACGTACAACGAGGC

CCTGGCGCGCGTGCAGCGCGCTGTGCACATCGATGAGCTCGTGCCCCTGCCTGAACTG

ACCAAGCACAGCACATCAGCGGTGGATCTATCCAACTGCTTTGCCCAGATCAGCCACA

CTGCCCGGCAGCTGGACTGGCCAGACCCAAGAGAGGCCTTCATGATTACCGTCAAGTT

TGTGGAGGACACCTGTCGCCTGGCCCTGGTGTACTCCAGCCTTATAAAGGCCCGGGCC

CGCGAGCTCTCTTCAGGCCAGAAGGACCAAGGCCAGGCAGCCAACATGCTGTGTGTGG

TGGTGAATGACATGGAGCAGCTGCGGCTGGTGATCGGCAAGTTGCTCGCCCAGCTGGC

ATGGGAGGCCCTGGAGCAGCGGGTAGGGGCCGTGCTGGAGCAGGGGCAGCTGCACAAC

ACGCTGCATGCCCAGCTGCAGAGCGCGCTGGCCGGGCTGGGCCATGAGATCCGCACTG

GCGTCCGCACCCTGGCCGAGCAGTTGGAGGTGGGCATCGCCAAGCACATCCAGAAACT

GGTGGGCGTCAGGGAGTCTGTCCTGCCTGACGATGCCATTCTGCCCCTGATGAAGTTC

CTGGAGGTGGAGCTTTGCTACATGAACACCAACTTGGTGCAGGAGAACTTCAGCAGCC

TCCTGACCCTCCTCTGGACCCACACACTCACAGTGCTGGTGGAGGCGGCCGCCTCCCA

GCGCAGCTCATCCCTGGCTTCCAACAGGCTGAAGATTCCCCTGCAGAACCTCGAGATC

TGCTTCCACGCTGAGGGCTGTGGCCTGCCACCCAAGGCCCTGCACACTGCCACCTTCC

AGGCTCTGCAGAGGGACCTGGAGCTGCAGGCGACCTCCAGCGGGGAACTCATCCGGAA

GTACTTCTGCAGCCCAATCCAGCAGCAGCCAGAAACCACCTCTGACGAGCTGGGGGCT

GTGACAGTCAAGGCCTCCTACCGCGCCTCTCACCAGAAGCTGCCTGTCGAGCTGCTCA

GCGCCTCCAGCCTGCTGCCCCTGGACTCCAATGGTTCCAGCGACCCCTTTGTCCAGCT

GACCTTGGAGCCCAGGCATGAGTTCCCTGACCTGGCCGCCCGGGAGACCCAGAAGCAC

AAGAAGGACCTTCACCCATTGTTTGATGAGACCTTTGAATTCCTGGTGCCTGCTGAGC

CGTGCCGCAACGCTCGGGCATGCCTCCTGCTCACCGTGCTGGACTACGACACGCTGGG

GGCCGACGACCTGGAAGGCGAGGCCTTCCTGCCGCTGCGTGAGGTGCCCGGGCTGACT

GGCTCTGAGGAGCCTGGTGAGGTGCCTCAGACCCGCCTGCCCCTCACGTACCCCGCAC

CCAACGGGGACCCAATCCTCCAGCTGCTGGAGGGCCGGAAGGGTGACCCAGAAGCCCA

TABLE 58A-continued

NOV58 Sequence Analysis

GGTCTTTGTGAGGCTGCGGCGGCACCGGGCCAAGCAGCCCTCCCAGCATGCCTTGCGG

CCGGCACCGTAGCCGTAGAGGTTTGCGGTGGGGCTCCGTCCCCGGTGGGGACTTGCAA

GGGCCTTCCTGTAGGGTCTGGGGCTTCCCCGCCACATCGCGGCCCTCCAGCCTGGCCT

AACACTTGGCGAGCCCCAGCATGCGGAGTGCCCAGAGTGCAGACCTCCCCTGCCTCCC

ATGGTGATGGGGGCTCAGCAGCGACATCTCTACTCCCGCCTCCCTGCCTCCAGCCCTG

GCTGCAATGTCTCTACCACATCCCAGCACCAGGGGGAGCAAACCCTGCCCCTGCCCGC

CTCTCAGAAAAGCTGCTGTGGTGGGCAGCGGATTGGGCCATCTGTCTCCTGGCCCTGG

CCCATCTGCCTCCTGGCCTTCCTGTTCCAGCCACTGGGGTGGGGGCCAGGTTCACTGG

GACCAGGGCTACACGCACAGAGTCTCCTGGAAAAGGGACAGGGGACCCTGCCAAAGAT

GAGGCTCCAGCTCCCCTGGCGGAGGGTGGTGGCCATTACTAGAGCGGGCCTGGGTCC

TCTCCCCAGGGGCTGCCAGCATCCAGGCCAGCAAGCCTGGAGCCAAGAACCTTCTGGC

TCTGAGGGAGCAAGAGCTGCCAGGCGGCAGGGCTGGCACAGACAGACGGAAGCAGAAA

GGACAGTTTGGCTGCTGTGTCTGCTGCGCACGCCCCTCCCCGGACAGCACCTGCCAC

CTAGAAACTTTCTTAGCAAAAAAATTAATAAAAACAAATCCATTGTCCTCTTAAAATA

TCCTTTGGCCTACAGTCGCGCCTGGAATGCGAGCCAGGCCGGCTAGCTTCCTCCCCAG

CCCTCAGGGACTTTGACGTACCGCCACCTTGGGGTAGCTACAAACCAGGGGGTAGG

TGTGGAAATAACTCAGGCAGAGCCACGGCTAGGGTCATTTPTGGCCGTGCGCTTTGAA

TAAATTGCTTTACCACGCATACCACTTCCTGTGGTCACACCCAGGACAGCGACCCGTT

CCTCGGGGACCACAGTGAGCACGCGCCTCCCCAGGGTGCAGGTTGAGGCCTGAGGGC

TGCTCTTGAGACAGTAGGGCGTAGAGCAACTGGGTCCTTCCCCTCCCTGGGGGTCAA

AACCTGAGCCTGGGCTG

NOV58a,

CG92541-01 Protein Sequence

ORF Start: ATG at 101  ORF Stop: TAG at 3374
SEQ ID NO:146  1091 aa MW at 123545.0 kD

MATLLSHPQQRPPFLRQAIKIRRRRVRDLQDPPPQMAPRIQPPSHHFSPEQRALLYED

ALYTVLHRLGHPEPNHVTEASELLRYLQEAFHVEPEEEQQTLQRVRELEKPIFCLKAT

VKQAKGILGKDVSGFSDPYCLLGIEQGVGVFGGSPGSRHRQKAVVRHTTPEEETHRTQ

VITQTLNPVWDETFTLEFEDITNASFHLDMWDLDTVESVRQKLGELTDLHGLRRIFKE

ARKDKGQDDPLRNVVLRLQDLRCREDQWYPLEPRTETYPDRGQCHLQFQLIHKRQRAT

SASRSQPSYTVHLHLLQQLVSHEVTQHQACSTSWDGSLSPQAATVLFLHATQKDLSDF

HQSMAQWLAYSRLYQSLEFPSSCLLHPITSIEYQWIQGRLKAEQQEELAASFNSLMTY

GLSLIRRFRSVIHLSVSDSPARLQSLLRVLVQMCKMKAFGELCPNTAPLPQLVTEALQ

TGTTEWFHLKQQHHQPMVQGIPEAGKALLGLVQDVIGDLHQCQRTWDKIFHSTLKIHL

FSMAFRELQWLVAKRVQDHTTVVGDVVSPEMGESLFQLYISLKELCQLRNSSSERDGV

LALDNFHRWFQPAIPSWLQKTYNEALARVQRAVQMDELVPLGELTKHSTSAVDLSNCF

AQISHTARQLDWPDPREAFMITVKFVEDTCRLALVYCSLIKARARELSSGQKDQGQAA

NMLCVVVNDMEQLRLVIGKLLAQLAWEALEQRVGAVLEQGQLQNTLHAQLQSALAGLG

HEIRTGVRTLAEQLEVGIAKHIQKLVGVRESVLPEDAILPLMKFLEVELCYMNTNLVQ

ENFSSLLTLLWTHTLTVLVEAAASQRSSSLASNRLKIALQNLEICFHAEGCGLPPKAL

HTATFQALQRDLELQATSSGELIRKYFCSRIQQQAETTSEELGAVTVKASYRASEQKL

RVELLSASSLLPLDSNGSSDPFVQLTLEPRHEFPELAARETQKHKKDLHPLFDSTFEF

TABLE 58A-continued

NOV58 Sequence Analysis

LVPAEPCRKAGACLLLTVLDYDTLGADDLEGEAFLPLREVPGLSGSEEPGEVPQTRLP

LTYPAPNCDPILQLLEGRKGDREAQVFVRLRRHRAKQASQHALRPAP

Further analysis of the NOV58a protein yielded the following properties shown in Table 58B.

TABLE 58B

Protein Sequence Properties NOV58a

| | |
|---|---|
| PSort analysis: | 0.9600 probability located in nucleus: 0.3092 probability located in microbody (peroxisome); 0.1776 probability located in lysosome (lumen); 0.1000 probability located in mitochondrial matrix space |
| SignalP analysis: | No Known Signal Sequence Predicted |

A search of the NOV58a protein against the Geneseq database, a proprietary database that contains sequences published in patents and patent publication, yielded several homologous proteins shown in Table 58C.

TABLE 58C

Geneseq Results for NOV58a

| Geneseq Identifier | Protein/Organism/Length [Patent #, Date] | NOV58a Residues/ Match Residues | Identities/ Similarities for the Matched Region | Expect Value |
|---|---|---|---|---|
| AAB41695 | Human ORFX ORF1459 polypeptide sequence SEQ ID NO:2918 - *Homo sapiens*, 509 aa. [WO200058473-A2, Oct. 5, 2000] | 587 ... 1091 5 ... 509 | 498/505 (98%) 498/505 (98%) | 0.0 |
| ABG08373 | Novel human diagnostic protein #8364 - *Homo sapiens*, 1433 aa. [WO200175067-A2, Oct. 11, 2001] | 48 ... 1049 132 ... 1168 | 356/1048 (33%) 547/1048 (51%) | e-155 |
| ABG08373 | Novel human diagnostic protein #8364 - *Homo sapiens*, 1433 aa. [WO200175067-A2, Oct. 11, 2001] | 48 ... 1049 132 ... 1168 | 356/1048 (33%) 547/1048 (51%) | e-155 |
| AAU19712 | Human novel extracellular matrix protein, Seq ID No 362 - *Homo sapiens*, 191 aa. [WO200155368-A1, Aug. 2, 2001] | 1 ... 158 32 ... 189 | 152/158 (96%) 154/158 (97%) | 5e-86 |
| AAM83868 | Human immune/haematopoietic antigen SEQ ID NO:11461 - *Homo sapiens*, 140 aa. [WO200157182-A2, Aug. 9, 2001] | 1 ... 88 36 ... 123 | 87/88 (98%) 87/88 (98%) | 3e-45 |

In a BLAST search of public sequence datbases, the NOV58a protein was found to have homology to the proteins shown in the BLASTP data in Table 58D.

TABLE 58D

Public BLASTP Results for NOV58a

| Protein Accession Number | Protein/Organism/Length | NOV58a Residues/ Match Residues | Identities/ Similarities for the Matched Portion | Expect Value |
|---|---|---|---|---|
| Q9R189 | MUNC13-4 PROTEIN - *Rattus norvegicus* (Rat), 1088 aa. | 1 ... 1091 1 ... 1088 | 941/1091 (86%) 992/1091 (90%) | 0.0 |
| Q9H7K5 | FLJ00067 PROTEIN - *Homo sapiens* (Human), 574 aa (fragment). | 318 ... 816 8 ... 506 | 491/499 (98%) 494/499 (98%) | 0.0 |
| Q96RZ3 | BAI ASSOCIATED PROTEIN 3 - *Homo sapiens* (Human), 1187 aa. | 48 ... 1073 132 ... 1174 | 359/1055 (34%) 556/1055 (52%) | e-160 |
| Q9UJK1 | C316G12.1 (KIAA0734 (C2 DOMAIN PROTEIN)) - *Homo sapiens* (Human), 1152 aa. | 48 ... 1073 97 ... 1139 | 359/1055 (34%) 556/1055 (52%) | e-160 |

TABLE 58D-continued

Public BLASTP Results for NOV58a

| Protein Accession Number | Protein/Organism/Length | NOV58a Residues/ Match Residues | Identities/ Similarities for the Matched Portion | Expect Value |
|---|---|---|---|---|
| O94839 | KIAA0734 PROTEIN - *Homo sapiens* (Human), 1186 aa (fragment). | 48 ... 1073<br>131 ... 1173 | 359/1055 (34%)<br>556/1055 (52%) | e-160 |

PFam analysis predicts that the NOV58a protein contains the domains shown in the Table 58E.

TABLE 58E

Domain Analysis of NOV58a

| Pfam Domain | NOV58a Match Region | Identities/ Similarities for the Matched Region | Expect Value |
|---|---|---|---|
| C2: domain 1 of 2 | 113 ... 214 | 28/116 (24%)<br>74/116 (64%) | 0.075 |

TABLE 58E-continued

Domain Analysis of NOV58a

| Pfam Domain | NOV58a Match Region | Identities/ Similarities for the Matched Region | Expect Value |
|---|---|---|---|
| C2: domain 2 of 2 | 928 ... 1020 | 31/101 (31%)<br>66/101 (65%) | 2e-07 |

Example 59

The NOV59 clone was analyzed, and the nucleotide and encoded polypeptide sequences are shown in Table 59A.

TABLE 59A

NOV59 Sequence Analysis

NOV 59a,
CG92662-01 DNA Sequence

SEQ ID NO:147     1006 bp
CTGTGGGTGGTGATGGATCTCAACCAAAGCCATTCCGTGACGCTGAATGATGGACATG

TCATGCCGATGCTGGGATTTCGCACTTATGCTCCTGATCATGTACCCAAGAGCAAGGC

TGGTGAAGCCACCCAAGTGGCTATTGATGCAGCCTTCCCTCACATTGATGCGGCGTTC

TTCTACCAAAACGAGGAGGAGGTCGGAAAGGCCATTCCACAGAAGATTCCTGATGGCC

CTGTGAACAGAGAGGACATTTTCTACACCACTGAGCTTTGGACAACTTTCTTTAGACC

AGAATTAGTTCGCCCAGCCCTGGAAGGCTCACTGAAGAAACTTCAACTGGACTATGTC

GATCTCTTCATTATCCACAATCCATTGGCTATGAAGCCTGGGGAGGAATTGCTGCCTA

AGGATGCCAGTGGAAACATTATTTTTGATACTGTGCATCTTCCTGACACATGGGAGGT

ACTGGAGAAGTGCAAAGAAGCAGGTTTAACCAAGTCCATCGGGGTGTCCAATTTCAAT

CACAAACTGCTGGAACTCATCCTCAACAAGCCAGGGCTCAAGTACAAGCCCACCTGCA

ACCAGGTCCAATGTCACCCTTACCTCAACCAGACCAAACTCCTGGAGTTCTGCAAGTC

CAAGGACATTGTTCTAGTTGCCTACAGGGCCCTGGCATCTCACACAGACCCAAACTGG

ATGGACCCAGATAGCCCATATCTCTTAGAGCAGCCAACCTTGAAATCCATTGCCAAGA

AATACAATAGAAGCCCAGGCCAGGTTGCCCTGTGCTATGAGCTGCACCGGGGGGTGGT

GGTCCTGGCCAAGAGCTTCTCTGAGAAGAGAATCAAAGAGAACTTCCAGCAGGTTTTT

GACTTTCAGTTGACTCCAGAGGACATGAAAGCCACTGATGGCCTCAACAGAAATTTCC

GATATGAAACTCTAGACTTTTATCTCAGATATCAAGAGGAAAACCACATGAATAAATA

CCTGTTTCTTTTAAAGCTGAT

ORF Start: ATG at 13      ORF Stop: TAA at 997
SEQ ID NO:148             328 aa MW at 37820.9 kD NOV59a,
CG92662-01 Protein Sequence MDLKQSHSVRLNDGHVMPMLGFGTYAPDHVPKSKAGEATEVAIDAGFRHIDAAFFYQN
EEVGKAIREKIADGPVKREDTFYTTELWTTFFRPELVRPALEGSLKKLQLDYVDLFI

TABLE 59A-continued

NOV59 Sequence Analysis

IHNPLAMKPGEELLPKDASGNIIFDTVDLRDTWEVLEKCKEAGLTKSIGVSNFNHKLL

ELILNKPGLKYKPTCNQVECHPYLNQSKLLEFCKSKDIVLVAYRALASHRDFNWMDPD

SPYLLEEPTLKSIAKKYNRSPGQVALCYELQRGVSVLAKSFSEKRIKENFQQVFDFEL

TPEDMKATDGLNRNPRYETLDFYLRYQEENHMNKYLFL

Further analysis of the NOV59a protein yielded the following properties shown in Table 59B.

TABLE 59B

| | Protein Sequence Properties NOV59a |
|---|---|
| PSort analysis: | 0.4500 probability located in cytoplasm; 0.3726 probability located in microbody (peroxisome); 0.1000 probability located in mitochondrial matrix space; 0.1000 probability located in lysosome (lumen) |
| SignalP analysis: | No Known Signal Sequence Predicted |

A search of the NOV59a protein against the Geneseq database, a proprietary database that contains sequences published in patents and patent publication, yielded several homologous proteins shown in Table 59C.

TABLE 59C

Geneseq Results for NOV59a

| Geneseq Identifier | Protein/Organism/Length [Patent #, Date] | NOV59a Residues/ Match Residues | Identities/ Similarities for the Matched Region | Expect Value |
|---|---|---|---|---|
| AAM79455 | Human protein SEQ ID NO 3101- Homo sapiens, 325 aa. [WO200157190-A2, Aug. 9, 2001] | 1 ... 325<br>3 ... 325 | 218/325 (67%)<br>265/325 (81%) | e-127 |
| AAM78471 | Human protein SEQ ID NO 1133 - Homo sapiens, 323 aa. [WO200157190-A2, Aug. 9, 2001] | 1 ... 325<br>1 ... 323 | 218/325 (67%)<br>265/325 (81%) | e-127 |
| AAW14799 | Type 5 17-beta-hydroxysteroid dehydrogenase - Homo sapiens, 323 aa. [WO9711162-A1, Mar. 27, 1997] | 1 ... 325<br>1 ... 323 | 218/325 (67%)<br>265/325 (81%) | e-127 |
| AAB43444 | Human cancer associated protein sequence SEQ ID NO:889 - Homo sapiens, 336 aa. [WO200055350-A1, Sep. 21, 2000] | 9 ... 313<br>21 ... 324 | 215/305 (70%)<br>257/305 (83%) | e-126 |
| AAB76865 | Human lung tumour protein related protein sequence SEQ ID NO:783 - Homo sapiens, 364 aa. [WO200100828-A2, Jan. 4, 2001] | 30 ... 313<br>70 ... 352 | 201/284 (70%)<br>242/284 (84%) | e-117 |

In a BLAST search of public sequence datbases, the NOV59a protein was found to have homology to the proteins shown in the BLASTP data in Table 59D.

TABLE 59D

Public BLASTP Results for NOV59a

| Protein Accession Number | Protein/Organism/Length Residues | NOV59a Residues/ Match Region | Identities/ Similarities for the Matched Value | Expect |
|---|---|---|---|---|
| AAH20744 | ALDO-KETO REDUCTASE FAMILY 1, MEMBER C4 (CHLORDECONE REDUCTASE, 3-ALPHA HYDROXYSTEROID DEHYDROGENASE, TYPE I, | 9 ... 325<br>8 ... 323 | 214/317 (67%)<br>267/317 (83%) | e-128 |

TABLE 59D-continued

Public BLASTP Results for NOV59a

| Protein Accession Number | Protein/Organism/Length Residues | NOV59a Residues/ Match Region | Identities/ Similarities for the Matched Value | Expect |
|---|---|---|---|---|
| P80508 | DIHYDRODIOL DEHYDROGENASE 4) - *Homo sapiens* (Human), 323 aa. Prostaglandin-E2 9-reductase (EC 1.1.1.189) (20-alpha-hydroxysteroid dehydrogenase) (EC 1.1.1.149) (20-alpha-HSD) - *Oryctolagus cuniculus* (Rabbit), 323 aa. | 9 ... 325 8 ... 323 | 218/317 (68%) 260/317 (81%) | e-128 |
| Q96A71 | ALDO-KETO REDUCTASE FAMILY 1, MEMBER C2 (DIHYDRODIOL DEHYDROGENASE 2, BILE ACID BINDING PROTEIN, 3-ALPHA HYDROXYSTEROID DEHYDROGENASE, TYPE III) (DD2/BILE ACID-BINDING PROTEIN/AKR1C2/3ALPHA-HYDROXYSTEROID DEHYDROGENASE TYPE 3) - *Homo sapiens* (Human), 323 aa. | 9 ... 313 8 ... 311 | 217/305 (71%) 260/305 (85%) | e-128 |
| P17516 | Chlordecone reductase (EC 1.1.1.225) (CDR) (3-alpha-hydroxysteroid dehydrogenase) (EC 1.1.1.50) (3-alpha-HSD) (Dihydrodiol dehydrogenase 4) (DD4) (HAKRA) - *Homo sapiens* (Human), 323 aa. | 9 ... 325 8 ... 323 | 214/317 (67%) 266/317 (83%) | e-127 |
| Q9NS54 | 3ALPHA-HYDROXYSTEROID DEHYDROGENASE VARIANT (EC 1.1.1.213) - *Homo sapiens* (Human), 323 aa. | 9 ... 325 8 ... 323 | 214/317 (67%) 266/317 (83%) | e-127 |

PFam analysis predicts that the NOV59a protein contains the domains shown in the Table 59E.

TABLE 59E

Domain Analysis of NOV59a

| Pfam Domain | NOV59a Match Region | Identities/ Similarities for the Matched Region | Expect Value |
|---|---|---|---|
| aldo_ket_red: domain 1 of 1 | 11 ... 305 | 160/368 (43%) 216/368 (71%) | 9.7e-140 |

Example 60

The NOV60 clone was analyzed, and the nucleotide and encoded polypeptide sequences are shown in Table 60A.

TABLE 60A

NOV60 Sequence Analysis

| | SEQ ID NO:149 | 1922 bp |
|---|---|---|
| NOV60a, CG92683-01 DNA Sequence | CTGTGGCTTGACCCTGAGCTTGCCCATATTCCCTGGCTGGATGGAGTGGCTAAGCCCT GATATCGCTCTGCCCAGAAGAGATGAGTCGACTCAAACTTCTCCAGCCAGGAAGAGGA TCACGCATGCCAAAGTCCACGGTGCAGGTCAGCTCAGGCTGTCCATTGATGCCCAGGA CCGGGTTCTGCTGCTTCACGTTATACAAGGTAAAGGCCTGATCAGCAAACAGCCTGGC ACCTGTGATCCGTATGTGAAGGTATCTTTGATCCCTGAAGATAGTAGACTACGCCACC AGAAGACGCAGACCGTTCCAGACTGCAGAGACCCGGCTTTCCACGAGCACTTCTTCTT TCCTGTCCAAGAGCAGGATGATCAGAAGCGTCTCTTGGTTACTGTCTGGAACAGGGCC | |

TABLE 60A-continued

NOV60 Sequence Analysis

```
AGCCAGTCCAGGAGACAGAGTCTCATTGGCTGCATGAGCTTTGGGGTGAAGTCTCTCC
TGACTCCAGACAAGCAGATCAGTGGTTGGTACTACCTCCTAGGGGACCACCTGGGCCG
GACCAAGCACTTGAAGGTGGCCAGGCGGCGACTGCGGCCGCTGAGAGACCCGCTGCTG
AGAATGCCAGGAGGTGGGGACACTGAGAATGGGAAGAAACTAAAGATCACCATCCCGA
GGGGAAAGGACGGCTTTCGCTTCACCATCTGCTGCCACTCTCCAGTTCGAGTCCAGGC
CGTGGATTCCGGTGGTCCGGCGGAACGGGCAGGGCTGCAGCAGCTGGACACGGTGCTG
CAGCTGAATGAGAGGCCTGTGGAGCACTCGAAATGTGTGGACCTGGCCCACGAGATCC
GGAGCTGCCCCAGTGAGATCATCCTACTCGTGTGGCGCATGGTCCCCCAGGTCAAGCC
AGGACCAGATGGCGGGGTCCTGCGGCGGGCCTCCTGCAAGTCCAGACATGACCTCCAG
TCACCCCCCAACAAACGGGAGAAGAACTGCACCCATGGGGTCCAGGCACGGCCTGAGC
AGCGCCACAGCTGCCACCTGGTATGTGACAGCTCTGATGGGCTGCTGCTCGGCGGCTG
GGAGCGCTACACCGAGGTGGCCAAGCGCGGGGGCCAGCACACCCTGCCTGCACTGTCC
CGTGCCACTGCCCCCACCGACCCCAACTACATCATCCTGGCCCCGCTGAATCCTGGGA
GCCAGCTGCTCCGGCCTGTGTACCAGGACGATACCATCCCCGAACAATCAGGGAGTCC
CAGTAAAGGGAAGTCCTACACAGGCCTCGGGAAGAAGTCCCGGCTCATGAAGACAGTG
CAGACCATGAAGGGCCACGGGAACTACCAAAACTGCCCGGTTGTGAGGCCGCATGCCA
CGCACTCAAGCTATGGCACCTACGTCACCCTGGCCCCCAAAGTCCTGGTGTTCCCTGT
CTTTGTTCAGCCTCTAGATCTCTGTAATCCTGCCCGGACCCTCCTGCTGTCAGAGGAG
CTGCTGCTGTATGAAGGGAGCAACAAGTCAACCCAGGTGACACTGTTTGCCTATTCGG
ACCTGCTGCTCTTCACCAAGGAGGACGAGCCTGGCCGCTGCGACCTCCTGAGGAACCC
CCTCTACCTCCAGAGTGTGAAGCTGCAGGAAGGTTCTTCAGAAGACCTGAAATTCTGC
GTGCTCTATCTAGCACAGAAGGCAGAGTGCTTATTCACTTTGGAAGCGCACTCGCAGG
AGCAGAAGAAGAGAGTGTGCTGGTGCCTGTCGGAGAACATCCCCAAGCAGCAACAGCT
GGCAGCACCCCCGGACAGCAAGCACAAACTCCACCCTTTCGGCTCTCTCCAGCAGGAG
ATGGGGCCGGTCAACTCAACCAATGCCACCCAGGATAGAAGCTTTACCTCACCAGGAC
AGACTCTGATTGGCTGAGCAAACCCAAGGGCGGGACTCTGCTTCTGGCAACTTAACCC
TTTCTTGG
```

| | |
|---|---|
| | ORF Start: ATG at 41     ORF Stop: TGAat 1871 |
| | SEQ ID NO:150     610 aa MW at 68306.6 kD |
| NOV60a, | MEWLSPDIALPRRDEWTQTSPARKRITHAKVQGAGQLRLSIDAQDRVLLLHVTEGKGL |
| CG92683-01 Protein Sequence | ISKQPGTCDPYVKVSLIPEDSRLHQKTQTVPDCRDPAFHEHFFFPVQEEDDQKRLLV |
| | TVWNRASQSRRQSLICCMSFCVKSLLTPDKEISGWYYLLGEHLGRTKHLKVARRRLRP |
| | LRDPLLRMPGGGDTENGKKLKITIPRGKDGFGFTICCDSPVRVQAVDSGGPAERAGLQ |
| | QLDTVLQLNERPVEHWKCVELAHEIRSCPSEIILLVWPNVPQVKPGPDGGVLRRASCK |
| | STHDLQSPPNKREKNCTHGVQARPEQRESCHLVCDSSDGLLLGGWERYTEVAKRGGQH |
| | TLPALSRATAPTDPNYIILAPLNPGSQLLRPVYQEDTIPEESGSPSKCKSYTGLGKKS |
| | RLMKTVQTMKGEGNYQNCPVVRPHATHSSYGTYVTLAPKVLVPPVPVQPLDLCNPART |
| | LLLSEELLLYEGRNKSTQVTLFAYSDLLLPTKEDEPGRCDVLRNPLYLQSVKLQEGSS |
| | EDLKFCVLYLAQKAECLFTLEAESQEQKKRVCWCLSENIAKQQQLAAPPDSKQKLHPF |
| | GSLQQEMGPVNSTNATQDRSFTSPGQTLIG |

TABLE 60A-continued

NOV60 Sequence Analysis

| | |
|---|---|
| NOV60b, <br><br> CG92683-02 DNA Sequence | SEQ ID NO:151        2874 bp <br> <u>GCAGGACCCGCAGCC</u>ATGAACCGCTTCAATGGGCTCTGCAACGTGTGCTCGGAGCGCC <br> GCTACCGCCAGATCACCATCCCCAGCGGAAAGGACGGCTTTCGCTTCACCATCTGCTG <br> CGACTCTCCAGTTCGAGTCCAGGCCGTGGATTCCGGTGGTCCGGCGGAACCGGCAGGG <br> CTGCAGCAGCTGGACACGGTGCTGCAGCTGAATGAGAGGCCTGTGCACCACTGGAAAT <br> GTGTGGACCTGGCCCACGACATCCCCAGCTGCCCCAGTGAGATCATCCTACTCGTGTG <br> GCGCATGGTCCCCCAGGTCAAGCCAGGACCAGATGGCGGGGTCCTGCGGCCGGCCTCC <br> TGCAAGTCGACACATGACCTCCAGTCACCCCCCAACAAACGGGAGAAGAACTGCACCC <br> ATGGGGTCCAGGCACGGCCTGAGCAGCGCCACAGCTGCCACCTGGTATGTGACAGCTC <br> TGATGGGCTGCTGCTCGGCGGCTGGGAGCGCTACACCGAGGTGGCCAAGCGCGGGGGC <br> CAGCACACCCTGCCTGCACTGTCCCGTGCCACTGCCCCCACCGACCCCAACTACATCA <br> TCCTGGCCCCGCTGAATCCTGCGAGCCAGGTACCTGTCTTTCCCTTGCAGCTGCTCCG <br> GCCTGTGTACCAGGAGGATACCATCCCCGAAGAATCACGGAGTCCCAGTAAAGGGAAG <br> TCCTACACAGGCCTGGGGAAGAAGTCCCCGCTCATGAAGACAGTGCAGACCATGAAGG <br> GCCACGGGAACTACCAAAACTGCCCGGTTCTGAGGCCGCATGCCACGCACTCAAGCTA <br> TGGCACCTACGTCACCCTCGCCCCCAAAGTCCTGGTCTTCCCTGTCTTTGTTCAGCCT <br> CTAGATCTCTGTAATCCTGCCCGGACCCTCCTGCTGTCAGAGGAGCTGCTGCTGTATG <br> AAGGGAGGAACAACTCAACCCAGGTGACACTGTTTGCCTATTCGGACCTCCTCCTCTT <br> CACCAAGGAGGACGAGCCTCGCCGCTGCGACGTCCTGAGGAACCCCCTCTACCTCCAG <br> AGTGTGAAGCTGCAGGAACGTTCTTCAGAAGACCTGAAATTCTGCGTGCTCTATCTAG <br> CAGAGAAGGCAGAGTGCTTATTCACTTTGGAAGCGCACTCGCAGGAGCACAAGAAGAG <br> AGTGTGCTGGTGCCTGTCGGAGAACATCGCCAAGCAGCAACAGCTGGCACCATCACCC <br> CCGGACAGCAAGATGTTTGAGACGGAGGCAGATGAGAAGAGGGAGATGGCCTTGGAGG <br> AAGGGAAGGGGCCTGGTGCCGAGGATTCCCCACCCAGCAAGGAGCCCTCTCCTGGCCA <br> GGAGCTTCCTCCACGACAAGACCTTCCACCCAACAAGGACTCCCCTTCTGCGCAGGAA <br> CCCGCTCCCAGCCAAGAACCACTGTCCAGCAAAGACTCAGCTACCTCTGAAGGATCCC <br> CTCCAGGCCCAGATGCTCCGCCCAGCAAGGATGTGCCACCATGCCAGGAACCCCCTCC <br> AGCCCAAGACCTCTCACCCTGCCAGGACCTACCTGCTGGTCAAGAACCCCTGCCTCAC <br> CAGGACCCTCTACTCACCAAAGACCTCCCTGCCATCCAGGAATCCCCCACCCGGGACC <br> TTCCACCCTGTCAAGATCTGCCTCCTAGCCAGGTCTCCCTGCCAGCCAAGGCCCTTAC <br> TGAGGACACCATGAGCTCCGGGGACCTACTAGCAGCTACTGGGGACCCACCTGCGGCC <br> CCCAGGCCAGCCTTCGTGATCCCTGAGGTCCGGCTGGATAGCACCTACAGCCAGAAGG <br> CAGGGGCAGAGCAGGGCTGCTCGGGAGATGACGAGGATGCAGAAGACGCCGAGGAGGT <br> GGAGGAGGGGAGGAAGGGGAGGAGGACGAGGATGAGGACACCAGCGATGACAACTAC <br> GGAGAGCGCAGTGAGGCCAAGCGCAGCAGCATGATCGACACGGGCCAGGGGCTGAGG <br> GTGGCCTCTCACTGCGTGTGCAGAACTCGCTGCGGCGCCGGACGCACAGCGAGGGCAG <br> CCTGCTGCAGGAGCCCCGAGGGCCCTGCTTTGCCTCCGACACCACCTTGCACTGCTCA <br> GACGGTGAGGCCGCCGCCTCCACCTGGGGCATGCCTTCGCCCAGCACCCTCAAGAAAG <br> AGCTGGGCCGCAATGGTGGCTCCATGCACCACCTTTCCCTCTTCTTCACAGGACACAG |

TABLE 60A-continued

NOV60 Sequence Analysis

GAAGATGAGCGGGGCTGACACCGTTGGGGATGATGACGAAGCCTCCCGGAAGAGAAAG

AGCAAAAACCTGGCCAAGGACATGAAGAACAAGCTGGGGATCTTCACACGGCGGAATG

AGTCCCCTGGAGCCCCTCCCGCGGGCAAGGCAGACAAAATGATGAACTCATTCAAGCC

CACCTCAGAGGAAGCCCTCAAGTGGGGCGAGTCCTTCGAGAAGCTGCTGGTTCACAAA

GGGTTAGCAGTGTTCCAAGCCTTCCTTCGCACTGAGTTCAGTGAGGAGAATCTGGAGT

TCTGGTTGGCTTGTGAGGACTTCAAGAAGGTCAAGTCACAGTCCAAGATGGCATCCAA

GGCCAAGAAGATCTTTGCTGAATACATCGCGATCCAGGCATGCAAGGAGGTAAACCTG

GACTCCTACACGCGGGAGCACACCAAGGACAACCTGCAGAGCGTCACGCGGGGCTGCT

TCGACCTGGCACAGAAGCGCATCTTCGGGCTCATGGAAAAGGACTCGTACCCTCGCTT

TCTCCGTTCTGACCTCTACCTGGACCTTATTAACCAGAAGAAGATGAGTCCCCCGCTT

TAGGGGCCACTGGAGTCGAGCTCACCGTTCACACCAGGCGGGCTGGGTCCCCTGCCCA

CCTGCCTCCCTGCCCCCTGTGACGGAGCGGGC

| | |
|---|---|
| | ORF Start: ATG at 16     ORF Stop: TAG at 2785 |
| | SEQ ID NO:152           923 aa MW at 101609.2 kD |
| NOV60b, | MNRFNGLCKVCSERRYRQITIPRGKDGFGFTICCDSPVRVQAVDSGGPAERAGLQQLD |
| CG92683-02 Protein Sequence | TVLQLNERPVEHWKCVELAHETRSCPSEIILLVWRNVPQVKPGPDGGVLRRASCKSTH |
| | DLQSPPNKREKNCTHGVQARFEQRHSCHLVCDSSDGLLLGGWERYTEVAKRGGQHTLP |
| | ALSRATAPTDPNYIILAPLNPGSQVPVFPLQLLRPVYQEDTIPEESGSPSKGKSYTGL |
| | GKKSRLMKTVQTMKGHGNYQNCPVVRPHATHSSYGTYVTLAPKVLVFPVFVQPLDLCN |
| | PARTLLLSEELLLYEGRNKSTQVTLFAYSDLLLFTKEDEPGRCDVLRNPLYLQSVKLQ |
| | EGSSEDLKPCVLYLAEKAECLFTLEAHSQEQKKRVCWCLSENIAKQQQLAASPPDSKM |
| | FETEADEKREMALEEGKGPGAEDSPPSKEPSPGQELPPCQDLPPNKDSPSGQEPAPSQ |
| | EPLSSKDSATSEGSPPGPDAPPSKDVPPCQEPPPAQDLSPCQDLPAGQEPLPHQDPLL |
| | TKDLPAIQESPTRDLPPCQDLPPSQVSLPAKALTEDTMSSGDLLAATGDPPAAPRPAF |
| | VIPEVRLDSTYSQKAGAEQGCSCDEEDAEEAEEVEEGEEGEEDEDEDTSDDNYGERSE |
| | AKRSSMIETGQGAEGGLSLRVQNSLRRRTHSEGSLLQEPRGPCFASDTTLHCSDGEGA |
| | ASTWGMPSPSTLKKELGRNGGSMHHLSLFFTGHRKMSGADTVGDDDEASRKRKSKNLA |
| | KDMKNKLGIFRRRNESPGAPPAGKADKMMKSFKPTSEEALKWGESLEKLLVHKGLAVF |
| | QAFLRTEFSEENLEFWLACEDPKKVKSQSKMASKAKKIFAEYIAIQACKEVNLDSYTR |
| | EHTKDNLQSVTRGCEDIAQKRIFGLMEKDSYPRFLRSDLYLDLINQKKMSPPL |

Sequence comparison of the above protein sequences yields the following sequence relationships shown in Table 60B.

TABLE 60B

Comparison of NOV60a against NOV60b.

| Protein Sequence | NOV60a Residues/ Match Residues | Identities/Similarities for the Matched Region |
|---|---|---|
| NOV60b | 195 ... 574 | 367/388 (94%) |
| | 18 ... 405 | 369/388 (94%) |

Further analysis of the NOV60a protein yielded the following properties shown in Table 60C.

TABLE 60C

Protein Sequence Properties NOV60a

| | |
|---|---|
| PSort analysis: | 0.3000 probability located in microbody (peroxisome); 0.3000 probability located in nucleus; 0.1000 probability located in mitochondrial matrix space; 0.1000 probability located in lysosome (lumen) |
| SignalP analysis: | No Known Signal Sequence Predicted |

A search of the NOV60a protein against the Geneseq database, a proprietary database that contains sequences published in patents and patent publication, yielded several homologous proteins shown in Table 60D.

TABLE 60D

Geneseq Results for NOV60a

| Geneseq Identifier | Protein/Organism/Length [Patent #, Date] | NOV60a Residues/ Match Residues | Identities/ Similarities for the Matched Region | Expect Value |
|---|---|---|---|---|
| AAM93446 | Human polypeptide, SEQ ID NO: 3092 - *Homo sapiens*, 602 aa. [EP1130094-A2, Sep. 5, 2001] | 35 ... 610 27 ... 602 | 560/576 (97%) 567/576 (98%) | 0.0 |
| AAU17386 | Novel signal transduction pathway protein, Seq ID 951 - *Homo sapiens*, 212 aa. [WO200154733-A1, Aug. 2, 2001] | 195 ... 363 45 ... 212 | 148/170 (87%) 149/170 (87%) | 2e−80 |
| ABG01916 | Novel human diagnostic protein #1907 - *Homo sapiens*, 336 aa. [WO200175067-A2, Oct. 11, 2001] | 453 ... 601 14 ... 216 | 123/203 (60%) 134/203 (65%) | 2e−57 |
| ABG01916 | Novel human diagnostic protein #1907 - *Homo sapiens*, 336 aa. [WO200175067-A2, Oct. 11, 2001] | 453 ... 601 14 ... 216 | 123/203 (60%) 134/203 (65%) | 2e−57 |
| ABG01914 | Novel human diagnostic protein #1905 - *Homo sapiens*, 66 aa. [WO200175067-A2, Oct. 11, 2001] | 455 ... 519 1 ... 65 | 61/65 (93%) 64/65 (97%) | 8e−29 |

In a BLAST search of public sequence datbases, the NOV60a protein was found to have homology to the proteins shown in the BLASTP data in Table 60E.

TABLE 60E

Public BLASTP Results for NOV60a

| Protein Accession Number | Protein/Organism/Length | NOV60a Residues/ Match Residues | Identities/ Similarities for the Matched Portion | Expect Value |
|---|---|---|---|---|
| Q9QXA2 | C2PA PROTEIN - *Mus musculus* (Mouse), 610 aa. | 1 ... 610 1 ... 610 | 530/610 (86%) 564/610 (91%) | 0.0 |
| AAL37173 | ENDOTHELIAL PDZ PROTEIN-1 - *Mus musculus* (Mouse), 433 aa. | 195 ... 610 18 ... 433 | 381/416 (91%) 396/416 (94%) | 0.0 |
| AAL68829 | PDZ-RGS3 - *Homo sapiens* (Human), 917 aa. | 195 ... 574 18 ... 398 | 374/381 (98%) 378/381 (99%) | 0.0 |
| Q925G9 | PDZ-RGS3 PROTEIN - *Mus musculus* (Mouse), 930 aa. | 195 ... 608 18 ... 434 | 359/418 (85%) 378/418 (89%) | 0.0 |
| Q920Q9 | SRB-RGS - *Rattus norvegicus* (Rat), 967 aa. | 195 ... 575 18 ... 398 | 349/381 (91%) 362/381 (94%) | 0.0 |

PFam analysis predicts that the NOV60a protein contains the domains shown in the Table 60F.

TABLE 60F

Domain Analysis of NOV60a

| Pfam Domain | NOV60a Match Region | Identities/ Similarities for the Matched Region | Expect Value |
|---|---|---|---|
| C2: domain 1 of 1 | 48 ... 135 | 29/97 (30%) 68/97 (70%) | 7.8e−13 |
| PDZ: domain 1 of 1 | 195 ... 271 | 24/86 (28%) 56/86 (65%) | 1.5e−07 |
| PH: domain 1 of 1 | 465 ... 552 | 12/88 (14%) 61/88 (69%) | 3.4 |

Example 61

The NOV61 clone was analyzed, and the nucleotide and encoded polypeptide sequences are shown in Table 61A.

TABLE 61A

NOV61 Sequence Analysis

| | |
|---|---|
| NOV61a, CG92694-01 DNA Sequence | SEQ ID NO: 153    1482 bp<br>TCAGAGTAGGAGTCCATGCGGACATCGGCTAAGATTCCAGAATGACTACCGTCTTGAC<br>TTACACTTTTAAAAAGTGCACTTCTGATGCACTTCTCACTGCATCAGAATGGTCCCTC<br>AGATTTTCCATAAGACCTCTGAGCTATTCCTCCCAGTTGCGACCTGCCCCAGCCATCC<br>AGACCGAAACGAGCAAGACATTAGCCAAACCCAATATAAGGAATATTGTGGTGGTGGA<br>TGGTGTTCGCACTCCATTTTTGCTGTCAGGCACTTCGTATAAAGACCTGATACCACAT<br>GATTTGGCTAGAGCAACACTTACGGGTTTGTTGCATCAGCCCAGTGTCCCCAAGGAAG<br>TAGTTGATTATATCATCTTTGGCACAGTCATTCACGAACTGAAAACAAGCCATGTGGC<br>TGGAGAGGCTGCCCTTGGAACTGCCTTCTCTGACAAGACTCCTGCTCACACTGTCACC<br>ATGGCTTGTATCTCTGCCAACCAAGCCATGACCACAGGTGTTGGTTTCATTGCTTCTG<br>GCCAGTGTGATGTGATCATGGCAGGTCGTGTCGAGTTGATGTTCCATGTCCCTATTCG<br>TCAGTCAAGGAAAATGAGAAAACTGATGCTTGATCTAAGTAAGGCCAAATTTGTGGGC<br>CAGAGACTGTCTTCAATCTCTAAATGCCAATTGAATTTCCCAGCACCTGAGCTCCCTG<br>AGGTTTCTGAGTTCTCCACCAGTGAGACCACGGGCCACTCTGCAGACCAATTGGCTGT<br>TTCTCGACTGGAACAGGATGAATATGCACTGCGCTGTCCCAGTCTGGCCAAGAAGGCA<br>CAGGATGAAGGACTCCTTTCTGATGTCGTACCCTTCAAAGTACCAGGAAAAGATACAG<br>TTACCAAACATAATGGCATCCGTCCTTCCTCACTGGAGCAGATGGCTAAACTAAAACC<br>TGCATTCATCAAGCCCTACGGCACACCGACAGCTGCAAATTCTTCTTTCTTGACTGAT<br>GGCGCATCTGAGGCAGAGGAAAAGGCTCTGGCAATGGGTTATAAGCCGAAGGAGTGTT<br>TGAGGGATTTTATGTACGTGTCTCACAATCTGAAAGATCAACTATTATTCACACCAAC<br>ATATGCGACTCCAAAAATTCTAGAAAAGGCAGCATTAACCATGAGTGATATTGATGCT<br>TTTGAATTTCACAAAGCTTTCTCAGGTAAGATTTTAGCTAATTTTAAAGCCATGGATT<br>CTGATTGGTTTGCACAAAATTACATGGGTAGAAAAACCAAGGTTACATTGCTTCCTTC<br>GGAGAAGTTTAATAACTGGGGTGGATCTCTGTCCCTGGAACACCCATTTGGAGCTACT<br>GGCTGCAGGTTGGTCGTCGCAGCTGCCAACAGATTACGGAAGGAAGCAGGCCAGTATG<br>CCTTAGCGGCTGCCTGTGCAGCTGGAGGGCAGGGCCATGGTATGATAGTGGAAGCTTA<br>CCCAAAATAATAGATCCAGAAGAAATGACCAG |
| NOV61a, CG92694-01 Protein Sequence | ORF Start: ATG at 42    ORF Stop: TAA at 1458<br>SEQ ID NO: 154    472 aa    MW at 51283.5kD<br>MTTVLTYTFKKCTSDALLTASEWSLRFSIRPLSYSSQLRAAPAIQTETRKTLAKPNIR<br>NIVVVDGVRTPFLLSGTSYKDLIPHDLARATLTGLLHQPSVPKEVVDYIIFGTVTQEV<br>KTSHVAGEAALGTAFSDKTPAHTVTMACISANQAMTTGVGLIASGQCDVIMAGGVELM<br>FHVPIRQSRKMRKLMLDLSKAKFVGQRLSSISKCQLNFPAPELPEVSEFSTSETTGHS<br>ADQLAVSRLEQDEYALRCPSLAKKAQDEGLLSDVVPFKVPGKDTVTKHNGIRPSSLEQ<br>MAKLKPAFIKPYGTATAANSSFLTDGASEAEEKALAMGYKPKECLRDFMYVSHNLKDQ<br>LLFRPTYATPKILEKAGLPMSDIDAFEFHKAFSGKILAIFKANDSDWFAQNYMGRKSK<br>VTLLPSEKFNNWGGSLSLEHPFGATGCRLVVAAANRLRKEGGQYALAAACAACGQGHG<br>MIVEAYPK |

Further analysis of the NOV61a protein yielded the following properties shown in Table 61B.

TABLE 61B

Protein Sequence Properties NOV61a

| | |
|---|---|
| PSort analysis: | 0.6079 probability located in mitochondrial matrix space; 0.3717 probability located in microbody (peroxisome); 0.3122 probability located in mitochondrial inner membrane 0.3122 probability located in mitochondrial intermembrane space |
| SignalP analysis: | No Known Signal Sequence Predicted |

A search of the NOV61a protein against the Geneseq database, a proprietary database that contains sequences published in patents and patent publication, yielded several homologous proteins shown in Table 61C.

TABLE 61C

Geneseq Results for NOV61a

| Geneseq Identifier | Protein/Organism/Length [Patent #, Date] | NOV61a Residues/ Match Residues | Identities/ Similarities for the Matched Region | Expect Value |
|---|---|---|---|---|
| ABG11653 | Novel human diagnostic protein #11644 - *Homo sapiens*, 417 aa. [WO200175067-A2, Oct. 11, 2001] | 125 ... 472 62 ... 417 | 305/356 (85%) 318/356 (88%) | e-168 |
| ABG11653 | Novel human diagnostic protein #11644 - *Homo sapiens*, 417 aa. [WO200175067-A2, Oct. 11, 2001] | 125 ... 472 62 ... 417 | 305/356 (85%) 318/356 (88%) | e-168 |
| ABG11657 | Novel human diagnostic protein #11648 - *Homo sapiens*, 470 aa. [WO200175067-A2, Oct. 11, 2001] | 125 ... 472 110 ... 470 | 294/361 (81%) 308/361 (84%) | e-156 |
| ABG11657 | Novel human diagnostic protein #11648 - *Homo sapiens*, 470 aa. [WO200175067-A2, Oct. 11, 2001] | 125 ... 472 110 ... 470 | 294/361 (81%) 308/361 (84%) | e-156 |
| AAU30648 | Novel human secreted protein #1139 - *Homo sapiens*, 478 aa. [WO200179449-A2, Oct. 25, 2001] | 90 ... 472 76 ... 478 | 295/403 (73%) 318/403 (78%) | e-144 |

In a BLAST search of public sequence datbases, the NOV61a protein was found to have homology to the proteins shown in the BLASTP data in Table 61D.

TABLE 61D

Public BLASTP Results for NOV61a

| Protein Accession Number | Protein/Organism/Length | NOV61a Residues/ Match Residues | Identities/ Similarities for the Matched Portion | Expect Value |
|---|---|---|---|---|
| Q9H3F5 | MSTP029 - *Homo sapiens* (Human), 475 aa. | 1 ... 472 1 ... 475 | 407/480 (84%) 430/480 (88%) | 0.0 |
| Q96C77 | HYPOTHETICAL 51.4 KDA PROTEIN - *Homo sapiens* (Human), 475 aa. | 1 ... 472 1 ... 475 | 406/480 (84%) 429/480 (88%) | 0.0 |
| P55084 | Trifunctional enzyme beta subunit, mitochondrial precursor (TP-beta) [Includes: 3-ketoacyl-CoA thiolase (EC 2.3.1.16) (Acetyl-CoA acyltransferase) (Beta-ketothiolase)] - *Homo sapiens* (Human), 474 aa. | 3 ... 472 2 ... 474 | 405/478 (84%) 428/478 (88%) | 0.0 |
| O46629 | Trifunctional enzyme beta subunit, mitochondrial precursor (TP-beta) [Includes: 3-ketoacyl-CoA thiolase (EC 2.3.1.16) (Acetyl-CoA acyltransferase) (Beta-ketothiolase)] - *Bos taurus* (Bovine), 475 aa. | 1 ... 472 1 ... 475 | 385/480 (80%) 420/480 (87%) | 0.0 |
| Q99JY0 | SIMILAR TO HYDROXYACYL-COENZYME A DEHYDROGENASE/ 3-KETOACYL-COENZYME A | 1 ... 472 1 ... 475 | 378/480 (78%) 423/480 (87%) | 0.0 |

TABLE 61D-continued

Public BLASTP Results for NOV61a

| Protein Accession Number | Protein/Organism/Length | NOV61a Residues/ Match Residues | Identities/ Similarities for the Matched Portion | Expect Value |
|---|---|---|---|---|
| | THIOLASE/ENOYL-COENZYME A HYDRATASE (TRIFUNCTIONAL PROTEIN), BETA SUBUNIT - *Mus musculus* (Mouse), 475 aa. | | | |

PFam analysis predicts that the NOV61a protein contains the domains shown in the Table 61E.

TABLE 61E

Domain Analysis of NOV61a

| Pfam Domain | NOV61a Match Region | Identities/ Similarities for the Matched Region | Expect Value |
|---|---|---|---|
| thiolase: domain 1 of 1 | 52...323 | 99/294 (34%) 229/294 (78%) | 1.6e-83 |
| thiolase_C: domain 1 of 1 | 327...469 | 59/144 (41%) 121/144 (84%) | 1.4e-58 |

Example 62

The NOV62 clone was analyzed, and the nucleotide and encoded polypeptide sequences are shown in Table 62A.

TABLE 62A

NOV62 Sequence Analysis

| | |
|---|---|
| NOV62a, CG92896-01 DNA Sequence | SEQ ID NO: 155    1280 bp<br>ACTATGGCCTCCTCCTCGGTCCCACCAGCCACGGTATCCGCGGCGACAGCAGGCCCCG<br>GCCCAGGTTTCGGCTTCGCCTCCAAGACCAAGAAGAAGCATTTCGTGCAGCAGAAGGT<br>GAAGGTGTTCCGGGCGGCCCACCCGCTGGTGCGTGTGTTCCTGTGGGCCGTAGCCCAC<br>TCGATCAATGAGCTCAGCCAGGTGCCTCCCCCGGTGATGCTCCTGCCAGATGACTTTA<br>AGGCCAGCTCCAAGATCAAGGTCAACAATCACCTTTTCCACAGGGAAAATCTGCCCAG<br>TCATTTCAAGTTCAAGGACTATTGTCCCCAGGTCTTCAGGAACCTCCGTGATCGATTT<br>GGCATTGATGACCAAGATTACTTGGTGTCCCTTACCCGAAACCCCCCCAGCGAAAGTG<br>AAGGCAGTGATGGTCGCTTCCTTATCTCCTACGATCGGACTCTGGTCATCAAAGAAGT<br>ATCCAGTGAGGACATTGCTGACATGCATAGCAACCTCTCCAACTATCACCAGTACATT<br>GTGAAGTGCCATGGCAACACGCTTCTGCCCCAGTTCCTGGGGATGTACCGAGTCAGTG<br>TGGACAACGAAGACAGCTACATGCTTGTGATGCGCAATATGTTTAGCCACCGTCTTCC<br>TGTGCACAGGAAGTATGACCTCAAGGGTTCCCTAGTGTCCCGGGAAGCCAGCGATAAG<br>GAAAAGGTGAAAGAATTGCCCACCCTTAACGATATGGACTTTCTCAACAAGAACCAGA<br>AAGTATATATTGGTGAAGAGGAGAACAAAATATTTCTGGAGAAGCTGAAGAGAGATGT<br>GGAGTTTCTAGTGCAGCTGAAGATCATGGACTACAGCCTTCTGCTAGGCATCCACGAC<br>ATCATTCGGGGCTCTGAACCAGAGGAGGAAGCGCCCGTGCGGGAGGATGAGTCAGAGG<br>TGGATGGGGACTGCAGCCTGACTGGACCTCCTGCTCTTGTGGGCTCCTATGGCACCTC<br>CCCAGAGGGTATCGGAGGCTACATCCATTCCCATCCGCCCCTGGCCCCACGACAGTTT |

TABLE 62A-continued

NOV62 Sequence Analysis

GAGTCCTTCATTGATGTCTATGCCATCCGGAGTGCTGAAGCTGCCCCCCAGAAGGAGG

TCTACTTCATGGGCCTCATTGATATCCTTACACAGTATGATGCTAAGAAGAAAGCAGC

TCATGCAGCCAAAACTGTCAAGCATGGGGCTGGGGCAGAGATCTCTACTGTCCATCCG

GAGCAGTATGCTAAGCGATTCCTGGATTTTATTACCAACATCTTTGCCTAAGAGACTG

CCTG

NOV62a,
CG92896-01 Protein Sequence

ORF Start: ATG at 4     ORF Stop: TAA at 1267
SEQ ID NO: 156          421 aa    MW at 47299.4kD
MASSSVPPATVSAATAGPGPGFGFASKTKKKHFVQQKVKVFRAADPLVGVFLWGVAHS

INELSQVPPPVMLLPDDFKASSKIKVNNHLFHRENLPSHFKFKEYCPQVFRNLRDRFG

IDDQDYLVSLTRNPPSESEGSDGRFLISYDRTLVIKEVSSEDIADMHSNLSNYHQYIV

KCHGNTLLPQFLGMYRVSVDNEDSYMLVMRNMFSHRLPVHRKYDLKGSLVSREASDKE

KVKELPTLKDMDFLNKNQKVYIGEEEKKIFLEKLKRDVEFLVQLKIMDYSLLLGIHDI

IRGSEPEEEAPVREDESEVDGDCSLTGPPALVGSYGTSPEGIGGYIHSHRPLGPGEFE

SFIDVYAIRSAEGAPQKEVYPMGLIDILTQYDAKKKAAHAAKTVKHCAGAETSTVHPE

QYAKRFLDFITNIFA

NOV62b,
CG92896-02 DNA Sequence

SEQ ID NO: 157       1280 bp
ACTATGGCGTCCTCCTCGGTCCCACCAGCCACGGTATCGGCGGCGACAGCAGGCCCCG

GCCCAGGTTTCGGCTTCGCCTCCAAGACCAACAAGAAGCATTTCGTGCAGCAGAAGGT

GAAGGTGTTCCGGGCGGCCGACCCCCTGGTGGGTGTGTTCCTGTGGGCCGTAGCCCAC

TCGATCAATGAGCTCAGCCAGGTGCCTCCCCCGGTGATGCTGCTGCCAGATGACTTTA

AGGCCAGCTCCAAGATCAAGGTCAACAATCACCTTTTCCACAGGGAAAATCTGCCCAG

TCATTTCAAGTTCAAGGAGTATTGTCCCCAGGTCTTCAGGAACCTCCGTGATCGATTT

GGCATTGATGACCAAGATTACTTGGTGTCCCTTACCCGAAACCCCCCCAGCGAAAGTG

AAGGCAGTGATGGTCGCTTCCTTATCTCCTACGATCGGACTCTGGTCATCAAAGAAGT

ATCCAGTGAGGACATTGCTGACATGCATAGCAACCTCTCCAACTATCACCAGTACATT

GTGAAGTGCCATGCCAACACGCTTCTGCCCCAGTTCCTGGGGATCTACCCAGTCAGTG

TGGACAACGAAGACAGCTACATGCTTGTGATGCGCAATATGTTTAGCCACCGTCTTCC

TGTGCACAGGAAGTATGACCTCAAGGGTTCCCTAGTGTCCCGGGAAGCCAGCGATAAG

GAAAAGGTTAAAGAATTGCCCACCCTTAAGGATATGGACTTTCTCAACAAGAACCAGA

AAGTATATATTGGTGAAGAGGAGAAGAAAATATTTCTGGAGAAGCTGAAGAGAGATGT

GGAGTTTCTAGTGCAGCTGAAGATCATGGACTACAGCCTTCTGCTAGGCATCCACGAC

ATCATTCGGGGCTCTGAACCAGACGAGGAAGCGCCCGTGCCGGAGGATGAGTCAGAGG

TGGATGGGGACTGCAGCCTGACTCCACCTCCTGCTCTGGTGGGCTCCTATGCCACCTC

CCCAGAGGGTATCCGAGGCTACATCCATTCCCATCGGCCCCTGGGCCCAGGAGAGTTT

GAGTCCTTCATTGATCTCTATGCCATCCGGAGTGCTGAAGGAGCCCCCCAGAAGGAGG

TCTACTTCATGGGCCTCATTGATATCCTTACACAGTATGATGCCAAGAAGAAAGCAGC

TCATGCAGCCAAAACTGTCAAGCATGGGGCTGGGGCAGAGATCTCTACTGTCCATCCG

GAGCAGTATCCTAAGCGATTCCTGGATTTTATTACCAACATCTTTGCCTAAGAGACTG

CCTG

TABLE 62A-continued

NOV62 Sequence Analysis

NOV62b,
CG92896-02 Protein Sequence

ORF Start: ATG at 4    ORF Stop: TAA at 1267
SEQ ID NO: 158    421 aa    MW at 47299.4kD

MASSSVPPATVSAATAGPGPGPGFASKTKKKHFVQQKVKVFRAADPLVGVFLWGVAHS

INELSQVPPPVMLLPDDFKASSKIKVNNHLFHRENLPSHFKFKEYCPQVFRNLRDRFG

IDDQDYLVSLTRNPPSESEGSDGRFLISYDRTLVIKEVSSEDIADMHSNLSNYHGYIV

KCHGNTLLPQFLGMYRVSVDNEDSYMLVMRNMFSHRLPVHRKYDLKGSLVSREASDKE

KVKELPTLKDMDFLNKNQKVYIGEEEKKIFLEKLKRDVEELVQLKIMDYSLLLGIHDI

IRGSEPEEEAPVREDESEVDGDCSLTGPPALVGSYGTSPEGIGGYIHSHRPLGPGEFE

SFIDVYAIRSAEGAPQKEVYFMGLIDILTQYDAKKKAAHAAKTVKHGAGAEISTVHPE

QYAKRFLDFITNIFA

Sequence comparison of the above protein sequences yields the following sequence relationships shown in Table 62B.

TABLE 62B

Comparison of NOV62a against NOV62b.

| Protein Sequence | NOV62a Residues/ Match Residues | Identities/Similarities for the Matched Region |
|---|---|---|
| NOV62b | 42 ... 421 | 334/380 (87%) |
|  | 42 ... 421 | 334/380 (87%) |

Further analysis of the NOV62a protein yielded the following properties shown in Table 62C.

TABLE 62C

Protein Sequence Properties NOV62a

| PSort analysis: | 0.3000 probability located in nucleus; 0.2053 probability located in microbody (peroxisome); 0.1000 probability located in mitochondrial matrix space; 0.1000 probability located in lysosome (lumen) |
|---|---|
| SignalP analysis: | Cleavage site between residues 59 and 60 |

A search of the NOV62a protein against the Geneseq database, a proprietary database that contains sequences published in patents and patent publication, yielded several homologous proteins shown in Table 62D.

TABLE 62D

Geneseq Results for NOV62a

| Geneseq Identifier | Protein/Organism/Length [Patent #, Date] | NOV62a Residues/ Match Residues | Identities/ Similarities for the Matched Region | Expect Value |
|---|---|---|---|---|
| AAG63222 | Amino acid sequence of a human lipid metabolism enzyme-*Homo sapiens*, 421 aa. [WO200153468-A2, 26-JUL-2001] | 1 ... 421<br>1 ... 421 | 421/421 (100%)<br>421/421 (100%) | 0.0 |
| AAB88462 | Human membrane or secretory protein clone PSEC0253-*Homo sapiens*, 265 aa. [EP1067182-A2, 10-JAN-2001] | 1 ... 262<br>1 ... 262 | 234/262 (89%)<br>245/262 (93%) | e-135 |
| ABB12247 | Human PI 5-phosphate 4-kinase gamma homologue, SEQ ID NO:2617-*Homo sapiens*, 223 aa. [WO200157188-A2, 09-AUG-2001] | 1 ... 171<br>15 ... 185 | 171/171 (100%)<br>171/171 (100%) | 1e-96 |
| ABG09799 | Novel human diagnostic protein #9790-*Homo sapiens*, 605 aa. [WO200175067-A2, 11-OCT-2001] | 47 ... 418<br>128 ... 490 | 125/381 (32%)<br>182/381 (46%) | 6e-40 |
| ABG09796 | Novel human diagnostic protein #9787-*Homo sapiens*, 556 aa. [WO200175067-A2, 11-OCT-2001] | 47 ... 418<br>128 ... 490 | 125/381 (32%)<br>182/381 (46%) | 6e-40 |

In a BLAST search of public sequence datbases, the NOV62a protein was found to have homology to the proteins shown in the BLASTP data in Table 62E.

TABLE 62E

Public BLASTP Results for NOV62a

| Protein Accession Number | Protein/Organism/Length | NOV62a Residues/ Match Residues | Identities/ Similarities for the Matched Portion | Expect Value |
|---|---|---|---|---|
| Q91XU3 | PHOSPHATIDYL INOSITOL PHOSPHATE KINASE TYPE II GAMMA-*Mus musculus* (Mouse), 421 aa. | 1 . . . 421<br>1 . . . 421 | 404/421 (95%)<br>410/421 (96%) | 0.0 |
| O88370 | PHOSPHATIDYLINOSITOL 5-PHOSPHATE 4-KINASE GAMMA-*Rattus norvegicus* (Rat), 420 aa. | 1 . . . 421<br>1 . . . 420 | 401/421 (95%)<br>409/421 (96%) | 0.0 |
| O88377 | PHOSPHATIDYLINOSITOL 5-PHOSPHATE 4-KINASE BETA-*Rattus norvegicus* (Rat), 416 aa. | 26 . . . 419<br>21 . . . 414 | 270/397 (68%)<br>323/397 (81%) | e-154 |
| P78356 | PHOSPHATIDYLINOSITOL-4-PHOSPHATE 5-KINASE TYPE II BETA (EC 2.7.1.68)-*Homo sapiens* (Human), 416 aa. | 26 . . . 419<br>21 . . . 414 | 267/397 (67%)<br>324/397 (81%) | e-153 |
| AAL18245 | PHOSPHATIDYLINOSITOL-4-PHOSPHATE 5-KINASE TYPE II BETA-*Mus musculus* (Mouse), 392 aa (fragment). | 30 . . . 419<br>1 . . . 390 | 267/393 (67%)<br>322/393 (80%) | e-152 |

PFam analysis predicts that the NOV62a protein contains the domains shown in the Table 62F.

TABLE 62F

Domain Analysis of NOV62a

| Pfam Domain | NOV62a Match Region | Identities/ Similarities for the Matched Region | Expect Value |
|---|---|---|---|
| PIP5K: domain 1 of 1 | 124 . . . 420 | 139/359 (39%)<br>279/359 (78%) | 1.5e−155 |

Example 63

The NOV63 clone was analyzed, and the nucleotide and encoded polypeptide sequences are shown in Table 63A.

TABLE 63A

NOV63 Sequence Analysis

| | |
|---|---|
| NOV63a,<br>CG92987-01 DNA Sequence | SEQ ID NO: 159    2056 bp<br>ATGGCCAAACCAGCACAGGGTGCCAAGTACCGGGGCTCCATCCATGACTTCCCAGGCT<br><br>TTGACCCCAACCAGGATGCCGAGGCTCTGTACACTGCCATGAAGGGCTTTGGCAGTGA<br><br>CAAGGAGGCCATATTGGACATAATCACCTCACGGAGCAACAGGCAGAGGCAGGAGGTC<br><br>TGCCAGAGCTACAAGTCCCTCTACCCCAACCACCTCATTGCTGATTTAAAGTATGAAT<br><br>TGACGGGCAAGTTTGAACGGTTGATTGTGGGCCTGATGAGGCCACCTGCCTATTGTGA<br><br>TGCCAAAGAAATTAAAGATGCCATCTCGGGCATTGGCACTGATGAGAAGTCCCTCATT<br><br>GAGATCTTCGCTTCCCGGACCAATGAGCAGATGCACCAGCTGGTGGCAGCATACAAAG<br><br>ATGCCTACGACCGGGACCTGGAGGCTGACATCATCGGCGACACCTCTGGCCACTTCCA<br><br>GAAGATCCTTGTGGTCCTGCTCCAGGGAACCAGGGAGGAGGATGACGTAGTGAGCGAG<br><br>GACCTCCTACAACACGATCTCCAGGACCTATACCAGGCACGCGAACTGAAATGCGGAA |

TABLE 63A-continued

NOV63 Sequence Analysis

CAGATGAAGCCCAGTTCATTTACATCTTGGGAAATCGCAGCAAGCAGCATCTTCGGTT
GGTGTTCGATGAGTATCTGAACACCACAGGGAAGCCGATTGAAGCCAGCATCCCAGGG
GAGCTGTCTGGGGACTTTGAGAAGCTAATGCTGGCCGTAGTGAAGTGTATCCGGAGCA
CCCCGGAATATTTTGCTGAAAGGCTCTTCAAGGCTATGAAGGCCCTGGGGACTCGGGA
CAACACCCTGATCCGCATCATGGTCTCCCGTAGTGAGTTGGACATGCTCGACATTCGG
GAGATCTTCCGGACCAAGTATGAGAAGTCCCTCTACACCATGATCAAGAATGACACCT
CTGGCGAGTACAAGAAGACTCTGCTGAAGCTGTCTGGCGGAGATGATGATGCTGCTGG
CCAGTTCTTCCCGCAGGCACCGCAGCTGGCCTATCAGATGTCGGAACTTAGTGCAGTC
GCCCGAGTAGAGCTGAAGGCAGTGGCCCGAGTAGAGCTGAAGGGAACTGTGCGCCCAG
CCAATGACTTCAACCCTGACGCAGATGCCAAAGCCCTGCGGAAAGCCAPGAAGGGACT
CCCGACTGACGAAGACACAATCATCGATATCATCACGCACCGCAGCAATGTCCAGCGG
CAGCAGATCCGGCAGACCTTCAACTCTCACTTTCGCCGGGACTTAATGACTGACCTGA
AGTCTGAGATCTCTGGAGACCTGGCAAGGCTCATTCTGGCGCTCATCATCCCACCCGC
CCATTACGATGCCAAGCAGTTGAAGAAGGCCATGGAGGGAGCCGGCACAGATGAAAAG
GCTCTTATTCAAATCCTGGCCACTCGGACCAATGCTGAAATCCGGGCCATCAATCAGG
CCTATAACGAGGACTATCACAAGTCCCTGGAGGATGCTCTGAGCTCAGACACAPCTGG
CCACTTCAGGAGGATCCTCATTTCTCTGCCCACGGCQCATCGTGAGGAGGGAGGAGAA
AACCTGGACCAGGCACGGGAAGATGCCCAGGAAATAGCAGACACACCCAGTGGAGACA
AAACTTCCTTGGAGACACGTTTCATGACGATCCTGTGTACCCGGAGCTATCCGCACCT
CCGCAGAGTCTTCCAGGAGTTCATCAAGATGACCAACTATGACGTGGAGCACACCATC
AAGAACGACATGTCTGGGGATGTCACGCATGCATTTGTGCCCATTGTTCAAAGTGTCA
AGAACAAGCCTCTCTTCTTTGCCGACAAACTTTACAAATCCATCAACGGTGCTGGCAC
AGATGAGAAGACTCTGACCAGCATCATCGTATCCCACAGTGAGATTGACCTGCTCAAC
ATCCGGAGGGAATTCATTGAGAAATAPGACAAGTCTCTCCACCAAGCCATTCAGGGTG
ACACCTCCGGAGACTTCCTGAAGGCCTTGCTGGCTCTCTGTGGTGGTGAGGACTAGGG
CCACTGCTTTCAGGTGTGATATCTAT

ORF Start: ATG at 1    ORF Stop: TAG at 2026
SEQ ID NO: 160         675 aa    MW at 76123.6kD NOV63a, CG92987-01 Protein Sequence MAKPAQGAKYRGSIHDFPGFDPNQDAEALYTANKGFGSDKEAILDIITSRSNRQRQEV
CQSYKSLYGKDLIADLKYELTGKFERLIVGLMRPPAYCKAKEIKDAISIGTDEKCLI
EILASRTNEQMHQLVAAYKDAYERDLEADIIGDTSGHFQKMLVVLLQGTREEDDVVSE
DLVQQDVQDLYEAGELKWCTDEAQFIYILGNRSKQHLRLVFDEYLKTTGKPIEASIRG
ELSCDFEKLMLAVVKCIRSTPEYFAERLFKAMKGLGTRDNTLIRIMVSRSELDMLDIR
EIFRTKYEKSLYSMIKNDTSGEYKKTLLKLSGGDDDAAGQFFPEAAQVAYQMWELSAV
ARVELKAVARVELKGTVRPANDFNPDADAKALRKANKGLCTOEDTIIDIITERSNVQR
QQIRQTFKSHFGRDLMTDLKSEISGDLARLILGLMMPFAHYDAKQLKKAEEGAGTDEK
ALIEILATRTNAEIRAINEAYKEDYHKSLEDALSSDTSGHFRRILISLATGHREEGE
NLDQAREDAQEIADTPSGDKTSLETRFMTILCTRSYPHLRRVFQEFIKMTNYDVEHTI
KKEMSGDVRDAFVAIVQSVKNKPLFFADKLYKSMKGAGTDEKTLTRIMVSHSEIDLLN
IRREFIEKYDKSLHQAIEGDTSGDFLKALLALCGGED Further analysis of the NOV63a protein yielded the following properties shown in Table 63B.

TABLE 63B

Protein Sequence Properties NOV63a

| | |
|---|---|
| PSort analysis: | 0.4500 probability located in cytoplasm; 0.3000 probability located in microbody (peroxisome); 0.1000 probability located in mitochondrial matrix space; 0.1000 probability located in lysosome (lumen) |

TABLE 63B-continued

Protein Sequence Properties NOV63a

| | |
|---|---|
| SignalP analysis: | No Known Signal Sequence Predicted |

A search of the NOV63a protein against the Gene seq database, a proprietary database that contains sequences published in patents and patent publication, yielded several homologous proteins shown in Table 63C.

TABLE 63C

Geneseq Results for NOV63a

| Geneseq Identifier | Protein/Organism/Length [Patent #, Date] | NOV63a Residues/ Match Residues | Identities/ Similarities for the Matched Region | Expect Value |
|---|---|---|---|---|
| AAR03726 | Human placenta-derived coagulation inhibitor protein-Homo sapiens, 786 aa. [EP351826-A, Jan. 24, 1990] | 1 ... 675<br>1 ... 673 | 665/681 (97%)<br>665/681 (97%) | 0.0 |
| AAR03725 | Human placenta-derived coagulation inhibitor-*Homo sapiens*, 672 aa. [EP351826-A, Jan. 24, 1990] | 2 ... 675<br>1 ... 672 | 662/680 (97%)<br>664/680 (97%) | 0.0 |
| ABG19948 | Novel human diagnostic protein #19939-*Homo sapiens*, 736 aa. [WO200175067-A2, Oct. 11, 2001] | 1 ... 673<br>60 ... 736 | 633/685 (92%)<br>641/685 (93%) | 0.0 |
| ABG19948 | Novel human diagnostic protein #19939-*Homo sapiens*, 736 aa. [WO200175067-A2, Oct. 11, 2001] | 1 ... 673<br>60 ... 736 | 633/685 (92%)<br>641/685 (93%) | 0.0 |
| ABB57067 | Mouse ischaemic condition related protein sequence SEQ ID NO: 136-*Mus musculus*, 319 aa. [WO200188188-A2, Nov. 22, 2001] | 11 ... 326<br>4 ... 319 | 180/316 (56%)<br>237/316 (74%) | e-101 |

In a BLAST search of public sequence datbases, the NOV63a protein was found to have homology to the proteins shown in the BLASTP data in Table 63D.

TABLE 63D

Public BLASTP Results for NOV63a

| Protein Accession Number | Protein/Organisn/Length | NOV63a Residues/ Match Residues | Identities/ Similarities for the Matched Portion | Expect Value |
|---|---|---|---|---|
| AAH17046 | ANNEXIN A6-*Homo sapiens* (Human), 673 aa. | 1 ... 675<br>1 ... 673 | 666/681 (97%)<br>666/681 (97%) | 0.0 |
| P08133 | Annexin VI (Lipocortin VI) (P68) (P70) (Protein III) (Chromobindin 20) (67 kDa calelectrin) (Calphobindin-II) (CPB-II)-*Homo sapiens* (Human), 672 aa. | 2 ... 675<br>1 ... 672 | 665/680 (97%)<br>665/680 (97%) | 0.0 |
| Q99JX6 | SIMILAR TO ANNEXIN A6-*Mus musculus* (Mouse), 667 aa. | 1 ... 675<br>1 ... 667 | 629/675 (93%)<br>646/675 (95%) | 0.0 |
| S01786 | annexin VI-mouse, 673 aa. | 1 ... 675<br>1 ... 673 | 629/681 (92%)<br>646/681 (94%) | 0.0 |
| S52844 | annexin VI-rat, 673 aa. | 1 ... 675<br>1 ... 673 | 629/681 (92%)<br>647/681 (94%) | 0.0 |

PFam analysis predicts that the NOV63a protein contains the domains shown in the Table 63E.

TABLE 63E

Domain Analysis of NOV63a

| Pfam Domain | NOV63a Match Region | Identities/ Similarities for the Matched Region | Expect Value |
| --- | --- | --- | --- |
| annexin: domain 1 of 8 | 22 . . . 89 | 28/68 (41%) 46/68 (68%) | 1e−7 |
| annexin: domain 2 of 8 | 94 . . . 161 | 26/68 (38%) 46/68 (68%) | 8.9e−18 |
| annexin: domain 3 of 8 | 178 . . . 245 | 23/68 (34%) 43/68 (63%) | 1.2e−14 |
| annexin: domain 4 of 8 | 253 . . . 320 | 27/68 (40%) 46/68 (68%) | 5.1e−19 |

TABLE 63E-continued

Domain Analysis of NOV63a

| Pfam Domain | NOV63a Match Region | Identities/ Similarities for the Matched Region | Expect Value |
| --- | --- | --- | --- |
| annexin: domain 5 of 8 | 373 . . . 440 | 31/68 (46%) 49/68 (72%) | 2.7e−22 |
| annexin: domain 6 of 8 | 445 . . . 512 | 29/68 (43%) 55/68 (81%) | 1.7e−24 |
| annexin: domain 7 of 8 | 527 . . . 595 | 19/69 (28%) 41/69 (59%) | 5.3e−06 |
| annexin: domain 8 of 8 | 603 . . . 670 | 30/68 (44%) 50/68 (74%) | 5e−20 |

Example 64

The NOV64 clone was analyzed, and the nucleotide and encoded polypeptide sequences are shown in Table 64A.

TABLE 64A

NOV64 Sequence Analysis

NOV64a,
CG93042-01 DNA Sequence

SEQ ID NO: 161   987 bp
TCTGAAGCAATGCTAATACAACCTCAGTCACTGAATTTCTCCTTTTCGCAGTGACAG

ACATTCAAGAACTGCAGCCTTTTCTCTTCGTTCTTTTCCTTACCATCTACTTCATCAG

TGTGGCTGGGAATGGAGCCATTCTGATGATTCTCATCTCPGATCATAGAGTCCATTCC

CCTATGTATTTCTTCCTGCGAAACCTGTCCTGCCTGGACATCTGCTACTCCAGCGTAA

CACTGCCAAAAATGCTGCAGAACTTCCTCTCTCCACACAAAGCAATTTCTTTCTTGGG

ATGCATAAGCCAACTCCATTTCTTCCACTTCCTGGGCACCACAGAGGCCATGTTGTTG

GCCGTGATGGCATTTGACCGCTTTGTCGCTATTTGCAAGCCACTTCGCTACACTGTCA

TTATGAACCCTCAGCTCTGTACCCACATGGCCATCACAATCTGGATGATTGGTTTTTT

CCATGCCCTGCTGCACTCCCTAATGACCTCTCGCTTGAACTTCTGTGGTTCTAACCGT

ATCTATCACTTCTTCTGTGATGTGAAGCCATTGCTAAAGCTGGCCTGTGGGAACACTG

AGCTTAATCAGTGGCTGCTCAGTACTGTCACACGGACAAPCGCCATGGGCCCCTTCTT

TCTCACATTACTCTCCTATTTCTACATTATCACCCATCTCTTCPTCAAGACTCATTCT

TTTAGCATGCTCCGCAAACCACTGTCCACTTGTCCCTCCCACTTCATGGTAGTTATTC

TTTTGTATGCACCTGTTCTCTTCACCTATATTCATCATGCCTCAGCCACCTCCATGGA

CCAGGACCGGATCACTGCCATCATGTATACTGTGGTCACTCCAGTACTAAACCCACTG

ATCTACACTTTGAAGCGAACCAAAGGAAAGTGAAAAGGGGCCTTTATATATGAGCCAA

TGAAAAAGGTGCCTTTCGCCTAAAGAAATCTTGAAGAACTCTTTTGAACCATAAATAA

A
ORF Start: ATG at 10    ORF Stop: TGA at 901
SEQ ID NO: 162    297 aa    MW at 33589.7dK NOV64a,
CG93042-01 Protein Sequence

MLNTTSVTEFLLLGVTDIQELQPFLFVVFLTIYFISVAGNGAILMIVISDHRLHSPMY

FFLGNLSCLDICYSSVTLPKMLQNFLSAHKAISFLGCISQLHFFHFLGSTEAMLLAVM

AFDRFVAICKPLRYTVTMNPQLCTQMAPTIWMICFFHALLHSLMTSRLNFCOSNRIYH

FFCDVKPLLKLACGNTELNQWLLSTVTGTIAMGPFFLTLLSYFYIITHLFFKTHSFSM

LRKALSTCASEFMVVILLYAPVLFTYIHHASGTSMDQDRITAIMYTVVTPVLNPLTYT
LKGTKGK

Further analysis of the NOV64a protein yielded the following properties shown in Table 64B.

TABLE 64B

Protein Sequence Properties NOV64a

| | |
|---|---|
| PSort analysis: | 0.6000 probability located in plasma membrane; 0.4000 probability located in Golgi body; 0.3000 probability located in endoplasmic reticulum (membrane); 0.3000 probability located in microbody (peroxisome) |

TABLE 64B-continued

Protein Sequence Properties NOV64a

| | |
|---|---|
| SignalP analysis: | Cleavage site between residues 39 and 40 |

A search of the NOV64a protein against the Geneseq database, a proprietary database that contains sequences published in patents and patent publication, yielded several homologous proteins shown in Table 64C.

TABLE 64C

Geneseq Results for NOV64a

| Geneseq Identifier | Protein/Organism/Length [Patent #, Date] | NOV64a Residues/ Match Residues | Identities/ Similarities for the Matched Region | Expect Value |
|---|---|---|---|---|
| AAG72212 | Human olfactory receptor polypeptide, SEQ ID NO: 1893 - Homo sapiens, 309 aa. [WO200127158-A2, 19-APR-2001] | 1 . . . 297 1 . . . 292 | 281/297 (94%) 286/297 (95%) | e−159 |
| AAG71661 | Human olfactory receptor polypeptide, SEQ ID NO: 1342 - Homo sapiens, 309 aa. [WO200127158-A2, 19-APR-2001] | 1 . . . 297 1 . . . 292 | 281/297 (94%) 286/297 (95%) | e−159 |
| AAG72870 | Human olfactory receptor data exploratorium sequence, SEQ ID NO: 2552 - Homo sapiens, 315 aa. [WO200127158-A2, 19-APR-2001] | 1 . . . 297 7 . . . 303 | 265/297 (89%) 276/297 (92%) | e−151 |
| AAG72203 | Human olfactory receptor polypeptide, SEQ ID NO: 1884 - Homo sapiens, 307 aa. [WO200127158-A2, 19-APR-2001] | 1 . . . 297 1 . . . 297 | 265/297 (89%) 276/297 (92%) | e−151 |
| AAG72658 | Murine OR-like polypeptide query sequence, SEQ ID NO: 2340 - Mus musculus, 325 aa. [WO200127158-A2, 19-APR-2001] | 1 . . . 292 7 . . . 298 | 235/292 (80%) 260/292 (88%) | e−138 |

In a BLAST search of public sequence datbases, the NOV64a protein was found to have homology to the proteins shown in the BLASTP data in Table 64D.

TABLE 64D

Public BLASTP Results for NOV64a

| Protein Accession Number | Protein/Organism/Length | NOV64a Residues/ Match Residues | Identities/ Similarities for the Matched Portion | Expect Value |
|---|---|---|---|---|
| P58182 | Olfactory receptor 12D2 (Hs6M1-20) - Homo sapiens (Human), 307 aa. | 1 . . . 297 1 . . . 297 | 265/297 (89%) 276/297 (92%) | e−151 |
| Q920Y9 | BM332P19.2 (NOVEL 7 TRANSMEMBRANE RECEPTOR (RHODOPSIN FAMILY) (OLFACTORY RECEPTOR LIKE) PROTEIN (MM17M1-13), ORTHOLOG OF HUMAN DJ994E9.8 (HS6M1-20)) - Mus musculus (Mouse), 308 aa. | 1 . . . 292 1 . . . 292 | 235/292 (80%) 260/292 (88%) | e−138 |
| Q920Y8 | BM332P19.3 (NOVEL 7 TRANSMEMBRANE RECEPTOR (RHODOPSIN FAMILY) (OLFACTORY RECEPTOR LIKE) PROTEIN (MM17M1-14)) - Mus musculus (Mouse), 313 aa. | 1 . . . 292 1 . . . 292 | 228/292 (78%) 257/292 (87%) | e−133 |
| Q920Z0 | BM332P19.1 (NOVEL 7 TRANSMEMBRANE RECEPTOR (RHODOPSIN FAMILY) (OLFACTORY RECEPTOR LIKE) PROTEIN (MM17M1-12)) - Mus musculus (Mouse), 308 aa. | 1 . . . 292 1 . . . 292 | 228/292 (78%) 253/292 (86%) | e−133 |
| AAL60921 | OLFACTORY RECEPTOR MOR250-1 - Mus musculus (Mouse), 314 aa. | 1 . . . 292 1 . . . 294 | 210/294 (71%) 243/294 (82%) | e−120 |

PFam analysis predicts that the NOV64a protein contains the domains shown in the Table 64E.

TABLE 64E

Domain Analysis of NOV64a

| Pfam Domain | NOV64a Match Region | Identities/ Similarities for the Matched Region | Expect Value |
|---|---|---|---|
| 7tm_1: domain 1 of 1 | 39 ... 289 | 46/269 (17%) 169/269 (63%) | 4.9e−33 |

Example 65

The NOV65 clone was analyzed, and the nucleotide and encoded polypeptide sequences are shown in Table 65A.

TABLE 65A

NOV65 Sequence Analysis

NOV65a, CG93265-01 DNA Sequence

SEQ ID NO: 163     1137 bp

GGGCAGGAGCTGGGGCCACGCTGGTCTGGGATAGTTGGGCAGGGAGGCTGTCTACCTG
GTCTCCAGAATGGACGGCCCTGTGGCAGAGCATGCCAAGCAGGAGGCCTTTCACGTGG
TCACACCTCTGTTGGAGAGCTGGGCGCTGTCCCAGGTGGCGGGCATGCCTGTCTTCCT
CAAGTGTGAGAATGTGCAGCCCAGCGGCTCCTTCAAGATTCGGGGCATTGGGCATTTC
TGCCAGGAGATGGCCAAGAAGGGATGCAGACACCTGGTGTGCTCCTCAGGGGGTAATG
CGGGCATCGCTGCTGCCTATGCTGCTAGGAAGCTGGGCATTCCTGCCACCATCGTGCT
CCCCGAGAGCACCTCCCTGCAGGTGGTGCAGAGGCTGCAGGGGGAGGGGGCCGAGGTT
CAGCTGACTGGAAAGGTCTGGGACGAGGCCAATCTGAGGGCCCAAGAGTTGGCCAAGA
GGGACGGCTGGGAGAATGTCCCCCCGTTTGACCACCCCTAATATGGAAAGGCCACGC
CAGCCTGGTGCAGGAGCTGAAAGCAGTGCTGAGGACCCCACCAGGTGCCCTGGTGCTG
GCAGTTGGGGGTGGGGGTCTCCTGGCCGGGGTGGTGGCTGGCCTGCTGGAGGTGGGCT
GGCAGCATGTACCCATCATTGCCATGGAGACCCATGGGCACACTGCTTCAATGCGGC
CATCACAGCCGGCAAGCTGGTCACACTTCCAGACATCACCAGTGTGGCCAAGAGCCTG
GGTGCCAAGACGGTGGCCGCTCGGGCCCTTAGTTCGATGCAGGTGTGCAAGATTCACT
CTGAAGTGGTGGAGGACACCGAGGCTGTGAGCGCTGTGCAGCAGCTCCTGGATGATGA
GCGTATGCTGGTGGAGCCTGCCTGTGGGGCAGCCTTAGCAGCCATCTACTCAGGCCTC
CTGCGGAGGCTCCAGGCCGAGGGCTGCCTGCCCCCTTCCCTGACTTCAGTTGTGGTAA
TCGTGTGTGGAGGCAACAACATCAACAGCCGAGAGCTGCAGGCTTTGAAAACCCACCT
GGGCCAGGTCTGAGGGGTCCCATCCTGGCCCCAAAGACCCCTGAGAGGCCCATGGACA
GTCCTGTGTCTGGATGAGGAGGACTCAGTGCTGGC

ORF Start ATG at 68    ORF Stop: TGA at 1055

NOV65a, CG93265-01 Protein Sequence

SEQ ID NO: 164    329 aa    MW at 34615.8kD

NDGPVAEHAKQEPFHVVTPLLESWALSQVAGMPVFLKCENVQPSGSFKIRGIGHFCQE
MAKKGCRHLVCSSGGNAGIAAAYAARKLGIPATIVLPESTSLQVVQRLQGEGAEVQLT
GKVWDEANLRAQELAKRDGWENVPPFDHPLIWKGHASLVQELKAVLRTPPGALVLAVG
GGGLLAGVVAGLLEVGWQHVPIIANETHGAHCFNAAITAGKLVTLPDITSVAKSLGAK
TVAARALSSMQVCKIHSEVVEDTEAVSAVQQLLDDERMLVEPACGAALAAIYSGLLRR
LQAEGCLPPSLTSVVVIVCGGNNINSRELQALKTHLGQV

SEQ ID NO: 165    1137 bp

TABLE 65A-continued

NOV65 Sequence Analysis

NOV65b, CG93265-02 DNA Sequence

<u>GGGCAGGAGCTGGGGCCACGCTGGTCTGGGATAGTTGGGCAGGGAGGCTGTCTACCTG</u>

<u>GTCTCCAGA</u>ATGGACGGCCCTGGGCCAGAGCATGCCAAGCAGGAGCCCTTCACGTGG

TCACACCTCTGTTGGAGAGCTGGGCGCTGTCCCAGGTGGCGGGCATGCCTGTCTTCCT

CAAGTGTGAGAATGTGCAGCCCAGCGGCTCCTTCAAGATTCGGGGCATTGGGCATTTC

TGCCAGGAGATGGCCAAGAAGGGATGCAGACACCTGGTGTGCTCCTCAGGGGGTAATG

CGGGCATCGCTGCTGCCTATGCTGCTAGGAAGCTGGGCATTCCTGCCACCATCGTGCT

CCCCGAGAGCACCTCCCTGCAGGTGGTGCAGAGGCTGCAGGGGGAGGGGCCGAGGTT

CAGCTGACTGGAAAGGTCTGGGACGAGGCCAATCTGAGGGCGCAAGAGTTGGCCAAGA

GGGACGGCTGGGAGAATGTCCCCCCGTTTGACCACCCCCTAATATGGAAAGGCCACGC

CAGCCTGGTGCAGGAGCTGAAAGCAGTGCTGAGGACCCCACCAGGTGCCCTGGTGCTG

GCAGTTGGGGGTGGGGGTCTCCTGGCCGGGGTGGTGGCTGGCCTGCTGGAGGTGGGCT

GGCAGCATGTACCCATCATTGCCATGGAGACCCATGGGCACACTGCTTCAATGCGGC

CATCACAGCCGGCAAGCTGGTCACACTTCCAGACATCACCAGTGTGGCCAAGAGCCTG

GGTGCCAAGACGGTGGCCGCTCGGGCCCTTAGTTCGATGCAGGTGTGCAAGATTCACT

CTGAAGTGGTGGAGGACACCGAGGCTGTGAGCGCTGTGCAGCAGCTCCTGGATGATGA

GCGTATGCTGGTGGAGCCTGCCTGTGGGCAGCCTTAGCAGCCATCTACTCAGGCCTC

CTGCGGAGGCTCCAGGCCGACGGCTGCCTGCCCCCTTCCCTGACTTCAGTTGTGGTAA

TCGTGTGTGGAGGCAACAACATCAACAGCCGAGAGCTGCAGGCTTTGAAAACCCACCT

GGGCCAGGTCTGA<u>GGGGTCCCATCCTGGCCCCAAAGACCCCTGAGAGGCCCATGGACA</u>

<u>GTCCTGTGTCTGGATGAGGAGGACTCAGTGCTGGC</u>

ORF Start: ATG at 68    ORF Stop: TGA at 1055
SEQ ID NO: 166    329 aa    MW at 346 15.8kD NOV65b, CG93265-02 Protein Sequence

MDGPVAEHAKQEPFHVVTPLLESWALSQVAGMPVFLKCENVQPSGSFKIRGIGHFCQE

MAKKGCRHLVCSSGGNAGIAAAYAARKLGIPATIVLPESTSLQVVQRLQGEGAEVQLT

GKVWDEANLRAQELAKRDGWENVPPFDHPLIWKGHASLVQELKAVLRTPPGALVLAVG

GGGLLAGVVAGLLEVGWQHVPIIAMETHGAHCFNAAITAGKLVTLPDITSVAKSLGAK

TVAARALSSMQVCKIHSEVVEDTEAVSAVQQLLDDERMLVEPACGAALAAIYSGLLRR

LQAEGCLPPSLTSVVVIVCGGNNINSRELQALKTHLGQV

Sequence comparison of the above protein sequences yields the following sequence relationships shown in Table 65B.

TABLE 65B

Comparison of NOV65a against NOV65b.

| Protein Sequence | NOV65a Residues/ Match Residues | Identities/Similarities for the Matched Region |
|---|---|---|
| NOV65b | 1 ... 329 | 284/329 (86%) |
|  | 1 ... 329 | 284/329 (86%) |

Further analysis of the NOV65a protein yielded the following properties shown in Table 65C.

TABLE 65C

Protein Sequence Properties NOV65a

| PSort analysis: | 0.8500 probability located in endoplasmic reticulum (membrane); 0.4400 probability located in plasma membrane; 0.1000 probability located in mitochondrial inner membrane; 0.1000 probability located in Golgi body |
| SignalP analysis: | No Known Signal Sequence Predicted |

A search of the NOV65a protein against the Geneseq database, a proprietary database that contains sequences published in patents and patent publication, yielded several homologous proteins shown in Table 65D.

TABLE 65D

Geneseq Results for NOV65a

| Geneseq Identifier | Protein/Organism/Length [Patent #, Date] | NOV65a Residues/ Match Residues | Identities/ Similarities for the Matched Region | Expect Value |
|---|---|---|---|---|
| AAM40622 | Human polypeptide SEQ ID NO: 5553 - *Homo sapiens*, 340 aa. [WO200153312-A1, 26-JUL-2001] | 1 . . . 329<br>12 . . . 340 | 327/329 (99%)<br>327/329 (99%) | 0.0 |
| AAM38836 | Human polypeptide SEQ ID NO: 1981 - *Homo sapiens*, 329 aa. [WO200153312-A1, 26-JUL-2001] | 1 . . . 329<br>1 . . . 329 | 327/329 (99%)<br>327/329 (99%) | 0.0 |
| AAU23238 | Novel human enzyme polypeptide #324 - *Homo sapiens*, 340 aa. [WO200155301-A2, 02-AUG-2001] | 1 . . . 329<br>12 . . . 340 | 327/329 (99%)<br>327/329 (99%) | 0.0 |
| AAM52238 | Human DHY SEQ ID NO: 2 - *Homo sapiens*, 329 aa. [WO200181559-A2, 01-NOV-2001] | 1 . . . 329<br>1 . . . 329 | 326/329 (99%)<br>326/329 (99%) | 0.0 |
| AAU23764 | Novel human enzyme polypeptide #850 - *Homo sapiens*, 340 aa. [WO200155301-A2, 02-AUG-2001] | 1 . . . 329<br>12 . . . 340 | 326/329 (99%)<br>326/329 (99%) | 0.0 |

In a BLAST search of public sequence datbases, the NOV65a protein was found to have homology to the proteins shown in the BLASTP data in Table 65E.

TABLE 65E

Public BLASTP Results for NOV65a

| Protein Accession Number | Protein/Organism/Length | NOV65a Residues/ Match Residues | Identities/ Similarities for the Matched Portion | Expect Value |
|---|---|---|---|---|
| Q96GA7 | UNKNOWN (PROTEIN FOR MGC: 15400) - *Homo sapiens* (Human), 329 aa. | 1 . . . 329<br>1 . . . 329 | 327/329 (99%)<br>327/329 (99%) | 0.0 |
| AAH22601 | RIKEN CDNA 4432411H13 GENE - *Mus musculus* (Mouse), 329 aa. | 1 . . . 327<br>1 . . . 327 | 263/327 (80%)<br>290/327 (88%) | e–149 |
| AAL56988 | SERINE DEHYDRATASE (EC 4.2.1.13) - *Mus musculus* (Mouse), 359 aa. | 1 . . . 324<br>1 . . . 324 | 262/324 (80%)<br>289/324 (88%) | e–148 |
| DWRTT | L-serine dehydratase (EC 4.2.1.13) - rat, 327 aa. | 9 . . . 327<br>2 . . . 321 | 197/320 (61%)<br>243/320 (75%) | e–107 |
| AAH21605 | SIMILAR TO SERINE DEHYDRATASE - *Mus musculus* (Mouse), 327 aa. | 9 . . . 327<br>2 . . . 321 | 199/320 (62%)<br>242/320 (75%) | e–106 |

PFam analysis predicts that the NOV65a protein contains the domains shown in the Table 65F.

TABLE 65F

Domain Analysis of NOV65a

| Pfam Domain | NOV65a Match Region | Identities/ Similarities for the Matched Region | Expect Value |
|---|---|---|---|
| Adaptin_N: domain 1 of 1 | 238 . . . 272 | 10/35 (29%)<br>28/35 (80%) | 8.9 |
| PALP: domain 1 of 1 | 11 . . . 311 | 96/385 (25%)<br>226/385 (59%) | 1.4e–64 |

Example 66

The NOV66 clone was analyzed, and the nucleotide and encoded polypeptide sequences are shown in Table 66A.

TABLE 66A

| NOV66 Sequence Analysis | |
|---|---|
| NOV66a, CG93464-01 DNA Sequence | SEQ ID NO: 167  2786 bp<br>CTTGATACACACAGCCACATATGCACACAGATGTATAAAACGGAAAAGTTTCACAAAG<br>CAACATCCTGTGAACAATATGTTAATATTACAGGAAACAGCTATGACCATGATTACGA<br>ATTCGAGCTCGGTACCCATAAAGCTGTCCTGGAAGACCCAATGTTGAAGTTCTCAGGA<br>ACTATATCAAGAGACATGCTCTGATCTTTATGTTACTTGTCAAGTTTTTGCAGAAGGGA<br>AGCCTTTGGCCTTGCCAGTTAGAACATCCTCCCCAGCATTTAGTACAAGATGGAGCTG<br>GAATGAATGGCTGAAACTACCAGTAAAATACCCTGACCTGCCCAGGAATGCCCAAGTG<br>GCCCTCACCATATGGGATGTGTATGGTCCCGGAAAAGCAGTGCCTGTAGGAGGAACAA<br>CGGTTTCGCTCTTTGGAAAATACGGGATGTTTCGCCAAGGGATGCATGACTTGAAAGT<br>CTGGCCTAATGTAGAAGCAGATGGATCAGAACCCACAAAAACTCCTGGCAGAACAAGT<br>AGCACTCTCTCAGAAGATCAGATGAGCCGTCTTGCCAAGCTCACCAAAGCTCATCGAC<br>AAGGACACATGGTGAAAGTAGATTGGCTGGATAGATTGACATTTAGAGAAATAGAAAT<br>GATAAATGAGAGTGAAAAACGAAGTTCTAATTTCATGTACCTGATGGTTGAATTTCGA<br>TGTGTCAAGTGTGATGATAAGGAATATGGTATTGTTTATTATGAAAAGGACGGTGATG<br>AATCATCTCCAATTTTAACAAGTTTTGAATTAGTGAAAGTTCCTGACCCCCAGATGTC<br>TATGGAGAATTTAGTTGAGAGCAAACACCACAAGCTTGCCCGGAGTTTAAGAAGTGGA<br>CCTTCTGACCACGATCTGAAACCCAATGCTGCCACGAGAGATCAGTTAAATATTATTG<br>TGAGTTATCCACCAACCAAGCAACTTACATATGAAGAACAAGATCTTGTTTGGAAGTT<br>TAGATATTATCTTACGAATCAAGAAAAAGCCTTGACAAAATTCTTGAAATGTGTTAAT<br>TGGGATCTACCTCAAGAGGCCAAACAGGCCTTGGAACTTCTGGGAAAATGGAAGCCGA<br>TGGATGTAGAGGACTCCTTGGAGCTGTTATCCTCTCATTACACCAACCCAACTGTGAG<br>GCGTTATGCTGTTGCCCGGTTGCGACAGGCCGATGATGAGGATTTGTTGATGTACCTA<br>TTACAATTGGTCCAGGCTCTCAAATATGAAAATTTTGATGATATAAAGAATGGATTGG<br>AACCTACCAAGAAGGATAGTCAGAGTTCAGTGTCAGAAAATGTGTCAAATTCTGGAAT<br>AAATTCTGCAGAAATAGATAGCTCCCAAATTATAACCAGCCCCCTTCCTTCAGTCTCT<br>TCACCTCCTCCTGCATCAAAAACAAAAGAAGTTCCAGATGGCGAAAATCTGGAACAAG<br>ATCTCTGTACCTTCTTGATATCGAGAGCCTGCAAAAACTCAACACTGGCTAATTATTT<br>ATACTGGTATGTGATAGTGGAATGTGAAGATCAAGATACTCAGCAGAGAGATCCAAAG<br>ACCCATGAGATGTACTTGAACGTAATGAGAAGATTCAGCCAAGCATTGTTGAAGGGTG<br>ATAAGTCTGTCAGAGTTATGCGTTCTTTGCTGGCTGCACAACAGACATTTGTAGATCG<br>GTTGGTGCATCTAATGAAGGCAGTACAACGCGAAAGTGGAAATCGTAAGAAAAAGAAT<br>GAGAGACTACAGGCATTGCTTGGAGATAATGAAAAGATGAATTTGTCAGATGTGGAAC<br>TTATCCCGTTGCCTTTAGAACCCCAAGTGAAAATTAGAGGAATAATTCCGGAAACAGC<br>TACACTGTTTAAAAGTGCCCTTATGCCTGCACAGTTGTTTTTTAAGACGGAAGATGGA<br>GGCAAATATCCAGTTATATTTAAGCATGGAGATGATTTACGTCAAGATCAACTTATTC<br>TTCAAATCATTTCACTCATGGACAAGCTGTTACGGAAAGAAAATCTGGACTTGAAATT<br>GACACCTTATAAGGTGTTAGCCACCAGTACAAAACATGGTTTCATGCAGTTTATCCAG<br>TCAGTTCCTGTGGCTGAAGTTCTTGATACAGAGGGAAGCATTCAGAACTTTTTTAGAA<br>AATATGCACCAAGTGAGAATGGGCCAAATGGGATTAGTGCTGAGGTCATGGACACTTA |

TABLE 66A-continued

NOV66 Sequence Analysis

```
CGTTAAAAGCTGTGCTGGATATTGCGTGATCACCTATATACTTGGAGTTGGAGACAGG
CACCTGGATAACCTTTTGCTAACAAAAACAGGTAAACTCTTCCACATAGACTTTGGAT
ATATTTTGGGTCGGGATCCAAAGCCTCTTCCTCCACCAATGAAGCTGAATAAAGAAAT
GGTAGAAGGAATGGGGGGCACACAGAGTGAGCAGTACCAAGAGTTCCGTAAACAGTGT
TACACGGCTTTCCTCCACCTGCGAAGGTATTCTAATCTGATTTTGAACTTGTTTTCCT
TGATGGTTGATGCAAACATTCCAGATATTGCACTTGAACCAGATAAAACTGTGAAAAA
GGTTCAGGATAAATTCCGCTTAGACCTGTCGGATGAAGAGGCTGTGCATTACATGCAG
AGTCTGATTGATGAGAGTGTCCATGCTCTTTTTGCTGCAGTGGTGGAACAGATTCACA
AGTTTGCCCAGGTAAGTTCCCTGAGTGCAGTGCATTTTTCTCACCTTCTCCGTCTATA
CTGCCCCAGAGTCCTTGGAGAGCCATGCATTTCTCCTGCCAGTTGACATCTTTTCTGT
TT
```

NOV66a,
CG93464-01 Protein Sequence

ORF Start: ATG at 31    ORF Stop: TGA at 2770
SEQ ID NO: 168          913 aa    MW at 104082.1 kD

```
MYKTEKFHKATSCEQYVNITGNSYDHDYEFELGTHKAVLEDPMLKFSGLYQETCSDLY
VTCQVFAEGKPLALPVRTSSPAFSTRWSWNEWLKLPVKYPDLPRNAQVALTIWDVYGP
GKAVPKGGTTVSLFGKYGMFRQGMHDLKVWPNVEADGSEPTKTPGRTSSTLSEDQMSR
LAKLTKAHRQGHMVKVDWLDRLTFREIEMINESEKRSSNFMYLMVEFRCVKCDDKEYG
IVYYEKDGDESSPILTSFELVKVPDPQMSMENLVESKHHKLARSLRSGPSDHDLKPNA
ATRDQLNIIVSYPPTKQLTYEEQDLVWKFRYYLTNQEKALTKFLKCVNWDLPQEAKQA
LELLGKWKPMDVEDSLELLSSHYTNPTVRRYAVARLRQADDEDLLMYLLQLVQALKYE
NFDDIKNGLEPTKKDSQSSVSENVSNSGINSAEIDSSQIITSPLPSVSSPPPASKTKE
VPDGENLEQDLCTFLISRACKNSTLANYLYWYVIVECEDQDTQQRDPKTHEMYLNVMR
RFSQALLKGDKSVRVMRSLLAAQQTFVDRLVHLMKAVQRESGNRKKKNERLQALLGGN
EKMNLSDVELIPLPLEPQVKIRGIIPETATLFKSALMPAQLFFKTEDGGKYPVIFKHG
DDLRQDQLILQIISLMDKLLRKENLDLKLTPYKVLATSTKHGFMQFIQSVPVAEVLDT
EGSIQNFFRKYAPSENGPNGISAEVMDTYVKSCAGYCVITYILGVGDRHLDNLLLTKT
GKLFHIDFGYILGRDPKPLPPPMKLNKEMVEGMGGTQSEQYQEFRKQCYTAFLHLRRY
SNLILNLFSLMVDANIPDIALEPDKTVKKVQDKFRLDLSDEEAVHYNQQSLIDESVHAL
FAAVVEQIHKFAQVSSLSAVHFSHLLRVYCPRVLGEPCISPAS
```

NOV66b,
CG93464-02 DNA Sequence

SEQ ID NO: 169    3040 bp

```
TGTAGGTGGTACCTTTGCAGACGGTGCGATGGGGGAAGCAGAGAAGTTTCACTACATC
TATAGTTGTGACCTGGATATCAACGTCCAGCTTAAGATAGGAAGCTTGGAAGGGAAGA
GAGAACAAAAGAGTTATAAAGCTGTCCTGGAAGACCCAATGTTGAAGTTCTCAGGACT
ATATCAAGAGACATGCTCTGATCTTTAGGGTACTTGTCAAGTTTTTGCAGAAGGGAAG
CCTTTGGCCTTGCCAGTTAGAACATCCTCCCCAGCATTTAGTACAAGATGGAGCTGGA
ATGAATGGCTGAAACTACCAGTAAAATATCCTGACCTGCCCAGGAATGCCCAAGTGGC
CCTCACCATATGGGATGTGTATGGTCCCGGAAAAGCAGTGCCTGTAGGAGGAACAACG
GTTTCGCTCTTTGGAAAATACGGGATGTTTCGCCAAGGGATGCATGACTTGAAAGTCT
GGCCTAATGTAGAAGCAGATGGATCAGAACCCACAAAAACTCCTGGCAGAACAAGTAG
CACTCTCTCAGAAGATCAGATGAGCCGTCTTGCCAAGCTCACCAAAGCTCATCGACAA
```

TABLE 66A-continued

NOV66 Sequence Analysis

TAAATGAGAGTGAAAAACGAAGTTCTAATTTCATGTACCTGATGGTTGAATTTCGATG

TGTCAAGTGTGATGATAAGGAATATGGTATTGTTTATTATGAAAAGGACGGTGATGAA

TCATCTCCAATTTTAACAAGTTTTGAATTAGTGAAAGTTCCTGACCCCCAGATGTCTA

TGGAGAATTTAGTTGAGAGCAAACACCACAAGCTTGCCCGGAGTTTAAGAAGTCGACC

TTCTGACCACGATCTGAAACCCAATGCTGCCACGAGAGATCAGTTAAATATTATTGTG

AGTTATCCACCAACCAAGCAACTTACATATGAAGAACAAGATCTTGTTTGGAAGTTTA

GATATTATCTTACGAATCAAGAAAAAGCCTTGACAAAATTCTTGAAATGTGTTAATTG

GGATCTACCTCAAGAGGCCAAACAGGCCTTGGAACTTCTGGGAAAATGGAAGCCGATG

GATGTAGAGGACTCCTTGGAGCTGTTATCCTCTCATTACACCAACCCAACTGTGAGGC

GTTATGCTGTTGCCCGGTTGCGACAGGCCGATGATGAGGATTTGTTGATGTACCTATT

ACAATTGGTCCAGGCTCTCAAATATGAAAATTTTGATGATATAAAGAATGGATTGGAA

CCTACCAAGAAGGATAGTCAGAGTTCAGTGTCAGAAAATGTGTCAAATTCTGGAATAA

ATTCTGCAGAATAGATAGCTCCCAAATTATAACCAGCCCCCTTCCTTCAGTCTCTTC

ACCTCCTCCTGCATCAAAAACAAAAGAAGTTCCAGATGGCGAAAATCTGGAACAAGAT

CTCTGTACCTTCTTGATATCGAGAGCCTGCAAAAACTCAACACTGGCTAATTATTTAT

ACTGGTATGTGATAGTGGAATGTGAAGATCAAGATACTCAGCAGAGAGATCCAAAGAC

CCATGAGATGTACTTGAACGTAATGAGAAGATTCAGCCAAGCATTGTTGAAGGGTGAT

AAGTCTGTCAGAGTTATGCGTTCTTTGCTGGCTGCACAACAGACATTTGTAGATCGGT

TGGTGCATCTAATGAAGGCAGTACAACGCGAAAGTGGAAATCGTAAGAAAAAGAATGA

GAGACTACAGGCATTGCTTGGAGATAATGAAAAGATGAATTTGTCAGATGTGGAACTT

ATCCCGTTGCCTTTAGAACCCCAAGTGAAAATTAGAGGAATAATTCCGGAAACAGCTA

CACTGTTTAAAAGTGCCCTTATGCCTGCACAGTTGTTTTTTAAGACGGAAGATGGAGG

CAAATATCCAGTTATATTTAAGCATGGAGATGATTTACGTCAAGATCAACTTATTCTT

CAAATCATTTCACTCATGGACAAGCTGTTACGGAAAGAAAATCTGGACTTGAAATTGA

CACCTTATAAGGTGTTAGCCACCAGTACAAAACATGGCTTCATGCAGTTTATCCAGTC

AGTTCCTGTGGCTGAAGTTCTTGATACAGAGGGAAGCATTCAGAACTTTTTTAGAAAA

TATGCACCAAGTGAGAATGGGCCAAATGGGATTAGTGCTGAGGTCATGGACACTTACG

TTAAAAGCTGTGCTGGATATTGCGTGATCACCTATATACTTGGAGTTGGAGACAGGCA

CCTGGATAACCTTTTGCTAACAAAAACAGGCAAACTCTTCCACATAGACTTTGGATAT

ATTTTGGGTCGGGATCCAAAGCCTCTTCCTCCACCAATGAAGCTGAATAAAGAAATGG

TAGAAGGAATGGGGGGCACACAGAGTGAGCAGTACCAAGAGTTCCGTAAACAGTGTTA

CACGGCTTTCCTCCACCTGCGAAGGTATTCTAATCTGATTTTGAACTTGTTTTCCTTG

ATGGTTGATGCAAACATTCCAGATATTGCACTTGAACCAGATAAAACTGTGAAAAAGG

TTCAGGATAAATTCCGCTTAGACCTGTCGGATGAAGAGGCTGTGCATTACATGCAGAG

TCTGATTGATGAGAGTGTCCATGCTCTTTTTGCTGCAGTGGTGGAACAGATTCACAAG

TTTGCCCAGTACTGGAGAAAATGAAACTGGGATTGACCCATCAAGATGCTTGGCTCAA

TAAGAAAACCACGTTAGGAGCAACCTTTGTATATTGGAGACTTCAGAGTAACCAGCAA

GGAAGAGAAATCTTAATCTTCAAGTTACCATATTTTCCAAATATTACATGGTACCTGA

GTTCTGCTTCCTTGGATGTCATTGCTTAAATATAGTCTTGAAGGGCTTGTTTTGAAAT

TABLE 66A-continued

NOV66 Sequence Analysis

ATTGTATATATTTTTTCAAATGTATACATTGTTAATAAATTAAGAAATGAGAAACATT

CTTATTTATGTACATGTTATGAGAGTTCTGGAGGAAGTAATATGTTGAAATAGTAAAC

CCTTTTAGTTTTTGAGTTTAAAAA

| | |
|---|---|
| NOV66b, CG93464-02 Protein Sequence | ORF Start: ATG at 29     ORF Stop: TGA at 2690<br>SEQ ID NO: 170     887 aa    MW at 101414.2kD<br>MGEAEKFHYIYSCDLDINVQLKIGSLEGKREQKSYKAVLEDPMLKFSGLYQETCSDLY<br><br>VTCQVFAEGKPLALPVRTSSPAFSTRWSWNEWLKLPVKYPDLPRNAQVALTIWDVYGP<br><br>GKAVPVGGTTVSLFGKYGMFRQGMHDLKVWPNVEADGSEPTKTPGRTSSTLSEDQMSR<br><br>LAKLTKAHRQGHMVKVDWLDRLTFREIEMINESEKRSSNFMYLMVEFRCVKCDDKEYG<br><br>IVYYEKDGDESSPILTSFELVKVPDPQMSMENLVESKHHKLARSLRSGSPDHDLKPNA<br><br>ATRDQLNIIVSYPPTKQLTYEEQDLVWKFRYYLTNQEKALTKFLKCVNWDLPQEAKQA<br><br>LELLGKWKPMDVEDSLELLSSHYTNPTVRRYAVARLRQADDEDLLMYLLQLVQALKYE<br><br>NFDDIKNGLEPTKKDSQSSVSENVSNSGINSAEIDSSQIITSPLPSVSSPPPASKTKE<br><br>VPDGENLEQDLCTFLISRACKNSTLANYLYWYVIVECEDQDTQQRDPKTHEMYLNVMR<br><br>RFSQALLKGDKSVRVMRSLLAAQQTFVDRLVHLMKAVQRESGNRKKKNERLQALLGDN<br><br>EKMNLSDVELIPLPLEPQVKIRGIIPETATLFKSALMPAQLFFKTEDGGKYPVIFKHG<br><br>DDLRQDQLILQIISLMDKLLRKENLDLKLTPYKVLATSTKHGFMQFIQSVPVAEVLDT<br><br>EGSIQNFFRKYAPSENGPNGISAEVMDTYVKSCAGYCVITYILGVGDRHLDNLLLTKT<br><br>GKLFHIDFGYILGRDPKPLPPPMKLNKEMVEGMGGTQSEQYQEFRKQCYTAFLHLRRY<br><br>SNLILNLFSLMVDANIPDIALEPDKTVKKVQDKFRLDLSDEEAVHYMQSLIDESVHAL<br><br>FAAVVEQIHKFAQYWRK |
| NOV66c, CG93464-03 DNA Sequence | SEQ ID NO: 171      2654 bp<br><u>TGTAGGTGGTACCTTTGCAGACGGTGCG</u>ATGGGGGAAGCAGAGAAGTTTCACTACATC<br><br>TATAGTTGTGACCTGGATATCAACGTCCAGCTTAAGATAGGAAGCTTGGAAGGGAAGA<br><br>GAGAACAAAAGAGTTATAAAGCTGTCCTGGAAGACCCAATGTTGAAGTTCTCAGGACT<br><br>ATATCAAGAGACATGCTCTGATCTTTATGTTACTTGTCAAGTTTTTGCAGAAGGGAAG<br><br>CCTTTGGCCTTGCCAGTTAGAACATCCTCCCCAGCATTTAGTACAAGATGGAGCTGGA<br><br>ATGAATGGCTGAAACTACCAGTAAAATACCCTGACCTGCCCAGGAATGCCCAAGTGGC<br><br>CCTCACCATATGGGATGTGTATGGTCCCGGAAAAGCAGTGCCTGTAGGAGGAACAACG<br><br>GTTTCGCTCTTTGGAAAATACGGGATGTTTCGCCAAGGGATGCATGACTTGAAAGTCT<br><br>GGCCTAATGTAGAAGCAGATGGATCAGAACCCACAAAAACTCCTGGCAGAACAAGTAG<br><br>CACTCTCTCAGAAGATCAGATGAGCCGTCTTGCCAAGCTCACCAAAGCTCATCGACAA<br><br>GGACACATGGTGAAAGTAGATTGGCTGGATAGATTGACATTTAGAGAAATAGAAATGA<br><br>TAAATGAGAGTGAAAAACGAAGTTCTAATTTCATGTACCTGATGGTTGAATTTCGATG<br><br>TGTCAAGTGTGATGATAAGGAATATGGTATTGTTTATTATGAAAAGGACGGTGATGAA<br><br>TCATCTCCAATTTTAACAAGTTTTGAATTAGTGAAAGTTCCTGACCCCCAGATGTCTA<br><br>TGGAGAATTTAGTTGAGAGCAAACACCACAAGCTTGCCCGGAGTTTAAGAAGTGGACC<br><br>TTCTGACCACGATCTGAAACCCAATGCTGCCACGAGAGATCAGTTAAATATTATTGTG<br><br>AGTTATCCACCAACCAAGCAACTTACATATGAAGAACAAGATCTTGTTTGGAAGTTTA<br><br>GATATTATCTTACGAATCAAGAAAAAGCCTTGACAAAATTCTTGAAATGTGTTAATTG |

TABLE 66A-continued

NOV66 Sequence Analysis

```
GGATCTACCTCAAGAGGCCAAACAGGCCTTGGAACTTCTGGGAAAATGGAAGCCGATG
GTTATGCTGTTGCCCGGTTGCGACAGGCCGATGATGAGGATTTGTTGATGTACCTATT
ACAATTGGTCCAGGCTCTCAAATATGAAAATTTTGATGATATAAAGAATGGATTGGAA
CCTACCAAGAAGGATAGTCAGAGTTCAGTGTCAGAAAATGTGTCAAATTCTGGAATAA
ATTCTGCAGAAATAGATAGCTCCCAAATTATAACCAGCCCCCTTCCTTCAGTCTCTTC
ACCTCCTCCTGCATCAAAAACAAAAGAAGTTACAGATGGCGAAAATCTGGAACAAGAT
CTCTGTACCTTCTTGATATCGAGAGCCTGCAAAAACTCAACACTGGCTAATTATTTAT
ACTGGTATGTGATAGTGGAATGTGAAGATCAAGATACTCAGCAGAGAGATCCAAAGAC
CCATGAGATGTACTTGAACGTAATGAGAAGATTCAGCCAAGCATTGTTGAAGGGTGAT
AAGTCTGTCAGAGTTATGCGTTCTTTGCTGGCTGCACAACAGACATTTGTAGATCGGT
TGGTGCATCTAATGAAGGCAGTACAACGCGAAAGTGGAAATCGTAAGAAAAAGAATGA
GAGACTACAGGCATTGCTTGGAGATAATGAAAAGATGAATTTGTCAGATGTGGAACTT
ATCCCGTTGCCTTTAGAACCCCAAGTGAAAATTAGAGGAATAATTCCGGAAACAGCTA
CACTGTTTAAAAGTGCCCTTATGCCTGCACAGTTGTTTTTTAAGACGGAAGATGGAGG
CAAATATCCAGTTATATTTAAGCATGGAGATGATTTACGTCAAGATCAACTTATTCTT
CAAATCATTTCACTCATGGACAAGCTGTTACGGAAAGAAAATCTGGACTTGAAATTGA
CACCTTATAAGGTGTTAGCCACCAGTACAAAACATGGCTTCATGCAGTTTATCCAGTC
AGTTCCTGTGGCTGAAGTTCTTGATACAGAGGGAAGCATTCAGAACTTTTTTAGAAAA
TATGCACCAAGTGAGAATGGGCCAAATGGGATTAGTGCTGAGGTCATGGACACTTACG
TTAAAAGCTGTGCTGGATATTGCGTGATCACCTATATACTTGGAGTTGGAGACAGGCA
CCTGGATAACCTTTTGCTAACAAAAACAGTACTGGAGAAAATGAAACTGGGATTGACC
CATCAAGATGCTTGGCTCAATAAGAAAACCACGTTAGGAGCAACCTTTGTATATTGGA
GACTTCAGAGTAACCAGCAAGGAAGAGAAATCTTAATCTTCAAGTTACCATATTTTCC
AAATATTACATGGTACCTGAGTTCTGCTTCCTTGGATGTCATTGCTTAAATATAGTCT
TGAAGGGCTTGTTTTGAAATATTGTATATATTTTTTCAAATGTATACATTGTTAATAA
ATTAAGAAATGAGAAACATTCTTATTTATGTACATGTTATGAGAGTTCTGGAGGAAGT
AATATGTTGAAATAGTAAACCCTTTTAGTTTTTGAGTTTAAAAA
```

|  |  |
|---|---|
| | ORF Start: ATG at 29   ORF Stop: TAA at 2483 |
| | SEQ ID NO: 172    818 aa    MW at 93341.0kD |
| NOV66c,<br>CG93464-03 Protein Sequence | MGEAEKFHYIYSCDLDINVQLKIGSLEGKREQKSYKAVLEDPMLKFSGLYQETCSDLY<br>VTCQVFAEGKPLALPVRTSSPAFSTRWSNEWLKLPVKYPDLPRNAQVALTIWDVYGP<br>GKAVPVGGTTVSLFGKYGMFRQGMHDLKVWPNVEADGSEPTKTPORTSSTLSEDQMSR<br>LAKLTKAHRQGHMVKVDWLDRLTFREIEMINESEKRSSNFMYLMVEFRCVKCDDKEYG<br>IVYYEKDGDESSPILTSFELVKVPDPQMSMENLVESKHHKLARSLRSGPSDHDLKPNA<br>ATRDQLNIIVSYPPTKQLTYEEQDLVWKFRYYLTNQEKALTKFLKCVNWDLPQEAKQA<br>LELLGKWKPMDVEDSLELLSSHYTNPTVRRYAVARLRQADDEDLLMYLLQLVQALKYE<br>NFDDIKNGLEPTKKDSQSSVSENVSNSGINSAEIDSSQIITSPLPSVSSPPPASKTKE<br>VPDGENLEQDLCTFLISRACKNSTLANYLYWYVIVECEDQDTQQRDPKTHEMYLNVMR<br>RFSQALLKGDKSVRVMRSLLAAQQTFVDRLVHLMKAVQRESGNRKKKNERLQALLGDN<br>EKMNLSDVELIPLPLEPQVKIRGIIPETATLFKSALMPAQLFFKTEDGGKYPVIFKHG |

TABLE 66A-continued

NOV66 Sequence Analysis

```
DDLRQDQLILQIISLMDKLLRKENLDLKLTPYKVLATSTKHGFMQFIQSVPVAEVLDT

EGSIQNFFRKYAPSENGPNGISAEVMDTYVKSCAGYCVITYILGVGDRHLDNLLLTKT

VLEKMKLGLTHQDAWLNKKTTLGATFVYWRLQSNQQGREILIFKLPYFPNITWYLSSA

SLDVIA
```

Sequence comparison of the above protein sequences yields the following sequence relationships shown in Table 66B.

TABLE 66B

Comparison of NOV66a against NOV66b and NOV66c.

| Protein Sequence | NOV66a Residues/ Match Residues | Identities/Similarities for the Matched Region |
|---|---|---|
| NOV66b | 1 ... 883 | 806/883 (91%) |
|  | 1 ... 883 | 814/883 (91%) |
| NOV66c | 1 ... 754 | 687/754 (91%) |
|  | 1 ... 754 | 695/754 (92%) |

Further analysis of the NOV66a protein yielded the following properties shown in Table 66C.

TABLE 66C

Protein Sequence Properties NOV66a

| PSort analysis: | 0.4600 probability located in nucleus; 0.3000 probability located in microbody (peroxisome); 0.1000 probability located in mitochondrial matrix space; 0.1000 probability located in lysosome (lumen) |
|---|---|
| SignalP analysis: | No Known Signal Sequence Predicted |

A search of the NOV66a protein against the Geneseq database, a proprietary database that contains sequences published in patents and patent publication, yielded several homologous proteins shown in Table 66D.

TABLE 66D

Geneseq Results for NOV66a

| Geneseq Identifier | Protein/Organism/Length [Patent #, Date] | NOV66a Residues/ Match Residues | Identities/ Similarities for the Matched Region | Expect Value |
|---|---|---|---|---|
| AAM39431 | Human polypeptide SEQ ID NO 2576 - Homo sapiens, 887 aa. [WO200153312-A1, 26 Jul. 2001] | 1 ... 883<br>1 ... 883 | 844/883 (95%)<br>855/883 (96%) | 0.0 |
| AAM41217 | Human polypeptide SEQ ID NO 6148 - Homo sapiens, 901 aa. [WO200153312-A1, 26 Jul. 2001] | 1 ... 883<br>13 ... 897 | 822/885 (92%)<br>838/885 (93%) | 0.0 |
| AAW97880 | Maize phosphatidylinositol-3-kinase - Zea mays, 803 aa. [WO9905298-A1, 04 Feb. 1999] | 49 ... 883<br>32 ... 800 | 328/839 (39%)<br>475/839 (56%) | e-163 |
| AAG00176 | Human secreted protein, SEQ ID NO: 4257 - Homo sapiens, 149 aa. [EP1033401-A2, 06 Sep. 2000] | 358 ... 506<br>1 ... 149 | 149/149 (100%)<br>149/149 (100%) | 1e-80 |
| AAR46552 | Human PITR-c, 127 aa. [WO9321328-A, 28 Oct. 1993] | 638 ... 764<br>1 ... 127 | 126/127 (99%)<br>127/127 (99%) | 1e-67 |

In a BLAST search of public sequence datbases, the NOV66a protein was found to have homology to the proteins shown in the BLASTP data in Table 66E.

TABLE 66E

Public BLASTP Results for NOV66a

| Protein Accession Number | Protein/Organism/Length | NOV66a Residues/ Match Residues | Identities/ Similarities for the Matched Portion | Expect Value |
|---|---|---|---|---|
| O88763 | PHOSPHATIDYLINOSITOL 3-KINASE - *Rattus norvegicus* (Rat), 887 aa. | 1 ... 883<br>1 ... 883 | 837/883 (94%)<br>858/883 (96%) | 0.0 |
| Q15134 | PHOSPHATIDYLINOSITOL 3-KINASE - *Homo sapiens* (Human), 887 aa. | 1 ... 883<br>1 ... 883 | 820/883 (92%)<br>836/883 (93%) | 0.0 |
| S57219 | phosphatidylinositol 3-kinase - human, 887 aa. | 1 ... 883<br>1 ... 883 | 819/883 (92%)<br>834/883 (93%) | 0.0 |
| AAH24675 | SIMILAR TO PHOSPHATIDYLINOSITOL 3-KINASE - *Mus musculus* (Mouse), 847 aa. | 1 ... 842<br>1 ... 841 | 792/842 (94%)<br>812/842 (96%) | 0.0 |
| Q9TXI7 | HYPOTHETICAL 103.1 KDA PROTEIN - *Caenorhabditis elegans*, 901 aa. | 23 ... 883<br>12 ... 898 | 349/915 (38%)<br>520/915 (56%) | e-154 |

PFam analysis predicts that the NOV66a protein contains the domains shown in the Table 66F.

TABLE 66F

Domain Analysis of NOV66a

| Pfam Domain | NOV66a Match Region | Identities/ Similarities for the Matched Region | Expect Value |
|---|---|---|---|
| PI3K_C2: domain 1 of 1 | 34 ... 202 | 68/197 (35%)<br>153/197 (78%) | 6.4e-64 |
| PI3Ka: domain 1 of 1 | 283 ... 530 | 88/273 (32%)<br>192/273 (70%) | 1.6e-69 |

TABLE 66F-continued

Domain Analysis of NOV66a

| Pfam Domain | NOV66a Match Region | Identities/ Similarities for the Matched Region | Expect Value |
|---|---|---|---|
| PI3_PI4_kinase: domain 1 of 1 | 630 ... 833 | 103/286 (36%)<br>191/286 (67%) | 8.4e-105 |

Example 67

The NOV67 clone was analyzed, and the nucleotide and encoded polypeptide sequences are shown in Table 67A.

TABLE 67A

NOV67 Sequence Analysis

| NOV67a, CG93495-01 DNA Sequence | SEQ ID NO: 173      5873 bp<br>CACGTGCATGTGTAGCATGCCTTGGTTTTTCCTTTGGCATCTGAAAAAGGCACAACCT<br>GAAAGACCTAGAACCCAGTGTCGGTCCCCAGGCCCTTTGGGACAGGAAGAGAAGAGCC<br>GTGTGGCCGCGGGGAGGATGTCCTGCGGCGGGGCTGTCCTCGCGGACTGACTGGACTC<br>CATCTCCCAGCGGGCGCCGCGGCGCGGCCACGCCCCCCACTCCCCGCGCGCGCCCGG<br>TGGAGACTTCGATTTTCAGAATTCCTCCTGGGAATGCTGACTCCTTGCTTGGTGCCCT<br>GATGCTTCTCTGAGATAAACTGATGAATTGGAACCATGGTGCAAAAGAAGAAGTTCTG<br>TCCTCGGTTACTTGACTATCTAGTGATCGTAGGGGCCAGGCACCCGAGCAGTGATAGC<br>GTGGCCCAGACTCCTGAATTGCTACGGCGATACCCCTTGGAGGATCACACTGAGTTTC<br>CCCTGCCCCAGATGTAGTGTTCTTCTGCCAGCCCGAGGGCTGCCTGAGCGTGCGGCA<br>GCGGCGCATGAGCCTTCGGGATGATACCTCTTTTGTCTTCACCCTCACTGACAAGGAC<br>ACTGGAGTCACGCGATATGGCATCTGTGTTAACTTCTACCGCTCCTTCCAAAAGCGAA<br>TCTCTAAGGAGAAGGGGGAAGGTGGGGCAGGGTCCCGTGGGAAGGAAGGAACCCATGC |

TABLE 67A-continued

NOV67 Sequence Analysis

```
CACCTGTGCCTCAGAAGAGGGTGGCACTGAGAGCTCAGAGAGTGGCTCATCCCTGCAG
CCTCTCAGTGCTGACTCTACCCCTGATGTGAACCAGTCTCCTCGGGGCAAACGCCGGG
CCAAGGCGGGGAGCCGCTCCCGCAACAGTACTCTCACGTCCCTGTGCGTGCTCAGCCA
CTACCCTTTCTTCTCCACCTTCCGAGAGTGTTTGTATACTCTCAAGCGCCTGGTGGAC
TGCTGTAGTGAGCGCCTTCTGGGCAAGAAACTGGGCATCCCTCGAGGCGTACAAAGGG
ACACCATGTGGCGGATCTTTACTGGATCGCTGCTGGTAGAGGAGAAGTCAAGTGCCCT
TCTGCATGACCTTCGAGAGATTGAGGCCTGGATCTATCGATTGCTGCGCTCCCCAGTA
CCCGTCTCTGGGCAGAAGCGAGTAGACATCGAGGTCCTACCCCAAGAGCTCCAGCCAG
CTCTGACCTTTGCTCTTCCAGACCCATCTCGATTCACCCTAGTGGATTTCCCACTGCA
CCTTCCCTTGGAACTTCTAGGTGTGGACGCCTGTCTCCAGGTGCTAACCTGCATTCTG
TTAGAGCACAAGGTGGTGCTACAGTCCCGAGACTACAATGCACTCTCCATGTCTGTGA
TGGCATTCGTGGCAATGATCTACCCACTGGAATATATGTTTCCTGTCATCCCGCTGCT
ACCCACCTGCATGGCATCAGCAGAGCAGCTGCTGTTGGCTCCAACCCCGTACATCATT
GGGGTTCCTGCCAGCTTCTTCCTCTACAAACTGGACTTCAAAATGCCTGATGATGTAT
GGCTAGTGGATCTGGACAGCAATAGGGTGATTGCCCCCACCAATGCAGAAGTGCTGCC
TATCCTGCCAGAACCAGAATCACTAGAGCTGAAAAAGCATTTAAAGCAGGCCTTGGCC
AGCATGAGTCTCAACACCCAGCCCATCCTCAATCTGGAGAAATTTCATGAGGGCCAGG
AGATCCCCCTTCTCTTGGGAAGGCCTTCTAATGACCTGCAGTCCACACCGTCCACTGA
ATTCAACCCACTCATCTATGGCAATGATGTGGATTCTGTGGATGTTGCAACCAGGGTT
GCCATGGTACGGTTCTTCAATTCCGCCAACGTGCTGCAGGGATTTCAGATGCACACGC
GTACCCTGCGCCTCTTTCCTCGGCCTGTGGTAGCTTTTCAAGCTGGCTCCTTTCTAGC
CTCACGTCCCCGGCAGACTCCTTTTGCCGAGAAATTGGCCAGGACTCAGGCTGTGGAG
TACTTTGGGGAATGGATCCTTAACCCCACCAACTATGCCTTTCAGCGAATTCACAACA
ATATGTTTGATCCAGCCCTGATTGGTGACAAGCCAAAGTGGTATGCTCATCAGCTGCA
GCCTATCCACTATCGCGTCTATGACAGCAATTCCCAGCTGGCTGAGGCCCTGAGTGTA
CCACCAGAGCGGGACTCTGACTCCGAACCTACTGATGATAGTGGCAGTGATAGTATGG
ATTATGACGATTCAAGCTCTTCTTACTCCTCCCTTGGTGACTTTGTCAGTGAAATGAT
GAAATGTGACATTAATGGTGATACTCCCAATGTGGACCCTCTGACACATGCAGCACTG
GGGGATGCCAGCGAGGTGGAGATTGACGAGCTGCAGAATCAGAAGGAAGCAGAAGAGC
CTGGCCCAGACAGTGAGAACTCTCAGGAAAACCCCCCACTGCGCTCCAGCTCTAGCAC
CACAGCCAGCAGCAGCCCCAGCACTGTCATCCACGGAGCCAACTCTGAACCTGCTGAC
TCTACGGAGATGGATGATAAGGCAGCAGTAGGCGTCTCCAAGCCCCTCCCTTCCGTGC
CTCCCAGCATTGGCAAATCGGACGTGGACAGACGTCAGGCAGAAATTGGAGAGGGGGC
TCAAAAGCTGCTGCGGCCCAACAGCTTGAGACTGGCAAGTGACTGAGATGCAGAGTCA
GACTCTCGGGCAAGCTCTCCCAACTCCACCGTCTCCAACACCAGCACCGAGGGCTTCG
GGGGCATCATGTCTTTTGCCAGCAGCCTCTATCGGAACCACAGTACCAGCTTCAGTCT
TTCAAACCTCACACTGCCCACCAAAGGTGCCCGAGAGAAGGCCACGCCCTTCCCCAGT
CTGAAAGGAAACAGGAGGGCGTTAGTGGATCAGAAGTCATCTGTCATTAAACACAGCC
CAACAGTGAAAAGAGAACCTCCATCACCCCAGGGTCGATCCAGCAATTCTAGTGAGAA
```

TABLE 67A-continued

NOV67 Sequence Analysis

CCAGCAGTTCCTGAAGGAGGTGGTGCACAGCGTGCTGGACGGCCAGGGAGTTGGCTGG

CTCAACATGAAAAAGGTGCGCCGGCTGCTGGAGAGCGAGCAGCTGCGAGTTCTTGTCC

TGAGCAAGCTGAACCGCATGGTGCAGTCAGAGGACGATGCCCGGCAGGACATCATCCC

GGATGTGGAGATCAGTCGGAAGGTGTACAAGGGAATGTTAGACCTCCTCAAGTGTACA

GTCCTCAGCTTGGAGCAGTCCTATGCCCACGCGGGTCTGGGTGGCATGGCCAGCATCT

TTGGGCTTTTGGAGATTGCCCAGACCCACTACTATAGTAAAGAACCAGACAAGCGGAA

GAGAAGTCCAACAGAAAGTGTAAATACCCCAGTTGGCAAGGATCCTGGCCTAGCTGGG

CGGGGGGACCCAAAGGCTATGGCACAACTGAGAGTTCCACAACTGGGACCTCGGGCAC

CAAGTGCCACAGGAAAGGGTCCTAAGGAACTGGACACCAGAAGTTTAAAGGAAGAAAA

TTTTATAGCATCTATTGGGCCTGAAGTAATCAAACCTGTCTTTGACCTTGGTGAGACA

GAGGAGAAAAAGTCCCAGATCAGCGCAGACAGTGGTGTGAGCCTGACGTCTAGTTCCC

AGAGGACTGATCAAGACTCTGTCATCGGCGTGAGTCCAGCTGTTATGATCCGCAGCTC

AAGTCAGGATTCTGAAGTTAGCACCGTGGTGAGTAATAGCTCTGGAGAGACCCTTGGA

GCTGACAGTGACTTGAGCAGCAATGCAGGTGATGGACCAGGTGGCGAGGGCAGTGTTC

ACCTGGCAAGCTCTCGGGGCACTTTGTCTGATAGTGAAATTGAGACCAACTCTGCCAC

AAGCACCATCTTTGGTAAAGCCCACAGCTTGAAGCCAAGCATAAAGGAGAAGCTGGCA

GGCAGCCCCATTCGTACTTCTGAAGATGTGAGCCAGCGAGTCTATCTCTATGAGGGAC

TCCTAGGCAAAGAGCGTTCTACTTTATGGGACCAAATGCAATTCTGGGAAGATGCCTT

CTTAGATGCTGTGATGTTGGAGAGAGAAGGGATGGGTATGGACCAGGGTCCCCAGGAA

ATGATCGACAGGTACCTGTCCCTTGGAGAACATGACCGGAAGCGCCTGGAAGATGATG

AAGATCGCTTGCTGGCCACACTTCTGCACAACCTCATCTCCTACATGCTGCTGATGAA

GGTAAATAAGAATGACATCCGCAAGAAGGTGAGGCGCCTAATGGGAAAGTCGCACATT

GGGCTTGTGTACAGCCAGCAAATCAATGAGGTGCTTGATCAGCTGGCGAACCTGAATG

GACGCGATCTCTCTATCTGGTCCAGTGGCAGCCGGCACATGAAGAAGCAGACATTTGT

GGTACATGCAGGGACAGATACAAACGGAGATATCTTTTTCATGGAGGTGTGCGATGAC

TGTGTGGTGTTGCGTAGTAACATCGGAACAGTGTATGAGCGCTGGTGGTACGAGAAGC

TCATCAACATGACCTACTGTCCCAAGACGAAGGTGTTGTGCTTGTGGCGTAGAAATGG

CTCTGAGACCCAGCTCAACAAGTTCTATACTAAAAAGTGTCGGGAGCTGTACTACTGT

GTGAAGGACAGCATGGAGCGCGCTGCCGCCCGACAGCAAAGCATCAAACCCGGACCTG

AATTGGGTGGCGAGTTCCCTGTGCAGGACCTGAAGACTGGTGAGGGTGGCCTGCTGCA

GGTGACCCTGGAAGGGATCAACCTCAAATTCATGCACAATCACGTTTTCATAGAGCTG

AATCACATTAAAAAGTGCAATACAGTTCGACGCGTCTTTGTCCTGGAGGAATTTGTTC

CTGAAATTAAAGAAGTGGTGAGCCACAAGTACAAGACACCAATGGCCCACGAAATCTG

CTACTCCGTATTATGTCTCTTCTCGTACGTGGCTGCAGTTCATAGCAGTGAGGAAGAT

CTCAGAACCCCGCCCCGGCCTGTCTCTAGCTGA<u>TGGAGAGGGGCTACGCAGCTGCCCC</u>

<u>AGCCCAGGGCACGCCCCTGGCCCCTTGCTGTTCCCAAGTGCACGATGCTGCTGTGACT</u>

<u>GAGGAGTGGATGATGCTCGTGTGTCCTCTGCAAGCCCCCTGCTGTGGCTTGGTTGGTT</u>

<u>ACCGGTTATGTGTCCCTCTGAGTCTGTCTTGAGCGTGTCCACCTTCTCCCTCTCCACT</u>

<u>CCCAGAAGACCAAACTGCCTTCCCCTCAGGGCTCAAGAATGTGTACAGTCTGTGGGGC</u>

TABLE 67A-continued

NOV67 Sequence Analysis

CGGTGTGAACCCACTATTTTGTGTCCTTGAGACATTTGTGTTGTGGTTCCTTGTCCTT
GTCCCTGGCGTTATAACTGTCCACTGCAAGAGTCTGGCTCTCCCTTCTCTGTGACCCG
GCATGACTGGGCGCCTGGAGCAGTTTCACTCTGTGAGGAGTGAGGGAACCCTGGGGCT
CACCCTCTCAGAGGAAGGGCACAGAGAGGAAGGGAAGAATTGGGGGGCAGCCGGAGTG
AGTGGCAGCCTCCCTGCTTCCTTGTGCATTCCCAAGCCGGCAGCTACTGCCCACGGCC
CGCAGTGTTGGCTGCTGCCTGCCACAGCCTCTGTGACTGCAGTGGAGCGGCGAATTCC
CTGTGGCCTGCCACGCCTTCGGCATCAGAGGATGGAGTGGTCGAGGCTAGTGGAGTCC
CAGGGACCGCTGGCTGCTCTGCCTGAGCATCAGGGAGGGGCAGGAAAGACCAAGCTG
GGTTTGCACATCTGTCTGCAGGCTGTCTCTCCAGGCACCGGGTGTCACGAGGGAGAGA
CAGCCTGGGTATGGGCAAGAAATGACTGTAAATATTTCAGCCCCACATTATTTATAGA
AAATGTACAGTTGTGTGAATGTGAAATAAATGTCCTCAACTCCCAAAAAAAAAAAAAA
AAAAAAAAAAAAAA

ORF Start: ATG at 326   ORF Stop: TGA at 4961
SEQ ID NO: 174   1545 aa   MW at 171357.1kD NOV67a,
CG93495-01 Protein Sequence MVQKKKFCPRLLDYLVIVGARHPSSDSVAQTPELLRRYPLEDHTEFPLPPDVVFFCQP
EGCLSVRQRRMSLRDDTSFVFTLTDKDTGVTRYGICVNFYRSFQKRISKEKGEGGAGS
RGKEGTHATCASEEGGTESSESGSSLQPLSADSTPDVNQSPRGKRRAKAGSRSRNSTL
TSLCVLSHYPFFSTFRECLYTLKRLVDCCSERLLGKKLGIPRGVQRDTMWRIFTGSLL
VEEKSSALLHDLREIEAWIYRLLRSPVPVSGQKRVDIEVLPQELQPALTFALPDPSRF
TLVDFPLHLPLELLGVDACLQVLTCILLEHKVVLQSRDYNALSMSVMAFVAMIYPLEY
MFPVIPLLPTCMASAEQLLLAPTPYIIGVPASFFLYKLDFKMPDDVWLVDLDSNRVIA
PTNAEVLPILPEPESLELKKHLKQALASMSLNTQPILNLEKFHEGQBIPLLLGRPSND
LQSTPSTEFNPLIYGNDVDSVDVATRVAMVRFFNSANVLQGFQMHTRTLRLFPRPVVA
FQAGSFLASRPRQTPFAEKLARTQAVEYFGEWILNPTNYAFQRIHNNMFDPALIGDKP
KWYAHQLQPIHYRVYDSNSQLAEALSVPPERDSDSEPTDDSGSDSMDYDDSSSSYSSL
GDFVSEMMKCDINGDTPNVDPLTHAALGDASEVEIDELQNQKEAEEPGPDSENSQENP
PLRSSSSTTASSSPSTVIHGANSEPADSTEMDDKAAVGVSKPLPSVPPSIGKSDVDRR
QAEIGEGAQKLLRPNSLRLASDSDAESDSRASSPNSTVSNTSTEGFGGIMSFASSLYR
NHSTSFSLSNLTLPTKGAREKATPFPSLKGNRRALVDQKSSVIKHSPTVKREPPSPQG
RSSNSSENQQFLKEVVHSVLDGQGVGWLNMKKVRRLLESEQLRVLVLSKLNRMVQSED
DARQDIIPDVEISRKVYKGMLDLLKCTVLSLEQSYAHAGLGGMASIFGLLEIAQTHYY
SKEPDKRKRSPTESVNTPVGKDPGLAGRGDPKAMAQLRVPQLGPRAPSATGKGPKELD
TRSLKEENFIASAGPEVIKPVFDLGETEEKKSQISADSGVSLTSSSQRTDQDSVIGVS
PAVMIRSSSQDSEVSTVVSNSSGETLGADSDLSSNAGDGPGGEGSVHLASSRGTLSDS
EIETNSATSTIFGKAHSLKPSIKEKLAGSPIRTSEDVSQRVYLYEGLLGKERSTLWDQ
MQFWEDAFLDAVMLEREGMGMDQGPQEMIDRYLSLGEHDRKRLEDDEDRLLATLLHNL
ISYMLLMKVNKNDIRKKVRRLMGKSHIGLVYSQQINEVLDQLANLNGRDLSIWSSGSR
HMKKQTFVVHAGTDTNGDIFFMEVCDDCVVLRSNIGTVYERWWYEKLINMTYCPKTKV

TABLE 67A-continued

NOV67 Sequence Analysis

LCLWRRNGSETQLNKFYTKKCRELYYCVKDSMERAAARQQSIKPGPELGGEFPVQDLK

TGEGGLLQVTLEGINLKFMHNQVFIELNHIKKCNTVRGVFVLEEFVPEIKEVVSHKYK

TPMAHEICYSVLCLFSYVAAVHSSEEDLRTPPRPVSS

Further analysis of the NOV67a protein yielded the following properties shown in Table 67B.

TABLE 67B

Protein Sequence Properties NOV67a

| | |
|---|---|
| PSort analysis: | 0.8200 probability located in endoplasmic reticulum (membrane); 0.1900 probability located in plasma membrane; 0.1000 probability located in endoplasmic reticulum (lumen); 0.1000 probability located in outside |
| SignalP analysis: | No Known Signal Sequence Predicted |

A search of the NOV67a protein against the Geneseq database, a proprietary database that contains sequences published in patents and patent publication, yielded several homologous proteins shown in Table 67C.

TABLE 67C

Geneseq Results for NOV67a

| Geneseq Identifier | Protein/Organism/Length [Patent #, Date] | NOV67a Residues/ Match Residues | Identities/ Similarities for the Matched Region | Expect Value |
|---|---|---|---|---|
| AAW35576 | TNF-R1-DD ligand protein clone 57TU4A - *Homo sapiens*, 1588 aa. [WO9730084-A1, 21 Aug. 1997] | 1 . . . 1545<br>1 . . . 1588 | 1542/1588 (97%)<br>1544/1588 (97%) | 0.0 |
| AAW64453 | Rat brain Rab3 GEP protein - *Rattus sp*, 1602 aa. [EP856583-A2, 05 Aug. 1998] | 1 . . . 1545<br>1 . . . 1602 | 1477/1609 (91%)<br>1501/1609 (92%) | 0.0 |
| AAB37805 | Human TNF receptor death domain ligand protein #4 - *Homo sapiens*, 607 aa. [WO200064479-A1, 02 Nov. 2000] | 939 . . . 1545<br>1 . . . 607 | 607/607 (100%)<br>607/607 (100%) | 0.0 |
| AAW35574 | TNF-R1-DD ligand protein clone 27TU - *Homo sapiens*, 607 aa. [WO9730084-A1, 21 Aug. 1997] | 939 . . . 1545<br>1 . . . 607 | 607/607 (100%)<br>607/607 (100%) | 0.0 |
| AAR95331 | Tumor necrosis factor receptor 1 death domain ligand (clone 27TU) - *Homo sapiens*, 607 aa. [WO9612735-A1, 02 May 1996] | 939 . . . 1545<br>1 . . . 607 | 607/607 (100%)<br>607/607 (100%) | 0.0 |

In a BLAST search of public sequence datbases, the NOV67a protein was found to have homology to the proteins shown in the BLASTP data in Table 67D.

TABLE 67D

Public BLASTP Results for NOV67a

| Protein Accession Number | Protein/Organism/Length | NOV67a Residues/ Match Residues | Identities/ Similarities for the Matched Portion | Expect Value |
|---|---|---|---|---|
| AAL40268 | INSULINOMA-GLUCAGONOMA PROTEIN 20 SPLICE VARIANT 3 - *Homo sapiens* (Human), 1545 aa. | 1 . . . 1545<br>1 . . . 1545 | 1538/1545 (99%)<br>1540/1545 (99%) | 0.0 |
| AAL40267 | INSULINOMA-GLUCAGONOMA PROTEIN 20 SPLICE VARIANT 2 - *Homo sapiens* (Human), 1565 aa. | 1 . . . 1545<br>1 . . . 1565 | 1538/1565 (98%)<br>1540/1565 (98%) | 0.0 |

TABLE 67D-continued

Public BLASTP Results for NOV67a

| Protein Accession Number | Protein/Organism/Length | NOV67a Residues/ Match Residues | Identities/ Similarities for the Matched Portion | Expect Value |
|---|---|---|---|---|
| O15293 | MAP KINASE-ACTIVATING DEATH DOMAIN PROTEIN - *Homo sapiens* (Human), 1588 aa. | 1 . . . 1545<br>1 . . . 1588 | 1542/1588 (97%)<br>1544/1588 (97%) | 0.0 |
| AAL35261 | INSULINOMA- GLUCAGONOMA PROTEIN 20 SPLICE VARIANT 4 - *Homo sapiens* (Human), 1479 aa. | 1 . . . 1477<br>1 . . . 1476 | 1467/1477 (99%)<br>1471/1477 (99%) | 0.0 |
| O08873 | RAB3 GDP/GTP EXCHANGE PROTEIN - *Rattus norvegicus* (Rat), 1602 aa. | 1 . . . 1545<br>1 . . . 1602 | 1477/1609 (91%)<br>1501/1609 (92%) | 0.0 |

PFam analysis predicts that the NOV67a protein contains the domains shown in the Table 67E.

TABLE 67E

Domain Analysis of NOV67a

| Pfam Domain | NOV67a Match Region | Identities/ Similarities for the Matched Region | Expect Value |
|---|---|---|---|
| DENN: domain 1 of 1 | 254 . . . 402 | 83/154 (54%)<br>147/154 (95%) | 7e−86 |
| Latrophilin: domain 1 of 1 | 759 . . . 1048 | 83/419 (20%)<br>142/419 (34%) | 4.4 |
| Ribosomal_L14: domain 1 of 1 | 1046 . . . 1062 | 9/19 (47%)<br>15/19 (79%) | 5 |
| Ribosomal_L30: domain 1 of 1 | 1460 . . . 1478 | 6/19 (32%)<br>17/19 (89%) | 6.4 |

Example 68

The NOV68 clone was analyzed, and the nucleotide and encoded polypeptide sequences are shown in Table 68A.

TABLE 68A

NOV68 Sequence Analysis

| NOV68a,<br>CG93529-01 DNA Sequence | SEQ ID NO: 175    6327 bp<br>ATGGCCTTCTGGACACAGCTGATGCTGCTGCTCTGGAAGAATTTCATGTATCGCCGGA<br>GGACAGCCGGTCCAGCTCCTGGTCGAATTGCTGTGGCCTCTCTTCCTCTTCTTCATCCT<br>GGTGGCTGTTCGCCACTCCCACCCGCCCCTGGAGCACCATGAATGCCACTTCCCAAAC<br>GAAGCCACTGCCATCGGCGGGCACCGTGCCCTGGCTCCAGGGTCTCATCTGTAATGTGA<br>GACAACACCTGCTTTCCGCAGCTGACACCGGGCGAGGAGCCCGGGCGCCTGAGCAACTT<br>GCAACGACTCCCTGGTCTCCCGGCTGCTAGCCGATGCCCGCACTGTGCTGGGAGGGGCC<br>GAGTGCCCACAGGACGCTGGCTGGCCTAGGGAAGCTGATCGCCACGCTGAGGGCTGCAC<br>GGCAGCACGGCCCAGCCTCAACCAACCAAGCAGTCTCCACTGGAACCACCCATGCTGGA<br>GTGTCGCGGAGCTGCTGACGTCACTGCTGCGCACGGAATCCCTGGGGTTGGCACTGGGC<br>GCAAGCCCAGGAGCCCTTGCACAGCTTGTTGGAGGCCGCTGAGGACCTGGCCCAGGAGC<br>GTCCTGGCGCTGCGCAGCCTGGTGGAGCTTCGGGCACTGCTGCAGAGACCCCGAGGGAC<br>GCAGCGGCCCCTGGAGTTGCTGTCAGAGGCCCTCTGCAGTGTCAGGGGACCTAGCAGC<br>GACAGTGGGCCCCTCCCTCAACTGGTACGAGGCTAGTGACCTGATGGAGCTGGTGGGGC<br>GAGGAGCCAGAATCCGCCCTGCCAGACAGCAGCCTGAGCCCCGCCTGCTCGGAGCTGAT<br>GTGGAGCCCTGGACAGCCACCCGCTGTCCCGCCTGCTCTGGAGACGCCTGAAGCCTCTG<br>GATCCTCGGGAAGCTACTCTTTGCACCAGATACACCTTTTACCCGGAAGCTCATGGCCC |

TABLE 68A-continued

NOV68 Sequence Analysis

GAGGTCAACCGGACCTTCGAGGAGCTCACCCTGCTGAGGGATGTCCGGGAGGTGTGGGA

GGATGCTGGGACCCCGGATCTTCACCTTCATGAACGACAGTTCCAATGTGGCCATGCTG

GCAGCGGCTCCTGCAGATGCAGGATGAAGGAAGAAGGCAGCCCAGACCTGGAGGCCGGG

GACCACATGGAGGCCCTGCGATCCTTTCTGGACCCTGGGAGCGGTGGCTACAGCTGGCA

GGGACGCACACGCTGATGTGGGGCACCTGGTGGGCACGCTGGGCCGAGTGACGGAGTGC

GCTGTCCTTGGACAAGCTGGAGGCGGCACCCTCAGAGGCAGCCCTGGTGTCGCGGGCCC

GTGCAACTGCTCGCGGAACATCGATTCTGGGCCGGCGTCGTCTTCTTGGGACCTGAGGA

GCTCTTCAGACCCCACAGAGCACCCAACCCCAGACCTGGGCCCCGGCCACGTGCGCATC

GAAAATCCGCATGGACATTGACGTGGTCACGAGGACCAATAAGATCAGGGACAGGTTTT

GGGGACCCTGGCCCAGCCGCGGACCCCCTGACCGACCTGCGCTACGTGTGGGGCGGCTT

GCGTGTACCTGCAAGACCTGGTGGAGCGTGCAGCCGTCCGCGTGCTCAGCGGCGCCAAC

GCCCCGGGCCGGCCTCTACCTGCAGCAGATGCCCTATCCGTGCTATGTGGACGACGTGT

GTCCTGCGTGTGCTGAGCCGGTCGCTGCCGCTCTTCCTGACGCTGGCCTGGATCTACTC

GCGTGACACTGACAGTGAAGGCCGTGGTGCGGGAGAAGGAGACGCGGCTGCGGGACACC

GATGCGCGCCATGGGCTCAGCCGCGCGGTGCTCTGGCTAGGCTGGTTCCTCAGCTGCC

GTCGGGCCCTTCCTGCTCAGCGCCGCACTGCTGGTTCTGGTGCTCAAGCTGGGAGACAT

GCCTCCCCTACAGCCACCCGGGCGTGGTCTTCCTGTTCTTGGCAGCCTTCGCGGTGGCC

GACGGTGACCCAGAGCTTCCTGCTCAGCGCCTTCTTCTCCCGCGCCAACCTGGCTGCGG

GCCTGCGGCGGCCTGGCCTACTTCTCCCTCTACCTGCCCTACGTGCTGTGTGTGGCTTG

GGCGGGACCGGCTGCCCGCGGGTGGCCGCGTGGCCGCGAGCCTGCTGTCGCCCGTGGCC

GTTCGGCTTCGGCTGCGAGAGCCTGGCTCTGCTGGAGGAGCAGGGCGAGGGCGCGCAGT

GGGCACAACGTGGGCACCCGGCCTACGGCAGACGTCTTCAGCCTGGCCCAGGTCTCTGG

GCCTTCTGCTGCTGGACGCGGCGCTCTACGGCCTCGCCACCTGGTACCTGGAAGCTGTG

GTGCCCAGGCCAGTACGGGATCCCTGAACCATGGAATTTTCCTTTTCGGAGGAGCTACT

GGGTGCGGACCTCGGCCCCCCAAGAGTCCAGCCCCTTGCCCCACCCCGCTGGACCCAAA

GGGTGCTGGTAGAAGAGGCACCGCCCGGCCTGAGTCCTGGCGTCTCCGTTCGCAGCCTG

GGAGAAGCGCTTTCCTGGAAGCCCGCAGCCAGCCCTGCGGGGGCTCAGCCTGGACTTCT

GACCAGGGCCACATCACCGCCTTCCTGGGCCACAACGGGGCCGGCAAGACCACCACCCT

GGTCCATCTTGAGTGGCCTCTTCCCACCCAGTGGTGGCTCTGCCTTCATCCTGGGCCAC

GGACGTCCGCTCCAGCATGGCCGCCATCCGGCCCCACCTGGGCGTCTGTCCTCAGTACA

GACGTGCTGTTTGACATGCTGACCGTGGACGAGCACGTCTGGTTCTATGGGCGGCTGAA

GGGGTCTGAGTGCCGCTGTAGTGGGCCCCGAGCAGGACCGTCTGCTGCAGGATGTGGGG

GCTGGTCTCCAAGCACAGTGTGCAGACTCGCCACCTCTCTGGTGGGATGCAACGGAAGC

GTGTCCGTGGCCATTGCCTTTGTGGGCGGCTCCCAAGTTGTTATCCTGGACGAGCCTAC

GGGCTGGCGTGGATCCTGCTTCCCGCCGCGGTATTTGGGAGCTGCTGCTCAAATACCGA

GGAAGGTCGCACGCTGATCCTCTCCACCCACCACCTGGATGAGGCAGAGCTGCTGGGAG

GACCGTGTGGCTGTGGTGGCAGGTGGCCGCTTGTGCTGCTGTGGCTCCCCACTCTTCCT

GGCGCCGTCACCTGGGCTCCGGCTACTACCTGACGCTGGTGAAGGCCCGCCTGCCCCTG

GACCACCAATGAGAAGGCTGACACTGACATGGAGGGCAGTGTGGACACCAGGCAGGAAA

TABLE 68A-continued

NOV68 Sequence Analysis

GAGAAGAATGGCAGCCAGGGCAGCAGAGTCGGCACTCCTCAGCTGCTGGCCCTGGTACA

GGCACTGGGTGCCCGGGGCACGGCTGGTGGAGGAGCTGCCACACGAGCTGGTGCTGGTG

GCTGCCCTACACGGGTGCCCATGACGGCAGCTTCGCCACACTCTTCCGAGAGCTAGACA

GCGCGGCTGGCGGAGCTGAGGCTCACTGGCTACGGGATCTCCGACACCAGCCTCGAGGA

GGATCTTCCTGAAGGTGGTGGAGGAGTGTGCTGCGGACACAGATATGGAGGATGGCAGC

GTGCGGGCAGCACCTATGCACAGGCATTGCTGGCCTAGACGTAACCCTGCGGCTCAAGA

GTGCCGCCACAGGAGACAGCGCTGGAGAACGGGGAACCAGCTGGGTCAGCCCCAGAGAC

GTGACCAGGGCTCTGGGCCAGACGCCGTGGGCCCGGTACAGGGCTGGGCACTGACCCGC

GCAGCAGCTCCAGGCCCTGCTTCTCAAGCGCTTTCTGCTTGCCCGCCGCAGCCGCCGCG

GGCCTGTTCGCCCAGATCGTGCTGCCTGCCCTCTTTGTGGGCCTGGCCCTCGTGTTCAG

GCCTCATCGTGCCTCCTTTCGGGCACTACCCGGCTCTGCGGCTCAGTCCCACCATGTAC

GGGTGCTCAGGTGTCCTTCTTCAGTGAGGACGCCCCAGGGGACCCTGGACGTGCCCGGC

GTGCTCGAGGCGCTGCTGCAGGAGGCAGGACTGGAGGAGCCCCCAGTGCAGCATAGCTC

GCCACAGGTTCTCGGCACCAGAAGTTCCTGCTGAAGTGGCCAAGGTCTTGGCCAGTGGC

GAACTGGACCCCAGAGTCTCCATCCCCAGCCTGCCAGTGTAGCCAGCCCGGTGCCCGGC

GGCCTGCTGCCCGACTGCCCGGCTGCAGCTGGTGGTCCCCCTCCGCCCCAGGCAGTGAC

GCGGCTCTGGGGAAGTGGTTCAGAACCTGACAGGCCGGAACCTGTCTGACTTCCTGGTC

GAAGACCTACCCGCGCCTGGTGCGCCAGGGCCTGAAGACTAAGAAGTGGGTGAATGAGG

GTCAGGTACGGAGGCTTCTCGCTGGGGGGCCGAGACCCAGGCCTGCCCTCTGGCCAAGA

GGTTGGGCCGCTCAGTGGAGGAGTTGTGGGCGCTGCTGAGTCCCCTGCCTGGCGGGGCC

GCTCGACCGTGTCCTGAAAAAACCTCACAGCCTGGGCTCACAGCCTGGATGCTCAGGACA

GGTCTCAAGATCTGGTTCAACAACAAAGGCTGGCACTCCATGGTGACCTTTGTCAACCG

GAGCCAGCAACGCAATCCTCCGTGCTCACCTGCCCCCAGGCCCGGCCCGCCACGCCCAC

GAGCATCACCACACTCAACCACCCCTTGAACCTCACCAAGGAGCAGCTGTCTGAGGCTG

GCACTGATGGCCTCCTCGGTGGACGTCCTCGTCTCCATCTGTGTGGTCTTTGCCATGTC

GCTTTGTCCCGGCCAGCTTCACTCTTGTCCTCATTGAGGAGCGAGTCACCCGGGCCAAG

GCACCTGCAGCTCATGGGGGCCTGTCCCCACCCTCTACTGGCTTGGCAACTTTCTCT

GGGGACATGAAGCTGCAGGAGGTGAGCCGGATCTTGAAACAGGTCTTCCTTATCTTCCC

GCCACTTCTGCTTGGGCCGGGGGCTCATTGACATGGTGCGGAACCAGGCCATGGCTGAT

GGCCTTTGAGCGCTTGGGAGACAGGCAGTTCCAGTCACCCCTGCGCTGGGAGGTGGTCG

GGCAAGAACCTCTTGGCCATGGTGATACAGGGGCCCCTCTTCCTTCTCTTCACACTACT

GGCTGCAGCACGAAGCCAACTTCCTGCCACAGCCCAGGGTGAGGTCTCTGCCACTCCTG

GGGAGAGGAGGACGAGGATGTAGCCCGTGAACGGGAGCGGGTGGTCCAAGGAGCCACCC

GAGGGGGATGTGTTGGTGCTGAGGAACTTGACCAAGGTATACCGTGGGCAGAGGATGCC

GACCTGTTGACCGCTTGTGCCTGGGGATTCCCCCTGGTGAGTGTTTTGGGCTGCTGGGT

GGTGAATGGAGCAGGGAAGACGTCCACGTTTCGCATGGTGACGGGGACACATTGGCCA

GGCAGGGGCGAGGCTGTGCTGGCAGGCCACAGCGTGGCCCGGGAACCCAGTGCTGCGCA

GCCTCAGCATGGGATACTGCCCTCAATCCGATGCCATCTTTGAGCTGCTGACGGGCCGC

GGAGCACCTGGAGCTGCTTGCGCGCCTGCGCGGTGTCCCGGAGGCCCAGGTTGCCCAGA

TABLE 68A-continued

NOV68 Sequence Analysis

```
GCCGCTGGCTCGGGCCTGGCGCGTCTGGGACTCTCATGGTACGCAGACCGGCCTGCAGG
GCACCTACAGCGGAGGCAACAAACGCAAGCTGGCGACGGCCCTGGCGCTGGTTGGGGAC
GCCAGCCGTGGTGTTTCTGGACGAGCCGACCACAGGCATGGACCCCAGCGCGCGGCGCT
GTCCTTTGGAACAGCCTTTTGGCCGTGGTGCGGGAGGGCCGTTCAGTGATGCTCACCTC
GCCATAGCATGGAGGAGTGTGAAGCGCTCTGCTCGCGCCTAGCCATCATGGTGAATGGG
GCGGTTCCGCTGCCTGGGCAGCCCGCAACATCTCAAGGGCAGATTCGCGGCGGGTCACA
GCACTGACCCTGCGGGTGCCCGCCGCAAGGTCCCAGCCGGCAGCGGCCTTCGTGGCGGC
GCGAGTTCCCTGGGTCGGAGCTGCGCGAGGCACATGGAGGCCGCCTGCGCTTCCAGCTG
GCCGCCGGGAGGGCGCTGCGCCCTGGCGCGCGTCTTTGGAGAGCTGGCGGTGCACGGCG
GCAGAGCACGGCGTGGAGGACTTTTCCGTGAGCCAGACGATGCTGGAGGAGGTATTCTT
GGTACTTCTCCAAGGACCAGGGGAAGGACGAGGACACCGAAGAGCAGAAGGAGGCAGGA
GGTGGGAGTGGACCCCGCGCCAGGCCTGCAGCACCCCAAACGCGTCAGCCAGTTCCTCG
GATGACCCTAGCACTGCCGAGACTGTGCTCTGAGCCTCCCTCCCCTGCGGGGCCGCGGG
GGAGGCCCTGGGAATGGCAAGGGCAAGGTAGAGTGCCTAGGAGCCCTGGACTCAGGCTG
GGCAGAGGGGCTGGTGCCCTGGAGAAAATAAAGAGAAGGCTGGAGAGAAGCCGTGCTTG
GGTGAA
```

NOV68a,
CG93529-01 Protein Sequence

ORF Start: ATG at 1      ORF Stop: TGA at 6178
SEQ ID NO: 176    2059 aa    MW at 224783.2kD MAFWTQLMLLLWKNFMYRRRQPVQLLVELLWPLFLFFILVAVRHSPPLEHHECHFPN
KPLPSAGTVPWLQGLICNVNNTCFPQLTPGEEPGRLSNFNDSLVSRLLADARTVLGGA
SAHRTLAGLGKLIATLRAARSTAQPQPTKQSPLEPPMLDVAELLTSLLRTESLGLALG
QAQEPLHSLLEAAEDLAQELLALRSLVELRALLQRPRGTSGPLELLSEALCSVRGPSS
TVGPSLNWYEASDLMELVGQEPESALPDSSLSPACSELIGALDSHPLSRLLWRRLKPL
ILGKLLFAPDTPFTRKLMAQVNRTFEELTLLRDVREVWEMLGPRIFTFMNDSSNVAML
QRLLQNQDEGRRQPRPGGRDHMEALRSFLDPGSGGYSWQDAHADVGHLVGTLGRVTEC
LSLDKLEAAPSEAALVSRALQLLAEHRFWAGVVFLGPEDSSDPTEHPTPDLGPGHVRI
KIRMDIDVVTRTNKIRDRFWDPGPAADPLTDLRYVWGGFVYLQDLVERAAVRVLSGAN
PRAGLYLQQMPYPCYVDDVFLRVLSRSLPLFLTLAWIYSVTLTVKAVVREKETRLRDT
MRAMGLSRAVLWLGWFLSCLGPFLLSAALLVLVLKLGDILPYSHPGVVFLFLAAFAVA
TVTQSFLLSAFFSRANLAAACGGLAYFSLYLPYVLCVAWRDRLPAGGRVAASLLSPVA
FGFGCESLALLEEQGEGAQWHNVGTRPTADVFSLAQVSGLLLLDAALYGLATWYLEAV
CPGQYGIPEPWNFPFRRSYWCGPRPPKSPAPCPTPLDPKVLVEEAPPGLSPGVSVRSL
EKRFPGSPQPALRGLSLDFYQGHITAFLGHNGAGKTTTLSILSGLFPPSGGSAFILGH
DVRSSMAAIRPHLGVCPQYNVLFDMLTVDEHVWFYGRLKGLSAAVVGPEQDRLLQDVG
LVSKQSVQTRHLSGGMQRKLSVAIAFVGGSQVVILDEPTAGVDPASRRGIWELLLKYR
EGRTLILSTHHLDEAELLGDRVAVVAGGRLCCCGSPLFLRRHLGSGYYLTLVKARLPL
TTNEKADTDMEGSVDTRQEKKNGSQGSRVGTPQLLALVQHWVPGARLVEELPHELVLV
LPYTGAHDGSFATLFRELDTRLAELRLTGYGISDTSLEEIFLKVVEECAADTDMEDGS
CGQHLCTGIAGLDVTLRLKMPPQETALENGEPAGSAPETDQGSGPDAVGRVQGWALTR
QQLQALLLKRFLLARRSRRGLFAQIVLPALFVGLALVFSLIVPPFGHYPALRLSPTMY TABLE 68A-continued NOV68 Sequence Analysis

NWTPESPSPACQCSQPGARRLLPDCPAAAGGPPPPQAVTGSGEVVQNLTGRNLSDFLV

KTYPRLVRQGLKTKKWVNEVRYGGFSLGGRDPGLPSGQELGRSVEELWALLSPLPGGA

LDRVLKNLTAWAHSLDAQDSLKIWFNNKGWHSMVTFVNRASNAILRAHLPPGPARHAH

SITTLNHPLNLTKEQLSEAALMASSVDVLVSICVVFAMSFVPASFTLVLIEERVTRAK

HLQLMGGLSPTLYWLGNFLWDMKLQEVSRILKQVFLIFPHFCLGRGLIDMVRNQAMAD

AFERLGDRQFQSPLRWEVVGKNLLAMVIQGPLFLLFTLLLQHRSQLLPQPRVRSLPLL

GEEDEDVARERERVVQGATQGDVLVLRNLTKVYRGQRMPAVDRLCLGIPPGECFGLLG

VNGAGKTSTFRNVTGDTLASRGEAVLAGHSVAREPSAAHLSMGYCPQSDAIFELLTGR

EHLELLARLRGVPEAQVAQTAGSGLARLGLSWYADRPAGTYSGGNKRKLATALALVGD

PAVVFLDEPTTGMDPSARRFLWNSLLAVVREGRSVMLTSHSMEECEALCSRLAIMVNG

RFRCLGSPQHLKGRFAAGHTLTLRVPAARSQPAAAFVAAEFPGSELREAHGGRLRFQL

PPGGRCALARVFGELAVHGAEHGVEDFSVSQTMLEEVFLYFSKDQGKDEDTEEQKEAG

VGVDPAPGLQHPKRVSQFLDDPSTAETVL

Further analysis of the NOV68a protein yielded the following properties shown in Table 68B.

TABLE 68B

Protein Sequence Properties NOV68a

PSort analysis: 0.8000 probability located in plasma membrane; 0.7548 probability located in mitochondrial inner membrane; 0.6258 probability located in mitochondrial intermembrane space; 0.5172 probability located in mitochondrial matrix space TABLE 68B-continued Protein Sequence Properties NOV68a SignalP analysis: Cleavage site between residues 46 and 47

A search of the NOV68a protein against the Geneseq database, a proprietary database that contains sequences published in patents and patent publication, yielded several homologous proteins shown in Table 68C.

TABLE 68C

Geneseq Results for NOV68a

| Geneseq Identifier | Protein/Organism/Length [Patent #, Date] | NOV68a Residues/ Match Residues | Identities/ Similarities for the Matched Region | Expect Value |
| --- | --- | --- | --- | --- |
| AAU04484 | Human PD-ATP-binding cassette (PD-ABC) protein form #2 - *Homo sapiens*, 1873 aa. [WO200153490-A1, 26-Jul-2001] | 1 . . . 1588<br>1 . . . 1588 | 1585/1588 (99%)<br>1586/1588 (99%) | 0.0 |
| AAU04483 | Human PD-ATP-binding cassette (PD-ABC) protein form #1 - *Homo sapiens*, 2146 aa. [WO200153490-A1, 26-Jul-2001] | 1 . . . 1588<br>1 . . . 1588 | 1585/1588 (99%)<br>1586/1588 (99%) | 0.0 |
| AAB38114 | Human ABC1 cholesterol transporter mutant, E1172D - *Homo sapiens*, 2261 aa. [WO200055318-A2, 21-Sep-2000] | 158 . . . 1588<br>234 . . . 1707 | 732/1482 (49%)<br>982/1482 (65%) | 0.0 |
| AAB38111 | Human ABC1 cholesterol transporter mutant, V771M - *Homo sapiens*, 2261 aa. [WO200055318-A2, 21-Sep-2000] | 158 . . . 1588<br>234 . . . 1707 | 732/1482 (49%)<br>982/1482 (65%) | 0.0 |
| AAB31365 | Amino acid sequence of a human ABC1 polypeptide - *Homo sapiens*, 2261 aa. [WO200078971-A2, 28-Dec-2000] | 158 . . . 1588<br>234 . . . 1707 | 732/1482 (49%)<br>982/1482 (65%) | 0.0 |

In a BLAST search of public sequence datbases, the NOV68a protein was found to have homology to the proteins shown in the BLASTP data in Table 68D.

TABLE 68D

Public BLASTP Results for NOV68a

| Protein Accession Number | Protein/Organism/Length | NOV68a Residues/ Match Residues | Identities/ Similarities for the Matched Portion | Expect Value |
|---|---|---|---|---|
| Q9BZC4 | ABC TRANSPORTER MEMBER 7 - *Homo sapiens* (Human), 2146 aa. | 1 ... 1588<br>1 ... 1588 | 1585/1588 (99%)<br>1586/1588 (99%) | 0.0 |
| Q9NR73 | MACROPHAGE ABC TRANSPORTER - *Homo sapiens* (Human), 2146 aa. | 1 ... 1588<br>1 ... 1588 | 1585/1588 (99%)<br>1585/1588 (99%) | 0.0 |
| Q96S58 | ABCA-SSN - *Homo sapiens* (Human), 2008 aa. | 167 ... 1588<br>29 ... 1450 | 1419/1422 (99%)<br>1419/1422 (99%) | 0.0 |
| Q91V24 | ATP-BINDING CASSETTE TRANSPORTER SUB-FAMILY A MEMBER 7 - *Mus musculus* (Mouse), 2159 aa. | 1 ... 1588<br>1 ... 1602 | 1200/1625 (73%)<br>1334/1625 (81%) | 0.0 |
| AAL56247 | ATP-BINDTNG CASSETTE TRANSPORTER 1 - *Gallus gallus* (Chicken), 2260 aa. | 136 ... 1588<br>210 ... 1706 | 740/1508 (49%)<br>995/1508 (65%) | 0.0 |

PFam analysis predicts that the NOV68a protein contains the domains shown in the Table 68E.

TABLE 68E

Domain Analysis of NOV68a

| Pfam Domain | NOV68a Match Region | Identities/ Similarities for the Matched Region | Expect Value |
|---|---|---|---|
| Ca_channel_B: domain 1 of 1 | 224 ... 247 | 12/25 (48%)<br>15/25 (60%) | 1.3 |
| photoRC: domain 1 of 1 | 591 ... 608 | 9/20 (45%)<br>15/20 (75%) | 0.31 |
| SRP54: domain 1 of 2 | 832 ... 851 | 7/20 (35%)<br>15/20 (75%) | 0.28 |
| ABC_tran: domain 1 of 2 | 834 ... 1014 | 73/199 (37%)<br>139/199 (70%) | 2.3e-58 |

TABLE 68E-continued

Domain Analysis of NOV68a

| Pfam Domain | NOV68a Match Region | Identities/ Similarities for the Matched Region | Expect Value |
|---|---|---|---|
| Pterin_4a: domain 1 of 1 | 1440 ... 1539 | 25/111 (23%)<br>46/111 (41%) | 1.1 |
| SRP54: domain 2 of 2 | 1738 ... 1749 | 7/12 (58%)<br>11/12 (92%) | 13 |
| ABC_tran: domain 2 of 2 | 1733 ... 1914 | 61/199 (31%)<br>132/199 (66%) | 2.4e-39 |

Example 69

The NOV69 clone was analyzed, and the nucleotide and encoded polypeptide sequences are shown in Table 69A.

TABLE 69A

NOV69 Sequence Analysis

| | |
|---|---|
| NOV69a,<br>CG93594-01 DNA Sequence | SEQ ID NO: 177    1702 bp<br>TAATCTGGCTCAATTTCTGACACAAGAACAATATGCAGCTGAGATGAGTAAAGCTATT<br><br>GCTTTTGAGATCATTCAGAAATACGAGCCTATCGAAGAAGTTAGGAAAGCACACCAAA<br><br>TGTCATTAGAAGGTTTTACAAGATACATGGATTCACGTGAATGTCTACTGTTTAAAAA<br><br>TGAATGTAGAAAAGTTTATCAAGATATGACTCATCCATTAAATGATTATTTTATTTCA<br><br>TCTTCACATAACACATATTTGGTATCTGATCAATTATTGGGACCAAGTGACCTTTGGG<br><br>GATATGTAAGTGCCCTTGTGAAAGGATGCCGTTGTTTGGAGATTGACTGCTGGGATGG<br><br>AGCACAAAATGAACCTGTTGTATATCATGGCTACACACTCACAAGCAAACTTCTGTTT<br><br>AAAACTGTTATCCAAGCTATACACAAGTATGCATTCATGACATCTGACTACCCAGTGG<br><br>TGCTCTCTTTAGAAAATCACTGCTCCACTGCCCAACAAGAAGTAATGGCAGACAATTT |

TABLE 69A-continued

NOV69 Sequence Analysis

GCAGGCTACTTTTGGAGAGTCCTTGCTTTCTGATATGCTTGATGATTTTCCTGATACT

CTACCATCACCAGAGGCACTAAAATTCAAAATATTAGTTAAAAATAAGAAAATAGGAA

CCTTAAAGGAAACCCATGAAAGAAAAGGTTCTGATAAGCGTGGTAAGGTGGAGGAATG

GGAAGAAGAAGTGGCAGATGGAGAGGAGGAGGAGGAGGAGGAGGAGGAGGAGGAGGAG

GAGGAGGAGGATAAATTCAAAGAATCAGAAGTATTGGAATCTGTTTTAGGAGACAATC

AAGACAAGGAAACAGGGGTAAAAAGGAAGCTAAAAATTGCTCTGTCCTTATCTGATCT

TGTCATTTATACGAAAGCTGAGAAATTCAAAAGCTTTCAACATTCAAGATTATATCAG

CAATTTAATGAAAATAATTCTATTGGGGAGACACAAGCCCGAAAACTTTCAAAATTGC

GAGTCCATGAGTTTATTTTTCACACCAGGAAGTTCATTACCAGAATATATCCCAAAGC

AACAAGAGCAGACTCTTCTAATTTTAATCCCCAAGAATTTTGGAATATAGGTTGTCAA

ATGGTGGCTTTAAATTTCCAGACCCCTGGTCTGCCCATGGATCTGCAAAATGGGAAAT

TTTTGGATAATGGTGGTTCTGGATATATTTTGAAACCACATTTCTTAAGAGAGAGTAA

ATCATACTTTAACCCAAGTAACATAAAAGAGGGTATGCCAATTACACTTACAATAAGG

CTCATCAGTGGTATCCAGTTGCCTCTTACTCATTCATCATCTAACAAAGGTGATTCAT

TAGTAATTATAGAAGTTTTTGGTGTTCCAAATGATCAAATGAAGCAGCAGACTCGTGT

AATTAAAAAAAATGCTTTTAGTCCAAGATGGAATGAAACATTCACATTTATTATTCAT

GTCCCAGAATTGGCATTGATACGTTTTGTTGTTGAAGGTCAAGGTTTAATAGCAGGAA

ATGAATTTCTTGGGCAATATACTTTGCCACTTCTATGCATGAACAAAGGTTATCGTCG

TATTCCTCTGTTTTCCAGAATGGGTGAGAGCCTTGAGCCTGCTTCACTGTTTGTTTAT

GTTTGGTACGTCAGATAA<u>CAGCTAATGATAAATGACATATCATTAGCTATGCATCGCA

ATAAAACAGCCAAAATGAAT</u>

ORE Start: ATG at 44   JRF Stop: TAA at 1640
SEQ ID NO: 178        532 aa   MW at 61203.1kD NOV69a,
CG93594-01 Protein Sequence

MSKAIAFEIIQKYEPIEEVRKAHQMSLEGFTRYMDSRECLLFKNECRKVYQDMTHPLN

DYFISSSHNTYLVSDQLLGPSDLWGYVSALVKGCRCLEIDCWDGAQNEPVVYHGYTLT

SKLLFKTVIQAIHKYAFMTSDYPVVLSLENHCSTAQQEVMADNLQATFGESLLSDMLD

DFPDTLPSPEALKFKILVKNKKIGTLKETHERKGSDKRGKVEEWEEEVADGEEEEEEE

EEEEEEEDKFKESEVLESVLGDNQDKETGVKRKLKIALALSDLVIYTKAEKFKSFQH

SRLYQQFNENNSIGETQARKLSKLRVHEFIFHTRKFITRIYPKATRADSSNFNPQEFW

NIGCQMVALNFQTPGLPMDLQNGKFLDNGGSGYILKPHFLRESKSYFNPSNIKEGMPI

TLTIRLISGIQLPLTHSSSNKGDSLVIIEVFGVPNDQMKQQTRVIKKNAFSPRWNETF

TFIIHVPELALIRFVVEGQGLIAGNEFLGQYTLPLLCMNKGYRRIPLFSRMGESLEPA

SLFVYVWYVR

Further analysis of the NOV69a protein yielded the following properties shown in Table 69B.

TABLE 69B

Protein Sequence Properties NOV69a

| | |
|---|---|
| PSort analysis: | 0.4500 probability located in cytoplasm; 0.4223 probability located in microbody (peroxisome); 0.1000 probability located in mitochondrial matrix space; 0.1000 probability located in lysosome (lumen) |
| SignalP analysis: | No Known Signal Sequence Predicted |

A search of the NOV69a protein against the Geneseq database, a proprietary database that contains sequences published in patents and patent publication, yielded several homologous proteins shown in Table 69C.

TABLE 69C

Geneseq Results for NOV69a

| Geneseq Identifier | Protein/Organism/Length [Patent #, Date] | NOV69a Residues/ Match Residues | Identities/ Similarities for the Matched Region | Expect Value |
|---|---|---|---|---|
| AAM95867 | Human reproductive system related antigen SEQ ID NO: 4525 - *Homo sapiens*, 254 aa. [WO200155320-A2, 02-Aug-2001] | 279 . . . 532<br>1 . . . 254 | 253/254 (99%)<br>253/254 (99%) | e−147 |
| AAU22938 | Novel human enzyme polypeptide #24 - *Homo sapiens*, 254 aa. [WO200155301-A2, 02-Aug-2001] | 279 . . . 532<br>1 . . . 254 | 253/254 (99%)<br>253/254 (99%) | e−147 |
| AAE14268 | Human phospholipase C delta 5 (PLCD5) protein #1 - *Homo sapiens*, 762 aa. [WO200183771-A2, 08-Nov-2001] | 5 . . . 528<br>244 . . . 751 | 249/528 (47%)<br>335/528 (63%) | e−133 |
| AAE10440 | Novel human phospholipase protein #7 - *Homo sapiens*, 762 aa. [WO200168871-A2, 20-Sep-2001] | 5 . . . 528<br>244 . . . 751 | 249/528 (47%)<br>335/528 (63%) | e−133 |
| AAE14270 | Human phospholipase C delta 5 (PLCD5) protein #3 - *Homo sapiens*, 759 aa. [WO200183771-A2, 08-Nov-2001] | 5 . . . 528<br>241 . . . 748 | 247/529 (46%)<br>333/529 (62%) | e−129 |

In a BLAST search of public sequence datbases, the NOV69a protein was found to have homology to the proteins shown in the BLASTP data in Table 69D.

TABLE 69D

Public BLASTP Results for NOV69a

| Protein Accession Number | Protein/Organism/Length | NOV69a Residues/ Match Residues | Identities/ Similarities for the Matched Portion | Expect Value |
|---|---|---|---|---|
| Q95JS1 | HYPOTHETICAL 74.6 KDA PROTEIN - *Macaca fascicularis* (Crab eating macaque) (Cynomolgus monkey), 641 aa. | 1 . . . 532<br>105 . . . 641 | 503/545 (92%)<br>513/545 (93%) | 0.0 |
| Q95JS0 | HYPOTHETICAL 74.4 KDA PROTEIN - *Macaca fascicularis* (Crab eating macaque) (Cynomolgus monkey), 640 aa. | 1 . . . 532<br>105 . . . 640 | 501/545 (91%)<br>512/545 (93%) | 0.0 |
| Q96J70 | TESTIS-DEVELOPMENT RELATED NYD-SP27 - *Homo sapiens* (Human), 504 aa. | 1 . . . 532<br>1 . . . 504 | 489/545 (89%)<br>490/545 (89%) | 0.0 |
| Q9D9N4 | ADULT MALE TESTIS CDNA, RIKEN FULL-LENGTH ENRICHED LIBRARY, CLONE: 1700041H07, FULL INSERT SEQUENCE - *Mus musculus* (Mouse), 537 aa. | 8 . . . 532<br>10 . . . 536 | 388/533 (72%)<br>452/533 (84%) | 0.0 |
| Q9BRC7 | HYPOTHETICAL 87.6 KDA PROTEIN - *Homo sapiens* (Human), 762 aa. | 5 . . . 528<br>244 . . . 751 | 249/528 (47%)<br>335/528 (63%) | e−133 |

PFam analysis predicts that the NOV69a protein contains the domains shown in the Table 69E.

TABLE 69E

Domain Analysis of NOV69a

| Pfam Domain | NOV69a Match Region | Identities/ Similarities for the Matched Region | Expect Value |
|---|---|---|---|
| PI-PLC-X: domain 1 of 1 | 52 ... 196 | 78/153 (51%) 115/153 (75%) | 3.9e–64 |
| UvrD-helicase: domain 1 of 1 | 187 ... 240 | 11/64 (17%) 40/64 (62%) | 9.5 |

TABLE 69E-continued

Domain Analysis of NOV69a

| Pfam Domain | NOV69a Match Region | Identities/ Similarities for the Matched Region | Expect Value |
|---|---|---|---|
| PI-PLC-Y: domain 1 of 1 | 272 ... 389 | 63/128 (49%) 89/128 (70%) | 1.6e–50 |
| C2: domain 1 of 1 | 408 ... 496 | 33/97 (34%) 73/97 (75%) | 4.9e–20 |

Example 70

The NOV70 clone was analyzed, and the nucleotide and encoded polypeptide sequences are shown in Table 70A.

TABLE 70A

NOV70 Sequence Analysis

| | |
|---|---|
| NOV70a, CG93669-01 DNA Sequence | SEQ ID NO:179  2257 bp<br>CCGCAAGTCCCTCGCCGCCTTGGGGTCTGGGCGCGCGGTCCGTGGGGGTCAGCAGGGC<br><br>GAGCGGCTTTTCCAGGAGAAAGGGCCCTCACGGGTGAGCGGGGCGACTGGGCTCCCCC<br><br>GCGGTGCAGTTGCCCCGCGCGACCGGCCCCGGCTTCAACGGATTCTTCTCGCTCGCTG<br><br>CCCGGAAAGAACCATTTGGGAGAGCCCATGGTGACTGCGTGAGTGGAGCCCAGCTGTG<br><br>TGGATGCCCCAGCATGGATGACTACATGGTCCTGAGAATGATTGGGGAGGGCTCCTTC<br><br>GGCAGAGCTCTTTTGGTTCAGCATGAAAGCAGTAATCAGATGTTTGCCATGAAAGAAA<br><br>TAAGGCTTCCCAAGGTCACTACTAATACACAGAATTCTAGGAAGGAGGCTGTTCTTTT<br><br>AGCCAAAATGAAACACCCTAATATTGTTGCCTTCAAAGAATCATTTGAAGCTGAAGGA<br><br>CACTTCTATATTGTGATGGAATACTGTGATGGAGGGGATCTAATGCAAAAGATTAAAC<br><br>AGCAGAAAGGAAAGTTATTTCCTGAAGACCAGATACTTAATTGGTTTACCCAAATGTG<br><br>CCTTGGAGTAAATCACATTCACAAGAAACGTGTGCTACACAGAGATATCAAGTCCCAG<br><br>AATATCTTCCTCACTCAGAATGGAAAAGTGAAATTGGGAGACTTTGGATCTGCCCGTC<br><br>TTCTCTCCAATCCGATGGCATTTGCTTGTACCTATGTGGGAACTCCTTATTATGTGCC<br><br>TCCAGAAATTTGGGAAAACCTGCCTTATAACAATAAAAGTGACATCTGGTCCTTGGGT<br><br>TGCATCCTGTATGAACTCTGTACCCTTAAGCATCCATTTCAGGCAAATAGTTGGAAAA<br><br>ATCTTATCCTCAAAGTATGTCAAGGGTGCATCAGTCCACTGCCGTCTCATTACTCCTA<br><br>TGAACTTCAGTTCCTAGTCAAGCAGATGTTTAAAAGGAATCCCTCACATCGCCCCTCG<br><br>GCTACAACGCTTCTCTCTCGAGGCATCGTAGCTCGGCTTGTCCAGAAGTGCTTACCCC<br><br>CCGAGATCATCATGGAATATGGTGAGGAAGTATTAGAAGAAATAAAAAATTCGAAGCA<br><br>TAACACACCAAGAAAAAAAACAAACCCCAGCAGAATCAGGATAGCTTTGGGAAATGAA<br><br>GCAAGCACAGTGCAAGAGGAAGAACAAGATAGAAAGGGTAGCCATACTGATTTGGAAA<br><br>GCATTAATGAAAATTTAGTTGAAAGTGCATTGAGAAGAGTAAACAGAGAAGAAAAAGG<br><br>TAATAAGTCAGTCCATCTGAGGAAAGCCAGTTCACCAAATCTTCATAGACGACAGTGG<br><br>GAGAAAAATGTACCCAATACAGCTCTTACAGCTTTGGAAAATGCATCCATACTCACCT<br><br>CCAGTTTAACAGCAGAGGACGATAGAGGTGGTTCTGTAATAAAGTACAGCAAAAATAC<br><br>TACTCGTAAGCAGTGGCTCAAAGAGACCCCTGACACTTTGTTGAACATCCTTAAGAAT |

TABLE 70A-continued

NOV70 Sequence Analysis

|  |  |
|---|---|
|  | GCTGATCTCAGCTTGGCTTTTCAAACATACACAATATATAGACCAGGTTCAGAAGGGT |
|  | TCTTGAAAGGCCCCCTGTCTGAAGAAACAGAAGCATCGGACAGTGTTGATGGAGGTCA |
|  | CGATTCTGTCATTTTGGATCCAGAGCGACTTGAGCCTGGGCTAGATGAGGAGGACACG |
|  | GACTTTGAGGAGGAAGATGACAACCCCGACTGGGTGTCAGAGCTGAAGAAGCGAGCTG |
|  | GATGGCAAGGCCTGTGCGACAGATAATGCCTGAGGAAATGTTCCTGAGTCACGCTGAG |
|  | GAGAGCCTTCACTCAGGAGTTCATGCTGAGATGATCATGAGTTCATGCGACGTATATT |
|  | TTCCTTTGGAAACAGAATGAAGCAGAGGAAACTCTTAATACTTAAAATCGTTCTTGAT |
|  | TAGTATCGTGAGTTTGAAAAGTCTAGAACTCCTGTAAGTTTTTGAACTCAAGGGAGAA |
|  | GGTATAGTGGAATGAGTGTGAGCATCGGGCTTTGCAGTCCCATAGAACAGAAATGGGA |
|  | TGCTAGCGTGCCACTACCTACTTGTGTGATTGTGGGAAATTACTTAACCTCTTCAAGC |
|  | CCCAATTTCCTCAACCATAAAATGAAGATAATAATGCCTACCTCAGAGGGATGCTGAC |
|  | CACAGACCTTTATAGCAGCCCGTATGATATTATTCACATTATGATATGTGTTTATTAT |
|  | TATGTGACTCTTTTTACATTTCCTAAAGGTTTGAGAATTAAATATATTTAATT |
| NOV70a,<br>CG93669-01 Protein Sequence | ORF Start: ATG at 246            ORF Stop: TAA at 1764<br>SEQ ID NO:180     506 aa     MW at 57681.0 kD<br>MDDYMVLRMIGEGSFGRALLVQHESSNQMFAMKEIRLPKVTTNTQNSRKEAVLLAKMK<br>HPNIVAFKESFEAEGHLYIVMEYCDGGDLMQKIKQQKGKLFPEDQILNWFTQMCLGVN<br>HIHKKRVLHRDIKSQNIFLTQNGKVKLGDFGSARLLSNPMAFACTYVGTPYYVPPEIW<br>ENLPYNNKSDIWSLGCILYELCTLKHPFQANSWKNLILKVCQGCISPLPSHYSYELQF<br>LVKQMFKRNPSHRPSATTLLSRGIVARLVQKCLPPEIIMEYGEEVLEEIKNSKHNTPR<br>KKTNPSRIRIALGNEASTVQEEEQDRKGSHTDLESINENLVESALRRVNREEKGNKSV<br>HLRKASSPNLHRRQWEKNVPNTALTALENASILTSSLTAEDDRGGSVIKYSKNTTRKQ<br>WLKETPDTLLNILKNADLSLAFQTYTIYRPGSEGFLKGPLSEETEASDSVDGGHDSVI<br>LDPERLEPGLDEEDTDFEEEDDNPDWVSELKKRAGWQGLCDR |
| NOV70b,<br>CG93669-02 DNA Sequence | SEQ ID NO:181         1781 bp<br>CCGCAAGTCCCTCGCCGCCTTGGGGTCTGGGCGCGCGGTCCGTGGGGGTCAGCAGGGC |
|  | GAGCGGCTTTTCCAGGAGAAAGGGCCCTCACGGGTGAGCGGGGCGACTGGGCTCCCCC |
|  | GCGGTGCAGTTGCCCCGCGCGACCGGCCCCGGCTTCAACGGATTCTTCTCGCTCGCTG |
|  | CCCGGAAAGAACCATTTGGGAGAGCCCATGGTGACTGCGTGAGTGGAGCCCAGCTGTG |
|  | TGGATGCCCCAGCATGGATGACTACATGGTCCTGAGAATGATTGGGGAGGGCTCCTTC |
|  | GGCAGAGCTCTTTTGGTTCAGCATGAAAGCAGTAATCAGATGTTTGCCATGAAAGAAA |
|  | TAAGGCTTCCCAAGGTCACTACTAATACACAGAATTCTAGGAAGGAGGCTGTTCTTTT |
|  | AGCCAAAATGAAACACCCTAATATTGTTGCCTTCAAAGAATCATTTGAAGCTGAAGGA |
|  | CACTTGTATATTGTGATGGAATACTGTGATGGAGGGGATCTAATGCAAAAGATTAAAC |
|  | AGCAGAAAGGAAAGTTATTTCCTGAAGACCAGATACTTAATTGGTTTACCCAAATGTG |
|  | CCTTGGAGTAAATCACATTCACAAGAAACGTGTGCTACACAGAGATATCAAGTCCCAG |
|  | AATATCTTCCTCACTCAGAATGGAAAAGTGAAATTGGGAGACTTTGGATCTGCCCGTC |
|  | TTCTCTCCAATCCGATGGCATTTGCTTGTACCTATGTGGGAACTCCTTATTATGTGCC |
|  | TCCAGAAATTTGGGAAAACCTGCCTTATAACAATAAAAGTGACATCTGGTCCTTGGGT |
|  | TGCATCCTGTATGAACTCTGTACCCTTAAGCATCCATTTCAGGCAAATAGTTGGAAAA |

TABLE 70A-continued

NOV70 Sequence Analysis

|  | |
|---|---|
| | ATCTTATCCTCAAAGTATGTCAAGGGTGCATCAGTCCACTGCCGTCTCATTACTCCTA |
| | TGAACTTCAGTTCCTAGTCAAGCAGATGTTTAAAAGGAATCCCTCACATCGCCCCTCG |
| | GCTACAACGCTTCTCTCTCGAGGCATCGTAGCTCGGCTTGTCCAGAAGTGCTTACCCC |
| | CCGAGATCATCATGGAATATGGTGAGGAAGTATTAGAAGAAATAAAAAATTCGAAGCA |
| | TAACACACCAAGAAAAAAACAAGAGGAAGAACAAGATAGAAAGGGTAGCCATACTGAT |
| | TTGGAAAGCATTAATGAAAATTTAGTTGAAAGTGCATTGAGAAGAGTAAACAGAGAAG |
| | AAAAAGGTAATAAGTCAGTCCATCTGAGGAAAGCCAGTTCACCAAATCTTCATAGACG |
| | ACAGTGGGAGAAAAATGTACCCAATACAGCTCTTACAGCTTTGGAAAATGCATCCATA |
| | CTCACCTCCAGTTTAACAGCAGAGGACGATAGAGGTGGTTCTGTAATAAAGTACAGCA |
| | AAAATACTACTCGTAAGCAGTGGCTCAAAGAGACCCCTGACACTTTGTTGAACATCCT |
| | TAAGAATGCTGATCTCAGCTTGGCTTTTCAAACATACACAATATATAGACCAGGTTCA |
| | GAAGGGTTCTTGAAAGGCCCCCTGTCTGAAGAAACAGAAGCATCGGACAGTGTTGATG |
| | GAGGTCACGATTCTGTCATTTTGGATCCAGAGCGACTTGAGCCTGGGCTAGATGAGGA |
| | GGACACGGACTTTGAGGAGGAAGATGACAACCCCGACTGGGTGTCAGAGCTGAAGAAG |
| | CGAGCTGGATGGCAAGGCCTGTGCGACAGATAATGCCTGAGGAAATGTTCCTGAGTCA |
| | CGCTGAGGAGAGGCTTCACTCTAGGAGTTCATGCTGAGATG |
| NOV70b, CG93669-02 Protein Sequence | ORF Start: ATG at 246    ORF Stop: TAA at 1713<br>SEQ ID NO:182    489 aa    MW at 55900.0 kD<br>MDDYMVLRMIGEGSFGRALLVQHESSNQMFAMKEIRLPKVTTNTQNSREAVLLAKMK<br><br>HPNIVAFKESFEAEGHLYIVMEYCDGGDLMQKIKQQKGKLFPEDQILNWFTQMCLGVN<br><br>HIHKKRVLHRDIKSQNIFLTQNGKVKLGDFGSARLLSNPMAFACTYVGTPYYVPPEIW<br><br>ENLPYNNKSDIWSLGCILYELCTLKHPFQANSWKNLILKVCQGCISPLPSHYSYELQF<br><br>LVKQMFKRNPSHRPSATTLLSRGIVARLVQKCLPPEIIMEYGEEVLEEIKNSKHNTPR<br><br>KKQEEEQDRKGSHTDLESINENLVESALRRVNREEKGNKSVHLRKASSPNLHRRQWEK<br><br>NVPNTALTALENASILTSSLTAEDDRGGSVIKYSKNTTRKQWLKETPDTLLNILKNAD<br><br>LSLAFQTYTIYRPGSEGFLKGPLSEETEASDSVDGGHDSVILDPERLEPGLDEEDTDF<br><br>EEEDDNPDWVSELKKRAGWQGLCDR |
| NOV70c, CG93669-03 DNA Sequence | SEQ ID NO:183    1588 bp<br>CCGCAAGTCCCTCGCCGCCTTGGGGTCTGGGCGCGCGGTCCGTGGGGGTCAGCAGGGC<br><br>GAGCGGCTTTTCCAGGAGAAAGGGCCCTCACGGGTGAGCGGGGCGACTGGGCTCCCCC<br><br>GCGGTGCAGTTGCCCCGCGCGACCGGCCCCGGCTTCAACGGATTCTTCTCGCTCGCTG<br><br>CCCGGAAAGAACCATTTGGGAGAGCCCATGGTGACTGCGTGAGTGGAGCCCAGCTGTG<br><br>TGGATGCCCCAGCATGGATGACTACATGGTCCTGAGAATGATTGGGGAGGGCTCCTTC<br><br>GGCAGAGCTCTTTTGGTTCAGCATGAAAGCAGTAATCAGATGTTTGCCATGAAAGAAA<br><br>TAAGGCTTCCCAAGGTCACTACTAATACACAGAATTCTAGGAAGGAGGCTGTTCTTTT<br><br>AGCCAAAATGAAACACCCTAATATTGTTGCCTTCAAAGAATCATTTGAAGCTGAAGGA<br><br>CACTTGTATATTGTGATGGAATACTGTGATGGAGGGATCTAATGCAAAAGATTAAAC<br><br>AGCAGAAAGGAAAGTTATTTCCTGAAGACCAGATACTTAATTGGTTTACCCAAATGTG<br><br>CCTTGGAGTAAATCACATTCACAAGAAACGTGTGCTACACAGAGATATCAAGTCCCAG<br><br>AATATCTTCCTCACTCAGAATGGAAAAGTGAAATTGGGAGACTTTGGATCTGCCCGTC |

TABLE 70A-continued

NOV70 Sequence Analysis

TCCTCTCCAATCCGATGGCATTTGCTTGTACCTATGTGGGAACTCCTTATTATGTGCC

TCCAGAAATTTGGGAAAACCTGCCTTATAACAATAAAAGTGACATCTGGTCCTTGGGT

TGCATCCTGTATGAACTCTGTACCCTTAAGCATCCATTTCAGGCAAATAGTTGGAAAA

ATCTTATCCTCAAAGTATGTCAAGGGTGCATCAGTCCACTGCCGTCTCATTACTCCTA

TGAACTTCAGTTCCTAGTCAAGCAGATGTTTAAAAGGAATCCCTCACATCGCCCCTCG

GCTACAGCGCTTCTCTCTCGAGGCATCGTAGCTCGGCTTGTCCAGAAGTGCTTACCCC

CCGAGATCATCATGGAATATGGTGAGGAAGTATTAGAAGAAATAAAAAATTCGAAGCA

TAACACACCAAGAAAAAAACAAGAGGAAGAACAAGATAGAAAGGGTAGCCATACTGAT

TTGGAAAGCATTAATGAAAATTTAGTTGAAAGTGCATTGAGAAGAGTAAACAGAGAAG

AAAAAGGTAATAAGTCAGTCCATCTGAGGAAAGCCAGTTCACCAAATCTTCATAGACG

ACAGTGGGAGAAAAATGTACCCAATACAGCTCTTACAGCTTTGGAAAATGCATCCATA

CTCACCTCCAGTTTAACAGCAGAGGACGATAGAGGTTCAGAAGGGTTCTTGAAAGGCC

CCCTGTCTGAAGAAACAGAAGCATCGGACAGTGTTGAGGAGGACACGGACTTTGAGGA

GGAAGATGACAACCCCGACTGGGTGTCAGAGCTGAAGAAGCGAGCTGGATGGCAAGGC

CTGTGCGACAGATAATGCCTGAGGAAATGTACCTGAGTCACGCTGAGGAGAGGCTTCA

CTCAGGAGTTCATGCTGAGATG

ORF Start: ATG at 246         ORF Stop: TAA at 1521
SEQ ID NO:184     425 aa    MW at 48684.0 kD NOV70c, CG93669-03 Protein Sequence

MDDYMVLRMIGEGSFGRALLVQHESSNQMFAMKEIRLPKVTTNTQNSRKEAVLLAKMK

HPNIVAFKESFEAEGHLYIVMEYCDGGDLMQKIKQQKGKLFPEDQILNWFTQMCLGVN

HIHKKRVLHRDIKSQNIFLTQNGKVKLGDFGSARLLSNPMAFACTYVGTPYYVPPEIW

ENLPYNNKSDIWSLGCILYELCTLKHPFQANSWKNLILKVCQGCISPLPSHYSYELQF

LVKQMFKRNPSHRPSATALLSRGIVARLVQKCLPPEIIMEYGEEVLEEIKNSKHNTPR

KKQEEEQDRKGSHTDLESINENLVESALRRVNREEKGNKSVHLRKASSPNLHRRQWEK

NVPNTALTALENASILTSSLTAEDDRGSEGFLKGPLSEETEASDSVEEDTDFEEEDDN

PDWVSELKKRAGWQGLCDR

Sequence comparison of the above protein sequences yields the following sequence relationships shown in Table 70B.

TABLE 70B

Comparison of NOV70a against NOV70b and NOV70c.

| Protein Sequence | NOV70a Residues/ Match Residues | Identities/Similarities for the Matched Region |
|---|---|---|
| NOV70b | 1 ... 506 | 477/506 (94%) |
| | 1 ... 489 | 477/506 (94%) |
| NOV70c | 1 ... 506 | 410/506 (81%) |
| | 1 ... 425 | 410/506 (81%) |

Further analysis of the NOV70a protein yielded the following properties shown in Table 70C.

TABLE 70C

Protein Sequence Properties NOV70a

| | |
|---|---|
| PSort analysis: | 0.6000 probability located in nucleus; 0.3000 probability located in microbody (peroxisome); 0.1000 probability located in mitochondrial matrix space; 0.1000 probability located in lysosome (lumen) |
| SignalP analysis: | No Known Signal Sequence Predicted |

A search of the NOV70a protein against the Geneseq database, a proprietary database that contains sequences published in patents and patent publication, yielded several homologous proteins shown in Table 70D.

TABLE 70D

Geneseq Results for NOV70a

| Geneseq Identifier | Protein/Organism/Length [Patent #, Date] | NOV70a Residues/ Match Residues | Identities/ Similarities for the Matched Region | Expect Value |
|---|---|---|---|---|
| AAM78344 | Human protein SEQ ID NO 1006 - Homo sapiens, 506 aa. [WO200157190-A2, 09 Aug. 2001] | 1 . . . 506<br>1 . . . 506 | 501/506 (99%)<br>503/506 (99%) | 0.0 |
| AAM79328 | Human protein SEQ ID NO 2974 - Homo sapiens, 527 aa. [WO200157190-A2, 09 Aug. 2001] | 1 . . . 506<br>22 . . . 527 | 500/506 (98%)<br>502/506 (98%) | 0.0 |
| AAY68778 | Amino acid sequence of a human phosphorylation effector PHSP-10 - Homo sapiens, 510 aa. [WO200006728-A2, 10 Feb. 2000] | 42 . . . 506<br>46 . . . 510 | 462/465 (99%)<br>464/465 (99%) | 0.0 |
| AAU07102 | Human novel human protein, NHP #2 Homo sapiens, 1214 aa. [WO200161016-A2, 23 Aug. 2001] | 1 . . . 272<br>1 . . . 273 | 152/273 (55%)<br>209/273 (75%) | 3e-92 |
| AAM39211 | Human polypeptide SEQ ID NO 2356 - Homo sapiens, 1214 aa. [WO200153312-A1, 26 Jul. 2001] | 1 . . . 272<br>1 . . . 273 | 152/273 (55%)<br>209/273 (75%) | 3e-92 |

In a BLAST search of public sequence datbases, the NOV70a protein was found to have homology to the proteins shown in the BLASTP data in Table 70E.

TABLE 70E

Public BLASTP Results for NOV70a

| Protein Accession Number | Protein/Organism/Length | NOV70a Residues/ Match Residues | Identities/ Similarities for the Matched Portion | Expect Value |
|---|---|---|---|---|
| P51956 | Serine/threonine-protein kinase NEK3 (EC 2.7.1.-) (NimA-related protein kinase 3) (HSPK 36) - Homo sapiens (Human), 459 aa (fragment). | 48 . . . 506<br>1 . . . 459 | 456/459 (99%)<br>457/459 (99%) | 0.0 |
| AAH19916 | HYPOTHETICAL 51.3 KDA PROTEIN - Homo sapiens (Human), 450 aa. | 57 . . . 506<br>1 . . . 450 | 448/450 (99%)<br>449/450 (99%) | 0.0 |
| Q99K72 | SIMILAR TO NIMA (NEVER IN MITOSIS GENE A)-RELATED EXPRESSED KINASE 3 - Mus musculus (Mouse), 509 aa. | 1 . . . 500<br>1 . . . 496 | 369/503 (73%)<br>423/503 (83%) | 0.0 |
| Q9R0A5 | Serine/threonine-protein kinase NEK3 (EC 2.7.1.-) (NimA-related protein kinase 3) - Mus musculus (Mouse), 511 aa. | 1 . . . 500<br>1 . . . 498 | 370/505 (73%)<br>423/505 (83%) | 0.0 |
| Q96PY6 | KIAA1901 PROTEIN - Homo sapiens (Human), 1265 aa (fragment). | 1 . . . 272<br>8 . . . 280 | 152/273 (55%)<br>209/273 (75%) | 8e-92 |

PFam analysis predicts that the NOV70a protein contains the domains shown in the Table 70F.

TABLE 70F

Domain Analysis of NOV70a

| Pfam Domain | NOV70a Match Region | Identities/ Similarities for the Matched Region | Expect Value |
|---|---|---|---|
| RIO1: domain 1 of 1 | 5 . . . 183 | 34/234 (15%)<br>86/234 (37%) | 6.5 |
| pkinase: domain 1 of 1 | 4 . . . 257 | 95/293 (32%)<br>212/293 (72%) | 1.4e-88 |
| Vmethyltransf: domain 1 of 1 | 248 . . . 263 | 7/16 (44%)<br>15/16 (94%) | 6.8 |

Example 71

The NOV71 clone was analyzed, and the nucleotide and encoded polypeptide sequences are shown in Table 71A.

TABLE 71A

NOV71 Sequence Analysis

| | |
|---|---|
| NOV71 a,<br>CG93896-01 DNA Sequence | SEQ ID NO: 185    1453 bp<br>ATGGATAAGTACGATGTGATTAAGGCCATCGGGCAAGGTGCCTTCGGGAAAGCATACT<br>TAGCTAAAGGGAAATCAGATAGCAAGCACTGTGTCATAAAAGAGATCAATTTTGAAAA<br>GCAAGAAAAGAAGCTTCAAAGAAAGAAGTGATTCTTCTGGAAAAGATGAAACATCCC<br>AACATTGTAGCCTTCTTCAATTCATTTCAAGAGAATGGCAGGCTGTTTATTGTAATGG<br>AATATTGTGATGGAGGGGATCTCATGAAAAGGATCAATAGACAACGGGGTGTGTTATT<br>TAGTGAAGATCAGATCCTCGGTTGGTTTGTACAGATTTCTCTAGGACTAAAACATATT<br>CATGACAGGAAGATATTACACAGGGACATAAAAGCTCAGAACATTTTTCTTAGCAAGA<br>ACGGAATGGTGGCAAAGCTTGGGGACTTTGGTATAGCAAGAGTCCTGAATAATTCCAT<br>GGAACTTGCTCGAACTTGTATTGGAACACCTTACTACCTGTCCCCAGAGATCTGTCAG<br>AATAAACCCTACAACAATAAAACGGATATTTGGTCTCTTGGCTGTGTCTTATATGAGC<br>TCTGCACACTTAAACATCCTTTTGAGGGTAACAACTTACAGCAGCTGGTTCTGAAGAT<br>TTGTCAAGCACATTTTGCCCCAATATCTCCGGGGTTTTCTCGTGAGCTCCATTCCTTG<br>ATATCTCAGCTCTTTCAAGTATCTCCTCGAGACCGACCATCCATAAATTCCATTTTGA<br>AAAGGCCCTTTTTAGAGAATCTTATTCCCAAATATTTGACTCCTGAGGTCATTCAGGA<br>AGAATTCAGTCACATGCTTATATGCAGAGCAGGAGCGCCAGCTTCTCGACATGCTGGG<br>AAGGTGGTCCAGAAGTGTAAAATACAAAAAGTGAGATTCCAGGGAAAGTGCCCACCAA<br>GATCAAGGATATCTGTGCCAATTAAAAGGAATGCTATATTGCATAGAAATGAATGGAG<br>ACCACCAGCTGGAGCCCAGAAGGCCAGATCTATAAAAATGATAGAAAGACCCAAAATT<br>GCTGCTGTCTGTGGACATTATGATTATTATTATGCTCAACTTGATATGCTGAGGAGGA<br>GAGCCCACAAACCAAGTTATCACCCCATTCCTCAAGAAAATACTGGAGTTGAGGATTA<br>CGGTCAGGAAACGAGGCATGGTCCATCCCCAAGTCAATGA<u>TTCTGTAACTGTGAACTA</u><br><u>CTTCTTGAACTTGGAACTTCAAGCCACTGGTGAATTGTGAATCTCATTACTAAACTGA</u><br><u>AAATTACTCGTCAAATTGGTGCCTAAGATTCGTTCAAGTTTCTACTTAAGCTGAACAT</u><br><u>TCTTATTTTCTAAGGCCTGCTGAGTACCTTCAGAGAAAATTTGAAGCTCAACAATATA</u><br><u>AGTTGAAAGTGGAGAAGCAATTGGGTCTTCGTCCATCTTCTGCCGAGCCAAATTACAA</u><br><u>CCA</u> |
| | ORE Start: ATG at 1    ORF Stop: TGA at 1198<br>SEQ ID NO: 186    399 aa    MW at 45662.6kD |
| NOV71a,<br>CG93896-01 Protein Sequence | MDKYDVIKAIGQGAFGKAYLAKGKSDSKHCVIKEINFEKQEKEASKKEVILLEKMKHP<br>NIVAFFNSFQENGRLFIVMEYCDGGDLMKRINRQRGVLFSEDQILGWFVQISLGLKHI<br>HDRKILHRDIKAQNIFLSKNGMVAKLGDFGIARVLNNSMELARTCIGTPYYLSPEICQ<br>NKPYNNKTDIWSLGCVLYELCTLKHPFEGNNLQQLVLKICQAHFAPISPGFSRELHSL<br>ISQLFQVSPRDRPSINSILKRPFLENLIPKYLTPEVIQEEFSHMLICRAGAPASRHAG<br>KVVQKCKIQKVRFQGKCPPRSRISVPIKRNAILHRNEWRPPAGAQKARSIKMIERPKI<br>AAVCGHYDYYYAQLDMLRRRAHKPSYHPIPQENTGVEDYGQETRHGPSPSQ |
| NOV71b, | SEQ ID NO: 187    1587 bp<br><u>TGGACACTGACATGGACTGAAGGAGTAGAAAATCCTTCCGGGACGCTTCGTTGGCCCC</u> |

TABLE 71A-continued

NOV71 Sequence Analysis

CG93896-02 DNA Sequence

GCGGAGCCGGCGGAGCAGGAAACTCAGCCCATTGGAGACCATGGATAAGTACGATGTG
ATTAAGGCCATCGGGCAAGGTGCCTTCGGGAAAGCATACTTAGCTAAAGGGAAATCAG
ATAGCAAGCACTGTGTCATAAAAGAGATCAATTTTCAAAAGATCCCCATACAAGAAAA
AGAAGCTTCAAAGAAAGAAGTGATTCTTCTGGAAAAGATGAAACATCCCAACATTGTA
GCCTTCTTCAATTCATTTCAAGAATGGCAGGCTGTTTATTGTAATGGAATATTGTG
ATGGAGGGGATCTCATGAAAAGGATCAATAGACAACGGGGTGTGTTATTTAGTGAAGA
TCAGATCCTCGGTTGGTTTGTACAGATTTCTCTAGGACTAAAACATATTCATGACAGG
AAGATATTACACAGGGACATAAAAGCTCAGAACATTTTTCTTAGCAAGAACGGAATGG
TGGCAAAGCTTGGGGACTTTGGTATAGCAAGAGTCCTGAATAGTTCCATGGAACTTGC
TCGAACTTGTATTGGAACACCTTACTACCTGTCCCCAGAGATCTGTCAGAATAAACCC
TACAACAATAAAACGGATATTTGGTCTCTTGGCTGTGTCTTATATGAGCTCTGCACAC
TTAAACATCCTTTTGAGGGTAACAACTTACAGCAGCTGGTTCTGAAGATTTGTCAAGC
ACATTTTGCCCCAATATCTCCGGGGTTTTCTCGTGAGCTCCATTCCTTGATATCTCAG
CTCTTTCAAGTATCTCCTCGAGACCGACCATCCATAAATTCCATTTTGAAAAGGCCCT
TTTTAGAGAATCTTATTCCCAAATATTTGACTCCTGAGGTCAGTTTTGAGGAAGAATT
CAGTCACATGCTTATATGCAGAGCAGGAGCGCCAGCTTCTCGACATGCTGGGAAGGTG
GTCCAGAAGTGTAAAATACAAAAAGTGAGATTCCAGGGAAAGTGCCCACCAAGATCAA
GGATATCTGTGCCAATTAAAAGGAATGCTATATTGCATAGAAATGAATGGAGACCACC
AGCTGGAGCCCAGAAGGCCAGATCTATAAAAATGATAGAAAGACCCAAAATTGCTGCT
GTCTGTGGACATTATGATTATTATGCTCAACTTGATATGCTGAGGAGGAGAGCCC
ACAAACCAAGTTATCACCCCATTCCTCAAGAAAATACTGGAGTTGAGGATTACGGTCA
GGAAACGAGGCATGGTCCATCCCCAAGTCAATGATTCTGTAACTGTGAACTACTTCTT
GAACTTGGAACTTCAAGCCACTGGTGAATTGTGAATCTCATTACTAAACTGAAAATTA
CTCGTCAAATTGGTGCCTAAGATTCGTTCAAGTTTCTACTTAAGCTGAACATTCTTAT
TTTCTAAGGCCTGCTGAGTACCTTCAGAGAAAATTTGAAGCTCAACAATATAAGTTGA
AAGTGGAGAAGCAATTGGGTCTTCGTCCATCTTCTGCCGAGCCAAATTACAACCAAAA
AAAAAAAAAAAAAAAAAACGG

ORF Start: ATG at 99    ORF Stop: TGA at 1308
SEQ ID NO: 188          403 aa    MW at 46099.1kD NOV71b,
CG93896-02 Protein Sequence MDKYDVIKAIGQGAFGKAYLAKGKSDSKHCVIKEINFEKMPIQEKEASKKEVILLEKM
KHPNIVAFFNSFQENGRLFIVMEYCDGGDLMKRINRQRGVLFSEDQILGWFVQISLGL
KHIHDRKILHRDIKAQNIFLSKNGMVAKLGDFGIARVLNSSMELARTCIGTPYYLSPE
ICQNKPYNNKTDIWSLGCVLYELCTLKHPFEGNNLQQLVLKICQAHFAPISPGFSREL
HSLISQLFQVSPRDRPSINSILKRPFLENLIPKYLTPEVSFEEEFSHMLICRAGAPAS
RHAGKVVQKCKIQKVRFQCKCPPRSRISVPIKRNAILHRNEWRPPAGAQKARSIKMIE
RPKIAAVCGHYDYYYAQLDMLRRRAHKPSYHPIPQENTGVEDYGQETRHGPSPSQ Sequence comparison of the above protein sequences yields the following sequence relationships shown in Table 71B.

TABLE 71B

Comparison of NOV71a against NOV71b.

| Protein Sequence | NOV71a Residues/ Match Residues | Identities/ Similarities for the Matched Region |
|---|---|---|
| NOV71b | 1 . . . 399 | 396/403 (98%) |
|  | 1 . . . 403 | 398/403 (98%) |

Further analysis of the NOV71a protein yielded the following properties shown in Table 71C.

TABLE 71C

Protein Sequence Properties NOV71a

| PSort analysis: | 0.4500 probability located in cytoplasm; 0.3000 probability located in microbody (peroxisome); 0.1000 probability located in mitochondrial matrix space; 0.1000 probability located in lysosome (lumen) |
|---|---|
| SignalP analysis: | No Known Signal Sequence Predicted |

A search of the NOV71a protein against the Geneseq database, a proprietary database that contains sequences published in patents and patent publication, yielded several homologous proteins shown in Table 71D.

TABLE 71D

Geneseq Results for NOV71a

| Geneseq Identifier | Protein/Organism/Length [Patent #, Date] | NOV71a Residues/ Match Residues | Identities/ Similarities for the Matched Region | Expect Value |
|---|---|---|---|---|
| AAU03545 | Human protein kinase #45 - *Homo sapiens*, 649 aa. [WO200138503-A2, 31 May 2001] | 1 . . . 399<br>1 . . . 377 | 338/402 (84%)<br>344/402 (85%) | 0.0 |
| AAU07102 | Human novel human protein, NHP #2 - *Homo sapiens*, 1214 aa. [WO200161016-A2, 23 Aug. 2001] | 1 . . . 289<br>1 . . . 294 | 183/295 (62%)<br>231/295 (78%) | e−103 |
| AAM39211 | Human polypeptide SEQ ID NO 2356 - *Homo sapiens*, 1214 aa. [WO200153312-A1, 26 Jul. 2001] | 1 . . . 289<br>1 . . . 294 | 183/295 (62%)<br>231/295 (78%) | e−103 |
| AAM39210 | Human polypeptide SEQ ID NO 2355 - *Homo sapiens*, 1242 aa. [WO2001533 12-A1, 26 Jul. 2001] | 1 . . . 289<br>1 . . . 294 | 183/295 (62%)<br>231/295 (78%) | e−103 |
| AAM78344 | Human protein SEQ ID NO 1006 - *Homo sapiens*, 506 aa. [WO200157190-A2, 09 Aug. 2001] | 1 . . . 271<br>1 . . . 272 | 148/273 (54%)<br>200/273 (73%) | 3e−85 |

In a BLAST search of public sequence datbases, the NOV71a protein was found to have homology to the proteins shown in the BLASTP data in Table 71E.

TABLE 71E

Public BLASTP Results for NOV71a

| Protein Accession Number | Protein/Organism/Length | NOV71a Residues/ Match Residues | Identities/ Similarities for the Matched Portion | Expect Value |
|---|---|---|---|---|
| P51954 | Serine/threonine-protein kinase NEK1 (EC 2.7.1.-) (NimA-related protein kinase 1) - *Mus musculus* (Mouse), 774 aa. | 1 . . . 347<br>1 . . . 375 | 197/379 (51%)<br>261/379 (67%) | e−105 |
| Q96PY6 | KIAA1901 PROTEIN - *Homo sapiens* (Human), 1265 aa (fragment). | 1 . . . 289<br>8 . . . 301 | 183/295 (62%)<br>231/295 (78%) | e−103 |
| Q9R0A5 | Serine/threonine-protein kinase NEK3 (EC 2.7.1.-) (NimA-related protein kinase 3) - *Mus musculus* (Mouse), 511 aa. | 1 . . . 271<br>1 . . . 270 | 149/271 (54%)<br>199/271 (72%) | 2e−85 |
| Q99K72 | SIMILAR TO NIMA (NEVER IN MITOSIS GENE A)-RELATED EXPRESSED KINASE 3 - *Mus musculus* (Mouse), 509 aa. | 1 . . . 271<br>1 . . . 270 | 148/271 (54%)<br>199/271 (72%) | 9e−85 |

TABLE 71E-continued

Public BLASTP Results for NOV71a

| Protein Accession Number | Protein/Organism/Length | NOV71a Residues/ Match Residues | Identities/ Similarities for the Matched Portion | Expect Value |
|---|---|---|---|---|
| P51956 | Serine/threonine-protein kinase NEK3 (EC 2.7.1.-) (NimA-related protein kinase 3) (HSPK 36) - *Homo sapiens* (Human), 459 aa (fragment). | 46 ... 271<br>1 ... 225 | 130/226 (57%)<br>171/226 (75%) | 1e-75 |

PFam analysis predicts that the NOV71a protein contains the domains shown in the Table 71F.

TABLE 71F

Domain Analysis of NOV71a

| Pfam Domain | NOV71a Match Region | Identities/ Similarities for the Matched Region | Expect Value |
|---|---|---|---|
| NadA: domain 1 of 1 | 31 ... 213 | 47/369 (13%)<br>112/369 (30%) | 7.5 |
| pkinase: domain 1 of 1 | 4 ... 256 | 89/292 (30%)<br>205/292 (70%) | 7.1e-88 |

Example 72

The NOV72 clone was analyzed, and the nucleotide and encoded polypeptide sequences are shown in Table 72A.

TABLE 72A

NOV72 Sequence Analysis

NOV72a, CG93939-01 DNA Sequence

SEQ ID NO: 189  2290 bp

GTGGCATCAATGCCGAAGAACAGCAAAGTGACCCAGCGTGAGCACAGCAGTGAGCATG

TCACTGAGTCCGTGGCCGACCTGCTGGCCCTCCACGAGCCTGTGGACTATAAGCAGAG

TGTACTGAATCTGGCTGGTGAGGCAGCCGGCAAGCACAAGGCGGTGGAGGACGACCTG

GATGCAGAGGACCGGCCGGCCTGGAACAGTAAGCTGCAGTACATCCTGGCCCACATTG

GCTTCTCTGTGGGCCTCGGCAACATCTGGAGGTTCCCCTACCTGTGCCAGAAAAATGG

AGGAGGTGCTTACCTGGTGCCCTACCTGGTGCTGCTGATCATCATCGGGATCCCCCTC

TTCTTCCTGGAGCTGGCTGTGGGTCAGAGGATCCGCCGCGGCAGCATCGGTGTGTGGC

ACTATATATGTCCCCGCCTGGGGGCATCGGCTTCTCCAGCTGCAPAGTCTGTCTCTT

TGTGGGGCTGTATTATAATGTGATCATCGGGTGGAGCATCTTCTATTTCTTCAAGTCC

TTCCAGTACCCGCTGCCCTGGAGTGAATGTCCTGTCGTCAGGAATGGCAGCGTCGCAG

TGGTGGAGGCAGAGTGTGAAAAGAGCTCAGCCACTACCTACTTCTGGTACCGAGAGGC

CTTGGACATCTCTCACTCCATCTCGGAGAGTCGGGGCCTCAACTGGAAGATGACCCTG

TGCCTCCTCGTGGCCTGGAGCATCGTCGGGATGGCTGTCGTTAAGGGCATCCAGTCCT

CGGGGAAGGTGATGTATTTCAGCTCCCTCTTCCCCTACGTGGTGCTGGCCTGCTTCCT

GGTCCGGGGGCTGTTGCTGCGAGGGGCAGTTGATGGCATCCTACACATGTTCACTCCC

AAGCTGGACAAGATGCTGGACCCCCAGGTGTGGCGGGAGGCAGCTACCCAGGTCTTCT

TTGCCTTGGGCCTCGGCTTTGCTGGTGTCATTGCCTTCTCCAGCTACAATAAGCAGGA

TABLE 72A-continued

NOV72 Sequence Analysis

CAACAACTGCCACTTCGATGCCGCCCTGGTGTCCTTCATCAACTTCTTCACGTCAGTG
TTGGCCACCCTCGTGGTGTTTGCTGTGCTGCGCTTCAAGGCCAACATCATGAATGAGA
AGTGTGTGGTCGAGAATGCTGAGAAAATCCTAGGGTACCTTAACACCAACGTCCTGAG
CCGGGACCTCATCCCACCCCACGTCAACTTCTCCCACCTCACCACAAAGGACTACATG
GAGATGTACAATGTCATCATGACCGTGAAGGAGGACCAGTTCTCAGCCCTGGGTCTTG
ACCCCTGCCTTCTGGAGGACGAGCTCGACAAGTCCGTGCAGGGCACACGCCTGGCCTT
CATCGCCTTCACTGAGGCCATGACGCACTTCCCCGCCTCCCCGTTCTGGTCCGTCATC
TTCTTCTTGATGCTTATCAACCTGGGCCTGGGCAGCATGATCGGGACCATGGCAGGCA
TCACCACGCCCATCATCGACACCTTCAACGTGCCCAAGGAGATGTTCACACTGGCCTG
CTGTGTCTTTGCATTCCTCGTGGGCTGTTGTTCGTCCAGCGCTCCGGAAACTACTTT
GTCACCATGTTCGATGACTACTCAGCCACCCTGCCACTCACTCTCATCGTCATCCTTG
AGAACATCGCTGTGGCCTGGATTTATGGAACCAAGAAGTTCATGCAGGAGCTGACGGA
GATGCTGGGCTTCCGCCCCTACCGCTTCTATTTCTACATGTGGAAGTTCGTGTCTCCA
CTATGCATGGCTGTGCTCACCACAGCCAGCATCATCCAGCTGGGGGTCACGCCCCCGG
GCTACAGCGCCTGGATCAAGGAGGAGGCTGCCGAGCGCTACCTGTATTTCCCCAACTG
CGCCATGGCACTCCTGATCACCCTCATCGTCGTGGCGACGCTGCCCATCCCTGTCGTG
TTCGTCCTGCGGCACTTCCACCTGCTCTGTGATGGCTCCAACACCCTCTCCGTGTCCT
ACAAGAAGCGCCGCATGATGAAGGACATCTCCAACCTGGAGGAGAACCATGAGACCCG
CTTCATCCTCAGCAAGGTGCCCAGTGAGGCACCTTCCCCCATGCCCACTCACCGTTCC
TATCTGGGGCCCGGCAGCACATCACCCCTGGAGACCAGCGGTAACCCCAATGGACGCT
ATGGGAGCGGCTACCTGCTGGCCAGCACCCCTGAGTCGGAGCTGTGA<u>CCACTGCCCAA</u>
<u>GCCCT</u>

ORF Start: ATG at 10     ORF Stop: TGA at 2191
SEQ ID NO: 190          727 aa    MW at 81000.5kD NOV72a,
CG93939-01 Protein Sequence MPKNSKVTQREHSSEHVTESVADLLALEEPVDYKQSVLNVAGEAGGKQKAVEEELDAE
DRPAWNSKLQYILAQIGFSVGLGNIWRFPYLCQKNGGGAYLVPYLVLLIIIGIPLFFL
ELAVGQRIRRGSIGVWHYICPRLGGIGFSSCIVCLFVGLYYNVIIGWSIFYFFKSFQY
PLPWSECPVVRNGSVAVVEAECEKSSATTYFWYREALDISDSISESGGLNWKMTLCLL
VAWSIVGMAVVKGIQSSGKVMYFSSLFPYVVLACFLVRGLLLRGAVDGILHMFTPKLD
KMLDPQVWREAATQVFFALGLGFGGVIAFSSYNKQDNNCHFDAALVSFINFFTSVLAT
LVVFAVLGFKANIMNEKCVVENAEKILGYLNTNVLSRDLIPPHVNFSHLTTKDYMEMY
NVIMTVKEDQFSALGLDPCLLEDELDSKSQGTGLAFIAFTEAMTHFPASPFWSVMFFL
MLINLGLGSMIGTMAGITTPIIDTFKVPKEMFTVGCCVFAFLVGLLFVQRSGNYFVTM
FDDYSATLPLTLIVILENIAVAWIYGTKKFMQELTEMLGFRPYRFYFYMWKFVSPLCM
AVLTTASIIQLGVTPPGYSAWIKEEAAERYLYFPNWAMALLITLIVVATLPIPVVFVL
RHFHLLSDGSNTLSVSYKKGRMMKDISNLEENDETRFILSKVPSEAPSPMPTHRSYLG
PGSTSPLETSGNPNGRYGSGYLLASTPESEL Further analysis of the NOV72a protein yielded the following properties shown in Table 72B.

TABLE 72B

| Protein Sequence Properties NOV72a | |
|---|---|
| PSort analysis: | 0.8000 probability located in plasma membrane; 0.4000 probability located in Golgi body; 0.3000 probability located in endoplasmic reticulum (membrane); 0.3000 probability located in microbody (peroxisome) |

TABLE 72B-continued

| Protein Sequence Properties NOV72a | |
|---|---|
| SignalP analysis: | No Known Signal Sequence Predicted |

A search of the NOV72a protein against the Geneseq database, a proprietary database that contains sequences published in patents and patent publication, yielded several homologous proteins shown in Table 72C.

TABLE 72C

Geneseq Results for NOV72a

| Geneseq Identifier | Protein/Organism/Length [Patent #, Date] | NOV72a Residues/ Match Residues | Identities/ Similarities for the Matched Region | Expect Value |
|---|---|---|---|---|
| AAR88390 | Human neurotransmitter transporter protein - *Homo sapiens*, 727 aa. [WO9531539-A1, 23 Nov. 1995] | 1 . . . 727<br>1 . . . 727 | 706/727 (97%)<br>706/727 (97%) | 0.0 |
| AAY72908 | Human NTT7 protein - *Homo sapiens*, 730 aa. [WO200119854-A2, 22 Mar. 2001] | 1 . . . 727<br>1 . . . 730 | 487/735 (66%)<br>603/735 (81%) | 0.0 |
| AAG67159 | Amino acid sequence of a human 579 transporter polypeptide - *Homo sapiens*, 730 aa. [WO200164875-A2, 07 Sep. 2001] | 1 . . . 727<br>1 . . . 730 | 487/735 (66%)<br>603/735 (81%) | 0.0 |
| AAE05100 | *Drosophila melanogaster*dmNTT4 protein - *Drosophila melanogaster*, 675 aa. [WO200149848-A2, 12 Jul. 2001] | 59 . . . 684<br>54 . . . 662 | 280/629 (44%)<br>407/629 (64%) | e−168 |
| AAG64193 | Human nerve mass-transferring protein - *Homo sapiens*, 616 aa. [CN1287170-A, 14 Mar. 2001] | 25 . . . 634<br>3 . . . 596 | 262/617 (42%)<br>390/617 (62%) | e−147 |

In a BLAST search of public sequence datbases, the NOV72a protein was found to have homology to the proteins shown in the BLASTP data in Table 72D.

TABLE 72D

Public BLASTP Results for NOV72a

| Protein Accession Number | Protein/Organism/Length | NOV72a Residues/ Match Residues | Identities/ Similarities for the Matched Portion | Expect Value |
|---|---|---|---|---|
| P31662 | Orphan sodium- and chloride-dependent neurotransmitter transporter NTT4 - *Rattus norvegicus* (Rat), 727 aa. | 1 . . . 727<br>1 . . . 727 | 705/727 (96%)<br>718/727 (97%) | 0.0 |
| I56506 | Na+/Cl(−)-dependent neurotransmitter transporter, brain - rat, 727 aa. | 1 . . . 727<br>1 . . . 727 | 703/727 (96%)<br>716/727 (97%) | 0.0 |
| Q9H2J7 | Orphan sodium- and chloride-dependent neurotransmitter transporter NTT73 (Orphan transporter v7-3) - *Homo sapiens* (Human), 730 aa. | 1 . . . 727<br>1 . . . 730 | 487/735 (66%)<br>603/735 (81%) | 0.0 |
| Q9XS59 | Orphan sodium- and chloride-dependent neurotransmitter transporter NTT73 (Orphan transporter v7-3) - *Bos taurus* (Bovine), 729 aa. | 1 . . . 724<br>1 . . . 723 | 480/727 (66%)<br>593/727 (81%) | 0.0 |
| Q08469 | Orphan sodium- and chloride-dependent neurotransmitter transporter NTT73 (Orphan transporter v7-3) - *Rattus norvegicus* (Rat), 729 aa. | 1 . . . 724<br>1 . . . 723 | 484/734 (65%)<br>595/734 (80%) | 0.0 |

PFam analysis predicts that the NOV72a protein contains the domains shown in the Table 72E.

TABLE 72E

Domain Analysis of NOV72a

| Pfam Domain | NOV72a Match Region | Identities/ Similarities for the Matched Region | Expect Value |
|---|---|---|---|
| SNF: domain 1 of 1 | 60 ... 657 | 310/638 (49%) 572/638 (90%) | 0 |

Example 73

The NOV73 clone was analyzed, and the nucleotide and encoded polypeptide sequences are shown in Table 73A.

TABLE 73A

NOV73 Sequence Analysis

NOV73a, CG94245-01 DNA Sequence

SEQ ID NO: 191    1547 bp

<u>GGAATTATATTAAATCTGTAAATCAATTGAAAAATAATTGTCAAAACTGTGGCGCCAG</u>

<u>ATACCGCGGTTGAGGTGG</u>ATGGAAGGGACCTGCTGCAGGGAGATGAGGAGGCTGCAGG

GCAGTGACTGCAGCTCCACAGCTCCCGCAGTGGCTCTGCCCAGGTACTTCTGCCCCAG

AGAGGACAAATATGAATACCCAGACAACAGTCTCATCTGTCTTTTTGCTATATGTGAG

TCAAGGGCAACAGGAAAACACTGTGCGGCATCGAGCTGTGGTCGGTGCAACGGCTTCT

TCAGATGCAGCATATGCAAGAGTAACGTTTATTCTTGCAGGTTCCGTCGGCAATGTTT

TGTTGACAAGGCCAAAAGAAATGAATGTACATACAGTCAATTAAGAAAGTGTTTTAGA

GCAGGAATGGAAAAAGAAGTTGTGCATAATGAATGCAATAGAACAAGCACCAGAAGAA

GCACATGTGATGGCAGCAATATCCCCTCCATTAACACACTGGCACAAGCTGAAGTTCT

GTCTTGCCAGATCTCAGTCTCAAGCCTTGGGGCAAGTACTGATATACATGTTAAAAAA

AATAAAAGTGTTGGTGATGTCTGTCAATTTCTGAAACAGCAGCTCTTAGTCTTGGTGG

AATGGGCTAAATATATTCCTGCCTTCTGTCAGTTACCATTGGATGACAAGGTCGCGCT

GTTGAGATATCATGCAGGAGAACACTTACTGCCTGGAGCTATAAAGAGATCCATGATG

TATAAAGATATTTTGCTTTTGGGAAACAACTATATTATTCACTGCAACAGCTGTGAAT

TTGAGATTAGCAGTGTAATCAGTCGGGTTCTAGTTGAGCTGGTTCAACCATTTCAAGA

AATCCAAAAGGCAATTGTATTTTTTGGCCCAGATGTGAAAGGGCTACACGATCCAATA

AACATTAAGAACATGCAATTCCAAGGGCGGATGGGTTTGCAGAACTCCGTCAATGATT

CCGCACGCAGTATGGCTCCCTGGGGGAGGTTTGGACAGTTGCTTCTGCTGCTGCCCAC

ACTGCTGCGCATCATTTGGCAAATGATTGAGCAAATAAGTTTGTTTAAAAAACTTTTG

CGGTTGACTAAAATTGGCCACCTACTTCAGGAAATGTTAAATGGGGCTTCCAATGATA

GTAGTCATCTCCATCATCCAATACATCCACATTCATCTCAAGATCCATTAACTGGACA

AACTGTACTTTTACGTCCCATGTACACACTGGTACACACTGGTTCTTATGAAGACCAC

ATCAGAACTCCTGAAACCCCACTCCCTTCCCCACCACAAGGCTTTGCACAAGAAGATT

ACAGAACAGCTACAAATCAAGCTTCAGTCATTTCACCAGCCTCTCTTCAAACAAAAAC

AATTGTTTCAAACAAAAACAATTGTGAAAATGTGTTTATTTCTGAACAGCACTGCATA

AATGTGAAAAGCTGTTTGTCTTGAAACATCTCAAGATAGTACTTTTGGCAAACTCTGA

<u>TCCAAGGCTTCTTCATGGAACTGTTATAAGACAGTATCC</u>

ORF Start: ATG at 77    ORF Stop: TGA at 1472
SEQ ID NO: 192    465 aa    MW AT 52258.7kD

TABLE 73A-continued

NOV73 Sequence Analysis

| | |
|---|---|
| NOV73a, CG94245-01 Protein Sequence | MEGTCCREMRRLQGSDCSSRAPGVALRRYFCPREDKYEYPDNSLICLFAICESRATGK HCGASSCGGCKGFFRCSICKSNVYSCRFRRQCFVDKAKRNQCRYSQLRKCFRAGMEKE VVHNECNRTSTRRSTCDGSNIPSINTLAQAEVLSCQISVSSLGASTDIHVKKNKSVGD VCEFLKQQLLVLVEWAKYIPAFCQLPLDDKVALLRYHAGEHLLPGAIKRSMMYKDILL LGNNYIIHCNSCEFEISSVISRVLVELVQPFQEIQKAIVFFGPDVKGLHDPINIKNMQ FQGRMGLENSVNDSARSMAPWGRFGELLLLLPTLLRIIWQMIEQISLFKKLLRLTKIG HLLQEMLNGASNDSSHLHHPIHPHSSQDPLTGQTVLLGPMYTLVHTGSYEDHIRTPET PLPSPPQGFAQEDYRTATNQASVISPASLQTKTIVSNKNNCENVFISEQHCINVKSCL S |

Further analysis of the NOV73a protein yielded the following properties shown in Table 73B.

TABLE 73B

Protein Sequence Properties NOV73a

| | |
|---|---|
| PSort analysis: | 0.4721 probability located in mitochondrial matrix space; 0.3000 probability located in microbody (peroxisome); 0.1752 probability located in mitochondrial inner membrane; 0.1752 probability located in mitochondrial intermembrane space |
| SignalP analysis: | No Known Signal Sequence Predicted |

A search of the NOV73a protein against the Geneseq database, a proprietary database that contains sequences published in patents and patent publication, yielded several homologous proteins shown in Table 73C.

TABLE 73C

Geneseq Results for NOV73a

| Geneseq Identifier | Protein/Organism/Length [Patent #, Date] | NOV73a Residues/ Match Residues | Identities/ Similarities for the Matched Region | Expect Value |
|---|---|---|---|---|
| AAM79298 | Human protein SEQ ID NO 1960 - Homo sapiens, 474 aa. [WO200157190-A2, 09 Aug. 2001] | 47 . . . 434 59 . . . 461 | 230/407 (56%) 279/407 (68%) | e-116 |
| AAW71574 | Human native hepatocyte nuclear factor 4 alpha - Homo sapiens, 465 aa. [WO9811254-A1, 19 Mar. 1998] | 47 . . . 434 50 . . . 452 | 230/407 (56%) 279/407 (68%) | e-116 |
| AAW71587 | Human hepatocyte nuclear factor 4 alpha - Homo sapiens, 516 aa. [WO9811254-A1, 19 Mar. 1998] | 47 . . . 434 101 . . . 503 | 230/407 (56%) 279/407 (68%) | e-115 |
| AAM80282 | Human protein SEQ ID NO 3928 - Homo sapiens, 505 aa. [WO200157190-A2, 09 Aug. 2001] | 47 . . . 434 90 . . . 492 | 228/407 (56%) 277/407 (68%) | e-115 |
| AAY77496 | Rat hepatocyte nuclear factor 4 (HNF-4) - Rattus sp, 455 aa. [US6025196-A, 15 Feb. 2000] | 47 . . . 444 50 . . . 453 | 226/412 (54%) 281/412 (67%) | e-115 |

In a BLAST search of public sequence datbases, the NOV73a protein was found to have homology to the proteins shown in the BLASTP data in Table 73D.

TABLE 73D

Public BLASTP Results for NOV73a

| Protein Accession Number | Protein/Organism/Length | NOV73a Residues/ Match Residues | Identities/ Similarities for the Matched Portion | Expect Value |
| --- | --- | --- | --- | --- |
| JC6095 | hepatocyte nuclear factor 4 gamma chain - human, 774 aa. | 41 ... 431<br>371 ... 764 | 293/401 (73%)<br>320/401 (79%) | e−158 |
| Q14541 | Hepatocyte nuclear factor 4-gamma (HNF-4-gamma) - *Homo sapiens* (Human), 408 aa. | 41 ... 431<br>5 ... 398 | 292/401 (72%)<br>320/401 (78%) | e−158 |
| Q9WUU6 | Hepatocyte nuclear factor 4-gamma (HNF-4-gamma) - *Mus musculus* (Mouse), 408 aa. | 41 ... 435<br>5 ... 402 | 288/405 (71%)<br>319/405 (78%) | e−156 |
| Q91766 | Hepatocyte nuclear factor 4-alpha (HNF-4-alpha) - *Xenopus laevis* (African clawed frog), 455 aa. | 47 ... 444<br>50 ... 453 | 235/411 (57%)<br>283/411 (68%) | e−118 |
| JC4937 | hepatocyte nuclear factor 4, splice form B - human, 465 aa. | 47 ... 434<br>50 ... 452 | 231/407 (56%)<br>280/407 (68%) | e−116 |

PFam analysis predicts that the NOV73a protein contains the domains shown in the Table 73E.

TABLE 73E

Domain Analysis of NOV73a

| Pfam Domain | NOV73a Match Region | Identities/ Similarities for the Matched Region | Expect Value |
| --- | --- | --- | --- |
| zf-C4: domain 1 of 1 | 49 ... 121 | 35/74 (47%)<br>60/74 (81%) | 9.9e−25 |
| hormone_rec: domain 1 of 1 | 180 ... 355 | 59/205 (29%)<br>128/205 (62%) | 6.3e−27 |

Example 74

The NOV74 clone was analyzed, and the nucleotide and encoded polypeptide sequences are shown in Table 74A.

TABLE 74A

NOV74 Sequence Analysis

| NOV74a, CG94302-01 DNA Sequence | SEQ ID NO: 193    7386 bp<br>TCAAAAAAGCCAAGTTTGATGGTGCCCAAGAGAAATTCAACACGTACGTGACCCTGAA<br><br>AGTGCAGAATGTCAAGAGCACGACCATCGCGGTGCGGGGCAGCCAGCCCAGCTGGGAG<br><br>CAGGATTTCATGTTCGAGATTAACCGTCTGGATTTGGGACTGACGGTGGAGGTGTGGA<br><br>ATAAGGGTCTCATCTGGGACACAATGGTGGGCACTGTGTGCATCCCACTGAGGACCAT<br><br>CCGCCAGTCCAATGAGGAGGGCCCTGGAGAGTGGCTCACGCTGGACTCCCACGTCATC<br><br>ATGGCAGACAGTGAGATCTGTGGCACAAAGGACCCCACCTTCCACCGCATCCTCCTGG<br><br>ACACGCGCTTTGAGCTACCCTTAGACATTCCTGAAGAGGACGCTCGCTACTGGGCCAA<br><br>GAAGCTGGAGCAGCTCAATGCTATGCGGGACCAGGATGAATATTCGTTCCAAGATGAG<br><br>CAAGACAAGCCTCTGCCTGTCCCCAGCAACCAGTGCTGTAAGTACTTCCCATACCGCC<br><br>TCTCTCTTCCACACGATGACCCCGACAGTCCAGTGGATGATCGTGACAGTGACTACCG<br><br>CAGTGAAACGAGCAACAGCATCCCGCCGCCCTATTATACTACGTCACAACCCAACGCC<br><br>TCAGTCCACCAATATTCTGTTCGCCCACCACCCCTGGGCTCCCGGGAGTCCTACAGTG |

TABLE 74A-continued

| NOV74 Sequence Analysis |
|---|
| ACTCCATGCACAGTTACGAGGAGTTCTCTGAGCCACAAGCCCTCAGCCCCACGGGTAG |
| CAGCCGCTATGCCTCTTCCGGGGAGCTGAGCCAGGGAAGCTCTCAGCTGAGCGAGGAC |
| TTCGACCCTGACCAGCACAGCCTGCAGGGCTCCGACATGGACGATGAGCGGCACCGGG |
| ACTCCTACCACTCCTGCCACAGCTCGGTCAGCTACCACAAAGACTCGCCTCGCTGGGA |
| CCAGGATGAGGAAGAGCTGGAGGAGGACCTGGAGGACTTCCTGGAGCAGGAGGAGCTG |
| CCTGAAGATGAGGAGCAGCTGGAGGAGGAGGAGGAGGAGGTGCCTGACCATTTGGGCA |
| GCTATGCCCAGCGTGAAGACGTAGCTGTGGCTGAGCCCAAAGACTTCAAACGCATCAG |
| CCTCCCGCCAGCTGCCCCAGGGAAGGAGGACAACGCCCCAGTCGCACCCACCGAGGCC |
| CCCGACATGGCCAAGGTGGCCCCCAAGCCAGCCACGCCCGACAAGGTGCCTGCAGCTG |
| AGCAGATCCCTGAGGCTGAGCCACCCAAGGACGAGGAGAGTTTCAGGCCGAGAGAGGA |
| TGAGGAAGGCCAGGAGGGGCAGGACTCCATGTCCAGGGCCAAGGCCAACTGGCTGCGT |
| GCCTTCAACAAGGTGCGGATGCAGCTGCAGGAGGCCCGGGGAGAAGGAGAGATGTCTA |
| AATCCCTATGGTTCAAAGGCGGGCCAGGGGCGGTCTCATCATCATCGACAGCATGCC |
| AGACATCCGCAAGAGGAAACCTATCCCACTCGTGAGCGACTTGGTACTGTCCCTGGTC |
| CAGTCCAGGAAAGCGGGCATCACCTCGGCCTTGGCCTCCAGCACGTTGAACAACGAGG |
| AGCTGAAAAACCACGTTTACAAGAAGACCCTGCAAGCCTTAATCTACCCCATCTCGTG |
| CACGACGCCACACAACTTCGAAGTGTCGACGGCCACCACGCCCACCTACTGCTACGAG |
| TGCGAGGGGCTGCTGTGGGCATCGCGAGGCAGGGCATGCGCTGCACCGAGTGCGGTG |
| TCAAGTGCCACGAGAAGTGCCAGGACCTGCTCAACGCCGACTGCCTGCAGCGTGCTGC |
| GGAGAAGAGCTCCAAGCACGGGGCGGAGGACCGGACACACAACATCATCATGGTGCTC |
| AAGGACCGCATGAAGATCCGGGAGCGCAACAAGCCCGAGATCTTCGAGCTCATCCAGG |
| AGATCTTCGCGGTGACCAAGACGGCGCACACGCACCACATGAAGGCGGTCAAGCAGAG |
| CGTGCTGGACGGCACGTCCAAGTGGTCCGCCAACATCAGCATCACCGTGGTCTGCGCC |
| CAGGGCTTGCAGGCAAAGGACAAGACAGGATCCAGTGACCCCTATGTCACCGTCCAGG |
| TCGGGAAGACCAAGAAACGGACAAAAACCATCTATGGGAACCTCAACCCGGTGTGGGA |
| GGAGAATTTCCACTTTGAATGTCACAATTCCTCCGACCGCATCAAGGTGCGCGTCTGG |
| GACGAGGATGACGACATCAAATCCCGCGTGAAACAGAGGTTCAAGAGGGAATCTGACG |
| ATTTCCTGGGGCAGACGATCATTGAGGTGCGGACGCTCAGCGGCGAGATGGACGTGTG |
| GTACAACCTGGACAAGCGAACTGACAAATCTGCCGTGTCGGGTGCCATCCGGCTCCAC |
| ATCAGTGTGGAGATCAAAGGCGAGGAGAAGGTGGCCCCGTACCATGTCCAGTACACCT |
| GTCTGCATGAGAACCTGTTCCACTTCGTCACCGACGTGCAGAACAATGGGGTCGTGAA |
| GATCCCAGATGCCAAGGGTGACGATGCCTGGAAGGTTTACTACGATGAGACAGCCCAG |
| GAGATTGTCGACGAGTTTGCCATGCGCTACCGCGTCGAGTCCATCTACCAAGCCATGA |
| CCCACTTTGCCTCCCTCTCCTCCAAGTATATGTCCCCAGGGGTGCCTGCCGTCATGAG |
| CACCCTGCTCGCCAACATCAATGCCTACTACGCACACACCACCGCCTCCACCAACGTG |
| TCTGCCTCCGACCGCTTCGCCGCCTCCAACTTTGGGAAAGAGCCCTTCCTGAAACTCC |
| TGGACCAGCTGCATAACTCCCTGCGGATTGACCTCTCCATGTACCGGAATAACTTCCC |
| AGCCAGCAGCCCGGAGAGACTCCAGGACCTCAAATCCACTGTGGACCTTCTCACCAGC |
| ATCACCTTCTTTCGGATGAAGGTACAAGAACTCCAGAGCCCGCCCCGAGCCAGCCAGG |

TABLE 74A-continued

NOV74 Sequence Analysis

TGGTAAAGGACTGTGTGAAAGCCTGCCTTAATTCTACCTACGACTACATCTTCAATAA

CTGCCATGAACTGTACAGCCGGGAGTACCAGACAGACCCGGCCAAGAAGGGGGAAGTT

CCCCCAGAGGAACAGGGGCCCAGCATCAAGAACCTCGACTTCTGGTCCAAGCTGATTA

CCCTCATAGTGTCCATCATTGACGAAGACAAGAATTCCTACACTCCCTGCCTCAACCA

GTTTCCCCAGGAGCTGAATGTGGGTAAAATCAGCGCTGAAGTGATGTGGAATCTGTTT

GCCCAAGACATGAACTACGCCATGGAGGAGCACGACAAGCATCGTCTATGCAAGAGTG

CCGACTACATGAACCTCCACTTCAAGGTGAAATCCCTCTACAATGAGTATGTCACGGA

ACTTCCCTCCTTCAAGGACCGCGTGCCTGAGTACCCTGCATGGTTTGAACCCTTCGTC

ATCCAGTGGCTGGATGAGAATGAGGAGGTGTCCCGGGATTTCCTGCACGGTGCCCTGG

AGCGAGACAAGAAGGATGGGTTCCAGCAGACCTCAGAGCATGCCCTATTCTCCTGCTC

CGTGGTGGATGTTTTCTCCCAACTCAACCAGAGCTTTGAAATCATCAAGAAACTCGAG

TGTCCCGACCCTCAGATCGTGGGGCACTACATGAGGCGCTTTGCCAAGACCATCAGTA

ATGTGCTCCTCCAGTATGCAGACATCATCTCCAAGGACTTTGCCTCCTACTGCTCCAA

GGAGAAGGACAAAGTGCCCTGCATTCTCATGAATAACACTCAACAGCTACCAGTTCAG

CTGGAGAAGATGTTCGAAGCCATGGGAGGAAAGGAGCTGGATGCTGAAGCCAGTGACA

TCCTGAAGGAGCTTCAGGTGAAACTCAATAACGTCTTGGATGAGCTCAGCCGGGTGTT

TGCTACCAGCTTCCAGCCGCACATTGAAGAGTGTGTCAAACAGATGGGTGACATCCTT

AGCCAGGTTAAGGGCACAGGCAATGTGCCAGCCAGTGCCTGCAGCAGCGTGGCCCAGG

ACGCGGACAATGTGTTGCAGCCCATCATGGACCTGCTGGACAGCAACCTGACCCTCTT

TGCCAAAATCTGTGAGAAGACTGTGCTCAAGCCAGTGCTGAAGGAGCTGTGGAAGCTG

GTTATGAACACCATGGAGAAAACCATCGTCCTGCCGCCCCTCACTGACCAGACGATGA

TCGGGAACCTCTTGAGAAAACATGGCAAGGGATTAGAAAAGGGCAGGGTGAAATTGCC

AAGCCACTCAGACGGAACCCAGATGATCTTCAATGCAGCCAAGGAGCTGGGTCAGCTG

TCCAAACTCAAGGATCACATGGTACGAGAAGAAGCCAAGAGCTTCACCCCAAACCAGT

GCGCGGTTGTTGAGTTGGCCCTGGACACCATCAAGCAATATTTCCACGCCGGTGGCGT

GGGCCTCAAGAAGACCTTCCTGGAGAAGAGCCCGGACCTGCAATCCTTGCGCTATGCC

CTGTCACTCTACACGCAGCCCACCGACCTGCTAATCAAGACCTTTGTACAGACGCAAT

CGGCCCGAGGTCCATGGTGGAAAAGGTACTAGGTTACCCTTAGTGAAGACATTTATCC

TGAGAAGGGTACGGGTGTAGAAGACCCTCTGGGTGAAGTCTCTCTCCATGTTGAGCTG

TTCACTCATCGAGGAACTGGGTAACACAAGGTCACAGTGAAAGTGGTGGCTGCCAATG

ACCTCAAGTGGCAGACTTCTGGCATCTTCCGGCCGTTCATCGAGGTCAACATCATTGG

GCCCCAGCTCAGCCACAACAAACGCAAGTTTCCCACCAAATCCAAGAACAATAGCTGG

GCTCCCAAGTACAATGAGAGCTTCCAGTTCACCCTGAGCGCCGACGCGGGTCCCCAGT

GGGGCTGGCCGTGCTGCAGCTGCGTGAGCTGGCCCAGCGCGGGAGCGCCGCCTGCTGG

CTGCCGCTCGGCCGCCGCATCCACATGGACGACACGGGCCTCACGGTGCTGCGAATCC

TCTCGCAGCGCAGCAACGACGAGGTGGCCAAGGAGTTCGTGAAGCTCAAGTCGGACAC

GCGCTCCGCCGAGGAGGGCGGTGCCGCGCCTGCGCCTTAG<u>CGCGGGCGGTCGGCCGAG</u>

<u>CGGCACTGCGCCTGCGCGGACGGCGCTGCGCGGGGAGGGACGGGGCTTGCGCCTTGGT</u>

<u>GGGACCTCCCCAGGGGCGGGGCTCGGGGGGCTCCACGCCAAGGGTGGGCTGCGCCTAC</u>

TABLE 74A-continued

NOV74 Sequence Analysis

GCCCTTGACTCAGCTTTCCCTTTTGGGGAATTAGGAATGCAGGATGCCCCGCCCTCTC

GGGAGGCCACGCCCAAGGGCGCGACGAAGGAAGGAGCCACATCCCCAACTTGAGGCCA

CGCCCCCAGCACCTAGGGGGCATTTTGAGCTGGGATGGGGGAAACCTCGTCCCTATGG

AGGAGGCCACATCCCGGGGCTCTGGTACCGGGAGGCACCACCTCATGTCCCCTGGAAA

AGCCATAAGATGGGACCCAGACCCCTGGGACCCCAGACCAATTGCCAAGTATGGAAAT

CTCAGCTCCCTCGAGGGGGGCCCTGGGCAAGGGGTAGGGCTCTCTGGAGCGCCCCTC

TAGGTGGCCTGGGGACTGGAGGGACCAGGATGCTGGTTGGAGGGCCCCGGAATACCGG

AGTCCCTTTAGATATTTGTGCAAAAAATAAATGGGCCGAGGGGGGACGATGGGATTTC

AAAAGCACATGCGCCCTTGGGCGCCCAAACCCTGGGGGCCGAGGGGACGGCTCTGGTT

CCCCACGCTGCCCCTACTTCCCTTTGGGAGTTTGCCTCTCCCTCTCCCCAACAAACC

CAGTCCTCATATCATAGAGTTCAACACACCCATTTGACAGATGGCAAAACTGAGGCTT

AAAGAGCTGCTTCAGACTTGGCCAAGGTTCCAGGTGCCATACCCTCTGTGCCCCTCCC

TTAGGCCTGTGTGCCCCATGGAAGGGTGGGCTGAGATCGGGATGACCTGACACAGCTC

CCTATTGCTGCTAATTCCCCCTCGGCCTCCTCCAAGGGGTGGAAATTCCAGGCCAAGA

CCCCTACTTCGCCTTTCCTTCTCCGGCTGCCAAGCAGGACCTTTGCCCTCAGCCCTTT

CTCCTGGGATCTCCATGGGGATGCCATGAGGGCCTCCCACCACAAAAGAGAATTTGG

GATCCCCTGGTCCCAGGTTTCTCCATCCCTTCTTCCTTTTCCAGAATTTTCCAAATAG

GAAAGAACAGAAGGAGACCAGAAACTCTAGGGGGAGAAAGAGAATGAGAGAAAGAGA

ATGAGAGAGAGAAACACAAACACAGTGACACAGTGAGAGCTTAGTCTCCAAGAGCC

TATTCATTGATTCAAACACCCAAGCCACAGGATACCTCAGATGGCCCTCTTGCCAGCT

GGAAGCTCTTTCTCCAATGAGCAAAGTTACAGTGACCTGGCTGGAGTTACCTGGTGCA

CATAGGACCTTAGGGGAAAGTTCAGCGTGGACTACACTTGCTCTGGGATCTGCTTTTC

CACATGTGTCTATGGCACGCCTTTTTCTGCTGGATTGGGAAGGACAAGATTTTGCTGT

GCTAGGGAGAAATGAAAACGGGGTGAGCTGAGTAGCTGGGTTTCTGGAGGATAGAACA

TCAGATGGGGAGGCTTTCCGAGGTGAAGAATGAGAGGGAACCACTTACTAGAGAGAAA

AGAGCTCCAGGCCTGGGCAACAGCACGTGCGAAGGCCAGCAGAGAAGAACTGTTGAAA

CAACGAGAAGGGTGGCACGGCTGGAGCTGAGCCAGCAAGGGGGATCGTGAGGAGCCTT

GGGGTTGGGGAGATCTGCAGAAGCATCAGACCAGGCAGGGCCTCGTACGCAGTCCTGA

GGAGTTTTACTTTTATTCTAAGACAGTTGGGGAGCTCCAGGAGCTGTTTTAAGTTGGG

GAGAGACTGGATTCCAGCCTGCAAAAGCTGTTTTGTGAAGACTAAAACCAGTGAGGAG

AGGTGGAGGTTGCTTTGGGGACACTGAAATGGATTCTTGGAAAGATTCTGAAGGCTGT

GTTGAAAAGACACCTATAGCTGTGGGACATGACTATAATCCCAGCATTTGGGGAGAC

CGAGGCTGGCAGATCACTTAAGGTCAGGAGTTTGAGACCAGCCTGGCCAACATGGCGA

AACCCCATCTCTGCTAAAAATACAAAAATTAGCTGGGTCCAGTGGTGCATGCCTGTAG

TCCCAGCTACTCAGGACACTGACGCGGGACAATTGTTTGAACCCTCGAGGCAGAGGTT

GTAGTGAGTCGTGATCACACAACTGCACTCCAGCCTGGGCAACAGAACAATACTCCAT

TCCCTCCCCTCTACCCCACC

ORF Start: at 3  ORF Stop: TAG at 5142
SEQ ID NO: 194  1713 aa  MW at 194170.2kD NOV74a, KKAKFDGAQEKFNTYVTLKVQNVKSTTIAVRGSQPSWEQDFMFEINRLDLGLTVEVWN

TABLE 74A-continued

NOV74 Sequence Analysis

CG94302-01 Protein Sequence

KGLIWDTMVGTVWIPLRTIRQSNEEGPGEWLTLDSQVIMADSEICGTKDPTFHRILLD
TRFELPLDIPEEEARYWAKKLEQLNAMRDQDEYSFQDEQDKPLPVPSNQCCKYFPYRL
SLPDDDPDSAVDDRDSDYRSETSNSIPPPYYTTSQPNASVHQYSVRPPPLGSRESYSD
SMHSYEEFSEPQALSPTGSSRYASSGELSQGSSQLSEDFDPDEHSLQGSDMEDERDRD
SYHSCHSSVSYHKDSPRWDQDEEELEEDLEDFLEEEELPEDEEELEEEEEVPDDLGS
YAQREDVAVAEPKDFKRISLPPAAPGKEDKAPVAPTEAPDMAKVAPKPATPDKVPAAE
QIPEAEPPKDEESFRPREDEEGQEGQDSMSRAKANWLRAFNKVRMQLQEARGEGEMSK
SLWFKGGPGGGLIIDSMPDIRKRKPIPLVSDLVLSLVQSRKAGITSALASSTLNNEE
LKNHVYKKTLQALIYPISCTTPHNFEVWTATTPTYCYECEGLLWGIARQGMRCTECGV
KCHEKCQDLLNADCLQRAAEKSSKHGAEDRTQNIIMVLKDRMKIRERNKPEIFELIQE
IFAVTKTAHTQQMKAVKQSVLDGTSKWSAKISITVVCAQGLQAKDKTGSSDPYVTQV
GKTKKRTKTIYGNLNPVWEENFHFECHNSSDRIKVRVWDEDDDIKSRVKQRFKRESDD
FLGQTIIEVRTLSGEMDVWYNLDKRTDKSAVSGAIRLHISVELKGEEKVAPYHVQYTC
LHENLFHFVTDVQNNGVVKIPDAKGDDAWKVYYDETAQEIVDEFAMRYGVESIYQAMT
HFACLSSKYMCPGVPAVMSTLLANINAYYAHTTASTNVSASDRFAASNFGKERFVKLL
DQLHNSLRIDLSMYRNNFPASSPERLQDLKSTVDLLTSITFFRMKVQELQSPPRASQV
VKDCVKACLNSTYEYIFNNCHELYSREYQTDPAKKGEVPPEEQGPSIKNLDFWSKLIT
LIVSIIEEDKNSYTPCLNQFPQELNVGKISAEVMWNLFAQDMKYAMEEHDKHRLCKSA
DYMNLHFKVKWLYNEYVTELPSFKDRVPEYPAWFEPFVIQWLDENEEVSRDFLHGALE
RDKKDGFQQTSEHALFSCSVVDVFSQLNQSFEIIKKLECPDPQIVGHYMRRFAKTISN
VLLQYADIISKDFASYCSKEKEKVPCILMNNTQQLRVQLEKMFEAMGGKELDAEASDI
LKELQVKLNNVLDELSRVFATSFQPHIEECVKQMGDILSQVKGTGNVPASACSSVAQD
ADNVLQPIMDLLDSNLTLFAKICEKTVLKRVLKELWKLVMNTMEKTIVLPPLTDQTIM
GNLLRKHGKGLEKGRVKLPSHSDGTQMIFNAAKELGQLSKLKDHMVREEAKSLTPKQC
AVVELALDTIKQYFHAGGVGLKKTFLEKSPDLQSLRYALSLYTQATDLLIKTFVQTQS
AQVHGGKGTRFTLSEDIYPEKGTGVEDPVGEVSVHVELFTHPGTGEHKVTVKVVAAND
LKWQTSGIFRPFIEVNIIGPQLSDKKRKFATKSKNNSWAPKYNESFQFTLSADAGPEC
YELQVCVKDYCFAREDRTVGLAVLQLRELAQRGSAACWLPLGRRIHMDDTGLTVLRIL
SQRSNDEVAKEFVKLKSDTRSAEEGGAAPAP

Further analysis of the NOV74a protein yielded the following properties shown in Table 74B.

TABLE 74B

Protein Sequence Properties NOV74a

| | |
|---|---|
| PSort analysis: | 0.7000 probability located in nucleus; 0.3000 probability located in microbody (peroxisome); 0.1000 probability located in mitochondrial matrix space; 0.1000 probability located in lysosome (lumen) |
| SignalP analysis: | No Known Signal Sequence Predicted |

A search of the NOV74a protein against the Geneseq database, a proprietary database that contains sequences published in patents and patent publication, yielded several homologous proteins shown in Table 74C.

TABLE 74C

Geneseq Results for NOV74a

| Geneseq Identifier | Protein/Organism/Length [Patent #, Date] | NOV74a Residues/ Match Residues | Identities/ Similarities for the Matched Region | Expect Value |
|---|---|---|---|---|
| AAW83431 | Rat Munc13-1 - Rattus sp, 1763 aa. [JP10313866-A, Dec. 2, 1998] | 1 . . . 1713<br>37 . . . 1763 | 1635/1727 (94%)<br>1665/1727 (95%) | 0.0 |
| AAY27134 | Human munc13 (Hmunc13) polypeptide - Homo sapiens, 1591 aa. [WO9931134-A1, Jun. 24, 1999] | 1 . . . 1707<br>9 . . . 1590 | 1242/1717 (72%)<br>1390/1717 (80%) | 0.0 |
| AAW83428 | Munc13-1-interacting domain of Doc2-alpha - Rattus sp, 611 aa. [JP10313866-A, Dec. 2, 1998] | 801 . . . 1411<br>1 . . . 611 | 600/611 (98%)<br>605/611 (98%) | 0.0 |
| AAB47279 | PN7098 - Homo sapiens, 1230 aa. [WO200140794-A1, 07 Jun. 2001] | 119 . . . 677<br>684 . . . 1230 | 226/589 (38%)<br>305/589 (51%) | 4e-88 |
| ABG02226 | Novel human diagnostic protein #2217 - Homo sapiens, 146 aa. [WO200175067-A2, Oct. 11, 2001] | 406 . . . 540<br>12 . . . 146 | 131/135 (97%)<br>133/135 (98%) | 3e-69 |

In a BLAST search of public sequence datbases, the NOV74a protein was found to have homology to the proteins shown in the BLASTP data in Table 74D.

TABLE 74D

Public BLASTP Results for NOV74a

| Protein Accession Number | Protein/Organism/Length | NOV74a Residues/ Match Residues | Identities/ Similarities for the Matched Portion | Expect Value |
|---|---|---|---|---|
| Q62768 | MUNC13-1 - Rattus norvegicus (Rat), 1735 aa. | 1 . . . 1713<br>9 . . . 1735 | 1635/1727 (94%)<br>1665/1727 (95%) | 0.0 |
| Q9WV40 | MUNC13-2 PROTEIN - Rattus norvegicus (Rat), 1622 aa. | 1 . . . 1707<br>9 . . . 1621 | 1236/1720 (71%)<br>1393/1720 (80%) | 0.0 |
| O14795 | MUNC13 - Homo sapiens (Human), 1591 aa. | 1 . . . 1707<br>9 . . . 1590 | 1242/1717 (72%)<br>1390/1717 (80%) | 0.0 |
| Q9Z1N9 | RENAL MUNC13 - Mus musculus (Mouse), 1591 aa. | 1 . . . 1707<br>9 . . . 1590 | 1218/1719 (70%)<br>1375/1719 (79%) | 0.0 |
| Q62769 | MUNC13-2 - Rattus norvegicus (Rat), 1985 aa. | 459 . . . 1707<br>767 . . . 1984 | 1016/1250 (81%)<br>1121/1250 (89%) | 0.0 |

PFam analysis predicts that the NOV74a protein contains the domains shown in the Table 75B. Table 74E.

TABLE 74E

Domain Analysis of NOV74a

| Pfam Domain | NOV74a Match Region | Identities/ Similarities for the Matched Region | Expect Value |
|---|---|---|---|
| DAG_PE-bind: domain 1 of 1 | 545 . . . 594 | 20/51 (39%)<br>44/51 (86%) | 1.3e-19 |
| C2: domain 1 of 2 | 669 . . . 760 | 37/106 (35%)<br>76/106 (72%) | 3.3e-21 |
| sigma70: domain 1 of 1 | 1203 . . . 1371 | 32/242 (13%)<br>108/242 (45%) | 2.6 |
| SPX: domain 1 of 1 | 1211 . . . 1375 | 30/351 (9%) | 0.96 |

TABLE 74E-continued

Domain Analysis of NOV74a

| Pfam Domain | NOV74a Match Region | Identities/ Similarities for the Matched Region | Expect Value |
|---|---|---|---|
| NTF2: domain 1 of 1 | 1499 . . . 1614 | 105/351 (30%)<br>29/135 (21%)<br>78/135 (58%) | 2.7 |
| C2: domain 2 of 2 | 1557 . . . 1647 | 24/97 (25%)<br>58/97 (60%) | 0.00069 |

Example 75

The NOV75 clone was analyzed, and the nucleotide and encoded polypeptide sequences are shown in Table 75A.

TABLE 75A

NOV75 Sequence Analysis

NOV75a, CG94356-01 DNA Sequence

SEQ ID NO: 195      1746 bp

ATGGTGGTGGTGCCTTTCACAATTCCATTCGATTCATCAGTCTGGCTGCTGCAGAAGT
TGAACATCAAGGTCCAAGGAGGGCCTTCTGCTGAAGGGCCACAGAGGAACACCAGGCT
GGGATGGATTCAGGGCAAGCAAGTCACTGTGCTGGGAAGCCCTGTGCCTGTGAACGTG
TTCCTCGGAGTCCCCTTTGCTGCTCCCCCGCTGGGATCCCTGCGATTTACGAACCCGC
AGCCTGCATCGCCCTGGGATAACTTGCGAGAAGCCACCTCCTACCCTAATTTGTGCCT
CCAGAACTCAGAGTGGCTGCTCTTAGATCAACATATGCTCAAGGTGCATTACCCGAAA
TTCGGAGTGTCAGAAGACTGCCTCTACCTGAACATCTATGCGCCTGCCCACGCCGATA
CAGGCTCCAAGCTCCCCGTCTTGGTGTGGTTCCCAGGAGGTGCCTTCAAGACTGGCTC
AGCCTCCATCTTTGATGGGTCCGCCCTGGCTGCCTATGAGGACGTGCTGGTTGTGGTC
GTCCAGTACCGGCTAGGAATATTTGGTTTCTTCACCACATGGGATCAGCATGCTCCGG
GGAACTGGGCCTTCAAGGACCAGGTGGCTGCTCTGTCCTGGGTCCAGAAGAACATCGA
GTTCTTCGGTGGGGACCCCAGCTCTGTGACCATCTTTGGCGAGTCCGCGGGAGCCATA
AGTGTTTCTAGTCTTATACTGTCTCCCATGGCCAAAGGCTTATTCCACAAAGCCATCA
TGGAGAGTGGGGTGGCCATCATCCCTTACCTGGAGGCCCATGATTATGAAGAGTGA
GGACCTGCAGGTGGTTGCACATTTCTGTGGTAACAATGCGTCAGACTCTGAGGCCCTG
CTGAGGTGCCTGAGGACAAAACCCTCCAAGGAGCTGCTGACCCTCAGCCAGAAAACAA
AGTCTTTCACTCGAGTGGTTGATGGTGCTTTCTTTCCTAATGAGCCTCTAGATCTATT
GTCTCAGAAAGCATTTAAAGCAATTCCTTCCATCATCGGAGTCAATAACCACGAGTGT
GGCTTCCTGCTGCCTATGGTAAGAATTCTGGCTGTCCATACTGCCACTCCCTCAAACC
GTGATGCAGCTTTGGCTTCAACAGCTGGGCATTTCCACAGAAGACATATCCCGCCTCA
GTATTTGCACCTTGTGGCTAATGAATACTTCCATGACAAGCACTCCCTGACTGAAATC
CGAGACAGTCTTCTGGACTTGCTTGGAGATGTGTTCTTTGTGGTCCCTGCACTGATCA
CAGCTCGATATCACAGAGATGCTGGTGCACCTGTCTACTTCTATGAGTTTCGGCACCG
GCCTCAGTGCTTTGAAGACACGAAGCCAGCTTTTGTCAAAGCCGACCACGCTGATGAA
GTCCGCTTTGTGTTCGGTGGTGCCTTCCTGAAGGGGGACATTGTTATGTTCGAAGGAG
CCACGGAGGAGGAGAAGTTACTGAGCCGGAAGATGATGAAATACTGGGCTACCTTTGC
TCGAACCGGGAATCCTAATGGGAACGACCTGTCTCTGTGGCCAGCTTATAATCTGACT
GAGCAGTACCTCCAGCTGGACTTGAACATGAGCCTCGGACAGAGACTCAAAGAACCGC
GGAGAGATGTGTGGGTGACGGGGTATCCTCAGCCATGGAAAGCTGCCATCATCCAGAA
TAAAAAACCTAGAAGTCAAATTCTAGGCATCAAGGGTCGGATCAGCAATGCCAAGAAG
AAATGA

ORF Start: ATG at 1     ORF Stop: TGA at 1744

SEQ ID NO: 196      581 aa     MW at 64717.6kD

NOV75a, CG94356-01 Protein Sequence

MVVVPFTIPFDSSVWLLQKLNIKVQGGPSAEGPQRNTRLGWIQGKQVTVLGSPVPVNV

FLGVPFAAPPLGSLRFTNPQPASPWDNLREATSYPNLCLQNSEWLLLDQHMLKVHYPK

FGVSEDCLYLNIYAPAHADTGSKLPVLVWFPGGAFKTGSASIFDGSALAAYEDVLVVV

VQYRLGIFGFFTTWDQHAPGNWAFKDQVAALSWVQKNIEFFGGDPSSVTIFGESAGAI

SVSSLILSPMAKGLFHKAIMESGVAIIPYLEAHDYEKSEDLQVVAHFCGNNASDSEAL

LRCLRTKPSKELLTLSQKTKSFTRVVDGAFFPNEPLDLLSQKAFKAIPSIIGVNNHEC

TABLE 75A-continued

NOV75 Sequence Analysis

GFLLPMVRILAVHTATPSNRDAALASTAGHFHRRHIPPQYLHLVANEYFHDKHSLTEI

RDSLLDLLGDVFFVVPALITARYHRDAGAPVYFYEFRHRPQCFEDTKPAFVKADHADE

VRFVFGGAFLKGDIVMFEGATEEEKLLSRKMMKYWATFARTGNPNGNDLSLWPAYNLT

EQYLQLDLNMSLGQRLKEPRRDVWVTGYPQPWKAAIIQNKKPRSQILGIKGRISNAKK

K

Further analysis of the NOV75a protein yielded the following properties shown in Table 75B.

TABLE 75B

| Protein Sequence Properties NOV75a | |
|---|---|
| PSort analysis: | 0.6000 probability located in plasma membrane: 0.4109 probability located in mitochondrial inner membrane; 0.4000 probability located in Golgi body; 0.3000 probability located in endoplasmic reticulum (membrane) |
| SignalP analysis: | No Known Signal Sequence Predicted |

A search of the NOV75a protein against the Geneseq database, a proprietary database that contains sequences published in patents and patent publication, yielded several homologous proteins shown in Table 75C.

TABLE 75C

Geneseq Results for NOV75a

| Geneseq Identifier | Protein/Organism/Length [Patent #, Date] | NOV75a Residues/ Match Residues | Identities/ Similarities for the Matched Region | Expect Value |
|---|---|---|---|---|
| AAB58981 | Breast and ovarian cancer associated antigen protein sequence SEQ ID 689 - Homo sapiens, 549 aa. [WO200055173-A1, SEP. 21, 2000] | 15 . . . 552<br>3 . . . 534 | 252/544 (46%)<br>342/544 (62%) | e−133 |
| AAB31700 | Protein encoded by an intestinal carboxylesterase (iCE) cDNA - Homo sapiens, 559 aa. [WO200100784-A2, JAN. 4, 2001] | 20 . . . 552<br>20 . . . 544 | 252/538 (46%)<br>341/538 (62%) | e−132 |
| ABG10273 | Novel human diagnostic protein #10264 - Homo sapiens, 583 aa. [WO200175067-A2, OCT. 11, 2001] | 20 . . . 552<br>42 . . . 568 | 249/540 (46%)<br>337/540 (62%) | e−126 |
| ABG10273 | Novel human diagnostic protein #10264 - Homo sapiens, 583 aa. [WO200175067-A2, OCT. 11, 2001] | 20 . . . 552<br>42 . . . 568 | 249/540 (46%)<br>337/540 (62%) | e−126 |
| AAE04101 | Human gene 2 encoded secreted protein HWLFE89, SEQ ID NO: 87 - Homo sapiens, 571 aa. [WO200134643-A1, MAY 17, 2001] | 27 . . . 554<br>28 . . . 558 | 242/536 (45%)<br>331/536 (61%) | e−125 |

In a BLAST search of public sequence datbases, the NOV75a protein was found to have homology to the proteins shown in the BLASTP data in Table 75D.

TABLE 75D

Public BLASTP Results for NOV75a

| Protein Accession Number | Protein/Organism/Length | NOV75a Residues/ Match Residues | Identities/ Similarities for the Matched Portion | Expect Value |
|---|---|---|---|---|
| Q96DN9 | CDNA FLJ31547 FIS, CLONE NT2RI2001010, WEAKLY SIMILAR | 27 . . . 551<br>25 . . . 494 | 446/525 (84%)<br>449/525 (84%) | 0.0 |

TABLE 75D-continued

Public BLASTP Results for NOV75a

| Protein Accession Number | Protein/Organism/Length | NOV75a Residues/ Match Residues | Identities/ Similarities for the Matched Portion | Expect Value |
|---|---|---|---|---|
| | TO FATTY ACYL-COA HYDROLASE PRECURSOR, MEDIUM CHAIN (EC 3.1.2.14) - *Homo sapiens* (Human), 525 aa. | | | |
| Q95KH3 | HYPOTHETICAL 41.0 KDA PROTEIN - *Macaca fascicularis* (Crab eating macaque) (Cynomolgus monkey), 361 aa. | 238 ... 551<br>17 ... 324 | 274/314 (87%)<br>282/314 (89%) | e-155 |
| O35533 | CARBOXYLESTERASE PRECURSOR (EC 3.1.1.1) (ALI-ESTERASE) (B-ESTERASE) (MONOBUTYRASE) (COCAINE ESTERASE) (PROCAINE ESTERASE) (METHYLBUTYRASE) - *Mesocricetus auratus* (Golden hamster), 559 aa. | 16 ... 552<br>18 ... 544 | 262/540 (48%)<br>343/540 (63%) | e-138 |
| Q91WG0 | SIMILAR TO CARBOXYLESTERASE 2 (INTESTINE, LIVER) - *Mus musculus* (Mouse), 561 aa. | 20 ... 552<br>20 ... 546 | 267/542 (49%)<br>337/542 (61%) | e-137 |
| O70177 | CARBOXYLESTERASE PRECURSOR (EC 3.1.1.1) - *Rattus norvegicus* (Rat), 561 aa. | 20 ... 552<br>20 ... 546 | 268/541 (49%)<br>340/541 (62%) | e-136 |

PFam analysis predicts that the NOV75a protein contains the domains shown in the Table 75E.

TABLE 75E

Domain Analysis of NOV75a

| Pfam Domain | NOV75a Match Region | Identities/ Similarities for the Matched Region | Expect Value |
|---|---|---|---|
| COesterase: domain 1 of 1 | 40 ... 546 | 204/578 (35%)<br>388/578 (67%) | 3.1e-157 |

Example 76

The NOV76 clone was analyzed, and the nucleotide and encoded polypeptide sequences are shown in Table 76A.

TABLE 76A

NOV76 Sequence Analysis

| | |
|---|---|
| NOV76a<br>CG94421-01 DNA Sequence | SEQ ID NO: 197    2025 bp<br>CTCAAGTTGACCTGCCACTTCACCCAAGGAGGGTAAGGAGCTGGGACCAGAGTCGCCA<br><br>ATTCCTGCCTTCTAGATCCTGGGCAAGCTCTTGCCTCTGACAGTGTATTTGCCAACAT<br><br>GGCACCCAAAAAGAAGATTGTCAAAAAGAACAAAGGAGATATCAATGAGATGACTATA<br><br>ATCGTAGAAGATAGCCCCCTAAACAAACTGAATGCTTTGAATGGGCTCCTAGAGGGAG<br><br>GCAATGGCCTTAGCTGCATTTCTTCTGAACTAACAGATGCTTCTTATGGCCCCAACCT<br><br>CTTGGAAGGTTTAAGTAAAATGCGGCAGGAGAACTTCTTATGTGACTTAGTCATTGGT<br><br>ACCAAAACCAAATCCTTTGATGTTCATAAGTCAGTCATGGCTTCATCCAGTGAGTATT<br><br>TTTACAACATCCTAAAAAAAGACCCGTCAATTCAGAGCGTGGATCTCAATGATATCTC<br><br>ACCACTAGGCCTGGCCACTGTCATTGCATATGCCTACACTGGAAAGCTCACTCTCTCC<br><br>TTGTATACAATAGGAAGCATTATTTCTGCTGCTCTTTATCTTCAGATCCATACTCTTA<br><br>TAAAGATGTGCAGTGATTTTCTGATACGGGAGATGAGTGTTGAGAATTGCATGTATGT |

TABLE 76A-continued

NOV76 Sequence Analysis

TGTTAATATTGCTGAAACATACTCCCTAAAAAATGCAAAAGCAGCAGCCCAGAAATTT

ATTCGGGATAACTTCCTTGAATTTGCAGAATCGGATCAGTTTATGAAACTTACATTTG

AACAAATTAATGAACTTCTTATAGATGATGACTTACAGTTGCCTTCTGAGATAGTAGC

ATTCCAGATTGCAATGAAATGGTTAGAATTTGACCAAAAGAGAGTAAAATACGCTGCA

GATCTTTTGAGCAATATTCGCTTTGGTACCATCTCTGCACAAGACCTGGTCAATTATG

TTCAATCCGTACCAAGAATGATGCAAGATGCTGATTGTCACAGACTTCTCGTAGATGC

TATGAACTACCACTTGCTTCCATATCATCAAAACACATTCCAATCTAGGCGAACAAGA

ATCCGAGGTGGCTGCCGAGTCCTCGTCACTGTTGGGGGACGCCCAGGCCTTACTGAGA

AGTCCCTTAGCAGAGACATCCTGTATAGACACCCTGAAAATGGATGGACCAAGCTTAC

GGAAATGCCAGCCAAAAGTTTTAATCAGTCTGTGGCTGTGATCGATGGATTTCTTTAT

GTAGCCGGTGGTGAAGACCAGAATGATGCAAGAAATCAAGCCAAGCATGCAGTCAGCA

ATTTCTGCAGATACGATCCCCGCTTCAACACCTGGATACACCTGGCCAGCATGAACCA

GAAGCGCACGCACTTCAGCCTGAGCGTGTTCAACGGGCTCGTGTACGCCGCGGGCGGC

CGCAACGCAGAAGGAAGCCTGGCCTCGCTGGAGTGCTACGTGCCCTCCACCAATCAGT

GGCAGCCGAAGACGCCCCTGGAGGTGGCGCGCTGCTGCCACGCTAGCGCGGTCGCCGA

CGGCCGCGTGCTGGTGACCGGAGGCTACATCGCCAACGCCTACTCGCGCTCTGTGTGC

GCCTACGACCCGGCCAGCGACTCGTGGCAGGAGCTGCCGAACCTCAGCACACCCCGGG

GCTGGCACTGCGCGGTCACGCTGAGCGACAGAGTGTACGTGATGGGCGGCAGCCAGCT

GGGGCCGCGCGGGGAGCGCGTGGACGTGCTCACCGTCGAGTGCTACAGCCCCGCGACC

GGCCAGTGGAGCTACGCGGCGCCGCTGCAGGTGGGAGTGAGCACTGCGGGCGTCTCGG

CGCTGCATGGCCGCGCCTACCTGGTGGGGGGCTGGAACGAGGGCGAGAAGAAGTACAA

GAAGTGCATCCAGTGCTTCAGCCCCGAGCTCAACGAGTGGACGGAGGACGACGAGCTA

CCCGAGGCCACTGTCGGCGTGTCCTGCTGCACCCTCTCGATGCCCAACAACGTGACTC

GGGAATCCCGGGCCAGTTCGGTATCTTCTGTGCCAGTCAGTATCTGAGCCCAG

ORF Start: ATG at 115    ORF Stop: TGA at 2017
SEQ ID NO: 198           634 aa    MW at 70259.3kD NOV76a,
CG94421-01 Protein Sequence

MAPKKKIVKKNKGDINEMTIIVEDSPLNKLNALNGLLEGGNGLSCISSELTDASYGPN

LLEGLSKMRQENFLCDLVIGTKTKSFDVHKSVMASCSEYFYNILKKDPSIQRVDLNDI

SPLGLATVIAYAYTGKLTLSLYTIGSIISAAVYLQIHTLIKMCSDFLIREMSVENCMY

VVNIAETYSLKNAKAAAQKFIRDNFLEFAESDQFMKLTFEQINELLIDDDLQLPSEIV

AFQIAMKWLEFDQKRVKYAADLLSNIRFGTISAQDLVNYVQSVPRMMQDADCHRLLVD

AMNYHLLPYHQNTLQSRRTIRGGCRVLVTVGGRPGLTEKSLSRDILYRDPENGWSKL

TEMPAKSFNQCVAVMDGFLYVAGGEDQNDARNQAKHAVSNFCRYDPRFNTWIHLASMN

QKRTHFSLSVFNGLVYAAGGRNAEGSLASLECYVPSTNQWQPKTPLEVARCCHASAVA

DGRVLVTGGYIANAYSRSVCAYDPASDSWQELPNLSTPRGWHCAVTLSDRVYVMGGSQ

LGPRGERVDVLTVECYSPATGQWSYAAPLQVGVSTAGVSALHGRAYLVGGWNEGEKKY

KKCIQCFSPELNEWTEDDELPEATVGVSCCTLSMPNNVTRESRASSVSSVPVSI

Further analysis of the NOV76a protein yielded the following properties shown in Table 76B.

TABLE 76B

Protein Sequence Properties NOV76a

| | |
|---|---|
| PSort analysis: | 0.3000 probability located in microbody (peroxisome); 0.3000 probability located in nucleus; 0.1000 probability located in mitochondrial matrix space; 0.1000 probability located in lysosome (lumen) |

TABLE 76B-continued

Protein Sequence Properties NOV76a

| | |
|---|---|
| SignalP analysis: | No Known Signal Sequence Predicted |

A search of the NOV76a protein against the Geneseq database, a proprietary database that contains sequences published in patents and patent publication, yielded several homologous proteins shown in Table 76C.

TABLE 76C

Geneseq Results for NOV76a

| Geneseq Identifier | Protein/Organism/Length [Patent #, Date] | NOV76a Residues/ Match Residues | Identities/ Similarities for the Matched Region | Expect Value |
|---|---|---|---|---|
| ABG10610 | Novel human diagnostic protein #10601 - Homo sapiens, 604 aa. [WO200175067-A2, OCT. 11, 2001] | 38 . . . 631<br>3 . . . 604 | 209/607 (34%)<br>329/607 (53%) | e-104 |
| ABG10610 | Novel human diagnostic protein #10601 - Homo sapiens, 604 aa. [WO200175067-A2, OCT. 11, 2001] | 38 . . . 631<br>3 . . . 604 | 209/607 (34%)<br>329/607 (53%) | e-104 |
| AAU28187 | Novel human secretory protein, Seq ID No: 356 - Homo sapiens, 615 aa. [WO200166689-A2, SEP. 13, 2001] | 34 . . . 620<br>27 . . . 614 | 209/595 (35%)<br>336/595 (56%) | e-102 |
| AAB93480 | Human protein sequence SEQ ID NO: 12768 - Homo sapiens, 615 aa. [EP1074617-A2, FEB. 7, 2001] | 34 . . . 620<br>27 . . . 614 | 209/595 (35%)<br>336/595 (56%) | e-102 |
| AAB95123 | Human protein sequence SEQ ID NO: 17120 - Homo sapiens, 616 aa. [EP1074617-A2, FEB. 7, 2001] | 53 . . . 614<br>26 . . . 595 | 184/572 (32%)<br>300/572 (52%) | 2e-84 |

In a BLAST search of public sequence datbases, the NOV76a protein was found to have homology to the proteins shown in the BLASTP data in Table 76D.

TABLE 76D

Public BLASTP Results for NOV76a

| Protein Accession Number | Protein/Organism/Length | NOV76a Residues/ Match Residues | Identities/ Similarities for the Matched Portion | Expect Value |
|---|---|---|---|---|
| Q9H511 | BA345L23.2 (NOVEL PROTEIN WITH BTB/POZ (BROAD COMPLEX TRAMTRACK BRIC-A-BRAC/POX VIRUS AND ZINC FINGER) DOMAIN) - Homo sapiens (Human), 634 aa. | 1 . . . 634<br>1 . . . 634 | 633/634 (99%)<br>634/634 (99%) | 0.0 |
| CAD28475 | HYPOTHETICAL 69.4 KDA PROTEIN - Homo sapiens (Human), 617 aa. | 40 . . . 628<br>6 . . . 614 | 216/613 (35%)<br>335/613 (54%) | e-106 |
| Q9P2J3 | Hypothetical protein KIAA1354 - Homo sapiens (Human), 632 aa (fragment). | 40 . . . 628<br>21 . . . 629 | 216/613 (35%)<br>335/613 (54%) | e-106 |
| Q9DBY7 | 1200009K10RIK PROTEIN - Mus musculus (Mouse), 638 aa. | 51 . . . 631<br>53 . . . 638 | 207/590 (35%)<br>324/590 (54%) | e-106 |
| Q9P2N7 | Hypothetical protein KIAA1309 - Homo sapiens (Human), 639 aa (fragment). | 39 . . . 631<br>32 . . . 639 | 210/613 (34%)<br>333/613 (54%) | e-105 |

PFam analysis predicts that the NOV76a protein contains the domains shown in the Table 76E.

TABLE 76E

Domain Analysis of NOV76a

| Pfam Domain | NOV76a Match Region | Identities/ Similarities for the Matched Region | Expect Value |
|---|---|---|---|
| BTB: domain 1 of 1 | 57 . . . 167 | 33/143 (23%) 85/143 (59%) | 1.4e−17 |
| Kelch: domain 1 of 5 | 354 . . . 406 | 15/53 (28%) 37/53 (70%) | 1.1e−05 |
| Kelch: domain 2 of 5 | 408 . . . 453 | 10/47 (21%) 36/47 (77%) | 8.2e−07 |
| Kelch: domain 3 of 5 | 455 . . . 500 | 12/47 (26%) 36/47 (77%) | 3e−07 |

TABLE 76E-continued

Domain Analysis of NOV76a

| Pfam Domain | NOV76a Match Region | Identities/ Similarities for the Matched Region | Expect Value |
|---|---|---|---|
| Kelch: domain 4 of 5 | 502 . . . 552 | 12/51 (24%) 39/51 (76%) | 1.2e−06 |
| Kelch: domain 5 of 5 | 554 . . . 601 | 13/48 (27%) 32/48 (67%) | 0.16 |

Example 77

The NOV77 clone was analyzed, and the nucleotide and encoded polypeptide sequences are shown in Table 77A.

TABLE 77A

NOV77 Sequence Analysis

NOV77A,

CG94465-01 DNA Sequence

SEQ ID NO:199    2880 bp

ACGAGGGCGGGGCGCGCCGGCGGGGTGACGTCACGGCCGCGCGCGGCGTCGGCGGAGC

CTCACTTTGAACCCAGTTGGCGGGAGTGGCTGCTCGCGGAGGGGCAGTGTCTGCGGGG

CCGCTGTATGCTGTCCAGCGATGGATCCCACCGCGGGAAGCAAGAAGGAGCCTGGAGG

AGGCGCGGCGACTGAGGAGGGCGTGAATAGGATCGCAGTGCCAAAACCGCCCTCCATT

GAGGAATTCAGCATAGTGAAGCCCATTAGCCGGGGCGCCTTCGGGAAAGTGTATCTGG

GGCAGAAAGGCGGCAAATTGTATGCAGTAAAGGTAGTTAAAAAAGCAGACATGATCAA

CAAAAATATGACTCATCAGGTCCAAGCTGACAGAGATGCACTGGCACTAAGCAAAAGC

CCATTCATTGTCCATTTGTATTATTCACTGCAGTCTGCAAACAATGTCTACTTGGTGA

TGGAATATCTTATTGGGGGAGATGTCAAGTCTCTCCTACATATATATGGTTATTTTGA

TGAAGAGATGGCTGTGAAATATATTTCTGAAGTAGCACTGGCTCTAGACTACCTTCAC

AGACATGGAATCATCCACAGGGACTTGAAACCGGACAATATGCTTATTTCTAATGAGG

GTCATATTAAACTGACGGATTTTGGCCTTTCAAAAGTTACTTTGAATAGAGATATTAA

TATGATCGATATCCTTACAACACCATCAATGGCAAAACCTAGACAAGATTATTCAAGA

ACCCCAGGACAAGTGTTATCGCTTATCAGCTCGTTGGGATTTAACACACCAATTGCAG

AAAAAAATCAAGACCCTGCAAACATCCTTTCAGCCTGTCTGTCTGAAACATCACAGCT

TTCTCAAGGACTCGTATGCCCTATGTCTGTAGATCAAAAGGACACTACGCCTTATTCT

AGCAAATTACTAAAATCATGTGAAACAGTTGCCTCCAACCCAGGAATGCCTGTGAAGT

GTCTAACTTCTAATTTACTCCAGTCTAGGAAAAGGCTGGCCACATCCAGTGCCAGTAG

TCAATCCCACACCTTCATATCCAGTGTGGAATCAGAATGCCACAGCAGTCCCAAATGG

GAAAAAGATTGCCAGGAAAGTGATGAAGCATTGGGCCCAACAATGATGAGTTGGAATG

CAGTTGAAAAGTTATGCGCAAAATCTGCAAATGCCATTGAGACGAAAGGTTTCAATAA

AAAGGATCTGGAGTTAGCTCTTTCTCCCATTCATAACAGCAGTGCCCTTCCCACCACT

GGACGCTCTTGTGTAAACCTTGCTAAAAAATGCTTCTCTGGGGAAGTTTCTTGGGAAG

CAGTAGAACTGGATGTAAATAATATAAATATGGACACTGACACAAGTCAGTTAGGTTT

CCATCAGTCAAATCAGTGGGCTGTGGATTCTGGTGGGATATCTGAAGAGCACCTTGGG

TABLE 77A-continued

NOV77 Sequence Analysis

AAAAGAAGTTTAAAAAGAAATTTTGAGTTGGTTGACTCCAGTCCTTGTAAAAAAATTA
TACAGAATAAAAAAACTTGTGTAGAGTATAAGCATAACGAAATGACAAATTGTTATAC
AAATCAAAATACAGGCTTAACAGTTGAAGTGCAGGACCTTAAGCTATCAGTGCACAAA
AGTCAACAAAATGACTCTGCTAATAAGGAGAACATTGTCAATTCTTTTACTGATAAAC
AACAAACACCAGAAAAATTACCTATACCAATGATAGCAAAAAACCTTATGTGTGAACT
CGATGAAGACTGTGAAAAGAATAGTAAGAGGGACTACTTAAGTTCTAGTTTTCTATGT
TCTGATGATGATAGAGCTTCTAAAAATATTTCTATGAACTCTGATTCATCTTTTCCTG
GAATTTCTATAATGGAAAGTCCATTAGAAAGTCAGCCCTTAGATTCAGATACAAGCAT
CAAAGAATCCTCTTTTGAAGAATCAAATATTGAAGATCCACTTATTGTAACACCAGAT
TGCCAAGAAAAGACCTCACCAAAAGGTGTCGAGAACCCTGCTGTACAAGAGAGTAACC
AAAAAATGTTAGGTCCTCCTTTGGAGGTGCTGAAAACGTTAGCCTCTAAAAGAAATGC
TGTTGCTTTTCGAAGTTTTAACAGTCATATTAATGCATCCAATAACTCAGAACCATCC
AGAATGAACATGACTTCTTTAGATGCAATGGATATTTCGTGTGCCTACAGTGGTTCAT
ATCCCATGGCTATAACCCCTACTCAAAAAGAAGATCCTGTATGCCACATCAGCAGAC
CCCAAATCAGATCAAGTCGGGAACTCCATACCGAACTCCGAAGAGTGTGAGAAGAGGG
GTGGCCCCCGTTGATGATGGGCGAATTCTAGGAACCCCAGACTACCTTGCACCTGAGC
TGTTACTAGGCAGGGCCCATGGTAAGGCATGCATGCCTGCGGTAGACTGGTGGGCACT
TGGAGTTTGCTTGTTTGAATTTCTAACAGGAATTCCCCCTTTCAATGATGAAACACCA
CAACAAGTATTCCAGAATATTCTGAAAAGAGATATCCCTTGGCCAGAAGGTGAAGAAA
AGTTATCTGATAATGCTCAAAGTGCAGTAGAAATACTTTTAACCATTGATGATACAAA
GAGAGCTGGAATGAAACGTCATCCTCTCTTCAGTGATGTGGACTGGGAAAATCTGCAG
CATCAGACTATGCCTTTCATCCCCCAGCCAGATGATGAAACAGATACCTCCTATTTTG
AAGCCAGGAATACTGCTCAGCACCTGACTGTATCTGGATTTAGTCTGTAG<u>CACAAAAA</u>
<u>TTTTCCTTTTAGTCTAGCCTTGTGTTATAGAATGAACTTGCATAATTATATACTCCTT</u>
<u>AATACTAGATTGATCTAAGGGGGAAAGATCANNNNNNNN</u>

ORF Staff: ATG at 137        ORF Stop: TAG at 2774
SEQ ID NO: 200               879 aa MW at 97267.9 kD NOV77a,
CG94465-01 Protein Sequence MDPTAGSKKEPGGGAATEEGVNRIAVPKPPSIEEFSIVKPISRGAFGKVYLGQKGGKL
YAVKVVKKADMINKNMTHQVQAERDALALSKSPFIVHLYYSLQSANNVYLVMEYLIGG
DVKSLLHIYGYFDEEMAVKYISEVALALDYLHRHGIIHRDLKPDNMLISNEGHIKLTD
FGLSKVTLNRDINMMDILTTPSMAKPRQDYSRTPGQVLSLISSLGFNTPIAEKNQDPA
NILSACLSETSQLSQGLVCPMSVDQKDTTPYSSKLLKSCETVASNPGMPVKCLTSNLL
QSRKRLATSSASSQSHTFISSVESECHSSPKWEKDCQESDEALGPTMMSWNAVEKLCA
KSANAIETKGFNKKDLELALSPIHNSSALPTTGRSCVNLAKKCFSGEVSWEAVELDVN
NINMDTDTSQLGFHQSNQWAVDSGGISEEHLGKRSLKRNFELVDSSPCKKIIQNKKTC
VEYKHNEMTNCYTNQNTGLTVEVQDLKLSVHKSQQNDCANKENIVNSFTDKQQTPEKL
PIPMIAKNLMCELDEDCEKNSKRDYLSSSFLCSDDDRASKNISMNSDSSFPGISIMES
PLESQPLDSDRSIKESSFEESNIEDPLIVTPDCQEKTSPKGVENPAVQESNQKMLGPP
LEVLKTLASKRNAVAFRSFNSHINASNNSEPSRMNMTSLDAMDISCAYSGSYPMAITP
TQKRRSCMPHQQTPNQIKSGTPYRTPKSVRRGVAPVDDGRILGTPDYLAPELLLGRAH

TABLE 77A-continued

NOV77 Sequence Analysis

|  |  |
|---|---|
|  | GKACMPAVDWWALGVCLFEFLTGIPPFNDETPQQVFQNILKRDIPWPEGEEKLSDNAQ |
|  | SAVEILLTIDDTKRAGMKRHPLFSDVDWENLQHQTMPFIPQPDDETDTSYFEARNTAQ |
|  | HLTVSGFSL |
| NOV77b, | SEQ ID NO:201                  2702 bp |
|  | <u>GAGCCTCACTTTGAACCCAGTTGGCGGGAATGGCTGCTCGCGGAGGGGCAGTGTACGC</u> |
| CG94465-02 DNA Sequence | <u>GGGGCCGCTGTAGGCTGTCCAGCG</u>ATGGATCCCACCGCGGGAAGCAAGAAGGAGCCTG |
|  | GAGGAGGCGCGGCGACTGAGGAGGGCGTGAATAGGATCGCAGTGCCAAAACCGCCCCTC |
|  | CATTGAGGAATTCAGCATAGTGAAGCCCATTAGCCGGGGCGCCTTCGGGAAAGTGTAT |
|  | CTGGGGCAGAAAGGCGGCAAATTGTATGCAGTAAAGGTTGTTAAAAAAGCAGACATGA |
|  | TCAACAAAAATATGACTCATCAGGTCCAAGCTGAGAGAGATCCACTGGCACTAAGCAA |
|  | AAGCCCATTCATTGTCCATTTGTATTATTCACTGCACTCTGCAAACAATGTCTACTTG |
|  | GTAATGGAATATCTTATTGGGGAGATGTCAAGTCTCTCCTACATATATATGGTTATT |
|  | TTGATGAAGAGATGGCTGTGAAATATATTTCTGAAGTAGCACTGGCTCTAGACTACCT |
|  | TCACAGACATGGAATCATCCACAGGGACTTGAAACCGGACAATATGCTTATTTCTAAT |
|  | GAGGGTCATATTAAACTGACGGATTTTGGCCTTTCAAAAGTTACTTTGAATAGAGATA |
|  | TTAATATGATGGATATCCTTACAACACCATCAATGGCAAAACCTAGACAAGATTATTC |
|  | AAGAACCCCAGGACAAGTGTTATCGCTTATCAGCTCGTTGGGATTTAACACACCAATT |
|  | GCAGAAAAAAATCAAGACCCTGCAAACATCCTTTCAGCCTGTCTCTGTGAAACATCAC |
|  | AGCTTTCTCAAGGACTCGTATGCCCTATGTCTGTAGATCAAAAGGACACTACGCCTTA |
|  | TTCTAGCAAATTACTAAAATCATGTCTTGAAACAGTTGCCTCCAACCCAGGAATGCCT |
|  | GTGAAGTGTCTAACTTCTAATTTACTCCAGTCTAGGAAAAGGCTGGCCACATCCAGTG |
|  | CCAGTAGTCAATCCCACACCTTCATATCCAGTGTGGAATCAGAATGCCACAGCAGTCC |
|  | CAAATGGGAAAAAGATTGCCAGGAAAGTGATGAAGCATTGGGCCCAACAATGATGAGT |
|  | TGGAATGCAGTTGAAAAGTTATGCGCAAAATCTGCAAATGCCATTGAGACGAAAGGTT |
|  | TCAATAAAAAGGATCTGGAGTTAGCTCTTTCTCCCATTCATAACAGCAGTGCCCTTCC |
|  | CACCACTGGACGCTCTTGTGTAAACCTTGCTAAAAAATGCTTCTCTGGGGAAGTTTCT |
|  | TGGGAAGCAGTAGAACTGGATGTAAATAATATAAATATGGACACTGACACAAGTCAGT |
|  | TAGGTTTCCATCAGTCAAATCAGTGGGCTGTGGATTCTGGTGGGATATCTGAAGAGCA |
|  | CCTTGGGAAAAGAAGTTTAAAAAGAAATTTTGAGTTGGTTGACTCCAGTCCTTGTAAA |
|  | AAAATTATACAGAATAAAAAAACTTGTGTAGAGTATAAGCATAACGAAATGGCAAATT |
|  | GTTATACAAATCAAAATACAGGCTTAACAGTTGAAGTGCAGGACCTTAAGCTATCAGT |
|  | GCACAAAAGTCAACAAAATGACTGTGCTAATAAGGAGAACATTGTCAATTCTTTTACT |
|  | GATAAACAACAAACACCAGAAAAATTACCTATACCAATGATAGCAAAAAACCTTATGT |
|  | GTGAACTCGATGAAGACTGTGAAAAGAATAGTAAGAGGGACTACTTAAGTTCTAGTTT |
|  | TCTATGTTCTGATGATGATAGAGCTTCTAAAAATATTTCTATGAACTCTGATTCATCT |
|  | TTTCCTGGAATTTCTATAATGGAAAGTCCATTAGAAAGTCAGCCCTTAGATTCAGATA |
|  | GAAGCATTAAAGAATCCTCTTTTGAAGAATCAAATATTGAAGATCCACTTATTGTAAC |
|  | ACCAGATTGCCAAGAAAACACCTCACCAAAAGGTCTCGAGAACCCTGCTGTACAAGAG |
|  | AGTAACCAAAAAATGTTAGGTCCTCCTTTGGAGGTGCTGAAAACGTTAGCCTCTAAAA |

TABLE 77A-continued

NOV77 Sequence Analysis

```
GAAATGCTGTTGCTTTTCGAAGTTTTAACAGTCATATTAATGCATCCAATAACTCAGA

ACCATCCAGAATGAACATGACTTCTTTAGATGCAATGGATATTTCGTGTGCCTACAGT

GGTTCATATCCCATGCTATAACCCCTACTCAAAAAAGAAGATCCTGTATGCCACATC

AGACCCCAAATCAGATCAAGTCGGGAACTCCATACCGAACTCCGAAGAGTGTGAGAAG

AGGGGTGGCCCCCGTTGATGATGGGCGAATTCTAGGAACCCCAGACTACCTTGCACCT

GAGCTGTTACTAGGCAGGGCCCATGATATCCCTTGGCCAGAAGGTGAAGAAAAGTTAT

CTGATAATGCTCAAAGTGCAGTAGAAATACTTTTAACCATTGATGATACAAAGAGAGC

TGGAATGAAAGAGCTAAAACGTCATCCTCTCTTCAGTGATGTCGACTGGGAAAATCTG

CAGCATCAGACTATGCCTTTCATCCCCCAGCCAGATGATGAAACAGATACCTCCTATT

TTGAAGCCAGGAATACTGCTCAGCACCTGACCGTATCTGGATTTAGTCTGTAGCACAA

AAATTTTCCTTTTAGTCTAGCCTCGTGTTATAGAATGAACTTGCATAATTATATACTC

CTTAATACTAGATTGATCTAAGGGGGAAAGATCA
```

| | |
|---|---|
| NOV77b, | ORF Start: ATG at 83     ORF Stop: TAG at 2603<br>SEQ ID NO:202     840 aa MW at 92829.8 kD |
| CG94465-02 Protein Sequence | MDPTAGSKKEPGGGAATEEGVNRIAVPKPPSIEEFSIVKPISRGAFGKVYLGQKGGKL<br>YAVKVVKKADMINKMTHQVQAERDALALSKSPFIVHLYYSLQSANNVYLVMEYLIGG<br>DVKSLLHIYGYFDEEMAVKYISEVALALDYLHRHGIIHRDLKPDNMLISNEGHIKLTD<br>FGLSKVTLNRDINMMDILTTPSMAKPRQDYSRTPGQVLSLISSLGFNTPIAEKNQDPA<br>NILSACLSETSQLSQGLVCPMSVDQKDTTPYSSKLLKSCLETVASNPGMPVKCLTSNL<br>LQSRKRLATSSASSQSHTFISSVESECHSSPKWEKDCQESDEALGPTMMSWNAVEKLC<br>AKSANAIETKGFNKKDLELALSPIHNSSALPTTGRSCVNLAKKCFSGEVSWEAVELDV<br>NNINMDTDTSQLGFHQSNQWAVDSGGISEEHLGKRSLKRNFELVDSSPCKKIIQNKKT<br>CVEYKHNEMANCYTNQNTGLTVEVQDLKLSVHKSQQNDCANKENIVNSFTDKQQTPEK<br>LPIPMIAKNLMCELDEDCEKNSKRDYLSSSFLCSDDDRASKNISMNSDSSFPGISIME<br>SPLESQPLDSDRSIKESSFEESNIEDPLIVTPDCQEKTSPKGVENPAVQESNQKMLGP<br>PLEVLKTLASKRNAVAFRSFNSHINASNNSEPSRMNMTSLDAMDISCAYSGSYPMAIT<br>PTQKRRSCMPHQTPNQIKSGTPYRTPKSVRRGVAPVDDGRILGTPDYLAPELLLGRAH<br>DIPWPEGEEKLSDNAQSAVEILLTIDDTKRAGMKELKRHPLFSDVDWENLQHQTMPFI<br>PQPDDETDTSYFEARNTAQHLTVSCFSL |
| NOV77c,<br>CG94465-03 DNA Sequence | SEQ ID NO:203     1415 bp<br>GAGCCTCACTTTGAACCCAGTTGGCCGGAATGGCTGCTCGCGGAGGGGCAGTGTACGC<br>GGGCCGCTGTAGGCTGTCCAGCGATGGATCCCACCGCGGGAAGCAAGAAGGAGCCTG<br>GAGGAGGCGCGGCGACTGAGGAGGGCGTGAATAGGATCGCAGTGCCAAAACCGCCCTC<br>CATTGAGGAATTCAGCATAGTGAAGCCCATTAGCCGGGGCGCCTTCGGGAAAGTGTAT<br>CTGGGGCAGAAAGGCGGCAAATTGTATGCAGTAAAGGTTGTTAAAAAAGCAGACATGA<br>TCAACAAAAATATGACTCATCAGGTCCAAGCTGAGAGAGATGCACTGGCACTAAGCAA<br>AAGCCCATTCATTGTCCATTTGTATTATTCACTGCAGTCTGCAAACAATGTCTACTTG<br>GTAATGGAATATCTTATTGGGGGAGATGTCAAGTCTCTCCTACATATATATGGTTATT<br>TTGATGAAGAGATGGCTGTGAAATATATTTCTGAAGTAGCACTGGCTCTAGACTACCT<br>TCACAGACATGGAATCATCCACAGGGACTTGAAACCGGACAATATGCTTATTTCTAAT |

TABLE 77A-continued

NOV77 Sequence Analysis

GAGGGTCATATTAAACTGACGGATTTTGGCCTTTCAAAAGTTACTTTGAATAGAGATA
TTAATATGATGGATATCCTTACAACACCATCAATGGCAAAACCTAGACAAGATTATTC
AAGAACCCCACGACAAGTGTTATCGCTTATCAGCTCGTTGGGATTTAACACACCAATT
GCAGAAAAAAATCAAGACCCTGCAAACATCCTTTCAGCCTGTCTGTCTGAAACATCAC
AGCTTTCTCAAGGACTCGTATGCCCTATGTCTGTAGATCAAAAGGACACTACGCCTTA
TTCTAGCAAATTACTAAAATCATCTCTTGAAACAGTTGCCTCCAACCCAGGAATGCCT
GTGAAGTGTCTAACTTCTAATTTACTCCAGTCTAGGAAAAGGCTGGCCACATCCAGTG
CCAGTAGTCAATCCCACACCTTCATATCCAGTGTGGAATCAGAATGCCACACCAGTCC
CAAATGGGAAAAAGATTGCCAGCACACCCCAAATCAGATCAAGTCGGGAACTCCATAC
CGAACTCCGAAGAGTGTGAGAAGAGGGGTGGCCCCCGTTGATGATGGGCGAATTCTAG
GAACCCCAGACTACCTTGCACCTGAGCTGTTACTAGGCAGGGCCCATGAGCTAAAACG
TCATCCTCTCTTCAGTGATGTGGACTGGGAAAATCTGCAGCATCAGACTATGCCTTTC
ATCCCCCAGCCAGATGATGAACAGATACCTCCTATTTTGAAGCCAGGAATACTGCTC
AGCACCTGACTGTATCTCGATTTAGTCTGTAGCACAAAATTTTCCTTTTAGTCTAGCC
TTGTGTTATAGAATGAACTTGCA

| | ORF Start: ATG at 83 | ORF Stop: TAG at 1364 |
|---|---|---|
| | SEQ ID NO:204 | 427 aa MW at 47124.2 kD |

NOV77c,

CG94465-03 Protein Sequence

MDPTAGSKKEPGGGAATEEGVNRIAVPKPPSIEEFSIVKPISRGAFGKVYLGQKGGKL
YAVKVVKKADMINKNMTHQVQAERDALALSKSPFIVHLYYSLQSANNVYLVMEYLIGG
DVKSLLHIYGYFDEEMAVKYISEVALALDYLHRHGIIHRDLKPDNMLISNEGHIKLTD
FGLSKVTLNRDINMMDILTTPSMAKPRQDYSRTPGQVLSLISSLGFNTPIAEKNQDPA
NILSACLSETSQLSQGLVCPMSVDQKDTTPYSSKLLKSCLETVASNPGMPVKCLTSNL
LQSRKRLATSSASSQSHTFISSVESECHSSPKWEKDCQQTPNQIKSGTPYRTPKSVRR
GVAPVDDGRILGTPDYLAPELLLGRAHELKRHPLFSDVDWENLQHQTMPFIPQPDDET
DTSYFEARNTAQHLTVSGFSL

Sequence comparison of the above protein sequences yields the following sequence relationships shown in Table 77B.

TABLE 77B

Comparison of NOV77a against NOV77b and NOV77c.

| Protein Sequence | NOV77a Residues/ Match Residues | Identities/Similarities for the Matched Region |
|---|---|---|
| NOV77b | 1 ... 879 | 835/883 (94%) |
| | 1 ... 840 | 835/883 (94%) |
| NOV77c | 1 ... 329 | 327/330 (99%) |
| | 1 ... 330 | 329/330 (99%) |

Further analysis of the NOV77a protein yielded the following properties shown in Table 77C.

TABLE 77C

Protein Sequence Properties NOV77a

| | |
|---|---|
| PSort analysis: | 0.4500 probability located in cytoplasm; 0.3000 probability located in microbody (peroxisome); 0.1000 probability located in mitochondrial matrix space; 0.1000 probability located in lysosome (lumen) |
| SignalP analysis: | No Known Signal Sequence Predicted |

A search of the NOV77a protein against the Geneseq database, a proprietary database that contains sequences published in patents and patent publication, yielded several homologous proteins shown in Table 77D.

TABLE 77D

Geneseq Results for NOV77a

| Geneseq Identifier | Protein/Organism/Length [Patent #, Date] | NOV77a Residues/ Match Residues | Identities/ Similarities for the Matched Region | Expect Value |
|---|---|---|---|---|
| AAG66515 | Human 18477 protein kinase - *Homo sapiens*, 879 aa. [WO200159080-A1, 16-AUG-2001] | 1...879<br>1...879 | 875/883 (99%)<br>875/883 (99%) | 0.0 |
| AAB93303 | Human protein sequence SEQ ID NO: 12373 - *Homo sapiens*, 878 aa. [EP1074617-A2, 07-FEB-2001] | 1...879<br>1...878 | 872/883 (98%)<br>872/883 (98%) | 0.0 |
| AAM93339 | Human polypeptide, SEQ ID NO: 2877 - *Homo sapiens*, 840 aa. [EP1130094-A2, 05-SEP-2001] | 1...879<br>1...840 | 834/883 (94%)<br>835/883 (94%) | 0.0 |
| AAB65602 | Novel protein kinase, SEQ ID NO: 127 - *Homo sapiens*, 329 aa. [WO200073469-A2, 07-DEC-2000] | 1...327<br>1...328 | 327/328 (99%)<br>327/328 (99%) | 0.0 |
| AAM48169 | CEK1-34 protein sequence - Unidentified, 312 aa. [CN1315336-A, 03-OCT-2001] | 566...879<br>1...312 | 308/317 (97%)<br>309/317 (97%) | e-177 |

In a BLAST search of public sequence datbases, the NOV77a protein was found to have homology to the proteins shown in the BLASTP data in Table 77E.

TABLE 77E

Public BLASTP Results for NOV77a

| Protein Accession Number | Protein/Organism/Length | NOV77a Residues/ Match Residues | Identities/ Similarities for the Matched Portion | Expect Value |
|---|---|---|---|---|
| Q96GX5 | UNKNOWN (PROTEIN FOR MGC: 17352) - *Homo sapiens* (Human), 879 aa. | 1...879<br>1...879 | 875/883 (99%)<br>875/883 (99%) | 0.0 |
| Q96SJ5 | CDNA FLJ14813 FIS, CLONE NT2RP4002408, MODERATELY SIMILAR TO PROTEIN KINASE CEK1 (EC 2.7.1.-) - *Homo sapiens* (Human), 878 aa. | 1...879<br>1...878 | 872/883 (98%)<br>872/883 (98%) | 0.0 |
| Q95K03 | HYPOTHETICAL 53.7 KDA PROTEIN - *Macaca fascicularis* (Crab eating macaque) (Cynomolgus monkey), 487 aa. | 162...633<br>1...473 | 451/473 (95%)<br>459/473 (96%) | 0.0 |
| Q9D9V0 | 2700091H24RIK PROTEIN - *Mus musculus* (Mouse), 615 aa. | 253...879<br>1...615 | 439/632 (69%)<br>508/632 (79%) | 0.0 |
| Q9CZH9 | 2700091H24RIK PROTEIN - *Mus musculus* (Mouse), 615 aa. | 253...879<br>1...615 | 439/632 (69%)<br>507/632 (79%) | 0.0 |

PFam analysis predicts that the NOV77a protein contains the domains shown in the Table 77F.

TABLE 77F

Domain Analysis of NOV77a

| Pfam Domain | NOV77a Match Region | Identities/ Similarities for the Matched Region | Expect Value |
|---|---|---|---|
| pkinase: domain 1 of 2 | 35...180 | 53/148 (36%)<br>122/148 (82%) | 1.2e-44 |
| RIO1: domain 1 of 1 | 48...208 | 43/226 (19%)<br>77/226 (34%) | 2 |
| wap: domain 1 of 1 | 515...550 | 12/55 (22%)<br>27/55 (49%) | 8.1 |
| pkinase: domain 2 of 2 | 739...835 | 34/138 (25%)<br>74/138 (54%) | 3.2e-10 |
| pkinase_C: domain 1 of 1 | 836...864 | 10/31 (32%)<br>23/31 (74%) | 0.027 |

Example 78

The NOV78 clone was analyzed, and the nucleotide and encoded polypeptide sequences are shown in Table 78A.

TABLE 78A

NOV78 Sequence Analysis

| | | |
|---|---|---|
| NOV78a, CG94511-01 DNA Sequence | SEQ ID NO:205      1173 bp<br>CCTATCCATGAATATTATGTTCCCTTAAAAAATGTCTGTGGGCCTGCAGCCTGGTGCA<br>GAGTATAATAACGGGCTCACCCACAAGCCAGCTAGCAGAGTGCTGGTAGCATTCTGTA<br>ATTTTGCAAATGAGGCAAACTTGAAATTAAGAAATCTGGAAGAGGGCTCGCCTATCAC<br>AATAGTACTCACCAGGGAAGACGGACTCAAATATTACAGGATGACGCAGACTGTTCAT<br>CAAATGGAATTTAAATATATTGGCACCAAAAATGACAGAAAATATTCACATTTCTGTC<br>ATTTTTGTCATGTGAGGAACACTGCTGGGATGGGACTTGAAGCCAGGATAAATCCCAC<br>AGATCATCTCATCACAGCCTATTTAGGCTCTGGCTTTAGCTTTACTCATGAACTTTCT<br>GTCCCAGAAATTGTTCTAGAGCTTACAGGACAAAGAGGAGGTTGTGCTAAAGGAAAAG<br>TAGGATCAATGCATATGTATGCCAAGAACTTCTACAGGAGCCATGGCACTGTCAGAGC<br>TCAGGTCTCCCTGGGAGCTGGTATTGGCTTGGCCTGTGAGTATAACGGAAAAGATCAG<br>GTCGGTCTGAATGACTTTATATTTGAGGCCTACAATATAGCCGCTTTGTGGAAATTAC<br>CTCCTATTTTCATCTGTGAGAATAACTGCTATGGAATAAGAGCATCTGTTGAGACAGC<br>AGCACCTAGCACTGATTACTATAAGACAGGCAATTTTGTACCTGGACTAAGGATAGAC<br>AGAATGAATATTCTATGTGTCCATGAGGCAACAAAGTTTGCCTGTTGTATATTTGGAA<br>AGGGGACCATACTGATGAAGCTGCAGACTTACCATTATCAAGGCCACAGTGTAAGTGA<br>TCCTGGAGTCAGCTGTACACAAGAAGAAATTCAAGAAGCAAGAAGCAAGAGGACTGAC<br>TCTATTATGCTTCTCAAAGATAAAATGGTAAATAGCAATCTTGCCAATGTTAAAGAAG<br>CCTGGGCTACAGAGCGAGACTCTGTCTCAAAAAACAAAAGAAAGGAAACCGATGTTGA<br>TACAACTGATCCCAAACTACCTTTGGAAGAATTAGGCCGTTACATTTATTTACATTTA<br>TTGCATTTTGAAGTTTATGATGTAAATCAGTGGATCCAGTTTAAGTAG<u>ATTTTTATTT<br>TTTTTAAGACAGG</u> |
| NOV78a, CG94511-01 Protein Sequence | ORF Staff: ATG at 32      ORF Stop: TAG at 1148<br>SEQ ID NO:206      372 aa MW at 41908.5 kD<br>MSVGLQPGAEYNNGLTQKPASRVLVAFCNFANEANLKLRNLEEGSPITIVLTREDGLK<br>YYRMTQTVHQMEFKYIGTKNDRKYSHFCHFCDVRKTAGMGLEARINPTDHLITAYLGS<br>GFSFTHELSVPEILVELTGQRGGCAKGKVGSMHMYAKNFYRSHGTVRAQVSLGAGIGL<br>ACEYNGKDEVGLNDFIFEAYNIAALWKLPPIFICENNCYGIRASVETAAPSTDYYKTG<br>NFVPGLRIDRMNILCVHEATKFACCIFGKGTILMKLQTYHYQGHSVSDPGVSCTQEEI<br>QEARSKRTDSIMLLDKMVNSNLANVKEAWATERDSVSKNKRKETDVDTTDPKLPLEE<br>LGRYIYLHLLHFEVYDVNQWIQFK |

Further analysis of the NOV78a protein yielded the following properties shown in Table 78B.

TABLE 78B

Protein Sequence Properties NOV78a

| | |
|---|---|
| PSort analysis: | 0.6500 probability located in cytoplasm; 0.1000 probability located in mitochondrial matrix space; 0.1000 probability located in lysosome (lumen); 0.0436 probability located in microbody (peroxisome) |

TABLE 78B-continued

Protein Sequence Properties NOV78a

| | |
|---|---|
| SignalP analysis: | No Known Signal Sequence Predicted |

A search of the NOV78a protein against the Geneseq database, a proprietary database that contains sequences published in patents and patent publication, yielded several homologous proteins shown in Table 78C.

TABLE 78C

Geneseq Results for NOV78a

| Geneseq Identifier | Protein/Organism/Length [Patent #, Date] | NOV78a Residues/ Match Residues | Identities/ Similarities for the Matched Region | Expect Value |
| --- | --- | --- | --- | --- |
| AAG38280 | *Arabidopsis thaliana* protein fragment SEQ ID NO: 47202 - *Arabidopsis thaliana*, 389 aa. [EP1033405-A2, 06-SEP-2000] | 57 ... 336 60 ... 346 | 114/293 (38%) 160/293 (53%) | 7e−47 |
| AAG38279 | *Arabidopsis thaliana* protein fragment SEQ ID NO: 47201 - *Arabidopsis thaliana*, 413 aa. [EP1033405-A2, 06-SEP-2000] | 57 ... 336 84 ... 370 | 114/293 (38%) 160/293 (53%) | 7e−47 |
| AAG32461 | *Arabidopsis thaliana* protein fragment SEQ ID NO: 39163 - *Arabidopsis thaliana*, 389 aa. [EP1033405-A2, 06-SEP-2000] | 57 ... 336 60 ... 346 | 114/293 (38%) 160/293 (53%) | 7e−47 |
| AAG38281 | *Arabidopsis thaliana* protein fragment SEQ ID NO: 47203 - *Arabidopsis thaliana*, 324 aa. [EP1033405-A2, 06-SEP-2000] | 85 ... 336 23 ... 281 | 110/265 (41%) 151/265 (56%) | 5e−46 |
| AAG32463 | *Arabidopsis thaliana* protein fragment SEQ ID NO: 39165 - *Arabidopsis thaliana*, 321 aa. [EP1033405-A2, 06-SEP-2000] | 85 ... 336 20 ... 278 | 110/265 (41%) 151/265 (56%) | 5e−46 |

In a BLAST search of public sequence datbases, the NOV78a protein was found to have homology to the proteins shown in the BLASTP data in Table 78D.

TABLE 78D

Public BLASTP Results for NOV78a

| Protein Accession Number | Protein/Organism/Length | NOV78a Residues/ Match Residues | Identities/ Similarities for the Matched Portion | Expect Value |
| --- | --- | --- | --- | --- |
| P08559 | Pyruvate dehydrogenase E1 component alpha subunit, somatic form, mitochondrial precursor (EC 1.2.4.1) (PDHE1-A type I) - *Homo sapiens* (Human), 390 aa. | 13 ... 372 13 ... 387 | 232/377 (61%) 269/377 (70%) | e−118 |
| P29804 | Pyruvate dehydrogenase E1 component alpha subunit, somatic form, mitochondrial precursor (EC 1.2.4.1) (PDHE1-A type I) - *Sus scrofa* (Pig), 389 aa (fragment). | 13 ... 372 12 ... 386 | 230/377 (61%) 268/377 (71%) | e−117 |
| DERTP1 | pyruvate dehydrogenase (lipoamide) (EC 1.2.4.1) alpha chain 1 precursor - rat, 390 aa. | 14 ... 372 14 ... 387 | 232/376 (61%) 265/376 (69%) | e−117 |
| P35486 | Pyruvate dehydrogenase E1 component alpha subunit, somatic form, mitochondrial precursor (EC 1.2.4.1) (PDHE1-A type I) - *Mus musculus* (Mouse), 390 aa. | 14 ... 372 14 ... 387 | 232/376 (61%) 265/376 (69%) | e−117 |
| P26284 | Pyruvate dehydrogenase E1 component alpha subunit, somatic form, mitochondrial precursor (EC 1.2.4.1) (PDHE1-A type I) - *Rattus norvegicus* (Rat), 390 aa. | 14 ... 372 14 ... 387 | 229/376 (60%) 265/376 (69%) | e−116 |

PFam analysis predicts that the NOV78a protein contains the domains shown in the Table 78E.

TABLE 78E

Domain Analysis of NOV78a

| Pfam Domain | NOV78a Match Region | Identities/ Similarities for the Matched Region | Expect Value |
| --- | --- | --- | --- |
| E1_dehydrog: domain 1 of 1 | 61 . . . 347 | 111/329 (34%) 217/329 (66%) | 3.2e−51 |

Example 79

The NOV79 clone was analyzed, and the nucleotide and encoded polypeptide sequences are shown in Table 79A.

TABLE 79A

NOV79 Sequence Analysis

| | |
| --- | --- |
| NOV79a, CG94551-01 DNA Sequence | SEQ ID NO:207  6757 bp<br>TCCTGATACTTGTTTACTTTTCTGGGGCAGAAAAGCTTGCACTAATTGCTCTCCATGG TGGCTAATTTTTTCAAGAGCTTGATTTTACCTTACATTCATAAGCTTTGCAAAGGAAT GTTTACAAAGAAATTGGGAAATACAAACAAAAACAAAGAGTATCGTCAGCAGAAAAAG GATCAAGACTTCCCCACTGCTGGCCAGACCAAATCCCCCAAATTTTCTTACACTTTTA AAAGCACTGTAAAGAAGATTGCAAAGTGTTCATCCACTCACAACTTATCCACTCAGGA AGACGAGGCCAGTAAAGAGTTTTCCCTCTCACCAACATTCAGTTACCGAGTAGCTATT GCCAATGGCCTACAACCCTCTCACCAACATTCAGACAATGAGGATCTGCTTCAAGAGC TCTCTTCAATCGAGAGTTCCTACTCAGAATCATTAAATGAACTAAGGAGTAGCACAGA AAACCAGGCACAATCAACACACACAATGCCAGTTAGACGCAACAGAAAGAGTTCAAGC AGCCTTGCACCCTCTGAGGGCAGCTCTGACGGGGAGCGTACTCTACATGGCTTAAAAC TGGGAGCTTTACGAAAACTGAGAAAATGGAAAAAGAGTCAAGAATGTGTCTCCTCAGA CTCAGAGTTAAGCACCATGAAAAAATCCTGGGGAATAAGAAGTAAGTCTTTGGACAGA ACTGTCCGAAACCCAAACACAAATGCCCTGGAGCCAGGGTTCAGTTCCTCTGGCTGCA TTAGCCAAACACATGATGTCATGGAAATGATCTTTAAGGAACTTCAGGGAATAAGTCA GATTGAAACAGAACTTTCTGAACTACGAGGGCACGTCAATGCTCTCAAGCACTCCATC GATGAGATCTCCAGCAGTGTGGAGGTTGTACAAAGTGAAATTCAGCACTTGCGCACAG GGTTTGTCCAGTCTCGGAGGGAAACTAGAGACATCCATGATTATATTAAGCACTTACG TCATATGGGTAGCAAGGCAAGCCTCAGATTTTTAAATGTGACTGAAGAAAGATTTGAA TATGTTGAAAGCGTGGTGTACCAAATTCTAATAGATAAAATGGGTTTTTCAGATGCAC CAAATGCTATTAAAATTGAATTTGCTCAGAGGATAGGACACCAGAGACACTGCCCAAA TGCAAAGCCTCGACCCATACTTGTGTACTTTGAAACCCCTCAACAAAGGGATTCTGTC TTAAAAAAGTCATATAAACTCAAAGGAACAGGCATTGGAATCTCAACAGATATTCTAA CTCATGACATCAGAGAAAGAAAAGAGAAAGGGATACCATCCTCCCAGACATATGAGAG CATGGCTATAAAGTTGTCTACTCCAGAGCCAAAAATCAAGAAGAACAATTGGCAGTCA CCTGATGACAGTGATGAAGATCTTGAATCTGACCTCAATAGAAACAGTTACGCTGTGC TTTCCAAGTCAGAGCTTCTAACAAAGGGAAGTACTTCCAAGCCAAGCTCAAAATCACA CAGTGCTAGATCCAAGAATAAAACTGCTAATAGCAGCAGAATTTCAAATAAATCAGAT |

TABLE 79A-continued

NOV79 Sequence Analysis

TATGATAAAATCTCCTCACAGTTGCCAGAATCAGATATCTTGGAAAAGCAAACCACAA

CCCATTATGCAGATGCAACACCTCTCTGGGACTCACAGAGTGATTTTTTCACTGCTAA

ACTTAGTCGTTCTGAATCAGATTTTTCCAAATTGTGTCAGTCTTACTCAGAAGATTTT

TCAGAAAATCAGTTTTTCACTAGAACTAATGGAAGCTCTCTCCTGTCATCTTCGGACC

GGGAGCTATGGCACAGGAAACAGGAAGGAACAGCGACCCTGTATGACAGTCCCAAGGA

CCAGCATTTGAATGGAGGTGTTCAGGGTATCCAAGGGCAGACTGAAACTGAAAACACA

GAAACTGTGGATAGTGGAATGAGTAATGGCATGGTGTGTGCATCTGGAGACCGGAGTC

ATTACAGTGATTCTCAGCTCTCTTTACATGAGGATCTTTCTCCATGGAAGGAATGGAA

TCAAGGAGCTGATTTAGGCTTGGATTCATCCACCCAGGAAGGTTTTGATTATGAAACA

AACAGTCTTTTTGACCAACAGCTTGATGTTTACAATAAAGACCTAGAATACTTGGGAA

AGTGCCACAGTGATCTTCAAGATGACTCAGAGAGCTACGACTTAACTCAAGATGACAA

TTCTTCTCCATGCCCTGGCTTGGATAATGAACCACAAGGCCAGTGGGTTGGCCAATAT

GATTCTTATCACGGAGCTAATTCTAATGAGCTATACCAAAATCAAAACCAGTTGTCCA

TGATGTATCGAAGTCAAAGTGAATTGCAAAGTGATGATTCAGAGGATGCCCCACCCAA

ATCATGGCATAGTCGATTAAGCATTGACCTTTCTGATAAGACTTTCAGCTTCCCAAAA

TTTGGATCTACACTGCAGAGGGCTAAATCAGCCTTGGAAGTAGTATGGAACAAAAGCA

CACAGAGTCTGAGTGGGTATGAGGACAGTGGCTCTTCATTAATGGGGAGATTTCGGAC

ATTATCTCAATCAACTGCAAATGAGTCAAGTACCACACTTGACTCTGATGTCTACACG

GAGCCCTATTACTATAAAGCAGAGGATGAGGAAGATTATACTGAACCACTGGCTGACA

ATGAAACAGATTATGTTGAAGTCATGGAACAAGTCCTTGCTAAACTAGAAAACAGGAC

TAGTATTACTGAAACAGATGAACAAATGCAAGCATATGATCACCTTTCATATGAAACA

CCTTATGAAACCCCACAAGATGAGGGTTATGATGGTCCAGCAGATGATATGGTTAGTG

AAGAGGGGTTAGAACCCTTAAATGAAACATCAGCTGAGATGGAAATAAGAGAAGATGA

AAACCAAAACATTCCTGAACAGCCAGTGGAGATCACAAAGCCAAAGAGAATTCGTCCT

TCTTTCAAAGAAGCAGCTTTAAGGGCCTATAAAAAGCAAATGGCAGAGTTGGAAGAGA

AGATCTTGGCTGGATCTTACTCTTCATTTAAGGCTCGAATAGTAAGTGGCAATGATTT

GGATGCTTCCAAATTTTCTGCACTCCAGGTGTGTGGTGGGGCTGGAGGTGGACTTTAT

GGTATTGACAGCATGCCGGATCTTCGCAGAAAAAAAACTTTGCCTATTGTCCGAGATG

TGGTAAGTACCCTGGCTGCCCGGAAATCTGGACTCTCCCTGGCTATGGTGATTAGGAC

ATCCCTAAATAATGAGGAACTGAAAATGCACGTCTTCAAGAAGACCTTGCAGGCACTG

ATCTACCCTATGTCTTCTACCATCCCACACAATTTTGAGGTCTGGACGGCTACCACAC

CCACCTACTCTTATGAGTGTGAAGGGCTCCTGTGGGCATTGCAAGGCAAGGCATGAA

GTGTCTGGAGTGTGGAGTGAAATGCCACGAAAAGTGTCAGGACCTGCTAAACGCTGAC

TGCTTGCAGAGTGCAGCAGAAAAGAGTTCTAAACATGGTGCCGAAGACAAGACTCAGA

CCATTATTACAGCAATGAAAGAAAGAATGAAGATCAGGGAGAAAAACCGGCCAGAACT

ATTTGAAGTAATCCAGGAAATGTTTCAGATTTCTAAAGAAGATTTTGTGCAGTTTACA

AAGGCGGCCAAACAGAGTGTACTGGATGGGACATCTAAGTGGTCTGCAAAAATAACCA

TTACAGTGGTTTCTGCACAGGGTCTACAGGCAAAAGATAAAACAGGGTCTAGTGATCC

ATATGTTACAGTTCAAGTTGGAAAGAACAAAAGAAGAACAAAAACCATTTTTGGAAAT

TABLE 79A-continued

NOV79 Sequence Analysis

TTGAATCCAGTATGGGATGAGAAGTTTTATTTGGAGTGTCATAACTCCACAGATCGAA

TCAAAGTCAGAGTATGGGATGAAGATGATGATATTAAATCCAGAGTCAAGCAACATTT

CAAAAAGGAGTCAGATGATTTTCTGGGACAAACAATTGTAGAAGTGAGGACCTTGAGT

GGAGAAATGGATGTCTGGTACAACTTAGAGAAAAGGACAGATAAGTCAGCTGTATCTG

GGGCCATACGATTGAAAATCAATGTGGAGATAAAAGGAGAAGAGAAGGTTGCTCCATA

TCATATTCAATATACATGTTTACATGAGAATCTGTTCCATTACTTGACTGAAGTGAAA

TCTAATGGTGGAGTGAAAATCCCAGAAGTCAAAGGGGATGAAGCCTGGAAGGTTTTCT

TTGATGATGCTTCCCAAGAAATAGTTGATGAATTTGCTATGCGTTATGGAATTGAATC

CATTTATCAAGCTATGACGCACTTTTCATGTCTGTCTTCTAAATACATGTGCCCCGGT

GTCCCTGCCGTCATGAGCACCTTGCTGGCTAATATAAATGCTTTTTATGCTCACACAA

CAGTTTCAACAAACATACAGGTTTCTGCCTCAGATCGATTTGCTGCTACCAACTTTGG

TAGGGAAAAATTCATAAAACTACTGGACCAGTTACATAACTCTTTGAGGATTGATCTG

TCAAAGTATAGGCAGGAAAACTTTCCTGCAAGCAATACTGAAAGACTGCAAGACCTGA

AATCAACTGTTGACCTGTTAACAAGTATCACCTTTTTTAGGATGAAGGTACTGGAGCT

GCAAACCCCCCAAAAGCGAGCATGGTGGTGAAGGACTGTGTAAGGGCTTGCCTGCAT

TCTACATACAAGTATATTTTTGACAACTGCCATGAACTCTACTCCCAGCTAACAGACC

CAAGTAAGAAACAGGATATTCCTCGTGAAGATCAGGGACCAACCACCAAGAATTTGGA

TTTTTGGCCCCAACTTATTACACTGATGGTTACTATTATTGATGAGGATAAAACTGCC

TACACACCTGTCCTGAATCAGTTTCCTCAAGAGCTGAACATGGGAAAAATAAGTGCCG

AAATTATGTGGACTCTTTTTGCTCTGGATATGAAATATGCATTAGAAGAACATGAAAA

TCAGCGCTTATGCAAGAGCACCGATTATATGAATTTGCATTTCAAAGTTAAATGGTTT

TATAATGAATATGTGCGTGAACTTCCTGCCTTGAAGGATGCTGTTCCTCAATACTCCT

TGTGGTTTGAACCTTTTGTCATGCAATGCCTAGATGAAAACGAAGATGTGTCAATGGA

ATTCCTTCATGGAGCACTGGGAAGAGACAAAAAAGATGGATTCCAGCAGACATCTGAG

CATGCTCTCTTTTGTTGCTCCGTGGTTGATGTCTTTGCTCAGCTGAATCAGAGCTTTG

AAATTATTAAGAAACTGGAATGCCCTAATCCTGAAGCATTATCTCACTTAATGAGAAG

ATTTGCAAAGACTATCAATAAAGTGCTGCTCCAGTATGCTGCAATTGTATCAAGTGAT

TTCAGTTCACATTGTGATAAGGAAAATGTGCCCTGTATCTTGATGAACAATATTCAAC

AATTGCGGGTCCAGCTGGAAAAAATGTTTGAATCCATGGGAGGGAAGGAGCTAGATTC

TGAAGCTAGTACTATTCTAAAAGAACTTCAGGTTAAGCTCAGTGGGGTCCTGGATGAG

CTCAGCGTCACTTATGGTGAAAGTTTCCAGGTTATAATTGAAGAGTGTATAAAACAGA

TGAGTTTCGAACTAAATCAAATGAGAGCAAATGGAAACACCACATCTAATAAGAACAG

TGCAGCAATGGATGCAGAGATTGTGTTAAGATCTCTTATGGATTTTTTGGACAAAACG

AGTCTCTCAGCAAAAATCTGTGAGAAAACAGTCCTAAAGCGAGTTTTAAAAGAGTTAT

GGAAGCTAGTTCTCAACAAAATAGAAAAACAAATTGTTCTTCCTCCTCTGACAGATCA

AACAGGACCCCAGATGATTTTCATTGCAGCTAAAGATCTTGGACAATTATCCAAACTG

AAGCAGGAGCACATGATTCGAGAGGATGCCAGGGGTCTGACGCCAAGACAATGCGCTT

TAATGGAGGTAGTGCTGGCTACCATCAAGTCCTTGTACCAATATTTTCATGCAGAAGA

TABLE 79A-continued

NOV79 Sequence Analysis

AATGGGCCTGAAGAACAATTTTCTGAGAAAAGGCCCGAATCTCCAGTTTCTTAAATGC

GCTCCCAGTCTTTATACCCAAACTACTGATGCCTTGATCAAGAAATTCATAGATACTC

AAACCTCACAGAGTCGTTCCTCCAAAGATGCCGTGGGTCAGATATCTGTTCATGTGGA

CATCACTCCCACCCCAGGAACGGGAGATCATAAAGTCACTGTAAAAGTGATTGCTATT

AATGACCTAAACTGGCAGACCACAGCAATGTTCCGCCCCTTTGTGGAAGTTTCTATAC

TGGGACCCAACCTTGGAGACAAGAAGAGAAAACAAGGCACAAAAACAAAAAGCAACAC

ATGGTCACCAAAGTACAATGAAACATTTCAGTTGATTCTCGGAAAGGAAAATCGACCA

GGCGCTTATGAACTTCATCTCTCAGTTAAGGATTACTGCTTTGCCACAGAAGATCGAA

TTATCGGAATGACAGTCATTCAGCTACAGAACATAGCAGAAAAGGGAAGCTATGGGGC

ATGGTATCCTCTTCTGAAAAATATCTCTATGGATGAAACTGGTTTGACTATCCTTAGA

ATACTCTCAGAGGACCAGTGATGATGTGGCTAAAGAATTTGTAAGACTTAAATCTG

AAACAAGATCTACTGAAGAGAGTGCTTGAAACAAAGACTGCAAGCTAAATACATAACT

ATAATTGTTTGACTACTGCATGCATGTGC

ORF Staff: ATG at 55        ORF Stop: TGA at 6697
SEQ ID NO:208               2214 aa MW at 251058.0 kD NOV79a,
CG94551-01 Protein Sequence

MVANFFKSLTLPYIHKLCKGMFTKKLGNTNKNKEYRQQKKDQDPPTAGQTKSPKFSYT

FKSTVKKIAKCSSTHNLSTEEDEASKEFSLSPTFSYRVAIANGLQPSHQHSDNEDLLQ

ELSSIESSYSESLNELRSSTEHQAQSTHTMPVRRNRKSSSSLAPSEGSSDGERTLHGL

KLGALRKLRKWKKSQECVSSDSELSTMKKSWGIRSKSLDRTVRNPKTNALEPGFSSSG

CISQTHDVMEMIFKELQGISQIETELSELRGHVNALKHSIDEISSSVEVVQSEIEQLR

TGFVQSRRETRDIHDYIKHLGHMGSKASLRFLNVTEERFEYVESVVYQILIDKMGFSD

APNAIKIEFAQRIGHQRDCPNAKPRPILVYFETPQQRDSVLKKSYKLKGTGIGISTDI

LTHDIRERKEKGIPSSQTYESMAIKLSTPEPKIKKNNWQSPDDSDEDLESDLNRNSYA

VLSKSELLTKGSTSKPSSKSHSARSKNKTANSSRISNKSDYDKISSQLPESDILEKQT

TTHYADATPLWHSQSDFFTAKLSRSESDFSKLCQSYSEDFSENQFFTRTNGSSLLSSS

DRELWQRKQEGTATLYDSPKDQHLNGGVQGIQGQTETENTETVDSGMSNGMVCASGDR

SHYSDSQLSLHEDLSPWKEWNQGADLGLDSSTQEGFDYETNSLFDQQLDVYNKDLEYL

GKCHSDLQDDSESYDLTQDDNSSPCPGLDNEPQGQWVGQYDSYQGANSNELYQNQNQL

SMMYRSQSELQSDDSEDAPPKSWHSRLSIDLSDKTFSFPKFGSTLQRAKSALEVVWNK

STQSLSGYEDSGSSLMGRFRTLSQSTANESSTTLDSDVYTEPYYYKAEDEEDYTEPVA

DNETDYVEVMEQVLAKLENRTSITETDEQMQAYDHLSYETPYETPQDEGYDCPADDMV

SEEGLEPLNETSAEMEIREDENQNIPEQPVEITKPKRIRPSFKEAALRAYKKQMAELE

EKILAGSYSSFKARIVSGNDLDASKFSALQVCGGAGGGLYGIDSMPDLRRKKTLPIVR

DVVSTLAARKSGLSLAMVIRTSLNNEELKMHVFKKTLQALIYPMSSTIPHNFEVWTAT

TPTYCYECEGLLWGIARQGMKCLECGVKCHEKCQDLLNADCLQSAAEKSSKHGAEDKT

QTIITAMKERMKIREKNRPEVFEVIQEMFQISKEDFVQFTKAAKQSVLDGTSKWSAKI

TITVVSAQGLQAKDKTGSSDPYVTVQVGKNKRRTKTIFGNLNPVWDEKFYLECHNSTD

RIKVRVWDEDDDIKSRVKQHFKKESDDFLGQTIVEVRTLSGEMDVWYNLEKRTDKSAV

SGAIRLKINVEIKGEEKVAPYHIQYTCLHENLFHYLTEVKSNGGVKIPEVKGDEAWKV

FFDDASQEIVDEFAMRYGIESIYQAMTHFSCLSSKYMCPGVPAVMSTLLANINAFYAH

TABLE 79A-continued

NOV79 Sequence Analysis

TTVSTNIQVSASDRFAATNFGREKFIKLLDQLHNSLRIDLSKYRQENFPASNTERLQD

LKSTVDLLTSITFFRMKVLELQSPPKASMVVKDCVRACLDSTYKYIFDNCHELYSQLT

DPSKKQDIPREDQGPTTKNLDFWPQLITLMVTIIDEDKTAYTPVLNQFPQELNMGKIS

AEIMWTLFALDMKYALEEHENQRLCKSTDYMNLHFKVKWFYNEYVRELPAFKDAVPEY

SLWFEPFVMQWLDENEDVSMEFLHGALGRDKKDGFQQTSEHALFSCSVVDVFAQLNQS

FEIIKKLECPNPEALSHLMRRFAKTINKVLLQYAAIVSSDFSSHCDKENVPCILMNNI

QQLRVQLEKMFESMGGKELDSEASTILKELQVKLSGVLDELSVTYGESFQVIIEECIK

QMSFELNQMRANGNTTSNKESAAMDAEIVLRSLMDFLDKTSLSAKICEKTVLKRVLKE

LWKLVLNKIEKQIVLPPLTDQTGPQMIFIAAKDLGQLSKLKQEHMIREDARGLTPRQC

ALMEVVLATIKSLYQYFHAEEMGLKKNFLRKGPNLQFLKCAPSLYTQTTDALIKKFID

TQTSQSRSSKDAVGQISVHVDITATPGTGDHKVTVKVIAINDLNWQTTAMFRPFVEVC

ILGPNLGDKKRKQGTKTKSNTWSPKYNETFQLILGKENRPGAYELHLSVKDYCFARED

RIIGMTVIQLQNIAEKGSYGAWYPLLKNISMDETGLTILRILSQRTSDDVAKEFVRLK

SETRSTEESA

Further analysis of the NOV79a protein yielded the following properties shown in Table 79B.

TABLE 79B

Protein Sequence Properties NOV79a

| | |
|---|---|
| PSort analysis: | 0.9800 probability located in nucleus; 0.3000 probability located in microbody (peroxisome); 0.1000 probability located in mitochondrial matrix space; 0.1000 probability located in lysosome (lumen) |
| SignalP analysis: | No Known Signal Sequence Predicted |

A search of the NOV79a protein against the Geneseq database, a proprietary database that contains sequences published in patents and patent publication, yielded several homologous proteins shown in Table 79C.

TABLE 79C

Geneseq Results for NOV79a

| Geneseq Identifier | Protein/Organism/Length [Patent #, Date] | NOV79a Residues/ Match Residues | Identities/ Similarities for the Matched Region | Expect Value |
|---|---|---|---|---|
| AAB47279 | PN7098 - *Homo sapiens*, 1230 aa. [WO200140794-A1, 07-JUN-2001] | 1 . . . 1226<br>1 . . . 1230 | 1214/1230 (98%)<br>1216/1230 (98%) | 0.0 |
| AAY27134 | Human munc13 (Hmunc13) polypeptide - *Homo sapiens*, 1591 aa. [WO9931134-A1, 24-JUN-1999] | 1020 . . . 2214<br>405 . . . 1591 | 880/1197 (73%)<br>1027/1197 (85%) | 0.0 |
| AAW83431 | Rat Munc13-1 - Rattus sp, 1763 aa. [JP10313866-A, 02-DEC-1998] | 705 . . . 2212<br>222 . . . 1756 | 948/1582 (59%)<br>1144/1582 (71%) | 0.0 |
| AAW83428 | Munc13-1-interacting domain of Doc2-alpha - Rattus sp, 611 aa. [JP10313866-A, 02-DEC-1998] | 1350 . . . 1936<br>1 . . . 590 | 449/593 (75%)<br>520/593 (86%) | 0.0 |
| ABG13673 | Novel human diagnostic protein #13664 - *Homo sapiens*, 183 aa. [WO200175067-A2, 11-OCT-2001] | 2037 . . . 2214<br>6 . . . 183 | 176/178 (98%)<br>177/178 (98%) | 6e-98 |

In a BLAST search of public sequence datbases, the NOV79a protein was found to have homology to the proteins shown in the BLASTP data in Table 79D.

TABLE 79D

Public BLASTP Results for NOV79a

| Protein Accession Number | Protein/Organism/Length | NOV79a Residues/ Match Residues | Identities/ Similarities for the Matched Portion | Expect Value |
|---|---|---|---|---|
| T42759 | Munc13-3 protein - rat, 2207 aa. | 1 . . . 2214<br>4 . . . 2207 | 1980/2221 (89%)<br>2065/2221 (92%) | 0.0 |
| Q62770 | MUNC13-3 - *Rattus norvegicus* (Rat), 2207 aa. | 1 . . . 2214<br>4 . . . 2207 | 1980/2221 (89%)<br>2065/2221 (92%) | 0.0 |
| O14795 | MUNC13 - *Homo sapiens* (Human), 1591 aa. | 1020 . . . 2214<br>405 . . . 1591 | 880/1197 (73%)<br>1027/1197 (85%) | 0.0 |
| Q62769 | MUNC13-2 - *Rattus norvegicus* (Rat), 1985 aa. | 1020 . . . 2214<br>779 . . . 1985 | 879/1217 (72%)<br>1026/1217 (84%) | 0.0 |
| Q9WV40 | MUNC13-2 PROTEIN - *Rattus norvegicus* (Rat), 1622 aa. | 1020 . . . 2214<br>416 . . . 1622 | 879/1217 (72%)<br>1026/1217 (84%) | 0.0 |

PFam analysis predicts that the NOV79a protein contains the domains shown in the Table 79E.

TABLE 79E

Domain Analysis of NOV79a

| Pfam Domain | NOV79a Match Region | Identities/ Similarities for the Matched Region | Expect Value |
|---|---|---|---|
| Transposase_22: domain 1 of 1 | 146 . . . 492 | 73/394 (19%)<br>146/394 (37%) | 0.46 |
| DAG_PE-bind: domain 1 of 1 | 1094 . . . 1143 | 21/51 (41%)<br>43/51 (84%) | 1.8e-18 |

TABLE 79E-continued

Domain Analysis of NOV79a

| Pfam Domain | NOV79a Match Region | Identities/ Similarities for the Matched Region | Expect Value |
|---|---|---|---|
| C2: domain 1 of 2 | 1218 . . . 1309 | 33/106 (31%)<br>73/106 (69%) | 2.3e-19 |
| C2: domain 2 of 2 | 2063 . . . 2153 | 26/97 (27%)<br>57/97 (59%) | 0.0054 |

Example 80

The NOV80 clone was analyzed, and the nucleotide and encoded polypeptide sequences are shown in Table 80A.

TABLE 80A

NOV80 Sequence Analysis

NOV80a,
CG94682-02 DNA Sequence

SEQ ID NO:209  1683 bp
GTCAGGCCTATGGCCATGGCCTTCACAGACCTGCTGGATGCTCTGGGCAGCATGGCCC
GCTTCCAGCTCAACCACACAGCCCTGCTGCTGCTGCCCTGCGGCCTCCTGGCCTGCCA
CAACTTCCTGCAGAACTTCACCGCCGCTGTCCCCCCCCACCACTGCCGGGGCCCTGCC
AACCACACTGAGGCCTCCACCAACGACTCGGGGGCCTGGCTCAGGCCCACCATACCCC
TGGACCAGCTTGGGGCCCCTCAGCCCTGCCGGCGCTTCACCAACCCTCAGTGGGCCCT
GCTGAGCCCCAACTCCTCCATCCCGGGCGCGGCCACGGAGGGCTGCAAGGACGGCTGG
GTCTATAACCGCAGTGTTTTCCCGTCCACCATCGTGATGGAGTGGGATCTGGTGTGTG
AGGCCCGCACTCTCCGAGACCTGGCGCAGTCCGTCTACATTGCCGGGGTGCTGGTGGG
GGCTGCCGTCTTTGGCAGCTTGGCAGACAGGCTGGGCTGCAAGGGCCCCCTGGTCTGG
TCCTACCTGCAGCTGGCAGCTTCGGGGGCCGCCACAGCGTATTTCAGCTCCTTCAGTG
CCTATTGCGTCTTCCGGTTCCTGATGGGCATGACCTTCTCTGGCATCATCCTCAACTC
CGTCTCCCTGATTGTGGAGTGGATGCCCACACGGGGCCGGACTGTGGCGGGTATTTTG
CTGGGGTATTCCTTCACCCTGGCCCAGCTCATCCTGGCTGGGGTAGCCTACCTGATTC
GCCCCTGGCGGTGCCTGCAGTTTGCCATCTCTGCTCCTTTCCTGATCTTTTTCCTCTA

TABLE 80A-continued

NOV80 Sequence Analysis

```
TTCTTGGTGGCTTCCAGAGTCATCCCGCTGGCTCCTCCTGCATGGCAAGTCCCACTTA
GCTGTACAGAATCTGCAGAAGGTGGCTGCAATGAACGGGAGGAAGCAGGAAGGGGAAA
GGCTGACCAAGGAGGTGATGAGCTCCTACATCCAAAGCGAGTTTGCAAGTGTCTGCAC
CTCCAACTCAATCTTGGACCTCTTCCGAACCCCGGCCATCCGCAAGGTCACATGCTGT
CTCATGGTGATTTGGTGGGGCCATTCTGTGGCTTACTATGGCCTGGCCATGGACCTGC
AGAAGTTTGGGCTCAGCCTATACCTGGTGCAGGCCCTGTTTGGAATCATCAACATCCC
GGCCATGCTGGTGGCCACCGCCACCATGATTTACGTGGGCCGCCGTGCCACGGTGGCC
TCCTTCCTCATCCTGGCCGGGCTCATGGTGATCGCCAACATGTTTGTGCCAGAAGGCA
CGCAGATCCTGTGCACAGCCCAGGCAGCGCTGGGCAAAGCTGCCTGGCCAGCTCCTT
CATCTGTGTGTACCTGTTTACCGGCGAGCTGTACCCCACCGAGATCAGGCAGATGGGG
ATGGGCTTTGCCTCTGTCCACGCCCGCCTCGGGGGCCTGACGGCGCCCCTGGTTACCA
CACTTGGGGAATACAGCACCATCCTGCCACCCGTGAGCTTTGGGGCCACCGCAATCCT
GGCTGGGCTGGCCGTCTGCTTCCTGACTGAGACCCGCAACATGCCCCTGGTGGAGACC
ATCGCAGCCATGGAGAGGAGGGTCAAAGAAGGCTCTTCCAAGAAACATGTAGAAGAGA
AGAGTGAAGAAATTTCTCTTCAGCAGCTGAGAGCATCTCCCCTCAAAGAGACCATCTA
A
```

NOV80a,
CG94682-02 Protein Sequence

ORF Start: ATG at 10  ORF Stop: TAA at 1681
SEQ ID NO:210  557 aa MW at 60747.4 kD MAMAFTDLLDALGSMGRFQLNHTALLLLPCGLLACHNFLQNPTAAVPPHHCRGPANHT
EASTNDSGAWLRATIPLDQLGAPEPCRRFTKPQWALLSPNSSIPGAATEGCKDGWVYN
RSVFPSTIVMEWDLVCEARTLRDLAQSVYIAGVLVCAAVFGSLADRLGCKGPLVWSYL
QLAASGAATAYFSSFSAYCVFRFLMGMTFSGIILNSVSLIVEWMPTRCRTVAGILLGY
SFTLGQLILAGVAYLIRPWRCLQFAISAPFLIFFLYSWWLPESSRWLLLHGKSQLAVQ
NLQKVAAMNGRKQEGERLTKEVMSSYIQSEFASVCTSNSILDLFRTPAIRKVTCCLMV
IWWGHSVAYYGLAMDLQKFGLSLYLVQALFGIINIPAMLVATATMIYVGRRATVASFL
ILAGLMVIANMFVPEGTQILCTAQAALGKGCLASSFICVYLFTGELYPTEIRQMGMGF
ASVHARLGGLTAPLVTTLGEYSTILPPVSFGATAILAGLAVCFLTETRNMPLVETIAA
MERRVKEGSSKSSEEKSEEISLQQLRASPLKETI Further analysis of the NOV80a protein yielded the following properties shown in Table 80B.

TABLE 80B

Protein Sequence Properties NOV80a

| | |
|---|---|
| PSort analysis: | 0.6000 probability located in plasma membrane; 0.4000 probability located in Golgi body; 0.3142 probability located in mitochondrial inner membrane; 0.3000 probability located in endoplasmic reticulum (membrane) |
| SignalP analysis: | Cleavage site between residues 35 and 36 |

A search of the NOV80a protein against the Geneseq database, a proprietary database that contains sequences published in patents and patent publication, yielded several homologous proteins shown in Table 80C.

TABLE 80C

Geneseq Results for NOV80a

| Geneseq Identifier | Protein/Organism/Length [Patent #, Date] | NOV80a Residues/ Match Residues | Identities/ Similarities for the Matched Region | Expect Value |
|---|---|---|---|---|
| AAE13280 | Human transporters and ion channels (TRICH)-7 - *Homo sapiens*, 589 aa. [WO200177174-A2, 18-OCT-2001] | 1 . . . 557<br>34 . . . 589 | 548/558 (98%)<br>551/558 (98%) | 0.0 |
| AAB47271 | hOAT1 - *Homo sapiens*, 550 aa. [WO200104283-A2, 18-JAN-2001] | 3 . . . 546<br>1 . . . 541 | 253/546 (46%)<br>343/546 (62%) | e–141 |
| AAY44278 | Human organic anion transporter - *Homo sapiens*, 550 aa. [WO9964459-A2, 16-DEC-1999] | 3 . . . 546<br>1 . . . 541 | 253/546 (46%)<br>343/546 (62%) | e–141 |
| AAW88489 | Human organic anion transporter OAT-1 - *Homo sapiens*, 563 aa. [WO9853064-A1, 26-NOV-1998] | 3 . . . 526<br>1 . . . 522 | 249/526 (47%)<br>334/526 (63%) | e–141 |
| AAW88488 | Rat organic anion transporter OAT-1 - *Rattus sp.* 551 aa. [WO9853064-A1, 26-NOV-1998] | 3 . . . 546<br>1 . . . 542 | 247/546 (45%)<br>344/546 (62%) | e–141 |

In a BLAST search of public sequence datbases, the NOV80a protein was found to have homology to the proteins shown in the BLASTP data in Table 80D.

TABLE 80D

Public BLASTP Results for NOV80a

| Protein Accession Number | Protein/Organism/Length | NOV80a Residues/ Match Residues | Identities/ Similarities for the Matched Portion | Expect Value |
|---|---|---|---|---|
| O57379 | RENAL ORGANIC ANION TRANSPORTER - *Pseudopleuronecta americanus* (Winter flounder), 562 aa. | 3 . . . 556<br>1 . . . 561 | 261/565 (46%)<br>361/565 (63%) | e–144 |
| O35956 | RENAL ORGANIC ANION TRANSPORT PROTEIN 1 - *Rattus norvegicus* (Rat), 551 aa. | 3 . . . 546<br>1 . . . 542 | 248/546 (45%)<br>346/546 (62%) | e–141 |
| Q9TSY7 | RENAL ORGANIC ANION TRANSPORTER 1 (RBOAT1) - *Oryctolagus cuniculus* (Rabbit), 551 aa. | 3 . . . 546<br>1 . . . 542 | 252/546 (46%)<br>342/546 (62%) | e–141 |
| O95742 | RENAL ORGANIC ANION TRANSPORT PROTEIN 1 - *Homo sapiens* (Human), 563 aa. | 3 . . . 526<br>1 . . . 522 | 249/526 (47%)<br>334/526 (63%) | e–141 |
| Q9R1U7 | ORGANIC ANION TRANSPORTER 3 - *Rattus norvegicus* (Rat), 536 aa. | 3 . . . 546<br>1 . . . 533 | 255/550 (46%)<br>350/550 (63%) | e–139 |

PFam analysis predicts that the NOV80a protein contains the domains shown in the Table 80E.

TABLE 80E

Domain Analysis of NOV80a

| Pfam Domain | NOV80a Match Region | Identities/ Similarities for the Matched Region | Expect Value |
|---|---|---|---|
| Chal_stil_syntC: domain 1 of 1 | 200 . . . 212 | 5/13 (38%)<br>11/13 (85%) | 9.8 |
| sugar_tr: domain 1 of 1 | 100 . . . 521 | 95/504 (19%)<br>284/504 (56%) | 1.3e–07 |

Example 81

The clone was analyzed, and the nucleotide and encoded polypeptide sequences are shown in Table 81A.

TABLE 81A

NOV81 Sequence Analysis

| | |
|---|---|
| NOV81a, CG90214-01 DNA Sequence | SEQ ID NO:211    1537 bp<br>AGCTCGAGATTTCTGTGGCTCCTCAAGATATTGGTCATAATCCTGGTACTTGGCATTG<br>TTGGATTTATGTTCGGAAGCATGTTCCTTCAAGCAGTGTTCAGCAGCCCCAAGCCAGA<br>ACTCCCAAGTCCTGCCCCGGGTGTCCAGAAGCTGAAGCTTCTGCCTGAGGAACGTCTC<br>AGGAACCTCTTTTCCTACGATGGAATCTGGCTGTTCCCGAAAAATCAGTGCAAATGTG<br>AGGAACCTCTTTTCCTACGATGGAATCTGGCTGTTCCCGAAAAATCAGTGCAAATGTG<br>AAGCCAACAAAGAGCAGGGAGGTTACAACTTTCAGGATGCCTATGGCCAGAGCGACCT<br>CCCAGCGGTGAAAGCGAGGAGACAGGCTGAATTTGAACACTTTCAGAGGAGGTGCAGA<br>GAAGGCCTGCCCCGCCCACTGCCCCTGCTGGTCCAGCCCAACCTCCCCTTTGGGTACC<br>CAGTCCACGGAGTGGAGGTGATGCCCCTGCACACGGTTCCCATCCCAGGTAAGTACAT<br>CCACATACCAAGAGACCCCGTCACCCTGACAGCTTCTCTGGGGACACTGAACACCCTT<br>GCTGATGTCCCAGACAGTGTGGTGCAGGGCAGAGGCCAGAAGCAGCTGATCATTTCTA<br>CCAGTGACCGGAAGCTGTTGAAGTTCATTCTTCAGCACGTGACATACACCAGCACGGG<br>GTACCAGCACCAGAAGGTAGACATAGGTGTGAGTCTGGAGTCCAGGTCCTCAGTGGCC<br>AAGTTTCCAGTGACCATCCGCCATCCTGTCATACCCAAGCTATACGACCCTGGACCAG<br>AGAGGAAGCTCAGAAACCTGGTTACCATTGCTACCAAGACTTTCCTCCGCCCCCACAA<br>GCTCATGATCATGCTCCGGAGTATTCGAGAGTATTACCCAGACTTGACCGTAATAGTG<br>GCTGATGACAGCCAGAAGCCCCTGGAAATTAAAGACAACCACGTGGAGTATTACACTA<br>TGCCCTTTGGGAAGGGTTGGTTTGCTGGTAGGAACCTGGCCATATCTCAGGTCACCAC<br>CAAATACGTTCTCTGGGTGGACGATGATTTTCTCTTCAACGAGGAGACCAACATTGAG<br>GTGCTGGTGGATGTCCTGGAGAAAACAGAACTGGACGTGGTAGGGGCCTGCCTTCACA<br>AGAGGATGGGATTTTTCCAACCCCTGGATGGCTTCCCCAGCTGCGTGGTGACCAGTGG<br>CGTGGTCAACTTCTTCCTGGCCCACACGGAGCGACTCCAAAGAGTTGGCTTTGATCCC<br>CGCCTGCAACGAGTGGCTCACGAATTCTTCATTGATGGGCTAGGGACCCTACTCGTGG<br>GGTCATGCCCAGAAGTGATTATAGGTCACCAGTCTCGGTCTCCAGTGGTGGACTCAGA<br>ACTGGCTGCCCTAGAGAAGACCTACAATACATACCGGTCCAACACCCTCACCCGGGTC<br>CAGTTCAAGCTGGCCCTCCACTACTTCAAGAACCATCTCCAATGTGCCGCATAA<u>ACGT</u><br><u>GTGAGGGCATAGCAGAPACACTAGCCTGGCTGGTTATGGTATCTATAGCAGGCCACCA</u><br><u>AAAACTGGACTCCTGATAGGTGAACGTTG</u> |
| NOV81a, CG90214-01 Protein Sequence | ORF Start: AGC at 1    ORF Stop: TAA at 1444<br>SEQ ID NO:212    481 aa MW at 54526.8 kD<br>SSRFLWLLKILVIILVLGIVGFMFGSMFLQAVFSSPKPELPSPAPGVQKLKLLPEERL<br>RNLFSYDGIWLFPKNQCKCEANKEQGGYNFQDAYGQSDLPAVKARRQAEFEHFQRRCR<br>EGLPRPLPLLVQPNLPFGYPVHGVEVMPLHTVPIPGKYTHIPRDPVTLTASLGTLNTL<br>ADVPDSVVQGRGQKQLIISTSDRKLLKFILQHVTYTSTGYQHQKVDIGVSLESRSSVA<br>KFPVTIRHPVIPKLYDPGPERKLRNLVTIATKTFLRPHKLMIMLRSIREYYPDLTVIV<br>ADDSQKPLEIKDNHVEYYTMPFGKGWFAGRNLAISQVTTKYVLWVDDDFLFNEETKIE<br>VLVDVLEKTELDVVGACLHKRMGFFQPLDGFPSCVVTSGVVNFFLAHTERLQRVCFDP<br>RLQRVAHEFFIDGLGTLLVCSCPEVIIGHQSRSPVVDSELAALEKTYNTYRSNTLTRV<br>QFKLALHYFKNHLQCAA |

Further analysis of the NOV81a protein yielded the following properties shown in Table 81B.

TABLE 81B

Protein Sequence Properties NOV81a

| | |
|---|---|
| PSort analysis: | 0.4600 probability located in plasma membrane |
| SignalP analysis: | Cleavage site between residues 34 and 35 |

A search of the NOV81a protein against the Geneseq database, a proprietary database that contains sequences published in patents and patent publication, yielded several homologous proteins shown in Table 81C.

TABLE 81C

Geneseq Results for NOV81a

| Geneseq Identifier | Protein/Organism/Length [Patent #, Date] | NOV81a Residues/ Match Residues | Identities/ Similarities for the Matched Region | Expect Value |
|---|---|---|---|---|
| AAE03702 | Novel human transferase-related protein #1, 506 aa. | 2 . . . 363<br>6 . . . 367 | 352/362 (97%)<br>352/362 (97%) | 1.2 e−247 |
| AAE03719 | Novel human transferase-related protein #18, 566 aa. | 2 . . . 363<br>66 . . . 427 | 352/362 (97%)<br>352/362 (97%) | 1.2 e−247 |
| AAE03717 | Novel human transferase-related protein #16, 572 aa. | 2 . . . 363<br>66 . . . 433 | 351/368 (95%)<br>351/368 (95%) | 3.0 e−244 |
| AAE03718 | Novel human transferase-related protein #17, 512 aa. | 2 . . . 363<br>6 . . . 373 | 351/368 (95%)<br>351/368 (95%) | 3.0 e−244 |
| AAE03711 | Novel human transferase-related protein #10, 448 aa. | 2 . . . 362<br>66 . . . 426 | 351/361 (97%)<br>351/368 (97%) | 1.1 e−183 |

In a BLAST search of public sequence datbases, the NOV81a protein was found to have homology to the proteins shown in the BLASTP data in Table 81D.

TABLE 81D

Public BLASTP Results for NOV81a

| Protein Accession Number | Protein/Organism/Length | NOV81a Residues/ Match Residues | Identities/ Similarities for the Matched Portion | Expect Value |
|---|---|---|---|---|
| Q09199 | Beta-1,4 N-acetylgalactosaminyltransferase - *Mus musculus* (Mouse), 510 aa. | 22 . . . 480<br>30 . . . 509 | 341/483 (70%)<br>378/483 (77%) | 0.0 |
| Q00973 | Beta-1,4 N-acetylgalactosaminyltransferase (EC 2.4.1.92) ((N-acetylneuraminyl)-galactosylglucosylceramide) (GM2/GD2 synthase) (GalNAc-T) - *Homo sapiens* (Human), 533 aa. | 34 . . . 479<br>45 . . . 529 | 205/496 (41%)<br>274/496 (54%) | 1e−90 |
| Q09200 | Beta-1,4 N-acetylgalactosaminyltransferase (EC 2.4.1.92) ((N-acetylneuraminyl)-galactosylglucosylceramide) (GM2/GD2 synthase) (GalNAc-T) - *Mus musculus* (Mouse), 533 aa. | 29 . . . 479<br>20 . . . 529 | 209/514 (40%)<br>281/514 (54%) | 3e−90 |
| Q10468 | Beta-1,4 N-acetylgalactosaminyltransferase (EC 2.4.1.92) ((N-acetylneuraminyl)-galactosylglucosylceramide) (GM2/GD2 synthase) (GalNAc-T) - *Rattus norvegicus* (Rat), 533 aa. | 41 . . . 479<br>43 . . . 529 | 200/491 (40%)<br>272/491 (54%) | 5e−89 |
| BC022180 | UDP-N-acetyl-alpha-D-galactosamine: (N-acetylneuraminyl)-galactosylglucosylceramide-beta-1,4-N-acetylgalactosaminyltransferase - *Mus musculus* (Mouse), 244 aa. | 29 . . . 222<br>20 . . . 238 | 65/222 (29%)<br>98/222 (43%) | 2e−13 |

PFam analysis predicts that the NOV81a protein contains the domains shown in the Table 81E.

TABLE 81E

Domain Analysis of NOV81a

| Pfam Domain | NOV81a Match Region | Score | Expect Value |
|---|---|---|---|
| gnl\|Pfam\|pfam00535; Glycos_transf_2, Glycosyl transferase | 260 . . . 420 | 49.6 | 4.2e−12 |

Example 82

Sequencing Methodology and Identification of NOVX Clones

1. GeneCalling™ Technology: This is a proprietary method of performing differential gene expression profiling between two or more samples developed at CuraGen and described by Shimkets, et al., "Gene expression analysis by transcript profiling coupled to a gene database query" Nature Biotechnology 17:198–803 (1999). cDNA was derived from various human samples representing multiple tissue types, normal and diseased states, physiological states, and developmental states from different donors. Samples were obtained as whole tissue, primary cells or tissue cultured primary cells or cell lines. Cells and cell lines may have been treated with biological or chemical agents that regulate gene expression, for example, growth factors, chemokines or steroids. The cDNA thus derived was then digested with up to as many as 120 pairs of restriction enzymes and pairs of linker-adaptors specific for each pair of restriction enzymes were ligated to the appropriate end. The restriction digestion generates a mixture of unique cDNA gene fragments. Limited PCR amplification is performed with primers homologous to the linker adapter sequence where one primer is biotinylated and the other is fluorescently labeled. The doubly labeled material is isolated and the fluorescently labeled single strand is resolved by capillary gel electrophoresis. A computer algorithm compares the electropherograms from an experimental and control group for each of the restriction digestions. This and additional sequence-derived information is used to predict the identity of each differentially expressed gene fragment using a variety of genetic databases. The identity of the gene fragment is confirmed by additional, gene-specific competitive PCR or by isolation and sequencing of the gene fragment.

2. SeqCalling™ Technology: cDNA was derived from various human samples representing multiple tissue types, normal and diseased states, physiological states, and developmental states from different donors. Samples were obtained as whole tissue, primary cells or tissue cultured primary cells or cell lines. Cells and cell lines may have been treated with biological or chemical agents that regulate gene expression, for example, growth factors, chemokines or steroids. The cDNA thus derived was then sequenced using CuraGen's proprietary SeqCalling technology. Sequence traces were evaluated manually and edited for corrections if appropriate. cDNA sequences from all samples were assembled together, sometimes including public human sequences, using bioinformatic programs to produce a consensus sequence for each assembly. Each assembly is included in CuraGen Corporation's database. Sequences were included as components for assembly when the extent of identity with another component was at least 95% over 50 bp. Each assembly represents a gene or portion thereof and includes information on variants, such as splice forms single nucleotide polymorphisms (SNPs), insertions, deletions and other sequence variations.

3. PathCalling™ Technology:

The NOVX nucleic acid sequences are derived by laboratory screening of cDNA library by the two-hybrid approach. cDNA fragments covering either the full length of the DNA sequence, or part of the sequence, or both, are sequenced. In silico prediction was based on sequences available in CuraGen Corporation's proprietary sequence databases or in the public human sequence databases, and provided either the full length DNA sequence, or some portion thereof.

The laboratory screening was performed using the methods summarized below:

cDNA libraries were derived from various human samples representing multiple tissue types, normal and diseased states, physiological states, and developmental states from different donors. Samples were obtained as whole tissue, primary cells or tissue cultured primary cells or cell lines. Cells and cell lines may have been treated with biological or chemical agents that regulate gene expression, for example, growth factors, chemokines or steroids. The cDNA thus derived was then directionally cloned into the appropriate two-hybrid vector (Gal4-activation domain (Gal4-AD) fusion). Such cDNA libraries as well as commercially available cDNA libraries from Clontech (Palo Alto, Calif.) were then transferred from E.coli into a CuraGen Corporation proprietary yeast strain (disclosed in U.S. Pat. Nos. 6,057, 101 and 6,083,693, incorporated herein by reference in their entireties).

Gal4-binding domain (Gal4-BD) fusions of a CuraGen Corportion proprietary library of human sequences was used to screen multiple Gal4-AD fusion cDNA libraries resulting in the selection of yeast hybrid diploids in each of which the Gal4-AD fusion contains an individual cDNA. Each sample was amplified using the polymerase chain reaction (PCR) using non-specific primers at the cDNA insert boundaries. Such PCR product was sequenced; sequence traces were evaluated manually and edited for corrections if appropriate. cDNA sequences from all samples were assembled together, sometimes including public human sequences, using bioinformatic programs to produce a consensus sequence for each assembly. Each assembly is included in CuraGen Corporation's database. Sequences were included as components for assembly when the extent of identity with another component was at least 95% over 50 bp. Each assembly represents a gene or portion thereof and includes information on variants, such as splice forms single nucleotide polymorphisms (SNPs), insertions, deletions and other sequence variations.

Physical clone: the cDNA fragment derived by the screening procedure, covering the entire open reading frame is, as a recombinant DNA, cloned into pACT2 plasmid (Clontech) used to make the cDNA library. The recombinant plasmid is inserted into the host and selected by the yeast hybrid diploid generated during the screening procedure by the mating of both CuraGen Corporation proprietary yeast strains N106' and YULH (U.S. Pat. Nos. 6,057,101 and 6,083,693).

4. RACE: Techniques based on the polymerase chain reaction such as rapid amplification of cDNA ends (RACE), were used to isolate or complete the predicted sequence of the cDNA of the invention. Usually multiple clones were sequenced from one or more human samples to derive the sequences for fragments. Various human tissue samples from different donors were used for the RACE reaction. The sequences derived from these procedures were included in the SeqCalling Assembly process described in preceding paragraphs.

5. Exon Linking: The NOVX target sequences identified in the present invention were subjected to the exon linking process to confirm the sequence. PCR primers were designed by starting at the most upstream sequence available, for the forward primer, and at the most downstream sequence available for the reverse primer. In each case, the sequence was examined, walking inward from the respective termini toward the coding sequence, until a suitable sequence that is either unique or highly selective was encountered, or, in the case of the reverse primer, until the stop codon was reached. Such primers were designed based on in silico predictions for the full length cDNA, part (one or more exons) of the DNA or protein sequence of the target sequence, or by translated homology of the predicted exons to closely related human sequences from other species. These primers were then employed in PCR amplification based on the following pool of human cDNAs: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea, uterus. Usually the resulting amplicons were gel purified, cloned and sequenced to high redundancy. The PCR product derived from exon linking was cloned into the pCR2.1 vector from Invitrogen. The resulting bacterial clone has an insert covering the entire open reading frame cloned into the pCR2.1 vector. The resulting sequences from all clones were assembled with themselves, with other fragments in CuraGen Corporation's database and with public ESTs. Fragments and ESTs were included as components for an assembly when the extent of their identity with another component of the assembly was at least 95% over 50 bp. In addition, sequence traces were evaluated manually and edited for corrections if appropriate. These procedures provide the sequence reported herein.

6. Physical Clone:

Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene sequence. The DNA sequence was then manually corrected for apparent inconsistencies thereby obtaining the sequences encoding the full-length protein.

The PCR product derived by exon linking, covering the entire open reading frame, was cloned into the pCR2.1 vector from Invitrogen to provide clones used for expression and screening purposes.

Example 83

Quantitative Expression Analysis of Clones in Various Cells and Tissues

The quantitative expression of various clones was assessed using microtiter plates containing RNA samples from a variety of normal and pathology-derived cells, cell lines and tissues using real time quantitative PCR (RTQ PCR). RTQ PCR was performed on an Applied Biosystems ABI PRISM® 7700 or an ABI PRISM® 7900 HT Sequence Detection System. Various collections of samples are assembled on the plates, and referred to as Panel 1 (containing normal tissues and cancer cell lines), Panel 2 (containing samples derived from tissues from normal and cancer sources), Panel 3 (containing cancer cell lines), Panel 4 (containing cells and cell lines from normal tissues and cells related to inflammatory conditions), Panel 5D/5I (containing human tissues and cell lines with an emphasis on metabolic diseases), AI_comprehensive_panel (containing normal tissue and samples from autoimmune diseases), Panel CNSD.01 (containing central nervous system samples from normal and diseased brains) and CNS_neurodegeneration_panel (containing samples from normal and Alzheimer's diseased brains).

RNA integrity from all samples is controlled for quality by visual assessment of agarose gel electropherograms using 28S and 18S ribosomal RNA staining intensity ratio as a guide (2:1 to 2.5:1 28s: 18s) and the absence of low molecular weight RNAs that would be indicative of degradation products. Samples are controlled against genomic DNA contamination by RTQ PCR reactions run in the absence of reverse transcriptase using probe and primer sets designed to amplify across the span of a single exon.

First, the RNA samples were normalized to reference nucleic acids such as constitutively expressed genes (for example, β-actin and GAPDH). Normalized RNA (5 μl) was converted to cDNA and analyzed by RTQ-PCR using One Step RT-PCR Master Mix Reagents (Applied Biosystems; Catalog No. 4309169) and gene-specific primers according to the manufacturer's instructions.

In other cases, non-normalized RNA samples were converted to single strand cDNA (sscDNA) using Superscript II (Invitrogen Corporation; Catalog No. 18064-147) and random hexamers according to the manufacturer's instructions. Reactions containing up to 10 μg of total RNA were performed in a volume of 20 μl and incubated for 60 minutes at 42° C. This reaction can be scaled up to 50 μg of total RNA in a final volume of 100 μl. sscDNA samples are then normalized to reference nucleic acids as described previously, using 1× TaqMan® Universal Master mix (Applied Biosystems; catalog No. 4324020), following the manufacturer's instructions.

Probes and primers were designed for each assay according to Applied Biosystems Primer Express Software package (version I for Apple Computer's Macintosh Power PC) or a similar algorithm using the target sequence as input. Default settings were used for reaction conditions and the following parameters were set before selecting primers: primer concentration=250 nM, primer melting temperature (Tm) range=58°–60° C., primer optimal Tm=59° C., maximum primer difference=2° C., probe does not have 5'G, probe Tm must be 10° C. greater than primer Tm, amplicon size 75 bp to 100 bp. The probes and primers selected (see below) were synthesized by Synthegen (Houston, Tex., USA). Probes were double purified by HPLC to remove uncoupled dye and evaluated by mass spectroscopy to verify coupling of reporter and quencher dyes to the 5' and 3' ends of the probe, respectively. Their final concentrations were: forward and reverse primers, 900 nM each, and probe, 200 nM.

PCR conditions: When working with RNA samples, normalized RNA from each tissue and each cell line was spotted in each well of either a 96 well or a 384-well PCR plate (Applied Biosystems). PCR cocktails included either a single gene specific probe and primers set, or two multiplexed probe and primers sets (a set specific for the target clone and another gene-specific set multiplexed with the target probe). PCR reactions were set up using TaqMan (V One-Step RT-PCR Master Mix (Applied Biosystems, Catalog No. 4313803) following manufacturer's instructions. Reverse transcription was performed at 48° C. for 30 minutes followed by amplification/PCR cycles as follows: 95° C. 10 min, then 40 cycles of 95° C. for 15 seconds, 60° C. for 1 minute. Results were recorded as CT values (cycle at which a given sample crosses a threshold level of fluorescence) using a log scale, with the difference in RNA concentration between a given sample and the sample with the lowest CT value being represented as 2 to the power of delta CT. The percent relative expression is then obtained by taking the reciprocal of this RNA difference and multiplying by 100.

When working with sscDNA samples, normalized sscDNA was used as described previously for RNA samples. PCR reactions containing one or two sets of probe and primers were set up as described previously, using 1×TaqMan® Universal Master mix (Applied Biosystems; catalog No. 4324020), following the manufacturer's instructions. PCR amplification was performed as follows: 95° C. 10 min, then 40 cycles of 95° C. for 15 seconds, 60° C. for 1 minute. Results were analyzed and processed as described previously.

Panels 1, 1.1, 1.2, and 1.3D

The plates for Panels 1, 1.1, 1.2 and 1.3D include 2 control wells (genomic DNA control and chemistry control) and 94 wells containing cDNA from various samples. The samples in these panels are broken into 2 classes: samples derived from cultured cell lines and samples derived from primary normal tissues. The cell lines are derived from cancers of the following types: lung cancer, breast cancer, melanoma, colon cancer, prostate cancer, CNS cancer, squamous cell carcinoma, ovarian cancer, liver cancer, renal cancer, gastric cancer and pancreatic cancer. Cell lines used in these panels are widely available through the American Type Culture Collection (ATCC), a repository for cultured cell lines, and were cultured using the conditions recommended by the ATCC. The normal tissues found on these panels are comprised of samples derived from all major organ systems from single adult individuals or fetuses. These samples are derived from the following organs: adult skeletal muscle, fetal skeletal muscle, adult heart, fetal heart, adult kidney, fetal kidney, adult liver, fetal liver, adult lung, fetal lung, various regions of the brain, the spleen, bone marrow, lymph node, pancreas, salivary gland, pituitary gland, adrenal gland, spinal cord, thymus, stomach, small intestine, colon, bladder, trachea, breast, ovary, uterus, placenta, prostate, testis and adipose.

In the results for Panels 1, 1.1, 1.2 and 1.3D, the following abbreviations are used:
ca.=carcinoma,
*=established from metastasis,
met=metastasis,
s cell var=small cell variant,
non-s=non-sm=non-small,
squam=squamous,
pl. eff=pl effusion=pleural effusion,
glio=glioma,
astro=astrocytoma, and
neuro=neuroblastoma.

General_Screening_Panel_v1.4 and General_Screening_Panel_v1.5

The plates for Panels 1.4 and 1.5 include 2 control wells (genomic DNA control and chemistry control) and 94 wells containing cDNA from various samples. The samples in Panels 1.4 and 1.5 are broken into 2 classes: samples derived from cultured cell lines and samples derived from primary normal tissues. The cell lines are derived from cancers of the following types: lung cancer, breast cancer, melanoma, colon cancer, prostate cancer, CNS cancer, squamous cell carcinoma, ovarian cancer, liver cancer, renal cancer, gastric cancer and pancreatic cancer. Cell lines used in Panel 1.4 are widely available through the American Type Culture Collection (ATCC), a repository for cultured cell lines, and were cultured using the conditions recommended by the ATCC. The normal tissues found on Panels 1.4 and 1.5 are comprised of pools of samples derived from all major organ systems from 2 to 5 different adult individuals or fetuses. These samples are derived from the following organs: adult skeletal muscle, fetal skeletal muscle, adult heart, fetal heart, adult kidney, fetal kidney, adult liver, fetal liver, adult lung, fetal lung, various regions of the brain, the spleen, bone marrow, lymph node, pancreas, salivary gland, pituitary gland, adrenal gland, spinal cord, thymus, stomach, small intestine, colon, bladder, trachea, breast, ovary, uterus, placenta, prostate, testis and adipose. Abbreviations are as described for Panels 1, 1.1, 1.2, and 1.3D.

Panels 2D and 2.2

The plates for Panels 2D and 2.2 generally include 2 control wells and 94 test samples composed of RNA or cDNA isolated from human tissue procured by surgeons working in close cooperation with the National Cancer Institute's Cooperative Human Tissue Network (CHTN) or the National Disease Research Initiative (NDR1). The tissues are derived from human malignancies and in cases where indicated many malignant tissues have "matched margins" obtained from noncancerous tissue just adjacent to the tumor. These are termed normal adjacent tissues and are denoted "NAT" in the results below. The tumor tissue and the "matched margins" are evaluated by two independent pathologists (the surgical pathologists and again by a pathologist at NDRI or CHTN). This analysis provides a gross histopathological assessment of tumor differentiation grade. Moreover, most samples include the original surgical pathology report that provides information regarding the clinical stage of the patient. These matched margins are taken from the tissue surrounding (i.e. immediately proximal) to the zone of surgery (designated "NAT", for normal adjacent tissue, in Table RR). In addition, RNA and cDNA samples were obtained from various human tissues derived from autopsies performed on elderly people or sudden death victims (accidents, etc.). These tissues were ascertained to be free of disease and were purchased from various commercial sources such as Clontech (Palo Alto, Calif.), Research Genetics, and Invitrogen.

Panel 3D

The plates of Panel 3D are comprised of 94 cDNA samples and two control samples. Specifically, 92 of these samples are derived from cultured human cancer cell lines, 2 samples of human primary cerebellar tissue and 2 controls. The human cell lines are generally obtained from ATCC (American Type Culture Collection), NCI or the German tumor cell bank and fall into the following tissue groups: Squamous cell carcinoma of the tongue, breast cancer, prostate cancer, melanoma, epidermoid carcinoma, sarcomas, bladder carcinomas, pancreatic cancers, kidney cancers, leukemias/lymphomas, ovarian/uterine/cervical, gastric, colon, lung and CNS cancer cell lines. In addition, there are two independent samples of cerebellum. These cells are all cultured under standard recommended conditions and RNA extracted using the standard procedures. The cell lines in panel 3D and 1.3D are of the most common cell lines used in the scientific literature.

Panels 4D, 4R, and 4.1D

Panel 4 includes samples on a 96 well plate (2 control wells, 94 test samples) composed of RNA (Panel 4R) or cDNA (Panels 4D/4.1D) isolated from various human cell lines or tissues related to inflammatory conditions. Total RNA from control normal tissues such as colon and lung (Stratagene, La Jolla, Calif.) and thymus and kidney (Clontech) was employed. Total RNA from liver tissue from cirrhosis patients and kidney from lupus patients was obtained from BioChain (Biochain Institute, Inc., Hayward, Calif.). Intestinal tissue for RNA preparation from patients diagnosed as having Crohn's disease and ulcerative colitis was obtained from the National Disease Research Interchange (NDR1) (Philadelphia, Pa.).

Astrocytes, lung fibroblasts, dermal fibroblasts, coronary artery smooth muscle cells, small airway epithelium, bronchial epithelium, microvascular dermal endothelial cells, microvascular lung endothelial cells, human pulmonary aortic endothelial cells, human umbilical vein endothelial cells were all purchased from Clonetics (Walkersville, MD) and grown in the media supplied for these cell types by Clonetics. These primary cell types were activated with various cytokines or combinations of cytokines for 6 and/or 12–14 hours, as indicated. The following cytokines were used; IL-1 beta at approximately 1–5 ng/ml, TNF alpha at approximately 5–10 ng/ml, IFN gamma at approximately 20–50 ng/ml, IL-4 at approximately 5–10 ng/ml, IL-9 at approximately 5–10 ng/ml, IL-13 at approximately 5–10 ng/ml. Endothelial cells were sometimes starved for various times by culture in the basal media from Clonetics with 0.1% serum.

Mononuclear cells were prepared from blood of employees at CuraGen Corporation, using Ficoll. LAK cells were prepared from these cells by culture in DMEM 5% FCS (Hyclone), 100 μM non essential amino acids (Gibco/Life Technologies, Rockville, Md.), 1 mM sodium pyruvate (Gibco), mercaptoethanol $5.5 \times 10^{-5}$M (Gibco), and 10 mM Hepes (Gibco) and Interleukin 2 for 4–6 days. Cells were then either activated with 10–20 ng/ml PMA and 1–2 μg/ml ionomycin, IL-12 at 5–10 ng/ml, IFN gamma at 20–50 ng/ml and IL-18 at 5–10 ng/ml for 6 hours. In some cases, mononuclear cells were cultured for 4–5 days in DMEM 5% FCS (Hyclone), 100 μM non essential amino acids (Gibco), 1 mM sodium pyruvate (Gibco), mercaptoethanol $5.5 \times 10^{-5}$M (Gibco), and 10 mM Hepes (Gibco) with PHA (phytohemagglutinin) or PWM (pokeweed mitogen) at approximately 5 μg/ml. Samples were taken at 24, 48 and 72 hours for RNA preparation. MLR (mixed lymphocyte reaction) samples were obtained by taking blood from two donors, isolating the mononuclear cells using Ficoll and mixing the isolated mononuclear cells 1:1 at a final concentration of approximately $2 \times 10^6$ cells/ml in DMEM 5% FCS (Hyclone), 100 μM non essential amino acids (Gibco), 1 mM sodium pyruvate (Gibco), mercaptoethanol ($5.5 \times 10^{-5}$M) (Gibco), and 10 mM Hepes (Gibco). The MLR was cultured and samples taken at various time points ranging from 1–7 days for RNA preparation.

Monocytes were isolated from mononuclear cells using CD14 Miltenyi Beads, +ve VS selection columns and a Vario Magnet according to the manufacturer's instructions. Monocytes were differentiated into dendritic cells by culture in DMEM 5% fetal calf serum (FCS) (Hyclone, Logan, Utah), 100 μM non essential amino acids (Gibco), 1 mM sodium pyruvate (Gibco), mercaptoethanol $5.5 \times 10^{-5}$M (Gibco), and 10 mM Hepes (Gibco), 50 ng/ml GMCSF and 5 ng/ml IL-4 for 5–7 days. Macrophages were prepared by culture of monocytes for 5–7 days in DMEM 5% FCS (Hyclone), 100 μM non essential amino acids (Gibco), 1 mM sodium pyruvate (Gibco), mercaptoethanol $5.5 \times 10^{-5}$M (Gibco), 10 mM Hepes (Gibco) and 10% AB Human Serum or MCSF at approximately 50 ng/ml. Monocytes, macrophages and dendritic cells were stimulated for 6 and 12–14 hours with lipopolysaccharide (LPS) at 100 ng/ml. Dendritic cells were also stimulated with anti-CD40 monoclonal antibody (Pharmingen) at 10 g/ml for 6 and 12–14 hours.

CD4 lymphocytes, CD8 lymphocytes and NK cells were also isolated from mononuclear cells using CD4, CD8 and CD56 Miltenyi beads, positive VS selection columns and a Vario Magnet according to the manufacturer's instructions. CD45RA and CD45RO CD4 lymphocytes were isolated by depleting mononuclear cells of CD8, CD56, CD14 and CD19 cells using CD8, CD56, CD14 and CD19 Miltenyi beads and positive selection. CD45RO beads were then used to isolate the CD45RO CD4 lymphocytes with the remaining cells being CD45RA CD4 lymphocytes. CD45RA CD4, CD45RO CD4 and CD8 lymphocytes were placed in DMEM 5% FCS (Hyclone), 100M non essential amino acids (Gibco), 1 mM sodium pyruvate (Gibco), mercaptoethanol $5.5 \times 10^{-5}$M (Gibco), and 10 mM Hepes (Gibco) and plated at $10^6$ cells/ml onto Falcon 6 well tissue culture plates that had been coated overnight with 0.5 μg/ml anti-CD28 (Pharmingen) and 3 μg/ml anti-CD3 (OKT3, ATCC) in PBS. After 6 and 24 hours, the cells were harvested for RNA preparation. To prepare chronically activated CD8 lymphocytes, we activated the isolated CD8 lymphocytes for 4 days on anti-CD28 and anti-CD3 coated plates and then harvested the cells and expanded them in DMEM 5% FCS (Hyclone), 100 μM non essential amino acids (Gibco), 1 mM sodium pyruvate (Gibco), mercaptoethanol $5.5 \times 10^{-5}$M (Gibco), and 10 mM Hepes (Gibco) and IL-2. The expanded CD8 cells were then activated again with plate bound anti-CD3 and anti-CD28 for 4 days and expanded as before. RNA was isolated 6 and 24 hours after the second activation and after 4 days of the second expansion culture. The isolated NK cells were cultured in DMEM 5% FCS (Hyclone), 100 μM non essential amino acids (Gibco), 1 mM sodium pyruvate (Gibco), mercaptoethanol $5.5 \times 10^{-5}$M (Gibco), and 10 mM Hepes (Gibco) and IL-2 for 4–6 days before RNA was prepared.

To obtain B cells, tonsils were procured from NDR1. The tonsil was cut up with sterile dissecting scissors and then passed through a sieve. Tonsil cells were then spun down and resupended at $10^6$ cells/ml in DMEM 5% FCS (Hyclone), 100 μM non essential amino acids (Gibco), 1 mM sodium pyruvate (Gibco), mercaptoethanol $5.5 \times 10^{-5}$M (Gibco), and 10 mM Hepes (Gibco). To activate the cells, we used PWM at 5 μg/ml or anti-CD40 (Pharmingen) at approximately 10 μg/ml and IL-4 at 5–10 ng/ml. Cells were harvested for RNA preparation at 24, 48 and 72 hours.

To prepare the primary and secondary Th1/Th2 and Tr1 cells, six-well Falcon plates were coated overnight with 10 μg/ml anti-CD28 (Pharmingen) and 2 μg/ml OKT3 (ATCC), and then washed twice with PBS. Umbilical cord blood CD4 lymphocytes (Poietic Systems, German Town, Md.) were cultured at $10^5$–$10^6$ cells/ml in DMEM 5% FCS (Hyclone), 100 μM non essential amino acids (Gibco), 1 mM sodium pyruvate (Gibco), mercaptoethanol $5.5 \times 10^{-5}$M (Gibco), 10 mM Hepes (Gibco) and IL-2 (4 ng/ml). IL-12 (5 ng/ml) and anti-IL-4 (1 μg/ml) were used to direct to Th1, while IL-4 (5 ng/ml) and anti-IFN gamma (1 μg/ml) were used to direct to Th2 and IL-10 at 5 ng/ml was used to direct to Tr1. After 4–5 days, the activated Th1, Th2 and Tr1 lymphocytes were washed once in DMEM and expanded for 4–7 days in DMEM 5% FCS (Hyclone), 100 µM non essential amino acids (Gibco), 1 mM sodium pyruvate (Gibco), mercaptoethanol $5.5 \times 10^{-5}$M (Gibco), 10 mM Hepes (Gibco) and IL-2 (1 ng/ml). Following this, the activated Th1, Th2 and Tr1 lymphocytes were re-stimulated for 5 days with anti-CD28/OKT3 and cytokines as described above, but with the addition of anti-CD95L (1 µg/ml) to prevent apoptosis. After 4–5 days, the Th1, Th2 and Tr1 lymphocytes were washed and then expanded again with IL-2 for 4–7 days. Activated Th1 and Th2 lymphocytes were maintained in this way for a maximum of three cycles. RNA was prepared from primary and secondary Th1, Th2 and Tr1 after 6 and 24 hours following the second and third activations with plate bound anti-CD3 and anti-CD28 mAbs and 4 days into the second and third expansion cultures in Interleukin 2.

The following leukocyte cells lines were obtained from the ATCC: Ramos, EOL-1, KU-812. EOL cells were further differentiated by culture in 0.1 mM dbcAMP at $5 \times 10^5$ cells/ml for 8 days, changing the media every 3 days and adjusting the cell concentration to $5 \times 10^5$ cells/ml. For the culture of these cells, we used DMEM or RPMI (as recommended by the ATCC), with the addition of 5% FCS (Hyclone), 100 µM non essential amino acids (Gibco), 1 mM sodium pyruvate (Gibco), mercaptoethanol $5.5 \times 10^{-5}$M (Gibco), 10 mM Hepes (Gibco). RNA was either prepared from resting cells or cells activated with PMA at 10 ng/ml and ionomycin at 1 µg/ml for 6 and 14 hours. Keratinocyte line CCD106 and an airway epithelial tumor line NCI-H292 were also obtained from the ATCC. Both were cultured in DMEM 5% FCS (Hyclone), 100 M non essential amino acids (Gibco), 1 mM sodium pyruvate (Gibco), mercaptoethanol $5.5 \times 10^{-5}$M (Gibco), and 10 mM Hepes (Gibco). CCD1106 cells were activated for 6 and 14 hours with approximately 5 ng/ml TNF alpha and 1 ng/ml IL-1 beta, while NCI-H292 cells were activated for 6 and 14 hours with the following cytokines: 5 ng/ml IL-4, 5 ng/ml IL-9, 5 ng/ml IL-13 and 25 ng/ml IFN gamma.

For these cell lines and blood cells, RNA was prepared by lysing approximately $10^7$ cells/ml using Trizol (Gibco BRL). Briefly, 1/10 volume of bromochloropropane (Molecular Research Corporation) was added to the RNA sample, vortexed and after 10 minutes at room temperature, the tubes were spun at 14,000 rpm in a Sorvall SS34 rotor. The aqueous phase was removed and placed in a 15 ml Falcon Tube. An equal volume of isopropanol was added and left at −20° C. overnight. The precipitated RNA was spun down at 9,000 rpm for 15 min in a Sorvall SS34 rotor and washed in 70% ethanol. The pellet was redissolved in 3001 µl of RNAse-free water and 35 µl buffer (Promega) 5 µl DTT, 7 µl RNAsin and 8 µl DNAse were added. The tube was incubated at 37° C. for 30 minutes to remove contaminating genomic DNA, extracted once with phenol chloroform and re-precipitated with 1/10 volume of 3M sodium acetate and 2 volumes of 100% ethanol. The RNA was spun down and placed in RNAse free water. RNA was stored at −80° C.

AI_Comprehensive Panel_v1.0

The plates for AI_comprehensive panel_v1.0 include two control wells and 89 test samples comprised of cDNA isolated from surgical and postmortem human tissues obtained from the Backus Hospital and Clinomics (Frederick, Md.). Total RNA was extracted from tissue samples from the Backus Hospital in the Facility at CuraGen. Total RNA from other tissues was obtained from Clinomics.

Joint tissues including synovial fluid, synovium, bone and cartilage were obtained from patients undergoing total knee or hip replacement surgery at the Backus Hospital. Tissue samples were immediately snap frozen in liquid nitrogen to ensure that isolated RNA was of optimal quality and not degraded. Additional samples of osteoarthritis and rheumatoid arthritis joint tissues were obtained from Clinomics. Normal control tissues were supplied by Clinomics and were obtained during autopsy of trauma victims.

Surgical specimens of psoriatic tissues and adjacent matched tissues were provided as total RNA by Clinomics. Two male and two female patients were selected between the ages of 25 and 47. None of the patients were taking prescription drugs at the time samples were isolated.

Surgical specimens of diseased colon from patients with ulcerative colitis and Crohns disease and adjacent matched tissues were obtained from Clinomics. Bowel tissue from three female and three male Crohn's patients between the ages of 41–69 were used. Two patients were not on prescription medication while the others were taking dexamethasone, phenobarbital, or tylenol. Ulcerative colitis tissue was from three male and four female patients. Four of the patients were taking lebvid and two were on phenobarbital.

Total RNA from post mortem lung tissue from trauma victims with no disease or with emphysema, asthma or COPD was purchased from Clinomics. Emphysema patients ranged in age from 40–70 and all were smokers, this age range was chosen to focus on patients with cigarette-linked emphysema and to avoid those patients with alpha-1antitrypsin deficiencies. Asthma patients ranged in age from 36–75, and excluded smokers to prevent those patients that could also have COPD. COPD patients ranged in age from 35–80 and included both smokers and non-smokers. Most patients were taking corticosteroids, and bronchodilators.

In the labels employed to identify tissues in the $AI_{13}$ comprehensive panel_v1.0 panel, the following abbreviations are used:

AI=Autoimmunity
Syn=Synovial
Normal=No apparent disease
Rep22/Rep20=individual patients
RA=Rheumatoid arthritis
Backus=From Backus Hospital
OA=Osteoarthritis
(SS)(BA)(MF)=Individual patients
Adj=Adjacent tissue
Match control=adjacent tissues
−M=Male
−F=Female
COPD=Chronic obstructive pulmonary disease Panels 5D and 5I The plates for Panel 5D and 5I include two control wells and a variety of cDNAs isolated from human tissues and cell lines with an emphasis on metabolic diseases. Metabolic tissues were obtained from patients enrolled in the Gestational Diabetes study. Cells were obtained during different stages in the differentiation of adipocytes from human mesenchymal stem cells. Human pancreatic islets were also obtained.

In the Gestational Diabetes study subjects are young (18–40 years), otherwise healthy women with and without gestational diabetes undergoing routine (elective) Caesarean section. After delivery of the infant, when the surgical incisions were being repaired/closed, the obstetrician removed a small sample (<1 cc) of the exposed metabolic tissues during the closure of each surgical level. The biopsy material was rinsed in sterile saline, blotted and fast frozen within 5 minutes from the time of removal. The tissue was then flash frozen in liquid nitrogen and stored, individually, in sterile screw-top tubes and kept on dry ice for shipment to or to be picked up by CuraGen. The metabolic tissues of interest include uterine wall (smooth muscle), visceral adipose, skeletal muscle (rectus) and subcutaneous adipose. Patient descriptions are as follows:

Patient 2: Diabetic Hispanic, overweight, not on insulin
Patient 7–9: Nondiabetic Caucasian and obese (BMI>30)
Patient 10: Diabetic Hispanic, overweight, on insulin
Patient 11: Nondiabetic African American and overweight
Patient 12: Diabetic Hispanic on insulin Adipocyte differentiation was induced in donor progenitor cells obtained from Osirus (a division of Clonetics/BioWhittaker) in triplicate, except for Donor 3U which had only two replicates. Scientists at Clonetics isolated, grew and differentiated human mesenchymal stem cells (HuMSCs) for CuraGen based on the published protocol found in Mark F. Pittenger, et al., Multilineage Potential of Adult Human Mesenchymal Stem Cells Science Apr. 2, 1999: 143–147. Clonetics provided Trizol lysates or frozen pellets suitable for mRNA isolation and ds cDNA production. A general description of each donor is as follows:

Donor 2 and 3 U: Mesenchymal Stem cells, Undifferentiated Adipose
Donor 2 and 3 AM: Adipose, AdiposeMidway Differentiated
Donor 2 and 3 AD: Adipose, Adipose Differentiated Human cell lines were generally obtained from ATCC (American Type Culture Collection), NCI or the German tumor cell bank and fall into the following tissue groups: kidney proximal convoluted tubule, uterine smooth muscle cells, small intestine, liver HepG2 cancer cells, heart primary stromal cells, and adrenal cortical adenoma cells. These cells are all cultured under standard recommended conditions and RNA extracted using the standard procedures. All samples were processed at CuraGen to produce single stranded cDNA.

Panel 5I contains all samples previously described with the addition of pancreatic islets from a 58 year old female patient obtained from the Diabetes Research Institute at the University of Miami School of Medicine. Islet tissue was processed to total RNA at an outside source and delivered to CuraGen for addition to panel 5I.

In the labels employed to identify tissues in the 5D and 5I panels, the following abbreviations are used:
GO Adipose=Greater Omentum Adipose
SK=Skeletal Muscle
UT=Uterus
PL=Placenta
AD=Adipose Differentiated
AM=Adipose Midway Differentiated
U=Undifferentiated Stem Cells Panel CNSD.01

The plates for Panel CNSD.01 include two control wells and 94 test samples comprised of cDNA isolated from postmortem human brain tissue obtained from the Harvard Brain Tissue Resource Center. Brains are removed from calvaria of donors between 4 and 24 hours after death, sectioned by neuroanatomists, and frozen at −80° C. in liquid nitrogen vapor. All brains are sectioned and examined by neuropathologists to confirm diagnoses with clear associated neuropathology.

Disease diagnoses are taken from patient records. The panel contains two brains from each of the following diagnoses: Alzheimer's disease, Parkinson's disease, Huntington's disease, Progressive Supernuclear Palsy, Depression, and "Normal controls". Within each of these brains, the following regions are represented: cingulate gyrus, temporal pole, globus palladus, substantia nigra, Brodman Area 4 (primary motor strip), Brodman Area 7 (parietal cortex), Brodman Area 9 (prefrontal cortex), and Brodman area 17 (occipital cortex). Not all brain regions are represented in all cases; e.g., Huntington's disease is characterized in part by neurodegeneration in the globus palladus, thus this region is impossible to obtain from confirmed Huntington's cases. Likewise Parkinson's disease is characterized by degeneration of the substantia nigra making this region more difficult to obtain. Normal control brains were examined for neuropathology and found to be free of any pathology consistent with neurodegeneration.

In the labels employed to identify tissues in the CNS panel, the following abbreviations are used:
PSP=Progressive supranuclear palsy
Sub Nigra=Substantia nigra
Glob Palladus=Globus palladus
Temp Pole=Temporal pole
Cing Gyr=Cingulate gyrus
BA 4=Brodman Area 4

Panel CNS_Neurodegeneration_V1.0

The plates for Panel CNS_Neurodegeneration_V1.0 include two control wells and 47 test samples comprised of cDNA isolated from postmortem human brain tissue obtained from the Harvard Brain Tissue Resource Center (McLean Hospital) and the Human Brain and Spinal Fluid Resource Center (VA Greater Los Angeles Healthcare System). Brains are removed from calvaria of donors between 4 and 24 hours after death, sectioned by neuroanatomists, and frozen at −80° C. in liquid nitrogen vapor. All brains are sectioned and examined by neuropathologists to confirm diagnoses with clear associated neuropathology.

Disease diagnoses are taken from patient records. The panel contains six brains from Alzheimer's disease (AD) patients, and eight brains from "Normal controls" who showed no evidence of dementia prior to death. The eight normal control brains are divided into two categories: Controls with no dementia and no Alzheimer's like pathology (Controls) and controls with no dementia but evidence of severe Alzheimer's like pathology, (specifically senile plaque load rated as level 3 on a scale of 0–3; 0=no evidence of plaques, 3=severe AD senile plaque load). Within each of these brains, the following regions are represented: hippocampus, temporal cortex (Brodman Area 21), parietal cortex (Brodman area 7), and occipital cortex (Brodman area 17). These regions were chosen to encompass all levels of neurodegeneration in AD. The hippocampus is a region of early and severe neuronal loss in AD; the temporal cortex is known to show neurodegeneration in AD after the hippocampus; the parietal cortex shows moderate neuronal death in the late stages of the disease; the occipital cortex is spared in AD and therefore acts as a "control" region within AD patients. Not all brain regions are represented in all cases.

In the labels employed to identify tissues in the CNS_Neurodegeneration_V1.0 panel, the following abbreviations are used:
AD=Alzheimer's disease brain; patient was demented and showed AD-like pathology upon autopsy
Control=Control brains; patient not demented, showing no neuropathology
Control (Path)=Control brains; pateint not demented but showing sever AD-like pathology
SupTemporal Ctx=Superior Temporal Cortex
Inf Temporal Ctx=Inferior Temporal Cortex

A. CG55912-01: CACNG4

Expression of gene CG55912-01 was assessed using the primer-probe set Ag2841, described in Table AA. Results of the RTQ-PCR runs are shown in Tables AB, AC, and AD.

TABLE AA

Probe Name Ag2841

| Primers | Sequences | Length | Start Position | SEQ ID NO: |
|---|---|---|---|---|
| Forward | 5'-gtctgcgtgaagatcaatcatt-3' | 22 | 283 | 213 |
| Probe | TET-5'-aggacacggactacgaccacgacag-3'-TAMRA | 25 | 311 | 214 |
| Reverse | 5'-cggaccgtacggagtagatact-3' | 22 | 341 | 215 |

TABLE AB

CNS_neurodegeneration_v1.0

| Tissue Name | Rel. Exp. (%) Ag2841, Run 209779166 | Tissue Name | Rel. Exp. (%) Ag2841, Run 209779166 |
|---|---|---|---|
| AD 1 Hippo | 15.8 | Control (Path) 3 Temporal Ctx | 0.0 |
| AD 2 Hippo | 34.6 | Control (Path) 4 Temporal Ctx | 25.9 |
| AD 3 Hippo | 15.9 | AD 1 Occipital Ctx | 6.8 |
| AD 4 Hippo | 17.0 | AD 2 Occipital Ctx (Missing) | 0.0 |
| AD 5 hippo | 85.3 | AD 3 Occipital Ctx | 24.0 |
| AD 6 Hippo | 51.1 | AD 4 Occipital Ctx | 21.8 |
| Control 2 Hippo | 21.0 | AD 5 Occipital Ctx | 0.0 |
| Control 4 Hippo | 0.0 | AD 6 Occipital Ctx | 51.8 |
| Control (Path) 3 Hippo | 0.0 | Control 1 Occipital Ctx | 6.0 |
| AD 1 Temporal Ctx | 6.3 | Control 2 Occipital Ctx | 100.0 |
| AD 2 Temporal Ctx | 16.3 | Control 3 Occipital Ctx | 39.2 |
| AD 3 Temporal Ctx | 5.0 | Control 4 Occipital Ctx | 5.1 |
| AD 4 Temporal Ctx | 7.9 | Control (Path) 1 Occipital Ctx | 46.7 |
| AD 5 Inf Temporal Ctx | 64.6 | Control (Path) 2 Occipital Ctx | 23.0 |
| AD 5 SupTemporal Ctx | 38.4 | Control (Path) 3 Occipital Ctx | 6.3 |
| AD 6 Inf Temporal Ctx | 46.3 | Control (Path) 4 Occipital Ctx | 25.3 |
| AD 6 Sup Temporal Ctx | 88.3 | Control 1 Parietal Ctx | 0.0 |
| Control 1 Temporal Ctx | 10.4 | Control 2 Parietal Ctx | 51.4 |
| Control 2 Temporal Ctx | 42.9 | Control 3 Parietal Ctx | 18.9 |
| Control 3 Temporal Ctx | 20.3 | Control (Path) 1 Parietal Ctx | 86.5 |
| Control 4 Temporal Ctx | 8.4 | Control (Path) 2 Parietal Ctx | 31.0 |
| Control (Path) 1 Temporal Ctx | 58.2 | Control (Path) 3 Parietal Ctx | 7.5 |
| Control (Path) 2 Temporal Ctx | 49.7 | Control (Path) 4 Parietal Ctx | 63.7 |

TABLE AC

Panel 1.3D

| Tissue Name | Rel. Exp. (%) Ag2841, Run 161922470 | Rel. Exp. (%) Ag2841, Run 165721032 | Tissue Name | Rel. Exp. (%) Ag2841, Run 161922470 | Rel. Exp. (%) Ag2841, Run 165721032 |
|---|---|---|---|---|---|
| Liver adenocarcinoma | 3.1 | 7.2 | Kidney (fetal) | 0.0 | 0.0 |
| Pancreas | 0.0 | 0.0 | Renal ca. 786-0 | 0.0 | 0.0 |
| Pancreatic ca. CAPAN 2 | 5.7 | 5.9 | Renal ca. A498 | 0.0 | 0.0 |
| Adrenal gland | 0.0 | 0.0 | Renal ca. RXF 393 | 0.0 | 0.0 |

TABLE AC-continued

Panel 1.3D

| Tissue Name | Rel. Exp. (%) Ag2841, Run 161922470 | Rel. Exp. (%) Ag2841, Run 165721032 | Tissue Name | Rel. Exp. (%) Ag2841, Run 161922470 | Rel. Exp. (%) Ag2841, Run 165721032 |
|---|---|---|---|---|---|
| Thyroid | 0.0 | 0.0 | Renal ca. ACHN | 0.0 | 0.0 |
| Salivary gland | 0.0 | 0.0 | Renal ca. UO-31 | 0.0 | 0.0 |
| Pituitary gland | 0.0 | 0.0 | Renal ca. TK-10 | 0.0 | 0.0 |
| Brain (fetal) | 18.3 | 27.0 | Liver | 0.0 | 0.0 |
| Brain (whole) | 27.0 | 19.5 | Liver (fetal) | 0.0 | 0.0 |
| Brain (amygdala) | 77.4 | 54.3 | Liver ca. (hepatoblast) HepG2 | 0.0 | 0.0 |
| Brain (cerebellum) | 0.0 | 0.0 | Lung | 3.0 | 9.2 |
| Brain (hippocampus) | 100.0 | 100.0 | Lung (fetal) | 0.0 | 0.0 |
| Brain (substantia nigra) | 0.0 | 3.5 | Lung ca. (small cell) LX-1 | 0.0 | 0.0 |
| Brain (thalamus) | 7.9 | 0.0 | Lung ca. (small cell) NCI-H69 | 0.0 | 0.0 |
| Cerebral Cortex | 90.8 | 8.4 | Lung ca. (s.cell var.) SHP-77 | 0.0 | 3.9 |
| Spinal cord | 3.9 | 0.0 | Lung ca. (large cell)NCI-H460 | 0.0 | 0.0 |
| glio/astro U87-MG | 2.7 | 6.5 | Lung ca. (non-sm. cell) A549 | 15.0 | 0.0 |
| glio/astro U-118-MG | 0.0 | 0.0 | Lung ca. (non-s.cell) NCI-H23 | 7.2 | 12.5 |
| astrocytoma SW1783 | 0.0 | 6.6 | Lung ca. (non-s.cell) HOP-62 | 0.0 | 0.0 |
| neuro*; met SK-N-AS | 8.4 | 0.0 | Lung ca. (non-s.cl) NCI-H522 | 12.9 | 3.2 |
| astrocytoma SF-539 | 0.0 | 0.0 | Lung ca. (squam.) SW 900 | 0.0 | 0.0 |
| astrocytoma SNB-75 | 0.0 | 0.0 | Lung ca. (squam.) NCI-H596 | 0.0 | 0.0 |
| glioma SNB-19 | 27.2 | 6.2 | Mammary gland | 0.0 | 0.0 |
| glioma U251 | 0.0 | 0.0 | Breast ca.* (pl.ef) MCF-7 | 0.0 | 0.0 |
| glioma SF-295 | 0.0 | 3.4 | Breast ca.* (pl.ef) MDA-MB-231 | 0.0 | 0.0 |
| Heart (fetal) | 0.0 | 0.0 | Breast ca.* (pl.ef) T47D | 0.0 | 0.0 |
| Heart | 0.0 | 0.0 | Breast ca. BT-549 | 0.0 | 0.0 |
| Skeletal muscle (fetal) | 0.0 | 0.0 | Breast ca. MDA-N | 0.0 | 0.0 |
| Skeletal muscle | 0.0 | 0.0 | Ovary | 0.0 | 0.0 |
| Bone marrow | 3.8 | 0.0 | Ovarian ca. OVCAR-3 | 0.0 | 0.0 |
| Thymus | 0.0 | 0.0 | Ovarian ca. OVCAR-4 | 0.0 | 22.1 |
| Spleen | 0.0 | 0.0 | Ovarian ca. OVCAR-5 | 7.0 | 0.0 |
| Lymph node | 0.0 | 0.0 | Ovarian ca. OVCAR-8 | 0.0 | 0.0 |
| Colorectal | 0.0 | 0.0 | Ovarian ca. IGROV-1 | 0.0 | 0.0 |
| Stomach | 0.0 | 0.0 | Ovarian ca.* (ascites) SK-OV-3 | 0.0 | 0.0 |
| Small intestine | 0.0 | 0.0 | Uterus | 0.0 | 2.6 |
| Colon ca. SW480 | 0.0 | 2.6 | Placenta | 0.0 | 0.0 |
| Colon ca.* SW620(SW480 met) | 0.0 | 0.0 | Prostate | 0.0 | 0.0 |
| Colon ca. HT29 | 0.0 | 0.0 | Prostate ca.* (bone met)PC-3 | 0.0 | 2.0 |
| Colon ca. HCT-116 | 0.0 | 0.0 | Testis | 21.0 | 0.0 |
| Colon ca. CaCo-2 | 0.0 | 0.0 | Melanoma Hs688(A).T | 0.0 | 0.0 |
| Colon ca. tissue(ODO3866) | 0.0 | 0.0 | Melanoma* (met) Hs688(B).T | 0.0 | 0.0 |
| Colon ca. HCC-2998 | 8.4 | 0.0 | Melanoma UACC-62 | 0.0 | 0.0 |
| Gastric ca.* (liver met) NCI-N87 | 18.0 | 4.2 | Melanoma M14 | 0.0 | 0.0 |

TABLE AC-continued

Panel 1.3D

| Tissue Name | Rel. Exp. (%) Ag2841, Run 161922470 | Rel. Exp. (%) Ag2841, Run 165721032 | Tissue Name | Rel. Exp. (%) Ag2841, Run 161922470 | Rel. Exp. (%) Ag2841, Run 165721032 |
|---|---|---|---|---|---|
| Bladder | 0.0 | 0.0 | Melanoma LOX IMVI | 0.0 | 11.0 |
| Trachea | 0.0 | 0.0 | Melanoma* (met) SK-MEL-5 | 0.0 | 0.0 |
| Kidney | 0.0 | 0.0 | Adipose | 0.0 | 0.0 |

TABLE AD

Panel 4D

| Tissue Name | Rel. Exp. (%) Ag2841, Run 159616564 | Tissue Name | Rel. Exp. (%) Ag2841, Run 159616564 |
|---|---|---|---|
| Secondary Th1 act | 0.0 | HUVEC IL-1 beta | 2.7 |
| Secondary Th2 act | 0.0 | HUVEC IFN gamma | 8.8 |
| Secondary Tr1 act | 0.0 | HUVEC TNF alpha + IFN gamma | 15.9 |
| Secondary Th1 rest | 0.0 | HUVEC TNF alpha + IL4 | 2.2 |
| Secondary Th2 rest | 0.0 | HUVEC IL-11 | 13.6 |
| Secondary Tr1 rest | 0.0 | Lung Microvascular EC none | 21.5 |
| Primary Th1 act | 0.0 | Lung Microvascular EC TNF alpha + IL-1 beta | 33.7 |
| Primary Th2 act | 0.0 | Microvascular Dermal EC none | 12.1 |
| Primary Tr1 act | 0.0 | Microsvascular Dermal EC TNF alpha + IL-1 beta | 0.0 |
| Primary Th1 rest | 0.0 | Bronchial epithelium TNF alpha + IL1 beta | 0.0 |
| Primary Th2 rest | 0.0 | Small airway epithelium none | 2.4 |
| Primary Tr1 rest | 0.0 | Small airway epithelium TNF alpha + IL-1 beta | 0.0 |
| CD45RA CD4 lymphocyte act | 0.0 | Coronery artery SMC rest | 10.8 |
| CD45RO CD4 lymphocyte act | 0.0 | Coronery artery SMC TNF alpha + IL-1 beta | 8.3 |
| CD8 lymphocyte act | 0.0 | Astrocytes rest | 0.0 |
| Secondary CD8 lymphocyte rest | 0.0 | Astrocytes TNF alpha + IL-1 beta | 9.8 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1 beta | 0.0 |
| LAK cells IL-2 | 0.0 | Liver cirrhosis | 15.1 |
| LAK cells IL-2 + IL-12 | 0.0 | Lupus kidney | 0.0 |
| LAK cells IL-2 + IFN gamma | 0.0 | NCI-H292 none | 0.0 |
| LAK cells IL-2 + IL-18 | 0.0 | NCI-H292 IL-4 | 0.0 |
| LAK cells PMA/ionomycin | 0.0 | NCI-H292 IL-9 | 0.0 |
| NK Cells IL-2 rest | 0.0 | NCI-H292 IL-13 | 0.0 |
| Two Way MLR 3 day | 0.0 | NCI-H292 IFN gamma | 0.0 |
| Two Way MLR 5 day | 0.0 | HPAEC none | 19.6 |
| Two Way MLR 7 day | 0.0 | HPAEC TNF alpha + IL-1 beta | 7.0 |
| PBMC rest | 5.9 | Lung fibroblast none | 0.0 |
| PBMC PWM | 0.0 | Lung fibroblast TNF alpha + IL-1 beta | 0.0 |
| PBMC PHA-L | 0.0 | Lung fibroblast IL-4 | 0.0 |
| Ramos (B cell) none | 0.0 | Lung fibroblast IL-9 | 0.0 |
| Ramos (B cell) ionomycin | 0.0 | Lung fibroblast IL-13 | 0.0 |
| B lymphocytes PWM | 0.0 | Lung fibroblast IFN gamma | 0.0 |
| B lymphocytes CD40L and IL-4 | 0.0 | Dermal fibroblast CCD1070 rest | 3.6 |
| EOL-1 dbcAMP | 0.0 | Dermal fibroblast CCD1070 TNF alpha | 0.0 |

TABLE AD-continued

Panel 4D

| Tissue Name | Rel. Exp. (%) Ag2841, Run 159616564 | Tissue Name | Rel. Exp. (%) Ag2841, Run 159616564 |
|---|---|---|---|
| EOL-1 dbcAMP PMA/ionomycin | 0.0 | Dermal fibroblast CCD1070 IL-1 beta | 0.0 |
| Dendritic cells none | 0.0 | Dermal fibroblast IFN gamma | 0.0 |
| Dendritic cells LPS | 0.0 | Dermal fibroblast IL-4 | 0.0 |
| Dendritic cells anti-CD40 | 0.0 | IBD Colitis 2 | 0.0 |
| Monocytes rest | 0.0 | IBD Crohn's | 0.0 |
| Monocytes LPS | 0.0 | Colon | 100.0 |
| Macrophages rest | 0.0 | Lung | 40.1 |
| Macrophages LPS | 0.0 | Thymus | 0.0 |
| HUVEC none | 5.8 | Kidney | 0.0 |
| HUVEC starved | 6.9 | | |

CNS_neurodegeneration_v1.0 Summary: Ag2841 Expression of the CG55912-01 gene is low (CTs>35) across all of the samples on this panel. Although levels are low for this gene, there is a significant difference in expression levels between non-demented controls and patients suffering from Alzheimer's disease, such that the levels of mRNA appear to be downregulated 2-fold in the postmortem AD brain (p=0.0018 when analyzed by ANCOVA; estimate of RNA loaded per well used as a covariate). This gene may therefore represent a drug target for the treatment of Alzheimer's disease or other dementias.

Panel 1.3D Summary: Ag2841 Two experiments with same primer and probe set are in excellent agreement, with highest expression of the CG55912-01 gene in the hippocampus region of the brain (CT=34). In addition, expression of this gene is exclusive to brain region. Therefore, expression of this gene can be used to distinguish this sample from other samples in the panel. In addition, this gene may play a role in central nervous system disorders such as Alzheimer's disease, Parkinson's disease, epilepsy, multiple sclerosis, schizophrenia and depression.

The CG55912-01 gene encodes a homolog of a neuronal voltage-gated calcium channel. In *Caenorhabditis elegans* voltage-gated calcium channels have been shown to direct neuronal migration. In *C. elegans* mutants carrying loss-of-function alleles of the calcium channel gene unc-2, the touch receptor neuron AVM and the interneuron SDQR often migrated inappropriately, leading to misplacement of their cell bodies (Tam T, Mathews E, Snutch T P, Schafer W R. (2000) Voltage-gated calcium channels direct neuronal migration in *Caenorhabditis elegans*. Dev Biol 226(1):104–17). Therefore, in analogy with *C. elegan* unc-2, neuronal voltage-gated calcium channel encoded by the CG55912-01 gene may also play a role in directing neuronal migration. In addition, calcium channels have been implicated in number of neurological diseases such as familial hemiplegic migraine, episodic ataxia type 2, spinocerebellar ataxia 6, and Lambert-Eaton myasthenic syndrome and other diseases (Greenberg D A. (1997) Calcium channels in neurological disease. Ann Neurol 42(3):275–82). Therefore, therapeutic modulation of the activity of this gene may prove useful in the treatment of the different neurological diseases.

Panel 2D Summary: Ag2841 Expression of the CG55912-01 gene is low/undetectable (CTs>35) across all of the samples on this panel (data not shown).

Panel 3D Summary: Ag2841 Expression of the CG55912-01 gene is low/undetectable (CTs>35) across all of the samples on this panel (data not shown).

Panel 4D Summary: Ag2841 Low but significant expression of the CG55912-01 gene is detected exclusively in colon. Therefore, expression of this gene may be used to distinguish colon from the other tissues on this panel. Furthermore, expression of this gene is decreased in colon samples from patients with IBD colitis and Crohn's disease relative to normal colon. Therefore, therapeutic modulation of the activity of the calcium channel encoded by this gene may be useful in the treatment of inflammatory bowel disease.

Panel CNS_1 Summary: Ag2841 Expression of the CG55912-01 gene is low/undetectable (CTs>35) across all of the samples on this panel (data not shown).

B. CG55918-01 and CG55918-02: Zinc Transporter 2 (ZNT-2)

Expression of gene CG55918-01 and full length clone CG55918-02 was assessed using the primer-probe set Ag2845, described in Table BA. Results of the RTQ-PCR runs are shown in Tables BB, BC, BD and BE. Please note that CG55918-02 represents a full-length physical clone of the CG55918-01 gene, validating the prediction of the gene sequence.

TABLE BA

Probe Name Ag2845

| Primers | Sequences | Length | Start Position | SEQ ID NO: |
|---|---|---|---|---|
| Forward | 5'-aagggtcctgacagtcactgt-3' | 21 | 123 | 216 |
| Probe | TET-5'-cagcgccagctgtatgtagcctctg-3'-TAMRA | 25 | 165 | 217 |
| Reverse | 5'-atcatgaacaacaggcagatg-3' | 21 | 191 | 218 |

TABLE BB

Panel 1.3D

| Tissue Name | Rel. Exp. (%) Ag2845, Run 161590530 | Rel. Exp. (%) Ag2845, Run 165701936 | Tissue Name | Rel. Exp. (%) Ag2845, Run 161590530 | Rel. Exp. (%) Ag2845, Run 165701936 |
|---|---|---|---|---|---|
| Liver adenocarcinoma | 0.8 | 0.4 | Kidney (fetal) | 3.4 | 4.5 |
| Pancreas | 4.9 | 16.3 | Renal ca. 786-0 | 0.0 | 0.0 |
| Pancreatic ca. CAPAN 2 | 0.0 | 0.0 | Renal ca. A498 | 0.0 | 0.0 |
| Adrenal gland | 0.5 | 0.7 | Renal ca. RXF 393 | 0.0 | 0.0 |
| Thyroid | 4.7 | 7.8 | Renal ca. ACHN | 0.0 | 0.0 |
| Salivary gland | 0.4 | 0.7 | Renal ca. UO-31 | 0.0 | 0.0 |
| Pituitary gland | 0.0 | 0.0 | Renal ca. TK-10 | 0.0 | 0.0 |
| Brain (fetal) | 0.0 | 0.0 | Liver | 0.0 | 0.0 |
| Brain (whole) | 0.0 | 0.0 | Liver (fetal) | 0.0 | 0.0 |
| Brain (amygdala) | 0.0 | 1.1 | Liver ca. (hepatoblast) HepG2 | 0.2 | 0.0 |
| Brain (cerebellum) | 0.0 | 0.0 | Lung | 0.0 | 0.0 |
| Brain (hippocampus) | 0.1 | 0.0 | Lung (fetal) | 0.0 | 0.0 |
| Brain (substantia nigra) | 0.0 | 0.0 | Lung ca. (small cell) LX-1 | 0.0 | 0.0 |
| Brain (thalamus) | 0.0 | 0.0 | Lung ca. (small cell) NCI-H69 | 0.0 | 0.0 |
| Cerebral Cortex | 0.0 | 0.0 | Lung ca. (s.cell var.) SHP-77 | 0.0 | 0.0 |
| Spinal cord | 0.0 | 0.0 | Lung ca. (large cell)NCI-H460 | 0.0 | 0.0 |
| glio/astro U87-MG | 0.0 | 0.0 | Lung ca. (non-sm. cell) A549 | 0.0 | 0.0 |
| glio/astro U-118-MG | 0.0 | 0.0 | Lung ca. (non-s.cell) NCI-H23 | 0.0 | 0.9 |
| astrocytoma SW1783 | 0.1 | 0.5 | Lung ca. (non-s.cell) HOP-62 | 0.0 | 0.0 |
| neuro*; met SK-N-AS | 0.0 | 0.0 | Lung ca. (non-s.cl) NCI-H522 | 0.3 | 0.0 |
| astrocytoma SF-539 | 0.0 | 0.0 | Lung ca. (squam.) SW 900 | 0.0 | 0.2 |
| astrocytoma SNB-75 | 0.0 | 0.5 | Lung ca. (squam.) NCI-H596 | 0.0 | 0.0 |
| glioma SNB-19 | 0.1 | 0.0 | Mammary gland | 0.3 | 0.9 |
| glioma U251 | 0.0 | 0.0 | Breast ca.* (pl.ef) MCF-7 | 0.0 | 0.0 |
| glioma SF-295 | 0.0 | 0.2 | Breast ca.* (pl.ef) MDA-MB-231 | 0.0 | 0.0 |
| Heart (fetal) | 2.1 | 1.3 | Breast ca.* (pl.ef) T47D | 0.0 | 0.0 |
| Heart | 2.8 | 2.1 | Breast ca. BT-549 | 0.0 | 1.0 |
| Skeletal muscle (fetal) | 2.9 | 0.0 | Breast ca. MDA-N | 0.0 | 0.0 |
| Skeletal muscle | 0.4 | 2.5 | Ovary | 0.3 | 0.0 |
| Bone marrow | 0.0 | 0.0 | Ovarian ca. OVCAR-3 | 0.0 | 1.1 |
| Thymus | 0.0 | 0.0 | Ovarian ca. OVCAR-4 | 0.0 | 0.0 |
| Spleen | 0.0 | 0.0 | Ovarian ca. OVCAR-5 | 0.0 | 0.0 |
| Lymph node | 0.0 | 0.0 | Ovarian ca. OVCAR-8 | 0.0 | 0.0 |
| Colorectal | 0.3 | 0.0 | Ovarian ca. IGROV-1 | 0.0 | 0.0 |
| Stomach | 0.0 | 0.2 | Ovarian ca.* (ascites) SK-OV-3 | 0.0 | 0.0 |
| Small intestine | 0.0 | 0.6 | Uterus | 0.1 | 0.6 |
| Colon ca. SW480 | 1.6 | 3.7 | Placenta | 30.6 | 80.7 |
| Colon ca.* SW620(SW480 met) | 0.0 | 0.4 | Prostate | 0.0 | 0.0 |
| Colon ca. HT29 | 0.0 | 0.0 | Prostate ca.* (bone met)PC-3 | 0.0 | 0.0 |
| Colon ca. HCT-116 | 0.2 | 0.0 | Testis | 0.5 | 2.3 |
| Colon ca. CaCo-2 | 1.6 | 2.5 | Melanoma Hs688(A).T | 0.0 | 0.0 |

TABLE BB-continued

Panel 1.3D

| Tissue Name | Rel. Exp. (%) Ag2845, Run 161590530 | Rel. Exp. (%) Ag2845, Run 165701936 | Tissue Name | Rel. Exp. (%) Ag2845, Run 161590530 | Rel. Exp. (%) Ag2845, Run 165701936 |
| --- | --- | --- | --- | --- | --- |
| Colon ca. tissue(ODO3866) | 0.3 | 1.8 | Melanoma* (met) Hs688(B).T | 0.0 | 0.0 |
| Colon ca. HCC-2998 | 6.7 | 16.8 | Melanoma UACC-62 | 0.0 | 0.0 |
| Gastric ca.* (liver met) NCI-N87 | 0.0 | 0.0 | Melanoma M14 | 0.1 | 0.0 |
| Bladder | 100.0 | 100.0 | Melanoma LOX IMVI | 0.0 | 0.0 |
| Trachea | 0.5 | 0.7 | Melanoma* (met) SK-MEL-5 | 0.0 | 0.0 |
| Kidney | 10.9 | 11.8 | Adipose | 0.1 | 0.3 |

TABLE BC

Panel 2D

| Tissue Name | Rel. Exp. (%) Ag2845, Run 161590724 | Tissue Name | Rel. Exp. (%) Ag2845, Run 161590724 |
| --- | --- | --- | --- |
| Normal Colon | 0.1 | Kidney Margin 8120608 | 50.7 |
| CC Well to Mod Diff (ODO3866) | 0.5 | Kidney Cancer 8120613 | 0.0 |
| CC Margin (ODO3866) | 0.0 | Kidney Margin 8120614 | 30.1 |
| CC Gr.2 rectosigmoid (ODO3868) | 0.0 | Kidney Cancer 9010320 | 0.0 |
| CC Margin (ODO3868) | 0.0 | Kidney Margin 9010321 | 72.7 |
| CC Mod Diff (ODO3920) | 1.6 | Normal Uterus | 0.0 |
| CC Margin (ODO3920) | 0.1 | Uterus Cancer 064011 | 0.0 |
| CC Gr.2 ascend colon (ODO3921) | 0.3 | Normal Thyroid | 7.6 |
| CC Margin (ODO3921) | 0.3 | Thyroid Cancer 064010 | 42.9 |
| CC from Partial Hepatectomy (ODO4309) Mets | 1.2 | Thyroid Cancer A302152 | 14.4 |
| Liver Margin (ODO4309) | 0.0 | Thyroid Margin A302153 | 1.1 |
| Colon mets to lung (OD04451-01) | 0.0 | Normal Breast | 0.3 |
| Lung Margin (OD04451-02) | 0.0 | Breast Cancer (OD04566) | 0.7 |
| Normal Prostate 6546-1 | 0.1 | Breast Cancer (OD04590-01) | 0.0 |
| Prostate Cancer (OD04410) | 0.1 | Breast Cancer Mets (OD04590-03) | 0.0 |
| Prostate Margin (OD04410) | 0.0 | Breast Cancer Metastasis (OD04655-05) | 0.0 |
| Prostate Cancer (OD04720-01) | 0.2 | Breast Cancer 064006 | 0.3 |
| Prostate Margin (OD04720-02) | 0.2 | Breast Cancer 1024 | 2.0 |
| Normal Lung 061010 | 0.4 | Breast Cancer 9100266 | 0.1 |
| Lung Met to Muscle (ODO4286) | 0.2 | Breast Margin 9100265 | 0.1 |
| Muscle Margin (ODO4286) | 0.7 | Breast Cancer A209073 | 0.1 |
| Lung Malignant Cancer (OD03126) | 0.0 | Breast Margin A209073 | 0.2 |
| Lung Margin (OD03126) | 0.0 | Normal Liver | 0.1 |
| Lung Cancer (OD04404) | 0.0 | Liver Cancer 064003 | 0.1 |
| Lung Margin (OD04404) | 0.2 | Liver Cancer 1025 | 0.0 |
| Lung Cancer (OD04565) | 0.0 | Liver Cancer 1026 | 0.8 |
| Lung Margin (OD04565) | 0.0 | Liver Cancer 6004-T | 0.0 |
| Lung Cancer (OD04237-01) | 0.2 | Liver Tissue 6004-N | 0.1 |
| Lung Margin (OD04237-02) | 0.3 | Liver Cancer 6005-T | 0.5 |
| Ocular Mel Met to Liver (ODO4310) | 2.6 | Liver Tissue 6005-N | 0.1 |
| Liver Margin (ODO4310) | 0.0 | Normal Bladder | 100.0 |
| Melanoma Mets to Lung (OD04321) | 0.2 | Bladder Cancer 1023 | 0.0 |
| Lung Margin (OD04321) | 0.0 | Bladder Cancer A302173 | 0.1 |
| Normal Kidney | 12.2 | Bladder Cancer (OD04718-01) | 0.3 |
| Kidney Ca, Nuclear grade 2 (OD04338) | 3.6 | Bladder Normal Adjacent (OD04718-03) | 0.2 |
| Kidney Margin (OD04338) | 15.9 | Normal Ovary | 0.0 |

TABLE BC-continued

Panel 2D

| Tissue Name | Rel. Exp. (%) Ag2845, Run 161590724 | Tissue Name | Rel. Exp. (%) Ag2845, Run 161590724 |
|---|---|---|---|
| Kidney Ca Nuclear grade 1/2 (OD04339) | 0.1 | Ovarian Cancer 064008 | 0.1 |
| Kidney Margin (OD04339) | 20.9 | Ovarian Cancer (OD04768-07) | 0.2 |
| Kidney Ca, Clear cell type (OD04340) | 0.0 | Ovary Margin (OD04768-08) | 0.0 |
| Kidney Margin (OD04340) | 16.0 | Normal Stomach | 0.0 |
| Kidney Ca, Nuclear grade 3 (OD04348) | 0.0 | Gastric Cancer 9060358 | 0.2 |
| Kidney Margin (OD04348) | 8.8 | Stomach Margin 9060359 | 0.0 |
| Kidney Cancer (OD04622-01) | 0.2 | Gastric Cancer 9060395 | 1.0 |
| Kidney Margin (OD04622-03) | 5.8 | Stomach Margin 9060394 | 0.8 |
| Kidney Cancer (OD04450-01) | 1.2 | Gastric Cancer 9060397 | 0.2 |
| Kidney Margin (OD04450-03) | 2.6 | Stomach Margin 9060396 | 0.0 |
| Kidney Cancer 8120607 | 0.3 | Gastric Cancer 064005 | 0.0 |

TABLE BD

Panel 3D

| Tissue Name | Rel. Exp. (%) Ag2845, Run 164843786 | Tissue Name | Rel. Exp. (%) Ag2845, Run 164843786 |
|---|---|---|---|
| Daoy-Medulloblastoma | 0.0 | Ca Ski-Cervical epidermoid carcinoma (metastasis) | 0.0 |
| TE671-Medulloblastoma | 0.4 | ES-2-Ovarian clear cell carcinoma | 0.0 |
| D283 Med-Medulloblastoma | 0.0 | Ramos-Stimulated with PMA/ionomycin 6 h | 0.0 |
| PFSK-1-Primitive Neuroectodermal | 0.0 | Ramos-Stimulated with PMA/ionomycin 14 h | 0.0 |
| XF-498-CNS | 0.0 | MEG-01-Chronic myelogenous leukemia (megokaryoblast) | 1.0 |
| SNB-78-Glioma | 0.0 | Raji-Burkitt's lymphoma | 0.0 |
| SF-268-Glioblastoma | 0.0 | Daudi-Burkitt's lymphoma | 0.0 |
| T98G-Glioblastoma | 1.0 | U266-B-cell plasmacytoma | 0.0 |
| SK-N-SH-Neuroblastoma (metastasis) | 0.0 | CA46-Burkitt's lymphoma | 0.0 |
| SF-295-Glioblastoma | 0.0 | RL-non-Hodgkin's B-cell lymphoma | 0.0 |
| Cerebellum | 0.0 | JM1-pre-B-cell lymphoma | 0.0 |
| Cerebellum | 0.0 | Jurkat-T cell leukemia | 0.0 |
| NCI-H292-Mucoepidermoid lung carcinoma | 0.0 | TF-1-Erythroleukemia | 0.0 |
| DMS-114-Small cell lung cancer | 2.4 | HUT 78-T-cell lymphoma | 0.0 |
| DMS-79-Small cell lung cancer | 84.1 | U937-Histiocytic lymphoma | 0.0 |
| NCI-H146-Small cell lung cancer | 0.0 | KU-812-Myelogenous leukemia | 0.0 |
| NCI-H526-Small cell lung cancer | 1.0 | 769-P-Clear cell renal carcinoma | 0.0 |
| NCI-N417-Small cell lung cancer | 0.1 | Caki-2-Clear cell renal carcinoma | 0.2 |
| NCI-H82-Small cell lung cancer | 0.0 | SW 839-Clear cell renal carcinoma | 0.0 |
| NCI-H157-Squamous cell lung cancer (metastasis) | 0.0 | G401-Wilms' tumor | 0.9 |
| NCI-H1155-Large cell lung cancer | 3.4 | Hs766T-Pancreatic carcinoma (LN metastasis) | 0.0 |
| NCI-H1299-Large cell lung cancer | 0.0 | CAPAN-1-Pancreatic adenocarcinoma (liver metastasis) | 0.6 |
| NCI-H727-Lung carcinoid | 0.0 | SU86.86-Pancreatic carcinoma (liver metastasis) | 1.7 |
| NCI-UMC-11-Lung carcinoid | 0.0 | BxPC-3-Pancreatic adenocarcinoma | 0.0 |
| LX-1-Small cell lung cancer | 0.0 | HPAC-Pancreatic adenocarcinoma | 0.5 |
| Colo-205-Colon cancer | 0.0 | MIA PaCa-2-Pancreatic carcinoma | 0.0 |
| KM12-Colon cancer | 0.0 | CFPAC-1-Pancreatic ductal adenocarcinoma | 100.0 |
| KM20L2-Colon cancer | 1.9 | PANC-1-Pancreatic epithelioid ductal carcinoma | 0.0 |

TABLE BD-continued

Panel 3D

| Tissue Name | Rel. Exp. (%) Ag2845, Run 164843786 | Tissue Name | Rel. Exp. (%) Ag2845, Run 164843786 |
|---|---|---|---|
| NCI-H716-Colon cancer | 0.0 | T24-Bladder carcinma (transitional cell) | 0.0 |
| SW-48-Colon adenocarcinoma | 0.0 | 5637-Bladder carcinoma | 0.0 |
| SW1116-Colon adenocarcinoma | 0.0 | HT-1197-Bladder carcinoma | 54.7 |
| LS 174T-Colon adenocarcinoma | 2.7 | UM-UC-3-Bladder carcinma (transitional cell) | 0.0 |
| SW-948-Colon adenocarcinoma | 0.0 | A204-Rhabdomyosarcoma | 0.0 |
| SW-480-Colon adenocarcinoma | 0.0 | HT-1080-Fibrosarcoma | 0.0 |
| NCI-SNU-5-Gastric carcinoma | 15.8 | MG-63-Osteosarcoma | 0.0 |
| KATO III-Gastric carcinoma | 0.6 | SK-LMS-1-Leiomyosarcoma (vulva) | 0.0 |
| NCI-SNU-16-Gastric carcinoma | 0.0 | SJRH30-Rhabdomyosarcoma (met to bone marrow) | 0.0 |
| NCI-SNU-1-Gastric carcinoma | 0.0 | A431-Epidermoid carcinoma | 0.0 |
| RF-1-Gastric adenocarcinoma | 0.0 | WM266-4-Melanoma | 1.0 |
| RF-48-Gastric adenocarcinoma | 0.0 | DU 145-Prostate carcinoma (brain metastasis) | 0.0 |
| MKN-45-Gastric carcinoma | 0.0 | MDA-MB-468-Breast adenocarcinoma | 0.5 |
| NCI-N87-Gastric carcinoma | 0.0 | SCC-4-Squamous cell carcinoma of tongue | 0.0 |
| OVCAR-5-Ovarian carcinoma | 0.0 | SCC-9-Squamous cell carcinoma of tongue | 0.0 |
| RL95-2-Uterine carcinoma | 0.0 | SCC-15-Squamous cell carcinoma of tongue | 0.0 |
| HelaS3-Cervical adenocarcinoma | 0.0 | CAL 27-Squamous cell carcinoma of tongue | 0.0 |

TABLE BE

Panel 4D

| Tissue Name | Rel. Exp. (%) Ag2845, Run 159841918 | Tissue Name | Rel. Exp. (%) Ag2845, Run 159841918 |
|---|---|---|---|
| Secondary Th1 act | 0.0 | HUVEC IL-1 beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1 beta | 0.0 |
| Primary Th2 act | 0.0 | Microvascular Dermal EC none | 0.0 |
| Primary Tr1 act | 0.0 | Microsvascular Dermal EC TNF alpha + IL-1 beta | 0.7 |
| Primary Th1 rest | 0.0 | Bronchial epithelium TNF alpha + IL1 beta | 0.0 |
| Primary Th2 rest | 0.0 | Small airway epithelium none | 0.0 |
| Primary Tr1 rest | 0.0 | Small airway epithelium TNF alpha + IL-1 beta | 0.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1 beta | 0.0 |
| CD8 lymphocyte act | 0.0 | Astrocytes rest | 0.0 |
| Secondary CD8 lymphocyte rest | 0.0 | Astrocytes TNF alpha + IL-1 beta | 0.0 |
| Secondary CD8 lymphocyte act | 0.0 | KU-812 (Basophil) rest | 0.7 |
| CD4 lymphocyte none | 0.0 | KU-812 (Basophil) PMA/ionomycin | 1.4 |

TABLE BE-continued

Panel 4D

| Tissue Name | Rel. Exp. (%) Ag2845, Run 159841918 | Tissue Name | Rel. Exp. (%) Ag2845, Run 159841918 |
|---|---|---|---|
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1 beta | 0.0 |
| LAK cells IL-2 | 0.0 | Liver cirrhosis | 6.3 |
| LAK cells IL-2 + IL-12 | 0.0 | Lupus kidney | 6.2 |
| LAK cells IL-2 + IFN gamma | 0.0 | NCI-H292 none | 0.0 |
| LAK cells IL-2 + IL-18 | 0.0 | NCI-H292 IL-4 | 0.0 |
| LAK cells PMA/ionomycin | 0.0 | NCI-H292 IL-9 | 0.0 |
| NK Cells IL-2 rest | 0.0 | NCI-H292 IL-13 | 0.0 |
| Two Way MLR 3 day | 0.0 | NCI-H292 IFN gamma | 0.7 |
| Two Way MLR 5 day | 0.0 | HPAEC none | 0.0 |
| Two Way MLR 7 day | 0.0 | HPAEC TNF alpha + IL-1 beta | 1.1 |
| PBMC rest | 0.0 | Lung fibroblast none | 0.0 |
| PBMC PWM | 0.0 | Lung fibroblast TNF alpha + IL-1 beta | 0.0 |
| PBMC PHA-L | 0.0 | Lung fibroblast IL-4 | 0.0 |
| Ramos (B cell) none | 0.0 | Lung fibroblast IL-9 | 0.0 |
| Ramos (B cell) ionomycin | 0.0 | Lung fibroblast IL-13 | 0.0 |
| B lymphocytes PWM | 0.0 | Lung fibroblast IFN gamma | 0.0 |
| B lymphocytes CD40L and IL-4 | 0.0 | Dermal fibroblast CCD1070 rest | 0.0 |
| EOL-1 dbcAMP | 0.0 | Dermal fibroblast CCD1070 TNF alpha | 0.0 |
| EOL-1 dbcAMP PMA/ionomycin | 0.0 | Dermal fibroblast CCD1070 IL-1 beta | 0.0 |
| Dendritic cells none | 0.0 | Dermal fibroblast IFN gamma | 0.0 |
| Dendritic cells LPS | 0.0 | Dermal fibroblast IL-4 | 0.0 |
| Dendritic cells anti-CD40 | 0.0 | IBD Colitis 2 | 0.5 |
| Monocytes rest | 0.0 | IBD Crohn's | 0.5 |
| Monocytes LPS | 0.0 | Colon | 12.8 |
| Macrophages rest | 0.0 | Lung | 5.1 |
| Macrophages LPS | 0.0 | Thymus | 100.0 |
| HUVEC none | 0.0 | Kidney | 0.7 |
| HUVEC starved | 0.0 | | |

Panel 1.3D Summary: Ag2845 Two experiments with same primer and probe sets are in excellent agreement, with highest expression of the CG55918-01 gene in bladder (CTs=27–30). In addition, high expression of this gene is also seen in placenta. Thus, expression of this gene can be used to distinguish these tissue samples from other samples in the panel. Furthermore, therapeutic modulation of the activity of the zinc transporter encoded by this gene may be useful in the treatment diseases associated with bladder and placenta including fertility and reproductive disorders.

Among tissues with metabolic or endocrine function, this gene is expressed at low levels in pancreas, adrenal gland, thyroid, skeletal muscle, and heart. Therefore, therapeutic modulation of the activity of this gene may prove useful in the treatment of endocrine/metabolically related diseases, such as obesity and diabetes.

Panel 2D Summary: Ag2845 Highest expression of the CG55918-01 gene is detected in bladder (CT=26.7). Interestingly, expression of this gene is down regulated in bladder and kidney cancer samples (CTs>35) as compared to the corresponding control margin samples (CTs=27–30). Therefore, therapeutic modulation of the activity of the zinc transporter encoded by this gene may be useful in the treatment bladder and kidney cancers.

In addition, expression of this gene is up-regulated in thyroid cancer A302152 (CT=29.6) as compared to control margin sample (CT=33.4). Therefore, expression of this gene can be used as a diagnostic marker for thyroid cancer and therapeutic modulation of the activity of the zinc transporter encoded by this gene may be useful in the treatment this cancer.

Panel 3D Summary: Ag2845 Highest expression of the CG55918-01 gene is detected in the CFPAC-1-pancreatic ductal adenocarcinoma cell line (CT=29.6). In addition, high expression of this gene is also detected in HT-1197-bladder carcinoma, and DMS-79-small cell lung cancer cell line. Therefore, expression of this gene can be used as a diagnostic marker for these cancers and also, therapeutic modulation of the activity of the zinc transporter encoded by this gene may be useful in the treatment of these cancers.

Panel 4D Summary: Ag2845 Highest expression of the CG55918-01 gene is detected in thymus (CT=29.6). The zinc transporter encoded by this gene could therefore play an important role in T cell development. Small molecule therapeutics, or antibody therapeutics designed against the protein encoded for by this gene could be utilized to modulate immune function (T cell development) and be important for organ transplant, AIDS treatment or post chemotherapy immune reconstitution.

In addition, low but significant expression of this gene is also seen in colon (CT=33). Furthermore, expression of this gene is decreased in colon samples from patients with IBD colitis and Crohn's disease relative to normal colon. Therefore, therapeutic modulation of the activity of the protein encoded by this gene may be useful in the treatment of inflammatory bowel disease.

Low expression of this gene is also observed in lung, liver cirrhosis and lupus kidney samples (CTs=34). Therefore, therapeutic modulation of the activity of the zinc transporter encoded by this gene may be useful in the treatment of disease associated with lung, liver cirrhosis and lupus disease.

C. CG56832-01 and CG56832-02 and CG56832-03: Guanylate Kinase

Expression of gene CG56832-01, variant CG56832-03 and clone CG56832-02 was assessed using the primer-probe sets Ag3O33 and Ag3718, described in Tables CA and CB. Results of the RTQ-PCR runs are shown in Tables CC, CD and CE.

TABLE CA

Probe Name Ag3033

| Primers | Sequences | Length | Start Position | SEQ ID NO: |
|---|---|---|---|---|
| Forward | 5'-tgtggacatgaagttcaaggat-3' | 22 | 1154 | 219 |
| Probe | TET-5'-cctacaagagatggaaaatttagccca-3'-TAMRA | 27 | 1181 | 220 |
| Reverse | 5'-gccaaactgagtttccattctt-3' | 22 | 1208 | 221 |

TABLE CB

Probe Name Ag3718

| Primers | Sequences | Length | Start Position | SEQ ID NO: |
|---|---|---|---|---|
| Forward | 5'-tgtggacatgaagttcaaggat-3' | 22 | 1154 | 222 |
| Probe | TET-5'-cctacaagagatggaaaatttagccca-3'-TAMRA | 27 | 1181 | 223 |
| Reverse | 5'-gccaaactgagtttccattctt-3' | 22 | 1208 | 224 |

TABLE CC

General_screening_panel_v1.4

| Tissue Name | Rel. Exp.(%) Ag3718, Run 218267394 | Tissue Name | Rel. Exp.(%) Ag3718, Run 218267394 |
|---|---|---|---|
| Adipose | 0.4 | Renal ca. TK-10 | 0.6 |
| Melanoma* Hs688(A).T | 1.9 | Bladder | 0.2 |
| Melanoma* Hs688(B).T | 2.3 | Gastric ca. (liver met.) NCI-N87 | 0.6 |
| Melanoma* M14 | 0.8 | Gastric ca. KATO III | 0.0 |
| Melanoma* LOXIMVI | 100.0 | Colon ca. SW-948 | 0.0 |
| Melanoma* SK-MEL-5 | 0.2 | Colon ca. SW480 | 1.4 |
| Squamous cell carcinoma SCC-4 | 0.3 | Colon ca.* (SW480 met) SW620 | 0.0 |
| Testis Pool | 0.0 | Colon ca. HT29 | 0.0 |
| Prostate ca.* (bone met) PC-3 | 1.2 | Colon ca. HCT-116 | 0.4 |
| Prostate Pool | 0.0 | Colon ca. CaCo-2 | 0.1 |
| Placenta | 0.0 | Colon cancer tissue | 0.2 |
| Uterus Pool | 0.0 | Colon ca. SW1116 | 0.0 |
| Ovarian ca. OVCAR-3 | 0.0 | Colon ca. Colo-205 | 0.0 |
| Ovarian ca. SK-OV-3 | 1.0 | Colon ca. SW-48 | 0.0 |
| Ovarian ca. OVCAR-4 | 0.0 | Colon Pool | 0.0 |
| Ovarian ca. OVCAR-5 | 0.6 | Small Intestine Pool | 0.0 |
| Ovarian ca. IGROV-1 | 2.3 | Stomach Pool | 0.0 |
| Ovarian ca. OVCAR-8 | 0.0 | Bone Marrow Pool | 0.1 |
| Ovary | 0.2 | Fetal Heart | 0.2 |
| Breast ca. MCF-7 | 0.0 | Heart Pool | 0.0 |
| Breast ca. MDA-MB-231 | 2.3 | Lymph Node Pool | 0.2 |
| Breast ca. BT 549 | 1.1 | Fetal Skeletal Muscle | 0.2 |
| Breast ca. T47D | 0.5 | Skeletal Muscle Pool | 0.4 |
| Breast ca. MDA-N | 0.0 | Spleen Pool | 4.0 |
| Breast Pool | 0.2 | Thymus Pool | 0.2 |
| Trachea | 0.2 | CNS cancer (glio/astro) U87-MG | 42.9 |

TABLE CC-continued

General_screening_panel_v1.4

| Tissue Name | Rel. Exp.(%) Ag3718, Run 218267394 | Tissue Name | Rel. Exp.(%) Ag3718, Run 218267394 |
|---|---|---|---|
| Lung | 0.3 | CNS cancer (glio/astro) U-118-MG | 33.9 |
| Fetal Lung | 0.0 | CNS cancer (neuro; met) SK-N-AS | 4.2 |
| Lung ca. NCI-N417 | 0.0 | CNS cancer (astro) SF-539 | 0.2 |
| Lung Ca. LX-1 | 0.0 | CNS cancer (astro) SNB-75 | 14.9 |
| Lung ca. NCI-H146 | 0.0 | CNS cancer (glio) SNB-19 | 2.4 |
| Lung ca. SHP-77 | 0.0 | CNS cancer (glio) SF-295 | 0.8 |
| Lung ca. A549 | 0.0 | Brain (Amygdala) Pool | 0.2 |
| Lung ca. NCI-H526 | 0.0 | Brain (cerebellum) | 1.3 |
| Lung ca. NCI-H23 | 0.2 | Brain (fetal) | 0.3 |
| Lung ca. NCI-H460 | 4.5 | Brain (Hippocampus) Pool | 0.8 |
| Lung ca. HOP-62 | 0.7 | Cerebral Cortex Pool | 1.0 |
| Lung ca. NCI-H522 | 0.0 | Brain (Substantia nigra) Pool | 0.1 |
| Liver | 0.0 | Brain (Thalamus) Pool | 1.1 |
| Fetal Liver | 0.0 | Brain (whole) | 0.5 |
| Liver ca. HepG2 | 0.0 | Spinal Cord Pool | 0.3 |
| Kidney Pool | 0.0 | Adrenal Gland | 0.0 |
| Fetal Kidney | 0.4 | Pituitary gland Pool | 0.2 |
| Renal ca. 786-0 | 0.3 | Salivary Gland | 0.0 |
| Renal ca. A498 | 0.4 | Thyroid (female) | 0.0 |
| Renal Ca. ACHN | 0.4 | Pancreatic ca. CAPAN2 | 0.2 |
| Renal ca. UO-31 | 5.8 | Pancreas Pool | 0.0 |

TABLE CD

Panel 1.3D

| Tissue Name | Rel. Exp. (%) Ag3033, Run 167962289 | Tissue Name | Rel. Exp. (%) Ag3033, Run 167962289 |
|---|---|---|---|
| Liver adenocarcinoma | 2.0 | Kidney (fetal) | 0.0 |
| Pancreas | 0.0 | Renal ca. 786-0 | 1.0 |
| Pancreatic ca. CAPAN 2 | 0.0 | Renal ca. A498 | 6.5 |
| Adrenal gland | 0.0 | Renal ca. RXF 393 | 0.0 |
| Thyroid | 0.0 | Renal ca. ACHN | 0.0 |
| Salivary gland | 0.0 | Renal ca. UO-31 | 19.9 |
| Pituitary gland | 1.5 | Renal ca. TK-10 | 0.0 |
| Brain (fetal) | 4.0 | Liver | 0.0 |
| Brain (whole) | 5.1 | Liver (fetal) | 0.0 |
| Brain (amygdala) | 3.6 | Liver ca. (hepatoblast) HepG2 | 0.0 |
| Brain (cerebellum) | 13.1 | Lung | 0.0 |
| Brain (hippocampus) | 4.3 | Lung (fetal) | 2.3 |
| Brain (substantia nigra) | 1.0 | Lung ca. (small cell) LX-1 | 0.0 |
| Brain (thalamus) | 1.4 | Lung ca. (small cell) NCI-H69 | 8.5 |
| Cerebral Cortex | 0.0 | Lung ca. (s.cell var.) SHP-77 | 0.0 |
| Spinal cord | 2.8 | Lung ca. (large cell)NCI-H460 | 2.5 |
| glio/astro U87-MG | 40.9 | Lung ca. (non-sm. cell) A549 | 0.0 |
| glio/astro U-118-MG | 31.4 | Lung ca. (non-s.cell) NCI-H23 | 0.9 |
| astrocytoma SW1783 | 27.7 | Lung ca. (non-s.cell) HOP-62 | 0.9 |
| neuro*; met SK-N-AS | 1.0 | Lung ca. (non-s.cl) NCI-H522 | 0.0 |
| astrocytoma SF-539 | 1.1 | Lung ca. (squam.) SW 900 | 0.0 |
| astrocytoma SNB-75 | 9.2 | Lung ca. (squam.) NCI-H596 | 0.0 |
| glioma SNB-19 | 3.7 | Mammary gland | 0.0 |
| glioma U251 | 0.3 | Breast ca.* (pl.ef) MCF-7 | 0.0 |
| glioma SF-295 | 1.0 | Breast ca.* (pl.ef) MDA MB-231 | 3.8 |
| Heart (fetal) | 0.0 | Breast ca.* (pl.ef) T47D | 0.0 |
| Heart | 0.0 | Breast ca. BT-549 | 3.6 |
| Skeletal muscle (fetal) | 0.0 | Breast ca. MDA-N | 3.3 |

TABLE CD-continued

Panel 1.3D

| Tissue Name | Rel. Exp. (%) Ag3033, Run 167962289 | Tissue Name | Rel. Exp. (%) Ag3033, Run 167962289 |
| --- | --- | --- | --- |
| Skeletal muscle | 2.0 | Ovary | 0.0 |
| Bone marrow | 0.0 | Ovarian ca. OVCAR-3 | 0.0 |
| Thymus | 0.0 | Ovarian ca. OVCAR-4 | 0.0 |
| Spleen | 5.4 | Ovarian ca. OVCAR-5 | 3.7 |
| Lymph node | 0.0 | Ovarian ca. OVCAR-8 | 1.0 |
| Colorectal | 0.0 | Ovarian ca. IGROV-1 | 0.0 |
| Stomach | 0.0 | Ovarian ca.* (ascites) SK-OV-3 | 7.7 |
| Small intestine | 0.0 | Uterus | 0.0 |
| Colon ca. SW480 | 0.0 | Placenta | 0.0 |
| Colon ca.* SW620(SW480 met) | 1.1 | Prostate | 0.0 |
| Colon ca. HT29 | 0.0 | Prostate ca.* (bone met)PC-3 | 2.5 |
| Colon ca. HCT-116 | 0.0 | Testis | 2.7 |
| Colon ca. CaCo-2 | 0.0 | Melanoma Hs688(A).T | 3.0 |
| Colon ca. tissue(ODO3866) | 0.0 | Melanoma* (met) Hs688(B).T | 2.0 |
| Colon ca. HCC-2998 | 2.1 | Melanoma UACC-62 | 0.0 |
| Gastric ca.* (liver met) NCI-N87 | 1.0 | Melanoma M14 | 0.0 |
| Bladder | 0.0 | Melanoma LOX IMVI | 100.0 |
| Trachea | 1.3 | Melanoma* (met) SK-MEL-5 | 0.0 |
| Kidney | 0.0 | Adipose | 1.1 |

TABLE CE

Panel 4D

| Tissue Name | Rel. Exp. (%) Ag3033, Run 162427946 | Tissue Name | Rel. Exp. (%) Ag3033, Run 162427946 |
| --- | --- | --- | --- |
| Secondary Th1 act | 0.0 | HUVEC IL-1 beta | 19.3 |
| Secondary Th2 act | 0.0 | HUVEC IFN gamma | 4.1 |
| Secondary Tr1 act | 0.0 | HUVEC TNF alpha + IFN gamma | 18.4 |
| Secondary Th1 rest | 0.0 | HUVEC TNF alpha + IL4 | 18.3 |
| Secondary Th2 rest | 0.0 | HUVEC IL-11 | 7.2 |
| Secondary Tr1 rest | 0.0 | Lung Microvascular EC none | 10.8 |
| Primary Th1 act | 0.0 | Lung Microvascular EC TNF alpha + IL-1 beta | 12.3 |
| Primary Th2 act | 0.0 | Microvascular Dermal EC none | 30.1 |
| Primary Tr1 act | 0.4 | Microsvascular Dermal EC TNF alpha + IL-1 beta | 18.7 |
| Primary Th1 rest | 0.0 | Bronchial epithelium TNF alpha + IL1 beta | 0.7 |
| Primary Th2 rest | 0.0 | Small airway epithelium none | 1.9 |
| Primary Tr1 rest | 0.0 | Small airway epithelium TNF alpha + IL-1 beta | 1.3 |
| CD45RA CD4 lymphocyte act | 2.7 | Coronery artery SMC rest | 36.6 |
| CD45RO CD4 lymphocyte act | 0.0 | Coronery artery SMC TNF alpha + IL-1 beta | 16.8 |
| CD8 lymphocyte act | 0.0 | Astrocytes rest | 8.8 |
| Secondary CD8 lymphocyte rest | 0.0 | Astrocytes TNF alpha + IL-1 beta | 7.1 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.5 |
| LAK cells rest | 0.0 | CCD1106 (Keratinocytes) TNF alpha + IL-1 beta | 0.0 |
| LAK cells IL-2 | 0.0 | Liver cirrhosis | 0.0 |
| LAK cells IL-2 + IL-12 | 0.0 | Lupus kidney | 0.0 |
| LAK cells IL-2 + IFN gamma | 0.5 | NCI-H292 none | 0.0 |
| LAK cells IL-2 + IL-18 | 0.0 | NCI-H292 IL-4 | 0.4 |

TABLE CE-continued

Panel 4D

| Tissue Name | Rel. Exp. (%) Ag3033, Run 162427946 | Tissue Name | Rel. Exp. (%) Ag3033, Run 162427946 |
|---|---|---|---|
| LAK cells PMA/ionomycin | 0.0 | NCI-H292 IL-9 | 0.0 |
| NK Cells IL-2 rest | 1.2 | NCI-H292 IL-13 | 0.0 |
| Two Way MLR 3 day | 0.0 | NCI-H292 IFN gamma | 0.0 |
| Two Way MLR 5 day | 0.0 | HPAEC none | 10.4 |
| Two Way MLR 7 day | 0.0 | HPAEC TNF alpha + IL-1 beta | 36.6 |
| PBMC rest | 0.0 | Lung fibroblast none | 0.9 |
| PBMC PWM | 0.0 | Lung fibroblast TNF alpha + IL-1 beta | 0.4 |
| PBMC PHA-L | 0.0 | Lung fibroblast IL-4 | 1.2 |
| Ramos (B cell) none | 0.0 | Lung fibroblast IL-9 | 5.6 |
| Ramos (B cell) ionomycin | 0.0 | Lung fibroblast IL-13 | 0.3 |
| B lymphocytes PWM | 0.0 | Lung fibroblast IFN gamma | 0.4 |
| B lymphocytes CD40L and IL-4 | 0.0 | Dermal fibroblast CCD1070 rest | 13.5 |
| EOL-1 dbcAMP | 0.0 | Dermal fibroblast CCD1070 TNF alpha | 38.2 |
| EOL-1 dbcAMP PMA/ionomycin | 0.4 | Dermal fibroblast CCD1070 IL-1 beta | 19.9 |
| Dendritic cells none | 0.0 | Dermal fibroblast IFN gamma | 1.2 |
| Dendritic cells LPS | 0.0 | Dermal fibroblast IL-4 | 2.2 |
| Dendritic cells anti-CD40 | 0.0 | IBD Colitis 2 | 0.0 |
| Monocytes rest | 0.0 | IBD Crohn's | 0.0 |
| Monocytes LPS | 0.0 | Colon | 0.5 |
| Macrophages rest | 0.0 | Lung | 0.0 |
| Macrophages LPS | 0.0 | Thymus | 0.0 |
| HUVEC none | 62.9 | Kidney | 0.4 |
| HUVEC starved | 100.0 | | |

CNS neurodegeneration v1.0 Summary: Ag3718 Expression of the CG56832-01 gene is low/undetectable (CTs>35) across all of the samples on this panel (data not shown).

General_screeningpanel_v1.4 Summary: Ag3718 Highest expression of the CG56832-01 gene is detected in melanoma LOXIMVI cell line (CT=28.6). Thus, expression of this gene can be used to distinguish this sample from other samples in this panel. In addition, significant expression of this gene is associated with number of CNS cancer, renal cancer UO-31, lung cancer NCI-H460, breast cancer MDA-MB-231, and ovarian cancer IGROV-1 cell lines. The CG56832-01 gene codes for a homologue of Drosophila the tumour suppressor protein D1g, a membrane-associated guanylate kinase homolog (MAGUK). In Drosophila, genetic loss of the tumour suppressor protein D1g (in d1g mutants) or p 127 (in 1 g1 mutants) leads to loss of epithelial structure and excess proliferation in the imaginal discs and brain of the developing larva. These phenotypes show most of the characteristic features of human neoplasia (De Lorenzo C, Mechler B M, Bryant P J. (1999) What is Drosophila telling us about cancer? Cancer Metastasis Rev 18(2):295–311). Therefore, therapeutic modulation of the activity of this gene or its protein product, through the use of small molecule drugs, or antibodies, might be beneficial in the treatment of these cancers.

Panel 1.3D Summary: Ag3033 Highest expression of the CG56832-01 gene is detected in melanoma LOXIMVI cell line (CT=31.3). Thus, expression of this gene can be used to distinguish this sample from other samples in this panel. In addition, significant expression of this gene is associated with number of CNS cancer, renal cancer UO-31, lung cancer NCI-H69, and ovarian cancer SK-OV-3 cell lines. Please see Panel 1.4 for a discussion of the potential utility of this gene.

In addition, low but significant expression of this gene is also seen in brain cerebellum sample (CT=34.2). Therefore, therapeutic modulation of the activity of this gene or its protein product, through the use of small molecule drugs, might be beneficial in the treatment of ataxia and autism.

Panel 4D Summary: Ag3033 Highest expression of the CG56832-01 gene is detected in starved HUVEC cells (CT=30). In addition, significant expression of this gene is seen in dermal fibroblasts, IL-9 treated lung fibroblast, HPAEC, astrocytes, coronery artery SMC, microvascular dermal EC, lung microvascular EC, and HUVEC. Therefore, therapeutic modulation of the activity of this gene or its protein product, through the use of small molecule drugs, might be beneficial in the treatment of autoimmune and inflammatory diseases such as asthma, allergies, inflammatory bowel disease, lupus erythematosus, psoriasis, rheumatoid arthritis, and osteoarthritis.

CG59580-01: GPCR

Expression of gene CG59580-01 was assessed using the primer-probe set Ag3481, described in Table DA. Results of the RTQ-PCR runs are shown in Table DB.

TABLE DA

Probe Name Ag3481

| Primers | Sequences | Length | Start Position | SEQ ID NO: |
|---|---|---|---|---|
| Forward | 5'-ccatgtacttcttcctctccaa-3' | 22 | 273 | 225 |
| Probe | TET-5'-tgtctaccactgtcccaaagatgctg-3'-TAMRA | 26 | 321 | 226 |
| Reverse | 5'-gctctgtgtctggatgttcac-3' | 21 | 347 | 227 |

TABLE DB

Panel 4D

| Tissue Name | Rel. Exp. (%) Ag3481, Run 166441541 | Tissue Name | Rel. Exp. (%) Ag3481, Run 166441541 |
|---|---|---|---|
| Secondary Th1 act | 0.0 | HUVEC IL-1 beta | 0.0 |
| Secondary Th2 act | 0.3 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1 beta | 0.0 |
| Primary Th2 act | 0.0 | Microvascular Dermal EC none | 0.0 |
| Primary Tr1 act | 0.0 | Microvasular Dermal EC TNF alpha + IL-1 beta | 0.0 |
| Primary Th1 rest | 0.0 | Bronchial epithelium TNF alpha + IL1 beta | 0.0 |
| Primary Th2 rest | 0.0 | Small airway epithelium none | 0.0 |
| Primary Tr1 rest | 0.0 | Small airway epithelium TNF alpha + IL-1 beta | 0.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1 beta | 0.0 |
| CD8 lymphocyte act | 0.0 | Astrocytes rest | 0.4 |
| Secondary CD8 lymphocyte rest | 0.0 | Astrocytes TNF alpha + IL-1 beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1 beta | 0.0 |
| LAK cells IL-2 | 0.0 | Liver cirrhosis | 100.0 |
| LAK cells IL-2 + IL-12 | 0.0 | Lupus kidney | 8.4 |
| LAK cells IL-2 + IFN gamma | 0.0 | NCI-H292 none | 0.0 |
| LAK cells IL-2 + IL-18 | 0.0 | NCI-H292 IL-4 | 0.0 |
| LAK cells PMA/ionomycin | 0.0 | NCI-H292 IL-9 | 0.0 |
| NK Cells IL-2 rest | 0.0 | NCI-H292 IL-13 | 0.0 |
| Two Way MLR 3 day | 0.0 | NCI-H292 IFN gamma | 0.0 |
| Two Way MLR 5 day | 0.0 | HPAEC none | 0.0 |
| Two Way MLR 7 day | 0.0 | HPAEC TNF alpha + IL-1 beta | 0.0 |
| PBMC rest | 0.0 | Lung fibroblast none | 0.0 |
| PBMC PWM | 0.0 | Lung fibroblast TNF alpha + IL-1 beta | 0.0 |
| PBMC PHA-L | 0.0 | Lung fibroblast IL-4 | 0.0 |
| Ramos (B cell) none | 0.0 | Lung fibroblast IL-9 | 0.0 |
| Ramos (B cell) ionomycin | 0.0 | Lung fibroblast IL-13 | 0.0 |
| B lymphocytes PWM | 0.0 | Lung fibroblast IFN gamma | 0.0 |
| B lymphocytes CD40L and IL-4 | 0.0 | Dermal fibroblast CCD1070 rest | 0.0 |
| EOL-1 dbcAMP | 0.0 | Dermal fibroblast CCD1070 TNF alpha | 0.0 |
| EOL-1 dbcAMP PMA/ionomycin | 0.0 | Dermal fibroblast CCD1070 IL-1 beta | 0.0 |
| Dendritic cells none | 0.0 | Dermal fibroblast IFN gamma | 0.0 |
| Dendritic cells LPS | 0.0 | Dermal fibroblast IL-4 | 0.0 |
| Dendritic cells anti-CD40 | 0.0 | IBD Colitis 2 | 6.3 |
| Monocytes rest | 0.0 | IBD Crohn's | 0.0 |
| Monocytes LPS | 0.0 | Colon | 9.2 |
| Macrophages rest | 0.0 | Lung | 0.0 |
| Macrophages LPS | 0.0 | Thymus | 0.4 |
| HUVEC none | 0.0 | Kidney | 0.0 |
| HUVEC starved | 0.0 | | |

CNS_neurodegeneration_v1.0 Summary: Ag3481 Expression of the CG59580-01 gene is low/undetectable in all samples on this panel (CTs>35). (Data not shown.)

General_screening_panel_v1.4 Summary: Ag3481 Expression of the CG59580-01 gene is low/undetectable in all samples on this panel (CTs>35). (Data not shown.)

Panel 4D Summary: Ag3481 Expression of the CG59580-01 gene is detected in a liver cirrhosis sample (CT 31.3). Furthermore, expression of this gene is not detected in normal liver in Panel 1.3D, suggesting that its expression is unique to liver cirrhosis. This gene encodes a putative GPCR; therefore, antibodies or small molecule therapeutics could reduce or inhibit fibrosis that occurs in liver cirrhosis. In addition, antibodies to this putative GPCR could also be used for the diagnosis of liver cirrhosis.

E. CG59611-01: Odorant Receptor

Expression of gene CG59611-01 was assessed using the primer-probe set Ag3495, described in Table EA.

TABLE EA

Probe Name Ag3495

| Primers | Sequences | Length | Start Position | SEQ ID NO: |
|---|---|---|---|---|
| Forward | 5'-ctatccacctcacaccttcact-3' | 22 | 152 | 228 |
| Probe | TET-5'-cacgtacttcctgctcagcaacctgt-3'-TAMRA | 26 | 178 | 229 |
| Reverse | 5'-gaggacaggcacatgtcaatat-3' | 22 | 207 | 230 |

CNS_neurodegeneration_v1.0 Summary: Ag3495 Expression of the CG59611-01 gene is low/undetectable in all samples on this panel (CTs>35). (Data not shown.) The amp plot indicates that there is a high probability of a probe failure.

General_screening_panel_v1.4 Summary: Ag3495 Results from one experiment with the CG59611-01 gene are not included. The amp plot indicates that there were experimental difficulties with this run.

Panel 4.1D Summary: Ag3495 Expression of the CG59611-01 gene is low/undetectable in all samples on this panel (CTs>35). (Data not shown.) The amp plot indicates that there is a high probability of a probe failure.

F. CG59617-01: GPCR

Expression of gene CG59617-01 was assessed using the primer-probe set Ag3497, described in Table FA.

TABLE FA

Probe Name Ag3497

| Primers | Sequences | Length | Start Position | SEQ ID NO: |
|---|---|---|---|---|
| Forward | 5'-gccagttgcttcatgttaattc-3' | 22 | 649 | 231 |
| Probe | TET-5'-tgccaacatagtaaatgccatcctga-3'-TAMRA | 26 | 681 | 232 |
| Reverse | 5'-cccatcagtggtgcgtatc-3' | 19 | 708 | 233 |

CNS_neurodegeneration_v1.0 Summary: Ag3497 Expression of the CG59617-01 gene is low/undetectable in all samples on this panel (CTs>35). (Data not shown.)

General_screening_panel_v1.4 Summary: Ag3497 Expression of the CG59617-01 gene is low/undetectable in all samples on this panel (CTs>35). (Data not shown.)

Panel 4.1D Summary: Ag3497 Expression of the CG59617-01 gene is limited to a few samples, with highest expression in a 7 day post MLR (CT=28.4).

G. CG59826-01: Transformation-Sensitive Protein IEF SSP like Protein

Expression of gene CG59826-01 was assessed using the primer-probe set Ag3599, described in Table GA. Results of the RTQ-PCR runs are shown in Tables GB, GC and GD.

TABLE GA

Probe Name Ag3599

| Primers | Sequences | Length | Start Position | SEQ ID NO: |
|---|---|---|---|---|
| Forward | 5'-agctgcctgttacaccaaact-3' | 21 | 1213 | 234 |
| Probe | TET-5'-atttccagctggcactcaaggactgt-3'-TAMRA | 26 | 1239 | 235 |
| Reverse | 5'-aaggtcggttctagctggatac-3' | 22 | 1272 | 236 |

TABLE GB

CNS_neurodegeneration_v1.0

| Tissue Name | Rel. Exp. (%) Ag3599, Run 211010105 | Rel. Exp. (%) Ag3599, Run 224079046 | Tissue Name | Rel. Exp. (%) Ag3599, Run 211010105 | Rel. Exp. (%) Ag3599, Run 224079046 |
|---|---|---|---|---|---|
| AD 1 Hippo | 28.1 | 26.8 | Control (Path) 3 Temporal Ctx | 5.3 | 5.8 |
| AD 2 Hippo | 29.5 | 33.0 | Control (Path) 4 Temporal Ctx | 21.6 | 26.8 |
| AD 3 Hippo | 24.8 | 25.3 | AD 1 Occipital Ctx | 35.4 | 37.9 |
| AD 4 Hippo | 6.2 | 7.3 | AD 2 Occipital Ctx (Missing) | 0.0 | 0.0 |
| AD 5 hippo | 87.7 | 100.0 | AD 3 Occipital Ctx | 24.3 | 29.3 |
| AD 6 Hippo | 71.2 | 85.9 | AD 4 Occipital Ctx | 24.3 | 18.7 |
| Control 2 Hippo | 36.9 | 44.8 | AD 5 Occipital Ctx | 37.6 | 76.8 |
| Control 4 Hippo | 9.6 | 10.7 | AD 6 Occipital Ctx | 61.1 | 41.5 |
| Control (Path) 3 Hippo | 7.4 | 8.4 | Control 1 Occipital Ctx | 6.0 | 7.2 |
| AD 1 Temporal Ctx | 28.7 | 28.1 | Control 2 Occipital Ctx | 69.3 | 65.5 |

TABLE GB-continued

CNS_neurodegeneration_v1.0

| Tissue Name | Rel. Exp. (%) Ag3599, Run 211010105 | Rel. Exp. (%) Ag3599, Run 224079046 | Tissue Name | Rel. Exp. (%) Ag3599, Run 211010105 | Rel. Exp. (%) Ag3599, Run 224079046 |
|---|---|---|---|---|---|
| AD 2 Temporal Ctx | 35.4 | 40.6 | Control 3 Occipital Ctx | 13.0 | 14.7 |
| AD 3 Temporal Ctx | 16.8 | 18.4 | Control 4 Occipital Ctx | 7.3 | 8.2 |
| AD 4 Temporal Ctx | 20.0 | 20.3 | Control (Path) 1 Occipital Ctx | 57.4 | 67.4 |
| AD 5 Inf Temporal Ctx | 100.0 | 95.9 | Control (Path) 2 Occipital Ctx | 8.4 | 11.3 |
| AD 5 SupTemporal Ctx | 47.0 | 49.0 | Control (Path) 3 Occipital Ctx | 3.2 | 3.3 |
| AD 6 Inf Temporal Ctx | 60.7 | 77.9 | Control (Path) 4 Occipital Ctx | 9.9 | 11.0 |
| AD 6 Sup Temporal Ctx | 61.6 | 73.2 | Control 1 Parietal Ctx | 9.0 | 10.7 |
| Control 1 Temporal Ctx | 7.9 | 9.4 | Control 2 Parietal Ctx | 33.2 | 40.3 |
| Control 2 Temporal Ctx | 40.1 | 47.0 | Control 3 Parietal Ctx | 18.0 | 21.6 |
| Control 3 Temporal Ctx | 15.8 | 17.8 | Control (Path) 1 Parietal Ctx | 59.9 | 72.2 |
| Control 4 Temporal Ctx | 6.2 | 7.4 | Control (Path) 2 Parietal Ctx | 21.6 | 24.3 |
| Control (Path) 1 Temporal Ctx | 41.5 | 50.3 | Control (Path) 3 Parietal Ctx | 4.5 | 4.4 |
| Control (Path) 2 Temporal Ctx | 28.9 | 34.2 | Control (Path) 4 Parietal Ctx | 33.7 | 40.3 |

TABLE GC

General_screening_panel_v1.4

| Tissue Name | Rel. Exp. (%) Ag3599, Run 217676501 | Tissue Name | Rel. Exp. (%) Ag3599, Run 217676501 |
|---|---|---|---|
| Adipose | 3.9 | Renal ca. TK-10 | 33.0 |
| Melanoma* Hs688(A).T | 14.9 | Bladder | 7.6 |
| Melanoma* Hs688(B).T | 14.3 | Gastric ca. (liver met.) NCI-N87 | 29.7 |
| Melanoma* M14 | 50.0 | Gastric ca. KATO III | 97.3 |
| Melanoma* LOXIMVI | 54.3 | Colon ca. SW-948 | 9.7 |
| Melanoma* SK-MEL-5 | 56.6 | Colon ca. SW480 | 88.3 |
| Squamous cell carcinoma SCC-4 | 54.7 | Colon ca.* (SW480 met) SW620 | 39.8 |
| Testis Pool | 10.3 | Colon ca. HT29 | 29.7 |
| Prostate ca.* (bone met) PC-3 | 34.2 | Colon ca. HCT-116 | 100.0 |
| Prostate Pool | 3.0 | Colon ca. CaCo-2 | 33.9 |
| Placenta | 6.4 | Colon cancer tissue | 10.4 |
| Uterus Pool | 1.7 | Colon ca. SW1116 | 7.9 |
| Ovarian ca. OVCAR-3 | 39.5 | Colon ca. Colo-205 | 11.3 |
| Ovarian ca. SK-OV-3 | 37.9 | Colon ca. SW-48 | 15.1 |
| Ovarian ca. OVCAR-4 | 29.3 | Colon Pool | 2.2 |
| Ovarian ca. OVCAR-5 | 33.0 | Small Intestine Pool | 4.6 |
| Ovarian ca. IGROV-1 | 17.0 | Stomach Pool | 3.5 |
| Ovarian ca. OVCAR-8 | 13.0 | Bone Marrow Pool | 1.7 |
| Ovary | 4.8 | Fetal Heart | 5.9 |
| Breast ca. MCF-7 | 19.8 | Heart Pool | 2.7 |
| Breast ca. MDA-MB-231 | 60.7 | Lymph Node Pool | 6.0 |
| Breast ca. BT 549 | 65.1 | Fetal Skeletal Muscle | 4.3 |
| Breast ca. T47D | 57.4 | Skeletal Muscle Pool | 15.7 |
| Breast ca. MDA-N | 28.3 | Spleen Pool | 4.2 |
| Breast Pool | 5.3 | Thymus Pool | 5.1 |
| Trachea | 5.0 | CNS cancer (glio/astro) U87-MG | 41.2 |
| Lung | 1.0 | CNS cancer (glio/astro) U-118-MG | 74.2 |
| Fetal Lung | 11.3 | CNS cancer (neuro; met) SK-N-AS | 34.4 |

TABLE GC-continued

General_screening_panel_v1.4

| Tissue Name | Rel. Exp. (%) Ag3599, Run 217676501 | Tissue Name | Rel. Exp. (%) Ag3599, Run 217676501 |
|---|---|---|---|
| Lung ca. NCI-N417 | 8.9 | CNS cancer (astro) SF-539 | 24.1 |
| Lung ca. LX-1 | 33.2 | CNS cancer (astro) SNB-75 | 36.3 |
| Lung ca. NCI-H146 | 18.0 | CNS cancer (glio) SNB-19 | 14.7 |
| Lung ca. SHP-77 | 42.0 | CNS cancer (glio) SF-295 | 39.0 |
| Lung ca. A549 | 43.5 | Brain (Amygdala) Pool | 6.0 |
| Lung ca. NCI-H526 | 19.6 | Brain (cerebellum) | 26.4 |
| Lung ca. NCI-H23 | 27.5 | Brain (fetal) | 11.8 |
| Lung ca. NCI-H460 | 17.1 | Brain (Hippocampus) Pool | 6.3 |
| Lung ca. HOP-62 | 12.5 | Cerebral Cortex Pool | 9.1 |
| Lung ca. NCI-H522 | 38.4 | Brain (Substantia nigra) Pool | 7.9 |
| Liver | 1.3 | Brain (Thalamus) Pool | 9.5 |
| Fetal Liver | 13.6 | Brain (whole) | 9.2 |
| Liver ca. HepG2 | 10.0 | Spinal Cord Pool | 7.2 |
| Kidney Pool | 5.8 | Adrenal Gland | 15.0 |
| Fetal Kidney | 5.3 | Pituitary gland Pool | 1.5 |
| Renal ca. 786-0 | 17.7 | Salivary Gland | 3.0 |
| Renal ca. A498 | 8.7 | Thyroid (female) | 4.3 |
| Renal ca. ACHN | 9.9 | Pancreatic ca. CAPAN2 | 28.1 |
| Renal ca. UO-31 | 26.2 | Pancreas Pool | 7.3 |

TABLE GD

Panel 4.1D

| Tissue Name | Rel. Exp. (%) Ag3599, Run 169910500 | Tissue Name | Rel. Exp. (%) Ag3599, Run 169910500 |
|---|---|---|---|
| Secondary Th1 act | 95.9 | HUVEC IL-1beta | 46.0 |
| Secondary Th2 act | 100.0 | HUVEC IFN gamma | 32.5 |
| Secondary Tr1 act | 91.4 | HUVEC TNF alpha + IFN gamma | 26.8 |
| Secondary Th1 rest | 6.1 | HUVEC TNF alpha + IL4 | 30.4 |
| Secondary Th2 rest | 14.5 | HUVEC IL-11 | 17.1 |
| Secondary Tr1 rest | 9.5 | Lung Microvascular EC none | 28.3 |
| Primary Th1 act | 90.1 | Lung Microvascular EC TNF alpha + IL-1beta | 25.0 |
| Primary Th2 act | 54.7 | Microvascular Dermal EC none | 25.5 |
| Primary Tr1 act | 84.1 | Microsvascular Dermal EC TNF alpha + IL-1beta | 26.1 |
| Primary Th1 rest | 14.2 | Bronchial epithelium TNF alpha + IL1beta | 18.7 |
| Primary Th2 rest | 10.4 | Small airway epithelium none | 12.3 |
| Primary Tr1 rest | 22.5 | Small airway epithelium TNF alpha + IL-1beta | 19.5 |
| CD45RA CD4 lymphocyte act | 51.4 | Coronery artery SMC rest | 25.5 |
| CD45RO CD4 lymphocyte act | 55.9 | Coronery artery SMC TNF alpha + IL-1beta | 20.0 |
| CD8 lymphocyte act | 68.3 | Astrocytes rest | 19.2 |
| Secondary CD8 lymphocyte rest | 68.3 | Astrocytes TNF alpha + IL-1beta | 13.8 |
| Secondary CD8 lymphocyte act | 41.5 | KU-812 (Basophil) rest | 47.3 |
| CD4 lymphocyte none | 3.1 | KU-812 (Basophil) PMA/ionomycin | 75.8 |
| 2ry Th1/Th2/Tr1_anti-CD95 CH11 | 10.1 | CCD1106 (Keratinocytes) none | 29.1 |
| LAK cells rest | 32.8 | CCD1106 (Keratinocytes) TNF alpha + IL-1beta | 27.7 |
| LAK cells IL-2 | 44.4 | Liver cirrhosis | 2.9 |
| LAK cells IL-2 + IL-12 | 61.6 | NCI-H292 none | 22.7 |
| LAK cells IL-2 + IFN gamma | 53.2 | NCI-H292 IL-4 | 42.0 |
| LAK cells IL-2 + IL-18 | 50.3 | NCI-H292 IL-9 | 53.6 |
| LAK cells PMA/ionomycin | 44.8 | NCI-H292 IL-13 | 45.7 |
| NK Cells IL-2 rest | 28.7 | NCI-H292 IFN gamma | 42.6 |
| Two Way MLR 3 day | 27.7 | HPAEC none | 22.1 |

TABLE GD-continued

Panel 4.1D

| Tissue Name | Rel. Exp. (%) Ag3599, Run 169910500 | Tissue Name | Rel. Exp. (%) Ag3599, Run 169910500 |
|---|---|---|---|
| Two Way MLR 5 day | 51.1 | HPAEC TNF alpha + IL-1beta | 39.5 |
| Two Way MLR 7 day | 28.7 | Lung fibroblast none | 21.6 |
| PBMC rest | 4.9 | Lung fibroblast TNF alpha + IL-1beta | 15.5 |
| PBMC PWM | 59.9 | Lung fibroblast IL-4 | 31.2 |
| PBMC PHA-L | 50.0 | Lung fibroblast IL-9 | 34.4 |
| Ramos (B cell) none | 44.1 | Lung fibroblast IL-13 | 25.3 |
| Ramos (B cell) ionomycin | 39.0 | Lung fibroblast IFN gamma | 25.3 |
| B lymphocytes PWM | 48.6 | Dermal fibroblast CCD1070 rest | 37.6 |
| B lymphocytes CD40L and IL-4 | 27.7 | Dermal fibroblast CCD1070 TNF alpha | 52.9 |
| EOL-1 dbcAMP | 25.7 | Dermal fibroblast CCD1070 IL-1beta | 24.7 |
| EOL-1 dbcAMP PMA/ionomycin | 28.3 | Dermal fibroblast IFN gamma | 15.8 |
| Dendritic cells none | 43.8 | Dermal fibroblast IL-4 | 35.8 |
| Dendritic cells LPS | 17.8 | Dermal Fibroblast rest | 20.6 |
| Dendritic cells anti-CD40 | 47.0 | Neutrophils TNFa + LPS | 2.8 |
| Monocytes rest | 8.5 | Neutrophils rest | 1.9 |
| Monocytes LPS | 18.4 | Colon | 5.0 |
| Macrophages rest | 50.7 | Lung | 10.7 |
| Macrophages LPS | 13.8 | Thymus | 11.5 |
| HUVEC none | 25.2 | Kidney | 9.4 |
| HUVEC starved | 29.1 | | |

CNS_neurodegeneration_v1.0 Summary: Ag3599 Two experiments with the same probe and primer produce results that are in excellent agreement. The CG59826-01 gene appears to be slightly upregulated in the temporal cortex of Alzheimer's disease patients. Therefore, blockade of this receptor may decrease neuronal death and be of use in the treatment of Alzheimer's disease and other neurodegenerative disorders.

General_screening_panel_v1.4 Summary: Ag3599 Highest expression of the CG59826-01 gene is seen in a colon cancer cell line (CT=23.8). Significant levels of expression are seen in a cluster of samples derived from ovarian, breast, brain, colon, gastric, melanoma, pancreatic and lung cancer cell lines. Thus, expression of this gene could be used to differentiate between these samples and other samples on this panel and as a marker to detect the presence of these cancers. Furthermore, therapeutic modulation of the expression or function of this gene may be effective in the treatment of ovarian, breast, brain, colon, gastric, melanoma, pancreatic and lung cancers. Overall, this gene is more highly expressed in cancer cell lines and some fetal cell lines than in the samples derived from normal tissues. This expression profile suggests a role for this gene in cellular growth and differentiation.

In addition, this gene is expressed at much higher levels in fetal lung and liver and skeletal muscle tissue (CTs= 26–27) when compared to expression in the adult counterpart (CTs=30). Thus, expression of this gene may be used to differentiate between the fetal and adult source of these tissues.

Among tissues with metabolic function, this gene is expressed at moderate to high levels in pituitary, adipose, adrenal gland, pancreas, thyroid, and adult and fetal skeletal muscle, heart, and liver. This widespread expression among these tissues suggests that this gene product may play a role in normal neuroendocrine and metabolic and that disregulated expression of this gene may contribute to neuroendocrine disorders or metabolic diseases, such as obesity and diabetes.

This molecule is also expressed at high levels in the CNS, including the hippocampus, thalamus, substantia nigra, amygdala, cerebellum and cerebral cortex. Therefore, therapeutic modulation of the expression or function of this gene may be useful in the treatment of neurologic disorders, such as Alzheimer's disease, Parkinson's disease, schizophrenia, multiple sclerosis, stroke and epilepsy. Please see Panel CNS_neurodegeneration_v1.0 for further discussion of utility of this gene in the central nervous system.

Panel 4.1D Summary: Ag3599 The CG59826-01 gene is ubiquitously expressed in this panel, with highest expression in activated secondary Th2 cells (CT=26). This gene appears to be more highly expressed in activated T cells than in resting T cells. Thus, expression of this gene could be used to identify activated T cells. Furthermore, therapeutic regulation of the transcript or the protein encoded by the transcript could be important in the treatment of T cell-mediated diseases such as asthma, arthritis, psoriasis, IBD, and lupus.

H. CG59839-01: Cation-Transporting ATPase

Expression of gene CG59839-01 was assessed using the primer-probe sets Ag1417 and Ag3604, described in Tables HA and HB. Results of the RTQ-PCR runs are shown in Tables HC, HD and HE.

TABLE HA

Probe Name Ag1417

| Primers | Sequences | Length | Start Position | SEQ ID NO: |
|---|---|---|---|---|
| Forward | 5'-ataggaaaatggacgcctacat-3' | 22 | 730 | 237 |
| Probe | TET-5'-ccattgccggtctctgtaaacctgaa-3'-TAMRA | 26 | 769 | 238 |
| Reverse | 5'-ttttgaaaatcgacaggaactg-3' | 22 | 796 | 239 |

TABLE HB

Probe Name Ag3604

| Primers | Sequences | Length | Start Position | SEQ ID NO: |
|---|---|---|---|---|
| Forward | 5'-gcaattgagaacaacatggatt-3' | 22 | 924 | 240 |
| Probe | TET-5'-caaattaaagcaagaaaccctgcag-3'-TAMRA | 26 | 971 | 241 |
| Reverse | 5'-tgttggctttatgcaaatcttc-3' | 22 | 1002 | 242 |

TABLE HC

CNS_neurodegeneration_v1.0

| Tissue Name | Rel. Exp. (%) Ag3604, Run 210997046 | Tissue Name | Rel. Exp. (%) Ag3604, Run 210997046 |
|---|---|---|---|
| AD 1 Hippo | 8.8 | Control (Path) 3 Temporal Ctx | 9.1 |
| AD 2 Hippo | 26.8 | Control (Path) 4 Temporal Ctx | 39.8 |
| AD 3 Hippo | 7.3 | AD 1 Occipital Ctx | 14.3 |
| AD 4 Hippo | 10.7 | AD 2 Occipital Ctx (Missing) | 0.0 |
| AD 5 hippo | 97.9 | AD 3 Occipital Ctx | 5.0 |
| AD 6 Hippo | 87.7 | AD 4 Occipital Ctx | 23.3 |
| Control 2 Hippo | 28.9 | AD 5 Occipital Ctx | 47.3 |
| Control 4 Hippo | 18.9 | AD 6 Occipital Ctx | 48.6 |
| Control (Path) 3 Hippo | 11.3 | Control 1 Occipital Ctx | 5.8 |
| AD 1 Temporal Ctx | 15.5 | Control 2 Occipital Ctx | 74.7 |
| AD 2 Temporal Ctx | 35.4 | Control 3 Occipital Ctx | 26.6 |
| AD 3 Temporal Ctx | 6.0 | Control 4 Occipital Ctx | 6.8 |
| AD 4 Temporal Ctx | 23.8 | Control (Path) 1 Occipital Ctx | 100.0 |
| AD 5 Inf Temporal Ctx | 94.0 | Control (Path) 2 Occipital Ctx | 13.9 |
| AD 5 SupTemporal Ctx | 55.1 | Control (Path) 3 Occipital Ctx | 5.0 |
| AD 6 Inf Temporal Ctx | 65.5 | Control (Path) 4 Occipital Ctx | 30.8 |
| AD 6 Sup Temporal Ctx | 66.0 | Control 1 Parietal Ctx | 10.7 |
| Control 1 Temporal Ctx | 9.3 | Control 2 Parietal Ctx | 46.7 |
| Control 2 Temporal Ctx | 42.3 | Control 3 Parietal Ctx | 16.5 |
| Control 3 Temporal Ctx | 15.6 | Control (Path) 1 Parietal Ctx | 88.9 |
| Control 4 Temporal Ctx | 12.8 | Control (Path) 2 Parietal Ctx | 25.7 |
| Control (Path) 1 Temporal Ctx | 52.9 | Control (Path) 3 Parietal Ctx | 6.3 |
| Control (Path) 2 Temporal Ctx | 48.3 | Control (Path) 4 Parietal Ctx | 52.5 |

TABLE HD

General_screening_panel_v1.4

| Tissue Name | Rel. Exp. (%) Ag3604, Run 217674539 | Tissue Name | Rel. Exp. (%) Ag3604, Run 217674539 |
|---|---|---|---|
| Adipose | 5.6 | Renal ca. TK-10 | 17.9 |
| Melanoma* Hs688(A).T | 17.9 | Bladder | 10.9 |
| Melanoma* Hs688(B).T | 24.0 | Gastric ca. (liver met.) NCI-N87 | 17.0 |
| Melanoma* M14 | 12.3 | Gastric ca. KATO III | 38.7 |
| Melanoma* LOXIMVI | 13.4 | Colon ca. SW-948 | 4.4 |

TABLE HD-continued

General_screening_panel_v1.4

| Tissue Name | Rel. Exp. (%) Ag3604, Run 217674539 | Tissue Name | Rel. Exp. (%) Ag3604, Run 217674539 |
|---|---|---|---|
| Melanoma* SK-MEL-5 | 17.8 | Colon ca. SW480 | 31.9 |
| Squamous cell carcinoma SCC-4 | 11.9 | Colon ca.* (SW480 met) SW620 | 17.0 |
| Testis Pool | 1.3 | Colon ca. HT29 | 9.1 |
| Prostate ca.* (bone met) PC-3 | 15.5 | Colon ca. HCT-116 | 27.9 |
| Prostate Pool | 1.4 | Colon ca. CaCo-2 | 14.8 |
| Placenta | 0.9 | Colon cancer tissue | 10.2 |
| Uterus Pool | 1.4 | Colon ca. SW1116 | 1.5 |
| Ovarian ca. OVCAR-3 | 12.4 | Colon ca. Colo-205 | 4.1 |
| Ovarian ca. SK-OV-3 | 24.3 | Colon ca. SW-48 | 5.8 |
| Ovarian ca. OVCAR-4 | 10.8 | Colon Pool | 4.0 |
| Ovarian ca. OVCAR-5 | 50.3 | Small Intestine Pool | 2.5 |
| Ovarian ca. IGROV-1 | 9.0 | Stomach Pool | 3.0 |
| Ovarian ca. OVCAR-8 | 5.4 | Bone Marrow Pool | 1.2 |
| Ovary | 2.1 | Fetal Heart | 5.6 |
| Breast ca. MCF-7 | 12.0 | Heart Pool | 2.1 |
| Breast ca. MDA-MB-231 | 15.3 | Lymph Node Pool | 4.7 |
| Breast ca. BT 549 | 9.2 | Fetal Skeletal Muscle | 0.6 |
| Breast ca. T47D | 100.0 | Skeletal Muscle Pool | 1.7 |
| Breast ca. MDA-N | 15.2 | Spleen Pool | 4.8 |
| Breast Pool | 3.9 | Thymus Pool | 2.9 |
| Trachea | 3.0 | CNS cancer (glio/astro) U87-MG | 84.7 |
| Lung | 0.5 | CNS cancer (glio/astro) U-118-MG | 30.8 |
| Fetal Lung | 8.0 | CNS cancer (neuro; met) SK-N-AS | 14.5 |
| Lung ca. NCI-N417 | 1.5 | CNS cancer (astro) SF-539 | 13.1 |
| Lung ca. LX-1 | 10.9 | CNS cancer (astro) SNB-75 | 39.8 |
| Lung ca. NCI-H146 | 11.7 | CNS cancer (glio) SNB-19 | 9.8 |
| Lung ca. SHP-77 | 5.3 | CNS cancer (glio) SF-295 | 30.6 |
| Lung ca. A549 | 9.6 | Brain (Amygdala) Pool | 1.9 |
| Lung ca. NCI-H526 | 4.5 | Brain (cerebellum) | 1.4 |
| Lung ca. NCI-H23 | 25.7 | Brain (fetal) | 4.4 |
| Lung ca. NCI-H460 | 5.9 | Brain (Hippocampus) Pool | 2.1 |
| Lung ca. HOP-62 | 5.8 | Cerebral Cortex Pool | 2.7 |
| Lung ca. NCI-H522 | 8.8 | Brain (Substantia nigra) Pool | 1.9 |
| Liver | 0.6 | Brain (Thalamus) Pool | 2.8 |
| Fetal Liver | 11.1 | Brain (whole) | 2.4 |
| Liver ca. HepG2 | 6.2 | Spinal Cord Pool | 1.9 |
| Kidney Pool | 5.2 | Adrenal Gland | 2.5 |
| Fetal Kidney | 4.2 | Pituitary gland Pool | 0.7 |
| Renal ca. 786-0 | 44.1 | Salivary Gland | 0.8 |
| Renal ca. A498 | 10.2 | Thyroid (female) | 5.0 |
| Renal ca. ACHN | 6.4 | Pancreatic ca. CAPAN2 | 12.0 |
| Renal ca. UO-31 | 37.9 | Pancreas Pool | 5.6 |

TABLE HE

Panel 4.1D

| Tissue Name | Rel. Exp. (%) Ag3604, Run 169910577 | Tissue Name | Rel. Exp. (%) Ag3604, Run 169910577 |
|---|---|---|---|
| Secondary Th1 act | 14.2 | HUVEC IL-1beta | 8.5 |
| Secondary Th2 act | 18.0 | HUVEC IFN gamma | 5.2 |
| Secondary Tr1 act | 17.9 | HUVEC TNF alpha + IFN gamma | 7.4 |
| Secondary Th1 rest | 1.6 | HUVEC TNF alpha + IL4 | 11.3 |
| Secondary Th2 rest | 3.8 | HUVEC IL-11 | 1.8 |
| Secondary Tr1 rest | 2.5 | Lung Microvascular EC none | 8.0 |
| Primary Th1 act | 11.8 | Lung Microvascular EC TNF alpha + IL-1beta | 24.1 |
| Primary Th2 act | 13.6 | Microvascular Dermal EC none | 4.1 |
| Primary Tr1 act | 12.1 | Microvascular Dermal EC TNF alpha + IL-1beta | 12.2 |

TABLE HE-continued

Panel 4.1D

| Tissue Name | Rel. Exp. (%) Ag3604, Run 169910577 | Tissue Name | Rel. Exp. (%) Ag3604, Run 169910577 |
| --- | --- | --- | --- |
| Primary Th1 rest | 3.6 | Bronchial epithelium TNF alpha + 1beta | 11.7 |
| Primary Th2 rest | 3.4 | Small airway epithelium none | 4.2 |
| Primary Tr1 rest | 3.4 | Small airway epithelium TNF alpha + IL-1beta | 13.6 |
| CD45RA CD4 lymphocyte act | 13.5 | Coronery artery SMC rest | 37.1 |
| CD45RO CD4 lymphocyte act | 14.8 | Coronery artery SMC TNF alpha + IL-1beta | 48.6 |
| CD8 lymphocyte act | 14.1 | Astrocytes rest | 6.7 |
| Secondary CD8 lymphocyte rest | 11.9 | Astrocytes TNF alpha + IL-1beta | 15.1 |
| Secondary CD8 lymphocyte act | 7.2 | KU-812 (Basophil) rest | 9.3 |
| CD4 lymphocyte none | 1.6 | KU-812 (Basophil) PMA/ionomycin | 23.0 |
| 2ry Th1/Th2/Tr1_anti-CD95 CH11 | 2.8 | CCD1106 (Keratinocytes) none | 10.6 |
| LAK cells rest | 15.7 | CCD1106 (Keratinocytes) TNF alpha + IL-1beta | 16.2 |
| LAK cells IL-2 | 6.7 | Liver cirrhosis | 3.5 |
| LAK cells IL-2 + IL-12 | 7.2 | NCI-H292 none | 6.0 |
| LAK cells IL-2 + IFN gamma | 10.4 | NCI-H292 IL-4 | 13.3 |
| LAK cells IL-2 + IL-18 | 9.4 | NCI-H292 IL-9 | 13.6 |
| LAK cells PMA/ionomycin | 60.7 | NCI-H292 IL-13 | 12.5 |
| NK Cells IL-2 rest | 7.2 | NCI-H292 IFN gamma | 13.7 |
| Two Way MLR 3 day | 15.1 | HPAEC none | 5.3 |
| Two Way MLR 5 day | 13.1 | HPAEC TNF alpha + IL-1beta | 54.7 |
| Two Way MLR 7 day | 8.7 | Lung fibroblast none | 11.1 |
| PBMC rest | 1.6 | Lung fibroblast TNF alpha + IL-1beta | 7.4 |
| PBMC PWM | 12.8 | Lung fibroblast IL-4 | 18.6 |
| PBMC PHA-L | 10.1 | Lung fibroblast IL-9 | 24.7 |
| Ramos (B cell) none | 10.0 | Lung fibroblast IL-13 | 13.8 |
| Ramos (B cell) ionomycin | 8.4 | Lung fibroblast IFN gamma | 20.4 |
| B lymphocytes PWM | 9.7 | Dermal fibroblast CCD1070 rest | 11.8 |
| B lymphocytes CD40L and IL-4 | 6.7 | Dermal fibroblast CCD1070 TNF alpha | 23.2 |
| EOL-1 dbcAMP | 7.9 | Dermal fibroblast CCD1070 IL-1beta | 25.7 |
| EOL-1 dbcAMP PMA/ionomycin | 24.0 | Dermal fibroblast IFN gamma | 12.2 |
| Dendritic cells none | 23.3 | Dermal fibroblast IL-4 | 12.6 |
| Dendritic cells LPS | 28.7 | Dermal fibroblasts rest | 8.7 |
| Dendritic cells anti-CD40 | 18.6 | Neutrophils TNFa + LPS | 7.5 |
| Monocytes rest | 2.8 | Neutrophils rest | 0.6 |
| Monocytes LPS | 100.0 | Colon | 1.6 |
| Macrophages rest | 27.7 | Lung | 3.7 |
| Macrophages LPS | 24.8 | Thymus | 5.7 |
| HUVEC none | 3.5 | Kidney | 6.6 |
| HUVEC starved | 4.2 | | |

CNS_neurodegeneration_v1.0 Summary: Ag3604 This panel does not show differential expression of the CG59839-01 gene in Alzheimer's disease. However, this expression profile confirms the presence of this gene in the brain, with highest expression in the occipital cortex of a control patient (CT=28.5). Please see Panel 1.4 for discussion of utility of this gene in the central nervous system.

General_screening_panel_v1.4 Summary: Ag3604 Highest expression of the CG59839-01 gene is seen in a breast cancer cell line (CT=24). High levels of expression are also seen in all the cell lines on this panel. In addition, higher levels of expression are seen in the fetal tissue samples. Expression in fetal liver and lung (CTs=27) is significantly higher than in the adult liver and lung (CTs=31.5). Therefore, expression of this gene could be used to differentiate between the adult and fetal sources of these tissues. Furthermore, this expression profile suggests a role for this gene product in cell growth and proliferation.

Among tissues with metabolic function, this gene is expressed at moderate to low levels in pituitary, adipose, adrenal gland, pancreas, thyroid, and adult and fetal skeletal muscle, heart, and liver. This widespread expression among these tissues suggests that this gene product may play a role in normal neuroendocrine and metabolic and that disregulated expression of this gene may contribute to neuroendocrine disorders or metabolic diseases, such as obesity and diabetes.

This gene is also expressed at moderate levels in the CNS, including the hippocampus, thalamus, substantia nigra, amygdala, cerebellum and cerebral cortex. Therefore, therapeutic modulation of the expression or function of this gene may be useful in the treatment of neurologic disorders, such as Alzheimer's disease, Parkinson's disease, schizophrenia, multiple sclerosis, stroke and epilepsy.

Panel 4.1D Summary: Ag3604 Highest expression of the CG59839-01 gene is seen in LPS stimulated monocytes (CT=25.3). The protein encoded by this gene may therefore be involved in the activation of monocytes in their function as antigen-presenting cells. This suggests that therapeutics that block the function of this membrane protein may be useful as anti-inflammatory therapeutics for the treatment of autoimmune and inflammatory diseases. Furthermore, antibodies or small molecule therapeutics that stimulate the function of this protein may be useful therapeutics for the treatment of immunosupressed individuals.

This gene is also expressed at moderate to low levels in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. This ubiquitous pattern of expression suggests that this gene product may be involved in homeostatic processes for these and other cell types and tissues. This pattern is in agreement with the expression profile in General_screening_panel_v1.4 and also suggests a role for the gene product in cell survival and proliferation. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

I. CG59847-01: Novel Intracellular Protein

Expression of gene CG59847-01 was assessed using the primer-probe set Ag3608, described in Table IA. Results of the RTQ-PCR runs are shown in Tables IB, IC and ID.

TABLE IA

Probe Name Ag3608

| Primers | Sequences | Length | Start Position | SEQ ID NO: |
|---|---|---|---|---|
| Forward | 5'-cataacgaaatgaaggcagaaa-3' | 22 | 786 | 243 |
| Probe | TET-5'-tgttctttgaaaccaacaagaacaaaga-3'-TAMRA | 28 | 814 | 244 |
| Reverse | 5'-cccagagattctggtatgttgt-3' | 22 | 843 | 245 |

TABLE IB

CNS_neurodegeneration_v1.0

| Tissue Name | Rel. Exp. (%) Ag3608, Run 210998067 | Tissue Name | Rel. Exp. (%) Ag3608, Run 210998067 |
|---|---|---|---|
| AD 1 Hippo | 16.7 | Control (Path) 3 Temporal Ctx | 16.0 |
| AD 2 Hippo | 32.5 | Control (Path) 4 Temporal Ctx | 83.5 |
| AD 3 Hippo | 22.1 | AD 1 Occipital Ctx | 37.4 |
| AD 4 Hippo | 0.0 | AD 2 Occipital Ctx (Missing) | 0.9 |
| AD 5 hippo | 95.9 | AD 3 Occipital Ctx | 14.8 |
| AD 6 Hippo | 80.7 | AD 4 Occipital Ctx | 43.5 |
| Control 2 Hippo | 16.0 | AD 5 Occipital Ctx | 38.2 |
| Control 4 Hippo | 24.3 | AD 6 Occipital Ctx | 40.3 |
| Control (Path) 3 Hippo | 12.9 | Control 1 Occipital Ctx | 7.4 |
| AD 1 Temporal Ctx | 38.7 | Control 2 Occipital Ctx | 39.0 |
| AD 2 Temporal Ctx | 43.2 | Control 3 Occipital Ctx | 58.6 |
| AD 3 Temporal Ctx | 23.8 | Control 4 Occipital Ctx | 14.8 |
| AD 4 Temporal Ctx | 46.0 | Control (Path) 1 Occipital Ctx | 97.9 |
| AD 5 Inf Temporal Ctx | 98.6 | Control (Path) 2 Occipital Ctx | 51.1 |
| AD 5 SupTemporal Ctx | 91.4 | Control (Path) 3 Occipital Ctx | 4.6 |
| AD 6 Inf Temporal Ctx | 87.7 | Control (Path) 4 Occipital Ctx | 44.4 |
| AD 6 Sup Temporal Ctx | 100.0 | Control 1 Parietal Ctx | 20.7 |
| Control 1 Temporal Ctx | 18.2 | Control 2 Parietal Ctx | 87.7 |
| Control 2 Temporal Ctx | 21.5 | Control 3 Parietal Ctx | 20.7 |
| Control 3 Temporal Ctx | 42.6 | Control (Path) 1 Parietal Ctx | 87.1 |
| Control 4 Temporal Ctx | 27.0 | Control (Path) 2 Parietal Ctx | 0.0 |
| Control (Path) 1 Temporal Ctx | 90.1 | Control (Path) 3 Parietal Ctx | 12.9 |
| Control (Path) 2 Temporal Ctx | 93.3 | Control (Path) 4 Parietal Ctx | 71.2 |

TABLE IC

General_screening_panel_v1.4

| Tissue Name | Rel. Exp. (%) Ag3608, Run 217675976 | Tissue Name | Rel. Exp. (%) Ag3608, Run 217675976 |
|---|---|---|---|
| Adipose | 19.5 | Renal ca. TK-10 | 39.8 |
| Melanoma* Hs688(A).T | 16.5 | Bladder | 45.1 |
| Melanoma* Hs688(B).T | 11.8 | Gastric ca. (liver met.) NCI-N87 | 52.5 |
| Melanoma* M14 | 11.3 | Gastric ca. KATO III | 18.3 |
| Melanoma* LOXIMVI | 11.6 | Colon ca. SW-948 | 3.0 |
| Melanoma* SK-MEL-5 | 44.1 | Colon ca. SW480 | 26.6 |
| Squamous cell carcinoma SCC-4 | 17.0 | Colon ca.* (SW480 met) SW620 | 16.6 |
| Testis Pool | 17.7 | Colon ca. HT29 | 28.5 |
| Prostate ca.* (bone met) PC-3 | 30.6 | Colon ca. HCT-116 | 24.3 |
| Prostate Pool | 15.1 | Colon ca. CaCo-2 | 30.1 |
| Placenta | 4.0 | Colon cancer tissue | 25.0 |
| Uterus Pool | 9.7 | Colon ca. SW1116 | 5.3 |
| Ovarian ca. OVCAR-3 | 50.0 | Colon ca. Colo-205 | 4.4 |
| Ovarian ca. SK-OV-3 | 24.3 | Colon ca. SW-48 | 3.2 |
| Ovarian ca. OVCAR-4 | 3.6 | Colon Pool | 39.0 |
| Ovarian ca. OVCAR-5 | 65.1 | Small Intestine Pool | 53.2 |
| Ovarian ca. IGROV-1 | 9.5 | Stomach Pool | 18.6 |
| Ovarian ca. OVCAR-8 | 5.6 | Bone Marrow Pool | 26.2 |
| Ovary | 20.9 | Fetal Heart | 58.6 |
| Breast ca. MCF-7 | 18.2 | Heart Pool | 17.6 |
| Breast ca. MDA-MB-231 | 17.2 | Lymph Node Pool | 55.1 |
| Breast ca. BT 549 | 38.2 | Fetal Skeletal Muscle | 16.2 |
| Breast ca. T47D | 87.7 | Skeletal Muscle Pool | 22.1 |
| Breast ca. MDA-N | 16.6 | Spleen Pool | 27.2 |
| Breast Pool | 50.0 | Thymus Pool | 41.8 |
| Trachea | 13.4 | CNS cancer (glio/astro) U87-MG | 31.2 |
| Lung | 52.5 | CNS cancer (glio/astro) U-118-MG | 27.0 |
| Fetal Lung | 62.9 | CNS cancer (neuro; met) SK-N-AS | 21.9 |
| Lung ca. NCI-N417 | 54.3 | CNS cancer (astro) SF-539 | 13.0 |
| Lung ca. LX-1 | 27.2 | CNS cancer (astro) SNB-75 | 36.6 |
| Lung ca. NCI-H146 | 13.5 | CNS cancer (glio) SNB-19 | 11.6 |
| Lung ca. SHP-77 | 43.8 | CNS cancer (glio) SF-295 | 85.9 |
| Lung ca. A549 | 17.9 | Brain (Amygdala) Pool | 8.3 |
| Lung ca. NCI-H526 | 7.2 | Brain (cerebellum) | 15.8 |
| Lung ca. NCI-H23 | 26.8 | Brain (fetal) | 24.3 |
| Lung ca. NCI-H460 | 15.2 | Brain (Hippocampus) Pool | 14.1 |
| Lung ca. HOP-62 | 18.7 | Cerebral Cortex Pool | 17.8 |
| Lung ca. NCI-H522 | 26.8 | Brain (Substantia nigra) Pool | 9.8 |
| Liver | 0.9 | Brain (Thalamus) Pool | 26.1 |
| Fetal Liver | 15.5 | Brain (whole) | 10.4 |
| Liver ca. HepG2 | 11.6 | Spinal Cord Pool | 15.1 |
| Kidney Pool | 55.5 | Adrenal Gland | 8.5 |
| Fetal Kidney | 100.0 | Pituitary gland Pool | 9.2 |
| Renal ca. 786-0 | 23.7 | Salivary Gland | 6.0 |
| Renal ca. A498 | 17.8 | Thyroid (female) | 5.4 |
| Renal ca. ACHN | 28.9 | Pancreatic ca. CAPAN2 | 27.0 |
| Renal ca. UO-31 | 15.3 | Pancreas Pool | 44.4 |

TABLE ID

Panel 4.1D

| Tissue Name | Rel. Exp. (%) Ag3608, Run 169943567 | Tissue Name | Rel. Exp. (%) Ag3608, Run 169943567 |
|---|---|---|---|
| Secondary Th1 act | 16.8 | HUVEC IL-1beta | 18.8 |
| Secondary Th2 act | 33.2 | HUVEC IFN gamma | 27.4 |
| Secondary Tr1 act | 24.8 | HUVEC TNF alpha + IFN gamma | 7.9 |
| Secondary Th1 rest | 23.2 | HUVEC TNF alpha + IL4 | 9.8 |
| Secondary Th2 rest | 24.7 | HUVEC IL-11 | 15.6 |

TABLE ID-continued

Panel 4.1D

| Tissue Name | Rel. Exp. (%) Ag3608, Run 169943567 | Tissue Name | Rel. Exp. (%) Ag3608, Run 169943567 |
|---|---|---|---|
| Secondary Tr1 rest | 32.1 | Lung Microvascular EC none | 19.1 |
| Primary Th1 act | 32.8 | Lung Microvascular EC TNF alpha + IL-1beta | 19.9 |
| Primary Th2 act | 40.9 | Microvascular Dermal EC none | 17.6 |
| Primary Tr1 act | 34.4 | Microsvasular Dermal EC TNF alpha + IL-1beta | 9.7 |
| Primary Th1 rest | 24.5 | Bronchial epithelium TNF alpha + IL1beta | 18.4 |
| Primary Th2 rest | 28.1 | Small airway epithelium none | 6.3 |
| Primary Tr1 rest | 29.1 | Small airway epithelium TNF alpha + IL-1beta | 15.4 |
| CD45RA CD4 lymphocyte act | 20.7 | Coronery artery SMC rest | 9.6 |
| CD45RO CD4 lymphocyte act | 37.1 | Coronery artery SMC TNF alpha + IL-1beta | 12.2 |
| CD8 lymphocyte act | 27.9 | Astrocytes rest | 12.3 |
| Secondary CD8 lymphocyte rest | 28.9 | Astrocytes TNF alpha + IL-1beta | 11.8 |
| Secondary CD8 lymphocyte act | 14.2 | KU-812 (Basophil) rest | 18.7 |
| CD4 lymphocyte none | 24.3 | KU-812 (Basophil) PMA/ionomycin | 12.1 |
| 2ry Th1/Th2/Tr1_anti-CD95 CH11 | 16.3 | CCD1106 (Keratinocytes) none | 15.6 |
| LAK cells rest | 3.9 | CCD1106 (Keratinocytes) TNF alpha + IL-1beta | 14.1 |
| LAK cells IL-2 | 32.3 | Liver cirrhosis | 61.6 |
| LAK cells IL-2 + IL-12 | 32.5 | NCI-H292 none | 20.7 |
| LAK cells IL-2 + IFN gamma | 41.5 | NCI-H292 IL-4 | 30.4 |
| LAK cells IL-2 + IL-18 | 36.3 | NCI-H292 IL-9 | 42.6 |
| LAK cells PMA/ionomycin | 15.0 | NCI-H292 IL-13 | 22.8 |
| NK Cells IL-2 rest | 24.1 | NCI-H292 IFN gamma | 24.3 |
| Two Way MLR 3 day | 38.2 | HPAEC none | 23.8 |
| Two Way MLR 5 day | 19.2 | HPAEC TNF alpha + IL-1beta | 29.9 |
| Two Way MLR 7 day | 20.7 | Lung fibroblast none | 14.8 |
| PBMC rest | 11.7 | Lung fibroblast TNF alpha + IL-1beta | 9.2 |
| PBMC PWM | 22.4 | Lung fibroblast IL-4 | 15.7 |
| PBMC PHA-L | 16.4 | Lung fibroblast IL-9 | 19.1 |
| Ramos (B cell) none | 21.2 | Lung fibroblast IL-13 | 16.6 |
| Ramos (B cell) ionomycin | 24.8 | Lung fibroblast IFN gamma | 12.2 |
| B lymphocytes PWM | 18.3 | Dermal fibroblast CCD1070 rest | 26.8 |
| B lymphocytes CD40L and IL-4 | 24.8 | Dermal fibroblast CCD1070 TNF alpha | 37.6 |
| EOL-1 dbcAMP | 49.3 | Dermal fibroblast CCD1070 IL-1beta | 11.4 |
| EOL-1 dbcAMP PMA/ionomycin | 31.4 | Dermal fibroblast IFN gamma | 10.9 |
| Dendritic cells none | 16.4 | Dermal fibroblast IL-4 | 50.3 |
| Dendritic cells LPS | 10.3 | Dermal Fibroblasts rest | 14.3 |
| Dendritic cells anti-CD40 | 17.7 | Neutrophils TNFa + LPS | 13.0 |
| Monocytes rest | 10.7 | Neutrophils rest | 21.0 |
| Monocytes LPS | 29.5 | Colon | 27.9 |
| Macrophages rest | 8.2 | Lung | 15.6 |
| Macrophages LPS | 11.1 | Thymus | 100.0 |
| HUVEC none | 11.7 | Kidney | 40.9 |
| HUVEC starved | 27.7 | | |

CNS_neurodegeneration_v1.0 Summary: Ag3608 This panel does not show differential expression of the CG59847-01 gene in Alzheimer's disease. However, this expression profile confirms the presence of this gene in the brain. Please see Panel 1.4 for discussion of utility of this gene in the central nervous system.

General_screeningpanel_v1.4 Summary: Ag3608 The CG59847-01 gene is expressed ubiquitously throughout this panel, with highest expression in fetal kidney (CT=25.4). Overall, this expression profile suggests that this gene product may be involved in cellular growth and proliferation.

Among tissues with metabolic function, this gene is expressed at high to moderate levels in pituitary, adipose, adrenal gland, pancreas, thyroid, and adult and fetal skeletal muscle, heart, and liver. This widespread expression among these tissues suggests that this gene product may play a role in normal neuroendocrine and metabolic and that disregulated expression of this gene may contribute to neuroendocrine disorders or metabolic diseases, such as obesity and diabetes.

In addition, this gene is expressed at much higher levels in fetal liver tissue (CT=27) when compared to expression in the adult counterpart (CT=31). Thus, expression of this gene may be used to differentiate between the fetal and adult source of this tissue.

This gene is also expressed at high levels in the CNS, including the hippocampus, thalamus, substantia nigra, amygdala, cerebellum and cerebral cortex. Therefore, therapeutic modulation of the expression or function of this gene may be useful in the treatment of neurologic disorders, such as Alzheimer's disease, Parkinson's disease, schizophrenia, multiple sclerosis, stroke and epilepsy.

Panel 4.1D Summary: Ag3608 The CG59847-01 gene is expressed ubiquitously throughout this panel, with highest expression in the thymus (CT=28). In addition, this gene is expressed at high to moderate levels in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. This ubiquitous pattern of expression suggests that this gene product may be involved in homeostatic processes for these and other cell types and tissues. This pattern is in agreement with the expression profile in General_screening_panel_v1.4 and also suggests a role for the gene product in cell survival and proliferation. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

J. CG59905-01: Sushi Containing Membrane Protein

Expression of gene CG59905-01 was assessed using the primer-probe set Ag2443, described in Table JA. Results of the RTQ-PCR runs are shown in Tables JB, JC, JD, JE and JF.

TABLE JA

Probe Name Ag2443

| Primers | Sequences | Length | Start Position | SEQ ID NO: |
|---|---|---|---|---|
| Forward | 5'-cagtttgggaccgacttca-3' | 19 | 652 | 246 |
| Probe | TET-5'-caagactgtgagctatcagtgtaaccca-3'-TAMRA | 28 | 678 | 247 |
| Reverse | 5'-tgactgcttccatgacatagc-3' | 21 | 707 | 248 |

TABLE JB

CNS_neurodegeneration_v1.0

| Tissue Name | Rel. Exp. (%) Ag2443, Run 228397047 | Tissue Name | Rel. Exp. (%) Ag2443, Run 228397047 |
|---|---|---|---|
| AD 1 Hippo | 14.6 | Control (Path) 3 Temporal Ctx | 6.9 |
| AD 2 Hippo | 31.6 | Control (Path) 4 Temporal Ctx | 41.2 |
| AD 3 Hippo | 9.1 | AD 1 Occipital Ctx | 23.5 |
| AD 4 Hippo | 9.5 | AD 2 Occipital Ctx (Missing) | 0.0 |
| AD 5 Hippo | 100.0 | AD 3 Occipital Ctx | 8.1 |
| AD 6 Hippo | 34.6 | AD 4 Occipital Ctx | 31.0 |
| Control 2 Hippo | 22.7 | AD 5 Occipital Ctx | 39.2 |
| Control 4 Hippo | 7.4 | AD 6 Occipital Ctx | 19.8 |
| Control (Path) 3 Hippo | 5.8 | Control 1 Occipital Ctx | 3.0 |
| AD 1 Temporal Ctx | 13.8 | Control 2 Occipital Ctx | 52.5 |
| AD 2 Temporal Ctx | 36.1 | Control 3 Occipital Ctx | 36.9 |
| AD 3 Temporal Ctx | 11.3 | Control 4 Occipital Ctx | 8.7 |
| AD 4 Temporal Ctx | 33.7 | Control (Path) 1 Occipital Ctx | 94.0 |
| AD 5 Inf Temporal Ctx | 76.3 | Control (Path) 2 Occipital Ctx | 27.9 |
| AD 5 Sup Temporal Ctx | 40.9 | Control (Path) 3 Occipital Ctx | 2.2 |
| AD 6 Inf Temporal Ctx | 43.5 | Control (Path) 4 Occipital Ctx | 25.9 |
| AD 6 Sup Temporal Ctx | 52.5 | Control 1 Parietal Ctx | 8.7 |
| Control 1 Temporal Ctx | 10.1 | Control 2 Parietal Ctx | 37.4 |
| Control 2 Temporal Ctx | 36.1 | Control 3 Parietal Ctx | 25.5 |
| Control 3 Temporal Ctx | 27.7 | Control (Path) 1 Parietal Ctx | 81.8 |
| Control 3 Temporal Ctx | 15.7 | Control (Path) 2 Parietal Ctx | 32.8 |
| Control (Path) 1 Temporal Ctx | 65.1 | Control (Path) 3 Parietal Ctx | 5.5 |
| Control (Path) 2 Temporal Ctx | 50.7 | Control (Path) 4 Parietal Ctx | 62.0 |

TABLE JC

Panel 1.3D

| Tissue Name | Rel. Exp. (%) Ag2443, Run 165517738 | Tissue Name | Rel. Exp. (%) Ag2443, Run 165517738 |
|---|---|---|---|
| Liver adenocarcinoma | 16.6 | Kidney (fetal) | 2.5 |
| Pancreas | 0.0 | Renal ca. 786-0 | 0.0 |
| Pancreatic ca. CAPAN 2 | 0.0 | Renal ca. A498 | 0.0 |
| Adrenal gland | 1.5 | Renal ca. RXF 393 | 0.0 |
| Thyroid | 0.0 | Renal ca. ACHN | 0.0 |
| Salivary gland | 0.0 | Renal ca. UO-31 | 0.0 |
| Pituitary gland | 2.2 | Renal ca. TK-10 | 0.0 |
| Brain (fetal) | 51.4 | Liver | 0.0 |
| Brain (whole) | 92.0 | Liver (fetal) | 0.0 |
| Brain (amygdala) | 52.1 | Liver ca. (hepatoblast) HepG2 | 0.0 |
| Brain (cerebellum) | 47.6 | Lung | 0.0 |
| Brain (hippocampus) | 78.5 | Lung (fetal) | 1.4 |
| Brain (substantia nigra) | 8.0 | Lung ca. (small cell) LX-1 | 0.0 |
| Brain (thalamus) | 12.9 | Lung ca. (small cell) NCI-H69 | 0.0 |
| Cerebral Cortex | 100.0 | Lung ca. (s. cell var.) SHP-77 | 16.8 |
| Spinal cord | 6.5 | Lung ca. (large cell)NCI-H460 | 1.6 |
| glio/astro U87-MG | 0.0 | Lung ca. (non-sm. cell) A549 | 0.0 |
| glio/astro U-118-MG | 0.0 | Lung ca. (non-s. cell) NCI-H23 | 11.2 |
| astrocytoma SW1783 | 0.0 | Lung ca. (non-s. cell) HOP-62 | 0.0 |
| neuro*; met SK-N-AS | 0.0 | Lung ca. (non-s. cl) NCI-H522 | 0.0 |
| astrocytoma SF-539 | 0.0 | Lung ca. (squam.) SW 900 | 0.0 |
| astrocytoma SNB-75 | 0.0 | Lung ca. (squam.) NCI-H596 | 4.8 |
| glioma SNB-19 | 0.6 | Mammary gland | 2.1 |
| glioma U251 | 29.9 | Breast ca.* (pl. ef) MCF-7 | 0.0 |
| glioma SF-295 | 1.9 | Breast ca.* (pl. ef) MDA-MB-231 | 0.0 |
| Heart (fetal) | 0.0 | Breast ca.* (pl. ef) T47D | 10.9 |
| Heart | 0.0 | Breast ca. BT-549 | 0.0 |
| Skeletal muscle (fetal) | 6.2 | Breast ca. MDA-N | 9.3 |
| Skeletal muscle | 0.8 | Ovary | 1.1 |
| Bone marrow | 0.0 | Ovarian ca. OVCAR-3 | 11.5 |
| Thymus | 0.0 | Ovarian ca. OVCAR-4 | 0.0 |
| Spleen | 5.4 | Ovarian ca. OVCAR-5 | 0.0 |
| Lymph node | 0.5 | Ovarian ca. OVCAR-8 | 0.0 |
| Colorectal | 0.7 | Ovarian ca. IGROV-1 | 0.0 |
| Stomach | 0.0 | Ovarian ca.* (ascites) SK-OV-3 | 0.8 |
| Small intestine | 1.5 | Uterus | 2.8 |
| Colon ca. SW480 | 0.0 | Placenta | 2.9 |
| Colon ca.* SW620(SW480 met) | 0.0 | Prostate | 0.9 |
| Colon ca. HT29 | 0.0 | Prostate ca.* (bone met)PC-3 | 0.0 |
| Colon ca. HCT-116 | 0.0 | Testis | 20.9 |
| Colon ca. CaCo-2 | 0.0 | Melanoma Hs688(A).T | 0.0 |
| Colon ca. tissue(ODO3866) | 0.0 | Melanoma* (met) Hs688(B).T | 0.6 |
| Colon ca. HCC-2998 | 0.0 | Melanoma UACC-62 | 19.5 |
| Gastric ca.* (liver met) NCI-N87 | 0.0 | Melanoma M14 | 15.1 |
| Bladder | 1.2 | Melanoma LOX IMVI | 0.7 |
| Trachea | 2.0 | Melanoma* (met) SK-MEL-5 | 7.3 |
| Kidney | 4.1 | Adipose | 0.4 |

TABLE JD

Panel 2D

| Tissue Name | Rel. Exp. (%) Ag2443, Run 164988396 | Tissue Name | Rel. Exp. (%) Ag2443, Run 164988396 |
|---|---|---|---|
| Normal Colon | 12.6 | Kidney Margin 8120608 | 37.1 |
| CC Well to Mod Diff (ODO3866) | 1.2 | Kidney Cancer 8120613 | 0.0 |
| CC Margin (ODO3866) | 2.9 | Kidney Margin 8120614 | 31.6 |
| CC Gr.2 rectosigmoid (ODO3868) | 1.9 | Kidney Cancer 9010320 | 4.2 |
| CC Margin (ODO3868) | 3.2 | Kidney Margin 9010321 | 62.9 |
| CC Mod Diff (ODO3920) | 1.5 | Normal Uterus | 1.4 |
| CC Margin (ODO3920) | 2.6 | Uterus Cancer 064011 | 19.6 |
| CC Gr.2 ascend colon (ODO3921) | 9.3 | Normal Thyroid | 0.6 |
| CC Margin (ODO3921) | 2.9 | Thyroid Cancer 064010 | 6.6 |
| CC from Partial Hepatectomy (ODO4309) Mets | 0.0 | Thyroid Cancer A302152 | 0.0 |
| Liver Margin (ODO4309) | 0.0 | Thyroid Margin A302153 | 1.9 |
| Colon mets to lung (OD04451-01) | 2.5 | Normal Breast | 22.2 |
| Lung Margin (OD04451-02) | 18.0 | Breast Cancer (OD04566) | 0.8 |
| Normal Prostate 6546-1 | 4.2 | Breast Cancer (OD04590-01) | 2.6 |
| Prostate Cancer (OD04410) | 0.0 | Breast Cancer Mets (OD04590-03) | 2.0 |
| Prostate Margin (OD04410) | 5.3 | Breast Cancer Metastasis (OD04655-05) | 2.9 |
| Prostate Cancer (OD04720-01) | 6.0 | Breast Cancer 064006 | 4.3 |
| Prostate Margin (OD04720-02) | 4.5 | Breast Cancer 1024 | 6.5 |
| Normal Lung 061010 | 29.9 | Breast Cancer 9100266 | 6.5 |
| Lung Met to Muscle (ODO4286) | 2.4 | Breast Margin 9100265 | 15.7 |
| Muscle Margin (ODO4286) | 3.1 | Breast Cancer A209073 | 10.7 |
| Lung Malignant Cancer (OD03126) | 12.2 | Breast Margin A209073 | 31.4 |
| Lung Margin (OD03126) | 20.4 | Normal Liver | 0.0 |
| Lung Cancer (OD04404) | 3.0 | Liver Cancer 064003 | 26.6 |
| Lung Margin (OD04404) | 30.1 | Liver Cancer 1025 | 0.0 |
| Lung Cancer (OD04565) | 0.8 | Liver Cancer 1026 | 0.0 |
| Lung Margin (OD04565) | 9.0 | Liver Cancer 6004-T | 0.0 |
| Lung Cancer (OD04237-01) | 7.8 | Liver Tissue 6004-N | 29.1 |
| Lung Margin (OD04237-02) | 3.1 | Liver Cancer 6005-T | 0.0 |
| Ocular Mel Met to Liver (ODO4310) | 3.2 | Liver Tissue 6005-N | 0.0 |
| Liver Margin (ODO4310) | 1.1 | Normal Bladder | 0.4 |
| Melanoma Mets to Lung (OD04321) | 0.0 | Bladder Cancer 1023 | 0.0 |
| Lung Margin (OD04321) | 17.2 | Bladder Cancer A302173 | 39.0 |
| Normal Kidney | 100.0 | Bladder Cancer (OD04718-01) | 0.0 |
| Kidney Ca, Nuclear grade 2 (OD04338) | 0.0 | Bladder Normal Adjacent (OD04718-03) | 4.5 |
| Kidney Margin (OD04338) | 16.8 | Normal Ovary | 2.6 |
| Kidney Ca Nuclear grade 1/2 (OD04339) | 6.3 | Ovarian Cancer 064008 | 0.0 |
| Kidney Margin (OD04339) | 59.0 | Ovarian Cancer (OD04768-07) | 0.0 |
| Kidney Ca, Clear cell type (OD04340) | 10.7 | Ovary Margin (OD04768-08) | 0.0 |
| Kidney Margin (OD04340) | 38.4 | Normal Stomach | 2.2 |
| Kidney Ca, Nuclear grade 3 (OD04348) | 0.8 | Gastric Cancer 9060358 | 0.0 |
| Kidney Margin (OD04348) | 18.4 | Stomach Margin 9060359 | 1.3 |
| Kidney Cancer (OD04622-01) | 1.8 | Gastric Cancer 9060395 | 4.6 |
| Kidney Margin (OD04622-03) | 8.9 | Stomach Margin 9060394 | 5.3 |
| Kidney Cancer (OD04450-01) | 1.6 | Gastric Cancer 9060397 | 2.5 |
| Kidney Margin (OD04450-03) | 21.3 | Stomach Margin 9060396 | 0.8 |
| Kidney Cancer 8120607 | 0.0 | Gastric Cancer 064005 | 0.0 |

TABLE JE

Panel 4D

| Tissue Name | Rel. Exp. (%) Ag2443, Run 164337611 | Tissue Name | Rel. Exp. (%) Ag2443, Run 164337611 |
|---|---|---|---|
| Secondary Th1 act | 0.0 | HUVEC IL-1beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 0.0 | Microvasular Dermal EC TNF alpha + IL-1beta | 0.0 |
| Primary Th1 rest | 0.0 | Bronchial epithelium TNF alpha + IL1beta | 0.0 |
| Primary Th2 rest | 0.0 | Small airway epithelium none | 0.0 |
| Primary Tr1 rest | 0.0 | Small airway epithelium TNF alpha + IL-1beta | 0.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1beta | 0.0 |
| CD8 lymphocyte act | 0.0 | Astrocytes rest | 0.0 |
| Secondary CD8 lymphocyte rest | 0.0 | Astrocytes TNF alpha + IL-1beta | 0.0 |
| Secondary CD8 lymphocyte act | 0.0 | KU-812 (Basophil) rest | 0.7 |
| CD4 lymphocyte none | 0.0 | KU-812 (Basophil) PMA/ionomycin | 0.4 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1beta | 0.0 |
| LAK cells IL-2 | 0.0 | Liver cirrhosis | 0.2 |
| LAK cells IL-2 + IL-12 | 0.0 | Lupus kidney | 0.1 |
| LAK cells IL-2 + IFN gamma | 0.0 | NCI-H292 none | 0.0 |
| LAK cells IL-2 + IL-18 | 0.0 | NCI-H292 IL-4 | 0.0 |
| LAK cells PMA/ionomycin | 0.0 | NCI-H292 IL-9 | 0.0 |
| NK Cells IL-2 rest | 0.0 | NCI-H292 IL-13 | 0.0 |
| Two Way MLR 3 day | 0.0 | NCI-H292 IFN gamma | 0.0 |
| Two Way MLR 5 day | 0.0 | HPAEC none | 0.2 |
| Two Way MLR 7 day | 0.0 | HPAEC TNF alpha + IL-1beta | 0.1 |
| PBMC rest | 0.1 | Lung fibroblast none | 0.0 |
| PBMC PWM | 0.0 | Lung fibroblast TNF alpha + IL-1beta | 0.0 |
| PBMC PHA-L | 0.0 | Lung fibroblast IL-4 | 0.0 |
| Ramos (B cell) none | 35.6 | Lung fibroblast IL-9 | 0.0 |
| Ramos (B cell) ionomycin | 100.0 | Lung fibroblast IL-13 | 0.0 |
| B lymphocytes PWM | 0.0 | Lung fibroblast IFN gamma | 0.0 |
| B lymphocytes CD40L and IL-4 | 0.0 | Dermal fibroblast CCD1070 rest | 0.0 |
| EOL-1 dbcAMP | 0.5 | Dermal fibroblast CCD1070 TNF alpha | 0.0 |
| EOL-1 dbcAMP PMA/ionomycin | 0.0 | Dermal fibroblast CCD1070 IL-1beta | 0.0 |
| Dendritic cells none | 0.2 | Dermal fibroblast IFN gamma | 0.0 |
| Dendritic cells LPS | 0.0 | Dermal fibroblast IL-4 | 0.0 |
| Dendritic cells anti-CD40 | 0.0 | IBD Colitis 2 | 0.0 |
| Monocytes rest | 0.1 | IBD Crohn's | 0.0 |
| Monocytes LPS | 0.0 | Colon | 0.1 |
| Macrophages rest | 0.0 | Lung | 0.1 |
| Macrophages LPS | 0.0 | Thymus | 2.5 |
| HUVEC none | 0.0 | Kidney | 0.1 |
| HUVEC starved | 0.0 | | |

TABLE JF

Panel CNS_1

| Tissue Name | Rel. Exp. (%) Ag2443, Run 171656290 | Tissue Name | Rel. Exp. (%) Ag2443, Run 171656290 |
|---|---|---|---|
| BA4 Control | 21.0 | BA17 PSP | 14.1 |
| BA4 Control2 | 17.2 | BA17 PSP2 | 12.0 |
| BA4 Alzheimer's2 | 7.6 | Sub Nigra Control | 12.6 |
| BA4 Parkinson's | 42.9 | Sub Nigra Control2 | 6.5 |
| BA4 Parkinson's2 | 46.3 | Sub Nigra Alzheimer's2 | 2.3 |
| BA4 Huntington's | 18.8 | Sub Nigra Parkinson's2 | 9.7 |
| BA4 Huntington's2 | 17.0 | Sub Nigra Huntington's | 11.7 |
| BA4 PSP | 6.1 | Sub Nigra Huntington's2 | 9.2 |
| BA4 PSP2 | 19.1 | Sub Nigra PSP2 | 0.0 |
| BA4 Depression | 9.5 | Sub Nigra Depression | 0.0 |
| BA4 Depression2 | 2.9 | Sub Nigra Depression2 | 0.5 |
| BA7 Control | 27.9 | Glob Palladus Control | 5.9 |
| BA7 Control2 | 22.8 | Glob Palladus Control2 | 3.7 |
| BA7 Alzheimer's2 | 15.7 | Glob Palladus Alzheimer's | 4.5 |
| BA7 Parkinson's | 19.6 | Glob Palladus Alzheimer's2 | 3.2 |
| BA7 Parkinson's2 | 28.1 | Glob Palladus Parkinson's | 49.7 |
| BA7 Huntington's | 27.9 | Glob Palladus Parkinson's2 | 5.3 |
| BA7 Huntington's2 | 0.0 | Glob Palladus PSP | 1.0 |
| BA7 PSP | 24.7 | Glob Palladus PSP2 | 0.6 |
| BA7 PSP2 | 19.3 | Glob Palladus Depression | 1.6 |
| BA7 Depression | 13.0 | Temp Pole Control | 14.1 |
| BA9 Control | 14.2 | Temp Pole Control2 | 23.8 |
| BA9 Control2 | 31.6 | Temp Pole Alzheimer's | 4.4 |
| BA9 Alzheimer's | 3.3 | Temp Pole Alzheimer's2 | 7.8 |
| BA9 Alzheimer's2 | 22.5 | Temp Pole Parkinson's | 29.9 |
| BA9 Parkinson's | 31.4 | Temp Pole Parkinson's2 | 35.4 |
| BA9 Parkinson's2 | 38.7 | Temp Pole Huntington's | 24.7 |
| BA9 Huntington's | 29.1 | Temp Pole PSP | 1.8 |
| BA9 Huntington's2 | 21.8 | Temp Pole PSP2 | 5.6 |
| BA9 PSP | 7.4 | Temp Pole Depression2 | 8.5 |
| BA9 PSP2 | 4.6 | Cing Gyr Control | 46.7 |
| BA9 Depression | 6.0 | Cing Gyr Control2 | 17.9 |
| BA9 Depression2 | 8.6 | Cing Gyr Alzheimer's | 8.7 |
| BA17 Control | 54.3 | Cing Gyr Alzheimer's2 | 15.7 |
| BA17 Control2 | 28.5 | Cing Gyr Parkinson's | 13.1 |
| BA17 Alzheimer's2 | 21.9 | Cing Gyr Parkinson's2 | 21.9 |
| BA17 Parkinson's | 47.3 | Cing Gyr Huntington's | 24.3 |
| BA17 Parkinson's2 | 100.0 | Cing Gyr Huntington's2 | 13.4 |
| BA17 Huntington's | 34.9 | Cing Gyr PSP | 10.4 |
| BA17 Huntington's2 | 33.4 | Cing Gyr PSP2 | 4.4 |
| BA17 Depression | 13.8 | Cing Gyr Depression | 5.3 |
| BA17 Depression2 | 32.5 | Cing Gyr Depression2 | 4.9 |

CNS_neurodegeneration_v1.0 Summary: Ag2443 This panel confirms the expression of the CG59905-01 gene at low levels in the brains of an independent group of individuals. However, no differential expression of this gene was detected between Alzheimer's diseased postmortem brains and those of non-demented controls in this experiment. Please see Panel 1.4 for a discussion of the potential utility of this gene in treatment of central nervous system disorders. Results from a second experiment with the same probe and primer set are not included. The data suggests that there were experimental difficulties with this run.

Panel 1.3D Summary: Ag2443 Highest expression of the CG59905-01 gene is detected in cerebral cortex of brain (CT=30.9). In addition, high expression of this gene is observed exclusively in all the brain regions (CTs=31). Thus, expression of this gene can be used to distinguish these brain samples from other samples used in this panel. Low but significant expression is also seen in spinal cord region. Therefore, therapeutic modulation of the activity of this gene or its protein product, through the use of small molecule drugs, protein therapeutics or antibodies, might be beneficial in the treatment of central nervous system disorders such as Alzheimer's disease, Parkinson's disease, epilepsy, multiple sclerosis, schizophrenia and depression.

The CG59905-01 gene encodes a variant of cub and sushi multiple domains 1 protein (CSMD 1). A related protein, SEZ-6, has recently been shown to be associated with neuronal bursting activity of seizures (Shimizu-Nishikawa K, Kajiwara K, Kimura M, Katsuki M, Sugaya E. (1995) Cloning and expression of SEZ-6, a brain-specific and seizure-related cDNA. Brain Res Mol Brain Res 28(2):201–10). Thus, the protein encoded by the CG59905-01 may also play a role in neuronal siezures.

In addition, low to moderate expression of this gene is seen in melanoma, ovarian cancer OVCAR-3, breast cancer, lung cancer, liver adenocarcinoma and glioma U251 cell lines. Therefore, therapeutic modulation of the activity of this gene or its protein product, through the use of small molecule drugs, or antibodies, might be beneficial in the treatment of these cancers.

Significant expression is also detected in fetal skeletal muscle. Interestingly, this gene is expressed at much higher levels in fetal (CT=34.9) when compared to adult skeletal muscle (CT=37.9). This observation suggests that expression of this gene can be used to distinguish fetal from adult skeletal muscle. In addition, the relative overexpression of this gene in fetal skeletal muscle suggests that the protein product may enhance muscular growth or development in the fetus and thus may also act in a regenerative capacity in the adult. Therefore, therapeutic modulation of the GPCR encoded by this gene could be useful in treatment of muscle related diseases. More specifically, treatment of weak or dystrophic muscle with the protein encoded by this gene could restore muscle mass or function.

Panel 2D Summary: Ag2443 Highest expression of the CG59905-01 gene is detected in kidney (CT=31). Expression of this gene is down-regulated in kidney and lung cancer. In addition, there appears to be substantial expression in other samples derived from bladder cancer, liver cancer, uterine cancer, breast cancer, kidney cancer and lung cancer. The CG59905-01 gene encodes a variant of cub and sushi multiple domains 1 protein (CSMD1). Recently, CSMD1 has been shown to be a candidate for tumor suppressor of multiple types of cancer (Sun P C, Uppaluri R, Schmidt A P, Pashia M E, Quant E C, Sunwoo J B, Gollin S M, Scholnick S B. (2001) Transcript map of the 8p23 putative tumor suppressor region. Genomics 75(1–3):17–25). Therefore, therapeutic modulation of the activity of this gene or its protein product, through the use of small molecule drugs, or antibodies, might be beneficial in the treatment of bladder, liver, uterine, breast, kidney and lung cancers.

Panel 4D Summary: Ag2443 Highest expression of the CG59905-01 gene is seen y in Ramos B cells (CTs=26–27). Thus, expression of this gene can be used to distinguish these samples from other samples in this panel. In addition, expression of this gene in B cells suggests that this gene may be involved in rheumatic disease including rheumatoid arthritis, lupus, osteoarthritis, and hyperproliferative B cell disorders.

Low but significant expression of this gene is also detected in thymus. Therefore, drugs that inhibit the function of this protein may regulate T cell development in the thymus and reduce or eliminate the symptoms of T cell mediated autoimmune or inflammatory diseases, including asthma, allergies, inflammatory bowel disease, lupus erythematosus, or rheumatoid arthritis. Additionally, small molecule or antibody therapeutics designed against this putative protein may disrupt T cell development in the thymus and function as an immunosuppresant for tissue transplant.

Panel CNS_1 Summary: Ag2443 This panel confirms the expression of the CG59905-01 gene at low levels in the brains of an independent group of individuals. Please see Panel 1.4 for a discussion of the potential utility of this gene in treatment of central nervous system disorders.

K. CG59930-01 and CG59930-02: Leucine-Rich Repeat-Containing Protein

Expression of gene CG59930-01 and full length clone CG59930-02 was assessed using the primer-probe sets Ag1106 and Ag1614, described in Tables KA and KB. Results of the RTQ-PCR runs are shown in Tables KC, KD, KE, KF and KG. Please note that CG59930-02 represents a full-length physical clone of the CG59930-01 gene, validating the prediction of the gene sequence.

TABLE KA

Probe Name Ag1106

| Primers | Sequences | Length | Start Position | SEQ ID NO: |
|---|---|---|---|---|
| Forward | 5'-ccagggattggactgcttac-3' | 20 | 614 | 249 |
| Probe | TET-5'-caacaaaatcaagactgtccccaagga-3'-TAMRA | 27 | 661 | 250 |
| Reverse | 5'-tctccaagctggcacaatta-3' | 20 | 694 | 251 |

TABLE KB

Probe Name Ag1614

| Primers | Sequences | Length | Start Position | SEQ ID NO: |
|---|---|---|---|---|
| Forward | 5'-tgaaaattcctgaattcattgg-3' | 22 | 534 | 252 |
| Probe | TET-5'-ccagaacctcattgtgttagatttatctcg-3'-TAMRA | 30 | 562 | 253 |
| Reverse | 5'-ccctggtggtatctctgaaatt-3' | 22 | 598 | 254 |

TABLE KC

Panel 1.3D

| Tissue Name | Rel. Exp. (%) Ag1614, Run 165920458 | Tissue Name | Rel. Exp. (%) Ag1614, Run 165920458 |
|---|---|---|---|
| Liver adenocarcinoma | 0.0 | Kidney (fetal) | 0.1 |
| Pancreas | 0.2 | Renal ca. 786-0 | 0.0 |
| Pancreatic ca. CAPAN 2 | 0.3 | Renal ca. A498 | 0.1 |
| Adrenal gland | 0.3 | Renal ca. RXF 393 | 0.0 |
| Thyroid | 0.4 | Renal ca. ACHN | 0.1 |
| Salivary gland | 0.5 | Renal ca. UO-31 | 0.0 |
| Pituitary gland | 0.5 | Renal ca. TK-10 | 0.1 |

TABLE KC-continued

Panel 1.3D

| Tissue Name | Rel. Exp. (%) Ag1614, Run 165920458 | Tissue Name | Rel. Exp. (%) Ag1614, Run 165920458 |
|---|---|---|---|
| Brain (fetal) | 0.6 | Liver | 0.2 |
| Brain (whole) | 1.8 | Liver (fetal) | 0.1 |
| Brain (amygdala) | 1.3 | Liver ca. (hepatoblast) HepG2 | 0.0 |
| Brain (cerebellum) | 1.2 | Lung | 0.1 |
| Brain (hippocampus) | 1.1 | Lung (fetal) | 0.3 |
| Brain (substantia nigra) | 0.9 | Lung ca. (small cell) LX-1 | 0.1 |
| Brain (thalamus) | 2.4 | Lung ca. (small cell) NCI-H69 | 0.1 |
| Cerebral Cortex | 0.1 | Lung ca. (s.cell var.) SHP-77 | 0.0 |
| Spinal cord | 0.4 | Lung ca. (large cell) NCI-H460 | 0.0 |
| glio/astro U87-MG | 0.1 | Lung ca. (non-sm. cell) A549 | 0.0 |
| glio/astro U-118-MG | 0.0 | Lung ca. (non-s.cell) NCI-H23 | 0.2 |
| astrocytoma SW1783 | 0.2 | Lung ca. (non-s.cell) HOP-62 | 0.1 |
| neuro; met SK-N-AS | 0.0 | Lung ca. (non-s.cl) NCI-H522 | 0.0 |
| astrocytoma SF-539 | 0.4 | Lung ca. (squam.) SW 900 | 0.2 |
| astrocytoma SNB-75 | 0.0 | Lung ca. (squam.) NCI-H596 | 0.1 |
| glioma SNB-19 | 0.4 | Mammary gland | 0.0 |
| glioma U251 | 0.3 | Breast ca.* (pl.ef) MCF-7 | 0.2 |
| glioma SF-295 | 0.1 | Breast ca.* (pl.ef) MDA-MB-231 | 0.0 |
| Heart (fetal) | 3.1 | Breast ca.* (pl.ef) T47D | 0.3 |
| Heart | 18.0 | Breast ca. BT-549 | 0.0 |
| Skeletal muscle (fetal) | 1.5 | Breast ca. MDA-N | 0.0 |
| Skeletal muscle | 100.0 | Ovary | 0.0 |
| Bone marrow | 0.1 | Ovarian ca. OVCAR-3 | 0.1 |
| Thymus | 0.5 | Ovarian ca. OVCAR-4 | 0.1 |
| Spleen | 1.0 | Ovarian ca. OVCAR-5 | 0.0 |
| Lymph node | 0.2 | Ovarian ca. OVCAR-8 | 0.0 |
| Colorectal | 0.0 | Ovarian ca. IGROV-1 | 0.1 |
| Stomach | 0.3 | Ovarian ca.* (ascites) SK-OV-3 | 0.2 |
| Small intestine | 0.2 | Uterus | 0.0 |
| Colon ca. SW480 | 0.1 | Placenta | 0.2 |
| Colon ca.* SW620(SW480 met) | 0.2 | Prostate | 0.2 |
| Colon ca. HT29 | 0.0 | Prostate ca.* (bone met)PC-3 | 0.2 |
| Colon ca. HCT-116 | 0.0 | Testis | 0.8 |
| Colon ca. CaCo-2 | 0.0 | Melanoma Hs688(A).T | 0.0 |
| Colon ca. tissue(ODO3866) | 0.1 | Melanoma* (met) Hs688(B).T | 0.1 |
| Colon ca. HCC-2998 | 0.0 | Melanoma UACC-62 | 0.0 |
| Gastric ca.* (liver met) NCI-N87 | 0.1 | Melanoma M14 | 0.1 |
| Bladder | 0.3 | Melanoma LOX IMVI | 0.0 |
| Trachea | 0.1 | Melanoma* (met) SK-MEL-5 | 0.9 |
| Kidney | 0.2 | Adipose | 0.8 |

TABLE KD

Panel 2.2

| Tissue Name | Rel. Exp. (%) Ag1614, Run 173968961 | Tissue Name | Rel. Exp. (%) Ag1614, Run 173968961 |
|---|---|---|---|
| Normal Colon | 3.5 | Kidney Margin (OD04348) | 20.9 |
| Colon cancer (OD06064) | 1.9 | Kidney malignant cancer (OD06204B) | 0.0 |
| Colon Margin (OD06064) | 0.5 | Kidney normal adjacent tissue (OD06204E) | 1.9 |

TABLE KD-continued

Panel 2.2

| Tissue Name | Rel. Exp. (%) Ag1614, Run 173968961 | Tissue Name | Rel. Exp. (%) Ag1614, Run 173968961 |
|---|---|---|---|
| Colon cancer (OD06159) | 0.0 | Kidney Cancer (OD04450-01) | 6.7 |
| Colon Margin (OD06159) | 2.0 | Kidney Margin (OD04450-03) | 8.8 |
| Colon cancer (OD06297-04) | 0.0 | Kidney Cancer 8120613 | 0.0 |
| Colon Margin (OD06297-05) | 5.7 | Kidney Margin 8120614 | 1.2 |
| CC Gr.2 ascend colon (ODO3921) | 0.0 | Kidney Cancer 9010320 | 0.0 |
| CC Margin (ODO3921) | 2.8 | Kidney Margin 9010321 | 1.4 |
| Colon cancer metastasis (OD06104) | 1.2 | Kidney Cancer 8120607 | 0.0 |
| Lung Margin (OD06104) | 23.7 | Kidney Margin 8120608 | 0.0 |
| Colon mets to lung (OD04451-01) | 26.6 | Normal Uterus | 10.7 |
| Lung Margin (OD04451-02) | 7.2 | Uterine Cancer 064011 | 1.1 |
| Normal Prostate | 5.6 | Normal Thyroid | 5.2 |
| Prostate Cancer (OD04410) | 2.0 | Thyroid Cancer 064010 | 0.5 |
| Prostate Margin (OD04410) | 0.0 | Thyroid Cancer A302152 | 3.8 |
| Normal Ovary | 0.0 | Thyroid Margin A302153 | 2.2 |
| Ovarian cancer (OD06283-03) | 0.0 | Normal Breast | 7.0 |
| Ovarian Margin (OD06283-07) | 0.0 | Breast Cancer (OD04566) | 3.2 |
| Ovarian Cancer 064008 | 4.0 | Breast Cancer 1024 | 3.8 |
| Ovarian cancer (OD06145) | 0.0 | Breast Cancer (OD04590-01) | 2.5 |
| Ovarian Margin (OD06145) | 2.1 | Breast Cancer Mets (OD04590-03) | 1.5 |
| Ovarian cancer (OD06455-03) | 3.6 | Breast Cancer Metastasis (OD04655-05) | 8.1 |
| Ovarian Margin (OD06455-07) | 0.0 | Breast Cancer 064006 | 10.2 |
| Normal Lung | 6.1 | Breast Cancer 9100266 | 0.0 |
| Invasive poor diff. lung adeno (ODO4945-01 | 5.6 | Breast Margin 9100265 | 1.5 |
| Lung Margin (ODO4945-03) | 25.7 | Breast Cancer A209073 | 0.5 |
| Lung Malignant Cancer (OD03126) | 2.4 | Breast Margin A2090734 | 1.7 |
| Lung Margin (OD03126) | 4.3 | Breast cancer (OD06083) | 15.5 |
| Lung Cancer (OD05014A) | 0.5 | Breast cancer node metastasis (OD06083) | 5.2 |
| Lung Margin (OD05014B) | 7.3 | Normal Liver | 6.8 |
| Lung cancer (OD06081) | 4.6 | Liver Cancer 1026 | 0.0 |
| Lung Margin (OD06081) | 16.6 | Liver Cancer 1025 | 4.2 |
| Lung Cancer (OD04237-01) | 3.1 | Liver Cancer 6004-T | 2.2 |
| Lung Margin (OD04237-02) | 6.0 | Liver Tissue 6004-N | 1.7 |
| Ocular Melanoma Metastasis | 100.0 | Liver Cancer 6005-T | 0.0 |
| Ocular Melanoma Margin (Liver) | 8.8 | Liver Tissue 6005-N | 0.0 |
| Melanoma Metastasis | 3.2 | Liver Cancer 064003 | 5.3 |
| Melanoma Margin (Lung) | 4.7 | Normal Bladder | 4.7 |
| Normal Kidney | 6.3 | Bladder Cancer 1023 | 0.0 |
| Kidney Ca, Nuclear grade 2 (OD04338) | 26.1 | Bladder Cancer A302173 | 1.3 |
| Kidney Margin (OD04338) | 5.6 | Normal Stomach | 5.8 |
| Kidney Ca Nuclear grade 1/2 (OD04339) | 20.4 | Gastric Cancer 9060397 | 0.0 |
| Kidney Margin (OD04339) | 3.8 | Stomach Margin 9060396 | 0.0 |
| Kidney Ca, Clear cell type (OD04340) | 1.2 | Gastric Cancer 9060395 | 1.6 |
| Kidney Margin (OD04340) | 11.0 | Stomach Margin 9060394 | 1.4 |
| Kidney Ca, Nuclear grade 3 (OD04348) | 1.2 | Gastric Cancer 064005 | 1.2 |

TABLE KE

Panel 3D

| Tissue Name | Rel. Exp. (%) Ag1614, Run 170188914 | Tissue Name | Rel. Exp. (%) Ag1614, Run 170188914 |
|---|---|---|---|
| Daoy-Medulloblastoma | 0.0 | Ca Ski-Cervical epidermoid carcinoma (metastasis) | 0.1 |
| TE671-Medulloblastoma | 0.0 | ES-2-Ovarian clear cell carcinoma | 0.0 |
| D283 Med-Medulloblastoma | 0.1 | Ramos-Stimulated with PMA/ionomycin 6 h | 0.0 |
| PFSK-1-Primitive Neuroectodermal | 0.0 | Ramos-Stimulated with PMA/ionomycin 14 h | 0.0 |
| XF-498-CNS | 0.0 | MEG-01-Chronic myelogenous leukemia (megokaryoblast) | 0.1 |
| SNB-78-Glioma | 0.0 | Raji-Burkitt's lymphoma | 0.0 |
| SF-268-Glioblastoma | 0.0 | Daudi-Burkitt's lymphoma | 0.0 |
| T98G-Glioblastoma | 0.0 | U266-B-cell plasmacytoma | 0.1 |
| SK-N-SH-Neuroblastoma (metastasis) | 0.0 | CA46-Burkitt's lymphoma | 0.0 |
| SF-295-Glioblastoma | 0.0 | RL-non-Hodgkin's B-cell lymphoma | 0.0 |
| Cerebellum | 0.3 | JM1-pre-B-cell lymphoma | 0.0 |
| Cerebellum | 0.0 | Jurkat-T cell leukemia | 0.0 |
| NCI-H292-Mucoepidermoid lung carcinoma | 100.0 | TF-1-Erythroleukemia | 0.1 |
| DMS-114-Small cell lung cancer | 0.0 | HUT 78-T-cell lymphoma | 0.0 |
| DMS-79-Small cell lung cancer | 0.6 | U937-Histiocytic lymphoma | 0.0 |
| NCI-H146-Small cell lung cancer | 0.2 | KU-812-Myelogenous leukemia | 0.1 |
| NCI-H526-Small cell lung cancer | 0.1 | 769-P-Clear cell renal carcinoma | 0.0 |
| NCI-N417-Small cell lung cancer | 0.0 | Caki-2-Clear cell renal carcinoma | 0.0 |
| NCI-H82-Small cell lung cancer | 0.0 | SW 839-Clear cell renal carcinoma | 0.0 |
| NCI-H157-Squamous cell lung cancer (metastasis) | 0.0 | G401-Wilms' tumor | 0.0 |
| NCI-H1155-Large cell lung cancer | 0.0 | Hs766T-Pancreatic carcinoma (LN metastasis) | 0.0 |
| NCI-H1299-Large cell lung cancer | 0.0 | CAPAN-1-Pancreatic adenocarcinoma (liver metastasis) | 0.0 |
| NCI-H727-Lung carcinoid | 0.0 | SU86.86-Pancreatic carcinoma (liver metastasis) | 0.1 |
| NCI-UMC-11-Lung carcinoid | 0.0 | BxPC-3-Pancreatic adenocarcinoma | 0.0 |
| LX-1-Small cell lung cancer | 0.1 | HPAC-Pancreatic adenocarcinoma | 0.0 |
| Colo-205-Colon cancer | 0.0 | MIA PaCa-2-Pancreatic carcinoma | 0.0 |
| KM12-Colon cancer | 0.0 | CFPAC-1-Pancreatic ductal adenocarcinoma | 0.0 |
| KM20L2-Colon cancer | 0.0 | PANC-1-Pancreatic epithelioid ductal carcinoma | 0.0 |
| NCI-H716-Colon cancer | 0.0 | T24-Bladder carcinma (transitional cell) | 0.1 |
| SW-48-Colon adenocarcinoma | 0.0 | 5637-Bladder carcinoma | 0.0 |
| SW1116-Colon adenocarcinoma | 0.0 | HT-1197-Bladder carcinoma | 0.0 |
| LS 174T-Colon adenocarcinoma | 0.0 | UM-UC-3-Bladder carcinma (transitional cell) | 0.0 |
| SW-948-Colon adenocarcinoma | 0.0 | A204-Rhabdomyosarcoma | 0.0 |
| SW-480-Colon adenocarcinoma | 0.0 | HT-1080-Fibrosarcoma | 0.0 |
| NCI-SNU-5-Gastric carcinoma | 0.0 | MG-63-Osteosarcoma | 0.0 |
| KATO III-Gastric carcinoma | 0.0 | SK-LMS-1-Leiomyosarcoma (vulva) | 0.1 |
| NCI-SNU-16-Gastric carcinoma | 0.0 | SJRH30-Rhabdomyosarcoma (met to bone marrow) | 0.0 |
| NCI-SNU-1-Gastric carcinoma | 0.0 | A431-Epidermoid carcinoma | 0.0 |
| RF-1-Gastric adenocarcinoma | 0.0 | WM266-4-Melanoma | 0.0 |
| RF-48-Gastric adenocarcinoma | 0.0 | DU 145-Prostate carcinoma (brain metastasis) | 0.0 |

TABLE KE-continued

Panel 3D

| Tissue Name | Rel. Exp. (%) Ag1614, Run 170188914 | Tissue Name | Rel. Exp. (%) Ag1614, Run 170188914 |
|---|---|---|---|
| MKN-45-Gastric carcinoma | 0.0 | MDA-MB-468-Breast adenocarcinoma | 0.1 |
| NCI-N87-Gastric carcinoma | 0.0 | SCC-4-Squamous cell carcinoma of tongue | 0.0 |
| OVCAR-5-Ovarian carcinoma | 0.0 | SCC-9-Squamous cell carcinoma of tongue | 0.0 |
| RL95-2-Uterine carcinoma | 0.0 | SCC-15-Squamous cell carcinoma of tongue | 0.0 |
| HelaS3-Cervical adenocarcinoma | 0.0 | CAL 27-Squamous cell carcinoma of tongue | 0.0 |

TABLE KF

Panel 4D

| Tissue Name | Rel. Exp. (%) Ag1614, Run 165762852 | Tissue Name | Rel. Exp. (%) Ag1614, Run 165762852 |
|---|---|---|---|
| Secondary Th1 act | 13.9 | HUVEC IL-1beta | 11.5 |
| Secondary Th2 act | 19.5 | HUVEC IFN gamma | 9.0 |
| Secondary Tr1 act | 25.5 | HUVEC TNF alpha + IFN gamma | 3.6 |
| Secondary Th1 rest | 39.2 | HUVEC TNF alpha + IL4 | 1.4 |
| Secondary Th2 rest | 17.0 | HUVEC IL-11 | 3.1 |
| Secondary Tr1 rest | 19.5 | Lung Microvascular EC none | 5.2 |
| Primary Th1 act | 10.8 | Lung Microvascular EC TNF alpha + IL-1beta | 3.1 |
| Primary Th2 act | 12.8 | Microvascular Dermal EC none | 12.7 |
| Primary Tr1 act | 25.7 | Microsvascular Dermal EC TNF alpha + IL-1beta | 5.7 |
| Primary Th1 rest | 77.4 | Bronchial epithelium TNF alpha + IL1beta | 10.9 |
| Primary Th2 rest | 40.3 | Small airway epithelium none | 6.7 |
| Primary Tr1 rest | 17.2 | Small airway epithelium TNF alpha + IL-1beta | 25.2 |
| CD45RA CD4 lymphocyte act | 21.0 | Coronery artery SMC rest | 6.0 |
| CD45RO CD4 lymphocyte act | 28.3 | Coronery artery SMC TNF alpha + IL-1beta | 6.7 |
| CD8 lymphocyte act | 34.2 | Astrocytes rest | 19.9 |
| Secondary CD8 lymphocyte rest | 19.8 | Astrocytes TNF alpha + IL-1beta | 18.3 |
| Secondary CD8 lymphocyte act | 11.7 | KU-812 (Basophil) rest | 15.2 |
| CD4 lymphocyte none | 33.9 | KU-812 (Basophil) PMA/ionomycin | 67.4 |
| 2ry Th1/Th2/Tr1_anti-CD95 CH11 | 40.6 | CCD1106 (Keratinocytes) none | 2.9 |
| LAK cells rest | 8.1 | CCD1106 (Keratinocytes) TNF alpha + IL-1beta | 10.9 |
| LAK cells IL-2 | 33.2 | Liver cirrhosis | 28.5 |
| LAK cells IL-2 + IL-12 | 13.8 | Lupus kidney | 8.5 |
| LAK cells IL-2 + IFN gamma | 39.8 | NCI-H292 none | 27.7 |
| LAK cells IL-2 + IL-18 | 25.3 | NCI-H292 IL-4 | 28.1 |
| LAK cells PMA/ionomycin | 3.0 | NCI-H292 IL-9 | 19.5 |
| NK Cells IL-2 rest | 19.2 | NCI-H292 IL-13 | 20.3 |
| Two Way MLR 3 day | 22.1 | NCI-H292 IFN gamma | 12.1 |
| Two Way MLR 5 day | 16.3 | HPAEC none | 9.1 |
| Two Way MLR 7 day | 15.5 | HPAEC TNF alpha + IL-1beta | 3.3 |
| PBMC rest | 16.3 | Lung fibroblast none | 12.3 |
| PBMC PWM | 14.1 | Lung fibroblast TNF alpha + IL-1beta | 11.5 |
| PBMC PHA-L | 18.9 | Lung fibroblast IL-4 | 7.3 |
| Ramos (B cell) none | 12.9 | Lung fibroblast IL-9 | 10.2 |
| Ramos (B cell) ionomycin | 22.1 | Lung fibroblast IL-13 | 8.7 |
| B lymphocytes PWM | 26.4 | Lung fibroblast IFN gamma | 5.6 |
| B lymphocytes CD40L and IL-4 | 100.0 | Dermal fibroblast CCD1070 rest | 15.4 |

TABLE KF-continued

Panel 4D

| Tissue Name | Rel. Exp. (%) Ag1614, Run 165762852 | Tissue Name | Rel. Exp. (%) Ag1614, Run 165762852 |
|---|---|---|---|
| EOL-1 dbcAMP | 10.4 | Dermal fibroblast CCD1070 TNF alpha | 20.9 |
| EOL-1 dbcAMP PMA/ionomycin | 8.0 | Dermal fibroblast CCD1070 IL-1beta | 2.3 |
| Dendritic cells none | 16.0 | Dermal fibroblast IFN gamma | 4.6 |
| Dendritic cells LPS | 9.3 | Dermal fibroblast IL-4 | 7.1 |
| Dendritic cells anti-CD40 | 18.0 | IBD Colitis 2 | 3.9 |
| Monocytes rest | 33.0 | IBD Crohn's | 19.1 |
| Monocytes LPS | 2.9 | Colon | 27.4 |
| Macrophages rest | 26.4 | Lung | 13.0 |
| Macrophages LPS | 13.2 | Thymus | 33.4 |
| HUVEC none | 8.6 | Kidney | 51.8 |
| HUVEC starved | 12.0 | | |

TABLE KG

Panel 5D

| Tissue Name | Rel. Exp. (%) Ag1614, Run 169269227 | Tissue Name | Rel. Exp. (%) Ag1614, Run 169269227 |
|---|---|---|---|
| 97457_Patient-02go_adipose | 0.3 | 94709_Donor 2 AM - A_adipose | 0.2 |
| 97476_Patient-07sk_skeletal muscle | 10.0 | 94710_Donor 2 AM - B_adipose | 0.1 |
| 97477_Patient-07ut_uterus | 0.3 | 94711_Donor 2 AM - C_adipose | 0.3 |
| 97478_Patient-07pl_placenta | 1.3 | 94712_Donor 2 AD - A_adipose | 0.5 |
| 97481_Patient-08sk_skeletal muscle | 17.4 | 94713_Donor 2 AD - B_adipose | 0.3 |
| 97482_Patient-08ut_uterus | 0.0 | 94714_Donor 2 AD - C_adipose | 0.4 |
| 97483_Patient-08pl_placenta | 1.1 | 94742_Donor 3 U - A_Mesenchymal Stem Cells | 0.0 |
| 97486_Patient-09sk_skeletal muscle | 23.3 | 94743_Donor 3 U - B_Mesenchymal Stem Cells | 0.1 |
| 97487_Patient-09ut_uterus | 0.4 | 94730_Donor 3 AM - A_adipose | 0.0 |
| 97488_Patient-09pl_placenta | 0.7 | 94731_Donor 3 AM - B_adipose | 0.1 |
| 97492_Patient-10ut_uterus | 0.0 | 94732_Donor 3 AM - C_adipose | 0.4 |
| 97493_Patient-10pl_placenta | 1.6 | 94733_Donor 3 AD - A_adipose | 0.3 |
| 97495_Patient-11go_adipose | 0.3 | 94734_Donor 3 AD - B_adipose | 0.1 |
| 97496_Patient-11sk_skeletal muscle | 88.3 | 94735_Donor 3 AD - C_adipose | 0.1 |
| 97497_Patient-11ut_uterus | 0.1 | 77138_Liver_HepG2untreated | 0.2 |
| 97498_Patient-11pl_placenta | 0.5 | 73556_Heart_Cardiac stromal cells (primary) | 0.0 |
| 97500_Patient-12go_adipose | 0.3 | 81735_Small Intestine | 0.5 |
| 97501_Patient-12sk_skeletal muscle | 100.0 | 72409_Kidney_Proximal Convoluted Tubule | 0.1 |
| 97502_Patient-12ut_uterus | 0.3 | 82685_Small intestine_Duodenum | 0.1 |
| 97503_Patient-12pl_placenta | 1.1 | 90650_Adrenal_Adrenocortical adenoma | 0.6 |
| 94721_Donor 2 U - A_Mesenchymal Stem Cells | 0.0 | 72410_Kidney_HRCE | 0.4 |
| 94722_Donor 2 U - B_Mesenchymal Stem Cells | 0.2 | 72411_Kidney_HRE | 0.1 |
| 94723_Donor 2 U - C_Mesenchymal Stem Cells | 0.1 | 73139_Uterus_Uterine smooth muscle cells | 0.2 |

Panel 1.3D Summary: Ag1614 Expression of the CG59930-01 gene is limited to a few samples with highest expression in skeletal muscle (CT=27). Moderate levels of expression are seen in heart and low but significant levels are seen in fetal heart, fetal skeletal muscle, amygdala, thalamus, cerebellum, substantia nigra and hippocampus. Thus, expression of this gene could be used to differentiate skeletal muscle from other samples on this panel, particularly from fetal skeletal muscle (CT=33.8), and as a marker of skeletal tissue.

This gene encodes a putative leucine-rich repeat protein. Leucine rich repeats (LRR) mediate reversible protein-protein interactions and have diverse cellular functions, including cellular adhesion and signaling. Several of these proteins, such as connectin, slit, chaoptin, and Toll have pivotal roles in neuronal development in *Drosophila* and may play significant but distinct roles in neural development and in the adult nervous system of humans (Ref. 2). In *Drosophilia*, the LRR region of axon guidance proteins has been shown to be critical for their function (especially in axon repulsion). Therefore, therapeutic modulation of the levels of this protein, or possible signaling via this protein, may be of utility in enhancing/directing compensatory synaptogenesis and fiber growth in the CNS in response to neuronal death (stroke, head trauma), axon lesion (spinal cord injury), or neurodegeneration (Alzheimer's, Parkinson's, Huntington's, vascular dementia or any neurodegenerative disease).

Panel 2.2 Summary: Ag1614 Highest expression of the CG59930-01 gene is seen in an ocular melanoma metastasis to the liver (CT=31.9). Thus, expression of this gene could be used to differentiate between this sample and other samples on this panel.

Panel 3D Summary: Ag1614 Expression of the CG59930-01 gene is highest in a lung cancer cell line (CT=25.6). Thus, expression of this gene could be used to differentiate between this sample and other samples on this panel and as a marker to detect the presence of lung cancer. Furthermore, therapeutic modulation of the expression or function of this gene may be effective in the treatment of lung cancer.

Panel 4D Summary: Ag1614 The CG59930-01 gene is expressed ubiquitously in this panel, with highest expression in CD40/IL-4 treated B lymphocytes (CT=31.3). In addition, this gene is expressed at high to moderate levels in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. This ubiquitous pattern of expression suggests that this gene product may be involved in homeostatic processes for these and other cell types and tissues. This pattern suggests a role for the gene product in cell survival and proliferation. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

Panel 5D Summary: Ag1614 Expression of the CG59930-01 gene is in agreement with the profile in Panel 1.3D. Highest expression is in skeletal muscle (CT=27.8) and several samples of skeletal muscle show prominent expression of this gene. Thus, this gene may be involved in the pathogenesis and/or treatment of metabolic disorders that involve skeletal muscle, including obesity and diabetes.

L. CG59934-01 and CG59934-02: Leucine-Rich Repeat Protein

Expression of gene CG59934-01 and full length clone CG59934-02 was assessed using the primer-probe sets Ag3633 and Ag4659, described in Tables LA and LB. Results of the RTQ-PCR runs are shown in Tables LC, LD and LE. Please note that the Ag3633 probe and primer set is specific to CG59934-01 only.

TABLE LA

Probe Name Ag3633

| Primers | Sequences | Length | Start Position | SEQ ID NO: |
|---|---|---|---|---|
| Forward | 5'-gctgaacgtccagctctct-3' | 19 | 1701 | 255 |
| Probe | TET-5'-ctccctgggactgcagtacaatgct-3'-TAMRA | 25 | 1731 | 256 |
| Reverse | 5'-ctcaggtcccactcctgact-3' | 20 | 1756 | 257 |

TABLE LB

Probe Name Ag4659

| Primers | Sequences | Length | Start Position | SEQ ID NO: |
|---|---|---|---|---|
| Forward | 5'-cacaggcagtagcttcttgaac-3' | 22 | 510 | 258 |
| Probe | TET-5'-cagcaccaacatcttctccaacctga-3'-TAMRA | 26 | 534 | 259 |
| Reverse | 5'-cctccagcatgttgaagttg-3' | 20 | 582 | 260 |

TABLE LC

CNS_neurodegeneration_v1.0

| Tissue Name | Rel. Exp. (%) Ag4659, Run 224723494 | Tissue Name | Rel. Exp. (%) Ag4659, Run 224723494 |
|---|---|---|---|
| AD 1 Hippo | 0.0 | Control (Path) 3 Temporal Ctx | 0.0 |
| AD 2 Hippo | 54.0 | Control (Path) 4 Temporal Ctx | 0.0 |
| AD 3 Hippo | 100.0 | AD 1 Occipital Ctx | 0.0 |
| AD 4 Hippo | 0.0 | AD 2 Occipital Ctx (Missing) | 0.0 |
| AD 5 Hippo | 57.4 | AD 3 Occipital Ctx | 0.0 |
| AD 6 Hippo | 0.0 | AD 4 Occipital Ctx | 0.0 |
| Control 2 Hippo | 0.0 | AD 5 Occipital Ctx | 0.0 |
| Control 4 Hippo | 0.0 | AD 6 Occipital Ctx | 0.0 |
| Control (Path) 3 Hippo | 0.0 | Control 1 Occipital Ctx | 0.0 |
| AD 1 Temporal Ctx | 0.0 | Control 2 Occipital Ctx | 0.0 |
| AD 2 Temporal Ctx | 80.7 | Control 3 Occipital Ctx | 0.0 |
| AD 3 Temporal Ctx | 0.0 | Control 4 Occipital Ctx | 0.0 |
| AD 4 Temporal Ctx | 0.0 | Control (Path) 1 Occipital Ctx | 0.0 |
| AD 5 Inf Temporal Ctx | 0.0 | Control (Path) 2 Occipital Ctx | 0.0 |

TABLE LC-continued

CNS_neurodegeneration_v1.0

| Tissue Name | Rel. Exp. (%) Ag4659, Run 224723494 | Tissue Name | Rel. Exp. (%) Ag4659, Run 224723494 |
|---|---|---|---|
| AD 5 SupTemporal Ctx | 0.0 | Control (Path) 3 Occipital Ctx | 0.0 |
| AD 6 Inf Temporal Ctx | 0.0 | Control (Path) 4 Occipital Ctx | 0.0 |
| AD 6 Sup Temporal Ctx | 0.0 | Control 1 Parietal Ctx | 0.0 |
| Control 1 Temporal Ctx | 0.0 | Control 2 Parietal Ctx | 0.0 |
| Control 2 Temporal Ctx | 0.0 | Control 3 Parietal Ctx | 0.0 |
| Control 3 Temporal Ctx | 0.0 | Control (Path) 1 Parietal Ctx | 0.0 |
| Control 3 Temporal Ctx | 0.0 | Control (Path) 2 Parietal Ctx | 0.0 |
| Control (Path) 1 Temporal Ctx | 0.0 | Control (Path) 3 Parietal Ctx | 0.0 |
| Control (Path) 2 Temporal Ctx | 0.0 | Control (Path) 4 Parietal Ctx | 0.0 |

TABLE LD

General_screening_panel_v1.4

| Tissue Name | Rel. Exp. (%) Ag3633, Run 217218047 | Rel. Exp. (%) Ag3633, Run 218233757 | Tissue Name | Rel. Exp. (%) Ag3633, Run 217218047 | Rel. Exp. (%) Ag3633, Run 218233757 |
|---|---|---|---|---|---|
| Adipose | 0.0 | 0.0 | Renal ca. TK-10 | 8.7 | 5.8 |
| Melanoma* Hs688(A).T | 0.8 | 1.1 | Bladder | 0.0 | 0.9 |
| Melanoma* Hs688(B).T | 0.4 | 0.0 | Gastric ca. (liver met.) NCI-N87 | 0.2 | 0.0 |
| Melanoma* M14 | 0.0 | 0.0 | Gastric ca. KATO III | 0.0 | 0.0 |
| Melanoma* LOXIMVI | 0.0 | 0.0 | Colon ca. SW-948 | 0.0 | 0.0 |
| Melanoma* SK-MEL-5 | 0.0 | 0.0 | Colon ca. SW480 | 0.0 | 0.0 |
| Squamous cell carcinoma SCC-4 | 0.0 | 0.0 | Colon ca.* (SW480 met) SW620 | 0.0 | 0.0 |
| Testis Pool | 0.7 | 0.0 | Colon ca. HT29 | 0.0 | 0.0 |
| Prostate ca.* (bone met) PC-3 | 0.0 | 0.0 | Colon ca. HCT-116 | 0.2 | 0.0 |
| Prostate Pool | 0.0 | 0.0 | Colon ca. CaCo-2 | 0.4 | 0.3 |
| Placenta | 0.0 | 0.0 | Colon cancer tissue | 0.0 | 0.6 |
| Uterus Pool | 0.0 | 0.0 | Colon ca. SW1116 | 0.0 | 0.3 |
| Ovarian ca. OVCAR-3 | 0.0 | 0.0 | Colon ca. Colo-205 | 0.0 | 0.0 |
| Ovarian ca. SK-OV-3 | 0.0 | 1.6 | Colon ca. SW-48 | 0.0 | 0.0 |
| Ovarian ca. OVCAR-4 | 0.0 | 0.0 | Colon Pool | 0.6 | 0.0 |
| Ovarian ca. OVCAR-5 | 0.0 | 0.6 | Small Intestine Pool | 0.0 | 0.5 |
| Ovarian ca. IGROV-1 | 0.0 | 0.0 | Stomach Pool | 0.0 | 0.4 |
| Ovarian ca. OVCAR-8 | 0.0 | 0.0 | Bone Marrow Pool | 0.4 | 0.0 |
| Ovary | 0.0 | 0.0 | Fetal Heart | 0.1 | 0.0 |
| Breast ca. MCF-7 | 0.0 | 0.0 | Heart Pool | 0.5 | 0.1 |
| Breast ca. MDA-MB-231 | 0.7 | 0.0 | Lymph Node Pool | 0.0 | 1.1 |
| Breast ca. BT 549 | 0.4 | 0.0 | Fetal Skeletal Muscle | 0.0 | 0.0 |
| Breast ca. T47D | 0.0 | 0.4 | Skeletal Muscle Pool | 0.0 | 0.0 |
| Breast ca. MDA-N | 0.0 | 0.0 | Spleen Pool | 0.1 | 0.0 |
| Breast Pool | 0.3 | 0.4 | Thymus Pool | 0.3 | 0.3 |
| Trachea | 0.0 | 0.0 | CNS cancer (glio/astro) U87-MG | 3.3 | 1.4 |

TABLE LD-continued

General_screening_panel_v1.4

| Tissue Name | Rel. Exp. (%) Ag3633, Run 217218047 | Rel. Exp. (%) Ag3633, Run 218233757 | Tissue Name | Rel. Exp. (%) Ag3633, Run 217218047 | Rel. Exp. (%) Ag3633, Run 218233757 |
|---|---|---|---|---|---|
| Lung | 0.4 | 0.0 | CNS cancer (glio/astro) U-118-MG | 1.7 | 1.9 |
| Fetal Lung | 0.5 | 0.0 | CNS cancer (neuro; met) SK-N-AS | 0.0 | 0.0 |
| Lung ca. NCI-N417 | 0.0 | 0.0 | CNS cancer (astro) SF-539 | 0.0 | 0.0 |
| Lung ca. LX-1 | 0.0 | 0.0 | CNS cancer (astro) SNB-75 | 0.0 | 0.4 |
| Lung ca. NCI-H146 | 0.0 | 0.0 | CNS cancer (glio) SNB-19 | 0.0 | 0.0 |
| Lung ca. SHP-77 | 0.0 | 0.0 | CNS cancer (glio) SF-295 | 0.0 | 0.4 |
| Lung ca. A549 | 0.0 | 0.0 | Brain (Amygdala) Pool | 0.0 | 0.0 |
| Lung ca. NCI-H526 | 0.0 | 0.0 | Brain (cerebellum) | 0.0 | 0.0 |
| Lung ca. NCI-H23 | 0.6 | 0.0 | Brain (fetal) | 0.0 | 0.0 |
| Lung ca. NCI-H460 | 0.0 | 0.0 | Brain (Hippocampus) Pool | 0.0 | 0.0 |
| Lung ca. HOP-62 | 0.0 | 0.0 | Cerebral Cortex Pool | 0.0 | 0.0 |
| Lung ca. NCI-H522 | 0.0 | 0.0 | Brain (Substantia nigra) Pool | 0.4 | 0.0 |
| Liver | 100.0 | 100.0 | Brain (Thalamus) Pool | 0.0 | 0.6 |
| Fetal Liver | 48.6 | 54.0 | Brain (whole) | 2.7 | 2.0 |
| Liver ca. HepG2 | 23.2 | 21.8 | Spinal Cord Pool | 0.4 | 0.0 |
| Kidney Pool | 0.5 | 0.5 | Adrenal Gland | 3.3 | 3.1 |
| Fetal Kidney | 0.5 | 0.0 | Pituitary gland Pool | 0.0 | 0.0 |
| Renal ca. 786-0 | 0.0 | 0.0 | Salivary Gland | 0.0 | 0.0 |
| Renal ca. A498 | 0.0 | 0.5 | Thyroid (female) | 0.8 | 0.0 |
| Renal ca. ACHN | 0.0 | 0.0 | Pancreatic ca. CAPAN2 | 0.0 | 0.0 |
| Renal ca. UO-31 | 0.0 | 0.4 | Pancreas Pool | 0.5 | 2.2 |

TABLE LE

Panel 4.1D

| Tissue Name | Rel. Exp. (%) Ag3633, Run 169960871 | Rel. Exp. (%) Ag4659, Run 200690190 | Tissue Name | Rel. Exp. (%) Ag3633, Run 169960871 | Rel. Exp. (%) Ag4659, Run 200690190 |
|---|---|---|---|---|---|
| Secondary Th1 act | 0.0 | 0.0 | HUVEC IL-1beta | 0.0 | 0.0 |
| Secondary Th2 act | 0.0 | 1.1 | HUVEC IFN gamma | 0.0 | 0.0 |
| Secondary Tr1 act | 0.0 | 0.0 | HUVEC TNF alpha + IFN gamma | 0.0 | 0.0 |
| Secondary Th1 rest | 0.0 | 0.0 | HUVEC TNF alpha + IL4 | 0.0 | 0.0 |
| Secondary Th2 rest | 0.0 | 0.0 | HUVEC IL-11 | 0.0 | 0.0 |
| Secondary Tr1 rest | 0.0 | 0.0 | Lung Microvascular EC none | 0.0 | 0.0 |
| Primary Th1 act | 0.0 | 0.0 | Lung Microvascular EC TNF alpha + IL-1beta | 0.0 | 0.0 |
| Primary Th2 act | 0.0 | 0.0 | Microvascular Dermal EC none | 0.0 | 0.0 |
| Primary Tr1 act | 0.0 | 0.0 | Microvasular Dermal EC TNF alpha + IL-1beta | 0.0 | 0.0 |
| Primary Th1 rest | 0.0 | 0.0 | Bronchial epithelium TNF alpha + IL1beta | 0.0 | 0.0 |
| Primary Th2 rest | 0.0 | 0.0 | Small airway epithelium none | 0.0 | 0.0 |

TABLE LE-continued

Panel 4.1D

| Tissue Name | Rel. Exp. (%) Ag3633, Run 169960871 | Rel. Exp. (%) Ag4659, Run 200690190 | Tissue Name | Rel. Exp. (%) Ag3633, Run 169960871 | Rel. Exp. (%) Ag4659, Run 200690190 |
|---|---|---|---|---|---|
| Primary Tr1 rest | 0.0 | 0.0 | Small airway epithelium TNF alpha + IL-1beta | 0.0 | 0.0 |
| CD45RA CD4 lymphocyte act | 0.0 | 0.0 | Coronery artery SMC rest | 0.0 | 0.0 |
| CD45RO CD4 lymphocyte act | 0.0 | 0.0 | Coronery artery SMC TNF alpha + IL-1beta | 0.0 | 0.0 |
| CD8 lymphocyte act | 0.0 | 0.0 | Astrocytes rest | 0.0 | 0.0 |
| Secondary CD8 lymphocyte rest | 0.0 | 0.0 | Astrocytes TNF alpha + IL-1beta | 0.0 | 0.0 |
| Secondary CD8 lymphocyte act | 0.0 | 0.0 | KU-812 (Basophil) rest | 0.0 | 0.0 |
| CD4 lymphocyte none | 0.0 | 0.0 | KU-812 (Basophil) PMA/ionomycin | 0.0 | 0.0 |
| 2ry Th1/Th2/Tr1_anti-CD95 CH11 | 0.0 | 0.0 | CCD1106 (Keratinocytes) none | 0.0 | 0.0 |
| LAK cells rest | 0.0 | 0.0 | CCD1106 (Keratinocytes) TNF alpha + IL-1beta | 0.0 | 0.0 |
| LAK cells IL-2 | 0.0 | 0.0 | Liver cirrhosis | 87.1 | 47.3 |
| LAK cells IL-2 + IL-12 | 0.0 | 0.0 | NCI-H292 none | 0.0 | 0.0 |
| LAK cells IL-2 + IFN gamma | 0.0 | 0.0 | NCI-H292 IL-4 | 0.0 | 0.0 |
| LAK cells IL-2 + IL-18 | 0.0 | 0.0 | NCI-H292 IL-9 | 0.0 | 0.0 |
| LAK cells PMA/ionomycin | 0.0 | 0.0 | NCI-H292 IL-13 | 0.0 | 0.0 |
| NK Cells IL-2 rest | 0.0 | 0.0 | NCI-H292 IFN gamma | 0.0 | 0.0 |
| Two Way MLR 3 day | 0.0 | 0.0 | HPAEC none | 0.0 | 0.0 |
| Two Way MLR 5 day | 0.0 | 0.0 | HPAEC TNF alpha + IL-1beta | 0.0 | 0.0 |
| Two Way MLR 7 day | 0.0 | 0.0 | Lung fibroblast none | 0.0 | 0.0 |
| PBMC rest | 0.0 | 0.0 | Lung fibroblast TNF alpha + IL-1beta | 0.0 | 0.5 |
| PBMC PWM | 0.0 | 0.0 | Lung fibroblast IL-4 | 0.0 | 0.0 |
| PBMC PHA-L | 0.0 | 0.0 | Lung fibroblast IL-9 | 0.0 | 0.0 |
| Ramos (B cell) none | 0.0 | 0.0 | Lung fibroblast IL-13 | 0.0 | 0.0 |
| Ramos (B cell) ionomycin | 0.0 | 0.0 | Lung fibroblast IFN gamma | 0.0 | 0.0 |
| B lymphocytes PWM | 0.0 | 0.0 | Dermal fibroblast CCD1070 rest | 0.0 | 0.0 |
| B lymphocytes CD40L and IL-4 | 0.0 | 0.0 | Dermal fibroblast CCD1070 TNF alpha | 0.0 | 0.0 |
| EOL-1 dbcAMP | 0.0 | 0.0 | Dermal fibroblast CCD1070 IL-1beta | 5.7 | 0.0 |
| EOL-1 dbcAMP PMA/ionomycin | 0.0 | 0.0 | Dermal fibroblast IFN gamma | 0.0 | 0.0 |
| Dendritic cells none | 5.9 | 0.0 | Dermal fibroblast IL-4 | 0.0 | 0.8 |
| Dendritic cells LPS | 0.0 | 0.0 | Dermal Fibroblasts rest | 0.0 | 0.5 |
| Dendritic cells anti-CD40 | 0.0 | 0.0 | Neutrophils TNFa + LPS | 0.0 | 0.0 |
| Monocytes rest | 0.0 | 0.0 | Neutrophils rest | 0.0 | 0.0 |
| Monocytes LPS | 1.6 | 0.0 | Colon | 0.0 | 0.0 |
| Macrophages rest | 0.0 | 0.0 | Lung | 0.0 | 0.0 |
| Macrophages LPS | 0.0 | 0.0 | Thymus | 0.0 | 6.5 |
| HUVEC none | 0.0 | 0.0 | Kidney | 100.0 | 100.0 |
| HUVEC starved | 0.0 | 0.0 | | | |

CNS_neurodegeneration_v1.0 Summary: Ag3633/Ag4659 Expression of the CG59934-01 gene is low/undetectable in all samples on this panel (CTs>35). (Data not shown.)

General_screening_panel_v1.4 Summary: Ag3633/Ag4659 Two experiments with two different probe and primer sets produce results that are in excellent agreement. Significant expression of the CG59934-01 gene is primarily limited to liver derived samples, with moderate expression in fetal and adult liver and liver cancer (CTs=28–30). Thus, expression of this gene could be used to differentiate between these liver derived samples and other samples on this panel and as a marker of liver tissue.

Panel 4.1D Summary: Ag3633/Ag4659 Two experiments with two different probe and primer sets produce results that are in excellent agreement. Significant expression of the CG59934-01 gene is limited to kidney and liver cirrhosis (CTs=30–33). The expression in liver cirrhosis is consistent with the liver specific expression in Panel 1.4. Thus, expression of this gene could be used to differentiate between these samples and other samples on this panel and as a marker of kidney and liver tissue.

M. CG88565-01: UDP N-Acetylglucosamine Transporter

Expression of gene CG88565-01 was assessed using the primer-probe set Ag3646, described in Table MA. Results of the RTQ-PCR runs are shown in Tables MB, MC and MD.

TABLE MA

Probe Name Ag3646

| Primers | Sequences | Length | Start Position | SEQ ID NO: |
|---|---|---|---|---|
| Forward | 5'-ttcgtcttcttggcttctgata-3' | 22 | 646 | 261 |
| Probe | TET-5'-tgaccatgcagttctattcaataagtctga-3'-TAMRA | 30 | 672 | 262 |
| Reverse | 5'-cgatgacgggaatttcataa-3' | 22 | 703 | 263 |

TABLE MB

CNS_neurodegeneration_v1.0

| Tissue Name | Rel. Exp. (%) Ag3646, Run 211019282 | Tissue Name | Rel. Exp. (%) Ag3646, Run 211019282 |
|---|---|---|---|
| AD 1 Hippo | 8.4 | Control (Path) 3 Temporal Ctx | 2.3 |
| AD 2 Hippo | 28.9 | Control (Path) 4 Temporal Ctx | 25.7 |
| AD 3 Hippo | 2.6 | AD 1 Occipital Ctx | 6.2 |
| AD 4 Hippo | 3.8 | AD 2 Occipital Ctx (Missing) | 0.0 |
| AD 5 Hippo | 100.0 | AD 3 Occipital Ctx | 1.9 |
| AD 6 Hippo | 31.6 | AD 4 Occipital Ctx | 15.7 |
| Control 2 Hippo | 27.7 | AD 5 Occipital Ctx | 57.0 |
| Control 4 Hippo | 7.6 | AD 6 Occipital Ctx | 11.7 |
| Control (Path) 3 Hippo | 2.4 | Control 1 Occipital Ctx | 1.5 |
| AD 1 Temporal Ctx | 7.5 | Control 2 Occipital Ctx | 74.7 |
| AD 2 Temporal Ctx | 21.9 | Control 3 Occipital Ctx | 9.5 |
| AD 3 Temporal Ctx | 2.0 | Control 4 Occipital Ctx | 5.4 |
| AD 4 Temporal Ctx | 14.7 | Control (Path) 1 Occipital Ctx | 94.0 |
| AD 5 Inf Temporal Ctx | 94.0 | Control (Path) 2 Occipital Ctx | 7.0 |
| AD 5 Sup Temporal Ctx | 36.9 | Control (Path) 3 Occipital Ctx | 1.1 |
| AD 6 Inf Temporal Ctx | 27.0 | Control (Path) 4 Occipital Ctx | 14.1 |
| AD 6 Sup Temporal Ctx | 26.2 | Control 1 Parietal Ctx | 2.9 |
| Control 1 Temporal Ctx | 3.2 | Control 2 Parietal Ctx | 26.8 |
| Control 2 Temporal Ctx | 71.2 | Control 3 Parietal Ctx | 16.6 |
| Control 3 Temporal Ctx | 11.0 | Control (Path) 1 Parietal Ctx | 74.2 |
| Control 3 Temporal Ctx | 4.5 | Control (Path) 2 Parietal Ctx | 16.8 |
| Control (Path) 1 Temporal Ctx | 69.3 | Control (Path) 3 Parietal Ctx | 2.2 |
| Control (Path) 2 Temporal Ctx | 35.8 | Control (Path) 4 Parietal Ctx | 47.0 |

TABLE MC

General_screening_panel_v1.4

| Tissue Name | Rel. Exp. (%) Ag3646, Run 218341951 | Tissue Name | Rel. Exp. (%) Ag3646, Run 218341951 |
| --- | --- | --- | --- |
| Adipose | 1.8 | Renal ca. TK-10 | 13.7 |
| Melanoma* Hs688(A).T | 11.0 | Bladder | 3.3 |
| Melanoma* Hs688(B).T | 12.3 | Gastric ca. (liver met.) NCI-N87 | 2.9 |
| Melanoma* M14 | 43.2 | Gastric ca. KATO III | 23.7 |
| Melanoma* LOXIMVI | 18.9 | Colon ca. SW-948 | 2.2 |
| Melanoma* SK-MEL-5 | 100.0 | Colon ca. SW480 | 28.7 |
| Squamous cell carcinoma SCC-4 | 4.5 | Colon ca.* (SW480 met) SW620 | 22.2 |
| Testis Pool | 3.3 | Colon ca. HT29 | 3.8 |
| Prostate ca.* (bone met) PC-3 | 31.2 | Colon ca. HCT-116 | 20.3 |
| Prostate Pool | 1.9 | Colon ca. CaCo-2 | 17.2 |
| Placenta | 6.4 | Colon cancer tissue | 11.9 |
| Uterus Pool | 0.8 | Colon ca. SW1116 | 3.2 |
| Ovarian ca. OVCAR-3 | 7.8 | Colon ca. Colo-205 | 1.4 |
| Ovarian ca. SK-OV-3 | 13.9 | Colon ca. SW-48 | 1.7 |
| Ovarian ca. OVCAR-4 | 5.5 | Colon Pool | 5.5 |
| Ovarian ca. OVCAR-5 | 9.7 | Small Intestine Pool | 3.4 |
| Ovarian ca. IGROV-1 | 9.7 | Stomach Pool | 2.5 |
| Ovarian ca. OVCAR-8 | 8.4 | Bone Marrow Pool | 1.9 |
| Ovary | 5.9 | Fetal Heart | 1.5 |
| Breast ca. MCF-7 | 6.7 | Heart Pool | 2.1 |
| Breast ca. MDA-MB-231 | 39.8 | Lymph Node Pool | 7.8 |
| Breast ca. BT 549 | 24.0 | Fetal Skeletal Muscle | 1.6 |
| Breast ca. T47D | 23.2 | Skeletal Muscle Pool | 2.0 |
| Breast ca. MDA-N | 41.8 | Spleen Pool | 2.7 |
| Breast Pool | 7.0 | Thymus Pool | 3.8 |
| Trachea | 3.0 | CNS cancer (glio/astro) U87-MG | 69.3 |
| Lung | 1.4 | CNS cancer (glio/astro) U-118-MG | 39.2 |
| Fetal Lung | 7.0 | CNS cancer (neuro; met) SK-N-AS | 28.3 |
| Lung ca. NCI-N417 | 11.9 | CNS cancer (astro) SF-539 | 13.3 |
| Lung ca. LX-1 | 7.7 | CNS cancer (astro) SNB-75 | 59.0 |
| Lung ca. NCI-H146 | 5.0 | CNS cancer (glio) SNB-19 | 8.8 |
| Lung ca. SHP-77 | 25.0 | CNS cancer (glio) SF-295 | 29.7 |
| Lung ca. A549 | 41.5 | Brain (Amygdala) Pool | 7.3 |
| Lung ca. NCI-H526 | 1.4 | Brain (cerebellum) | 20.0 |
| Lung ca. NCI-H23 | 20.0 | Brain (fetal) | 9.2 |
| Lung ca. NCI-H460 | 13.0 | Brain (Hippocampus) Pool | 9.1 |
| Lung ca. HOP-62 | 9.7 | Cerebral Cortex Pool | 14.3 |
| Lung ca. NCI-H522 | 23.0 | Brain (Substantia nigra) Pool | 11.1 |
| Liver | 1.1 | Brain (Thalamus) Pool | 15.3 |
| Fetal Liver | 6.0 | Brain (whole) | 13.8 |
| Liver ca. HepG2 | 6.0 | Spinal Cord Pool | 5.3 |
| Kidney Pool | 8.2 | Adrenal Gland | 9.3 |
| Fetal Kidney | 3.6 | Pituitary gland Pool | 1.7 |
| Renal ca. 786-0 | 19.5 | Salivary Gland | 0.8 |
| Renal ca. A498 | 8.2 | Thyroid (female) | 1.4 |
| Renal ca. ACHN | 7.4 | Pancreatic ca. CAPAN2 | 8.4 |
| Renal ca. UO-31 | 13.0 | Pancreas Pool | 7.1 |

TABLE MD

Panel 4.1D

| Tissue Name | Rel. Exp. (%) Ag3646, Run 169975208 | Tissue Name | Rel. Exp. (%) Ag3646, Run 169975208 |
| --- | --- | --- | --- |
| Secondary Th1 act | 16.0 | HUVEC IL-1beta | 15.7 |
| Secondary Th2 act | 22.5 | HUVEC IFN gamma | 11.0 |
| Secondary Tr1 act | 19.1 | HUVEC TNF alpha + IFN gamma | 14.1 |
| Secondary Th1 rest | 4.1 | HUVEC TNF alpha + IL4 | 11.1 |
| Secondary Th2 rest | 5.6 | HUVEC IL-11 | 5.0 |
| Secondary Tr1 rest | 3.7 | Lung Microvascular EC none | 20.4 |

TABLE MD-continued

Panel 4.1D

| Tissue Name | Rel. Exp. (%) Ag3646, Run 169975208 | Tissue Name | Rel. Exp. (%) Ag3646, Run 169975208 |
|---|---|---|---|
| Primary Th1 act | 12.2 | Lung Microvascular EC TNF alpha + IL-1beta | 18.2 |
| Primary Th2 act | 13.5 | Microvascular Dermal EC none | 10.8 |
| Primary Tr1 act | 12.1 | Microsvasular Dermal EC TNF alpha + IL-1beta | 8.6 |
| Primary Th1 rest | 4.7 | Bronchial epithelium TNF alpha + IL1beta | 6.5 |
| Primary Th2 rest | 5.1 | Small airway epithelium none | 4.5 |
| Primary Tr1 rest | 9.7 | Small airway epithelium TNF alpha + IL-1beta | 7.6 |
| CD45RA CD4 lymphocyte act | 14.1 | Coronery artery SMC rest | 7.4 |
| CD45RO CD4 lymphocyte act | 12.7 | Coronery artery SMC TNF alpha + IL-1beta | 9.2 |
| CD8 lymphocyte act | 12.5 | Astrocytes rest | 6.3 |
| Secondary CD8 lymphocyte rest | 10.7 | Astrocytes TNF alpha + IL-1beta | 4.1 |
| Secondary CD8 lymphocyte act | 8.7 | KU-812 (Basophil) rest | 4.6 |
| CD4 lymphocyte none | 1.7 | KU-812 (Basophil) PMA/ionomycin | 5.3 |
| 2ry Th1/Th2/Tr1_anti-CD95 CH11 | 4.8 | CCD1106 (Keratinocytes) none | 14.6 |
| LAK cells rest | 9.6 | CCD1106 (Keratinocytes) TNF alpha + IL-1beta | 8.4 |
| LAK cells IL-2 | 9.7 | Liver cirrhosis | 1.5 |
| LAK cells IL-2 + IL-12 | 10.3 | NCI-H292 none | 7.3 |
| LAK cells IL-2 + IFN gamma | 12.5 | NCI-H292 IL-4 | 8.2 |
| LAK cells IL-2 + IL-18 | 13.2 | NCI-H292 IL-9 | 13.8 |
| LAK cells PMA/ionomycin | 3.3 | NCI-H292 IL-13 | 8.8 |
| NK Cells IL-2 rest | 11.6 | NCI-H292 IFN gamma | 6.6 |
| Two Way MLR 3 day | 8.3 | HPAEC none | 7.4 |
| Two Way MLR 5 day | 9.4 | HPAEC TNF alpha + IL-1beta | 9.6 |
| Two Way MLR 7 day | 6.7 | Lung fibroblast none | 10.2 |
| PBMC rest | 2.2 | Lung fibroblast TNF alpha + IL-1beta | 8.3 |
| PBMC PWM | 14.2 | Lung fibroblast IL-4 | 14.9 |
| PBMC PHA-L | 9.5 | Lung fibroblast IL-9 | 21.2 |
| Ramos (B cell) none | 77.9 | Lung fibroblast IL-13 | 13.2 |
| Ramos (B cell) ionomycin | 100.0 | Lung fibroblast IFN gamma | 11.6 |
| B lymphocytes PWM | 9.0 | Dermal fibroblast CCD1070 rest | 16.6 |
| B lymphocytes CD40L and IL-4 | 10.1 | Dermal fibroblast CCD1070 TNF alpha | 19.3 |
| EOL-1 dbcAMP | 24.3 | Dermal fibroblast CCD1070 IL-1beta | 11.0 |
| EOL-1 dbcAMP PMA/ionomycin | 11.1 | Dermal fibroblast IFN gamma | 8.8 |
| Dendritic cells none | 17.7 | Dermal fibroblast IL-4 | 14.0 |
| Dendritic cells LPS | 10.2 | Dermal Fibroblasts rest | 11.3 |
| Dendritic cells anti-CD40 | 18.2 | Neutrophils TNFa + LPS | 0.0 |
| Monocytes rest | 4.5 | Neutrophils rest | 0.4 |
| Monocytes LPS | 4.2 | Colon | 2.6 |
| Macrophages rest | 14.0 | Lung | 5.5 |
| Macrophages LPS | 13.7 | Thymus | 8.1 |
| HUVEC none | 10.3 | Kidney | 15.9 |
| HUVEC starved | 15.2 | | |

CNS_neurodegeneration_v1.0 Summary: Ag3646 This panel confirms the expression of the CG88565-01 gene at low levels in the brains of an independent group of individuals. However, no differential expression of this gene was detected between Alzheimer's diseased postmortem brains and those of non-demented controls in this experiment. Please see Panel 1.4 for a discussion of the potential utility of this gene in treatment of central nervous system disorders.

General_screening_panel_v1.4 Summary: Ag3646 Highest expression of the CG88565-01 gene is detected in melanoma SK-MEL-5 cell line (CT=28.3). In addition, high to moderate expression of this gene is also seen in number of cancer cell lines (CNS, colon, renal, lung, breast, ovarian, prostate, and melanomas). Therefore, therapeutic modulation of the activity of this gene or its protein product, through the use of small molecule drugs, protein therapeutics or antibodies, might be beneficial in the treatment of these cancers.

Among tissues with metabolic or endocrine function, this gene is expressed at low to moderate levels in pancreas, adipose, adrenal gland, thyroid, pituitary gland, skeletal muscle, heart, liver and the gastrointestinal tract. Therefore, therapeutic modulation of the activity of this gene may prove useful in the treatment of endocrine/metabolically related diseases, such as obesity and diabetes.

In addition, this gene is expressed at moderate levels in all regions of the central nervous system examined, including amygdala, hippocampus, substantia nigra, thalamus, cerebellum, cerebral cortex, and spinal cord. Therefore, this gene may play a role in central nervous system disorders such as Alzheimer's disease, Parkinson's disease, epilepsy, multiple sclerosis, schizophrenia and depression.

Panel 4.1D Summary: Ag3646 Highest expression of the CG88565-01 gene is detected in Ramos B cells (CTs=29). This gene is expressed at high to moderate levels in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. This ubiquitous pattern of expression suggests that this gene product may be involved in homeostatic processes for these and other cell types and tissues. This pattern is in agreement with the expression profile in General_screening_panel_v1.4 and also suggests a role for the gene product in cell survival and proliferation. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

N. CG88623-01: Potassium Channel, Alpha Subunit like Gene

Expression of gene CG88623-01 was assessed using the primer-probe set Ag3648, described in Table NA. Results of the RTQ-PCR runs are shown in Tables NB, NC and ND.

TABLE NA

Probe Name Ag3648

| Primers | Sequences | Length | Start Position | SEQ ID NO: |
|---|---|---|---|---|
| Forward | 5'-cggagacatgtacccagaga-3' | 20 | 1186 | 264 |
| Probe | TET-5'-ttttgccttcctctgcattgcttttg-3'-TAMRA | 26 | 1222 | 265 |
| Reverse | 5'-gcatcccgttgagaatgat-3' | 19 | 1250 | 266 |

TABLE NB

CNS_neurodegeneration_v1.0

| Tissue Name | Rel. Exp. (%) Ag3648, Run 211019463 | Tissue Name | Rel. Exp. (%) Ag3648, Run 211019463 |
|---|---|---|---|
| AD 1 Hippo | 31.2 | Control (Path) 3 Temporal Ctx | 12.1 |
| AD 2 Hippo | 36.6 | Control (Path) 4 Temporal Ctx | 49.0 |
| AD 3 Hippo | 9.0 | AD 1 Occipital Ctx | 6.9 |
| AD 4 Hippo | 24.8 | AD 2 Occipital Ctx (Missing) | 0.0 |
| AD 5 Hippo | 77.9 | AD 3 Occipital Ctx | 6.9 |
| AD 6 Hippo | 39.2 | AD 4 Occipital Ctx | 23.7 |
| Control 2 Hippo | 26.4 | AD 5 Occipital Ctx | 24.7 |
| Control 4 Hippo | 25.5 | AD 6 Occipital Ctx | 10.5 |
| Control (Path) 3 Hippo | 9.1 | Control 1 Occipital Ctx | 3.6 |
| AD 1 Temporal Ctx | 35.8 | Control 2 Occipital Ctx | 17.0 |
| AD 2 Temporal Ctx | 31.2 | Control 3 Occipital Ctx | 16.0 |
| AD 3 Temporal Ctx | 8.9 | Control 4 Occipital Ctx | 8.2 |
| AD 4 Temporal Ctx | 24.1 | Control (Path) 1 Occipital Ctx | 68.3 |
| AD 5 Inf Temporal Ctx | 78.5 | Control (Path) 2 Occipital Ctx | 10.7 |
| AD 5 Sup Temporal Ctx | 51.1 | Control (Path) 3 Occipital Ctx | 1.2 |
| AD 6 Inf Temporal Ctx | 43.5 | Control (Path) 4 Occipital Ctx | 21.9 |
| AD 6 Sup Temporal Ctx | 41.8 | Control 1 Parietal Ctx | 6.5 |
| Control 1 Temporal Ctx | 8.4 | Control 2 Parietal Ctx | 40.1 |
| Control 2 Temporal Ctx | 32.1 | Control 3 Parietal Ctx | 21.5 |
| Control 3 Temporal Ctx | 9.2 | Control (Path) 1 Parietal Ctx | 100.0 |
| Control 3 Temporal Ctx | 22.4 | Control (Path) 2 Parietal Ctx | 33.2 |
| Control (Path) 1 Temporal Ctx | 76.8 | Control (Path) 3 Parietal Ctx | 10.9 |
| Control (Path) 2 Temporal Ctx | 61.1 | Control (Path) 4 Parietal Ctx | 57.8 |

TABLE NC

General_screening_panel_v1.4

| Tissue Name | Rel. Exp. (%) Ag3648, Run 21978045 | Tissue Name | Rel. Exp. (%) Ag3648, Run 219798045 |
|---|---|---|---|
| Adipose | 2.3 | Renal ca. TK-10 | 33.2 |
| Melanoma* Hs688(A).T | 6.8 | Bladder | 17.1 |
| Melanoma* Hs688(B).T | 7.2 | Gastric ca. (liver met.) NCI-N87 | 50.0 |
| Melanoma* M14 | 5.8 | Gastric ca. KATO III | 32.8 |
| Melanoma* LOXIMVI | 4.2 | Colon ca. SW-948 | 4.4 |
| Melanoma* SK-MEL-5 | 32.5 | Colon ca. SW480 | 18.6 |
| Squamous cell carcinoma SCC-4 | 6.7 | Colon ca.* (SW480 met) SW620 | 30.1 |
| Testis Pool | 26.2 | Colon ca. HT29 | 4.4 |
| Prostate ca.* (bone met) PC-3 | 11.3 | Colon ca. HCT-116 | 79.0 |
| Prostate Pool | 4.2 | Colon ca. CaCo-2 | 13.6 |
| Placenta | 0.5 | Colon cancer tissue | 4.3 |
| Uterus Pool | 7.1 | Colon ca. SW1116 | 0.5 |
| Ovarian ca. OVCAR-3 | 29.5 | Colon ca. Colo-205 | 1.4 |
| Ovarian ca. SK-OV-3 | 21.6 | Colon ca. SW-48 | 0.3 |
| Ovarian ca. OVCAR-4 | 8.8 | Colon Pool | 7.9 |
| Ovarian ca. OVCAR-5 | 13.8 | Small Intestine Pool | 15.0 |
| Ovarian ca. IGROV-1 | 8.8 | Stomach Pool | 13.6 |
| Ovarian ca. OVCAR-8 | 2.1 | Bone Marrow Pool | 6.2 |
| Ovary | 9.5 | Fetal Heart | 2.3 |
| Breast ca. MCF-7 | 14.6 | Heart Pool | 3.1 |
| Breast ca. MDA-MB-231 | 30.6 | Lymph Node Pool | 16.4 |
| Breast ca. BT 549 | 100.0 | Fetal Skeletal Muscle | 7.6 |
| Breast ca. T47D | 13.6 | Skeletal Muscle Pool | 15.0 |
| Breast ca. MDA-N | 7.9 | Spleen Pool | 5.1 |
| Breast Pool | 13.5 | Thymus Pool | 10.2 |
| Trachea | 6.2 | CNS cancer (glio/astro) U87-MG | 35.6 |
| Lung | 6.6 | CNS cancer (glio/astro) U-118-MG | 26.4 |
| Fetal Lung | 9.0 | CNS cancer (neuro; met) SK-N-AS | 7.3 |
| Lung ca. NCI-N417 | 1.6 | CNS cancer (astro) SF-539 | 6.6 |
| Lung ca. LX-1 | 15.6 | CNS cancer (astro) SNB-75 | 56.3 |
| Lung ca. NCI-H146 | 9.0 | CNS cancer (glio) SNB-19 | 6.1 |
| Lung ca. SHP-77 | 3.2 | CNS cancer (glio) SF-295 | 15.7 |
| Lung ca. A549 | 23.5 | Brain (Amygdala) Pool | 8.3 |
| Lung ca. NCI-H526 | 2.0 | Brain (cerebellum) | 2.9 |
| Lung ca. NCI-H23 | 40.1 | Brain (fetal) | 14.3 |
| Lung ca. NCI-H460 | 29.7 | Brain (Hippocampus) Pool | 11.4 |
| Lung ca. HOP-62 | 12.2 | Cerebral Cortex Pool | 9.2 |
| Lung ca. NCI-H522 | 4.5 | Brain (Substantia nigra) Pool | 5.8 |
| Liver | 0.2 | Brain (Thalamus) Pool | 13.8 |
| Fetal Liver | 5.5 | Brain (whole) | 7.2 |
| Liver ca. HepG2 | 8.7 | Spinal Cord Pool | 7.4 |
| Kidney Pool | 25.7 | Adrenal Gland | 6.2 |
| Fetal Kidney | 14.7 | Pituitary gland Pool | 1.7 |
| Renal ca. 786-0 | 11.0 | Salivary Gland | 1.7 |
| Renal ca. A498 | 5.1 | Thyroid (female) | 1.4 |
| Renal ca. ACHN | 15.1 | Pancreatic ca. CAPAN2 | 1.3 |
| Renal ca. UO-31 | 3.6 | Pancreas Pool | 19.2 |

TABLE ND

Panel 4.1D

| Tissue Name | Rel. Exp. (%) Ag3648, Run 169975756 | Tissue Name | Rel. Exp. (%) Ag3648, Run 169975756 |
|---|---|---|---|
| Secondary Th1 act | 12.9 | HUVEC IL-1beta | 11.3 |
| Secondary Th2 act | 15.2 | HUVEC IFN gamma | 23.0 |
| Secondary Tr1 act | 16.3 | HUVEC TNF alpha + IFN gamma | 4.9 |
| Secondary Th1 rest | 1.2 | HUVEC TNF alpha + IL4 | 6.0 |
| Secondary Th2 rest | 5.8 | HUVEC IL-11 | 2.7 |
| Secondary Tr1 rest | 1.6 | Lung Microvascular EC none | 48.6 |

TABLE ND-continued

Panel 4.1D

| Tissue Name | Rel. Exp. (%) Ag3648, Run 169975756 | Tissue Name | Rel. Exp. (%) Ag3648, Run 169975756 |
|---|---|---|---|
| Primary Th1 act | 15.2 | Lung Microvascular EC TNF alpha + IL-1beta | 21.0 |
| Primary Th2 act | 29.7 | Microvascular Dermal EC none | 6.1 |
| Primary Tr1 act | 19.8 | Microsvasular Dermal EC TNF alpha + IL-1beta | 10.7 |
| Primary Th1 rest | 12.2 | Bronchial epithelium TNF alpha + IL1beta | 20.9 |
| Primary Th2 rest | 15.2 | Small airway epithelium none | 2.7 |
| Primary Tr1 rest | 19.8 | Small airway epithelium TNF alpha + IL-1beta | 14.0 |
| CD45RA CD4 lymphocyte act | 39.0 | Coronery artery SMC rest | 4.8 |
| CD45RO CD4 lymphocyte act | 55.5 | Coronery artery SMC TNF alpha + IL-1beta | 2.7 |
| CD8 lymphocyte act | 44.1 | Astrocytes rest | 19.5 |
| Secondary CD8 lymphocyte rest | 47.0 | Astrocytes TNF alpha + IL-1beta | 12.1 |
| Secondary CD8 lymphocyte act | 10.2 | KU-812 (Basophil) rest | 29.7 |
| CD4 lymphocyte none | 4.2 | KU-812 (Basophil) PMA/ionomycin | 25.3 |
| 2ry Th1/Th2/Tr1_anti-CD95 CH11 | 3.2 | CCD1106 (Keratinocytes) none | 48.0 |
| LAK cells rest | 15.2 | CCD1106 (Keratinocytes) TNF alpha + IL-1beta | 55.1 |
| LAK cells IL-2 | 22.1 | Liver cirrhosis | 5.4 |
| LAK cells IL-2 + IL-12 | 18.7 | NCI-H292 none | 11.0 |
| LAK cells IL-2 + IFN gamma | 20.4 | NCI-H292 IL-4 | 29.1 |
| LAK cells IL-2 + IL-18 | 37.9 | NCI-H292 IL-9 | 25.5 |
| LAK cells PMA/ionomycin | 21.6 | NCI-H292 IL-13 | 34.6 |
| NK Cells IL-2 rest | 14.3 | NCI-H292 IFN gamma | 36.1 |
| Two Way MLR 3 day | 35.1 | HPAEC none | 15.1 |
| Two Way MLR 5 day | 14.8 | HPAEC TNF alpha + IL-1beta | 23.7 |
| Two Way MLR 7 day | 4.4 | Lung fibroblast none | 19.5 |
| PBMC rest | 4.2 | Lung fibroblast TNF alpha + IL-1beta | 4.4 |
| PBMC PWM | 13.5 | Lung fibroblast IL-4 | 45.4 |
| PBMC PHA-L | 14.6 | Lung fibroblast IL-9 | 52.5 |
| Ramos (B cell) none | 54.0 | Lung fibroblast IL-13 | 29.5 |
| Ramos (B cell) ionomycin | 48.3 | Lung fibroblast IFN gamma | 24.0 |
| B lymphocytes PWM | 25.0 | Dermal fibroblast CCD1070 rest | 14.6 |
| B lymphocytes CD40L and IL-4 | 13.5 | Dermal fibroblast CCD1070 TNF alpha | 15.4 |
| EOL-1 dbcAMP | 100.0 | Dermal fibroblast CCD1070 IL-1beta | 9.0 |
| EOL-1 dbcAMP PMA/ionomycin | 89.5 | Dermal fibroblast IFN gamma | 20.9 |
| Dendritic cells none | 16.6 | Dermal fibroblast IL-4 | 42.3 |
| Dendritic cells LPS | 11.4 | Dermal fibroblasts rest | 7.4 |
| Dendritic cells anti-CD40 | 5.9 | Neutrophils TNFa + LPS | 0.0 |
| Monocytes rest | 1.4 | Neutrophils rest | 0.0 |
| Monocytes LPS | 3.1 | Colon | 5.3 |
| Macrophages rest | 11.0 | Lung | 4.5 |
| Macrophages LPS | 1.4 | Thymus | 9.2 |
| HUVEC none | 7.0 | Kidney | 13.8 |
| HUVEC starved | 12.2 | | |

CNS_neurodegeneration_v1.0 Summary: Ag3648 This panel does not show differential expression of the CG99623-01 gene in Alzheimer's disease. However, this expression profile confirms the presence of this gene in the brain. Please see Panel 1.4 for discussion of utility of this gene in the central nervous system.

General_screening_panel_v1.4 Summary: Ag3648 Highest expression of the CG88623-01 gene is seen in a breast cancer cell line (CT=29.3). Moderate levels of expression are also seen in samples derived from colon, gastric, brain, lung, ovarian and melanoma cancer cell lines. Thus, expression of this gene could be used to differentiate the breast cancer sample from the other samples on this panel and as a marker for breast cancer. Furthermore, the consistent levels of expression in the cancer cell lines on this panel suggest that this gene product may be involved in cellular growth and proliferation. Thus, therapeutic modulation of the expression or function of this gene may be effective in the treatment of these cancers.

Among tissues with metabolic function, this gene is expressed at low but significant levels in adipose, adrenal gland, pancreas, fetal liver and adult and fetal skeletal muscle and heart. This expression pattern suggests that this gene product may play a role in normal neuroendocrine and metabolic and that disregulated expression of this gene may contribute to neuroendocrine disorders or metabolic diseases, such as obesity and type 2 diabetes.

This gene, a potassium channel homolog, also shows low but significant expression in the brain, including the hippocampus, cortex, amygdala, substantia nigra and thalamus. These regions are succeptable to the neurodegeneration associated with Alzheimer's disease, Parkinson's disease, Huntington's disease and other pathological neurodegenerative conditions. In fact, potassium channels have been implicated in neurodegenerative diseases, including Alzheimer's disease. It has been suggested that modulating these channels to reduce outward $K^+$ current may provide an approach to reducing neuronal degeneration in patients with Alzheimer's disease. Therefore, agents that modulate the function of this gene product could potentially reduce neuronal degeneration in patients with Alzheimer's disease and other neurodegenerative diseases.

In addition, defective potassium channels are known to cause several CNS disorders, including epilepsy and episodic ataxia with myokymia. Therefore, modulation of the expression or function of this gene product may potentially be useful as a treatment for the symptoms produced by ataxia and epilepsy (Jhamandas J H, Cho C, Jassar B, Harris K, MacTavish D, Easaw J. Cellular Mechanisms for Amyloid beta-Protein Activation of Rat Cholinergic Basal Forebrain Neurons. J Neurophysiol 2001 September;86(3) :1312–20; Chi X, Sutton E T, Hellermann G, Price J M. Potassium channel openers prevent beta-amyloid toxicity in bovine vascular endothelial cells. Neurosci Lett 2000 Aug. 18;290(1):9–12; Piccini A, Ciotti M T, Vitolo O V, Calissano P, Tabaton M, Galli C. Endogenous APP derivatives oppositely modulate apoptosis through an autocrine loop. Neuroreport 2000 May 15;11(7):1375–9; Yu S P, Farhangrazi Z S, Ying H S, Yeh C H, Choi D W. Enhancement of outward potassium current may participate in beta-amyloid peptide-induced cortical neuronal death. Neurobiol Dis 1998 August;5(2):81–8; Colom L V, Diaz M E, Beers D R, Neely A, Xie W J, Appel S H. Role of potassium channels in amyloid-induced cell death. J Neurochem 1998 May;70(5) :1925–34).

Panel 4.1D Summary: Ag3648 Highest expression of the CG88623-01 gene is seen in untreated eosinophils and eosinophils stimulated with PMA/ionomycin (CTs=31.5). Thus, expression of this gene could be used to differentiate between the eosinophil derived samples and other samples on this panel and as a marker for eosinophils. Furthermore, therapeutic modulation of the expression or function of this gene product may be useful in the treatment of hematopoietic disorders involving eosinphils, parasitic infections and asthma.

Low but significant levels of expression are also seen in other cells important to the immune respones, including lung and dermal fibroblasts, basophils, the B cell line Ramos, activated and resting primary Th1, Th2 and Tr1 cells, activated CD4 and CD8 lymphocytes, and resting secondary CD8 lymphocytes. Since many of these cells play an important role in lung pathology, inflammatory bowel disease and autoimmune disorders, therapies designed with the protein encoded by this gene may block or inhibit inflammation or tissue damage due to lung conditions including asthma, allergies, hypersensitivity reactions, inflammatory bowel disease, rheumatoid arthritis, viral infections and autoimmune disease.

O. CG88645-01: Cardiac Potassium Channel Subunit (KV6.2)-like Protein

Expression of gene CG88645-01 was assessed using the primer-probe set Ag3650, described in Table OA. Results of the RTQ-PCR runs are shown in Tables OB, OC and OD.

TABLE OA

Probe Name Ag3650

| Primers | Sequences | Length | Start Position | SEQ ID NO: |
|---|---|---|---|---|
| Forward | 5'-ctggagtcaccttgagggtact-3' | 22 | 980 | 267 |
| Probe | TET-5'-attaagcttgcccgtcacttcattgg-3'-TAMRA | 26 | 1027 | 268 |
| Reverse | 5'-agagtcaaaccgagtgtctgaa-3' | 22 | 1055 | 269 |

TABLE OB

CNS_neurodegeneration_v1.0

| Tissue Name | Rel. Exp. (%) Ag3650, Run 211019100 | Tissue Name | Rel. Exp. (%) Ag3650, Run 211019100 |
|---|---|---|---|
| AD 1 Hippo | 17.0 | Control (Path) 3 Temporal Ctx | 0.7 |
| AD 2 Hippo | 15.7 | Control (Path) 4 Temporal Ctx | 21.8 |
| AD 3 Hippo | 6.7 | AD 1 Occipital Ctx | 5.1 |
| AD 4 Hippo | 4.4 | AD 2 Occipital Ctx (Missing) | 0.0 |
| AD 5 Hippo | 40.1 | AD 3 Occipital Ctx | 1.4 |
| AD 6 Hippo | 100.0 | AD 4 Occipital Ctx | 9.2 |
| Control 2 Hippo | 26.8 | AD 5 Occipital Ctx | 19.3 |
| Control 4 Hippo | 3.5 | AD 6 Occipital Ctx | 9.8 |
| Control (Path) 3 Hippo | 1.7 | Control 1 Occipital Ctx | 0.3 |
| AD 1 Temporal Ctx | 6.2 | Control 2 Occipital Ctx | 11.4 |
| AD 2 Temporal Ctx | 24.3 | Control 3 Occipital Ctx | 6.7 |
| AD 3 Temporal Ctx | 3.1 | Control 4 Occipital Ctx | 0.0 |
| AD 4 Temporal Ctx | 11.3 | Control (Path) 1 Occipital Ctx | 46.0 |
| AD 5 Inf Temporal Ctx | 64.2 | Control (Path) 2 Occipital Ctx | 3.6 |

TABLE OB-continued

CNS_neurodegeneration_v1.0

| Tissue Name | Rel. Exp. (%) Ag3650, Run 211019100 | Tissue Name | Rel. Exp. (%) Ag3650, Run 211019100 |
|---|---|---|---|
| AD 5 Sup Temporal Ctx | 53.6 | Control (Path) 3 Occipital Ctx | 0.1 |
| AD 6 Inf Temporal Ctx | 35.1 | Control (Path) 4 Occipital Ctx | 2.7 |
| AD 6 Sup Temporal Ctx | 47.6 | Control 1 Parietal Ctx | 3.0 |
| Control 1 Temporal Ctx | 1.7 | Control 2 Parietal Ctx | 26.8 |
| Control 2 Temporal Ctx | 24.7 | Control 3 Parietal Ctx | 10.4 |
| Control 3 Temporal Ctx | 12.1 | Control (Path) 1 Parietal Ctx | 58.6 |
| Control 3 Temporal Ctx | 4.1 | Control (Path) 2 Parietal Ctx | 13.7 |
| Control (Path) 1 Temporal Ctx | 61.1 | Control (Path) 3 Parietal Ctx | 0.0 |
| Control (Path) 2 Temporal Ctx | 23.7 | Control (Path) 4 Parietal Ctx | 19.3 |

TABLE OC

General_screening_panel_V1.4

| Tissue Name | Rel. Exp. (%) Ag3650, Run 218952325 | Tissue Name | Rel. Exp. (%) Ag3650, Run 218952325 |
|---|---|---|---|
| Adipose | 0.8 | Renal ca. TK-10 | 38.7 |
| Melanoma* Hs688(A).T | 0.0 | Bladder | 12.3 |
| Melanoma* Hs688(B).T | 0.3 | Gastric ca. (liver met.) NCI-N87 | 10.3 |
| Melanoma* M14 | 11.7 | Gastric ca. KATO III | 0.0 |
| Melanoma* LOXIMVI | 0.0 | Colon ca. SW-948 | 0.0 |
| Melanoma* SK-MEL-5 | 40.6 | Colon ca. SW480 | 2.3 |
| Squamous cell carcinoma SCC-4 | 0.0 | Colon ca.* (SW480 met) SW620 | 0.0 |
| Testis Pool | 15.5 | Colon ca. HT29 | 1.1 |
| Prostate ca.* (bone met) PC-3 | 0.6 | Colon ca. HCT-116 | 36.6 |
| Prostate Pool | 3.9 | Colon ca. CaCo-2 | 17.7 |
| Placenta | 0.0 | Colon cancer tissue | 0.5 |
| Uterus Pool | 0.7 | Colon ca. SW1116 | 0.0 |
| Ovarian ca. OVCAR-3 | 16.4 | Colon ca. Colo-205 | 0.0 |
| Ovarian ca. SK-OV-3 | 100.0 | Colon ca. SW-48 | 0.0 |
| Ovarian ca. OVCAR-4 | 16.3 | Colon Pool | 6.0 |
| Ovarian ca. OVCAR-5 | 33.4 | Small Intestine Pool | 4.2 |
| Ovarian ca. IGROV-1 | 9.0 | Stomach Pool | 5.4 |
| Ovarian ca. OVCAR-8 | 5.6 | Bone Marrow Pool | 0.6 |
| Ovary | 30.4 | Fetal Heart | 0.0 |
| Breast ca. MCF-7 | 1.3 | Heart Pool | 1.2 |
| Breast ca. MDA-MB-231 | 0.4 | Lymph Node Pool | 10.6 |
| Breast ca. BT 549 | 41.8 | Fetal Skeletal Muscle | 0.7 |
| Breast ca. T47D | 46.7 | Skeletal Muscle Pool | 0.4 |
| Breast ca. MDA-N | 0.0 | Spleen Pool | 2.5 |
| Breast Pool | 5.1 | Thymus Pool | 23.0 |
| Trachea | 4.9 | CNS cancer (glio/astro) U87-MG | 1.8 |
| Lung | 4.0 | CNS cancer (glio/astro) U-118-MG | 0.0 |
| Fetal Lung | 2.8 | CNS cancer (neuro; met) SK-N-AS | 7.9 |
| Lung ca. NCI-N417 | 30.4 | CNS cancer (astro) SF-539 | 1.7 |
| Lung ca. LX-1 | 0.8 | CNS cancer (astro) SNB-75 | 2.0 |
| Lung ca. NCI-H146 | 56.6 | CNS cancer (glio) SNB-19 | 6.8 |
| Lung ca. SHP-77 | 85.9 | CNS cancer (glio) SF-295 | 11.1 |
| Lung ca. A549 | 16.0 | Brain (Amygdala) Pool | 24.5 |
| Lung ca. NCI-H526 | 23.5 | Brain (cerebellum) | 0.4 |
| Lung ca. NCI-H23 | 38.4 | Brain (fetal) | 10.7 |
| Lung ca. NCI-H460 | 5.6 | Brain (Hippocampus) Pool | 42.3 |
| Lung ca. HOP-62 | 0.9 | Cerebral Cortex Pool | 38.7 |
| Lung ca. NCI-H522 | 67.8 | Brain (Substantia nigra) Pool | 33.2 |
| Liver | 0.0 | Brain (Thalamus) Pool | 51.8 |

TABLE OC-continued

General_screening_panel_V1.4

| Tissue Name | Rel. Exp. (%) Ag3650, Run 218952325 | Tissue Name | Rel. Exp. (%) Ag3650, Run 218952325 |
|---|---|---|---|
| Fetal Liver | 0.7 | Brain (whole) | 41.2 |
| Liver ca. HepG2 | 12.9 | Spinal Cord Pool | 5.4 |
| Kidney Pool | 1.9 | Adrenal Gland | 48.3 |
| Fetal Kidney | 21.5 | Pituitary gland Pool | 10.3 |
| Renal ca. 786-0 | 0.0 | Salivary Gland | 0.0 |
| Renal ca. A498 | 4.0 | Thyroid (female) | 0.1 |
| Renal ca. ACHN | 41.8 | Pancreatic ca. CAPAN2 | 5.2 |
| Renal ca. UO-31 | 2.7 | Pancreas Pool | 21.2 |

TABLE OD

Panel 4.1D

| Tissue Name | Rel. Exp. (%) Ag3650, Run 169975768 | Tissue Name | Rel. Exp. (%) Ag3650, Run 169975768 |
|---|---|---|---|
| Secondary Th1 act | 7.1 | HUVEC IL-1beta | 0.0 |
| Secondary Th2 act | 13.8 | HUVEC IFN gamma | 0.0 |
| Secondary Tr1 act | 10.2 | HUVEC TNF alpha + IFN gamma | 0.0 |
| Secondary Th1 rest | 1.7 | HUVEC TNF alpha + IL4 | 0.0 |
| Secondary Th2 rest | 1.7 | HUVEC IL-11 | 0.0 |
| Secondary Tr1 rest | 0.0 | Lung Microvascular EC none | 0.0 |
| Primary Th1 act | 16.0 | Lung Microvascular EC TNF alpha + IL-1beta | 0.0 |
| Primary Th2 act | 18.9 | Microvascular Dermal EC none | 0.0 |
| Primary Tr1 act | 8.8 | Microsvascular Dermal EC TNF alpha + IL-1beta | 0.0 |
| Primary Th1 rest | 3.1 | Bronchial epithelium TNF alpha + IL1beta | 0.0 |
| Primary Th2 rest | 0.0 | Small airway epithelium none | 0.0 |
| Primary Tr1 rest | 4.5 | Small airway epithelium TNF alpha + IL-1beta | 0.0 |
| CD45RA CD4 lymphocyte act | 5.2 | Coronery artery SMC rest | 0.0 |
| CD45RO CD4 lymphocyte act | 13.1 | Coronery artery SMC TNF alpha + IL-1beta | 0.0 |
| CD8 lymphocyte act | 3.2 | Astrocytes rest | 0.0 |
| Secondary CD8 lymphocyte rest | 1.3 | Astrocytes TNF alpha + IL-1beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.8 | CCD1106 (Keratinocytes) none | 0.0 |
| LAK cells rest | 1.4 | CCD1106 (Keratinocytes) TNF alpha + IL-1beta | 0.6 |
| LAK cells IL-2 | 0.0 | Liver cirrhosis | 0.0 |
| LAK cells IL-2 + IL-12 | 1.6 | NCI-H292 none | 0.0 |
| LAK cells IL-2 + IFN gamma | 9.5 | NCI-H292 IL-4 | 0.0 |
| LAK cells IL-2 + IL-18 | 7.1 | NCI-H292 IL-9 | 3.3 |
| LAK cells PMA/ionomycin | 0.0 | NCI-H292 IL-13 | 0.0 |
| NK Cells IL-2 rest | 0.0 | NCI-H292 IFN gamma | 3.4 |
| Two Way MLR 3 day | 3.0 | HPAEC none | 0.0 |
| Two Way MLR 5 day | 2.8 | HPAEC TNF alpha + IL-1beta | 0.0 |
| Two Way MLR 7 day | 1.6 | Lung fibroblast none | 0.0 |
| PBMC rest | 0.0 | Lung fibroblast TNF alpha + IL-1beta | 0.0 |
| PBMC PWM | 3.3 | Lung fibroblast IL-4 | 0.0 |
| PBMC PHA-L | 3.4 | Lung fibroblast IL-9 | 0.0 |
| Ramos (B cell) none | 0.0 | Lung fibroblast IL-13 | 0.0 |
| Ramos (B cell) ionomycin | 4.2 | Lung fibroblast IFN gamma | 0.0 |
| B lymphocytes PWM | 13.2 | Dermal fibroblast CCD1070 rest | 0.0 |
| B lymphocytes CD40L and IL-4 | 0.7 | Dermal fibroblast CCD1070 TNF alpha | 0.0 |
| EOL-1 dbcAMP | 0.0 | Dermal fibroblast CCD1070 IL-1beta | 0.0 |

TABLE OD-continued

Panel 4.1D

| Tissue Name | Rel. Exp. (%) Ag3650, Run 169975768 | Tissue Name | Rel. Exp. (%) Ag3650, Run 169975768 |
|---|---|---|---|
| EOL-1 dbcAMP PMA/ionomycin | 0.0 | Dermal fibroblast IFN gamma | 0.0 |
| Dendritic cells none | 0.0 | Dermal fibroblast IL-4 | 0.0 |
| Dendritic cells LPS | 1.7 | Dermal Fibroblasts rest | 0.0 |
| Dendritic cells anti-CD40 | 0.0 | Neutrophils TNFa + LPS | 0.0 |
| Monocytes rest | 0.0 | Neutrophils rest | 0.0 |
| Monocytes LPS | 0.0 | Colon | 6.6 |
| Macrophages rest | 4.6 | Lung | 3.2 |
| Macrophages LPS | 0.0 | Thymus | 100.0 |
| HUVEC none | 0.0 | Kidney | 11.8 |
| HUVEC starved | 0.0 | | |

CNS_neurodegeneration_v1.0 Summary: Ag3650 This panel confirms the expression of the CG88645-01 gene at low levels in the brains of an independent group of individuals. However, no differential expression of this gene was detected between Alzheimer's diseased postmortem brains and those of non-demented controls in this experiment. Please see Panel 1.4 for a discussion of the potential utility of this gene in treatment of central nervous system disorders.

General_screening$_{13}$ panel_v1.4 Summary: Ag3650 Highest expression of the CG88645-01 gene is detected in ovarian cancer SK-OV-3 cell line (CT=29.9). In addition high expression of this gene is also seen in cluster of lung, ovarian, colon, renal, and breast cancer cell line. The CG88645-01 gene codes for a potassium channel subunit. Therefore, therapeutic modulation of the activity of this gene or its protein product, through the use of small molecule drugs, protein therapeutics or antibodies, might be beneficial in the treatment of these cancers.

Among tissues with metabolic or endocrine function, this gene is expressed at high to moderate levels in pancreas, adipose, adrenal gland, pituitary gland and the gastrointestinal tract. Potassium channel in pancrease have been implicated in regulation of insulin secretion (Ref. 1). Therefore, therapeutic modulation of the activity of this gene may prove useful in the treatment of endocrine/metabolically related diseases, such as obesity and diabetes.

In addition, this gene is expressed at high levels in all regions of the central nervous system examined, including amygdala, hippocampus, substantia nigra, thalamus, cerebellum, cerebral cortex, and spinal cord. Therefore, this gene may play a role in central nervous system disorders such as Alzheimer's disease, Parkinson's disease, epilepsy, multiple sclerosis, schizophrenia and depression. Furthermore, mutations in K+ channel genes have been implicated in diseases as diverse as persistent hyperinsulinemia of infancy, cardiac long QT syndrome, cerebellar degeneration, epilepsy, and certain ataxias (Dukes I D, Philipson L H. (1996) K+ channels: generating excitement in pancreatic beta-cells. Diabetes 45(7):845–53; Moulard B, Picard F, le Hellard S, Agulhon C, Weiland S, Favre I, Bertrand S, Malafosse A, Bertrand D. (2001) Ion channel variation causes epilepsies. Brain Res Brain Res Rev 36(2–3):275–84). Therefore, therapeutic modulation of the activity of this gene may prove useful in the treatment of these diseases.

Panel 4.1D Summary: Ag3650 Highest expression of the CG88645-01 gene is detected in thymus (CT=32). Thus, expression of this gene may be used to identify thymic tissue. In addition, expression of this gene is stimulated in activated primary Th1 and Th2 cells (CTs=34.5–34.8). Therefore, drugs that inhibit the function of this protein may regulate T cell development in the thymus and reduce or eliminate the symptoms of T cell mediated autoimmune or inflammatory diseases, including asthma, allergies, inflammatory bowel disease, lupus erythematosus, or rheumatoid arthritis. Additionally, small molecule or antibody therapeutics designed against this putative protein may disrupt T cell development in the thymus and function as an immunosuppresant for tissue transplant.

P. CG88738-01: Synaptotagmin Interacting Protein STIP1

Expression of gene CG88738-01 was assessed using the primer-probe set Ag3676, described in Table PA.

TABLE PA

Probe Name Ag3676

| Primers | Sequences | Length | Start Position | SEQ ID NO: |
|---|---|---|---|---|
| Forward | 5'-tcgatcttcctcgacgtaagta-3' | 22 | 137 | 270 |
| Probe | TET-5'-tcctttgaagaattcaaagcatattttgca-3'-TAMRA | 30 | 179 | 271 |
| Reverse | 5'-tcttctccactgagaacaccat-3' | 22 | 210 | 272 |

CNS_neurodegeneration_v1.0 Summary: Ag3676 Expression of the CG88738-01 gene is low/undetectable in all samples on this panel (CTs>35). (Data not shown.)

General_screening_panel_v1.4 Summary: Ag3676 Expression of the CG88738-01 gene is low/undetectable in all samples on this panel (CTs>35). (Data not shown.)

Panel 4.1D Summary: Ag3676 Expression of the CG88738-01 gene is low/undetectable in all samples on this panel (CTs>35). (Data not shown.)

Q. CG88902-01 and CG88902-02: UDP Glucuronosyltransferase

Expression of gene CG88902-01 and full length clone CG88902-02 was assessed using the primer-probe set Ag3680, described in Table QA. Results of the RTQ-PCR runs are shown in Tables QB and QC. Please note that CG88902-02 represents a full-length physical clone of the CG88902-01 gene, validating the prediction of the gene sequence.

TABLE QA

Probe Name Ag3680

| Primers | Sequences | Length | Start Position | SEQ ID NO: |
|---|---|---|---|---|
| Forward | 5'-tttactgagggctttgagaaca-3' | 22 | 1366 | 273 |
| Probe | TET-5'-ccgattcctcttataaagagaatgctatga-3'-TAMRA | 30 | 1395 | 274 |
| Reverse | 5'-caggttgatcatggtgaattct-3' | 22 | 1433 | 275 |

TABLE QB

Panel 2.2

| Tissue Name | Rel. Exp. (%) Ag3680, Run 174441543 | Tissue Name | Rel. Exp. (%) Ag3680, Run 174441543 |
|---|---|---|---|
| Normal Colon | 19.2 | Kidney Margin (OD04348) | 19.5 |
| Colon cancer (OD06064) | 1.2 | Kidney malignant cancer (OD06204B) | 0.0 |
| Colon Margin (OD06064) | 30.4 | Kidney normal adjacent tissue (OD06204E) | 10.9 |
| Colon cancer (OD06159) | 0.4 | Kidney Cancer (OD04450-01) | 100.0 |
| Colon Margin (OD06159) | 19.3 | Kidney Margin (OD04450-03) | 6.3 |
| Colon cancer (OD06297-04) | 1.1 | Kidney Cancer 8120613 | 0.0 |
| Colon Margin (OD06297-05) | 16.3 | Kidney Margin 8120614 | 7.7 |
| CC Gr.2 ascend colon (ODO3921) | 1.7 | Kidney Cancer 9010320 | 0.9 |
| CC Margin (ODO3921) | 7.8 | Kidney Margin 9010321 | 3.2 |
| Colon cancer metastasis (OD06104) | 2.8 | Kidney Cancer 8120607 | 0.6 |
| Lung Margin (OD06104) | 37.6 | Kidney Margin 8120608 | 5.1 |
| Colon mets to lung (OD04451-01) | 0.5 | Normal Uterus | 0.0 |
| Lung Margin (OD04451-02) | 0.0 | Uterine Cancer 064011 | 0.0 |
| Normal Prostate | 0.0 | Normal Thyroid | 0.0 |
| Prostate Cancer (OD04410) | 0.0 | Thyroid Cancer 064010 | 0.0 |
| Prostate Margin (OD04410) | 0.0 | Thyroid Cancer A302152 | 0.0 |
| Normal Ovary | 0.0 | Thyroid Margin A302153 | 0.0 |
| Ovarian cancer (OD06283-03) | 0.0 | Normal Breast | 0.0 |
| Ovarian Margin (OD06283-07) | 0.0 | Breast Cancer (OD04566) | 0.0 |
| Ovarian Cancer 064008 | 0.3 | Breast Cancer 1024 | 0.0 |
| Ovarian cancer (OD06145) | 0.0 | Breast Cancer (OD04590-01) | 0.0 |
| Ovarian Margin (OD06145) | 0.0 | Breast Cancer Mets (OD04590-03) | 0.0 |
| Ovarian cancer (OD06455-03) | 0.0 | Breast Cancer Metastasis (OD04655-05) | 0.0 |
| Ovarian Margin (OD06455-07) | 0.0 | Breast Cancer 064006 | 0.0 |
| Normal Lung | 0.0 | Breast Cancer 9100266 | 0.0 |
| Invasive poor diff. lung adeno (ODO4945-01) | 0.0 | Breast Margin 9100265 | 0.0 |
| Lung Margin (ODO4945-03) | 0.0 | Breast Cancer A209073 | 0.0 |
| Lung Malignant Cancer (OD03126) | 0.0 | Breast Margin A2090734 | 0.0 |
| Lung Margin (OD03126) | 0.0 | Breast cancer (OD06083) | 0.0 |
| Lung Cancer (OD05014A) | 0.0 | Breast cancer node metastasis (OD06083) | 0.0 |
| Lung Margin (OD05014B) | 0.0 | Normal Liver | 6.0 |
| Lung cancer (OD06081) | 0.0 | Liver Cancer 1026 | 0.8 |
| Lung Margin (OD06081) | 0.0 | Liver Cancer 1025 | 4.8 |
| Lung Cancer (OD04237-01) | 0.0 | Liver Cancer 6004-T | 2.6 |
| Lung Margin (OD04237-02) | 0.0 | Liver Tissue 6004-N | 0.5 |
| Ocular Melanoma Metastasis | 0.0 | Liver Cancer 6005-T | 2.3 |
| Ocular Melanoma Margin (Liver) | 3.9 | Liver Tissue 6005-N | 4.0 |
| Melanoma Metastasis | 0.0 | Liver Cancer 064003 | 1.7 |

TABLE QB-continued

Panel 2.2

| Tissue Name | Rel. Exp. (%) Ag3680, Run 174441543 | Tissue Name | Rel. Exp. (%) Ag3680, Run 174441543 |
|---|---|---|---|
| Melanoma Margin (Lung) | 0.0 | Normal Bladder | 2.9 |
| Normal Kidney | 12.0 | Bladder Cancer 1023 | 0.0 |
| Kidney Ca, Nuclear grade 2 (OD04338) | 8.2 | Bladder Cancer A302173 | 0.6 |
| Kidney Margin (OD04338) | 8.0 | Normal Stomach | 0.3 |
| Kidney Ca Nuclear grade 1/2 (OD04339) | 54.0 | Gastric Cancer 9060397 | 0.0 |
| Kidney Margin (OD04339) | 27.9 | Stomach Margin 9060396 | 0.0 |
| Kidney Ca, Clear cell type (OD04340) | 23.8 | Gastric Cancer 9060395 | 0.0 |
| Kidney Margin (OD04340) | 9.9 | Stomach Margin 9060394 | 2.5 |
| Kidney Ca, Nuclear grade 3 (OD04348) | 0.5 | Gastric Cancer 064005 | 2.6 |

TABLE QC

Panel 4.1D

| Tissue Name | Rel. Exp. (%) Ag3680, Run 169988038 | Tissue Name | Rel. Exp. (%) Ag3680, Run 169988038 |
|---|---|---|---|
| Secondary Th1 act | 0.0 | HUVEC IL-1beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 0.0 | Microsvasular Dermal EC TNF alpha + IL-1beta | 0.0 |
| Primary Th1 rest | 0.0 | Bronchial epithelium TNF alpha + IL1beta | 0.0 |
| Primary Th2 rest | 0.0 | Small airway epithelium none | 0.0 |
| Primary Tr1 rest | 0.0 | Small airway epithelium TNF alpha + IL-1beta | 0.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1beta | 0.0 |
| CD8 lymphocyte act | 0.0 | Astrocytes rest | 0.0 |
| Secondary CD8 lymphocyte rest | 0.0 | Astrocytes TNF alpha + IL-1beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.1 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1beta | 0.0 |
| LAK cells IL-2 | 0.0 | Liver cirrhosis | 7.8 |
| LAK cells IL-2 + IL-12 | 0.0 | NCI-H292 none | 0.0 |
| LAK cells IL-2 + IFN gamma | 0.0 | NCI-H292 IL-4 | 0.0 |
| LAK cells IL-2 + IL-18 | 0.0 | NCI-H292 IL-9 | 0.0 |
| LAK cells PMA/ionomycin | 0.0 | NCI-H292 IL-13 | 0.0 |
| NK Cells IL-2 rest | 0.0 | NCI-H292 IFN gamma | 0.0 |
| Two Way MLR 3 day | 0.0 | HPAEC none | 0.0 |
| Two Way MLR 5 day | 0.0 | HPAEC TNF alpha + IL-1beta | 0.0 |
| Two Way MLR 7 day | 0.0 | Lung fibroblast none | 0.0 |
| PBMC rest | 0.0 | Lung fibroblast TNF alpha + IL-1beta | 0.0 |
| PBMC PWM | 0.0 | Lung fibroblast IL-4 | 0.0 |
| PBMC PHA-L | 0.0 | Lung fibroblast IL-9 | 0.0 |
| Ramos (B cell) none | 0.0 | Lung fibroblast IL-13 | 0.0 |
| Ramos (B cell) ionomycin | 0.0 | Lung fibroblast IFN gamma | 0.0 |
| B lymphocytes PWM | 0.0 | Dermal fibroblast CCD1070 rest | 0.0 |

TABLE QC-continued

Panel 4.1D

| Tissue Name | Rel. Exp. (%) Ag3680, Run 169988038 | Tissue Name | Rel. Exp. (%) Ag3680, Run 169988038 |
|---|---|---|---|
| B lymphocytes CD40L and IL-4 | 0.0 | Dermal fibroblast CCD1070 TNF alpha | 0.0 |
| EOL-1 dbcAMP | 0.0 | Dermal fibroblast CCD1070 IL-1beta | 0.0 |
| EOL-1 dbcAMP PMA/ionomycin | 0.0 | Dermal fibroblast IFN gamma | 0.0 |
| Dendritic cells none | 0.0 | Dermal fibroblast IL-4 | 0.0 |
| Dendritic cells LPS | 0.0 | Dermal Fibroblasts rest | 0.0 |
| Dendritic cells anti-CD40 | 0.0 | Neutrophils TNFa + LPS | 0.0 |
| Monocytes rest | 0.0 | Neutrophils rest | 0.0 |
| Monocytes LPS | 0.0 | Colon | 37.1 |
| Macrophages rest | 0.0 | Lung | 0.1 |
| Macrophages LPS | 0.0 | Thymus | 0.0 |
| HUVEC none | 0.0 | Kidney | 100.0 |
| HUVEC starved | 0.0 | | |

CNS_neurodegeneration_v1.0 Summary: Ag3680 Expression of the CG88902-01 gene is low/undetectable (CTs>35) across all of the samples on this panel (data not shown).

General_screening_panel_v1.4 Summary: Ag3680 Results from one experiment with the CG88902-01 gene are not included. The amp plot indicates that there were experimental difficulties with this run.

Panel 2.2 Summary: Ag3680 Highest expression of the CG88902-01 gene is detected in kidney cancer (OD04450-01) sample (CT=31.2). Interestingly, expression of this gene is higher in OD04450-01 cancer sample as compared to the control margin (OD04450-03) sample (CT=35.2). Thus, expression of this gene can be used as diagnostic marker to detection of kidney cancer and also, therapeutic modulation of the activity of the protein encoded by this gene may be beneficial in the treatment of kidney cancer.

In addition, expression of this gene is downregulated in colon cancer and colon cancer metastasis to lung. Therefore, therapeutic modulation to increase the activity of the protein encoded by this gene may be beneficial in the treatment of colon cancer.

Panel 4.1D Summary: Ag3680 Highest expression of the CG88902-01 gene is detected in kidney (CT=39.4). Significant expression of this gene is also seen in colon sample (Ct30.8). Thus, expression of this gene can be used to distinguish colon and kidney sample from other samples in this panel. In addition, therapeutic modulation of the activity of the protein encoded by this gene may be useful in the treatment of inflammatory bowel disease and inflammatory or autoimmune diseases that affect the kidney, including lupus and glomerulonephritis.

Moderate expression of this gene is also detected in liver cirrhosis sample (Ct33). The presence of this gene in liver cirrhosis (a component of which involves liver inflammation and fibrosis) suggests that antibodies to the protein encoded by this gene could also be used for the diagnosis of liver cirrhosis. Furthermore, therapeutic agents involving this gene may be useful in reducing or inhibiting the inflammation associated with fibrotic and inflammatory diseases.

R. CG89098-01: F-Box Protein

Expression of gene CG89098-01 was assessed using the primer-probe set Ag3688, described in Table RA. Results of the RTQ-PCR runs are shown in Tables RB, RC and RD.

TABLE RA

Probe Name Ag3688

| Primers | Sequences | Length | Start Position | SEQ ID NO: |
|---|---|---|---|---|
| Forward | 5'-acagcggctgtatgtacagact-3' | 22 | 607 | 276 |
| Probe | TET-5'-ccaacttctagacgccaaccagactg-3'-TAMRA | 26 | 635 | 277 |
| Reverse | 5'-tcaggcacagcagagaatttat-3' | 22 | 667 | 278 |

TABLE RB

CNS_neurodegeneration_v1.0

| Tissue Name | Rel. Exp. (%) Ag3688, Run 211144702 | Tissue Name | Rel. Exp. (%) Ag3688, Run 211144702 |
|---|---|---|---|
| AD 1 Hippo | 14.9 | Control (Path) 3 Temporal Ctx | 8.0 |
| AD 2 Hippo | 38.4 | Control (Path) 4 Temporal Ctx | 34.2 |
| AD 3 Hippo | 7.5 | AD 1 Occipital Ctx | 13.3 |
| AD 4 Hippo | 5.5 | AD 2 Occipital Ctx (Missing) | 0.0 |
| AD 5 Hippo | 94.6 | AD 3 Occipital Ctx | 9.7 |
| AD 6 Hippo | 33.7 | AD 4 Occipital Ctx | 12.2 |

TABLE RB-continued

CNS_neurodegeneration_v1.0

| Tissue Name | Rel. Exp. (%) Ag3688, Run 211144702 | Tissue Name | Rel. Exp. (%) Ag3688, Run 211144702 |
|---|---|---|---|
| Control 2 Hippo | 28.3 | AD 5 Occipital Ctx | 52.1 |
| Control 4 Hippo | 12.9 | AD 6 Occipital Ctx | 16.8 |
| Control (Path) 3 Hippo | 10.7 | Control 1 Occipital Ctx | 4.4 |
| AD 1 Temporal Ctx | 16.4 | Control 2 Occipital Ctx | 65.1 |
| AD 2 Temporal Ctx | 40.1 | Control 3 Occipital Ctx | 15.7 |
| AD 3 Temporal Ctx | 9.8 | Control 4 Occipital Ctx | 8.1 |
| AD 4 Temporal Ctx | 19.8 | Control (Path) 1 Occipital Ctx | 84.7 |
| AD 5 Inf Temporal Ctx | 100.0 | Control (Path) 2 Occipital Ctx | 14.3 |
| AD 5 Sup Temporal Ctx | 43.2 | Control (Path) 3 Occipital Ctx | 4.7 |
| AD 6 Inf Temporal Ctx | 47.3 | Control (Path) 4 Occipital Ctx | 15.8 |
| AD 6 Sup Temporal Ctx | 49.7 | Control 1 Parietal Ctx | 7.8 |
| Control 1 Temporal Ctx | 7.6 | Control 2 Parietal Ctx | 50.7 |
| Control 2 Temporal Ctx | 49.3 | Control 3 Parietal Ctx | 17.3 |
| Control 3 Temporal Ctx | 15.5 | Control (Path) 1 Parietal Ctx | 90.8 |
| Control 3 Temporal Ctx | 13.5 | Control (Path) 2 Parietal Ctx | 26.2 |
| Control (Path) 1 Temporal Ctx | 83.5 | Control (Path) 3 Parietal Ctx | 4.5 |
| Control (Path) 2 Temporal Ctx | 36.6 | Control (Path) 4 Parietal Ctx | 43.5 |

TABLE RC

General_screening_panel_v1.4

| Tissue Name | Rel. Exp. (%) Ag3688, Run 217130888 | Tissue Name | Rel. Exp. (%) Ag3688, Run 217130888 |
|---|---|---|---|
| Adipose | 10.8 | Renal ca. TK-10 | 20.7 |
| Melanoma* Hs688(A).T | 10.2 | Bladder | 2.7 |
| Melanoma* Hs688(B).T | 8.4 | Gastric ca. (liver met.) NCI-N87 | 1.3 |
| Melanoma* M14 | 13.0 | Gastric ca. KATO III | 0.2 |
| Melanoma* LOXIMVI | 0.0 | Colon ca. SW-948 | 0.0 |
| Melanoma* SK-MEL-5 | 6.8 | Colon ca. SW480 | 100.0 |
| Squamous cell carcinoma SCC-4 | 49.7 | Colon ca.* (SW480 met) SW620 | 25.2 |
| Testis Pool | 6.1 | Colon ca. HT29 | 0.0 |
| Prostate ca.* (bone met) PC-3 | 45.4 | Colon ca. HCT-116 | 43.8 |
| Prostate Pool | 6.2 | Colon ca. CaCo-2 | 10.6 |
| Placenta | 1.3 | Colon cancer tissue | 1.4 |
| Uterus Pool | 1.9 | Colon ca. SW1116 | 0.0 |
| Ovarian ca. OVCAR-3 | 19.1 | Colon ca. Colo-205 | 0.1 |
| Ovarian ca. SK-OV-3 | 6.3 | Colon ca. SW-48 | 0.1 |
| Ovarian ca. OVCAR-4 | 45.1 | Colon Pool | 9.4 |
| Ovarian ca. OVCAR-5 | 23.7 | Small Intestine Pool | 5.8 |
| Ovarian ca. IGROV-1 | 14.0 | Stomach Pool | 3.8 |
| Ovarian ca. OVCAR-8 | 12.7 | Bone Marrow Pool | 5.6 |
| Ovary | 10.9 | Fetal Heart | 7.7 |
| Breast ca. MCF-7 | 19.6 | Heart Pool | 4.2 |
| Breast ca. MDA-MB-231 | 57.0 | Lymph Node Pool | 10.5 |
| Breast ca. BT 549 | 3.6 | Fetal Skeletal Muscle | 2.4 |
| Breast ca. T47D | 50.3 | Skeletal Muscle Pool | 0.5 |
| Breast ca. MDA-N | 0.0 | Spleen Pool | 0.8 |
| Breast Pool | 9.4 | Thymus Pool | 4.1 |
| Trachea | 8.7 | CNS cancer (glio/astro) U87-MG | 50.7 |
| Lung | 4.1 | CNS cancer (glio/astro) U-118-MG | 16.3 |
| Fetal Lung | 7.3 | CNS cancer (neuro; met) SK-N-AS | 0.3 |
| Lung ca. NCI-N417 | 0.0 | CNS cancer (astro) SF-539 | 0.9 |
| Lung ca. LX-1 | 35.4 | CNS cancer (astro) SNB-75 | 7.5 |

TABLE RC-continued

General_screening_panel_v1.4

| Tissue Name | Rel. Exp. (%) Ag3688, Run 217130888 | Tissue Name | Rel. Exp. (%) Ag3688, Run 217130888 |
|---|---|---|---|
| Lung ca. NCI-H146 | 20.7 | CNS cancer (glio) SNB-19 | 12.3 |
| Lung ca. SHP-77 | 0.0 | CNS cancer (glio) SF-295 | 5.8 |
| Lung ca. A549 | 12.1 | Brain (Amygdala) Pool | 14.5 |
| Lung ca. NCI-H526 | 5.3 | Brain (cerebellum) | 90.8 |
| Lung ca. NCI-H23 | 65.1 | Brain (fetal) | 24.3 |
| Lung ca. NCI-H460 | 0.1 | Brain (Hippocampus) Pool | 16.5 |
| Lung ca. HOP-62 | 10.0 | Cerebral Cortex Pool | 27.5 |
| Lung ca. NCI-H522 | 18.2 | Brain (Substantia nigra) Pool | 22.4 |
| Liver | 1.8 | Brain (Thalamus) Pool | 21.6 |
| Fetal Liver | 11.8 | Brain (whole) | 27.9 |
| Liver ca. HepG2 | 1.3 | Spinal Cord Pool | 10.3 |
| Kidney Pool | 9.2 | Adrenal Gland | 3.6 |
| Fetal Kidney | 7.1 | Pituitary gland Pool | 2.8 |
| Renal ca. 786-0 | 17.7 | Salivary Gland | 6.4 |
| Renal ca. A498 | 11.7 | Thyroid (female) | 2.1 |
| Renal ca. ACHN | 35.1 | Pancreatic ca. CAPAN2 | 2.9 |
| Renal ca. UO-31 | 33.7 | Pancreas Pool | 7.3 |

TABLE RD

Panel 4.1D

| Tissue Name | Rel. Exp. (%) Ag3688, Run 169988046 | Tissue Name | Rel. Exp. (%) Ag3688, Run 169988046 |
|---|---|---|---|
| Secondary Th1 act | 1.6 | HUVEC IL-1beta | 12.3 |
| Secondary Th2 act | 4.6 | HUVEC IFN gamma | 16.4 |
| Secondary Tr1 act | 3.1 | HUVEC TNF alpha + IFN gamma | 5.4 |
| Secondary Th1 rest | 0.0 | HUVEC TNF alpha + IL4 | 3.9 |
| Secondary Th2 rest | 1.6 | HUVEC IL-11 | 11.9 |
| Secondary Tr1 rest | 0.5 | Lung Microvascular EC none | 16.7 |
| Primary Th1 act | 1.4 | Lung Microvascular EC TNF alpha + IL-1beta | 4.7 |
| Primary Th2 act | 5.6 | Microvascular Dermal EC none | 9.6 |
| Primary Tr1 act | 1.3 | Microsvascular Dermal EC TNF alpha + IL-1beta | 2.8 |
| Primary Th1 rest | 2.6 | Bronchial epithelium TNF alpha + IL1beta | 34.9 |
| Primary Th2 rest | 1.5 | Small airway epithelium none | 11.0 |
| Primary Tr1 rest | 0.4 | Small airway epithelium TNF alpha + IL-1beta | 19.1 |
| CD45RA CD4 lymphocyte act | 6.4 | Coronery artery SMC rest | 7.9 |
| CD45RO CD4 lymphocyte act | 10.8 | Coronery artery SMC TNF alpha + IL-1beta | 6.3 |
| CD8 lymphocyte act | 11.7 | Astrocytes rest | 6.7 |
| Secondary CD8 lymphocyte rest | 1.6 | Astrocytes TNF alpha + IL-1beta | 9.9 |
| Secondary CD8 lymphocyte act | 2.8 | KU-812 (Basophil) rest | 2.5 |
| CD4 lymphocyte none | 1.2 | KU-812 (Basophil) PMA/ionomycin | 4.6 |
| 2ry Th1/Th2/Tr1_anti-CD95 CH11 | 0.4 | CCD1106 (Keratinocytes) none | 58.6 |
| LAK cells rest | 0.3 | CCD1106 (Keratinocytes) TNF alpha + IL-1beta | 45.1 |
| LAK cells IL-2 | 2.7 | Liver cirrhosis | 6.7 |
| LAK cells IL-2 + IL-12 | 1.2 | NCI-H292 none | 72.2 |
| LAK cells IL-2 + IFN gamma | 2.0 | NCI-H292 IL-4 | 85.9 |
| LAK cells IL-2 + IL-18 | 0.7 | NCI-H292 IL-9 | 100.0 |
| LAK cells PMA/ionomycin | 0.4 | NCI-H292 IL-13 | 87.1 |
| NK Cells IL-2 rest | 1.4 | NCI-H292 IFN gamma | 98.6 |
| Two Way MLR 3 day | 0.0 | HPAEC none | 10.4 |
| Two Way MLR 5 day | 6.2 | HPAEC TNF alpha + IL-1beta | 8.9 |
| Two Way MLR 7 day | 19.2 | Lung fibroblast none | 14.8 |
| PBMC rest | 0.0 | Lung fibroblast TNF alpha + IL-1beta | 6.9 |

TABLE RD-continued

Panel 4.1D

| Tissue Name | Rel. Exp. (%) Ag3688, Run 169988046 | Tissue Name | Rel. Exp. (%) Ag3688, Run 169988046 |
|---|---|---|---|
| PBMC PWM | 1.5 | Lung fibroblast IL-4 | 7.7 |
| PBMC PHA-L | 6.2 | Lung fibroblast IL-9 | 18.2 |
| Ramos (B cell) none | 0.0 | Lung fibroblast IL-13 | 10.5 |
| Ramos (B cell) ionomycin | 0.0 | Lung fibroblast IFN gamma | 12.3 |
| B lymphocytes PWM | 2.7 | Dermal fibroblast CCD1070 rest | 15.8 |
| B lymphocytes CD40L and IL-4 | 4.0 | Dermal fibroblast CCD1070 TNF alpha | 6.3 |
| EOL-1 dbcAMP | 0.0 | Dermal fibroblast CCD1070 IL-1beta | 10.2 |
| EOL-1 dbcAMP PMA/ionomycin | 0.0 | Dermal fibroblast IFN gamma | 5.4 |
| Dendritic cells none | 2.3 | Dermal fibroblast IL-4 | 13.3 |
| Dendritic cells LPS | 1.4 | Dermal Fibroblasts rest | 21.2 |
| Dendritic cells anti-CD40 | 0.4 | Neutrophils TNFa + LPS | 0.0 |
| Monocytes rest | 0.0 | Neutrophils rest | 0.0 |
| Monocytes LPS | 0.0 | Colon | 14.1 |
| Macrophages rest | 0.6 | Lung | 7.8 |
| Macrophages LPS | 0.4 | Thymus | 7.2 |
| HUVEC none | 11.7 | Kidney | 32.3 |
| HUVEC starved | 9.1 | | |

CNS_neurodegeneration_v1.0 Summary: Ag3688 This panel does not show differential expression of the CG89098-01 gene in Alzheimer's disease. However, this expression profile confirms the presence of this gene in the brain. Please see Panel 1.4 for discussion of utility of this gene in the central nervous system.

General_screening_panel_v1.4 Summary: Ag3688 Highest expression of the CG89098-01 gene, which encodes a putative F box protein, is seen in a colon cancer cell line (CT=27). This gene also shows high to moderate levels of expression in many of the cancer cell lines on this panel, including samples derived from brain, renal, lung, breast, ovarian and prostate cancer cell lines. Thus, expression of this gene could be used as a marker for colon cancer. It has been suggested that F-box proteins are involved in the regulation of many processes, including cell division. Therefore, therapeutic modulation of the expression or function of this gene may be effective in the treatment of these cancers.

Among tissues with metabolic function, this gene is expressed at moderate to low levels in pituitary, adipose, adrenal gland, pancreas, thyroid, and adult and fetal skeletal muscle, heart, and liver. This widespread expression among these tissues suggests that this gene product may play a role in normal neuroendocrine and metabolic and that disregulated expression of this gene may contribute to neuroendocrine disorders or metabolic diseases, such as obesity and diabetes.

This gene is also expressed at high to moderate levels in the CNS, including the hippocampus, thalamus, substantia nigra, amygdala, cerebellum and cerebral cortex. Therefore, therapeutic modulation of the expression or function of this gene may be useful in the treatment of neurologic disorders, such as Alzheimer's disease, Parkinson's disease, schizophrenia, multiple sclerosis, stroke and epilepsy.

Overall, this gene shows widespread expression in the samples on this panel, perhaps reflecting a broader role for this gene product in cellular processes, as has been suggested for F box proteins.

Panel 4.1D Summary: Ag3688 Expression of the CG89098-01 gene is highest in a cluster of treated and untreated samples from the NCI-H292 mucoepidermoid cell line (CTs=30). Significant levels of expression are also seen in treated and untreated keratinocytes. Low but significant levels of expression are also seen in a variety of nonhematopoietic cell samples including lung and dermal fibroblasts, small airway and bronchial epithelium, lung and dermal microvasculature, human pulmonary aortic endothelial cells, HUVECs, and smooth muscle cells. Given this distribution of expression in cells involved in inflammatory processes of the lung and skin, therapeutic modulation of the expression or function of this gene product may reduce or eliminate symptoms in patients suffering from asthma, allergy, emphysema and psoriasis.

S. CG89126-01: Cytochrome P450

Expression of gene CG89126-01 was assessed using the primer-probe set Ag3689, described in Table SA. Results of the RTQ-PCR runs are shown in Table SB.

TABLE SA

Probe Name Ag3689

| Primers | Sequences | Length | Start Position | SEQ ID NO: |
|---|---|---|---|---|
| Forward | 5'-cgccttccatttcaacatc-3' | 19 | 477 | 279 |
| Probe | TET-5'-tcctatataacgatcttcaacaagagtgca-3'-TAMRA | 30 | 502 | 280 |
| Reverse | 5'-ccacttgtcaagcatgatgtt-3' | 21 | 532 | 281 |

TABLE SB

Panel 2.2

| Tissue Name | Rel. Exp. (%) Ag3689, Run 174441628 | Tissue Name | Rel. Exp. (%) Ag3689, Run 174441628 |
|---|---|---|---|
| Normal Colon | 0.1 | Kidney Margin (OD04348) | 0.0 |
| Colon cancer (OD06064) | 0.0 | Kidney malignant cancer (OD06204B) | 0.0 |
| Colon Margin (OD06064) | 30.4 | Kidney normal adjacent tissue (OD06204E) | 0.0 |
| Colon cancer (OD06159) | 0.0 | Kidney Cancer (OD04450-01) | 0.0 |
| Colon Margin (OD06159) | 0.9 | Kidney Margin (OD04450-03) | 0.0 |
| Colon cancer (OD06297-04) | 0.0 | Kidney Cancer 8120613 | 0.0 |
| Colon Margin (OD06297-05) | 0.0 | Kidney Margin 8120614 | 0.0 |
| CC Gr.2 ascend colon (ODO3921) | 0.0 | Kidney Cancer 9010320 | 0.0 |
| CC Margin (ODO3921) | 0.0 | Kidney Margin 9010321 | 0.0 |
| Colon cancer metastasis (OD06104) | 0.0 | Kidney Cancer 8120607 | 0.0 |
| Lung Margin (OD06104) | 0.0 | Kidney Margin 8120608 | 0.0 |
| Colon mets to lung (OD04451-01) | 0.0 | Normal Uterus | 0.0 |
| Lung Margin (OD04451-02) | 0.0 | Uterine Cancer 064011 | 0.0 |
| Normal Prostate | 0.0 | Normal Thyroid | 0.0 |
| Prostate Cancer (OD04410) | 0.0 | Thyroid Cancer 064010 | 0.0 |
| Prostate Margin (OD04410) | 0.0 | Thyroid Cancer A302152 | 0.0 |
| Normal Ovary | 0.0 | Thyroid Margin A302153 | 0.0 |
| Ovarian cancer (OD06283-03) | 0.0 | Normal Breast | 0.0 |
| Ovarian Margin (OD06283-07) | 0.0 | Breast Cancer (OD04566) | 0.0 |
| Ovarian Cancer 064008 | 0.0 | Breast Cancer 1024 | 0.0 |
| Ovarian cancer (OD06145) | 0.0 | Breast Cancer (OD04590-01) | 0.0 |
| Ovarian Margin (OD06145) | 0.0 | Breast Cancer Mets (OD04590-03) | 0.0 |
| Ovarian cancer (OD06455-03) | 0.0 | Breast Cancer Metastasis (OD04655-05) | 1.4 |
| Ovarian Margin (OD06455-07) | 0.0 | Breast Cancer 064006 | 0.0 |
| Normal Lung | 0.0 | Breast Cancer 9100266 | 0.0 |
| Invasive poor diff. lung adeno (ODO4945-01 | 0.0 | Breast Margin 9100265 | 0.0 |
| Lung Margin (ODO4945-03) | 0.0 | Breast Cancer A209073 | 0.0 |
| Lung Malignant Cancer (OD03126) | 0.0 | Breast Margin A2090734 | 0.0 |
| Lung Margin (OD03126) | 0.0 | Breast cancer (OD06083) | 0.0 |
| Lung Cancer (OD05014A) | 0.0 | Breast cancer node metastasis (OD06083) | 0.0 |
| Lung Margin (OD05014B) | 0.0 | Normal Liver | 22.2 |
| Lung cancer (OD06081) | 0.0 | Liver Cancer 1026 | 0.0 |
| Lung Margin (OD06081) | 0.0 | Liver Cancer 1025 | 80.7 |
| Lung Cancer (OD04237-01) | 0.0 | Liver Cancer 6004-T | 88.3 |
| Lung Margin (OD04237-02) | 0.0 | Liver Tissue 6004-N | 0.0 |
| Ocular Melanoma Metastasis | 0.0 | Liver Cancer 6005-T | 0.0 |
| Ocular Melanoma Margin (Liver) | 0.7 | Liver Tissue 6005-N | 100.0 |
| Melanoma Metastasis | 0.0 | Liver Cancer 064003 | 0.0 |
| Melanoma Margin (Lung) | 0.0 | Normal Bladder | 0.0 |
| Normal Kidney | 0.0 | Bladder Cancer 1023 | 0.0 |
| Kidney Ca, Nuclear grade 2 (OD04338) | 0.0 | Bladder Cancer A302173 | 0.0 |
| Kidney Margin (OD04338) | 0.0 | Normal Stomach | 0.1 |
| Kidney Ca Nuclear grade 1/2 (OD04339) | 0.0 | Gastric Cancer 9060397 | 0.0 |
| Kidney Margin (OD04339) | 0.0 | Stomach Margin 9060396 | 2.0 |
| Kidney Ca, Clear cell type (OD04340) | 0.0 | Gastric Cancer 9060395 | 0.0 |
| Kidney Margin (OD04340) | 0.0 | Stomach Margin 9060394 | 3.2 |
| Kidney Ca, Nuclear grade 3 (OD04348) | 0.0 | Gastric Cancer 064005 | 0.0 |

CNS_neurodegeneration v1.0 Summary: Ag3689 Expression of the CG89126-01 gene is low/undetectable in all samples on this panel (CTs>35). (Data not shown.)

General_screening_panel_v1.4 Summary: Ag3689 Expression of the CG89126-01 gene is low/undetectable in all samples on this panel (CTs>35). (Data not shown.)

Panel 2.2 Summary: Ag3689 Expression of the CG89126-01 gene is essentially restricted to liver derived tissue, with highest expression in normal liver tissue (CT=29.8). Moderate levels of expression of this gene are also seen in samples derived from liver cancer. Thus, expression of this gene could be used as a marker of liver tissue and to differentiate between liver derived samples and other samples on this panel.

Panel 4.1D Summary: Ag3689 Expression of the CG89126-01 gene is low/undetectable in all samples on this panel (CTs>35). (Data not shown.)

T. CG89677-01: Arylsulfatase

Expression of gene CG89677-01 was assessed using the primer-probe set Ag3695, described in Table TA. Results of the RTQ-PCR runs are shown in Tables TB, and TC.

TABLE TA

Probe Name Ag3695

| Primers | Sequences | Length | Start Position | SEQ ID NO: |
|---|---|---|---|---|
| Forward | 5'-gtacgctacccagctgagaac-3' | 21 | 1474 | 282 |
| Probe | TET-5'-ccccgggctcatcctgactttaat-3'-TAMRA | 24 | 1495 | 283 |
| Reverse | 5'-cttcctcctcttcctcatcact-3' | 22 | 1543 | 284 |

TABLE TB

General_screening_panel_v1.4

| Tissue Name | Rel. Exp. (%) Ag3695, Run 213406518 | Tissue Name | Rel. Exp. (%) Ag3695, Run 213406518 |
|---|---|---|---|
| Adipose | 0.6 | Renal ca. TK-10 | 17.9 |
| Melanoma* Hs688(A).T | 9.3 | Bladder | 3.5 |
| Melanoma* Hs688(B).T | 7.7 | Gastric ca. (liver met.) NCI-N87 | 0.0 |
| Melanoma* M14 | 0.0 | Gastric ca. KATO III | 0.0 |
| Melanoma* LOXIMVI | 0.0 | Colon ca. SW-948 | 0.0 |
| Melanoma* SK-MEL-5 | 0.0 | Colon ca. SW480 | 0.0 |
| Squamous cell carcinoma SCC-4 | 4.0 | Colon ca.* (SW480 met) SW620 | 0.0 |
| Testis Pool | 0.0 | Colon ca. HT29 | 0.0 |
| Prostate ca.* (bone met) PC-3 | 2.1 | Colon ca. HCT-116 | 0.4 |
| Prostate Pool | 1.8 | Colon ca. CaCo-2 | 0.6 |
| Placenta | 21.9 | Colon cancer tissue | 13.2 |
| Uterus Pool | 1.8 | Colon ca. SW1116 | 0.0 |
| Ovarian ca. OVCAR-3 | 3.4 | Colon ca. Colo-205 | 0.0 |
| Ovarian ca. SK-OV-3 | 4.5 | Colon ca. SW-48 | 0.3 |
| Ovarian ca. OVCAR-4 | 2.5 | Colon Pool | 8.0 |
| Ovarian ca. OVCAR-5 | 0.0 | Small Intestine Pool | 0.4 |
| Ovarian ca. IGROV-1 | 0.0 | Stomach Pool | 2.2 |
| Ovarian ca. OVCAR-8 | 16.5 | Bone Marrow Pool | 1.3 |
| Ovary | 0.5 | Fetal Heart | 0.4 |
| Breast ca. MCF-7 | 0.0 | Heart Pool | 2.6 |
| Breast ca. MDA-MB-231 | 30.8 | Lymph Node Pool | 6.0 |
| Breast ca. BT 549 | 9.0 | Fetal Skeletal Muscle | 2.3 |
| Breast ca. T47D | 0.9 | Skeletal Muscle Pool | 0.6 |
| Breast ca. MDA-N | 0.0 | Spleen Pool | 2.4 |
| Breast Pool | 5.2 | Thymus Pool | 4.3 |
| Trachea | 1.9 | CNS cancer (glio/astro) U87-MG | 100.0 |
| Lung | 0.0 | CNS cancer (glio/astro) U-118-MG | 4.9 |
| Fetal Lung | 26.6 | CNS cancer (neuro; met) SK-N-AS | 0.0 |
| Lung ca. NCI-N417 | 0.0 | CNS cancer (astro) SF-539 | 24.8 |
| Lung ca. LX-1 | 0.0 | CNS cancer (astro) SNB-75 | 74.7 |
| Lung ca. NCI-H146 | 1.3 | CNS cancer (glio) SNB-19 | 0.0 |
| Lung ca. SHP-77 | 0.0 | CNS cancer (glio) SF-295 | 0.8 |
| Lung ca. A549 | 9.5 | Brain (Amygdala) Pool | 2.6 |
| Lung ca. NCI-H526 | 0.0 | Brain (cerebellum) | 0.0 |
| Lung ca. NCI-H23 | 9.9 | Brain (fetal) | 0.0 |
| Lung ca. NCI-H460 | 0.0 | Brain (Hippocampus) Pool | 1.7 |
| Lung ca. HOP-62 | 87.1 | Cerebral Cortex Pool | 2.0 |
| Lung ca. NCI-H522 | 0.0 | Brain (Substantia nigra) Pool | 4.5 |
| Liver | 0.0 | Brain (Thalamus) Pool | 2.2 |
| Fetal Liver | 0.0 | Brain (whole) | 0.5 |
| Liver ca. HepG2 | 22.2 | Spinal Cord Pool | 4.2 |
| Kidney Pool | 9.0 | Adrenal Gland | 0.0 |

TABLE TB-continued

General_screening_panel_v1.4

| Tissue Name | Rel. Exp. (%) Ag3695, Run 213406518 | Tissue Name | Rel. Exp. (%) Ag3695, Run 213406518 |
|---|---|---|---|
| Fetal Kidney | 2.8 | Pituitary gland Pool | 0.0 |
| Renal ca. 786-0 | 0.0 | Salivary Gland | 0.0 |
| Renal ca. A498 | 1.6 | Thyroid (female) | 0.0 |
| Renal ca. ACHN | 42.9 | Pancreatic ca. CAPAN2 | 3.9 |
| Renal ca. UO-31 | 9.3 | Pancreas Pool | 4.6 |

TABLE TC

Panel 4.1D

| Tissue Name | Rel. Exp. (%) Ag3695, Run 169987358 | Tissue Name | Rel. Exp. (%) Ag3695, Run 169987358 |
|---|---|---|---|
| Secondary Th1 act | 8.5 | HUVEC IL-1beta | 1.5 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 0.0 | Microsvascular Dermal EC TNF alpha + IL-1beta | 0.0 |
| Primary Th1 rest | 0.0 | Bronchial epithelium TNF alpha + IL1beta | 32.5 |
| Primary Th2 rest | 0.0 | Small airway epithelium none | 2.8 |
| Primary Tr1 rest | 0.0 | Small airway epithelium TNF alpha + IL-1beta | 1.9 |
| CD45RA CD4 lymphocyte act | 19.6 | Coronery artery SMC rest | 2.6 |
| CD45RO CD4 lymphocyte act | 0.0 | Coronery artery SMC TNF alpha + IL-1beta | 12.8 |
| CD8 lymphocyte act | 0.0 | Astrocytes rest | 15.3 |
| Secondary CD8 lymphocyte rest | 0.0 | Astrocytes TNF alpha + IL-1beta | 12.6 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 100.0 |
| LAK cells rest | 0.0 | CCD1106 (Keratinocytes) TNF alpha + IL-1beta | 69.3 |
| LAK cells IL-2 | 0.0 | Liver cirrhosis | 0.0 |
| LAK cells IL-2 + IL-12 | 0.0 | NCI-H292 none | 19.9 |
| LAK cells IL-2 + IFN gamma | 0.0 | NCI-H292 IL-4 | 24.8 |
| LAK cells IL-2 + IL-18 | 0.0 | NCI-H292 IL-9 | 15.2 |
| LAK cells PMA/ionomycin | 0.0 | NCI-H292 IL-13 | 26.8 |
| NK Cells IL-2 rest | 0.0 | NCI-H292 IFN gamma | 24.7 |
| Two Way MLR 3 day | 0.0 | HPAEC none | 0.0 |
| Two Way MLR 5 day | 0.0 | HPAEC TNF alpha + IL-1beta | 0.0 |
| Two Way MLR 7 day | 0.0 | Lung fibroblast none | 5.4 |
| PBMC rest | 0.0 | Lung fibroblast TNF alpha + IL-1beta | 4.4 |
| PBMC PWM | 0.0 | Lung fibroblast IL-4 | 6.8 |
| PBMC PHA-L | 0.0 | Lung fibroblast IL-9 | 12.0 |
| Ramos (B cell) none | 0.0 | Lung fibroblast IL-13 | 1.6 |
| Ramos (B cell) ionomycin | 0.0 | Lung fibroblast IFN gamma | 0.0 |
| B lymphocytes PWM | 0.0 | Dermal fibroblast CCD1070 rest | 35.8 |
| B lymphocytes CD40L and IL-4 | 0.0 | Dermal fibroblast CCD1070 TNF alpha | 10.8 |
| EOL-1 dbcAMP | 0.0 | Dermal fibroblast CCD1070 IL-1beta | 40.1 |
| EOL-1 dbcAMP PMA/ionomycin | 0.0 | Dermal fibroblast IFN gamma | 2.6 |
| Dendritic cells none | 0.0 | Dermal fibroblast IL-4 | 1.7 |
| Dendritic cells LPS | 0.0 | Dermal Fibroblast rest | 2.0 |

TABLE TC-continued

Panel 4.1D

| Tissue Name | Rel. Exp. (%) Ag3695, Run 169987358 | Tissue Name | Rel. Exp. (%) Ag3695, Run 169987358 |
|---|---|---|---|
| Dendritic cells anti-CD40 | 0.0 | Neutrophils TNFa + LPS | 0.0 |
| Monocytes rest | 0.0 | Neutrophils rest | 3.0 |
| Monocytes LPS | 0.0 | Colon | 1.3 |
| Macrophages rest | 0.0 | Lung | 23.5 |
| Macrophages LPS | 0.0 | Thymus | 1.4 |
| HUVEC none | 0.0 | Kidney | 6.3 |
| HUVEC starved | 0.0 | | |

CNS_neurodegeneration_v1.0 Summary: Ag3695 Expression of the CG89677-01 gene is low/undetectable (CTs>35) across all of the samples on this panel (data not shown).

General_screening_panel_v1.4 Summary: Ag3695 Expression of teh CG89677-01 gene is limited to a few samples in this panel, with highest expression in a brain cancer cell line (CT=31.6). Moderate levels of expression are also seen in a lung cancer cell line. Thus, expression of this gene could be used to differentiate between these samples and other samples on this panel, and as a marker for these cancers. Furthermore, therapeutic modulation of the expression or function of this gene may be effective in the treatment of lung or brain cancer.

Panel 2.2 Summary: Ag3695 Expression of the CG89677-01 gene is low/undetectable in all samples on this panel (CTs>35). (Data not shown.)

Panel 4.1D Summary: Ag3695 Expression of the CG89677-01 gene is restricted to untreated keratinocytes and keratinocytes treated with the inflammatory cytokines TNF-a and IL-1b (CTs=33–34). Therefore, modulation of the expression or activity of the protein encoded by this transcript through the application of small molecule therapeutics may be useful in the treatment of psoriasis and wound healing.

U. CG89697-01 and CG89697-02: RIS

Expression of gene CG89697-01 and full length clone CG89697-02 was assessed using the primer-probe sets Ag4699 and Ag4523, described in Tables UA and UB. Results of the RTQ-PCR runs are shown in Tables UC, UD and UE. Please note that CG89697-02 represents a full-length physical clone of the CG89697-01 gene, validating the prediction of the gene sequence.

TABLE UA

Probe Name Ag4699

| Primers | Sequences | Length | Start Position | SEQ ID NO: |
|---|---|---|---|---|
| Forward | 5'-ctggtcaccgtgaagtcatc-3' | 20 | 766 | 285 |
| Probe | TET-5'-cctaccctgactctcctgaagggctt-3'-TAMRA | 26 | 811 | 286 |
| Reverse | 5'-ggggcctcagaagatcttg-3' | 19 | 837 | 287 |

TABLE UB

Probe Name Ag4523

| Primers | Sequences | Length | Start Position | SEQ ID NO: |
|---|---|---|---|---|
| Forward | 5'-ggctcagtacaggcaagtca-3' | 20 | 462 | 288 |
| Probe | TET-5'-aggcaggtttgggtgcctgtttt-3'-TAMRA | 23 | 507 | 289 |
| Reverse | 5'-caaagtccagacaggcagag-3' | 20 | 537 | 290 |

TABLE UC

CNS_neurodegeneration_v1.0

| Tissue Name | Rel. Exp. (%) Avg4699, Run 224710805 | Rel. Exp. (%) Ag4699, Run 230510316 | Tissue Name | Rel. Exp. (%) Ag4699, Run 224710805 | Rel. Exp. (%) Ag4699, Run 230510316 |
|---|---|---|---|---|---|
| AD 1 Hippo | 14.0 | 4.6 | Control (Path) 3 Temporal Ctx | 1.0 | 3.2 |
| AD 2 Hippo | 21.9 | 19.1 | Control (Path) 4 Temporal Ctx | 3.4 | 3.7 |
| AD 3 Hippo | 4.9 | 6.1 | AD 1 Occipital Ctx | 3.4 | 2.1 |
| AD 4 Hippo | 9.6 | 9.8 | AD 2 Occipital Ctx (Missing) | 0.0 | 0.0 |
| AD 5 hippo | 11.5 | 12.1 | AD 3 Occipital Ctx | 2.0 | 2.9 |
| AD 6 Hippo | 100.0 | 100.0 | AD 4 Occipital Ctx | 8.2 | 6.4 |
| Control 2 Hippo | 10.0 | 6.6 | AD 5 Occipital Ctx | 3.5 | 0.0 |

TABLE UC-continued

CNS_neurodegeneration_v1.0

| Tissue Name | Rel. Exp. (%) Avg4699, Run 224710805 | Rel. Exp. (%) Ag4699, Run 230510316 | Tissue Name | Rel. Exp. (%) Ag4699, Run 224710805 | Rel. Exp. (%) Ag4699, Run 230510316 |
|---|---|---|---|---|---|
| Control 4 Hippo | 23.7 | 17.8 | AD 6 Occipital Ctx | 3.4 | 3.8 |
| Control (Path) 3 Hippo | 3.9 | 1.4 | Control 1 Occipital Ctx | 3.1 | 2.0 |
| AD 1 Temporal Ctx | 7.4 | 5.6 | Control 2 Occipital CTx | 6.3 | 3.9 |
| AD 2 Temporal Ctx | 7.3 | 9.9 | Control 3 Occipital Ctx | 2.5 | 2.8 |
| AD 3 Temporal Ctx | 4.9 | 3.4 | Control 4 Occipital Ctx | 6.6 | 5.3 |
| AD 4 Temporal Ctx | 7.9 | 3.0 | Control (Path) 1 Occipital Ctx | 12.2 | 10.7 |
| AD 5 Inf Temporal Ctx | 23.3 | 27.52 | Control (Path) 2 Occipital Ctx | 2.8 | 0.0 |
| AD 5 SupTemporal Ctx | 40.6 | 44.4 | Control (Path) 3 Occipital Ctx | 0.7 | 1.4 |
| AD 6 Inf Temporal Ctx | 36.9 | 53.2 | Control (Path) 4 Occipital Ctx | 4.1 | 5.1 |
| AD 6 Sup Temporal Ctx | 23.2 | 31.0 | Control 1 Parietal Ctx | 4.0 | 4.9 |
| Control 1 Temporal Ctx | 2.3 | 3.1 | Control 2 Parietal Ctx | 16.4 | 19.8 |
| Control 2 Temporal Ctx | 4.3 | 2.0 | Control 3 Parietal Ctx | 3.4 | 0.5 |
| Control 3 Temporal Ctx | 1.6 | 2.5 | Control (Path) 1 Parietal Ctx | 4.3 | 4.8 |
| Control 4 Temporal Ctx | 5.3 | 6.2 | Control (Path) 2 Parietal Ctx | 2.3 | 4.4 |
| Control (Path) 1 Temporal Ctx | 8.0 | 4.5 | Control (Path) 3 Parietal Ctx | 1.3 | 1.4 |
| Control (Path) 2 Temporal Ctx | 1.7 | 3.1 | Control (Path) 4 Parietal Ctx | 6.4 | 3.3 |

TABLE UD

General_screening_panel_v1.4

| Tissue Name | Rel. Exp.(%) Ag4523, Run 222714393 | Rel. Exp.(%) Ag4699, Run 222812001 | Tissue Name | Rel. Exp.(%) Ag4523, Run 222714393 | Rel. Exp.(%) Ag4699, Run 222812001 |
|---|---|---|---|---|---|
| Adipose | 6.9 | 3.8 | Renal ca. TK-10 | 0.0 | 0.1 |
| Melanoma* Hs688(A).T | 0.0 | 0.0 | Bladder | 7.1 | 6.5 |
| Melanoma* Hs688(B).T | 0.0 | 0.1 | Gastric Ca. (liver met.) NCI-N87 | 0.4 | 0.0 |
| Melanoma* M14 | 0.0 | 0.0 | Gastric ca. KATO III | 0.0 | 0.2 |
| Melanoma* LOXIMVI | 0.4 | 0.0 | Colon ca. SW-948 | 0.0 | 0.0 |
| Melanoma* SK-MEL-5 | 0.2 | 0.0 | Colon ca. SW480 | 0.0 | 0.0 |
| Squamous cell carcinoma SCC-4 | 0.3 | 0.0 | Colon ca.* (SW480 met) SW620 | 0.0 | 0.0 |
| Testis Pool | 17.7 | 17.7 | Colon ca. HT29 | 0.0 | 0.1 |
| Prostate ca.* (bone met) PC-3 | 0.0 | 0.0 | Colon ca. HCT-116 | 0.0 | 0.0 |
| Prostate Pool | 16.3 | 14.7 | Colon ca. CaCo-2 | 10.2 | 8.6 |
| Placenta | 11.9 | 9.9 | Colon cancer tissue | 4.9 | 5.1 |
| Uterus Pool | 7.5 | 16.7 | Colon. SW1116 | 0.0 | 0.2 |
| Ovarian ca. OVCAR-3 | 4.5 | 3.6 | Colon ca. Colo-205 | 0.0 | 0.0 |
| Ovarian ca. SK-OV-3 | 12.7 | 13.3 | Colon ca. SW-48 | 1.7 | 2.1 |
| Ovarian ca. OVCAR-4 | 1.6 | 1.1 | Colon Pool | 44.1 | 45.1 |
| Ovarian ca. OVCAR-5 | 0.4 | 0.4 | Small Intestine Pool | 18.9 | 18.3 |

TABLE UD-continued

General_screening_panel_v1.4

| Tissue Name | Rel. Exp.(%) Ag4523, Run 222714393 | Rel. Exp.(%) Ag4699, Run 222812001 | Tissue Name | Rel. Exp.(%) Ag4523, Run 222714393 | Rel. Exp.(%) Ag4699, Run 222812001 |
|---|---|---|---|---|---|
| Ovarian ca. IGROV-1 | 0.0 | 0.1 | Stomach Pool | 12.8 | 15.9 |
| Ovarian ca. OVCAR-8 | 0.0 | 0.0 | Bone Marrow Pool | 12.6 | 12.7 |
| Ovary | 6.4 | 7.4 | Fetal Heart | 23.2 | 18.4 |
| Breast ca. MCF-7 | 0.0 | 0.0 | Heart Pool | 11.8 | 10.7 |
| Breast ca. MDA-MB-231 | 0.0 | 0.0 | Lymph Node Pool | 52.5 | 58.2 |
| Breast ca. BT 549 | 0.4 | 0.5 | Fetal Skeletal Muscle | 5.3 | 7.3 |
| Breast ca. T47D | 0.9 | 0.4 | Skeletal Muscle Pool | 9.3 | 9.1 |
| Breast ca. MDA-N | 0.0 | 0.0 | Spleen Pool | 3.5 | 5.0 |
| Breast Pool | 42.0 | 40.6 | Thymus Pool | 12.2 | 11.1 |
| Trachea | 18.8 | 18.6 | CNS cancer (glio/astro) U87-MG | 0.0 | 0.0 |
| Lung | 3.2 | 4.3 | CNS cancer (glio/astro) U-118-MG | 0.3 | 0.2 |
| Fetal Lung | 100.0 | 100.0 | CNS cancer (neuro;met) SK-N-AS | 0.2 | 0.1 |
| Lung ca. NCI-N417 | 0.0 | 0.0 | CNS cancer (astro) SF-539 | 0.0 | 0.0 |
| Lung ca. LX-1 | 0.4 | 0.5 | CNS cancer (astro) SNB-75 | 0.5 | 0.3 |
| Lung ca. NCI-H146 | 0.7 | 0.5 | CNS cancer (glio) SNB-19 | 0.0 | 0.3 |
| Lung ca. SHP-77 | 0.0 | 0.1 | CNS cancer (glio) SF-295 | 0.3 | 0.1 |
| Lung ca. A549 | 0.4 | 1.0 | Brain (Amygdala) Pool | 6.0 | 9.7 |
| Lung ca. NCI-H526 | 0.0 | 0.0 | Brian (cerebellum) | 9.8 | 11.4 |
| Lung ca. NCI-H23 | 5.4 | 3.3 | Brain (fetal) | 3.7 | 2.4 |
| Lung ca. NCI-H460 | 0.0 | 0.0 | Brain (Hippocampus) Pool | 13.3 | 13.7 |
| Lung ca. HOP-62 | 0.7 | 0.2 | Cerebral Cortex Pool | 7.0 | 4.7 |
| Lung ca. NCI-H522 | 0.7 | 0.0 | Brain (Substantia nigra) Pool | 9.1 | 7.9 |
| Liver | 0.1 | 0.1 | Brain (Thalamus) Pool | 11.4 | 12.7 |
| Fetal Liver | 1.7 | 1.3 | Brain (whole) | 6.7 | 6.1 |
| Liver ca. HepG2 | 0.0 | 0.1 | Spinal Cord Pool | 18.8 | 16.5 |
| Kidney Pool | 50.3 | 64.2 | Adrenal Gland | 4.4 | 2.2 |
| Fetal Kidney | 3.3 | 3.5 | Pituitary gland Pool | 0.5 | 0.7 |
| Renal ca. 786-0 | 0.0 | 0.2 | Salivary Gland | 3.4 | 3.0 |
| Renal ca. A498 | 0.0 | 0.0 | Thyroid (female) | 2.5 | 2.5 |
| Renal ca. ACHN | 1.2 | 0.0 | Pancreatic ca. CAPAN2 | 0.5 | 0.0 |
| Renal ca. UO-31 | 0.2 | 0.0 | Pancreas Pool | 26.6 | 31.6 |

TABLE UE

Panel 4.1D

| Tissue Name | Rel. Exp. (%) Ag4699, Run 200924185 | Tissue Name | Rel. Exp. (%) Ag4699, Run 200924185 |
|---|---|---|---|
| Secondary Th1 act | 0.0 | HUVEC IL-1beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |

TABLE UE-continued

Panel 4.1D

| Tissue Name | Rel. Exp. (%) Ag4699, Run 200924185 | Tissue Name | Rel. Exp. (%) Ag4699, Run 200924185 |
| --- | --- | --- | --- |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1beta | 2.6 |
| Primary Th2 act | 0.0 | Microvascular Dermal EC none | 0.0 |
| Primary Tr1 act | 0.0 | Microsvasular Dermal EC TNF alpha + IL-1beta | 0.0 |
| Primary Th1 rest | 0.0 | Bronchial epithelium TNF alpha + IL1beta | 0.0 |
| Primary Th2 rest | 0.0 | Small airway epithelium none | 1.7 |
| Primary Tr1 rest | 0.0 | Small airway epithelium TNF alpha + IL-1beta | 0.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1beta | 0.0 |
| CD8 lymphocyte act | 0.0 | Astrocytes rest | 1.4 |
| Secondary CD8 lymphocyte rest | 0.0 | Astrocytes TNF alpha + IL-1beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1beta | 0.0 |
| LAK cells IL-2 | 0.0 | Liver cirrhosis | 15.5 |
| LAK cells IL-2 + IL-12 | 0.0 | NCI-H292 none | 0.0 |
| LAK cells IL-2 + IFN gamma | 0.0 | NCI-H292 IL-4 | 0.0 |
| LAK cells IL-2 + IL-18 | 0.0 | NCI-H292 IL-9 | 0.0 |
| LAK cells PMA/ionomycin | 0.0 | NCI-H292 IL-13 | 0.0 |
| NK Cells IL-2 rest | 0.0 | NCI-H292 IFN gamma | 0.0 |
| Two Way MLR 3 day | 0.0 | HPAEC none | 0.0 |
| Two Way MLR 5 day | 0.0 | HPAEC TNF alpha + IL-1beta | 0.0 |
| Two Way MLR 7 day | 0.0 | Lung fibroblast none | 70.7 |
| PBMC rest | 0.0 | Lung fibroblast TNF alpha + IL-1beta | 39.2 |
| PBMC PWM | 0.0 | Lung fibroblast IL-4 | 26.4 |
| PBMC PHA-L | 0.0 | Lung fibroblast IL-9 | 9.0 |
| Ramos (B cell) none | 0.0 | Lung fibroblast IL-13 | 27.7 |
| Ramos (B cell) ionomycin | 0.0 | Lung fibroblast IFN gamma | 34.4 |
| B lymphocytes PWM | 0.0 | Dermal fibroblast CCD1070 rest | 3.7 |
| B lymphocytes CD40L and IL-4 | 2.9 | Dermal fibroblast CCD1070 TNF alpha | 5.1 |
| EOL-1 dbcAMP | 0.0 | Dermal fibroblast CCD1070 IL-1beta | 1.2 |
| EOL-1 dbcAMP PMA/ionomycin | 0.0 | Dermal fibroblast IFN gamma | 11.7 |
| Dendritic cells none | 0.0 | Dermal fibroblast IL-4 | 8.4 |
| Dendritic cells LPS | 0.0 | Dermal Fibroblasts rest | 5.1 |
| Dendritic cells anti-CD40 | 1.1 | Neutrophils TNFa + LPS | 0.0 |
| Monocytes rest | 0.0 | Neutrophils rest | 0.0 |
| Monocytes LPS | 0.0 | Colon | 5.2 |
| Macrophages rest | 3.1 | Lung | 100.0 |
| Macrophages LPS | 1.9 | Thymus | 7.4 |
| HUVEC none | 0.0 | Kidney | 39.8 |
| HUVEC starved | 0.0 | | |

CNS_neurodegeneration_v1.0 Summary: Ag4699 Two experiments with the same probe and primer set produce results that are in excellent agreement, with highest expression of the CG89697-01 gene in the hippocampus of an Alzheimer's patient (CTs=29–30). In both cases, the expression of this gene is up-regulated in the temporal cortex of Alzheimer's disease patients when compared to non-demented controls. This difference is apparent when data are analyzed via ANCOVA, using overall RNA quality and/or quantity as a covariate. The temporal cortex is a region that shows degeneration at the mid-stages of this disease. Thus, it is likely that the phenomenon of neurodegeneration is captured in this region, as opposed to the hippocampus and entorhinal cortex where a large number of neurons are already lost by the time of death in AD. Furthermore, in the occipital cortex (where neurodegeneration does not occur in Alzheimer's) this gene is not found to be up-regulated in the same patients. Taken together, these data suggest that this gene is at least a marker of Alzheimer's-like neurodegeneration, and is probably involved in the process of neurodegeneration.

General_screening_13 panel_v1.4 Summary: Ag4253/Ag4699 Two experiments with the same probe and primer set produce results that are in excellent agreement, with highest expression of the CG89697-01 gene in the fetal lung (CTs=28). In addition, this gene is expressed at much higher levels in fetal when compared to expression in the adult counterpart (CTs=32–33). Thus, expression of this gene may be used to differentiate between the fetal and adult source of this tissue.

Among tissues with metabolic function, this gene is expressed at moderate to low levels in adipose, adrenal gland, pancreas, thyroid, fetal liver and adult and fetal skeletal muscle and heart. This expression suggests that this gene product may play a role in normal neuroendocrine and metabolic and that disregulated expression of this gene may contribute to neuroendocrine disorders or metabolic diseases, such as obesity and diabetes.

This gene is also expressed at low levels in the CNS, including the hippocampus, thalamus, substantia nigra, amygdala, cerebellum and cerebral cortex. Therefore, therapeutic modulation of the expression or function of this gene may be useful in the treatment of neurologic disorders, such as Alzheimer's disease, Parkinson's disease, schizophrenia, multiple sclerosis, stroke and epilepsy.

Panel 4.1D Summary: Ag4699 Highest expression of the CG89697-01 gene is seen in the lung (CT=31.2), in agreement with expression in Panel 1.4. In addition, this gene shows a very restricted pattern of expression in lung fibroblasts, with higher expression in untreated lung fibroblasts. This lung prominent expression suggests that expression of this gene could be used to identify lung derived tissue. In addition, this gene product may be involved in the normal homeostasis of this organ. Therefore, therapeutic modulation of the expression or function of this gene product may be useful in the treatment of pathological and inflammatory lung conditions such as asthma, emphysema, and allergy.

V. CG90001-01: Peptidylprolyl Isomerase A

Expression of gene CG90001-01 was assessed using the primer-probe set Ag3699, described in Table VA. Results of the RTQ-PCR runs are shown in Table VB.

TABLE VA

Probe Name Ag3699

| Primers | Sequences | Length | Start Position | SEQ ID NO: |
|---|---|---|---|---|
| Forward | 5'-caacacaaatgattcccagttt-3' | 22 | 317 | 291 |
| Probe | TET-5'-ttcatctgcactgccaagactgagtg-3'-TAMRA | 26 | 339 | 292 |
| Reverse | 5'-atctttcaccttgccaaagac-3' | 21 | 384 | 293 |

TABLE VB

CNS_neurodegeneration_v1.0

| Tissue Name | Rel. Exp. (%) Ag3699, Run 211291161 | Tissue Name | Rel. Exp. (%) Ag3699, Run 211291161 |
|---|---|---|---|
| AD 1 Hippo | 8.0 | Control (Path) 3 Temporal Ctx | 3.5 |
| AD 2 Hippo | 34.4 | Control (Path) 4 Temporal Ctx | 40.1 |
| AD 3 Hippo | 3.7 | AD 1 Occipital Ctx | 21.6 |
| AD 4 Hippo | 8.9 | AD 2 Occipital Ctx (Missing) | 0.0 |
| AD 5 Hippo | 60.3 | AD 3 Occipital Ctx | 4.5 |
| AD 6 Hippo | 58.2 | AD 4 Occipital Ctx | 25.7 |
| Control 2 Hippo | 19.2 | AD 5 Occipital Ctx | 20.2 |
| Control 4 Hippo | 5.2 | AD 6 Occipital Ctx | 17.9 |
| Control (Path) 3 Hippo | 3.8 | Control 1 Occipital Ctx | 0.0 |
| AD 1 Temporal Ctx | 10.0 | Control 2 Occipital Ctx | 18.7 |
| AD 2 Temporal Ctx | 22.2 | Control 3 Occipital Ctx | 17.7 |
| AD 3 Temporal Ctx | 5.4 | Control 4 Occipital Ctx | 4.8 |
| AD 4 Temporal Ctx | 30.1 | Control (Path) 1 Occipital Ctx | 100.0 |
| AD 5 Inf Temporal Ctx | 79.6 | Control (Path) 2 Occipital Ctx | 17.9 |
| AD 5 Sup Temporal Ctx | 27.4 | Control (Path) 3 Occipital Ctx | 2.6 |
| AD 6 Inf Temporal Ctx | 31.0 | Control (Path) 4 Occipital Ctx | 16.5 |
| AD 6 Sup Temporal Ctx | 71.7 | Control 1 Parietal Ctx | 2.4 |
| Control 1 Temporal Ctx | 15.5 | Control 2 Parietal Ctx | 39.5 |
| Control 2 Temporal Ctx | 17.8 | Control 3 Parietal Ctx | 18.4 |
| Control 3 Temporal Ctx | 19.9 | Control (Path) 1 Parietal Ctx | 69.3 |
| Control 3 Temporal Ctx | 10.7 | Control (Path) 2 Parietal Ctx | 29.3 |
| Control (Path) 1 Temporal Ctx | 47.6 | Control (Path) 3 Parietal Ctx | 3.3 |
| Control (Path) 2 Temporal Ctx | 42.3 | Control (Path) 4 Parietal Ctx | 42.9 |

CNS_neurodegeneration_v1.0 Summary: Ag3699 Expression of the CG90001-01 gene is low seen at low levels in the brain in this panel, with highest expression in occipital cortex of a control patient (CT=33.7). Low but significant expression of this gene is also seen in the hippocampus. Thus, this gene product may be involved in the function of the CNS.

General_screening_panel_v1.4 Summary: Ag3699 Expression of the CG90001-01 gene is low/undetectable in all samples on this panel (CTs>35). (Data not shown.) Panel 4.1D Summary: Ag3699 Expression of the CG90001-01 gene is low/undetectable in all samples on this panel (CTs>35). (Data not shown.)

W. CG90011-01: ATP Specific Succinyl COA Synthetase Beta Subunit Precursor

Expression of gene CG90011-01 was assessed using the primer-probe set Ag3700, described in Table WA.

TABLE WA

Probe Name Ag3700

| Primers | Sequences | Length | Start Position | SEQ ID NO: |
|---|---|---|---|---|
| Forward | 5'-tggtgctacagtccatcaagt-3' | 21 | 1034 | 294 |
| Probe | TET-5'-cagaagcatttaagcctatcacttcaga-3'-TAMRA | 28 | 1057 | 295 |
| Reverse | 5'-ctccacaaatgttgaccagaat-3' | 22 | 1101 | 296 |

CNS_neurodegeneration_v1.0 Summary: Ag3700 Expression of the CG90011-01 gene is low/undetectable (CTs>35) across all of the samples on this panel (data not shown).

General_screening_panel_v1.4 Summary: Ag3700 Expression of the CG90011-01 gene is low/undetectable (CTs>35) across all of the samples on this panel (data not shown).

Panel 4.1D Summary: Ag3700 Expression of the CG90011-01 gene is low/undetectable (CTs>35) across all of the samples on this panel (data not shown).

Panel 5 Islet Summary: Ag3700 Expression of the CG90011-01 gene is low/undetectable (CTs>35) across all of the samples on this panel (data not shown).

X. CG90204-01: Semaphorin Cytoplasmic Domain-Associated Protein

Expression of gene CG90204-01 was assessed using the primer-probe set Ag3706, described in Table XA. Results of the RTQ-PCR runs are shown in Tables XB, XC and XD.

TABLE XA

Probe Name Ag3706

| Primers | Sequences | Length | Start Position | SEQ ID NO: |
|---|---|---|---|---|
| Forward | 5'-caagaagaagaaggcacaa-3' | 22 | 1599 | 297 |
| Probe | TET-5'-ctgcaacatcctcatccaacaaccat-3'-TAMRA | 26 | 1627 | 298 |
| Reverse | 5'-atttcgcaagctttcatctgt-3' | 21 | 1677 | 299 |

TABLE XB

CNS_neurodegeneration_v1.0

| Tissue Name | Rel. Exp. (%) Ag3706, Run 211291164 | Tissue Name | Rel. Exp. (%) Ag3706, Run 211291164 |
|---|---|---|---|
| AD 1 Hippo | 11.0 | Control (Path) 3 Temporal Ctx | 7.2 |
| AD 2 Hippo | 17.4 | Control (Path) 4 Temporal Ctx | 59.9 |
| AD 3 Hippo | 5.3 | AD 1 Occipital Ctx | 37.9 |
| AD 4 Hippo | 7.8 | AD 2 Occipital Ctx (Missing) | 0.0 |
| AD 5 hippo | 64.6 | AD 3 Occipital Ctx | 9.2 |
| AD 6 Hippo | 21.5 | AD 4 Occipital Ctx | 22.8 |
| Control 2 Hippo | 25.3 | AD 5 Occipital Ctx | 25.3 |
| Control 4 Hippo | 9.5 | AD 6 Occipital Ctx | 48.0 |
| Control (Path) 3 Hippo | 11.0 | Control 1 Occipital Ctx | 2.9 |
| AD 1 Temporal Ctx | 19.9 | Control 2 Occipital Ctx | 70.2 |
| AD 2 Temporal Ctx | 37.4 | Control 3 Occipital Ctx | 2.7 |
| AD 3 Temporal Ctx | 9.2 | Control 4 Occipital Ctx | 5.4 |
| AD 4 Temporal Ctx | 27.0 | Control (Path) 1 Occipital Ctx | 100.0 |
| AD 5 Inf Temporal Ctx | 66.0 | Control (Path) 2 Occipital Ctx | 16.2 |
| AD 5 SupTemporal Ctx | 24.8 | Control (Path) 3 Occipital Ctx | 3.1 |
| AD 6 Inf Temporal Ctx | 74.7 | Control (Path) 4 Occipital Ctx | 41.2 |
| AD 6 Sup Temporal Ctx | 56.6 | Control 1 Parietal Ctx | 6.6 |
| Control 1 Temporal Ctx | 8.6 | Control 2 Parietal Ctx | 44.8 |
| Control 2 Temporal Ctx | 32.3 | Control 3 Parietal Ctx | 12.8 |
| Control 3 Temporal Ctx | 33.0 | Control (Path) 1 Parietal Ctx | 69.3 |
| Control 4 Temporal Ctx | 12.2 | Control (Path) 2 Parietal Ctx | 23.0 |
| Control (Path) 1 Temporal Ctx | 55.1 | Control (Path) 3 Parietal Ctx | 4.2 |
| Control (Path) 2 Temporal Ctx | 42.3 | Control (Path) 4 Parietal Ctx | 57.0 |

TABLE XC

General_screening_panel_v1.4

| Tissue Name | Rel. Exp. (%) Ag3706, Run 218253760 | Tissue Name | Rel. Exp. (%) Ag3706, Run 218253760 |
| --- | --- | --- | --- |
| Adipose | 14.0 | Renal ca. TK-10 | 0.0 |
| Melanoma* Hs688(A).T | 0.0 | Bladder | 4.7 |
| Melanoma* Hs688(B).T | 0.0 | Gastric ca. (liver met.) NCI-N87 | 0.0 |
| Melanoma* M14 | 0.0 | Gastric ca. KATO III | 0.0 |
| Melanoma* LOXIMVI | 8.2 | Colon ca. SW-948 | 0.0 |
| Melanoma* SK-MEL-5 | 0.0 | Colon ca. SW480 | 0.0 |
| Squamous cell carcinoma SCC-4 | 0.0 | Colon ca.* (SW480 met) SW620 | 0.0 |
| Testis Pool | 80.1 | Colon ca. HT29 | 0.0 |
| Prostate ca.* (bone met) PC-3 | 0.2 | Colon ca. HCT-116 | 0.0 |
| Prostate Pool | 94.0 | Colon ca. CaCo-2 | 0.4 |
| Placenta | 0.9 | Colon cancer tissue | 6.1 |
| Uterus Pool | 9.7 | Colon ca. SW1116 | 0.0 |
| Ovarian ca. OVCAR-3 | 6.0 | Colon ca. Colo-205 | 0.0 |
| Ovarian ca. SK-OV-3 | 0.2 | Colon ca. SW-48 | 0.0 |
| Ovarian ca. OVCAR-4 | 0.0 | Colon Pool | 7.6 |
| Ovarian ca. OVCAR-5 | 0.0 | Small Intestine Pool | 84.1 |
| Ovarian ca. IGROV-1 | 0.0 | Stomach Pool | 24.3 |
| Ovarian ca. OVCAR-8 | 0.0 | Bone Marrow Pool | 5.6 |
| Ovary | 44.8 | Fetal Heart | 2.8 |
| Breast ca. MCF-7 | 0.4 | Heart Pool | 8.5 |
| Breast ca. MDA-MB-231 | 0.0 | Lymph Node Pool | 12.6 |
| Breast ca. BT 549 | 0.0 | Fetal Skeletal Muscle | 5.4 |
| Breast ca. T47D | 0.2 | Skeletal Muscle Pool | 1.5 |
| Breast ca. MDA-N | 0.0 | Spleen Pool | 6.2 |
| Breast Pool | 6.2 | Thymus Pool | 6.6 |
| Trachea | 13.4 | CNS cancer (glio/astro) U87-MG | 0.0 |
| Lung | 29.5 | CNS cancer (glio/astro) U-118-MG | 0.0 |
| Fetal Lung | 4.2 | CNS cancer (neuro; met) SK-N-AS | 0.0 |
| Lung ca. NCI-N417 | 0.0 | CNS cancer (astro) SF-539 | 1.4 |
| Lung ca. LX-1 | 0.0 | CNS cancer (astro) SNB-75 | 0.0 |
| Lung ca. NCI-H146 | 2.5 | CNS cancer (glio) SNB-19 | 0.0 |
| Lung ca. SHP-77 | 0.2 | CNS cancer (glio) SF-295 | 0.3 |
| Lung ca. A549 | 0.3 | Brain (Amygdala) Pool | 19.5 |
| Lung ca. NCI-H526 | 0.0 | Brain (cerebellum) | 8.1 |
| Lung ca. NCI-H23 | 1.9 | Brain (fetal) | 100.0 |
| Lung ca. NCI-H460 | 0.0 | Brain (Hippocampus) Pool | 25.7 |
| Lung ca. HOP-62 | 0.0 | Cerebral Cortex Pool | 36.1 |
| Lung ca. NCI-H522 | 0.2 | Brain (Substantia nigra) Pool | 19.2 |
| Liver | 0.2 | Brain (Thalamus) Pool | 35.1 |
| Fetal Liver | 1.7 | Brain (whole) | 22.2 |
| Liver ca. HepG2 | 0.0 | Spinal Cord Pool | 29.1 |
| Kidney Pool | 40.3 | Adrenal Gland | 2.1 |
| Fetal Kidney | 24.7 | Pituitary gland Pool | 2.9 |
| Renal ca. 786-0 | 0.7 | Salivary Gland | 0.9 |
| Renal ca. A498 | 0.0 | Thyroid (female) | 3.2 |
| Renal ca. ACHN | 0.0 | Pancreatic ca. CAPAN2 | 0.0 |
| Renal ca. UO-31 | 0.3 | Pancreas Pool | 4.0 |

TABLE XD

Panel 4.1D

| Tissue Name | Rel. Exp. (%) Ag3706, Run 169987426 | Tissue Name | Rel. Exp. (%) Ag3706, Run 169987426 |
| --- | --- | --- | --- |
| Secondary Th1 act | 0.0 | HUVEC IL-1beta | 0.0 |
| Secondary Th2 act | 0.0 | HUVEC IFN gamma | 1.7 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |

TABLE XD-continued

Panel 4.1D

| Tissue Name | Rel. Exp. (%) Ag3706, Run 169987426 | Tissue Name | Rel. Exp. (%) Ag3706, Run 169987426 |
|---|---|---|---|
| Secondary Tr1 rest | 0.0 | Lung Microvascular EC none | 0.0 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 0.0 | Microsvasular Dermal EC TNF alpha + IL-1beta | 0.0 |
| Primary Th1 rest | 0.0 | Bronchial epithelium TNF alpha + IL1beta | 0.0 |
| Primary Th2 rest | 0.0 | Small airway epithelium none | 0.0 |
| Primary Tr1 rest | 0.0 | Small airway epithelium TNF alpha + IL-1beta | 0.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1beta | 0.0 |
| CD8 lymphocyte act | 0.0 | Astrocytes rest | 0.0 |
| Secondary CD8 lymphocyte rest | 0.0 | Astrocytes TNF alpha + IL-1beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 1.2 | CCD1106 (Keratinocytes) none | 0.0 |
| LAK cells rest | 6.6 | CCD1106 (Keratinocytes) TNF alpha + IL-1beta | 0.0 |
| LAK cells IL-2 | 0.0 | Liver cirrhosis | 87.7 |
| LAK cells IL-2 + IL-12 | 0.0 | NCI-H292 none | 0.0 |
| LAK cells IL-2 + IFN gamma | 0.0 | NCI-H292 IL-4 | 0.0 |
| LAK cells IL-2 + IL-18 | 0.0 | NCI-H292 IL-9 | 0.0 |
| LAK cells PMA/ionomycin | 0.0 | NCI-H292 IL-13 | 0.0 |
| NK Cells IL-2 rest | 0.0 | NCI-H292 IFN gamma | 0.0 |
| Two Way MLR 3 day | 0.0 | HPAEC none | 0.0 |
| Two Way MLR 5 day | 0.0 | HPAEC TNF alpha + IL-1beta | 0.0 |
| Two Way MLR 7 day | 0.0 | Lung fibroblast none | 0.0 |
| PBMC rest | 0.0 | Lung fibroblast TNF alpha + IL-1beta | 0.0 |
| PBMC PWM | 0.0 | Lung fibroblast IL-4 | 1.7 |
| PBMC PHA-L | 0.0 | Lung fibroblast IL-9 | 0.0 |
| Ramos (B cell) none | 0.0 | Lung fibroblast IL-13 | 0.0 |
| Ramos (B cell) ionomycin | 0.0 | Lung fibroblast IFN gamma | 0.0 |
| B lymphocytes PWM | 0.0 | Dermal fibroblast CCD1070 rest | 0.0 |
| B lymphocytes CD40L and IL-4 | 0.0 | Dermal fibroblast CCD1070 TNF alpha | 0.0 |
| EOL-1 dbcAMP | 0.0 | Dermal fibroblast CCD1070 IL-1beta | 0.0 |
| EOL-1 dbcAMP PMA/ionomycin | 0.0 | Dermal fibroblast IFN gamma | 0.0 |
| Dendritic cells none | 0.0 | Dermal fibroblast IL-4 | 0.0 |
| Dendritic cells LPS | 12.9 | Dermal Fibroblasts rest | 0.0 |
| Dendritic cells anti-CD40 | 4.1 | Neutrophils TNF a + LPS | 0.0 |
| Monocytes rest | 0.0 | Neutrophils rest | 0.0 |
| Monocytes LPS | 0.0 | Colon | 100.0 |
| Macrophages rest | 0.0 | Lung | 12.9 |
| Macrophages LPS | 0.0 | Thymus | 1.7 |
| HUVEC none | 0.0 | Kidney | 17.1 |
| HUVEC starved | 0.0 | | |

CNS_neurodegeneration_v1.0 Summary: Ag3706 This panel does not show differential expression of the CG90204-01 gene in Alzheimer's disease. However, this expression profile confirms the presence of this gene in the brain. Please see Panel 1.4 for discussion of utility of this gene in the central nervous system.

General_screening_panel_v1.4 Summary: Ag3706 The CG90204-01 gene shows moderate levels of expression in most of the CNS regions examined, with highest expression in the fetal brain (CT=30). Therefore, therapeutic modulation of the expression or function of this gene may be useful in the treatment of neurologic disorders, such as Alzheimer's disease, Parkinson's disease, schizophrenia, multiple sclerosis, stroke and epilepsy.

Moderate levels of expression are also expressed in other normal tissue samples, including prostate, ovary and testis.

Panel 4.1D Summary: Ag3706 Expression of the CG90204-01 gene is restricted to a few samples, with highest expression in the colon and liver cirrhosis (CTs=31.7). Thus, expression of this gene could be used to differentiate between these samples and other samples on this panel. In addition, expression in liver cirrhosis, but not liver on Panel 1.4 suggests that this gene product may be useful as in the diagnosis and/or treatment of liver cirrhosis.

Y. CG90214-01: BETA-1,4 N Acetylgalactosaminyltransferase

Expression of gene CG90214-01 was assessed using the primer-probe set Ag3708, described in Table YA. Results of the RTQ-PCR runs are shown in Tables YB and YC.

TABLE YA

Probe Name Ag3708

| Primers | Sequences | Length | Start Position | SEQ ID NO: |
|---|---|---|---|---|
| Forward | 5'-cccagacttgaccgtaatagtg-3' | 22 | 849 | 300 |
| Probe | TET-5'-acagccagaagcccctggaaattaaa-3'-TAMRA | 26 | 878 | 301 |
| Reverse | 5'-tcccaaagggcatagtgtaata-3' | 22 | 919 | 302 |

TABLE YB

Panel 2.2

| Tissue Name | Rel. Exp. (%) Ag3708, Run 173764403 | Tissue Name | Rel. Exp. (%) Ag3708, Run 173764403 |
|---|---|---|---|
| Normal Colon | 29.5 | Kidney Margin (OD04348) | 21.0 |
| Colon cancer (OD06064) | 11.8 | Kidney malignant cancer (OD06204B) | 0.0 |
| Colon Margin (OD06064) | 66.9 | Kidney normal adjacent tissue (OD06204E) | 2.2 |
| Colon cancer (OD06159) | 3.6 | Kidney Cancer (OD04450-01) | 0.0 |
| Colon Margin (OD06159) | 100.0 | Kidney Margin (OD04450-03) | 9.0 |
| Colon cancer (OD06297-04) | 2.6 | Kidney Cancer 8120613 | 5.3 |
| Colon Margin (OD06297-05) | 24.1 | Kidney Margin 8120614 | 2.0 |
| CC Gr.2 ascend colon (ODO3921) | 12.0 | Kidney Cancer 9010320 | 0.6 |
| CC Margin (ODO3921) | 29.1 | Kidney Margin 9010321 | 3.3 |
| Colon cancer metastasis (OD06104) | 4.5 | Kidney Cancer 8120607 | 0.0 |
| Lung Margin (OD06104) | 6.9 | Kidney Margin 8120608 | 1.4 |
| Colon mets to lung (OD04451-01) | 0.0 | Normal Uterus | 0.0 |
| Lung Margin (OD04451-02) | 2.0 | Uterine Cancer 064011 | 0.0 |
| Normal Prostate | 0.0 | Normal Thyroid | 0.7 |
| Prostate Cancer (OD04410) | 0.0 | Thyroid Cancer 064010 | 4.6 |
| Prostate Margin (OD04410) | 0.0 | Thyroid Cancer A302152 | 1.5 |
| Normal Ovary | 0.0 | Thyroid Margin A302153 | 5.0 |
| Ovarian cancer (OD06283-03) | 2.5 | Normal Breast | 0.0 |
| Ovarian Margin (OD06283-07) | 0.0 | Breast Cancer (OD04566) | 1.7 |
| Ovarian Cancer 064008 | 8.7 | Breast Cancer 1024 | 17.8 |
| Ovarian cancer (OD06145) | 1.3 | Breast Cancer (OD04590-01) | 0.7 |
| Ovarian Margin (OD06145) | 0.6 | Breast Cancer Mets (OD04590-03) | 0.0 |
| Ovarian cancer (OD06455-03) | 0.0 | Breast Cancer Metastasis (OD04655-05) | 0.0 |
| Ovarian Margin (OD06455-07) | 0.0 | Breast Cancer 064006 | 2.2 |
| Normal Lung | 0.5 | Breast Cancer 9100266 | 1.2 |
| Invasive poor diff. lung adeno (ODO4945-01) | 2.0 | Breast Margin 9100265 | 0.4 |
| Lung Margin (ODO4945-03) | 0.0 | Breast Cancer A209073 | 3.7 |

TABLE YB-continued

Panel 2.2

| Tissue Name | Rel. Exp. (%) Ag3708, Run 173764403 | Tissue Name | Rel. Exp. (%) Ag3708, Run 173764403 |
|---|---|---|---|
| Lung Malignant Cancer (OD03126) | 8.5 | Breast Margin A2090734 | 1.0 |
| Lung Margin (OD03126) | 0.0 | Breast cancer (OD06083) | 0.8 |
| Lung Cancer (OD05014A) | 9.0 | Breast cancer node metastasis (OD06083) | 1.2 |
| Lung Margin (OD05014B) | 0.0 | Normal Liver | 0.0 |
| Lung cancer (OD06081) | 0.6 | Liver Cancer 1026 | 22.7 |
| Lung Margin (OD06081) | 0.5 | Liver Cancer 1025 | 0.0 |
| Lung Cancer (OD04237-01) | 0.0 | Liver Cancer 6004-T | 1.1 |
| Lung Margin (OD04237-02) | 0.0 | Liver Tissue 6004-N | 1.3 |
| Ocular Melanoma Metastasis | 0.0 | Liver Cancer 6005-T | 35.4 |
| Ocular Melanoma Margin (Liver) | 0.0 | Liver Tissue 6005-N | 0.0 |
| Melanoma Metastasis | 0.0 | Liver Cancer 064003 | 0.0 |
| Melanoma Margin (Lung) | 0.0 | Normal Bladder | 0.0 |
| Normal Kidney | 4.0 | Bladder Cancer 1023 | 1.1 |
| Kidney Ca, Nuclear grade 2 (OD04338) | 36.6 | Bladder Cancer A302173 | 0.0 |
| Kidney Margin (OD04338) | 1.6 | Normal Stomach | 16.2 |
| Kidney Ca Nuclear grade 1/2 (OD04339) | 6.1 | Gastric Cancer 9060397 | 0.0 |
| Kidney Margin (OD04339) | 1.4 | Stomach Margin 9060396 | 0.6 |
| Kidney Ca, Clear cell type (OD04340) | 2.5 | Gastric Cancer 9060395 | 5.3 |
| Kidney Margin (OD04340) | 31.0 | Stomach Margin 9060394 | 4.3 |
| Kidney Ca, Nuclear grade 3 (OD04348) | 0.0 | Gastric Cancer 064005 | 0.0 |

TABLE YC

Panel 4.1D

| Tissue Name | Rel. Exp. (%) Ag3708, Run 169960432 | Tissue Name | Rel. Exp. (%) Ag3708, Run 169960432 |
|---|---|---|---|
| Secondary Th1 act | 0.0 | HUVEC IL-1beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 1.5 | Microvasular Dermal EC TNF alpha + IL-1beta | 0.0 |
| Primary Th1 rest | 0.0 | Bronchial epithelium TNF alpha + IL1beta | 17.7 |
| Primary Th2 rest | 0.0 | Small airway epithelium none | 34.6 |
| Primary Tr1 rest | 0.0 | Small airway epithelium TNF alpha + IL-1beta | 30.4 |
| CD45RA CD4 lymphocyte act | 0.0 | Coronery artery SMC rest | 0.0 |
| CD45RO CD4 lymphocyte act | 1.1 | Coronery artery SMC TNF alpha + IL-1beta | 0.0 |
| CD8 lymphocyte act | 0.0 | Astrocytes rest | 0.0 |
| Secondary CD8 lymphocyte rest | 0.0 | Astrocytes TNF alpha + IL-1beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 18.7 |
| LAK cells rest | 0.0 | CCD1106 (Keratinocytes) TNF alpha + IL-1beta | 33.4 |
| LAK cells IL-2 | 0.0 | Liver cirrhosis | 3.7 |
| LAK cells IL-2 + IL-12 | 0.0 | NCI-H292 none | 0.0 |

TABLE YC-continued

Panel 4.1D

| Tissue Name | Rel. Exp. (%) Ag3708, Run 169960432 | Tissue Name | Rel. Exp. (%) Ag3708, Run 169960432 |
| --- | --- | --- | --- |
| LAK cells IL-2 + IFN gamma | 0.0 | NCI-H292 IL-4 | 0.0 |
| LAK cells IL-2 + IL-18 | 0.0 | NCI-H292 IL-9 | 2.3 |
| LAK cells PMA/ionomycin | 0.0 | NCI-H292 IL-13 | 0.0 |
| NK Cells IL-2 rest | 0.0 | NCI-H292 IFN gamma | 0.0 |
| Two Way MLR 3 day | 0.0 | HPAEC none | 0.0 |
| Two Way MLR 5 day | 0.0 | HPAEC TNF alpha + IL-1beta | 0.0 |
| Two Way MLR 7 day | 0.0 | Lung fibroblast none | 0.0 |
| PBMC rest | 0.0 | Lung fibroblast TNF alpha + IL-1beta | 0.0 |
| PBMC PWM | 0.0 | Lung fibroblast IL-4 | 0.0 |
| PBMC PHA-L | 0.0 | Lung fibroblast IL-9 | 1.3 |
| Ramos (B cell) none | 0.0 | Lung fibroblast IL-13 | 0.0 |
| Ramos (B cell) ionomycin | 0.0 | Lung fibroblast IFN gamma | 0.0 |
| B lymphocytes PWM | 0.0 | Dermal fibroblast CCD1070 rest | 0.0 |
| B lymphocytes CD40L and IL-4 | 0.0 | Dermal fibroblast CCD1070 TNF alpha | 1.6 |
| EOL-1 dbcAMP | 0.0 | Dermal fibroblast CCD1070 IL-1beta | 1.8 |
| EOL-1 dbcAMP PMA/ionomycin | 0.0 | Dermal fibroblast IFN gamma | 0.0 |
| Dendritic cells none | 0.0 | Dermal fibroblast IL-4 | 0.0 |
| Dendritic cells LPS | 0.0 | Dermal Fibroblasts rest | 0.0 |
| Dendritic cells anti-CD40 | 0.0 | Neutrophils TNFa + LPS | 0.0 |
| Monocytes rest | 0.0 | Neutrophils rest | 0.0 |
| Monocytes LPS | 0.0 | Colon | 71.7 |
| Macrophages rest | 0.0 | Lung | 0.0 |
| Macrophages LPS | 0.0 | Thymus | 0.0 |
| HUVEC none | 0.0 | Kidney | 100.0 |
| HUVEC starved | 0.0 | | |

CNS_neurodegeneration_v1.0 Summary: Ag3708 Expression of the CG90214-01 gene is low/undetectable (CTs>35) across all of the samples on this panel (data not shown).

General_screening_panel_v1.4 Summary: Ag3708 Results from one experiment with the CG90214-01 gene are not included. The amp plot indicates that there were experimental difficulties with this run.

Panel 2.2 Summary: Ag3708 Highest expression of the CG90214-01 gene is detected in colon margin (OD06159) sample (CT=31.6). Interestingly, expression of this gene is down-regulated in colon and kidney cancer. Therefore, therapeutic modulation of the activity of this gene or its protein product, through the use of small molecule drug, might be beneficial in the treatment of these cancers.

In addition, expression of this gene is higher in two of the liver cancer (1026, 6005-T) and kidney cancer nuclear grade 2 (OD04338) samples. Therefore, expression of this gene can be used as diagnostic marker for kidney and liver cancer. Furthermore, therapeutic modulation of the activity of this gene or its protein product, through the use of small molecule drugs, might be beneficial in the treatment of these cancers.

Panel 4.1D Summary: Ag3708 Highest expression of the CG90214-01 gene is detected in kidney sample (CT=33). Significant expression of this gene is also seen in colon (CT=33.6). Thus, expression of this gene can be used to distinguish this sample from other samples used in this panel. In addition, low but significant expression of this gene is also seen in small airway epithelium and TNFalpha+IL-1beta treated keratinocytes. Therefore, therapeutic modulation of the activity of the protein encoded by this gene may be useful in the treatment of inflammatory bowel disease, psoriasis, wound healing, asthma, COPD, and emphysema, and inflammatory or autoimmune diseases that affect the kidney, including lupus and glomerulonephritis.

Panel CNS_1 Summary: Ag3708 Expression of the CG90214-01 gene is low/undetectable (CTs>35) across all of the samples on this panel (data not shown).

Z. CG90385-01: Mitogen Activated Protein Kinase

Expression of gene CG90385-01 was assessed using the primer-probe sets Ag658 and Ag3979, described in Tables ZA and ZB. Results of the RTQ-PCR runs are shown in Tables ZC, ZD and ZE.

TABLE ZA

| Probe Name Ag658 | | | | |
| --- | --- | --- | --- | --- |
| Primers | Sequences | Length | Start Position | SEQ ID NO: |
| Forward | 5'-gctccttcaagacggtgtatc-3' | 21 | 512 | 303 |
| Probe | TET-5'-ctagacaccgacaccacagtggaggt-3'-TAMRA | 26 | 538 | 304 |
| Reverse | 5'-ccgctcagctctagacagttt-3' | 21 | 589 | 305 |

TABLE ZB

| | Probe Name Ag3979 | | | |
|---|---|---|---|---|
| Primers | Sequences | Length | Start Position | SEQ ID NO: |
| Forward | 5'-gctccttcaagacggtgtatc-3' | 21 | 512 | 306 |
| Probe | TET-5'-ctagacaccgacaccacagtggaggt-3'-TAMRA | 26 | 538 | 307 |
| Reverse | 5'-ccgctcagctctagacagttt-3' | 21 | 589 | 308 |

TABLE ZC

| | General_screening_panel_v1.4 | | |
|---|---|---|---|
| Tissue Name | Rel. Exp. (%) Ag3979, Run 217534174 | Tissue Name | Rel. Exp. (%) Ag3979, Run 217534174 |
| Adipose | 1.3 | Renal ca. TK-10 | 14.5 |
| Melanoma* Hs688(A).T | 20.7 | Bladder | 0.6 |
| Melanoma* Hs688(B).T | 91.4 | Gastric ca. (liver met.) NCI-N87 | 6.7 |
| Melanoma* M14 | 8.6 | Gastric ca. KATO III | 0.3 |
| Melanoma* LOXIMVI | 4.2 | Colon ca. SW-948 | 3.4 |
| Melanoma* SK-MEL-5 | 0.8 | Colon ca. SW480 | 4.5 |
| Squamous cell carcinoma SCC-4 | 0.5 | Colon ca.* (SW480 met) SW620 | 5.9 |
| Testis Pool | 0.8 | Colon ca. HT29 | 24.3 |
| Prostate ca.* (bone met) PC-3 | 100.0 | Colon ca. HCT-116 | 5.1 |
| Prostate Pool | 15.4 | Colon ca. CaCo-2 | 39.8 |
| Placenta | 0.0 | Colon cancer tissue | 24.1 |
| Uterus Pool | 0.3 | Colon ca. SW1116 | 0.6 |
| Ovarian ca. OVCAR-3 | 0.5 | Colon ca. Colo-205 | 0.2 |
| Ovarian ca. SK-OV-3 | 0.7 | Colon ca. SW-48 | 15.8 |
| Ovarian ca. OVCAR-4 | 0.5 | Colon Pool | 0.0 |
| Ovarian ca. OVCAR-5 | 11.5 | Small Intestine Pool | 2.9 |
| Ovarian ca. IGROV-1 | 1.3 | Stomach Pool | 0.5 |
| Ovarian ca. OVCAR-8 | 2.4 | Bone Marrow Pool | 0.6 |
| Ovary | 3.2 | Fetal Heart | 0.5 |
| Breast ca. MCF-7 | 0.8 | Heart Pool | 0.1 |
| Breast ca. MDA-MB-231 | 6.1 | Lymph Node Pool | 0.3 |
| Breast ca. BT 549 | 21.8 | Fetal Skeletal Muscle | 0.0 |
| Breast ca. T47D | 16.0 | Skeletal Muscle Pool | 0.0 |
| Breast ca. MDA-N | 0.9 | Spleen Pool | 0.3 |
| Breast Pool | 0.2 | Thymus Pool | 0.1 |
| Trachea | 6.3 | CNS cancer (glio/astro) U87-MG | 0.3 |
| Lung | 1.2 | CNS cancer (glio/astro) U-118-MG | 0.3 |
| Fetal Lung | 2.9 | CNS cancer (neuro; met) SK-N-AS | 0.1 |
| Lung ca. NCI-N417 | 0.0 | CNS cancer (astro) SF-539 | 0.0 |
| Lung ca. LX-1 | 6.9 | CNS cancer (astro) SNB-75 | 1.7 |
| Lung ca. NCI-H146 | 0.1 | CNS cancer (glio) SNB-19 | 0.7 |
| Lung ca. SHP-77 | 1.0 | CNS cancer (glio) SF-295 | 11.4 |
| Lung ca. A549 | 5.4 | Brain (Amygdala) Pool | 0.3 |
| Lung ca. NCI-H526 | 0.1 | Brain (cerebellum) | 1.7 |
| Lung ca. NCI-H23 | 3.1 | Brain (fetal) | 2.1 |
| Lung ca. NCI-H460 | 0.8 | Brain (Hippocampus) Pool | 1.3 |
| Lung ca. HOP-62 | 12.8 | Cerebral Cortex Pool | 0.5 |
| Lung ca. NCI-H522 | 5.6 | Brain (Substantia nigra) Pool | 0.2 |
| Liver | 0.0 | Brain (Thalamus) Pool | 0.3 |
| Fetal Liver | 52.5 | Brain (whole) | 1.0 |
| Liver ca. HepG2 | 28.7 | Spinal Cord Pool | 0.4 |
| Kidney Pool | 0.0 | Adrenal Gland | 0.2 |
| Fetal Kidney | 24.5 | Pituitary gland Pool | 0.6 |
| Renal ca. 786-0 | 0.9 | Salivary Gland | 0.6 |
| Renal ca. A498 | 1.6 | Thyroid (female) | 0.0 |
| Renal ca. ACHN | 32.1 | Pancreatic ca. CAPAN2 | 1.5 |
| Renal ca. UO-31 | 20.7 | Pancreas Pool | 1.6 |

TABLE ZD

Panel 2.1

| Tissue Name | Rel. Exp. (%) Ag3979, Run 170721574 | Tissue Name | Rel. Exp. (%) Ag3979, Run 170721574 |
|---|---|---|---|
| Normal Colon | 9.9 | Kidney Cancer 9010320 | 0.0 |
| Colon cancer (OD06064) | 0.2 | Kidney margin 9010321 | 44.4 |
| Colon cancer margin (OD06064) | 2.6 | Kidney Cancer 8120607 | 1.5 |
| Colon cancer (OD06159) | 3.5 | Kidney margin 8120608 | 8.7 |
| Colon cancer margin (OD06159) | 2.4 | Normal Uterus | 0.0 |
| Colon cancer (OD06298-08) | 30.8 | Uterus Cancer | 0.6 |
| Colon cancer margin (OD06298-018) | 12.7 | Normal Thyroid | 0.0 |
| Colon Cancer Gr.2 ascend colon (ODO3921) | 4.7 | Thyroid Cancer | 0.0 |
| Colon Cancer margin (ODO3921) | 4.1 | Thyroid Cancer A302152 | 0.0 |
| Colon cancer metastasis (OD06104) | 0.8 | Thyroid margin A302153 | 0.0 |
| Lung margin (OD06104) | 1.2 | Normal Breast | 3.2 |
| Colon mets to lung (OD04451-01) | 9.5 | Breast Cancer | 3.4 |
| Lung margin (OD04451-02) | 0.0 | Breast Cancer | 2.9 |
| Normal Prostate | 9.3 | Breast Cancer (OD04590-01) | 1.3 |
| Prostate Cancer (OD04410) | 6.4 | Breast Cancer Mets (OD04590-03) | 2.3 |
| Prostate margin (OD04410) | 9.0 | Breast Cancer Metastasis | 100.0 |
| Normal Lung | 0.2 | Breast Cancer | 0.0 |
| Invasive poor diff. lung adeno 1 (ODO4945-01) | 0.3 | Breast Cancer 9100266 | 2.8 |
| Lung margin (ODO4945-03) | 0.0 | Breast margin 9100265 | 2.9 |
| Lung Malignant Cancer (OD03126) | 2.8 | Breast Cancer A209073 | 0.5 |
| Lung margin (OD03126) | 0.6 | Breast margin A2090734 | 3.5 |
| Lung Cancer (OD05014A) | 0.0 | Normal Liver | 0.0 |
| Lung margin (OD05014B) | 0.0 | Liver Cancer 1026 | 2.6 |
| Lung Cancer (OD04237-01) | 0.0 | Liver Cancer 1025 | 0.3 |
| Lung margin (OD04237-02) | 0.0 | Liver Cancer 6004-T | 0.6 |
| Ocular Mel Met to Liver (ODO4310) | 3.9 | Liver Tissue 6004-N | 1.4 |
| Liver margin (ODO4310) | 0.0 | Liver Cancer 6005-T | 4.4 |
| Melanoma Mets to Lung (OD04321) | 13.9 | Liver Tissue 6005-N | 0.0 |
| Lung margin (OD04321) | 0.0 | Liver Cancer | 1.7 |
| Normal Kidney | 19.9 | Normal Bladder | 0.0 |
| Kidney Ca, Nuclear grade 2 (OD04338) | 76.8 | Bladder Cancer | 6.7 |
| Kidney margin (OD04338) | 1.5 | Bladder Cancer | 0.0 |
| Kidney Ca Nuclear grade 1/2 (OD04339) | 0.7 | Normal Ovary | 1.8 |
| Kidney margin (OD04339) | 19.1 | Ovarian Cancer | 0.0 |
| Kidney Ca, Clear cell type (OD04340) | 0.0 | Ovarian cancer (OD06145) | 0.0 |
| Kidney margin (OD04340) | 15.4 | Ovarian cancer margin (OD06145) | 0.0 |
| Kidney Ca, Nuclear grade 3 (OD04348) | 0.0 | Normal Stomach | 1.8 |
| Kidney margin (OD04348) | 20.7 | Gastric Cancer 9060397 | 2.5 |
| Kidney Cancer (OD04450-01) | 1.4 | Stomach margin 9060396 | 1.2 |

TABLE ZD-continued

Panel 2.1

| Tissue Name | Rel. Exp. (%) Ag3979, Run 170721574 | Tissue Name | Rel. Exp. (%) Ag3979, Run 170721574 |
|---|---|---|---|
| Kidney margin (OD04450-03) | 42.9 | Gastric Cancer 9060395 | 1.0 |
| Kidney Cancer 8120613 | 0.0 | Stomach margin 9060394 | 2.2 |
| Kidney margin 8120614 | 9.9 | Gastric Cancer 064005 | 1.0 |

TABLE ZE

Panel 4.1D

| Tissue Name | Rel. Exp. (%) Ag3979, Run 170721251 | Tissue Name | Rel. Exp. (%) Ag3979, Run 170721251 |
|---|---|---|---|
| Secondary Th1 act | 0.0 | HUVEC IL-1beta | 1.2 |
| Secondary Th2 act | 0.0 | HUVEC IFN gamma | 1.8 |
| Secondary Tr1 act | 0.0 | HUVEC TNF alpha + IFN gamma | 0.2 |
| Secondary Th1 rest | 0.0 | HUVEC TNF alpha + IL4 | 0.3 |
| Secondary Th2 rest | 0.0 | HUVEC IL-11 | 0.9 |
| Secondary Tr1 rest | 0.0 | Lung Microvascular EC none | 100.0 |
| Primary Th1 act | 0.1 | Lung Microvascular EC TNF alpha + IL-1beta | 58.2 |
| Primary Th2 act | 0.0 | Microvascular Dermal EC none | 72.2 |
| Primary Tr1 act | 0.0 | Microsvascular Dermal EC TNF alpha + IL-1beta | 48.0 |
| Primary Th1 rest | 0.0 | Bronchial epithelium TNF alpha + IL1beta | 3.4 |
| Primary Th2 rest | 0.0 | Small airway epithelium none | 0.0 |
| Primary Tr1 rest | 0.0 | Small airway epithelium TNF alpha + IL-1beta | 0.7 |
| CD45RA CD4 lymphocyte act | 5.2 | Coronery artery SMC rest | 39.5 |
| CD45RO CD4 lymphocyte act | 0.0 | Coronery artery SMC TNF alpha + IL-1beta | 40.6 |
| CD8 lymphocyte act | 0.0 | Astrocytes rest | 12.1 |
| Secondary CD8 lymphocyte rest | 0.0 | Astrocytes TNF alpha + IL-1beta | 27.5 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 1.7 |
| LAK cells rest | 0.0 | CCD1106 (Keratinocytes) TNF alpha + IL-1beta | 1.3 |
| LAK cells IL-2 | 0.0 | Liver cirrhosis | 0.6 |
| LAK cells IL-2 + IL-12 | 0.0 | NCI-H292 none | 0.5 |
| LAK cells IL-2 + IFN gamma | 0.0 | NCI-H292 IL-4 | 0.8 |
| LAK cells IL-2 + IL-18 | 0.0 | NCI-H292 IL-9 | 1.2 |
| LAK cells PMA/ionomycin | 0.0 | NCI-H292 IL-13 | 0.3 |
| NK Cells IL-2 rest | 0.0 | NCI-H292 IFN gamma | 0.6 |
| Two Way MLR 3 day | 0.0 | HPAEC none | 3.4 |
| Two Way MLR 5 day | 0.0 | HPAEC TNF alpha + IL-1beta | 7.5 |
| Two Way MLR 7 day | 0.2 | Lung fibroblast none | 0.3 |
| PBMC rest | 0.0 | Lung fibroblast TNF alpha + IL-1beta | 0.1 |
| PBMC PWM | 0.0 | Lung fibroblast IL-4 | 0.0 |
| PBMC PHA-L | 0.0 | Lung fibroblast IL-9 | 0.0 |
| Ramos (B cell) none | 0.0 | Lung fibroblast IL-13 | 0.6 |
| Ramos (B cell) ionomycin | 0.4 | Lung fibroblast IFN gamma | 0.9 |
| B lymphocytes PWM | 0.0 | Dermal fibroblast CCD1070 rest | 14.3 |
| B lymphocytes CD40L and IL-4 | 0.0 | Dermal fibroblast CCD1070 TNF alpha | 9.9 |
| EOL-1 dbcAMP | 0.9 | Dermal fibroblast CCD1070 IL-1beta | 11.2 |
| EOL-1 dbcAMP PMA/ionomycin | 1.8 | Dermal fibroblast IFN gamma | 0.9 |
| Dendritic cells none | 0.0 | Dermal fibroblast IL-4 | 0.2 |

TABLE ZE-continued

Panel 4.1D

| Tissue Name | Rel. Exp. (%) Ag3979, Run 170721251 | Tissue Name | Rel. Exp. (%) Ag3979, Run 170721251 |
|---|---|---|---|
| Dendritic cells LPS | 0.0 | Dermal Fibroblasts rest | 0.0 |
| Dendritic cells anti-CD40 | 0.3 | Neutrophils TNF a + LPS | 0.3 |
| Monocytes rest | 0.0 | Neutrophils rest | 0.3 |
| Monocytes LPS | 0.0 | Colon | 2.0 |
| Macrophages rest | 0.0 | Lung | 0.0 |
| Macrophages LPS | 0.0 | Thymus | 4.5 |
| HUVEC none | 3.5 | Kidney | 29.1 |
| HUVEC starved | 1.5 | | |

CNS_neurodegeneration_v1.0 Summary: Ag3979 Expression of this gene is low/undetectable (CTs>35) across all of the samples on this panel (data not shown).

General_screening_panel_v1.4 Summary: Ag3979 Expression of this gene is highest in prostate cancer cell line PC-3 and a melanoma cell line (CT=28). Thus, the expression of this gene could be used to distinguish the cells from the other samples in the panel. In addition, there is substantial expression associated with kidney cancer cell lines and colon cancer cell lines. Therefore, therapeutic modulation of the activity of this gene or its protein product, through the use of small molecule drugs, protein therapeutics or antibodies, might be of benefit in the treatment of kidney cancer, prostate cancer, colon cancer or melanoma. Finally, expression of this gene is much higher in fetal liver (CT=29) than adult liver (CT=40), as well as in fetal kidney (CT=30) than adult kidney (CT=40). This observation suggests that expression of this gene may be used to distinguish fetal from adult liver or kidney.

This gene encodes a protein with homology to kinases and is expressed at very low levels in the fetal brain, hippocampus, and cerebellum. This gene is predominantly expressed in fetal tissues and in cancer cell lines, suggesting that it plays a role in cell division or differentiation. Thus, this gene may therefore be of use in regulation of the cell cycle in stem cell research or therapy.

Panel 2.1 Summary: Ag3979 Expression of this gene is highest in a sample derived from a metastatic breast cancer (CT=30.9). Thus, the expression of this gene could be used to distinguish this metastatic breast cancer specimen from other samples in the panel. In addition, there appears to be substantial expression associated with a number of normal kidney tissue samples adjacent to malignant kidney. Therefore, therapeutic modulation of the activity of this gene, through the use of small molecule drugs, protein therapeutics or antibodies, might be of benefit in the treatment of breast and kidney cancer.

Panel 4.1D Summary: Ag3979 Expression of this gene is highest in lung microvascular endothelial cells (CT=29.7). The transcript is also expressed by fibroblasts, endothelium and smooth muscle cells. This gene encodes a putative protien kinase that localizes to the nucleus based on PSORT analysis. The protein encoded for by this transcript may be important in the normal function of the fibroblasts, endothelial cells and smooth muscle cells. Therefore, therapies designed with the protein encoded for by this transcript could be used to regulate fibroblast, endothelium and smooth muscle cell function and may be important in the treatment of asthma, emphysema, arthritis, and inflammatory bowel disease.

AA. CG90635-01: Nuclear Body Associated Kinase 2B

Expression of gene CG90635-01 was assessed using the primer-probe sets Ag3709 and Ag3768, described in Tables AAA and AAB. Results of the RTQ-PCR runs are shown in Tables AAC, AAD and AAE.

TABLE AAA

Probe Name Ag3709

| Primers | Sequences | Length | Start Position | SEQ ID NO: |
|---|---|---|---|---|
| Forward | 5'-caaagctgtgtgctcaacct-3' | 20 | 1067 | 309 |
| Probe | TET-5'-acagagctcctgaaattatccttgga-3'-TAMRA | 26 | 1105 | 310 |
| Reverse | 5'-tgaccacatgtcaatagcttca-3' | 22 | 1142 | 311 |

TABLE AAB

Probe Name Ag3768

| Primers | Sequences | Length | Start Position | SEQ ID No: |
|---|---|---|---|---|
| Forward | 5'-ccagatttgcactcagacaga-3' | 21 | 1952 | 312 |
| Probe | TET-5'-tccaacagacatttatagtatgtccacctg-3'-TAMRA | 30 | 1978 | 313 |
| Reverse | 5'-gcttgtagtccactttgaaacg-3' | 22 | 2008 | 314 |

TABLE AAC

CNS_neurodegeneration_v1.0

| Tissue Name | Rel. Exp. (%) Ag3768, Run 211176319 | Tissue Name | Rel. Exp. (%) Ag3768, Run 211176319 |
|---|---|---|---|
| AD 1 Hippo | 20.2 | Control (Path) 3 Temporal Ctx | 16.2 |
| AD 2 Hippo | 32.5 | Control (Path) 4 Temporal Ctx | 28.5 |
| AD 3 Hippo | 19.5 | AD 1 Occipital Ctx | 27.4 |
| AD 4 Hippo | 7.9 | AD 2 Occipital Ctx (Missing) | 0.0 |
| AD 5 Hippo | 100.0 | AD 3 Occipital Ctx | 15.4 |
| AD 6 Hippo | 76.3 | AD 4 Occipital Ctx | 15.5 |
| Control 2 Hippo | 24.0 | AD 5 Occipital Ctx | 36.1 |
| Control 4 Hippo | 26.1 | AD 6 Occipital Ctx | 28.7 |
| Control (Path) 3 Hippo | 15.0 | Control 1 Occipital Ctx | 9.5 |
| AD 1 Temporal Ctx | 35.4 | Control 2 Occipital Ctx | 46.3 |
| AD 2 Temporal Ctx | 22.5 | Control 3 Occipital Ctx | 24.7 |
| AD 3 Temporal Ctx | 9.4 | Control 4 Occipital Ctx | 11.3 |
| AD 4 Temporal Ctx | 28.1 | Control (Path) 1 Occipital Ctx | 71.7 |
| AD 5 Inf Temporal Ctx | 73.2 | Control (Path) 2 Occipital Ctx | 17.1 |
| AD 5 Sup Temporal Ctx | 63.3 | Control (Path) 3 Occipital Ctx | 13.0 |
| AD 6 Inf Temporal Ctx | 64.2 | Control (Path) 4 Occipital Ctx | 7.9 |
| AD 6 Sup Temporal Ctx | 64.2 | Control 1 Parietal Ctx | 15.7 |
| Control 1 Temporal Ctx | 10.3 | Control 2 Parietal Ctx | 49.7 |
| Control 2 Temporal Ctx | 30.6 | Control 3 Parietal Ctx | 16.8 |
| Control 3 Temporal Ctx | 20.0 | Control (Path) 1 Parietal Ctx | 11.6 |
| Control 3 Temporal Ctx | 5.4 | Control (Path) 2 Parietal Ctx | 19.2 |
| Control (Path) 1 Temporal Ctx | 57.4 | Control (Path) 3 Parietal Ctx | 12.9 |
| Control (Path) 2 Temporal Ctx | 39.2 | Control (Path) 4 Parietal Ctx | 16.6 |

TABLE AAD

General_screening_panel_v1.4

| Tissue Name | Rel. Exp. (%) Ag3768, Run 218981616 | Tissue Name | Rel. Exp. (%) Ag3768, Run 218981616 |
|---|---|---|---|
| Adipose | 6.8 | Renal ca. TK-10 | 26.6 |
| Melanoma* Hs688(A).T | 17.6 | Bladder | 14.1 |
| Melanoma* Hs688(B).T | 15.6 | Gastric ca. (liver met.) NCI-N87 | 36.6 |
| Melanoma* M14 | 20.0 | Gastric ca. KATO III | 26.8 |
| Melanoma* LOXIMVI | 14.7 | Colon ca. SW-948 | 5.7 |
| Melanoma* SK-MEL-5 | 11.3 | Colon ca. SW480 | 20.6 |
| Squamous cell carcinoma SCC-4 | 14.7 | Colon ca.* (SW480 met) SW620 | 14.9 |
| Testis Pool | 26.1 | Colon ca. HT29 | 11.1 |
| Prostate ca.* (bone met) PC-3 | 20.7 | Colon ca. HCT-116 | 23.5 |
| Prostate Pool | 4.1 | Colon ca. CaCo-2 | 19.3 |
| Placenta | 8.2 | Colon cancer tissue | 18.7 |
| Uterus Pool | 3.7 | Colon ca. SW1116 | 4.2 |
| Ovarian ca. OVCAR-3 | 12.0 | Colon ca. Colo-205 | 7.7 |
| Ovarian ca. SK-OV-3 | 66.0 | Colon ca. SW-48 | 7.1 |
| Ovarian ca. OVCAR-4 | 8.3 | Colon Pool | 16.6 |
| Ovarian ca. OVCAR-5 | 28.1 | Small Intestine Pool | 10.4 |
| Ovarian ca. IGROV-1 | 14.8 | Stomach Pool | 12.7 |
| Ovarian ca. OVCAR-8 | 17.3 | Bone Marrow Pool | 5.2 |
| Ovary | 9.4 | Fetal Heart | 13.7 |
| Breast ca. MCF-7 | 100.0 | Heart Pool | 6.1 |
| Breast ca. MDA-MB-231 | 25.5 | Lymph Node Pool | 16.2 |
| Breast ca. BT 549 | 39.2 | Fetal Skeletal Muscle | 7.2 |

TABLE AAD-continued

General_screening_panel_v1.4

| Tissue Name | Rel. Exp. (%) Ag3768, Run 218981616 | Tissue Name | Rel. Exp. (%) Ag3768, Run 218981616 |
|---|---|---|---|
| Breast ca. T47D | 47.3 | Skeletal Muscle Pool | 8.5 |
| Breast ca. MDA-N | 6.1 | Spleen Pool | 10.1 |
| Breast Pool | 18.0 | Thymus pool | 20.6 |
| Trachea | 20.4 | CNS cancer (glio/astro) U87-MG | 28.1 |
| Lung | 4.6 | CNS cancer (glio/astro) U-118-MG | 36.9 |
| Fetal Lung | 51.1 | CNS cancer (neuro; met) SK-N-AS | 18.0 |
| Lung ca. NCI-N417 | 6.8 | CNS cancer (astro) SF-539 | 23.2 |
| Lung ca. LX-1 | 14.2 | CNS cancer (astro) SNB-75 | 43.8 |
| Lung ca. NCI-H146 | 4.1 | CNS cancer (glio) SNB-19 | 14.4 |
| Lung ca. SHP-77 | 14.0 | CNS cancer (glio) SF-295 | 37.4 |
| Lung ca. A549 | 15.4 | Brain (Amygdala) Pool | 8.1 |
| Lung ca. NCI-H526 | 9.5 | Brain (cerebellum) | 37.6 |
| Lung ca. NCI-H23 | 33.0 | Brain (fetal) | 13.5 |
| Lung ca. NCI-H460 | 12.3 | Brain (Hippocampus) Pool | 11.3 |
| Lung ca. HOP-62 | 7.4 | Cerebral Cortex Pool | 13.6 |
| Lung ca. NCI-H522 | 16.8 | Brain (Substantia nigra) Pool | 12.0 |
| Liver | 1.6 | Brain (Thalamus) Pool | 15.9 |
| Fetal Liver | 34.4 | Brain (whole) | 29.1 |
| Liver ca. HepG2 | 8.5 | Spinal Cord Pool | 17.9 |
| Kidney Pool | 18.6 | Adrenal Gland | 21.5 |
| Fetal Kidney | 7.0 | Pituitary gland Pool | 7.1 |
| Renal ca. 786-0 | 18.9 | Salivary Gland | 5.7 |
| Renal ca. A498 | 7.7 | Thyroid (female) | 6.0 |
| Renal ca. ACHN | 9.1 | Pancreatic ca. CAPAN2 | 10.7 |
| Renal ca. UO-31 | 15.7 | Pancreas Pool | 16.3 |

TABLE AAE

Panel 4.1D

| Tissue Name | Rel. Exp. (%) Ag3768, Run 170069115 | Tissue Name | Rel. Exp. (%) Ag3768, Run 170069115 |
|---|---|---|---|
| Secondary Th1 act | 30.8 | HUVEC IL-1beta | 22.4 |
| Secondary Th2 act | 44.1 | HUVEC IFN gamma | 11.8 |
| Secondary Tr1 act | 51.1 | HUVEC TNF alpha + IFN gamma | 15.9 |
| Secondary Th1 rest | 13.3 | HUVEC TNF alpha + IL4 | 17.7 |
| Secondary Th2 rest | 16.5 | HUVEC IL-11 | 12.3 |
| Secondary Tr1 rest | 19.6 | Lung Microvascular EC none | 22.7 |
| Primary Th1 act | 16.7 | Lung Microvascular EC TNF alpha + IL-1beta | 19.1 |
| Primary Th2 act | 32.5 | Microvascular Dermal EC none | 16.7 |
| Primary Tr1 act | 26.6 | Microsvascular Dermal EC TNF alpha + IL-1beta | 19.3 |
| Primary Th1 rest | 20.3 | Bronchial epithelium TNF alpha + IL1beta | 12.3 |
| Primary Th2 rest | 14.8 | Small airway epithelium none | 4.1 |
| Primary Tr1 rest | 19.8 | Small airway epithelium TNF alpha + IL-1beta | 14.6 |
| CD45RA CD4 lymphocyte act | 21.5 | Coronery artery SMC rest | 8.7 |
| CD45RO CD4 lymphocyte act | 25.9 | Coronery artery SMC TNF alpha + IL-1beta | 8.8 |
| CD8 lymphocyte act | 31.6 | Astrocytes rest | 11.5 |
| Secondary CD8 lymphocyte rest | 32.3 | Astrocytes TNF alpha + IL-1beta | 6.8 |
| Secondary CD8 lymphocyte act | 25.5 | KU-812 (Basophil) rest | 30.8 |
| CD4 lymphocyte none | 14.9 | KU-812 (Basophil) PMA/ionomycin | 56.3 |
| 2ry Th1/Th2/Tr1_anti-CD95 CH11 | 22.1 | CCD1106 (Keratinocytes) none | 8.4 |
| LAK cells rest | 35.6 | CCD1106 (Keratinocytes) TNF alpha + IL-1beta | 15.2 |

TABLE AAE-continued

Panel 4.1D

| Tissue Name | Rel. Exp. (%) Ag3768, Run 170069115 | Tissue Name | Rel. Exp. (%) Ag3768, Run 170069115 |
| --- | --- | --- | --- |
| LAK cells IL-2 | 26.4 | Liver cirrhosis | 6.6 |
| LAK cells IL-2 + IL-12 | 30.8 | NCI-H292 none | 7.8 |
| LAK cells IL-2 + IFN gamma | 31.4 | NCI-H292 IL-4 | 16.5 |
| LAK cells IL-2 + IL-18 | 31.2 | NCI-H292 IL-9 | 19.6 |
| LAK cells PMA/ionomycin | 19.1 | NCI-H292 IL-13 | 11.0 |
| NK Cells IL-2 rest | 63.3 | NCI-H292 IFN gamma | 17.9 |
| Two Way MLR 3 day | 46.3 | HPAEC none | 12.9 |
| Two Way MLR 5 day | 26.8 | HPAEC TNF alpha + IL-1beta | 28.9 |
| Two Way MLR 7 day | 25.9 | Lung fibroblast none | 7.0 |
| PBMC rest | 27.7 | Lung fibroblast TNF alpha + IL-1beta | 7.4 |
| PBMC PWM | 33.2 | Lung fibroblast IL-4 | 17.1 |
| PBMC PHA-L | 19.2 | Lung fibroblast IL-9 | 12.9 |
| Ramos (B cell) none | 34.4 | Lung fibroblast IL-13 | 9.6 |
| Ramos (B cell) ionomycin | 31.0 | Lung fibroblast IFN gamma | 15.3 |
| B lymphocytes PWM | 21.9 | Dermal fibroblast CCD1070 rest | 17.2 |
| B lymphocytes CD40L and IL-4 | 41.5 | Dermal fibroblast CCD1070 TNF alpha | 48.6 |
| EOL-1 dbcAMP | 17.1 | Dermal fibroblast CCD1070 IL-1beta | 9.2 |
| EOL-1 dbcAMP PMA/ionomycin | 17.0 | Dermal fibroblast IFN gamma | 7.9 |
| Dendritic cells none | 26.8 | Dermal fibroblast IL-4 | 15.7 |
| Dendritic cells LPS | 18.9 | Dermal Fibroblasts rest | 6.0 |
| Dendritic cells anti-CD40 | 22.4 | Neutrophils TNF a + LPS | 7.1 |
| Monocytes rest | 34.6 | Neutrophils rest | 35.4 |
| Monocytes LPS | 48.0 | Colon | 10.5 |
| Macrophages rest | 22.7 | Lung | 18.3 |
| Macrophages LPS | 18.0 | Thymus | 100.0 |
| HUVEC none | 15.8 | Kidney | 15.5 |
| HUVEC starved | 16.2 | | |

CNS$_{13}$ neurodegeneration_v1.0 Summary: Ag3768 The CG90853-01 gene appears to be slightly upregulated in the temporal cortex of Alzheimer's disease patients and also in patient not demented but showing severe AD-like pathology as compared to non-demented patient with no neuropathology. The temporal cortex is a region that shows degeneration at the mid-stages of this disease. These results suggest that this gene may be a marker of Alzheimer's-like neurodegeneration, and may also be involved in the process of neurodegeneration.

General_screening$_{13}$ panel_v1.4 Summary: Ag3768 Expression of the CG90635-01 gene is ubiquitous in this panel, with highest expression in a breast cancer cell line (CT=28.6). Significant expression is also seen in a cluster of breast and ovarian cancer cell lines. Thus, therapeutic modulation of the expression or function of this gene may be effective in the treatment of these cancers.

In addition, this gene is expressed at much higher levels in fetal lung and liver tissue (CTs=30) when compared to expression in the adult counterpart (CTs=33–34). Thus, expression of this gene may be used to differentiate between the fetal and adult source of these tissues.

Among tissues with metabolic function, this gene is expressed at moderate to low levels in pituitary, adipose, adrenal gland, pancreas, thyroid, and adult and fetal skeletal muscle, heart, and liver. This widespread expression among these tissues suggests that this gene product may play a role in normal neuroendocrine and metabolic and that disregulated expression of this gene may contribute to neuroendocrine disorders or metabolic diseases, such as obesity and diabetes.

This gene is also expressed at moderate levels in the CNS, including the hippocampus, thalamus, substantia nigra, amygdala, cerebellum and cerebral cortex. Therefore, therapeutic modulation of the expression or function of this gene may be useful in the treatment of neurologic disorders, such as Alzheimer's disease, Parkinson's disease, schizophrenia, multiple sclerosis, stroke and epilepsy.

A second experiment with the probe/primer set Ag3709 shows undetectable levels of expression in all samples on this panel (CTs=40). The data suggest that there is a possibility of an experimental failure.

Panel 4.1D Summary: Ag3678 Expression of the CG90635-01 gene is ubiquitous in this panel, with highest expression in the thymus (CT=29.6). This gene also is expressed at moderate to low levels in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. This ubiquitous pattern of expression suggests that this gene product may be involved in homeostatic processes for these and other cell types and tissues. This pattern is in agreement with the expression profile in General_screening_panel_v1.4 and also suggests a role for the gene product in cell survival and proliferation. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

Two additional experiments with the probe/primer set Ag3709 show undetectable levels of expression in all samples on this panel (CTs=40). The data suggest that there is a possibility of an experimental failure.

AB. CG90729-01: Proline-Rich Inositol Polyphosphate 5-Phosphatase

Expression of gene CG90729-01 was assessed using the primer-probe set Ag3713, described in Table ABA. Results of the RTQ-PCR runs are shown in Tables ABB, ABC and ABD.

TABLE ABA

Probe Name Ag3713

| Primers | Sequences | Length | Start Position | SEQ ID NO: |
|---|---|---|---|---|
| Forward | 5'-ggatgggaatacctaccaggta-3' | 22 | 2457 | 315 |
| Probe | TET-5'-cattcagtgaggaatcactgcccaag-3'-TAMRA | 26 | 2480 | 316 |
| Reverse | 5'-aggatgctgtggttgtgactat-3' | 22 | 2534 | 317 |

TABLE ABB

CNS_neurodegeneration_v1.0

| Tissue Name | Rel. Exp. (%) Ag3713, Run 211295018 | Tissue Name | Rel. Exp. (%) Ag3713, Run 211295018 |
|---|---|---|---|
| AD 1 Hippo | 13.1 | Control (Path) 3 Temporal Ctx | 3.9 |
| AD 2 Hippo | 37.4 | Control (Path) 4 Temporal Ctx | 6.5 |
| AD 3 Hippo | 3.0 | AD 1 Occipital Ctx | 12.5 |
| AD 4 Hippo | 2.0 | AD 2 Occipital Ctx (Missing) | 0.0 |
| AD 5 hippo | 100.0 | AD 3 Occipital Ctx | 2.4 |
| AD 6 Hippo | 73.7 | AD 4 Occipital Ctx | 4.2 |
| Control 2 Hippo | 7.5 | AD 5 Occipital Ctx | 23.0 |
| Control 4 Hippo | 8.9 | AD 6 Occipital Ctx | 19.5 |
| Control (Path) 3 Hippo | 1.8 | Control 1 Occipital Ctx | 1.1 |
| AD 1 Temporal Ctx | 11.3 | Control 2 Occipital Ctx | 25.5 |
| AD 2 Temporal Ctx | 30.4 | Control 3 Occipital Ctx | 18.4 |
| AD 3 Temporal Ctx | 3.7 | Control 4 Occipital Ctx | 1.6 |
| AD 4 Temporal Ctx | 3.4 | Control (Path) 1 Occipital Ctx | 62.9 |
| AD 5 Inf Temporal Ctx | 63.3 | Control (Path) 2 Occipital Ctx | 21.3 |
| AD 5 Sup Temporal Ctx | 39.8 | Control (Path) 3 Occipital Ctx | 1.7 |
| AD 6 Inf Temporal Ctx | 29.3 | Control (Path) 4 Occipital Ctx | 6.7 |
| AD 6 Sup Temporal Ctx | 42.3 | Control 1 Parietal Ctx | 6.5 |
| Control 1 Temporal Ctx | 4.1 | Control 2 Parietal Ctx | 29.9 |
| Control 2 Temporal Ctx | 10.7 | Control 3 Parietal Ctx | 23.7 |
| Control 3 Temporal Ctx | 19.5 | Control (Path) 1 Parietal Ctx | 45.7 |
| Control 4 Temporal Ctx | 6.1 | Control (Path) 2 Parietal Ctx | 31.6 |
| Control (Path) 1 Temporal Ctx | 36.1 | Control (Path) 3 Parietal Ctx | 3.3 |
| Control (Path) 2 Temporal Ctx | 45.4 | Control (Path) 4 Parietal Ctx | 17.1 |

TABLE ABC

General_screening_panel_v1.4

| Tissue Name | Rel. Exp. (%) Ag3713, Run 218267257 | Tissue Name | Rel. Exp. (%) Ag3713, Run 218267257 |
|---|---|---|---|
| Adipose | 0.2 | Renal ca. TK-10 | 0.6 |
| Melanoma* Hs688(A).T | 0.1 | Bladder | 1.1 |

TABLE ABC-continued

General_screening_panel_v1.4

| Tissue Name | Rel. Exp. (%) Ag3713, Run 218267257 | Tissue Name | Rel. Exp. (%) Ag3713, Run 218267257 |
|---|---|---|---|
| Melanoma* Hs688(B).T | 0.2 | Gastric ca. (liver met.) NCI-N87 | 4.1 |
| Melanoma* M14 | 0.0 | Gastric ca. KATO III | 2.4 |
| Melanoma* LOXIMVI | 0.5 | Colon ca. SW-948 | 1.7 |
| Melanoma* SK-MEL-5 | 0.8 | Colon ca. SW480 | 3.6 |
| Squamous cell carcinoma SCC-4 | 0.0 | Colon ca.* (SW480 met) SW620 | 4.6 |
| Testis Pool | 0.7 | Colon ca. HT29 | 0.1 |
| Prostate ca.* (bone met) PC-3 | 3.2 | Colon ca. HCT-116 | 4.0 |
| Prostate Pool | 0.9 | Colon ca. CaCo-2 | 2.6 |
| Placenta | 0.1 | Colon cancer tissue | 3.9 |
| Uterus Pool | 0.3 | Colon ca. SW1116 | 1.0 |
| Ovarian ca. OVCAR-3 | 1.6 | Colon ca. Colo-205 | 0.2 |
| Ovarian ca. SK-OV-3 | 0.2 | Colon ca. SW-48 | 0.3 |
| Ovarian ca. OVCAR-4 | 0.6 | Colon Pool | 1.9 |
| Ovarian ca. OVCAR-5 | 38.2 | Small Intestine Pool | 1.1 |
| Ovarian ca. IGROV-1 | 2.6 | Stomach Pool | 0.6 |
| Ovarian ca. OVCAR-8 | 4.9 | Bone Marrow Pool | 0.5 |
| Ovary | 1.7 | Fetal Heart | 3.2 |
| Breast ca. MCF-7 | 8.0 | Heart Pool | 2.5 |
| Breast ca. MDA-MB-231 | 1.0 | Lymph Node Pool | 1.2 |
| Breast ca. BT 549 | 1.3 | Fetal Skeletal Muscle | 0.1 |
| Breast ca. T47D | 100.0 | Skeletal Muscle Pool | 1.3 |
| Breast ca. MDA-N | 0.0 | Spleen Pool | 0.1 |
| Breast Pool | 1.7 | Thymus Pool | 0.6 |
| Trachea | 5.5 | CNS cancer (glio/astro) U87-MG | 1.4 |
| Lung | 0.1 | CNS cancer (glio/astro) U-118-MG | 0.4 |
| Fetal Lung | 1.2 | CNS cancer (neuro; met) SK-N-AS | 3.1 |
| Lung ca. NCI-N417 | 0.0 | CNS cancer (astro) SF-539 | 0.2 |
| Lung ca. LX-1 | 4.0 | CNS cancer (astro) SNB-75 | 0.4 |
| Lung ca. NCI-H146 | 0.5 | CNS cancer (glio) SNB-19 | 1.9 |
| Lung ca. SHP-77 | 2.0 | CNS cancer (glio) SF-295 | 2.3 |
| Lung ca. A549 | 1.2 | Brain (Amygdala) Pool | 1.9 |
| Lung ca. NCI-H526 | 0.3 | Brain (cerebellum) | 52.5 |
| Lung ca. NCI-H23 | 3.0 | Brain (fetal) | 7.2 |
| Lung ca. NCI-H460 | 2.9 | Brain (Hippocampus) Pool | 2.0 |
| Lung ca. HOP-62 | 1.2 | Cerebral Cortex Pool | 3.1 |
| Lung ca. NCI-H522 | 1.7 | Brain (Substantia nigra) Pool | 4.2 |
| Liver | 0.1 | Brain (Thalamus) Pool | 3.0 |
| Fetal Liver | 0.3 | Brain (whole) | 12.3 |
| Liver ca. HepG2 | 0.0 | Spinal Cord Pool | 0.7 |
| Kidney Pool | 2.0 | Adrenal Gland | 0.5 |
| Fetal Kidney | 1.9 | Pituitary gland Pool | 0.9 |
| Renal ca. 786-0 | 1.0 | Salivary Gland | 9.6 |
| Renal ca. A498 | 0.0 | Thyroid (female) | 69.3 |
| Renal ca. ACHN | 3.1 | Pancreatic ca. CAPAN2 | 0.6 |
| Renal ca. UO-31 | 2.4 | Pancreas Pool | 2.0 |

TABLE ABD

Panel 4.1D

| Tissue Name | Rel. Exp. (%) Ag3713, Run 169987477 | Tissue Name | Rel. Exp. (%) Ag3713, Run 169987477 |
|---|---|---|---|
| Secondary Th1 act | 0.0 | HUVEC IL-1beta | 0.0 |
| Secondary Th2 act | 0.8 | HUVEC IFN gamma | 0.3 |
| Secondary Tr1 act | 0.0 | HUVEC TNF alpha + IFN gamma | 0.1 |
| Secondary Th1 rest | 0.6 | HUVEC TNF alpha + IL4 | 0.2 |
| Secondary Th2 rest | 0.0 | HUVEC IL-11 | 0.0 |
| Secondary Tr1 rest | 0.0 | Lung Microvascular EC none | 1.2 |
| Primary Th1 act | 0.0 | Lung Microvascular EC TNF alpha + IL-1beta | 0.0 |
| Primary Th2 act | 1.0 | Microvascular Dermal EC none | 0.1 |

TABLE ABD-continued

Panel 4.1D

| Tissue Name | Rel. Exp. (%) Ag3713, Run 169987477 | Tissue Name | Rel. Exp. (%) Ag3713, Run 169987477 |
|---|---|---|---|
| Primary Tr1 act | 1.3 | Microvasular Dermal EC TNF alpha + IL-1beta | 0.0 |
| Primary Th1 rest | 0.0 | Bronchial epithelium TNF alpha + IL1beta | 1.5 |
| Primary Th2 rest | 0.0 | Small airway epithelium none | 0.8 |
| Primary Tr1 rest | 0.0 | Small airway epithelium TNF alpha + IL-1beta | 0.8 |
| CD45RA CD4 lymphocyte act | 0.8 | Coronery artery SMC rest | 0.0 |
| CD45RO CD4 lymphocyte act | 0.3 | Coronery artery SMC TNF alpha + IL-1beta | 0.0 |
| CD8 lymphocyte act | 0.0 | Astrocytes rest | 6.4 |
| Secondary CD8 lymphocyte rest | 0.1 | Astrocytes TNF alpha + IL-1beta | 1.6 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 4.6 |
| LAK cells rest | 0.0 | CCD1106 (Keratinocytes) TNF alpha + IL-1beta | 4.3 |
| LAK cells IL-2 | 0.8 | Liver cirrhosis | 1.8 |
| LAK cells IL-2 + IL-12 | 0.0 | NCI-H292 none | 1.5 |
| LAK cells IL-2 + IFN gamma | 0.4 | NCI-H292 IL-4 | 1.1 |
| LAK cells IL-2 + IL-18 | 0.0 | NCI-H292 IL-9 | 3.0 |
| LAK cells PMA/ionomycin | 0.4 | NCI-H292 IL-13 | 2.0 |
| NK Cells IL-2 rest | 0.0 | NCI-H292 IFN gamma | 1.2 |
| Two Way MLR 3 day | 0.0 | HPAEC none | 1.1 |
| Two Way MLR 5 day | 0.0 | HPAEC TNF alpha + IL-1beta | 0.0 |
| Two Way MLR 7 day | 0.0 | Lung fibroblast none | 2.4 |
| PBMC rest | 0.0 | Lung fibroblast TNF alpha + IL-1beta | 0.0 |
| PBMC PWM | 1.4 | Lung fibroblast IL-4 | 0.0 |
| PBMC PHA-L | 0.3 | Lung fibroblast IL-9 | 0.8 |
| Ramos (B cell) none | 0.0 | Lung fibroblast IL-13 | 0.0 |
| Ramos (B cell) ionomycin | 0.0 | Lung fibroblast IFN gamma | 0.7 |
| B lymphocytes PWM | 0.6 | Dermal fibroblast CCD1070 rest | 0.1 |
| B lymphocytes CD40L and IL-4 | 0.9 | Dermal fibroblast CCD1070 TNF alpha | 0.0 |
| EOL-1 dbcAMP | 0.0 | Dermal fibroblast CCD1070 IL-1beta | 0.0 |
| EOL-1 dbcAMP PMA/ionomycin | 0.0 | Dermal fibroblast IFN gamma | 0.0 |
| Dendritic cells none | 0.0 | Dermal fibroblast IL-4 | 0.5 |
| Dendritic cells LPS | 1.0 | Dermal Fibroblast rest | 1.2 |
| Dendritic cells anti-CD40 | 0.0 | Neutrophils TNFa + LPS | 0.0 |
| Monocytes rest | 0.0 | Neutrophils rest | 0.1 |
| Monocytes LPS | 0.2 | Colon | 75.3 |
| Macrophages rest | 0.0 | Lung | 9.0 |
| Macrophages LPS | 0.0 | Thymus | 1.4 |
| HUVEC none | 2.3 | Kidney | 100.0 |
| HUVEC starved | 0.4 | | |

CNS_neurodegeneration_v1.0 Summary: Ag3713 This panel confirms the expression of the CG90729-01 gene at low levels in the brains of an independent group of individuals. However, no differential expression of this gene was detected between Alzheimer's diseased postmortem brains and those of non-demented controls in this experiment. Please see Panel 1.4 for a discussion of the potential utility of this gene in treatment of central nervous system disorders.

General_screening_panel_v1.4 Summary: Ag3713 Highest expression of the CG90729-01 gene is detected in breast cancer T47D cell line (CT=25.4). In addition, significant expression of this gene is associated with number of cancer (CNS, colon, gastric, lung, renal, breast, ovarian and prostate) cell lines. Therefore, therapeutic modulation of the activity of this gene or its protein product, through the use of small molecule drugs, protein therapeutics or antibodies, might be beneficial in the treatment of these cancers.

Among tissues with metabolic or endocrine function, this gene is expressed at low to moderate levels in pancreas, adipose, adrenal gland, thyroid, pituitary gland, skeletal muscle, heart, liver and the gastrointestinal tract. Therefore, therapeutic modulation of the activity of this gene may prove useful in the treatment of endocrine/metabolically related diseases, such as obesity and diabetes.

Interestingly, this gene is expressed at much higher levels in adult (CT=31.7) when compared to fetal skeletal muscle (CT=35). This observation suggests that expression of this gene can be used to distinguish fetal from adult skeletal muscle.

In addition, this gene is expressed at high levels in all regions of the central nervous system examined, including amygdala, hippocampus, substantia nigra, thalamus, cerebellum, cerebral cortex, and spinal cord. Therefore, this gene may play a role in central nervous system disorders such as Alzheimer's disease, Parkinson's disease, epilepsy, multiple sclerosis, schizophrenia and depression.

Panel 4.1D Summary: Ag3713 Highest expression of the CG90729-01 gene is detected in kidney (CT=30). In addition, significant expression is also seen in colon sample (CT=30.5). Thus, expression of this gene can be used to distinguish these two tissue samples from other samples in the panel. Low expression of this gene is also observed in lung, keratinocytes and astrocytes. Therefore, therapeutic modulation of the activity of this gene may prove useful in the treatment of inflammatory or autoimmune diseases that affect the kidney, including lupus and glomerulonephritis, inflammatory bowel disease, allergy, asthma, psoriasis and wound healing.

AC. CG90760-01: Transcription Factor 20

Expression of gene CG90760-01 was assessed using the primer-probe set Ag3715, described in Table ACA. Results of the RTQ-PCR runs are shown in Tables ACB, ACC and ACD.

TABLE ACA

| Probe Name Ag3715 | | | | |
|---|---|---|---|---|
| Primers | Sequences | Length | Start Position | SEQ ID NO: |
| Forward | 5'-cttcatctgggcctctgatt-3' | 20 | 18 | 318 |
| Probe | TET-5'-tctttattccctccatcatctagacttga-3'-TAMRA | 29 | 40 | 319 |
| Reverse | 5'-cgcatctccttggtacaaataa-3' | 22 | 71 | 320 |

TABLE ACB

CNS_neurodegeneration_v1.0

| Tissue Name | Rel. Exp. (%) Ag3715, Run 211295020 | Tissue Name | Rel. Exp. (%) Ag3715, Run 211295020 |
|---|---|---|---|
| AD 1 Hippo | 17.3 | Control (Path) 3 Temporal Ctx | 3.4 |
| AD 2 Hippo | 27.7 | Control (Path) 4 Temporal Ctx | 32.1 |
| AD 3 Hippo | 12.9 | AD 1 Occipital Ctx | 27.0 |
| AD 4 Hippo | 4.6 | AD 2 Occipital Ctx (Missing) | 0.0 |
| AD 5 hippo | 66.4 | AD 3 Occipital Ctx | 5.9 |
| AD 6 Hippo | 31.2 | AD 4 Occipital Ctx | 8.9 |
| Control 2 Hippo | 4.6 | AD 5 Occipital Ctx | 10.5 |
| Control 4 Hippo | 4.0 | AD 6 Occipital Ctx | 18.3 |
| Control (Path) 3 Hippo | 0.0 | Control 1 Occipital Ctx | 0.0 |
| AD 1 Temporal Ctx | 22.5 | Control 2 Occipital Ctx | 14.9 |
| AD 2 Temporal Ctx | 40.1 | Control 3 Occipital Ctx | 10.4 |
| AD 3 Temporal Ctx | 9.0 | Control 4 Occipital Ctx | 6.8 |
| AD 4 Temporal Ctx | 17.1 | Control (Path) 1 Occipital Ctx | 73.7 |
| AD 5 Inf Temporal Ctx | 100.0 | Control (Path) 2 Occipital Ctx | 13.8 |
| AD 5 Sup Temporal Ctx | 34.2 | Control (Path) 3 Occipital Ctx | 6.0 |
| AD 6 Inf Temporal Ctx | 51.4 | Control (Path) 4 Occipital Ctx | 24.0 |
| AD 6 Sup Temporal Ctx | 42.9 | Control 1 Parietal Ctx | 9.3 |
| Control 1 Temporal Ctx | 3.3 | Control 2 Parietal Ctx | 66.0 |
| Control 2 Temporal Ctx | 0.0 | Control 3 Parietal Ctx | 13.4 |
| Control 3 Temporal Ctx | 15.9 | Control (Path) 1 Parietal Ctx | 41.2 |
| Control 4 Temporal Ctx | 3.6 | Control (Path) 2 Parietal Ctx | 39.5 |
| Control (Path) 1 Temporal Ctx | 76.8 | Control (Path) 3 Parietal Ctx | 1.9 |
| Control (Path) 2 Temporal Ctx | 37.4 | Control (Path) 4 Parietal Ctx | 39.5 |

TABLE ACC

General_screening_panel_v1.4

| Tissue Name | Rel. Exp. (%) Ag3715, Run 218267374 | Tissue Name | Rel. Exp. (%) Ag3715, Run 218267374 |
|---|---|---|---|
| Adipose | 3.9 | Renal ca. TK-10 | 16.4 |
| Melanoma* Hs688(A).T | 1.9 | Bladder | 23.5 |
| Melanoma* Hs688(B).T | 2.5 | Gastric ca. (liver met.) NCI-N87 | 40.1 |

TABLE ACC-continued

General_screening_panel_v1.4

| Tissue Name | Rel. Exp. (%) Ag3715, Run 218267374 | Tissue Name | Rel. Exp. (%) Ag3715, Run 218267374 |
|---|---|---|---|
| Melanoma* M14 | 7.5 | Gastric ca. KATO III | 29.9 |
| Melanoma* LOXIMVI | 4.5 | Colon ca. SW-948 | 7.1 |
| Melanoma* SK-MEL-5 | 27.7 | Colon ca. SW480 | 19.6 |
| Squamous cell carcinoma SCC-4 | 8.5 | Colon ca.* (SW480 met) SW620 | 33.4 |
| Testis Pool | 11.0 | Colon ca. HT29 | 18.9 |
| Prostate ca.* (bone met) PC-3 | 11.3 | Colon ca. HCT-116 | 19.1 |
| Prostate Pool | 6.8 | Colon ca. CaCo-2 | 32.8 |
| Placenta | 6.4 | Colon cancer tissue | 7.3 |
| Uterus Pool | 0.9 | Colon ca. SW1116 | 3.2 |
| Ovarian ca. OVCAR-3 | 14.3 | Colon ca. Colo-205 | 2.0 |
| Ovarian ca. SK-OV-3 | 16.8 | Colon ca. SW-48 | 0.8 |
| Ovarian ca. OVCAR-4 | 7.2 | Colon Pool | 8.3 |
| Ovarian ca. OVCAR-5 | 100.0 | Small Intestine Pool | 6.5 |
| Ovarian ca. IGROV-1 | 2.3 | Stomach Pool | 6.2 |
| Ovarian ca. OVCAR-8 | 0.5 | Bone Marrow Pool | 7.3 |
| Ovary | 6.7 | Fetal Heart | 5.6 |
| Breast ca. MCF-7 | 10.5 | Heart Pool | 3.0 |
| Breast ca. MDA-MB-231 | 4.9 | Lymph Node Pool | 14.3 |
| Breast ca. BT 549 | 13.9 | Fetal Skeletal Muscle | 6.7 |
| Breast ca. T47D | 30.8 | Skeletal Muscle Pool | 4.3 |
| Breast ca. MDA-N | 3.9 | Spleen Pool | 10.7 |
| Breast Pool | 14.1 | Thymus Pool | 13.3 |
| Trachea | 13.5 | CNS cancer (glio/astro) U87-MG | 15.1 |
| Lung | 3.5 | CNS cancer (glio/astro) U-118-MG | 13.2 |
| Fetal Lung | 23.0 | CNS cancer (neuro; met) SK-N-AS | 4.2 |
| Lung ca. NCI-N417 | 2.1 | CNS cancer (astro) SF-539 | 2.8 |
| Lung ca. LX-1 | 38.7 | CNS cancer (astro) SNB-75 | 23.7 |
| Lung ca. NCI-H146 | 4.7 | CNS cancer (glio) SNB-19 | 2.0 |
| Lung ca. SHP-77 | 18.2 | CNS cancer (glio) SF-295 | 32.8 |
| Lung ca. A549 | 15.5 | Brain (Amygdala) Pool | 4.0 |
| Lung ca. NCI-H526 | 0.5 | Brain (cerebellum) | 22.8 |
| Lung ca. NCI-H23 | 41.8 | Brain (fetal) | 57.4 |
| Lung ca. NCI-H460 | 12.3 | Brain (Hippocampus) Pool | 8.7 |
| Lung ca. HOP-62 | 24.7 | Cerebral Cortex Pool | 2.1 |
| Lung ca. NCI-H522 | 16.3 | Brain (Substantia nigra) Pool | 5.9 |
| Liver | 0.5 | Brain (Thalamus) Pool | 8.4 |
| Fetal Liver | 8.5 | Brain (whole) | 6.7 |
| Liver ca. HepG2 | 5.8 | Spinal Cord Pool | 7.8 |
| Kidney Pool | 23.0 | Adrenal Gland | 13.0 |
| Fetal Kidney | 34.9 | Pituitary gland Pool | 5.7 |
| Renal ca. 786-0 | 9.5 | Salivary Gland | 4.9 |
| Renal ca. A498 | 1.4 | Thyroid (female) | 0.8 |
| Renal ca. ACHN | 14.0 | Pancreatic ca. CAPAN2 | 56.6 |
| Renal ca. UO-31 | 6.5 | Pancreas Pool | 17.8 |

TABLE ACD

Panel 4.1D

| Tissue Name | Rel. Exp. (%) Ag3715, Run 169992420 | Tissue Name | Rel. Exp. (%) Ag3715, Run 169992420 |
|---|---|---|---|
| Secondary Th1 act | 55.5 | HUVEC IL-1beta | 24.3 |
| Secondary Th2 act | 82.4 | HUVEC IFN gamma | 38.4 |
| Secondary Tr1 act | 68.3 | HUVEC TNF alpha + IFN gamma | 27.0 |
| Secondary Th1 rest | 40.9 | HUVEC TNF alpha + IL4 | 15.2 |
| Secondary Th2 rest | 52.1 | HUVEC IL-11 | 12.9 |
| Secondary Tr1 rest | 36.1 | Lung Microvascular EC none | 27.7 |
| Primary Th1 act | 81.2 | Lung Microvascular EC TNF alpha + IL-1beta | 28.5 |
| Primary Th2 act | 97.3 | Microvascular Dermal EC none | 28.1 |
| Primary Tr1 act | 60.3 | Microvasular Dermal EC TNF alpha + IL-1beta | 21.3 |

TABLE ACD-continued

Panel 4.1D

| Tissue Name | Rel. Exp. (%) Ag3715, Run 169992420 | Tissue Name | Rel. Exp. (%) Ag3715, Run 169992420 |
|---|---|---|---|
| Primary Th1 rest | 75.3 | Bronchial epithelium TNF alpha + IL1beta | 23.5 |
| Primary Th2 rest | 59.9 | Small airway epithelium none | 16.8 |
| Primary Tr1 rest | 52.5 | Small airway epithelium TNF alpha + IL-1beta | 34.2 |
| CD45RA CD4 lymphocyte act | 43.8 | Coronery artery SMC rest | 9.6 |
| CD45RO CD4 lymphocyte act | 100.0 | Coronery artery SMC TNF alpha + IL-1beta | 7.9 |
| CD8 lymphocyte act | 54.3 | Astrocytes rest | 11.5 |
| Secondary CD8 lymphocyte rest | 69.3 | Astrocytes TNF alpha + IL-1beta | 6.8 |
| Secondary CD8 lymphocyte act | 25.5 | KU-812 (Basophil) rest | 27.7 |
| CD4 lymphocyte none | 27.9 | KU-812 (Basophil) PMA/ionomycin | 13.5 |
| 2ry Th1/Th2/Tr1_anti-CD95 CH11 | 61.1 | CCD1106 (Keratinocytes) none | 85.9 |
| LAK cells rest | 41.8 | CCD1106 (Keratinocytes) TNF alpha + IL-1beta | 50.3 |
| LAK cells IL-2 | 71.7 | Liver cirrhosis | 5.8 |
| LAK cells IL-2 + IL-12 | 45.7 | NCI-H292 none | 18.2 |
| LAK cells IL-2 + IFN gamma | 70.7 | NCI-H292 IL-4 | 53.2 |
| LAK cells IL-2 + IL-18 | 72.7 | NCI-H292 IL-9 | 40.9 |
| LAK cells PMA/ionomycin | 88.9 | NCI-H292 IL-13 | 25.0 |
| NK Cells IL-2 rest | 30.4 | NCI-H292 IFN gamma | 15.9 |
| Two Way MLR 3 day | 86.5 | HPAEC none | 13.4 |
| Two Way MLR 5 day | 53.6 | HPAEC TNF alpha + IL-1beta | 34.4 |
| Two Way MLR 7 day | 32.5 | Lung fibroblast none | 12.9 |
| PBMC rest | 39.8 | Lung fibroblast TNF alpha + IL-1beta | 12.4 |
| PBMC PWM | 32.8 | Lung fibroblast IL-4 | 9.2 |
| PBMC PHA-L | 47.3 | Lung fibroblast IL-9 | 18.7 |
| Ramos (B cell) none | 70.2 | Lung fibroblast IL-13 | 15.3 |
| Ramos (B cell) ionomycin | 55.5 | Lung fibroblast IFN gamma | 1.5 |
| B lymphocytes PWM | 41.8 | Dermal fibroblast CCD1070 rest | 15.9 |
| B lymphocytes CD40L and IL-4 | 48.3 | Dermal fibroblast CCD1070 TNF alpha | 67.8 |
| EOL-1 dbcAMP | 50.7 | Dermal fibroblast CCD1070 IL-1beta | 0.0 |
| EOL-1 dbcAMP PMA/ionomycin | 56.6 | Dermal fibroblast IFN gamma | 13.4 |
| Dendritic cells none | 29.9 | Dermal fibroblast IL-4 | 24.5 |
| Dendritic cells LPS | 6.7 | Dermal Fibroblast rest | 11.1 |
| Dendritic cells anti-CD40 | 12.8 | Neutrophils TNFa + LPS | 11.9 |
| Monocytes rest | 15.0 | Neutrophils rest | 40.3 |
| Monocytes LPS | 75.8 | Colon | 20.3 |
| Macrophages rest | 17.3 | Lung | 8.4 |
| Macrophages LPS | 9.9 | Thymus | 84.1 |
| HUVEC none | 7.3 | Kidney | 56.6 |
| HUVEC starved | 29.3 | | |

CNS_neurodegeneration_v1.0 Summary: Ag3715 This panel does not show differential expression of the CG90760-01 gene in Alzheimer's disease. However, this expression profile confirms the presence of this gene in the brain, with highest expression in the temporal cortex of an Alzheimer's patient (CT=32.6). Please see Panel 1.4 for discussion of utility of this gene in the central nervous system.

General_screening_panel_v1.4 Summary: Ag3715 Expression of the CG90760-01 gene is widespread in this panel, with highest expression in an ovarian cancer cell line (CT=30.5). Thus, expression of this gene could be used to differentiate between this sample and other samples on this panel.

In addition, the widespread expression of this gene suggests a broader role for this gene product in cell survival and growth.

Among tissues with metabolic function, this gene is expressed at low levels in pituitary, adrenal gland, pancreas, fetal heart and liver and adult and fetal skeletal muscle. This expression suggests that this gene product may play a role in normal neuroendocrine and metabolic and that disregulated expression of this gene may contribute to neuroendocrine disorders or metabolic diseases, such as obesity and diabetes.

This gene is also expressed at low levels in the CNS, including the hippocampus, thalamus, substantia nigra, and cerebellum. Therefore, therapeutic modulation of the expression or function of this gene may be useful in the treatment of neurologic disorders, such as Alzheimer's disease, Parkinson's disease, schizophrenia, multiple sclerosis, stroke and epilepsy.

Panel 4.1D Summary: Ag3715 Results from one experiment with the CG90760-01 gene are not included. The amp plot indicates that there were experimental difficulties with this run.

AC. CG90760-01: Transcription Factor 20

Expression of gene CG90760-01 was assessed using the primer-probe set Ag3715, described in Table ACA. Results of the RTQ-PCR runs are shown in Tables ACB, ACC and ACD.

TABLE ACA

Probe Name Ag3715

| Primers | Sequences | Length | Start Position | SEQ ID No |
|---|---|---|---|---|
| Forward | 5'-cttcatctgggcctctgatt-3' | 20 | 18 | |
| Probe | TET-5'-tctttattccctccatcatctagacttga-3'-TAMRA | 29 | 40 | |
| Reverse | 5'-cgcatctccttggtacaaataa-3' | 22 | 71 | |

TABLE ACB

CNS_neurodegeneration_v1.0

| Tissue Name | Rel. Exp. (%) Ag3715, Run 211295020 | Tissue Name | Rel. Exp. (%) Ag3715, Run 211295020 |
|---|---|---|---|
| AD 1 Hippo | 17.3 | Control (Path) 3 Temporal Ctx | 3.4 |
| AD 2 Hippo | 27.7 | Control (Path) 4 Temporal Ctx | 32.1 |
| AD 3 Hippo | 12.9 | AD 1 Occipital Ctx | 27.0 |
| AD 4 Hippo | 4.6 | AD 2 Occipital Ctx (Missing) | 0.0 |
| AD 5 hippo | 66.4 | AD 3 Occipital Ctx | 5.9 |
| AD 6 Hippo | 31.2 | AD 4 Occipital Ctx | 8.9 |
| Control 2 Hippo | 4.6 | AD 5 Occipital Ctx | 10.5 |
| Control 4 Hippo | 4.0 | AD 6 Occipital Ctx | 18.3 |
| Control (Path) 3 Hippo | 0.0 | Control 1 Occipital Ctx | 0.0 |
| AD 1 Temporal Ctx | 22.5 | Control 2 Occipital Ctx | 14.9 |
| AD 2 Temporal Ctx | 40.1 | Control 3 Occipital Ctx | 10.4 |
| AD 3 Temporal Ctx | 9.0 | Control 4 Occipital Ctx | 6.8 |
| AD 4 Temporal Ctx | 17.1 | Control (Path) 1 Occipital Ctx | 73.7 |
| AD 5 Inf Temporal Ctx | 100.0 | Control (Path) 2 Occipital Ctx | 13.8 |
| AD 5 Sup Temporal Ctx | 34.2 | Control (Path) 3 Occipital Ctx | 6.0 |
| AD 6 Inf Temporal Ctx | 51.4 | Control (Path) 4 Occipital Ctx | 24.0 |
| AD 6 Sup Temporal Ctx | 42.9 | Control 1 Parietal Ctx | 9.3 |
| Control 1 Temporal Ctx | 3.3 | Control 2 Parietal Ctx | 66.0 |
| Control 2 Temporal Ctx | 0.0 | Control 3 Parietal Ctx | 13.4 |
| Control 3 Temporal Ctx | 15.9 | Control (Path) 1 Parietal Ctx | 41.2 |
| Control 4 Temporal Ctx | 3.6 | Control (Path) 2 Parietal Ctx | 39.5 |
| Control (Path) 1 Temporal Ctx | 76.8 | Control (Path) 3 Parietal Ctx | 1.9 |
| Control (Path) 2 Temporal Ctx | 37.4 | Control (Path) 4 Parietal Ctx | 39.5 |

TABLE ACC

General_screening_panel_v1.4

| Tissue Name | Rel. Exp. (%) Ag3715, Run 218267374 | Tissue Name | Rel. Exp. (%) Ag3715, Run 218267374 |
|---|---|---|---|
| Adipose | 3.9 | Renal ca. TK-10 | 16.4 |
| Melanoma* Hs688(A).T | 1.9 | Bladder | 23.5 |
| Melanoma* Hs688(B).T | 2.5 | Gastric ca. (liver met.) NCI-N87 | 40.1 |

TABLE ACC-continued

General_screening_panel_v1.4

| Tissue Name | Rel. Exp. (%) Ag3715, Run 218267374 | Tissue Name | Rel. Exp. (%) Ag3715, Run 218267374 |
|---|---|---|---|
| Melanoma* M14 | 7.5 | Gastric ca. KATO III | 29.9 |
| Melanoma* LOXIMVI | 4.5 | Colon ca. SW-948 | 7.1 |
| Melanoma* SK-MEL-5 | 27.7 | Colon ca. SW480 | 19.6 |
| Squamous cell carcinoma SCC-4 | 8.5 | Colon ca.* (SW480 met) SW620 | 33.4 |
| Testis Pool | 11.0 | Colon ca. HT29 | 18.9 |
| Prostate ca.* (bone met) PC-3 | 11.3 | Colon ca. HCT-116 | 19.1 |
| Prostate Pool | 6.8 | Colon ca. CaCo-2 | 32.8 |
| Placenta | 6.4 | Colon cancer tissue | 7.3 |
| Uterus Pool | 0.9 | Colon ca. SW1116 | 3.2 |
| Ovarian ca. OVCAR-3 | 14.3 | Colon ca. Colo-205 | 2.0 |
| Ovarian ca. SK-OV-3 | 16.8 | Colon ca. SW-48 | 0.8 |
| Ovarian ca. OVCAR-4 | 7.2 | Colon Pool | 8.3 |
| Ovarian ca. OVCAR-5 | 100.0 | Small Intestine Pool | 6.5 |
| Ovarian ca. IGROV-1 | 2.3 | Stomach Pool | 6.2 |
| Ovarian ca. OVCAR-8 | 0.5 | Bone Marrow Pool | 7.3 |
| Ovary | 6.7 | Fetal Heart | 5.6 |
| Breast ca. MCF-7 | 10.5 | Heart Pool | 3.0 |
| Breast ca. MDA-MB-231 | 4.9 | Lymph Node Pool | 14.3 |
| Breast ca. BT 549 | 13.9 | Fetal Skeletal Muscle | 6.7 |
| Breast ca. T47D | 30.8 | Skeletal Muscle Pool | 4.3 |
| Breast ca. MDA-N | 3.9 | Spleen Pool | 10.7 |
| Breast Pool | 14.1 | Thymus Pool | 13.3 |
| Trachea | 13.5 | CNS cancer (glio/astro) U87-MG | 15.1 |
| Lung | 3.5 | CNS cancer (glio/astro) U-118-MG | 13.2 |
| Fetal Lung | 23.0 | CNS cancer (neuro; met) SK-N-AS | 4.2 |
| Lung ca. NCI-N417 | 2.1 | CNS cancer (astro) SF-539 | 2.8 |
| Lung ca. LX-1 | 38.7 | CNS cancer (astro) SNB-75 | 23.7 |
| Lung ca. NCI-H146 | 4.7 | CNS cancer (glio) SNB-19 | 2.0 |
| Lung ca. SHP-77 | 18.2 | CNS cancer (glio) SF-295 | 32.8 |
| Lung ca. A549 | 15.5 | Brain (Amygdala) Pool | 4.0 |
| Lung ca. NCI-H526 | 0.5 | Brain (cerebellum) | 22.8 |
| Lung ca. NCI-H23 | 41.8 | Brain (fetal) | 57.4 |
| Lung ca. NCI-H460 | 12.3 | Brain (Hippocampus) Pool | 8.7 |
| Lung ca. HOP-62 | 24.7 | Cerebral Cortex Pool | 2.1 |
| Lung ca. NCI-H522 | 16.3 | Brain (Substantia nigra) Pool | 5.9 |
| Liver | 0.5 | Brain (Thalamus) Pool | 8.4 |
| Fetal Liver | 8.5 | Brain (whole) | 6.7 |
| Liver ca. HepG2 | 5.8 | Spinal Cord Pool | 7.8 |
| Kidney Pool | 23.0 | Adrenal Gland | 13.0 |
| Fetal Kidney | 34.9 | Pituitary gland Pool | 5.7 |
| Renal ca. 786-0 | 9.5 | Salivary Gland | 4.9 |
| Renal ca. A498 | 1.4 | Thyroid (female) | 0.8 |
| Renal ca. ACHN | 14.0 | Pancreatic ca. CAPAN2 | 56.6 |
| Renal ca. UO-31 | 6.5 | Pancreas Pool | 17.8 |

TABLE ACD

Panel 4.1D

| Tissue Name | Rel. Exp. (%) Ag3715, Run 169992420 | Tissue Name | Rel. Exp. (%) Ag3715, Run 169992420 |
|---|---|---|---|
| Secondary Th1 act | 55.5 | HUVEC IL-1beta | 24.3 |
| Secondary Th2 act | 82.4 | HUVEC IFN gamma | 38.4 |
| Secondary Tr1 act | 68.3 | HUVEC TNF alpha + IFN gamma | 27.0 |
| Secondary Th1 rest | 40.9 | HUVEC TNF alpha + IL4 | 15.2 |
| Secondary Th2 rest | 52.1 | HUVEC IL-11 | 12.9 |
| Secondary Tr1 rest | 36.1 | Lung Microvascular EC none | 27.7 |
| Primary Th1 act | 81.2 | Lung Microvascular EC TNF alpha + IL-1beta | 28.5 |
| Primary Th2 act | 97.3 | Microvascular Dermal EC none | 28.1 |
| Primary Tr1 act | 60.3 | Microsvasular Dermal EC TNF alpha + IL-1beta | 21.3 |

TABLE ACD-continued

Panel 4.1D

| Tissue Name | Rel. Exp. (%) Ag3715, Run 169992420 | Tissue Name | Rel. Exp. (%) Ag3715, Run 169992420 |
|---|---|---|---|
| Primary Th1 rest | 75.3 | Bronchial epithelium TNF alpha + IL1beta | 23.5 |
| Primary Th2 rest | 59.9 | Small airway epithelium none | 16.8 |
| Primary Tr1 rest | 52.5 | Small airway epithelium TNF alpha + IL-1beta | 34.2 |
| CD45RA CD4 lymphocyte act | 43.8 | Coronery artery SMC rest | 9.6 |
| CD45RO CD4 lymphocyte act | 100.0 | Coronery artery SMC TNF alpha + IL-1beta | 7.9 |
| CD8 lymphocyte act | 54.3 | Astrocytes rest | 11.5 |
| Secondary CD8 lymphocyte rest | 69.3 | Astrocytes TNF alpha + IL-1beta | 6.8 |
| Secondary CD8 lymphocyte act | 25.5 | KU-812 (Basophil) rest | 27.7 |
| CD4 lymphocyte none | 27.9 | KU-812 (Basophil) PMA/ionomycin | 13.5 |
| 2ry Th1/Th2/Tr1_anti-CD95 CH11 | 61.1 | CCD1106 (Keratinocytes) none | 85.9 |
| LAK cells rest | 41.8 | CCD1106 (Keratinocytes) TNF alpha + IL-1beta | 50.3 |
| LAK cells IL-2 | 71.7 | Liver cirrhosis | 5.8 |
| LAK cells IL-2 + IL-12 | 45.7 | NCI-H292 none | 18.2 |
| LAK cells IL-2 + IFN gamma | 70.7 | NCI-H292 IL-4 | 53.2 |
| LAK cells IL-2 + IL-18 | 72.7 | NCI-H292 IL-9 | 40.9 |
| LAK cells PMA/ionomycin | 88.9 | NCI-H292 IL-13 | 25.0 |
| NK Cells IL-2 rest | 30.4 | NCI-H292 IFN gamma | 15.9 |
| Two Way MLR 3 day | 86.5 | HPAEC none | 13.4 |
| Two Way MLR 5 day | 53.6 | HPAEC TNF alpha + IL-1beta | 34.4 |
| Two Way MLR 7 day | 32.5 | Lung fibroblast none | 12.9 |
| PBMC rest | 39.8 | Lung fibroblast TNF alpha + IL-1beta | 12.4 |
| PBMC PWM | 32.8 | Lung fibroblast IL-4 | 9.2 |
| PBMC PHA-L | 47.3 | Lung fibroblast IL-9 | 18.7 |
| Ramos (B cell) none | 70.2 | Lung fibroblast IL-13 | 15.3 |
| Ramos (B cell) ionomycin | 55.5 | Lung fibroblast IFN gamma | 1.5 |
| B lymphocytes PWM | 41.8 | Dermal fibroblast CCD1070 rest | 15.9 |
| B lymphocytes CD40L and IL-4 | 48.3 | Dermal fibroblast CCD1070 TNF alpha | 67.8 |
| EOL-1 dbcAMP | 50.7 | Dermal fibroblast CCD1070 IL-1beta | 0.0 |
| EOL-1 dbcAMP PMA/ionomycin | 56.6 | Dermal fibroblast IFN gamma | 13.4 |
| Dendritic cells none | 29.9 | Dermal fibroblast IL-4 | 24.5 |
| Dendritic cells LPS | 6.7 | Dermal Fibroblasts rest | 11.1 |
| Dendritic cells anti-CD40 | 12.8 | Neutrophils TNFa + LPS | 11.9 |
| Monocytes rest | 15.0 | Neutrophils rest | 40.3 |
| Monocytes LPS | 75.8 | Colon | 20.3 |
| Macrophages rest | 17.3 | Lung | 8.4 |
| Macrophages LPS | 9.9 | Thymus | 84.1 |
| HUVEC none | 7.3 | Kidney | 56.6 |
| HUVEC starved | 29.3 | | |

CNS_neurodegeneration_v1.0 Summary: Ag3715 This panel does not show differential expression of the CG90760-01 gene in Alzheimer's disease. However, this expression profile confirms the presence of this gene in the brain, with highest expression in the temporal cortex of an Alzheimer's patient (CT=32.6). Please see Panel 1.4 for discussion of utility of this gene in the central nervous system.

General_screening_panel_v1.4 Summary: Ag3715 Expression of the CG90760-01 gene is widespread in this panel, with highest expression in an ovarian cancer cell line (CT=30.5). Thus, expression of this gene could be used to differentiate between this sample and other samples on this panel.

In addition, the widespread expression of this gene suggests a broader role for this gene product in cell survival and growth.

Among tissues with metabolic function, this gene is expressed at low levels in pituitary, adrenal gland, pancreas, fetal heart and liver and adult and fetal skeletal muscle. This expression suggests that this gene product may play a role in normal neuroendocrine and metabolic and that disregulated expression of this gene may contribute to neuroendocrine disorders or metabolic diseases, such as obesity and diabetes.

This gene is also expressed at low levels in the CNS, including the hippocampus, thalamus, substantia nigra, and cerebellum. Therefore, therapeutic modulation of the expression or function of this gene may be useful in the treatment of neurologic disorders, such as Alzheimer's disease, Parkinson's disease, schizophrenia, multiple sclerosis, stroke and epilepsy.

Panel 4.1D Summary: Ag3715 Results from one experiment with the CG90760-01 gene are not included. The amp plot indicates that there were experimental difficulties with this run.

AD. CG90770-01: 9530058B02RIK Protein

Expression of gene CG90770-01 was assessed using the primer-probe set ag3668, described in Table ADA. Results of the RTQ-PCR runs are shown in Table ADB.

TABLE ADA

Probe Name ag3668

| Primers | Sequences | Length | Start Position | SEQ ID NO: |
|---|---|---|---|---|
| Forward | 5'-cattgacttggacgagtggt-3' | 20 | 453 | 321 |
| Probe | TET-5'-gcacttcctggctagaatcaccagct-3'-TAMRA | 26 | 480 | 322 |
| Reverse | 5'-aggtagaccatagcagcgct-3' | 20 | 529 | 323 |

TABLE ADB

Panel 4.1D

| Tissue Name | Rel. Exp. (%) ag3668, Run 169990916 | Tissue Name | Rel. Exp. (%) ag3668, Run 169990916 |
|---|---|---|---|
| Secondary Th1 act | 16.5 | HUVEC IL-1beta | 1.7 |
| Secondary Th2 act | 3.6 | HUVEC IFN gamma | 0.3 |
| Secondary Tr1 act | 8.3 | HUVEC TNF alpha + IFN gamma | 0.0 |
| Secondary Th1 rest | 0.6 | HUVEC TNF alpha + IL4 | 0.0 |
| Secondary Th2 rest | 1.6 | HUVEC IL-11 | 1.3 |
| Secondary Tr1 rest | 0.7 | Lung Microvascular EC none | 0.0 |
| Primary Th1 act | 14.2 | Lung Microvascular EC TNF alpha + IL-1beta | 2.2 |
| Primary Th2 act | 9.5 | Microvascular Dermal EC none | 1.5 |
| Primary Tr1 act | 4.4 | Microsvascular Dermal EC TNF alpha + IL-1beta | 0.0 |
| Primary Th1 rest | 4.0 | Bronchial epithelium TNF alpha + IL1beta | 4.4 |
| Primary Th2 rest | 5.8 | Small airway epithelium none | 0.0 |
| Primary Tr1 rest | 15.7 | Small airway epithelium TNF alpha + IL-1beta | 0.0 |
| CD45RA CD4 lymphocyte act | 0.3 | Coronery artery SMC rest | 1.1 |
| CD45RO CD4 lymphocyte act | 8.9 | Coronery artery SMC TNF alpha + IL-1beta | 0.0 |
| CD8 lymphocyte act | 8.8 | Astrocytes rest | 0.0 |
| Secondary CD8 lymphocyte rest | 9.9 | Astrocytes TNF alpha + IL-1beta | 1.7 |
| Secondary CD8 lymphocyte act | 0.0 | KU-812 (Basophil) rest | 63.3 |
| CD4 lymphocyte none | 5.7 | KU-812 (Basophil) PMA/ionomycin | 31.4 |
| 2ry Th1/Th2/Tr1_anti-CD95 CH11 | 1.7 | CCD1106 (Keratinocytes) none | 0.0 |
| LAK cells rest | 11.9 | CCD1106 (Keratinocytes) TNF alpha + IL-1beta | 0.0 |
| LAK cells IL-2 | 11.4 | Liver cirrhosis | 1.1 |
| LAK cells IL-2 + IL-12 | 8.8 | NCI-H292 none | 4.3 |
| LAK cells IL-2 + IFN gamma | 4.9 | NCI-H292 IL-4 | 4.5 |
| LAK cells IL-2 + IL-18 | 4.3 | NCI-H292 IL-9 | 5.0 |
| LAK cells PMA/ionomycin | 0.0 | NCI-H292 IL-13 | 3.8 |
| NK Cells IL-2 rest | 3.8 | NCI-H292 IFN gamma | 9.1 |

TABLE ADB-continued

Panel 4.1D

| Tissue Name | Rel. Exp. (%) ag3668, Run 169990916 | Tissue Name | Rel. Exp. (%) ag3668, Run 169990916 |
|---|---|---|---|
| Two Way MLR 3 day | 3.6 | HPAEC none | 2.5 |
| Two Way MLR 5 day | 3.8 | HPAEC TNF alpha + IL-1beta | 0.0 |
| Two Way MLR 7 day | 5.3 | Lung fibroblast none | 0.0 |
| PBMC rest | 0.0 | Lung fibroblast TNF alpha + IL-1beta | 0.0 |
| PBMC PWM | 13.3 | Lung fibroblast IL-4 | 0.0 |
| PBMC PHA-L | 13.9 | Lung fibroblast IL-9 | 0.0 |
| Ramos (B cell) none | 100.0 | Lung fibroblast IL-13 | 0.0 |
| Ramos (B cell) ionomycin | 55.1 | Lung fibroblast IFN gamma | 0.0 |
| B lymphocytes PWM | 13.1 | Dermal fibroblast CCD1070 rest | 0.0 |
| B lymphocytes CD40L and IL-4 | 3.2 | Dermal fibroblast CCD1070 TNF alpha | 1.7 |
| EOL-1 dbcAMP | 19.9 | Dermal fibroblast CCD1070 IL-1beta | 0.0 |
| EOL-1 dbcAMP PMA/ionomycin | 5.2 | Dermal fibroblast IFN gamma | 0.0 |
| Dendritic cells none | 10.7 | Dermal fibroblast IL-4 | 0.0 |
| Dendritic cells LPS | 16.7 | Dermal Fibroblasts rest | 0.0 |
| Dendritic cells anti-CD40 | 1.1 | Neutrophils TNFa + LPS | 0.0 |
| Monocytes rest | 2.7 | Neutrophils rest | 0.0 |
| Monocytes LPS | 13.3 | Colon | 0.0 |
| Macrophages rest | 1.2 | Lung | 0.0 |
| Macrophages LPS | 32.5 | Thymus | 19.3 |
| HUVEC none | 0.0 | Kidney | 2.6 |
| HUVEC starved | 4.1 | | |

CNS_neurodegeneration_v1.0 Summary: Ag3668 Expression of the CG90770-01 gene is low/undetectable in all samples on this panel (CTs>35). (Data not shown.)

General_screening_panel_v1.5 Summary: Ag3668 Results from one experiment with the CG90770-01 gene are not included. The amp plot indicates that there were experimental difficulties with this run.

Panel 4.1D Summary: Ag3668 Highest expression of the CG90770-01 gene is seen in an untreated sample derived from the B cell line Ramos (CT=31.5). Lower but still significant levels of expression are seen in Ramos B cells stimulated with ionomycin. B cells represent a principle component of immunity and contribute to the immune response in a number of important functional roles, including antibody production. Production of antibodies against self-antigens is a major component in autoimmune disorders. Since B cells play an important role in autoimmunity, inflammatory processes and inflammatory cascades, therapeutic modulation of this gene product may reduce or eliminate the symptoms of patients suffering from asthma, allergies, chronic obstructive pulmonary disease, emphysema, Crohn's disease, ulcerative colitis, rheumatoid arthritis, psoriasis, osteoarthritis, systemic lupus erythematosus and other autoimmune disorders.

This transcript is also expressed at low but significant levels in induced in the basophil cell line KU-812. Basophils release histamines and other biological modifiers in response to allergens and play an important role in the pathology of asthma and hypersensitivity reactions. Therefore, therapeutics designed against the putative protein encoded by this gene may reduce or inhibit inflammation by blocking basophil function in these diseases.

AE. CG91002-01: 3Beta-Hydroxy-Delta5-Steroid Dehydrogenase

Expression of gene CG91002-01 was assessed using the primer-probe set Ag3721, described in Table AEA. Results of the RTQ-PCR runs are shown in Tables AEB and AEC.

TABLE AEA

Probe Name Ag3721

| Primers | Sequences | Length | Start Position | SEQ ID NO: |
|---|---|---|---|---|
| Forward | 5'-tagaaccgtggagtgggttt-3' | 20 | 1101 | 324 |
| Probe | TET-5'-accgtgaagtccaagactcagcgatt-3'-TAMRA | 26 | 1144 | 325 |
| Reverse | 5'-atacccacatgcacatctctgt-3' | 22 | 1178 | 326 |

TABLE AEB

CNS_neurodegeneration_v1.0

| Tissue Name | Rel. Exp. (%) Ag3721, Run 211295023 | Tissue Name | Rel. Exp. (%) Ag3721, Run 211295023 |
|---|---|---|---|
| AD 1 Hippo | 10.6 | Control (Path) 3 Temporal Ctx | 2.8 |
| AD 2 Hippo | 12.9 | Control (Path) 4 Temporal Ctx | 26.4 |

TABLE AEB-continued

CNS_neurodegeneration_v1.0

| Tissue Name | Rel. Exp. (%) Ag3721, Run 211295023 | Tissue Name | Rel. Exp. (%) Ag3721, Run 211295023 |
|---|---|---|---|
| AD 3 Hippo | 3.6 | AD 1 Occipital Ctx | 10.4 |
| AD 4 Hippo | 1.7 | AD 2 Occipital Ctx (Missing) | 0.0 |
| AD 5 Hippo | 100.0 | AD 3 Occipital Ctx | 6.7 |
| AD 6 Hippo | 10.7 | AD 4 Occipital Ctx | 7.8 |
| Control 2 Hippo | 2.2 | AD 5 Occipital Ctx | 18.8 |
| Control 4 Hippo | 1.4 | AD 6 Occipital Ctx | 10.3 |
| Control (Path) 3 Hippo | 1.9 | Control 1 Occipital Ctx | 2.2 |
| AD 1 Temporal Ctx | 6.7 | Control 2 Occipital Ctx | 31.9 |
| AD 2 Temporal Ctx | 20.6 | Control 3 Occipital Ctx | 13.2 |
| AD 3 Temporal Ctx | 4.2 | Control 4 Occipital Ctx | 3.3 |
| AD 4 Temporal Ctx | 9.5 | Control (Path) 1 Occipital Ctx | 50.3 |
| AD 5 Inf Temporal Ctx | 79.6 | Control (Path) 2 Occipital Ctx | 8.4 |
| AD 5 Sup Temporal Ctx | 23.8 | Control (Path) 3 Occipital Ctx | 2.9 |
| AD 6 Inf Temporal Ctx | 28.1 | Control (Path) 4 Occipital Ctx | 8.6 |
| AD 6 Sup Temporal Ctx | 26.8 | Control 1 Parietal Ctx | 2.5 |
| Control 1 Temporal Ctx | 2.2 | Control 2 Parietal Ctx | 33.9 |
| Control 2 Temporal Ctx | 11.5 | Control 3 Parietal Ctx | 16.0 |
| Control 3 Temporal Ctx | 8.7 | Control (Path) 1 Parietal Ctx | 26.2 |
| Control 3 Temporal Ctx | 6.3 | Control (Path) 2 Parietal Ctx | 17.2 |
| Control (Path) 1 Temporal Ctx | 34.9 | Control (Path) 3 Parietal Ctx | 1.2 |
| Control (Path) 2 Temporal Ctx | 33.9 | Control (Path) 4 Parietal Ctx | 30.4 |

TABLE AEC

Panel 4.1D

| Tissue Name | Rel. Exp. (%) Ag3721, Run 169993119 | Tissue Name | Rel. Exp. (%) Ag3721, Run 169993119 |
|---|---|---|---|
| Secondary Th1 act | 0.0 | HUVEC IL-1beta | 17.4 |
| Secondary Th2 act | 0.0 | HUVEC IFN gamma | 19.1 |
| Secondary Tr1 act | 0.0 | HUVEC TNF alpha + IFN gamma | 16.5 |
| Secondary Th1 rest | 0.8 | HUVEC TNF alpha + IL4 | 26.2 |
| Secondary Th2 rest | 0.0 | HUVEC IL-11 | 10.4 |
| Secondary Tr1 rest | 0.7 | Lung Microvascular EC none | 32.3 |
| Primary Th1 act | 0.0 | Lung Microvascular EC TNF alpha + IL-1beta | 39.0 |
| Primary Th2 act | 0.0 | Microvascular Dermal EC none | 17.9 |
| Primary Tr1 act | 0.5 | Microsvascular Dermal EC TNF alpha + IL-1beta | 13.4 |
| Primary Th1 rest | 0.0 | Bronchial epithelium TNF alpha + IL1beta | 21.8 |
| Primary Th2 rest | 0.0 | Small airway epithelium none | 2.8 |
| Primary Tr1 rest | 0.0 | Small airway epithelium TNF alpha + IL-1beta | 16.8 |
| CD45RA CD4 lymphocyte act | 5.4 | Coronery artery SMC rest | 6.6 |
| CD45RO CD4 lymphocyte act | 0.0 | Coronery artery SMC TNF alpha + IL-1beta | 7.9 |
| CD8 lymphocyte act | 0.0 | Astrocytes rest | 0.4 |
| Secondary CD8 lymphocyte rest | 1.0 | Astrocytes TNF alpha + IL-1beta | 1.7 |
| Secondary CD8 lymphocyte act | 0.6 | KU-812 (Basophil) rest | 0.0 |
| CD4 lymphocyte none | 0.0 | KU-812 (Basophil) PMA/ionomycin | 0.4 |
| 2ry Th1/Th2/Tr1_anti-CD95 CH11 | 0.5 | CCD1106 (Keratinocytes) none | 6.4 |
| LAK cells rest | 60.7 | CCD1106 (Keratinocytes) TNF alpha + IL-1beta | 8.3 |

TABLE AEC-continued

Panel 4.1D

| Tissue Name | Rel. Exp. (%) Ag3721, Run 169993119 | Tissue Name | Rel. Exp. (%) Ag3721, Run 169993119 |
|---|---|---|---|
| LAK cells IL-2 | 0.0 | Liver cirrhosis | 0.4 |
| LAK cells IL-2 + IL-12 | 1.1 | NCI-H292 none | 0.8 |
| LAK cells IL-2 + IFN gamma | 0.8 | NCI-H292 IL-4 | 20.2 |
| LAK cells IL-2 + IL-18 | 0.0 | NCI-H292 IL-9 | 3.9 |
| LAK cells PMA/ionomycin | 23.8 | NCI-H292 IL-13 | 20.3 |
| NK Cells IL-2 rest | 0.0 | NCI-H292 IFN gamma | 3.8 |
| Two Way MLR 3 day | 23.2 | HPAEC none | 6.0 |
| Two Way MLR 5 day | 9.8 | HPAEC TNF alpha + IL-1beta | 16.8 |
| Two Way MLR 7 day | 1.4 | Lung fibroblast none | 6.9 |
| PBMC rest | 0.3 | Lung fibroblast TNF alpha + IL-1beta | 11.0 |
| PBMC PWM | 2.7 | Lung fibroblast IL-4 | 10.9 |
| PBMC PHA-L | 3.5 | Lung fibroblast IL-9 | 5.8 |
| Ramos (B cell) none | 0.0 | Lung fibroblast IL-13 | 8.7 |
| Ramos (B cell) ionomycin | 0.0 | Lung fibroblast IFN gamma | 6.0 |
| B lymphocytes PWM | 0.0 | Dermal fibroblast CCD1070 rest | 1.8 |
| B lymphocytes CD40L and IL-4 | 0.0 | Dermal fibroblast CCD1070 TNF alpha | 13.9 |
| EOL-1 dbcAMP | 0.8 | Dermal fibroblast CCD1070 IL-1beta | 8.6 |
| EOL-1 dbcAMP PMA/ionomycin | 63.7 | Dermal fibroblast IFN gamma | 0.5 |
| Dendritic cells none | 66.9 | Dermal fibroblast IL-4 | 2.4 |
| Dendritic cells LPS | 42.9 | Dermal Fibroblasts rest | 0.0 |
| Dendritic cells anti-CD40 | 91.4 | Neutrophils TNFa + LPS | 2.4 |
| Monocytes rest | 18.4 | Neutrophils rest | 1.1 |
| Monocytes LPS | 100.0 | Colon | 1.6 |
| Macrophages rest | 64.6 | Lung | 10.3 |
| Macrophages LPS | 11.7 | Thymus | 1.0 |
| HUVEC none | 8.5 | Kidney | 62.9 |
| HUVEC starved | 11.3 | | |

CNS_neurodegeneration_v1.0 Summary: Ag3721 This panel does not show differential expression of the CG91002-01 gene in Alzheimer's disease. However, this expression profile confirms the presence of this gene in the brain, with highest expression in the hippocampus of an Alzheimer's patient (CT=29.2). This gene encodes a homolog of a steroid dehydrogenase, an enzyme that is known to function in the processing of hormones. Brain hormone regulation mediates numerous clinically significant conditions, including psychiatric disorders such as anxiety, overeating and memory disorders. Therefore, agents that modulate the activity of this gene product have potential utility in the treatment of these disorders. In addition, steroid treatment is used in a number of clinical conditions including Alzheimer's disease (estrogen), menopause associated symptoms (estrogen), multiple sclerosis (glucocorticoids), and spinal cord injury (methylprednisolone). Treatment with an antagonist of this gene product, or reduction of the levels of this gene product could slow steroid degradation and lower the necessary amount given for therapeutic effect, thus reducing peripheral side effects (Biswas M G, Russell D W. Expression cloning and characterization of oxidative 17beta- and 3alpha-hydroxysteroid dehydrogenases from rat and human prostate. J Biol Chem 1997 Jun. 20;272(25): 15959–66; Matsumoto T, Tamaki T, Kawakami M, Yoshida M, Ando M, Yamada H. Early complications of high-dose methylprednisolone sodium succinate treatment in the follow-up of acute cervical spinal cord injury. Spine Feb. 15, 2001;26(4):426–30; Holinka C F. Design and conduct of clinical trials in hormone replacement therapy. Ann NY Acad Sci 2001 September;943:89–108; Burkman R T, Collins J A, Greene R A. Current perspectives on benefits and risks of hormone replacement therapy. Am J Obstet Gynecol 2001 August; 185(2 Suppl):S13–23; Gaillard P J, van Der Meide P H, de Boer A G, Breimer D D. Glucocorticoid and type 1 interferon interactions at the blood-brain barrier: relevance for drug therapies for multiple sclerosis. Neuroreport 2001 Jul. 20; 12(10):2189–93; Penning T M, Burczynski M E, Jez J M, Hung C F, Lin H K, Ma H, Moore M, Palackal N, Ratnam K. Human 3alpha-hydroxysteroid dehydrogenase isoforms (AKR1C1-AKR1C4) of the aldo-keto reductase superfamily: functional plasticity and tissue distribution reveals roles in the inactivation and formation of male and female sex hormones. Biochem J 2000 Oct. 1;351(Pt 1):67–77).

General_screening_panel_v1.4 Summary: Ag3721 Results from one experiment with the CG91002-01 gene are not included. The amp plot indicates that there were experimental difficulties with this run.

Panel 4.1D Summary: Ag3721 Highest expression of the CG91002-01 gene is seen in LPS treated monocytes. Expression in monocytes, macrophages, and dendritic cells suggests that small molecule drugs that antagonize the function of this gene product may reduce or eliminate the symptoms of autoimmune and inflammatory diseases, such as, but not limited to, Crohn's disease, ulcerative colitis, multiple sclerosis, chronic obstructive pulmonary disease, asthma, emphysema, rheumatoid arthritis, lupus erythematosus, or psoriasis.

AF. CG91002-02: 3Beta-Hydroxy-Delta5-Steroid Dehydrogenase

Expression of gene CG91002-02 was assessed using the primer-probe set Ag3722, described in Table AFA. Results of the RTQ-PCR runs are shown in Tables AFB, AFC and AFD.

TABLE AFA

Probe Name Ag3722

| Primers | Sequences | Length | Start Position | SEQ ID NO: |
|---|---|---|---|---|
| Forward | 5'-tgcatgtgggtattgttagga-3' | 21 | 1172 | 327 |
| Probe | TET-5'-aagctccatcctcctggcttcataca-3'-TAMRA | 26 | 1202 | 328 |
| Reverse | 5'-ctggacttttgcccttgtc-3' | 19 | 1231 | 329 |

TABLE AFB

CNS_neurodegeneration_v1.0

| Tissue Name | Rel. Exp. (%) Ag3722, Run 211295024 | Tissue Name | Rel. Exp. (%) Ag3722, Run 211295024 |
|---|---|---|---|
| AD 1 Hippo | 7.4 | Control (Path) 3 Temporal Ctx | 7.4 |
| AD 2 Hippo | 14.7 | Control (Path) 4 Temporal Ctx | 35.4 |
| AD 3 Hippo | 8.2 | AD 1 Occipital Ctx | 29.7 |
| AD 4 Hippo | 6.3 | AD 2 Occipital Ctx (Missing) | 0.0 |
| AD 5 hippo | 100.0 | AD 3 Occipital Ctx | 9.8 |
| AD 6 Hippo | 13.7 | AD 4 Occipital Ctx | 26.1 |
| Control 2 Hippo | 6.5 | AD 5 Occipital Ctx | 12.9 |
| Control 4 Hippo | 3.1 | AD 6 Occipital Ctx | 21.2 |
| Control (Path) 3 Hippo | 3.9 | Control 1 Occipital Ctx | 3.6 |
| AD 1 Temporal Ctx | 16.7 | Control 2 Occipital Ctx | 24.7 |
| AD 2 Temporal Ctx | 34.2 | Control 3 Occipital Ctx | 31.6 |
| AD 3 Temporal Ctx | 10.7 | Control 4 Occipital Ctx | 6.3 |
| AD 4 Temporal Ctx | 29.7 | Control (Path) 1 Occipital Ctx | 48.6 |
| AD 5 Inf Temporal Ctx | 63.3 | Control (Path) 2 Occipital Ctx | 13.9 |
| AD 5 Sup Temporal Ctx | 22.5 | Control (Path) 3 Occipital Ctx | 1.5 |
| AD 6 Inf Temporal Ctx | 41.5 | Control (Path) 4 Occipital Ctx | 22.5 |
| AD 6 Sup Temporal Ctx | 53.6 | Control 1 Parietal Ctx | 12.4 |
| Control 1 Temporal Ctx | 7.4 | Control 2 Parietal Ctx | 51.1 |
| Control 2 Temporal Ctx | 12.2 | Control 3 Parietal Ctx | 17.6 |
| Control 3 Temporal Ctx | 22.4 | Control (Path) 1 Parietal Ctx | 56.3 |
| Control 4 Temporal Ctx | 13.5 | Control (Path) 2 Parietal Ctx | 28.3 |
| Control (Path) 1 Temporal Ctx | 30.8 | Control (Path) 3 Parietal Ctx | 4.6 |
| Control (Path) 2 Temporal Ctx | 49.3 | Control (Path) 4 Parietal Ctx | 52.9 |

TABLE AFC

General_screening_panel_v1.4

| Tissue Name | Rel. Exp. (%) Ag3722, Run 218296850 | Tissue Name | Rel. Exp. (%) Ag3722, Run 218296850 |
|---|---|---|---|
| Adipose | 47.6 | Renal ca. TK-10 | 35.1 |
| Melanoma* Hs688(A).T | 1.5 | Bladder | 26.8 |
| Melanoma* Hs688(B).T | 6.5 | Gastric ca. (liver met.) NCI-N87 | 50.3 |
| Melanoma* M14 | 25.7 | Gastric ca. KATO III | 0.0 |
| Melanoma* LOXIMVI | 0.0 | Colon ca. SW-948 | 0.0 |
| Melanoma* SK-MEL-5 | 73.7 | Colon ca. SW480 | 7.4 |
| Squamous cell carcinoma SCC-4 | 0.0 | Colon ca.* (SW480 met) SW620 | 13.3 |
| Testis Pool | 6.8 | Colon ca. HT29 | 0.0 |

TABLE AFC-continued

General_screening_panel_v1.4

| Tissue Name | Rel. Exp. (%) Ag3722, Run 218296850 | Tissue Name | Rel. Exp. (%) Ag3722, Run 218296850 |
|---|---|---|---|
| Prostate ca.* (bone met) PC-3 | 1.5 | Colon ca. HCT-116 | 1.8 |
| Prostate Pool | 22.4 | Colon ca. CaCo-2 | 5.4 |
| Placenta | 78.5 | Colon cancer tissue | 9.3 |
| Uterus Pool | 4.4 | Colon ca. SW1116 | 0.0 |
| Ovarian ca. OVCAR-3 | 10.7 | Colon ca. Colo-205 | 1.7 |
| Ovarian ca. SK-OV-3 | 0.0 | Colon ca. SW-48 | 0.0 |
| Ovarian ca. OVCAR-4 | 3.6 | Colon Pool | 19.1 |
| Ovarian ca. OVCAR-5 | 3.3 | Small Intestine Pool | 36.3 |
| Ovarian ca. IGROV-1 | 12.4 | Stomach Pool | 31.6 |
| Ovarian ca. OVCAR-8 | 2.7 | Bone Marrow Pool | 9.3 |
| Ovary | 95.3 | Fetal Heart | 63.3 |
| Breast ca. MCF-7 | 0.0 | Heart Pool | 14.9 |
| Breast ca. MDA-MB-231 | 3.7 | Lymph Node Pool | 23.0 |
| Breast ca. BT 549 | 4.8 | Fetal Skeletal Muscle | 14.4 |
| Breast ca. T47D | 3.2 | Skeletal Muscle Pool | 22.7 |
| Breast ca. MDA-N | 24.5 | Spleen Pool | 13.4 |
| Breast Pool | 33.7 | Thymus Pool | 26.4 |
| Trachea | 2.6 | CNS cancer (glio/astro) U87-MG | 10.4 |
| Lung | 17.1 | CNS cancer (glio/astro) U-118-MG | 3.1 |
| Fetal Lung | 92.7 | CNS cancer (neuro; met) SK-N-AS | 0.0 |
| Lung ca. NCI-N417 | 0.0 | CNS cancer (astro) SF-539 | 0.0 |
| Lung ca. LX-1 | 43.5 | CNS cancer (astro) SNB-75 | 26.2 |
| Lung ca. NCI-H146 | 0.0 | CNS cancer (glio) SNB-19 | 7.7 |
| Lung ca. SHP-77 | 44.4 | CNS cancer (glio) SF-295 | 16.3 |
| Lung ca. A549 | 0.0 | Brain (Amygdala) Pool | 31.4 |
| Lung ca. NCI-H526 | 0.0 | Brain (cerebellum) | 16.0 |
| Lung ca. NCI-H23 | 4.3 | Brain (fetal) | 51.4 |
| Lung ca. NCI-H460 | 0.0 | Brain (Hippocampus) Pool | 37.1 |
| Lung ca. HOP-62 | 6.6 | Cerebral Cortex Pool | 99.3 |
| Lung ca. NCI-H522 | 0.0 | Brain (Substantia nigra) Pool | 99.3 |
| Liver | 1.6 | Brain (Thalamus) Pool | 76.8 |
| Fetal Liver | 12.6 | Brain (whole) | 100.0 |
| Liver ca. HepG2 | 0.0 | Spinal Cord Pool | 29.5 |
| Kidney Pool | 83.5 | Adrenal Gland | 17.9 |
| Fetal Kidney | 99.3 | Pituitary gland Pool | 11.3 |
| Renal ca. 786-0 | 0.0 | Salivary Gland | 4.2 |
| Renal ca. A498 | 6.7 | Thyroid (female) | 2.3 |
| Renal ca. ACHN | 0.0 | Pancreatic ca. CAPAN2 | 1.3 |
| Renal ca. UO-31 | 0.0 | Pancreas Pool | 13.4 |

TABLE AFD

Panel 4.1D

| Tissue Name | Rel. Exp. (%) Ag3722, Run 169993268 | Tissue Name | Rel. Exp (%) Ag3722, Run 169993268 |
|---|---|---|---|
| Secondary Th1 act | 0.0 | HUVEC IL-1beta | 2.9 |
| Secondary Th2 act | 0.0 | HUVEC IFN gamma | 4.6 |
| Secondary Tr1 act | 0.0 | HUVEC TNF alpha + IFN gamma | 6.3 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 42.6 |
| Primary Th1 act | 0.0 | Lung Microvascular EC TNF alpha + IL-1beta | 1.0 |
| Primary Th2 act | 0.0 | Microvascular Dermal EC none | 0.0 |
| Primary Tr1 act | 0.0 | Microvsasular Dermal EC TNF alpha + IL-1beta | 6.4 |
| Primary Th1 rest | 0.0 | Bronchial epithelium TNF alpha + IL1beta | 6.8 |
| Primary Th2 rest | 0.0 | Small airway epithelium none | 0.0 |
| Primary Tr1 rest | 0.0 | Small airway epithelium TNF alpha + IL-1beta | 9.5 |
| CD45RA CD4 lymphocyte act | 0.0 | Coronery artery SMC rest | 1.5 |

TABLE AFD-continued

Panel 4.1D

| Tissue Name | Rel. Exp. (%) Ag3722, Run 169993268 | Tissue Name | Rel. Exp (%) Ag3722, Run 169993268 |
| --- | --- | --- | --- |
| CD45RO CD4 lymphocyte act | 0.0 | Coronery artery SMC TNF alpha + IL-1beta | 0.0 |
| CD8 lymphocyte act | 0.0 | Astrocytes rest | 5.4 |
| Secondary CD8 lymphocyte rest | 0.0 | Astrocytes TNF alpha + IL-1beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 3.2 |
| LAK cells rest | 71.2 | CCD1106 (Keratinocytes) TNF alpha + IL-1beta | 4.1 |
| LAK cells IL-2 | 0.0 | Liver cirrhosis | 1.0 |
| LAK cells IL-2 + IL-12 | 0.0 | NCI-H292 none | 0.0 |
| LAK cells IL-2 + IFN gamma | 1.7 | NCI-H292 IL-4 | 31.4 |
| LAK cells IL-2 + IL-18 | 0.0 | NCI-H292 IL-9 | 3.0 |
| LAK cells PMA/ionomycin | 17.9 | NCI-H292 IL-13 | 16.8 |
| NK Cells IL-2 rest | 0.0 | NCI-H292 IFN gamma | 1.2 |
| Two Way MLR 3 day | 20.0 | HPAEC none | 0.0 |
| Two Way MLR 5 day | 3.6 | HPAEC TNF alpha + IL-1beta | 7.1 |
| Two Way MLR 7 day | 0.0 | Lung fibroblast none | 0.0 |
| PBMC rest | 1.7 | Lung fibroblast TNF alpha + IL-1beta | 4.1 |
| PBMC PWM | 0.0 | Lung fibroblast IL-4 | 0.0 |
| PBMC PHA-L | 0.0 | Lung fibroblast IL-9 | 0.9 |
| Ramos (B cell) none | 0.0 | Lung fibroblast IL-13 | 0.0 |
| Ramos (B cell) ionomycin | 0.0 | Lung fibroblast IFN gamma | 1.8 |
| B lymphocytes PWM | 0.0 | Dermal fibroblast CCD1070 rest | 0.0 |
| B lymphocytes CD40L and IL-4 | 0.0 | Dermal fibroblast CCD1070 TNF alpha | 9.5 |
| EOL-1 dbcAMP | 0.0 | Dermal fibroblast CCD1070 IL-1beta | 3.2 |
| EOL-1 dbcAMP PMA/ionomycin | 24.1 | Dermal fibroblast IFN gamma | 0.0 |
| Dendritic cells none | 72.2 | Dermal fibroblast IL-4 | 0.9 |
| Dendritic cells LPS | 64.6 | Dermal Fibroblasts rest | 0.0 |
| Dendritic cells anti-CD40 | 100.0 | Neutrophils TNFa + LPS | 0.0 |
| Monocytes rest | 2.1 | Neutrophils rest | 0.0 |
| Monocytes LPS | 84.7 | Colon | 0.0 |
| Macrophages rest | 66.9 | Lung | 6.7 |
| Macrophages LPS | 2.9 | Thymus | 0.0 |
| HUVEC none | 0.9 | Kidney | 84.1 |
| HUVEC starved | 0.0 | | |

CNS_neurodegeneration_v1.0 Summary: Ag3722 This panel does not show differential expression of the CG91002-02 gene in Alzheimer's disease. However, this expression profile confirms the presence of this gene in the brain, with highest expression in the hippocampus of an Alzheimer's patient (CT=29.4). This gene encodes a homolog of a steroid dehydrogenase, an enzyme that is known to function in the processing of hormones. Brain hormone regulation mediates numerous clinically significant conditions, including psychiatric disorders such as anxiety, overeating and memory disorders. Therefore, agents that modulate the activity of this gene product have potential utility in the treatment of these disorders. In addition, steroid treatment is used in a number of clinical conditions including Alzheimer's disease (estrogen), menopause associated symptoms (estrogen), multiple sclerosis (glucocorticoids), and spinal cord injury (methylprednisolone). Treatment with an antagonist of this gene product, or reduction of the levels of this gene product could slow steroid degredation and lower the necessary amount given for therapeutic effect, thus reducing peripheral side effects (Biswas M G, Russell D W. Expression cloning and characterization of oxidative 17beta- and 3alpha-hydroxysteroid dehydrogenases from rat and human prostate. J Biol Chem 1997 Jun. 20;272(25):15959–66; Matsumoto T, Tamaki T, Kawakami M, Yoshida M, Ando M, Yamada H. Early complications of high-dose methylprednisolone sodium succinate treatment in the follow-up of acute cervical spinal cord injury. Spine 2001 Feb. 15;26(4):426–30; Holinka C F. Design and conduct of clinical trials in hormone replacement therapy. Ann NY Acad Sci 2001 September;943:89–108; Burkman R T, Collins J A, Greene R A. Current perspectives on benefits and risks of hormone replacement therapy. Am J Obstet Gynecol 2001 August;185(2 Suppl):S13–23; Gaillard P J, van Der Meide P H, de Boer A G, Breimer D D. Glucocorticoid and type 1 interferon interactions at the blood-brain barrier: relevance for drug therapies for multiple sclerosis. Neuroreport 2001 Jul. 20;12(10):2189–93; Penning T M, Burczynski M E, Jez J M, Hung C F, Lin H K, Ma H, Moore M, Palackal N, Ratnam K. Human 3alpha-hydroxysteroid dehydrogenase isoforms (AKR1C1-AKR1C4) of the aldo-keto reductase superfamily: functional plasticity and tissue distribution reveals roles in the inactivation and formation of male and female sex hormones. Biochem J 2000 Oct. 1;351(Pt 1):67–77).

General_screening_panel_v1.4 Summary: Ag3722 Highest expression of the CG91002-02 gene is seen in the brain (CT=31.6). Prominent expression is seen at low but significant levels throughout the CNS. Please see CNS_neurodegeneration_v1.0 for discussion of utility of this gene in the central nervous system.

Among tissues with metabolic function, this gene is expressed at moderate to low levels in adipose, adrenal gland, pancreas, thyroid, fetal liver and adult and fetal skeletal muscle, and heart. This widespread expression among these tissues suggests that this gene product may play a role in normal neuroendocrine and metabolic and that disregulated expression of this gene may contribute to neuroendocrine disorders or metabolic diseases, such as obesity and diabetes.

Low but significant levels of expression are also seen in lung cancer and melanoma cell lines and may suggest involvement of this gene product in those cancers.

Panel 4.1D Summary: Ag3722 Highest expression of the CG91002-02 gene is seen in anti CD40 dendritic cells (CT=33.1). Expression in monocytes, macrophages, and dendritic cells suggests that small molecule drugs that antagonize the function of this gene product may reduce or eliminate the symptoms of autoimmune and inflammatory diseases, such as, but not limited to, Crohn's disease, ulcerative colitis, multiple sclerosis, chronic obstructive pulmonary disease, asthma, emphysema, rheumatoid arthritis, lupus erythematosus, or psoriasis.

AG. CG91298-01: Phosphatidylglycerophosphate Synthase

Expression of gene CG91298-01 was assessed using the primer-probe set Ag3727, described in Table AGA. Results of the RTQ-PCR runs are shown in Tables AGB and AGC.

TABLE AGA

Probe Name Ag3727

| Primers | Sequences | Length | Start Position | SEQ ID NO: |
|---|---|---|---|---|
| Forward | 5'-acctggatttatccgctgatt-3' | 21 | 904 | 330 |
| Probe | TET-5'-aagcccttcgagattcaaatcgatga-3'-TAMRA | 26 | 931 | 331 |
| Reverse | 5'-agtcaacagggtctcagtgaca-3' | 22 | 960 | 332 |

TABLE AGB

CNS_neurodegeneration_v1.0

| Tissue Name | Rel. Exp. (%) Ag3727, Run 212143355 | Tissue Name | Rel. Exp. (%) Ag3727, Run 212143355 |
|---|---|---|---|
| AD 1 Hippo | 18.8 | Control (Path) 3 Temporal Ctx | 5.7 |
| AD 2 Hippo | 19.3 | Control (Path) 4 Temporal Ctx | 20.4 |
| AD 3 Hippo | 10.7 | AD 1 Occipital Ctx | 27.5 |
| AD 4 Hippo | 9.5 | AD 2 Occipital Ctx (Missing) | 0.0 |
| AD 5 hippo | 100.0 | AD 3 Occipital Ctx | 12.1 |
| AD 6 Hippo | 62.4 | AD 4 Occipital Ctx | 15.9 |
| Control 2 Hippo | 40.9 | AD 5 Occipital Ctx | 20.0 |
| Control 4 Hippo | 10.2 | AD 6 Occipital Ctx | 61.6 |
| Control (Path) 3 Hippo | 6.9 | Control 1 Occipital Ctx | 5.3 |
| AD 1 Temporal Ctx | 45.7 | Control 2 Occipital Ctx | 63.3 |
| AD 2 Temporal Ctx | 23.5 | Control 3 Occipital Ctx | 20.4 |
| AD 3 Temporal Ctx | 9.7 | Control 4 Occipital Ctx | 7.7 |
| AD 4 Temporal Ctx | 20.4 | Control (Path) 1 Occipital Ctx | 61.6 |
| AD 5 Inf Temporal Ctx | 84.1 | Control (Path) 2 Occipital Ctx | 11.6 |
| AD 5 SupTemporal Ctx | 53.6 | Control (Path) 3 Occipital Ctx | 5.9 |
| AD 6 Inf Temporal Ctx | 71.7 | Control (Path) 4 Occipital Ctx | 17.2 |
| AD 6 Sup Temporal Ctx | 78.5 | Control 1 Parietal Ctx | 10.6 |
| Control 1 Temporal Ctx | 5.8 | Control 2 Parietal Ctx | 89.5 |
| Control 2 Temporal Ctx | 33.4 | Control 3 Parietal Ctx | 19.3 |
| Control 3 Temporal Ctx | 34.2 | Control (Path) 1 Parietal Ctx | 50.0 |
| Control 4 Temporal Ctx | 8.2 | Control (Path) 2 Parietal Ctx | 16.2 |
| Control (Path) 1 Temporal Ctx | 38.4 | Control (Path) 3 Parietal Ctx | 5.4 |
| Control (Path) 2 Temporal Ctx | 34.9 | Control (Path) 4 Parietal Ctx | 48.0 |

TABLE AGC

Panel 4.1D

| Tissue Name | Rel. Exp. (%) Ag3727, Run 170047715 | Rel. Exp. (%) Ag3727, Run 170128711 | Tissue Name | Rel. Exp. (%) Ag3727, Run 170047715 | Rel. Exp. (%) Ag3727, Run 170128711 |
|---|---|---|---|---|---|
| Secondary Th1 act | 29.1 | 0.3 | HUVEC IL-1beta | 9.2 | 13.9 |
| Secondary Th2 act | 34.4 | 100.0 | HUVEC IFN gamma | 19.6 | 11.5 |
| Secondary Tr1 act | 33.7 | 5.4 | HUVEC TNF alpha + IFN gamma | 12.8 | 6.9 |
| Secondary Th1 rest | 14.5 | 14.2 | HUVEC TNF alpha + IL4 | 13.5 | 5.1 |
| Secondary Th2 rest | 28.7 | 6.6 | HUVEC IL-11 | 9.5 | 6.7 |
| Secondary Tr1 rest | 15.5 | 2.5 | Lung Microvascular EC none | 19.1 | 7.6 |
| Primary Th1 act | 18.9 | 6.0 | Lung Microvascular EC TNF alpha + IL-1beta | 16.6 | 48.6 |
| Primary Th2 act | 25.5 | 8.5 | Microvascular Dermal EC none | 13.2 | 21.9 |
| Primary Tr1 act | 17.6 | 20.2 | Microsvascular Dermal EC TNF alpha + IL-1beta | 12.8 | 9.6 |
| Primary Th1 rest | 20.4 | 5.8 | Bronchial epithelium TNF alpha + IL1beta | 11.1 | 9.3 |
| Primary Th2 rest | 21.6 | 11.4 | Small airway epithelium none | 6.6 | 9.6 |
| Primary Tr1 rest | 27.5 | 6.2 | Small airway epithelium TNF alpha + IL-1beta | 8.3 | 12.9 |
| CD45RA CD4 lymphocyte act | 20.6 | 12.6 | Coronery artery SMC rest | 7.9 | 10.7 |
| CD45RO CD4 lymphocyte act | 27.4 | 6.9 | Coronery artery SMC TNF alpha + IL-1beta | 6.4 | 22.4 |
| CD8 lymphocyte act | 20.9 | 6.3 | Astrocytes rest | 5.1 | 8.8 |
| Secondary CD8 lymphocyte rest | 32.3 | 5.4 | Astrocytes TNF alpha + IL-1beta | 4.4 | 8.5 |
| Secondary CD8 lymphocyte act | 16.4 | 6.9 | KU-812 (Basophil) rest | 21.6 | 9.6 |
| CD4 lymphocyte none | 8.9 | 6.0 | KU-812 (Basophil) PMA/ionomycin | 26.6 | 12.7 |
| 2ry Th1/Th2/Tr1_anti-CD95 CH11 | 18.9 | 7.0 | CCD1106 (Keratinocytes) none | 14.8 | 14.0 |
| LAK cells rest | 17.1 | 6.4 | CCD1106 (Keratinocytes) TNF alpha + IL-1beta | 12.6 | 5.0 |
| LAK cells IL-2 | 20.6 | 11.4 | Liver cirrhosis | 6.3 | 7.2 |
| LAK cells IL-2 + IL-12 | 25.5 | 8.7 | NCI-H292 none | 8.6 | 15.3 |
| LAK cells IL-2 + IFN gamma | 23.7 | 8.7 | NCI-H292 IL-4 | 15.5 | 10.7 |
| LAK cells IL-2 + IL-18 | 27.9 | 7.2 | NCI-H292 IL-9 | 18.7 | 19.5 |
| LAK cells PMA/ionomycin | 33.7 | 9.2 | NCI-H292 IL-13 | 13.0 | 12.2 |
| NK Cells IL-2 rest | 23.2 | 6.7 | NCI-H292 IFN gamma | 13.4 | 11.5 |
| Two Way MLR 3 day | 27.2 | 4.3 | HPAEC none | 12.9 | 11.7 |
| Two Way MLR 5 day | 16.8 | 31.0 | HPAEC TNF alpha + IL-1beta | 19.3 | 12.6 |
| Two Way MLR 7 day | 15.4 | 5.0 | Lung fibroblast none | 9.3 | 9.1 |
| PBMC rest | 11.3 | 7.5 | Lung fibroblast TNF alpha + IL-1beta | 12.3 | 11.8 |
| PBMC PWM | 30.8 | 10.3 | Lung fibroblast IL-4 | 9.9 | 4.3 |
| PBMC PHA-L | 27.5 | 11.6 | Lung fibroblast IL-9 | 9.6 | 6.5 |
| Ramos (B cell) none | 17.2 | 11.9 | Lung fibroblast IL-13 | 8.5 | 18.4 |
| Ramos (B cell) ionomycin | 15.1 | 4.3 | Lung fibroblast IFN gamma | 14.5 | 11.8 |
| B lymphocytes PWM | 16.4 | 3.3 | Dermal fibroblast CCD1070 rest | 13.5 | 13.9 |
| B lymphocytes CD40L and IL-4 | 36.6 | 4.9 | Dermal fibroblast CCD1070 TNF alpha | 20.0 | 9.2 |
| EOL-1 dbcAMP | 18.3 | 3.5 | Dermal fibroblast CCD1070 IL-1beta | 10.4 | 13.7 |
| EOL-1 dbcAMP PMA/ionomycin | 20.9 | 3.8 | Dermal fibroblast IFN gamma | 13.0 | 12.9 |

TABLE AGC-continued

Panel 4.1D

| Tissue Name | Rel. Exp. (%) Ag3727, Run 170047715 | Rel. Exp. (%) Ag3727, Run 170128711 | Tissue Name | Rel. Exp. (%) Ag3727, Run 170047715 | Rel. Exp. (%) Ag3727, Run 170128711 |
|---|---|---|---|---|---|
| Dendritic cells none | 18.3 | 2.9 | Dermal fibroblast IL-4 | 12.5 | 10.5 |
| Dendritic cells LPS | 14.7 | 4.7 | Dermal Fibroblasts rest | 10.2 | 8.1 |
| Dendritic cells anti-CD40 | 20.9 | 6.5 | Neutrophils TNFa + LPS | 16.5 | 10.6 |
| Monocytes rest | 27.5 | 6.9 | Neutrophils rest | 32.3 | 9.5 |
| Monocytes LPS | 100.0 | 8.8 | Colon | 5.8 | 10.4 |
| Macrophages rest | 12.8 | 12.1 | Lung | 10.1 | 17.8 |
| Macrophages LPS | 14.3 | 8.1 | Thymus | 29.5 | 6.9 |
| HUVEC none | 11.1 | 7.1 | Kidney | 9.4 | 17.2 |
| HUVEC starved | 15.4 | 5.7 | | | |

CNS_neurodegeneration_v1.0 Summary: Ag3727 This panel does not show differential expression of the CG91298-01 gene in Alzheimer's disease. However, this expression profile confirms the presence of this gene in the brain, with highest expression in the hippocampus of an Alzheimer's patient. Moderate to low levels of expression in the CNS suggests that therapeutic modulation of the expression or function of this gene may be useful in the treatment of neurologic disorders, such as Alzheimer's disease, Parkinson's disease, schizophrenia, multiple sclerosis, stroke and epilepsy.

General_screening_panel_v1.4 Summary: Ag3727 Results from one experiment with the CG91298-01 gene are not included. The amp plot indicates that there were experimental difficulties with this run.

Panel 4.1D Summary: Ag3727 Two experiments with the same probe and primer both show ubiquitous expression of the CG91298-01 gene on this panel. Highest expression is seen in LPS stimulated monocytes and chronically activated Th2 cells (CTs=26–28). In addition, this gene is expressed at moderate to low levels in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. This ubiquitous pattern of expression suggests that this gene product may be involved in homeostatic processes for these and other cell types and tissues. This gene encodes a homolog of phosphatidylglycerophosphate synthase, an enzyme that has been shown to be necessary for cell growth. The expression profile in this experiment supports a role for this gene product in cell growth and survival, as well. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis (Ohtsuka T, Nishijima M, Akamatsu Y. A somatic cell mutant defective in phosphatidylglycerophosphate synthase, with impaired phosphatidylglycerol and cardiolipin biosynthesis. J Biol Chem 1993 Oct. 25;268(30):22908–13).

AH. CG91383-01: Aldehyde Dehydrogenase

Expression of gene CG91383-01 was assessed using the primer-probe set Ag3719, described in Table AHA.

TABLE AHA

Probe Name Ag3719

| Primers | Sequences | Length | Start Position | SEQ ID NO: |
|---|---|---|---|---|
| Forward | 5'-acctgagcaaaagtgaactcaa-3' | 22 | 151 | 333 |
| Probe | TET-5'-cagtcatgaagtcattaccatccttgga-3'-TAMRA | 28 | 179 | 334 |
| Reverse | 5'-aggaagattccccaacataaaa-3' | 22 | 215 | 335 |

CNS_neurodegeneration_v1.0 Summary: Ag3719 Expression of the CG91383-01 gene is low/undetectable (CTs>35) across all of the samples on this panel (data not shown).

General_screening_panel_v1.4 Summary: Ag3719 Results from one experiment with the CG91383-01 gene are not included. The amp plot indicates that there were experimental difficulties with this run.

Panel 2.2 Summary: Ag3719 Expression of the CG91383-01 gene is low/undetectable (CTs>35) across all of the samples on this panel (data not shown).

Panel 4.1D Summary: Ag3719 Expression of the CG91383-01 gene is low/undetectable (CTs>35) across all of the samples on this panel (data not shown). Panel 5 Islet Summary: Ag3719 Expression of the CG91383-01 gene is low/undetectable (CTs>35) across all of the samples on this panel (data not shown).

AI. CG91403-01: Proline Rich Synapse Associated Protein 2

Expression of gene CG91403-01 was assessed using the primer-probe set Ag3728, described in Table AIA. Results of the RTQ-PCR runs are shown in Tables AIB, AIC, AID and AIE.

TABLE AIA

Probe Name Ag3728

| Primers | Sequences | Length | Start Position | SEQ ID NO: |
|---|---|---|---|---|
| Forward | 5'-agaacctcatcgatgataagca-3' | 22 | 590 | 336 |
| Probe | TET-5'-aaagcttcacacaaaggcgaacctga-3'-TAMRA | 26 | 618 | 337 |
| Reverse | 5'-tggacgtagtccatgaacttct-3' | 22 | 644 | 338 |

TABLE AIB

| AI_comprehensive_panel_v1.0 | | | |
|---|---|---|---|
| Tissue Name | Rel. Exp. (%) Ag3728, Run 248445826 | Tissue Name | Rel. Exp. (%) Ag3728, Run 248445826 |
| 110967 COPD-F | 1.1 | 112427 Match Control Psoriasis-F | 4.2 |
| 110980 COPD-F | 1.1 | 112418 Psoriasis-M | 0.6 |
| 110968 COPD-M | 0.9 | 112723 Match Control Psoriasis-M | 0.1 |
| 110977 COPD-M | 2.5 | 112419 Psoriasis-M | 0.8 |
| 110989 Emphysema-F | 2.2 | 112424 Match Control Psoriasis-M | 0.6 |
| 110992 Emphysema-F | 0.8 | 112420 Psoriasis-M | 0.8 |
| 110993 Emphysema-F | 1.2 | 112425 Match Control Psoriasis-M | 1.7 |
| 110994 Emphysema-F | 0.8 | 104689 (MF) OA Bone-Backus | 6.6 |
| 110995 Emphysema-F | 1.2 | 104690 (MF) Adj "Normal" Bone-Backus | 3.7 |
| 110996 Emphysema-F | 0.1 | 104691 (MF) OA Synovium-Backus | 1.6 |
| 110997 Asthma-M | 0.4 | 104692 (BA) OA Cartilage-Backus | 0.0 |
| 111001 Asthma-F | 1.4 | 104694 (BA) OA Bone-Backus | 2.4 |
| 111002 Asthma-F | 1.8 | 104695 (BA) Adj "Normal" Bone-Backus | 3.7 |
| 111003 Atopic Asthma-F | 1.6 | 104696 (BA) OA Synovium-Backus | 1.3 |
| 111004 Atopic Asthma-F | 0.6 | 104700 (SS) OA Bone-Backus | 2.4 |
| 111005 Atopic Asthma-F | 0.8 | 104701 (SS) Adj "Normal" Bone-Backus | 4.0 |
| 111006 Atopic Asthma-F | 0.2 | 104702 (SS) OA Synovium-Backus | 5.3 |
| 111417 Allergy-M | 0.7 | 117093 OA Cartilage Rep7 | 0.8 |
| 112347 Allergy-M | 0.0 | 112672 OA Bone5 | 1.2 |
| 112349 Normal Lung-F | 0.0 | 112673 OA Synovium5 | 0.7 |
| 112357 Normal Lung-F | 0.8 | 112674 OA Synovial Fluid cells5 | 0.6 |
| 112354 Normal Lung-M | 0.4 | 117100 OA Cartilage Rep14 | 0.4 |
| 112374 Crohns-F | 0.5 | 112756 OA Bone9 | 0.1 |
| 112389 Match Control Crohns-F | 0.6 | 112757 OA Synovium9 | 0.6 |
| 112375 Crohns-F | 0.6 | 112758 OA Synovial Fluid Cells9 | 0.9 |
| 112732 Match Control Crohns-F | 0.4 | 117125 RA Cartilage Rep2 | 1.4 |
| 112725 Crohns-M | 0.1 | 113492 Bone2 RA | 1.1 |
| 112387 Match Control Crohns-M | 1.0 | 113493 Synovium2 RA | 0.4 |
| 112378 Crohns-M | 0.0 | 113494 Syn Fluid Cells RA | 0.8 |
| 112390 Match Control Crohns-M | 1.6 | 113499 Cartilage4 RA | 0.9 |
| 112726 Crohns-M | 0.8 | 113500 Bone4 RA | 1.4 |
| 112731 Match Control Crohns-M | 0.9 | 113501 Synovium4 RA | 0.8 |
| 112380 Ulcer Col-F | 0.5 | 113502 Syn Fluid Cells4 RA | 0.5 |
| 112734 Match Control Ulcer Col-F | 0.8 | 113495 Cartilage3 RA | 1.1 |
| 112384 Ulcer Col-F | 1.4 | 113496 Bone3 RA | 1.0 |
| 112737 Match Control Ulcer Col-F | 0.4 | 113497 Synovium3 RA | 0.3 |
| 112386 Ulcer Col-F | 0.4 | 113498 Syn Fluid Cells3 RA | 1.4 |
| 112738 Match Control Ulcer Col-F | 100.0 | 117106 Normal Cartilage Rep20 | 1.2 |
| 112381 Ulcer Col-M | 0.0 | 113663 Bone3 Normal | 0.0 |
| 112735 Match Control Ulcer Col-M | 0.4 | 113664 Synovium3 Normal | 0.0 |
| 112382 Ulcer Col-M | 0.4 | 113665 Syn Fluid Cells3 Normal | 0.0 |
| 112394 Match Control Ulcer Col-M | 0.2 | 117107 Normal Cartilage Rep22 | 0.3 |
| 112383 Ulcer Col-M | 1.1 | 113667 Bone4 Normal | 0.4 |
| 112736 Match Control Ulcer Col-M | 0.4 | 113668 Synovium4 Normal | 0.3 |
| 112423 Psoriasis-F | 0.8 | 113669 Syn Fluid Cells4 Normal | 0.9 |

TABLE AIC

CNS_neurodegeneration_v1.0

| Tissue Name | Rel. Exp. (%) Ag3728, Run 212143476 | Tissue Name | Rel. Exp. (%) Ag3728, Run 212143476 |
|---|---|---|---|
| AD 1 Hippo | 16.3 | Control (Path) 3 Temporal Ctx | 14.0 |
| AD 2 Hippo | 31.4 | Control (Path) 4 Temporal Ctx | 56.6 |
| AD 3 Hippo | 17.3 | AD 1 Occipital Ctx | 19.1 |
| AD 4 Hippo | 10.0 | AD 2 Occipital Ctx (Missing) | 0.0 |
| AD 5 Hippo | 95.3 | AD 3 Occipital Ctx | 13.3 |
| AD 6 Hippo | 52.1 | AD 4 Occipital Ctx | 17.3 |
| Control 2 Hippo | 44.8 | AD 5 Occipital Ctx | 39.2 |
| Control 4 Hippo | 8.6 | AD 6 Occipital Ctx | 12.8 |
| Control (Path) 3 Hippo | 10.4 | Control 1 Occipital Ctx | 7.5 |
| AD 1 Temporal Ctx | 51.1 | Control 2 Occipital Ctx | 66.9 |
| AD 2 Temporal Ctx | 34.9 | Control 3 Occipital Ctx | 28.7 |
| AD 3 Temporal Ctx | 12.4 | Control 4 Occipital Ctx | 7.2 |
| AD 4 Temporal Ctx | 26.4 | Control (Path) 1 Occipital Ctx | 84.7 |
| AD 5 Inf Temporal Ctx | 92.0 | Control (Path) 2 Occipital Ctx | 15.8 |
| AD 5 Sup Temporal Ctx | 41.5 | Control (Path) 3 Occipital Ctx | 10.0 |
| AD 6 Inf Temporal Ctx | 42.0 | Control (Path) 4 Occipital Ctx | 22.2 |
| AD 6 Sup Temporal Ctx | 55.5 | Control 1 Parietal Ctx | 11.0 |
| Control 1 Temporal Ctx | 10.4 | Control 2 Parietal Ctx | 54.7 |
| Control 2 Temporal Ctx | 48.0 | Control 3 Parietal Ctx | 18.6 |
| Control 3 Temporal Ctx | 24.7 | Control (Path) 1 Parietal Ctx | 100.0 |
| Control 3 Temporal Ctx | 13.9 | Control (Path) 2 Parietal Ctx | 27.7 |
| Control (Path) 1 Temporal Ctx | 93.3 | Control (Path) 3 Parietal Ctx | 8.3 |
| Control (Path) 2 Temporal Ctx | 55.1 | Control (Path) 4 Parietal Ctx | 58.2 |

TABLE AID

General_screening_panel_v1.4

| Tissue Name | Rel. Exp. (%) Ag3728, Run 218297645 | Tissue Name | Rel. Exp. (%) Ag3728, Run 218297645 |
|---|---|---|---|
| Adipose | 18.8 | Renal ca. TK-10 | 1.6 |
| Melanoma* Hs688(A).T | 1.0 | Bladder | 21.6 |
| Melanoma* Hs688(B).T | 0.3 | Gastric ca. (liver met.) NCI-N87 | 10.8 |
| Melanoma* M14 | 1.4 | Gastric ca. KATO III | 1.3 |
| Melanoma* LOXIMVI | 0.0 | Colon ca. SW-948 | 0.1 |
| Melanoma* SK-MEL-5 | 10.7 | Colon ca. SW480 | 2.8 |
| Squamous cell carcinoma SCC-4 | 6.1 | Colon ca.* (SW480 met) SW620 | 0.3 |
| Testis Pool | 3.6 | Colon ca. HT29 | 0.0 |
| Prostate ca.* (bone met) PC-3 | 2.5 | Colon ca. HCT-116 | 20.2 |
| Prostate Pool | 5.0 | Colon ca. CaCo-2 | 3.3 |
| Placenta | 23.0 | Colon cancer tissue | 14.1 |
| Uterus Pool | 10.1 | Colon ca. SW1116 | 1.3 |
| Ovarian ca. OVCAR-3 | 2.4 | Colon ca. Colo-205 | 0.0 |
| Ovarian ca. SK-OV-3 | 70.2 | Colon ca. SW-48 | 0.0 |
| Ovarian ca. OVCAR-4 | 2.8 | Colon Pool | 36.9 |
| Ovarian ca. OVCAR-5 | 2.3 | Small Intestine Pool | 15.7 |
| Ovarian ca. IGROV-1 | 1.1 | Stomach Pool | 9.4 |
| Ovarian ca. OVCAR-8 | 1.3 | Bone Marrow Pool | 9.0 |
| Ovary | 6.7 | Fetal Heart | 23.3 |
| Breast ca. MCF-7 | 0.9 | Heart Pool | 16.2 |
| Breast ca. MDA-MB-231 | 10.2 | Lymph Node Pool | 22.8 |
| Breast ca. BT 549 | 4.5 | Fetal Skeletal Muscle | 14.0 |

TABLE AID-continued

General_screening_panel_v1.4

| Tissue Name | Rel. Exp. (%) Ag3728, Run 218297645 | Tissue Name | Rel. Exp. (%) Ag3728, Run 218297645 |
|---|---|---|---|
| Breast ca. T47D | 3.9 | Skeletal Muscle Pool | 15.3 |
| Breast ca. MDA-N | 0.0 | Spleen Pool | 75.8 |
| Breast Pool | 25.2 | Thymus Pool | 12.1 |
| Trachea | 10.5 | CNS cancer (glio/astro) U87-MG | 0.0 |
| Lung | 1.8 | CNS cancer (glio/astro) U-118-MG | 0.1 |
| Fetal Lung | 100.0 | CNS cancer (neuro; met) SK-N-AS | 0.0 |
| Lung ca. NCI-N417 | 0.0 | CNS cancer (astro) SF-539 | 1.1 |
| Lung ca. LX-1 | 0.8 | CNS cancer (astro) SNB-75 | 1.5 |
| Lung ca. NCI-H146 | 1.6 | CNS cancer (glio) SNB-19 | 1.1 |
| Lung ca. SHP-77 | 0.0 | CNS cancer (glio) SF-295 | 1.4 |
| Lung ca. A549 | 0.6 | Brain (Amygdala) Pool | 26.4 |
| Lung ca. NCI-H526 | 0.2 | Brain (cerebellum) | 11.6 |
| Lung ca. NCI-H23 | 3.7 | Brain (fetal) | 32.8 |
| Lung ca. NCI-H460 | 0.2 | Brain (Hippocampus) Pool | 27.4 |
| Lung ca. HOP-62 | 0.7 | Cerebral Cortex Pool | 44.8 |
| Lung ca. NCI-H522 | 3.2 | Brain (Substantia nigra) Pool | 31.4 |
| Liver | 2.6 | Brain (Thalamus) Pool | 42.9 |
| Fetal Liver | 11.3 | Brain (whole) | 55.5 |
| Liver ca. HepG2 | 3.3 | Spinal Cord Pool | 3.7 |
| Kidney Pool | 42.9 | Adrenal Gland | 12.4 |
| Fetal Kidney | 15.0 | Pituitary gland Pool | 1.3 |
| Renal ca. 786-0 | 0.0 | Salivary Gland | 1.6 |
| Renal ca. A498 | 0.2 | Thyroid (female) | 9.2 |
| Renal ca. ACHN | 0.4 | Pancreatic ca. CAPAN2 | 15.7 |
| Renal ca. UO-31 | 1.0 | Pancreas Pool | 26.1 |

TABLE AIE

Panel 4.1D

| Tissue Name | Rel. Exp. (%) Ag3728, Run 170222884 | Tissue Name | Rel. Exp. (%) Ag3728, Run 170222884 |
|---|---|---|---|
| Secondary Th1 act | 0.0 | HUVEC IL-1beta | 52.9 |
| Secondary Th2 act | 0.2 | HUVEC IFN gamma | 57.8 |
| Secondary Tr1 act | 0.0 | HUVEC TNF alpha + IFN gamma | 13.8 |
| Secondary Th1 rest | 0.0 | HUVEC TNF alpha + IL4 | 12.9 |
| Secondary Th2 rest | 0.0 | HUVEC IL-11 | 42.9 |
| Secondary Tr1 rest | 0.0 | Lung Microvascular EC none | 100.0 |
| Primary Th1 act | 0.1 | Lung Microvascular EC TNF alpha + IL-1beta | 55.1 |
| Primary Th2 act | 0.0 | Microvascular Dermal EC none | 62.9 |
| Primary Tr1 act | 0.0 | Microvasular Dermal EC TNF alpha + IL-1beta | 38.4 |
| Primary Th1 rest | 0.0 | Bronchial epithelium TNF alpha + IL1beta | 2.4 |
| Primary Th2 rest | 0.0 | Small airway epithelium none | 0.8 |
| Primary Tr1 rest | 0.0 | Small airway epithelium TNF alpha + IL-1beta | 4.0 |
| CD45RA CD4 lymphocyte act | 0.2 | Coronery artery SMC rest | 0.0 |
| CD45RO CD4 lymphocyte act | 0.1 | Coronery artery SMC TNF alpha + IL-1beta | 0.0 |
| CD8 lymphocyte act | 0.1 | Astrocytes rest | 0.3 |
| Secondary CD8 lymphocyte rest | 0.0 | Astrocytes TNF alpha + IL-1beta | 0.2 |
| Secondary CD8 lymphocyte act | 0.0 | KU-812 (Basophil) rest | 6.8 |
| CD4 lymphocyte none | 0.0 | KU-812 (Basophil) PMA/ionomycin | 6.3 |
| 2ry Th1/Th2/Tr1_anti-CD95 CH11 | 0.0 | CCD1106 (Keratinocytes) none | 2.8 |
| LAK cells rest | 0.0 | CCD1106 (Keratinocytes) TNF alpha + IL-1beta | 2.9 |

TABLE AIE-continued

Panel 4.1D

| Tissue Name | Rel. Exp. (%) Ag3728, Run 170222884 | Tissue Name | Rel. Exp. (%) Ag3728, Run 170222884 |
|---|---|---|---|
| LAK cells IL-2 | 0.0 | Liver cirrhosis | 2.2 |
| LAK cells IL-2 + IL-12 | 0.1 | NCI-H292 none | 0.0 |
| LAK cells IL-2 + IFN gamma | 0.0 | NCI-H292 IL-4 | 0.3 |
| LAK cells IL-2 + IL-18 | 0.0 | NCI-H292 IL-9 | 0.2 |
| LAK cells PMA/ionomycin | 0.5 | NCI-H292 IL-13 | 0.4 |
| NK Cells IL-2 rest | 0.0 | NCI-H292 IFN gamma | 0.6 |
| Two Way MLR 3 day | 0.1 | HPAEC none | 57.4 |
| Two Way MLR 5 day | 0.0 | HPAEC TNF alpha + IL-1beta | 54.0 |
| Two Way MLR 7 day | 0.1 | Lung fibroblast none | 0.0 |
| PBMC rest | 0.0 | Lung fibroblast TNF alpha + IL-1beta | 0.1 |
| PBMC PWM | 0.0 | Lung fibroblast IL-4 | 0.0 |
| PBMC PHA-L | 0.2 | Lung fibroblast IL-9 | 0.2 |
| Ramos (B cell) none | 0.0 | Lung fibroblast IL-13 | 0.0 |
| Ramos (B cell) ionomycin | 0.0 | Lung fibroblast IFN gamma | 0.0 |
| B lymphocytes PWM | 0.0 | Dermal fibroblast CCD1070 rest | 0.2 |
| B lymphocytes CD40L and IL-4 | 0.0 | Dermal fibroblast CCD1070 TNF alpha | 0.0 |
| EOL-1 dbcAMP | 0.0 | Dermal fibroblast CCD1070 IL-1beta | 0.1 |
| EOL-1 dbcAMP PMA/ionomycin | 0.0 | Dermal fibroblast IFN gamma | 0.2 |
| Dendritic cells none | 0.3 | Dermal fibroblast IL-4 | 0.2 |
| Dendritic cells LPS | 0.5 | Dermal Fibroblasts rest | 0.3 |
| Dendritic cells anti-CD40 | 1.6 | Neutrophils TNFa + LPS | 0.0 |
| Monocytes rest | 0.0 | Neutrophils rest | 0.0 |
| Monocytes LPS | 0.0 | Colon | 2.2 |
| Macrophages rest | 3.4 | Lung | 19.3 |
| Macrophages LPS | 0.1 | Thymus | 3.5 |
| HUVEC none | 35.8 | Kidney | 12.4 |
| HUVEC starved | 46.0 | | |

AI_comprehensive panel_v1.0 Summary: Ag3728 Highest expression of the CG91403-01 gene is detected in 112738 match control ulcerative colitis sample (CT=24). Interestingly, expression of this gene is lower in 2 samples derived from ulcerative colitis patients and 2 samples derived from Crohn's patient as compared to their matched control sample. Therefore, therapeutic modulation of the activity of the protein encoded by this gene may be useful in the treatment of inflammatory bowel disease. In addition, this gene shows low to moderate expression in all the samples used in this panel. Taken together with the expression of this gene in activated endothelial, as shown on Panel 4.1D, therapeutic modulation of the activity of the protein encoded by this gene with small molecule antagonists may reduce or eliminate the symptoms of autoimmune and inflammatory diseases that involve activated endothelial cells, such as, but not limited to, Crohn's disease, ulcerative colitis, multiple sclerosis, chronic obstructive pulmonary disease, asthma, emphysema, rheumatoid arthritis, lupus erythematosus, or psoriasis.

CNS_neurodegeneration_v1.0 Summary: Ag3728 This panel confirms the expression of the CG91403-01 gene at low levels in the brains of an independent group of individuals. However, no differential expression of this gene was detected between Alzheimer's diseased postmortem brains and those of non-demented controls in this experiment. Please see Panel 1.4 for a discussion of the potential utility of this gene in treatment of central nervous system disorders.

General_screening_panel_v1.4 Summary: Ag3728 Highest expression of the CG91403-01 gene is detected in fetal lung (CT=27). Interestingly, this gene is expressed at much higher levels in fetal when compared to adult lung (CT=33). This observation suggests that expression of this gene can be used to distinguish fetal from adult lung. In addition, the relative overexpression of this gene in fetal lung suggests that the protein product may be required for the lung development in the fetus and thus may also act in a regenerative capacity in the adult.

High to moderate expression is seen in some of the cancer (ovarian, colon, pancreatic, breast, squamous cell carcinoma, prostate) cell lines. Therefore, therapeutic modulation of the activity of this gene or its protein product, through the use of small molecule drugs might be beneficial in the treatment of these cancers.

Among tissues with metabolic or endocrine function, this gene is expressed at high to moderate levels in pancreas, adipose, adrenal gland, thyroid, pituitary gland, skeletal muscle, heart, liver and the gastrointestinal tract. Therefore, therapeutic modulation of the activity of this gene may prove useful in the treatment of endocrine/metabolically related diseases, such as obesity and diabetes.

In addition, this gene is expressed at high levels in all regions of the central nervous system examined, including amygdala, hippocampus, substantia nigra, thalamus, cerebellum, cerebral cortex, and spinal cord. Therefore, this gene may play a role in central nervous system disorders such as Alzheimer's disease, Parkinson's disease, epilepsy, multiple sclerosis, schizophrenia and depression.

The CG91403-01 gene codes for a homolog of rat proline rich synapse associated protein 2 (ProSAP2). Recently, ProSAP2 haploinsufficiency has been shown to be associated with the 22q13.3 deletion syndrome (Bonaglia M C, Giorda R. Borgatti R. Felisari G. Gagliardi C, Selicorni A, Zuffardi O. (2001) Disruption of the ProSAP2 gene in at (12;22)(q24.1;q13.3) is associated with the 22q13.3 deletion syndrome. Am J Hum Genet 69(2):261–8). Therefore, therapeutic modulation of the activity of this gene or its protein product, through the use of small molecule drugs might be beneficial in the treatment of the 22q13.3 deletion syndrome.

Panel 4.1D Summary: Ag3728 Highest expression of the CG91403-01 gene is detected in lung microvascular EC (CT=28.6). High to moderate expression of this gene is also seen in HUVFC, HPAEC, lung microvascular EC, microvascular dermal EC, TNFalpha+ IL-1beta treated small airway epithelium, basophils and keratinocytes, lung, kidney, thymus, and lung. Therefore, modulation of the expression or activity of the protein encoded by this gene through the application of small molecule therapeutics may be useful in the treatment of asthma, COPD, emphysema, psoriasis, lupus erythematosus, inflammatory bowel diseases, such as Crohn's and ulcerative colitis, rheumatoid arthritis, osteoarthritis and wound healing.

AJ. CG91434-01: Aldehyde Dehydrogenase

Expression of gene CG91434-01 was assessed using the primer-probe sets Ag3729 and Ag5999, described in Tables AJA and AJB. Results of the RTQ-PCR runs are shown in Tables AJC and AJD.

TABLE AJA

Probe Name Ag3729

| Primers | Sequences | Length | Start Position | SEQ ID NO: |
|---|---|---|---|---|
| Forward | 5'-ttcaagaaaacaagcagcttct-3' | 22 | 122 | 339 |
| Probe | TET-5'-cccaggacctgcataagccagct-3'-TAMRA | 23 | 158 | 340 |
| Reverse | 5'-ctcagatatgtctgcctcgaa-3' | 21 | 181 | 341 |

TABLE AJB

Probe Name Ag5999

| Primers | Sequences | Length | Start Position | SEQ ID NO: |
|---|---|---|---|---|
| Forward | 5'-cctgtacgccttctccaaca-3' | 20 | 1101 | 342 |
| Probe | TET-5'-agccaggtggtcaagcgggtgctg-3'-TAMRA | 24 | 1123 | 343 |
| Reverse | 5'-actcctccaaaaggcaggct-3' | 20 | 1207 | 344 |

TABLE AJC

Panel 2.2

| Tissue Name | Rel. Exp.(%) Ag3729, Run 174441818 | Rel. Exp.(%) Ag3729, Run 259034396 | Tissue Name | Rel. Exp.(%) Ag3729, Run 174441818 | Rel. Exp.(%) Ag3729, Run 259034396 |
|---|---|---|---|---|---|
| Normal Colon | 0.4 | 0.3 | Kidney Margin (OD04348) | 0.0 | 0.0 |
| Colon Cancer (OD06064) | 1.4 | 1.0 | Kidney malignant cancer (OD06204B) | 0.0 | 0.0 |
| Colon Margin (OD06064) | 0.0 | 0.0 | Kidney normal adjacent tissue (OD06204E) | 0.0 | 0.0 |
| Colon cancer (OD06159) | 0.2 | 0.1 | Kidney Cancer (OD04450-01) | 0.0 | 0.0 |
| Colon Margin (OD06159) | 0.0 | 0.0 | Kidney Margin (OD04450-03) | 1.3 | 0.9 |
| Colon cancer (OD06297-04) | 0.0 | 0.0 | Kidney Cancer 8120613 | 0.0 | 0.0 |
| Colon Margin (OD06297-05) | 0.0 | 0.0 | Kidney Margin 8120614 | 0.0 | 0.0 |
| CC Gr.2 ascend colon (ODO3921) | 1.1 | 0.8 | Kidney Cancer 9010320 | 0.5 | 0.3 |
| CC Margin (ODO3921) | 0.0 | 0.0 | Kidney Margin 9010321 | 1.8 | 1.4 |
| Colon cancer metastasis (OD06104) | 0.2 | 0.1 | Kidney Cancer 8120607 | 0.0 | 0.0 |
| Lung Margin (OD06104) | 0.0 | 0.0 | Kidney Margin 8120608 | 1.0 | 0.8 |
| Colon mets to lung (OD04451-01) | 0.2 | 0.2 | Normal Uterus | 0.0 | 0.0 |
| Lung Margin (OD04451-02) | 0.0 | 0.0 | Uterine Cancer 064011 | 1.8 | 1.2 |
| Normal Prostate | 2.3 | 1.8 | Normal Thyroid | 0.0 | 0.0 |
| Prostate Cancer (OD04410) | 2.2 | 1.6 | Thyroid Cancer 064010 | 0.0 | 0.0 |
| Prostate Margin (OD04410) | 5.1 | 3.8 | Thyroid Cancer A302152 | 0.0 | 0.0 |
| Normal Ovary | 0.7 | 0.3 | Thyroid Margin A302153 | 0.0 | 0.0 |

TABLE AJC-continued

Panel 2.2

| Tissue Name | Rel. Exp.(%) Ag3729, Run 174441818 | Rel. Exp.(%) Ag3729, Run 259034396 | Tissue Name | Rel. Exp.(%) Ag3729, Run 174441818 | Rel. Exp.(%) Ag3729, Run 259034396 |
|---|---|---|---|---|---|
| Ovarian cancer (OD06283-03) | 2.5 | 1.7 | Normal Breast | 9.2 | 6.5 |
| Ovarian Margin (OD06283-07) | 0.0 | 0.0 | Breast Cancer (OD04566) | 17.4 | 12.9 |
| Ovarian Cancer 064008 | 1.0 | 0.6 | Breast Cancer 1024 | 100.0 | 100.0 |
| Ovarian cancer (OD06145) | 0.4 | 0.3 | Breast Cancer (OD04590-01) | 3.9 | 2.5 |
| Ovarian Margin (OD06145) | 0.5 | 0.3 | Breast Cancer Mets (OD04590-03) | 1.2 | 0.9 |
| Ovarian cancer (OD06455-03) | 0.9 | 0.5 | Breast Cancer Metastasis (OD04655-05) | 48.6 | 34.4 |
| Ovarian Margin (OD06455-07) | 0.0 | 0.0 | Breast Cancer 064006 | 2.4 | 2.1 |
| Normal Lung | 0.0 | 0.0 | Breast Cancer 9100266 | 55.1 | 43.8 |
| Invasive poor diff. lung adeno (ODO4945-01) | 9.2 | 7.5 | Breast Margin 9100265 | 14.7 | 10.8 |
| Lung Margin (ODO4945-03) | 0.0 | 0.0 | Breast Cancer A209073 | 32.1 | 24.5 |
| Lung Malignant Cancer (OD03126) | 0.5 | 0.4 | Breast Margin A2090734 | 9.1 | 6.4 |
| Lung Margin (OD03126) | 0.4 | 0.3 | Breast cancer (OD06083) | 69.7 | 61.6 |
| Lung Cancer (OD05014A) | 0.0 | 0.0 | Breast cancer node metastasis (OD06083) | 28.5 | 23.3 |
| Lung Margin (OD05014B) | 0.8 | 0.6 | Normal Liver | 0.0 | 0.0 |
| Lung cancer (OD06081) | 44.8 | 0.3 | Liver Cancer 1026 | 0.0 | 0.0 |
| Lung Margin (OD06081) | 0.0 | 0.0 | Liver Cancer 1025 | 0.8 | 0.6 |
| Lung Cancer (OD04237-01) | 3.1 | 2.6 | Liver Cancer 6004-T | 0.2 | 0.1 |
| Lung Margin (OD04237-02) | 0.4 | 0.3 | Liver Tissue 6004-N | 0.4 | 0.3 |
| Ocular Melanoma Metastasis | 0.0 | 0.0 | Liver Cancer 6005-T | 0.0 | 0.0 |
| Ocular Melanoma Margin (Liver) | 0.0 | 0.0 | Liver Tissue 6005-N | 0.0 | 0.0 |
| Melanoma Metastatis | 0.0 | 0.0 | Liver Cancer 064003 | 0.0 | 0.0 |
| Melanoma Margin (Lung) | 0.3 | 0.2 | Normal Bladder | 0.0 | 0.0 |
| Normal Kidney | 0.0 | 0.0 | Bladder Cancer 1023 | 3.2 | 2.3 |
| Kidney Ca, Nuclear grade 2 (OD04338) | 1.5 | 1.2 | Bladder Cancer A302173 | 4.5 | 3.2 |
| Kidney Margin (OD04338) | 0.4 | 0.3 | Normal Stomach | 0.0 | 0.0 |
| Kidney Ca Nuclear grade 1/2 (OD04339) | 0.0 | 0.0 | Gastric Cancer 9060397 | 0.5 | 0.3 |
| Kidney Margin (OD04339) | 0.0 | 0.0 | Stomach Margin 9060396 | 2.1 | 1.4 |
| Kidney Ca, Clear cell type (OD04340) | 0.0 | 0.0 | Gastric Cancer 9060395 | 2.5 | 1.7 |
| Kidney Margin (OD04340) | 0.4 | 0.3 | Stomach Margin 9060394 | 1.8 | 1.1 |
| Kidney Ca, Nuclear grade (OD04348) | 0.0 | 0.0 | Gastric Cancer 064005 | 0.0 | 0.0 |

TABLE AJD

Panel 4.1D

| Tissue Name | Rel. Exp. (%) Ag3729, Run 170222887 | Tissue Name | Rel. Exp. (%) Ag3729, Run 170222887 |
|---|---|---|---|
| Secondary Th1 act | 0.0 | HUVEC IL-1beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 0.0 | Microsvasular Dermal EC TNF alpha + IL-1beta | 0.0 |
| Primary Th1 rest | 0.0 | Bronchial epithelium TNF alpha + IL1beta | 26.8 |
| Primary Th2 rest | 0.0 | Small airway epithelium none | 25.5 |
| Primary Tr1 rest | 0.0 | Small airway epithelium TNF alpha + IL-1beta | 46.7 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1beta | 0.0 |
| CD8 lymphocyte act | 0.0 | Astrocytes rest | 0.0 |
| Secondary CD8 lymphocyte rest | 0.0 | Astrocytes TNF alpha + IL-1beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1beta | 6.7 |
| LAK cells IL-2 | 0.0 | Liver cirrhosis | 0.0 |
| LAK cells IL-2 + IL-12 | 0.0 | NCI-H292 none | 100.0 |
| LAK cells IL-2 + IFN gamma | 0.0 | NCI-H292 IL-4 | 55.9 |
| LAK cells IL-2 + IL-18 | 0.0 | NCI-H292 IL-9 | 82.9 |
| LAK cells PMA/ionomycin | 0.0 | NCI-H292 IL-13 | 58.2 |
| NK Cells IL-2 rest | 0.0 | NCI-H292 IFN gamma | 60.3 |
| Two Way MLR 3 day | 0.0 | HPAEC none | 0.0 |
| Two Way MLR 5 day | 0.0 | HPAEC TNF alpha + IL-1beta | 0.0 |
| Two Way MLR 7 day | 0.0 | Lung fibroblast none | 0.0 |
| PBMC rest | 0.0 | Lung fibroblast TNF alpha + IL-1beta | 0.0 |
| PBMC PWM | 0.0 | Lung fibroblast IL-4 | 0.0 |
| PBMC PHA-L | 0.0 | Lung fibroblast IL-9 | 0.0 |
| Ramos (B cell) none | 7.4 | Lung fibroblast IL-13 | 0.0 |
| Ramos (B cell) ionomycin | 3.1 | Lung fibroblast IFN gamma | 0.0 |
| B lymphocytes PWM | 0.0 | Dermal fibroblast CCD1070 rest | 0.0 |
| B lymphocytes CD40L and IL-4 | 0.0 | Dermal fibroblast CCD1070 TNF alpha | 0.0 |
| EOL-1 dbcAMP | 0.0 | Dermal fibroblast CCD1070 IL-1beta | 0.0 |
| EOL-1 dbcAMP PMA/ionomycin | 0.0 | Dermal fibroblast IFN gamma | 0.0 |
| Dendritic cells none | 0.0 | Dermal fibroblast IL-4 | 0.0 |
| Dendritic cells LPS | 0.0 | Dermal Fibroblasts rest | 0.0 |
| Dendritic cells anti-CD40 | 0.0 | Neutrophils TNFa + LPS | 0.0 |
| Monycytes rest | 0.0 | Neutrophils rest | 0.0 |
| Monocytes LPS | 0.0 | Colon | 0.0 |
| Macrophages rest | 0.0 | Lung | 6.3 |
| Macrophages LPS | 0.0 | Thymus | 7.8 |
| HUVEC none | 0.0 | Kidney | 2.6 |
| HUVEC starved | 0.0 | | |

CNS_neurodegeneration_v1.0 Summary: Ag3729 Expression of the CG91434-01 gene is low/undetectable in all samples on this panel (CTs>35). (Data not shown.)

General_screening_panel_v1.4 Summary: Ag3729 Results from one experiment with this probe and primer and the CG91434-01 gene are not included. The data suggests that there were experimental difficulties with this run.

General_screening_panel_v1.5 Summary: Ag5999 Results from one experiment with this probe and primer and the CG91434-01 gene are not included. The data suggests that there were experimental difficulties with this run.

Panel 2.2 Summary: Ag3729 Highest expression of the CG91434-01 gene is seen in breast cancer (CT=29). In addition, this gene is more highly expressed in breast cancer than in the normal adjacent tissue. Thus, expression of this gene could be used to differentiate between the breast cancer samples and other samples on this panel and as a marker for breast cancer. Furthermore, therapeutic modulation of the expression or function of this gene may be effective in the treatment of breast cancer (Rekha G K, Devaraj V R, Sreerama L, Lee M J, Nagasawa H T, Sladek N E. Inhibition of human class 3 aldehyde dehydrogenase, and sensitization of tumor cells that express significant amounts of this enzyme to oxazaphosphorines, by chlorpropamide analogues. Biochem Pharmacol 1998 Feb. 15;55(4):465–74).

Panel 4.1D Summary: Ag3729 Expression of the CG91434-01 gene is restricted to a few samples, with highest expression is seen in untreated NCI-H292 cells (CT=31.4). The gene is also expressed in a cluster of treated and untreated samples derived from the NCI-H292 cell line, a human airway epithelial cell line that produces mucins. Mucus overproduction is an important feature of bronchial asthma and chronic obstructive pulmonary disease samples. Interestingly, the transcript is also expressed at lower but still significant levels in small airway and bronchial epithelium treated with IL-1 beta and TNF-alpha and untreated small airway epithelium. The expression of the transcript in this mucoepidermoid cell line that is often used as a model for airway epithelium (NCI-H292 cells) suggests that this transcript may be important in the proliferation or activation of airway epithelium. Therefore, therapeutics designed with the protein encoded by the transcript may reduce or eliminate symptoms caused by inflammation in lung epithelia in chronic obstructive pulmonary disease, asthma, allergy, and emphysema.

AK. CG91484-01: GPCR

Expression of gene CG91484-01 was assessed using the primer-probe set Ag3732, described in Table AKA.

TABLE AKA

Probe Name Ag3732

| Primers | Sequences | Length | Start Position | SEQ ID NO: |
|---|---|---|---|---|
| Forward | 5'-acaatgattctgccatttatgg-3' | 22 | 238 | 345 |
| Probe | TET-5'-cctcccaacttcaagacaatcactgg-3'-TAMRA | 26 | 263 | 346 |
| Reverse | 5'-ccattgaagaccttgcacaa-3' | 20 | 304 | 347 |

CNS_neurodegeneration_v1.0 Summary: Ag3732 Expression of the CG91484-01 gene is low/undetectable in all samples on this panel (CTs>35). (Data not shown.)

General_screening_panel_v1.4 Summary: Ag3732 Expression of the CG91484-01 gene is low/undetectable in all samples on this panel (CTs>35). (Data not shown.)

Panel 4.1D Summary: Ag3732 Expression of the CG91484-01 gene is low/undetectable in all samples on this panel (CTs>35). (Data not shown.)

AL. CG91514-01: Telokin

Expression of gene CG91514-01 was assessed using the primer-probe sets Ag3772 and Ag3795, described in Tables ALA and ALB. Results of the RTQ-PCR runs are shown in Tables ALC, ALD, ALE, ALF and ALG.

TABLE ALA

Probe Name Ag3772

| Primers | Sequences | Length | Start Position | SEQ ID NO: |
|---|---|---|---|---|
| Forward | 5'-actcccttttggaatgcaataaa-3' | 22 | 602 | 348 |
| Probe | TET-5'-attgtgtgccctgcttgccctcat-3'-TAMRA | 24 | 630 | 349 |
| Reverse | 5'-ctccacagacctccaacca-3' | 19 | 660 | 350 |

TABLE ALB

Probe Name Ag3795

| Primers | Sequences | Length | Start Position | SEQ ID NO: |
|---|---|---|---|---|
| Forward | 5'-cctgcatcgtcacaggatac-3' | 20 | 312 | 351 |
| Probe | TET-5'-agagccagaggtgacctggtacaagg-3'-TAMRA | 26 | 334 | 352 |
| Reverse | 5'-catattttggcaagccacag-3' | 20 | 382 | 353 |

TABLE ALC

CNS_neurodegeneration_v1.0

| Tissue Name | Rel. Exp. (%) Ag3772, Run 211176609 | Tissue Name | Rel. Exp. (%) Ag3772, Run 211176609 |
|---|---|---|---|
| AD 1 Hippo | 11.5 | Control (Path) 3 Temporal Ctx | 5.4 |
| AD 2 Hippo | 30.1 | Control (Path) 4 Temporal Ctx | 17.7 |

TABLE ALC-continued

CNS_neurodegeneration_v1.0

| Tissue Name | Rel. Exp. (%) Ag3772, Run 211176609 | Tissue Name | Rel. Exp. (%) Ag3772, Run 211176609 |
|---|---|---|---|
| AD 3 Hippo | 5.5 | AD 1 Occipital Ctx | 4.3 |
| AD 4 Hippo | 6.9 | AD 2 Occipital Ctx (Missing) | 0.0 |
| AD 5 Hippo | 100.0 | AD 3 Occipital Ctx | 3.5 |
| AD 6 Hippo | 75.8 | AD 4 Occipital Ctx | 16.2 |
| Control 2 Hippo | 14.0 | AD 5 Occipital Ctx | 22.5 |
| Control 4 Hippo | 25.7 | AD 6 Occipital Ctx | 33.0 |
| Control (Path) 3 Hippo | 6.0 | Control 1 Occipital Ctx | 7.0 |
| AD 1 Temporal Ctx | 19.5 | Control 2 Occipital Ctx | 55.5 |
| AD 2 Temporal Ctx | 39.2 | Control 3 Occipital Ctx | 6.1 |
| AD 3 Temporal Ctx | 2.9 | Control 4 Occipital Ctx | 7.3 |
| AD 4 Temporal Ctx | 13.9 | Control (Path) 1 Occipital Ctx | 76.3 |
| AD 5 Inf Temporal Ctx | 42.0 | Control (Path) 2 Occipital Ctx | 14.3 |
| AD 5 Sup Temporal Ctx | 36.3 | Control (Path) 3 Occipital Ctx | 2.7 |
| AD 6 Inf Temporal Ctx | 71.2 | Control (Path) 4 Occipital Ctx | 14.1 |
| AD 6 Sup Temporal Ctx | 93.3 | Control 1 Parietal Ctx | 3.3 |
| Control 1 Temporal Ctx | 5.9 | Control 2 Parietal Ctx | 34.9 |
| Control 2 Temporal Ctx | 18.0 | Control 3 Parietal Ctx | 12.3 |
| Control 3 Temporal Ctx | 14.9 | Control (Path) 1 Parietal Ctx | 0.0 |
| Control 3 Temporal Ctx | 12.4 | Control (Path) 2 Parietal Ctx | 21.6 |
| Control (Path) 1 Temporal Ctx | 48.0 | Control (Path) 3 Parietal Ctx | 3.4 |
| Control (Path) 2 Temporal Ctx | 20.0 | Control (Path) 4 Parietal Ctx | 24.3 |

TABLE ALD

General_screening_panel_v1.4

| Tissue Name | Rel. Exp. (%) Ag3772, Run 219514529 | Tissue Name | Rel. Exp. (%) Ag3772, Run 219514529 |
|---|---|---|---|
| Adipose | 2.3 | Renal ca. TK-10 | 18.4 |
| Melanoma* Hs688(A).T | 0.1 | Bladder | 4.0 |
| Melanoma* Hs688(B).T | 0.1 | Gastric ca. (liver met.) NCI-N87 | 0.9 |
| Melanoma* M14 | 0.0 | Gastric ca. KATO III | 0.1 |
| Melanoma* LOXIMVI | 0.0 | Colon ca. SW-948 | 3.0 |
| Melanoma* SK-MEL-5 | 0.1 | Colon ca. SW480 | 0.1 |
| Squamous cell carcinoma SCC-4 | 1.9 | Colon ca.* (SW480 met) SW620 | 0.4 |
| Testis Pool | 2.0 | Colon ca. HT29 | 22.1 |
| Prostate ca.* (bone met) PC-3 | 0.1 | Colon ca. HCT-116 | 0.4 |
| Prostate Pool | 0.8 | Colon ca. CaCo-2 | 0.4 |
| Placenta | 7.0 | Colon cancer tissue | 1.1 |
| Uterus Pool | 0.4 | Colon ca. SW1116 | 0.2 |
| Ovarian ca. OVCAR-3 | 0.1 | Colon ca. Colo-205 | 0.2 |
| Ovarian ca. SK-OV-3 | 0.5 | Colon ca. SW-48 | 0.1 |
| Ovarian ca. OVCAR-4 | 0.2 | Colon Pool | 1.7 |
| Ovarian ca. OVCAR-5 | 2.5 | Small Intestine Pool | 1.6 |
| Ovarian ca. IGROV-1 | 1.0 | Stomach Pool | 1.0 |
| Ovarian ca. OVCAR-8 | 0.4 | Bone Marrow Pool | 1.1 |
| Ovary | 0.5 | Fetal Heart | 59.5 |
| Breast ca. MCF-7 | 0.8 | Heart Pool | 4.8 |
| Breast ca. MDA-MB-231 | 0.1 | Lymph Node Pool | 2.3 |
| Breast ca. BT 549 | 2.0 | Fetal Skeletal Muscle | 32.8 |
| Breast ca. T47D | 2.2 | Skeletal Muscle Pool | 100.0 |
| Breast ca. MDA-N | 0.0 | Spleen Pool | 0.9 |
| Breast Pool | 3.2 | Thymus Pool | 1.7 |
| Trachea | 1.7 | CNS cancer (glio/astro) U87-MG | 0.1 |

TABLE ALD-continued

General_screening_panel_v1.4

| Tissue Name | Rel. Exp. (%) Ag3772, Run 219514529 | Tissue Name | Rel. Exp. (%) Ag3772, Run 219514529 |
|---|---|---|---|
| Lung | 0.4 | CNS cancer (glio/astro) U-118-MG | 0.3 |
| Fetal Lung | 18.0 | CNS cancer (neuro; met) SK-N-AS | 0.2 |
| Lung ca. NCI-N417 | 2.0 | CNS cancer (astro) SF-539 | 0.2 |
| Lung ca. LX-1 | 0.3 | CNS cancer (astro) SNB-75 | 0.2 |
| Lung ca. NCI-H146 | 0.0 | CNS cancer (glio) SNB-19 | 0.9 |
| Lung ca. SHP-77 | 17.7 | CNS cancer (glio) SF-295 | 0.8 |
| Lung ca. A549 | 0.3 | Brain (Amygdala) Pool | 0.6 |
| Lung ca. NCI-H526 | 0.9 | Brain (cerebellum) | 0.8 |
| Lung ca. NCI-H23 | 0.3 | Brain (fetal) | 1.5 |
| Lung ca. NCI-H460 | 0.1 | Brain (Hippocampus) Pool | 1.0 |
| Lung ca. HOP-62 | 0.2 | Cerebral Cortex Pool | 0.5 |
| Lung ca. NCI-H522 | 0.1 | Brain (Substantia nigra) Pool | 0.5 |
| Liver | 0.4 | Brain (Thalamus) Pool | 1.0 |
| Fetal Liver | 4.9 | Brain (whole) | 1.1 |
| Liver ca. HepG2 | 0.0 | Spinal Cord Pool | 0.8 |
| Kidney Pool | 2.4 | Adrenal Gland | 7.3 |
| Fetal Kidney | 8.7 | Pituitary gland Pool | 4.8 |
| Renal ca. 786-0 | 7.7 | Salivary Gland | 0.5 |
| Renal ca. A498 | 0.6 | Thyroid (female) | 0.8 |
| Renal ca. ACHN | 0.0 | Pancreatic ca. CAPAN2 | 8.6 |
| Renal ca. UO-31 | 5.7 | Pancreas Pool | 2.3 |

TABLE ALE

General_screening_panel_v1.5

| Tissue Name | Rel. Exp. (%) Ag3795, Run 258001456 | Tissue Name | Rel. Exp. (%) Ag3795, Run 258001456 |
|---|---|---|---|
| Adipose | 0.9 | Renal ca. TK-10 | 12.6 |
| Melanoma* Hs688(A).T | 0.0 | Bladder | 2.2 |
| Melanoma* Hs688(B).T | 0.1 | Gastric ca. (liver met.) NCI-N87 | 0.2 |
| Melanoma* M14 | 0.0 | Gastric ca. KATO III | 0.0 |
| Melanoma* LOXIMVI | 0.0 | Colon ca. SW-948 | 1.3 |
| Melanoma* SK-MEL-5 | 0.0 | Colon ca. SW480 | 0.1 |
| Squamous cell carcinoma SCC-4 | 0.0 | Colon ca.* (SW480 met) SW620 | 0.1 |
| Testis Pool | 0.5 | Colon ca. HT29 | 13.1 |
| Prostate ca.* (bone met) PC-3 | 0.0 | Colon ca. HCT-116 | 0.1 |
| Prostate Pool | 0.6 | Colon ca. CaCo-2 | 0.2 |
| Placenta | 0.3 | Colon cancer tissue | 0.7 |
| Uterus Pool | 0.2 | Colon ca. SW1116 | 0.0 |
| Ovarian ca. OVCAR-3 | 0.0 | Colon ca. Colo-205 | 0.0 |
| Ovarian ca. SK-OV-3 | 0.1 | Colon ca. SW-48 | 0.0 |
| Ovarian ca. OVCAR-4 | 0.0 | Colon Pool | 0.4 |
| Ovarian ca. OVCAR-5 | 0.3 | Small Intestine Pool | 0.6 |
| Ovarian ca. IGROV-1 | 0.3 | Stomach Pool | 0.5 |
| Ovarian ca. OVCAR-8 | 0.2 | Bone Marrow Pool | 0.1 |
| Ovary | 0.1 | Fetal Heart | 13.1 |
| Breast ca. MCF-7 | 0.3 | Heart Pool | 2.6 |
| Breast ca. MDA-MB-231 | 0.1 | Lymph Node Pool | 0.0 |
| Breast ca. BT 549 | 0.1 | Fetal Skeletal Muscle | 6.7 |
| Breast ca. T47D | 0.0 | Skeletal Muscle Pool | 100.0 |
| Breast ca. MDA-N | 0.0 | Spleen Pool | 0.5 |
| Breast Pool | 0.6 | Thymus Pool | 0.5 |
| Trachea | 0.4 | CNS cancer (glio/astro) U87-MG | 0.0 |
| Lung | 0.0 | CNS cancer (glio/astro) U-118-MG | 0.1 |
| Fetal Lung | 4.2 | CNS cancer (neuro; met) SK-N-AS | 0.0 |
| Lung ca. NCI-N417 | 0.0 | CNS cancer (astro) SF-539 | 0.1 |
| Lung ca. LX-1 | 0.1 | CNS cancer (astro) SNB-75 | 0.1 |
| Lung ca. NCI-H146 | 0.0 | CNS cancer (glio) SNB-19 | 0.4 |
| Lung ca. SHP-77 | 12.8 | CNS cancer (glio) SF-295 | 0.4 |
| Lung ca. A549 | 0.0 | Brain (Amygdala) Pool | 0.4 |

TABLE ALE-continued

General_screening_panel_v1.5

| Tissue Name | Rel. Exp. (%) Ag3795, Run 258001456 | Tissue Name | Rel. Exp. (%) Ag3795, Run 258001456 |
|---|---|---|---|
| Lung ca. NCI-H526 | 0.4 | Brain (cerebellum) | 0.3 |
| Lung ca. NCI-H23 | 0.1 | Brain (fetal) | 0.5 |
| Lung ca. NCI-H460 | 0.0 | Brain (Hippocampus) Pool | 0.5 |
| Lung ca. HOP-62 | 0.1 | Cerebral Cortex Pool | 0.3 |
| Lung ca. NCI-H522 | 0.0 | Brain (Substantia nigra) Pool | 0.3 |
| Liver | 0.2 | Brain (Thalamus) Pool | 0.5 |
| Fetal Liver | 1.8 | Brain (whole) | 0.8 |
| Liver ca. HepG2 | 0.0 | Spinal Cord Pool | 0.4 |
| Kidney Pool | 0.8 | Adrenal Gland | 3.5 |
| Fetal Kidney | 1.7 | Pituitary gland Pool | 2.5 |
| Renal ca. 786-0 | 6.4 | Salivary Gland | 0.3 |
| Renal ca. A498 | 0.1 | Thyroid (female) | 0.3 |
| Renal ca. ACHN | 0.0 | Pancreatic ca. CAPAN2 | 5.2 |
| Renal ca. UO-31 | 2.2 | Pancreas Pool | 0.7 |

TABLE ALF

Panel 4.1D

| Tissue Name | Rel. Exp. (%) Ag3795, Run 172208559 | Tissue Name | Rel. Exp. (%) Ag3795, Run 172208559 |
|---|---|---|---|
| Secondary Th1 act | 0.4 | HUVEC IL-1beta | 97.3 |
| Secondary Th2 act | 0.5 | HUVEC IFN gamma | 92.0 |
| Secondary Tr1 act | 0.0 | HUVEC TNF alpha + IFN gamma | 23.7 |
| Secondary Th1 rest | 0.0 | HUVEC TNF alpha + IL4 | 88.3 |
| Secondary Th2 rest | 1.3 | HUVEC IL-11 | 66.4 |
| Secondary Tr1 rest | 0.9 | Lung Microvascular EC none | 100.0 |
| Primary Th1 act | 0.0 | Lung Microvascular EC TNF alpha + IL-1beta | 68.3 |
| Primary Th2 act | 0.9 | Microvascular Dermal EC none | 0.0 |
| Primary Tr1 act | 0.0 | Microsvascular Dermal EC TNF alpha + IL-1beta | 76.3 |
| Primary Th1 rest | 0.0 | Bronchial epithelium TNF alpha + IL1beta | 1.5 |
| Primary Th2 rest | 0.0 | Small airway epithelium none | 1.3 |
| Primary Tr1 rest | 0.5 | Small airway epithelium TNF alpha + IL-1beta | 0.6 |
| CD45RA CD4 lymphocyte act | 0.0 | Coronery artery SMC rest | 0.5 |
| CD45RO CD4 lymphocyte act | 3.3 | Coronery artery SMC TNF alpha + IL-1beta | 2.1 |
| CD8 lymphocyte act | 0.0 | Astrocytes rest | 2.9 |
| Secondary CD8 lymphocyte rest | 0.4 | Astrocytes TNF alpha + IL-1beta | 4.8 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.8 |
| 2ry Th1/Th2/Tr1_anti-CD95 CH11 | 0.0 | CCD1106 (Keratinocytes) none | 0.5 |
| LAK cells rest | 0.0 | CCD1106 (Keratinocytes) TNF alpha + IL-1beta | 0.0 |
| LAK cells IL-2 | 0.0 | Liver cirrhosis | 7.2 |
| LAK cells IL-2 + IL-12 | 0.9 | NCI-H292 none | 1.4 |
| LAK cells IL-2 + IFN gamma | 1.5 | NCI-H292 IL-4 | 1.0 |
| LAK cells IL-2 + IL-18 | 0.0 | NCI-H292 IL-9 | 1.0 |
| LAK cells PMA/ionomycin | 0.3 | NCI-H292 IL-13 | 0.6 |
| NK Cells IL-2 rest | 0.6 | NCI-H292 IFN gamma | 0.0 |
| Two Way MLR 3 day | 0.0 | HPAEC none | 46.0 |
| Two Way MLR 5 day | 0.0 | HPAEC TNF alpha + IL-1beta | 6.0 |
| Two Way MLR 7 day | 0.0 | Lung fibroblast none | 1.2 |
| PBMC rest | 0.2 | Lung fibroblast TNF alpha + IL-1beta | 0.9 |
| PBMC PWM | 1.0 | Lung fibroblast IL-4 | 0.0 |
| PBMC PHA-L | 1.0 | Lung fibroblast IL-9 | 0.0 |
| Ramos (B cell) none | 0.0 | Lung fibroblast IL-13 | 0.0 |

TABLE ALF-continued

Panel 4.1D

| Tissue Name | Rel. Exp. (%) Ag3795, Run 172208559 | Tissue Name | Rel. Exp. (%) Ag3795, Run 172208559 |
|---|---|---|---|
| Ramos (B cell) ionomycin | 0.0 | Lung fibroblast IFN gamma | 0.0 |
| B lymphocytes PWM | 0.5 | Dermal fibroblast CCD1070 rest | 1.8 |
| B lymphocytes CD40L and IL-4 | 0.0 | Dermal fibroblast CCD1070 TNF alpha | 1.5 |
| EOL-1 dbcAMP | 0.3 | Dermal fibroblast CCD1070 IL-1beta | 0.6 |
| EOL-1 dbcAMP PMA/ionomycin | 0.4 | Dermal fibroblast IFN gamma | 0.0 |
| Dendritic cells none | 2.3 | Dermal fibroblast IL-4 | 0.0 |
| Dendritic cells LPS | 1.1 | Dermal Fibroblasts rest | 0.0 |
| Dendritic cells anti-CD40 | 1.6 | Neutrophils TNFa + LPS | 0.5 |
| Monocytes rest | 0.0 | Neutrophils rest | 2.6 |
| Monocytes LPS | 0.0 | Colon | 3.6 |
| Macrophages rest | 11.0 | Lung | 17.0 |
| Macrophages LPS | 1.1 | Thymus | 6.1 |
| HUVEC none | 66.9 | Kidney | 30.8 |
| HUVEC starved | 75.8 | | |

TABLE ALG

Panel 5 Islet

| Tissue Name | Rel. Exp. (%) Ag3795, Run 256791465 | Tissue Name | Rel. Exp. (%) Ag3795, Run 256791465 |
|---|---|---|---|
| 97457_Patient-02go_adipose | 0.3 | 94709_Donor 2 AM - A_adipose | 0.5 |
| 97476_Patient-07sk_skeletal muscle | 5.1 | 94710_Donor 2 AM - B_adipose | 0.0 |
| 97477_Patient-07ut_uterus | 0.0 | 94711_Donor 2 AM - C_adipose | 0.0 |
| 97478_Patient-07pl_placenta | 0.4 | 94712_Donor 2 AD - A_adipose | 0.0 |
| 99167_Bayer Patient 1 | 42.9 | 94713_Donor 2 AD - B_adipose | 0.1 |
| 97482_Patient-08ut_uterus | 0.5 | 94714_Donor 2 AD - C_adipose | 0.4 |
| 97483_Patient-08pl_placenta | 0.7 | 94742_Donor 3 U - A_Mesenchymal Stem Cells | 0.1 |
| 97486_Patient-09sk_skeletal muscle | 8.1 | 94743_Donor 3 U - B_Mesenchymal Stem Cells | 0.0 |
| 97487_Patient-09ut_uterus | 0.2 | 94730_Donor 3 AM - A_adipose | 0.3 |
| 97488_Patient-09pl_placenta | 0.4 | 94731_Donor 3 AM - B_adipose | 0.3 |
| 97492_Patient-10ut_uterus | 0.5 | 94732_Donor 3 AM - C_adipose | 0.4 |
| 97493_Patient-10pl_placenta | 2.6 | 94733_Donor 3 AD - A_adipose | 0.1 |
| 97495_Patient-11go_adipose | 0.5 | 94734_Donor 3 AD - B_adipose | 0.0 |
| 97496_Patient-11sk_skeletal muscle | 48.0 | 94735_Donor 3 AD - C_adipose | 0.0 |
| 97497_Patient-11ut_uterus | 0.8 | 77138_Liver_HepG2untreated | 0.3 |
| 97498_Patient-11pl_placenta | 0.6 | 73556_Heart_Cardiac stromal cells (primary) | 5.8 |
| 97500_Patient-12go_adipose | 0.8 | 81735_Small Intestine | 2.5 |
| 97501_Patient-12sk_skeletal muscle | 100.0 | 72409_Kidney_Proximal Convoluted Tubule | 1.0 |
| 97502_Patient-12ut_uterus | 0.0 | 82685_Small intestine_Duodenum | 0.0 |
| 97503_Patient-12pl_placenta | 0.3 | 90650_Adrenal_Adrenocortical adenoma | 2.4 |
| 94721_Donor 2 U - A_Mesenchymal Stem Cells | 0.0 | 72410_Kidney_HRCE | 5.2 |
| 94722_Donor 2 U - B_Mesenchymal Stem Cells | 0.1 | 72411_Kidney_HRE | 16.0 |
| 94723_Donor 2 U - C_Mesenchymal Stem Cells | 0.1 | 73139_Uterus_Uterine smooth muscle cells | 0.0 |

CNS_neurodegeneration_v1.0 Summary: Ag3772 This panel does not show differential expression of the CG91514-01 gene in Alzheimer's disease. However, this expression profile confirms the presence of this gene in the brain, with highest expression in the hippocampus of an Alzheimer's patient (CT=30.3). Please see Panel 1.4 for discussion of utility of this gene in the central nervous system.

General_screening_panel_v1.4 Summary: Ag3772 Highest expression of the CG91514-01, a telokin homolog, is seen in skeletal muscle (CT=24.6). This gene is ubiquitously expressed in this panel, with high levels of expression also seen in fetal heart, skeletal muscle and lung and renal, lung and colon cancer cell lines. Thus, expression of this gene could be used to differentiate between skeletal muscle and other samples on this panel and as a marker of skeletal muscle. Telokin is the name for the carboxy-terminal 154 codons of muscle light chain kinase that are expressed as an independent protein in smooth muscle. This expression profile supports the identification of this gene product as a telokin homolog. This gene is also expressed in other metabolic tissues including pancreas, thyroid, pituitary, adrenal, heart, and adult and fetal liver. This expression profile suggests that this gene product may be involved in the pathogenesis and/or treatment of metabolic disorders, including obesity and type 2 diabetes.

In addition, this gene is expressed at much higher levels in fetal lung and heart tissue (CTs=25–27) when compared to expression in the adult counterpart (CTs=29–32). Thus, expression of this gene may be used to differentiate between the fetal and adult source of these tissues.

This gene is also expressed at moderate to low levels in the CNS, including the hippocampus, thalamus, substantia nigra, amygdala, cerebellum and cerebral cortex. Therefore, therapeutic modulation of the expression or function of this gene may be useful in the treatment of neurologic disorders, such as Alzheimer's disease, Parkinson's disease, schizophrenia, multiple sclerosis, stroke and epilepsy.

Results from a second experiment with the probe/primer set Ag3795 are not included. The amp plot indicates there were experimental difficulties with this run.

General_screening_panel_v1.5 Summary: Ag3795 Highest expression of the CG91514-01 gene is seen in skeletal muscle (CT=26.6). Expression in this panel is in excellent agreement with expression in Panel 1.4. Please see that Panel 1.4 for discussion of utility of this gene in the central nervous system and metabolic disorders.

Panel 4.1D Summary: Ag3795 Highest expression of the CG91514-01 gene is seen in untreated lung microvacular EC (CT=31). Significant expression of this gene appears to be limited to a cluster of cells derived from treated and untreated HUVEC and lung microvasculature and untreated dermal EC. Endothelial cells are known to play important roles in inflammatory responses by altering the expression of surface proteins that are involved in activation and recruitment of effector inflammatory cells. The expression of this gene in dermal microvascular endothelial cells suggests that this protein product may be involved in inflammatory responses to skin disorders, including psoriasis. Expression in lung microvascular endothelial cells suggests that the protein encoded by this transcript may also be involved in lung disorders including asthma, allergies, chronic obstructive pulmonary disease, and emphysema. Therefore, therapeutic modulation of the protein encoded by this gene may lead to amelioration of symptoms associated with psoriasis, asthma, allergies, chronic obstructive pulmonary disease, and emphysema.

Expression of this transcript in the microvasculature of the lung and the dermis also suggests a role for this gene in the maintenance of the integrity of the microvasculature. Therefore, therapeutics designed for this putative protein could be beneficial for the treatment of diseases associated with damaged microvasculature including heart diseases or inflammatory diseases, such as psoriasis, asthma, and chronic obstructive pulmonary diseases.

Results from a second experiment with the probe and primer set Ag3772 are not included. The amp plot indicates that there were experimental difficulties with this run.

Panel 5 Islet Summary: Ag3795 Expression of the CG91514-05 gene confirms the expression seen in Panels 1.4 and 1.5, with prominent expression in skeletal muscle (CTs=29–33). Please see Panel 1.4 for discussion of utility of this gene in the central nervous system.

AM. CG91587-01: Tripartite Motif Protein TRIM4 Isoform Alpha

Expression of gene CG91587-01 was assessed using the primer-probe sets Ag1115, Ag1166 and Ag759, described in Tables AMA, AMB and AMC. Results of the RTQ-PCR runs are shown in Table AMD.

TABLE AMA

Probe Name Ag1115

| Primers | Sequences | Length | Start Position | SEQ ID NO: |
|---------|-----------|--------|----------------|------------|
| Forward | 5'-gccaactgcttttgtagagaga-3' | 22 | 1150 | 354 |
| Probe | TET-5'-tcagcacttaccctgtgttctgggaa-3'-TAMRA | 26 | 1174 | 355 |
| Reverse | 5'-aatgtttccctgaggtgaaaac-3' | 22 | 1205 | 356 |

TABLE AMB

Probe Name Ag1166

| Primers | Sequences | Length | Start Position | SEQ ID NO: |
|---------|-----------|--------|----------------|------------|
| Forward | 5'-gccaactgcttttgtagagaga-3' | 22 | 1150 | 357 |
| Probe | TET-5'-tcagcacttaccctgtgttctgggaa-3'-TAMRA | 26 | 1174 | 358 |
| Reverse | 5'-aatgtttccctgaggtgaaaac-3' | 22 | 1205 | 359 |

TABLE AMC

Probe Name Ag759

| Primers | Sequences | Length | Start Position | SEQ ID NO: |
|---------|-----------|--------|----------------|------------|
| Forward | 5'-agtgcacctgcacaccttt-3' | 19 | 1480 | 360 |
| Probe | TET-5'-cttgttcttctgtctcacgcctccg-3'-TAMRA | 25 | 1500 | 361 |
| Reverse | 5'-atcagtcactggtggaatgact-3' | 22 | 1558 | 362 |

TABLE AMD

Panel 4D

| Tissue Name | Rel. Exp. (%) Ag1166, Run 140171235 | Tissue Name | Rel. Exp. (%) Ag1166, Run 140171235 |
|---|---|---|---|
| Secondary Th1 act | 39.5 | HUVEC IL-1beta | 8.1 |
| Secondary Th2 act | 38.4 | HUVEC IFN gamma | 31.0 |
| Secondary Tr1 act | 41.5 | HUVEC TNF alpha + IFN gamma | 11.5 |
| Secondary Th1 rest | 20.9 | HUVEC TNF alpha + IL4 | 18.4 |
| Secondary Th2 rest | 26.1 | HUVEC IL-11 | 10.7 |
| Secondary Tr1 rest | 24.3 | Lung Microvascular EC none | 31.6 |
| Primary Th1 act | 29.5 | Lung Microvascular EC TNF alpha + IL-1beta | 20.6 |
| Primary Th2 act | 40.9 | Microvascular Dermal EC none | 73.7 |
| Primary Tr1 act | 52.1 | Microsvascular Dermal EC TNF alpha + IL-1beta | 45.7 |
| Primary Th1 rest | 82.4 | Bronchial epithelium TNF alpha + IL1beta | 44.4 |
| Primary Th2 rest | 44.8 | Small airway epithelium none | 13.5 |
| Primary Tr1 rest | 54.3 | Small airway epithelium TNF alpha + IL-1beta | 67.8 |
| CD45RA CD4 lymphocyte act | 15.6 | Coronery artery SMC rest | 19.9 |
| CD45RO CD4 lymphocyte act | 33.0 | Coronery artery SMC TNF alpha + IL-1beta | 24.3 |
| CD8 lymphocyte act | 28.9 | Astrocytes rest | 9.9 |
| Secondary CD8 lymphocyte rest | 33.7 | Astrocytes TNF alpha + IL-1beta | 21.3 |
| Secondary CD8 lymphocyte act | 18.3 | KU-812 (Basophil) rest | 27.0 |
| CD4 lymphocyte none | 18.3 | KU-812 (Basophil) PMA/ionomycin | 58.2 |
| 2ry Th1/Th2/Tr1_anti-CD95 CH11 | 42.9 | CCD1106 (Keratinocytes) none | 5.4 |
| LAK cells rest | 43.2 | CCD1106 (Keratinocytes) TNF alpha + IL-1beta | 17.9 |
| LAK cells IL-2 | 42.3 | Liver cirrhosis | 7.5 |
| LAK cells IL-2 + IL-12 | 42.3 | Lupus kidney | 16.4 |
| LAK cells IL-2 + IFN gamma | 41.8 | NCI-H292 none | 50.3 |
| LAK cells IL-2 + IL-18 | 36.6 | NCI-H292 IL-4 | 40.1 |
| LAK cells PMA/ionomycin | 13.0 | NCI-H292 IL-9 | 42.0 |
| NK Cells IL-2 rest | 21.3 | NCI-H292 IL-13 | 34.9 |
| Two Way MLR 3 day | 41.2 | NCI-H292 IFN gamma | 19.3 |
| Two Way MLR 5 day | 30.4 | HPAEC none | 22.1 |
| Two Way MLR 7 day | 19.5 | HPAEC TNF alpha + IL-1beta | 17.1 |
| PBMC rest | 12.8 | Lung fibroblast none | 17.8 |
| PBMC PWM | 100.0 | Lung fibroblast TNF alpha + IL-1beta | 11.8 |
| PBMC PHA-L | 77.4 | Lung fibroblast IL-4 | 33.4 |
| Ramos (B cell) none | 59.9 | Lung fibroblast IL-9 | 19.1 |
| Ramos (B cell) ionomycin | 88.9 | Lung fibroblast IL-13 | 51.8 |
| B lymphocytes PWM | 34.4 | Lung fibroblast IFN gamma | 40.3 |
| B lymphocytes CD40L and IL-4 | 17.7 | Dermal fibroblast CCD1070 rest | 29.9 |
| EOL-1 dbcAMP | 20.9 | Dermal fibroblast CCD1070 TNF alpha | 46.7 |
| EOL-1 dbcAMP PMA/ionomycin | 24.3 | Dermal fibroblast CCD1070 IL-1beta | 23.2 |
| Dendritic cells none | 25.2 | Dermal fibroblast IFN gamma | 20.2 |
| Dendritic cells LPS | 19.2 | Dermal fibroblast IL-4 | 38.4 |
| Dendritic cells anti-CD40 | 32.5 | IBD Colitis 2 | 3.4 |
| Monocytes rest | 26.4 | IBD Crohn's | 3.0 |
| Monocytes LPS | 31.6 | Colon | 17.1 |
| Macrophages rest | 35.4 | Lung | 23.7 |
| Macrophages LPS | 30.4 | Thymus | 87.1 |
| HUVEC none | 21.5 | Kidney | 43.2 |
| HUVEC starved | 33.4 | | |

Panel 4D Summary: Ag1166 Highest expression of the CG91587-01 gene is detected in PWM treated PBMC cells (CT=28.8). This gene is expressed at high to moderate levels in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. This ubiquitous pattern of expression suggests that this gene product may be involved in homeostatic processes for these and other cell types and tissues. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

AN. CG91911-01: Mitogen-Activated Protein Kinase Kinase Kinase 8 (MAP3K8)

Expression of gene CG91911-01 was assessed using the primer-probe sets Ag3116, Ag3551 and Ag4828, described in Tables ANA, ANB and ANC. Results of the RTQ-PCR runs are shown in Tables AND, ANE, ANF, ANG, ANH and ANI.

TABLE ANA

Probe Name Ag3116

| Primers | Sequences | Length | Start Position | SEQ ID NO: |
|---|---|---|---|---|
| Forward | 5'-catgttctcaagggacttgatt-3' | 22 | 802 | 363 |
| Probe | TET-5'-cactcaaagaaagtgatccatcatga-3'-TAMRA | 26 | 829 | 364 |
| Reverse | 5'-ttttgtggacatgaaaacaatg-3' | 22 | 870 | 365 |

TABLE ANB

Probe Name Ag3551

| Primers | Sequences | Length | Start Position | SEQ ID NO: |
|---|---|---|---|---|
| Forward | 5'-catgttctcaagggacttgatt-3' | 22 | 802 | 366 |
| Probe | TET-5'-cactcaaagaaagtgatccatcatga-3'-TAMRA | 26 | 829 | 367 |
| Reverse | 5'-ttttgtggacatgaaaacaatg-3' | 22 | 870 | 368 |

TABLE ANC

Probe Name Ag4828

| Primers | Sequences | Length | Start Position | SEQ ID NO: |
|---|---|---|---|---|
| Forward | 5'-gaggaatctgagatgctcaaga-3' | 22 | 1393 | 369 |
| Probe | TET-5'-caacgctctctctacatcgacctcgg-3'-TAMRA | 26 | 1417 | 370 |
| Reverse | 5'-tccccgaacaagattgaagt-3' | 20 | 1457 | 371 |

TABLE AND

CNS_neurodegeneration_v1.0

| Tissue Name | Rel. Exp. (%) Ag3551, Run 209990366 | Tissue Name | Rel. Exp. (%) Ag3551, Run 209990366 |
|---|---|---|---|
| AD 1 Hippo | 20.0 | Control (Path) 3 Temporal Ctx | 14.6 |
| AD 2 Hippo | 44.1 | Control (Path) 4 Temporal Ctx | 18.8 |
| AD 3 Hippo | 7.1 | AD 1 Occipital Ctx | 13.5 |
| AD 4 Hippo | 5.6 | AD 2 Occipital Ctx (Missing) | 0.0 |
| AD 5 hippo | 100.0 | AD 3 Occipital Ctx | 4.0 |
| AD 6 Hippo | 57.0 | AD 4 Occipital Ctx | 15.8 |
| Control 2 Hippo | 24.7 | AD 5 Occipital Ctx | 34.6 |
| Control 4 Hippo | 51.4 | AD 6 Occipital Ctx | 46.0 |
| Control (Path) 3 Hippo | 48.6 | Control 1 Occipital Ctx | 21.0 |
| AD 1 Temporal Ctx | 21.3 | Control 2 Occipital Ctx | 41.5 |
| AD 2 Temporal Ctx | 39.5 | Control 3 Occipital Ctx | 16.3 |
| AD 3 Temporal Ctx | 6.1 | Control 4 Occipital Ctx | 13.0 |
| AD 4 Temporal Ctx | 16.8 | Control (Path) 1 Occipital Ctx | 95.3 |
| AD 5 Inf Temporal Ctx | 100.0 | Control (Path) 2 Occipital Ctx | 10.2 |
| AD 5 SupTemporal Ctx | 91.4 | Control (Path) 3 Occipital Ctx | 21.5 |
| AD 6 Inf Temporal Ctx | 58.2 | Control (Path) 4 Occipital Ctx | 24.0 |
| AD 6 Sup Temporal Ctx | 65.5 | Control 1 Parietal Ctx | 17.2 |
| Control 1 Temporal Ctx | 20.3 | Control 2 Parietal Ctx | 57.4 |
| Control 2 Temporal Ctx | 21.2 | Control 3 Parietal Ctx | 16.5 |
| Control 3 Temporal Ctx | 10.8 | Control (Path) 1 Parietal Ctx | 28.3 |
| Control 4 Temporal Ctx | 6.9 | Control (Path) 2 Parietal Ctx | 15.8 |
| Control (Path) 1 Temporal Ctx | 42.0 | Control (Path) 3 Parietal Ctx | 19.6 |
| Control (Path) 2 Temporal Ctx | 26.4 | Control (Path) 4 Parietal Ctx | 61.1 |

TABLE ANE

General_screening_panel_v1.4

| Tissue Name | Rel. Exp. (%) Ag3116, Run 219923407 | Rel. Exp. (%) Ag3551, Run 218328114 | Rel. Exp. (%) Ag4828, Run 217081802 | Tissue Name | Rel. Exp. (%) Ag3116, Run 219923407 | Rel. Exp. (%) Ag3551, Run 218328114 | Rel. Exp. (%) Ag4828, Run 217081802 |
|---|---|---|---|---|---|---|---|
| Adipose | 100.0 | 58.2 | 53.6 | Renal ca. TK-10 | 6.4 | 8.2 | 10.6 |
| Melanoma* Hs688(A).T | 18.8 | 9.0 | 15.5 | Bladder | 32.5 | 24.1 | 31.9 |
| Melanoma* Hs688(B).T | 21.3 | 10.7 | 17.4 | Gastric ca. (liver met.) NCI-N87 | 26.8 | 23.5 | 36.3 |
| Melanoma* M14 | 1.0 | 0.9 | 3.5 | Gastric ca. KATO III | 8.7 | 8.0 | 12.2 |
| Melanoma* LOXIMVI | 2.9 | 1.5 | 3.2 | Colon ca. SW-948 | 2.6 | 2.6 | 5.4 |
| Melanoma* SK-MEL-5 | 0.8 | 0.8 | 0.9 | Colon ca. SW480 | 13.5 | 12.3 | 25.0 |
| Squamous cell carcinoma SCC-4 | 1.0 | 2.2 | 7.0 | Colon ca.* (SW480 met) SW620 | 1.6 | 1.4 | 2.5 |
| Testis Pool | 3.5 | 3.3 | 4.7 | Colon ca. HT29 | 7.2 | 5.7 | 14.3 |
| Prostate ca.* (bone met) PC-3 | 6.4 | 1.8 | 6.3 | Colon ca. HCT-116 | 2.1 | 1.7 | 2.1 |
| Prostate Pool | 2.1 | 2.0 | 3.9 | Colon ca. CaCo-2 | 13.5 | 15.7 | 15.9 |
| Placenta | 30.8 | 25.9 | 39.0 | Colon cancer tissue | 34.9 | 42.3 | 39.8 |
| Uters Pool | 7.7 | 4.7 | 9.0 | Colon ca. SW1116 | 0.1 | 0.3 | 3.4 |
| Ovarian ca. OVCAR-3 | 4.4 | 6.1 | 15.7 | Colon ca. Colo-205 | 2.7 | 2.6 | 8.8 |
| Ovarian ca. SK-OV-3 | 9.7 | 18.2 | 46.3 | Colon ca. SW-48 | 3.3 | 4.7 | 5.4 |
| Ovarian ca. OVCAR-4 | 3.7 | 5.4 | 7.1 | Colon Pool | 16.6 | 9.8 | 16.2 |
| Ovarian ca. OVCAR-5 | 19.2 | 19.9 | 30.6 | Small Intestine Pool | 7.3 | 5.5 | 9.3 |
| Ovarian ca. IGROV-1 | 7.0 | 9.1 | 14.1 | Stomach Pool | 6.6 | 8.0 | 17.3 |
| Ovarian ca. OVCAR-8 | 1.8 | 1.9 | 2.7 | Bone Marrow Pool | 5.2 | 3.3 | 7.0 |
| Ovary | 2.7 | 2.5 | 4.5 | Fetal Heart | 4.5 | 4.6 | 2.9 |
| Breast ca. MCF-7 | 64.6 | 81.8 | 100.0 | Heart Pool | 9.2 | 6.8 | 7.9 |
| Breast ca. MDA-MB-231 | 3.1 | 2.1 | 9.2 | Lymph Node Pool | 10.4 | 9.9 | 15.2 |
| Breast ca. BT 549 | 24.5 | 36.3 | 73.2 | Fetal Skeletal Muscle | 2.4 | 2.9 | 1.7 |
| Breast ca. T47D | 37.4 | 60.3 | 66.0 | Skeletal Muscle Pool | 7.7 | 8.5 | 9.8 |
| Breast ca. MDA-N | 0.3 | 0.5 | 0.9 | Spleen Pool | 16.0 | 22.8 | 45.7 |
| Breast Pool | 33.2 | 9.8 | 24.1 | Thymus Pool | 7.5 | 6.9 | 15.9 |
| Trachea | 14.5 | 15.5 | 18.0 | CNS cancer (glio/astro) U87-MG | 2.1 | 2.4 | 7.6 |
| Lung | 4.2 | 3.4 | 6.7 | CNS cancer (glio/astro) U-118-MG | 5.4 | 2.7 | 7.9 |
| Fetal Lung | 83.5 | 100.0 | 68.3 | CNS cancer (neuro; met) SK-N-AS | 0.7 | 1.2 | 2.6 |
| Lung ca. NCI-N417 | 0.0 | 0.0 | 0.2 | CNS cancer (astro) SF-539 | 1.4 | 1.8 | 2.3 |
| Lung ca. LX-1 | 8.0 | 6.0 | 11.8 | CNS cancer (astro) SNB-75 | 4.7 | 5.9 | 14.1 |
| Lung ca. NCI-H146 | 0.0 | 0.0 | 0.0 | CNS cancer (glio) SNB-19 | 6.2 | 10.7 | 11.1 |
| Lung ca. SHP-77 | 0.0 | 0.0 | 0.1 | CNS cancer (glio) SF-295 | 16.0 | 18.8 | 31.9 |
| Lung ca. A549 | 35.4 | 0.0 | 36.6 | Brain (Amygdala) Pool | 1.6 | 0.7 | 2.7 |
| Lung ca. NCI-H526 | 0.0 | 0.0 | 0.0 | Brain (cerebellum) | 1.1 | 0.3 | 1.4 |

TABLE ANE-continued

General_screening_panel_v1.4

| Tissue Name | Rel. Exp. (%) Ag3116, Run 219923407 | Rel. Exp. (%) Ag3551, Run 218328114 | Rel. Exp. (%) Ag4828, Run 217081802 | Tissue Name | Rel. Exp. (%) Ag3116, Run 219923407 | Rel. Exp. (%) Ag3551, Run 218328114 | Rel. Exp. (%) Ag4828, Run 217081802 |
|---|---|---|---|---|---|---|---|
| Lung ca. NCI-H23 | 10.9 | 13.0 | 13.4 | Brain (fetal) | 6.0 | 4.1 | 4.9 |
| Lung ca. NCI-H460 | 7.4 | 5.8 | 17.6 | Brain (Hippocampus) Pool | 3.6 | 1.5 | 3.7 |
| Lung ca. HOP-62 | 11.4 | 4.3 | 13.2 | Cerebral Cortex Pool | 2.1 | 2.0 | 3.5 |
| Lung ca. NCI-H522 | 1.6 | 1.5 | 2.1 | Brain (Substantia nigra) Pool | 2.4 | 2.0 | 2.7 |
| Liver | 0.6 | 0.2 | 1.0 | Brain (Thalamus) Pool | 2.6 | 2.2 | 4.5 |
| Fetal Liver | 5.0 | 4.0 | 2.8 | Brain (whole) | 2.7 | 2.5 | 4.5 |
| Liver ca. HepG2 | 4.5 | 5.4 | 8.1 | Spinal Cord Pool | 2.1 | 3.2 | 3.8 |
| Kidney Pool | 26.6 | 21.0 | 31.4 | Adrenal Gland | 11.7 | 3.8 | 9.5 |
| Fetal Kidney | 9.0 | 10.7 | 7.7 | Pituitary gland Pool | 0.7 | 0.7 | 1.4 |
| Renal ca. 786-0 | 6.0 | 7.9 | 10.9 | Salivary Gland | 1.9 | 1.5 | 2.5 |
| Renal ca. A498 | 1.2 | 2.3 | 5.2 | Thyroid (female) | 3.3 | 3.6 | 7.7 |
| Renal ca. ACHN | 1.9 | 0.8 | 2.5 | Pancreatic ca. CAPAN2 | 14.9 | 21.9 | 34.4 |
| Renal ca. UO-31 | 11.1 | 10.7 | 14.9 | Pancreas Pool | 15.0 | 17.8 | 19.6 |

TABLE ANF

Panel 1.3D

| Tissue Name | Rel. Exp. (%) Ag3116, Run 167617379 | Tissue Name | Rel. Exp. (%) Ag3116, Run 167617379 |
|---|---|---|---|
| Liver adenocarcinoma | 24.8 | Kidney (fetal) | 34.2 |
| Pancreas | 3.4 | Renal ca. 786-0 | 3.7 |
| Pancreatic ca. CAPAN 2 | 12.1 | Renal ca. A498 | 3.3 |
| Adrenal gland | 2.6 | Renal ca. RXF 393 | 17.1 |
| Thyroid | 1.3 | Renal ca. ACHN | 1.7 |
| Salivary gland | 0.0 | Renal ca. UO-31 | 0.8 |
| Pituitary gland | 2.1 | Renal ca. TK-10 | 4.4 |
| Brain (fetal) | 3.1 | Liver | 2.4 |
| Brain (whole) | 3.1 | Liver (fetal) | 4.5 |
| Brain (amygdala) | 1.0 | Liver ca. (hepatoblast) HepG2 | 4.4 |
| Brain (cerebellum) | 1.0 | Lung | 25.0 |
| Brain (hippocampus) | 3.0 | Lung (fetal) | 29.7 |
| Brain (substantia nigra) | 3.7 | Lung ca. (small cell) LX-1 | 5.5 |
| Brain (thalamus) | 1.2 | Lung ca. (small cell) NCI-H69 | 0.0 |
| Cerebral Cortex | 2.5 | Lung ca. (s.cell var.) SHP-77 | 0.0 |
| Spinal cord | 3.0 | Lung ca. (large cell)NCI-H460 | 2.3 |
| glio/astro U87-MG | 1.5 | Lung ca. (non-sm. cell) A549 | 14.3 |
| glio/astro U-118-MG | 2.8 | Lung ca. (non-s.cell) NCI-H23 | 5.0 |
| astrocytoma SW1783 | 2.0 | Lung ca. (non-s.cell) HOP-62 | 5.7 |
| neuro*; met SK-N-AS | 1.5 | Lung ca. (non-s.cl) NCI-H522 | 1.2 |
| astrocytoma SF-539 | 2.4 | Lung ca. (squam.) SW 900 | 24.1 |
| astrocytoma SNB-75 | 14.5 | Lung ca. (squam.) NCI-H596 | 0.0 |
| glioma SNB-19 | 0.0 | Mammary gland | 7.7 |
| glioma U251 | 0.7 | Breast ca.* (pl.ef) MCF-7 | 57.8 |

TABLE ANF-continued

Panel 1.3D

| Tissue Name | Rel. Exp. (%) Ag3116, Run 167617379 | Tissue Name | Rel. Exp. (%) Ag3116, Run 167617379 |
| --- | --- | --- | --- |
| glioma SF-295 | 6.9 | Breast ca.* (pl.ef) MDA-MB-231 | 0.8 |
| Heart (fetal) | 5.8 | Breast ca.* (pl.ef) T47D | 3.5 |
| Heart | 3.2 | Breast ca. BT-549 | 4.8 |
| Skeletal muscle (fetal) | 4.6 | Breast ca. MDA-N | 0.0 |
| Skeletal muscle | 2.1 | Ovary | 6.1 |
| Bone marrow | 4.0 | Ovarian ca. OVCAR-3 | 3.0 |
| Thymus | 3.4 | Ovarian ca. OVCAR-4 | 26.1 |
| Spleen | 10.6 | Ovarian ca. OVCAR-5 | 44.8 |
| Lymph node | 10.3 | Ovarian ca. OVCAR-8 | 1.4 |
| Colorectal | 6.4 | Ovarian ca. IGROV-1 | 6.4 |
| Stomach | 1.8 | Ovarian ca.* (ascites) SK-OV-3 | 33.2 |
| Small intestine | 3.0 | Uterus | 4.4 |
| Colon ca. SW480 | 6.0 | Placenta | 6.8 |
| Colon ca.* SW620(SW480 met) | 6.1 | Prostate | 0.0 |
| Colon ca. HT29 | 6.6 | Prostate ca.* (bone met)PC-3 | 2.1 |
| Colon ca. HCT-116 | 0.0 | Testis | 0.0 |
| Colon ca. CaCo-2 | 11.3 | Melanoma Hs688(A).T | 1.0 |
| Colon ca. tissue(ODO3866) | 13.1 | Melanoma* (met) Hs688(B).T | 3.5 |
| Colon ca. HCC-2998 | 17.6 | Melanoma UACC-62 | 0.0 |
| Gastric ca.* (liver met) NCI-N87 | 11.0 | Melanoma M14 | 1.1 |
| Bladder | 10.2 | Melanoma LOX IMVI | 1.2 |
| Trachea | 3.9 | Melanoma* (met) SK-MEL-5 | 0.0 |
| Kidney | 5.0 | Adipose | 100.0 |

TABLE ANG

Panel 2D

| Tissue Name | Rel. Exp. (%) Ag3116, Run 169556216 | Tissue Name | Rel. Exp. (%) Ag3116, Run 169556216 |
| --- | --- | --- | --- |
| Normal Colon | 58.2 | Kidney Margin 8120608 | 2.0 |
| CC Well to Mod Diff (ODO3866) | 22.7 | Kidney Cancer 8120613 | 3.5 |
| CC Margin (ODO3866) | 14.4 | Kidney Margin 8120614 | 2.9 |
| CC Gr.2 rectosigmoid (ODO3868) | 7.5 | Kidney Cancer 9010320 | 42.0 |
| CC Margin (ODO3868) | 3.4 | Kidney Margin 9010321 | 7.7 |
| CC Mod Diff (ODO3920) | 7.0 | Normal Uterus | 7.0 |
| CC Margin (ODO3920) | 6.9 | Uterus Cancer 064011 | 18.8 |
| CC Gr.2 ascend colon (ODO3921) | 27.7 | Normal Thyroid | 5.8 |
| CC Margin (ODO3921) | 8.4 | Thyroid Cancer 064010 | 6.9 |
| CC from Partial Hepatectomy (ODO4309) Mets | 34.9 | Thyroid Cancer A302152 | 3.0 |
| Liver Margin (ODO4309) | 8.5 | Thyroid Margin A302153 | 12.1 |
| Colon mets to lung (OD04451-01) | 12.2 | Normal Breast | 28.9 |
| Lung Margin (OD04451-02) | 21.8 | Breast Cancer (OD04566) | 6.3 |
| Normal Prostate 6546-1 | 2.9 | Breast Cancer (OD04590-01) | 44.4 |
| Prostate Cancer (OD04410) | 7.4 | Breast Cancer Mets (OD04590-03) | 43.5 |
| Prostate Margin (OD04410) | 8.2 | Breast Cancer Metastasis (OD04655-05) | 6.9 |
| Prostate Cancer (OD04720-01) | 6.6 | Breast Cancer 064006 | 12.0 |
| Prostate Margin (OD04720-02) | 21.8 | Breast Cancer 1024 | 12.9 |
| Normal Lung 061010 | 42.6 | Breast Cancer 9100266 | 6.9 |
| Lung Met to Muscle (ODO4286) | 15.0 | Breast Margin 9100265 | 6.9 |
| Muscle Margin (ODO4286) | 9.5 | Breast Cancer A209073 | 7.2 |
| Lung Malignant Cancer (OD03126) | 17.4 | Breast Margin A209073 | 4.3 |
| Lung Margin (OD03126) | 59.5 | Normal Liver | 2.3 |

TABLE ANG-continued

Panel 2D

| Tissue Name | Rel. Exp. (%) Ag3116, Run 169556216 | Tissue Name | Rel. Exp. (%) Ag3116, Run 169556216 |
|---|---|---|---|
| Lung Cancer (OD04404) | 53.6 | Liver Cancer 064003 | 2.1 |
| Lung Margin (OD04404) | 45.1 | Liver Cancer 1025 | 5.8 |
| Lung Cancer (OD04565) | 10.4 | Liver Cancer 1026 | 4.2 |
| Lung Margin (OD04565) | 10.8 | Liver Cancer 6004-T | 6.1 |
| Lung Cancer (OD04237-01) | 39.8 | Liver Tissue 6004-N | 6.4 |
| Lung Margin (OD04237-02) | 65.5 | Liver Cancer 6005-T | 7.4 |
| Ocular Mel Met to Liver (ODO4310) | 1.6 | Liver Tissue 6005-N | 3.9 |
| Liver Margin (ODO4310) | 9.9 | Normal Bladder | 37.1 |
| Melanoma Mets to Lung (OD04321) | 2.0 | Bladder Cancer 1023 | 6.5 |
| Lung Margin (OD04321) | 50.7 | Bladder Cancer A302173 | 14.8 |
| Normal Kidney | 13.0 | Bladder Cancer (OD04718-01) | 27.9 |
| Kidney Ca, Nuclear grade 2 (OD04338) | 16.4 | Bladder Normal Adjacent (OD04718-03) | 100.0 |
| Kidney Margin (OD04338) | 18.4 | Normal Ovary | 6.3 |
| Kidney Ca Nuclear grade 1/2 (OD04339) | 10.3 | Ovarian Cancer 064008 | 31.9 |
| Kidney Margin (OD04339) | 6.5 | Ovarian Cancer (OD04768-07) | 21.9 |
| Kidney Ca, Clear cell type (OD04340) | 28.7 | Ovary Margin (OD04768-08) | 32.5 |
| Kidney Margin (OD04340) | 22.7 | Normal Stomach | 18.8 |
| Kidney Ca, Nuclear grade 3 (OD04348) | 4.5 | Gastric Cancer 9060358 | 14.6 |
| Kidney Margin (OD04348) | 6.7 | Stomach Margin 9060359 | 16.2 |
| Kidney Cancer (OD04622-01) | 12.2 | Gastric Cancer 9060395 | 33.2 |
| Kidney Margin (OD04622-03) | 1.8 | Stomach Margin 9060394 | 24.8 |
| Kidney Cancer (OD04450-01) | 4.0 | Gastric Cancer 9060397 | 26.8 |
| Kidney Margin (OD04450-03) | 7.1 | Stomach Margin 9060396 | 7.4 |
| Kidney Cancer 8120607 | 3.3 | Gastric Cancer 064005 | 27.4 |

TABLE ANH

Panel 4D

| Tissue Name | Rel. Exp. (%) Ag3116, Run 164526105 | Rel. Exp. (%) Ag3551, Run 166453851 | Tissue Name | Rel. Exp. (%) Ag3116, Run 164526105 | Rel. Exp. (%) Ag3551, Run 166453851 |
|---|---|---|---|---|---|
| Secondary Th1 act | 15.6 | 38.4 | HUVEC IL-1 beta | 0.8 | 8.2 |
| Secondary Th2 act | 23.0 | 56.3 | HUVEC IFN gamma | 1.4 | 1.2 |
| Secondary Tr1 act | 23.2 | 78.5 | HUVEC TNF alpha + IFN gamma | 3.0 | 3.1 |
| Secondary Th1 rest | 2.9 | 22.8 | HUVEC TNF alpha + IL4 | 2.5 | 2.6 |
| Secondary Th2 rest | 2.5 | 4.5 | HUVEC IL-11 | 0.5 | 0.5 |
| Secondary Tr1 rest | 2.0 | 7.0 | Lung Microvascular EC none | 0.0 | 0.1 |
| Primary Th1 act | 13.5 | 18.3 | Lung Microvascular EC TNF alpha + IL-1 beta | 4.2 | 2.8 |
| Primary Th2 act | 6.6 | 15.5 | Microvascular Dermal EC none | 0.1 | 0.1 |
| Primary Tr1 act | 17.7 | 33.2 | Microvascular Dermal EC TNF alpha + IL-1 beta | 5.7 | 7.3 |
| Primary Th1 rest | 9.2 | 32.1 | Bronchial epithelium TNF alpha + IL1 beta | 2.4 | 1.5 |
| Primary Th2 rest | 1.2 | 2.9 | Small airway epithelium none | 0.6 | 1.1 |
| Primary Tr1 rest | 1.7 | 3.8 | Small airway epithelium TNF alpha + IL-1 beta | 5.5 | 5.0 |
| CD45RA CD4 lymphocyte act | 4.9 | 6.7 | Coronery artery SMC rest | 1.0 | 0.8 |
| CD45RO CD4 lymphocyte act | 11.1 | 44.8 | Coronery artery SMC TNF alpha + IL-1 beta | 0.7 | 0.6 |
| CD8 lymphocyte act | 5.3 | 12.2 | Astrocytes rest | 0.5 | 1.0 |

TABLE ANH-continued

Panel 4D

| Tissue Name | Rel. Exp. (%) Ag3116, Run 164526105 | Rel. Exp. (%) Ag3551, Run 166453851 | Tissue Name | Rel. Exp. (%) Ag3116, Run 164526105 | Rel. Exp. (%) Ag3551, Run 166453851 |
|---|---|---|---|---|---|
| Secondary CD8 lymphocyte rest | 4.9 | 16.0 | Astrocytes TNF alpha + IL-1 beta | 14.9 | 61.1 |
| Secondary CD8 lymphocyte act | 7.6 | 25.5 | KU-812 (Basophil) rest | 0.2 | 0.2 |
| CD4 lymphocyte none | 0.8 | 1.1 | KU-812 (Basophil) PMA/ionomycin | 1.0 | 1.5 |
| 2ry Th1/Th2/Tr1_anti-CD95 CH11 | 3.0 | 11.0 | CCD1106 (Keratinocytes) none | 0.4 | 0.5 |
| LAK cells rest | 6.8 | 5.3 | CCD1106 (Keratinocytes) TNF alpha + IL-1 beta | 0.8 | 12.4 |
| LAK cells IL-2 | 6.4 | 23.2 | Liver cirrhosis | 1.1 | 5.3 |
| LAK cells IL-2 + IL-12 | 22.4 | 73.7 | Lupus kidney | 1.1 | 4.8 |
| LAK cells IL-2 + IFN gamma | 17.4 | 44.1 | NCI-H292 none | 8.4 | 9.7 |
| LAK cells IL-2 + IL-18 | 12.2 | 25.0 | NCI-H292 IL-4 | 17.6 | 18.4 |
| LAK cells PMA/ionomycin | 12.3 | 20.7 | NCI-H292 IL-9 | 6.5 | 5.3 |
| NK Cells IL-2 rest | 12.9 | 23.0 | NCI-H292 IL-13 | 9.2 | 12.0 |
| Two Way MLR 3 day | 12.5 | 24.0 | NCI-H292 IFN gamma | 4.3 | 3.5 |
| Two Way MLR 5 day | 6.0 | 17.1 | HPAEC none | 0.5 | 0.5 |
| Two Way MLR 7 day | 3.0 | 6.3 | HPAEC TNF alpha + IL-1 beta | 8.2 | 11.0 |
| PBMC rest | 4.0 | 5.4 | Lung fibroblast none | 0.2 | 1.0 |
| PBMC PWM | 100.0 | 49.3 | Lung fibroblast TNF alpha + IL-1 beta | 1.7 | 9.8 |
| PBMC PHA-L | 11.8 | 5.6 | Lung fibroblast IL-4 | 3.3 | 3.2 |
| Ramos (B cell) none | 0.8 | 2.0 | Lung fibroblast IL-9 | 0.9 | 0.5 |
| Ramos (B cell) ionomycin | 16.7 | 6.5 | Lung fibroblast IL-13 | 1.4 | 1.8 |
| B lymphocytes PWM | 53.2 | 25.3 | Lung fibroblast IFN gamma | 3.4 | 4.0 |
| B lymphocytes CD40L and IL-4 | 61.1 | 81.8 | Dermal fibroblast CCD1070 rest | 1.9 | 1.1 |
| EOL-1 dbcAMP | 0.7 | 0.4 | Dermal fibroblast CCD1070 TNF alpha | 11.9 | 13.7 |
| EOL-1 dbcAMP PMA/ionomycin | 2.2 | 3.0 | Dermal fibroblast CCD1070 IL-1 beta | 6.1 | 6.3 |
| Dendritic cells none | 4.8 | 8.7 | Dermal fibroblast IFN gamma | 0.6 | 0.9 |
| Dendritic cells LPS | 12.3 | 25.2 | Dermal fibroblast IL-4 | 4.2 | 6.7 |
| Dendritic cells anti-CD40 | 3.2 | 6.8 | IBD Colitis 2 | 1.1 | 4.1 |
| Monocytes rest | 5.0 | 7.3 | IBD Crohn's | 1.8 | 6.0 |
| Monocytes LPS | 43.8 | 100.0 | Colon | 2.6 | 15.7 |
| Macrophages rest | 8.2 | 11.7 | Lung | 8.2 | 7.5 |
| Macrophages LPS | 26.8 | 57.4 | Thymus | 2.3 | 3.5 |
| HUVEC none | 0.2 | 0.5 | Kidney | 4.2 | 3.8 |
| HUVEC starved | 0.6 | 1.5 | | | |

TABLE ANI

Panel 5D

| Tissue Name | Rel. Exp. (%) Ag3116, Run 170863008 | Rel. Exp. (%) Ag4828, Run 219436967 | Tissue Name | Rel. Exp. (%) Ag3116, Run 170863008 | Rel. Exp. (%) Ag4828, Run 219436967 |
|---|---|---|---|---|---|
| 97457_Patient-02go_adipose | 33.4 | 33.9 | 94709_Donor 2 AM - A_adipose | 5.1 | 10.8 |
| 97476_Patient-07sk_skeletal muscle | 31.2 | 33.4 | 94710_Donor 2 AM - $B_N$_adipode | 3.2 | 9.3 |
| 97477_Patient-07ut_uterus | 7.7 | 59.5 | 94711_Donor 2 AM - C_adipose | 0.0 | 3.0 |
| 97478_Patient-07pl_placenta | 62.0 | 39.8 | 94712_Donor 2 AD - A_adipose | 12.9 | 13.7 |
| 97481_Patient-08sk_skeletal muscle | 20.0 | 25.9 | 94713_Donor 2 AD - B_adipose | 12.9 | 10.0 |
| 97482_Patient-08ut_uterus | 33.4 | 19.8 | 94714_Donor 2 AD - C_adipose | 8.8 | 6.7 |
| 97483_Patient-08pl_placenta | 58.6 | 41.5 | 94742_Donor 3 U - A_Mesenchymal Stem Cells | 1.6 | 4.7 |
| 97486_Patient-09sk_skeletal muscle | 3.7 | 6.5 | 94743_Donor 3 U - B_Mesenchymal Stem Cells | 4.8 | 2.8 |
| 97487_Patient-09ut_uterus | 13.6 | 8.1 | 94730_Donor 3 AM - A_adipose | 6.8 | 6.3 |
| 97488_Patient-09pl_placenta | 41.2 | 38.4 | 94731_Donor 3 AM - B_adipose | 5.3 | 2.4 |
| 97492_Patient-10ut_uterus | 31.9 | 30.6 | 94732_Donor 3 AM - C_adipose | 1.9 | 2.2 |
| 97493_Patient-10pl_placenta | 74.7 | 72.7 | 94733_Donor 3 AD - A_adipose | 2.5 | 10.2 |
| 97495_Patient-11go_adipose | 67.4 | 100.0 | 94734_Donor 3 AD - B_adipose | 2.9 | 5.5 |
| 97496_Patient-11sk_skeletal muscle | 9.0 | 5.8 | 94735_Donor 3 AD - C_adipose | 6.7 | 4.7 |
| 97497_Patient-11ut_uterus | 35.4 | 20.6 | 77138_Liver_HepG2untreated | 13.0 | 14.4 |
| 97498_Patient-11pl_placenta | 52.1 | 50.0 | 73556_Heart_Cardiac stromal cells (primary) | 9.1 | 1.9 |
| 97500_Patient-12go_adipose | 100.0 | 82.4 | 81735_Small Intestine | 20.0 | 17.2 |
| 97501_Patient-12sk_skeletal muscle | 14.2 | 19.2 | 72409_Kidney_Proximal Convoluted Tubule | 0.0 | 0.9 |
| 97502_Patient-12ut_uterus | 51.8 | 23.7 | 82685_Small intestine_Duodenum | 13.5 | 19.1 |
| 97503_Patient-12pl_placenta | 39.5 | 57.0 | 90650_Adrenal_Adrenocortical adenoma | 7.3 | 8.8 |
| 94721_Donor 2 U - A_Mesenchymal Stem Cells | 2.1 | 1.6 | 72410_Kidney_HRCE | 9.9 | 7.6 |
| 94722_Donor 2 U - B_Mesenchymal Stem Cells | 0.0 | 3.0 | 72411_Kidney_HRE | 5.9 | 13.5 |
| 94723_Donor 2 U - C_Mesenchymal Stem Cells | 1.8 | 2.1 | 73139_Uterus_Uterine smooth muscle cells | 2.5 | 2.0 |

CNS_neurodegeneration_v1.0 Summary: Ag3551 This panel confirms the expression of the CG91911-01 gene at low levels in the brains of an independent group of individuals. However, no differential expression of this gene was detected between Alzheimer's diseased postmortem brains and those of non-demented controls in this experiment. Please see Panel 1.4 for a discussion of the potential utility of this gene in treatment of central nervous system disorders.

General_screening_panel_v1.4 Summary: Ag3116/Ag3551/Ag4828 Results of three experiments with two different probes and primer sets are in excellent agreement. Highest expression of the CG91911-01 gene is detected in adipose (29.6), fetal lung (CT=30) and breast cancer MCF-7 cell line(CT=27.6). Interestingly, this gene is expressed at much higher levels in fetal (CT=28–30) when compared to adult lung (CT=31–35). This observation suggests that expression of this gene can be used to distinguish fetal from adult lung. In addition, the relative overexpression of this gene in fetal lung suggests that the protein product may enhance lung growth or development in the fetus and thus may also act in a regenerative capacity in the adult. Therefore, therapeutic modulation of the protein encoded by this gene could be useful in treatment of lung related diseases.

In addition significant expression of this gene is found in number of cancer (pancreatic, CNS, colon, lung, breast, ovary, prostate, melanoma) cell lines. Therefore, therapeutic modulation of the activity of this gene or its protein product, through the use of small molecule drugs, might be beneficial in the treatment of these cancers.

Among tissues with metabolic or endocrine function, this gene is expressed at high to moderate levels in pancreas, adipose, adrenal gland, thyroid, skeletal muscle, heart, fetal liver and the gastrointestinal tract. Therefore, therapeutic modulation of the activity of this gene may prove useful in the treatment of endocrine/metabolically related diseases, such as obesity and diabetes.

In addition, this gene is expressed at high levels in all regions of the central nervous system examined, including amygdala, hippocampus, substantia nigra, thalamus, cerebellum, cerebral cortex, and spinal cord. The CG91911-01 gene codes for mitogen-activated protein kinase kinase kinase 8 (MAP3K8). Recently, MKK6, a related protein has been shown to associated with Alzheimer's disease (Zhu X, Rottkamp C A, Hartzler A, Sun Z, Takeda A, Boux H, Shimohama S, Perry G, Smith M A. (2001) Activation of MKK6, an upstream activator of p38, in Alzheimer's disease. J Neurochem 79(2):311–8). Therefore, in analogy to MKK6 and the expression in brain, we predict that MAP3K8 may play a role in central nervous system disorders such as Alzheimer's disease, Parkinson's disease, epilepsy, multiple sclerosis, schizophrenia and depression.

Ag3551 Results from one experiment with the CG91911-01 gene are not included. The amp plot indicates that there were experimental difficulties with this run.

Panel 1.3D Summary: Ag3116 Highest expression of the CG91911-01 gene is detected in adipose (32.75). Low to moderate expression of this gene is also seen in number of ovarian cancer cell lines, liver adenocarcinoma and breast cancer MCF-7 cell line. Therefore, therapeutic modulation of the activity of this gene or its protein product, through the use of small molecule drugs, might be beneficial in the treatment of these cancers.

In addition, low expression of this gene is also seen in fetal kidney and lung. Interestingly, this gene is expressed at much higher levels in fetal (CT=34.3) when compared to adult kidney (CT=37). This observation suggests that expression of this gene can be used to distinguish fetal from adult kidney. In addition, the relative overexpression of this gene in fetal lung suggests that the protein product may enhance lung growth or development in the fetus and thus may also act in a regenerative capacity in the adult. Therefore, therapeutic modulation of the protein encoded by this gene could be useful in treatment of lung related diseases.

Panel 2D Summary: Ag3116 Highest expression of the CG91911-01 gene is detected in normal bladder (OD04718-03) sample (CT=31.4). Low to moderate expression of this gene is seen in large number of normal and cancer samples. Please see Panel 1.4 for a discussion of the potential utility of this gene.

Panel 4D Summary: Ag3116/Ag3551 Results from two experiments with same primer and probe set are in excellent agreement. Highest expression of the CG91911-01 gene is detected in PWM treated PBMC and LPS treated monocytes (CTs=28–29). Interestingly, expression of this gene is stimulated in activated primary Th2 and Tr1, activated secondary Th1, Th2, Tr1, PWM treated PBMC, LPS treated monocytes, TNFalpha+IL-1beta treated astrocytes and keratinocytes. Thus, expression of this gene can be used to distinguish between these activated or treated cells from the corresponding untreated or resting cells.

In addition low expression of this gene is seen in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

Panel 5D Summary: Ag3116/Ag4828 Results from two experiments with different primer and probe set are in excellent agreement. Highest expression of the CG91911-01 gene is detected in adipose tissue (CTs=29–33). Low to moderate expression of this gene is seen in wide range of samples used in this panel including adipose, skeletal muscle, uterus, and placenta. This wide spread expression of this gene in tissues with metabolic or endocrine function, suggests that this gene plays a role in endocrine/metabolically related diseases, such as obesity and diabetes.

The CG91911-01 gene codes for mitogen-activated protein kinase kinase kinase 8 (MAP3K8). Recently, activation of MAP kinase, ERK, a related protein, by modified LDL in vascular smooth muscle cells has been implicated in the development of atherosclerosis in diabetes (Velarde V, Jenkins A J, Christopher J, Lyons T J, Jaffa A A. (2001) Activation of MAPK by modified low-density lipoproteins in vascular smooth muscle cells. J Appl Physiol 91(3):1412–20). Therefore, MAP3K8 may also play a role in the development of this disease and therapeutic modulation of the activity of this gene or its protein product, through the use of small molecule drugs, might be beneficial in the treatment of artherosclerosis and diabetes.

AO. CG91941-01: Serine/Threonine-Protein Kinase

Expression of gene CG91941-01 was assessed using the primer-probe sets Ag3744 and Ag3746, described in Tables AOA and AOB. Results of the RTQ-PCR runs are shown in Tables AOC and AOD.

TABLE AOA

Probe Name Ag3744

| Primers | Sequences | Length | Start Position | SEQ ID NO: |
|---|---|---|---|---|
| Forward | 5'-ggctgcttgctgtatgagttat-3' | 22 | 631 | 372 |
| Probe | TET-5'-tgcattaatgcctccatttacagctt-3'-TAMRA | 26 | 654 | 373 |
| Reverse | 5'-tttcccagcgagttctttct-3' | 20 | 686 | 374 |

TABLE AOB

Probe Name Ag3746

| Primers | Sequences | Length | Start Position | SEQ ID NO: |
|---|---|---|---|---|
| Forward | 5'-ggctgcttgctgtatgagttat-3' | 22 | 631 | 375 |
| Probe | TET-5'-tgcattaatgcctccatttacagctt-3'-TAMRA | 26 | 654 | 376 |
| Reverse | 5'-tttcccagcgagttctttct-3' | 20 | 686 | 377 |

TABLE AOC

| | General_screening_panel_v1.4 | | | | |
|---|---|---|---|---|---|
| Tissue Name | Rel. Exp. (%) Ag3744, Run 218296857 | Rel. Exp. (%) Ag3746, Run 218297971 | Tissue Name | Rel. Exp. (%) Ag3744, Run 218296857 | Rel. Exp. (%) Ag3746, Run 218297971 |
| Adipose | 0.3 | 0.1 | Renal ca. TK-10 | 41.2 | 37.9 |
| Melanoma* Hs688(A).T | 1.2 | 1.5 | Bladder | 3.6 | 3.7 |
| Melanoma* Hs688(B).T | 1.9 | 1.9 | Gastric ca. (liver met.) NCI-N87 | 12.2 | 13.2 |
| Melanoma* M14 | 32.1 | 38.7 | Gastric ca. KATO III | 76.8 | 88.9 |
| Melanoma* LOXIMVI | 30.8 | 28.5 | Colon ca. SW-948 | 15.4 | 12.9 |
| Melanoma* SK-MEL-5 | 52.1 | 48.0 | Colon ca. SW480 | 48.0 | 44.1 |
| Squamous cell carcinoma SCC-4 | 40.9 | 42.6 | Colon ca.* (SW480 met) SW620 | 47.0 | 44.1 |
| Testis Pool | 40.9 | 37.9 | Colon ca. HT29 | 39.8 | 31.9 |
| Prostate ca.* (bone met) PC-3 | 17.2 | 18.2 | Colon ca. HCT-116 | 59.5 | 81.2 |
| Prostate Pool | 0.1 | 0.0 | Colon ca. CaCo-2 | 46.0 | 56.3 |
| Placenta | 0.3 | 0.2 | Colon cancer tissue | 8.9 | 9.3 |
| Uterus Pool | 0.1 | 0.0 | Colon ca. SW1116 | 11.7 | 11.7 |
| Ovarian ca. OVCAR-3 | 43.2 | 40.9 | Colon ca. Colo-205 | 27.9 | 23.5 |
| Ovarian ca. SK-OV-3 | 52.1 | 57.0 | Colon ca. SW-48 | 19.3 | 17.2 |
| Ovarian ca. OVCAR-4 | 11.3 | 7.7 | Colon Pool | 0.1 | 0.3 |
| Ovarian ca. OVCAR-5 | 33.0 | 28.9 | Small Intestine Pool | 0.2 | 0.2 |
| Ovarian ca. IGROV-1 | 9.7 | 9.3 | Stomach Pool | 0.3 | 0.2 |
| Ovarian ca. OVCAR-8 | 4.6 | 4.9 | Bone Marrow Pool | 0.2 | 0.1 |
| Ovary | 0.3 | 0.3 | Fetal Heart | 2.8 | 2.7 |
| Breast ca. MCF-7 | 16.2 | 19.3 | Heart Pool | 0.0 | 0.0 |
| Breast ca. MDA-MB-231 | 92.7 | 86.5 | Lymph Node Pool | 0.5 | 0.7 |
| Breast ca. BT 549 | 100.0 | 100.0 | Fetal Skeletal Muscle | 0.3 | 0.4 |
| Breast ca. T47D | 44.1 | 57.8 | Skeletal Muscle Pool | 0.0 | 0.0 |
| Breast ca. MDA-N | 19.9 | 21.6 | Spleen Pool | 1.0 | 1.4 |
| Breast Pool | 0.4 | 0.1 | Thymus Pool | 4.8 | 4.3 |
| Trachea | 0.6 | 0.8 | CNS cancer (glio/astro) U87-MG | 13.6 | 13.7 |
| Lung | 0.0 | 0.0 | CNS cancer (glio/astro) U-118-MG | 35.8 | 36.9 |
| Fetal Lung | 5.1 | 3.7 | CNS cancer (neuro; met) SK-N-AS | 45.7 | 48.3 |
| Lung ca. NCI-N417 | 5.6 | 5.7 | CNS cancer (astro) SF-539 | 25.9 | 30.4 |
| Lung ca. LX-1 | 43.8 | 42.9 | CNS cancer (astro) SNB-75 | 43.5 | 47.0 |
| Lung ca. NCI-H146 | 19.1 | 18.4 | CNS cancer (glio) SNB-19 | 5.7 | 7.5 |
| Lung ca. SHP-77 | 44.1 | 42.0 | CNS cancer (glio) SF-295 | 6.0 | 6.0 |
| Lung ca. A549 | 60.3 | 48.0 | Brain (Amygdala) Pool | 0.0 | 0.1 |
| Lung ca. NCI-H526 | 9.0 | 9.5 | Brain (cerebellum) | 0.0 | 0.0 |
| Lung ca. NCI-H23 | 41.8 | 38.7 | Brain (fetal) | 0.9 | 0.9 |
| Lung ca. NCI-H460 | 0.3 | 0.2 | Brain (Hippocampus) Pool | 0.0 | 0.1 |
| Lung ca. HOP-62 | 5.9 | 6.3 | Cerebral Cortex Pool | 0.2 | 0.2 |
| Lung ca. NCI-H522 | 32.8 | 28.5 | Brain (Substantia nigra) Pool | 0.1 | 0.0 |
| Liver | 0.0 | 0.0 | Brain (Thalamus) Pool | 0.1 | 0.2 |

TABLE AOC-continued

General_screening_panel_v1.4

| Tissue Name | Rel. Exp. (%) Ag3744, Run 218296857 | Rel. Exp. (%) Ag3746, Run 218297971 | Tissue Name | Rel. Exp. (%) Ag3744, Run 218296857 | Rel. Exp. (%) Ag3746, Run 218297971 |
|---|---|---|---|---|---|
| Fetal Liver | 12.2 | 14.6 | Brain (whole) | 0.2 | 0.2 |
| Liver ca. HepG2 | 14.7 | 13.8 | Spinal Cord Pool | 0.0 | 0.1 |
| Kidney Pool | 0.0 | 0.1 | Adrenal Gland | 0.1 | 0.1 |
| Fetal Kidney | 8.0 | 5.4 | Pituitary gland Pool | 0.0 | 0.1 |
| Renal ca. 786-0 | 43.5 | 43.8 | Salivary Gland | 0.0 | 0.0 |
| Renal ca. A498 | 6.5 | 6.2 | Thyroid (female) | 0.0 | 0.1 |
| Renal ca. ACHN | 17.2 | 14.9 | Pancreatic ca. CAPAN2 | 70.7 | 72.2 |
| Renal ca. UO-31 | 13.7 | 11.9 | Pancreas Pool | 0.5 | 0.3 |

TABLE AOD

Panel 4.1D

| Tissue Name | Rel. Exp. (%) Ag3744, Run 170068295 | Rel. Exp. (%) Ag3746, Run 170068664 | Rel. Exp. (%) Ag3746, Run 197450453 | Tissue Name | Rel. Exp. (%) Ag3744, Run 170068295 | Rel. Exp. (%) Ag3746, Run 170068664 | Rel. Exp. (%) Ag3746, Run 197450453 |
|---|---|---|---|---|---|---|---|
| Secondary Th1 act | 60.7 | 42.9 | 59.0 | HUVEC IL-1 beta | 32.8 | 29.3 | 33.0 |
| Secondary Th2 act | 40.9 | 30.8 | 47.3 | HUVEC IFN gamma | 27.7 | 25.2 | 39.2 |
| Secondary Tr1 act | 62.4 | 41.8 | 41.5 | HUVEC TNF alpha + IFN gamma | 24.3 | 13.5 | 20.3 |
| Secondary Th1 rest | 10.4 | 8.4 | 10.8 | HUVEC TNF alpha + IL4 | 22.7 | 16.0 | 26.1 |
| Secondary Th2 rest | 13.8 | 11.3 | 13.5 | HUVEC IL-11 | 14.2 | 10.9 | 18.3 |
| Secondary Tr1 rest | 7.7 | 9.6 | 5.0 | Lung Microvascular EC none | 15.3 | 10.8 | 21.0 |
| Primary Th1 act | 19.6 | 13.8 | 12.9 | Lung Microvascular EC TNF alpha + IL-1 beta | 12.4 | 10.4 | 18.8 |
| Primary Th2 act | 29.3 | 20.6 | 26.4 | Microvascular Dermal EC none | 28.9 | 15.3 | 32.3 |
| Primary Tr1 act | 28.9 | 20.2 | 29.3 | Microsvasular Dermal EC TNF alpha + IL-1 beta | 16.4 | 11.4 | 21.6 |
| Primary Th1 rest | 42.6 | 40.6 | 26.1 | Bronchial epithelium TNF alpha + IL1 beta | 2.0 | 2.8 | 3.3 |
| Primary Th2 rest | 31.2 | 20.2 | 13.4 | Small airway epithelium none | 1.5 | 0.9 | 1.0 |
| Primary Tr1 rest | 35.8 | 25.7 | 33.4 | Small airway epithelium TNF alpha + IL-1 beta | 4.2 | 2.8 | 3.9 |
| CD45RA CD4 lymphocyte act | 44.1 | 36.1 | 69.3 | Coronery artery SMC rest | 7.1 | 4.5 | 7.0 |
| CD45RO CD4 lymphocyte act | 36.1 | 26.8 | 38.4 | Coronery artery SMC TNF alpha + IL-1 beta | 6.8 | 3.8 | 4.6 |
| CD8 lymphocyte act | 51.1 | 33.9 | 36.1 | Astrocytes rest | 1.7 | 2.2 | 2.0 |
| Secondary CD8 lymphocyte rest | 25.5 | 18.4 | 27.2 | Astrocytes TNF alpha + IL-1 beta | 0.9 | 0.4 | 1.0 |
| Secondary CD8 lymphocyte act | 50.7 | 24.1 | 27.2 | KU-812 (Basophil) rest | 51.1 | 38.4 | 46.0 |
| CD4 lymphocyte none | 0.0 | 0.3 | 0.0 | KU-812 (Basophil) PMA/ionomycin | 40.1 | 32.3 | 52.1 |

TABLE AOD-continued

Panel 4.1D

| Tissue Name | Rel. Exp. (%) Ag3744, Run 170068295 | Rel. Exp. (%) Ag3746, Run 170068664 | Rel. Exp. (%) Ag3746, Run 197450453 | Tissue Name | Rel. Exp. (%) Ag3744, Run 170068295 | Rel. Exp. (%) Ag3746, Run 170068664 | Rel. Exp. (%) Ag3746, Run 197450453 |
|---|---|---|---|---|---|---|---|
| 2ry Th1/Th2/Tr1_anti-CD95 CH11 | 33.4 | 17.8 | 36.3 | CCD1106 (Keratinocytes) none | 39.2 | 19.8 | 35.8 |
| LAK cells rest | 4.5 | 1.9 | 2.6 | CCD1106 (Keratinocytes) TNF alpha + IL-1 beta | 16.6 | 11.3 | 12.8 |
| LAK cells IL-2 | 50.7 | 31.4 | 44.4 | Liver cirrhosis | 1.0 | 1.2 | 2.5 |
| LAK cells IL-2 + IL-12 | 27.5 | 20.3 | 25.9 | NCI-H292 none | 34.2 | 23.3 | 33.9 |
| LAK cells IL-2 + IFN gamma | 40.6 | 23.5 | 22.8 | NCI-H292 IL-4 | 61.1 | 42.0 | 45.4 |
| LAK cells IL-2 + IL-18 | 35.1 | 21.5 | 24.7 | NCI-H292 IL-9 | 88.9 | 51.1 | 66.0 |
| LAK cells PMA/ionomycin | 1.1 | 1.5 | 1.2 | NCI-H292 IL-13 | 56.3 | 40.1 | 53.6 |
| NK Cells IL-2 rest | 44.4 | 47.3 | 62.0 | NCI-H292 IFN gamma | 50.3 | 37.9 | 37.1 |
| Two Way MLR 3 day | 3.8 | 5.2 | 3.6 | HPAEC none | 20.0 | 11.7 | 10.5 |
| Two Way MLR 5 day | 17.3 | 18.7 | 23.8 | HPAEC TNF alpha + IL-1 beta | 13.7 | 9.0 | 11.2 |
| Two Way MLR 7 day | 24.1 | 22.7 | 23.3 | Lung fibroblast none | 8.2 | 4.5 | 7.3 |
| PBMC rest | 0.4 | 0.2 | 0.2 | Lung fibroblast TNF alpha + IL-1 beta | 12.2 | 12.2 | 13.9 |
| PBMC PWM | 25.5 | 18.6 | 23.2 | Lung fibroblast IL-4 | 2.1 | 0.5 | 0.9 |
| PBMC PHA-L | 41.5 | 27.9 | 48.3 | Lung fibroblast IL-9 | 4.4 | 3.0 | 3.1 |
| Ramos (B cell) none | 65.1 | 42.9 | 48.0 | Lung fibroblast IL-13 | 1.2 | 0.4 | 0.6 |
| Ramos (B cell) ionomycin | 45.7 | 32.1 | 54.0 | Lung fibroblast IFN gamma | 0.3 | 1.1 | 1.1 |
| B lymphocytes PWM | 24.7 | 19.5 | 38.4 | Dermal fibroblast CCD1070 rest | 87.1 | 69.3 | 83.5 |
| B lymphocytes CD40L and IL-4 | 27.9 | 20.7 | 25.3 | Dermal fibroblast CCD1070 TNF alpha | 100.0 | 100.0 | 100.0 |
| EOL-1 dbcAMP | 20.7 | 12.2 | 20.4 | Dermal fibroblast CCD1070 IL-1 beta | 52.5 | 37.1 | 52.9 |
| EOL-1 dbcAMP PMA/ionomycin | 21.5 | 14.0 | 15.8 | Dermal fibroblast IFN gamma | 20.2 | 14.0 | 23.3 |
| Dendritic cells none | 1.7 | 0.4 | 1.2 | Dermal fibroblast IL-4 | 32.8 | 20.6 | 29.3 |
| Dendritic cells LPS | 0.2 | 0.1 | 0.0 | Dermal Fibroblasts rest | 23.8 | 12.5 | 23.0 |
| Dendritic cells anti-CD40 | 0.0 | 0.0 | 0.2 | Neutrophils TNFa + LPS | 0.0 | 0.0 | 0.0 |
| Monocytes rest | 0.0 | 0.0 | 0.0 | Neutrophils rest | 0.0 | 0.0 | 0.0 |
| Monocytes LPS | 0.0 | 0.0 | 0.0 | Colon | 6.3 | 1.9 | 1.9 |
| Macrophages rest | 4.4 | 2.3 | 2.9 | Lung | 0.4 | 0.4 | 1.8 |
| Macrophages LPS | 1.0 | 0.4 | 0.9 | Thymus | 41.2 | 23.0 | 27.2 |
| HUVEC none | 30.4 | 23.7 | 28.1 | Kidney | 0.2 | 0.0 | 0.2 |
| HUVEC starved | 45.1 | 33.9 | 51.8 | | | | |

CNS_neurodegeneration_v1.0 Summary: Ag3744/Ag3746 Expression of the CG91941-01 gene is low/undetectable (CTs>35) across all of the samples on this panel (data not shown).

General_screening$_{13}$ panel_v1.4 Summary: Ag3744/Ag3746 Two experiments with same primer and probe sets are in excellent agreement with highest expression of the CG91941-01 gene in breast cancer BT 549 sample (CT=28). Interestingly, high expression of this gene is seen mainly in all the cancer cell lines (pancreatic, CNS, colon, renal, liver, lung, breast, ovarian, prostate, squamous cell carcinoma and melanoma). Thus, expression of this gene can be used as diagnostic marker for detection of these cancers and therapeutic modulation of the activity of this gene or its protein product, through the use of small molecule drugs, protein therapeutics or antibodies, might be beneficial in the treatment of these cancers.

Interestingly, this gene is expressed at much higher levels in fetal (CTs=31–34.8) when compared to adult liver, lung and heart (CTs=37–40). This observation suggests that expression of this gene can be used to distinguish fetal from adult liver, lung and hear. In addition, the relative overexpression of this gene in fetal liver, lung and heart suggests that the protein product may enhance growth or development of these tissues in the fetus and thus may also act in a regenerative capacity in the adult.

Panel 4.1D Summary: Ag3744/Ag3746 Three experiments with same primer and probe sets are in excellent agreement with highest expression of the CG91941-01 gene in TNF alpha treated dermal fibroblast CCD1070 (CT= 29–30). High to moderate expression of this gene is also seen in dermal fibroblasts, NCI-H292, basophils, keratinocytes, endothelial cells, EOL-1 dbcAMP, members of B and T cells, and thymus. Interestingly, expression of this gene is stimulated in PWM/PHA treated PBMC cells, and cytokine treated LAK cells. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

AP. CG91951-01: /Threonine-Protein Kinase

Expression of gene CG91951-01 was assessed using the primer-probe set Ag3747, described in Table APA. Results of the RTQ-PCR runs are shown in Tables APB and APC.

TABLE APA

Probe Name Ag3747

| Primers | Sequences | Length | Start Position | SEQ ID NO: |
|---|---|---|---|---|
| Forward | 5'-ttggggctagccagaatattaa-3' | 22 | 502 | 378 |
| Probe | TET-5'-accacgacacgagttttgcaaaa-3'-TAMRA | 23 | 524 | 379 |
| Reverse | 5'-aggacatgtgattcgtttgttc-3' | 22 | 580 | 380 |

TABLE APB

General_screening_panel_V1.4

| Tissue Name | Rel. Exp. (%) Ag3747, Run 218298221 | Tissue Name | Rel. Exp. (%) Ag3747, Run 218298221 |
|---|---|---|---|
| Adipose | 0.0 | Renal ca. TK-10 | 1.6 |
| Melanoma* Hs688(A).T | 0.4 | Bladder | 2.4 |
| Melanoma* Hs688(B).T | 0.0 | Gastric ca. (liver met.) NCI-N87 | 0.9 |
| Melanoma* M14 | 2.2 | Gastric ca. KATO III | 16.2 |
| Melanoma* LOXIMVI | 1.7 | Colon ca. SW-948 | 0.0 |
| Melanoma* SK-MEL-5 | 100.0 | Colon ca. SW480 | 1.3 |
| Squamous cell carcinoma SCC-4 | 0.4 | Colon ca.* (SW480 met) SW620 | 3.2 |
| Testis Pool | 33.7 | Colon ca. HT29 | 0.0 |
| Prostate ca.* (bone met) PC-3 | 0.9 | Colon ca. HCT-116 | 7.9 |
| Prostate Pool | 46.3 | Colon ca. CaCo-2 | 0.6 |
| Placenta | 0.0 | Colon cancer tissue | 0.0 |
| Uterus Pool | 0.0 | Colon ca. SW1116 | 0.6 |
| Ovarian ca. OVCAR-3 | 33.0 | Colon ca. Colo-205 | 0.3 |
| Ovarian ca. SK-OV-3 | 3.5 | Colon ca. SW-48 | 1.0 |
| Ovarian ca. OVCAR-4 | 0.0 | Colon Pool | 2.5 |
| Ovarian ca. OVCAR-5 | 0.9 | Small Intestine Pool | 0.0 |
| Ovarian ca. IGROV-1 | 6.7 | Stomach Pool | 0.0 |
| Ovarian ca. OVCAR-8 | 5.0 | Bone Marrow Pool | 0.0 |
| Ovary | 0.0 | Fetal Heart | 0.0 |
| Breast ca. MCF-7 | 1.3 | Heart Pool | 3.8 |
| Breast ca. MDA-MB-231 | 1.2 | Lymph Node Pool | 0.7 |
| Breast ca. BT 549 | 6.9 | Fetal Skeletal Muscle | 0.0 |
| Breast ca. T47D | 0.0 | Skeletal Muscle Pool | 0.0 |
| Breast ca. MDA-N | 12.2 | Spleen Pool | 0.0 |
| Breast Pool | 0.0 | Thymus Pool | 1.0 |
| Trachea | 0.0 | CNS cancer (glio/astro) U87-MG | 2.5 |
| Lung | 0.4 | CNS cancer (glio/astro) U-118-MG | 13.0 |
| Fetal Lung | 1.8 | CNS cancer (neuro; met) SK-N-AS | 3.4 |
| Lung ca. NCI-N417 | 0.0 | CNS cancer (astro) SF-539 | 2.2 |
| Lung ca. LX-1 | 2.5 | CNS cancer (astro) SNB-75 | 1.9 |
| Lung ca. NCI-H146 | 1.7 | CNS cancer (glio) SNB-19 | 6.6 |
| Lung ca. SHP-77 | 52.5 | CNS cancer (glio) SF-295 | 31.6 |
| Lung ca. A549 | 7.6 | Brain (Amygdala) Pool | 0.7 |
| Lung ca. NCI-H526 | 0.0 | Brain (cerebellum) | 0.0 |
| Lung ca. NCI-H23 | 15.9 | Brain (fetal) | 6.0 |
| Lung ca. NCI-H460 | 0.9 | Brain (Hippocampus) Pool | 1.8 |

TABLE APB-continued

General_screening_panel_V1.4

| Tissue Name | Rel. Exp. (%) Ag3747, Run 218298221 | Tissue Name | Rel. Exp. (%) Ag3747, Run 218298221 |
|---|---|---|---|
| Lung ca. HOP-62 | 0.7 | Cerebral Cortex Pool | 1.9 |
| Lung ca. NCI-H522 | 1.0 | Brain (Substantia nigra) Pool | 1.7 |
| Liver | 0.0 | Brain (Thalamus) Pool | 0.3 |
| Fetal Liver | 23.7 | Brain (whole) | 0.0 |
| Liver ca. HepG2 | 0.5 | Spinal Cord Pool | 0.9 |
| Kidney Pool | 0.5 | Adrenal Gland | 1.0 |
| Fetal Kidney | 0.0 | Pituitary gland Pool | 0.0 |
| Renal ca. 786-0 | 0.6 | Salivary Gland | 0.0 |
| Renal ca. A498 | 0.0 | Thyroid (female) | 0.0 |
| Renal ca. ACHN | 2.0 | Pancreatic ca. CAPAN2 | 0.0 |
| Renal ca. UO-31 | 3.6 | Pancreas Pool | 1.2 |

TABLE APC

Panel 4.1D

| Tissue Name | Rel. Exp. (%) Ag3747, Run 198383569 | Tissue Name | Rel. Exp. (%) Ag3747, Run 198383569 |
|---|---|---|---|
| Secondary Th1 act | 0.1 | HUVEC IL-1beta | 0.0 |
| Secondary Th2 act | 0.1 | HUVEC IFN gamma | 0.1 |
| Secondary Tr1 act | 0.1 | HUVEC TNF alpha + IFN gamma | 0.0 |
| Secondary Th1 rest | 0.0 | HUVEC TNF alpha + IL4 | 0.1 |
| Secondary Th2 rest | 0.0 | HUVEC IL-11 | 0.0 |
| Secondary Tr1 rest | 0.0 | Lung Microvascular EC none | 0.2 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 0.2 | Microsvascular Dermal EC TNF alpha + IL-1beta | 0.1 |
| Primary Th1 rest | 0.3 | Bronchial epithelium TNF alpha + IL1beta | 0.0 |
| Primary Th2 rest | 0.0 | Small airway epithelium none | 0.0 |
| Primary Tr1 rest | 0.0 | Small airway epithelium TNF alpha + IL-1beta | 0.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1beta | 0.0 |
| CD8 lymphocyte act | 0.1 | Astrocytes rest | 0.1 |
| Secondary CD8 lymphocyte rest | 0.0 | Astrocytes TNF alpha + IL-1beta | 0.0 |
| Secondary CD8 lymphocyte act | 0.0 | KU-812 (Basophil) rest | 0.1 |
| CD4 lymphocyte none | 0.1 | KU-812 (Basophil) PMA/ionomycin | 0.4 |
| 2ry Th1/Th2/Tr1_anti-CD95 CH11 | 0.1 | CCD1106 (Keratinocytes) none | 0.2 |
| LAK cells rest | 0.0 | CCD1106 (Keratinocytes) TNF alpha + IL-1beta | 0.0 |
| LAK cells IL-2 | 0.2 | Liver cirrhosis | 0.0 |
| LAK cells IL-2 + IL-12 | 0.0 | NCI-H292 none | 0.0 |
| LAK cells IL-2 + IFN gamma | 0.0 | NCI-H292 IL-4 | 0.1 |
| LAK cells IL-2 + IL-18 | 0.0 | NCI-H292 IL-9 | 0.3 |
| LAK cells PMA/ionomycin | 0.0 | NCI-H292 IL-13 | 0.0 |
| NK Cells IL-2 rest | 0.1 | NCI-H292 IFN gamma | 0.0 |
| Two Way MLR 3 day | 0.0 | HPAEC none | 0.0 |
| Two Way MLR 5 day | 0.0 | HPAEC TNF alpha + IL-1beta | 0.0 |
| Two Way MLR 7 day | 0.0 | Lung fibroblast none | 0.2 |
| PBMC rest | 0.0 | Lung fibroblast TNF alpha + IL-1beta | 0.0 |
| PBMC PWM | 0.0 | Lung fibroblast IL-4 | 0.0 |
| PBMC PHA-L | 0.0 | Lung fibroblast IL-9 | 0.0 |
| Ramos (B cell) none | 0.1 | Lung fibroblast IL-13 | 0.4 |
| Ramos (B cell) ionomycin | 0.1 | Lung fibroblast IFN gamma | 0.3 |
| B lymphocytes PWM | 0.0 | Dermal fibroblast CCD1070 rest | 0.6 |
| B lymphocytes CD40L | 0.0 | Dermal fibroblast CCD1070 | 0.3 |

TABLE APC-continued

Panel 4.1D

| Tissue Name | Rel. Exp. (%) Ag3747, Run 198383569 | Tissue Name | Rel. Exp. (%) Ag3747, Run 198383569 |
|---|---|---|---|
| and IL-4 | | TNF alpha | |
| EOL-1 dbcAMP | 0.0 | Dermal fibroblast CCD1070 IL-1beta | 0.0 |
| EOL-1 dbcAMP PMA/ionomycin | 0.2 | Dermal fibroblast IFN gamma | 0.2 |
| Dendritic cells none | 0.0 | Dermal fibroblast IL-4 | 0.2 |
| Dendritic cells LPS | 0.0 | Dermal Fibroblasts rest | 0.8 |
| Dendritic cells anti-CD40 | 0.0 | Neutrophils TNFa + LPS | 0.5 |
| Monocytes rest | 0.0 | Neutrophils rest | 0.3 |
| Monocytes LPS | 0.1 | Colon | 0.6 |
| Macrophages rest | 0.0 | Lung | 2.0 |
| Macrophages LPS | 0.0 | Thymus | 13.3 |
| HUVEC none | 0.0 | Kidney | 100.0 |
| HUVEC starved | 0.1 | | |

CNS_neurodegeneration_v1.0 Summary: Ag3747 Expression of the CG91951-01 gene is low/undetectable (CTs>34.5) across all of the samples on this panel (data not shown).

General_screening_panel_v1.4 Summary: Ag3747 Highest expression of the CG91951-01 gene is detected in melanoma SK-MEL-5 cell line (CT=31.4). In addition, low to moderated expression is also seen in 2 CNS cancer, gastric cancer KATO III, two lung cancer breast cancer MDA-N and Ovarian cancer OVCAR-3 cell lines. Therefore, expression of this gene can be used as diagnostic marker to detect these cancers and therapeutic modulation of the activity of this gene or its protein product, through the use of small molecule drugs might be beneficial in the treatment of these cancers.

Moderate expression of this gene is also seen in testis, prostate, and fetal liver. Interestingly, this gene is expressed at much higher levels in fetal (CT=33.5) when compared to adult liver (CT=40). This observation suggests that expression of this gene can be used to distinguish fetal from adult liver. In addition, the relative overexpression of this gene in fetal liver suggests that the protein product may enhance growth or development of liver in the fetus and thus may also act in a regenerative capacity in the adult. Therefore, therapeutic modulation of the protein encoded by this gene could be useful in treatment of liver related diseases.

Panel 4.1D Summary: Ag3747 High expression of the CG91951-01 gene is detected in exclusively in kidney (CT=28.7). Therefore, small molecule therapies designed with the protein encoded for by this gene could modulate kidney function and be important in the treatment of inflammatory or autoimmune diseases that affect the kidney, including lupus and glomerulonephritis.

Results from one experiment, Run 170068966, with this gene using same primer and probe set are not included. The amp plot indicates that there were experimental difficulties with this run.

Panel 5 Islet Summary: Ag3747 Expression of the CG91951-01 gene is low/undetectable (CTs>35) across all of the samples on this panel (data not shown).

AQ. CG92025-01: Gamma-Glutamyltransferase 1

Expression of gene CG92025-01 was assessed using the primer-probe set Ag3766, described in Table AQA. Results of the RTQ-PCR runs are shown in Tables AQB, AQC and AQD.

TABLE AQA

Probe Name Ag3766

| Primers | Sequences | Length | Start Position | SEQ ID NO: |
|---|---|---|---|---|
| Forward | 5'-ctggctgacacctatgagatg-3' | 21 | 692 | 381 |
| Probe | TET-5'-aggccttctacaacggcagcctcat-3'-TAMRA | 25 | 732 | 382 |
| Reverse | 5'-ctggatgtccttcacaatctg-3' | 21 | 761 | 383 |

TABLE AQB

CNS_neurodegeneration_v1.0

| Tissue Name | Rel. Exp. (%) Ag3766, Run 211176203 | Tissue Name | Rel. Exp. (%) Ag3766, Run 211176203 |
|---|---|---|---|
| AD 1 Hippo | 15.3 | Control (Path) 3 Temporal Ctx | 16.0 |
| AD 2 Hippo | 14.7 | Control (Path) 4 Temporal Ctx | 22.2 |
| AD 3 Hippo | 11.3 | AD 1 Occipital Ctx | 16.4 |
| AD 4 Hippo | 8.2 | AD 2 Occipital Ctx (Missing) | 0.0 |
| AD 5 Hippo | 37.6 | AD 3 Occipital Ctx | 18.0 |
| AD 6 Hippo | 35.4 | AD 4 Occipital Ctx | 86.5 |
| Control 2 Hippo | 29.9 | AD 5 Occipital Ctx | 44.8 |

TABLE AQB-continued

CNS_neurodegeneration_v1.0

| Tissue Name | Rel. Exp. (%) Ag3766, Run 211176203 | Tissue Name | Rel. Exp. (%) Ag3766, Run 211176203 |
|---|---|---|---|
| Control 4 Hippo | 14.1 | AD 6 Occipital Ctx | 10.7 |
| Control (Path) 3 Hippo | 5.1 | Control 1 Occipital Ctx | 13.3 |
| AD 1 Temporal Ctx | 8.7 | Control 2 Occipital Ctx | 35.4 |
| AD 2 Temporal Ctx | 25.2 | Control 3 Occipital Ctx | 32.1 |
| AD 3 Temporal Ctx | 7.2 | Control 4 Occipital Ctx | 14.0 |
| AD 4 Temporal Ctx | 10.3 | Control (Path) 1 Occipital Ctx | 38.7 |
| AD 5 Inf Temporal Ctx | 34.4 | Control (Path) 2 Occipital Ctx | 7.5 |
| AD 5 Sup Temporal Ctx | 0.0 | Control (Path) 3 Occipital Ctx | 7.2 |
| AD 6 Inf Temporal Ctx | 100.0 | Control (Path) 4 Occipital Ctx | 21.3 |
| AD 6 Sup Temporal Ctx | 79.6 | Control 1 Parietal Ctx | 29.1 |
| Control 1 Temporal Ctx | 17.2 | Control 2 Parietal Ctx | 73.2 |
| Control 2 Temporal Ctx | 41.2 | Control 3 Parietal Ctx | 10.2 |
| Control 3 Temporal Ctx | 17.0 | Control (Path) 1 Parietal Ctx | 44.4 |
| Control 3 Temporal Ctx | 24.0 | Control (Path) 2 Parietal Ctx | 28.1 |
| Control (Path) 1 Temporal Ctx | 28.9 | Control (Path) 3 Parietal Ctx | 10.3 |
| Control (Path) 2 Temporal Ctx | 24.3 | Control (Path) 4 Parietal Ctx | 43.8 |

TABLE AQC

General_screening_panel_v1.4

| Tissue Name | Rel. Exp. (%) Ag3766, Run 218902548 | Tissue Name | Rel. Exp. (%) Ag3766, Run 218902548 |
|---|---|---|---|
| Adipose | 0.5 | Renal ca. TK-10 | 24.0 |
| Melanoma* Hs688(A).T | 0.1 | Bladder | 8.0 |
| Melanoma* Hs688(B).T | 0.7 | Gastric ca. (liver met.) NCI-N87 | 25.9 |
| Melanoma* M14 | 0.1 | Gastric ca. KATO III | 2.2 |
| Melanoma* LOXIMVI | 2.6 | Colon ca. SW-948 | 5.3 |
| Melanoma* SK-MEL-5 | 3.4 | Colon ca. SW480 | 0.5 |
| Squamous cell carcinoma SCC-4 | 5.6 | Colon ca.* (SW480 met) SW620 | 1.7 |
| Testis Pool | 2.9 | Colon ca. HT29 | 3.2 |
| Prostate ca.* (bone met) PC-3 | 0.2 | Colon ca. HCT-116 | 5.5 |
| Prostate Pool | 6.6 | Colon ca. CaCo-2 | 9.3 |
| Placenta | 0.6 | Colon cancer tissue | 39.0 |
| Uterus Pool | 0.1 | Colon ca. SW1116 | 0.3 |
| Ovarian ca. OVCAR-3 | 0.9 | Colon ca. Colo-205 | 1.8 |
| Ovarian ca. SK-OV-3 | 0.4 | Colon ca. SW-48 | 3.4 |
| Ovarian ca. OVCAR-4 | 0.0 | Colon Pool | 0.7 |
| Ovarian ca. OVCAR-5 | 27.9 | Small Intestine Pool | 1.3 |
| Ovarian ca. IGROV-1 | 7.6 | Stomach Pool | 1.1 |
| Ovarian ca. OVCAR-8 | 3.0 | Bone Marrow Pool | 0.2 |
| Ovary | 0.3 | Fetal Heart | 0.3 |
| Breast ca. MCF-7 | 1.2 | Heart Pool | 0.2 |
| Breast ca. MDA-MB-231 | 2.5 | Lymph Node Pool | 0.2 |
| Breast ca. BT 549 | 0.6 | Fetal Skeletal Muscle | 0.3 |
| Breast ca. T47D | 50.0 | Skeletal Muscle Pool | 0.3 |
| Breast ca. MDA-N | 0.2 | Spleen Pool | 1.1 |
| Breast Pool | 0.6 | Thymus pool | 2.1 |
| Trachea | 1.8 | CNS cancer (glio/astro) U87-MG | 41.2 |
| Lung | 0.1 | CNS cancer (glio/astro) U-118-MG | 10.9 |
| Fetal Lung | 1.4 | CNS cancer (neuro; met) SK-N-AS | 0.6 |
| Lung ca. NCI-N417 | 0.0 | CNS cancer (astro) SF-539 | 1.0 |
| Lung ca. LX-1 | 1.7 | CNS cancer (astro) SNB-75 | 0.8 |
| Lung ca. NCI-H146 | 0.0 | CNS cancer (glio) SNB-19 | 6.8 |

TABLE AQC-continued

General_screening_panel_v1.4

| Tissue Name | Rel. Exp. (%) Ag3766, Run 218902548 | Tissue Name | Rel. Exp. (%) Ag3766, Run 218902548 |
|---|---|---|---|
| Lung ca. SHP-77 | 3.4 | CNS cancer (glio) SF-295 | 6.8 |
| Lung ca. A549 | 32.3 | Brain (Amygdala) Pool | 1.0 |
| Lung ca. NCI-H526 | 0.1 | Brain (cerebellum) | 0.8 |
| Lung ca. NCI-H23 | 1.2 | Brain (fetal) | 0.6 |
| Lung ca. NCI-H460 | 12.2 | Brain (Hippocampus) Pool | 0.9 |
| Lung ca. HOP-62 | 5.1 | Cerebral Cortex Pool | 0.6 |
| Lung ca. NCI-H522 | 0.5 | Brain (Substantia nigra) Pool | 1.0 |
| Liver | 2.5 | Brain (Thalamus) Pool | 1.1 |
| Fetal Liver | 25.9 | Brain (whole) | 0.8 |
| Liver ca. HepG2 | 7.3 | Spinal Cord Pool | 3.1 |
| Kidney Pool | 1.1 | Adrenal Gland | 0.2 |
| Fetal Kidney | 4.2 | Pituitary gland Pool | 0.3 |
| Renal ca. 786-0 | 100.0 | Salivary Gland | 0.8 |
| Renal ca. A498 | 29.5 | Thyroid (female) | 2.8 |
| Renal ca. ACHN | 17.8 | Pancreatic ca. CAPAN2 | 1.3 |
| Renal ca. UO-31 | 8.0 | Pancreas Pool | 12.1 |

TABLE AQD

Panel 4.1D

| Tissue Name | Rel. Exp. (%) Ag3766, Run 170069662 | Tissue Name | Rel. Exp. (%) Ag3766, Run 170069662 |
|---|---|---|---|
| Secondary Th1 act | 37.1 | HUVEC IL-1beta | 1.5 |
| Secondary Th2 act | 34.6 | HUVEC IFN gamma | 0.5 |
| Secondary Tr1 act | 54.7 | HUVEC TNF alpha + IFN gamma | 0.6 |
| Secondary Th1 rest | 26.2 | HUVEC TNF alpha + IL4 | 1.1 |
| Secondary Th2 rest | 18.2 | HUVEC IL-11 | 1.0 |
| Secondary Tr1 rest | 14.1 | Lung Microvascular EC none | 3.4 |
| Primary Th1 act | 15.1 | Lung Microvascular EC TNF alpha + IL-1beta | 3.0 |
| Primary Th2 act | 21.3 | Microvascular Dermal EC none | 2.0 |
| Primary Tr1 act | 25.0 | Microvasular Dermal EC TNF alpha + IL-1beta | 1.2 |
| Primary Th1 rest | 8.7 | Bronchial epithelium TNF alpha + IL1beta | 8.2 |
| Primary Th2 rest | 7.3 | Small airway epithelium none | 4.8 |
| Primary Tr1 rest | 13.9 | Small airway epithelium TNF alpha + IL-1beta | 2.8 |
| CD45RA CD4 lymphocyte act | 2.8 | Coronery artery SMC rest | 0.0 |
| CD45RO CD4 lymphocyte act | 12.3 | Coronery artery SMC TNF alpha + IL-1beta | 0.7 |
| CD8 lymphocyte act | 11.0 | Astrocytes rest | 1.2 |
| Secondary CD8 lymphocyte rest | 14.5 | Astrocytes TNF alpha + IL-1beta | 3.5 |
| Secondary CD8 lymphocyte act | 8.7 | KU-812 (Basophil) rest | 6.8 |
| CD4 lymphocyte none | 2.7 | KU-812 (Basophil) PMA/ionomycin | 6.0 |
| 2ry Th1/Th2/Tr1_anti-CD95 CH11 | 15.3 | CCD1106 (Keratinocytes) none | 2.3 |
| LAK cells rest | 9.5 | CCD1106 (Keratinocytes) TNF alpha + IL-1beta | 4.5 |
| LAK cells IL-2 | 6.0 | Liver cirrhosis | 10.7 |
| LAK cells IL-2 + IL-12 | 7.7 | NCI-H292 none | 0.9 |
| LAK cells IL-2 + IFN gamma | 10.7 | NCI-H292 IL-4 | 1.0 |
| LAK cells IL-2 + IL-18 | 7.3 | NCI-H292 IL-9 | 0.4 |
| LAK cells PMA/ionomycin | 18.9 | NCI-H292 IL-13 | 1.2 |
| NK Cells IL-2 rest | 4.9 | NCI-H292 IFN gamma | 2.0 |
| Two Way MLR 3 day | 12.4 | HPAEC none | 1.3 |
| Two Way MLR 5 day | 10.3 | HPAEC TNF alpha + IL-1beta | 0.0 |
| Two Way MLR 7 day | 11.2 | Lung fibroblast none | 1.1 |
| PBMC rest | 6.1 | Lung fibroblast TNF alpha + IL-1beta | 0.0 |
| PBMC PWM | 7.0 | Lung fibroblast IL-4 | 0.0 |

TABLE AQD-continued

Panel 4.1D

| Tissue Name | Rel. Exp. (%) Ag3766, Run 170069662 | Tissue Name | Rel. Exp. (%) Ag3766, Run 170069662 |
|---|---|---|---|
| PBMC PHA-L | 9.3 | Lung fibroblast IL-9 | 0.3 |
| Ramos (B cell) none | 3.2 | Lung fibroblast IL-13 | 0.4 |
| Ramos (B cell) ionomycin | 7.1 | Lung fibroblast IFN gamma | 0.0 |
| B lymphocytes PWM | 4.2 | Dermal fibroblast CCD1070 rest | 0.0 |
| B lymphocytes CD40L and IL-4 | 7.8 | Dermal fibroblast CCD1070 TNF alpha | 4.8 |
| EOL-1 dbcAMP | 11.5 | Dermal fibroblast CCD1070 IL-1beta | 0.6 |
| EOL-1 dbcAMP PMA/ionomycin | 2.1 | Dermal fibroblast IFN gamma | 0.0 |
| Dendritic cells none | 20.7 | Dermal fibroblast IL-4 | 0.0 |
| Dendritic cells LPS | 14.0 | Dermal Fibroblasts rest | 0.9 |
| Dendritic cells anti-CD40 | 29.3 | Neutrophils TNFa + LPS | 7.5 |
| Monocytes rest | 9.7 | Neutrophils rest | 4.9 |
| Monocytes LPS | 67.8 | Colon | 18.0 |
| Macrophages rest | 13.8 | Lung | 1.0 |
| Macrophages LPS | 13.0 | Thymus | 2.8 |
| HUVEC none | 1.8 | Kidney | 100.0 |
| HUVEC starved | 2.1 | | |

CNS_neurodegeneration_v1.0 Summary: Ag3766 This panel does not show differential expression of the CG92025-01 gene in Alzheimer's disease. However, this expression profile confirms the presence of this gene in the brain. Please see Panel 1.4 for discussion of utility of this gene in the central nervous system.

General_screening_panel_v1.4 Summary: Ag3766 Highest expression of the CG92025-01 gene is seen in a renal cancer cell line (CT=27.7). Moderate levels of expression are also seen in samples derived from ovarian, breast, brain, lung and colon cancer cell lines. Thus, expression of this gene could be used to differentiate these samples from other samples on this panel and as a marker of these types of cancers. This gene encodes a protein that is homologous to gamma-glutamyl transferase (GGT), an enzyme that acts as a glutathionase and is found in tissues involved in absorption and secretion. Elevated levels of this enzyme have been in found in renal cancers. Therefore, therapeutic modulation of the expression or function of this gene may be effective in the treatment of ovarian, breast, brain, lung and colon cancers.

Among metabolic tissues, this gene is expressed at moderate to low levels in pancreas, thyroid and adult and fetal liver. Elevated level of GGT have been linked to type 2 diabetes. Thus, the expression of this gene suggests that this gene product may play a role in normal neuroendocrine and metabolic and that disregulated expression of this gene may contribute to neuroendocrine disorders or metabolic diseases, such as obesity and diabetes.

This gene is also expressed at low levels in the CNS, including the hippocampus, thalamus, substantia nigra, amygdala, and cerebellum. GGT is important in repletion of intercellular glutathione and is upregulated in the face of oxidative stress. Therefore, therapeutic modulation of the expression or function of this gene may be useful in the treatment of neurologic disorders that result from oxidative stress, including Alzheimer's disease and schizophrenia (Perry I) Wannamethee S G, Shaper A G. Prospective study of serum gamma-glutamyltransferase and risk of NIDDM. Diabetes Care 1998 May;21(5):732–7; Lusini L, Tripodi S A, Rossi R, Giannerini F, Giustarini D, del Vecchio M T, Barbanti G, Cintorino M, Tosi P, Di Simplicio P. Altered glutathione anti-oxidant metabolism during tumor progression in human renal-cell carcinoma. Int J Cancer 2001 Jan. 1;91(1):55–9; Gupta A, Gupta A, Datta M, Shukla G S. Cerebral antioxidant status and free radical generation following glutathione depletion and subsequent recovery. Mol Cell Biochem 2000 June;209(1–2):55–61).

Panel 4.1D Summary: Ag3766 Highest expression of the CG92025-01 gene is seen in kidney (CT30.7). Moderate expression is also seen in LPS stimulated monocytes. Upon activation with pathogens such as LPS, monocytes contribute to the innate and specific immunity by migrating to the site of tissue injury and releasing inflammatory cytokines. This release contributes to the inflammation process. Therefore, modulation of the expression of the protein encoded by this transcript may prevent the recruitment of monocytes and the initiation it of the inflammatory process, and reduce the symptoms of patients suffering from autoimmune and inflammatory diseases such as asthma, allergies, inflammatory bowel disease, lupus erythematosus, or rheumatoid arthritis.

Low but significant levels of expression are seen in chronically stimulated T cells. Thus, therapeutics designed with the transcript may be important in the treatment of diseases such as asthma, IBD, psoriasis and arthritis in which T cells are chronically stimulated.

AR. CG92025-02: Gamma-Glutamyltranspepidase 2.

Expression of gene CG92025-02 was assessed using the primer-probe set Ag4127, described in Table ARA. Results of the RTQ-PCR runs are shown in Tables ARB and ARC.

TABLE ARA

Probe Name Ag4127

| Primers | Sequences | Length | Start Position | SEQ ID NO: |
|---|---|---|---|---|
| Forward | 5'-ccaggctggacagttcagt-3' | 19 | 27 | 384 |
| Probe | TET-5'-cccacagcagagttcaactggagaca-3'-TAMRA | 26 | 60 | 385 |
| Reverse | 5'-cctctgcctctagctggttt-3' | 20 | 89 | 386 |

TABLE ARB

General_screening_panel_v1.4

| Tissue Name | Rel. Exp. (%) Ag4127, Run 220361624 | Tissue Name | Rel. Exp. (%) Ag4127, Run 220361624 |
|---|---|---|---|
| Adipose | 0.4 | Renal ca TK-10 | 16.0 |
| Melanoma* Hs688(A).T | 0.1 | Bladder | 7.0 |
| Melanoma* Hs688(B).T | 0.2 | Gastric ca. (liver met.) NCI-N87 | 6.6 |
| Melanoma* M14 | 0.1 | Gastric ca. KATO III | 1.9 |
| Melanoma* LOXIMVI | 0.8 | Colon ca. SW-948 | 5.9 |
| Melanoma* SK-MEL-5 | 4.4 | Colon ca. SW480 | 0.6 |
| Squamous cell carcinoma SCC-4 | 1.6 | Colon ca.* (SW480 met) SW620 | 1.6 |
| Testis Pool | 2.1 | Colon ca. HT29 | 1.2 |
| Prostate ca.* (bone met) PC-3 | 0.1 | Colon ca. HCT-116 | 7.2 |
| Prostate Pool | 4.2 | Colon ca. CaCo-2 | 5.6 |
| Placenta | 1.0 | Colon cancer tissue | 55.5 |
| Uterus Pool | 0.1 | Colon ca. SW1116 | 0.1 |
| Ovarian ca. OVCAR-3 | 0.9 | Colon ca. Colo-205 | 2.2 |
| Ovarian ca. SK-OV-3 | 1.6 | Colon ca. SW-48 | 2.6 |
| Ovarian ca. OVCAR-4 | 0.3 | Colon Pool | 0.8 |
| Ovarian ca. OVCAR-5 | 23.5 | Small Intestine Pool | 0.5 |
| Ovarian ca. IGROV-1 | 4.8 | Stomach Pool | 0.8 |
| Ovarian ca. OVCAR-8 | 2.3 | Bone Marrow Pool | 0.3 |
| Ovary | 0.5 | Fetal Heart | 0.2 |
| Breast ca. MCF-7 | 1.4 | Heart Pool | 0.2 |
| Breast ca. MDA-MB-231 | 1.4 | Lymph Node Pool | 0.8 |
| Breast ca. BT 549 | 0.1 | Fetal Skeletal Muscle | 0.6 |
| Breast ca. T47D | 50.0 | Skeletal Muscle Pool | 0.3 |
| Breast ca. MDA-N | 0.0 | Spleen Pool | 0.5 |
| Breast Pool | 1.0 | Thymus Pool | 1.4 |
| Trachea | 0.8 | CNS cancer (glio/astro) U87-MG | 26.6 |
| Lung | 0.0 | CNS cancer (glio/astro) U-118-MG | 8.2 |
| Fetal Lung | 1.7 | CNS cancer (neuro; met) SK-N-AS | 0.8 |
| Lung ca. NCI-N417 | 0.1 | CNS cancer (astro) SF-539 | 0.9 |
| Lung ca. LX-1 | 2.7 | CNS cancer (astro) SNB-75 | 1.4 |
| Lung ca. NCI-H146 | 0.3 | CNS cancer (glio) SNB-19 | 4.0 |
| Lung ca. SHP-77 | 2.3 | CNS cancer (glio) SF-295 | 3.3 |
| Lung ca. A549 | 31.6 | Brain (Amygdala) Pool | 0.6 |
| Lung ca. NCI-H526 | 0.0 | Brain (cerebellum) | 1.4 |
| Lung ca. NCI-H23 | 0.6 | Brain (fetal) | 1.0 |
| Lung ca. NCI-H460 | 15.7 | Brain (Hippocampus) Pool | 0.5 |
| Lung ca. HOP-62 | 0.8 | Cerebral Cortex Pool | 0.5 |
| Lung ca. NCI-H522 | 0.6 | Brain (Substantia nigra) Pool | 0.7 |
| Liver | 7.1 | Brain (Thalamus) Pool | 0.6 |
| Fetal Liver | 24.3 | Brain (whole) | 1.1 |
| Liver ca. HepG2 | 4.4 | Spinal Cord Pool | 0.9 |
| Kidney Pool | 0.4 | Adrenal Gland | 0.3 |
| Fetal Kidney | 2.3 | Pituitary gland Pool | 0.5 |
| Renal ca. 786-0 | 100.0 | Salivary Gland | 0.6 |
| Renal ca. A498 | 15.5 | Thyroid (female) | 2.4 |
| Renal ca. ACHN | 17.6 | Pancreatic ca. CAPAN2 | 1.1 |
| Renal ca. UO-31 | 5.0 | Pancreas Pool | 8.1 |

TABLE ARC

Panel 4.1D

| Tissue Name | Rel. Exp. (%) Ag4127, Run 172859319 | Tissue Name | Rel. Exp. (%) Ag4127, Run 172859319 |
|---|---|---|---|
| Secondary Th1 act | 44.4 | HUVEC IL-1beta | 0.9 |
| Secondary Th2 act | 37.4 | HUVEC IFN gamma | 0.8 |
| Secondary Tr1 act | 30.8 | HUVEC TNF alpha + IFN gamma | 0.4 |
| Secondary Th1 rest | 28.7 | HUVEC TNF alpha + IL4 | 0.7 |
| Secondary Th2 rest | 28.7 | HUVEC IL-11 | 0.4 |
| Secondary Tr1 rest | 34.4 | Lung Microvascular EC none | 3.4 |

TABLE ARC-continued

Panel 4.1D

| Tissue Name | Rel. Exp. (%) Ag4127, Run 172859319 | Tissue Name | Rel. Exp. (%) Ag4127, Run 172859319 |
| --- | --- | --- | --- |
| Primary Th1 act | 30.1 | Lung Microvascular EC TNF alpha + IL-1beta | 1.2 |
| Primary Th2 act | 45.4 | Microvascular Dermal EC none | 0.4 |
| Primary Tr1 act | 40.3 | Microsvasular Dermal EC TNF alpha + IL-1beta | 0.4 |
| Primary Th1 rest | 13.0 | Bronchial epithelium TNF alpha + IL1beta | 8.1 |
| Primary Th2 rest | 13.2 | Small airway epithelium none | 4.9 |
| Primary Tr1 rest | 18.6 | Small airway epithelium TNF alpha + IL-1beta | 4.7 |
| CD45RA CD4 lymphocyte act | 3.4 | Coronery artery SMC rest | 0.0 |
| CD45RO CD4 lymphocyte act | 11.6 | Coronery artery SMC TNF alpha + IL-1beta | 3.0 |
| CD8 lymphocyte act | 12.4 | Astrocytes rest | 0.0 |
| Secondary CD8 lymphocyte rest | 19.3 | Astrocytes TNF alpha + IL-1beta | 0.2 |
| Secondary CD8 lymphocyte act | 8.2 | KU-812 (Basophil) rest | 3.2 |
| CD4 lymphocyte none | 3.5 | KU-812 (Basophil) PMA/ionomycin | 7.0 |
| 2ry Th1/Th2/Tr1_anti-CD95 CH11 | 26.1 | CCD1106 (Keratinocytes) none | 3.9 |
| LAK cells rest | 7.3 | CCD1106 (Keratinocytes) TNF alpha + IL-1beta | 6.6 |
| LAK cells IL-2 | 4.1 | Liver cirrhosis | 10.9 |
| LAK cells IL-2 + IL-12 | 12.9 | NCI-H292 none | 1.2 |
| LAK cells IL-2 + IFN gamma | 17.8 | NCI-H292 IL-4 | 1.3 |
| LAK cells IL-2 + IL-18 | 26.8 | NCI-H292 IL-9 | 2.4 |
| LAK cells PMA/ionomycin | 10.7 | NCI-H292 IL-13 | 2.6 |
| NK Cells IL-2 rest | 9.2 | NCI-H292 IFN gamma | 0.5 |
| Two Way MLR 3 day | 8.3 | HPAEC none | 1.2 |
| Two Way MLR 5 day | 4.7 | HPAEC TNF alpha + IL-1beta | 0.6 |
| Two Way MLR 7 day | 9.2 | Lung fibroblast none | 2.8 |
| PBMC rest | 0.9 | Lung fibroblast TNF alpha + IL-1beta | 1.4 |
| PBMC PWM | 9.5 | Lung fibroblast IL-4 | 0.4 |
| PBMC PHA-L | 7.5 | Lung fibroblast IL-9 | 0.4 |
| Ramos (B cell) none | 4.2 | Lung fibroblast IL-13 | 0.0 |
| Ramos (B cell) ionomycin | 12.3 | Lung fibroblast IFN gamma | 0.0 |
| B lymphocytes PWM | 15.1 | Dermal fibroblast CCD1070 rest | 1.2 |
| B lymphocytes CD40L and IL-4 | 16.5 | Dermal fibroblast CCD1070 TNF alpha | 7.3 |
| EOL-1 dbcAMP | 9.5 | Dermal fibroblast CCD1070 IL-1beta | 0.5 |
| EOL-1 dbcAMP PMA/ionomycin | 6.3 | Dermal fibroblast IFN gamma | 1.7 |
| Dendritic cells none | 17.4 | Dermal fibroblast IL-4 | 1.9 |
| Dendritic cells LPS | 5.5 | Dermal Fibroblasts rest | 1.9 |
| Dendritic cells anti-CD40 | 5.1 | Neutrophils TNFa + LPS | 6.6 |
| Monocytes rest | 9.3 | Neutrophils rest | 6.8 |
| Monocytes LPS | 39.2 | Colon | 13.8 |
| Macrophages rest | 8.7 | Lung | 4.6 |
| Macrophages LPS | 10.1 | Thymus | 13.7 |
| HUVEC none | 0.4 | Kidney | 100.0 |
| HUVEC starved | 0.2 | | |

CNS_neurodegeneration_v1.0 Summary: Ag4127 Results from one experiment with this probe and primer set and the CG92025-02 gene are not included. The amp plot indicates that there were experimental difficulties with this run.

General_screening_panel_v1.4 Summary: Ag4127 Highest expression of the CG92025-02 gene is seen in a renal cancer cell line (CT=26.6). High to moderate levels of expression are also seen in samples derived from colon, brain, breast, ovarian, and lung cancers. Thus, expression of this gene could be used to differentiate between these samples and other samples on this panel and as a marker for these cancers. This gene encodes a protein that is homologous to gamma-glutamyl transferase (GGT), an enzyme that acts as a glutathionase and is found in tissues involved in absorption and secretion. Elevated levels of this enzyme have been in found in renal cancers. Therefore, therapeutic modulation of the expression or function of this gene may be effective in the treatment of renal, colon, brain, breast, ovarian and lung cancers.

Among metabolic tissues, this gene is expressed at moderate to low levels in pancreas, thyroid, pituitary, adipose, fetal skeletal muscle and fetal and adult liver. Elevated level of GGT have been linked to type 2 diabetes. Thus, the expression of this genen suggests that this gene product may play a role in normal neuroendocrine and metabolic and that disregulated expression of this gene may contribute to neuroendocrine disorders or metabolic diseases, such as obesity and diabetes.

This gene is also expressed at low levels in the CNS, including the hippocampus, thalamus, substantia nigra, amygdala, cerebellum and cerebral cortex. GGT is important in repletion of intercellular glutathione and is upregulated in the face of oxidative stress. Therefore, therapeutic modulation of the expression or function of this gene may be useful in the treatment of neurologic disorders that result from oxidative stress, including Alzheimer's disease and schizophrenia (Perry I J, Wannamethee S G, Shaper A G. Prospective study of serum gamma-glutamyltransferase and risk of NIDDM. Diabetes Care 1998 May;21(5):732–7; Lusini L, Tripodi S A, Rossi R, Giannerini F, Giustarini D, del Vecchio M T, Barbanti G, Cintorino M, Tosi P, Di Simplicio P. Altered glutathione anti-oxidant metabolism during tumor progression in human renal-cell carcinoma. Int J Cancer 2001 Jan. 1;91(1):55–9; Gupta A, Gupta A, Datta M, Shukla G S. Cerebral antioxidant status and free radical generation following glutathione depletion and subsequent recovery. Mol Cell Biochem 2000 June;209(1–2):55–61).

Panel 4.1D Summary: Ag4127 Highest expression of the CG92025-02 gene is seen in kidney (CT=30.6). Moderate to low levels of expression are also seen in LPS stimulated monocytes, primary activated T cells, and resting and activated secondary T cells. Thus, expression of this gene could be used as to differentiate the kidney sample from other samples on this panel and as a marker of kidney tissue. In addition, expression stimulated monocytes and T cells suggests that modulation of the expression of the protein encoded by this transcript may prevent the recruitment of monocytes, the initiation of the inflammatory process, and reduce the symptoms of patients suffering from autoimmune and inflammatory diseases such as asthma, allergies, inflammatory bowel disease, lupus erythematosus, psoriasis, and rheumatoid arthritis.

AS. CG92078-01: Permease

Expression of gene CG92078-01 was assessed using the primer-probe set Ag3769, described in Table ASA. Results of the RTQ-PCR runs are shown in Tables ASB and ASC.

TABLE ASA

| Probe Name Ag3769 | | | | |
|---|---|---|---|---|
| Primers | Sequences | Length | Start Position | SEQ ID NO: |
| Forward | 5'-ttaggtccagaaatgaccagaa-3' | 22 | 1854 | 387 |
| Probe | TET-5'-cgcgtacttctgccctggttaattta-3'-TAMRA | 26 | 1876 | 388 |
| Reverse | 5'-tgactctccagcagatgagagt-3' | 22 | 1908 | 389 |

TABLE ASB

| General_screening_panel_v1.4 | | | |
|---|---|---|---|
| Tissue Name | Rel. Exp. (%) Ag3769, Run 218982365 | Tissue Name | Rel. Exp. (%) Ag3769, Run 218982365 |
| Adipose | 2.3 | Renal ca. TK-10 | 27.0 |
| Melanoma* Hs688(A).T | 6.8 | Bladder | 13.2 |
| Melanoma* Hs688(B).T | 3.7 | Gastric ca. (liver met.) NCI-N87 | 62.4 |
| Melanoma* M14 | 7.9 | Gastric ca. KATO III | 3.9 |
| Melanoma* LOXIMVI | 1.0 | Colon ca. SW-948 | 0.8 |
| Melanoma* SK-MEL-5 | 4.5 | Colon ca. SW480 | 7.4 |
| Squamous cell carcinoma SCC-4 | 1.0 | Colon ca.* (SW480 met) SW620 | 11.3 |
| Testis Pool | 2.5 | Colon ca. HT29 | 22.4 |
| Prostate ca.* (bone met) PC-3 | 22.7 | Colon ca. HCT-116 | 11.3 |
| Prostate Pool | 4.0 | Colon ca. CaCo-2 | 100.0 |
| Placenta | 3.4 | Colon cancer tissue | 5.0 |
| Uterus Pool | 1.4 | Colon ca. SW1116 | 2.2 |
| Ovarian ca. OVCAR-3 | 14.2 | Colon ca. Colo-205 | 0.0 |
| Ovarian ca. SK-OV-3 | 9.4 | Colon ca. SW-48 | 2.2 |
| Ovarian ca. OVCAR-4 | 2.5 | Colon Pool | 8.8 |
| Ovarian ca. OVCAR-5 | 16.2 | Small Intestine Pool | 8.7 |
| Ovarian ca. IGROV-1 | 6.0 | Stomach Pool | 7.0 |
| Ovarian ca. OVCAR-8 | 3.5 | Bone Marrow Pool | 4.0 |
| Ovary | 5.8 | Fetal Heart | 2.0 |
| Breast ca. MCF-7 | 4.4 | Heart Pool | 3.2 |
| Breast ca. MDA-MB-231 | 12.3 | Lymph Node Pool | 17.7 |
| Breast ca. BT 549 | 4.9 | Fetal Skeletal Muscle | 2.9 |
| Breast ca. T47D | 20.6 | Skeletal Muscle Pool | 1.9 |
| Breast ca. MDA-N | 15.4 | Spleen Pool | 5.8 |
| Breast Pool | 12.2 | Thymus Pool | 8.2 |
| Trachea | 0.0 | CNS cancer (glio/astro) U87-MG | 6.0 |
| Lung | 5.0 | CNS cancer (glio/astro) U-118-MG | 34.6 |
| Fetal Lung | 25.9 | CNS cancer (neuro; met) SK-N-AS | 5.9 |
| Lung ca. NCI-N417 | 0.0 | CNS cancer (astro) SF-539 | 1.0 |
| Lung ca. LX-1 | 20.7 | CNS cancer (astro) SNB-75 | 9.5 |
| Lung ca. NCI-H146 | 0.0 | CNS cancer (glio) SNB-19 | 4.5 |

TABLE ASB-continued

General_screening_panel_v1.4

| Tissue Name | Rel. Exp. (%) Ag3769, Run 218982365 | Tissue Name | Rel. Exp. (%) Ag3769, Run 218982365 |
|---|---|---|---|
| Lung ca. SHP-77 | 5.1 | CNS cancer (glio) SF-295 | 71.7 |
| Lung ca. A549 | 5.0 | Brain (Amygdala) Pool | 1.0 |
| Lung ca. NCI-H526 | 0.0 | Brain (cerebellum) | 3.1 |
| Lung ca. NCI-H23 | 25.7 | Brain (fetal) | 1.1 |
| Lung ca. NCI-H460 | 13.2 | Brain (Hippocampus) Pool | 0.0 |
| Lung ca. HOP-62 | 6.3 | Cerebral Cortex Pool | 0.0 |
| Lung ca. NCI-H522 | 12.5 | Brain (Substantia nigra) Pool | 0.0 |
| Liver | 1.3 | Brain (Thalamus) Pool | 1.9 |
| Fetal Liver | 5.0 | Brain (whole) | 1.2 |
| Liver ca. HepG2 | 6.5 | Spinal Cord Pool | 2.2 |
| Kidney Pool | 21.2 | Adrenal Gland | 1.6 |
| Fetal Kidney | 43.8 | Pituitary gland Pool | 0.0 |
| Renal ca. 786-0 | 3.8 | Salivary Gland | 1.4 |
| Renal ca. A498 | 2.3 | Thyroid (female) | 1.3 |
| Renal ca. ACHN | 15.0 | Pancreatic ca. CAPAN2 | 11.1 |
| Renal ca. UO-31 | 1.2 | Pancreas Pool | 15.8 |

TABLE ASC

Panel 4.1D

| Tissue Name | Rel. Exp. (%) Ag3769, Run 170069130 | Tissue Name | Rel. Exp. (%) Ag3769, Run 170069130 |
|---|---|---|---|
| Secondary Th1 act | 0.6 | HUVEC IL-1beta | 0.5 |
| Secondary Th2 act | 1.2 | HUVEC IFN gamma | 1.0 |
| Secondary Tr1 act | 0.7 | HUVEC TNF alpha + IFN gamma | 1.1 |
| Secondary Th1 rest | 0.9 | HUVEC TNF alpha + IL4 | 0.8 |
| Secondary Th2 rest | 1.7 | HUVEC IL-11 | 0.4 |
| Secondary Tr1 rest | 1.3 | Lung Microvascular EC none | 4.9 |
| Primary Th1 act | 1.0 | Lung Microvascular EC TNF alpha + IL-1beta | 2.8 |
| Primary Th2 act | 0.8 | Microvascular Dermal EC none | 1.6 |
| Primary Tr1 act | 1.1 | Microsvasular Dermal EC TNF alpha + IL-1beta | 0.7 |
| Primary Th1 rest | 0.7 | Bronchial epithelium TNF alpha + IL1beta | 1.9 |
| Primary Th2 rest | 1.5 | Small airway epithelium none | 0.4 |
| Primary Tr1 rest | 2.3 | Small airway epithelium TNF alpha + IL-1beta | 1.1 |
| CD45RA CD4 lymphocyte act | 0.6 | Coronery artery SMC rest | 0.3 |
| CD45RO CD4 lymphocyte act | 1.3 | Coronery artery SMC TNF alpha + IL-1beta | 0.0 |
| CD8 lymphocyte act | 0.9 | Astrocytes rest | 0.7 |
| Secondary CD8 lymphocyte rest | 1.1 | Astrocytes TNF alpha + IL-1beta | 0.2 |
| Secondary CD8 lymphocyte act | 0.3 | KU-812 (Basophil) rest | 0.0 |
| CD4 lymphocyte none | 0.4 | KU-812 (Basophil) PMA/ionomycin | 1.0 |
| 2ry Th1/Th2/Tr1_anti-CD95 CH11 | 1.0 | CCD1106 (Keratinocytes) none | 1.1 |
| LAK cells rest | 0.8 | CCD1106 (Keratinocytes) TNF alpha + IL-1beta | 0.4 |
| LAK cells IL-2 | 2.0 | Liver cirrhosis | 0.2 |
| LAK cells IL-2 + IL-12 | 1.2 | NCI-H292 none | 0.2 |
| LAK cells IL-2 + IFN gamma | 0.9 | NCI-H292 IL-4 | 0.5 |
| LAK cells IL-2 + IL-18 | 1.4 | NCI-H292 IL-9 | 1.7 |
| LAK cells PMA/ionomycin | 1.1 | NCI-H292 IL-13 | 0.5 |

TABLE ASC-continued

Panel 4.1D

| Tissue Name | Rel. Exp. (%) Ag3769, Run 170069130 | Tissue Name | Rel. Exp. (%) Ag3769, Run 170069130 |
|---|---|---|---|
| NK Cells IL-2 rest | 1.2 | NCI-H292 IFN gamma | 0.6 |
| Two Way MLR 3 day | 1.0 | HPAEC none | 0.6 |
| Two Way MLR 5 day | 0.6 | HPAEC TNF alpha + IL-1beta | 1.0 |
| Two Way MLR 7 day | 0.5 | Lung fibroblast none | 0.7 |
| PBMC rest | 0.0 | Lung fibroblast TNF alpha + IL-1beta | 0.0 |
| PBMC PWM | 1.5 | Lung fibroblast IL-4 | 0.3 |
| PBMC PHA-L | 1.2 | Lung fibroblast IL-9 | 0.8 |
| Ramos (B cell) none | 1.2 | Lung fibroblast IL-13 | 0.5 |
| Ramos (B cell) ionomycin | 1.3 | Lung fibroblast IFN gamma | 0.5 |
| B lymphocytes PWM | 0.2 | Dermal fibroblast CCD1070 rest | 0.6 |
| B lymphocytes CD40L and IL-4 | 1.9 | Dermal fibroblast CCD1070 TNF alpha | 0.8 |
| EOL-1 dbcAMP | 0.3 | Dermal fibroblast CCD1070 IL-1beta | 0.0 |
| EOL-1 dbcAMP PMA/ionomycin | 4.3 | Dermal fibroblast IFN gamma | 0.3 |
| Dendritic cells none | 1.0 | Dermal fibroblast IL-4 | 2.1 |
| Dendritic cells LPS | 0.8 | Dermal Fibroblasts rest | 0.3 |
| Dendritic cells anti-CD40 | 0.8 | Neutrophils TNFa + LPS | 0.0 |
| Monocytes rest | 0.8 | Neutrophils rest | 0.3 |
| Monocytes LPS | 1.0 | Colon | 17.7 |
| Macrophages rest | 0.9 | Lung | 48.0 |
| Macrophages LPS | 0.7 | Thymus | 1.0 |
| HUVEC none | 0.3 | Kidney | 100.0 |
| HUVEC starved | 1.1 | | |

CNS_neurodegeneration_v1.0 Summary: Ag3769 Expression of the CG92078-01 gene is low/undetectable (CTs>35) across all of the samples on this panel (data not shown).

General_screening$_{13}$ panel_v1.4 Summary: Ag3769 Highest expression of the CG92078-01 gene is detected in colon cancer CaCo-2 cell line (CT=33). In addition, significant expression of this gene is associated with two CNS cancer, and gastric cancer (liver metatstasis) NCI-N87 cell lines. Therefore, therapeutic modulation of the activity of this gene or its protein product, through the use of small molecule drugs, protein therapeutics or antibodies, might be beneficial in the treatment of these cancer.

Panel 4.1D Summary: Ag3769 Highest expression of the CG92078-01 gene is detected in kidney (CT=30.6). In addition, moderate to low expression of this gene is also seen in lung and colon samples. Therefore, expression of this gene can be used to distinguish these samples from other samples used in this panel. In addition, therapeutic modulation of the activity of the permease encoded by this gene may be useful in the treatment of inflammatory bowel disease, inflammatory or autoimmune diseases that affect the kidney and lung, including lupus and glomerulonephritis, asthma, COPD, allergies and emphysema.

Panel 5 Islet Summary: Ag3769 Expression of the CG92078-01 gene is low/undetectable (CTs>35) across all of the samples on this panel (data not shown).

AT. CG92088-01: IGb3 Synthase

Expression of gene CG92088-01 was assessed using the primer-probe sets Ag3773 and Ag4123, described in Tables ATA and ATB. Results of the RTQ-PCR runs are shown in Tables ATC and ATD.

TABLE ATA

Probe Name Ag3773

| Primers | Sequences | Length | Start Position | SEQ ID NO: |
|---|---|---|---|---|
| Forward | 5'-aagaggctagacagcagaacct-3' | 22 | 284 | 390 |
| Probe | TET-5'-caccattgggctgactatctttgctg-3'-TAMRA | 26 | 306 | 391 |
| Reverse | 5'-ccaggtacttctccaggtacct-3' | 22 | 337 | 392 |

TABLE ATB

Probe Name Ag4123

| Primers | Sequences | Length | Start Position | SEQ ID NO: |
|---|---|---|---|---|
| Forward | 5'-ttctgtatggcctccctaaatt-3' | 22 | 86 | 393 |
| Probe | TET-5'-atctggaagccctcatccccatg-3'-TAMRA | 23 | 113 | 394 |
| Reverse | 5'-gtctctcagctgggacattgt-3' | 21 | 154 | 395 |

TABLE ATC

CNS_neurodegeneration_v1.0

| Tissue Name | Rel. Exp. (%) Ag4123, Run 214301671 | Tissue Name | Rel. Exp. (%) Ag4123, Run 214301671 |
| --- | --- | --- | --- |
| AD 1 Hippo | 0.0 | Control (Path) 3 Temporal Ctx | 0.0 |
| AD 2 Hippo | 17.2 | Control (Path) 4 Temporal Ctx | 100.0 |
| AD 3 Hippo | 4.4 | AD 1 Occipital Ctx | 20.3 |
| AD 4 Hippo | 0.0 | AD 2 Occipital Ctx (Missing) | 0.0 |
| AD 5 hippo | 57.4 | AD 3 Occipital Ctx | 0.0 |
| AD 6 Hippo | 43.2 | AD 4 Occipital Ctx | 14.7 |
| Control 2 Hippo | 0.0 | AD 5 Occipital Ctx | 14.7 |
| Control 4 Hippo | 0.0 | AD 6 Occipital Ctx | 7.2 |
| Control (Path) 3 Hippo | 0.0 | Control 1 Occipital Ctx | 0.0 |
| AD 1 Temporal Ctx | 12.3 | Control 2 Occipital Ctx | 2.0 |
| AD 2 Temporal Ctx | 18.9 | Control 3 Occipital Ctx | 0.0 |
| AD 3 Temporal Ctx | 0.0 | Control 4 Occipital Ctx | 13.7 |
| AD 4 Temporal Ctx | 36.6 | Control (Path) 1 Occipital Ctx | 41.2 |
| AD 5 Inf Temporal Ctx | 88.9 | Control (Path) 2 Occipital Ctx | 0.0 |
| AD 5 Sup Temporal Ctx | 23.0 | Control (Path) 3 Occipital Ctx | 0.0 |
| AD 6 Inf Temporal Ctx | 60.7 | Control (Path) 4 Occipital Ctx | 0.0 |
| AD 6 Sup Temporal Ctx | 39.5 | Control 1 Parietal Ctx | 0.0 |
| Control 1 Temporal Ctx | 0.0 | Control 2 Parietal Ctx | 92.0 |
| Control 2 Temporal Ctx | 0.0 | Control 3 Parietal Ctx | 0.0 |
| Control 3 Temporal Ctx | 0.0 | Control (Path) 1 Parietal Ctx | 0.0 |
| Control 4 Temporal Ctx | 0.0 | Control (Path) 2 Parietal Ctx | 19.3 |
| Control (Path) 1 Temporal Ctx | 2.8 | Control (Path) 3 Parietal Ctx | 0.0 |
| Control (Path) 2 Temporal Ctx | 17.9 | Control (Path) 4 Parietal Ctx | 57.4 |

TABLE ATD

Panel 4.1D

| Tissue Name | Rel. Exp. (%) Ag4123, Run 172859311 | Tissue Name | Rel. Exp. (%) Ag4123, Run 172859311 |
| --- | --- | --- | --- |
| Secondary Th1 act | 0.0 | HUVEC IL-1beta | 0.0 |
| Secondary Th2 act | 0.0 | HUVEC IFN gamma | 11.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 18.3 | Lung Microvascular EC none | 0.0 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 0.0 | Microsvascular Dermal EC TNF alpha + IL-1beta | 0.0 |
| Primary Th1 rest | 0.0 | Bronchial epithelium TNF alpha + IL1beta | 0.0 |
| Primary Th2 rest | 0.0 | Small airway epithelium none | 0.0 |
| Primary Th1 rest | 24.3 | Small airway epithelium TNF alpha + IL-1beta | 26.6 |
| CD45RA CD4 lymphocyte act | 0.0 | Coronery artery SMC rest | 0.0 |
| CD45RO CD4 lymphocyte act | 10.0 | Coronery artery SMC TNF alpha + IL-1beta | 0.0 |
| CD8 lymphocyte act | 19.9 | Astrocytes rest | 0.0 |
| Secondary CD8 lymphocyte rest | 11.0 | Astrocytes TNF alpha + IL-1beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |

TABLE ATD-continued

Panel 4.1D

| Tissue Name | Rel. Exp. (%) Ag4123, Run 172859311 | Tissue Name | Rel. Exp. (%) Ag4123, Run 172859311 |
|---|---|---|---|
| 2ry Th1/Th2/Tr1_anti-CD95 CH11 | 24.5 | CCD1106 (Keratinocytes) none | 1.2 |
| LAK cells rest | 1.3 | CCD1106 (Keratinocytes) TNF alpha + IL-1beta | 1.3 |
| LAK cells IL-2 | 0.0 | Liver cirrhosis | 10.1 |
| LAK cells IL-2 + IL-12 | 0.0 | NCI-H292 none | 1.8 |
| LAK cells IL-2 + IFN gamma | 11.3 | NCI-H292 IL-4 | 0.0 |
| LAK cells IL-2 + IL-18 | 0.0 | NCI-H292 IL-9 | 0.0 |
| LAK cells PMA/ionomycin | 0.0 | NCI-H292 IL-13 | 0.0 |
| NK Cells IL-2 rest | 7.2 | NCI-H292 IFN gamma | 0.0 |
| Two Way MLR 3 day | 9.2 | HPAEC none | 0.0 |
| Two Way MLR 5 day | 29.3 | HPAEC TNF alpha + IL-1beta | 7.1 |
| Two Way MLR 7 day | 12.2 | Lung fibroblast none | 7.3 |
| PBMC rest | 9.7 | Lung fibroblast TNF alpha + IL-1beta | 0.0 |
| PBMC PWM | 0.0 | Lung fibroblast IL-4 | 26.8 |
| PBMC PHA-L | 0.0 | Lung fibroblast IL-9 | 42.9 |
| Ramos (B cell) none | 0.0 | Lung fibroblast IL-13 | 0.0 |
| Ramos (B cell) ionomycin | 0.0 | Lung fibroblast IFN gamma | 55.1 |
| B lymphocytes PWM | 0.0 | Dermal fibroblast CCD1070 rest | 10.5 |
| B lymphocytes CD40L and IL-4 | 9.0 | Dermal fibroblast CCD1070 TNF alpha | 8.8 |
| EOL-1 dbcAMP | 9.2 | Dermal fibroblast CCD1070 IL-1beta | 0.0 |
| EOL-1 dbcAMP PMA/ionomycin | 12.2 | Dermal fibroblast IFN gamma | 0.0 |
| Dendritic cells none | 17.9 | Dermal fibroblast IL-4 | 1.4 |
| Dendritic cells LPS | 29.9 | Dermal Fibroblasts rest | 0.0 |
| Dendritic cells anti-CD40 | 0.0 | Neutrophils TNFa + LPS | 100.0 |
| Monocytes rest | 40.1 | Neutrophils rest | 94.6 |
| Monocytes LPS | 21.2 | Colon | 0.0 |
| Macrophages rest | 0.0 | Lung | 0.0 |
| Macrophages LPS | 1.1 | Thymus | 0.0 |
| HUVEC none | 0.0 | Kidney | 9.1 |
| HUVEC starved | 11.7 | | |

AI_comprehensive panel_v1.0 Summary: Ag3773 Expression of the CG92088-01 gene is low/undetectable (CTs>35) across all of the samples on this panel (data not shown).

CNS_neurodegeneration_v1.0 Summary: Ag4123 Low expression of the CG92088-01 gene is exclusively seen in the temporal cortex of Alzheimer's disease patients. The CG92088-01 gene encodes a homolog of rat iGb3 synthase gene, which is a member of the ABO blood group glycosyltransferases. As seen in panel 4.1D, expression of this gene seems to be restricted to neutrophils. This suggests that this low expression could be from the infiltrating neutrophils in the diseased tissue. Therefore, blockade of this gene product may be of use in the treatment of this disease and decrease neuronal death. Ag3773 Expression of the CG92088-01 gene is low/undetectable (CTs>35) across all of the samples on this panel (data not shown).

General_screening_panel_v1.4 Summary: Ag3773 Expression of the CG92088-01 gene is low/undetectable (CTs>35) across all of the samples on this panel (data not shown).

Panel 2.2 Summary: Ag3773 Expression of the CG92088-01 gene is low/undetectable (CTs>35) across all of the samples on this panel (data not shown).

Panel 4.1D Summary: Ag4123 Expression of the CG92088-01 gene is exclusively seen in neutrophils. Thus, expression of this gene can be used to distinguish this sample from other samples in this panel. In addition, modulation of the expression or activity of the protein encoded by this gene through the application of small molecule therapeutics may be useful in the treatment of Crohn's disease, ulcerative colitis, multiple sclerosis, chronic obstructive pulmonary disease, asthma, emphysema, rheumatoid arthritis, lupus erythematosus, or psoriasis. Ag3773 Expression of the CG92088-01 gene is low/undetectable (CTs>35) across all of the samples on this panel (data not shown).

AU. CG92142-01: Glycerol-3-Phosphate Acyltransferase

Expression of gene CG92142-01 was assessed using the primer-probe set Ag3774, described in Table AUA. Results of the RTQ-PCR runs are shown in Tables AUB, AUC, AUD, AUE and AUF.

TABLE AUA

Probe Name Ag3774

| Primers | Sequences | Length | Start Position | SEQ ID NO: |
|---|---|---|---|---|
| Forward | 5'-ggtgctgctaaaactgttcaac-3' | 22 | 673 | 396 |
| Probe | TET-5'-tggaacattcaaattcacaaaggtca-3'-TAMRA | 26 | 704 | 397 |
| Reverse | 5'-attcgtctcagttgcagcttt-3' | 21 | 743 | 398 |

TABLE AUB

CNS_neurodegeneration_v1.0

| Tissue Name | Rel. Exp. (%) Ag3774, Run 206871268 | Tissue Name | Rel. Exp. (%) Ag3774, Run 206871268 |
|---|---|---|---|
| AD 1 Hippo | 29.1 | Control (Path) 3 Temporal Ctx | 29.3 |
| AD 2 Hippo | 73.7 | Control (Path) 4 Temporal Ctx | 50.3 |
| AD 3 Hippo | 10.0 | AD 1 Occipital Ctx | 22.4 |
| AD 4 Hippo | 14.6 | AD 2 Occipital Ctx (Missing) | 0.0 |
| AD 5 Hippo | 92.0 | AD 3 Occipital Ctx | 20.3 |
| AD 6 Hippo | 45.1 | AD 4 Occipital Ctx | 33.9 |
| Control 2 Hippo | 44.1 | AD 5 Occipital Ctx | 37.6 |
| Control 4 Hippo | 20.3 | AD 6 Occipital Ctx | 24.7 |
| Control (Path) 3 Hippo | 19.9 | Control 1 Occipital Ctx | 11.3 |
| AD 1 Temporal Ctx | 20.6 | Control 2 Occipital Ctx | 48.0 |
| AD 2 Temporal Ctx | 75.3 | Control 3 Occipital Ctx | 43.5 |
| AD 3 Temporal Ctx | 13.4 | Control 4 Occipital Ctx | 21.2 |
| AD 4 Temporal Ctx | 45.1 | Control (Path) 1 Occipital Ctx | 81.8 |
| AD 5 Inf Temporal Ctx | 100.0 | Control (Path) 2 Occipital Ctx | 12.9 |
| AD 5 Sup Temporal Ctx | 78.5 | Control (Path) 3 Occipital Ctx | 13.6 |
| AD 6 Inf Temporal Ctx | 43.5 | Control (Path) 4 Occipital Ctx | 45.1 |
| AD 6 Sup Temporal Ctx | 50.7 | Control 1 Parietal Ctx | 25.2 |
| Control 1 Temporal Ctx | 25.5 | Control 2 Parietal Ctx | 84.7 |
| Control 2 Temporal Ctx | 46.7 | Control 3 Parietal Ctx | 41.2 |
| Control 3 Temporal Ctx | 57.0 | Control (Path) 1 Parietal Ctx | 91.4 |
| Control 3 Temporal Ctx | 25.2 | Control (Path) 2 Parietal Ctx | 38.2 |
| Control (Path) 1 Temporal Ctx | 66.4 | Control (Path) 3 Parietal Ctx | 19.1 |
| Control (Path) 2 Temporal Ctx | 52.1 | Control (Path) 4 Parietal Ctx | 48.0 |

TABLE AUC

General_screening_panel_v1.4

| Tissue Name | Rel. Exp. (%) Ag3774, Run 213515543 | Tissue Name | Rel. Exp. (%) Ag3774, Run 213515543 |
|---|---|---|---|
| Adipose | 63.7 | Renal ca. TK-10 | 21.5 |
| Melanoma* Hs688(A).T | 16.0 | Bladder | 6.3 |
| Melanoma* Hs688(B).T | 74.7 | Gastric ca. (liver met.) NCI-N87 | 9.7 |
| Melanoma* M14 | 10.2 | Gastric ca. KATO III | 16.5 |
| Melanoma* LOXIMVI | 76.8 | Colon ca. SW-948 | 3.3 |
| Melanoma* SK-MEL-5 | 23.8 | Colon ca. SW480 | 12.9 |
| Squamous cell carcinoma SCC-4 | 5.8 | Colon ca.* (SW480 met) SW620 | 8.6 |
| Testis Pool | 12.8 | Colon ca. HT29 | 4.1 |
| Prostate ca.* (bone met) PC-3 | 10.3 | Colon ca. HCT-116 | 25.3 |
| Prostate Pool | 2.3 | Colon ca. CaCo-2 | 52.5 |
| Placenta | 1.3 | Colon cancer tissue | 10.4 |
| Uterus Pool | 1.6 | Colon ca. SW1116 | 3.0 |
| Ovarian ca. OVCAR-3 | 10.6 | Colon ca. Colo-205 | 2.9 |
| Ovarian ca. SK-OV-3 | 15.6 | Colon ca. SW-48 | 2.5 |
| Ovarian ca. OVCAR-4 | 5.4 | Colon Pool | 4.5 |
| Ovarian ca. OVCAR-5 | 6.3 | Small Intestine Pool | 5.9 |
| Ovarian ca. IGROV-1 | 5.5 | Stomach Pool | 3.3 |
| Ovarian ca. OVCAR-8 | 4.9 | Bone Marrow Pool | 2.8 |
| Ovary | 4.0 | Fetal Heart | 3.1 |
| Breast ca. MCF-7 | 11.7 | Heart Pool | 4.0 |
| Breast ca. MDA-MB-231 | 8.5 | Lymph Node Pool | 7.2 |
| Breast ca. BT 549 | 6.5 | Fetal Skeletal Muscle | 11.0 |
| Breast ca. T47D | 8.9 | Skeletal Muscle Pool | 10.9 |
| Breast ca. MDA-N | 10.7 | Spleen Pool | 5.3 |

TABLE AUC-continued

General_screening_panel_v1.4

| Tissue Name | Rel. Exp. (%) Ag3774, Run 213515543 | Tissue Name | Rel. Exp. (%) Ag3774, Run 213515543 |
|---|---|---|---|
| Breast Pool | 5.0 | Thymus pool | 7.6 |
| Trachea | 10.6 | CNS cancer (glio/astro) U87-MG | 9.7 |
| Lung | 1.0 | CNS cancer (glio/astro) U-118-MG | 19.1 |
| Fetal Lung | 6.2 | CNS cancer (neuro; met) SK-N-AS | 22.1 |
| Lung ca. NCI-N417 | 3.2 | CNS cancer (astro) SF-539 | 5.9 |
| Lung ca. LX-1 | 9.3 | CNS cancer (astro) SNB-75 | 22.5 |
| Lung ca. NCI-H146 | 2.9 | CNS cancer (glio) SNB-19 | 5.0 |
| Lung ca. SHP-77 | 16.2 | CNS cancer (glio) SF-295 | 100.0 |
| Lung ca. A549 | 7.6 | Brain (Amygdala) Pool | 2.9 |
| Lung ca. NCI-H526 | 1.9 | Brain (cerebellum) | 2.4 |
| Lung ca. NCI-H23 | 12.7 | Brain (fetal) | 17.9 |
| Lung ca. NCI-H460 | 7.7 | Brain (Hippocampus) Pool | 5.9 |
| Lung ca. HOP-62 | 6.0 | Cerebral Cortex Pool | 7.5 |
| Lung ca. NCI-H522 | 17.6 | Brain (Substantia nigra) Pool | 5.8 |
| Liver | 16.3 | Brain (Thalamus) Pool | 8.1 |
| Fetal Liver | 70.7 | Brain (whole) | 8.4 |
| Liver ca. HepG2 | 42.9 | Spinal Cord Pool | 4.8 |
| Kidney Pool | 8.5 | Adrenal Gland | 65.5 |
| Fetal Kidney | 6.6 | Pituitary gland Pool | 1.0 |
| Renal ca. 786-0 | 10.3 | Salivary Gland | 3.0 |
| Renal ca. A498 | 2.5 | Thyroid (female) | 3.8 |
| Renal ca. ACHN | 7.3 | Pancreatic ca. CAPAN2 | 5.4 |
| Renal ca. UO-31 | 7.2 | Pancreas Pool | 5.7 |

TABLE AUD

Panel 2.2

| Tissue Name | Rel. Exp. (%) Ag3774, Run 174448446 | Tissue Name | Rel. Exp. (%) Ag3774, Run 174448446 |
|---|---|---|---|
| Normal Colon | 7.9 | Kidney Margin (OD04348) | 8.7 |
| Colon cancer (OD06064) | 4.9 | Kidney malignant cancer (OD06204B) | 2.2 |
| Colon Margin (OD06064) | 3.6 | Kidney normal adjacent tissue (OD06204E) | 0.4 |
| Colon cancer (OD06159) | 0.2 | Kidney Cancer (OD04450-01) | 3.4 |
| Colon Margin (OD06159) | 2.8 | Kidney Margin (OD04450-03) | 3.3 |
| Colon cancer (OD06297-04) | 0.6 | Kidney Cancer 8120613 | 0.8 |
| Colon Margin (OD06297-05) | 2.3 | Kidney Margin 8120614 | 1.0 |
| CC Gr.2 ascend colon (ODO3921) | 0.5 | Kidney Cancer 9010320 | 1.6 |
| CC Margin (ODO3921) | 1.0 | Kidney Margin 9010321 | 0.2 |
| Colon cancer metastasis (OD06104) | 1.6 | Kidney Cancer 8120607 | 0.8 |
| Lung Margin (OD06104) | 1.1 | Kidney Margin 8120608 | 0.3 |
| Colon mets to lung (OD04451-01) | 2.2 | Normal Uterus | 5.0 |
| Lung Margin (OD04451-02) | 2.3 | Uterine Cancer 064011 | 1.1 |
| Normal Prostate | 0.6 | Normal Thyroid | 0.3 |
| Prostate Cancer (OD04410) | 1.2 | Thyroid Cancer 064010 | 0.6 |
| Prostate Margin (OD04410) | 1.2 | Thyroid Cancer A302152 | 2.2 |
| Normal Ovary | 1.0 | Thyroid Margin A302153 | 2.9 |
| Ovarian cancer (OD06283-03) | 1.0 | Normal Breast | 61.6 |
| Ovarian Margin (OD06283-07) | 10.1 | Breast Cancer (OD04566) | 2.7 |
| Ovarian Cancer 064008 | 3.3 | Breast Cancer 1024 | 4.8 |
| Ovarian cancer (OD06145) | 2.1 | Breast Cancer (OD04590-01) | 4.8 |
| Ovarian Margin (OD06145) | 2.4 | Breast Cancer Mets (OD04590-03) | 30.1 |
| Ovarian cancer (OD06455-03) | 1.7 | Breast Cancer Metastasis (OD04655-05) | 6.0 |

TABLE AUD-continued

Panel 2.2

| Tissue Name | Rel. Exp. (%) Ag3774, Run 174448446 | Tissue Name | Rel. Exp. (%) Ag3774, Run 174448446 |
|---|---|---|---|
| Ovarian Margin (OD06455-07) | 1.3 | Breast Cancer 064006 | 2.0 |
| Normal Lung | 3.1 | Breast Cancer 9100266 | 1.5 |
| Invasive poor diff. lung adeno (ODO4945-01) | 1.4 | Breast Margin 9100265 | 3.6 |
| Lung Margin (ODO4945-03) | 2.2 | Breast Cancer A209073 | 1.1 |
| Lung Malignant Cancer (OD03126) | 2.0 | Breast Margin A2090734 | 5.8 |
| Lung Margin (OD03126) | 0.7 | Breast cancer (OD06083) | 4.2 |
| Lung Cancer (OD05014A) | 1.2 | Breast cancer node metastasis (OD06083) | 12.6 |
| Lung Margin (OD05014B) | 7.1 | Normal Liver | 87.7 |
| Lung cancer (OD06081) | 0.1 | Liver Cancer 1026 | 12.5 |
| Lung Margin (OD06081) | 2.0 | Liver Cancer 1025 | 100.0 |
| Lung Cancer (OD04237-01) | 1.0 | Liver Cancer 6004-T | 63.7 |
| Lung Margin (OD04237-02) | 2.6 | Liver Tissue 6004-N | 4.8 |
| Ocular Melanoma Metastasis | 7.5 | Liver Cancer 6005-T | 28.5 |
| Ocular Melanoma Margin (Liver) | 19.5 | Liver Tissue 6005-N | 67.8 |
| Melanoma Metastasis | 2.0 | Liver Cancer 064003 | 12.2 |
| Melanoma Margin (Lung) | 3.6 | Normal Bladder | 2.3 |
| Normal Kidney | 1.6 | Bladder Cancer 1023 | 0.3 |
| Kidney Ca, Nuclear grade 2 (OD04338) | 3.3 | Bladder Cancer A302173 | 1.4 |
| Kidney Margin (OD04338) | 1.3 | Normal Stomach | 6.0 |
| Kidney Ca Nuclear grade 1/2 (OD04339) | 2.2 | Gastric Cancer 9060397 | 0.9 |
| Kidney Margin (OD04339) | 2.2 | Stomach Margin 9060396 | 1.7 |
| Kidney Ca, Clear cell type (OD04340) | 0.7 | Gastric Cancer 9060395 | 1.9 |
| Kidney Margin (OD04340) | 4.0 | Stomach Margin 9060394 | 2.3 |
| Kidney Ca, Nuclear grade 3 (OD04348) | 0.9 | Gastric Cancer 064005 | 1.9 |

TABLE AUE

Panel 4.1D

| Tissue Name | Rel. Exp. (%) Ag3774, Run 170130276 | Tissue Name | Rel. Exp. (%) Ag3774, Run 170130276 |
|---|---|---|---|
| Secondary Th1 act | 39.8 | HUVEC IL-1beta | 38.2 |
| Secondary Th2 act | 44.4 | HUVEC IFN gamma | 39.0 |
| Secondary Tr1 act | 33.7 | HUVEC TNF alpha + IFN gamma | 19.1 |
| Secondary Th1 rest | 9.5 | HUVEC TNF alpha + IL4 | 28.1 |
| Secondary Th2 rest | 11.4 | HUVEC IL-11 | 25.2 |
| Secondary Tr1 rest | 12.2 | Lung Microvascular EC none | 32.3 |
| Primary Th1 act | 36.6 | Lung Microvascular EC TNF alpha + IL-1beta | 36.3 |
| Primary Th2 act | 39.8 | Microvascular Dermal EC none | 26.4 |
| Primary Tr1 act | 28.9 | Microvascular Dermal EC TNF alpha + IL-1beta | 23.3 |
| Primary Th1 rest | 24.8 | Bronchial epithelium TNF alpha + IL1beta | 38.4 |
| Primary Th2 rest | 11.7 | Small airway epithelium none | 24.1 |
| Primary Tr1 rest | 23.2 | Small airway epithelium TNF alpha + IL-1beta | 28.9 |
| CD45RA CD4 lymphocyte act | 45.1 | Coronery artery SMC rest | 31.4 |
| CD45RO CD4 lymphocyte act | 45.1 | Coronery artery SMC TNF alpha + IL-1beta | 24.5 |
| CD8 lymphocyte act | 49.0 | Astrocytes rest | 46.3 |
| Secondary CD8 lymphocyte rest | 31.2 | Astrocytes TNF alpha + IL-1beta | 12.1 |
| Secondary CD8 lymphocyte act | 22.1 | KU-812 (Basophil) rest | 37.9 |
| CD4 lymphocyte none | 11.0 | KU-812 (Basophil) PMA/ionomycin | 49.3 |

TABLE AUE-continued

Panel 4.1D

| Tissue Name | Rel. Exp. (%) Ag3774, Run 170130276 | Tissue Name | Rel. Exp. (%) Ag3774, Run 170130276 |
|---|---|---|---|
| 2ry Th1/Th2/Tr1__anti-CD95 CH11 | 15.9 | CCD1106 (Keratinocytes) none | 56.3 |
| LAK cells rest | 18.7 | CCD1106 (Keratinocytes) TNF alpha + IL-1beta | 34.6 |
| LAK cells IL-2 | 31.4 | Liver cirrhosis | 38.4 |
| LAK cells IL-2 + IL-12 | 25.3 | NCI-H292 none | 25.2 |
| LAK cells IL-2 + IFN gamma | 46.7 | NCI-H292 IL-4 | 36.3 |
| LAK cells IL-2 + IL-18 | 32.8 | NCI-H292 IL-9 | 47.6 |
| LAK cells PMA/ionomycin | 3.9 | NCI-H292 IL-13 | 37.1 |
| NK Cells IL-2 rest | 30.8 | NCI-H292 IFN gamma | 49.3 |
| Two Way MLR 3 day | 23.3 | HPAEC none | 27.7 |
| Two Way MLR 5 day | 37.6 | HPAEC TNF alpha + IL-1beta | 31.9 |
| Two Way MLR 7 day | 17.8 | Lung fibroblast none | 44.1 |
| PBMC rest | 4.1 | Lung fibroblast TNF alpha + IL-1beta | 17.0 |
| PBMC PWM | 35.4 | Lung fibroblast IL-4 | 34.9 |
| PBMC PHA-L | 20.9 | Lung fibroblast IL-9 | 62.4 |
| Ramos (B cell) none | 76.8 | Lung fibroblast IL-13 | 42.0 |
| Ramos (B cell) ionomycin | 68.8 | Lung fibroblast IFN gamma | 25.2 |
| B lymphocytes PWM | 41.2 | Dermal fibroblast CCD1070 rest | 100.0 |
| B lymphocytes CD40L and IL-4 | 28.9 | Dermal fibroblast CCD1070 TNF alpha | 66.4 |
| EOL-1 dbcAMP | 17.4 | Dermal fibroblast CCD1070 IL-1beta | 38.2 |
| EOL-1 dbcAMP PMA/ionomycin | 20.9 | Dermal fibroblast IFN gamma | 17.0 |
| Dendritic cells none | 21.0 | Dermal fibroblast IL-4 | 47.3 |
| Dendritic cells LPS | 5.7 | Dermal Fibroblasts rest | 29.5 |
| Dendritic cells anti-CD40 | 22.5 | Neutrophils TNFa + LPS | 0.0 |
| Monocytes rest | 7.9 | Neutrophils rest | 2.3 |
| Monocytes LPS | 2.6 | Colon | 15.4 |
| Macrophages rest | 22.2 | Lung | 23.8 |
| Macrophages LPS | 4.5 | Thymus | 68.3 |
| HUVEC none | 29.7 | Kidney | 49.3 |
| HUVEC starved | 34.6 | | |

TABLE AUF

Panel 5D

| Tissue Name | Rel. Exp. (%) Ag3774, Run 223675472 | Tissue Name | Rel. Exp. (%) Ag3774, Run 223675472 |
|---|---|---|---|
| 97457__Patient-02go__adipose | 17.7 | 94709__Donor 2 AM - A__adipose | 19.6 |
| 97476__Patient-07sk__skeletal muscle | 3.6 | 94710__Donor 2 AM - B__adipose | 9.3 |
| 97477__Patient-07ut__uterus | 2.3 | 94711__Donor 2 AM - C__adipose | 7.5 |
| 97478__Patient-07pl__placenta | 2.2 | 94712__Donor 2 AD - A__adipose | 56.6 |
| 97481__Patient-08sk__skeletal muscle | 6.4 | 94713__Donor 2 AD - B__adipose | 72.2 |
| 97482__Patient-08ut__uterus | 1.6 | 94714__Donor 2 AD - C__adipose | 70.2 |
| 97483__Patient-08pl__placenta | 0.8 | 94742__Donor 3 U - A__Mesenchymal Stem Cells | 1.6 |
| 97486__Patient-09sk__skeletal muscle | 0.5 | 94743__Donor 3 U - B__Mesenchymal Stem Cells | 1.8 |
| 97487__Patient-09ut__uterus | 2.1 | 94730__Donor 3 AM - A__adipose | 13.1 |
| 97488__Patient-09pl__placenta | 0.8 | 94731__Donor 3 AM - B__adipose | 8.5 |
| 97492__Patient-10ut__uterus | 1.6 | 94732__Donor 3 AM - C__adipose | 8.7 |
| 97493__Patient-10pl__placenta | 1.4 | 94733__Donor 3 AD - A__adipose | 100.0 |
| 97495__Patient-11go__adipose | 10.4 | 94734__Donor 3 AD - B__adipose | 62.9 |
| 97496__Patient-11sk__skeletal muscle | 2.8 | 94735__Donor 3 AD - C__adipose | 53.2 |

TABLE AUF-continued

Panel 5D

| Tissue Name | Rel. Exp. (%) Ag3774, Run 223675472 | Tissue Name | Rel. Exp. (%) Ag3774, Run 223675472 |
|---|---|---|---|
| 97497_Patient-11ut_uterus | 2.1 | 77138_Liver_HepG2untreated | 56.6 |
| 97498_Patient-11pl_placenta | 1.8 | 73556_Heart_Cardiac stromal cells (primary) | 0.5 |
| 97500_Patient-12go_adipose | 13.5 | 81735_Small Intestine | 2.3 |
| 97501_Patient-12sk_skeletal muscle | 6.0 | 72409_Kidney_Proximal Convoluted Tubule | 1.0 |
| 97502_Patient-12ut_uterus | 2.6 | 82685_Small intestine_Duodenum | 1.6 |
| 97503_Patient-12pl_placenta | 0.4 | 90650_Adrenal_Adrenocortical adenoma | 4.6 |
| 94721_Donor 2 U - A_Mesenchymal Stem Cells | 3.5 | 72410_Kidney_HRCE | 3.3 |
| 94722_Donor 2 U - B_Mesenchymal Stem Cells | 3.7 | 72411_Kidney_HRE | 2.7 |
| 94723_Donor 2 U - C_Mesenchymal Stem Cells | 2.7 | 73139_Uterus_Uterine smooth muscle cells | 1.2 |

CNS_neurodegeneration_v1.0 Summary: Ag3774 This panel confirms the expression of the CG92142-01 gene at low levels in the brains of an independent group of individuals. However, no differential expression of this gene was detected between Alzheimer's diseased postmortem brains and those of non-demented controls in this experiment. Please see Panel 1.4 for a discussion of the potential utility of this gene in treatment of central nervous system disorders.

General_screening_panel_v1.4 Summary: Ag3774 Highest expression of the CG92142-01 gene is detected in CNS cancer (glio) SF-295 cell line (CT=26). High expression of this gene is also in number of cancer cell lines (pancreatic, CNS, colon, gastric, renal, lung, breast, ovarian, squamous cell carcinoma, prostate and melanoma). Therefore, therapeutic modulation of the activity of this gene or its protein product, through the use of small molecule drugs might be beneficial in the treatment of these cancers.

Among tissues with metabolic or endocrine function, this gene is expressed at high to moderate levels in pancreas, adipose, adrenal gland, thyroid, pituitary gland, skeletal muscle, heart, liver and the gastrointestinal tract. Therefore, therapeutic modulation of the activity of this gene may prove useful in the treatment of endocrine/metabolically related diseases, such as obesity and diabetes.

The CG92142-01 gene encodes a mitochondrial glycerol-3-phosphate acyltransferase (GPAT). GPAT is an adipocyte determination and differentiation factor 1 (ADD1) and sterol regulatory element-binding protein-1 (SREBP-1) regulated differentiation gene (Ericsson J, Jackson S M, Kim J B, Spiegelman B M, Edwards P A. (1997) Identification of glycerol-3-phosphate acyltransferase as an adipocyte determination and differentiation factor 1- and sterol regulatory element-binding protein-responsive gene. J Biol Chem 272 (11):7298–305). It is up-regulated by insulin and high-carbohydrate diets (Dircks L K, Sul H S. (1997) Mammalian mitochondrial glycerol-3-phosphate acyltransferase. Biochim Biophys Acta 1348(1–2):17–26). GPAT up-regulation increases triglyceride (TG) synthesis and fat deposition. Inhibition of GPAT activity could lead to decreased TG synthesis and fat deposition. Troglitazone, a thiazolidinedione compound used to treat non-insulin-dependent diabetes mellitus (NIDDM), was shown to decreases GPAT activity and adipogenesis in ZDF rat islets (Shimabukuro M, Zhou Y T, Lee Y, Unger R H. (1998) Troglitazone lowers islet fat and restores beta cell function of Zucker diabetic fatty rats. J Biol Chem 273(6):3547–50). Therefore, therapeutic modulation of the activity of this gene may prove useful in the treatment of diabetes.

In addition, this gene is expressed at moderate levels in all regions of the central nervous system examined, including amygdala, hippocampus, substantia nigra, thalamus, cerebellum, cerebral cortex, and spinal cord. Therefore, this gene may play a role in central nervous system disorders such as Alzheimer's disease, Parkinson's disease, epilepsy, multiple sclerosis, schizophrenia and depression.

Panel 2.2 Summary: Ag3774 Highest expression of the CG92142-01 gene is detected in liver cancer 1025 sample (CT=28.7). In addition, low to moderate expression of this gene is seen in number of cancer and normal samples used in this panel. Please see Panel 1.4 for a discussion of the potential utility of this gene.

Panel 4.1D Summary: Ag3774 Highest expression of the CG92142-01 gene is detected in resting dermal fibroblast CCD1070 (CT=31). This gene is expressed at low to moderate levels in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. This ubiquitous pattern of expression suggests that this gene product may be involved in homeostatic processes for these and other cell types and tissues. This pattern is in agreement with the expression profile in General_screening_panel_v1.4 and also suggests a role for the gene product in cell survival and proliferation. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

Interestingly, expression of this gene is stimulated in PWM treated PBMC cells (CT=32.5) as compared to resting PBMC (35.6). Therefore, expression of this gene can be used to distinguish between resting and stimulated PBMC cells.

Panel 5D Summary: Ag3774 Highest expression of the CG92142-01 gene is detected in 94733_Donor 3 AD-A_ adipose sample (CT=27.6). In addition, high to moderated expression of this gene is also seen in number of adipose, small intestine, uterus, skeletal muscle, placenta and mesenchymal stem cell samples. Please see Panel 1.4 for a discussion of the potential utility of this gene.

AV. CG92152-01: Plasminogen Activator SPA

Expression of gene CG92152-01 was assessed using the primer-probe set Ag3775, described in Table AVA. Results of the RTQ-PCR runs are shown in Tables AVB, AVC and AVD.

TABLE AVA

| Probe Name Ag3775 | | | | |
|---|---|---|---|---|
| Primers | Sequences | Length | Start Position | SEQ ID NO: |
| Forward | 5'-gcagattcaagtgcatgtgtta-3' | 22 | 517 | 399 |
| Probe | TET-5'-ttactattctgcccatccaggaggga-3'-TAMRA | 26 | 562 | 400 |
| Reverse | 5'-gcacagatcatcttctctgtga-3' | 22 | 588 | 401 |

TABLE AVB

CNS_neurodegeneration_v1.0

| Tissue Name | Rel. Exp. (%) Ag3775, Run 211176610 | Rel. Exp. (%) Ag3775, Run 224339887 | Tissue Name | Rel. Exp. (%) Ag3775, Run 211176610 | Rel. Exp. (%) Ag3775, Run 224339887 |
|---|---|---|---|---|---|
| AD 1 Hippo | 34.2 | 29.1 | Control (Path) 3 Temporal Ctx | 4.4 | 2.1 |
| AD 2 Hippo | 33.4 | 25.7 | Control (Path) 4 Temporal Ctx | 37.1 | 21.5 |
| AD 3 Hippo | 25.7 | 9.7 | AD 1 Occipital Ctx | 24.7 | 19.9 |
| AD 4 Hippo | 9.0 | 8.1 | AD 2 Occipital Ctx (Missing) | 0.0 | 0.0 |
| AD 5 hippo | 100.0 | 61.6 | AD 3 Occipital Ctx | 8.1 | 9.0 |
| AD 6 Hippo | 88.9 | 100.0 | AD 4 Occipital Ctx | 12.2 | 16.0 |
| Control 2 Hippo | 10.7 | 20.9 | AD 5 Occipital Ctx | 29.5 | 11.3 |
| Control 4 Hippo | 12.2 | 5.9 | AD 6 Occipital Ctx | 29.9 | 29.9 |
| Control (Path) 3 Hippo | 4.7 | 2.8 | Control 1 Occipital Ctx | 1.8 | 0.9 |
| AD 1 Temporal Ctx | 24.0 | 26.8 | Control 2 Occipital Ctx | 21.9 | 23.3 |
| AD 2 Temporal Ctx | 22.2 | 21.5 | Control 3 Occipital Ctx | 8.9 | 3.3 |
| AD 3 Temporal Ctx | 15.9 | 5.0 | Control 4 Occipital Ctx | 3.3 | 3.5 |
| AD 4 Temporal Ctx | 16.2 | 21.9 | Control (Path) 1 Occipital Ctx | 46.0 | 36.1 |
| AD 5 Inf Temporal Ctx | 79.0 | 36.1 | Control (Path) 2 Occipital Ctx | 3.9 | 3.3 |
| AD 5 SupTemporal Ctx | 73.2 | 47.3 | Control (Path) 3 Occipital Ctx | 4.6 | 1.3 |
| AD 6 Inf Temporal Ctx | 70.2 | 33.9 | Control (Path) 4 Occipital Ctx | 3.3 | 3.2 |
| AD 6 Sup Temporal Ctx | 74.2 | 51.1 | Control 1 Parietal Ctx | 3.7 | 3.3 |
| Control 1 Temporal Ctx | 1.4 | 3.7 | Control 2 Parietal Ctx | 26.8 | 34.9 |
| Control 2 Temporal Ctx | 18.7 | 12.9 | Control 3 Parietal Ctx | 9.3 | 3.1 |
| Control 3 Temporal Ctx | 8.4 | 6.5 | Control (Path) 1 Parietal Ctx | 44.4 | 27.7 |
| Control 4 Temporal Ctx | 14.2 | 2.9 | Control (Path) 2 Parietal Ctx | 13.1 | 17.7 |
| Control (Path) 1 Temporal Ctx | 53.6 | 29.5 | Control (Path) 3 Parietal Ctx | 1.4 | 4.5 |
| Control (Path) 2 Temporal Ctx | 43.2 | 21.8 | Control (Path) 4 Parietal Ctx | 32.8 | 23.3 |

TABLE AVC

General_screening_panel_v1.4

| Tissue Name | Rel. Exp. (%) Ag3775, Run 219514534 | Tissue Name | Rel. Exp. (%) Ag3775, Run 219514534 |
|---|---|---|---|
| Adipose | 17.1 | Renal ca. TK-10 | 0.0 |
| Melanoma* Hs688(A).T | 0.0 | Bladder | 3.9 |
| Melanoma* Hs688(B).T | 0.0 | Gastric ca. (liver met.) NCI-N87 | 0.0 |
| Melanoma* M14 | 21.6 | Gastric ca. KATO III | 0.0 |
| Melanoma* LOXIMVI | 0.0 | Colon ca. SW-948 | 0.0 |
| Melanoma* SK-MEL-5 | 5.2 | Colon ca. SW480 | 0.0 |
| Squamous cell carcinoma SCC-4 | 0.0 | Colon ca.* (SW480 met) SW620 | 0.0 |
| Testis Pool | 40.1 | Colon ca. HT29 | 0.0 |
| Prostate ca.* (bone met) PC-3 | 6.0 | Colon ca. HCT-116 | 0.0 |
| Prostate Pool | 5.7 | Colon ca. CaCo-2 | 0.0 |
| Placenta | 0.0 | Colon cancer tissue | 12.8 |
| Uterus Pool | 6.1 | Colon ca. SW1116 | 0.0 |
| Ovarian ca OVCAR-3 | 100.0 | Colon ca. Colo-205 | 0.0 |
| Ovarian ca. SK-OV-3 | 5.4 | Colon ca. SW-48 | 0.0 |
| Ovarian ca. OVCAR-4 | 0.0 | Colon Pool | 13.6 |
| Ovarian ca. OVCAR-5 | 0.0 | Small Intestine Pool | 12.2 |
| Ovarian ca. IGROV-1 | 12.5 | Stomach Pool | 15.6 |
| Ovarian ca. OVCAR-8 | 11.3 | Bone Marrow Pool | 10.5 |
| Ovary | 12.1 | Fetal Heart | 3.7 |
| Breast ca. MCF-7 | 10.4 | Heart Pool | 17.2 |
| Breast ca. MDA-MB-231 | 0.0 | Lymph Node Pool | 24.5 |
| Breast ca. BT 549 | 56.3 | Fetal Skeletal Muscle | 14.7 |
| Breast ca. T47D | 0.0 | Skeletal Muscle Pool | 61.1 |
| Breast ca. MDA-N | 6.2 | Spleen Pool | 90.8 |
| Breast Pool | 9.9 | Thymus Pool | 40.3 |
| Trachea | 11.2 | CNS cancer (glio/astro) U87-MG | 54.3 |
| Lung | 9.7 | CNS cancer (glio/astro) U-118-MG | 0.0 |
| Fetal Lung | 3.8 | CNS cancer (neuro; met) SK-N-AS | 2.3 |
| Lung ca. NCI-N417 | 0.0 | CNS cancer (astro) SF-539 | 3.0 |
| Lung ca. LX-1 | 0.0 | CNS cancer (astro) SNB-75 | 35.1 |
| Lung ca. NCI-H146 | 0.0 | CNS cancer (glio) SNB-19 | 3.8 |
| Lung ca. SHP-77 | 12.3 | CNS cancer (glio) SF-295 | 39.5 |
| Lung ca. A549 | 0.0 | Brain (Amygdala) Pool | 21.5 |
| Lung ca. NCI-H526 | 0.0 | Brain (cerebellum) | 6.4 |
| Lung ca. NCI-H23 | 0.0 | Brain (fetal) | 45.1 |
| Lung ca. NCI-H460 | 30.4 | Brain (Hippocampus) Pool | 25.7 |
| Lung ca. HOP-62 | 23.0 | Cerebral Cortex Pool | 34.4 |
| Lung ca. NCI-H522 | 0.0 | Brain (Substantia nigra) Pool | 12.9 |
| Liver | 3.8 | Brain (Thalamus) Pool | 36.3 |
| Fetal Liver | 3.1 | Brain (whole) | 33.7 |
| Liver ca. HepG2 | 1.2 | Spinal Cord Pool | 21.5 |
| Kidney Pool | 27.7 | Adrenal Gland | 20.3 |
| Fetal Kidney | 49.0 | Pituitary gland Pool | 6.1 |
| Renal ca. 786-0 | 0.0 | Salivary Gland | 6.6 |
| Renal ca. A498 | 0.0 | Thyroid (female) | 0.0 |
| Renal ca. ACHN | 1.9 | Pancreatic ca. CAPAN2 | 0.0 |
| Renal ca. UO-31 | 0.0 | Pancreas Pool | 18.9 |

TABLE AVD

Panel 4.1D

| Tissue Name | Rel. Exp. (%) Ag3775, Run 170129781 | Tissue Name | Rel. Exp. (%) Ag3775, Run 170129781 |
|---|---|---|---|
| Secondary Th1 act | 0.0 | HUVEC IL-1beta | 5.1 |
| Secondary Th2 act | 51.4 | HUVEC IFN gamma | 4.8 |
| Secondary Tr1 act | 29.1 | HUVEC TNF alpha + IFN gamma | 1.4 |
| Secondary Th1 rest | 4.0 | HUVEC TNF alpha + IL4 | 4.7 |
| Secondary Th2 rest | 20.0 | HUVEC IL-11 | 1.8 |

TABLE AVD-continued

Panel 4.1D

| Tissue Name | Rel. Exp. (%) Ag3775, Run 170129781 | Tissue Name | Rel. Exp. (%) Ag3775, Run 170129781 |
|---|---|---|---|
| Secondary Tr1 rest | 14.9 | Lung Microvascular EC none | 0.0 |
| Primary Th1 act | 6.7 | Lung Microvascular EC TNF alpha + IL-1beta | 0.0 |
| Primary Th2 act | 10.4 | Microvascular Dermal EC none | 0.0 |
| Primary Tr1 act | 8.8 | Microsvasular Dermal EC TNF alpha + IL-1beta | 0.0 |
| Primary Th1 rest | 0.9 | Bronchial epithelium TNF alpha + IL1beta | 4.2 |
| Primary Th2 rest | 2.1 | Small airway epithelium none | 0.0 |
| Primary Tr1 rest | 13.4 | Small airway epithelium TNF alpha + IL-1beta | 0.0 |
| CD45RA CD4 lymphocyte act | 7.8 | Coronery artery SMC rest | 2.8 |
| CD45RO CD4 lymphocyte act | 2.8 | Coronery artery SMC TNF alpha + IL-1beta | 2.0 |
| CD8 lymphocyte act | 6.6 | Astrocytes rest | 15.3 |
| Secondary CD8 lymphocyte rest | 3.5 | Astrocytes TNF alpha + IL-1beta | 9.1 |
| Secondary CD8 lymphocyte act | 0.0 | KU-812 (Basophil) rest | 4.3 |
| CD4 lymphocyte none | 3.9 | KU-812 (Basophil) PMA/ionomycin | 0.0 |
| 2ry Th1/Th2/Tr1_anti-CD95 CH11 | 10.7 | CCD1106 (Keratinocytes) none | 0.0 |
| LAK cells rest | 7.8 | CCD1106 (Keratinocytes) TNF alpha + IL-1beta | 2.2 |
| LAK cells IL-2 | 5.8 | Liver cirrhosis | 1.5 |
| LAK cells IL-2 + IL-12 | 11.2 | NCI-H292 none | 0.0 |
| LAK cells IL-2 +IFN gamma | 11.2 | NCI-H292 IL-4 | 0.0 |
| LAK cells IL-2 + IL-18 | 14.9 | NCI-H292 IL-9 | 0.0 |
| LAK cells PMA/ionomycin | 13.5 | NCI-H292 IL-13 | 0.0 |
| NK Cells IL-2 rest | 3.8 | NCI-H292 IFN gamma | 0.0 |
| Two Way MLR 3 day | 14.3 | HPAEC none | 0.0 |
| Two Way MLR 5 day | 2.5 | HPAEC TNF alpha + IL-1beta | 8.0 |
| Two Way MLR 7 day | 2.0 | Lung fibroblast none | 13.0 |
| PBMC rest | 0.0 | Lung fibroblast TNF alpha + IL-1beta | 2.3 |
| PBMC PWM | 3.8 | Lung fibroblast IL-4 | 32.1 |
| PBMC PHA-L | 17.6 | Lung fibroblast IL-9 | 56.6 |
| Ramos (B cell) none | 0.0 | Lung fibroblast IL-13 | 45.4 |
| Ramos (B cell) ionomycin | 0.0 | Lung fibroblast IFN gamma | 18.2 |
| B lymphocytes PWM | 1.9 | Dermal fibroblast CCD1070 rest | 9.0 |
| B lymphocytes CD40L and IL-4 | 10.1 | Dermal fibroblast CCD1070 TNF alpha | 4.7 |
| EOL-1 dbcAMP | 0.0 | Dermal fibroblast CCD1070 IL-1beta | 0.0 |
| EOL-1 dbcAMP PMA/ionomycin | 0.0 | Dermal fibroblast IFN gamma | 38.4 |
| Dendritic cells none | 8.3 | Dermal fibroblast IL-4 | 100.0 |
| Dendritic cells LPS | 0.0 | Dermal Fibroblasts rest | 5.3 |
| Dendritic cells anti-CD40 | 15.4 | Neutrophils TNFa + LPS | 4.0 |
| Monocytes rest | 1.1 | Neutrophils rest | 2.1 |
| Monocytes LPS | 9.4 | Colon | 0.0 |
| Macrophages rest | 7.2 | Lung | 21.8 |
| Macrophages LPS | 5.6 | Thymus | 57.4 |
| HUVEC none | 0.0 | Kidney | 2.2 |
| HUVEC starved | 0.0 | | |

CNS_neurodegeneration_v1.0 Summary: Ag3775 Two experiments with two probe and primer sets produce results that are in excellent agreement. This panel does not show differential expression of the CG92152-01 gene in Alzheimer's disease. However, this expression profile confirms the presence of this gene in the brain, with highest expression in the hippocampus of an Alzheimer's patient (CTs= 31–32). Please see Panel 1.4 for discussion of utility of this gene in the central nervous system.

General_screening_panel_v1.4 Summary: Ag3775 Highest expression of the CG92152-01 gene is seen in an ovarian cancer cell line (CT=32). Significant levels of expression are seen in a cluster of samples derived from breast and lung cancer cell lines. Thus, expression of this gene could be used to differentiate between these samples and other samples on this panel and as a marker to detect the presence of these cancers. Furthermore, therapeutic modulation of the expression or function of this gene may be effective in the treatment of ovarian, breast and lung cancers.

This gene is also expressed at low levels in the CNS, including the hippocampus, thalamus, substantia nigra, amygdala, cerebellum and cerebral cortex. Therefore, therapeutic modulation of the expression or function of this gene may be useful in the treatment of neurologic disorders, such as Alzheimer's disease, Parkinson's disease, schizophrenia, multiple sclerosis, stroke and epilepsy.

Among tissues with metabolic function, this gene is expressed at low but significant levels in adipose, adrenal gland, pancreas, heart and adult and fetal skeletal muscle. This expression among these tissues suggests that this gene product may play a role in normal neuroendocrine and metabolic and that disregulated expression of this gene may contribute to neuroendocrine disorders or metabolic diseases, such as obesity and diabetes.

Panel 4.1D Summary: Ag3775 Highest expression of the CG92152-01 gene in IL-4 treated with dermal fibroblasts (CTs=32.5). Low, but significant levels of expression are also seen in treated and untreated lung and dermal fibroblasts, and chronically activated Th2 cells. The expression of this gene in lung and skin derived fibroblasts suggests that this gene may be involved in normal conditions as well as pathological and inflammatory lung disorders that include chronic obstructive pulmonary disease, asthma, allergy, psoriasis, and emphysema.

AW. CG92228-01 and CG92228-02: Transmembrane Tryptase

Expression of gene CG92228-01 and variant CG92228-02 was assessed using the primer-probe sets Ag1291 and Ag749, described in Tables AWA and AWB. Results of the RTQ-PCR runs are shown in Table AWC.

TABLE AWA

Probe Name Ag1291

| Primers | Sequences | Length | Start Position | SEQ ID NO: |
|---|---|---|---|---|
| Forward | 5'-ccatcccaagtaccaagataca-3' | 22 | 511 | 402 |
| Probe | TET-5'-agacgtcgccttgttgaaactgtcct-3'-TAMRA | 26 | 538 | 403 |
| Reverse | 5'-gcagaagtgaaggtgacttgag-3' | 22 | 564 | 404 |

TABLE AWB

Probe Name Ag749

| Primers | Sequences | Length | Start Position | SEQ ID NO: |
|---|---|---|---|---|
| Forward | 5'-aatcgtcatccatcccaagt-3' | 20 | 502 | 405 |
| Probe | TET-5'-tcgccttgttgaaactgtcctctcaa-3'-TAMRA | 26 | 543 | 406 |
| Reverse | 5'-ataggcaggatggcagaagt-3' | 20 | 578 | 407 |

TABLE AWC

Panel 4D

| Tissue Name | Rel. Exp. (%) Ag1291, Run 138673859 | Tissue Name | Rel. Exp. (%) Ag1291, Run 138673859 |
|---|---|---|---|
| Secondary Th1 act | 0.0 | HUVEC IL-1beta | 21.6 |
| Secondary Th2 act | 0.0 | HUVEC IFN gamma | 31.4 |
| Secondary Tr1 act | 0.0 | HUVEC TNF alpha + IFN gamma | 10.2 |
| Secondary Th1 rest | 0.0 | HUVEC TNF alpha + IL4 | 22.1 |
| Secondary Th2 rest | 0.0 | HUVEC IL-11 | 20.7 |
| Secondary Tr1 rest | 0.0 | Lung Microvascular EC none | 39.8 |
| Primary Th1 act | 0.0 | Lung Microvascular EC TNF alpha + IL-1beta | 22.5 |
| Primary Th2 act | 0.0 | Microvascular Dermal EC none | 100.0 |
| Primary Tr1 act | 0.0 | Microvasular Dermal EC TNF alpha + IL-1beta | 44.4 |
| Primary Th1 rest | 0.0 | Bronchial epithelium TNF alpha + IL1beta | 42.3 |
| Primary Th2 rest | 0.0 | Small airway epithelium none | 12.3 |
| Primary Tr1 rest | 0.0 | Small airway epithelium TNF alpha + IL-1beta | 75.3 |
| CD45RA CD4 lymphocyte act | 0.0 | Coronery artery SMC rest | 3.1 |
| CD45RO CD4 lymphocyte act | 0.0 | Coronery artery SMC TNF alpha + IL-1beta | 6.1 |
| CD8 lymphocyte act | 0.0 | Astrocytes rest | 13.5 |
| Secondary CD8 lymphocyte rest | 0.6 | Astrocytes TNF alpha + IL-1beta | 8.8 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 22.4 |
| LAK cells rest | 0.0 | CCD1106 (Keratinocytes) TNF alpha + IL-1beta | 85.3 |
| LAK cells IL-2 | 0.0 | Liver cirrhosis | 18.8 |
| LAK cells IL-2 + IL-12 | 0.0 | Lupus kidney | 21.0 |
| LAK cells IL-2 + IFN gamma | 0.0 | NCI-H292 none | 55.9 |
| LAK cells IL-2 + IL-18 | 0.0 | NCI-H292 IL-4 | 52.9 |

TABLE AWC-continued

Panel 4D

| Tissue Name | Rel. Exp. (%) Ag1291, Run 138673859 | Tissue Name | Rel. Exp. (%) Ag1291, Run 138673859 |
|---|---|---|---|
| LAK cells PMA/ionomycin | 0.0 | NCI-H292 IL-9 | 53.6 |
| NK Cells IL-2 rest | 0.0 | NCI-H292 IL-13 | 50.0 |
| Two Way MLR 3 day | 0.0 | NCI-H292 IFN gamma | 37.6 |
| Two Way MLR 5 day | 0.0 | HPAEC none | 31.9 |
| Two Way MLR 7 day | 0.0 | HPAEC TNF alpha + IL-1beta | 37.4 |
| PBMC rest | 0.0 | Lung fibroblast none | 2.9 |
| PBMC PWM | 0.4 | Lung fibroblast TNF alpha + IL-1beta | 0.5 |
| PBMC PHA-L | 0.0 | lung fibroblast IL-4 | 0.5 |
| Ramos (B cell) none | 0.0 | Lung fibroblast IL-9 | 2.5 |
| Ramos (B cell) ionomycin | 0.0 | Lung fibroblast IL-13 | 1.9 |
| B lymphocytes PWM | 0.0 | Lung fibroblast IFN gamma | 1.7 |
| B lymphocytes CD40L and IL-4 | 0.6 | Dermal fibroblast CCD1070 rest | 14.0 |
| EOL-1 dbcAMP | 0.0 | Dermal fibroblast CCD1070 TNF alpha | 8.4 |
| EOL-1 dbcAMP PMA/ionomycin | 0.0 | Dermal fibroblast CCD1070 IL-1beta | 8.5 |
| Dendritic cells none | 0.0 | Dermal fibroblast IFN gamma | 6.9 |
| Dendritic cells LPS | 0.0 | Dermal fibroblast IL-4 | 16.6 |
| Dendritic cells anti-CD40 | 0.0 | IBD Colitis 2 | 1.7 |
| Monocytes rest | 0.0 | IBD Crohn's | 8.3 |
| Monocytes LPS | 0.0 | Colon | 45.1 |
| Macrophages rest | 0.4 | Lung | 16.4 |
| Macrophages LPS | 0.0 | Thymus | 76.8 |
| HUVEC none | 36.9 | Kidney | 5.7 |
| HUVEC starved | 59.0 | | |

Panel 4D Summary: Ag1291 Highest expression of the CG92228-01 gene is seen in untreated dermal microvascular endothelium (CT=29). Moderate levels of expression are also seen in other endothelial cells including treated and untreated HUVECs, lung microvascular EC, and HPAECs. Moderate levels of expression are also seen in untreated and activated keratinocytes, activated small airway and bronchial epithelium, normal thymus and colon and a cluster of samples from the mucoepidermoid NCI-H292 cell line. This expression in many cell types involved in the inflammatory and processes in the lung and skin suggest that this gene product may be involved in asthma, allergy, emphysema and psoriasis.

AX. CG92425-01 and CG92425-02: Retinol Dehydrogenase

Expression of gene CG92425-01 and full length clone CG92425-02 was assessed using the primer-probe set Ag3789, described in Table AXA. Please note that CG92425-02 represents a full-length physical clone of the CG92425-01 gene, validating the prediction of the gene sequence.

TABLE AXA

Probe Name Ag3789

| Primers | Sequences | Length | Start Position | SEQ ID NO: |
|---|---|---|---|---|
| Forward | 5'-ctacatccctctggctaagttg-3' | 22 | 889 | 408 |
| Probe | TET-5'-tcatcctaagccggtaccttccaagg-3'-TAMRA | 26 | 930 | 409 |
| Reverse | 5'-gatcctccccagtttagacact-3' | 22 | 965 | 410 |

CNS_neurodegeneration_v1.0 Summary: Ag3789 Results from one experiment with the CG92425-01 gene are not included. (All CTs=40). The data suggest that there is the possibility of an experimental failure.

General_screening13_panel_v1.4 Summary: Ag3789 Results from one experiment with the CG92425-01 gene are not included. (All CTs=40). The data suggest that there is the possibility of an experimental failure.

Panel 2.2 Summary: Ag3789 Results from one experiment with the CG92425-01 gene are not included. (All CTs=40). The data suggest that there is the possibility of an experimental failure.

Panel 4.1D Summary: Ag3789 Results from one experiment with the CG92425-01 gene are not included. (All CTs=40). The data suggest that there is the possibility of an experimental failure.

AY. CG92499-01: Putative Novel Seven Transmembrane Domain Protein

Expression of gene CG92499-01 was assessed using the primer-probe set Ag780, described in Table AYA. Results of the RTQ-PCR runs are shown in Table AYB.

TABLE AYA

Probe Name Ag780

| Primers | Sequences | Length | Start Position | SEQ ID NO: |
|---|---|---|---|---|
| Forward | 5'-ctcagcgtatcatccctgttac-3' | 22 | 568 | 411 |
| Probe | TET-5'-tcaaattttagcattggtcttccaagca-3'-TAMRA | 28 | 607 | 412 |
| Reverse | 5'-caaaatccatctggaaatacga-3' | 22 | 643 | 413 |

TABLE AYB

Panel 1.2

| Tissue Name | Rel. Exp. (%) Ag780, Run 117132955 | Tissue Name | Rel. Exp. (%) Ag780, Run 117132955 |
|---|---|---|---|
| Endothelial cells | 9.0 | Renal ca. 786-0 | 1.3 |
| Heart (Fetal) | 0.0 | Renal ca. A498 | 0.1 |
| Pancreas | 0.0 | Renal ca. RXF 393 | 0.0 |
| Pancreatic ca. CAPAN2 | 9.2 | Renal ca. ACHN | 0.1 |
| Adrenal Gland | 0.1 | Renal ca. UO-31 | 0.2 |
| Thyroid | 0.0 | Renal ca. TK-10 | 5.3 |
| Salivary gland | 0.1 | Liver | 16.7 |
| Pituitary gland | 0.0 | Liver (fetal) | 10.7 |
| Brain (fetal) | 5.2 | Liver ca. (hepatoblast) HepG2 | 11.6 |
| Brain (whole) | 0.0 | Lung | 0.0 |
| Brain (amygdala) | 0.3 | Lung (fetal) | 1.6 |
| Brain (cerebellum) | 0.2 | Lung ca. (small cell) LX-1 | 0.0 |
| Brain (hippocampus) | 0.0 | Lung ca. (small cell) NCI-H69 | 0.0 |
| Brain (thalamus) | 0.0 | Lung ca. (s. cell var.) SHP-77 | 0.0 |
| Cerebral Cortex | 0.0 | Lung ca. (large cell)NCI-H460 | 0.5 |
| Spinal cord | 0.5 | Lung ca. (non-sm. cell) A549 | 17.3 |
| glio/astro U87-MG | 0.0 | Lung ca. (non-s. cell) NCI-H23 | 1.9 |
| glio/astro U-118-MG | 0.0 | Lung ca. (non-s. cell) HOP-62 | 2.4 |
| astrocytoma SW1783 | 0.0 | Lung ca. (non-s. cl) NCI-H522 | 49.7 |
| neuro*; met SK-N-AS | 0.0 | Lung ca. (squam.) SW 900 | 11.6 |
| astrocytoma SF-539 | 0.0 | Lung ca. (squam.) NCI-H596 | 0.0 |
| astrocytoma SNB-75 | 0.1 | Mammary gland | 0.0 |
| glioma SNB-19 | 0.0 | Breast ca.* (pl. ef) MCF-7 | 8.1 |
| glioma U251 | 0.0 | Breast ca.* (pl. ef) MDA-MB-231 | 1.8 |
| glioma SF-295 | 0.0 | Breast ca.* (pl. ef) T47D | 2.0 |
| Heart | 0.0 | Breast ca. BT-549 | 0.0 |
| Skeletal Muscle | 0.0 | Breast ca. MDA-N | 0.2 |
| Bone marrow | 0.1 | Ovary | 0.0 |
| Thymus | 0.0 | Ovarian ca. OVCAR-3 | 0.0 |
| Spleen | 0.0 | Ovarian ca. OVCAR-4 | 0.0 |
| Lymph node | 0.0 | Ovarian ca. OVCAR-5 | 1.7 |
| Colorectal Tissue | 0.0 | Ovarian ca. OVCAR-8 | 0.5 |
| Stomach | 0.0 | Ovarian ca. IGROV-1 | 1.3 |
| Small intestine | 0.0 | Ovarian ca. (ascites) SK-OV-3 | 0.0 |
| Colon ca. SW480 | 0.0 | Uterus | 0.1 |
| Colon ca.* SW620 (SW480 met) | 0.0 | Placenta | 14.0 |
| Colon ca. HT29 | 0.2 | Prostate | 0.0 |
| Colon ca. HCT-116 | 5.8 | Prostate ca.* (bone met) PC-3 | 29.7 |
| Colon ca. CaCo-2 | 14.9 | Testis | 0.0 |
| Colon ca. Tissue (ODO3866) | 0.0 | Melanoma Hs688(A).T | 0.0 |
| Colon ca. HCC-2998 | 0.9 | Melanoma* (met) Hs688(B).T | 0.0 |
| Gastric ca.* (liver met) NCI-N87 | 5.7 | Melanoma UACC-62 | 26.1 |
| Bladder | 18.6 | Melanoma M14 | 9.2 |
| Trachea | 0.0 | Melanoma LOX IMVI | 3.5 |
| Kidney | 0.3 | Melanoma* (met) SK-MEL-5 | 100.0 |
| Kidney (fetal) | 0.5 | | |

Panel 1.2 Summary: Ag780 The CG92499-01 gene shows a restricted expression pattern, with highest expression in a melanoma cell line (CT=28). Moderate levels of expression are also seen in samples derived from prostate, lung, colon and liver cancer cell lines. Thus, expression of this gene could be used to differentiate between the melanoma cell line and other samples on this panel. Furthermore, therapeutic modulation of the expression or function of this gene may be effective in the treatment of these cancers.

Low but significant expression is also seen in the fetal brain (CT=32.4). Thus, expression of this gene could be used to differentiate between fetal and adult brain tissue (CT=40).

AZ. CG92541-01: MUNC13-4

Expression of gene CG92541-01 was assessed using the primer-probe set Ag3815, described in Table AZA. Results of the RTQ-PCR runs are shown in Tables AZB, AZC and AZD.

TABLE AZA

Probe Name Ag3815

| Primers | Sequences | Length | Start Position | SEQ ID NO: |
|---|---|---|---|---|
| Forward | 5'-ctggacccacacactcaca-3' | 19 | 2566 | 414 |
| Probe | TET-5'-cagctcatccctggcttccaacag-3'-TAMRA | 24 | 2614 | 415 |
| Reverse | 5'-gttctgcagggcaatcttc-3' | 19 | 2641 | 416 |

TABLE AZB

CNS_neurodegeneration_v1.0

| Tissue Name | Rel. Exp. (%) Ag3815, Run 211292378 | Tissue Name | Rel. Exp. (%) Ag3815, Run 211292378 |
|---|---|---|---|
| AD 1 Hippo | 45.1 | Control (Path) 3 Temporal Ctx | 4.9 |
| AD 2 Hippo | 50.0 | Control (Path) 4 Temporal Ctx | 32.5 |
| AD 3 Hippo | 26.6 | AD 1 Occipital Ctx | 36.1 |
| AD 4 Hippo | 17.9 | AD 2 Occipital Ctx (Missing) | 0.0 |
| AD 5 hippo | 46.7 | AD 3 Occipital Ctx | 41.2 |
| AD 6 Hippo | 61.6 | AD 4 Occipital Ctx | 3.3 |
| Control 2 Hippo | 59.0 | AD 5 Occipital Ctx | 18.7 |
| Control 4 Hippo | 44.4 | AD 6 Occipital Ctx | 23.7 |
| Control (Path) 3 Hippo | 6.2 | Control 1 Occipital Ctx | 11.0 |
| AD 1 Temporal Ctx | 26.2 | Control 2 Occipital Ctx | 32.3 |
| AD 2 Temporal Ctx | 49.7 | Control 3 Occipital Ctx | 16.8 |
| AD 3 Temporal Ctx | 42.0 | Control 4 Occipital Ctx | 14.0 |
| AD 4 Temporal Ctx | 29.5 | Control (Path) 1 Occipital Ctx | 100.0 |
| AD 5 Inf Temporal Ctx | 51.1 | Control (Path) 2 Occipital Ctx | 23.0 |
| AD 5 SupTemporal Ctx | 57.4 | Control (Path) 3 Occipital Ctx | 2.1 |
| AD 6 Inf Temporal Ctx | 48.6 | Control (Path) 4 Occipital Ctx | 34.6 |
| AD 6 Sup Temporal Ctx | 41.2 | Control 1 Parietal Ctx | 87.1 |
| Control 1 Temporal Ctx | 26.4 | Control 2 Parietal Ctx | 59.5 |
| Control 2 Temporal Ctx | 48.3 | Control 3 Parietal Ctx | 33.9 |
| Control 3 Temporal Ctx | 18.8 | Control (Path) 1 Parietal Ctx | 38.7 |
| Control 4 Temporal Ctx | 14.3 | Control (Path) 2 Parietal Ctx | 43.8 |
| Control (Path) 1 Temporal Ctx | 35.8 | Control (Path) 3 Parietal Ctx | 4.0 |
| Control (Path) 2 Temporal Ctx | 20.6 | Control (Path) 4 Parietal Ctx | 45.4 |

TABLE AZC

General_screening_panel_v1.4

| Tissue Name | Rel. Exp. (%) Ag3815, Run 218668399 | Tissue Name | Rel. Exp. (%) Ag3815, Run 218668399 |
|---|---|---|---|
| Adipose | 0.4 | Renal ca. TK-10 | 8.3 |
| Melanoma* Hs688(A).T | 0.0 | Bladder | 4.8 |
| Melanoma* Hs688(B).T | 0.0 | Gastric ca. (liver met.) NCI-N87 | 9.0 |
| Melanoma* M14 | 0.2 | Gastric ca. KATO III | 15.2 |

TABLE AZC-continued

General_screening_panel_v1.4

| Tissue Name | Rel. Exp. (%) Ag3815, Run 218668399 | Tissue Name | Rel. Exp. (%) Ag3815, Run 218668399 |
|---|---|---|---|
| Melanoma* LOXIMVI | 0.1 | Colon ca. SW-948 | 2.2 |
| Melanoma* SK-MEL-5 | 0.9 | Colon ca. SW480 | 45.1 |
| Squamous cell carcinoma SCC-4 | 1.8 | Colon ca.* (SW480 met) SW620 | 7.7 |
| Testis Pool | 0.3 | Colon ca. HT29 | 3.9 |
| Prostate ca.* (bone met) PC-3 | 1.2 | Colon ca. HCT-116 | 3.9 |
| Prostate Pool | 1.0 | Colon ca. CaCo-2 | 0.9 |
| Placenta | 9.2 | Colon cancer tissue | 13.7 |
| Uterus Pool | 1.1 | Colon ca. SW1116 | 0.1 |
| Ovarian ca. OVCAR-3 | 3.2 | Colon ca. Colo-205 | 0.0 |
| Ovarian ca. SK-OV-3 | 13.7 | Colon ca. SW-48 | 0.2 |
| Ovarian ca. OVCAR-4 | 3.2 | Colon Pool | 1.8 |
| Ovarian ca. OVCAR-5 | 37.9 | Small Intestine Pool | 4.4 |
| Ovarian ca. IGROV-1 | 1.2 | Stomach Pool | 1.3 |
| Ovarian ca. OVCAR-8 | 4.5 | Bone Marrow Pool | 0.8 |
| Ovary | 1.4 | Fetal Heart | 0.9 |
| Breast ca. MCF-7 | 5.9 | Heart Pool | 0.6 |
| Breast ca. MDA-MB-231 | 92.0 | Lymph Node Pool | 1.3 |
| Breast ca. BT 549 | 0.1 | Fetal Skeletal Muscle | 0.2 |
| Breast ca. T47D | 100.0 | Skeletal Muscle Pool | 2.2 |
| Breast ca. MDA-N | 0.0 | Spleen Pool | 7.9 |
| Breast Pool | 2.1 | Thymus Pool | 5.9 |
| Trachea | 2.0 | CNS cancer (glio/astro) U87-MG | 0.5 |
| Lung | 0.3 | CNS cancer (glio/astro) U-118-MG | 0.3 |
| Fetal Lung | 10.5 | CNS cancer (neuro; met) SK-N-AS | 0.5 |
| Lung ca. NCI-N417 | 0.0 | CNS cancer (astro) SF-539 | 0.1 |
| Lung ca. LX-1 | 11.0 | CNS cancer (astro) SNB-75 | 0.4 |
| Lung ca. NCI-H146 | 0.0 | CNS cancer (glio) SNB-19 | 0.7 |
| Lung ca. SHP-77 | 1.6 | CNS cancer (glio) SF-295 | 10.1 |
| Lung ca. A549 | 1.4 | Brain (Amygdala) Pool | 0.2 |
| Lung ca. NCI-H526 | 0.0 | Brain (cerebellum) | 0.9 |
| Lung ca. NCI-H23 | 0.2 | Brain (fetal) | 0.1 |
| Lung ca. NCI-H460 | 0.2 | Brain (Hippocampus) Pool | 0.8 |
| Lung ca. HOP-62 | 28.9 | Cerebral Cortex Pool | 0.9 |
| Lung ca. NCI-H522 | 1.0 | Brain (Substantia nigra) Pool | 1.4 |
| Liver | 0.2 | Brain (Thalamus) Pool | 0.5 |
| Fetal Liver | 3.7 | Brain (whole) | 0.6 |
| Liver ca. HepG2 | 15.2 | Spinal Cord Pool | 0.9 |
| Kidney Pool | 4.5 | Adrenal Gland | 0.6 |
| Fetal Kidney | 1.0 | Pituitary gland Pool | 0.8 |
| Renal ca. 786-0 | 0.2 | Salivary Gland | 0.6 |
| Renal ca. A498 | 0.2 | Thyroid (female) | 0.4 |
| Renal ca. ACHN | 0.2 | Pancreatic ca. CAPAN2 | 17.2 |
| Renal ca. UO-31 | 35.4 | Pancreas Pool | 3.1 |

TABLE AZD

Panel 4.1D

| Tissue Name | Rel. Exp. (%) Ag3815, Run 170129244 | Tissue Name | Rel. Exp. (%) Ag3815, Run 170129244 |
|---|---|---|---|
| Secondary Th1 act | 68.8 | HUVEC IL-1beta | 2.8 |
| Secondary Th2 act | 66.0 | HUVEC IFN gamma | 1.9 |
| Secondary Tr1 act | 87.1 | HUVEC TNF alpha + IFN gamma | 1.8 |
| Secondary Th1 rest | 29.5 | HUVEC TNF alpha + IL4 | 1.8 |
| Secondary Th2 rest | 50.3 | HUVEC IL-11 | 1.8 |
| Secondary Tr1 rest | 41.2 | Lung Microvascular EC none | 44.4 |
| Primary Th1 act | 55.5 | Lung Microvascular EC TNF alpha + IL-1beta | 16.5 |
| Primary Th2 act | 67.4 | Microvascular Dermal EC none | 4.9 |

TABLE AZD-continued

Panel 4.1D

| Tissue Name | Rel. Exp. (%) Ag3815, Run 170129244 | Tissue Name | Rel. Exp. (%) Ag3815, Run 170129244 |
|---|---|---|---|
| Primary Tr1 act | 84.1 | Microvasular Dermal EC TNF alpha + IL-1beta | 5.6 |
| Primary Th1 rest | 30.1 | Bronchial epithelium TNF alpha + IL1beta | 3.7 |
| Primary Th2 rest | 28.5 | Small airway epithelium none | 3.7 |
| Primary Tr1 rest | 52.9 | Small airway epithelium TNF alpha + IL-1beta | 9.0 |
| CD45RA CD4 lymphocyte act | 15.2 | Coronery artery SMC rest | 0.5 |
| CD45RO CD4 lymphocyte act | 37.6 | Coronery artery SMC TNF alpha + IL-1beta | 0.2 |
| CD8 lymphocyte act | 78.5 | Astrocytes rest | 0.0 |
| Secondary CD8 lymphocyte rest | 37.4 | Astrocytes TNF alpha + IL-1beta | 0.0 |
| Secondary CD8 lymphocyte act | 36.6 | KU-812 (Basophil) rest | 100.0 |
| CD4 lymphocyte none | 14.7 | KU-812 (Basophil) PMA/ionomycin | 72.2 |
| 2ry Th1/Th2/Tr1_anti-CD95 CH11 | 58.6 | CCD1106 (Keratinocytes) none | 13.3 |
| LAK cells rest | 37.6 | CCD1106 (Keratinocytes) TNF alpha + IL-1beta | 10.2 |
| LAK cells IL-2 | 34.9 | Liver cirrhosis | 7.2 |
| LAK cells IL-2 + IL-12 | 33.7 | NCI-H292 none | 33.7 |
| LAK cells IL-2 + IFN gamma | 30.1 | NCI-H292 IL-4 | 24.0 |
| LAK cells IL-2 + IL-18 | 31.4 | NCI-H292 IL-9 | 59.0 |
| LAK cells PMA/ionomycin | 9.9 | NCI-H292 IL-13 | 21.2 |
| NK Cells IL-2 rest | 50.7 | NCI-H292 IFN gamma | 28.7 |
| Two Way MLR 3 day | 56.3 | HPAEC none | 6.5 |
| Two Way MLR 5 day | 66.4 | HPAEC TNF alpha + IL-1beta | 4.9 |
| Two Way MLR 7 day | 43.2 | Lung fibroblast none | 0.6 |
| PBMC rest | 18.0 | Lung fibroblast TNF alpha + IL-1beta | 0.0 |
| PBMC PWM | 43.5 | Lung fibroblast IL-4 | 0.0 |
| PBMC PHA-L | 35.8 | Lung fibroblast IL-9 | 0.0 |
| Ramos (B cell) none | 0.2 | Lung fibroblast IL-13 | 0.8 |
| Ramos (B cell) ionomycin | 1.9 | Lung fibroblast IFN gamma | 0.0 |
| B lymphocytes PWM | 13.8 | Dermal fibroblast CCD1070 rest | 0.3 |
| B lymphocytes CD40L and IL-4 | 32.1 | Dermal fibroblast CCD1070 TNF alpha | 15.7 |
| EOL-1 dbcAMP | 24.0 | Dermal fibroblast CCD1070 IL-1beta | 0.0 |
| EOL-1 dbcAMP PMA/ionomycin | 14.8 | Dermal fibroblast IFN gamma | 0.2 |
| Dendritic cells none | 48.0 | Dermal fibroblast IL-4 | 0.9 |
| Dendritic cells LPS | 31.4 | Dermal Fibroblasts rest | 0.4 |
| Dendritic cells anti-CD40 | 29.9 | Neutrophils TNFa + LPS | 16.5 |
| Monocytes rest | 57.0 | Neutrophils rest | 57.8 |
| Monocytes LPS | 59.9 | Colon | 3.7 |
| Macrophages rest | 27.7 | Lung | 7.8 |
| Macrophages LPS | 30.4 | Thymus | 23.2 |
| HUVEC none | 2.6 | Kidney | 0.9 |
| HUVEC starved | 2.0 | | |

CNS_neurodegeneration_v1.0 Summary: Ag3815 This panel does not show differential expression of the CG925413-01 gene in Alzheimer's disease. However, this expression profile confirms the presence of this gene in the brain. Please see Panel 1.4 for discussion of utility of this gene in the central nervous system.

General_screening_panel_v1.4 Summary: Ag3815 Highest expression of the CG92541-01 gene is seen in a breast cancer cell line (C=27). Moderate levels of expression are also seen in samples derived from ovarian, renal, lung and colon cancers. Thus, expression of this gene could be used to differentiate the breast cancer cell lines from other samples on this panel and as a marker for these cancers. Furthermore, therapeutic modulation of the expression or function of this gene product may be useful in the treatment of breast, ovarian, lung, colon and renal cancers.

Among metabolic tissues, low levels of expression are seen in pancreas, adrenal, pituitary, skeletal muscle and fetal and adult heart and liver. This expression suggests that this gene product may be involved in the pathogenesis and/or treatment of metabolic disorders, including obesity and diabetes.

In addition, this gene is expressed at much higher levels in fetal lung and liver (CTs=30–32) when compared to expression in the adult counterparts (CTs—35). Thus, expression of this gene may be used to differentiate between the fetal and adult source of these tissues.

This gene is also expressed at low but significant levels in cerebellum, substantia nigra, hippocampus, and cerebral cortex. This gene encodes a homolog of MUNC 13, a protein involved in neurotransmitter release at the synaptic junction. Therefore, therapeutic modulation of the expression or function of this protein may be useful in the treatment of disease where reduction in neurotransmission has been shown to ameliorate symptomology (e.g., epilepsy or other seizure disorders, schizophrenia, bipolar disorder or anxiety) (Richmond J E, Weimer R M, Jorgensen E M. An open form of syntaxin bypasses the requirement for UNC-13 in vesicle priming. Nature 2001 Jul. 19;412(6844):338–41).

Panel 4.1D Summary: Ag3815 Highest expression of the CG92541-01 gene is seen the resting basophil cell line KU-812 (CT=29.3). In addition, moderate levels of expression are seen in many of the hematopoietic samples on this panel, including macrophages, monocytes, dendritic cells, T cells, neutrophils and B cells. In addition, this transcript appears to be slightly upregulated in activated T cells when compared to expression in resting T cells. Thus, this gene product may be involved in autoimmune or inflammatory conditions such as asthma, emphysema, inflammatory bowel disease, and rheumatoid arthritis.

BA. CG92662-01: Prostaglandin-E29-Reductase

Expression of gene CG92662-01 was assessed using the primer-probe set Ag3816, described in Table BAA. Results of the RTQ-PCR runs are shown in Tables BAB, BAC and BAD.

TABLE BAA

Probe Name Ag3816

| Primers | Sequences | Length | Start Position | SEQ ID NO: |
|---|---|---|---|---|
| Forward | 5'-ccctgtgaagagagaggacatt-3' | 22 | 231 | 417 |
| Probe | TET-5'-caccactgagctttggacaactttct-3'-TAMRA | 26 | 258 | 418 |
| Reverse | 5'-gggcgaactaattctggtctaa-3' | 22 | 284 | 419 |

TABLE BAB

General_screening_panel_v1.4

| Tissue Name | Rel. Exp. (%) Ag3816, Run 213515569 | Tissue Name | Rel. Exp. (%) Ag3816, Run 213515569 |
|---|---|---|---|
| Adipose | 0.4 | Renal ca. TK-10 | 0.3 |
| Melanoma* Hs688(A).T | 0.4 | Bladder | 0.0 |
| Melanoma* Hs688(B).T | 1.4 | Gastric ca. (liver met.) NCI-N87 | 6.7 |
| Melanoma* M14 | 0.0 | Gastric ca. KATO III | 5.4 |
| Melanoma* LOXIMVI | 16.8 | Colon ca. SW-948 | 3.6 |
| Melanoma* SK-MEL-5 | 0.0 | Colon ca. SW480 | 1.1 |
| Squamous cell carcinoma SCC-4 | 6.0 | Colon ca.* (SW480 met) SW620 | 1.0 |
| Testis Pool | 1.5 | Colon ca. HT29 | 1.3 |
| Prostate ca.* (bone met) PC-3 | 1.3 | Colon ca. HCT-116 | 0.0 |
| Prostate Pool | 0.0 | Colon ca. CaCo-2 | 0.3 |
| Placenta | 2.8 | Colon cancer tissue | 2.1 |
| Uterus Pool | 0.4 | Colon ca. SW1116 | 0.2 |
| Ovarian ca. OVCAR-3 | 0.0 | Colon ca. Colo-205 | 0.4 |
| Ovarian ca. SK-OV-3 | 27.0 | Colon ca. SW-48 | 2.1 |
| Ovarian ca. OVCAR-4 | 1.5 | Colon Pool | 0.4 |
| Ovarian ca. OVCAR-5 | 3.1 | Small Intestine Pool | 1.4 |
| Ovarian ca. IGROV-1 | 4.8 | Stomach Pool | 0.3 |
| Ovarian ca. OVCAR-8 | 0.0 | Bone Marrow Pool | 0.8 |
| Ovary | 0.2 | Fetal Heart | 0.0 |
| Breast ca. MCF-7 | 0.0 | Heart Pool | 0.3 |
| Breast ca. MDA-MB-231 | 14.4 | Lymph Node Pool | 0.8 |
| Breast ca. BT 549 | 1.7 | Fetal Skeletal Muscle | 0.0 |
| Breast ca. T47D | 6.4 | Skeletal Muscle Pool | 1.8 |
| Breast ca. MDA-N | 0.0 | Spleen Pool | 3.8 |
| Breast Pool | 0.8 | Thymus Pool | 3.0 |
| Trachea | 9.5 | CNS cancer (glio/astro) U87-MG | 100.0 |
| Lung | 0.0 | CNS cancer (glio/astro) U-118-MG | 0.0 |
| Fetal Lung | 1.4 | CNS cancer (neuro; met) SK-N-AS | 4.0 |
| Lung ca. NCI-N417 | 0.0 | CNS cancer (astro) SF-539 | 0.0 |
| Lung ca. LX-1 | 8.2 | CNS cancer (astro) SNB-75 | 2.7 |
| Lung ca. NCI-H146 | 4.8 | CNS cancer (glio) SNB-19 | 3.9 |
| Lung ca. SHP-77 | 39.2 | CNS cancer (glio) SF-295 | 51.4 |
| Lung ca. A549 | 71.2 | Brain (Amygdala) Pool | 0.3 |
| Lung ca. NCI-H526 | 0.0 | Brain (cerebellum) | 0.0 |
| Lung ca. NCI-H23 | 0.2 | Brain (fetal) | 0.0 |
| Lung ca. NCI-H460 | 26.4 | Brain (Hippocampus) Pool | 0.0 |
| Lung ca. HOP-62 | 18.6 | Cerebral Cortex Pool | 0.3 |
| Lung ca. NCI-H522 | 0.0 | Brain (Substantia nigra) Pool | 0.2 |

TABLE BAB-continued

General_screening_panel_v1.4

| Tissue Name | Rel. Exp. (%) Ag3816, Run 213515569 | Tissue Name | Rel. Exp. (%) Ag3816, Run 213515569 |
| --- | --- | --- | --- |
| Liver | 0.0 | Brain (Thalamus) Pool | 0.0 |
| Fetal Liver | 1.7 | Brain (whole) | 0.0 |
| Liver ca. HepG2 | 0.0 | Spinal Cord Pool | 0.0 |
| Kidney Pool | 0.6 | Adrenal Gland | 0.0 |
| Fetal Kidney | 0.3 | Pituitary gland Pool | 0.0 |
| Renal ca.786-0 | 0.0 | Salivary Gland | 3.0 |
| Renal ca. A498 | 0.8 | Thyroid (female) | 0.0 |
| Renal ca. ACHN | 1.1 | Pancreatic ca. CAPAN2 | 5.1 |
| Renal ca. UO-31 | 0.0 | Pancreas Pool | 2.0 |

TABLE BAC

Panel 2.2

| Tissue Name | Rel. Exp. (%) Ag3816, Run 174448448 | Tissue Name | Rel. Exp. (%) Ag3816, Run 174448448 |
| --- | --- | --- | --- |
| Normal Colon | 8.8 | Kidney Margin (OD04348) | 14.2 |
| Colon cancer (OD06064) | 0.0 | Kidney malignant cancer (OD06204B) | 0.0 |
| Colon Margin (OD06064) | 0.0 | Kidney normal adjacent tissue (OD06204E) | 1.5 |
| Colon cancer (OD06159) | 0.0 | Kidney Cancer (OD04450-01) | 0.0 |
| Colon Margin (OD06159) | 5.3 | Kidney Margin (OD04450-03) | 5.8 |
| Colon cancer (OD06297-04) | 2.0 | Kidney Cancer 8120613 | 2.7 |
| Colon Margin (OD06297-05) | 0.0 | Kidney Margin 8120614 | 0.0 |
| CC Gr.2 ascend colon (ODO3921) | 2.5 | Kidney Cancer 9010320 | 0.0 |
| CC Margin (ODO3921) | 0.0 | Kidney Margin 9010321 | 0.0 |
| Colon cancer metastasis (OD06104) | 0.0 | Kidney Cancer 8120607 | 3.0 |
| Lung Margin (OD06104) | 0.0 | Kidney Margin 8120608 | 0.0 |
| Colon mets to lung (OD04451-01) | 10.6 | Normal Uterus | 2.1 |
| Lung Margin (OD04451-02) | 0.0 | Uterine Cancer 064011 | 0.0 |
| Normal Prostate | 0.0 | Normal Thyroid | 0.0 |
| Prostate Cancer (OD04410) | 7.5 | Thyroid Cancer 064010 | 0.0 |
| Prostate Margin (OD04410) | 0.0 | Thyroid Cancer A302152 | 0.0 |
| Normal Ovary | 0.0 | Thyroid Margin A302153 | 0.0 |
| Ovarian cancer (OD06283-03) | 0.0 | Normal Breast | 6.0 |
| Ovarian Margin (OD06283-07) | 0.0 | Breast Cancer (OD04566) | 0.0 |
| Ovarian Cancer 064008 | 0.0 | Breast Cancer 1024 | 1.9 |
| Ovarian cancer (OD06145) | 0.0 | Breast Cancer (OD04590-01) | 0.0 |
| Ovarian Margin (OD06145) | 0.0 | Breast Cancer Mets (OD04590-03) | 6.8 |
| Ovarian cancer (OD06455-03) | 0.0 | Breast Cancer Metastasis (OD04655-05) | 100.0 |
| Ovarian Margin (OD06455-07) | 1.9 | Breast Cancer 064006 | 17.7 |
| Normal Lung | 5.4 | Breast Cancer 9100266 | 0.0 |
| Invasive poor diff. lung adeno (ODO4945-01 | 72.7 | Breast Margin 9100265 | 2.2 |
| Lung Margin (ODO4945-03) | 2.4 | Breast Cancer A209073 | 0.0 |
| Lung Malignant Cancer (OD03126) | 0.0 | Breast Margin A2090734 | 2.7 |
| Lung Margin (OD03126) | 0.0 | Breast cancer (OD06083) | 84.7 |
| Lung Cancer (OD05014A) | 0.0 | Breast cancer node metastasis (OD06083) | 49.0 |
| Lung Margin (OD05014B) | 4.9 | Normal Liver | 0.0 |
| Lung cancer (OD06081) | 8.3 | Liver Cancer 1026 | 0.0 |
| Lung Margin (OD06081) | 8.5 | Liver Cancer 1025 | 3.0 |
| Lung Cancer (OD04237-01) | 3.1 | Liver Cancer 6004-T | 0.0 |
| Lung Margin (OD04237-02) | 9.0 | Liver Tissue 6004-N | 0.0 |
| Ocular Melanoma Metastasis | 0.0 | Liver Cancer 6005-T | 2.6 |

TABLE BAC-continued

Panel 2.2

| Tissue Name | Rel. Exp. (%) Ag3816, Run 174448448 | Tissue Name | Rel. Exp. (%) Ag3816, Run 174448448 |
|---|---|---|---|
| Ocular Melanoma Margin (Liver) | 0.0 | Liver Tissue 6005-N | 0.0 |
| Melanoma Metastasis | 0.0 | Liver Cancer 064003 | 0.0 |
| Melanoma Margin (Lung) | 7.5 | Normal Bladder | 2.7 |
| Normal Kidney | 7.7 | Bladder Cancer 1023 | 0.0 |
| Kidney Ca, Nuclear grade 2 (OD04338) | 0.0 | Bladder Cancer A302173 | 0.0 |
| Kidney Margin (OD04338) | 5.3 | Normal Stomach | 2.9 |
| Kidney Ca Nuclear grade 1/2 (OD04339) | 5.6 | Gastric Cancer 9060397 | 0.0 |
| Kidney Margin (OD04339) | 0.0 | Stomach Margin 9060396 | 0.0 |
| Kidney Ca, Clear cell type (OD04340) | 0.0 | Gastric Cancer 9060395 | 2.2 |
| Kidney Margin (OD04340) | 7.7 | Stomach Margin 9060394 | 0.0 |
| Kidney Ca, Nuclear grade 3 (OD04348) | 0.0 | Gastric Cancer 064005 | 0.0 |

TABLE BAD

Panel 4.1D

| Tissue Name | Rel. Exp. (%) Ag3816, Run 170129269 | Tissue Name | Rel. Exp. (%) Ag3816, Run 170129269 |
|---|---|---|---|
| Secondary Th1 act | 8.0 | HUVEC IL-1beta | 3.7 |
| Secondary Th2 act | 3.8 | HUVEC IFN gamma | 1.9 |
| Secondary Tr1 act | 9.5 | HUVEC TNF alpha + IFN gamma | 0.7 |
| Secondary Th1 rest | 27.7 | HUVEC TNF alpha + IL4 | 1.8 |
| Secondary Th2 rest | 13.7 | HUVEC IL-11 | 0.7 |
| Secondary Tr1 rest | 17.2 | Lung Microvascular EC none | 22.1 |
| Primary Th1 act | 8.8 | Lung Microvascular EC TNF alpha + IL-1beta | 11.7 |
| Primary Th2 act | 1.4 | Microvascular Dermal EC none | 21.3 |
| Primary Tr1 act | 3.5 | Microvasular Dermal EC TNF alpha + IL-1beta | 14.1 |
| Primary Th1 rest | 20.6 | Bronchial epithelium TNF alpha + IL1beta | 8.4 |
| Primary Th2 rest | 13.7 | Small airway epithelium none | 0.9 |
| Primary Tr1 rest | 14.1 | Small airway epithelium TNF alpha + IL-1beta | 3.0 |
| CD45RA CD4 lymphocyte act | 4.1 | Coronery artery SMC rest | 0.6 |
| CD45RO CD4 lymphocyte act | 26.8 | Coronery artery SMC TNF alpha + IL-1beta | 0.0 |
| CD8 lymphocyte act | 3.7 | Astrocytes rest | 0.0 |
| Secondary CD8 lymphocyte rest | 20.4 | Astrocytes TNF alpha + IL-1beta | 0.0 |
| Secondary CD8 lymphocyte act | 1.0 | KU-812 (Basophil) rest | 16.3 |
| CD4 lymphocyte none | 31.2 | KU-812 (Basophil) PMA/ionomycin | 30.6 |
| 2ry Th1/Th2/Tr1_anti-CD95 CH11 | 15.6 | CCD1106 (Keratinocytes) none | 1.5 |
| LAK cells rest | 39.0 | CCD1106 (Keratinocytes) TNF alpha + IL-1beta | 1.3 |
| LAK cells IL-2 | 48.3 | Liver cirrhosis | 0.0 |
| LAK cells IL-2 + IL-12 | 31.6 | NCI-H292 none | 0.0 |
| LAK cells IL-2 + IFN gamma | 28.5 | NCI-H292 IL-4 | 1.1 |
| LAK cells IL-2 + IL-18 | 33.4 | NCI-H292 IL-9 | 0.9 |
| LAK cells PMA/ionomycin | 100.0 | NCI-H292 IL-13 | 0.8 |
| NK Cells IL-2 rest | 43.5 | NCI-H292 IFN gamma | 2.0 |
| Two Way MLR 3 day | 71.2 | HPAEC none | 0.6 |
| Two Way MLR 5 day | 31.4 | HPAEC TNF alpha + IL-1beta | 5.4 |
| Two Way MLR 7 day | 27.0 | Lung fibroblast none | 0.0 |
| PBMC rest | 13.0 | Lung fibroblast TNF alpha + IL-1beta | 0.0 |

TABLE BAD-continued

Panel 4.1D

| Tissue Name | Rel. Exp. (%) Ag3816, Run 170129269 | Tissue Name | Rel. Exp. (%) Ag3816, Run 170129269 |
|---|---|---|---|
| PBMC PWM | 23.2 | Lung fibroblast IL-4 | 0.0 |
| PBMC PHA-L | 9.1 | Lung fibroblast IL-9 | 0.0 |
| Ramos (B cell) none | 0.0 | Lung fibroblast IL-13 | 0.0 |
| Ramos (B cell) ionomycin | 0.0 | Lung fibroblast IFN gamma | 0.0 |
| B lymphocytes PWM | 12.4 | Dermal fibroblast CCD1070 rest | 0.0 |
| B lymphocytes CD40L and IL-4 | 14.0 | Dermal fibroblast CCD1070 TNF alpha | 3.8 |
| EOL-1 dbcAMP | 1.0 | Dermal fibroblast CCD1070 IL-1beta | 4.5 |
| EOL-1 dbcAMP PMA/ionomycin | 4.3 | Dermal fibroblast IFN gamma | 1.5 |
| Dendritic cells none | 23.8 | Dermal fibroblast IL-4 | 3.9 |
| Dendritic cells LPS | 14.9 | Dermal Fibroblasts rest | 2.7 |
| Dendritic cells anti-CD40 | 16.6 | Neutrophils TNFa + LPS | 3.6 |
| Monocytes rest | 3.2 | Neutrophils rest | 3.2 |
| Monocytes LPS | 11.6 | Colon | 1.4 |
| Macrophages rest | 7.4 | Lung | 1.9 |
| Macrophages LPS | 3.8 | Thymus | 2.1 |
| HUVEC none | 0.0 | Kidney | 0.6 |
| HUVEC starved | 2.1 | | |

CNS_neurodegeneration_v1.0 Summary: Ag3816 Expression of the CG92662-01 gene is low/undetectable in all samples on this panel (CTs>35). (Data not shown.)

General_screening_panel_v1.4 Summary: Ag3816 Expression of the CG92662-01 gene is predominantly associated with normal tissues, with highest expression in a brain cancer cell line (CT=30). Moderate levels of expression are also seen in a cluster of lung cancer cell lines, with low but significant expression in ovarian, breast and melanoma cancer cell lines. Thus, expression of this gene could be used to differentiate these cell line samples from other samples on this panel and as a diagnostic marker for the presence of these cancers. Furthermore, therapeutic modulation of the expression or function of this gene may be effective in the treatment of brain, ovarian, breast and melanoma cancers.

Panel 2.2 Summary: Ag3816 Expression of the CG92662-01 gene is almost exclusive to breast cancer (CTs=33–34). Thus, expression of this gene could be used to differentiate between the breast cancer cell lines and other samples on this panel and as a diagnostic marker for the presence of breast cancer. This gene encodes a protein homologous to the activity of 9-ketoreductase, the enzyme which converts prostaglandin E2 (PGE2) into prostaglandin F2 alpha (PGF2 alpha) and can influence estrogen synthesis and thus potentially the rate of breast cancer growth. Therefore, therapeutic modulation of the expression or function of this gene product may be useful in the treatment of breast cancer (Brueggemeier R W, Richards J A, Joomprabutra S, Bhat A S, Whetstone J L. Molecular pharmacology of aromatase and its regulation by endogenous and exogenous agents. J Steroid Biochem Mol Biol 2001 December;79(1–5):75–84; Brodie A M, Lu Q, Long B J, Fulton A, Chen T, Macpherson N, DeJong P C, Blankenstein M A, Nortier J W, Slee P H, van de Ven J, van Gorp J M, Elbers J R, Schipper M E, Blijham G H, Thijssen J H. Aromatase and COX-2 expression in human breast cancers. J Steroid Biochem Mol Biol 2001 December;79(1–5):41–7).

Panel 4.1D Summary: Ag3816 Expression of the CG92662-01 gene highest in LAK cells treated with PMA/ionomycin (CT=32.5). Low, but significant levels of expression are also seen in a cluster of both treated and untreated LAK cells, PMA/ionomycin treated basophils, untreated lung and dermal microvasculature, and resting TH1 cells (both primary and secondary). LAK cells are involved in tumor immunology and cell clearance of virally and bacterial infected cells as well as tumors. Therefore, modulation of the function of the protein encoded by this gene through the application of a small molecule drug or antibody may alter the functions of these cells and lead to improvement of symptoms associated with these conditions.

BB. CG92683-01: C2PA

Expression of gene CG92683-01 was assessed using the primer-probe set Ag3817, described in Table BBA.

TABLE BBA

Probe Name Ag3817

| Primers | Sequences | Length | Start Position | SEQ ID NO: |
|---|---|---|---|---|
| Forward | 5'-aggatgatcagaagcgtctctt-3' | 22 | 363 | 420 |
| Probe | TET-5'-ccagccagtccaggagacagagtct-3'-TAMRA | 25 | 405 | 421 |
| Reverse | 5'-aaagctcatgcagccaatg-3' | 19 | 430 | 422 |

CNS_neurodegeneration_v1.0 Summary: Ag3817 Expression of the CG92683-01 gene is low/undetectable (CTs>35) across all of the samples on this panel (data not shown).

General_screening_panel_v1.4 Summary: Ag3817 Expression of the CG92683-01 gene is low/undetectable (CTs>35) across all of the samples on this panel (data not shown).

Panel 4.1D Summary: Ag3817 Expression of the CG92683-01 gene is low/undetectable (CTs>35) across all of the samples on this panel (data not shown).

BC. CG92694-01: Long-Chain 3-Ketoacyl-COA Thiolase

Expression of gene CG92694-01 was assessed using the primer-probe set Ag3818, described in Table BCA.

TABLE BCA

Probe Name Ag3818

| Primers | Sequences | Length | Start Position | SEQ ID NO: |
|---|---|---|---|---|
| Forward | 5'-ctctgagctattcctcccagtt-3' | 22 | 133 | 423 |
| Probe | TET-5'-ccagccatccagaccgaaacgag-3'-TAMRA | 23 | 165 | 424 |
| Reverse | 5'-attgggtttggctaatgtcttc-3' | 22 | 188 | 425 |

CNS_neurodegeneration_v1.0 Summary: Ag3818 Expression of the CG92694-01 gene is low/undetectable (CTs>35) across all of the samples on this panel (data not shown).

General_screening_panel_v1.4 Summary: Ag3818 Expression of the CG92694-01 gene is low/undetectable (CTs>35) across all of the samples on this panel (data not shown).

Panel 4.1D Summary: Ag3818 Expression of the CG92694-01 gene is low/undetectable (CTs>35) across all of the samples on this panel (data not shown).

Panel 5 Islet Summary: Ag3818 Expression of the CG92694-01 gene is low/undetectable (CTs>35) across all of the samples on this panel (data not shown).

BD. CG92896-01 and CG92896-02: Phosphatidylinositol 5-Phoaphate 4-Kinase Gamma

Expression of gene CG92896-01 and full length clone CG92896-02 was assessed using the primer-probe set Ag3832, described in Table BDA. Results of the RTQ-PCR runs are shown in Tables BDB, BDC, BDD and BDE. Please note that CG92896-02 represents a full-length physical clone of the CG92896-01 gene, validating the prediction of the gene sequence.

TABLE BDA

Probe Name Ag3832

| Primers | Sequences | Length | Start Position | SEQ ID NO: |
|---|---|---|---|---|
| Forward | 5'-aagtatccagtgaggacattgc-3' | 22 | 461 | 426 |
| Probe | TET-5'-tgacatgcatagcaacctctccaact-3'-TAMRA | 26 | 483 | 427 |
| Reverse | 5'-catggcacttcacaatgtactg-3' | 22 | 514 | 428 |

TABLE BDB

CNS_neurodegeneration_v1.0

| Tissue Name | Rel. Exp. (%) Ag3832, Run 206873102 | Tissue Name | Rel. Exp. (%) Ag3832, Run 206873102 |
|---|---|---|---|
| AD 1 Hippo | 14.9 | Control (Path) 3 Temporal Ctx | 5.1 |
| AD 2 Hippo | 27.0 | Control (Path) 4 Temporal Ctx | 34.2 |
| AD 3 Hippo | 8.5 | AD 1 Occipital Ctx | 14.7 |
| AD 4 Hippo | 5.4 | AD 2 Occipital Ctx (Missing) | 0.0 |
| AD 5 Hippo | 100.0 | AD 3 Occipital Ctx | 6.7 |
| AD 6 Hippo | 42.9 | AD 4 Occipital Ctx | 17.9 |
| Control 2 Hippo | 32.1 | AD 5 Occipital Ctx | 52.9 |
| Control 4 Hippo | 6.8 | AD 6 Occipital Ctx | 27.0 |
| Control (Path) 3 Hippo | 4.3 | Control 1 Occipital Ctx | 1.9 |
| AD 1 Temporal Ctx | 12.8 | Control 2 Occipital Ctx | 80.1 |
| AD 2 Temporal Ctx | 34.9 | Control 3 Occipital Ctx | 12.6 |
| AD 3 Temporal Ctx | 5.0 | Control 4 Occipital Ctx | 4.7 |
| AD 4 Temporal Ctx | 21.8 | Control (Path) 1 Occipital Ctx | 74.2 |
| AD 5 Inf Temporal Ctx | 100.0 | Control (Path) 2 Occipital Ctx | 7.3 |
| AD 5 Sup Temporal Ctx | 33.9 | Control (Path) 3 Occipital Ctx | 2.6 |
| AD 6 Inf Temporal Ctx | 41.2 | Control (Path) 4 Occipital Ctx | 11.0 |
| AD 6 Sup Temporal Ctx | 51.4 | Control 1 Parietal Ctx | 5.1 |
| Control 1 Temporal Ctx | 3.4 | Control 2 Parietal Ctx | 37.1 |
| Control 2 Temporal Ctx | 47.0 | Control 3 Parietal Ctx | 26.4 |
| Control 3 Temporal Ctx | 14.8 | Control (Path) 1 Parietal Ctx | 92.7 |
| Control 3 Temporal Ctx | 7.3 | Control (Path) 2 Parietal Ctx | 20.4 |
| Control (Path) 1 Temporal Ctx | 55.5 | Control (Path) 3 Parietal Ctx | 3.8 |
| Control (Path) 2 Temporal Ctx | 34.6 | Control (Path) 4 Parietal Ctx | 41.5 |

TABLE BDC

General_screening_panel_v1.4

| Tissue Name | Rel. Exp. (%) Ag3832, Run 213603655 | Tissue Name | Rel. Exp. (%) Ag3832, Run 213603655 |
|---|---|---|---|
| Adipose | 4.2 | Renal ca. TK-10 | 32.3 |
| Melanoma* Hs688(A).T | 14.4 | Bladder | 15.5 |
| Melanoma* Hs688(B).T | 17.1 | Gastric ca. (liver met.) NCI-N87 | 57.8 |
| Melanoma* M14 | 47.0 | Gastric ca. KATO III | 40.9 |
| Melanoma* LOXIMVI | 22.2 | Colon ca. SW-948 | 14.6 |
| Melanoma* SK-MEL-5 | 44.4 | Colon ca. SW480 | 59.5 |
| Squamous cell carcinoma SCC-4 | 28.3 | Colon ca.* (SW480 met) SW620 | 20.9 |
| Testis Pool | 16.8 | Colon ca. HT29 | 17.8 |
| Prostate ca.* (bone met) PC-3 | 66.9 | Colon ca. HCT-116 | 42.3 |
| Prostate Pool | 6.6 | Colon ca. CaCo-2 | 34.9 |
| Placenta | 9.9 | Colon cancer tissue | 22.1 |
| Uterus Pool | 2.9 | Colon ca. SW1116 | 11.7 |
| Ovarian ca. OVCAR-3 | 33.2 | Colon ca. Colo-205 | 10.5 |
| Ovarian ca. SK-OV-3 | 33.2 | Colon ca. SW-48 | 9.9 |
| Ovarian ca. OVCAR-4 | 47.0 | Colon Pool | 6.1 |
| Ovarian ca. OVCAR-5 | 45.1 | Small Intestine Pool | 5.3 |
| Ovarian ca. IGROV-1 | 14.1 | Stomach Pool | 4.8 |
| Ovarian ca. OVCAR-8 | 16.0 | Bone Marrow Pool | 1.9 |
| Ovary | 7.4 | Fetal Heart | 2.7 |
| Breast ca. MCF-7 | 87.7 | Heart Pool | 2.6 |
| Breast ca. MDA-MB-231 | 18.7 | Lymph Node Pool | 6.1 |
| Breast ca. BT 549 | 32.1 | Fetal Skeletal Muscle | 2.0 |
| Breast ca. T47D | 100.0 | Skeletal Muscle Pool | 3.8 |
| Breast ca. MDA-N | 16.4 | Spleen Pool | 3.0 |
| Breast Pool | 8.0 | Thymus Pool | 3.9 |
| Trachea | 23.0 | CNS cancer (glio/astro) U87-MG | 43.5 |
| Lung | 1.1 | CNS cancer (glio/astro) U-118-MG | 32.8 |
| Fetal Lung | 10.8 | CNS cancer (neuro; met) SK-N-AS | 28.5 |
| Lung ca. NCI-N417 | 4.2 | CNS cancer (astro) SF-539 | 12.1 |
| Lung ca. LX-1 | 34.9 | CNS cancer (astro) SNB-75 | 18.3 |
| Lung ca. NCI-H146 | 16.7 | CNS cancer (glio) SNB-19 | 13.2 |
| Lung ca. SHP-77 | 45.1 | CNS cancer (glio) SF-295 | 45.4 |
| Lung ca. A549 | 39.0 | Brain (Amygdala) Pool | 11.2 |
| Lung ca. NCI-H526 | 13.1 | Brain (cerebellum) | 23.0 |
| Lung ca. NCI-H23 | 31.0 | Brain (fetal) | 10.9 |
| Lung ca. NCI-H460 | 19.3 | Brain (Hippocampus) Pool | 11.7 |
| Lung ca. HOP-62 | 16.0 | Cerebral Cortex Pool | 23.5 |
| Lung ca. NCI-H522 | 36.1 | Brain (Substantia nigra) Pool | 22.7 |
| Liver | 1.8 | Brain (Thalamus) Pool | 22.7 |
| Fetal Liver | 6.6 | Brain (whole) | 27.9 |
| Liver ca. HepG2 | 19.6 | Spinal Cord Pool | 9.2 |
| Kidney Pool | 15.0 | Adrenal Gland | 11.5 |
| Fetal Kidney | 5.0 | Pituitary gland Pool | 2.9 |
| Renal ca. 786-0 | 19.6 | Salivary Gland | 14.1 |
| Renal ca. A498 | 7.5 | Thyroid (female) | 6.6 |
| Renal ca. ACHN | 37.4 | Pancreatic ca. CAPAN2 | 44.1 |
| Renal ca. UO-31 | 33.0 | Pancreas Pool | 6.1 |

TABLE BDD

Panel 2.2

| Tissue Name | Rel. Exp. (%) Ag3832, Run 174448449 | Tissue Name | Rel. Exp. (%) Ag3832, Run 174448449 |
|---|---|---|---|
| Normal Colon | 21.2 | Kidney Margin (OD04348) | 100.0 |
| Colon cancer (OD06064) | 30.8 | Kidney malignant cancer (OD06204B) | 16.3 |
| Colon Margin (OD06064) | 14.0 | Kidney normal adjacent tissue (OD06204E) | 18.4 |

TABLE BDD-continued

Panel 2.2

| Tissue Name | Rel. Exp. (%) Ag3832, Run 174448449 | Tissue Name | Rel. Exp. (%) Ag3832, Run 174448449 |
|---|---|---|---|
| Colon cancer (OD06159) | 14.2 | Kidney Cancer (OD04450-01) | 38.4 |
| Colon Margin (OD06159) | 11.6 | Kidney Margin (OD04450-03) | 39.8 |
| Colon cancer (OD06297-04) | 8.8 | Kidney Cancer 8120613 | 11.3 |
| Colon Margin (OD06297-05) | 21.8 | Kidney Margin 8120614 | 26.6 |
| CC Gr.2 ascend colon (ODO3921) | 12.7 | Kidney Cancer 9010320 | 8.1 |
| CC Margin (ODO3921) | 7.9 | Kidney Margin 9010321 | 10.2 |
| Colon cancer metastasis (OD06104) | 9.7 | Kidney Cancer 8120607 | 28.1 |
| Lung Margin (OD06104) | 9.2 | Kidney Margin 8120608 | 19.9 |
| Colon mets to lung (OD04451-01) | 19.6 | Normal Uterus | 11.5 |
| Lung Margin (OD04451-02) | 27.9 | Uterine Cancer 064011 | 5.6 |
| Normal Prostate | 11.5 | Normal Thyroid | 4.0 |
| Prostate Cancer (OD04410) | 6.5 | Thyroid Cancer 064010 | 10.7 |
| Prostate Margin (OD04410) | 8.3 | Thyroid Cancer A302152 | 14.5 |
| Normal Ovary | 21.2 | Thyroid Margin A302153 | 3.1 |
| Ovarian cancer (OD06283-03) | 10.4 | Normal Breast | 16.3 |
| Ovarian Margin (OD06283-07) | 8.4 | Breast Cancer (OD04566) | 16.4 |
| Ovarian Cancer 064008 | 6.8 | Breast Cancer 1024 | 24.7 |
| Ovarian cancer (OD06145) | 3.1 | Breast Cancer (OD04590-01) | 45.1 |
| Ovarian Margin (OD06145) | 22.7 | Breast Cancer Mets (OD04590-03) | 33.4 |
| Ovarian cancer (OD06455-03) | 10.7 | Breast Cancer Metastasis (OD04655-05) | 49.3 |
| Ovarian Margin (OD06455-07) | 6.1 | Breast Cancer 064006 | 12.7 |
| Normal Lung | 15.4 | Breast Cancer 9100266 | 29.1 |
| Invasive poor diff. lung adeno (ODO4945-01) | 13.0 | Breast Margin 9100265 | 14.4 |
| Lung Margin (ODO4945-03) | 10.3 | Breast Cancer A209073 | 14.9 |
| Lung Malignant Cancer (OD03126) | 26.1 | Breast Margin A2090734 | 13.8 |
| Lung Margin (OD03126) | 9.9 | Breast cancer (OD06083) | 35.4 |
| Lung Cancer (OD05014A) | 29.3 | Breast cancer node metastasis (OD06083) | 19.3 |
| Lung Margin (OD05014B) | 24.1 | Normal Liver | 12.9 |
| Lung cancer (OD06081) | 8.2 | Liver Cancer 1026 | 7.3 |
| Lung Margin (OD06081) | 8.5 | Liver Cancer 1025 | 16.8 |
| Lung Cancer (OD04237-01) | 8.4 | Liver Cancer 6004-T | 12.3 |
| Lung Margin (OD04237-02) | 22.8 | Liver Tissue 6004-N | 7.7 |
| Ocular Melanoma Metastasis | 18.6 | Liver Cancer 6005-T | 24.3 |
| Ocular Melanoma Margin (Liver) | 7.8 | Liver Tissue 6005-N | 26.2 |
| Melanoma Metastasis | 12.5 | Liver Cancer 064003 | 15.3 |
| Melanoma Margin (Lung) | 27.5 | Normal Bladder | 11.0 |
| Normal Kidney | 20.4 | Bladder Cancer 1023 | 11.9 |
| Kidney Ca, Nuclear grade 2 (OD04338) | 68.8 | Bladder Cancer A302173 | 14.3 |
| Kidney Margin (OD04338) | 15.1 | Normal Stomach | 45.1 |
| Kidney Ca Nuclear grade 1/2 (OD04339) | 27.2 | Gastric Cancer 9060397 | 14.7 |
| Kidney Margin (OD04339) | 20.4 | Stomach Margin 9060396 | 43.5 |
| Kidney Ca, Clear cell type (OD04340) | 9.9 | Gastric Cancer 9060395 | 14.9 |
| Kidney Margin (OD04340) | 28.7 | Stomach Margin 9060394 | 48.3 |
| Kidney Ca, Nuclear grade 3 (OD04348) | 8.5 | Gastric Cancer 064005 | 11.3 |

TABLE BDE

Panel 4.1D

| Tissue Name | Rel. Exp. (%) Ag3832, Run 170127273 | Tissue Name | Rel. Exp. (%) Ag3832, Run 170127273 |
|---|---|---|---|
| Secondary Th1 act | 26.2 | HUVEC IL-1beta | 9.5 |
| Secondary Th2 act | 40.1 | HUVEC IFN gamma | 9.2 |
| Secondary Tr1 act | 36.9 | HUVEC TNF alpha + IFN gamma | 5.4 |
| Secondary Th1 rest | 13.6 | HUVEC TNF alpha + IL4 | 4.8 |
| Secondary Th2 rest | 18.8 | HUVEC IL-11 | 5.8 |
| Secondary Tr1 rest | 15.3 | Lung Microvascular EC none | 16.8 |
| Primary Th1 act | 20.7 | Lung Microvascular EC TNF alpha + IL-1beta | 13.9 |
| Primary Th2 act | 22.2 | Microvascular Dermal EC none | 12.3 |
| Primary Tr1 act | 18.9 | Microsvasular Dermal EC TNF alpha + IL-1beta | 6.1 |
| Primary Th1 rest | 15.3 | Bronchial epithelium TNF alpha + IL-1beta | 62.4 |
| Primary Th2 rest | 13.4 | Small airway epithelium none | 44.8 |
| Primary Tr1 rest | 17.4 | Small airway epithelium TNF alpha + IL-1beta | 90.1 |
| CD45RA CD4 lymphocyte act | 20.6 | Coronery artery SMC rest | 18.6 |
| CD45RO CD4 lymphocyte act | 39.0 | Coronery artery SMC TNF alpha + IL-1beta | 20.2 |
| CD8 lymphocyte act | 29.9 | Astrocytes rest | 36.1 |
| Secondary CD8 lymphocyte rest | 41.8 | Astrocytes TNF alpha + IL-1beta | 35.6 |
| Secondary CD8 lymphocyte act | 16.7 | KU-812 (Basophil) rest | 12.5 |
| CD4 lymphocyte none | 9.2 | KU-812 (Basophil) PMA/ionomycin | 27.4 |
| 2ry Th1/Th2/Tr1_anti-CD95 CH11 | 16.3 | CCD1106 (Keratinocytes) none | 80.1 |
| LAK cells rest | 35.6 | CCD1106 (Keratinocytes) TNF alpha + IL-1beta | 100.0 |
| LAK cells IL-2 | 26.1 | Liver cirrhosis | 7.6 |
| LAK cells IL-2 + IL-12 | 24.3 | NCI-H292 none | 33.0 |
| LAK cells IL-2 + IFN gamma | 29.9 | NCI-H292 IL-4 | 69.3 |
| LAK cells IL-2 + IL-18 | 37.1 | NCI-H292 IL-9 | 68.3 |
| LAK cells PMA/ionomycin | 14.4 | NCI-H292 IL-13 | 70.2 |
| NK Cells IL-2 rest | 34.6 | NCI-H292 IFN gamma | 71.2 |
| Two Way MLR 3 day | 32.3 | HPAEC none | 8.4 |
| Two Way MLR 5 day | 27.5 | HPAEC TNF alpha + IL-1beta | 10.5 |
| Two Way MLR 7 day | 20.6 | Lung fibroblast none | 23.8 |
| PBMC rest | 9.2 | Lung fibroblast TNF alpha + IL-1beta | 10.8 |
| PBMC PWM | 30.6 | Lung fibroblast IL-4 | 15.5 |
| PBMC PHA-L | 15.0 | Lung fibroblast IL-9 | 24.0 |
| Ramos (B cell) none | 26.8 | Lung fibroblast IL-13 | 16.8 |
| Ramos (B cell) ionomycin | 15.6 | Lung fibroblast IFN gamma | 18.2 |
| B lymphocytes PWM | 15.8 | Dermal fibroblast CCD1070 rest | 27.4 |
| B lymphocytes CD40L and IL-4 | 15.3 | Dermal fibroblast CCD1070 TNF alpha | 29.7 |
| EOL-1 dbcAMP | 17.9 | Dermal fibroblast CCD1070 IL-1beta | 8.6 |
| EOL-1 dbcAMP PMA/ionomycin | 21.3 | Dermal fibroblast IFN gamma | 5.6 |
| Dendritic cells none | 28.1 | Dermal fibroblast IL-4 | 8.5 |
| Dendritic cells LPS | 35.6 | Dermal Fibroblasts rest | 12.9 |
| Dendritic cells anti-CD40 | 32.8 | Neutrophils TNFa + LPS | 3.3 |
| Monocytes rest | 15.1 | Neutrophils rest | 14.4 |
| Monocytes LPS | 27.9 | Colon | 15.5 |
| Macrophages rest | 37.4 | Lung | 18.2 |
| Macrophages LPS | 33.9 | Thymus | 12.7 |
| HUVEC none | 7.1 | Kidney | 40.9 |
| HUVEC starved | 10.2 | | |

CNS_neurodegeneration_v1.0 Summary: Ag3832 This panel confirms the expression of the CG92896-01 gene at low levels in the brains of an independent group of individuals. However, no differential expression of this gene was detected between Alzheimer's diseased postmortem brains and those of non-demented controls in this experiment. Please see Panel 1.4 for a discussion of the potential utility of this gene in treatment of central nervous system disorders.

General_screening$_{13}$ panel_v1.4 Summary: Ag3832 Highest expression of the CG92896-01 gene is detected in breast cancer cell line T47D (CT=25.9). In addition high expression of this gene is also seen in cluster of cancer (pancreatic, CNS, colon, gastric, renal, breast, ovarian, prostate, squamous cell carcinoma, and melanoma) cell lines. Therefore, therapeutic modulation of the activity of this gene or its protein product, through the use of small molecule drugs might be beneficial in the treatment of these cancers.

Among tissues with metabolic or endocrine function, this gene is expressed at high to moderate levels in pancreas, adipose, adrenal gland, thyroid, pituitary gland, skeletal muscle, heart, liver and the gastrointestinal tract. Therefore, therapeutic modulation of the activity of this gene may prove useful in the treatment of endocrine/metabolically related diseases, such as obesity and diabetes.

In addition, this gene is expressed at high levels in all regions of the central nervous system examined, including amygdala, hippocampus, substantia nigra, thalamus, cerebellum, cerebral cortex, and spinal cord. Therefore, this gene may play a role in central nervous system disorders such as Alzheimer's disease, Parkinson's disease, epilepsy, multiple sclerosis, schizophrenia and depression.

High expression of this gene is also detected in fetal lung. Interestingly, this gene is expressed at much higher levels in fetal (CT=29) when compared to adult lung (CT=32.4). This observation suggests that expression of this gene can be used to distinguish fetal from adult lung. In addition, the relative overexpression of this gene in fetal lung suggests that the protein product may be required for growth or development of lung in the fetus and thus may also act in a regenerative capacity in the adult. Therefore, therapeutic modulation of the protein encoded by this gene could be useful in treatment of lung related diseases.

Panel 2.2 Summary: Ag3832 Highest expression of the CG92896-01 gene is detected in kidney margin (OD04348) sample (CT=29.5). Interestingly, expression of this gene is much higher in control kidney margin (OD04348) than in corresponding cancer sample (CT=33). Therefore, expression of this gene can be used to distinguish the kidney cancer from control sample. In addition, expression of this gene is seen in both normal and cancer tissue samples used in this panel. Please see Panel 1.4 for a discussion of the potential utility of this gene.

Panel 4.1D Summary: Ag3832 Highest expression of the CG92896-01 gene is detected in TNFalpha+IL-1beta treated keratinocytes (CT=27.6). This gene is expressed at high to moderate levels in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. This ubiquitous pattern of expression suggests that this gene product may be involved in homeostatic processes for these and other cell types and tissues. This pattern is in agreement with the expression profile in General_screening_panel_v1.4 and also suggests a role for the gene product in cell survival and proliferation. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

BE. CG93265-01 and CG93265-02: L-Serine Dehydratase

Expression of gene CG93265-01 and full length clone CG93265-02 was assessed using the primer-probe set Ag3847, described in Table BEA. Results of the RTQ-PCR runs are shown in Tables BEB, BEC, BED and BEE. Please note that CG93265-02 represents a full-length physical clone of the CG93265-01 gene, validating the prediction of the gene sequence.

TABLE BEA

Probe Name Ag3847

| Primers | Sequences | Length | Start Position | SEQ ID NO: |
|---|---|---|---|---|
| Forward | 5'-gccttagcagccatctactca-3' | 21 | 902 | 429 |
| Probe | TET-5'-ccccttccctgacttcagttgtg-3'-TAMRA | 23 | 960 | 430 |
| Reverse | 5'-tgcctccacacacgattac-3' | 19 | 983 | 431 |

TABLE BEB

CNS_neurodegeneration_v1.0

| Tissue Name | Rel. Exp. (%) Ag3847, Run 212186740 | Tissue Name | Rel. Exp. (%) Ag3847, Run 212186740 |
|---|---|---|---|
| AD 1 Hippo | 7.2 | Control (Path) 3 Temporal Ctx | 8.2 |
| AD 2 Hippo | 64.6 | Control (Path) 4 Temporal Ctx | 36.3 |
| AD 3 Hippo | 9.7 | AD 1 Occipital Ctx | 29.1 |
| AD 4 Hippo | 33.7 | AD 2 Occipital Ctx (Missing) | 0.0 |
| AD 5 Hippo | 72.7 | AD 3 Occipital Ctx | 10.8 |
| AD 6 Hippo | 39.0 | AD 4 Occipital Ctx | 38.7 |
| Control 2 Hippo | 34.2 | AD 5 Occipital Ctx | 95.9 |
| Control 4 Hippo | 67.4 | AD 6 Occipital Ctx | 27.5 |
| Control (Path) 3 Hippo | 1.9 | Control 1 Occipital Ctx | 32.3 |
| AD 1 Temporal Ctx | 21.8 | Control 2 Occipital Ctx | 100.0 |
| AD 2 Temporal Ctx | 63.3 | Control 3 Occipital Ctx | 56.3 |
| AD 3 Temporal Ctx | 7.0 | Control 4 Occipital Ctx | 36.3 |

TABLE BEB-continued

CNS_neurodegeneration_v1.0

| Tissue Name | Rel. Exp. (%) Ag3847, Run 212186740 | Tissue Name | Rel. Exp. (%) Ag3847, Run 212186740 |
|---|---|---|---|
| AD 4 Temporal Ctx | 25.5 | Control (Path) 1 Occipital Ctx | 98.6 |
| AD 5 Inf Temporal Ctx | 62.0 | Control (Path) 2 Occipital Ctx | 24.3 |
| AD 5 Sup Temporal Ctx | 29.7 | Control (Path) 3 Occipital Ctx | 4.8 |
| AD 6 Inf Temporal Ctx | 32.5 | Control (Path) 4 Occipital Ctx | 39.2 |
| AD 6 Sup Temporal Ctx | 37.6 | Control 1 Parietal Ctx | 35.8 |
| Control 1 Temporal Ctx | 35.6 | Control 2 Parietal Ctx | 12.7 |
| Control 2 Temporal Ctx | 30.6 | Control 3 Parietal Ctx | 31.9 |
| Control 3 Temporal Ctx | 24.0 | Control (Path) 1 Parietal Ctx | 64.2 |
| Control 3 Temporal Ctx | 18.4 | Control (Path) 2 Parietal Ctx | 66.9 |
| Control (Path) 1 Temporal Ctx | 62.4 | Control (Path) 3 Parietal Ctx | 6.6 |
| Control (Path) 2 Temporal Ctx | 48.3 | Control (Path) 4 Parietal Ctx | 73.7 |

TABLE BEC

General_screening_panel_v1.4

| Tissue Name | Rel. Exp. (%) Ag3847, Run 218906045 | Tissue Name | Rel. Exp. (%) Ag3847, Run 218906045 |
|---|---|---|---|
| Adipose | 11.4 | Renal ca. TK-10 | 40.6 |
| Melanoma* Hs688(A).T | 4.6 | Bladder | 30.6 |
| Melanoma* Hs688(B).T | 5.6 | Gastric ca. (liver met.) NCI-N87 | 55.1 |
| Melanoma* M14 | 4.8 | Gastric ca. KATO III | 25.5 |
| Melanoma* LOXIMVI | 1.5 | Colon ca. SW-948 | 8.7 |
| Melanoma* SK-MEL-5 | 20.9 | Colon ca. SW480 | 28.9 |
| Squamous cell carcinoma SCC-4 | 2.9 | Colon ca.* (SW480 met) SW620 | 6.2 |
| Testis Pool | 11.0 | Colon ca. HT29 | 11.7 |
| Prostate ca.* (bone met) PC-3 | 14.8 | Colon ca. HCT-116 | 43.8 |
| Prostate Pool | 8.5 | Colon ca. CaCo-2 | 9.9 |
| Placenta | 8.8 | Colon cancer tissue | 19.8 |
| Uterus Pool | 5.2 | Colon ca. SW1116 | 16.2 |
| Ovarian ca. OVCAR-3 | 42.3 | Colon ca. Colo-205 | 4.8 |
| Ovarian ca. SK-OV-3 | 9.2 | Colon ca. SW-48 | 5.0 |
| Ovarian ca. OVCAR-4 | 21.3 | Colon Pool | 7.2 |
| Ovarian ca. OVCAR-5 | 39.8 | Small Intestine Pool | 5.6 |
| Ovarian ca. IGROV-1 | 18.7 | Stomach Pool | 8.7 |
| Ovarian ca. OVCAR-8 | 22.4 | Bone Marrow Pool | 2.3 |
| Ovary | 13.2 | Fetal Heart | 2.2 |
| Breast ca. MCF-7 | 28.3 | Heart Pool | 6.8 |
| Breast ca. MDA-MB-231 | 48.6 | Lymph Node Pool | 22.8 |
| Breast ca. BT 549 | 35.4 | Fetal Skeletal Muscle | 2.2 |
| Breast ca. T47D | 100.0 | Skeletal Muscle Pool | 5.4 |
| Breast ca. MDA-N | 9.4 | Spleen Pool | 9.6 |
| Breast Pool | 9.9 | Thymus Pool | 10.3 |
| Trachea | 7.1 | CNS cancer (glio/astro) U87-MG | 48.0 |
| Lung | 2.4 | CNS cancer (glio/astro) U-118-MG | 50.3 |
| Fetal Lung | 5.5 | CNS cancer (neuro; met) SK-N-AS | 12.9 |
| Lung ca. NCI-N417 | 2.2 | CNS cancer (astro) SF-539 | 11.9 |
| Lung ca. LX-1 | 13.9 | CNS cancer (astro) SNB-75 | 29.7 |
| Lung ca. NCI-H146 | 6.6 | CNS cancer (glio) SNB-19 | 15.5 |
| Lung ca. SHP-77 | 23.5 | CNS cancer (glio) SF-295 | 48.3 |
| Lung ca. A549 | 34.2 | Brain (Amygdala) Pool | 15.9 |
| Lung ca. NCI-H526 | 1.5 | Brain (cerebellum) | 9.2 |

TABLE BEC-continued

General_screening_panel_v1.4

| Tissue Name | Rel. Exp. (%) Ag3847, Run 218906045 | Tissue Name | Rel. Exp. (%) Ag3847, Run 218906045 |
| --- | --- | --- | --- |
| Lung ca. NCI-H23 | 18.4 | Brain (fetal) | 2.3 |
| Lung ca. NCI-H460 | 17.1 | Brain (Hippocampus) Pool | 11.3 |
| Lung ca. HOP-62 | 4.1 | Cerebral Cortex Pool | 11.2 |
| Lung ca. NCI-H522 | 19.9 | Brain (Substantia nigra) Pool | 16.8 |
| Liver | 16.2 | Brain (Thalamus) Pool | 11.7 |
| Fetal Liver | 30.4 | Brain (whole) | 13.1 |
| Liver ca. HepG2 | 11.7 | Spinal Cord Pool | 36.1 |
| Kidney Pool | 4.8 | Adrenal Gland | 36.9 |
| Fetal Kidney | 21.8 | Pituitary gland Pool | 23.7 |
| Renal ca. 786-0 | 18.7 | Salivary Gland | 9.0 |
| Renal ca. A498 | 11.4 | Thyroid (female) | 25.5 |
| Renal ca. ACHN | 23.7 | Pancreatic ca. CAPAN2 | 3.7 |
| Renal ca. UO-31 | 21.6 | Pancreas Pool | 12.1 |

TABLE BED

Panel 4.1D

| Tissue Name | Rel. Exp. (%) Ag3847, Run 170126781 | Tissue Name | Rel. Exp. (%) Ag3847, Run 170126781 |
| --- | --- | --- | --- |
| Secondary Th1 act | 0.0 | HUVEC IL-1beta | 8.1 |
| Secondary Th2 act | 0.5 | HUVEC IFN gamma | 5.4 |
| Secondary Tr1 act | 1.1 | HUVEC TNF alpha + IFN gamma | 12.9 |
| Secondary Th1 rest | 2.5 | HUVEC TNF alpha + IL4 | 6.8 |
| Secondary Th2 rest | 2.4 | HUVEC IL-11 | 6.7 |
| Secondary Tr1 rest | 5.3 | Lung Microvascular EC none | 28.1 |
| Primary Th1 act | 0.6 | Lung Microvascular EC TNF alpha + IL-1beta | 8.3 |
| Primary Th2 act | 1.2 | Microvascular Dermal EC none | 4.0 |
| Primary Tr1 act | 2.4 | Microsvascular Dermal EC TNF alpha + IL-1beta | 5.5 |
| Primary Th1 rest | 0.0 | Bronchial epithelium TNF alpha + IL-1beta | 13.4 |
| Primary Th2 rest | 0.0 | Small airway epithelium none | 12.2 |
| Primary Tr1 rest | 0.0 | Small airway epithelium TNF alpha + IL-1beta | 15.7 |
| CD45RA CD4 lymphocyte act | 0.0 | Coronery artery SMC rest | 12.8 |
| CD45RO CD4 lymphocyte act | 0.0 | Coronery artery SMC TNF alpha + IL-1beta | 6.4 |
| CD8 lymphocyte act | 0.0 | Astrocytes rest | 11.6 |
| Secondary CD8 lymphocyte rest | 0.5 | Astrocytes TNF alpha + IL-1beta | 28.1 |
| Secondary CD8 lymphocyte act | 0.0 | KU-812 (Basophil) rest | 2.3 |
| CD4 lymphocyte none | 0.0 | KU-812 (Basophil) PMA/ionomycin | 14.7 |
| 2ry Th1/Th2/Tr1_anti-CD95 CH11 | 1.7 | CCD1106 (Keratinocytes) none | 17.2 |
| LAK cells rest | 49.0 | CCD1106 (Keratinocytes) TNF alpha + IL-1beta | 24.7 |
| LAK cells IL-2 | 7.3 | Liver cirrhosis | 100.0 |
| LAK cells IL-2 + IL-12 | 1.4 | NCI-H292 none | 13.0 |
| LAK cells IL-2 + IFN gamma | 2.0 | NCI-H292 IL-4 | 13.6 |
| LAK cells IL-2 + IL-18 | 0.0 | NCI-H292 IL-9 | 26.2 |
| LAK cells PMA/ionomycin | 9.3 | NCI-H292 IL-13 | 6.0 |
| NK Cells IL-2 rest | 3.7 | NCI-H292 IFN gamma | 27.4 |
| Two Way MLR 3 day | 28.3 | HPAEC none | 9.7 |
| Two Way MLR 5 day | 11.3 | HPAEC TNF alpha + IL-1beta | 4.0 |
| Two Way MLR 7 day | 3.9 | Lung fibroblast none | 34.9 |
| PBMC rest | 2.6 | Lung fibroblast TNF alpha + IL-1beta | 7.6 |
| PBMC PWM | 3.4 | Lung fibroblast IL-4 | 8.6 |
| PBMC PHA-L | 0.7 | Lung fibroblast IL-9 | 14.7 |

TABLE BED-continued

Panel 4.1D

| Tissue Name | Rel. Exp. (%) Ag3847, Run 170126781 | Tissue Name | Rel. Exp. (%) Ag3847, Run 170126781 |
|---|---|---|---|
| Ramos (B cell) none | 0.0 | Lung fibroblast IL-13 | 6.8 |
| Ramos (B cell) ionomycin | 0.0 | Lung fibroblast IFN gamma | 15.2 |
| B lymphocytes PWM | 0.0 | Dermal fibroblast CCD1070 rest | 2.3 |
| B lymphocytes CD40L and IL-4 | 1.4 | Dermal fibroblast CCD1070 TNF alpha | 0.8 |
| EOL-1 dbcAMP | 4.0 | Dermal fibroblast CCD1070 IL-1beta | 1.0 |
| EOL-1 dbcAMP PMA/ionomycin | 0.5 | Dermal fibroblast IFN gamma | 1.6 |
| Dendritic cells none | 62.0 | Dermal fibroblast IL-4 | 4.4 |
| Dendritic cells LPS | 22.1 | Dermal Fibroblasts rest | 4.6 |
| Dendritic cells anti-CD40 | 44.1 | Neutrophils TNFa + LPS | 0.0 |
| Monocytes rest | 4.4 | Neutrophils rest | 0.0 |
| Monocytes LPS | 24.7 | Colon | 3.8 |
| Macrophages rest | 84.1 | Lung | 14.9 |
| Macrophages LPS | 72.2 | Thymus | 3.6 |
| HUVEC none | 4.4 | Kidney | 55.5 |
| HUVEC starved | 4.1 | | |

TABLE BEE

Panel 5 Islet

| Tissue Name | Rel. Exp. (%) Ag3847, Run 226587525 | Tissue Name | Rel. Exp. (%) Ag3847, Run 226587525 |
|---|---|---|---|
| 97457_Patient-02go_adipose | 28.1 | 94709_Donor 2 AM - A_adipose | 14.9 |
| 97476_Patient-07sk_skeletal muscle | 3.1 | 94710_Donor 2 AM - B_adipose | 7.3 |
| 97477_Patient-07ut_uterus | 4.2 | 94711_Donor 2 AM - C_adipose | 4.5 |
| 97478_Patient-07pl_placenta | 11.2 | 94712_Donor 2 AD - A_adipose | 5.1 |
| 99167_Bayer Patient 1 | 100.0 | 94713_Donor 2 AD - B_adipose | 14.7 |
| 97482_Patient-08ut_uterus | 10.8 | 94714_Donor 2 AD - C_adipose | 6.7 |
| 97483_Patient-08pl_placenta | 8.3 | 94742_Donor 3 U - A_Mesenchymal Stem Cells | 8.3 |
| 97486_Patient-09sk_skeletal muscle | 0.0 | 94743_Donor 3 U - B_Mesenchymal Stem Cells | 0.0 |
| 97487_Patient-09ut_uterus | 3.6 | 94730_Donor 3 AM - A_adipose | 18.2 |
| 97488_Patient-09pl_placenta | 3.9 | 94731_Donor 3 AM - B_adipose | 0.0 |
| 97492_Patient-10ut_uterus | 13.7 | 94732_Donor 3 AM - C_adipose | 7.5 |
| 97493_Patient-10pl_placenta | 18.8 | 94733_Donor 3 AD - A_adipose | 24.3 |
| 97495_Patient-11go_adipose | 1.0 | 94734_Donor 3 AD - B_adipose | 7.7 |
| 97496_Patient-11sk_skeletal muscle | 1.7 | 94735_Donor 3 AD - C_adipose | 8.0 |
| 97497_Patient-11ut_uterus | 2.9 | 77138_Liver_HepG2untreated | 0.0 |
| 97498_Patient-11pl_placenta | 2.7 | 73556_Heart_Cardiac stromal cells (primary) | 9.3 |
| 97500 Patient-12go_adipose | 14.0 | 81735_Small Intestine | 14.8 |
| 97501_Patient-12sk_skeletal muscle | 7.7 | 72409_Kidney_Proximal Convoluted Tubule | 16.8 |
| 97502_Patient-12ut_uterus | 3.4 | 82685_Small intestine_Duodenum | 0.6 |
| 97503_Patient-12pl_placenta | 9.0 | 90650_Adrenal_Adrenocortical adenoma | 15.0 |
| 94721_Donor 2 U - A_Mesenchymal Stem Cells | 13.4 | 72410_Kidney_HRCE | 31.0 |
| 94722_Donor 2 U - B_Mesenchymal Stem Cells | 0.0 | 72411_Kidney_HRE | 25.2 |
| 94723_Donor 2 U - C_Mesenchymal Stem Cells | 15.8 | 73139_Uterus_Uterine smooth muscle cells | 12.3 |

CNS_neurodegeneration_v1.0 Summary: Ag3847 This panel confirms the expression of the CG93265-01 gene at low levels in the brains of an independent group of individuals. However, no differential expression of this gene was detected between Alzheimer's diseased postmortem brains and those of non-demented controls in this experiment. Please see Panel 1.4 for a discussion of the potential utility of this gene in treatment of central nervous system disorders.

General_screening_panel_v1.4 Summary: Ag3847 Highest expression of the CG93265-01 gene is detected in breast cancer T47D cell line (CT=26). In addition, high expression of this gene is seen in cluster of cancer cell lines (pancreatic, CNS, colon, renal, liver, breast, ovarian, prostate, squamous cell carcinoma and melanoma) used in this panel. Therefore, therapeutic modulation of the activity of this gene or its protein product, through the use of small molecule drugs, protein therapeutics or antibodies, might be beneficial in the treatment of these cancers.

This gene encodes a putative serine dehydratase, a gluconeogenic enzyme that produces pyruvate from serine. Among tissues with metabolic or endocrine function, this gene is expressed at high to moderate levels in pancreas, adipose, adrenal gland, thyroid, pituitary gland, skeletal muscle, heart, liver and the gastrointestinal tract. Inhibition of this enzyme in adipose or liver may decrease gluconeogenesis and be an adjunct therapy for the treatment of hyperglycemia and excess hepatic glucose production in Type 2 diabetes.

In addition, this gene is expressed at high levels in all regions of the central nervous system examined, including amygdala, hippocampus, substantia nigra, thalamus, cerebellum, cerebral cortex, and spinal cord. Therefore, this gene may play a role in central nervous system disorders such as Alzheimer's disease, Parkinson's disease, epilepsy, multiple sclerosis, schizophrenia and depression.

Panel 4.1D Summary: Ag3847 Highest expression of the CG93265-01 gene is detected in liver cirrhosis (CT=29.5). This gene encodes a homologue of rat L-serine dehydratase. Therefore, small molecule therapeutics could reduce or inhibit fibrosis that occurs in liver cirrhosis.

In addition, moderate to low expression of this gene is seen in normal tissues represented by kidney, thymus, lung and colon, as well as in lung fibroblasts, endothelial cells, NCI-H292 cells, keratinocytes, basophils, astrocytes, coronary artery SMC cells, small airway epithelium, macrophage, monocytes, dendritic cells, LAK cells, PBMC cells, two way MLR. Interestingly, expression of this gene is down-regulated in cytokine treated LAK cells (CTs>33) as compared to resting LAK cells (CT=30). Furthermore, expression of this gene is higher in LPS treated monocytes (CT=31) as compared to resting monocytes (CT-34). Therefore, expression of this gene can be used to distinguish between activated LAK cells/monocytes and resting cells and modulation of the gene product with a functional therapeutic may lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

Panel 5 Islet Summary: Ag3847 Highest expression of the CG93265-01 gene is detected in pancrease from patient 1 (CT=30.3). Moderate expression of this gene is also seen in samples derived from adipose, uterus, small intestine, kidney and placenta. This gene encodes a protein that is homologous to a gluconeogenic enzyme. Since gluconeogenesis is an energetically-expensive (ATP-consuming) process, and because insulin secretion is dependent upon increases in the ATP/ADP ratio, inhibition of this gene product may be an effective therapy to increase insulin secretion in Type 2 diabetes.

BF. CG93464-01: 3-Kinase

Expression of gene CG93464-01 was assessed using the primer-probe set Ag3856, described in Table BFA.

TABLE BFA

Probe Name Ag3856

| Primers | Sequences | Length | Start Position | SEQ ID NO: |
|---|---|---|---|---|
| Forward | 5'-ctgcagtggtggaacagatt-3' | 20 | 2645 | 432 |
| Probe | TET-5'-caagtttgcccaggtaagttccctga-3'-TAMRA | 26 | 2667 | 433 |
| Reverse | 5'-aggactctggggcagtatacac-3' | 22 | 2720 | 434 |

CNS_neurodegeneration_v1.0 Summary: Ag3856 Expression of the CG93464-01 gene is low/undetectable (CTs>35) across all of the samples on this panel (data not shown).

General_screening_panel_v1.4 Summary: Ag3856 Expression of the CG93464-01 gene is low/undetectable (CTs>35) across all of the samples on this panel (data not shown).

Panel 4.1D Summary: Ag3856 Expression of the CG93464-01 gene is low/undetectable (CTs>35) across all of the samples on this panel (data not shown).

Panel 5 Islet Summary: Ag3856 Expression of the CG93464-01 gene is low/undetectable (CTs>35) across all of the samples on this panel (data not shown).

BG. CG93495-01: MAP Kinase-Activating Death Domain Protein

Expression of gene CG93495-01 was assessed using the primer-probe set Ag3891, described in Table BGA. Results of the RTQ-PCR runs are shown in Tables BGB and BGC.

TABLE BGA

Probe Name Ag3891

| Primers | Sequences | Length | Start Position | SEQ ID NO: |
|---|---|---|---|---|
| Forward | 5'-gggatcaacctcaaattcatg-3' | 21 | 4712 | 435 |
| Probe | TET-5'-caatcaggttttcatagagctgaatcaca-3'TAMRA | 29 | 4735 | 436 |
| Reverse | 5'-aagacgcctcgaactgtattg-3' | 21 | 4774 | 437 |

TABLE BGB

CNS_neurodegeneration_v1.0

| Tissue Name | Rel. Exp. (%) Ag3891, Run 212195211 | Tissue Name | Rel. Exp. (%) Ag3891, Run 212195211 |
|---|---|---|---|
| AD 1 Hippo | 29.9 | Control (Path) 3 Temporal Ctx | 3.0 |
| AD 2 Hippo | 31.2 | Control (Path) 4 Temporal Ctx | 38.2 |
| AD 3 Hippo | 9.7 | AD 1 Occipital Ctx | 23.5 |
| AD 4 Hippo | 10.8 | AD 2 Occipital Ctx (Missing) | 0.0 |
| AD 5 hippo | 57.4 | AD 3 Occipital Ctx | 10.5 |
| AD 6 Hippo | 76.3 | AD 4 Occipital Ctx | 20.4 |
| Control 2 Hippo | 14.4 | AD 5 Occipital Ctx | 11.9 |
| Control 4 Hippo | 15.6 | AD 6 Occipital Ctx | 57.8 |
| Control (Path) 3 Hippo | 11.1 | Control 1 Occipital Ctx | 6.4 |
| AD 1 Temporal Ctx | 15.3 | Control 2 Occipital Ctx | 54.7 |
| AD 2 Temporal Ctx | 46.3 | Control 3 Occipital Ctx | 21.2 |
| AD 3 Temporal Ctx | 7.9 | Control 4 Occipital Ctx | 7.5 |
| AD 4 Temporal Ctx | 23.0 | Control (Path) 1 Occipital Ctx | 100.0 |
| AD 5 Inf Temporal Ctx | 81.2 | Control (Path) 2 Occipital Ctx | 6.0 |
| AD 5 Sup Temporal Ctx | 33.0 | Control (Path) 3 Occipital Ctx | 5.5 |
| AD 6 Inf Temporal Ctx | 60.7 | Control (Path) 4 Occipital Ctx | 6.8 |
| AD 6 Sup Temporal Ctx | 51.1 | Control 1 Parietal Ctx | 8.9 |
| Control 1 Temporal Ctx | 7.4 | Control 2 Parietal Ctx | 29.1 |
| Control 2 Temporal Ctx | 65.5 | Control 3 Parietal Ctx | 24.8 |
| Control 3 Temporal Ctx | 11.8 | Control (Path) 1 Parietal Ctx | 90.1 |
| Control 4 Temporal Ctx | 11.1 | Control (Path) 2 Parietal Ctx | 16.2 |
| Control (Path) 1 Temporal Ctx | 26.2 | Control (Path) 3 Parietal Ctx | 6.5 |
| Control (Path) 2 Temporal Ctx | 42.0 | Control (Path) 4 Parietal Ctx | 21.6 |

TABLE BGC

Panel 4.1D

| Tissue Name | Rel. Exp. (%) Ag3891, Run 170130430 | Tissue Name | Rel. Exp. (%) Ag3891, Run 170130430 |
|---|---|---|---|
| Secondary Th1 act | 41.2 | HUVEC IL-1beta | 20.4 |
| Secondary Th2 act | 55.9 | HUVEC IFN gamma | 25.5 |
| Secondary Tr1 act | 41.5 | HUVEC TNF alpha + IFN gamma | 10.4 |
| Secondary Th1 rest | 13.1 | HUVEC TNF alpha + IL4 | 9.7 |
| Secondary Th2 rest | 27.5 | HUVEC IL-11 | 7.6 |
| Secondary Tr1 rest | 27.9 | Lung Microvascular EC none | 25.5 |
| Primary Th1 act | 17.0 | Lung Microvascular EC TNF alpha + IL-1beta | 16.2 |
| Primary Th2 act | 45.4 | Microvascular Dermal EC none | 13.9 |
| Primary Tr1 act | 33.2 | Microvascular Dermal EC TNF alpha + IL-1beta | 9.1 |
| Primary Th1 rest | 14.8 | Bronchial epithelium TNF alpha + IL-1beta | 7.1 |
| Primary Th2 rest | 18.4 | Small airway epithelium none | 3.5 |
| Primary Tr1 rest | 26.4 | Small airway epithelium TNF alpha + IL-1beta | 7.5 |
| CD45RA CD4 lymphocyte act | 24.8 | Coronery artery SMC rest | 5.3 |
| CD45RO CD4 lymphocyte act | 47.6 | Coronery artery SMC TNF alpha + IL-1beta | 6.4 |
| CD8 lymphocyte act | 31.4 | Astrocytes rest | 4.4 |
| Secondary CD8 lymphocyte rest | 31.9 | Astrocytes TNF alpha + IL-1beta | 4.1 |
| Secondary CD8 lymphocyte act | 17.7 | KU-812 (Basophil) rest | 13.6 |

TABLE BGC-continued

Panel 4.1D

| Tissue Name | Rel. Exp. (%) Ag3891, Run 170130430 | Tissue Name | Rel. Exp. (%) Ag3891, Run 170130430 |
|---|---|---|---|
| CD4 lymphocyte none | 15.5 | KU-812 (Basophil) PMA/ionomycin | 31.9 |
| 2ry Th1/Th2/Tr1_anti-CD95 CH11 | 52.1 | CCD1106 (Keratinocytes) none | 12.4 |
| LAK cells rest | 38.4 | CCD1106 (Keratinocytes) TNF alpha + IL-1beta | 8.9 |
| LAK cells IL-2 | 25.0 | Liver cirrhosis | 4.6 |
| LAK cells IL-2 + IL-12 | 14.6 | NCI-H292 none | 14.9 |
| LAK cells IL-2 + IFN gamma | 11.2 | NCI-H292 IL-4 | 19.5 |
| LAK cells IL-2 + IL-18 | 22.8 | NCI-H292 IL-9 | 25.0 |
| LAK cells PMA/ionomycin | 27.7 | NCI-H292 IL-13 | 19.5 |
| NK Cells IL-2 rest | 61.6 | NCI-H292 IFN gamma | 20.2 |
| Two Way MLR 3 day | 39.0 | HPAEC none | 5.4 |
| Two Way MLR 5 day | 22.5 | HPAEC TNF alpha + IL-1beta | 17.7 |
| Two Way MLR 7 day | 21.3 | Lung fibroblast none | 11.0 |
| PBMC rest | 14.5 | Lung fibroblast TNF alpha + IL-1beta | 23.7 |
| PBMC PWM | 26.2 | Lung fibroblast IL-4 | 10.1 |
| PBMC PHA-L | 29.1 | Lung fibroblast IL-9 | 19.6 |
| Ramos (B cell) none | 14.4 | Lung fibroblast IL-13 | 13.0 |
| Ramos (B cell) ionomycin | 16.8 | Lung fibroblast IFN gamma | 15.4 |
| B lymphocytes PWM | 24.1 | Dermal fibroblast CCD1070 rest | 17.8 |
| B lymphocytes CD40L and IL-4 | 37.1 | Dermal fibroblast CCD1070 TNF alpha | 56.3 |
| EOL-1 dbcAMP | 27.9 | Dermal fibroblast CCD1070 IL-1beta | 20.0 |
| EOL-1 dbcAMP PMA/ionomycin | 23.8 | Dermal fibroblast IFN gamma | 10.8 |
| Dendritic cells none | 25.0 | Dermal fibroblast IL-4 | 15.6 |
| Dendritic cells LPS | 28.5 | Dermal Fibroblasts rest | 10.7 |
| Dendritic cells anti-CD40 | 24.7 | Neutrophils TNFa + LPS | 1.8 |
| Monocytes rest | 34.4 | Neutrophils rest | 5.8 |
| Monocytes LPS | 45.1 | Colon | 5.5 |
| Macrophages rest | 100.0 | Lung | 8.7 |
| Macrophages LPS | 51.4 | Thymus | 18.9 |
| HUVEC none | 9.1 | Kidney | 14.4 |
| HUVEC starved | 13.6 | | |

CNS_neurodegeneration_v1.0 Summary: Ag3891 This panel confirms the expression of the CG93495-01 gene at low levels in the brains of an independent group of individuals. However, no differential expression of this gene was detected between Alzheimer's diseased postmortem brains and those of non-demented controls in this experiment.

The CG93495-01 gene encodes a splice variant of MAP kinase-activating death domain protein (MADD). The MADD gene is differentially expressed in neoplastic versus normal cells and the protein is a substrate for c-Jun N-terminal kinase in the human central nervous system (Zhang Y, Zhou L, Miller C A. (1998) A splicing variant of a death domain protein that is regulated by a mitogen-activated kinase is a substrate for c-Jun N-terminal kinase in the human central nervous system. Proc Natl Acad Sci USA 95(5):2586–91). MADD homolog from C. elegans, AEX-3, a GDP/GTP exchange proteins specific for the Rab3 subfamily members has been shown to regulate exocytosis of neurotransmitters (Iwasaki K, Staunton J, Saifee O, Nonet M, Thomas J H. (1997) aex-3 encodes a novel regulator of presynaptic activity in C. elegans. Neuron 18(4):613–22). Therefore, therapeutic modulation of the activity of this gene may prove useful in the treatment of neurological disorders.

General_screening_panel_v1.4 Summary: Ag3891 Results from one experiment with the CG93495-01 gene are not included. The amp plot indicates that there were experimental difficulties with this run.

Panel 4.1D Summary: Ag3891 Highest expression of the CG93495-01 gene is detected in resting macrophage (CT= 27). This gene is expressed at high to moderate levels in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. This ubiquitous pattern of expression suggests that this gene product may be involved in homeostatic processes for these and other cell types and tissues. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

BH. CG93594-01: Phosphatidylinositol-Specific Phospholipase C

Expression of gene CG93594-01 was assessed using the primer-probe set Ag3861, described in Table BHA. Results of the RTQ-PCR runs are shown in Tables BHB and BHC.

TABLE BHA

Probe Name Ag3861

| Primers | Sequences | Length | Start Position | SEQ ID NO: |
|---|---|---|---|---|
| Forward | 5'-tgcgagtccatgagtttatttt-3' | 22 | 984 | 438 |
| Probe | TET-5'-tcacaccaggaagttcattaccagaa-3'-TAMRA | 26 | 1006 | 439 |
| Reverse | 5'-agagtctgctcttgttgctttg-3' | 22 | 1039 | 440 |

TABLE BHB

General_screening_panel_v1.4

| Tissue Name | Rel. Exp. (%) Ag3861, Run 213609049 | Tissue Name | Rel. Exp. (%) Ag3861, Run 213609049 |
|---|---|---|---|
| Adipose | 0.0 | Renal ca. TK-10 | 0.0 |
| Melanoma* Hs688(A).T | 0.0 | Bladder | 0.2 |
| Melanoma* Hs688(B).T | 0.0 | Gastric ca. (liver met.) NCI-N87 | 1.1 |
| Melanoma* M14 | 0.0 | Gastric ca. KATO III | 0.0 |
| Melanoma* LOXIMVI | 0.8 | Colon ca. SW-948 | 0.0 |
| Melanoma* SK-MEL-5 | 0.0 | Colon ca. SW480 | 0.0 |
| Squamous cell carcinoma SCC-4 | 0.0 | Colon ca.* (SW480 met) SW620 | 0.0 |
| Testis Pool | 100.0 | Colon ca. HT29 | 0.0 |
| Prostate ca.* (bone met) PC-3 | 0.0 | Colon ca. HCT-116 | 0.0 |
| Prostate Pool | 0.0 | Colon ca. CaCo-2 | 0.0 |
| Placenta | 0.0 | Colon cancer tissue | 0.0 |
| Uterus Pool | 0.0 | Colon ca. SW1116 | 0.0 |
| Ovarian ca. OVCAR-3 | 0.0 | Colon ca. Colo-205 | 0.0 |
| Ovarian ca. SK-OV-3 | 0.0 | Colon ca. SW-48 | 0.0 |
| Ovarian ca. OVCAR-4 | 1.9 | Colon Pool | 0.0 |
| Ovarian ca. OVCAR-5 | 0.0 | Small Intestine Pool | 0.0 |
| Ovarian ca. IGROV-1 | 0.0 | Stomach Pool | 0.2 |
| Ovarian ca. OVCAR-8 | 1.4 | Bone Marrow Pool | 0.0 |
| Ovary | 0.2 | Fetal Heart | 0.0 |
| Breast ca. MCF-7 | 0.0 | Heart Pool | 0.1 |
| Breast ca. MDA-MB-231 | 8.5 | Lymph Node Pool | 0.6 |
| Breast ca. BT 549 | 0.0 | Fetal Skeletal Muscle | 0.2 |
| Breast ca. T47D | 0.0 | Skeletal Muscle Pool | 0.0 |
| Breast ca. MDA-N | 0.0 | Spleen Pool | 0.3 |
| Breast Pool | 0.1 | Thymus Pool | 0.0 |
| Trachea | 0.8 | CNS cancer (glio/astro) U87-MG | 0.1 |
| Lung | 0.0 | CNS cancer (glio/astro) U-118-MG | 0.4 |
| Fetal Lung | 0.1 | CNS cancer (neuro;met) SK-N-AS | 0.5 |
| Lung ca. NCI-N417 | 0.0 | CNS cancer (astro) SF-539 | 0.0 |
| Lung ca. LX-1 | 0.0 | CNS cancer (astro) SNB-75 | 0.0 |
| Lung ca. NCI-H146 | 0.3 | CNS cancer (glio) SNB-19 | 0.0 |
| Lung ca. SHP-77 | 0.1 | CNS cancer (glio) SF-295 | 0.0 |
| Lung ca. A549 | 0.0 | Brain (Amygdala) Pool | 0.0 |
| Lung ca. NCI-H526 | 0.0 | Brain (cerebellum) | 0.0 |
| Lung ca. NCI-H23 | 0.5 | Brain (fetal) | 0.2 |
| Lung ca. NCI-H460 | 0.0 | Brain (Hippocampus) Pool | 0.0 |
| Lung ca. HOP-62 | 0.1 | Cerebral Cortex Pool | 0.5 |
| Lung ca. NCI-H522 | 0.0 | Brain (Substantia nigra) Pool | 0.0 |
| Liver | 0.0 | Brain (Thalamus) Pool | 0.1 |
| Fetal Liver | 1.5 | Brain (whole) | 0.3 |
| Liver ca. HepG2 | 0.0 | Spinal Cord Pool | 0.2 |
| Kidney Pool | 0.0 | Adrenal Gland | 0.0 |
| Fetal Kidney | 3.2 | Pituitary gland Pool | 0.0 |
| Renal ca. 786-0 | 0.0 | Salivary Gland | 0.1 |
| Renal ca. A498 | 0.2 | Thyroid (female) | 0.0 |
| Renal ca. ACHN | 0.0 | Pancreatic ca. CAPAN2 | 0.0 |
| Renal ca. UO-31 | 0.0 | Pancreas Pool | 0.1 |

TABLE BHC

Panel 4.1D

| Tissue Name | Rel. Exp. (%) Ag3861, Run 170128790 | Tissue Name | Rel. Exp. (%) Ag3861, Run 170128790 |
|---|---|---|---|
| Secondary Th1 act | 0.0 | HUVEC IL-1beta | 0.7 |
| Secondary Th2 act | 100.0 | HUVEC IFN gamma | 0.0 |
| Secondary Tr1 act | 5.5 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 0.0 | Microsvascular Dermal EC TNF alpha + IL-1beta | 0.0 |
| Primary Th1 rest | 0.0 | Bronchial epithelium TNF alpha + IL-1beta | 0.0 |
| Primary Th2 rest | 0.0 | Small airway epithelium none | 0.0 |
| Primary Tr1 rest | 0.0 | Small airway epithelium TNF alpha + IL-1beta | 0.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1beta | 0.0 |
| CD8 lymphocyte act | 0.0 | Astrocytes rest | 0.0 |
| Secondary CD8 lymphocyte rest | 0.0 | Astrocytes TNF alpha + IL-1beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.4 | CCD1106 (Keratinocytes) none | 0.0 |
| LAK cells rest | 0.0 | CCD1106 (Keratinocytes) TNF alpha + IL-1beta | 0.0 |
| LAK cells IL-2 | 0.0 | Liver cirrhosis | 0.0 |
| LAK cells IL-2 + IL-12 | 1.1 | NCI-H292 none | 0.0 |
| LAK cells IL-2 + IFN gamma | 0.0 | NCI-H292 IL-4 | 0.0 |
| LAK cells IL-2 + IL-18 | 0.0 | NCI-H292 IL-9 | 0.0 |
| LAK cells PMA/ionomycin | 0.0 | NCI-H292 IL-13 | 0.0 |
| NK Cells IL-2 rest | 0.0 | NCI-H292 IFN gamma | 0.0 |
| Two Way MLR 3 day | 0.0 | HPAEC none | 0.0 |
| Two Way MLR 5 day | 2.7 | HPAEC TNF alpha + IL-1beta | 0.0 |
| Two Way MLR 7 day | 0.0 | Lung fibroblast none | 0.0 |
| PBMC rest | 0.0 | Lung fibroblast TNF alpha + IL-1beta | 0.0 |
| PBMC PWM | 0.0 | Lung fibroblast IL-4 | 0.0 |
| PBMC PHA-L | 0.0 | Lung fibroblast IL-9 | 0.0 |
| Ramos (B cell) none | 0.0 | Lung fibroblast IL-13 | 0.0 |
| Ramos (B cell) ionomycin | 0.3 | Lung fibroblast IFN gamma | 0.0 |
| B lymphocytes PWM | 0.4 | Dermal fibroblast CCD1070 rest | 0.0 |
| B lymphocytes CD40L and IL-4 | 0.0 | Dermal fibroblast CCD1070 TNF alpha | 0.0 |
| EOL-1 dbcAMP | 0.0 | Dermal fibroblast CCD1070 IL-1beta | 0.0 |
| EOL-1 dbcAMP PMA/ionomycin | 0.0 | Dermal fibroblast IFN gamma | 0.0 |
| Dendritic cells none | 0.0 | Dermal fibroblast IL-4 | 0.0 |
| Dendritic cells LPS | 0.0 | Dermal Fibroblasts rest | 0.0 |
| Dendritic cells anti-CD40 | 0.0 | Neutrophils TNFa + LPS | 0.0 |
| Monocytes rest | 0.0 | Neutrophils rest | 0.0 |
| Monocytes LPS | 0.0 | Colon | 0.0 |
| Macrophages rest | 0.0 | Lung | 0.0 |
| Macrophages LPS | 0.3 | Thymus | 0.0 |
| HUVEC none | 0.0 | Kidney | 0.0 |
| HUVEC starved | 0.0 | | |

CNS_neurodegeneration_v1.0 Summary: Ag3861 Expression of the CG93594-01 gene is low/undetectable (CTs>35) across all of the samples on this panel (data not shown).

General_screening_panel_v1.4 Summary: Ag3861 High expression of the CG93594-01 gene is exclusively seen in testis (CT=28.6). Therefore, expression of this gene can be used to distinguish testis from other samples used in this panel. Furthermore, therapeutic modulation of the activity of this gene may prove useful in the treatment of testis related disorders including fertility and hypogonadism.

In addition, low expression of this gene is seen in breast cancer MDA-MB-231 and ovarian cancer OVCAR-4 cell lines. Therefore, therapeutic modulation of the activity of this gene or its protein product, through the use of small molecule drugs might be beneficial in the treatment of breast and ovarian cancer.

Significant expression is also detected in fetal kidney. Interestingly, this gene is expressed at much higher levels in fetal (CT=33.5) when compared to adult kidney (CT=40). This observation suggests that expression of this gene can be used to distinguish fetal from adult kidney. In addition, the relative overexpression of this gene in fetal kidney suggests that the protein product may enhance kidney growth or development in the fetus and thus may also act in a regenerative capacity in the adult. Therefore, therapeutic modulation of the protein encoded by this gene could be useful in treatment of kidney related diseases.

Panel 2.2 Summary: Ag3861 Expression of the CG93594-01 gene is low/undetectable (CTs>35) across all of the samples on this panel (data not shown).

Panel 4.1D Summary: Ag3861 High expression of the CG93594-01 gene is exclusively seen in activated secondary Th2 cells (CT=29.5). Therefore, expression of this gene can be used to distinguish activated secondary Th2 cells from other samples used in this panel. Furthermore, therapeutics designed with the protein encoded by this gene could be important in the regulation of T cell function and in the treatment of diseases such as asthma, IBD, psoriasis and arthritis in which T cells are chronically stimulated.

BI. CG93669-01 and CG93669-02 and CG93669-03: Serine/Threonine-Protein Kinase NEK3

Expression of gene CG93669-01 and variants CG93669-02 and CG93669-03 was assessed using the primer-probe set Ag3874, described in Table BIA.

TABLE BIA

Probe Name Ag3874

| Primers | Sequences | Length | Start Position | SEQ ID NO: |
|---|---|---|---|---|
| Forward | 5'-caagaaacgtgtgctacacaga-3' | 22 | 602 | 441 |
| Probe | TET-5'-tcaagtcccagaatatcttcctcactca-3'-TAMRA | 28 | 628 | 442 |
| Reverse | 5'-ctcccaatttcacttttccatt-3' | 22 | 657 | 443 |

CNS_neurodegeneration_v1.0 Summary: Ag3874 Expression of the CG93669-01 gene is low/undetectable (CTs>35) in all samples on this panel. (Data not shown.). The data suggest that there is a possibility of an experimental failure.

General_screening_panel_v1.4 Summary: Ag3874 Expression of the CG93669-01 gene is low/undetectable (CTs>35) in all samples on this panel. (Data not shown.). The data suggest that there is a possibility of an experimental failure.

Panel 4.1D Summary: Ag3874 Expression of the CG93669-01 gene is low/undetectable (CTs>35) in all samples on this panel. (Data not shown.). The data suggest that there is a possibility of an experimental failure.

BJ. CG93896-01 and CG93896-2: Protein Kinase (NEK like)

Expression of gene CG93896-01 and variant CG93896-02 was assessed using the primer-probe sets Ag3892 and Ag4153, described in Tables BJA and BJB. Results of the RTQ-PCR runs are shown in Tables BJC, BJD, BJE and BJF.

TABLE BJA

Probe Name Ag3892

| Primers | Sequences | Length | Start Position | SEQ ID NO: |
|---|---|---|---|---|
| Forward | 5'-acttgctcgaacttgtattgga-3' | 22 | 468 | 444 |
| Probe | TET-5'-acctgtccccagagatctgtcagaat-3'-TAMRA | 26 | 500 | 445 |
| Reverse | 5'-ccaagagaccaaatatccgttt-3' | 22 | 542 | 446 |

TABLE BJB

Probe Name Ag4153

| Primers | Sequences | Length | Start Position | SEQ ID NO: |
|---|---|---|---|---|
| Forward | 5'-gagagcccacaaaccaagttat-3' | 22 | 1101 | 447 |
| Probe | TET-5'-caccccattcctcaagaaaatactgga-3'-TAMRA | 27 | 1123 | 448 |
| Reverse | 5'-cctcgtttcctgaccgtaat-3' | 20 | 1157 | 449 |

TABLE BJC

CNS_neurodegeneration_v1.0

| Tissue Name | Rel. Exp. (%) Ag3892, Run 212247893 | Tissue Name | Rel. Exp. (%) Ag3892, Run 212247893 |
|---|---|---|---|
| AD 1 Hippo | 51.8 | Control (Path) 3 Temporal Ctx | 20.2 |
| AD 2 Hippo | 54.0 | Control (Path) 4 Temporal Ctx | 36.1 |
| AD 3 Hippo | 54.7 | AD 1 Occipital Ctx | 24.8 |
| AD 4 Hippo | 6.5 | AD 2 Occipital Ctx (Missing) | 0.0 |
| AD 5 Hippo | 27.4 | AD 3 Occipital Ctx | 27.9 |
| AD 6 Hippo | 81.2 | AD 4 Occipital Ctx | 14.1 |
| Control 2 Hippo | 25.5 | AD 5 Occipital Ctx | 25.0 |
| Control 4 Hippo | 60.3 | AD 6 Occipital Ctx | 28.1 |

TABLE BJC-continued

CNS_neurodegeneration_v1.0

| Tissue Name | Rel. Exp. (%) Ag3892, Run 212247893 | Tissue Name | Rel. Exp. (%) Ag3892, Run 212247893 |
|---|---|---|---|
| Control (Path) 3 Hippo | 60.3 | Control 1 Occipital Ctx | 8.6 |
| AD 1 Temporal Ctx | 61.6 | Control 2 Occipital Ctx | 19.3 |
| AD 2 Temporal Ctx | 28.5 | Control 3 Occipital Ctx | 9.8 |
| AD 3 Temporal Ctx | 27.0 | Control 4 Occipital Ctx | 43.8 |
| AD 4 Temporal Ctx | 29.5 | Control (Path) 1 Occipital Ctx | 100.0 |
| AD 5 Inf Temporal Ctx | 67.8 | Control (Path) 2 Occipital Ctx | 6.8 |
| AD 5 Sup Temporal Ctx | 97.3 | Control (Path) 3 Occipital Ctx | 6.8 |
| AD 6 Inf Temporal Ctx | 45.7 | Control (Path) 4 Occipital Ctx | 33.0 |
| AD 6 Sup Temporal Ctx | 48.0 | Control 1 Parietal Ctx | 11.7 |
| Control 1 Temporal Ctx | 12.4 | Control 2 Parietal Ctx | 75.3 |
| Control 2 Temporal Ctx | 19.3 | Control 3 Parietal Ctx | 2.2 |
| Control 3 Temporal Ctx | 31.0 | Control (Path) 1 Parietal Ctx | 49.7 |
| Control 3 Temporal Ctx | 15.3 | Control (Path) 2 Parietal Ctx | 48.0 |
| Control (Path) 1 Temporal Ctx | 54.0 | Control (Path) 3 Parietal Ctx | 21.6 |
| Control (Path) 2 Temporal Ctx | 25.2 | Control (Path) 4 Parietal Ctx | 33.2 |

TABLE BJD

General_screening_panel_v1.4

| Tissue Name | Rel. Exp. (%) Ag3892, Run 219166392 | Tissue Name | Rel. Exp. (%) Ag3892, Run 219166392 |
|---|---|---|---|
| Adipose | 8.0 | Renal ca. TK-10 | 5.4 |
| Melanoma* Hs688(A).T | 0.8 | Bladder | 4.9 |
| Melanoma* Hs688(B).T | 2.5 | Gastric ca. (liver met.) NCI-N87 | 45.1 |
| Melanoma* M14 | 5.2 | Gastric ca. KATO III | 9.3 |
| Melanoma* LOXIMVI | 0.5 | Colon ca. SW-948 | 2.7 |
| Melanoma* SK-MEL-5 | 3.9 | Colon ca. SW480 | 33.4 |
| Squamous cell carcinoma SSC-4 | 0.7 | Colon ca.* (SW480 met) SW620 | 2.7 |
| Testis Pool | 73.2 | Colon ca. HT29 | 3.8 |
| Prostate ca.* (bone met) PC-3 | 3.2 | Colon ca. HCT-116 | 18.9 |
| Prostate Pool | 4.5 | Colon ca. CaCo-2 | 3.4 |
| Placenta | 2.3 | Colon cancer tissue | 6.9 |
| Uterus Pool | 1.6 | Colon ca. SW1116 | 3.6 |
| Ovarian ca. OVCAR-3 | 7.2 | Colon ca. Colo-205 | 2.5 |
| Ovarian ca. SK-OV-3 | 7.6 | Colon ca. SW-48 | 3.3 |
| Ovarian ca. OVCAR-4 | 0.7 | Colon Pool | 8.8 |
| Ovarian ca. OVCAR-5 | 7.7 | Small Intestine Pool | 4.6 |
| Ovarian ca. IGROV-1 | 12.7 | Stomach Pool | 3.3 |
| Ovarian ca. OVCAR-8 | 1.2 | Bone Marrow Pool | 1.4 |
| Ovary | 2.9 | Fetal Heart | 2.2 |
| Breast ca. MCF-7 | 9.6 | Heart Pool | 3.1 |
| Breast ca. MDA-MB-231 | 1.6 | Lymph Node Pool | 2.9 |
| Breast ca. BT 549 | 1.6 | Fetal Skeletal Muscle | 1.4 |
| Breast ca. T47D | 31.9 | Skeletal Muscle Pool | 0.7 |
| Breast ca. MDA-N | 0.1 | Spleen Pool | 0.5 |
| Breast Pool | 5.9 | Thymus Pool | 5.3 |
| Trachea | 62.4 | CNS cancer (glio/astro) U87-MG | 0.7 |
| Lung | 1.8 | CNS cancer (glio/astro) U-118-MG | 0.8 |
| Fetal Lung | 100.0 | CNS cancer (neuro; met) SK-N-AS | 2.9 |
| Lung ca. NCI-N417 | 0.2 | CNS cancer (astro) SF-539 | 3.1 |
| Lung ca. LX-1 | 20.0 | CNS cancer (astro) SNB-75 | 0.6 |
| Lung ca. NCI-H146 | 0.5 | CNS cancer (glio) SNB-19 | 13.9 |
| Lung ca. SHP-77 | 0.6 | CNS cancer (glio) SF-295 | 5.0 |

TABLE BJD-continued

General_screening_panel_v1.4

| Tissue Name | Rel. Exp. (%) Ag3892, Run 219166392 | Tissue Name | Rel. Exp. (%) Ag3892, Run 219166392 |
|---|---|---|---|
| Lung ca. A549 | 2.2 | Brain (Amygdala) Pool | 2.0 |
| Lung ca. NCI-H526 | 0.2 | Brain (cerebellum) | 0.5 |
| Lung ca. NCI-H23 | 6.7 | Brain (fetal) | 4.7 |
| Lung ca. NCI-H460 | 1.2 | Brain (Hippocampus) Pool | 8.9 |
| Lung ca. HOP-62 | 0.3 | Cerebral Cortex Pool | 2.9 |
| Lung ca. NCI-H522 | 8.5 | Brain (Substantia nigra) Pool | 3.3 |
| Liver | 0.0 | Brain (Thalamus) Pool | 7.0 |
| Fetal Liver | 0.9 | Brain (whole) | 8.5 |
| Liver ca. HepG2 | 1.7 | Spinal Cord Pool | 8.8 |
| Kidney Pool | 5.0 | Adrenal Gland | 0.3 |
| Fetal Kidney | 24.0 | Pituitary gland Pool | 2.2 |
| Renal ca. 786-0 | 4.6 | Salivary Gland | 0.8 |
| Renal ca. A498 | 7.5 | Thyroid (female) | 2.5 |
| Renal ca. ACHN | 3.5 | Pancreatic ca. CAPAN2 | 1.3 |
| Renal ca. UO-31 | 1.0 | Pancreas Pool | 7.2 |

TABLE BJE

Panel 2.2

| Tissue Name | Rel. Exp. (%) Ag3892, Run 173768795 | Tissue Name | Rel. Exp. (%) Ag3892, Run 173768795 |
|---|---|---|---|
| Normal Colon | 16.4 | Kidney Margin (OD04348) | 84.1 |
| Colon cancer (OD06064) | 7.9 | Kidney malignant cancer (OD06204B) | 24.7 |
| Colon Margin (OD06064) | 6.3 | Kidney normal adjacent tissue (OD06204E) | 23.5 |
| Colon cancer (OD06159) | 4.3 | Kidney Cancer (OD04450-01) | 36.6 |
| Colon Margin (OD06159) | 9.6 | Kidney Margin (OD04450-03) | 36.9 |
| Colon cancer (OD06297-04) | 8.4 | Kidney Cancer 8120613 | 3.5 |
| Colon Margin (OD06297-05) | 15.1 | Kidney Margin 8120614 | 51.8 |
| CC Gr.2 ascend colon (ODO3921) | 11.6 | Kidney Cancer 9010320 | 38.7 |
| CC Margin (ODO3921) | 11.3 | Kidney Margin 9010321 | 18.6 |
| Colon cancer metastasis (OD06104) | 6.2 | Kidney Cancer 8120607 | 52.5 |
| Lung Margin (OD06104) | 22.2 | Kidney Margin 8120608 | 34.9 |
| Colon mets to lung (OD04451-01) | 5.7 | Normal Uterus | 26.8 |
| Lung Margin (OD04451-02) | 7.5 | Uterine Cancer 064011 | 9.5 |
| Normal Prostate | 7.7 | Normal Thyroid | 2.3 |
| Prostate Cancer (OD04410) | 8.1 | Thyroid Cancer 064010 | 8.0 |
| Prostate Margin (OD04410) | 11.9 | Thyroid Cancer A302152 | 37.1 |
| Normal Ovary | 49.0 | Thyroid Margin A302153 | 10.2 |
| Ovarian cancer (OD06283-03) | 16.2 | Normal Breast | 29.5 |
| Ovarian Margin (OD06283-07) | 7.5 | Breast Cancer (OD04566) | 42.6 |
| Ovarian Cancer 064008 | 22.1 | Breast Cancer 1024 | 17.1 |
| Ovarian cancer (OD06145) | 25.9 | Breast Cancer (OD04590-01) | 15.1 |
| Ovarian Margin (OD06145) | 31.6 | Breast Cancer Mets (OD04590-03) | 27.7 |
| Ovarian cancer (OD06455-03) | 25.9 | Breast Cancer Metastasis (OD04655-05) | 22.4 |
| Ovarian Margin (OD06455-07) | 10.7 | Breast Cancer 064006 | 19.3 |
| Normal Lung | 6.9 | Breast Cancer 9100266 | 4.6 |
| Invasive poor diff. lung adeno (ODO4945-01) | 14.5 | Breast Margin 9100265 | 7.9 |
| Lung Margin (ODO4945-03) | 11.0 | Breast Cancer A209073 | 10.3 |
| Lung Malignant Cancer (OD03126) | 8.1 | Breast Margin A2090734 | 26.6 |
| Lung Margin (OD03126) | 3.7 | Breast cancer (OD06083) | 32.8 |
| Lung Cancer (OD05014A) | 6.0 | Breast cancer node metastasis (OD06083) | 29.3 |
| Lung Margin (OD05014B) | 8.2 | Normal Liver | 40.3 |

TABLE BJE-continued

Panel 2.2

| Tissue Name | Rel. Exp. (%) Ag3892, Run 173768795 | Tissue Name | Rel. Exp. (%) Ag3892, Run 173768795 |
|---|---|---|---|
| Lung cancer (OD06081) | 18.4 | Liver Cancer 1026 | 27.4 |
| Lung Margin (OD06081) | 5.3 | Liver Cancer 1025 | 27.2 |
| Lung Cancer (OD04237-01) | 11.7 | Liver Cancer 6004-T | 32.8 |
| Lung Margin (OD04237-02) | 17.2 | Liver Tissue 6004-N | 21.8 |
| Ocular Melanoma Metastasis | 100.0 | Liver Cancer 6005-T | 57.0 |
| Ocular Melanoma Margin (Liver) | 25.9 | Liver Tissue 6005-N | 95.9 |
| Melanoma Metastasis | 12.5 | Liver Cancer 064003 | 32.3 |
| Melanoma Margin (Lung) | 10.2 | Normal Bladder | 8.1 |
| Normal Kidney | 16.3 | Bladder Cancer 1023 | 17.0 |
| Kidney Ca, Nuclear grade 2 (OD04338) | 57.8 | Bladder Cancer A302173 | 24.7 |
| Kidney Margin (OD04338) | 26.2 | Normal Stomach | 45.4 |
| Kidney Ca, Nuclear grade 1/2 (OD04339) | 35.4 | Gastric Cancer 9060397 | 3.3 |
| Kidney Margin (OD04339) | 29.9 | Stomach Margin 9060396 | 24.1 |
| Kidney Ca, Clear cell type (OD04340) | 11.7 | Gastric Cancer 9060395 | 22.1 |
| Kidney Margin (OD04340) | 24.8 | Stomach Margin 9060394 | 29.7 |
| Kidney Ca, Nuclear grade 3 (OD04348) | 6.0 | Gastric Cancer 064005 | 17.6 |

TABLE BJF

Panel 4.1D

| Tissue Name | Rel. Exp. (%) Ag3892, Run 170130819 | Tissue Name | Rel. Exp. (%) Ag3892, Run 170130819 |
|---|---|---|---|
| Secondary Th1 act | 0.0 | HUVEC IL-1beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 8.5 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 0.0 | Microsvasular Dermal EC TNF alpha + IL-1beta | 0.0 |
| Primary Th1 rest | 0.0 | Bronchial epithelium TNF alpha + IL1beta | 8.6 |
| Primary Th2 rest | 0.0 | Small airway epithelium none | 15.0 |
| Primary Tr1 rest | 0.0 | Small airway epithelium TNF alpha + IL-1beta | 17.4 |
| CD45RA CD4 lymphocyte act | 0.0 | Coronery artery SMC rest | 0.0 |
| CD45RO CD4 lymphocyte act | 6.4 | Coronery artery SMC TNF alpha + IL-1beta | 0.0 |
| CD8 lymphocyte act | 0.0 | Astrocytes rest | 26.6 |
| Secondary CD8 lymphocyte rest | 0.0 | Astrocytes TNF alpha + IL-1beta | 16.8 |
| Secondary CD8 lymphocyte act | 0.0 | KU-812 (Basophil) rest | 71.2 |
| CD4 lymphocyte none | 0.0 | KU-812 (Basophil) PMA/ionomycin | 100.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1beta | 0.0 |
| LAK cells IL-2 | 0.0 | Liver cirrhosis | 9.7 |
| LAK cells IL-2 + IL-12 | 0.0 | NCI-H292 none | 10.0 |
| LAK cells IL-2 + IFN gamma | 0.0 | NCI-H292 IL-4 | 7.2 |
| LAK cells IL-2 + IL-18 | 0.0 | NCI-H292 IL-9 | 25.9 |
| LAK cells PMA/ionomycin | 0.0 | NCI-H292 IL-13 | 21.0 |
| NK Cells IL-2 rest | 0.0 | NCI-H292 IFN gamma | 16.5 |
| Two Way MLR 3 day | 0.0 | HPAEC none | 0.0 |
| Two Way MLR 5 day | 0.0 | HPAEC TNF alpha + IL-1beta | 0.0 |

TABLE BJF-continued

Panel 4.1D

| Tissue Name | Rel. Exp. (%) Ag3892, Run 170130819 | Tissue Name | Rel. Exp. (%) Ag3892, Run 170130819 |
|---|---|---|---|
| Two Way MLR 7 day | 0.0 | Lung fibroblast none | 0.0 |
| PBMC rest | 0.0 | Lung fibroblast TNF alpha + IL-1beta | 0.0 |
| PBMC PWM | 0.0 | Lung fibroblast IL-4 | 5.5 |
| PBMC PHA-L | 6.4 | Lung fibroblast IL-9 | 0.0 |
| Ramos (B cell) none | 0.0 | Lung fibroblast IL-13 | 0.0 |
| Ramos (B cell) ionomycin | 0.0 | Lung fibroblast IFN gamma | 0.0 |
| B lymphocytes PWM | 12.4 | Dermal fibroblast CCD1070 rest | 1.4 |
| B lymphocytes CD40L and IL-4 | 0.0 | Dermal fibroblast CCD1070 TNF alpha | 0.0 |
| EOL-1 dbcAMP | 6.5 | Dermal fibroblast CCD1070 IL-1beta | 0.0 |
| EOL-1 dbcAMP PMA/ionomycin | 0.0 | Dermal fibroblast IFN gamma | 0.0 |
| Dendritic cells none | 0.0 | Dermal fibroblast IL-4 | 0.0 |
| Dendritic cells LPS | 0.0 | Dermal Fibroblasts rest | 17.1 |
| Dendritic cells anti-CD40 | 8.7 | Neutrophils TNFa + LPS | 0.0 |
| Monocytes rest | 0.0 | Neutrophils rest | 4.7 |
| Monocytes LPS | 0.0 | Colon | 0.0 |
| Macrophages rest | 0.0 | Lung | 22.1 |
| Macrophages LPS | 0.0 | Thymus | 30.8 |
| HUVEC none | 0.0 | Kidney | 85.3 |
| HUVEC starved | 0.0 | | |

CNS_neurodegeneration_v1.0 Summary: Ag3892 This panel confirms the expression of the CG93896-01 gene at low levels in the brain in an independent group of individuals. However, no differential expression of this gene was detected between Alzheimer's diseased postmortem brains and those of non-demented controls in this experiment. Please see Panel 1.4 for a discussion of the potential utility of this gene in treatment of central nervous system disorders.

Ag4153 Expression of the CG93896-01 gene is low/undetectable (CTs>35) across all of the samples on this panel (data not shown).

General_screening_panel_v1.4 Summary: Ag3892 Highest expression of the CG93896-01 gene is observed in fetal lung (CT=28.7). Interestingly, this gene is expressed at much higher levels in fetal when compared to adult lung (CT=34.5). This observation suggests that expression of this gene can be used to distinguish fetal from adult lung. In addition, the relative overexpression of this gene in fetal lung suggests that the protein product may enhance growth or development of lung in the fetus and thus may also act in a regenerative capacity in the adult. Therefore, therapeutic modulation of the protein encoded by this gene could be useful in treatment of lung related diseases.

In addition, high expression of this gene is seen in trachea and testis pool (CTs=29). Therefore, therapeutic modulation of the protein encoded by this gene could be useful in treatment of trachea and testis related diseases including fertility and hypogonadism.

Among tissues with metabolic or endocrine function, this gene is expressed at low to moderate levels in pancreas, adipose, thyroid, pituitary gland, skeletal muscle, heart, and the gastrointestinal tract. Therefore, therapeutic modulation of the activity of this gene may prove useful in the treatment of endocrine/metabolically related diseases, such as obesity and diabetes.

In addition, this gene is expressed at moderate levels in all regions of the central nervous system examined, including amygdala, hippocampus, substantia nigra, thalamus, cerebellum, cerebral cortex, and spinal cord. Therefore, this gene may play a role in central nervous system disorders such as Alzheimer's disease, Parkinson's disease, epilepsy, multiple sclerosis, schizophrenia and depression Ag4153 Expression of the CG93896-01 gene is low/undetectable (CTs>35) across all of the samples on this panel (data not shown).

Panel 2.2 Summary: Ag3892 Highest expression of the CG93896-01 gene is observed in ocular melenoma metastasis to liver (OD04310) (CT=31.4). Significant expression of this gene is associated with both normal and cancer tissue samples used in this panel. Interestingly, expression of this gene is higher in control kidney margin OD04348 and 8120614 and stomach margin 9060396 samples (CTs=32–33) as compared to their corresponding cancer tissue (CTs=36). Therefore, expression of this gene can be used as distinguish between normal and kidney/gastric cancer samples. Furthermore, therapeutic modulation of the protein encoded by this gene could be useful in treatment of these cancers.

Panel 4.1D Summary: Ag3892 Highest expression of the CG93896-01 gene is observed in PMA/ionomycin treated basophils (CT=33.5). Significant expression of this gene is also seen in resting basophils (CT=34). Therefore, therapeutic modulation of the protein encoded for by this gene could useful in treatment of asthma, allergies, hypersensitivity reactions, psoriasis, and viral infections.

In addition, moderate expression is also seen in kidney (CT=33.4). Therefore, expression of this gene could be used to distinguish basophils and kidney samples from other samples used in this panel. In addition, therapeutic modulation of the protein encoded for by this gene could useful in treatment of kidney related diseases such as lupus, glomerulonephritis. The CG93896-01 gene codes for NimA-related protein kinase (NEK). Mutation in one of the related protein NEK1 has recently been shown to be cause pleiotropic effects including facial dysmorphism, dwarfing, male sterility, anemia, cystic choroid plexus, and progressive polycystic kidney disease (PKD) in mice (Upadhya P, Birkenmeier E H, Birkenmeier C S, Barker J E. (2000) Mutations in a NIMA-related kinase gene, Nek1, cause pleiotropic effects including a progressive polycystic kidney disease in mice. Proc Natl Acad Sci USA 97(1):217–21). Therefore, therapeutic modulation of the NEK encoded for by this gene could useful in treatment of facial dysmorphism, dwarfing, male sterility, anemia, cystic choroid plexus, and progressive PKD.

Ag4153 Expression of the CG93896-01 gene is low/undetectable (CTs>35) across all of the samples on this panel (data not shown).

BK. CG94302-01: MUNC13-1

Expression of gene CG94302-01 was assessed using the primer-probe set Ag3911, described in Table BKA.

TABLE BKA

Probe Name Ag3911

| Primers | Sequences | Length | Start Position | SEQ ID NO: |
|---|---|---|---|---|
| Forward | 5'-ggtggtaaaggactgtgtgaaa-3' | 22 | 2957 | 468 |
| Probe | TET-5'-cgagtacatcttcaataactgccatga-3'-TAMRA | 27 | 2999 | 469 |
| Reverse | 5'-ggtactcccggctgtacagt-3' | 20 | 3026 | 470 |

CNS_neurodegeneration_v1.0 Summary: Ag3911 Results from one experiment with the CG94302-01 gene are not included. (All CTs=40). The data suggest that there is a possibility of an experimental failure.

General_screening_panel_v1.4 Summary: Ag3911 Results from one experiment with the CG94302-01 gene are not included. (All CTs=40). The data suggest that there is a possibility of an experimental failure.

Panel 4.1D Summary: Ag3911 Results from one experiment with the CG94302-01 gene are not included. (All CTs=40). The data suggest that there is a possibility of an experimental failure.

BL. CG94356-01: Carboxylesterase

Expression of gene CG94356-01 was assessed using the primer-probe set Ag3915, described in Table BLA. Results of the RTQ-PCR runs are shown in Tables BLB and BLC.

TABLE BLA

Probe Name Ag3915

| Primers | Sequences | Length | Start Position | SEQ ID NO: |
|---|---|---|---|---|
| Forward | 5'-agaagttactgagccggaagat-3' | 22 | 1463 | 450 |
| Probe | TET-5'-atactgggctacctttgctcgaaccg-3'-TAMRA | 26 | 1491 | 451 |
| Reverse | 5'-gattataagctggccacagaga-3' | 22 | 1540 | 452 |

TABLE BLB

CNS_neurodegeneration_v1.0

| Tissue Name | Rel. Exp. (%) Ag3915, Run 212248481 | Tissue Name | Rel. Exp. (%) Ag3915, Run 212248481 |
|---|---|---|---|
| AD 1 Hippo | 12.1 | Control (Path) 3 Temporal Ctx | 0.0 |
| AD 2 Hippo | 25.2 | Control (Path) 4 Temporal Ctx | 29.5 |
| AD 3 Hippo | 0.0 | AD 1 Occipital Ctx | 5.3 |
| AD 4 Hippo | 8.4 | AD 2 Occipital Ctx (Missing) | 0.0 |
| AD 5 Hippo | 28.9 | AD 3 Occipital Ctx | 0.0 |
| AD 6 Hippo | 29.5 | AD 4 Occipital Ctx | 9.2 |
| Control 2 Hippo | 26.2 | AD 5 Occipital Ctx | 12.8 |
| Control 4 Hippo | 9.1 | AD 6 Occipital Ctx | 22.2 |
| Control (Path) 3 Hippo | 0.0 | Control 1 Occipital Ctx | 0.0 |
| AD 1 Temporal Ctx | 5.4 | Control 2 Occipital Ctx | 30.4 |
| AD 2 Temporal Ctx | 24.8 | Control 3 Occipital Ctx | 9.2 |
| AD 3 Temporal Ctx | 0.0 | Control 4 Occipital Ctx | 6.1 |
| AD 4 Temporal Ctx | 10.3 | Control (Path) 1 Occipital Ctx | 70.2 |
| AD 5 Inf Temporal Ctx | 36.9 | Control (Path) 2 Occipital Ctx | 0.0 |
| AD 5 Sup Temporal Ctx | 8.0 | Control (Path) 3 Occipital Ctx | 11.6 |
| AD 6 Inf Temporal Ctx | 63.3 | Control (Path) 4 Occipital Ctx | 7.5 |
| AD 6 Sup Temporal Ctx | 52.5 | Control 1 Parietal Ctx | 7.1 |
| Control 1 Temporal Ctx | 0.0 | Control 2 Parietal Ctx | 22.1 |
| Control 2 Temporal Ctx | 65.1 | Control 3 Parietal Ctx | 35.4 |
| Control 3 Temporal Ctx | 22.7 | Control (Path) 1 Parietal Ctx | 71.2 |
| Control 3 Temporal Ctx | 9.5 | Control (Path) 2 Parietal Ctx | 9.9 |
| Control (Path) 1 Temporal Ctx | 100.0 | Control (Path) 3 Parietal Ctx | 0.0 |
| Control (Path) 2 Temporal Ctx | 35.8 | Control (Path) 4 Parietal Ctx | 58.6 |

TABLE BLC

General_screening_panel_v1.4

| Tissue Name | Rel. Exp. (%) Ag3915, Run 219174535 | Tissue Name | Rel. Exp. (%) Ag3915, Run 219174535 |
|---|---|---|---|
| Adipose | 0.0 | Renal ca. TK-10 | 0.0 |
| Melanoma* Hs688(A).T | 3.9 | Bladder | 0.0 |
| Melanoma* Hs688(B).T | 1.8 | Gastric ca. (liver met.) NCI-N87 | 0.0 |
| Melanoma* M14 | 0.0 | Gastric ca. KATO III | 0.0 |
| Melanoma* LOXIMVI | 0.0 | Colon ca. SW-948 | 0.0 |
| Melanoma* SK-MEL-5 | 33.7 | Colon ca. SW480 | 5.2 |
| Squamous cell carcinoma SCC-4 | 1.4 | Colon ca.* (SW480 met) SW620 | 5.0 |
| Testis Pool | 100.0 | Colon ca. HT29 | 0.0 |
| Prostate ca.* (bone met) PC-3 | 0.0 | Colon ca. HCT-116 | 0.0 |
| Prostate Pool | 0.0 | Colon ca. CaCo-2 | 0.0 |
| Placenta | 0.0 | Colon cancer tissue | 0.0 |
| Uterus Pool | 0.0 | Colon ca. SW1116 | 0.0 |
| Ovarian ca. OVCAR-3 | 0.0 | Colon ca. Colo-205 | 0.0 |
| Ovarian ca. SK-OV-3 | 0.0 | Colon ca. SW-48 | 0.0 |
| Ovarian ca. OVCAR-4 | 0.0 | Colon Pool | 0.0 |
| Ovarian ca. OVCAR-5 | 0.0 | Small Intestine Pool | 0.0 |
| Ovarian ca. IGROV-1 | 0.0 | Stomach Pool | 0.0 |
| Ovarian ca. OVCAR-8 | 0.0 | Bone Marrow Pool | 0.0 |
| Ovary | 1.8 | Fetal Heart | 0.0 |
| Breast ca. MCF-7 | 0.0 | Heart Pool | 1.4 |
| Breast ca. MDA-MB-231 | 0.0 | Lymph Node Pool | 0.0 |
| Breast ca. BT 549 | 0.0 | Fetal Skeletal Muscle | 0.0 |
| Breast ca. T47D | 0.0 | Skeletal Muscle Pool | 0.0 |
| Breast ca. MDA-N | 1.6 | Spleen Pool | 0.7 |
| Breast Pool | 0.0 | Thymus Pool | 3.6 |
| Trachea | 0.0 | CNS cancer (glio/astro) U87-MG | 1.9 |
| Lung | 0.0 | CNS cancer (glio/astro) U-118-MG | 0.0 |
| Fetal Lung | 0.0 | CNS cancer (neuro; met) SK-N-AS | 0.0 |
| Lung ca. NCI-N417 | 0.7 | CNS cancer (astro) SF-539 | 0.0 |
| Lung ca. LX-1 | 1.2 | CNS cancer (astro) SNB-75 | 0.0 |
| Lung ca. NCI-H146 | 0.0 | CNS cancer (glio) SNB-19 | 0.0 |
| Lung ca. SHP-77 | 0.0 | CNS cancer (glio) SF-295 | 1.8 |
| Lung ca. A549 | 1.8 | Brain (Amygdala) Pool | 18.0 |
| Lung ca. NCI-H526 | 0.0 | Brain (cerebellum) | 19.6 |
| Lung ca. NCI-H23 | 0.0 | Brain (fetal) | 20.6 |
| Lung ca. NCI-H460 | 0.0 | Brain (Hippocampus) Pool | 14.0 |
| Lung ca. HOP-62 | 0.0 | Cerebral Cortex Pool | 22.5 |
| Lung ca. NCI-H522 | 0.0 | Brain (Substantia nigra) Pool | 8.2 |
| Liver | 34.9 | Brain (Thalamus) Pool | 21.8 |
| Fetal Liver | 0.0 | Brain (whole) | 7.1 |
| Liver ca. HepG2 | 0.0 | Spinal Cord Pool | 5.2 |
| Kidney Pool | 0.0 | Adrenal Gland | 0.0 |
| Fetal Kidney | 0.0 | Pituitary gland Pool | 0.0 |
| Renal ca. 786-0 | 0.0 | Salivary Gland | 2.0 |
| Renal ca. A498 | 0.0 | Thyroid (female) | 0.0 |
| Renal ca. ACHN | 0.0 | Pancreatic ca. CAPAN2 | 0.0 |
| Renal ca. UO-31 | 0.0 | Pancreas Pool | 0.0 |

CNS_neurodegeneration_v1.0 Summary: Ag3915 The CG94356-01 gene is found to be down-regulated in the temporal cortex of Alzheimer's disease patients. Therefore, up-regulation of this gene or its protein product, or treatment with specific agonists of this enzyme may prevent, reduce or reverse the neuronal death, dementia, and memory loss associated with this disease.

General_screening_panel_v1.4 Summary: Ag3915 Highest expression of the CG94356-01 gene is seen in the testis (CT=32.4). Low, but significant levels of expression are also seen in amygdala, thalamus, cortex, cerebellum, and liver. This gene encodes a protein with homology to carboxylesterases, which catalyze the hydrolysis of a variety of compounds containing ester and amide bonds. They may also play an important role in lipid and drug metabolism by hydrolyzing endogenous long-chain fatty acid esters. Thus, expression of the CG94356-01 gene suggests that this gene product may play a similar role in the liver. In addition, the expression in the brain suggests that this gene may also play a role in central nervous system disorders such as Alzheimer's disease, Parkinson's disease, epilepsy, multiple sclerosis, schizophrenia and depression.

Panel 4.1D Summary: Ag3915 Expression of the CG94356-01 gene is low/undetectable in all samples on this panel (CTs>35). (Data not shown.)

BM. CG94421-01: Kelch-BTB Protein

Expression of gene CG94421-01 was assessed using the primer-probe set Ag3961, described in Table BMA. Results of the RTQ-PCR runs are shown in Tables BMB, BMC, BMD and BME.

TABLE BMA

Probe Name Ag3961

| Primers | Sequences | Length | Start Position | SEQ ID NO: |
|---|---|---|---|---|
| Forward | 5'-aatgatgcaagatgctgattgt-3' | 22 | 945 | 453 |
| Probe | TET-5'-cagacttctcgtagatgctatgaactacca-3'-TAMRA | 30 | 969 | 454 |
| Reverse | 5'-tgttttgatgatatggaagcaa-3' | 22 | 1000 | 455 |

TABLE BMB

AI_comprehensive_panel_v1.0

| Tissue Name | Rel. Exp. (%) Ag3961, Run 248079817 | Tissue Name | Rel. Exp. (%) Ag3961, Run 248079817 |
|---|---|---|---|
| 110967 COPD-F | 0.0 | 112427 Match Control Psoriasis-F | 1.2 |
| 110980 COPD-F | 0.0 | 112418 Psoriasis-M | 0.0 |
| 110968 COPD-M | 0.3 | 112723 Match Control Psoriasis-M | 1.7 |
| 110977 COPD-M | 0.2 | 112419 Psoriasis-M | 0.2 |
| 110989 Emphysema-F | 0.7 | 112424 Match Control Psoriasis-M | 0.1 |
| 110992 Emphysema-F | 0.2 | 112420 Psoriasis-M | 0.5 |
| 110993 Emphysema-F | 0.1 | 112425 Match Control Psoriasis-M | 1.5 |
| 110994 Emphysema-F | 0.1 | 104689 (MF) OA Bone-Backus | 0.5 |
| 110995 Emphysema-F | 0.4 | 104690 (MF) Adj "Normal" Bone-Backus | 0.5 |
| 110996 Emphysema-F | 0.3 | 104691 (MF) OA Synovium-Backus | 3.7 |
| 110997 Asthma-M | 0.1 | 104692 (BA) OA Cartilage-Backus | 1.7 |
| 111001 Asthma-F | 1.6 | 104694 (BA) OA Bone-Backus | 0.5 |
| 111002 Asthma-F | 5.1 | 104695 (BA) Adj "Normal" Bone-Backus | 1.0 |
| 111003 Atopic Asthma-F | 1.5 | 104696 (BA) OA Synovium-Backus | 2.6 |
| 111004 Atopic Asthma-F | 4.0 | 104700 (SS) OA Bone-Backus | 0.2 |
| 111005 Atopic Asthma-F | 2.0 | 104701 (SS) Adj "Normal" Bone-Backus | 1.2 |
| 111006 Atopic Asthma-F | 1.2 | 104702 (SS) OA Synovium-Backus | 23.3 |
| 111417 Allergy-M | 2.0 | 117093 OA Cartilage Rep7 | 0.5 |
| 112347 Allergy-M | 0.0 | 112672 OA Bone5 | 0.3 |
| 112349 Normal Lung-F | 0.0 | 112673 OA Synovium5 | 0.0 |
| 112357 Normal Lung-F | 0.6 | 112674 OA Synovial Fluid cells5 | 0.1 |
| 112354 Normal Lung-M | 1.5 | 117100 OA Cartilage Rep14 | 0.1 |
| 112374 Crohns-F | 0.6 | 112756 OA Bone9 | 0.0 |
| 112389 Match Control Crohns-F | 0.4 | 112757 OA Synovium9 | 100.0 |
| 112375 Crohns-F | 0.0 | 112758 OA Synovial Fluid Cells9 | 0.0 |
| 112732 Match Control Crohns-F | 0.5 | 117125 RA Cartilage Rep2 | 0.1 |
| 112725 Crohns-M | 0.0 | 113492 Bone2 RA | 0.5 |
| 112387 Match Control Crohns-M | 0.0 | 113493 Synovium2 RA | 0.3 |
| 112378 Crohns-M | 0.0 | 113494 Syn Fluid Cells RA | 0.1 |
| 112390 Match Control Crohns-M | 2.0 | 113499 Cartilage4 RA | 0.5 |
| 112726 Crohns-M | 0.4 | 113500 Bone4 RA | 0.9 |
| 112731 Match Control Crohns-M | 0.2 | 113501 Synovium4 RA | 0.7 |
| 112380 Ulcer Col-F | 0.6 | 113502 Syn Fluid Cells4 RA | 0.2 |

TABLE BMB-continued

AI_comprehensive_panel_v1.0

| Tissue Name | Rel. Exp. (%) Ag3961, Run 248079817 | Tissue Name | Rel. Exp. (%) Ag3961, Run 248079817 |
|---|---|---|---|
| 112734 Match Control Ulcer Col-F | 5.7 | 113495 Cartilage3 RA | 0.0 |
| 112384 Ulcer Col-F | 0.1 | 113496 Bone3 RA | 0.3 |
| 112737 Match Control Ulcer Col-F | 0.2 | 113497 Synovium3 RA | 0.0 |
| 112386 Ulcer Col-F | 0.0 | 113498 Syn Fluid Cells3 RA | 0.5 |
| 112738 Match Control Ulcer Col-F | 0.2 | 117106 Normal Cartilage Rep20 | 0.3 |
| 112381 Ulcer Col-M | 0.0 | 113663 Bone3 Normal | 0.0 |
| 112735 Match Control Ulcer Col-M | 0.0 | 113664 Synovium3 Normal | 0.0 |
| 112382 Ulcer Col-M | 0.5 | 113665 Syn Fluid Cells3 Normal | 0.0 |
| 112394 Match Control Ulcer Col-M | 0.0 | 117107 Normal Cartilage Rep22 | 0.0 |
| 112383 Ulcer Col-M | 0.5 | 113667 Bone4 Normal | 0.0 |
| 112736 Match Control Ulcer Col-M | 0.0 | 113668 Synovium4 Normal | 0.1 |
| 112423 Psoriasis-F | 0.2 | 113669 Syn Fluid Cells4 Normal | 0.0 |

TABLE BMC

CNS_neurodegeneration_v1.0

| Tissue Name | Rel. Exp. (%) Ag3961, Run 212343353 | Tissue Name | Rel. Exp. (%) Ag3961, Run 212343353 |
|---|---|---|---|
| AD 1 Hippo | 38.7 | Control (Path) 3 Temporal Ctx | 0.0 |
| AD 2 Hippo | 69.3 | Control (Path) 4 Temporal Ctx | 53.2 |
| AD 3 Hippo | 15.6 | AD 1 Occipital Ctx | 20.0 |
| AD 4 Hippo | 19.9 | AD 2 Occipital Ctx (Missing) | 0.0 |
| AD 5 Hippo | 48.3 | AD 3 Occipital Ctx | 19.8 |
| AD 6 Hippo | 68.8 | AD 4 Occipital Ctx | 16.7 |
| Control 2 Hippo | 27.5 | AD 5 Occipital Ctx | 30.6 |
| Control 4 Hippo | 52.1 | AD 6 Occipital Ctx | 30.8 |
| Control (Path) 3 Hippo | 17.8 | Control 1 Occipital Ctx | 0.0 |
| AD 1 Temporal Ctx | 3.8 | Control 2 Occipital Ctx | 32.3 |
| AD 2 Temporal Ctx | 0.0 | Control 3 Occipital Ctx | 20.0 |
| AD 3 Temporal Ctx | 8.3 | Control 4 Occipital Ctx | 33.9 |
| AD 4 Temporal Ctx | 40.3 | Control (Path) 1 Occipital Ctx | 35.1 |
| AD 5 Inf Temporal Ctx | 79.6 | Control (Path) 2 Occipital Ctx | 31.6 |
| AD 5 Sup Temporal Ctx | 100.0 | Control (Path) 3 Occipital Ctx | 0.0 |
| AD 6 Inf Temporal Ctx | 30.1 | Control (Path) 4 Occipital Ctx | 7.5 |
| AD 6 Sup Temporal Ctx | 19.5 | Control 1 Parietal Ctx | 9.6 |
| Control 1 Temporal Ctx | 0.0 | Control 2 Parietal Ctx | 8.2 |
| Control 2 Temporal Ctx | 59.5 | Control 3 Parietal Ctx | 40.9 |
| Control 3 Temporal Ctx | 10.5 | Control (Path) 1 Parietal Ctx | 21.9 |
| Control 3 Temporal Ctx | 30.1 | Control (Path) 2 Parietal Ctx | 0.0 |
| Control (Path) 1 Temporal Ctx | 24.3 | Control (Path) 3 Parietal Ctx | 19.2 |
| Control (Path) 2 Temporal Ctx | 38.2 | Control (Path) 4 Parietal Ctx | 57.4 |

TABLE BMD

General_screening_panel_v1.4

| Tissue Name | Rel. Exp. (%) Ag3961, Run 217332993 | Tissue Name | Rel. Exp. (%) Ag3961, Run 217332993 |
|---|---|---|---|
| Adipose | 9.0 | Renal ca. TK-10 | 0.3 |
| Melanoma* Hs688(A).T | 0.0 | Bladder | 0.2 |
| Melanoma* Hs688(B).T | 0.0 | Gastric ca. (liver met.) NCI-N87 | 0.2 |
| Melanoma* M14 | 0.0 | Gastric ca. KATO III | 0.4 |
| Melanoma* LOXIMVI | 0.0 | Colon ca. SW-948 | 0.0 |
| Melanoma* SK-MEL-5 | 0.1 | Colon ca. SW480 | 0.2 |
| Squamous cell carcinoma SCC-4 | 0.0 | Colon ca.* (SW480 met) SW620 | 0.1 |
| Testis Pool | 0.1 | Colon ca. HT29 | 0.0 |
| Prostate ca.* (bone met) PC-3 | 0.1 | Colon ca. HCT-116 | 0.3 |
| Prostate Pool | 0.7 | Colon ca. CaCo-2 | 0.5 |
| Placenta | 0.6 | Colon cancer tissue | 0.2 |
| Uterus Pool | 0.0 | Colon ca. SW1116 | 0.2 |
| Ovarian ca. OVCAR-3 | 0.1 | Colon ca. Colo-205 | 0.0 |
| Ovarian ca. SK-OV-3 | 0.0 | Colon ca. SW-48 | 0.0 |
| Ovarian ca. OVCAR-4 | 0.0 | Colon Pool | 0.2 |
| Ovarian ca. OVCAR-5 | 0.5 | Small Intestine Pool | 0.1 |
| Ovarian ca. IGROV-1 | 0.1 | Stomach Pool | 0.5 |
| Ovarian ca. OVCAR-8 | 0.3 | Bone Marrow Pool | 0.0 |
| Ovary | 0.1 | Fetal Heart | 20.2 |
| Breast ca. MCF-7 | 0.1 | Heart Pool | 25.3 |
| Breast ca. MDA-MB-231 | 0.0 | Lymph Node Pool | 0.3 |
| Breast ca. BT 549 | 0.0 | Fetal Skeletal Muscle | 24.7 |
| Breast ca. T47D | 0.5 | Skeletal Muscle Pool | 100.0 |
| Breast ca. MDA-N | 0.0 | Spleen Pool | 0.1 |
| Breast Pool | 0.6 | Thymus Pool | 0.6 |
| Trachea | 0.6 | CNS cancer (glio/astro) U87-MG | 0.0 |
| Lung | 0.1 | CNS cancer (glio/astro) U-118-MG | 0.1 |
| Fetal Lung | 0.9 | CNS cancer (neuro; met) SK-N-AS | 0.0 |
| Lung ca. NCI-N417 | 0.0 | CNS cancer (astro) SF-539 | 0.1 |
| Lung ca. LX-1 | 0.3 | CNS cancer (astro) SNB-75 | 0.0 |
| Lung ca. NCI-H146 | 0.0 | CNS cancer (glio) SNB-19 | 0.0 |
| Lung ca. SHP-77 | 0.0 | CNS cancer (glio) SF-295 | 0.4 |
| Lung ca. A549 | 0.1 | Brain (Amygdala) Pool | 0.0 |
| Lung ca. NCI-H526 | 0.0 | Brain (cerebellum) | 0.0 |
| Lung ca. NCI-H23 | 0.0 | Brain (fetal) | 0.1 |
| Lung ca. NCI-H460 | 0.1 | Brain (Hippocampus) Pool | 0.0 |
| Lung ca. HOP-62 | 0.5 | Cerebral Cortex Pool | 0.0 |
| Lung ca. NCI-H522 | 0.1 | Brain (Substantia nigra) Pool | 0.0 |
| Liver | 0.0 | Brain (Thalamus) Pool | 0.1 |
| Fetal Liver | 0.7 | Brain (whole) | 0.0 |
| Liver ca. HepG2 | 0.2 | Spinal Cord Pool | 0.4 |
| Kidney Pool | 0.1 | Adrenal Gland | 1.6 |
| Fetal Kidney | 1.8 | Pituitary gland Pool | 0.0 |
| Renal ca. 786-0 | 0.0 | Salivary Gland | 0.2 |
| Renal ca. A498 | 0.1 | Thyroid (female) | 0.0 |
| Renal ca. ACHN | 0.0 | Pancreatic ca. CAPAN2 | 0.2 |
| Renal ca. UO-31 | 1.1 | Pancreas Pool | 0.4 |

TABLE BME

Panel 4.1D

| Tissue Name | Rel. Exp. (%) Ag3961, Run 170739796 | Tissue Name | Rel. Exp. (%) Ag3961, Run 170739796 |
|---|---|---|---|
| Secondary Th1 act | 0.0 | HUVEC IL-1beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 3.4 |

TABLE BME-continued

Panel 4.1D

| Tissue Name | Rel. Exp. (%) Ag3961, Run 170739796 | Tissue Name | Rel. Exp. (%) Ag3961, Run 170739796 |
|---|---|---|---|
| Primary Th1 act | 3.2 | Lung Microvascular EC TNF alpha + IL-1beta | 0.0 |
| Primary Th2 act | 0.0 | Microvascular Dermal EC none | 0.0 |
| Primary Tr1 act | 0.0 | Microsvasular Dermal EC TNF alpha + IL-1beta | 0.0 |
| Primary Th1 rest | 0.0 | Bronchial epithelium TNF alpha + IL1beta | 37.6 |
| Primary Th2 rest | 3.3 | Small airway epithelium none | 3.5 |
| Primary Tr1 rest | 0.0 | Small airway epithelium TNF alpha + IL-1beta | 25.2 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1beta | 0.0 |
| CD8 lymphocyte act | 0.0 | Astrocytes rest | 7.7 |
| Secondary CD8 lymphocyte rest | 0.0 | Astrocytes TNF alpha + IL-1beta | 0.0 |
| Secondary CD8 lymphocyte act | 0.0 | KU-812 (Basophil) rest | 3.7 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1beta | 0.0 |
| LAK cells IL-2 | 0.0 | Liver cirrhosis | 6.5 |
| LAK cells IL-2 + IL-12 | 0.0 | NCI-H292 none | 6.0 |
| LAK cells IL-2 + IFN gamma | 0.0 | NCI-H292 IL-4 | 2.8 |
| LAK cells IL-2 + IL-18 | 0.0 | NCI-H292 IL-9 | 14.8 |
| LAK cells PMA/ionomycin | 0.0 | NCI-H292 IL-13 | 6.3 |
| NK Cells IL-2 rest | 0.0 | NCI-H292 IFN gamma | 7.5 |
| Two Way MLR 3 day | 0.0 | HPAEC none | 1.7 |
| Two Way MLR 5 day | 0.0 | HPAEC TNF alpha + IL-1beta | 0.0 |
| Two Way MLR 7 day | 0.0 | Lung fibroblast none | 0.0 |
| PBMC rest | 0.0 | Lung fibroblast TNF alpha + IL-1beta | 0.0 |
| PBMC PWM | 0.0 | Lung fibroblast IL-4 | 0.0 |
| PBMC PHA-L | 0.0 | Lung fibroblast IL-9 | 3.4 |
| Ramos (B cell) none | 0.0 | Lung fibroblast IL-13 | 0.0 |
| Ramos (B cell) ionomycin | 0.0 | Lung fibroblast IFN gamma | 0.0 |
| B lymphocytes PWM | 5.2 | Dermal fibroblast CCD1070 rest | 0.0 |
| B lymphocytes CD40L and IL-4 | 3.6 | Dermal fibroblast CCD1070 TNF alpha | 0.0 |
| EOL-1 dbcAMP | 0.0 | Dermal fibroblast CCD1070 IL-1beta | 0.0 |
| EOL-1 dbcAMP PMA/ionomycin | 0.0 | Dermal fibroblast IFN gamma | 0.0 |
| Dendritic cells none | 0.0 | Dermal fibroblast IL-4 | 0.0 |
| Dendritic cells LPS | 0.0 | Dermal Fibroblasts rest | 0.0 |
| Dendritic cells anti-CD40 | 0.0 | Neutrophils TNFa + LPS | 0.0 |
| Monocytes rest | 0.0 | Neutrophils rest | 0.0 |
| Monocytes LPS | 0.0 | Colon | 6.9 |
| Macrophages rest | 0.0 | Lung | 0.0 |
| Macrophages LPS | 0.0 | Thymus | 25.0 |
| HUVEC none | 0.0 | Kidney | 100.0 |
| HUVEC starved | 0.0 | | |

AI_comprehensive panel_v1.0 Summary: Ag3961 Expression of the CG94421-01 gene is highest in the synovium of an osteoarthritis (OA) patient (CT=28.4). Low, but significant levels are also seen in additional OA synovium samples and in asthma. Thus, this gene product may be involved in OA and asthma.

CNS_neurodegeneration_v1.0 Summary: Ag3961 This panel does not show differential expression of the CG94421-01 gene in Alzheimer's disease. However, this expression profile confirms the presence of this gene in the brain. This gene encodes a homolog of Kelch, a family of actin organizing proteins in Drosophila. Thus, this gene product may play a role in organizing the actin cytoskeleton in the brain.

General_screening_panel_v1.4 Summary: Ag3961 Highest expression of the CG94421-01 gene is seen in skeletal muscle (CT=25.3). High levels of expression are also seen in fetal skeletal muscle, heart, and fetal heart tissue. This gene encodes a putative kelch protein, which in Drosophila comprise a family of actin organizing proteins. Overall, this gene appears to be preferentially expressed in normal tissue samples and is expressed at moderate to low levels in other metabolic tissues, including pancreas, adrenal, fetal liver and adipose. Thus, this gene product may play a role in normal neuroendocrine and metabolic and that disregulated expression of this gene may contribute to neuroendocrine disorders or metabolic diseases, such as obesity and diabetes.

Panel 4.1D Summary: Ag3961 Expression of the CG94421-01 gene is highest in the kidney (CT=32.3). Low, but significant expression is also seen in TNF-alpha/IL-1 beta treated small airway and bronchial epithelium and in thymus. This expression is in agreement with the expression seen in Panel AI. Thus, this gene product may be involved in inflammatory conditions of the lung, including asthma.

BN. CG94465-01: Protein Kinase

Expression of gene CG94465-01 was assessed using the primer-probe set Ag3959, described in Table BNA. Results of the RTQ-PCR runs are shown in Tables BNB, BNC, BND and BNE.

TABLE BNA

Probe Name Ag3959

| Primers | Sequences | Length | Start Position | SEQ ID NO: |
|---|---|---|---|---|
| Forward | 5'-ggcaaattgtatgcagtaaagg-3' | 22 | 302 | 456 |
| Probe | TET-5'-aaatatgactcatcaggtccaagctg-3'-TAMRA | 26 | 352 | 457 |
| Reverse | 5'-cttagtgccagtgcatctctct-3' | 22 | 378 | 458 |

TABLE BNB

CNS_neurodegeneration_v1.0

| Tissue Name | Rel. Exp. (%) Ag3959, Run 212347482 | Tissue Name | Rel. Exp. (%) Ag3959, Run 212347482 |
|---|---|---|---|
| AD 1 Hippo | 6.1 | Control (Path) 3 Temporal Ctx | 6.8 |
| AD 2 Hippo | 24.1 | Control (Path) 4 Temporal Ctx | 10.9 |
| AD 3 Hippo | 9.4 | AD 1 Occipital Ctx | 14.9 |
| AD 4 Hippo | 7.3 | AD 2 Occipital Ctx (Missing) | 0.0 |
| AD 5 Hippo | 100.0 | AD 3 Occipital Ctx | 6.3 |
| AD 6 Hippo | 52.5 | AD 4 Occipital Ctx | 14.1 |
| Control 2 Hippo | 33.9 | AD 5 Occipital Ctx | 50.7 |
| Control 4 Hippo | 8.0 | AD 6 Occipital Ctx | 42.9 |
| Control (Path) 3 Hippo | 4.1 | Control 1 Occipital Ctx | 2.1 |
| AD 1 Temporal Ctx | 17.4 | Control 2 Occipital Ctx | 59.0 |
| AD 2 Temporal Ctx | 18.3 | Control 3 Occipital Ctx | 11.9 |
| AD 3 Temporal Ctx | 4.8 | Control 4 Occipital Ctx | 3.1 |
| AD 4 Temporal Ctx | 18.4 | Control (Path) 1 Occipital Ctx | 77.4 |
| AD 5 Inf Temporal Ctx | 66.4 | Control (Path) 2 Occipital Ctx | 0.0 |
| AD 5 Sup Temporal Ctx | 37.1 | Control (Path) 3 Occipital Ctx | 6.0 |
| AD 6 Inf Temporal Ctx | 75.3 | Control (Path) 4 Occipital Ctx | 29.5 |
| AD 6 Sup Temporal Ctx | 77.4 | Control 1 Parietal Ctx | 4.3 |
| Control 1 Temporal Ctx | 4.8 | Control 2 Parietal Ctx | 39.0 |
| Control 2 Temporal Ctx | 40.6 | Control 3 Parietal Ctx | 13.2 |
| Control 3 Temporal Ctx | 9.3 | Control (Path) 1 Parietal Ctx | 58.6 |
| Control 3 Temporal Ctx | 4.1 | Control (Path) 2 Parietal Ctx | 17.7 |
| Control (Path) 1 Temporal Ctx | 55.5 | Control (Path) 3 Parietal Ctx | 4.9 |
| Control (Path) 2 Temporal Ctx | 39.5 | Control (Path) 4 Parietal Ctx | 54.0 |

TABLE BNC

General_screening_panel_v1.4

| Tissue Name | Rel. Exp. (%) Ag3959, Run 222691601 | Tissue Name | Rel. Exp. (%) Ag3959, Run 222691601 |
|---|---|---|---|
| Adipose | 5.9 | Renal ca. TK-10 | 15.8 |
| Melanoma* Hs688(A).T | 4.9 | Bladder | 8.9 |
| Melanoma* Hs688(B).T | 4.4 | Gastric ca. (liver met.) NCI-N87 | 51.8 |
| Melanoma* M14 | 41.8 | Gastric ca. KATO III | 48.0 |
| Melanoma* LOXIMVI | 28.3 | Colon ca. SW-948 | 9.2 |
| Melanoma* SK-MEL-5 | 26.2 | Colon ca. SW480 | 51.8 |
| Squamous cell | 15.5 | Colon ca.* (SW480 met) | 26.2 |

TABLE BNC-continued

General_screening_panel_v1.4

| Tissue Name | Rel. Exp. (%) Ag3959, Run 222691601 | Tissue Name | Rel. Exp. (%) Ag3959, Run 222691601 |
|---|---|---|---|
| carcinoma SCC-4 | | SW620 | |
| Testis Pool | 6.8 | Colon ca. HT29 | 14.8 |
| Prostate ca.* (bone met) PC-3 | 5.3 | Colon ca. HCT-116 | 49.7 |
| Prostate Pool | 2.4 | Colon ca. CaCo-2 | 48.0 |
| Placenta | 3.3 | Colon cancer tissue | 9.2 |
| Uterus Pool | 2.6 | Colon ca. SW1116 | 2.9 |
| Ovarian ca. OVCAR-3 | 52.9 | Colon ca. Colo-205 | 3.9 |
| Ovarian ca. SK-OV-3 | 40.3 | Colon ca. SW-48 | 7.6 |
| Ovarian ca. OVCAR-4 | 44.1 | Colon Pool | 4.5 |
| Ovarian ca. OVCAR-5 | 25.2 | Small Intestine Pool | 3.2 |
| Ovarian ca. IGROV-1 | 9.3 | Stomach Pool | 3.2 |
| Ovarian ca. OVCAR-8 | 3.3 | Bone Marrow Pool | 1.9 |
| Ovary | 3.4 | Fetal Heart | 4.0 |
| Breast ca. MCF-7 | 22.8 | Heart Pool | 1.1 |
| Breast ca. MDA-MB-231 | 75.8 | Lymph Node Pool | 4.8 |
| Breast ca. BT 549 | 100.0 | Fetal Skeletal Muscle | 1.7 |
| Breast ca. T47D | 33.9 | Skeletal Muscle Pool | 1.9 |
| Breast ca. MDA-N | 27.5 | Spleen Pool | 7.7 |
| Breast Pool | 5.1 | Thymus Pool | 9.8 |
| Trachea | 4.5 | CNS cancer (glio/astro) U87-MG | 26.1 |
| Lung | 1.0 | CNS cancer (glio/astro) U-118-MG | 35.6 |
| Fetal Lung | 14.6 | CNS cancer (neuro; met) SK-N-AS | 50.7 |
| Lung ca. NCI-N417 | 10.2 | CNS cancer (astro) SF-539 | 23.8 |
| Lung ca. LX-1 | 39.0 | CNS cancer (astro) SNB-75 | 26.1 |
| Lung ca. NCI-H146 | 11.4 | CNS cancer (glio) SNB-19 | 7.9 |
| Lung ca. SHP-77 | 21.0 | CNS cancer (glio) SF-295 | 10.8 |
| Lung ca. A549 | 48.6 | Brain (Amygdala) Pool | 2.0 |
| Lung ca. NCI-H526 | 5.7 | Brain (cerebellum) | 1.4 |
| Lung ca. NCI-H23 | 29.7 | Brain (fetal) | 4.8 |
| Lung ca. NCI-H460 | 3.5 | Brain (Hippocampus) Pool | 2.1 |
| Lung ca. HOP-62 | 5.7 | Cerebral Cortex Pool | 3.1 |
| Lung ca. NCI-H522 | 28.9 | Brain (Substantia nigra) Pool | 1.9 |
| Liver | 0.2 | Brain (Thalamus) Pool | 3.7 |
| Fetal Liver | 14.0 | Brain (whole) | 2.5 |
| Liver ca. HepG2 | 8.6 | Spinal Cord Pool | 1.8 |
| Kidney Pool | 6.8 | Adrenal Gland | 3.8 |
| Fetal Kidney | 8.1 | Pituitary gland Pool | 2.7 |
| Renal ca. 786-0 | 40.3 | Salivary Gland | 1.1 |
| Renal ca. A498 | 8.2 | Thyroid (female) | 1.0 |
| Renal ca. ACHN | 7.0 | Pancreatic ca. CAPAN2 | 46.7 |
| Renal ca. UO-31 | 24.5 | Pancreas Pool | 6.0 |

TABLE BND

Panel 4.1D

| Tissue Name | Rel. Exp. (%) Ag3959, Run 170739792 | Rel. Exp. (%) Ag3959, Run 198383573 | Tissue Name | Rel. Exp. (%) Ag3959, Run 170739792 | Rel. Exp. (%) Ag3959, Run 198383573 |
|---|---|---|---|---|---|
| Secondary Th1 act | 63.7 | 56.3 | HUVEC IL-1beta | 14.3 | 16.6 |
| Secondary Th2 act | 100.0 | 100.0 | HUVEC IFN gamma | 13.5 | 11.1 |
| Secondary Tr1 act | 40.3 | 39.0 | HUVEC TNF alpha + IFN gamma | 14.2 | 16.0 |
| Secondary Th1 rest | 4.6 | 4.2 | HUVEC TNF alpha + IL4 | 9.9 | 10.4 |
| Secondary Th2 rest | 4.9 | 4.4 | HUVEC IL-11 | 7.2 | 6.9 |
| Secondary Tr1 rest | 6.2 | 5.6 | Lung Microvascular EC none | 11.3 | 11.5 |
| Primary Th1 act | 16.4 | 17.8 | Lung Microvascular EC TNF alpha + IL-1beta | 5.5 | 7.0 |
| Primary Th2 act | 28.1 | 28.9 | Microvascular Dermal EC none | 10.6 | 13.2 |

TABLE BND-continued

Panel 4.1D

| Tissue Name | Rel. Exp. (%) Ag3959, Run 170739792 | Rel. Exp. (%) Ag3959, Run 198383573 | Tissue Name | Rel. Exp. (%) Ag3959, Run 170739792 | Rel. Exp. (%) Ag3959, Run 198383573 |
|---|---|---|---|---|---|
| Primary Tr1 act | 27.4 | 31.6 | Microvascular Dermal EC TNF alpha + IL-1beta | 8.8 | 7.9 |
| Primary Th1 rest | 7.4 | 9.6 | Bronchial epithelium TNF alpha + IL1beta | 4.7 | 4.0 |
| Primary Th2 rest | 3.2 | 5.3 | Small airway epithelium none | 1.7 | 1.9 |
| Primary Tr1 rest | 7.9 | 10.0 | Small airway epithelium TNF alpha + IL-1beta | 5.1 | 7.0 |
| CD45RA CD4 lymphocyte act | 42.3 | 41.5 | Coronery artery SMC rest | 4.8 | 3.3 |
| CD45RO CD4 lymphocyte act | 71.2 | 64.6 | Coronery artery SMC TNF alpha + IL-1beta | 7.1 | 4.8 |
| CD8 lymphocyte act | 40.9 | 40.9 | Astrocytes rest | 2.1 | 2.7 |
| Secondary CD8 lymphocyte rest | 47.0 | 43.2 | Astrocytes TNF alpha + IL-1beta | 2.2 | 3.3 |
| Secondary CD8 lymphocyte act | 21.3 | 17.3 | KU-812 (Basophil) rest | 9.5 | 9.5 |
| CD4 lymphocyte none | 4.0 | 3.6 | KU-812 (Basophil) PMA/ionomycin | 21.6 | 21.8 |
| 2ry Th1/Th2/Tr1_anti-CD95 CH11 | 13.5 | 13.5 | CCD1106 (Keratinocytes) none | 29.7 | 29.7 |
| LAK cells rest | 12.1 | 13.5 | CCD1106 (Keratinocytes) TNF alpha + IL-1beta | 27.0 | 20.3 |
| LAK cells IL-2 | 27.4 | 30.4 | Liver cirrhosis | 3.2 | 2.1 |
| LAK cells IL-2 + IL-12 | 14.5 | 17.9 | NCI-H292 none | 17.4 | 14.8 |
| LAK cells IL-2 + IFN gamma | 17.7 | 20.0 | NCI-H292 IL-4 | 32.5 | 37.4 |
| LAK cells IL-2 + IL-18 | 54.7 | 23.3 | NCI-H292 IL-9 | 36.3 | 44.8 |
| LAK cells PMA/ionomycin | 28.1 | 30.1 | NCI-H292 IL-13 | 37.4 | 47.0 |
| NK Cells IL-2 rest | 46.7 | 46.3 | NCI-H292 IFN gamma | 32.3 | 32.8 |
| Two Way MLR 3 day | 11.0 | 13.9 | HPAEC none | 4.6 | 6.8 |
| Two Way MLR 5 day | 17.6 | 17.1 | HPAEC TNF alpha + IL-1beta | 13.7 | 13.4 |
| Two Way MLR 7 day | 15.5 | 17.3 | Lung fibroblast none | 5.9 | 4.5 |
| PBMC rest | 4.0 | 4.4 | Lung fibroblast TNF alpha + IL-1beta | 12.6 | 11.1 |
| PBMC PWM | 26.6 | 20.0 | Lung fibroblast IL-4 | 1.7 | 3.1 |
| PBMC PHA-L | 25.3 | 32.3 | Lung fibroblast IL-9 | 6.9 | 6.6 |
| Ramos (B cell) none | 24.3 | 22.4 | Lung fibroblast IL-13 | 3.0 | 3.8 |
| Ramos (B cell) ionomycin | 26.1 | 26.4 | Lung fibroblast IFN gamma | 4.0 | 3.5 |
| B lymphocytes PWM | 36.6 | 31.0 | Dermal fibroblast CCD1070 rest | 25.2 | 24.8 |
| B lymphocytes CD40L and IL-4 | 20.0 | 24.0 | Dermal fibroblast CCD1070 TNF alpha | 41.8 | 52.1 |
| EOL-1 dbcAMP | 23.8 | 14.6 | Dermal fibroblast CCD1070 IL-1beta | 23.8 | 31.2 |
| EOL-1 dbcAMP PMA/ionomycin | 24.8 | 27.7 | Dermal fibroblast IFN gamma | 13.3 | 18.0 |
| Dendritic cells none | 7.1 | 8.9 | Dermal fibroblast IL-4 | 16.4 | 18.0 |
| Dendritic cells LPS | 14.9 | 18.7 | Dermal Fibroblasts rest | 7.0 | 7.9 |
| Dendritic cells anti-CD40 | 6.5 | 5.4 | Neutrophils TNFa + LPS | 2.7 | 2.4 |
| Monocytes rest | 6.7 | 5.4 | Neutrophils rest | 3.4 | 4.2 |
| Monocytes LPS | 21.5 | 26.6 | Colon | 1.8 | 1.7 |
| Macrophages rest | 8.3 | 8.8 | Lung | 4.3 | 3.5 |
| Macrophages LPS | 20.7 | 23.3 | Thymus | 19.2 | 20.4 |
| HUVEC none | 13.5 | 13.7 | Kidney | 6.6 | 4.6 |
| HUVEC starved | 15.7 | 17.7 | | | |

TABLE BNE

Panel 5 Islet

| Tissue Name | Rel. Exp. (%) Ag3959, Run 229431860 | Tissue Name | Rel. Exp. (%) Ag3959, Run 229431860 |
|---|---|---|---|
| 97457_Patient-02go_adipose | 14.5 | 94709_Donor 2 AM - A_adipose | 29.1 |
| 97476_Patient-07sk_skeletal muscle | 10.8 | 94710_Donor 2 AM - B_adipose | 19.2 |
| 97477_Patient-07ut_uterus | 7.1 | 94711_Donor 2 AM - C_adipose | 7.7 |
| 97478_Patient-07pl_placenta | 14.0 | 94712_Donor 2 AD - A_adipose | 17.1 |
| 99167_Bayer Patient 1 | 22.1 | 94713_Donor 2 AD - B_adipose | 25.7 |
| 97482_Patient-08ut_uterus | 9.6 | 94714_Donor 2 AD - C_adipose | 17.9 |
| 97483_Patient-08pl_placenta | 33.0 | 94742_Donor 3 U - A_Mesenchymal Stem Cells | 2.8 |
| 97486_Patient-09sk_skeletal muscle | 0.8 | 94743_Donor 3 U - B_Mesenchymal Stem Cells | 13.0 |
| 97487_Patient-09ut_uterus | 14.7 | 94730_Donor 3 AM - A_adipose | 22.7 |
| 97488_Patient-09pl_placenta | 13.2 | 94731_Donor 3 AM - B_adipose | 27.4 |
| 97492_Patient-10ut_uterus | 13.9 | 94732_Donor 3 AM - C_adipose | 24.1 |
| 97493_Patient-10pl_placenta | 46.3 | 94733_Donor 3 AD - A_adipose | 24.7 |
| 97495_Patient-11go_adipose | 13.3 | 94734_Donor 3 AD - B_adipose | 8.7 |
| 97496_Patient-11sk_skeletal muscle | 1.6 | 94735_Donor 3 AD - C_adipose | 15.4 |
| 97497_Patient-11ut_uterus | 11.7 | 77138_Liver_HepG2untreated | 90.1 |
| 97498_Patient-11pl_placenta | 23.5 | 73556_Heart_Cardiac stromal cells (primary) | 12.9 |
| 97500_Patient-12go_adipose | 20.2 | 81735_Small Intestine | 20.7 |
| 97501_Patient-12sk_skeletal muscle | 11.0 | 72409_Kidney_Proximal Convoluted Tubule | 18.8 |
| 97502_Patient-12ut_uterus | 26.4 | 82685_Small intestine_Duodenum | 24.7 |
| 97503_Patient-12pl_placenta | 19.1 | 90650_Adrenal_Adrenocortical adenoma | 6.1 |
| 94721_Donor 2 U - A_Mesenchymal Stem Cells | 11.3 | 72410_Kidney_HRCE | 62.4 |
| 94722_Donor 2 U - B_Mesenchymal Stem Cells | 8.9 | 72411_Kidney_HRE | 100.0 |
| 94723_Donor 2 U - C_Mesenchymal Stem Cells | 4.3 | 73139_Uterus_Uterine smooth muscle cells | 22.8 |

CNS_neurodegeneration_v1.0 Summary: Ag3959 This panel confirms the expression of the CG94465-01 gene at low levels in the brains of an independent group of individuals. However, no differential expression of this gene was detected between Alzheimer's diseased postmortem brains and those of non-demented controls in this experiment. Please see Panel 1.4 for a discussion of the potential utility of this gene in treatment of central nervous system disorders.

General_screening_panel_v1.4 Summary: Ag3959 Highest expression of the CG94465-01 gene is detected in a breast cancer BT 549 cell line (CT=27.3). In addition, high expression of this gene is associated with a number of cancer cell lines (pancreatic, CNS, colon, lung, gastric, renal, breast, ovarian, prostate, squamous cell carcinoma, and melanoma). Therefore, therapeutic modulation of the activity of this gene may prove useful in the treatment of these cancers.

Among tissues with metabolic or endocrine function, this gene is expressed at high to moderate levels in pancreas, adipose, adrenal gland, thyroid, pituitary gland, skeletal muscle, heart, liver and the gastrointestinal tract. Therefore, therapeutic modulation of the activity of this gene may prove useful in the treatment of endocrine/metabolically related diseases, such as obesity and diabetes.

In addition, this gene is expressed at high levels in all regions of the central nervous system examined, including amygdala, hippocampus, substantia nigra, thalamus, cerebellum, cerebral cortex, and spinal cord. Therefore, this gene may play a role in central nervous system disorders such as Alzheimer's disease, Parkinson's disease, epilepsy, multiple sclerosis, schizophrenia and depression.

Panel 4.1D Summary: Ag3959 Two experiments with same primer and probe set are in excellent agreements with highest expression of the CG94465-01 gene in activated secondary Th2 cells (CTs=28). Expression of this gene is stimulated in activated secondary Th1 and Th2 cells (CTs=28–29) as compared to the resting cells (33). High expression of this gene is also detected in activated CD45RA CD4 lymphocyte and CD45RO CD4 lymphocyte. This expression pattern suggests that this gene may be important in T cell activation, polarization and proliferation. Thus, therapeutic regulation of the transcript or the protein encoded by this gene could be important in immune modulation and in the treatment of T cell-mediated diseases such as asthma, arthritis, psoriasis, IBD, and lupus.

In addition, this gene is expressed at low to moderate levels in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. This ubiquitous pattern of expression suggests that this gene product may be involved in homeostatic processes for these and other cell types and tissues. This pattern is in agreement with the expression profile in General_screening_panel_v1.4 and also suggests a role for the gene product in cell survival and proliferation. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

Panel 5 Islet Summary: Ag3959 Highest expression of the CG94465-01 gene is detected in 72411_kidney_HRE sample (CT=31). In addition, expression of this gene is ubiquitous throughout the samples used in this panel. Please see Panel 1.4 for a discussion of the potential utility of this gene in metabolic disorders.

BO. CG94511-01: Pyruvate Dehydrogenase

Expression of gene CG94511-01 was assessed using the primer-probe set Ag3922, described in Table BOA. Results of the RTQ-PCR runs are shown in Tables BOB, BOC and BOD.

TABLE BOA

| Probe Name Ag3922 | | | | |
|---|---|---|---|---|
| Primers | Sequences | Length | Start Position | SEQ ID NO: |
| Forward | 5'-ggctctggctttagctttactc-3' | 22 | 374 | 459 |
| Probe | TET-5'-tgaactttctgtcccagaaattcttg-3'-TAMRA | 26 | 397 | 460 |
| Reverse | 5'-ttagcacaacctcctctttgtc-3' | 22 | 435 | 461 |

TABLE BOB

| CNS_neurodegeneration_v1.0 | | | |
|---|---|---|---|
| Tissue Name | Rel. Exp. (%) Ag3922, Run 212343349 | Tissue Name | Rel. Exp. (%) Ag3922, Run 212343349 |
| AD 1 Hippo | 7.0 | Control (Path) 3 Temporal Ctx | 7.7 |
| AD 2 Hippo | 11.4 | Control (Path) 4 Temporal Ctx | 22.2 |
| AD 3 Hippo | 10.7 | AD 1 Occipital Ctx | 12.2 |
| AD 4 Hippo | 11.5 | AD 2 Occipital Ctx (Missing) | 0.0 |
| AD 5 Hippo | 100.0 | AD 3 Occipital Ctx | 5.3 |
| AD 6 Hippo | 66.0 | AD 4 Occipital Ctx | 9.7 |
| Control 2 Hippo | 25.7 | AD 5 Occipital Ctx | 20.4 |
| Control 4 Hippo | 5.1 | AD 6 Occipital Ctx | 20.3 |
| Control (Path) 3 Hippo | 9.9 | Control 1 Occipital Ctx | 10.9 |
| AD 1 Temporal Ctx | 26.8 | Control 2 Occipital Ctx | 25.5 |
| AD 2 Temporal Ctx | 19.1 | Control 3 Occipital Ctx | 11.7 |
| AD 3 Temporal Ctx | 7.0 | Control 4 Occipital Ctx | 2.0 |
| AD 4 Temporal Ctx | 34.6 | Control (Path) 1 Occipital Ctx | 65.5 |
| AD 5 Inf Temporal Ctx | 70.2 | Control (Path) 2 Occipital Ctx | 9.3 |
| AD 5 SupTemporal Ctx | 68.8 | Control (Path) 3 Occipital Ctx | 1.2 |
| AD 6 Inf Temporal Ctx | 42.6 | Control (Path) 4 Occipital Ctx | 21.6 |
| AD 6 Sup Temporal Ctx | 49.0 | Control 1 Parietal Ctx | 2.6 |
| Control 1 Temporal Ctx | 8.5 | Control 2 Parietal Ctx | 61.1 |
| Control 2 Temporal Ctx | 12.3 | Control 3 Parietal Ctx | 2.9 |
| Control 3 Temporal Ctx | 10.2 | Control (Path) 1 Parietal Ctx | 38.7 |
| Control 3 Temporal Ctx | 4.9 | Control (Path) 2 Parietal Ctx | 17.8 |
| Control (Path) 1 Temporal Ctx | 57.4 | Control (Path) 3 Parietal Ctx | 3.8 |
| Control (Path) 2 Temporal Ctx | 23.7 | Control (Path) 4 Parietal Ctx | 39.2 |

TABLE BOC

| General_screening_panel_v1.4 | | | |
|---|---|---|---|
| Tissue Name | Rel. Exp. (%) Ag3922, Run 219515088 | Tissue Name | Rel. Exp. (%) Ag3922, Run 219515088 |
| Adipose | 0.2 | Renal ca. TK-10 | 0.4 |
| Melanoma* Hs688(A).T | 0.1 | Bladder | 1.1 |
| Melanoma* Hs688(B).T | 0.2 | Gastric ca. (liver met.) NCI-N87 | 1.1 |

TABLE BOC-continued

General_screening_panel_v1.4

| Tissue Name | Rel. Exp. (%) Ag3922, Run 219515088 | Tissue Name | Rel. Exp. (%) Ag3922, Run 219515088 |
|---|---|---|---|
| Melanoma* M14 | 0.2 | Gastric ca. KATO III | 0.8 |
| Melanoma* LOXIMVI | 0.3 | Colon ca. SW-948 | 0.1 |
| Melanoma* SK-MEL-5 | 0.6 | Colon ca. SW480 | 100.0 |
| Squamous cell carcinoma SCC-4 | 0.2 | Colon ca.* (SW480 met) SW620 | 0.8 |
| Testis Pool | 0.3 | Colon ca. HT29 | 0.6 |
| Prostate ca.* (bone met) PC-3 | 1.1 | Colon ca. HCT-116 | 1.4 |
| Prostate Pool | 0.3 | Colon ca. CaCo-2 | 2.0 |
| Placenta | 0.1 | Colon cancer tissue | 0.4 |
| Uterus Pool | 0.1 | Colon ca. SW1116 | 0.1 |
| Ovarian ca. OVCAR-3 | 0.6 | Colon ca. Colo-205 | 0.0 |
| Ovarian ca. SK-OV-3 | 1.5 | Colon ca. SW-48 | 0.1 |
| Ovarian ca. OVCAR-4 | 0.2 | Colon Pool | 1.0 |
| Ovarian ca. OVCAR-5 | 1.4 | Small Intestine Pool | 1.1 |
| Ovarian ca. IGROV-1 | 0.3 | Stomach Pool | 0.6 |
| Ovarian ca. OVCAR-8 | 0.1 | Bone Marrow Pool | 0.4 |
| Ovary | 0.5 | Fetal Heart | 0.9 |
| Breast ca. MCF-7 | 0.3 | Heart Pool | 0.4 |
| Breast ca. MDA-MB-231 | 1.9 | Lymph Node Pool | 1.2 |
| Breast ca. BT 549 | 0.6 | Fetal Skeletal Muscle | 0.5 |
| Breast ca. T47D | 0.9 | Skeletal Muscle Pool | 1.3 |
| Breast ca. MDA-N | 0.3 | Spleen Pool | 24.3 |
| Breast Pool | 1.1 | Thymus Pool | 1.0 |
| Trachea | 1.4 | CNS cancer (glio/astro) U87-MG | 0.6 |
| Lung | 0.3 | CNS cancer (glio/astro) U-118-MG | 1.5 |
| Fetal Lung | 2.4 | CNS cancer (neuro; met) SK-N-AS | 0.5 |
| Lung ca. NCI-N417 | 0.1 | CNS cancer (astro) SF-539 | 0.2 |
| Lung ca. LX-1 | 0.3 | CNS cancer (astro) SNB-75 | 1.4 |
| Lung ca. NCI-H146 | 0.0 | CNS cancer (glio) SNB-19 | 0.2 |
| Lung ca. SHP-77 | 0.4 | CNS cancer (glio) SF-295 | 80.7 |
| Lung ca. A549 | 0.5 | Brain (Amygdala) Pool | 0.2 |
| Lung ca. NCI-H526 | 0.1 | Brain (cerebellum) | 0.4 |
| Lung ca. NCI-H23 | 0.9 | Brain (fetal) | 0.7 |
| Lung ca. NCI-H460 | 0.6 | Brain (Hippocampus) Pool | 0.3 |
| Lung ca. HOP-62 | 0.7 | Cerebral Cortex Pool | 0.3 |
| Lung ca. NCI-H522 | 0.9 | Brain (Substantia nigra) Pool | 0.1 |
| Liver | 0.0 | Brain (Thalamus) Pool | 0.5 |
| Fetal Liver | 0.3 | Brain (whole) | 0.2 |
| Liver ca. HepG2 | 0.6 | Spinal Cord Pool | 0.3 |
| Kidney Pool | 1.4 | Adrenal Gland | 1.0 |
| Fetal Kidney | 1.2 | Pituitary gland Pool | 0.1 |
| Renal ca. 786-0 | 0.7 | Salivary Gland | 0.1 |
| Renal ca. A498 | 0.1 | Thyroid (female) | 0.1 |
| Renal ca. ACHN | 0.0 | Pancreatic ca. CAPAN2 | 1.8 |
| Renal ca. UO-31 | 0.3 | Pancreas Pool | 1.3 |

TABLE BOD

Panel 4.1D

| Tissue Name | Rel. Exp. (%) Ag3922, Run 170552340 | Tissue Name | Rel. Exp. (%) Ag3922, Run 170552340 |
|---|---|---|---|
| Secondary Th1 act | 37.9 | HUVEC IL-1 beta | 8.2 |
| Secondary Th2 act | 49.7 | HUVEC IFN gamma | 14.9 |
| Secondary Tr1 act | 34.6 | HUVEC TNF alpha + IFN gamma | 8.0 |
| Secondary Th1 rest | 14.6 | HUVEC TNF alpha + IL4 | 9.2 |
| Secondary Th2 rest | 21.2 | HUVEC IL-11 | 6.9 |
| Secondary Tr1 rest | 19.9 | Lung Microvascular EC none | 14.4 |
| Primary Th1 act | 33.0 | Lung Microvascular EC TNF alpha + IL-1 beta | 20.3 |
| Primary Th2 act | 58.2 | Microvascular Dermal EC none | 9.5 |
| Primary Tr1 act | 35.4 | Microvasular Dermal EC TNF alpha + IL-1 beta | 3.1 |

TABLE BOD-continued

Panel 4.1D

| Tissue Name | Rel. Exp. (%) Ag3922, Run 170552340 | Tissue Name | Rel. Exp. (%) Ag3922, Run 170552340 |
|---|---|---|---|
| Primary Th1 rest | 9.5 | Bronchial epithelium TNF alpha + IL1 beta | 11.3 |
| Primary Th2 rest | 7.2 | Small airway epithelium none | 4.1 |
| Primary Tr1 rest | 31.0 | Small airway epithelium TNF alpha + IL-1 beta | 17.0 |
| CD45RA CD4 lymphocyte act | 19.2 | Coronery artery SMC rest | 4.9 |
| CD45RO CD4 lymphocyte act | 26.6 | Coronery artery SMC TNF alpha + IL-1 beta | 1.8 |
| CD8 lymphocyte act | 29.1 | Astrocytes rest | 14.0 |
| Secondary CD8 lymphocyte rest | 30.6 | Astrocytes TNF alpha + IL-1 beta | 6.8 |
| Secondary CD8 lymphocyte act | 18.6 | KU-812 (Basophil) rest | 4.9 |
| CD4 lymphocyte none | 16.6 | KU-812 (Basophil) PMA/ionomycin | 19.8 |
| 2ry Th1/Th2/Tr1_anti-CD95 CH11 | 31.4 | CCD1106 (Keratinocytes) none | 17.4 |
| LAK cells rest | 11.7 | CCD1106 (Keratinocytes) TNF alpha + IL-1 beta | 26.8 |
| LAK cells IL-2 | 33.4 | Liver cirrhosis | 2.8 |
| LAK cells IL-2 + IL-12 | 14.9 | NCI-H292 none | 15.2 |
| LAK cells IL-2 + IFN gamma | 14.0 | NCI-H292 IL-4 | 14.4 |
| LAK cells IL-2 + IL-18 | 19.1 | NCI-H292 IL-9 | 16.3 |
| LAK cells PMA/ionomycin | 15.2 | NCI-H292 IL-13 | 15.2 |
| NK Cells IL-2 rest | 23.3 | NCI-H292 IFN gamma | 18.3 |
| Two Way MLR 3 day | 28.3 | HPAEC none | 7.1 |
| Two Way MLR 5 day | 17.4 | HPAEC TNF alpha + IL-1 beta | 17.7 |
| Two Way MLR 7 day | 17.2 | Lung fibroblast none | 12.2 |
| PBMC rest | 8.0 | Lung fibroblast TNF alpha + IL-1 beta | 5.8 |
| PBMC PWM | 24.0 | Lung fibroblast IL-4 | 3.5 |
| PBMC PHA-L | 17.8 | Lung fibroblast IL-9 | 15.5 |
| Ramos (B cell) none | 23.7 | Lung fibroblast IL-13 | 7.4 |
| Ramos (B cell) ionomycin | 17.3 | Lung fibroblast IFN gamma | 15.4 |
| B lymphocytes PWM | 10.7 | Dermal fibroblast CCD1070 rest | 17.8 |
| B lymphocytes CD40L and IL-4 | 18.9 | Dermal fibroblast CCD1070 TNF alpha | 37.4 |
| EOL-1 dbcAMP | 15.4 | Dermal fibroblast CCD1070 IL-1 beta | 9.5 |
| EOL-1 dbcAMP PMA/ionomycin | 15.8 | Dermal fibroblast IFN gamma | 12.0 |
| Dendritic cells none | 14.8 | Dermal fibroblast IL-4 | 16.3 |
| Dendritic cells LPS | 12.3 | Dermal Fibroblasts rest | 2.5 |
| Dendritic cells anti-CD40 | 15.0 | Neutrophils TNFa + LPS | 8.5 |
| Monocytes rest | 33.9 | Neutrophils rest | 31.9 |
| Monocytes LPS | 40.1 | Colon | 7.0 |
| Macrophages rest | 11.5 | Lung | 24.5 |
| Macrophages LPS | 5.0 | Thymus | 58.6 |
| HUVEC none | 4.0 | Kidney | 100.0 |
| HUVEC starved | 13.6 | | |

CNS_neurodegeneration_v1.0 Summary: Ag3922 The CG94511-01 gene is found to be upregulated in the temporal cortex of Alzheimer's disease patients. Pyruvate dehydrogenase, which is a homolog of this gene product, plays a critical role in supplying the brain with glucose. The activity of pyruvate dehydrogenase may be affected in the Alzheimer's brain. Therefore, blockade of this enzyme may decrease neuronal death and be of use in the treatment of this disease. Impairment of the function of pyruvate dehydrogenase is associated with neurological deficits, neurodegeneration, and Parkinson's disease. Therefore, therapeutic modulation of this gene or gene product may therefore be of use in the treatment of these disorders (Bindoff L A, Birch-Machin M A, Farnsworth L, Gardner-Medwin D, Lindsay J G, Turnbull D M. Familial intermittent ataxia due to a defect of the E1 component of pyruvate dehydrogenase complex. J Neurol Sci 1989 November;93 (2–3):311–8; Li H, Dryhurst G. Oxidative metabolites of 5-S-cysteinyldopamine inhibit the pyruvate dehydrogenase complex. J Neural Transm 2001;108(12):1363–74; Casley C S, Canevari L, Land J M, Clark J B, Sharpe M A. Beta-amyloid inhibits integrated mitochondrial respiration and key enzyme activities. J Neurochem 2002 January;80(1):91–100; Krugel U, Bigl V, Eschrich K, Bigl M. Deafferentation of the septo-hippocampal pathway in rats as a model of the metabolic events in Alzheimer's disease. Int J Dev Neurosci 2001 June;19(3):263–77).

General_screening_13 panel_v1.4 Summary: Ag3922 The CG94511-01 gene is most highly expressed in a colon cancer cell line (CT=27). Thus, expression of this gene could be used to differentiate between this sample and other samples on this panel and as a marker to detect the presence of colon cancer. Furthermore, therapeutic modulation of the expression or function of this gene may be effective in the treatment of colon cancer.

Among tissues with metabolic function, this gene is expressed at moderate to low levels in adrenal gland, pancreas, fetal heart and adult and fetal skeletal muscle. This expression suggests that this gene product may play a role in normal neuroendocrine and metabolic and that disregulated expression of this gene may contribute to neuroendocrine disorders or metabolic diseases, such as obesity and diabetes.

Panel 4.1D Summary: Ag3922 The CG94511-01 gene is most highly expressed in the kidney (CT=31.6). In addition, this gene appears to be slightly upregulated in activated T cells when compared to expression in resting T cells. Thus, therapeutic regulation of the transcript or the protein encoded by the transcript could be important in immune modulation and in the treatment of T cell-mediated diseases such as asthma, arthritis, psoriasis, IBD, and lupus. In addition, this gene is expressed in many samples involved in the immune response, including B cells, LAK cells, macrophages, monocytes, dendritic cells and keratinocytes. This widespread expression among cells involved in immune function suggests that this gene product may be involved in homeostatic processes for these and other cell types and tissues. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

BP. CG94551-01: MUNC13-3

Expression of gene CG94551-01 was assessed using the primer-probe set Ag3925, described in Table BPA. Results of the RTQ-PCR runs are shown in Tables BPB, BPC, BPD and BPE.

TABLE BPA

Probe Name Ag3925

| Primers | Sequences | Length | Start Position | SEQ ID NO: |
|---|---|---|---|---|
| Forward | 5'-tctggagaccggagtcattac-3' | 21 | 1957 | 462 |
| probe | TET-5'-tctttacatgaggatctttctccatgg-3'-TAMRA | 27 | 1993 | 463 |
| Reverse | 5'-agctccttgattccattcctt-3' | 21 | 2020 | 464 |

TABLE BPB

CNS_neurodegeneration_v1.0

| Tissue Name | Rel. Exp. (%) Ag3925, Run 212344915 | Tissue Name | Rel. Exp. (%) Ag3925, Run 212344915 |
|---|---|---|---|
| AD 1 Hippo | 3.5 | Control (Path) 3 Temporal Ctx | 1.4 |
| AD 2 Hippo | 4.2 | Control (Path) 4 Temporal Ctx | 25.7 |
| AD 3 Hippo | 0.8 | AD 1 Occipital Ctx | 5.1 |
| AD 4 Hippo | 1.4 | AD 2 Occipital Ctx (Missing) | 0.0 |
| AD 5 Hippo | 100.0 | AD 3 Occipital Ctx | 2.6 |
| AD 6 Hippo | 12.5 | AD 4 Occipital Ctx | 10.7 |
| Control 2 Hippo | 13.0 | AD 5 Occipital Ctx | 22.4 |
| Control 4 Hippo | 3.1 | AD 6 Occipital Ctx | 24.1 |
| Control (Path) 3 Hippo | 1.2 | Control 1 Occipital Ctx | 1.2 |
| AD 1 Temporal Ctx | 4.7 | Control 2 Occipital Ctx | 50.3 |
| AD 2 Temporal Ctx | 12.1 | Control 3 Occipital Ctx | 6.9 |
| AD 3 Temporal Ctx | 1.3 | Control 4 Occipital Ctx | 1.9 |
| AD 4 Temporal Ctx | 8.1 | Control (Path) 1 Occipital Ctx | 48.3 |
| AD 5 Inf Temporal Ctx | 50.3 | Control (Path) 2 Occipital Ctx | 9.3 |
| AD 5 Sup Temporal Ctx | 16.3 | Control (Path) 3 Occipital Ctx | 0.9 |
| AD 6 Inf Temporal Ctx | 23.2 | Control (Path) 4 Occipital Ctx | 11.4 |
| AD 6 Sup Temporal Ctx | 24.3 | Control 1 Parietal Ctx | 3.5 |
| Control 1 Temporal Ctx | 2.3 | Control 2 Parietal Ctx | 11.7 |
| Control 2 Temporal Ctx | 15.5 | Control 3 Parietal Ctx | 8.1 |
| Control 3 Temporal Ctx | 8.1 | Control (Path) 1 Parietal Ctx | 42.9 |
| Control 3 Temporal Ctx | 2.2 | Control (Path) 2 Parietal Ctx | 18.6 |
| Control (Path) 1 Temporal Ctx | 31.6 | Control (Path) 3 Parietal Ctx | 1.8 |
| Control (Path) 2 Temporal Ctx | 22.4 | Control (Path) 4 Parietal Ctx | 45.4 |

TABLE BPC

General_screening_panel_v1.4

| Tissue Name | Rel. Exp. (%) Ag3925, Run 219515275 | Tissue Name | Rel. Exp. (%) Ag3925, Run 219515275 |
|---|---|---|---|
| Adipose | 0.6 | Renal ca. TK-10 | 0.0 |
| Melanoma* Hs688(A).T | 0.1 | Bladder | 0.2 |
| Melanoma* Hs688(B).T | 0.0 | Gastric ca. (liver met.) NCI-N87 | 0.0 |
| Melanoma* M14 | 0.0 | Gastric ca. KATO III | 0.0 |
| Melanoma* LOXIMVI | 1.3 | Colon ca. SW-948 | 0.0 |
| Melanoma* SK-MEL-5 | 0.0 | Colon ca. SW480 | 0.0 |
| Squamous cell carcinoma SCC-4 | 0.0 | Colon ca.* (SW480 met) SW620 | 0.0 |
| Testis Pool | 0.7 | Colon ca. HT29 | 0.1 |
| Prostate ca.* (bone met) PC-3 | 0.0 | Colon ca. HCT-116 | 0.0 |
| Prostate Pool | 0.4 | Colon ca. CaCo-2 | 14.3 |
| Placenta | 0.0 | Colon cancer tissue | 0.0 |
| Uterus Pool | 0.2 | Colon ca. SW1116 | 0.0 |
| Ovarian ca. OVCAR-3 | 0.0 | Colon ca. Colo-205 | 0.0 |
| Ovarian ca. SK-OV-3 | 0.2 | Colon ca. SW-48 | 0.0 |
| Ovarian ca. OVCAR-4 | 0.0 | Colon Pool | 0.0 |
| Ovarian ca. OVCAR-5 | 0.0 | Small Intestine Pool | 3.0 |
| Ovarian ca. IGROV-1 | 0.1 | Stomach Pool | 0.8 |
| Ovarian ca. OVCAR-8 | 0.0 | Bone Marrow Pool | 0.1 |
| Ovary | 5.5 | Fetal Heart | 0.4 |
| Breast ca. MCF-7 | 0.0 | Heart Pool | 0.2 |
| Breast ca. MDA-MB-231 | 0.0 | Lymph Node Pool | 0.2 |
| Breast ca. BT 549 | 0.0 | Fetal Skeletal Muscle | 0.7 |
| Breast ca. T47D | 0.0 | Skeletal Muscle Pool | 18.4 |
| Breast ca. MDA-N | 38.4 | Spleen Pool | 0.1 |
| Breast Pool | 0.0 | Thymus Pool | 0.4 |
| Trachea | 1.4 | CNS cancer (glio/astro) U87-MG | 0.0 |
| Lung | 2.3 | CNS cancer (glio/astro) U-118-MG | 0.0 |
| Fetal Lung | 47.0 | CNS cancer (neuro; met) SK-N-AS | 0.0 |
| Lung ca. NCI-H417 | 0.0 | CNS cancer (astro) SF-539 | 1.2 |
| Lung ca. LX-1 | 0.0 | CNS cancer (astro) SNB-75 | 88.9 |
| Lung ca. NCI-H146 | 0.0 | CNS cancer (glio) SNB-19 | 0.3 |
| Lung ca. SHP-77 | 0.3 | CNS cancer (glio) SF-295 | 0.0 |
| Lung ca. A549 | 1.4 | Brain (Amygdala) Pool | 19.8 |
| Lung ca. NCI-H526 | 0.0 | Brain (cerebellum) | 100.0 |
| Lung ca. NCI-H23 | 0.0 | Brain (fetal) | 15.6 |
| Lung ca. NCI-H460 | 0.0 | Brain (Hippocampus) Pool | 25.5 |
| Lung ca. HOP-62 | 0.0 | Cerebral Cortex Pool | 42.3 |
| Lung ca. NCI-H522 | 0.0 | Brain (Substantia nigra) Pool | 20.0 |
| Liver | 0.0 | Brain (Thalamus) Pool | 35.6 |
| Fetal Liver | 0.4 | Brain (whole) | 18.3 |
| Liver ca. HepG2 | 0.1 | Spinal Cord Pool | 7.3 |
| Kidney Pool | 1.4 | Adrenal Gland | 0.0 |
| Fetal Kidney | 47.6 | Pituitary gland Pool | 6.4 |
| Renal ca. 786-0 | 0.0 | Salivary Gland | 0.0 |
| Renal ca. A498 | 0.0 | Thyroid (female) | 5.0 |
| Renal ca. ACHN | 0.0 | Pancreatic ca. CAPAN2 | 0.0 |
| Renal ca. UO-31 | 71.2 | Pancreas Pool | 0.1 |

TABLE BPD

Panel 4.1D

| Tissue Name | Rel. Exp. (%) Ag3925, Run 170594009 | Tissue Name | Rel. Exp. (%) Ag3925, Run 170594009 |
|---|---|---|---|
| Secondary Th1 act | 0.0 | HUVEC IL-1 beta | 0.0 |
| Secondary Th2 act | 0.0 | HUVEC IFN gamma | 0.0 |
| Secondary Tr1 act | 0.6 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |

TABLE BPD-continued

Panel 4.1D

| Tissue Name | Rel. Exp. (%) Ag3925, Run 170594009 | Tissue Name | Rel. Exp. (%) Ag3925, Run 170594009 |
|---|---|---|---|
| Primary Th1 act | 0.0 | Lung Microvascular EC TNF alpha + IL-1 beta | 0.0 |
| Primary Th2 act | 0.0 | Microvascular Dermal EC none | 0.0 |
| Primary Tr1 act | 0.0 | Microsvasular Dermal EC TNF alpha + IL-1 beta | 0.0 |
| Primary Th1 rest | 0.0 | Bronchial epithelium TNF alpha + IL1 beta | 2.9 |
| Primary Th2 rest | 0.0 | Small airway epithelium none | 0.0 |
| Primary Tr1 rest | 0.0 | Small airway epithelium TNF alpha + IL-1 beta | 0.3 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1 beta | 0.0 |
| CD8 lymphocyte act | 0.0 | Astrocytes rest | 0.4 |
| Secondary CD8 lymphocyte rest | 0.0 | Astrocytes TNF alpha + IL-1 beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1 beta | 0.0 |
| LAK cells IL-2 | 0.0 | Liver cirrhosis | 0.3 |
| LAK cells IL-2 + IL-12 | 0.0 | NCI-H292 none | 2.5 |
| LAK cells IL-2 + IFN gamma | 0.0 | NCI-H292 IL-4 | 0.0 |
| LAK cells IL-2 + IL-18 | 0.0 | NCI-H292 IL-9 | 0.0 |
| LAK cells PMA/ionomycin | 0.0 | NCI-H292 IL-13 | 0.0 |
| NK Cells IL-2 rest | 0.0 | NCI-H292 IFN gamma | 0.5 |
| Two Way MLR 3 day | 0.0 | HPAEC none | 0.0 |
| Two Way MLR 5 day | 0.0 | HPAEC TNF alpha + IL-1 beta | 0.0 |
| Two Way MLR 7 day | 0.0 | Lung fibroblast none | 0.0 |
| PBMC rest | 0.0 | Lung fibroblast TNF alpha + IL-1 beta | 0.0 |
| PBMC PWM | 0.0 | Lung fibroblast IL-4 | 0.7 |
| PBMC PHA-L | 0.0 | Lung fibroblast IL-9 | 0.0 |
| Ramos (B cell) none | 0.0 | Lung fibroblast IL-13 | 2.9 |
| Ramos (B cell) ionomycin | 0.0 | Lung fibroblast IFN gamma | 4.1 |
| B lymphocytes PWM | 0.0 | Dermal fibroblast CCD1070 rest | 2.2 |
| B lymphocytes CD40L and IL-4 | 0.0 | Dermal fibroblast CCD1070 TNF alpha | 4.6 |
| EOL-1 dbcAMP | 0.0 | Dermal fibroblast CCD1070 IL-1 beta | 0.5 |
| EOL-1 dbcAMP PMA/ionomycin | 0.0 | Dermal fibroblast IFN gamma | 0.6 |
| Dendritic cells none | 0.0 | Dermal fibroblast IL-4 | 0.6 |
| Dendritic cells LPS | 0.0 | Dermal Fibroblasts rest | 4.1 |
| Dendritic cells anti-CD40 | 0.0 | Neutrophils TNFa + LPS | 0.8 |
| Monocytes rest | 0.0 | Neutrophils rest | 0.0 |
| Monocytes LPS | 0.0 | Colon | 9.3 |
| Macrophages rest | 0.0 | Lung | 10.8 |
| Macrophages LPS | 0.0 | Thymus | 39.5 |
| HUVEC none | 0.0 | Kidney | 100.0 |
| HUVEC starved | 0.0 | | |

TABLE BPE

Panel CNS_1

| Tissue Name | Rel. Exp. (%) Ag3925, Run 180912024 | Tissue Name | Rel. Exp. (%) Ag3925, Run 180912024 |
|---|---|---|---|
| BA4 Control | 37.6 | BA17 PSP | 41.5 |
| BA4 Control2 | 47.3 | BA17 PSP2 | 7.9 |
| BA4 Alzheimer's2 | 3.2 | Sub Nigra Control | 18.6 |
| BA4 Parkinson's | 34.6 | Sub Nigra Control2 | 49.0 |
| BA4 Parkinson's2 | 100.0 | Sub Nigra Alzheimer's2 | 8.2 |

TABLE BPE-continued

Panel CNS_1

| Tissue Name | Rel. Exp. (%) Ag3925, Run 180912024 | Tissue Name | Rel. Exp. (%) Ag3925, Run 180912024 |
|---|---|---|---|
| BA4 Huntington's | 42.3 | Sub Nigra Parkinson's2 | 24.1 |
| BA4 Huntington's2 | 3.3 | Sub Nigra Huntington's | 39.8 |
| BA4 PSP | 6.8 | Sub Nigra Huntington's2 | 43.8 |
| BA4 PSP2 | 24.8 | Sub Nigra PSP2 | 5.6 |
| BA4 Depression | 13.2 | Sub Nigra Depression | 1.8 |
| BA4 Depression2 | 6.2 | Sub Nigra Depression2 | 7.4 |
| BA7 Control | 29.9 | Glob Palladus Control | 0.4 |
| BA7 Control2 | 39.5 | Glob Palladus Control2 | 2.2 |
| BA7 Alzheimer's2 | 3.8 | Glob Palladus Alzheimer's | 7.7 |
| BA7 Parkinson's | 12.0 | Glob Palladus Alzheimer's2 | 0.7 |
| BA7 Parkinson's2 | 47.3 | Glob Palladus Parkinson's | 28.5 |
| BA7 Huntington's | 42.9 | Glob Palladus Parkinson's2 | 1.8 |
| BA7 Huntington's2 | 33.7 | Glob Palladus PSP | 1.5 |
| BA7 PSP | 75.8 | Glob Palladus PSP2 | 2.8 |
| BA7 PSP2 | 22.4 | Glob Palladus Depression | 0.5 |
| BA7 Depression | 15.5 | Temp Pole Control | 19.9 |
| BA9 Control | 17.0 | Temp Pole Control2 | 61.1 |
| BA9 Control2 | 65.5 | Temp Pole Alzheimer's | 2.6 |
| BA9 Alzheimer's | 4.7 | Temp Pole Alzheimer's2 | 2.6 |
| BA9 Alzheimer's2 | 10.2 | Temp Pole Parkinson's | 34.2 |
| BA9 Parkinson's | 20.0 | Temp Pole Parkinson's2 | 26.4 |
| BA9 Parkinson's2 | 58.2 | Temp Pole Huntington's | 27.7 |
| BA9 Huntington's | 34.4 | Temp Pole PSP | 9.1 |
| BA9 Huntington's2 | 9.2 | Temp Pole PSP2 | 2.3 |
| BA9 PSP | 18.2 | Temp Pole Depression2 | 4.3 |
| BA9 PSP2 | 2.9 | Cing Gyr Control | 43.5 |
| BA9 Depression | 5.1 | Cing Gyr Control2 | 28.5 |
| BA9 Depression2 | 8.5 | Cing Gyr Alzheimer's | 9.5 |
| BA17 Control | 71.2 | Cing Gyr Alzheimer's2 | 2.7 |
| BA17 Control2 | 64.6 | Cing Gyr Parkinson's | 15.6 |
| BA17 Alzheimer's2 | 6.3 | Cing Gyr Parkinson's2 | 25.5 |
| BA17 Parkinson's | 29.9 | Cing Gyr Huntington's | 43.5 |
| BA17 Parkinson's2 | 56.6 | Cing Gyr Huntington's2 | 6.6 |
| BA17 Huntington's | 37.9 | Cing Gyr PSP | 13.9 |
| BA17 Huntington's2 | 12.9 | Cing Gyr PSP2 | 1.6 |
| BA17 Depression | 8.0 | Cing Gyr Depression | 4.5 |
| BA17 Depression2 | 10.7 | Cing Gyr Depression2 | 6.1 |

CNS_neurodegeneration_v1.0 Summary: Ag3925 This panel does not show differential expression of the CG94551-01 gene in Alzheimer's disease. However, this expression profile confirms the presence of this gene in the brain. Please see Panel 1.4 for discussion of utility of this gene in the central nervous system.

General_screening_panel_v1.4 Summary: Ag3925 The CG94551-01 gene appears to be prefrentially expressed in the brain, with highest expression in the cerebellum (CT=27). Moderate levels of expression are also seen in amygdala, hippocampus, cerebral cortex, substantia nigra, and thalamus. This gene encodes a homolog of MUNC 13, a protein involved in neurotransmitter release at the synaptic junction. Therefore, therapeutic modulation of the expression or function of this protein may be useful in the treatment of disease where reduction in neurotransmission has been shown to ameliorate symptomology (e.g., epilepsy or other seizure disorders, schizophrenia, bipolar disorder or anxiety).

Moderate levels of expression are also seen in cell lines derived from brain, colon, renal and breast cancers. Therefore, expression of this gene may be used as a diagnostic marker for the presence of these cancers.

Among metabolic tissues, moderate to low levels of expression are seen in thyroid, pituitary, fetal liver, adipose and fetal and adult skeletal muscle. This widespread expression among metabolic tissues suggests that this gene product may be involved in the pathogenesis and/or treatment of metabolic disorders, including obesity and diabetes.

In addition, this gene is expressed at much higher levels in fetal lung, kidney and skeletal muscle tissue (CTs=28–29) when compared to expression in the adult counterpart (CTs=32–34). Thus, expression of this gene may be used to differentiate between the fetal and adult source of these tissues (Richmond J E, Weimer R M, Jorgensen E M. An open form of syntaxin bypasses the requirement for UNC-13 in vesicle priming. Nature 2001 Jul. 19;412(6844):338–41).

Panel 4.1D Summary: Ag3925 Expression of the CG94551-01 gene, a MUNC 13 homolog, is highest in the kidney (CT=31). MUNC 13 has been shown to act as a diacylglycerol receptor that induces apoptosis and may contribute to diabetic nephropathy.

Moderate levels of expression are also seen in normal lung, thymus, and colon. This expression profile suggests that this gene product may be involved in the normal homeostasis of these organs. Therefore, therapeutic modulation of the expression or function of this gene may be useful in maintaining or restoring function to these organs during inflammation (Song Y, Ailenberg M, Silverman M. Human munc 13 is a diacylglycerol receptor that induces apoptosis and may contribute to renal cell injury in hyperglycemia. Mol Biol Cell 1999 May; 10(5): 1609–19).

Panel CNS_1 Summary: Ag3925 This panel confirms the presence of the CG94551-01 gene in the brain. Please see Panel 1.4 for discussion of utility of this gene in the central nervous system.

BQ. CG94682-02: Renal Organic Anion Transporter 1

Expression of gene CG94682-02 was assessed using the primer-probe set Ag3948, described in Table BQA. Results of the RTQ-PCR runs are shown in Tables BQB, BQC, BQD and BQE.

TABLE BQA

Probe Name Ag3948

| Primers | Sequences | Length | Start Position | SEQ ID NO: |
|---|---|---|---|---|
| Forward | 5'-ctctattcttggtggcttcca-3' | 21 | 808 | 465 |
| Probe | TET-5'-ctcctgcatggcaagtcccagttag-3'-TAMRA | 25 | 847 | 466 |
| Reverse | 5'-ccaccttctgcagattctgtac-3' | 22 | 874 | 467 |

TABLE BQB

AI_comprehensive panel_v1.0

| Tissue Name | Rel. Exp.(%) Ag3948, Run 247842315 | Tissue Name | Rel. Exp.(%) Ag3948, Run 247842315 |
|---|---|---|---|
| 110967 COPD-F | 17.8 | 112427 Match Control Psoriasis-F | 12.1 |
| 110980 COPD-F | 6.7 | 112418 Psoriasis-M | 11.2 |
| 110968 COPD-M | 9.2 | 112723 Match Control Psoriasis-M | 9.6 |
| 110977 COPD-M | 20.0 | 112419 Psoriasis-M | 30.6 |
| 110989 Emphysema-F | 34.6 | 112424 Match Control Psoriasis-M | 18.4 |
| 110992 Emphysema-F | 0.0 | 112420 Psoriasis-M | 94.6 |
| 110993 Emphysema-F | 18.6 | 112425 Match Control Psoriasis-M | 42.6 |
| 110994 Emphysema-F | 9.2 | 104689 (MF) OA Bone-Backus | 20.2 |
| 110995 Emphysema-F | 100.0 | 104690 (MF) Adj "Normal" Bone-Backus | 7.2 |
| 110996 Emphysema-F | 5.2 | 104691 (MF) OA Synovium-Backus | 10.0 |
| 110997 Asthma-M | 18.0 | 104692 (BA) OA Cartilage-Backus | 0.0 |
| 111001 Asthma-F | 0.0 | 104694 (BA) OA Bone-Backus | 14.2 |
| 111002 Asthma-F | 8.8 | 104695 (BA) Adj "Normal" Bone-Backus | 7.5 |
| 111003 Atopic Asthma-F | 5.6 | 104696 (BA) OA Synovium-Backus | 13.9 |
| 111004 Atopic Asthma-F | 41.5 | 104700 (SS) OA Bone-Backus | 35.6 |
| 111005 Atopic Asthma-F | 17.6 | 104701 (SS) Adj "Normal" Bone-Backus | 8.7 |
| 111006 Atopic Asthma-F | 0.0 | 104702 (SS) OA Synovium-Backus | 26.8 |
| 111417 Allergy-M | 2.4 | 117093 OA Cartilage Rep7 | 18.9 |
| 112347 Allergy-M | 0.0 | 112672 OA Bone5 | 13.4 |
| 112349 Normal Lung-F | 10.1 | 112673 OA Synovium5 | 0.0 |
| 112357 Normal Lung-F | 9.2 | 112674 OA Synovial Fluid cells5 | 5.8 |
| 112354 Normal Lung-M | 19.2 | 117100 OA Cartilage Rep14 | 14.8 |
| 112374 Crohns-F | 28.3 | 112756 OA Bone9 | 21.0 |
| 112389 Match Control Crohns-F | 15.2 | 112757 OA Synovium9 | 20.3 |
| 112375 Crohns-F | 14.3 | 112758 OA Synovial Fluid Cells9 | 7.2 |
| 112732 Match Control Crohns-F | 92.7 | 117125 RA Cartilage Rep2 | 25.9 |
| 112725 Crohns-M | 23.5 | 113492 Bone2 RA | 10.9 |
| 112387 Match Control Crohns-M | 13.6 | 113493 Synovium2 RA | 8.8 |
| 112378 Crohns-M | 14.4 | 113494 Syn Fluid Cells RA | 16.8 |
| 112390 Match Control Crohns-M | 72.7 | 113499 Cartilage4 RA | 12.9 |
| 112726 Crohns-M | 12.8 | 113500 Bone4 RA | 20.7 |
| 112731 Match Control Crohns-M | 65.5 | 113501 Synovium4 RA | 13.8 |
| 112380 Ulcer Col-F | 18.6 | 113502 Syn Fluid Cells4 RA | 3.1 |
| 112734 Match Control Ulcer Col-F | 89.5 | 113495 Cartilage3 RA | 6.8 |
| 112384 Ulcer Col-F | 57.8 | 113496 Bone3 RA | 20.7 |

TABLE BQB-continued

AI_comprehensive_panel_v1.0

| Tissue Name | Rel. Exp.(%) Ag3948, Run 247842315 | Tissue Name | Rel. Exp.(%) Ag3948, Run 247842315 |
| --- | --- | --- | --- |
| 112737 Match Control Ulcer Col-F | 15.6 | 113497 Synovium3 RA | 8.7 |
| 112386 Ulcer Col-F | 2.7 | 113498 Syn Fluid Cells3 RA | 21.6 |
| 112738 Match Control Ulcer Col-F | 4.3 | 117106 Normal Cartilage Rep20 | 5.7 |
| 112381 Ulcer Col-M | 0.0 | 113663 Bone3 Normal | 16.2 |
| 112735 Match Control Ulcer Col-M | 58.2 | 113664 Synovium3 Normal | 2.6 |
| 112382 Ulcer Col-M | 8.4 | 113665 Syn Fluid Cells3 Normal | 5.2 |
| 112394 Match Control Ulcer Col-M | 17.1 | 117107 Normal Cartilage Rep22 | 11.0 |
| 112383 Ulcer Col-M | 47.3 | 113667 Bone4 Normal | 15.4 |
| 112736 Match Control Ulcer Col-M | 1.9 | 113668 Synovium4 Normal | 20.2 |
| 112423 Psoriasis-F | 27.4 | 113669 Syn Fluid Cells4 Normal | 40.9 |

TABLE BQC

CNS_neurodegeneration_v1.0

| Tissue Name | Rel. Exp.(%) Ag3948, Run 212345604 | Tissue Name | Rel. Exp.(%) Ag3948, Run 212345604 |
| --- | --- | --- | --- |
| AD 1 Hippo | 0.0 | Control (Path) 3 Temporal Ctx | 0.0 |
| AD 2 Hippo | 57.0 | Control (Path) 4 Temporal Ctx | 33.4 |
| AD 3 Hippo | 32.5 | AD 1 Occipital Ctx | 67.8 |
| AD 4 Hippo | 0.0 | AD 2 Occipital Ctx (Missing) | 5.3 |
| AD 5 Hippo | 47.0 | AD 3 Occipital Ctx | 0.0 |
| AD 6 Hippo | 20.3 | AD 4 Occipital Ctx | 0.0 |
| Control 2 Hippo | 0.0 | AD 5 Occipital Ctx | 18.4 |
| Control 4 Hippo | 0.0 | AD 6 Occipital Ctx | 39.2 |
| Control (Path) 3 Hippo | 0.0 | Control 1 Occipital Ctx | 0.0 |
| AD 1 Temporal Ctx | 0.0 | Control 2 Occipital Ctx | 79.6 |
| AD 2 Temporal Ctx | 16.7 | Control 3 Occipital Ctx | 42.0 |
| AD 3 Temporal Ctx | 14.9 | Control 4 Occipital Ctx | 0.0 |
| AD 4 Temporal Ctx | 0.0 | Control (Path) 1 Occipital Ctx | 46.0 |
| AD 5 Inf Temporal Ctx | 100.0 | Control (Path) 2 Occipital Ctx | 0.0 |
| AD 5 Sup Temporal Ctx | 0.0 | Control (Path) 3 Occipital Ctx | 0.0 |
| AD 6 Inf Temporal Ctx | 65.1 | Control (Path) 4 Occipital Ctx | 11.7 |
| AD 6 Sup Temporal Ctx | 91.4 | Control 1 Parietal Ctx | 10.3 |
| Control 1 Temporal Ctx | 0.0 | Control 2 Parietal Ctx | 49.3 |
| Control 2 Temporal Ctx | 0.0 | Control 3 Parietal Ctx | 0.0 |
| Control 3 Temporal Ctx | 0.0 | Control (Path) 1 Parietal Ctx | 67.8 |
| Control 3 Temporal Ctx | 18.0 | Control (Path) 2 Parietal Ctx | 14.4 |
| Control (Path) 1 Temporal Ctx | 32.1 | Control (Path) 3 Parietal Ctx | 0.0 |
| Control (Path) 2 Temporal Ctx | 9.7 | Control (Path) 4 Parietal Ctx | 20.4 |

TABLE BQD

General_screening_panel_v1.4

| Tissue Name | Rel. Exp.(%) Ag3948, Run 219279808 | Tissue Name | Rel. Exp.(%) Ag3948, Run 219279808 |
| --- | --- | --- | --- |
| Adipose | 0.3 | Renal ca. TK-10 | 2.1 |
| Melanoma* Hs688 (A).T | 0.5 | Bladder | 2.8 |
| Melanoma* Hs688 (B).T | 0.2 | Gastric ca. (liver met.) NCI-N87 | 22.2 |
| Melanoma* M14 | 0.2 | Gastric ca. KATO III | 4.0 |
| Melanoma* LOXIMVI | 0.0 | Colon ca. SW-948 | 0.1 |
| Melanoma* SK-MEL-5 | 0.1 | Colon ca. SW480 | 10.5 |
| Squamous cell carcinoma SCC-4 | 2.4 | Colon ca.* (SW480 met) SW620 | 1.6 |

TABLE BQD-continued

General_screening_panel_v1.4

| Tissue Name | Rel. Exp.(%) Ag3948, Run 219279808 | Tissue Name | Rel. Exp.(%) Ag3948, Run 219279808 |
|---|---|---|---|
| Testis Pool | 0.3 | Colon ca. HT29 | 1.5 |
| Prostate ca.* (bone met) PC-3 | 0.9 | Colon ca. HCT-116 | 2.3 |
| Prostate Pool | 0.3 | Colon ca. CaCo-2 | 0.7 |
| Placenta | 0.2 | Colon cancer tissue | 0.2 |
| Uterus Pool | 0.1 | Colon ca. SW1116 | 0.1 |
| Ovarian ca. OVCAR-3 | 11.5 | Colon ca. Colo-205 | 0.6 |
| Ovarian ca. SK-OV-3 | 1.3 | Colon ca. SW-48 | 0.8 |
| Ovarian ca. OVCAR-4 | 0.4 | Colon Pool | 0.6 |
| Ovarian ca. OVCAR-5 | 8.0 | Small Intestine Pool | 0.4 |
| Ovarian ca. IGROV-1 | 1.9 | Stomach Pool | 0.1 |
| Ovarian ca. OVCAR-8 | 0.5 | Bone Marrow Pool | 0.4 |
| Ovary | 0.4 | Fetal Heart | 0.1 |
| Breast ca. MCF-7 | 3.2 | Heart Pool | 0.3 |
| Breast ca. MDA-MB-231 | 2.3 | Lymph Node Pool | 0.7 |
| Breast ca. BT 549 | 0.2 | Fetal Skeletal Muscle | 0.6 |
| Breast ca. T47D | 9.6 | Skeletal Muscle Pool | 0.4 |
| Breast ca. MDA-N | 0.2 | Spleen Pool | 0.2 |
| Breast Pool | 0.7 | Thymus Pool | 0.3 |
| Trachea | 0.6 | CNS cancer (glio/astro) U87-MG | 0.5 |
| Lung | 0.2 | CNS cancer (glio/astro) U-118-MG | 0.1 |
| Fetal Lung | 1.7 | CNS cancer (neuro; met) SK-N-AS | 0.4 |
| Lung ca. NCI-N417 | 0.1 | CNS cancer (astro) SF-539 | 0.1 |
| Lung ca. LX-1 | 100.0 | CNS cancer (astro) SNB-75 | 0.1 |
| Lung ca. NCI-H146 | 1.0 | CNS cancer (glio) SNB-19 | 0.9 |
| Lung ca. SHP-77 | 0.1 | CNS cancer (glio) SF-295 | 9.3 |
| Lung ca. A549 | 2.2 | Brain (Amygdala) Pool | 0.1 |
| Lung ca. NCI-H526 | 0.1 | Brain (cerebellum) | 5.1 |
| Lung ca. NCI-H23 | 0.9 | Brain (fetal) | 2.3 |
| Lung ca. NCI-H460 | 0.2 | Brain (Hippocampus) Pool | 0.0 |
| Lung ca. HOP-62 | 0.5 | Cerebral Cortex Pool | 0.0 |
| Lung ca. NCI-H522 | 1.1 | Brain (Substantia nigra) Pool | 0.2 |
| Liver | 0.3 | Brain (Thalamus) Pool | 0.0 |
| Fetal Liver | 0.8 | Brain (whole) | 0.8 |
| Liver ca. HepG2 | 0.2 | Spinal Cord Pool | 0.0 |
| Kidney Pool | 0.7 | Adrenal Gland | 0.2 |
| Fetal Kidney | 0.7 | Pituitary gland Pool | 0.0 |
| Renal ca. 786-0 | 0.2 | Salivary Gland | 0.1 |
| Renal ca. A498 | 0.2 | Thyroid (female) | 0.7 |
| Renal ca. ACHN | 0.2 | Pancreatic ca. CAPAN2 | 3.8 |
| Renal ca. UO-31 | 1.6 | Pancreas Pool | 0.6 |

TABLE BQE

Panel 4.1D

| Tissue Name | Rel. Exp. (%) Ag3948, Run 170684837 | Tissue Name | Rel. Exp. (%) Ag3948, Run 170684837 |
|---|---|---|---|
| Secondary Th1 act | 1.6 | HUVEC IL-1 beta | 3.1 |
| Secondary Th2 act | 8.6 | HUVEC IFN gamma | 7.4 |
| Secondary Tr1 act | 4.4 | HUVEC TNF alpha + IFN gamma | 2.7 |
| Secondary Th1 rest | 0.3 | HUVEC TNF alpha + IL4 | 0.9 |
| Secondary Th2 rest | 3.9 | HUVEC IL-11 | 6.0 |
| Secondary Tr1 rest | 1.6 | Lung Microvascular EC none | 7.3 |
| Primary Th1 act | 0.3 | Lung Microvascular EC TNF alpha + IL-1 beta | 2.7 |
| Primary Th2 act | 1.6 | Microvascular Dermal EC none | 0.0 |
| Primary Tr1 act | 0.0 | Microsvascular Dermal EC TNF alpha + IL-1 beta | 0.5 |
| Primary Th1 rest | 0.0 | Bronchial epithelium TNF alpha + IL1 beta | 15.5 |
| Primary Th2 rest | 1.6 | Small airway epithelium none | 6.3 |
| Primary Tr1 rest | 0.4 | Small airway epithelium TNF alpha + IL-1 beta | 20.4 |
| CD45RA CD4 lymphocyte act | 0.0 | Coronery artery SMC rest | 6.0 |
| CD45RO CD4 lymphocyte act | 1.2 | Coronery artery SMC TNF alpha + IL-1 beta | 1.6 |
| CD8 lymphocyte act | 2.8 | Astrocytes rest | 0.3 |

TABLE BQE-continued

Panel 4.1D

| Tissue Name | Rel. Exp. (%) Ag3948, Run 170684837 | Tissue Name | Rel. Exp. (%) Ag3948, Run 170684837 |
|---|---|---|---|
| Secondary CD8 lymphocyte rest | 2.0 | Astrocytes TNF alpha + IL-1 beta | 1.5 |
| Secondary CD8 lymphocyte act | 1.2 | KU-812 (Basophil) rest | 3.4 |
| CD4 lymphocyte none | 1.6 | KU-812 (Basophil) PMA/ionomycin | 6.3 |
| 2ry Th1/Th2/Tr1_anti-CD95 CH11 | 4.6 | CCD1106 (Keratinocytes) none | 14.6 |
| LAK cells rest | 1.6 | CCD1106 (Keratinocytes) TNF alpha + IL-1 beta | 20.6 |
| LAK cells IL-2 | 1.7 | Liver cirrhosis | 0.0 |
| LAK cells IL-2 + IL-12 | 3.6 | NCI-H292 none | 49.7 |
| LAK cells IL-2 + IFN gamma | 0.0 | NCI-H292 IL-4 | 79.6 |
| LAK cells IL-2 + IL-18 | 1.7 | NCI-H292 IL-9 | 92.7 |
| LAK cells PMA/ionomycin | 0.0 | NCI-H292 IL-13 | 58.2 |
| NK Cells IL-2 rest | 4.9 | NCI-H292 IFN gamma | 50.0 |
| Two Way MLR 3 day | 3.1 | HPAEC none | 8.6 |
| Two Way MLR 5 day | 1.4 | HPAEC TNF alpha + IL-1 beta | 3.5 |
| Two Way MLR 7 day | 4.1 | Lung fibroblast none | 2.7 |
| PBMC rest | 2.5 | Lung fibroblast TNF alpha + IL-1 beta | 2.9 |
| PBMC PWM | 2.3 | Lung fibroblast IL-4 | 2.9 |
| PBMC PHA-L | 0.4 | Lung fibroblast IL-9 | 4.0 |
| Ramos (B cell) none | 0.0 | Lung fibroblast IL-13 | 5.5 |
| Ramos (B cell) ionomycin | 0.0 | Lung fibroblast IFN gamma | 5.8 |
| B lymphocytes PWM | 0.0 | Dermal fibroblast CCD1070 rest | 16.2 |
| B lymphocytes CD40L and IL-4 | 7.6 | Dermal fibroblast CCD1070 TNF alpha | 4.7 |
| EOL-1 dbcAMP | 1.9 | Dermal fibroblast CCD1070 IL-1 beta | 1.8 |
| EOL-1 dbcAMP PMA/ionomycin | 5.5 | Dermal fibroblast IFN gamma | 6.7 |
| Dendritic cells none | 1.6 | Dermal fibroblast IL-4 | 4.1 |
| Dendritic cells LPS | 0.0 | Dermal Fibroblasts rest | 12.2 |
| Dendritic cells anti-CD40 | 0.7 | Neutrophils TNFa + LPS | 0.7 |
| Monocytes rest | 2.8 | Neutrophils rest | 1.5 |
| Monocytes LPS | 9.3 | Colon | 5.5 |
| Macrophages rest | 0.0 | Lung | 11.6 |
| Macrophages LPS | 0.8 | Thymus | 40.6 |
| HUVEC none | 0.3 | Kidney | 100.0 |
| HUVEC starved | 9.9 | | |

AI_comprehensive panel_v1.0 Summary: Ag3948 This panel confirms expression of the CG94682-02 gene in tissue samples related to the immune and inflammatory response. Please see Panels 4 and 4.1D for discussion of utility of this gene in inflammation.

CNS_neurodegeneration_v1.0 Summary: Ag3948 This panel does not show differential expression of the CG94682-02 gene in Alzheimer's disease. However, this expression profile confirms the presence of this gene in the brain. Please see Panel General_screening_panel_v1.4 for discussion of utility of this gene in the central nervous system.

General_screening_panel_v1.4 Summary: Ag3948 The expression of the CG94682-02 gene, an organic anion transporter homolog, is highest in a small cell lung cancer line LX-1 (CT=28.2). This gene is also expressed in some ovarian, breast, CNS, gastric, pancreatic, renal and colon cancer cell lines. Therefore, expression of this gene may be associated with these forms of cancer and therapeutic modulation of this gene might be of use in the treatment or diagnosis of these cancers.

This gene is also expressed at low levels in the cerebellum and fetal brain. The organic anion transporters are involved in transport across the blood brain barrier. This gene may therefore be of use in drug delivery to the CNS, specifically for compounds such as nerve growth factors protein therapeutics which are believed to have numerous uses in the CNS, but lack a delivery system (Sugiyama D, Kusuhara H, Shitara Y, Abe T, Meier P J, Sekine T, Endou H, Suzuki H, Sugiyama Y. Characterization of the efflux transport of 17beta-estradiol-D-17beta-glucuronide from the brain across the blood-brain barrier. J Pharmacol Exp Ther 2001 July;298(1):316–22).

Ag3532 Results from one experiment with this gene are not included. The amp plot indicates that there were instrumental difficulties with this run.

Panel 4.1D Summary: Ag3498 The highest expression of the CG94682-02 gene is found in the kidney and in the pulmonary muco-epidermoid cell line NCI-H292 (CTs=31). The expression of this gene, although constitutive in the H292 cell line, is up regulated upon treatment with IL-4, IL-9 and IL-13, cytokines that have been linked to the pathogenesis of asthma and/or COPD.

This gene is also found in small airway epithelium and keratinocytes treated with the inflammatory cytokines TNF-a and IL-1b. Therefore, modulation of the expression or activity of the protein encoded by this transcript through the application of small molecule therapeutics may be useful in the treatment of asthma, COPD, emphysema, psoriasis and wound healing.

Example 84

Identification of Single Nucleotide Polymorphisms in NOVX Nucleic Acid Sequences Variant sequences are also included in this application. A variant sequence can include a single nucleotide polymorphism (SNP). A SNP can, in some instances, be referred to as a "cSNP" to denote that the nucleotide sequence containing the SNP originates as a cDNA. A SNP can arise in several ways. For example, a SNP may be due to a substitution of one nucleotide for another at the polymorphic site. Such a substitution can be either a transition or a transversion. A SNP can also arise from a deletion of a nucleotide or an insertion of a nucleotide, relative to a reference allele. In this case, the polymorphic site is a site at which one allele bears a gap with respect to a particular nucleotide in another allele. SNPs occurring within genes may result in an alteration of the amino acid encoded by the gene at the position of the SNP. Intragenic SNPs may also be silent, when a codon including a SNP encodes the same amino acid as a result of the redundancy of the genetic code. SNPs occurring outside the region of a gene, or in an intron within a gene, do not result in changes in any amino acid sequence of a protein but may result in altered regulation of the expression pattern. Examples include alteration in temporal expression, physiological response regulation, cell type expression regulation, intensity of expression, and stability of transcribed message.

SeqCalling assemblies produced by the exon linking process were selected and extended using the following criteria. Genomic clones having regions with 98% identity to all or part of the initial or extended sequence were identified by BLASTN searches using the relevant sequence to query human genomic databases. The genomic clones that resulted were selected for further analysis because this identity indicates that these clones contain the genomic locus for these SeqCalling assemblies. These sequences were analyzed for putative coding regions as well as for similarity to the known DNA and protein sequences. Programs used for these analyses include Grail, Genscan, BLAST, HMMER, FASTA, Hybrid and other relevant programs.

Some additional genomic regions may have also been identified because selected SeqCalling assemblies map to those regions. Such SeqCalling sequences may have overlapped with regions defined by homology or exon prediction. They may also be included because the location of the fragment was in the vicinity of genomic regions identified by similarity or exon prediction that had been included in the original predicted sequence. The sequence so identified was manually assembled and then may have been extended using one or more additional sequences taken from CuraGen Corporation's human SeqCalling database. SeqCalling fragments suitable for inclusion were identified by the CuraTools™ program SeqExtend or by identifying SeqCalling fragments mapping to the appropriate regions of the genomic clones analyzed.

The regions defined by the procedures described above were then manually integrated and corrected for apparent inconsistencies that may have arisen, for example, from miscalled bases in the original fragments or from discrepancies between predicted exon junctions, EST locations and regions of sequence similarity, to derive the final sequence disclosed herein. When necessary, the process to identify and analyze SeqCalling assemblies and genomic clones was reiterated to derive the full length sequence (Alderborn et al., Determination of Single Nucleotide Polymorphisms by Real-time Pyrophosphate DNA Sequencing. Genome Research. 10 (8) 1249–1265, 2000).

Variants are reported individually but any combination of all or a select subset of variants are also included as contemplated NOVX embodiments of the invention.

NOV2a SNP Data:

NOV2a has one SNP variant, whose variant positions for its nucleotide and amino acid sequences is numbered according to SEQ ID NOs:3 and 4, respectively. The nucleotide sequence of the NOV5a variant differs as shown in Table SNP1.

TABLE SNP1

| | Nucleotides | | | Amino Acids | | |
|---|---|---|---|---|---|---|
| Variant | Position | Initial | Modified | Position | Initial | Modified |
| 13377738 | 806 | C | T | 268 | Gly | Gly |

NOV3a SNP Data:

NOV3a has six SNP variants, whose variant positions for its nucleotide and amino acid sequences are numbered according to SEQ ID NOs:7 and 8, respectively. The nucleotide sequence of the NOV3a variant differs as shown in Table SNP2.

TABLE SNP2

| | Nucleotides | | | Amino Acids | | |
|---|---|---|---|---|---|---|
| Variant | Position | Initial | Modified | Position | Initial | Modified |
| 13375699 | 1355 | T | C | 388 | Phe | Leu |
| 13375696 | 1685 | T | C | 498 | Cys | Arg |
| 13375695 | 1698 | C | T | 502 | Ala | Val |
| 13375694 | 1723 | G | A | 510 | Gln | Gln |
| 13375693 | 1727 | C | T | 512 | Pro | Ser |
| 13375692 | 1769 | C | T | 0 | | |

NOV4a SNP Data:

NOV4a has five SNP variants, whose variant positions for its nucleotide and amino acid sequences are numbered according to SEQ ID NOs:9 and 10, respectively. The nucleotide sequence of the NOV4a variant differs as shown in Table SNP3.

TABLE SNP3

| | Nucleotides | | | Amino Acids | | |
|---|---|---|---|---|---|---|
| Variant | Position | Initial | Modified | Position | Initial | Modified |
| 13374823 | 769 | G | A | 242 | Gly | Glu |
| 13376034 | 827 | T | C | 261 | Ala | Ala |
| 13374824 | 835 | A | G | 264 | His | Arg |
| 13374825 | 1089 | A | G | 349 | Lys | Glu |
| 13376033 | 1095 | T | C | 351 | Ser | Pro |

NOV5a SNP Data:

NOV5a has one SNP variant, whose variant positions for its nucleotide and amino acid sequences is numbered according to SEQ ID NOs: 15 and 16, respectively. The nucleotide sequence of the NOV5a variant differs as shown in Table SNP4.

TABLE SNP4

| | Nucleotides | | | Amino Acids | | |
|---|---|---|---|---|---|---|
| Variant | Position | Initial | Modified | Position | Initial | Modified |
| 13377739 | 596 | G | A | 175 | Arg | Gln |

NOV15a SNP Data:

NOV15a has two SNP variants, whose variant positions for its nucleotide and amino acid sequences are numbered according to SEQ ID NOs:41 and 42, respectively. The nucleotide sequence of the NOV15a variant differs as shown in Table SNP5.

TABLE SNP5

| | Nucleotides | | | Amino Acids | | |
|---|---|---|---|---|---|---|
| Variant | Position | Initial | Modified | Position | Initial | Modified |
| 13377740 | 813 | A | G | 262 | Thr | Thr |
| 13377741 | 1030 | T | C | 0 | | |

NOV19a SNP Data:

NOV19a has eleven SNP variants, whose variant positions for its nucleotide and amino acid sequences are numbered according to SEQ ID NOs:49 and 50, respectively. The nucleotide sequence of the NOV19a variant differs as shown in Table SNP6.

TABLE SNP6

| | Nucleotides | | | Amino Acids | | |
|---|---|---|---|---|---|---|
| Variant | Position | Initial | Modified | Position | Initial | Modified |
| 13375979 | 157 | C | T | 19 | Gly | Gly |
| 13375978 | 210 | T | C | 37 | Leu | Pro |
| 13375977 | 219 | A | C | 40 | Lys | Thr |
| 13375976 | 269 | A | G | 57 | Thr | Ala |
| 13375975 | 324 | A | G | 75 | Glu | Gly |
| 13375974 | 374 | G | A | 92 | Asp | Asn |
| 13375973 | 454 | A | G | 118 | Arg | Arg |
| 13375972 | 475 | T | C | 125 | Cys | Cys |
| 13375971 | 781 | T | C | 227 | Tyr | Tyr |
| 13375970 | 1589 | G | A | 497 | Ala | Thr |
| 13377742 | 1818 | C | T | 0 | | |

NOV20a SNP Data:

NOV20a has one SNP variant, whose variant positions for its nucleotide and amino acid sequences is numbered according to SEQ ID NOs:53 and 54, respectively. The nucleotide sequence of the NOV20a variant differs as shown in Table SNP7.

TABLE SNP7

| | Nucleotides | | | Amino Acids | | |
|---|---|---|---|---|---|---|
| Variant | Position | Initial | Modified | Position | Initial | Modified |
| 13377746 | 267 | C | T | 87 | Pro | Pro |
| 13377745 | 802 | A | G | 266 | Met | Val |
| 13377744 | 1368 | C | A | 454 | Asn | Lys |
| 13377743 | 1671 | T | C | 555 | Tyr | Tyr |

NOV21a SNP Data:

NOV21 has one SNP variant, whose variant positions for its nucleotide and amino acid sequences is numbered according to SEQ ID NOs:57 and 58, respectively. The nucleotide sequence of the NOV21 variant differs as shown in Table SNP8.

TABLE SNP8

| | Nucleotides | | | Amino Acids | | |
|---|---|---|---|---|---|---|
| Variant | Position | Initial | Modified | Position | Initial | Modified |
| 13377747 | 360 | C | T | 114 | Leu | Phe |

NOV23a SNP Data:

NOV23a has two SNP variants, whose variant positions for its nucleotide and amino acid sequences are numbered according to SEQ ID NOs:61 and 62, respectively. The nucleotide sequence of the NOV23a variant differs as shown in Table SNP9.

TABLE SNP9

| | Nucleotides | | | Amino Acids | | |
|---|---|---|---|---|---|---|
| Variant | Position | Initial | Modified | Position | Initial | Modified |
| 13377748 | 2580 | G | A | 850 | Thr | Thr |
| 13377749 | 3243 | T | C | 1071 | Asn | Asn |

NOV24a SNP Data:

NOV24a has one SNP variant, whose variant positions for its nucleotide and amino acid sequences is numbered according to SEQ ID NOs:63 and 64, respectively. The nucleotide sequences of the NOV24a variant differs as shown in Table SNP10.

TABLE SNP10

| | Nucleotides | | | Amino Acids | | |
|---|---|---|---|---|---|---|
| Variant | Position | Initial | Modified | Position | Initial | Modified |
| 13377750 | 324 | G | T | 104 | Glu | Asp |

NOV26a SNP Data:

NOV26a has two SNP variants, whose variant positions for its nucleotide and amino acid sequences are numbered according to SEQ ID NOs:67 and 68, respectively. The nucleotide sequence of the NOV26a variant differs as shown in Table SNP 11.

TABLE SNP11

| | Nucleotides | | | Amino Acids | | |
|---|---|---|---|---|---|---|
| Variant | Position | Initial | Modified | Position | Initial | Modified |
| 13377752 | 681 | C | T | 192 | Thr | Thr |
| 13377751 | 796 | A | G | 231 | Ser | Gly |

NOV81a SNP Data:

NOV81a has seven SNP variants, whose variant positions for its nucleotide and amino acid sequences are numbered according to SEQ ID NOs:211 and 212, respectively. The nucleotide sequence of the NOV81a variant differs as shown in Table SNP 12.

TABLE SNP12

| Variant | Nucleotides | | | Amino Acids | | |
|---|---|---|---|---|---|---|
| | Position | Initial | Modified | Position | Initial | Modified |
| 13375651 | 256 | T | C | 86 | Tyr | His |
| 13375314 | 392 | T | C | 131 | Leu | Pro |
| 13375429 | 610 | C | T | 204 | Leu | Phe |
| 13375779 | 853 | G | A | 285 | Asp | Asn |
| 13375778 | 908 | A | G | 303 | Asn | Ser |
| 13377753 | 1186 | A | G | 396 | Thr | Ala |
| 13375652 | 1312 | C | T | 438 | Arg | Trp |

NOV30a SNP Data:

NOV30a has one SNP variant, whose variant positions for its nucleotide and amino acid sequences is numbered according to SEQ ID NOs:77 and 78, respectively. The nucleotide sequence of the NOV30a variant differs as shown in Table SNP13.

TABLE SNP13

| Variant | Nucleotides | | | Amino Acids | | |
|---|---|---|---|---|---|---|
| | Position | Initial | Modified | Position | Initial | Modified |
| 13377756 | 591 | A | G | 197 | Lys | Lys |

NOV32a SNP Data:

NOV32a has one SNP variant, whose variant positions for its nucleotide and amino acid sequences is numbered according to SEQ ID NOs:83 and 84 respectively. The nucleotide sequence of the NOV32a variant differs as shown in Table SNP 14.

TABLE SNP14

| Variant | Nucleotides | | | Amino Acids | | |
|---|---|---|---|---|---|---|
| | Position | Initial | Modified | Position | Initial | Modified |
| 13376298 | 2469 | C | A | 801 | Thr | Thr |

NOV38a SNP Data:

NOV38a has two SNP variants, whose variant positions for its nucleotide and amino acid sequences are numbered according to SEQ ID NOs:97 and 98, respectively. The nucleotide sequence of the NOV38a variant differs as shown in Table SNP 15.

TABLE SNP15

| Variant | Nucleotides | | | Amino Acids | | |
|---|---|---|---|---|---|---|
| | Position | Initial | Modified | Position | Initial | Modified |
| 13377760 | 4685 | G | A | 1540 | Arg | His |
| 13377759 | 4763 | A | G | 1566 | Asp | Gly |

NOV39a SNP Data:

NOV39a has four SNP variants, whose variant positions for its nucleotide and amino acid sequences are numbered according to SEQ ID NOs:99 and 100, respectively. The nucleotide sequence of the NOV39a variant differs as shown in Table SNP16.

TABLE SNP16

| Variant | Nucleotides | | | Amino Acids | | |
|---|---|---|---|---|---|---|
| | Position | Initial | Modified | Position | Initial | Modified |
| 13375856 | 187 | G | A | 59 | Ala | Thr |
| 13375855 | 798 | C | T | 262 | Pro | Pro |
| 13375854 | 1021 | G | A | 337 | Gly | Arg |
| 13375853 | 1337 | G | A | 442 | Arg | His |

NOV40a SNP Data:

NOV40a has one SNP variant, whose variant positions for its nucleotide and amino acid sequences is numbered according to SEQ ID NOs: 101 and 102 respectively. The nucleotide sequence of the NOV40a variant differs as shown in Table SNP 17.

TABLE SNP17

| Variant | Nucleotides | | | Amino Acids | | |
|---|---|---|---|---|---|---|
| | Position | Initial | Modified | Position | Initial | Modified |
| 13377761 | 178 | A | G | 58 | Met | Val |

NOV42A SNP Data:

NOV42A has three SNP variants, whose variant positions for its nucleotide and amino acid sequences are numbered according to SEQ ID NOs: 105 and 106, respectively. The nucleotide sequence of the NOV42A variant differs as shown in Table SNP 18.

TABLE SNP18

| Variant | Nucleotides | | | Amino Acids | | |
|---|---|---|---|---|---|---|
| | Position | Initial | Modified | Position | Initial | Modified |
| 13377766 | 824 | A | T | 230 | Lys | End |
| 13377770 | 913 | T | C | 259 | Ala | Ala |
| 13377771 | 1042 | A | G | 302 | Leu | Leu |

NOV44a SNP Data:

NOV44a has two SNP variants, whose variant positions for its nucleotide and amino acid sequences are numbered according to SEQ ID NOs: 109 and 110, respectively. The nucleotide sequence of the NOV44a variant differs as shown in Table SNP 19.

TABLE SNP19

| Variant | Nucleotides | | | Amino Acids | | |
|---|---|---|---|---|---|---|
| | Position | Initial | Modified | Position | Initial | Modified |
| 13377775 | 450 | C | T | 150 | Ile | Ile |
| 13377774 | 551 | A | G | 184 | Asp | Gly |

NOV45a NP Data:

NOV45a has eleven SNP variants, whose variant positions for its nucleotide and amino acid sequences are numbered according to SEQ ID NOs: 111 and 112, respectively. The nucleotide sequence of the NOV45a variant differs as shown in Table SNP20.

TABLE SNP20

| Variant | Nucleotides | | | Amino Acids | | |
|---|---|---|---|---|---|---|
| | Position | Initial | Modified | Position | Initial | Modified |
| 13376182 | 154 | C | T | 20 | His | Tyr |
| 13376181 | 273 | T | G | 59 | Arg | Arg |
| 13376178 | 977 | T | C | 294 | Met | Thr |
| 13376177 | 1052 | A | G | 319 | His | Arg |
| 13376176 | 1111 | T | C | 339 | Tyr | His |
| 13376175 | 1280 | A | T | 395 | Gln | Leu |
| 13376174 | 1343 | A | G | 416 | Glu | Gly |
| 13376173 | 1349 | A | G | 418 | Glu | Gly |
| 13376172 | 1361 | A | G | 422 | Asn | Ser |
| 13376171 | 1427 | T | C | 444 | Leu | Pro |
| 13376170 | 1913 | G | A | 0 | | |

NOV52a SNP Data:
NOV52a has seven SNP variants, whose variant positions for its nucleotide and amino acid sequences are numbered according to SEQ ID NOs:127 and 128, respectively. The nucleotide sequence of the NOV52a variant differs as shown in Table SNP21.

TABLE SNP21

| Variant | Nucleotides | | | Amino Acids | | |
|---|---|---|---|---|---|---|
| | Position | Initial | Modified | Position | Initial | Modified |
| 13375586 | 430 | T | C | 110 | Ser | Ser |
| 13375585 | 492 | A | G | 131 | Glu | Gly |
| 13375584 | 1711 | A | G | 537 | Ile | Met |
| 13375583 | 1756 | C | T | 552 | Asn | Asn |
| 13375582 | 2143 | T | A | 681 | Pro | Pro |
| 13377559 | 2550 | A | G | 817 | Lys | Arg |
| 13377776 | 2555 | C | T | 819 | Leu | Leu |

NOV53a SNP Data:
NOV53a has one SNP variant, whose variant positions for its nucleotide and amino acid sequences is numbered according to SEQ ID NOs: 129 and 130, respectively. The nucleotide sequence of the NOV53a variant differs as shown in Table SNP22.

TABLE SNP22

| Variant | Nucleotides | | | Amino Acids | | |
|---|---|---|---|---|---|---|
| | Position | Initial | Modified | Position | Initial | Modified |
| 13376019 | 384 | C | T | 123 | Ser | Phe |

NOV54a SNP Data:
NOV54a has one SNP variant, whose variant positions for its nucleotide and amino acid sequences is numbered according to SEQ ID NOs:135 and 136, respectively. The nucleotide sequence of the NOV54a variant differs as shown in Table SNP23.

TABLE SNP23

| Variant | Nucleotides | | | Amino Acids | | |
|---|---|---|---|---|---|---|
| | Position | Initial | Modified | Position | Initial | Modified |
| 13376037 | 485 | A | G | 148 | Lys | Glu |

NOV55a SNP Data:
NOV55a has one SNP variant, whose variant positions for its nucleotide and amino acid sequences is numbered according to SEQ ID NOs: 135 and 136, respectively. The nucleotide sequence of the NOV55a variant differs as shown in Table SNP24.

TABLE SNP24

| Variant | Nucleotides | | | Amino Acids | | |
|---|---|---|---|---|---|---|
| | Position | Initial | Modified | Position | Initial | Modified |
| 13377777 | 941 | C | T | 304 | Arg | Trp |

NOV56a SNP Data:
NOV56a has three SNP variants, whose variant positions for its nucleotide and amino acid sequences are numbered according to SEQ ID NOs: 139 and 140, respectively. The nucleotide sequence of the NOV56a variant differs as shown in Table SNP25.

TABLE SNP25

| Variant | Nucleotides | | | Amino Acids | | |
|---|---|---|---|---|---|---|
| | Position | Initial | Modified | Position | Initial | Modified |
| 13377780 | 311 | A | G | 102 | Lys | Lys |
| 13377779 | 403 | G | A | 133 | Arg | His |
| 13377778 | 1303 | T | C | 433 | Leu | Pro |

NOV57a SNP Data:
NOV57a has nine SNP variants, whose variant positions for its nucleotide and amino acid sequences are numbered according to SEQ ID NOs: 141 and 142, respectively. The nucleotide sequence of the NOV57a variant differs as shown in Table SNP26.

TABLE SNP26

| Variant | Nucleotides | | | Amino Acids | | |
|---|---|---|---|---|---|---|
| | Position | Initial | Modified | Position | Initial | Modified |
| 13377782 | 140 | C | A | 11 | Ser | Tyr |
| 13377783 | 193 | G | C | 29 | Ala | Pro |
| 13377784 | 201 | G | A | 31 | Arg | Arg |
| 13377785 | 261 | C | T | 51 | Ser | Ser |
| 13377786 | 282 | T | C | 58 | Asn | Asn |
| 13377787 | 291 | T | C | 61 | Ala | Ala |
| 13377788 | 317 | A | T | 70 | Asp | Val |
| 13377789 | 418 | C | T | 104 | Leu | Leu |
| 13377790 | 461 | A | G | 118 | Asp | Gly |

NOV61a SNP Data:
NOV61a has seven SNP variants, whose variant positions for its nucleotide and amino acid sequences are numbered according to SEQ ID NOs: 153 and 154, respectively. The nucleotide sequence of the NOV61a variant differs as shown in Table SNP27.

TABLE SNP27

| Variant | Nucleotides | | | Amino Acids | | |
|---|---|---|---|---|---|---|
| | Position | Initial | Modified | Position | Initial | Modified |
| 13376354 | 241 | G | A | 67 | Arg | His |
| 13376355 | 283 | T | C | 81 | Ile | Thr |
| 13376356 | 420 | C | T | 127 | Leu | Phe |
| 13376357 | 474 | A | G | 145 | Ile | Val |
| 13376358 | 588 | A | G | 183 | Arg | Gly |
| 13376359 | 904 | T | A | 288 | Leu | Gln |
| 13376360 | 1384 | G | A | 448 | Gly | Asp |

NOV62a SNP Data:
NOV62a has two SNP variants, whose variant positions for its nucleotide and amino acid sequences are numbered according to SEQ ID NOs: 155 and 156, respectively. The nucleotide sequence of the NOV62a variant differs as shown in Table SNP28.

TABLE SNP28

| | Nucleotides | | | Amino Acids | | |
|---|---|---|---|---|---|---|
| Variant | Position | Initial | Modified | Position | Initial | Modified |
| 13377799 | 135 | C | T | 44 | Ala | Ala |
| 13376511 | 1228 | G | A | 409 | Ala | Thr |

NOV65a SNP Data:

NOV65a has two SNP variants, whose variant positions for its nucleotide and amino acid sequences are numbered according to SEQ ID NOs: 163 and 164, respectively. The nucleotide sequence of the NOV65a variant differs as shown in Table SNP29.

TABLE SNP29

| | Nucleotides | | | Amino Acids | | |
|---|---|---|---|---|---|---|
| Variant | Position | Initial | Modified | Position | Initial | Modified |
| 13376363 | 1001 | A | G | 312 | Asn | Asp |
| 13376362 | 1007 | A | G | 314 | Ile | Val |

NOV67a SNP Data:

NOV67a has three SNP variants, whose variant positions for its nucleotide and amino acid sequences are numbered according to SEQ ID NOs: 173 and 174, respectively. The nucleotide sequence of the NOV67a variant differs as shown in Table SNP30.

TABLE SNP30

| | Nucleotides | | | Amino Acids | | |
|---|---|---|---|---|---|---|
| Variant | Position | Initial | Modified | Position | Initial | Modified |
| 13377801 | 533 | A | T | 70 | Ser | Cys |
| 13376280 | 1815 | T | C | 497 | Phe | Ser |
| 13377802 | 4683 | A | G | 1453 | Glu | Gly |

NOV69a SNP Data:

NOV69a has one SNP variant, whose variant positions for its nucleotide and amino acid sequences is numbered according to SEQ ID NOs: 177 and 178, respectively. The nucleotide sequence of the NOV69a variant differs as shown in Table SNP31.

TABLE SNP31

| | Nucleotides | | | Amino Acids | | |
|---|---|---|---|---|---|---|
| Variant | Position | Initial | Modified | Position | Initial | Modified |
| 13377803 | 118 | G | A | 25 | Met | Ile |

NOV70a SNP Data:

NOV70a has eight SNP variants, whose variant positions for its nucleotide and amino acid sequences are numbered according to SEQ ID NOs: 179 and 180, respectively. The nucleotide sequence of the NOV70a variant differs as shown in Table SNP32.

TABLE SNP32

| | Nucleotides | | | Amino Acids | | |
|---|---|---|---|---|---|---|
| Variant | Position | Initial | Modified | Position | Initial | Modified |
| 13376466 | 285 | T | C | 14 | Ser | Pro |
| 13376465 | 310 | A | T | 22 | Gln | Leu |
| 13376463 | 502 | A | G | 86 | Asp | Gly |
| 13376461 | 603 | A | G | 120 | Lys | Glu |
| 13376457 | 993 | A | C | 250 | Thr | Pro |
| 13376458 | 1165 | G | A | 307 | Ser | Asn |
| 13376460 | 1680 | A | G | 479 | Thr | Ala |
| 13376459 | 1711 | A | G | 489 | Asp | Gly |

NOV71a SNP Data:

NOV71a has two SNP variants, whose variant positions for its nucleotide and amino acid sequences are numbered according to SEQ ID NOs: 185 and 186, respectively. The nucleotide sequence of the NOV71a variant differs as shown in Table SNP33.

TABLE SNP33

| | Nucleotides | | | Amino Acids | | |
|---|---|---|---|---|---|---|
| Variant | Position | Initial | Modified | Position | Initial | Modified |
| 13374756 | 535 | A | G | 179 | Asn | Asp |
| 13374757 | 572 | T | C | 191 | Leu | Ser |

NOV72a SNP Data:

NOV72a has three SNP variants, whose variant positions for its nucleotide and amino acid sequences are numbered according to SEQ ID NOs: 189 and 190, respectively. The nucleotide sequence of the NOV72a variant differs as shown in Table SNP34.

TABLE SNP34

| | Nucleotides | | | Amino Acids | | |
|---|---|---|---|---|---|---|
| Variant | Position | Initial | Modified | Position | Initial | Modified |
| 13377805 | 47 | G | C | 13 | Ser | Thr |
| 13377806 | 196 | T | C | 63 | Trp | Arg |
| 13377807 | 1272 | T | C | 421 | Gly | Gly |

NOV77a SNP Data:

NOV77a has four SNP variants, whose variant positions for its nucleotide and amino acid sequences are numbered according to SEQ ID NOs: 199 and 200, respectively. The nucleotide sequence of the NOV77a variant differs as shown in Table SNP35.

TABLE SNP35

| | Nucleotides | | | Amino Acids | | |
|---|---|---|---|---|---|---|
| Variant | Position | Initial | Modified | Position | Initial | Modified |
| 13375891 | 201 | A | G | 22 | Asn | Ser |
| 13375890 | 2463 | C | T | 776 | Thr | Ile |
| 13375892 | 2692 | C | T | 852 | Pro | Pro |
| 13375889 | 2755 | T | C | 873 | Thr | Thr |

Other Embodiments

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims. The claims presented are representative of the inventions disclosed herein. Other, unclaimed inventions are also contemplated. Applicants reserve the right to pursue such inventions in later claims.

What is claimed is:

1. An isolated nucleic acid molecule comprising a nucleic acid sequence encoding a polypeptide comprising an amino acid sequence of SEQ ID NO: 32.

2. The nucleic acid molecule of claim 1, wherein said nucleic acid molecule comprises a nucleotide sequence of SEQ ID NO: 31.

3. An isolated nucleic acid molecule that hybridizes under stringent conditions to the nucleotide sequence SEQ ID NO: 31.

4. A vector comprising the nucleic acid molecule of claim 2.

5. The vector of claim 4, further comprising a promoter operably linked to said nucleic acid molecule.

6. A cell comprising the vector of claim 4.

7. An isolated nucleic acid sequence, said nucleic acid sequence comprising the complement of SEQ ID NO: 31.

* * * * *